US009896446B2

(12) United States Patent
Breslin et al.

(10) Patent No.: US 9,896,446 B2
(45) **Date of Patent: *Feb. 20, 2018**

(54) AZAQUINAZOLINE INHIBITORS OF ATYPICAL PROTEIN KINASE C

(71) Applicants: IGNYTA, INC., San Diego, CA (US); Cancer Research Technology Limited, London (GB)

(72) Inventors: Henry J. Breslin, Lansdale, PA (US); Bruce D. Dorsey, Ambler, PA (US); Benjamin J. Dugan, Glen Mills, PA (US); Robert L. Hudkins, Chester Springs, PA (US); Eugen F. Mesaros, Wallingford, PA (US); Gregory R. Ott, Media, PA (US); Craig A. Zificsak, Dowingtown, PA (US); Allison L. Zulli, Wayne, PA (US); Ming Tao, Maple Glen, PA (US); Katherine M. Fowler, Caversham (GB); Emma L. Morris, Biggleswade (GB); Gregoire A. Pave, London (GB); Jonathan R. A. Roffey, Reading (GB); Nathaniel J. T. Monck, Ascot (GB); Christelle N. Soudy, London (GB); Ikeoluwa Olowoye, Hemel Hempstead (GB)

(73) Assignee: CANCER RESEARCH TECHNOLOGY LIMITED, London (GB)

(*) Notice: Subject to any disclaimer, the term of this patent is extended or adjusted under 35 U.S.C. 154(b) by 26 days.

This patent is subject to a terminal disclaimer.

(21) Appl. No.: 14/975,605

(22) Filed: Dec. 18, 2015

(65) Prior Publication Data

US 2016/0102094 A1 Apr. 14, 2016

Related U.S. Application Data

(63) Continuation of application No. 14/038,915, filed on Sep. 27, 2013.

(60) Provisional application No. 61/707,340, filed on Sep. 28, 2012, provisional application No. 61/781,364, filed on Mar. 14, 2013.

(51) Int. Cl.

| | |
|---|---|
| ***A61K 31/407*** | (2006.01) |
| ***C07D 471/04*** | (2006.01) |
| ***C07D 519/00*** | (2006.01) |
| ***C07D 493/08*** | (2006.01) |
| ***C07D 498/04*** | (2006.01) |
| ***C07F 9/6584*** | (2006.01) |

(52) U.S. Cl.

CPC ......... *C07D 471/04* (2013.01); *C07D 493/08* (2013.01); *C07D 498/04* (2013.01); *C07D 519/00* (2013.01); *C07F 9/6584* (2013.01)

(58) Field of Classification Search

None

See application file for complete search history.

(56) References Cited

U.S. PATENT DOCUMENTS

| | | | | |
|---|---|---|---|---|
| 7,361,662 | B2 | 4/2008 | Rault et al. | |
| 2005/0038047 | A1 | 2/2005 | Edwards et al. | |
| 2014/0113882 | A1 * | 4/2014 | Breslin ................ | C07D 493/08 514/81 |

FOREIGN PATENT DOCUMENTS

| | | | |
|---|---|---|---|
| JP | 1974036700 | A | 4/1974 |
| JP | 2004-509116 | A | 3/2004 |
| WO | WO-02/22606 | A1 | 3/2002 |
| WO | WO/2008/032157 | | 3/2008 |

OTHER PUBLICATIONS

Berge et al., "Pharmaceutical Salts," *J. Pharm. Sci.* (1977), pp. 1-19, vol. 66.

Eder et al., "Atypical PKCι contributes to poor prognosis through loss of apical-basal polarity and Cyclin E overexpression in ovarian cancer," *Proc. Natl. Acad. Sci.* (2005), pp. 12519-1224, vol. 102.

Farese et al., "Muscle-specific knockout of PKC-λ impairs glucose transport and induces metabolic and diabetic syndromes," *J. Clin. Invest.* (2007), pp. 2289-2301, vol. 117.

Fields et al., "Protein kinase Cι: Human oncogene, prognostic marker and therapeutic target," *Pharmacol. Res.* (2007), pp. 487-497, vol. 55.

Filomenko et al., "Atypical Protein Kinase Cζ as a Target for Chemosensitization of Tumor Cells," *Cancer Res.* (2002), pp. 1815-1821, vol. 62.

Garcia-Cao et al., "Tumour-suppression activity of the proapoptotic regulator Par4," *Embo Reports* (2005), pp. 577-583, vol. 6.

Gonzalez Campos et al., "Estudio Oscillopolarpgrafico de dos Derivados [5,4-d] pirimidinicos", ARS Pharmaceutica, (1986) 273:255-261.

Inoue et al., "Requirement of Androgen-Dependent Activation of Protein Kinase Cζ for Androgen-Dependent Cell Proliferation in LNCaP Cells and Its Roles in Transition to Androgen-Independent Cells," *Molecular Endocrin.* (2006), pp. 3053-3069, vol. 20.

(Continued)

*Primary Examiner* — Sreeni Padmanabhan
*Assistant Examiner* — Jeanmarie Calvillo
(74) *Attorney, Agent, or Firm* — Foley & Lardner LLP

(57) ABSTRACT

The present application provides a compound of formula (I)

(I)

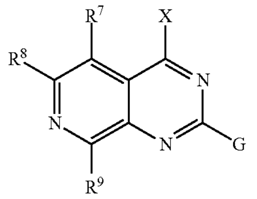

or a salt thereof, wherein $R^7$, $R^8$, $R^9$, G, and X are as defined herein. This application further describes compositions comprising the same. Compounds of formula (I) and their salts have aPKC inhibitory activity, and may be used to treat proliferative diseases.

14 Claims, No Drawings

(56) References Cited

OTHER PUBLICATIONS

Iorns et al., "Parallel RNAi and compound screens identify the PDK1 pathway as a target for tamoxifen sensitization," *Biochem J.* (2009), pp. 361-370, vol. 417.
Joshi et al., "Par-4 inhibits Akt and suppresses Ras-induced lung tumorigenesis," *Embo J.* (2008), pp. 2181-2193, vol. 27.
Kojima et al., "The overexpression and altered localization of the atypical protein kinase C lambda/iota in breast cancer correlates with the pathologic type of these tumors," *Human Pathology* (2008), pp. 824-831, vol. 39.
Leitges et al., "Targeted Disruption of the ζPKC Gene Results in the Impairment of the NF-κB Pathway," *Molecular Cell*, pp. 771-780, vol. 8.
Leseux et al., "PKCζ-mTOR pathway: a new target for rituximab therapy in follicular lymphoma," *Blood* (2008), vol. 111, pp. 285-291.
Murray et al., "Protein kinase Cι required for Ras transformation and colon carcinogenesis in vivo," *J. Cell Biology* (2004), vol. 164, pp. 797-802.
Nishikawa et al., "Structure-Activity Relationships of the Diuretic Activity of Triaza- and Tetraaza-naphthalene Compounds," *Chem. Pharm. Bull.* (1976), vol. 24, pp. 2057-2077.
Ono et al., "Protein Kinase Cζ subspecies from rat brain: Its structure, expression, and properties," *Proc. Natl. Acad. Sci.* (1989), vol. 86, pp. 3099-3103.
Osborne et al., "Role of the Estrogen Receptor Coactivator AIB1 (SRC-3) and HER-2/neu in Tamoxifen Resistance in Breast Cancer," *J. Natl. Cancer Inst.* (2003), vol. 95, pp. 353-361.
PCT Written Opinion dated Mar. 28, 2015 in PCT/US2013/062085.
Plo et al., "Overexpression of the Atypical Protein Kinase Cζ Reduces Topoisomerase II Catalytic Activity, Cleavable Complexes Formation, and Drug-induced Cytotoxicity in Monocytic U937 Leukemia Cells," *J. Biological Chem.* (2002), vol. 277, pp. 31407-31415.
Regala et al., "Atypical Protein Kinase CιIs an Oncogene in Human Non-small Cell Lung Cancer," *Cancer Res.* (2005), vol. 65, pp. 8905-8911.
Regala et al., "Atypical Protein Kinase Cι Expression and Aurothiomalate Sensitivity in Human Lung *Cancer Cells*," Cancer Res. (2008), vol. 68, pp. 5888-5895.
Regala et al., "Atypical Protein Kinase Cι Plays a Critical Role in Human Lung Cancer Cell Growth and Tumorigenicity," *J. Biological Chem.* (2005), vol. 280, pp. 31109-31115.
Search Report and Written Opinion for Application No. 11201502301Y dated Feb. 23.
Suzuki et al., "The PAR-aPKG system: lessons in polarity," *J. Cell Sci.* (2006), vol. 119, pp. 979-987.
Van Eis et al., 2,6-Naphthyridines as potent and selective inhibitors of the novel protein kinase C isozymes, Bioorganic & Medicinal Chemistry Letters, Pergamon GB, (2011) 21(24):7367-7372.
Xin et al., Protein Kinase Cζ Abrogates the Proapoptotic Function or Bax Through Phosphorylation, *J. Biological Chem.* (2007), vol. 282, pp. 21268-21277.
Yang et al., "Amplification of PRKCI, Located in 3q26, Is Associated with Lymph Node Metastasis in Esophageal Squamous Cell Carcinoma," *Genes, Chromosomes & Cancer* (2008), vol. 47, pp. 127-136.
Yi et al., "Atypical Protein Kinase C Regulates Dual Pathways for Degradation of the Oncogenic Coactivator SRC-3/AIBI," *Molecular Cell* (2008), vol. 29, pp. 465-476.
Zhang et al., "Integrative Geonomic Analysis of Protein Kinase C (PKC) Family Identifies PKCι as a Biomarker and Potential Oncogene in Ovarian Carcinoma," Cancer Res. (2006), vol. 66, pp. 4627-4635.

* cited by examiner

AZAQUINAZOLINE INHIBITORS OF ATYPICAL PROTEIN KINASE C

CROSS REFERENCE TO RELATED APPLICATIONS

This application is a continuation application and claims the benefit under 35 U.S.C. §120 of the priority date of U.S. application Ser. No. 14/038,915, filed Sep. 27, 2013, which claims the benefit under 35 U.S.C. §119(e) of the priority date of U.S. Provisional Application Nos. 61/707,340, filed Sep. 28, 2012 and 61/781,364, filed Mar. 14, 2013, the disclosures of each of which are incorporated herein by reference in their entireties.

BACKGROUND

PKCι and PKCζ (accession numbers NM_002740 and NM_002744 respectively) together define the atypical sub-class of the protein kinase C (PKC) family. The aPKCs are structurally and functionally distinct from the other PKC sub-classes, classic/conventional and novel, as their catalytic activity is not dependent on diacylglycerol and calcium (Ono, Y., Fujii, T., Ogita, K., Kikkawa, U., Igarashi, K., and Nishizuka, Y. (1989). Protein kinase C zeta subspecies from rat brain: its structure, expression, and properties. Proc Natl Acad Sci USA 86, 3099-3103). Structurally, PKCι and PKCζ contain a C-terminal serine/threonine kinase domain (AGC class) and an N-terminal regulatory region containing a Phox Bem 1 (PB 1) domain involved in mediating protein: protein interactions critical for aPKC function. At the amino acid level the aPKCs share 72% overall homology, however, the kinase domains share 84% identity and differ in the active site by just a single amino acid. This striking homology suggests an ATP-competitive ligand would not be expected to exhibit significant aPKC isoform selectivity.

The aPKCs have been implicated in a diverse number of signalling pathways, demonstrating both redundant and distinct signalling functions. Both isoforms have emerged as central players in the mechanisms that regulate the establishment and maintenance of cellular polarity in multiple cell types (reviewed in Suzuki, A., and Ohno, S. (2006). The PAR-aPKC system: lessons in polarity. J Cell Sci 119, 979-987). Genetic dissection of their functions using knockout mice have also revealed preferential roles for PKCζ in the regulation of NF-kB signalling (Leitges, M., Sanz, L., Martin, P., Duran, A., Braun, U., Garcia, J. F., Camacho, F., Diaz-Meco, M. T., Rennert, P. D., and Moscat, J. (2001). Targeted disruption of the zetaPKC gene results in the impairment of the NF-kappaB pathway. Mol Cell 8, 771-780), and PKCι in insulin secretion and action (Farese, R. V., Sajan, M. P., Yang, H., Li, P., Mastorides, S., Gower, W. R., Jr., Nimal, S., Choi, C. S., Kim, S., Shulman, G. I., et al. (2007). Muscle-specific knockout of PKC-lambda impairs glucose transport and induces metabolic and diabetic syndromes. J Clin Invest 117, 2289-2301). In addition, both isoforms have been implicated in the pathogenesis of cancer making a strong case for the inhibition of the aPKCs as a novel therapeutic avenue.

PKCι is a known oncogene in non-small cell lung cancer (NSCLC). In one study it was shown to be overexpressed in 69% of NSCLC cases at the protein level. Consistent with this, the PKCι gene (PRKCI residing on chromosome 3q26) was shown to be amplified in 36.5% of NSCLC tumours examined, including 96% of the squamous cell carcinoma sub-type (Regala, R. P., Weems, C., Jamieson, L., Khoor, A., Edell, E. S., Lohse, C. M., and Fields, A. P. (2005b).

Atypical protein kinase C iota is an oncogene in human non-small cell lung cancer. Cancer Res 65, 8905-8911). Amplification of 3q26 has also been reported in 44% of ovarian cancers, including >70% of serous epithelial ovarian cancers where 3q26 amplification is translated into increased PKCι protein expression. Moreover, increased PKCι expression is associated with poor prognosis in NSCLC and ovarian cancer where it may serve as a diagnostic biomarker of aggressive disease (Eder, A. M., Sui, X., Rosen, D. G., Nolden, L. K., Cheng, K. W., Lahad, J. P., Kango-Singh, M., Lu, K. H., Warneke, C. L., Atkinson, E. N., et al. (2005). Atypical PKCiota contributes to poor prognosis through loss of apical-basal polarity and cyclin E overexpression in ovarian cancer. Proc Natl Acad Sci USA 102, 12519-12524; Zhang, L., Huang, J., Yang, N., Liang, S., Barchetti, A., Giannakakis, A., Cadungog, M. G., O'Brien-Jenkins, A., Massobrio, M., Roby, K. F., et al. (2006). Integrative genomic analysis of protein kinase C (PKC) family identifies PKCiota as a biomarker and potential oncogene in ovarian carcinoma. Cancer Res 66, 4627-4635). 3q26 amplifications have been observed in many other cancers including oesophageal squamous cell carcinoma (Yang, Y. L., Chu, J. Y., Luo, M. L., Wu, Y. P., Zhang, Y., Feng, Y. B., Shi, Z. Z., Xu, X., Han, Y. L., Cai, Y., et al. (2008). Amplification of PRKCI, located in 3q26, is associated with lymph node metastasis in esophageal squamous cell carcinoma. Genes Chromosomes Cancer 47, 127-136) and breast cancer (Kojima, Y., Akimoto, K., Nagashima, Y., Ishiguro, H., Shirai, S., Chishima, T., Ichikawa, Y., Ishikawa, T., Sasaki, T., Kubota, Y., et al. (2008). The overexpression and altered localization of the atypical protein kinase C lambda/iota in breast cancer correlates with the pathologic type of these tumors. Hum Pathol 39, 824-831) suggesting that PKCι may also participate in the pathogenesis of these diseases.

In NSCLC the primary function of PKCι is to drive transformed growth via a Rac1/PAK/MEK/ERK signalling axis. However, PKCι also functions in NSCLC survival, resistance to chemotherapy, and invasion via distinct pathways (reviewed in Fields, A. P., and Regala, R. P. (2007). Protein kinase C iota: human oncogene, prognostic marker and therapeutic target. Pharmacol Res 55, 487-497). In ovarian cancer transformed growth is correlated with deregulated epithelial cell polarity and increased cycle E expression (Eder et al., 2005) suggesting that PKCι can influence the cancer phenotype through multiple mechanisms. Compelling evidence has emerged to suggest that inhibition of PKCι may be a useful therapeutic approach to combat tumours characterised by increased PKCι expression. In transgenic models, mice with elevated PKCι activity in the colon are more susceptible to carcinogen-induced colon carcinogenesis, and expression of a kinase-dead mutant of PKCι blocks the transformation of intestinal cells by oncogenic Ras (Murray, N. R., Jamieson, L., Yu, W., Zhang, J., Gokmen-Polar, Y., Sier, D., Anastasiadis, P., Gatalica, Z., Thompson, E. A., and Fields, A. P. (2004). Protein kinase Ciota is required for Ras transformation and colon carcinogenesis in vivo. J Cell Biol 164, 797-802). Finally, genetic or pharmacological inhibition of PKCι by a gold derivative—aurothiomalate (ATM)—blocks the growth of NSCLC cells in soft agar and significantly decreases tumour volume in xenograft models of NSCLC (Regala, R. P., Thompson, E. A., and Fields, A. P. (2008). Atypical protein kinase C iota expression and aurothiomalate sensitivity in human lung cancer cells. Cancer Res 68, 5888-5895; Regala, R. P., Weems, C., Jamieson, L., Copland, J. A., Thompson, E. A., and Fields, A. P. (2005a).

Atypical protein kinase Ciota plays a critical role in human lung cancer cell growth and tumorigenicity. J Biol Chem 280, 31109-31115).

Despite the high degree of similarity between aPKC isoforms, the role of PKCζ in cancer is distinct from that of PKCι. PKCζ plays a role in NSCLC cell survival by phosphorylating and antagonising the pro-apoptotic effects of Bax in response to nicotine (Xin, M., Gao, F., May, W. S., Flagg, T., and Deng, X. (2007). Protein kinase Czeta abrogates the proapoptotic function of Bax through phosphorylation. J Biol Chem 282, 21268-21277). PKCζ activity has also been linked to resistance against a wide range of cytotoxic and genotoxic agents. For instance, in human leukaemia cells, overexpression of PKCζ confers resistance against 1-β-D-arabinofuranosylcytosine (ara-C), daunorubicin, etoposide, and mitoxantrone-induced apoptosis (Filomenko, R., Poirson-Bichat, F., Billerey, C., Belon, J. P., Garrido, C., Solary, E., and Bettaieb, A. (2002). Atypical protein kinase C zeta as a target for chemosensitization of tumor cells. Cancer Res 62, 1815-1821; Plo, I., Hernandez, H., Kohlhagen, G., Lautier, D., Pommier, Y., and Laurent, G. (2002). Overexpression of the atypical protein kinase C zeta reduces topoisomerase II catalytic activity, cleavable complexes formation, and drug-induced cytotoxicity in monocytic U937 leukemia cells. J Biol Chem 277, 31407-31415). Furthermore, inhibition of PKCζ activity through expression of a kinase-dead mutant sensitises leukaemia cells to the cytotoxic effects of etoposide both in vitro and in vivo (Filomenko et al., 2002). Atypical protein kinase C regulates dual pathways for degradation of the oncogenic coactivator SRC-3/AIB1. Mol Cell 29, 465-476), and both of these proteins have been postulated to play a role in tamoxifen resistance in breast cancer (Iorns, E., Lord, C. J., and Ashworth, A. (2009). Parallel RNAi and compound screens identify the PDK1 pathway as a target for tamoxifen sensitization. Biochem J 417, 361-370; Osborne, C. K., Bardou, V., Hopp, T. A., Chamness, G. C., Hilsenbeck, S. G., Fuqua, S. A., Wong, J., Allred, D. C., Clark, G. M., and Schiff, R. (2003). Role of the estrogen receptor coactivator AIB1 (SRC-3) and HER-2/neu in tamoxifen resistance in breast cancer. J Natl Cancer Inst 95, 353-361). Together these studies suggest that inhibition of PKCζ activity may have beneficial therapeutic effects by acting as a chemosensitiser to a wide array of commonly used chemotoxic agents in the clinic.

Further evidence that small molecule inhibition of PKCζ could have important therapeutic benefits has recently emerged from tumour models that link PKCζ signalling to the mTOR pathway. PKCζ is constitutively activated in follicular lymphoma and has been identified as a novel target for the anti-CD20 therapeutic antibody rituximab (Leseux, L., Laurent, G., Laurent, C., Rigo, M., Blanc, A., Olive, D., and Bezombes, C. (2008). PKC zeta mTOR pathway: a new target for rituximab therapy in follicular lymphoma. Blood 111, 285-291). Rituximab inhibits follicular lymphoma proliferation by targeting a PKCζ-MAPK-mTOR pathway, suggesting that PKCζ is both a target of Rituximab, and a key regulator of its' anti-leukaemic effect. Regulation of the mTOR/p70S6K pathway by PKCζ has also been implicated in the transition of prostate cancer cells to an androgen-independent state (Inoue, T., Yoshida, T., Shimizu, Y., Kobayashi, T., Yamasaki, T., Toda, Y., Segawa, T., Kamoto, T., Nakamura, E., and Ogawa, O. (2006). Requirement of androgen-dependent activation of protein kinase Czeta for androgen-dependent cell proliferation in LNCaP Cells and its roles in transition to androgen-independent cells. Mol Endocrinol 20, 3053-3069). Finally, mice containing a homozygous deletion of Par4, a negative regulator of PKCζ, exhibit greatly enhanced PKCζ activity. These mice spontaneously develop tumours of the prostate and endometrium, and potentiate Ras-induced lung carcinogenesis consistent with a role for PKCζ in lung cancer (Garcia-Cao, I., Duran, A., Collado, M., Carrascosa, M. J., Martin-Caballero, J., Flores, J. M., Diaz-Meco, M. T., Moscat, J., and Serrano, M. (2005). Tumour-suppression activity of the proapoptotic regulator Par4. EMBO Rep 6, 577-583; Joshi, J., Fernandez-Marcos, P. J., Galvez, A., Amanchy, R., Linares, J. F., Duran, A., Pathrose, P., Leitges, M., Canamero, M., Collado, M., et al. (2008). Par-4 inhibits Akt and suppresses Ras-induced lung tumorigenesis. EMBO J 27, 2181-2193).

SUMMARY

The application provides a compound of formula (I)

(I)

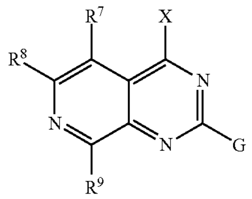

or a salt thereof, wherein $R^7$, $R^8$, $R^9$, G, and X are as defined herein.

A compound of formula (I) and its salts have aPKC inhibitory activity, and may be used to treat aPKC-dependent disorders or conditions.

The present application further provides a pharmaceutical composition comprising a compound of formula (I) or a pharmaceutically acceptable salt thereof together with at least one pharmaceutically acceptable carrier, diluent, or excipient therefor.

In another aspect, the present application provides a method of treating a subject suffering from an aPKC-dependent disorder or condition comprising: administering to the subject a compound of formula (I) or a pharmaceutically acceptable salt thereof.

The present application further provides a method of treating a proliferative disorder in a subject, comprising administering to the subject a therapeutically effective amount of a compound of formula (I) or a pharmaceutically acceptable salt thereof.

DETAILED DESCRIPTION

I. Definitions

"About" as used herein when referring to a measurable value such as an amount, a temporal duration, and the like, is meant to encompass reasonable variations of the value, such as, for example, ±10% from the specified value. For example, the phrase "about 50" encompasses reasonable variations of 50, such as ±10% of the numerical value 50, or from 45 to 55.

"Alkyl" or "alkyl group" refers to a monoradical of a branched or unbranched saturated hydrocarbon chain. Examples include, but are not limited to, methyl, ethyl, n-propyl, n-butyl, n-pentyl, n-hexyl, n-heptyl, n-octyl, n-nonyl, n-decyl, isopropyl, tert-butyl, isobutyl, etc. Alkyl groups typically contain 1-10 carbon atoms, such as 1-6 carbon atoms or 1-4 carbon atoms, and can be substituted or unsubstituted.

"Alkylene" or "alkylene group" refers to a diradical of a branched or unbranched saturated hydrocarbon chain. Examples include, but are not limited to, methylene ($—CH_2—$), the ethylene isomers ($—CH(CH_3)—$ and $—CH_2CH_2—$), the propylene isomers ($—CH(CH_3)CH_2—$, $—CH(CH_2CH_3)—$, $—C(CH_3)_2—$, and $—CH_2CH_2CH_2—$), etc. Alkylene groups typically contain 1-10 carbon atoms, such as 1-6 carbon atoms, and can be substituted or unsubstituted.

"Alkenyl" or "alkenyl group" refers to a monoradical of a branched or unbranched hydrocarbon chain containing at least one double bond. Examples include, but are not limited to, ethenyl, 3-buten-1-yl, 2-ethenylbutyl, and 3-hexen-1-yl. Alkenyl groups typically contain 2-10 carbon atoms, such as 2-6 carbon atoms or 2-4 carbon atoms, and can be substituted or unsubstituted.

"Alkynyl" or "alkynyl group" refers to a monoradical of a branched or unbranched hydrocarbon chain containing at least one triple bond. Examples include, but are not limited to, ethynyl, 3-butyn-1-yl, propynyl, 2-butyn-1-yl, and 3-pentyn-1-yl. Alkynyl groups typically contain 2-10 carbon atoms, such as 2-6 carbon atoms or 2-4 carbon atoms, and can be substituted or unsubstituted.

"Aryl" or "aryl group" refers to phenyl and 7-15 membered monoradical bicyclic or tricyclic hydrocarbon ring systems, including bridged, spiro, and/or fused ring systems, in which at least one of the rings is aromatic. Aryl groups can be substituted or unsubstituted. Examples include, but are not limited to, naphthyl, indanyl, 1,2,3,4-tetrahydronaphthalenyl, 6,7,8,9-tetrahydro-5H-benzocycloheptenyl, and 6,7,8,9-tetrahydro-5H-benzocycloheptenyl. An aryl group may contain 6 (i.e., phenyl) or 9 to 15 ring atoms, such as 6 (i.e., phenyl) or 9-11 ring atoms, e.g., 6 (i.e., phenyl), 9 or 10 ring atoms.

"Arylene" or "arylene group" refers to a phenylene ($—C_6H_4—$) or a 7-15 membered diradical bicyclic or tricyclic hydrocarbon ring systems, including bridged, spiro, and/or fused ring systems, in which at least one of the rings is aromatic. Arylene groups can be substituted or unsubstituted. For example, an arylene group may contain 6 (i.e., phenylene) or 9 to 15 ring atoms; such as 6 (i.e., phenylene) or 9-11 ring atoms; e.g., 6 (i.e., phenylene), 9 or 10 ring atoms. An arylene group can also include ring systems substituted on ring carbons with one or more —OH functional groups (which may further tautomerize to give a ring C═O group).

"Arylalkyl" or "arylalkyl group" refers to an alkyl group in which a hydrogen atom is replaced by an aryl group, wherein alkyl group and aryl group are as previously defined (i.e., arylalkyl-). Arylalkyl groups can be substituted or unsubstituted. Examples include, but are not limited to, benzyl ($C_6H_5CH_2—$).

"Cycloalkyl" or "cycloalkyl group" refers to a monoradical non-aromatic carbocyclic ring system, which may be saturated or unsaturated, substituted or unsubstituted, and may be monocyclic, bicyclic, or tricyclic, and may be bridged, spiro, and/or fused. Examples include, but are not limited to, cyclopropyl, cyclopropenyl, cyclobutyl, cyclobutenyl, cyclopentyl, cyclopentenyl, cyclohexyl, cyclohexenyl, norbornyl, norbornenyl, bicyclo[2.2.1]hexane, bicyclo[2.2.1]heptane, bicyclo[2.2.1]heptene, bicyclo[3.1.1]heptane, bicyclo[3.2.1]octane, bicyclo[2.2.2]octane, bicyclo[3.2.2]nonane, bicyclo[3.3.1]nonane, and bicyclo[3.3.2]decane. The cycloalkyl group may contain from 3 to 10 ring atoms, such as 3 to 7 ring atoms (e.g., 3 ring atoms, 5 ring atoms, 6 ring atoms, or 7 ring atoms).

"Cycloalkylalkyl" or "cycloalkylalkyl group" refers to an alkyl group in which a hydrogen atom is replaced by a cycloalkyl group, wherein alkyl group and cycloalkyl group are as previously defined (i.e., cycloalkylalkyl-). Cycloalkylalkyl groups can be substituted or unsubstituted. Examples include, but are not limited to, cyclohexylmethyl ($C_6H_{11}CH_2—$).

"Haloalkyl" or "haloalkyl group" refers to alkyl groups in which one or more hydrogen atoms are replaced by halogen atoms. Haloalkyl includes both saturated alkyl groups and unsaturated alkenyl and alkynyl groups, such as for example $—CF_3$, $—CHF_2$, $—CH_2F$, $—CF_2CF_3$, $—CHFCF_3$, $—CH_2CF_3$, $—CF_2CH_3$, $—CHFCH_3$, $—CF_2CF_2CF_3$, $—CF_2CH_2CH_3$, $—CF{=}CF_2$, $—CCl{=}CH_2$, $—CBr{=}CH_2$, $—CI{=}CH_2$, $—C{\equiv}C—CF_3$, $—CHFCH_2CH_3$ and $—CHFCH_2CF_3$.

"Halogen" includes fluorine, chlorine, bromine and iodine atoms.

"Heteroaryl" or "heteroaryl group" refers to (a) 5 and 6 membered monocyclic aromatic rings, which contain, in addition to carbon atom(s), at least one heteroatom, such as nitrogen, oxygen or sulfur, and (b) 7-15 membered bicyclic and tricyclic rings, which contain, in addition to carbon atom(s), at least one heteroatom, such as nitrogen, oxygen or sulfur, and in which at least one of the rings is aromatic. Heteroaryl groups can be substituted or unsubstituted, and may be bridged, spiro, and/or fused. Examples include, but are not limited to, 2,3-dihydrobenzofuranyl, 1,2-dihydroquinolinyl, 3,4-dihydroisoquinolinyl, 1,2,3,4-tetrahydroisoquinolinyl, 1,2,3,4-tetrahydroquinolinyl, benzoxazinyl, benzthiazinyl, chromanyl, furanyl, 2-furanyl, 3-furanyl, imidazolyl, isoxazolyl, isothiazolyl, oxadiazolyl, oxazolyl, pyridinyl, 2-, 3-, or 4-pyridinyl, pyrimidinyl, 2-, 4-, or 5-pyrimidinyl, pyrazolyl, pyrrolyl, 2- or 3-pyrrolyl, pyrazinyl, pyridazinyl, 3- or 4-pyridazinyl, 2-pyrazinyl, thienyl, 2-thienyl, 3-thienyl, tetrazolyl, thiazolyl, thiadiazolyl, triazinyl, triazolyl, pyridin-2-yl, pyridin-4-yl, pyrimidin-2-yl, pyridazin-4-yl, pyrazin-2-yl, naphthyridinyl, pteridinyl, phthalazinyl, purinyl, alloxazinyl, benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, isoquinolinyl, 10-aza-tricyclo[6.3.1.$0^{2,7}$]dodeca-2(7),3,5-trienyl, 12-oxa-10-aza-tricyclo[6.3.1.$0^{2,7}$]dodeca-2(7),3,5-trienyl, 12-aza-tricyclo[7.2.1.$0^{2,7}$]dodeca-2(7),3,5-trienyl, 10-aza-tricyclo[6.3.2.$0^{2,7}$]trideca-2(7),3,5-trienyl, 2,3,4,5-tetrahydro-1H-benzo[d]azepinyl, 1,3,4,5-tetrahydro-benzo[d]azepin-2-onyl, 1,3,4,5-tetrahydro-benzo[b]azepin-2-onyl, 2,3,4,5-tetrahydro-benzo[c]azepin-1-onyl, 1,2,3,4-tetrahydro-benzo[e][1,4]diazepin-5-onyl, 2,3,4,5-tetrahydro-1H-benzo[e][1,4]diazepinyl, 5,6,8,9-tetrahydro-7-oxa-benzocycloheptenyl, 2,3,4,5-tetrahydro-1H-benzo[b]azepinyl, 1,2,4,5-tetrahydro-benzo[e][1,3]diazepin-3-onyl, 3,4-dihydro-2H-benzo[b][1,4]dioxepinyl, 3,4-dihydro-2H-benzo[f][1,4]oxazepin-5-onyl, 6,7,8,9-tetrahydro-5-thia-8-aza-benzocycloheptenyl, 5,5-dioxo-6,7,8,9-tetrahydro-5-thia-8-aza-benzocycloheptenyl, and 2,3,4,5-tetrahydro-benzo[f][1,4]oxazepinyl. For example, a heteroaryl group may contain 5, 6, or 8-15 ring atoms. As another example, a heteroaryl group may contain 5 to 10 ring atoms, such as 5, 6, 9, or 10 ring atoms.

"Heteroarylalkyl" or "heteroarylalkyl group" refers to an alkyl group in which a hydrogen atom is replaced by a heteroaryl group, wherein alkyl group and heteroaryl group are as previously defined (i.e., heteroarylalkyl-). Heteroarylalkyl groups can be substituted or unsubstituted. Examples include, but are not limited to, the pyridinylmethyl isomers ( 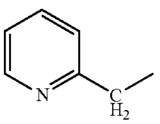 or 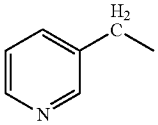 or 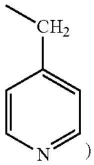 ).

"Heterocycloalkyl" or "heterocycloalkyl group" refers to 3-15 membered monocyclic, bicyclic, and tricyclic non-aromatic rings, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, tetrahydrofuranyl, pyrrolidinyl, pyrrolinyl, imidazolidinyl, imidazolinyl, pyrazolidinyl, pyrazolinyl, piperidyl, piperazinyl, indolinyl, isoindolinyl, morpholinyl, thiomorpholinyl, homomorpholinyl, homopiperidyl, homopiperazinyl, thiomorpholinyl-5-oxide, thiomorpholinyl-S,S-dioxide, pyrrolidinyl, tetrahydropyranyl, piperidinyl, tetrahydrothienyl, homopiperidinyl, homothiomorpholinyl-S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl-5-oxide, tetrahydrothienyl-S,S-dioxide, homothiomorpholinyl-5-oxide, quinuclidinyl, 2-oxa-5-azabicyclo[2.2.1]heptanyl, 8-oxa-3-aza-bicyclo[3.2.1]octanyl, 3,8-diaza-bicyclo[3.2.1]octanyl, 2,5-diaza-bicyclo[2.2.1]heptanyl, 3,8-diaza-bicyclo[3.2.1]octanyl, 3,9-diaza-bicyclo[4.2.1]nonanyl, 2,6-diaza-bicyclo[3.2.2]nonanyl, [1,4]oxaphosphinanyl-4-oxide, [1,4]azaphosphinanyl-4-oxide, [1,2]oxaphospholanyl-2-oxide, phosphinanyl-1-oxide, [1,3]azaphospholidinynl-3-oxide, [1,3]oxaphospholanyl-3-oxide and 7-oxabicyclo[2.2.1]heptanyl. A heterocycloalkyl group may contain, in addition to carbon atom(s), at least one nitrogen, oxygen, or sulfur. For example, a heterocycloalkyl group may contain, in addition to carbon atom(s), at least one nitrogen or oxygen. A heterocycloalkyl group may contain, in addition to carbon atom(s), at least one nitrogen. A heterocycloalkyl group may contain carbon atoms and 1 or 2 nitrogen atoms. A heterocycloalkyl group may contain carbon atoms and an oxygen atom. A heterocycloalkyl group may contain carbon atoms, a nitrogen atom, and an oxygen atom. A heterocycloalkyl group may contain carbon atoms, a nitrogen atom, and a sulfur atom. A heterocycloalkyl group may contain carbon atoms and a sulfur atom. A heterocycloalkyl group may contain from 3 to 10 ring atoms. A heterocycloalkyl group may contain from 3 to 7 ring atoms. A heterocycloalkyl group may contain from 5 to 7 ring atoms, such as 5 ring atoms, 6 ring atoms, or 7 ring atoms. Unless otherwise indicated, the foregoing heterocycloalkyl groups can be C-attached or N-attached where such is possible and results in the creation of a stable structure. For example, piperidinyl can be piperidin-1-yl (N-attached) or piperidin-4-yl (C-attached).

"Heterocycloalkylene" or "heterocycloalkylene group" refers to diradical, 3-15 membered monocyclic, bicyclic, or tricyclic non-aromatic ring systems, which may be saturated or unsaturated, can be substituted or unsubstituted, may be bridged, spiro, and/or fused, and which contain, in addition to carbon atom(s), at least one heteroatom, such as nitrogen, oxygen, sulfur or phosphorus. Examples include, but are not limited to, the azridinylene isomers ( 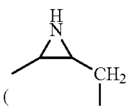 or 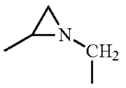 or 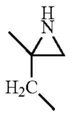 or 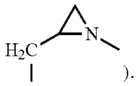 ).

The heterocycloalkylene group may contain, in addition to carbon atom(s), at least one nitrogen, oxygen, or sulfur. The heterocycloalkylene group may contain, in addition to carbon atom(s), at least one nitrogen or oxygen. The heterocycloalkylene group may contain, in addition to carbon atom(s), at least one nitrogen. For example, a heterocycloalkylene group may contain from 3 to 10 ring atoms; such as from 3 to 7 ring atoms. A heterocycloalkylene group may contain from 5 to 7 ring atoms, such as 5 ring atoms, 6 ring atoms, or 7 ring atoms. Unless otherwise indicated, the foregoing heterocycloalkylene groups can be C-attached and/or N-attached where such is possible and results in the creation of a stable structure. A heterocycloalkylene group can also include ring systems substituted on ring carbons with one or more —OH functional groups (which may further tautomerize to give a ring C═O group) and/or substituted on a ring sulfur atom by one (1) or two (2) oxygen atoms to give S═O or $SO_2$ groups, respectively, and/or substituted on a ring phosphorus by an oxygen atom to give P═O.

"Heterocycloalkylalkyl" or "heterocycloalkylalkyl group" refers to an alkyl group in which a hydrogen atom is replaced by a heterocycloalkyl group, wherein alkyl group and heterocycloalkyl group are as previously defined (i.e., heterocycloalkylalkyl-). Heteroycloalkylalkyl groups can be substituted or unsubstituted. Examples include, but are not limited to, pyrrolidinylmethyl ($C_4H_8NCH_2$—).

"Pharmaceutically acceptable" refers to physiologically tolerable materials, which do not typically produce an allergic or other untoward reaction, such as gastric upset, dizziness and the like, when administered to a human.

"Pharmaceutical composition" refers to a composition that can be used to treat a disease, condition, or disorder in a human.

"Pseudohalogen" refers to —OCN, —SCN, —$CF_3$, and —CN.

"Stable" or "chemically stable" refers to a compound that is sufficiently robust to be isolated to a useful degree of purity from a reaction mixture. The present application is directed solely to the preparation of stable compounds. When lists of alternative substituents include members which, owing to valency requirements, chemical stability, or other reasons, cannot be used to substitute a particular group, the list is intended to be read in context to include those members of the list that are suitable for substituting the particular group. For example, $R^1$ can be $C_{1-6}$alkyl optionally substituted by 1-13 $R^{19}$; when $R^1$ is methyl, the methyl group is optionally substituted by 1-3 $R^{19}$.

"Therapeutically effective amount" refers to an amount of a compound sufficient to inhibit, halt, or cause an improvement in a disorder or condition being treated in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated. It should be appreciated that determination of proper dosage forms, dosage amounts, and routes of administration is within the level of ordinary skill in the pharmaceutical and medical arts.

"Treatment" refers to the acute or prophylactic diminishment or alleviation of at least one symptom or characteristic associated or caused by a disorder being treated. For example, treatment can include diminishment of several symptoms of a disorder or complete eradication of a disorder.

II. Compounds

The compounds of the present application are defined by the following numbered Embodiments. When a higher numbered Embodiment refers back to multiple previous lower numbered Embodiments in the alternative and contains a new limitation not present in the lower numbered Embodiments, the higher numbered Embodiment is intended to be an express description of each and every one of the alternatives. For example, if Embodiment 2 refers back to Embodiment 1 and contains a limitation not present in Embodiment 1, Embodiment 3 refers back Embodiments 1 or 2 and contains a limitation(s) not present in Embodiments 1 or 2, and Embodiment 4 refers back to any of Embodiments 1-3 and contains a limitation(s) not present in Embodiments 1, 2, or 3, then Embodiment 4 is intended to be an explicit description of a genus having the limitations of Embodiments 1 and 4, an explicit description of a genus having the limitations of Embodiments 2 and 4 (i.e., 1, 2, and 4), and an explicit description of a genus having the limitations of Embodiments 3 and 4 (i.e., 1, 3, and 4, and 1, 2, 3 and 4). By way of example, if Embodiment 1 is a compound of formula (I) defining $R^7$, $R^8$ and $R^9$ independently as alkyl or aryl, Embodiment 2 is a compound of Embodiment 1 defining $R^7$ as alkyl, Embodiment 3 is a compound of Embodiments 1 or 2 defining $R^8$ as alkyl, and Embodiment 4 is a compound of any of Embodiments 1-3 defining $R^9$ as alkyl, then Embodiment 4 is an explicit description of a genus having the limitations of Embodiments 1 and 4 (i.e., a compound of formula (I) in which $R^7$ and $R^8$ are alkyl or aryl, and $R^9$ is alkyl), an explicit description of a genus having the limitations of Embodiments 2 and 4 (i.e., a compound of formula (I) in which $R^8$ is alkyl or aryl, and $R^7$ and $R^9$ are alkyl), an explicit description of a genus having the limitations of Embodiments 3 and 4 (i.e., a compound of formula (I) in which $R^7$ is alkyl or aryl, and $R^8$ and $R^9$ are alkyl; and a compound of formula (I) in which $R^7$, $R^8$ and $R^9$ are all alkyl). It should be noted in this regard that when a higher numbered Embodiment refers to a lower numbered Embodiment and contains limitations for a group(s) not present in the lower numbered Embodiment, the higher numbered Embodiment should be interpreted in context to ignore the missing group(s). For example, if Embodiment 1 recites a compound of formula (I) in which X is H, $C_{1-10}$alkyl, or —C(═O)$R^{28}$, Embodiment 2 recites a compound of Embodiment 1 in which X is H or $C_{1-10}$alkyl, and Embodiment 3 recites a compound of Embodiments 1 or 2 in which $R^{28}$ is alkyl, then Embodiment 3 defines a genus having the limitations of Embodiments 1 and 3 and a genus having the limitation of Embodiments 2 and 3 (i.e., 1, 2, and 3). In the genus defined by the limitations of Embodiments 2 and 3, X cannot be —C(═O)$R^{28}$; therefore this genus should be interpreted to ignore the Embodiment 3 definition of $R^{28}$=alkyl (i.e., the genus of Embodiments 2 and 3 has the same scope as the genus of Embodiment 2).

The compounds of the present application are defined herein using structural formulas that do not specifically recite the mass numbers or the isotope ratios of the constituent atoms. It is intended that the present application includes compounds in which the constituent atoms are present in any ratio of isotope forms. For example, carbon atoms may be present in any ratio of $^{12}C$, $^{13}C$, and $^{14}C$; hydrogen atoms may be present in any ratio of $^1H$, $^2H$, and $^3H$; etc. Preferably, the constituent atoms in the compounds of the present application are present in their naturally occurring ratios of isotope forms.

Embodiment 1

A compound of formula (I)

(I)

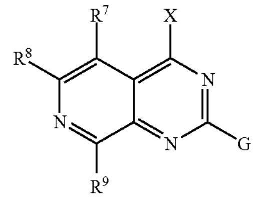

or a salt form thereof, wherein

G is a group of formula

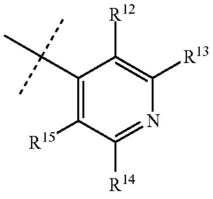

or

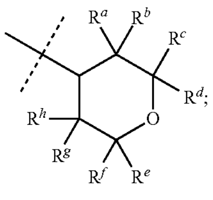

X is chosen from H, $C_{1-10}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{28}$, —C(═O)O$R^{28}$, —C(═O)N$R^{24}R^{28}$, —C(═O)C(═O)$R^{28}$, —N$R^{24}R^{28}$, —N$R^{24}$N$R^{24}R^{28}$, —N═N$R^{28}$, —NR$^{24}$OR$^{28}$, —NR$^{24}$C(═O)R$^{28}$, —NR$^{24}$C(═O)C(═O)R$^{28}$, —NR$^{24}$C(═O)OR$^{28}$, —NR$^{24}$C(═O)C(═O)OR$^{28}$, —NR$^{24}$C(═O)NR$^{24}$R$^{28}$, —NR$^{24}$C(═O)NR$^{24}$C(═O)R$^{28}$, —NR$^{24}$C(═O)NR$^{24}$C(═O)OR$^{28}$, —NR$^{24}$C(═O)C(═O)NR$^{24}$R$^{28}$, —NR$^{24}$S(═O)$_2$R$^{28}$, —NR$^{24}$S(═O)$_2$NR$^{24}$R$^{28}$, —OR$^{28}$, —OC(═O)R$^{28}$, —OC(═O)NR$^{24}$R$^{28}$, —OC(═O)OR$^{28}$, —OS(═O)R$^{28}$, —OS(═O)$_2$R$^{28}$, —OS(═O)$_2$OR$^{28}$, —OS(═O)$_2$NR$^{24}$R$^{28}$, —S(═O)$_n$R$^{28}$, —S(═O)$_2$NR$^{24}$R$^{28}$, and —S(═O)NR$^{24}$R$^{28}$;

R$^7$, R$^8$, R$^9$, R$^{12}$, R$^{13}$, R$^{14}$, R$^{15}$, R$^a$, R$^b$, R$^c$, R$^d$, R$^e$, R$^f$, R$^g$, and R$^h$ are independently chosen from H, C$_{1-6}$alkyl optionally substituted by 1-13 R$^{19}$, C$_{2-6}$alkenyl optionally substituted by 1-11 R$^{19}$, C$_{2-6}$alkynyl optionally substituted by 1-9 R$^{19}$, C$_{6-11}$aryl optionally substituted by 1-11 R$^{19}$, C$_{7-16}$arylalkyl optionally substituted by 1-19 R$^{19}$, C$_{3-11}$cycloalkyl optionally substituted by 1-21 R$^{19}$, C$_{4-17}$cycloalkylalkyl optionally substituted by 1-32 R$^{19}$, 3-15 membered heterocycloalkyl optionally substituted by 1-28 R$^{19}$, 4-21 membered heterocycloalkylalkyl optionally substituted by 1-40 R$^{19}$, 5-15 membered heteroaryl optionally substituted by 1-15 R$^{19}$, 6-21 membered heteroarylalkyl optionally substituted by 1-27 R$^{19}$, halogen, —CN, —C(═O)R$^{20}$, —C(═O)OR$^{20}$, —C(═O)NR$^{22}$R$^{23}$, —(═O)C(═O)R$^{20}$, —C(═NR$^{25}$)R$^{20}$, —C(═NR$^{25}$)NR$^{22}$R$^{23}$, —C(═NOH)NR$^{22}$R$^{23}$, —C(═NOR$^{26}$)R$^{20}$, —C(═NNR$^{22}$R$^{23}$)R$^{20}$, —C(═NNR$^{24}$C(═O)R$^{21}$)R$^{20}$, —C(═NNR$^{24}$C(═O)OR$^{21}$)R$^{20}$, —C(═S)NR$^{22}$R$^{23}$, —NC, —NO$_2$, —NR$^{22}$R$^{23}$, —NR$^{24}$NR$^{22}$R$^{23}$, —N═NR$^{24}$, —NR$^{24}$OR$^{26}$, —NR$^{24}$C(═O)R$^{20}$, —NR$^{24}$C(═O)C(═O)R$^{20}$, —NR$^{24}$C(═O)OR$^{21}$, —NR$^{24}$C(═O)C(═O)OR$^{21}$, —NR$^{24}$C(═O)NR$^{22}$R$^{23}$, —NR$^{24}$C(═O)NR$^{24}$C(═O)R$^{20}$, —NR$^{24}$C(═O)NR$^{24}$C(═O)OR$^{20}$, —NR$^{24}$C(═NR$^{25}$)NR$^{22}$R$^{23}$, —NR$^{24}$C(═O)C(═O)NR$^{22}$R$^{23}$, —NR$^{24}$C(═S)R$^{20}$, —NR$^{24}$C(═S)OR$^{20}$, —NR$^{24}$C(═S)NR$^{22}$R$^{23}$, —NR$^{24}$S(═O)$_2$R$^{21}$, —NR$^{24}$S(═O)$_2$NR$^{22}$R$^{23}$, —NR$^{24}$P(═O)R$^{78}$R$^{78}$, —NR$^{24}$P(═O)(NR$^{22}$R$^{23}$)(NR$^{22}$R$^{23}$), —NR$^{24}$P(═)(OR$^{20}$)(OR$^{20}$), —NR$^{24}$P(═O)(SR$^{20}$)(SR$^{20}$), —OR$^{20}$, —OCN, —OC(═O)R$^{20}$, —OC(═O)NR$^{22}$R$^{23}$, —OC(═O)OR$^{20}$, —OC(═NR$^{25}$)NR$^{22}$R$^{23}$, —OS(═O)R$^{20}$, —OS(═O)$_2$R$^{20}$, —OS(═O)$_2$OR$^{20}$, —OS(═O)$_2$NR$^{22}$R$^{23}$, —OP(═O)R$^{78}$R$^{78}$, —OP(═O)(NR$^{22}$R$^{23}$)(NR$^{22}$R$^{23}$), —OP(═O)(OR$^{20}$)(OR$^{20}$), —OP(═O)(SR$^{20}$)(SR$^{20}$), —Si(R$^{24}$)$_3$, —SCN, —S(═O)$_n$R$^{20}$, —S(═O)$_2$R$^{20}$, —SO$_3$R$^{27}$, —S(═O)$_2$NR$^{22}$R$^{23}$, —S(═O)NR$^{22}$R$^{23}$, —SP(═O)R$^{78}$R$^{78}$, —SP(═O)(NR$^{22}$R$^{23}$)(NR$^{22}$R$^{23}$), —SP(═O)(OR$^{20}$)(OR$^{20}$), —SP(═O)(SR$^{20}$)(SR$^{20}$), —P(═O)R$^{78}$R$^{78}$, —P(═O)(NR$^{22}$R$^{23}$)(NR$^{22}$R$^{23}$), —P(═O)(OR$^{20}$)(OR$^{20}$), and —P(═O)(SR$^{20}$)(SR$^{20}$);

or any of R$^7$ and R$^8$, R$^{12}$ and R$^{13}$, R$^{14}$ and R$^{15}$, R$^a$ and R$^b$, R$^a$ and R$^e$, R$^a$ and R$^e$, R$^a$ and R$^g$, R$^b$ and R$^d$, R$^b$ and R$^f$, R$^b$ and R$^h$, R$^c$ and R$^d$, R$^c$ and R$^e$, R$^c$ and R$^g$, R$^d$ and R$^f$, R$^d$ and R$^h$, R$^e$ and R$^f$, R$^e$ and R$^g$, R$^f$ and R$^h$, and R$^g$ and R$^h$ can, together with the atoms linking them, form a C$_{6-11}$aryl optionally substituted by 1-11 R$^{19}$, C$_{3-11}$cycloalkyl optionally substituted by 1-21 R$^{19}$, 3-15 membered heterocycloalkyl optionally substituted by 1-28 R$^{19}$ or a 5-15 membered heteroaryl optionally substituted by 1-15 R$^{19}$;

R$^{19}$ at each occurrence is independently chosen from C$_{1-6}$alkyl optionally substituted by 1-13 R$^{39}$, C$_{2-6}$alkenyl optionally substituted by 1-11 R$^{39}$, C$_{2-6}$alkynyl optionally substituted by 1-9 R$^{39}$, C$_{6-11}$aryl optionally substituted by 1-11 R$^{39}$, C$_{7-16}$arylalkyl optionally substituted by 1-19 R$^{39}$, C$_{3-11}$cycloalkyl optionally substituted by 1-21 R$^{39}$, C$_{4-17}$cycloalkylalkyl optionally substituted by 1-32 R$^{39}$, 3-15 membered heterocycloalkyl optionally substituted by 1-28 R$^{39}$, 4-21 membered heterocycloalkylalkyl optionally substituted by 1-40 R$^{39}$, 5-15 membered heteroaryl optionally substituted by 1-15 R$^{39}$, 6-21 membered heteroarylalkyl optionally substituted by 1-27 R$^{39}$, halogen, —CN, —C(═O)R$^{30}$, —C(═O)OR$^{30}$, —C(═O)NR$^{32}$R$^{33}$, —C(═O)C(═O)R$^{30}$, —C(═NR$^{35}$)R$^{30}$, —C(═NR$^{35}$)NR$^{32}$R$^{33}$, —C(═NOH)NR$^{32}$R$^{33}$, —C(═NOR$^{36}$)R$^{30}$, —C(═NNR$^{32}$R$^{33}$)R$^{30}$, —C(═NNR$^{34}$C(═O)R$^{31}$)R$^{30}$, —C(═NNR$^{34}$C(═O)OR$^{31}$)R$^{30}$, —C(═S)NR$^{32}$R$^{33}$, —NC, —NO$_2$, —NR$^{32}$R$^{33}$, —NR$^{34}$NR$^{32}$R$^{33}$, —N═NR$^{34}$, ═NR$^{30}$, ═NOR$^{30}$, —NR$^{34}$OR$^{36}$, —NR$^{34}$C(═O)R$^{30}$, —NR$^{34}$C(═O)C(═O)R$^{30}$, —NR$^{34}$C(═O)OR$^{31}$, —NR$^{34}$C(═O)C(═O)OR$^{31}$, —NR$^{34}$C(═O)NR$^{32}$R$^{33}$, —NR$^{34}$C(═O)NR$^{34}$C(═O)R$^{30}$, —NR$^{34}$C(═O)NR$^{34}$C(═O)OR$^{30}$, —NR$^{34}$C(═NR$^{35}$)NR$^{32}$R$^{33}$, —NR$^{34}$C(═O)C(═O)NR$^{32}$R$^{33}$, —NR$^{34}$C(═S)R$^{30}$, —NR$^{34}$C(═S)OR$^{30}$, —NR$^{34}$C(═S)NR$^{32}$R$^{33}$, —NR$^{34}$S(═O)$_2$R$^{31}$, —NR$^{34}$S(═O)$_2$NR$^{32}$R$^{33}$, —NR$^{34}$P(═O)R$^{78}$R$^{78}$, —NR$^{34}$P(═O)(NR$^{32}$R$^{33}$)(NR$^{32}$R$^{33}$), —NR$^{34}$P(═O)(OR$^{30}$)(OR$^{30}$), —NR$^{34}$P(═O)(SR$^{30}$)(SR$^{30}$), —OR$^{30}$, ═O, —OCN, —OC(═O)R$^{30}$, —OC(═O)NR$^{32}$R$^{33}$, —OC(═O)OR$^{30}$, —OC(═NR$^{35}$)NR$^{32}$R$^{33}$, —OS(═O)R$^{30}$, —OS(═O)$_2$R$^{30}$, —OS(═O)$_2$OR$^{30}$, —OS(═O)$_2$NR$^{32}$R$^{33}$, —OP(═O)R$^{78}$R$^{78}$, —OP(═O)(NR$^{32}$R$^{33}$)(NR$^{32}$R$^{33}$), —OP(═O)(OR$^{30}$)(OR$^{30}$), —OP(═O)(SR$^{30}$)(SR$^{30}$), —Si(R$^{34}$)$_3$, —SCN, ═S, —S(═O)$_n$R$^{30}$, —S(═O)$_2$OR$^{30}$, —SO$_3$R$^{37}$, —S(═O)$_2$NR$^{32}$R$^{33}$, —S(═O)NR$^{32}$R$^{33}$, —SP(═O)R$^{78}$R$^{78}$, —SP(═O)(NR$^{32}$R$^{32}$)(NR$^{32}$R$^{33}$), —SP(═O)(OR$^{30}$)(OR$^{30}$), —SP(═O)(SR$^{30}$)(SR$^{30}$), —P(═O)R$^{78}$R$^{78}$, —P(═O)(NR$^{32}$R$^{33}$)(NR$^{32}$R$^{33}$), —P(═O)(OR$^{30}$)(OR$^{30}$), and —P(═O)(SR$^{30}$)(SR$^{30}$);

R$^{20}$, R$^{21}$, R$^{24}$, R$^{25}$, R$^{26}$, R$^{27}$, R$^{30}$, R$^{31}$, R$^{34}$, R$^{35}$, R$^{36}$ and R$^{37}$ at each occurrence is independently chosen from H, C$_{1-6}$alkyl optionally substituted by 1-13 R$^{49}$, C$_{2-6}$alkenyl optionally substituted by 1-11 R$^{49}$, C$_{2-6}$alkynyl optionally substituted by 1-9 R$^{49}$, C$_{6-11}$aryl optionally substituted by 1-11 R$^{49}$, C$_{7-16}$arylalkyl optionally substituted by 1-19 R$^{49}$, C$_{3-11}$cycloalkyl optionally substituted by 1-21 R$^{49}$, C$_{4-17}$cycloalkylalkyl optionally substituted by 1-32 R$^{49}$, 3-15 membered heterocycloalkyl optionally substituted by 1-28 R$^{49}$, 4-21 membered heterocycloalkylalkyl optionally substituted by 1-40 R$^{49}$, 5-15 membered heteroaryl optionally substituted by 1-15 R$^{49}$, and 6-21 membered heteroarylalkyl optionally substituted by 1-27 R$^{49}$;

R$^{28}$ at each occurrence is independently chosen from C$_{1-10}$alkyl optionally substituted by 1-13 R$^{49}$, C$_{2-10}$alkenyl optionally substituted by 1-11 R$^{49}$, C$_{2-6}$alkynyl optionally substituted by 1-9 R$^{49}$, C$_{6-11}$aryl optionally substituted by 1-11 R$^{49}$, C$_{7-16}$arylalkyl optionally substituted by 1-19 R$^{49}$, C$_{3-11}$cycloalkyl optionally substituted by 1-21 R$^{49}$, C$_{4-17}$cycloalkylalkyl optionally substituted by 1-32 R$^{49}$, 3-15 membered heterocycloalkyl optionally substituted by 1-28 R$^{49}$, 4-21 membered heterocycloalkylalkyl optionally substituted by 1-40 R$^{49}$, 5-15 membered heteroaryl optionally substituted by 1-15 R$^{49}$, and 6-21 membered heteroarylalkyl optionally substituted by 1-27 R$^{49}$;

R$^{22}$, R$^{23}$, R$^{32}$ and R$^{33}$ at each occurrence is independently chosen from H, C$_{1-6}$alkyl optionally substituted by 1-13 R$^{59}$, C$_{2-6}$alkenyl optionally substituted by 1-11

$R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$;

or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$;

$R^{39}$, $R^{49}$, $R^{59}$ and $R^{69}$ at each occurrence is independently chosen from $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(═O)$R^{70}$, —C(═O)O$R^{70}$, —C(═O)N$R^{72}R^{73}$, —C(═O)C(═O)$R^{70}$, —C(═N$R^{75}$)$R^{70}$, —C(═N$R^{75}$)N$R^{72}R^{73}$, —C(═NOH)N$R^{72}R^{73}$, —C(═NO$R^{76}$)$R^{70}$, —C(═NN$R^{72}R^{73}$)$R^{70}$, —C(═NN$R^{74}$C(═O)$R^{71}$)$R^{70}$, —C(═NN$R^{74}$C(═O)O$R^{71}$)$R^{70}$, —C(═S)N$R^{72}R^{73}$, —NC, —$NO_2$, —N$R^{72}R^{73}$, —N$R^{74}$N$R^{72}R^{73}$, —N═N$R^{74}$, ═N$R^{70}$, ═NO$R^{70}$, —N$R^{74}$O$R^{76}$, —N$R^{74}$C(═O)$R^{70}$, —N$R^{74}$C(═O)C(═O)$R^{70}$, —N$R^{74}$C(═)O$R^{71}$, —N$R^{74}$C(═O)C(═O)O$R^{71}$, —N$R^{74}$C(═O)N$R^{72}R^{73}$, —N$R^{74}$C(═O)N$R^{74}$C(═O)$R^{70}$, —N$R^{74}$C(═O)N$R^{74}$C(═O)O$R^{70}$, —N$R^{74}$C(═N$R^{75}$)N$R^{72}R^{73}$, —N$R^{74}$C(═O)C(═O)N$R^{72}R^{73}$, —N$R^{74}$C(═S)$R^{70}$, —N$R^{74}$C(═S)O$R^{70}$, —N$R^{74}$C(═S)N$R^{72}R^{73}$, —N$R^{74}$S(═O)$_2R^{71}$, —N$R^{74}$S(═O)$_2$N$R^{72}R^{73}$, —N$R^{74}$P(═O)$R^{78}R^{78}$, —N$R^{74}$P(═O)(N$R^{72}R^{73}$)(N$R^{72}R^{73}$), —N$R^{74}$P(═O)(O$R^{70}$)(O$R^{70}$), —N$R^{74}$P(═O)(S$R^{70}$)(S$R^{70}$), —O$R^{70}$, ═O, —OCN, —OC(═O)$R^{70}$, —OC(═O)N$R^{72}R^{73}$, —OC(═O)O$R^{70}$, —OC(═N$R^{75}$)N$R^{72}R^{73}$, —OS(═O)$R^{70}$, —OS(═O)$_2R^{70}$, —OS(═O)$_2R^{70}$, —OS(═O)$_2$N$R^{72}R^{73}$, —OP(═O)$R^{78}R^{78}$, —OP(═O)(N$R^{72}R^{73}$)(N$R^{72}R^{73}$), —OP(═O)(O$R^{70}$)(O$R^{70}$), —OP(═O)(S$R^{70}$)(S$R^{70}$), —Si($R^{74}$)$_3$, —SCN, ═S, —S(═O)$_nR^{70}$, —S(═O)$_2$O$R^{70}$, —$SO_3R$, —S(═O)$_2$N$R^{72}R^{73}$, —S(═O)N$R^{72}R^{73}$, —SP(═O)$R^{78}R^{78}$, —SP(═O)(N$R^{72}R^{73}$)(N$R^{72}R^{73}$), —SP(═O)(O$R^{70}$)(O$R^{70}$), —SP(═O)(S$R^{70}$)(S$R^{70}$), —P(═O)$R^{78}R^{78}$, —P(═O)(N$R^{72}R^{73}$)(N$R^{72}R^{73}$), —P(═O)(O$R^{70}$)(O$R^{70}$), and —P(═O)(S$R^{70}$)(S$R^{70}$);

$R^{70}$, $R^{71}$, $R^{74}$, $R^{7}$, $R^{76}$ and $R^{77}$ at each occurrence is independently chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

$R^{72}$ and $R^{73}$ at each occurrence is independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, and 6-21 membered heteroarylalkyl optionally substituted by 1-27 $R^{99}$;

or any $R^{72}$ and $R^{73}$ may form, together with the nitrogen atom to which they are attached, a 3-15 membered heterocycloalkyl optionally substituted by 1-28 $R^{109}$ or a 5-15 membered heteroaryl optionally substituted by 1-15 $R^{109}$;

$R^{78}$ at each occurrence is independently chosen from $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

or any two $R^{78}$ attached to the same phosphorus atom can, together with the phosphorus atom linking them, form a 3-10 membered heterocycloalkyl optionally substituted by 1-6 $R^{89}$;

$R^{79}$, $R^{89}$, $R^{99}$ and $R^{109}$ at each occurrence is independently chosen from $C_{1-6}$alkyl optionally substituted by 1-13 $R^{119}$, $C_{2-6}$alkenyl optionally substituted by 1-11 $R^{119}$, $C_{2-6}$alkynyl optionally substituted by 1-9 $R^{119}$, $C_{6-11}$aryl optionally substituted by 1-11 $R^{119}$, $C_{7-16}$arylalkyl optionally substituted by 1-19 $R^{119}$, $C_{3-11}$cycloalkyl optionally substituted by 1-21 $R^{119}$, $C_{4-17}$cycloalkylalkyl optionally substituted by 1-32 $R^{119}$, 3-15 membered heterocycloalkyl optionally substituted by 1-28 $R^{119}$, 4-21 membered heterocycloalkylalkyl optionally substituted by 1-40 $R^{119}$, 5-15 membered heteroaryl optionally substituted by 1-15 $R^{119}$, 6-21 membered heteroarylalkyl optionally substituted by 1-27 $R^{119}$, halogen, —CN, —C(═O)$R^{110}$, —C(═O)O$R^{110}$, —C(═O)N$R^{112}R^{113}$, —C(═O)C(═O)$R^{110}$, —C(═N$R^{115}$)$R^{110}$, —C(═N$R^{115}$)N$R^{112}R^{113}$, —C(═NOH)N$R^{112}R^{113}$, —C(═NO$R^{116}$)$R^{110}$, —C(═NN$R^{112}R^{113}$)$R^{110}$, —C(═NN$R^{114}$C(═O)$R^{111}$)$R^{110}$, —C(═NN$R^{114}$C(═O)O$R^{111}$)$R^{110}$, —C(═S)N$R^{112}R^{113}$, —NC, —$NO_2$, —N$R^{112}R^{113}$, —N$R^{114}$N$R^{112}R^{113}$, —N═N$R^{114}$, ═N$R^{110}$, ═NO$R^{110}$, —N$R^{114}$O$R^{116}$, —N$R^{114}$C(═O)$R^{110}$, —N$R^{114}$C(═O)C(═O)$R^{110}$, —N$R^{114}$C(═O)O$R^{111}$, —N$R^{114}$C(═O)C(═O)O$R^{111}$, —N$R^{114}$C(═O)N$R^{112}R^{113}$, —N$R^{114}$C(═O)N$R^{114}$C(═O)$R^{110}$, —N$R^{114}$C(═O)N$R^{114}$C(═O)O$R^{110}$, —N$R^{114}$C(═N$R^{115}$)N$R^{112}R^{113}$, —N$R^{114}$C(═O)C(═O)

NR$^{112}$R$^{113}$, —NR$^{114}$C(=S)R$^{110}$, —NR$^{114}$C(=S)OR$^{110}$, —NR$^{114}$C(=S)NR$^{112}$R$^{113}$, —NR$^{114}$S(=O)$_2$R$^{11}$, —NR$^{114}$S(=O)$_2$NR$^{112}$R$^{113}$, —NR$^{114}$P(=O)R$^{118}$R$^{118}$, —NR$^{114}$P(=O)(NR$^{112}$R$^{113}$)(NR$^{112}$R$^{113}$), —NR$^{114}$P(=O)(OR$^{110}$)(OR$^{110}$)—NR$^{114}$P(=O)(SR$^{110}$)(SR$^{110}$), —OR$^{110}$, =O, —OCN, —OC(=O)R$^{110}$, —OC(=O)NR$^{112}$R$^{113}$, —OC(=O)OR$^{110}$, —OC(=NR$^{115}$)NR$^{112}$R$^{113}$, —OS(=O)R$^{110}$, —OS(=O)$_2$R$^{110}$, —OS(=O)$_2$OR$^{110}$, —OS(=O)$_2$NR$^{112}$R$^{113}$, —OP(=O)R$^{118}$R$^{118}$, —OP(=O)(NR$^{112}$R$^{113}$)(NR$^{112}$R$^{113}$), —OP(=O)(OR$^{110}$)(OR$^{110}$), —OP(=O)(SR$^{110}$)(SR$^{110}$), —Si(R$^{114}$)$_3$, —SCN, =S, —S(=O)$_n$R$^{110}$, —S(=O)$_2$OR$^{110}$, —SO$_3$R$^{1111}$, —S(=O)$_2$NR$^{112}$R$^{113}$, —S(=O)NR$^{112}$R$^{113}$, —SP(=O)R$^{118}$R$^{118}$, —SP(=O)(NR$^{112}$R$^{113}$)(NR$^{112}$R$^{113}$), —SP(=O)(OR$^{110}$)(OR$^{110}$), —SP(=O)(SR$^{110}$)(SR$^{110}$), —P(=O)R$^{118}$R$^{118}$, —P(=O)(NR$^{112}$R$^{113}$)(NR$^{112}$R$^{113}$), —P(=O)(OR$^{110}$)(OR$^{110}$), and —P(=O)(SR$^{110}$)(SR$^{110}$);

R$^{110}$, R$^{111}$, R$^{114}$, R$^{115}$, R$^{116}$ and R$^{117}$ at each occurrence is independently chosen from H, C$_{1-6}$alkyl optionally substituted by 1-13 R$^{129}$, C$_{2-6}$alkenyl optionally substituted by 1-11 R$^{129}$, C$_{2-6}$alkynyl optionally substituted by 1-9 R$^{129}$, C$_{6-11}$aryl optionally substituted by 1-11 R$^{129}$, C$_{7-16}$arylalkyl optionally substituted by 1-19 R$^{129}$, C$_{3-11}$cycloalkyl optionally substituted by 1-21 R$^{129}$, C$_{4-17}$cycloalkylalkyl optionally substituted by 1-32 R$^{129}$, 3-15 membered heterocycloalkyl optionally substituted by 1-28 R$^{129}$, 4-21 membered heterocycloalkylalkyl optionally substituted by 1-40 R$^{129}$, 5-15 membered heteroaryl optionally substituted by 1-15 R$^{129}$, and 6-21 membered heteroarylalkyl optionally substituted by 1-27 R$^{129}$;

R$^{112}$ and R$^{113}$ at each occurrence is independently chosen from H, C$_{1-6}$alkyl optionally substituted by 1-13 R$^{139}$, C$_{2-6}$alkenyl optionally substituted by 1-11 R$^{139}$, C$_{2-6}$alkynyl optionally substituted by 1-9 R$^{139}$, C$_{6-11}$aryl optionally substituted by 1-11 R$^{139}$, C$_{7-16}$arylalkyl optionally substituted by 1-19 R$^{139}$, C$_{3-11}$cycloalkyl optionally substituted by 1-21 R$^{139}$, C$_{4-17}$cycloalkylalkyl optionally substituted by 1-32 R$^{139}$, 3-15 membered heterocycloalkyl optionally substituted by 1-28 R$^{139}$, 4-21 membered heterocycloalkylalkyl optionally substituted by 1-40 R$^{139}$, 5-15 membered heteroaryl optionally substituted by 1-15 R$^{139}$, and 6-21 membered heteroarylalkyl optionally substituted by 1-27 R$^{39}$;

or any R$^{112}$ and R$^{113}$ may form, together with the nitrogen atom to which they are attached, a 3-15 membered heterocycloalkyl optionally substituted by 1-28 R$^{149}$ or a 5-15 membered heteroaryl optionally substituted by 1-15 R$^{149}$ R$^{118}$ at each occurrence is independently chosen from C$_{1-6}$alkyl optionally substituted by 1-13 R$^{129}$, C$_{2-6}$alkenyl optionally substituted by 1-11 R$^{129}$, C$_{2-6}$alkynyl optionally substituted by 1-9 R$^{129}$, C$_{6-11}$aryl optionally substituted by 1-11 R$^{129}$, C$_{7-16}$arylalkyl optionally substituted by 1-19 R$^{129}$, C$_{3-11}$cycloalkyl optionally substituted by 1-21 R$^{129}$, C$_{4-17}$cycloalkylalkyl optionally substituted by 1-32 R$^{129}$, 3-15 membered heterocycloalkyl optionally substituted by 1-28 R$^{129}$, 4-21 membered heterocycloalkylalkyl optionally substituted by 1-40 R$^{129}$, 5-15 membered heteroaryl optionally substituted by 1-15 R$^{129}$, and 6-21 membered heteroarylalkyl optionally substituted by 1-27 R$^{129}$;

R$^{119}$, R$^{129}$, R$^{139}$ and R$^{149}$ at each occurrence is independently chosen from C$_{1-6}$alkyl optionally substituted by 1-13 R$^{159}$, C$_{2-6}$alkenyl optionally substituted by 1-11 R$^{159}$, C$_{2-6}$alkynyl optionally substituted by 1-9 R$^{159}$, C$_{6-11}$aryl optionally substituted by 1-11 R$^{159}$, C$_{7-16}$arylalkyl optionally substituted by 1-19 R$^{159}$, C$_{3-11}$cycloalkyl optionally substituted by 1-21 R$^{159}$, C$_{4-17}$cycloalkylalkyl optionally substituted by 1-32 R$^{159}$, 3-15 membered heterocycloalkyl optionally substituted by 1-28 R$^{159}$, 4-21 membered heterocycloalkylalkyl optionally substituted by 1-40 R$^{159}$, 5-15 membered heteroaryl optionally substituted by 1-15 R$^{159}$, 6-21 membered heteroarylalkyl optionally substituted by 1-27 R$^{159}$, halogen, —CN, —C(=O)R$^{150}$, —C(=O)OR$^{150}$, —C(=O)NR$^{152}$R$^{153}$, —C(=O)C(=O)R$^{150}$, —C(=NR$^{155}$)R$^{150}$, —C(=NR$^{155}$)NR$^{152}$R$^{153}$, —C(=NOH)NR$^{152}$R$^{153}$, —C(=NOR$^{156}$)R$^{150}$, —C(=NNR$^{152}$R$^{153}$)R$^{150}$, —C(=NNR$^{154}$C(=O)R$^{151}$)R$^{150}$, —C(=NNR$^{154}$C(=O)OR$^{151}$)R$^{150}$, —C(=S)NR$^{152}$R$^{153}$, —NC, —NO$_2$, —NR$^{152}$R$^{150}$, —NR$^{154}$NR$^{152}$R$^{153}$, —N=NR$^{154}$, =NR$^{150}$, =NOR$^{15}$, —NR$^{154}$OR$^{156}$, —NR$^{154}$C(=O)R$^{150}$, —NR$^{154}$C(=O)C(=O)R$^{150}$, —NR$^{154}$C(=)OR$^{151}$, —NR$^{154}$C(=O)C(=O)OR$^{151}$, —NR$^{154}$C(=O)NR$^{152}$R$^{153}$, —NR$^{154}$C(=O)NR$^{154}$C(=O)R$^{150}$, —NR$^{154}$C(=O)NR$^{154}$C(=O)OR$^{150}$, —NR$^{154}$C(=NR$^{155}$)NR$^{152}$R$^{153}$, —NR$^{154}$C(=O)C(=O)NR$^{152}$R$^{153}$, —NR$^{154}$C(=S)R$^{150}$, —NR$^{154}$C(=S)OR$^{150}$, —NR$^{154}$C(=S)NR$^{152}$R$^{153}$, —NR$^{154}$S(=O)$_2$R$^{151}$, —NR$^{154}$S(=O)$_2$NR$^{152}$R$^{153}$, —NR$^{154}$P(=O)R$^{158}$R$^{158}$, —NR$^{154}$P(=O)(NR$^{152}$R$^{153}$)(NR$^{152}$R$^{153}$), —NR$^{154}$P(=O)(OR$^{150}$)(OR$^{150}$), —NR$^{154}$P(=O)(SR$^{150}$)(SR$^{150}$), —OR$^{150}$, =O, —OCN, —OC(=O)R$^{150}$, —OC(=O)NR$^{152}$R$^{153}$, —OC(=)OR$^{150}$, —OC(=NR$^{155}$)NR$^{152}$R$^{153}$, —OS(=O)R$^{150}$, —OS(=O)$_2$R$^{150}$, —OS(=O)$_2$OR$^{15}$, —OS(=O)$_2$NR$^{152}$R$^{153}$, —OP(=O)R$^{158}$R$^{158}$, —OP(=O)(NR$^{152}$R$^{153}$)(NR$^{152}$R$^{153}$), —OP(=O)(OR$^{150}$)(OR$^{150}$), —OP(=O)(SR$^{150}$)(SR$^{150}$), —Si(R$^{154}$)$_3$, —SCN, =S, —S(=O)$_n$R$^{150}$, —S(=O)$_2$OR$^{150}$, —SO$_3$R$^{1515}$, —S(=O)$_2$NR$^{152}$R$^{153}$, —S(=O)NR$^{152}$R$^{153}$, —SP(=O)R$^{158}$R$^{158}$, —SP(=O)(NR$^{152}$R$^{153}$)(NR$^{152}$R$^{153}$), —SP(=O)(OR$^{150}$)(OR$^{150}$), —SP(=O)(SR$^{150}$)(SR$^{150}$), —P(=O)R$^{158}$R$^{158}$, —P(=O)(NR$^{152}$R$^{153}$)(NR$^{152}$R$^{153}$), —P(=O)(OR$^{150}$)(OR$^{150}$), and —P(=O)(SR$^{150}$)(SR$^{150}$);

R$^{150}$, R$^{151}$, R$^{154}$, R$^{155}$, R$^{156}$ and R$^{157}$ at each occurrence is independently chosen from H, C$_{1-6}$alkyl optionally substituted by 1-13 R$^{169}$, C$_{2-6}$alkenyl optionally substituted by 1-11 R$^{169}$, C$_{2-6}$alkynyl optionally substituted by 1-9 R$^{169}$, C$_{6-11}$aryl optionally substituted by 1-11 R$^{169}$, C$_{7-16}$arylalkyl optionally substituted by 1-19 R$^{169}$, C$_{3-11}$cycloalkyl optionally substituted by 1-21 R$^{169}$, C$_{4-17}$cycloalkylalkyl optionally substituted by 1-32 R$^{169}$, 3-15 membered heterocycloalkyl optionally substituted by 1-28 R$^{169}$, 4-21 membered heterocycloalkylalkyl optionally substituted by 1-40 R$^{169}$, 5-15 membered heteroaryl optionally substituted by 1-15 R$^{169}$, and 6-21 membered heteroarylalkyl optionally substituted by 1-27 R$^{169}$;

R$^{152}$ and R$^{153}$ at each occurrence is independently chosen from H, C$_{1-6}$alkyl optionally substituted by 1-13 R$^{179}$, C$_{2-6}$alkenyl optionally substituted by 1-11 R$^{179}$, C$_{2-6}$alkynyl optionally substituted by 1-9 R$^{179}$, C$_{6-11}$aryl optionally substituted by 1-11 R$^{179}$, C$_{7-16}$arylalkyl optionally substituted by 1-19 R$^{179}$, C$_{3-11}$ cycloalkyl optionally substituted by 1-21 R$^{179}$, C$_{4-17}$cycloalkylalkyl optionally substituted by 1-32 R$^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, and 6-21 membered heteroarylalkyl optionally substituted by 1-27 $R^{179}$;

or any $R^{152}$ and $R^{153}$ may form, together with the nitrogen atom to which they are attached, a 3-15 membered heterocycloalkyl optionally substituted by 1-28 $R^{189}$ or a 5-15 membered heteroaryl optionally substituted by 1-15 $R^{189}$;

$R^{158}$ at each occurrence is independently chosen from $C_{1-6}$alkyl optionally substituted by 1-13 $R^{169}$, $C_{2-6}$alkenyl optionally substituted by 1-11 $R^{169}$, $C_{2-6}$alkynyl optionally substituted by 1-9 $R^{169}$, $C_{6-11}$aryl optionally substituted by 1-11 $R^{169}$, $C_{7-16}$arylalkyl optionally substituted by 1-19 $R^{169}$, $C_{3-11}$cycloalkyl optionally substituted by 1-21 $R^{169}$, $C_{4-17}$cycloalkylalkyl optionally substituted by 1-32 $R^{169}$, 3-15 membered heterocycloalkyl optionally substituted by 1-28 $R^{169}$, 4-21 membered heterocycloalkylalkyl optionally substituted by 1-40 $R^{169}$, 5-15 membered heteroaryl optionally substituted by 1-15 $R^{169}$, and 6-21 membered heteroarylalkyl optionally substituted by 1-27 $R^{69}$;

$R^{159}$, $R^{169}$, $R^{179}$ and $R^{189}$ at each occurrence is independently chosen from $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$aryl optionally substituted by 1-11 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, 6-21 membered heteroarylalkyl optionally substituted by 1-27 $R^{199}$, halogen, —CN, —C(=O)$R^{190}$, —C(=O)O$R^{190}$, —C(=O)N$R^{192}R^{193}$, —C(=O)C(=O)$R^{190}$, —C(=N$R^{195}$)$R^{190}$, —C(=N$R^{195}$)N$R^{192}R^{193}$, —C(=NOH)N$R^{192}R^{193}$, —C(=NO$R^{196}$)$R^{190}$, —C(=NN$R^{192}R^{193}$)$R^{190}$, —C(=NN$R^{194}$C(=O)$R^{191}$)$R^{190}$, —C(=NN$R^{194}$C(=O)O$R^{191}$)$R^{190}$, —C(=S)N$R^{192}R^{193}$, —NC, —$NO_2$, —N$R^{192}R^{193}$, —N$R^{194}$N$R^{192}R^{193}$, —N=N$R^{194}$, =N$R^{190}$, =NO$R^{190}$, —N$R^{194}$O$R^{196}$, —N$R^{194}$C(=O)$R^{190}$, —N$R^{194}$C(=O)C(=O)$R^{190}$, —N$R^{194}$C(=O)O$R^{191}$, —N$R^{194}$C(=O)C(=O)O$R^{191}$, —N$R^{194}$C(=O)N$R^{192}R^{193}$, —N$R^{194}$C(=O)N$R^{194}$C(=O)$R^{190}$, —N$R^{194}$C(=O)N$R^{194}$C(=)O$R^{190}$, —N$R^{194}$C(=N$R^{195}$)N$R^{192}R^{193}$, —N$R^{194}$C(=O)C(=O)N$R^{192}R^{193}$, —N$R^{194}$C(=S)$R^{190}$, —N$R^{194}$C(=S)O$R^{190}$, —N$R^{194}$C(=S)N$R^{192}R^{193}$, —N$R^{194}$S(=O)$_2R^{191}$, —N$R^{194}$S(=O)$_2$N$R^{192}R^{192}R^{193}$, —N$R^{194}$P(=O)$R^{198}R^{198}$, —N$R^{194}$P(=O)(N$R^{192}R^{193}$)(N$R^{192}R^{193}$)—N$R^{194}$P(=)(O$R^{190}$)(O$R^{190}$), —N$R^{194}$P(=O)(S$R^{190}$)(S$R^{190}$)—O$R^{190}$, =O, —OCN, —OC(=O)$R^{190}$, —OC(=O)N$R^{192}R^{193}$, —OC(=O)O$R^{190}$, —OC(=N$R^{195}$)N$R^{192}R^{193}$, —OS(=O)$R^{190}$, —OS(=O)$_2R^{190}$, —OS(=O)$_2$O$R^{190}$, —OS(=O)$_2$N$R^{192}R^{193}$, —OP(=O)$R^{198}R^{198}$, —OP(=O)(N$R^{192}R^{193}$)(N$R^{192}R^{193}$), —OP(=O)(O$R^{190}$)(O$R^{190}$), —OP(=O)(S$R^{190}$)(S$R^{190}$), —Si($R^{194}$)$_3$, —SCN, =S, —S(=O)$_n R^{190}$, —S(=O)$_2R^{190}$, —$SO_3R^{1919}$, —S(=O)$_2$N$R^{192}R^{193}$, —S(=O)N$R^{192}R^{193}$, —SP(=O)$R^{198}R^{198}$, —SP(=O)(N$R^{192}R^{193}$)(N$R^{192}R^{193}$), —SP(=O)(O$R^{190}$)(O$R^{190}$), —SP(=O)(S$R^{190}$)(S$R^{190}$), —P(=O)$R^{198}R^{198}$, —P(=O)(N$R^{192}R^{193}$)(N$R^{192}R^{193}$), —P(=O)(O$R^{190}$)(O$R^{190}$), and —P(=O)(S$R^{190}$)(S$R^{190}$);

$R^{190}$, $R^{91}$, $R^{94}$, $R^{195}$, $R^{196}$ and $R^{197}$ at each occurrence is independently chosen from H, $C_{1-6}$alkyl optionally substituted by 1-13 $R^{209}$, $C_{2-6}$alkenyl optionally substituted by 1-11 $R^{209}$, $C_{2-6}$alkynyl optionally substituted by 1-9 $R^{209}$, $C_{6-11}$aryl optionally substituted by 1-11 $R^{209}$, $C_{7-16}$arylalkyl optionally substituted by 1-19 $R^{209}$, $C_{3-11}$cycloalkyl optionally substituted by 1-21 $R^{209}$, $C_{4-17}$cycloalkylalkyl optionally substituted by 1-32 $R^{209}$, 3-15 membered heterocycloalkyl optionally substituted by 1-28 $R^{209}$, 4-21 membered heterocycloalkylalkyl optionally substituted by 1-40 $R^{209}$, 5-15 membered heteroaryl optionally substituted by 1-15 $R^{209}$, and 6-21 membered heteroarylalkyl optionally substituted by 1-27 $R^{209}$ $R^{192}$ and $R^{193}$ at each occurrence is independently chosen from H, $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, and 6-21 membered heteroarylalkyl optionally substituted by 1-27 $R^{219}$;

or any $R^{192}$ and $R^{193}$ may form, together with the nitrogen atom to which they are attached, a 3-15 membered heterocycloalkyl optionally substituted by 1-28 $R^{229}$ or a 5-15 membered heteroaryl optionally substituted by 1-15 $R^{229}$;

$R^{198}$ at each occurrence is independently chosen from $C_{1-6}$alkyl optionally substituted by 1-13 $R^{209}$, $C_{2-6}$alkenyl optionally substituted by 1-11 $R^{209}$, $C_{2-6}$alkynyl optionally substituted by 1-9 $R^{209}$, $C_{6-11}$aryl optionally substituted by 1-11 $R^{209}$, $C_{7-16}$arylalkyl optionally substituted by 1-19 $R^{209}$, $C_{3-11}$cycloalkyl optionally substituted by 1-21 $R^{209}$, $C_{4-17}$cycloalkylalkyl optionally substituted by 1-32 $R^{209}$, 3-15 membered heterocycloalkyl optionally substituted by 1-28 $R^{209}$, 4-21 membered heterocycloalkylalkyl optionally substituted by 1-40 $R^{209}$, 5-15 membered heteroaryl optionally substituted by 1-15 $R^{209}$, and 6-21 membered heteroarylalkyl optionally substituted by 1-27 $R^{209}$ $R^{199}$, $R^{209}$, $R^{219}$ and $R^{229}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(=O)$R^{230}$, —C(=)O$R^{230}$, —C(=O)N$R^{230}R^{230}$, —C(=O)C(=O)$R^{230}$, —C(=N$R^{230}$)$R^{230}$, —C(=N$R^{230}$)N$R^{230}R^{230}$, —C(=NOH)N$R^{230}R^{230}$, —C(=NO$R^{230}$)$R^{230}$, —C(=NN$R^{230}R^{230}$)$R^{230}$, —C(=NN$R^{230}$C(=O)$R^{230}$)$R^{230}$, —C(=NN$R^{230}$C(=O)O$R^{230}$)$R^{230}$, —C(=S)N$R^{230}R^{230}$, —NC, —$NO_2$, —N$R^{230}R^{230}$, —N$R^{230}$N$R^{230}R^{230}$, —N=N$R^{230}$, =N$R^{230}$, =NO$R^{230}$, —N$R^{230}$O$R^{230}$, —N$R^{230}$C(=O)$R^{230}$, —N$R^{230}$C(=O)C(=O)$R^{230}$, —N$R^{230}$C(=O)O$R^{230}$, —N$R^{230}$C(=O)C(=O)O$R^{230}$, —N$R^{230}$C(=O)N$R^{230}R^{230}$, —N$R^{230}$C(=O)N$R^{230}$C(=O)$R^{230}$, $-NR^{230}C(=O)NR^{230}C(=O)OR^{230}$, $-NR^{230}C(=NR^{230})NR^{230}R^{230}$, $-NR^{230}C(=O)C(=O)NR^{230}R^{230}$, $-NR^{230}C(=S)R^{230}$, $-NR^{230}C(=S)OR^{230}$, $-NR^{230}C(=S)NR^{230}R^{230}$, $-NR^{230}S(=)_2R^{230}$, $-NR^{230}S(=O)_2NR^{230}R^{230}$, $-NR^{230}P(=O)R^{231}R^{231}$, $-NR^{230}P(=O)(NR^{230}R^{230})(NR^{230}R^{230})$, $-NR^{230}P(=O)(OR^{230})(OR^{230})$, $-NR^{230}P(=O)(SR^{230})(SR^{230})$, $-OR^{230}$, $=O$, $-OCN$, $-OC(=O)R^{230}$, $-OC(=O)NR^{230}R^{230}$, $-OC(=O)OR^{230}$, $-OC(=NR^{230})NR^{230}R^{230}$, $-OS(=O)R^{230}$, $-OS(=)_2R^{230}$, $-OS(=O)_2OR^{230}$, $-OS(=O)_2NR^{230}R^{230}$, $-OP(=O)R^{231}R^{231}$, $-OP(=O)(NR^{230}R^{230})(NR^{230}R^{230})$, $-OP(=O)(OR^{230})(OR^{230})$, $-OP(=O)(SR^{230})(SR^{230})$, $-Si(R^{230})_3$, $-SCN$, $=S$, $-S(=O)_nR^{230}$, $-S(=O)_2R^{230}$, $-SO_3R^{230}$, $-S(=O)_2NR^{230}R^{230}$, $-S(=O)NR^{230}R^{230}$, $-SP(=O)R^{231}R^{231}$, $-SP(=O)(NR^{230}R^{230})(NR^{230}R^{230})$, $-SP(=O)(OR^{230})(OR^{230})$, $-SP(=)(SR^{230})(SR^{230})$, $-P(=O)R^{231}R^{231}$, $-P(=O)(NR^{230}R^{230})(NR^{230}R^{230})$, $-P(=O)(OR^{230})(OR^{230})$, and $-P(=O)(SR^{230})(SR^{230})$;

$R^{230}$ at each occurrence is independently chosen from H, $C_{1-6}$alkyl and $C_{1-6}$-haloalkyl;

$R^{231}$ at each occurrence is independently chosen from $C_{1-6}$alkyl and $C_{1-6}$-haloalkyl; and n at each occurrence is independently chosen from 0, 1, and 2;

with the proviso that the compound is not (a)

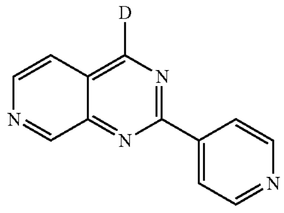

in which D is H or

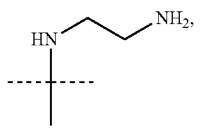

or a salt form thereof;

(b)

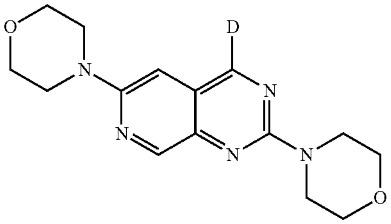

in which D is

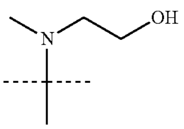

or

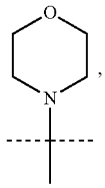

or a salt form thereof; or (c)

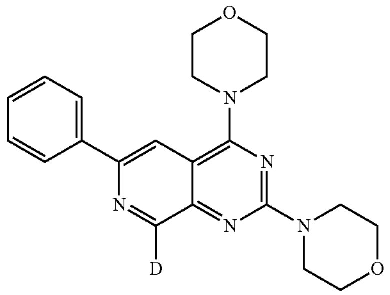

in which D is H or $-CH_3$, or a salt form thereof.

Embodiment 2

The compound of Embodiment 1, wherein G is a group of formula

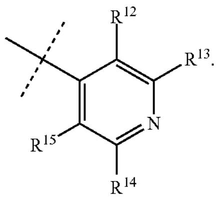

Embodiment 3

The compound of Embodiment 1, wherein G is a group of formula

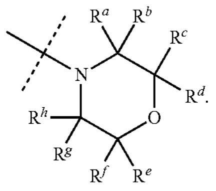

Embodiment 4

The compound of any of Embodiments 1-3, wherein X is chosen from H, $C_{1-10}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, —C(═O)$R^{28}$, —C(═O)O$R^{28}$, —C(═O)N$R^{24}R^{28}$, —C(═O)C(═O)$R^{28}$, —N$R^{24}R^{28}$, —N$R^{24}$N$R^{24}R^{28}$, —N═N$R^{28}$, —N$R^{24}$O$R^{28}$, —N$R^{24}$C(═O)$R^{28}$, —N$R^{24}$C(═O)C(═O)$R^{28}$, —N$R^{24}$C(═O)O$R^{28}$, —N$R^{24}$C(═O)C(═O)O$R^{28}$, —N$R^{24}$C(═O)N$R^{24}R^{28}$, —N$R^{24}$C(═O)N$R^{24}$C(═O)$R^{28}$, —N$R^{24}$C(═O)N$R^{24}$C(═O)O$R^{28}$, —N$R^{24}$C(═O)C(═O)N$R^{24}R^{28}$, —N$R^{24}$S(═O)$_2R^{28}$, —N$R^{24}$S(═O)$_2$N$R^{24}R^{28}$, —O$R^{28}$, —OC(═O)$R^{28}$, —OC(═O)N$R^{24}R^{28}$, —OC(═O)OR, —OS(═O)$R^{28}$, —OS(═O)$_2R^{28}$, —OS(═O)$_2$O$R^{28}$, —OS(═O)$_2$N$R^{24}R^{28}$, —S(═O)$_nR^{28}$, —S(═O)$_2$N$R^{24}R^{28}$, and —S(═O)N$R^{24}R^{28}$.

Embodiment 5

The compound of any of Embodiments 1-3, wherein X is chosen from H, $C_{1-10}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)O$R^{28}$, —N$R^{24}$C(═O)N$R^{24}R^{28}$, —N$R^{24}$S(═O)$_2R^{28}$, —N$R^{24}$S(═O)$_2$N$R^{24}R^{28}$, —O$R^{28}$, —OC(═O)$R^{28}$, —OC(═O)N$R^{24}R^{28}$, —OS(═O)$R^{28}$, —OS(═O)$_2R^{28}$, —OS(═O)$_2$N$R^{24}R^{28}$, —S(═O)$_nR^{28}$, —S(═O)$_2$N$R^{24}R^{28}$, and —S(═O)N$R^{24}R^{28}$.

Embodiment 6

The compound of any of Embodiments 1-3, wherein X is chosen from H, $C_{1-10}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)O$R^{28}$, —N$R^{24}$C(═O)N$R^{24}R^{28}$, —N$R^{24}$S(═O)$_2R^{28}$, —N$R^{24}$S(═O)$_2$N$R^{24}R^{28}$, —O$R^{28}$, —OC(═O)$R^{28}$, —OC(═O)N$R^{24}R^{28}$, —OS(═O)$R^{28}$, —OS(═O)$_2R^{28}$, —OS(═O)$_2$N$R^{24}R^{28}$, —S(═O)$_nR^{28}$, —S(═O)$_2$N$R^{24}R^{28}$, and —S(═O)N$R^{24}R^{28}$.

Embodiment 7

The compound of any of Embodiments 1-3, wherein X is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, $C_{4-7}$cycloalkylalkyl optionally substituted by 1-6 $R^{19}$, 3-10 membered heterocycloalkyl optionally substituted by 1-6 $R^{19}$, 4-7 membered heterocycloalkylalkyl optionally substituted by 1-6 $R^{19}$, 5-10 membered heteroaryl optionally substituted by 1-6 $R^{19}$, 6-11 membered heteroarylalkyl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)O$R^{28}$, —N$R^{24}$C(═O)N$R^{24}R^{28}$, —N$R^{24}$S(═O)$_2R^{28}$, —N$R^{24}$S(═O)$_2$N$R^{24}R^{28}$, —O$R^{28}$, —OC(═O)$R^{28}$, —OC(═O)N$R^{24}R^{28}$, —OS(═O)$R^{28}$, —OS(═O)$_2R^{28}$, —OS(═O)$_2$N$R^{24}R^{28}$, —S(═)$_nR^{28}$, —S(═O)$_2$N$R^{24}R^{28}$, and —S(═O)N$R^{24}R^{28}$.

Embodiment 8

The compound of any of Embodiments 1-3, wherein X is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, $C_{4-7}$cycloalkylalkyl optionally substituted by 1-6 $R^{19}$, 3-10 membered heterocycloalkyl optionally substituted by 1-6 $R^{19}$, 4-7 membered heterocycloalkylalkyl optionally substituted by 1-6 $R^{19}$, 5-10 membered heteroaryl optionally substituted by 1-6 $R^{19}$, 6-11 membered heteroarylalkyl optionally substituted by 1-6 $R^{19}$, —C(═O)$R^{28}$, —C(═)O$R^{28}$, —C(═O)N$R^{24}R^{28}$, —N$R^{24}R^{28}$, —N$R^{24}$C(═O)$R^{28}$, —N$R^{24}$C(═O)N$R^{24}R^{28}$, —N$R^{24}$S(═O)$_2R^{28}$, —O$R^{28}$, —OC(═O)$R^{28}$, —S(═O)$_nR^{28}$, and —S(═O)$_2$N$R^{24}R^{28}$.

Embodiment 9

The compound of any of Embodiments 1-3, wherein X is chosen from $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, $C_{4-7}$cycloalkylalkyl optionally substituted by 1-6 $R^{19}$, 3-10 membered heterocycloalkyl optionally substituted by 1-6 $R^{19}$, 4-7 membered heterocycloalkylalkyl optionally substituted by 1-6 $R^{19}$, 5-10 membered heteroaryl optionally substituted by 1-6 $R^{19}$, 6-11 membered heteroarylalkyl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)O$R^{28}$, —N$R^{24}$C(═O)N$R^{24}R^{28}$, —N$R^{24}$S(═O)$_2R^{28}$, —N$R^{24}$S(═O)$_2$N$R^{24}R^{28}$, —O$R^{28}$, —OC(═O)$R^{28}$, —OC(═O)N$R^{24}R^{28}$, —OS(═O)$R^{28}$, —OS(═)$_2R^{28}$, —OS(═O)$_2$N$R^{24}R^{28}$, —S(═)$_nR^{28}$, —S(═O)$_2$N$R^{24}R^{28}$, and —S(═O)N$R^{24}R^{28}$.

Embodiment 10

The compound of any of Embodiments 1-3, wherein X is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, $C_{4-7}$cycloalkylalkyl optionally substituted by 1-6 $R^{19}$, 3-10 membered heterocycloalkyl optionally substituted by 1-6 $R^{19}$, 4-7 membered heterocycloalkylalkyl optionally substituted by 1-6 $R^{19}$, 5-10 membered heteroaryl optionally substituted by 1-6 $R^{19}$, 6-11 membered heteroarylalkyl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)$_2$N$R^{24}R^{28}$, —N$R^{24}$S(═O)$_2R^{28}$, —O$R^{28}$, —OC(═O)$R^{28}$, —S(═O)$_n R^{28}$, and —S(═O)$_2$N$R^{24}R^{28}$.

Embodiment 11

The compound of any of Embodiments 1-3, wherein X is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)N$R^{24}R^{28}$, —N$R^{24}$S(═O)$_2R^{28}$, —O$R^{28}$, —OC(═O)$R^{28}$, —S(═O)$_n R^{28}$, and —S(═O)$_2$N$R^{24}R^{28}$.

Embodiment 12

The compound of any of Embodiments 1-3, wherein X is chosen from H, $C_{1-6}$alkyl optionally substituted by 1-6 $R^{19}$, $C_{6-10}$aryl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)N$R^{24}R^{28}$, —N$R^{24}$S(═O)$_2R^{28}$, —O$R^{28}$, —OC(═O)$R^{28}$, —S(═O)$_n R^{28}$, and —S(═O)$_2$N$R^{24}R^{28}$.

Embodiment 13

The compound of any of Embodiments 1-3, wherein X is chosen from H, $C_{1-6}$alkyl optionally substituted by 1-6 $R^{19}$, $C_{6-10}$aryl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —C(═O)$R^{28}$, —C(═O)N$R^{24}R^{28}$, —N$R^{24}R^{28}$, —N$R^{24}$C(═O)$R^{28}$, —N$R^{24}$S(═O)$_2R^{28}$, and —O$R^{28}$.

Embodiment 14

The compound of any of Embodiments 1-3, wherein X is chosen from H, 3-10 membered heterocycloalkyl optionally substituted by 1-6 $R^{19}$, 5-10 membered heteroaryl optionally substituted by 1-6 $R^{19}$, —C(═O)$R^{28}$, —C(═O)N$R^{24}R^{28}$, —N$R^{24}R^{28}$, —N$R^{24}$C(═O)$R^{28}$, —N$R^{24}$S(═O)$_2R^{28}$, and —O$R^{28}$.

Embodiment 15

The compound of any of Embodiments 1-3, wherein X is chosen from $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, $C_{4-7}$cycloalkylalkyl optionally substituted by 1-6 $R^{19}$, 3-10 membered heterocycloalkyl optionally substituted by 1-6 $R^{19}$, 4-7 membered heterocycloalkylalkyl optionally substituted by 1-6 $R^{19}$, 5-10 membered heteroaryl optionally substituted by 1-6 $R^{19}$, 6-11 membered heteroarylalkyl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)N$R^{24}R^{28}$, —N$R^{24}$S(═O)$_2R^{28}$, —O$R^{28}$, —OC(═O)$R^{28}$, —S(═O)$_n R^{28}$, and —S(═O)$_2$N$R^{24}R^{28}$.

Embodiment 16

The compound of any of Embodiments 1-3, wherein X is chosen from $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —C(═O)$R^{28}$, —C(═O)O$R^{28}$, —C(═O)N$R^{24}R^{28}$, —N$R^{24}R^{28}$, —N$R^{24}$C(═O)$R^{28}$, —N$R^{24}$C(═O)N$R^{24}R^{28}$, —N$R^{24}$S(═O)$_2R^{28}$, —O$R^{28}$, —OC(═O)$R^{28}$, —S(═O)$_n R^{28}$, and —S(═O)$_2$N$R^{24}R^{28}$.

Embodiment 17

The compound of any of Embodiments 1-3, wherein X is chosen from $C_{1-6}$alkyl optionally substituted by 1-6 $R^{19}$, $C_{6-10}$aryl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —C(═O)$R^{28}$, —C(═)O$R^{28}$, —C(═O)N$R^{24}R^{28}$, —N$R^{24}R^{28}$, —N$R^{24}$C(═O)$R^{28}$, —N$R^{24}$C(═O)N$R^{24}R^{28}$, —N$R^{24}$S(═O)$_2R^{28}$, —O$R^{28}$, —OC(═O)$R^{28}$, —S(═O)$_n R^{28}$, and —S(═O)$_2$N$R^{24}R^{28}$.

Embodiment 18

The compound of any of Embodiments 1-3, wherein X is chosen from $C_{1-6}$alkyl optionally substituted by 1-6 $R^{19}$, $C_{6-10}$aryl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —C(═O)$R^{28}$, —C(═O)N$R^{24}R^{28}$, —N$R^{24}R^{28}$, —N$R^{24}$C(═O)$R^{28}$, —N$R^{24}$S(═O)$_2R^{28}$, and —O$R^{28}$.

Embodiment 19

The compound of any of Embodiments 1-3, wherein X is chosen from 3-10 membered heterocycloalkyl optionally substituted by 1-6 $R^{19}$, 5-10 membered heteroaryl optionally substituted by 1-6 $R^{19}$, —C(═O)$R^{28}$, —C(═O)N$R^{24}R^{28}$, —N$R^{24}R^{28}$, —N$R^{24}$C(═O)$R^{28}$, —N$R^{24}$S(═O)$_2R^{28}$, and —O$R^{28}$.

Embodiment 20

The compound of any of Embodiments 1-3, wherein X is chosen from H, $C_{1-6}$alkyl optionally substituted by 1-6 $R^{19}$, $C_{6-10}$aryl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —N$R^{24}R^{28}$, and —O$R^{28}$.

Embodiment 21

The compound of any of Embodiments 1-3, wherein X is chosen from H, 3-10 membered heterocycloalkyl optionally substituted by 1-6 $R^{19}$, 5-10 membered heteroaryl optionally substituted by 1-6 $R^{19}$, —$NR^{24}R^{28}$, and —$OR^{28}$.

Embodiment 22

The compound of any of Embodiments 1-3, wherein X is chosen from $C_{1-6}$alkyl optionally substituted by 1-6 $R^{19}$, $C_{6-10}$aryl optionally substituted by 1-6 $R^{19}$, $C_{3-6}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, —$NR^{24}R^{28}$, and —$OR^{28}$.

Embodiment 23

The compound of any of Embodiments 1-3, wherein X is chosen from 3-10 membered heterocycloalkyl optionally substituted by 1-6 $R^{19}$, 5-10 membered heteroaryl optionally substituted by 1-6 $R^{19}$, —$NR^{24}R^{28}$, and —$OR^{28}$.

Embodiment 24

The compound of any of Embodiments 1-3, wherein X is chosen from H, 3-10 membered heterocycloalkyl optionally substituted by 1-6 $R^{19}$, 5-10 membered heteroaryl optionally substituted by 1-6 $R^{19}$, and —$NR^{24}R^{28}$.

Embodiment 25

The compound of any of Embodiments 1-3, wherein X is chosen from 3-10 membered heterocycloalkyl optionally substituted by 1-6 $R^{19}$, 5-10 membered heteroaryl optionally substituted by 1-6 $R^{19}$, and —$NR^{24}R^{28}$.

Embodiment 26

The compound of any of Embodiments 1-3, wherein X is chosen from H, 3-10 membered heterocycloalkyl optionally substituted by 1-6 $R^{19}$, —$NR^{24}R^{28}$, —$OR^{28}$, and —$SR^{28}$.

Embodiment 27

The compound of any of Embodiments 1-3, wherein X is chosen from 3-10 membered heterocycloalkyl optionally substituted by 1-6 $R^{19}$, and —$NR^{24}R^{28}$.

Embodiment 28

The compound of any of Embodiments 1-3, wherein X is chosen from H, 3-9 membered heterocycloalkyl optionally substituted by 1-6 $R^{19}$, and —$NR^{24}R^{28}$.

Embodiment 29

The compound of any of Embodiments 1-3, wherein X is chosen from 3-9 membered heterocycloalkyl optionally substituted by 1-6 $R^{19}$, and —$NR^{24}R^{28}$.

Embodiment 30

The compound of any of Embodiments 1-3, wherein X is chosen from H, 3-7 membered heterocycloalkyl optionally substituted by 1-6 $R^{19}$, and —$NR^{24}R^{28}$.

Embodiment 31

The compound of any of Embodiments 1-3, wherein X is chosen from 3-7 membered heterocycloalkyl optionally substituted by 1-6 $R^{19}$, and —$NR^{24}R^{28}$.

Embodiment 32

The compound of any of Embodiments 1-3, wherein X is 3-10 membered heterocycloalkyl optionally substituted by 1-6 $R^{19}$.

Embodiment 33

The compound of any of Embodiments 1-3, wherein X is 3-9 membered heterocycloalkyl optionally substituted by 1-6 $R^{19}$.

Embodiment 34

The compound of any of Embodiments 1-3, wherein X is 3-7 membered heterocycloalkyl optionally substituted by 1-6 $R^{19}$.

Embodiment 35

The compound of any of Embodiments 1-3, wherein X is 5-6 membered heterocycloalkyl optionally substituted by 1-6 $R^{19}$.

Embodiment 36

The compound of any of Embodiments 1-3, wherein X is 6 membered heterocycloalkyl optionally substituted by 1-6 $R^{19}$.

Embodiment 37

The compound of any of Embodiments 1-3, wherein X is morpholinyl, piperidinyl, or piperazinyl optionally substituted by 1-6 $R^{19}$.

Embodiment 38

The compound of any of Embodiments 1-3, wherein X is piperidinyl or piperazinyl optionally substituted by 1-6 $R^{19}$.

Embodiment 39

The compound of any of Embodiments 1-3, wherein X is piperidinyl optionally substituted by 1-6 $R^{19}$.

Embodiment 40

The compound of any of Embodiments 1-3, wherein X is piperazinyl optionally substituted by 1-6 $R^{19}$.

Embodiment 41

The compound of any of Embodiments 1-3, wherein X is —$NR^{24}R^{28}$.

Embodiment 42

The compound of any of Embodiments 1-3, wherein X is chosen from H and

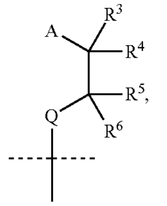

wherein

A is —$NR^{1}R^{2}$, —$CR^{i}R^{j}R^{k}$, —$OR^{18a}$, or —$SR^{18b}$;

Q is —$NR^{11}$—, —$CR^{m}R^{n}$—, —O—, or —S—;

$R^{k}$ is H, halogen, —CN, —$NO_2$, —$NR^{16}R^{17}$, —$OR^{18c}$, —$SR^{18d}$, or —$CR^{o}R^{p}R^{q}$;

$R^{q}$ is H, halogen, —CN, —$NO_2$, —$NR^{16a}R^{17a}$ or —$OR^{18e}$;

$R^{1}$, $R^{2}$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-13 $R^{79}$, $C_{2-6}$alkenyl optionally substituted by 1-19 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, and —$OR^{70}$;

$R^{3}$, $R^{4}$, $R^{5}$, $R^{6}$, $R^{i}$, $R^{j}$, $R^{m}$, $R^{n}$, $R^{o}$, and $R^{p}$ are independently chosen from H, $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$ aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(═O)$R^{70}$, —C(═O)$OR^{70}$, —C(═O)$NR^{72}R^{73}$, —C(═O)C(═O)$R^{70}$, —C(═$NR^{75}$)$R^{70}$, —C(═$NR^{75}$)$NR^{72}R^{73}$, —C(═NOH)$NR^{72}R^{73}$, —C(═$NOR^{76}$)$R^{70}$, —C(═$NNR^{72}R^{73}$)$R^{70}$, —C(═$NNR^{74}$C(═O)$R^{71}$)$R^{70}$, —C(═$NNR^{74}$C(═O)$OR^{71}$)$R^{70}$, —C(═S)$NR^{72}R^{73}$, —NC, —$NO_2$, —$NR^{72}R^{73}$, —$NR^{74}NR^{72}R^{73}$, —N═$NR^{74}$, —$NR^{74}OR^{76}$, —$NR^{74}$C(═O)$R^{70}$, —$NR^{74}$C(═O)C(═O)$R^{70}$, —$NR^{74}$C(═)$OR^{71}$, —$NR^{74}$C(═O)C(═O)$OR^{71}$, —$NR^{74}$C(═O)$NR^{72}R^{73}$, —$NR^{74}$C(═O)$NR^{74}$C(═O)$R^{70}$, —$NR^{74}$C(═O)$NR^{74}$C(═O)$OR^{70}$, —$NR^{74}$C(═$NR^{75}$)$NR^{72}R^{73}$, —$NR^{74}$C(═O)C(═O)$NR^{72}R^{73}$, —$NR^{74}$C(═S)$R^{70}$, —$NR^{74}$C(═S)$OR^{70}$, —$NR^{74}$C(═S)$NR^{72}R^{73}$, —$NR^{74}$S(═O)$_2R^{71}$, —$NR^{74}$S(═O)$_2NR^{72}R^{73}$, —$NR^{74}$P(═O)$R^{78}R^{78}$, —$NR^{74}$P(═O)($NR^{72}R^{73}$)($NR^{72}R^{73}$), —$NR^{74}$P(═O)($OR^{70}$)($OR^{70}$), —$NR^{74}$P(═O)($SR^{70}$)($SR^{70}$), —$OR^{70}$, —OCN, —OC(═O)$R^{70}$, —OC(═O)$NR^{72}R^{73}$, —OC(═O)$OR^{70}$, —OC(═$NR^{75}$)$NR^{72}R^{73}$, —OS(═O)$R^{70}$, —OS(═O)$_2R^{70}$, —OS(═O)$_2OR^{70}$, —OS(═O)$_2NR^{72}R^{73}$, —OP(═O)$R^{78}R^{78}$, —OP(═O)($NR^{72}R^{73}$)($NR^{72}R^{73}$), —OP(═O)($OR^{70}$)($OR^{70}$), —OP(═O)($SR^{70}$)($SR^{70}$), —Si($R^{74}$)$_3$, —SCN, —S(═O)$_nR^{70}$, —S(═O)$_2OR^{70}$, —$SO_3R^{77}$, —S(═O)$_2NR^{72}R^{73}$, —S(═O)$NR^{72}R^{73}$, —SP(═O)$R^{78}R^{78}$, —SP(═O)($NR^{72}R^{73}$)($NR^{72}R^{73}$), —SP(═O)($OR^{70}$)($OR^{70}$), —SP(═O)($SR^{70}$)($SR^{70}$), —P(═O)$R^{78}R^{78}$, —P(═O)($NR^{72}R^{73}$)($NR^{72}R^{73}$), —P(═O)($OR^{70}$)($OR^{70}$), and —P(═O)($SR^{70}$)($SR^{70}$);

or any of $R^{1}$ and $R^{2}$, $R^{1}$ and $R^{3}$, $R^{1}$ and $R^{5}$, $R^{1}$ and $R^{11}$, $R^{1}$ and $R^{n}$, $R^{4}$ and $R^{11}$, $R^{6}$ and $R^{11}$, $R^{16}$ and $R^{17}$, $R^{16}$ and $R^{i}$, $R^{16}$ and $R^{3}$, $R^{16}$ and $R^{5}$, $R^{16}$ and $R^{11}$, $R^{16}$ and $R^{n}$, $R^{j}$ and $R^{11}$, $R^{18a}$ and $R^{3}$, $R^{18a}$ and $R^{5}$, $R^{18a}$ and $R^{11}$, $R^{18a}$ and $R^{n}$, $R^{18b}$ and $R^{3}$, $R^{18b}$ and $R^{5}$, $R^{18b}$ and $R^{n}$, $R^{18b}$ and $R^{n}$, $R^{18c}$ and $R^{i}$, $R^{18}$ and $R^{3}$, $R^{18}$ and $R^{5}$, $R^{18c}$ and $R^{11}$, $R^{18c}$ and $R^{n}$, $R^{18d}$ and $R^{i}$, $R^{18d}$ and $R^{3}$, $R^{18d}$ and $R^{5}$, $R^{18d}$ and $R^{11}$, and $R^{18d}$ and $R^{n}$ can, together with the atoms linking them, form a 3-15 membered heterocycloalkyl optionally substituted by 1-28 $R^{79}$ or a 5-15 membered heteroaryl optionally substituted by 1-15 $R^{79}$;

or any of $R^{3}$ and $R^{4}$, $R^{3}$ and $R^{6}$, $R^{5}$ and $R^{6}$, $R^{i}$ and $R^{j}$, $R^{i}$ and $R^{4}$, $R^{i}$ and $R^{5}$, $R^{i}$ and $R^{n}$, $R^{m}$ and $R^{n}$, $R^{4}$ and $R^{m}$, and $R^{6}$ and $R^{m}$ can, together with the atoms linking them, form a $C_{6-11}$aryl optionally substituted by 1-11 $R^{79}$, $C_{3-11}$cycloalkyl optionally substituted by 1-21 $R^{79}$, 3-15 membered heterocycloalkyl optionally substituted by 1-28 $R^{79}$ or a 5-15 membered heteroaryl optionally substituted by 1-15 $R^{79}$;

or $R^{4}$ and $R^{5}$ or $R^{n}$ and $R^{5}$ can together form a double bond;

or any of $R^{3}$ and $R^{4}$, $R^{5}$ and $R^{6}$, $R^{i}$ and $R^{j}$, and $R^{m}$ and $R^{n}$ can together form ═O, ═$NR^{70}$, ═$NOR^{70}$, or ═S.

Embodiment 43

The compound of any of Embodiments 1-3, wherein X is

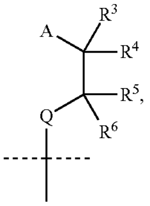

wherein

A is —$NR^{1}R^{2}$, —$CR^{i}R^{j}R^{k}$, —$OR^{18a}$, or —$SR^{18b}$;

Q is —$NR^{11}$—, —$CR^{m}R^{n}$—, —O—, or —S—;

$R^{k}$ is H, halogen, —CN, —$NO_2$, —$NR^{16}R^{17}$, —$OR^{18c}$, —$SR^{18d}$, or —$CR^{o}R^{p}R^{q}$;

$R^{q}$ is H, halogen, —CN, —$NO_2$, —$NR^{16a}R^{17a}$ or —$OR^{18e}$ $R^{1}$, $R^{2}$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$ aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, and —$OR^{70}$;

$R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(═O)$R^{70}$, —C(═O)O$R^{70}$, —C(═O)N$R^{72}R^{73}$, —C(═O)C(═O)$R^{70}$, —C(═N$R^{75}$)$R^{70}$, —C(═N$R^{75}$)N$R^{72}R^{73}$, —C(═NOH)N$R^{72}R^{73}$, —C(═NO$R^{76}$)$R^{70}$, —C(═NN$R^{72}R^{73}$)$R^{70}$, —C(═NN$R^{74}$C(═O)$R^{71}$)$R^{70}$, —C(═NN$R^{74}$C(═O)O$R^{71}$)$R^{70}$, —C(═S)N$R^{72}R^{73}$, —NC, —$NO_2$, —N$R^{72}R^{73}$, —N$R^{74}$N$R^{72}R^{73}$, —N═N$R^{74}$, —N$R^{74}$O$R^{76}$, —N$R^{74}$C(═O)$R^{70}$, —N$R^{74}$C(═O)C(═O)$R^{70}$, —N$R^{74}$C(═O)O$R^{71}$, —N$R^{74}$C(═O)C(═)O$R^{71}$, —N$R^{74}$C(═O)N$R^{72}R^{73}$, —N$R^{74}$C(═O)N$R^{74}$C(═O)$R^{70}$, —N$R^{74}$C(═O)N$R^{74}$C(═O)O$R^{70}$, —N$R^{74}$C(═N$R^{75}$)N$R^{72}R^{73}$, —N$R^{74}$C(═O)C(═O)N$R^{72}R^{73}$, —N$R^{74}$C(═S)$R^{70}$, —N$R^{74}$C(═S)O$R^{70}$, —N$R^{74}$C(═S)N$R^{72}R^{73}$, —N$R^{74}$S(═$O)_2R^{71}$, —N$R^{74}$S(═$O)_2$N$R^{72}R^{73}$, —N$R^{74}$P(═O)$R^{78}R^{78}$, —N$R^{74}$P(═O)(N$R^{72}R^{73}$)(N$R^{72}R^{73}$), —N$R^{74}$P(═)(O$R^{70}$)(O$R^{70}$), —N$R^{74}$P(═O)(S$R^{70}$)(S$R^{70}$), —O$R^{70}$, —OCN, —OC(═O)$R^{70}$, —OC(═O)N$R^{72}R^{73}$, —OC(═O)O$R^{70}$, —OC(═N$R^{75}$)N$R^{72}R^{73}$, —OS(═O)$R^{70}$, —OS(═$O)_2R^{70}$, —OS(═$O)_2$O$R^{70}$, —OS(═$O)_2$N$R^{72}R^{73}$, —OP(═O)$R^{78}R^{78}$, —OP(═O)(N$R^{72}R^{73}$)(N$R^{72}R^{73}$), —OP(═O)(O$R^{70}$)(O$R^{70}$), —OP(═O)(S$R^{70}$)(S$R^{70}$), —Si$(R^{74})_3$, —SCN, —S(═$O)_nR^{70}$, —S(═$O)_2$O$R^{70}$, —$SO_3R^{77}$, —S(═$O)_2$N$R^{72}R^{73}$, —S(═O)N$R^{72}R^{73}$, —SP(═O)$R^{78}R^{78}$, —SP(═O)(N$R^{72}R^{73}$)(N$R^{72}R^{73}$), —SP(═O)(O$R^{70}$)(O$R^{70}$), —SP(═O)(S$R^{70}$)(S$R^{70}$), —P(═O)$R^{78}R^{78}$, —P(═O)(N$R^{72}R^{73}$)(N$R^{72}R^{73}$), —P(═O)(O$R^{70}$)(O$R^{70}$), and —P(═O)(S$R^{70}$)(S$R^{70}$);

or any of $R^1$ and $R^2$, $R^1$ and $R^3$, $R^1$ and $R^5$, $R^1$ and $R^{11}$, $R^1$ and $R^n$, $R^4$ and $R^1$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18C}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-15 membered heterocycloalkyl optionally substituted by 1-28 $R^{79}$ or a 5-15 membered heteroaryl optionally substituted by 1-15 $R^{79}$;

or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-11 $R^{79}$, $C_{3-11}$cycloalkyl optionally substituted by 1-21 $R^{79}$, 3-15 membered heterocycloalkyl optionally substituted by 1-28 $R^{79}$ or a 5-15 membered heteroaryl optionally substituted by 1-15 $R^{79}$;

or $R^4$ and $R^5$ or $R^n$ and $R^5$ can together form a double bond;

or any of $R^3$ and $R^4$, $R^5$ and $R^6$, $R^i$ and $R^j$, and $R^m$ and $R^n$ can together form ═O, ═N$R^{70}$, ═NO$R^{70}$, or ═S.

Embodiment 44

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-10 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-10 $R^{79}$, $C_{3-11}$cycloalkyl optionally substituted by 1-10 $R^{79}$, $C_{4-17}$cycloalkylalkyl optionally substituted by 1-10 $R^{79}$, 3-15 membered heterocycloalkyl optionally substituted by 1-10 $R^{79}$, 4-21 membered heterocycloalkylalkyl optionally substituted by 1-10 $R^{79}$, 5-15 membered heteroaryl optionally substituted by 1-10 $R^{79}$, 6-21 membered heteroarylalkyl optionally substituted by 1-10 $R^{79}$, and —O$R^{70}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-10 $R^{79}$, $C_{2-6}$alkenyl optionally substituted by 1-10 $R^{79}$, $C_{2-6}$alkynyl optionally substituted by 1-9 $R^{79}$, $C_{6-11}$aryl optionally substituted by 1-10 $R^{79}$, $C_{7-16}$arylalkyl optionally substituted by 1-10 $R^{79}$, $C_{3-11}$cycloalkyl optionally substituted by 1-10 $R^{79}$, $C_{4-17}$cycloalkylalkyl optionally substituted by 1-10 $R^{79}$, 3-15 membered heterocycloalkyl optionally substituted by 1-10 $R^{79}$, 4-21 membered heterocycloalkylalkyl optionally substituted by 1-10 $R^{79}$, 5-15 membered heteroaryl optionally substituted by 1-10 $R^{79}$, 6-21 membered heteroarylalkyl optionally substituted by 1-10 $R^{79}$, halogen, —CN, —C(═O)$R^{70}$, —C(═O)O$R^{70}$, —C(═O)N$R^{72}R^{73}$, —(═O)C(═O)$R^{70}$, —NC, —$NO_2$, —N$R^{72}R^{73}$, —N$R^{74}$N$R^{72}R^{73}$, —N═N$R^{74}$, —N$R^{74}$O$R^{76}$, —N$R^{74}$C(═O)$R^{70}$, —N$R^{74}$C(═O)C(═O)$R^{70}$, —N$R^{74}$C(═O)O$R^{71}$, —N$R^{74}$C(═O)C(═)O$R^{71}$, —N$R^{74}$C(═O)N$R^{72}R^{73}$, —N$R^{74}$C(═O)N$R^{74}$C(═O)$R^{70}$, —N$R^{74}$C(═O)N$R^{74}$C(═O)O$R^{70}$, —N$R^{74}$C(═O)C(═O)N$R^{72}R^{73}$, —N$R^{74}$S(═$O)_2R^{71}$, —N$R^{74}$S(═$O)_2$N$R^{72}R^{73}$, —N$R^{74}$P(═O)$R^{78}R^{78}$, —N$R^{74}$P(═O)(N$R^{72}R^{73}$)(N$R^{72}R^{73}$), —N$R^{74}$P(═O)(O$R^{70}$)(O$R^{70}$), —O$R^{70}$, —OCN, —OC(═O)$R^{70}$, —OC(═O)N$R^{72}R^{73}$, —OC(═O)O$R^{70}$, —OS(═O)$R^{70}$, —OS(═$O)_2R^{70}$, —OS(═$O)_2$O$R^{70}$, —OS(═$O)_2$N$R^{72}R^{73}$, —OP(═O)$R^{78}R^{78}$, —OP(═O)(N$R^{72}R^{73}$)(N$R^{72}R^{73}$), —OP(═O)(O$R^{70}$)(O$R^{70}$), —Si$(R^{74})_3$, —SCN, —S(═$O)_nR^{70}$, —S(═$O)_2$O$R^{70}$, —$SO_3R^{77}$, —S(═$O)_2$N$R^{72}R^{73}$, —S(═O)N$R^{72}R^{73}$, —SP(═O)$R^{78}R^{78}$, —SP(═O)(N$R^{72}R^{73}$)(N$R^{72}R^{73}$), —SP(═O)(O$R^{70}$)(O$R^{70}$), —SP(═O)(S$R^{70}$)(S$R^{70}$), —P(═O)$R^{78}R^{78}$, —P(═O)(N$R^{72}R^{73}$)(N$R^{72}R^{73}$), and —P(═O)(O$R^{70}$)(O$R^{70}$); or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^{11}$, $R^{18e}$ and $R^{11}$, $R^{18e}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-15 membered heterocycloalkyl optionally substituted by 1-10 $R^{79}$ or a 5-15 membered heteroaryl optionally substituted by 1-10 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-10 $R^{79}$, $C_{3-11}$cycloalkyl optionally substituted by 1-10 $R^{79}$, 3-15 membered heterocycloalkyl optionally substituted by 1-10 $R^{79}$ or a 5-15 membered heteroaryl optionally substituted by 1-10 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form $=O$, $=NR^{70}$, $=NOR^{70}$, or $=S$.

Embodiment 45

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-10 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-10 $R^{79}$, $C_{3-11}$cycloalkyl optionally substituted by 1-10 $R^{79}$, $C_{4-17}$cycloalkylalkyl optionally substituted by 1-10 $R^{79}$, 3-15 membered heterocycloalkyl optionally substituted by 1-10 $R^{79}$, 4-21 membered heterocycloalkylalkyl optionally substituted by 1-10 $R^{79}$, 5-15 membered heteroaryl optionally substituted by 1-10 $R^{79}$, 6-21 membered heteroarylalkyl optionally substituted by 1-10 $R^{79}$, and $-OR^{70}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-10 $R^{79}$, $C_{2-6}$alkenyl optionally substituted by 1-10 $R^{79}$, $C_{2-6}$alkynyl optionally substituted by 1-9 $R^{79}$, $C_{6-11}$aryl optionally substituted by 1-10 $R^{79}$, $C_{7-16}$arylalkyl optionally substituted by 1-10 $R^{79}$, $C_{3-11}$cycloalkyl optionally substituted by 1-10 $R^{79}$, $C_{4-17}$cycloalkylalkyl optionally substituted by 1-10 $R^{79}$, 3-15 membered heterocycloalkyl optionally substituted by 1-10 $R^{79}$, 4-21 membered heterocycloalkylalkyl optionally substituted by 1-10 $R^{79}$, 5-15 membered heteroaryl optionally substituted by 1-10 $R^{79}$, 6-21 membered heteroarylalkyl optionally substituted by 1-10 $R^{79}$, halogen, $-CN$, $-C(=O)R^{70}$, $-C(=O)OR^{70}$, $-C(=O)NR^{72}R^{73}$, $-C(=O)C(=O)R^{70}$, $-NC$, $-NO_2$, $-NR^{72}R^{73}$, $-NR^{74}NR^{72}R^{73}$, $-N=NR^{74}$, $-NR^{74}OR^{76}$, $-NR^{74}C(=O)R^{70}$, $-NR^{74}C(=)OR^{71}$, $-NR^{74}C(=O)NR^{72}R^{73}$, $-NR^{74}S(=O)_2R^{71}$, $-NR^{74}S(=O)_2NR^{72}R^{73}$, $-NR^{74}P(=O)R^{78}R^{78}$, $-NR^{74}P(=O)(NR^{72}R^{73})(NR^{72}R^{73})$, $-NR^{74}P(=)(OR^{70})(OR^{70})$, $-OR^{70}$, $-OCN$, $-OC(=O)R^{70}$, $-OC(=O)NR^{72}R^{73}$, $-OC(=O)OR^{70}$, $-OS(=O)R^{70}$, $-OS(=O)_2R^{70}$, $-OS(=O)_2OR^{70}$, $-OS(=O)_2NR^{72}R^{73}$, $-OP(=O)R^{78}R^{78}$, $-OP(=O)(NR^{72}R^{73})(NR^{72}R^{73})$, $-OP(=O)(OR^{70})(OR^{70})$, $-SCN$, $-S(=O)_nR^{70}$, $-S(=O)_2R^{70}$, $-SO_3R^{77}$, $-S(=O)_2NR^{72}R^{73}$, $-S(=O)NR^{72}R^{73}$, $-SP(=O)R^{78}R^{78}$, $-SP(=O)(NR^{72}R^{73})(NR^{72}R^{73})$, $-SP(=O)(OR^{70})(OR^{70})$, $-SP(=O)(SR^{70})$, $-P(=O)R^{78}R^{78}$, $-P(=O)(NR^{72}R^{73})(NR^{72}R^{73})$, and $-P(=O)(OR^{70})(OR^{70})$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-15 membered heterocycloalkyl optionally substituted by 1-10 $R^{79}$ or a 5-15 membered heteroaryl optionally substituted by 1-10 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-10 $R^{79}$, $C_{3-11}$cycloalkyl optionally substituted by 1-10 $R^{79}$, 3-15 membered heterocycloalkyl optionally substituted by 1-10 $R^{79}$ or a 5-15 membered heteroaryl optionally substituted by 1-10 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form $=O$.

Embodiment 46

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-10 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-10 $R^{79}$, $C_{3-10}$cycloalkyl optionally substituted by 1-10 $R^{79}$, $C_{4-11}$cycloalkylalkyl optionally substituted by 1-10 $R^{79}$, 3-10 membered heterocycloalkyl optionally substituted by 1-10 $R^{79}$, 4-11 membered heterocycloalkylalkyl optionally substituted by 1-10 $R^{79}$, 5-11 membered heteroaryl optionally substituted by 1-10 $R^{79}$, and 6-12 membered heteroarylalkyl optionally substituted by 1-10 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-10 $R^{79}$, $C_{2-6}$alkenyl optionally substituted by 1-10 $R^{79}$, $C_{2-6}$alkynyl optionally substituted by 1-9 $R^{79}$, $C_{6-11}$aryl optionally substituted by 1-10 $R^{79}$, $C_{7-16}$arylalkyl optionally substituted by 1-10 $R^{79}$, $C_{3-10}$cycloalkyl optionally substituted by 1-10 $R^{79}$, $C_{4-11}$cycloalkylalkyl optionally substituted by 1-10 $R^{79}$, 3-10 membered heterocycloalkyl optionally substituted by 1-10 $R^{79}$, 4-11 membered heterocycloalkylalkyl optionally substituted by 1-10 $R^{79}$, 5-11 membered heteroaryl optionally substituted by 1-10 $R^{79}$, 6-12 membered heteroarylalkyl optionally substituted by 1-10 $R^{79}$, halogen, $-CN$, $-C(=O)R^{70}$, $-C(=O)OR^{70}$, $-C(=O)NR^{72}R^{73}$, $-NC$, $-NO_2$, $-NR^{72}R^{73}$, $-NR^{74}NR^{72}R^{73}$, $-NR^{74}OR^{76}$, $-NR^{74}C(=O)R^{70}$, $-NR^{74}C(=O)OR^{71}$, $-NR^{74}C(=O)NR^{72}R^{73}$, $-NR^{74}S(=O)_2R^{71}$, $-NR^{74}S(=O)_2NR^{72}R^{73}$, $-OR^{70}$, $-OCN$, $-OC(=O)R^{70}$, $-OC(=O)NR^{72}R^{73}$, $-OS(=O)R^{70}$, $-OS(=)_2R^{70}$, $-OS(=)_2OR^{70}$, $-OS(=)_2NR^{72}R^{73}$, $-SCN$, $-S(=O)_nR^{70}$, $-S(=O)_2OR^{70}$, $-SO_3R^{77}$, $-S(=O)_2NR^{72}R^{73}$, and $-S(=O)NR^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-10 $R^{79}$ or a 5-11 membered heteroaryl optionally substituted by 1-10 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-10 $R^{79}$, $C_{3-10}$cycloalkyl optionally substituted by 1-10 $R^{79}$, 3-11 membered heterocycloalkyl optionally substituted by 1-10 $R^{79}$ or a 5-11 membered heteroaryl optionally substituted by 1-10 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form $=O$.

Embodiment 47

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-10 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-10 $R^{79}$, $C_{3-10}$cycloalkyl optionally substituted by 1-10 $R^{79}$, $C_{4-11}$cycloalkylalkyl optionally substituted by 1-10 $R^{79}$, 3-10 membered heterocycloalkyl optionally substituted by 1-10 $R^{79}$, 4-11 membered heterocycloalkylalkyl optionally substituted by 1-10 $R^{79}$, 5-11 membered heteroaryl optionally substituted by 1-10 $R^{79}$, and 6-12 membered heteroarylalkyl optionally substituted by 1-10 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-10 $R^{79}$, $C_{2-6}$alkenyl optionally substituted by 1-10 $R^{79}$, $C_{2-6}$alkynyl optionally substituted by 1-9 $R^{79}$, $C_{6-11}$aryl optionally substituted by 1-10 $R^{79}$, $C_{7-16}$arylalkyl optionally substituted by 1-10 $R^{79}$, $C_{3-10}$cycloalkyl optionally substituted by 1-10 $R^{79}$, $C_{4-11}$cycloalkylalkyl optionally substituted by 1-10 $R^{79}$, 3-10 membered heterocycloalkyl optionally substituted by 1-10 $R^{79}$, 4-11 membered heterocycloalkylalkyl optionally substituted by 1-10 $R^{79}$, 5-11 membered heteroaryl optionally substituted by 1-10 $R^{79}$, 6-12 membered heteroarylalkyl optionally substituted by 1-10 $R^{79}$, halogen, —CN, —C(=O)$R^{70}$, —C(=O)O$R^{70}$, —C(=O)N$R^{72}R^{73}$, —NC, —NO$_2$, —N$R^{72}R^{73}$, —N$R^{74}$O$R^{76}$, —N$R^{74}$C(=O)$R^{70}$, —N$R^{74}$C(=O)O$R^{71}$, —N$R^{74}$C(=O)N$R^{72}R^{73}$, —N$R^{74}$S(=O)$_2R^{71}$, —N$R^{74}$S(=O)$_2$N$R^{72}R^{73}$, —O$R^{70}$, —OCN, —OC(=O)$R^{70}$, —OC(=O)N$R^{72}R^{73}$, —SCN, —S(=O)$_nR^{70}$, and —S(=O)$_2$N$R^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-10 $R^{79}$ or a 5-11 membered heteroaryl optionally substituted by 1-10 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-10 $R^{79}$, $C_{3-10}$cycloalkyl optionally substituted by 1-10 $R^{79}$, 3-11 membered heterocycloalkyl optionally substituted by 1-10 $R^{79}$ or a 5-11 membered heteroaryl optionally substituted by 1-10 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form =O.

Embodiment 48

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-10 $R^{79}$, $C_{6-11}$aryl optionally substituted by 1-11 $R^{79}$, $C_{7-16}$arylalkyl optionally substituted by 1-10 $R^{79}$, $C_{3-10}$cycloalkyl optionally substituted by 1-10 $R^{79}$, 3-10 membered heterocycloalkyl optionally substituted by 1-10 $R^{79}$, and 5-11 membered heteroaryl optionally substituted by 1-10 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-10 $R^{79}$, $C_{2-6}$alkenyl optionally substituted by 1-10 $R^{79}$, $C_{2-6}$alkynyl optionally substituted by 1-9 $R^{79}$, $C_{6-11}$aryl optionally substituted by 1-10 $R^{79}$, $C_{7-16}$arylalkyl optionally substituted by 1-10 $R^{79}$, $C_{3-10}$cycloalkyl optionally substituted by 1-10 $R^{79}$, 3-10 membered heterocycloalkyl optionally substituted by 1-10 $R^{79}$, 5-11 membered heteroaryl optionally substituted by 1-10 $R^{79}$, halogen, —CN, —C(=O)$R^{70}$, —C(=O)O$R^{70}$, —C(=O)N$R^{72}R^{73}$, —NC, —NO$_2$, —N$R^{72}R^{73}$, —N$R^{74}$O$R^{76}$, —N$R^{74}$C(=O)$R^{70}$, —N$R^{74}$C(=O)O$R^{71}$, —N$R^{74}$C(=O)N$R^{72}R^{73}$, —N$R^{74}$S(=O)$_2R^{71}$, —N$R^{74}$S(=O)$_2$N$R^{72}R^{73}$, —O$R^{70}$, —OC(=O)$R^{70}$, —OC(=O)N$R^{72}R^{73}$, —S(=O)$_nR^{70}$, and —S(=O)$_2$N$R^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-10 $R^{79}$ or a 5-11 membered heteroaryl optionally substituted by 1-10 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-10 $R^{79}$, $C_{3-10}$cycloalkyl optionally substituted by 1-10 $R^{79}$, 3-11 membered heterocycloalkyl optionally substituted by 1-10 $R^{79}$ or a 5-11 membered heteroaryl optionally substituted by 1-10 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form =O.

Embodiment 49

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, $C_{6-11}$aryl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, and 5-11 membered heteroaryl optionally substituted by 1-6 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, $C_{2-6}$alkenyl optionally substituted by 1-6 $R^{79}$, $C_{2-6}$alkynyl optionally substituted by 1-6 $R^{79}$, $C_{6-11}$aryl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, 5-11 membered heteroaryl optionally substituted by 1-6 $R^{79}$, halogen, —CN, —C(=O)$R^{70}$, —C(=O)O$R^{70}$, —C(=O)N$R^{72}R^{73}$, —NC, —NO$_2$, —N$R^{72}R^{73}$, —N$R^{74}$O$R^{76}$, —N$R^{74}$C(=O)$R^{70}$, —N$R^{74}$C(=O)O$R^{71}$, —N$R^{74}$C(=O)N$R^{72}R^{73}$, —N$R^{74}$S(=O)$_2R^{71}$, —N$R^{74}$S(=O)$_2$N$R^{72}R^{73}$, —O$R^{70}$, —OC(=O)$R^{70}$, —OC(=O)N$R^{72}R^{73}$, —S(=O)$_nR^{70}$, and —S(=O)$_2$N$R^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-6 $R^{79}$ or a 5-11 membered heteroaryl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-6 $R^{79}$, $C_{3-10}$cycloalkyl optionally substituted by 1-6 $R^{79}$, 3-11 membered heterocycloalkyl optionally substituted by 1-6 $R^{79}$ or a 5-11 membered heteroaryl optionally substituted by 1-6 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form =O.

Embodiment 50

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, halogen, —CN, —C(═O)$R^{70}$, —C(═O)O$R^{70}$, —C(═O)N$R^{72}R^{73}$, —$NO_2$, —N$R^{72}R^{73}$, —N$R^{74}$C(═O)$R^{70}$, —N$R^{74}$S(═O)$_2R^{71}$, —O$R^{70}$, —OC(═O)$R^{70}$, —S(═O)$_nR^{70}$, and —S(═O)$_2$N$R^{72}R^{73}$2R; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{3-10}$cycloalkyl optionally substituted by 1-6 $R^{79}$, or a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form ═O.

Embodiment 51

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-6 $R^{79}$, halogen, —CN, —C(═O)$R^{70}$, —C(═O)O$R^{70}$, —C(═O)N$R^{72}R^{73}$, —N$R^{72}R^{73}$, —N$R^{74}$C(═O)$R^{70}$, —N$R^{74}$S(═O)$_2R^{71}$, —O$R^{70}$, —OC(═O)$R^{70}$, —S(═O)$_nR^{70}$, and —S(═O)$_2$N$R^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18c}$ and $R^i$, $R^{18c}$ and $R^3$, $R^{18c}$ and $R^5$, $R^{18c}$ and $R^{11}$, and $R^{18c}$ and $R^n$ can, together with the atoms linking them, form a 3-11 membered heterocycloalkyl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{3-10}$cycloalkyl optionally substituted by 1-6 $R^{79}$, or a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form ═O.

Embodiment 52

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-3 $R^{79}$, halogen, —CN, —C(═O)$R^{70}$, —C(═O)O$R^{70}$, —C(═O)N$R^{72}R^{73}$, —N$R^{72}R^{73}$, —N$R^{74}$C(═O)$R^{70}$, —N$R^{74}$S(═O)$_2R^{71}$, —O$R^{70}$, —OC(═O)$R^{70}$, —S(═O)$_nR^{70}$, and —S(═O)$_2$N$R^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18c}$ and $R^i$, $R^{18c}$ and $R^3$, $R^{18c}$ and $R^5$, $R^{18c}$ and $R^{11}$, and $R^{18c}$ and $R^n$ can, together with the atoms linking them, form a 3-11 membered heterocycloalkyl optionally substituted by 1-6 $R^{79}$; or any of $R^3$ and $R^4$, $R^5$ and $R^6$, $R^i$ and $R^l$, and $R^m$ and $R^n$ can together form ═O.

Embodiment 53

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^l$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-3 $R^{79}$, halogen, —CN, —C(═O)$R^{70}$, —C(═O)O$R^{70}$, —C(═O)N$R^{72}R^{73}$, —N$R^{72}R^{73}$, —N$R^{74}$C(═O)$R^{70}$, —N$R^{74}$S(═O)$_2R^{71}$, —O$R^{70}$, —OC(═O)$R^{70}$, —S(═O)$_nR^{70}$, and —S(═O)$_2$N$R^{72}R^{73}$2R; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^1$, $R^{16}$ and $R^n$, $R^j$ and $R^{11}$, and $R^{18a}$ and $R^{11}$ can, together with the atoms linking them, form a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form ═O.

Embodiment 54

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^l$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, halogen, —CN, —C(═O)$R^{70}$, —C(═O)O$R^{70}$, —C(═O)N$R^{72}R^{73}$, —N$R^{72}R^{73}$, —N$R^{74}$C(═O)$R^{70}$, —N$R^{74}$S(═O)$_2R^{71}$, —O$R^{70}$, —OC(═O)$R^{70}$, —S(═)$_nR^{70}$, and —S(═O)$_2$N$R^{72}R^{73}$2R; or any of $R^1$ and $R^2$, $R^1$ and $R^3$, $R^1$ and $R^5$, $R^1$ and $R^{11}$, $R^1$ and $R^n$, $R^4$ and $R^{11}$, $R^{16}$ and $R^5$, $R^j$ and $R^{11}$, and $R^{18a}$ and $R^{11}$ can, together with the atoms linking them, form a 3-11 membered heterocycloalkyl optionally substituted by 1-6 $R^{79}$; or $R^3$ and $R^4$ can together form ═O.

Embodiment 55

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, —CN, —C(=O)OR$^{70}$, —C(=O)NR$^{72}$R$^{73}$, —NR$^{72}$R$^{73}$, and —OR$^{70}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^{16}$ and $R^5$, $R^j$ and $R^{11}$, and $R^{18a}$ and $R^{11}$ can, together with the atoms linking them, form a 3-11 membered heterocycloalkyl optionally substituted by 1-6 $R^{79}$; or $R^3$ and $R^4$ can together form =O.

Embodiment 56

The compound of Embodiments 42 or 43, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H and $C_{1-6}$alkyl optionally substituted by 1-6 $R^{79}$; $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, and $C_{7-16}$arylalkyl optionally substituted by 1-6 $R^{79}$; $R^3$ is chosen from H, $C_{1-6}$alkyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, halogen, —CN, —C(=O)R$^{70}$, —C(=O)OR$^{70}$, —C(=O)NR$^{72}$R$^{73}$, —NC, —NO$_2$, —NR$^{72}$R$^{73}$, —NR$^{74}$OR$^{76}$, —NR$^{74}$C(=O)R$^{70}$, —NR$^{74}$C(=O)OR$^{71}$, —NR$^{74}$C(=O)NR$^{72}$R$^{73}$, —NR$^{74}$S(=O)$_2$R$^{71}$, —NR$^{74}$S(=O)$_2$NR$^{72}$R$^{73}$, —OR$^{70}$, —OC(=O)R$^{70}$, —OC(=O)NR$^{72}$R$^{73}$, —S(=O)$_n$R$^{70}$, and —S(=O)$_2$NR$^{72}$R$^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{18d}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18e}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^1$, and $R^{18d}$ and $R^n$ can, together with the atoms linking them, form a 3-11 membered heterocycloalkyl optionally substituted by 1-6 $R^{79}$ or a 5-11 membered heteroaryl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-6 $R^{79}$, $C_{3-10}$cycloalkyl optionally substituted by 1-6 $R^{79}$, 3-11 membered heterocycloalkyl optionally substituted by 1-6 $R^{79}$ or a 5-11 membered heteroaryl optionally substituted by 1-6 $R^{79}$; or $R^4$ and $R^5$ or $R^n$ and $R^5$ can together form a double bond; or any of $R^3$ and $R^4$, $R^5$ and $R^6$, $R^i$ and $R^j$, and $R^m$ and $R^n$ can together form =O.

Embodiment 57

The compound of Embodiments 42 or 43, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H and $C_{1-6}$alkyl optionally substituted by 1-6 $R^{79}$; $R^2$ is chosen from H, $C_{1-6}$alkyl optionally substituted by 1-6 $R^{79}$, and $C_{7-16}$arylalkyl optionally substituted by 1-6 $R^{79}$; $R^4$, $R^5$, $R^6$, $R^i$, $R^j$, $R^m$, $R^n$, $R^o$, and $R^p$ are independently chosen from H and $C_{1-6}$alkyl optionally substituted by 1-6 $R^{79}$; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, halogen, —CN, —C(=O)R$^{70}$, —C(=O)OR$^{70}$, —C(=O)NR$^{72}$R$^{73}$, —NO$_2$, —NR$^{72}$R$^{73}$, —NR$^{74}$C(=O)R$^{70}$, —NR$^{74}$S(=O)$_2$R$^{71}$, —OR$^{70}$, —OC(=O)R$^{70}$, —S(=O)$_n$R$^{70}$, and —S(=O)$_2$NR$^{72}$R$^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{3-10}$cycloalkyl optionally substituted by 1-6 $R^{79}$, or a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form =O.

Embodiment 58

The compound of Embodiments 42 or 43, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H and $C_{1-6}$alkyl optionally substituted by 1-6 $R^{79}$; $R^2$ is chosen from H, $C_{1-6}$alkyl optionally substituted by 1-6 $R^{79}$, and $C_{7-16}$arylalkyl optionally substituted by 1-6 $R^{79}$; $R^4$, $R^5$, $R^6$, $R^i$, $R^j$, $R^m$, $R^n$, $R^o$, and $R^p$ are independently chosen from H and $C_{1-6}$alkyl optionally substituted by 1-6 $R^{79}$; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-6 $R^{79}$, halogen, —CN, —C(=O)R$^{70}$, —C(=O)OR$^{70}$, —C(=O)NR$^{72}$R$^{73}$, —NR$^{72}$R$^{73}$, —NR$^{74}$C(=O)R$^{70}$, —NR$^{74}$S(=O)$_2$R$^{71}$, —OR$^{70}$, —OC(=O)R$^{70}$, —S(=O)$_n$R$^{70}$, and —S(=O)$_2$NR$^{72}$R$^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18c}$ and $R^i$, $R^{18c}$ and $R^3$, $R^{18c}$ and $R^5$, $R^{18c}$ and $R^{11}$, and $R^{18c}$ and $R^n$ can, together with the atoms linking them, form a 3-11 membered heterocycloalkyl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{3-10}$-cycloalkyl optionally substituted by 1-6 $R^{79}$, or a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form =O.

Embodiment 59

The compound of Embodiments 42 or 43, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H and $C_{1-6}$alkyl optionally substituted by 1-6 $R^{79}$; $R^2$ is chosen from H, $C_{1-6}$alkyl optionally substituted by 1-6 $R^{79}$, and $C_{7-16}$arylalkyl optionally substituted by 1-6 $R^{79}$; $R^4$, $R^5$, $R^6$, $R^i$, $R^j$, $R^m$, $R^n$, $R^o$, and $R^p$ are independently chosen from H and $C_{1-6}$alkyl optionally substituted by 1-6 $R^{79}$; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-3 $R^{79}$, halogen, —CN, —C(═O)$R^{70}$, —C(═O)O$R^{70}$, —C(═O)N$R^{72}R^{73}$, —N$R^{72}R^{73}$, —N$R^{74}$C(═O)$R^{70}$, —N$R^{74}$S(═O)$_2R^{71}$, —O$R^{70}$, —OC(═O)$R^{70}$, —S(═O)$_nR^{70}$, and —S(═O)$_2$N$R^{72}R^{73}$; or any of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18c}$ and $R^3$, $R^{18c}$ and $R^5$, $R^{18c}$ and $R^{11}$, and $R^{18c}$ and $R''$ can, together with the atoms linking them, form a 3-11 membered heterocycloalkyl optionally substituted by 1-6 $R^{79}$; or any of $R^3$ and $R^4$, $R^5$ and $R^6$, $R^i$ and $R^j$, and $R'''$ and $R''$ can together form ═O.

Embodiment 60

The compound of any of Embodiments 42-59, wherein 0-3 of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl or an optionally substituted heteroaryl.

Embodiment 61

The compound of any of Embodiments 42-59, wherein 0-2 of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl or an optionally substituted heteroaryl.

Embodiment 62

The compound of any of Embodiments 42-59, wherein 1-2 of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl or an optionally substituted heteroaryl.

Embodiment 63

The compound of any of Embodiments 42-59, wherein none of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^i$, $R^{18d}$ and $R^3$, $R^{18d}$ and R, $R^{18d}$ and $R^{11}$, and $R^{18d}$ and $R''$, together with the atoms linking them, form an optionally substituted heterocycloalkyl or an optionally substituted heteroaryl.

Embodiment 64

The compound of any of Embodiments 42-59, wherein one of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl or an optionally substituted heteroaryl.

Embodiment 65

The compound of any of Embodiments 42-59, wherein two of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl or an optionally substituted heteroaryl.

Embodiment 66

The compound of any of Embodiments 42-59, wherein 0-3 of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl.

Embodiment 67

The compound of any of Embodiments 42-59, wherein 0-2 of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl.

Embodiment 68

The compound of any of Embodiments 42-59, wherein 1-2 of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ $R''$, together with the atoms linking them, form an optionally substituted heterocycloalkyl.

Embodiment 69

The compound of any of Embodiments 42-59, wherein none of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl.

Embodiment 70

The compound of any of Embodiments 42-59, wherein one of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18a}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18}$, $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl.

Embodiment 71

The compound of Embodiment 70, wherein said optionally substituted heterocarbocyclyl is a 3-7 membered heterocarbocycl optionally substituted with 1-4 $R^{79}$.

Embodiment 72

The compound of Embodiment 70, wherein said optionally substituted heterocarbocyclyl is a 5-6 membered heterocarbocycl optionally substituted with 1-4 $R^{79}$.

Embodiment 73

The compound of any of Embodiments 42-59, wherein two of $R^1$ and $R^2$, $R^1$ and $R^3$, $R^1$ and $R^5$, $R^1$ and $R^{11}$, $R^1$ and $R''$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R''$, $R^j$ and $R^{11}$, $R^{18a}$ and $R^3$, $R^{18a}$ and $R^5$, $R^{18}$ and $R^{11}$, $R^{18a}$ and $R''$, $R^{18b}$ and $R^3$, $R^{18b}$ and $R^5$, $R^{18b}$ and $R^{11}$, $R^{18b}$ and $R''$, $R^{18c}$ and $R^i$, $R^{18c}$ and $R^3$, $R^{18c}$ and $R^5$, $R^{18c}$ and $R^{11}$, $R^{18c}$ and $R''$, $R^{18d}$ and $R^i$, $R^{18d}$ and $R^3$, $R^{18d}$ and $R^5$, $R^{18d}$ and $R^{11}$, and $R^{18d}$ and $R''$, together with the atoms linking them, form an optionally substituted heterocycloalkyl.

Embodiment 74

The compound of any of Embodiments 42-73, wherein 0-2 of $R^3$ and $R^4$, $R^3$ and $R^6$, $R^5$ and $R^6$, $R^i$ and $R^j$, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited aryl, optionally substituted cycloalkyl, optionally substituted heterocycloalkyl, or optionally substituted heteroaryl.

Embodiment 75

The compound of any of Embodiments 42-73, wherein 0-1 of $R^3$ and $R^4$, $R^3$ and $R^6$, $R^5$ and $R^6$, $R^i$ and R, $R^i$ and $R^4$, $R^i$ and $R^5$, $R^1$ and $R''$, $R'''$ and $R''$, $R^4$ and $R'''$, and $R^6$ and $R'''$, together with the atoms linking them, form an optionally substitutited aryl, optionally substituted cycloalkyl, optionally substituted heterocycloalkyl, or optionally substituted heteroaryl.

Embodiment 76

The compound of any of Embodiments 42-73, wherein none of $R^3$ and $R^4$, $R^3$ and $R^6$, $R^5$ and $R^6$, $R^1$ and R, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited aryl, optionally substituted cycloalkyl, optionally substituted heterocycloalkyl, or optionally substituted heteroaryl.

Embodiment 77

The compound of any of Embodiments 42-73, wherein one of $R^3$ and $R^4$, $R^3$ and $R^6$, $R^5$ and $R^6$, $R^i$ and $R^j$, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited aryl, optionally substituted cycloalkyl, optionally substituted heterocycloalkyl, or optionally substituted heteroaryl.

Embodiment 78

The compound of any of Embodiments 42-73, wherein 0-2 of $R^3$ and $R^4$, $R^3$ and $R^6$, $R^5$ and $R^6$, $R^i$ and $R^j$, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited cycloalkyl or optionally substituted heterocycloalkyl.

Embodiment 79

The compound of any of Embodiments 42-73, wherein 0-1 of $R^3$ and $R^4$, $R^3$ and $R^6$, $R^5$ and $R^6$, $R^i$ and $R^j$, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited cycloalkyl or optionally substituted heterocycloalkyl.

Embodiment 80

The compound of any of Embodiments 42-73, wherein none of $R^3$ and $R^4$, $R^3$ and $R^6$, $R^5$ and $R^6$, $R^i$ and $R^j$, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited cycloalkyl or optionally substituted heterocycloalkyl.

Embodiment 81

The compound of any of Embodiments 42-73, wherein one of $R^3$ and $R^4$, $R^3$ and $R^6$, $R^5$ and $R^6$, $R^i$ and $R^j$, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited cycloalkyl or optionally substituted heterocycloalkyl.

Embodiment 82

The compound of any of Embodiments 42-73, wherein 0-2 of $R^3$ and $R^4$, $R^3$ and $R^6$, $R^5$ and $R^6$, $R^1$ and R, $R^i$ and $R^4$, $R^i$ and $R^5$, $R^i$ and $R''$, $R'''$ and $R''$, $R^4$ and $R'''$, and $R^6$ and $R'''$, together with the atoms linking them, form an optionally substitutited heterocycloalkyl.

Embodiment 83

The compound of any of Embodiments 42-73, wherein 0-1 of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$, together with the atoms linking them, form an optionally substitutited heterocycloalkyl.

Embodiment 84

The compound of any of Embodiments 42-73, wherein none of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$, together with the atoms linking them, form an optionally substitutited heterocycloalkyl.

Embodiment 85

The compound of any of Embodiments 42-73, wherein one of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$, together with the atoms linking them, form an optionally substitutited heterocycloalkyl.

Embodiment 86

The compound of Embodiment 85, wherein said optionally substituted heterocarbocyclyl is a 3-7 membered heterocarbocycl optionally substituted with 1-4 $R^{79}$.

Embodiment 87

The compound of Embodiment 85, wherein said optionally substituted heterocarbocyclyl is a 5-6 membered heterocarbocycl optionally substituted with 1-4 $R^{79}$.

Embodiment 88

The compound of any of Embodiments 42-87, wherein neither $R^4$ and $R^5$ nor $R^n$ and $R^5$ together form a double bond.

Embodiment 89

The compound of any of Embodiments 42-88, wherein none of $R^3$ and $R^4$, $R^5$ and $R^6$, $R^i$ and $R^j$, or $R^m$ and $R^n$ together form =O, =$NR^{70}$, =$NOR^{70}$, or =S.

Embodiment 90

The compound of Embodiments 42 or 43, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; $R^2$ is chosen from H and $C_{1-6}$alkyl optionally substituted by 1-6 $R^{79}$; $R^4$, $R^5$, $R^6$, $R^i$, $R^j$, $R^m$, $R^n$, $R^o$, and $R^p$ are H; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-3 $R^{79}$, halogen, —CN, —C(=O)$R^{70}$, —C(=O)$OR^{70}$, —C(=O)$NR^{72}R^{73}$, —$NR^{72}R^{73}$, —$NR^{74}$C(=O)$R^{70}$, —$NR^{74}S(=O)_2R^{71}$, —$OR^{70}$, —OC(=O)$R^{70}$, —S(=)$_nR^{70}$, and —$S(=O)_2NR^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, and $R^{18a}$ and $R^{11}$ can, together with the atoms linking them, form a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form =O.

Embodiment 91

The compound of Embodiments 42 or 43, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; $R^2$ is chosen from H and $C_{1-6}$alkyl optionally substituted by 1-6 $R^{79}$; $R^4$, $R^5$, $R^6$, $R^i$, $R^j$, $R^m$, $R^n$, $R^o$, and $R^p$ are H; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, halogen, —CN, —C(=O)$R^{70}$, —C(=O)$OR^{70}$, —C(=O)$NR^{72}R^{73}$, —$NR^{72}R^{73}$, —$NR^{74}$C(=O)$R^{70}$, —$NR^{74}S(=O)_2R^{71}$, —$OR^{70}$, —OC(=O)$R^{70}$, —S(=O)$_nR^{70}$, and —$S(=O)_2NR^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^1$, $R^{16}$ and $R^5$, $R^j$ and $R^1$, and $R^{18a}$ and $R^{11}$ can, together with the atoms linking them, form a 3-11 membered heterocycloalkyl optionally substituted by 1-6 $R^{79}$; or $R^3$ and $R^4$ can together form =O.

Embodiment 92

The compound of Embodiments 42 or 43, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; $R^2$ is chosen from H and $C_{1-6}$alkyl optionally substituted by 1-6 $R^{79}$; $R^4$, $R^5$, $R^6$, $R^i$, $R^j$, $R^m$, $R^n$, $R^o$, and $R^p$ are H; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, —CN, —C(=O)$OR^{70}$, —C(=O)$NR^{72}R^{73}$, —$NR^{72}R^{73}$, and —$OR^{70}$; or any of $R^1$ and $R^2$, $R^1$ and $R^3$, $R^1$ and $R^5$, $R^1$ and $R^{11}$, $R^1$ and $R^n$, $R^4$ and $R^1$, $R^{16}$ and $R^5$, $R^j$ and $R^{11}$, and $R^{18a}$ and $R^{11}$ can, together with the atoms linking them, form a 3-11 membered heterocycloalkyl optionally substituted by 1-6 $R^{79}$; or $R^3$ and $R^4$ can together form =O.

Embodiment 93

The compound of any of Embodiments 42-89, wherein at least five of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least four of $R^3$, $R^4$, $R^5$, $R^6$, $R^i$, $R^j$, $R^m$, $R^n$, $R^o$, and $R^p$ are H.

Embodiment 94

The compound of any of Embodiments 42-89, wherein at least five of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least five of $R^3$, $R^4$, $R^5$, $R^6$, $R^i$, $R^j$, $R^m$, $R^n$, $R^o$, and $R^p$ are H.

Embodiment 95

The compound of any of Embodiments 42-89, wherein at least six of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least five of $R^3$, $R^4$, $R^5$, $R^6$, $R^i$, $R^j$, $R^m$, $R^n$, $R^o$, and $R^p$ are H.

Embodiment 96

The compound of any of Embodiments 42-89, wherein at least six of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least six of $R^3$, $R^4$, $R^5$, $R^6$, $R^i$, $R^j$, $R^m$, $R^n$, $R^o$, and $R^p$ are H.

Embodiment 97

The compound of any of Embodiments 42-89, wherein at least seven of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least six of $R^3$, $R^4$, $R^5$, $R^6$, $R^i$, $R^j$, $R^m$, $R^n$, $R^o$, and $R^p$ are H.

Embodiment 98

The compound of any of Embodiments 42-89, wherein at least seven of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least seven of $R^3$, $R^4$, $R^5$, $R^6$, $R^i$, $R^j$, $R^m$, $R^n$, $R^o$, and $R^p$ are H.

Embodiment 99

The compound of any of Embodiments 42-89, wherein at least eight of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least seven of $R^3$, $R^4$, $R^5$, $R^6$, $R^i$, $R^j$, $R^m$, $R^n$, $R^o$, and $R^p$ are H.

Embodiment 100

The compound of any of Embodiments 42-89, wherein at least eight of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least eight of $R^3$, $R^4$, $R^5$, $R^6$, $R^i$, $R^j$, $R^m$, $R^n$, $R^o$, and $R^p$ are H.

Embodiment 101

The compound of any of Embodiments 42-89, wherein at least nine of R, $R^2$, $R^{11}$, $R^{16}$, $R^{17}$, $R^{16a}$, $R^{17a}$, $R^{18a}$, $R^{18b}$, $R^{18}$, $R^{18d}$, and $R^{18e}$ are H; and at least eight of $R^3$, $R^4$, $R^5$, $R^6$, $R^i$, $R^j$, $R^m$, $R^n$, $R^o$, and $R^p$ are H.

Embodiment 102

The compound of any of Embodiments 42-89, wherein at least nine of R, $R^2$, $R^{11}$, $R^{16}$, $R^{17}$, $R^{16a}$, $R^{17a}$, $R^{18a}$, $R^{18b}$, $R^{18}$, $R^{18d}$, and $R^{18e}$ are H; and at least nine of $R^3$, $R^4$, $R^5$, $R^6$, $R^i$, $R^j$, $R^m$, $R^n$, $R^o$, and $R^p$ are H.

Embodiment 103

The compound of any of Embodiments 42-89, wherein at least ten of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^e$ are H; and at least nine of $R^3$, $R^4$, $R^5$, $R^6$, $R^i$, $R^j$, $R^m$, $R^n$, $R^o$, and $R^p$ are H.

Embodiment 104

The compound of any of Embodiments 42-89, wherein at least eleven of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least nine of $R^3$, $R^4$, $R^5$, $R^6$, $R^i$, $R^j$, $R^m$, $R^n$, $R^o$, and $R^p$ are H.

Embodiment 105

The compound of any of Embodiments 42-89, wherein $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and at least nine of $R^3$, $R^4$, $R^5$, $R^6$, $R^i$ $R^j$, $R^m$, $R^n$, $R^o$, and $R^p$ are H.

Embodiment 106

The compound of any of Embodiments 42-89, wherein at least eleven of $R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; and $R^3$, $R^4$, $R^5$, $R^6$, $R^i$, $R^j$, $R^m$, $R^n$, $R^o$, and $R^p$ are H.

Embodiment 107

The compound of any of Embodiments 42-106, wherein $R^q$ is H, —$NR^{16a}R^{7a}$ or —$OR^{18e}$.

Embodiment 108

The compound of any of Embodiments 42-106, wherein $R^q$ is —$NR^{16a}R^{7a}$ or —$OR^{18e}$.

Embodiment 109

The compound of any of Embodiments 42-108, wherein $R^k$ is H, halogen, —CN, —$NR^{16}R^{17}$, —$OR^{18}$, —$SR^{18d}$, or —$CR^oR^pR^q$.

Embodiment 110

The compound of any of Embodiments 42-108, wherein $R^k$ is H, —CN, —$NR^{16}R^{17}$, —$OR^{18c}$, —$SR^{18d}$, or —$CR^oR^pR^q$.

Embodiment 111

The compound of any of Embodiments 42-108, wherein $R^k$ is H, —CN, —$NR^{16}R^{17}$, —$OR^{18c}$, or —$CR^oR^pR^q$.

Embodiment 112

The compound of any of Embodiments 42-108, wherein $R^k$ is H, —$NR^{16}R^{17}$, —$OR^{18c}$, or —$CR^oR^pR^q$.

Embodiment 113

The compound of any of Embodiments 42-108, wherein $R^k$ is —$NR^{16}R^{17}$, —$OR^{18c}$, or —$CR^oR^pR^q$.

Embodiment 114

The compound of any of Embodiments 42-106, wherein $R^k$ is H.

Embodiment 115

The compound of any of Embodiments 42-106, wherein $R^k$ is —$NR^{16}R^{17}$.

Embodiment 116

The compound of any of Embodiments 42-106, wherein $R^k$ is —$OR^{18c}$.

Embodiment 117

The compound of any of Embodiments 42-108, wherein $R^k$ is —$CR^oR^pR^q$.

Embodiment 118

The compound of any of Embodiments 42-117, wherein A is —$NR^1R^2$, —$CR^iR^jR^k$, or —$OR^{18a}$.

Embodiment 119

The compound of any of Embodiments 42-106, wherein A is —$NR^1R^2$ or —$OR^{18a}$.

Embodiment 120

The compound of any of Embodiments 42-117, wherein A is —$CR^iR^jR^k$.

Embodiment 121

The compound of any of Embodiments 42-106, wherein A is —$NR^1R^2$.

Embodiment 122

The compound of any of Embodiments 42-106, wherein A is —$OR^{18a}$.

Embodiment 123

The compound of any of Embodiments 42-122, wherein Q is —$NR^{11}$—, —$CR^mR^n$—, or —O—.

Embodiment 124

The compound of any of Embodiments 42-122, wherein Q is —$NR^{11}$—.

Embodiment 125

The compound of any of Embodiments 42-122, wherein Q is —$CR^mR^n$—.

Embodiment 126

The compound of any of Embodiments 42-122, wherein Q is —O—.

Embodiment 127

The compound of any of Embodiments 42-106, wherein A is —$NR^1R^2$, —$CR^iR^jR^k$, or —$OR^{18a}$; Q is —$NR^{11}$—, —$CR^mR^n$—, or —O—; and $R^k$ is —$NR^{16}R^{17}$, or —$OR^{18c}$.

Embodiment 128

The compound of any of Embodiments 42-106, wherein A is —$NR^1R^2$, —$CR^iR^jR^k$, or —$OR^{18a}$; Q is —$NR^{11}$—; and $R^k$ is —$NR^{16}R^{17}$, or —$OR^{18c}$.

Embodiment 129

The compound of any of Embodiments 42-106, wherein A is —$NR^1R^2$, —$CR^iR^jR^k$, or —$OR^{18a}$; Q is —$NR^{11}$—; and $R^k$ is —$OR^{18c}$.

Embodiment 130

The compound of any of Embodiments 42-106, wherein A is —$NR^1R^2$ or —$OR^{18a}$; and Q is —$NR^{11}$—.

Embodiment 131

The compound of any of Embodiments 42-106, wherein A is —$NR^1R^2$; and Q is —$NR^{11}$—.

Embodiment 132

The compound of any of Embodiments 1-3, wherein X is chosen from —$NHR^{28}$ and 3-10 membered heterocycloalkyl consisting of carbon atoms and 1 or 2 nitrogen atoms in which the heterocycloalkyl is optionally substituted by 1-6 $R^{19}$.

Embodiment 133

The compound of any of Embodiments 1-3, wherein X is chosen from —$NHR^{28}$ and 5-10 membered heterocycloalkyl consisting of carbon atoms and 1 or 2 nitrogen atoms in which the heterocycloalkyl is optionally substituted by 1-6 $R^{19}$.

Embodiment 134

The compound of any of Embodiments 1-3, wherein X is chosen from —$NHR^{28}$ and 5-9 membered heterocycloalkyl consisting of carbon atoms and 1 or 2 nitrogen atoms in which the heterocycloalkyl is optionally substituted by 1-6 $R^{19}$.

Embodiment 135

The compound of any of Embodiments 1-3, wherein X is chosen from —$NHR^{28}$ and 5-6 membered heterocycloalkyl consisting of carbon atoms and 1 or 2 nitrogen atoms in which the heterocycloalkyl is optionally substituted by 1-6 $R^{19}$.

Embodiment 136

The compound of any of Embodiments 1-3, wherein X is chosen from —$NHR^{28}$ and 5-10 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl optionally substituted by 1-3 $R^{39}$, $C_{6-11}$aryl optionally substituted by 1-3 $R^{39}$, $C_{7-16}$arylalkyl optionally substituted by 1-3 $R^{39}$, $C_{3-11}$cycloalkyl optionally substituted by 1-3 $R^{39}$, 3-15 membered heterocycloalkyl optionally substituted by 1-3 $R^{39}$, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 137

The compound of any of Embodiments 1-3, wherein X is chosen from —$NHR^{28}$ and 5-10 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 138

The compound of any of Embodiments 1-3, wherein X is chosen from —$NHR^{28}$ and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═)$OR^{30}$, —C(═O)$NR^{32}R^{33}$, —$NR^{32}R^{33}$, —$NR^{34}$C(═O)$R^{30}$, and —$OR^{30}$.

Embodiment 139

The compound of any of Embodiments 1-3, wherein X is chosen from —$NHR^{28}$ and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 140

The compound of any of Embodiments 1-3, wherein X is chosen from —$NHR^{28}$ and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, and —OH.

Embodiment 141

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-6 $R^{49}$), —NH(3-10 membered heterocycloalkyl optionally substituted by 1-6 $R^{49}$), —NH(4-11 membered heterocycloalkylalkyl optionally substituted by 1-6 $R^{49}$), and 3-10 membered heterocycloalkyl consisting of carbon atoms and 1 or 2 nitrogen atoms in which the heterocycloalkyl is optionally substituted by 1-6 $R^{19}$.

Embodiment 142

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-6 $R^{49}$), —NH(3-10 membered heterocycloalkyl), —NH(4-11 membered heterocycloalkylalkyl), and 3-10 membered heterocycloalkyl consisting of carbon atoms and 1 or 2 nitrogen atoms in which the heterocycloalkyl is optionally substituted by 1-6 $R^{19}$.

Embodiment 143

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-10 membered heterocycloalkyl consisting of carbon atoms and 1 or 2 nitrogen atoms in which the heterocycloalkyl is optionally substituted by 1-6 $R^{19}$.

Embodiment 144

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-9 membered heterocycloalkyl consisting of carbon atoms and 1 or 2 nitrogen atoms in which the heterocycloalkyl is optionally substituted by 1-6 $R^{19}$.

Embodiment 145

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1-6 $R^{19}$.

Embodiment 146

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-10 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl optionally substituted by 1-3 $R^{39}$, $C_{6-11}$aryl optionally substituted by 1-3 $R^{39}$, $C_{7-16}$arylalkyl optionally substituted by 1-3 $R^{39}$, $C_{3-11}$cycloalkyl optionally substituted by 1-3 $R^{39}$, 3-15 membered heterocycloalkyl optionally substituted by 1-3 $R^{39}$, halogen, —CN, —C(═O)$OR^{3}$, —C(═O)$NR^{32}R^{33}$, —$NR^{32}R^{33}$, —$NR^{34}$C(═O)$R^{30}$, and —$OR^{30}$.

Embodiment 147

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-10 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═O)$OR^{30}$, —C(═O)$NR^{32}R^{33}$, —$NR^{32}R^{33}$, —$NR^{34}$C(═O)$OR^{30}$, and —$OR^{30}$.

Embodiment 148

The compound of any of Embodiments 1-3, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 149

The compound of any of Embodiments 1-3, wherein X is chosen from —NH($C_{1-6}$alkyl optionally substituted by 1-6

$R^{49}$), —NH($C_{7-11}$arylalkyl), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 150

The compound of any of Embodiments 1-3, wherein X is chosen from —NH($C_{1-6}$alkyl optionally substituted by 1-6 $R^{49}$), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 151

The compound of any of Embodiments 1-3, wherein X is chosen from —NH($C_{1-6}$alkyl optionally substituted by 1-6 $R^{49}$), —NH(5-6 membered heterocycloalkyl), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, and —OH.

Embodiment 152

The compound of any of Embodiments 1-3, wherein X is chosen from —NH($C_{1-6}$alkyl optionally substituted by 1-6 $R^{49}$), —NH($C_{7-11}$arylalkyl), —NH(5-6 membered heterocycloalkyl consisting of carbon atoms and 1 or 2 nitrogen atoms), —NH(6-10 membered heterocycloalkylalkyl consisting of carbon atoms and 1 or 2 nitrogen atoms), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═O)$OR^{30}$, —C(═O)$NR^{32}R^{33}$, —$NR^{32}R^{33}$, —$NR^{34}$C(═O)$R^{3}$, and —$OR^{30}$.

Embodiment 153

The compound of any of Embodiments 1-3, wherein X is chosen from —NH($C_{1-6}$alkyl optionally substituted by 1-6 $R^{49}$), —NH(benzyl), —NH(5-6 membered heterocycloalkyl consisting of carbon atoms and 1 or 2 nitrogen atoms), —NH(6-10 membered heterocycloalkylalkyl consisting of carbon atoms and 1 or 2 nitrogen atoms), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 154

The compound of any of Embodiments 1-3, wherein X is chosen from —NH($C_{1-6}$alkyl optionally substituted by 1-6 $R^{49}$), —NH(5-6 membered heterocycloalkyl consisting of carbon atoms and 1 or 2 nitrogen atoms), —NH(6-10 membered heterocycloalkylalkyl consisting of carbon atoms and 1 or 2 nitrogen atoms), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

Embodiment 155

The compound of any of Embodiments 1-3, wherein X is chosen from —NH($C_{1-6}$alkyl optionally substituted by 1-6 $R^{49}$), —NH(5-6 membered heterocycloalkyl consisting of carbon atoms and 1 or 2 nitrogen atoms), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, and —OH.

Embodiment 156

The compound of any of Embodiments 1-3, wherein X is chosen from —NH($C_{1-6}$alkyl optionally substituted by 1-6 $R^{49}$) and —NH(5-6 membered heterocycloalkyl consisting of carbon atoms and 1 or 2 nitrogen atoms).

Embodiment 200

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{20}$, —C(═O)$OR^{20}$, —C(═O)$NR^{22}R^{23}$, —C(═O)C(═O)$R^{20}$, —C(═$NR^{25}$)$R^{20}$, —C(═$NR^{25}$)$NR^{22}R^{23}$, —C(═NOH)$NR^{22}R^{23}$, —C(═$NOR^{26}$)$R^{20}$, —C(═$NNR^{22}R^{23}$)$R^{20}$, —C(═$NNR^{24}$C(═O)$R^{21}$)$R^{20}$, —C(═$NNR^{24}$C(═O)$OR^{21}$)$R^{20}$, —C(═S)$NR^{22}R^{23}$, —NC, —$NO_2$, —$NR^{22}R^{23}$, —$NR^{24}NR^{22}R^{23}$, —N═$NR^{24}$, —$NR^{24}OR^{26}$, —$NR^{24}$C(═O)$R^{20}$, —$NR^{24}$C(═O)C(═O)$R^{20}$, —$NR^{24}$C(═O)$OR^{21}$, —$NR^{24}$C(═O)C(═O)$OR^{21}$, —$NR^{24}$C(═O)$NR^{22}R^{23}$, —$NR^{24}$C(═O)$NR^{24}$C(═O)$R^{20}$, —$NR^{24}$C(═O)$NR^{24}$C(═O)$OR^{20}$, —$NR^{24}$C(═$NR^{25}$)$NR^{22}R^{23}$, —$NR^{24}$C(═O)C(═O)$NR^{22}R^{23}$, —$NR^{24}$C(═S)$R^{20}$, —$NR^{24}$C(═S)$OR^{20}$, —$NR^{24}$C(═S)$NR^{22}R^{23}$, —$NR^{24}$S(═O)$_2R^{21}$, —$NR^{24}$S(═O)$_2NR^{22}R^{23}$, —$NR^4$P(═O)$R^{78}R^{78}$, —$NR^{24}$P(═O)($NR^{22}R^{23}$)($N^{22}R^{23}$), —$NR^{24}$P(═O)($OR^{20}$)($OR^{20}$), —$NR^{24}$P(═O)($SR^{20}$)($SR^{20}$), —$OR^{20}$, —OCN, —OC(═O)$R^{20}$, —OC(═O)$NR^{22}R^{23}$, —OC(═O)$OR^{20}$, —OC(═$NR^{25}$)$NR^{22}R^{23}$, —OS(═O)$R^{20}$, —OS(═O)$_2R^{20}$, —OS(═O)$_2OR^{20}$, —OS(═O)$_2NR^{22}R^{23}$, —OP(═O)$R^{78}R^{78}$, —OP(═O)($NR^{22}R^{23}$)($NR^{22}R^{23}$), —OP(═O)($OR^{20}$)($OR^{20}$), —OP(═O)($SR^{20}$)($SR^{20}$), —Si($R^{24}$)$_3$, —SCN, —S(═O)$_nR^{20}$, —S(═O)$_2OR^{20}$, —$SO_3R^{27}$, —S(═O)$_2NR^{22}R^{23}$, —S(═O)$NR^{22}R^{23}$, —SP(═O)$R^{78}R^{78}$, —SP (=O)($NR^{22}R^{23}$)($NR^{22}$)($NR^{23}$), —SP(=O)($OR^{20}$)($OR^{20}$), —SP(=O)($SR^{20}$)($SR^{20}$), —P(=O)$R^{78}R^{78}$, —P(=O)($NR^{22}R^{23}$)($NR^{22}R^{23}$), —P(=O)($OR^{20}$)($OR^{20}$), and —P(=O)($SR^{20}$)($SR^{20}$); or R and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 201

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=)$OR^{21}$, —$NR^{24}$C(=O)$NR^{22}R^{23}$, —$NR^{24}$S(=$O)_2R^{21}$, —$NR^{24}$S(=$O)_2NR^{22}R^{23}$, —$OR^{20}$, —OCN, —OC(=O)$R^{20}$, —OC(=O)$NR^{22}R^{23}$, —OC(=O)$OR^{20}$, —OS(=$O)_2R^{20}$, —OS(=O)$^{20}R^{20}$, —OS(=$O)_2NR^{22}R^{23}$, —S(=$O)_nR^{20}$, and —S(=$O)_2NR^{22}R^{23}$; or $R^7$ and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 202

The compound of any of Embodiments 1-156, wherein $R^7$, $R^8$, and $R^9$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=O)$OR^{21}$, —$NR^{24}$C(=O)$NR^{22}R^{23}$, —$NR^{24}$S(=$O)_2R^{21}$, —$NR^{24}$S(=$O)_2NR^{22}R^{23}$, —$OR^{20}$, —OCN, —OC(=O)$R^{20}$, —OC(=O)$NR^{22}R^{23}$, —OC(=O)$OR^{20}$, —OS(=$)_2R^{20}$, —OS(=$O)_2OR^{20}$, —OS(=$O)_2NR^{22}R^{23}$, —S(=$O)_nR^{20}$, and —S(=$O)_2NR^{22}R^{23}$; or $R^7$ and $R^8$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 203

The compound of any of Embodiments 1-156, wherein $R^7$, $R^8$, and $R^9$ are independently chosen from H, $C_{1-6}$alkyl optionally substituted by 1-4 $R^{19}$, $C_{2-6}$alkenyl optionally substituted by 1-4 $R^{19}$, $C_{2-6}$alkynyl optionally substituted by 1-4 $R^{19}$, $C_{6-10}$aryl optionally substituted by 1-4 $R^{19}$, $C_{7-11}$arylalkyl optionally substituted by 1-4 $R^{19}$, $C_{3-7}$cycloalkyl optionally substituted by 1-4 $R^{19}$, $C_{4-8}$cycloalkylalkyl optionally substituted by 1-4 $R^{19}$, 3-7 membered heterocycloalkyl optionally substituted by 1-4 $R^{19}$, 4-8 membered heterocycloalkylalkyl optionally substituted by 1-4 $R^{19}$, 5-6 membered heteroaryl optionally substituted by 1-4 $R^{19}$, 6-21 membered heteroarylalkyl optionally substituted by 1-4 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=)$OR^{21}$, —$NR^{24}$C(=O)$NR^{22}R^{23}$, —$NR^{24}$S(=$O)_2R^{21}$, —$NR^{24}$S(=$O)_2NR^{22}R^{23}$, —$OR^{20}$, —OCN, —OC(=O)$R^{20}$, —OC(=O)$NR^{22}R^{23}$, —OC(=)$OR^{20}$, —OS(=$O)_2R^{20}$, —OS(=$O)_2OR^{20}$, —OS(=$O)_2NR^{22}R^{23}$, —S(=$O)_nR^{20}$, and —S(=$O)_2NR^{22}R^{23}$; or $R^7$ and $R^8$ can, together with the atoms linking them, form a $C_{6-10}$aryl optionally substituted by 1-4 $R^{19}$, $C_{3-7}$cycloalkyl optionally substituted by 1-4 $R^{19}$, 3-7 membered heterocycloalkyl optionally substituted by 1-4 $R^{19}$ or a 5-6 membered heteroaryl optionally substituted by 1-4 $R^{19}$.

Embodiment 204

The compound of any of Embodiments 1-156, wherein $R^7$, $R^8$, and $R^9$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-7}$cycloalkyl optionally substituted by 1-3 $R^{19}$, $C_{4-8}$cycloalkylalkyl optionally substituted by 1-3 $R^{19}$, 3-7 membered heterocycloalkyl optionally substituted by 1-3 $R^{19}$, 4-8 membered heterocycloalkylalkyl optionally substituted by 1-3 $R^{19}$, 5-6 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}OR^{26}$, —$NR^{24}$C(=O)$R^{20}$, —$NR^{24}$C(=O)$OR^{21}$, —$NR^{24}$C(=O)$NR^{22}R^{23}$, —$NR^{24}$S(=$O)_2R^{21}$, —$NR^{24}$S(=$O)_2NR^{22}R^{23}$, —$OR^{20}$, —OCN, —OC(=O)$R^{20}$, —OC(=O)$NR^{22}R^{23}$, —OC(=O)$OR^{20}$, —OS(=$O)_2R^{20}$, —OS(=$O)_2OR^{20}$, —OS(=$O)_2NR^{22}R^{23}$, —S(=$)_nR^{20}$ and —S(=$O)_2NR^{22}R^{23}$; or $R^7$ and $R^8$ can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 205

The compound of any of Embodiments 1-156, wherein $R^7$, $R^8$, and $R^9$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-7}$cycloalkyl optionally substituted by 1-3 $R^{19}$, $C_{4-8}$cycloalkylalkyl optionally substituted by 1-3 $R^{19}$, 3-7 membered heterocycloalkyl optionally substituted by 1-3 $R^{19}$, 4-8 membered heterocycloalkylalkyl optionally substituted by 1-3 $R^{19}$, 5-6 membered heteroaryl optionally substituted by 1-3 $R^{19}$, 6-21 membered heteroarylalkyl optionally substituted by 1-3 $R^{19}$, halogen, —CN, —C(=O)$R^{20}$, —C(=O)

$OR^{20}$, —C(═O)$NR^{22}R^{23}$, —$NO_2$, —$NR^{22}R^{23}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —OC(═O)$NR^{22}R^{23}$, —OS(═O)$_2R^{20}$, —OS(═O)$_2NR^{22}R^{23}$, —S(═O)$_nR^{20}$, and —S(═O)$_2$ $NR^{22}R^{23}$; or $R^7$ and $R^8$ can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 206

The compound of any of Embodiments 1-156, wherein $R^7$, $R^8$, and $R^9$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-7}$cycloalkyl optionally substituted by 1-3 $R^{19}$, $C_{4-8}$cycloalkylalkyl optionally substituted by 1-3 $R^{19}$, 3-7 membered heterocycloalkyl optionally substituted by 1-3 $R^{19}$, 4-8 membered heterocycloalkylalkyl optionally substituted by 1-3 $R^{19}$, 5-6 membered heteroaryl optionally substituted by 1-3 $R^{19}$, 6-21 membered heteroarylalkyl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}$C(═O)$R^{20}$, —$NR^{24}$S(═O)$_2R^{21}$, —$OR^{20}$, —S(═O)$_nR^{20}$, and —S(═O)$_2NR^{22}R^{23}$; or $R^7$ and $R^8$ can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 207

The compound of any of Embodiments 1-156, wherein $R^7$, $R^8$, and $R^9$ are independently chosen from H, $C_{1-6}$alkyl, $C_{2-6}$alkenyl, $C_{2-6}$alkynyl, $C_{6-10}$aryl, $C_{7-11}$arylalkyl, $C_{3-7}$cycloalkyl, $C_{4-8}$cycloalkylalkyl, 3-7 membered heterocycloalkyl, 4-8 membered heterocycloalkylalkyl, 5-6 membered heteroaryl, 6-21 membered heteroarylalkyl, halogen, —CN, —C(═O)$R^{20}$, —C(═)$OR^{20}$, —C(═O)$NR^{22}R^{23}$, —$NO_2$, —$NR^{22}R^{23}$, —$NR^{24}$C(═O)$R^{20}$, —$NR^{24}$S(═O)$_2R^{21}$, —$OR^{20}$, —S(═O)$_nR^{20}$, and —S(═O)$_2NR^{22}$, $R^{23}$; or $R^7$ and $R^8$ can, together with the atoms linking them, form a $C_{6-10}$aryl, $C_{3-7}$cycloalkyl, 3-7 membered heterocycloalkyl or a 5-6 membered heteroaryl.

Embodiment 208

The compound of any of Embodiments 1-156, wherein $R^7$, $R^8$, and $R^9$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-7}$cycloalkyl optionally substituted by 1-3 $R^{19}$, $C_{4-8}$cycloalkylalkyl optionally substituted by 1-3 $R^{19}$, 3-7 membered heterocycloalkyl optionally substituted by 1-3 $R^{19}$, 4-8 membered heterocycloalkylalkyl optionally substituted by 1-3 $R^{19}$, 5-6 membered heteroaryl optionally substituted by 1-3 $R^{19}$, 6-21 membered heteroarylalkyl optionally substituted by 1-3 $R^{19}$, halogen, —CN, —C(═O)$R^{20}$, —C(═O)$NR^{22}R^{23}$, —$NO_2$, —$NR^{22}R^{23}$, —$NR^{24}$S(═O)$_2R^{21}$, —$OR^{20}$, —S(═O)$_nR^{20}$, and —S(═O)$_2NR^{22}R^{23}$; or $R^7$ and $R^8$ can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 209

The compound of any of Embodiments 1-156, wherein $R^7$, $R^8$, and $R^9$ are independently chosen from H, $C_{1-6}$alkyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$NR^{22}R^{23}$, —$NO_2$, —$NR^{22}R^{23}$, —$NR^{24}$S(═O)$_2R^{21}$, —$OR^{20}$, —S(═O)$_nR^{20}$, and —S(═O)$_2NR^{22}R^{23}$; or $R^7$ and $R^8$ can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 210

The compound of any of Embodiments 1-156, wherein $R^7$, $R^8$, and $R^9$ are independently chosen from H, $C_{1-6}$alkyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$NR^{22}R^{23}$, —$NO_2$, —$NR^{22}R^{23}$, —$NR^{24}$S(═O)$_2R^{21}$, —$OR^{20}$, —S(═O)$_nR^{20}$, and —S(═O)$_2NR^{22}R^{23}$; or $R^7$ and $R^8$ can, together with the atoms linking them, form a $C_{3-7}$cycloalkyl optionally substituted by 1-3 $R^{19}$, or a 3-7 membered heterocycloalkyl optionally substituted by 1-3 $R^{19}$.

Embodiment 211

The compound of any of Embodiments 1-156, wherein $R^7$, $R^8$, and $R^9$ are independently chosen from H, $C_{1-6}$alkyl, $C_{2-6}$alkynyl, $C_{6-10}$aryl, $C_{3-7}$cycloalkyl, 3-7 membered heterocycloalkyl, 5-6 membered heteroaryl, halogen, —CN, —C(═O)$R^{20}$, —C(═O)$NR^{22}R^{23}$, —$NO_2$, —$NR^{22}R^{23}$, —$NR^{24}$S(═O)$_2R^{21}$, —$OR^{20}$, —S(═O)$_nR^{20}$, and —S(═O)$_2NR^{22}R^{23}$; or $R^7$ and $R^8$ can, together with the atoms linking them, form a $C_{3-7}$cycloalkyl, or a 3-7 membered heterocycloalkyl.

Embodiment 212

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{20}$, —C(═O)O$R^{20}$, —C(═O)N$R^{22}R^{23}$, —$NO_2$, —N$R^{22}R^{23}$, and —O$R^{20}$; or $R^7$ and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^9$.

Embodiment 213

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)N$R^{22}R^{23}$, —$NO_2$, —N$R^{22}R^{23}$, and —O$R^{20}$; or $R^7$ and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 214

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{20}$, —C(═O)N$R^{22}R^{23}$, —N$R^{22}R^{23}$, —N$R^{24}$C(═O)$R^{20}$, and —O$R^{20}$; or $R^7$ and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 215

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{20}$, —C(═O)N$R^{22}R^{23}$, —N$R^{22}$R, —N$R^{24}$C(═O)$R^{20}$, and —O$R^{20}$; $R^8$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{7-16}$arylalkyl optionally substituted by 1-19 $R^{19}$, $C_{3-11}$cycloalkyl optionally substituted by 1-21 $R^{19}$, 3-15 membered heterocycloalkyl optionally substituted by 1-28 $R^{19}$, 6-21 membered heteroarylalkyl optionally substituted by 1-27 $R^{19}$, halogen, —CN, —C(═O)$R^{20}$, —C(═O)N$R^{22}R^{23}$, —N$R^{22}$R, —N$R^{24}$C(═O)$R^{20}$, and —O$R^{20}$; or $R^7$ and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 216

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, halogen, —CN, —C(═O)$R^{20}$, —C(═O)O$R^{20}$, —C(═O)N$R^{22}R^{23}$, —NC, —$NO_2$, —N$R^{22}R^{23}$, —N$R^{24}$N$R^{22}R^{23}$, —N═N$R^{24}$, —N$R^{24}$O$R^{26}$, —N$R^{24}$C(═O)$R^{20}$, —N$R^{24}$C(═O)C(═O)$R^{20}$, —N$R^{24}$C(═O)O$R^{21}$, —N$R^{24}$C(═O)N$R^{22}R^{23}$, —N$R^{24}$S(═O)$_2R^{21}$, —N$R^{24}$S(═O)$_2$N$R^{22}R^{23}$, —N$R^{24}$P(═O)$R^{78}R^{78}$, —N$R^{24}$P(═O)N$R^{22}R^{23}$)(NR)(N$R^{23}$), —N$R^{24}$P(═)(O$R^{20}$)(O$R^{20}$), —N$R^{24}$P(═O)(S$R^{20}$)(S$R^{20}$), —O$R^{20}$, —OCN, —OC(═O)$R^{20}$, —OC(═O)N$R^{22}R^{23}$, —OC(═)O$R^{20}$, —OS(═O)$R^{20}$, —OS(═O)$_2R^{20}$, —OS(═O)$_2$O$R^{20}$, —OS(═O)$_2$N$R^{22}R^{23}$, —OP(═O)$R^{78}R^{78}$, —OP(═O)(N$R^{22}R^{23}$)(N$R^{22}R^{23}$), —OP(═O)(O$R^{20}$)(O$R^{20}$), —OP(═O)(S$R^{20}$)(S$R^{20}$), —Si($R^{24}$)$_3$, —SCN, —S(═O)$_n R^{20}$, —S(═O)$_2$O$R^{20}$, —S$O_3R^{27}$, —S(═O)$_2$N$R^{22}R^{23}$, —S(═O)N$R^{22}R^{23}$, —SP(═O)$R^{78}R^{78}$, —SP(═O)(N$R^{22}R^{23}$)(N$R^{22}R^{23}$), —SP(═O)(O$R^{20}$)(O$R^{20}$), —SP(═O)(S$R^{20}$)(S$R^{20}$), —P(═O)$R^{78}R^{78}$, —P(═O)(N$R^{22}$R)(N$R^{22}R^{23}$), —P(═O)(O$R^{20}$)(O$R^{20}$), and —P(═O)(S$R^{20}$)(S$R^{20}$); or R and $R^8$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$.

Embodiment 217

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, halogen, —CN, —C(═O)$R^{20}$, —C(═O)O$R^{20}$, —C(═O)N$R^{22}R^{23}$, —NC, —$NO_2$, —N$R^{22}R^{23}$, —N$R^{24}$N$R^{22}R^{23}$, —N$R^{24}$O$R^{26}$, —N$R^{24}$C(═O)$R^{20}$, —N$R^{24}$C(═O)O$R^{21}$, —N$R^{24}$C(═O)N$R^{22}R^{23}$, —N$R^{24}$S(═O)$_2R^{21}$, —N$R^{24}$S(═O)$_2$N$R^{22}R^{23}$, —O$R^{20}$, —OCN, —OC(═O)$R^{20}$, —OC(═O)N$R^{22}R^{23}$, —OS(═O)$R^{20}$, —OS(═O)$_2R^{20}$, —OS(═O)$_2$O$R^{20}$, —OS(═O)$_2$N$R^{22}R^{23}$, —Si($R^{24}$)$_3$, —SCN, —S(═O)$_n R^{20}$, —S(═O)$_2R^{20}$, —S$O_3R^{27}$, —S(═O)$_2$N$R^{22}R^{23}$, and —S(═O)N$R^{22}R^{23}$; or $R^7$ and $R^8$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 218

The compound of any of Embodiments 1-156, wherein $R^7$, $R^8$, and $R^9$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-10 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}NR^{22}R^{23}$, —$NR^{24}OR^{26}$, —$NR^{24}$C(═O)$R^{20}$, —$NR^2$C(═)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OCN, —OC(═O)$R^{20}$, —OC(═O)$NR^{22}R^{23}$, —OS(═O)$R^{20}$, —OS(═O)$_2R^{20}$, —OS(═O)$_2R^{20}$, —OS(═O)$_2NR^{22}R^{23}$, —Si($R^{24}$)$_3$, —SCN, —S(═O)$_nR^{20}$, —S(═O)$_2OR^{20}$, —$SO_3R^{27}$, —S(═O)$_2NR^{22}R^{23}$, and —S(═O)$NR^{22}R^{23}$; or $R^7$ and $R^8$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 219

The compound of any of Embodiments 1-156, wherein $R^7$, $R^8$, and $R^9$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}$C(═O)$R^{20}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —Si($R^{24}$)$_3$, —S(═O)$_nR^{20}$, and —S(═O)$_2NR^{22}R^{23}$; or $R^7$ and $R^8$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 220

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}$C(═O)$R^{20}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —Si($R^{24}$)$_3$, —S(═O)$_nR^{20}$, and —S(═O)$_2NR^{22}R^{23}$.

Embodiment 221

The compound of any of Embodiments 1-156, wherein $R^7$, $R^8$, and $R^9$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, halogen, —$NR^{22}R^{23}$, —$NR^{24}$C(═O)$R^{20}$, —$NR^{24}$S(═O)$_2R^{21}$, —$OR^{20}$, —OC(═O)$R^{20}$, —S(═O)$_nR^{20}$, and —S(═O)$_2NR^{22}R^{23}$.

Embodiment 222

The compound of any of Embodiments 1-156, wherein $R^7$, $R^8$, and $R^9$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —$NR^{22}R^{23}$, —$NR^{24}$C(═O)$R^{20}$, —$NR^{24}$S(═O)$_2R^{21}$, —$OR^{20}$, —OC(═O)$R^{20}$, —S(═O)$_nR^{20}$, and —S(═O)$_2NR^{22}R^{23}$.

Embodiment 222

The compound of any of Embodiments 1-156, wherein $R^7$, $R^8$, and $R^9$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —$NR^{22}R^{23}$, —$OR^{20}$, and —S(═O)$_nR^{20}$.

Embodiment 223

The compound of any of Embodiments 1-156 or 200-222, wherein $R^8$ is not phenyl or morpholinyl.

Embodiment 224

The compound of any of Embodiments 1-156, wherein $R^7$ is chosen from H, $C_{1-6}$alkyl optionally substituted by 1-13 $R^{19}$, $C_{2-6}$alkenyl optionally substituted by 1-11 $R^{19}$, $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, halogen, —CN, —C(═O)$R^{20}$, —C(═)$OR^{20}$, —C(═O)$NR^{22}R^{23}$, —$NO_2$, —$NR^{22}R^{23}$, —$NR^{24}$C(═O)$R^{20}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; $R^8$ is chosen from H, $C_{1-6}$alkyl optionally substituted by 1-13 $R^{19}$, halogen, —$NR^{22}R^{23}$, and —$OR^{20}$; and $R^9$ is chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$, 5-15 membered heteroaryl optionally substituted by 1-15 $R^{19}$, halogen, —CN, —C(═O)$R^{20}$, —C(═O)

$OR^{20}$, —C(=O)$NR^{22}R^{23}$, —NC, —$NO_2$, —$NR^{22}R^{23}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{20}$, —$NR^{24}$S(=O)$_2NR^{22}R^{23}$, —$OR^{20}$, —OC(=O)$R^{20}$, —OC(=O)$NR^{22}R^{23}$, —S(=O)$_nR^{20}$, and —S(=O)$_2NR^{22}R^{23}$.

Embodiment 225

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{6-10}$aryl optionally substituted by 1-6 $R^{19}$, $C_{3-11}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, (=)$OR^{20}$, —C(=O)$NR^{22}R^{23}$, —$NO_2$, —$NR^{22}R^{23}$, —$NR^{24}$C(=O)$R^{20}$, —$NR^{24}$S(=O)$_2R^{21}$, —$NR^{24}$S(=O)$_2NR^{22}R^{23}$, —$OR^{20}$, —OC(=O)$R^{20}$, —S(=O)$_nR^{20}$, and —S(=O)$_2NR^{22}R^{23}$; $R^8$ is chosen from H, $C_{1-6}$alkyl optionally substituted by 1-6 $R^{19}$, halogen, —$NR^{22}R^{23}$, and —$OR^{20}$; and $R^9$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{21}$, —$NR^{24}$S(=O)$_2NR^{22}R^{23}$, —$OR^{20}$, —OC(=O)$R^{20}$, —OC(=O)$NR^{22}R^{23}$, —S(=O)$_nR^{20}$, and —S(=O)$_2NR^{22}R^{23}$.

Embodiment 226

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —(=)$OR^{20}$, —C(=O)$NR^{22}R^{23}$, —$NO_2$, —$NR^{22}R^{23}$, —$NR^{24}$C(=O)$R^{20}$, —$NR^{24}$S(=O)$_2R^{21}$, —$NR^{24}$S(=O)$_2NR^{22}R^{23}$, —$OR^{20}$, —OC(=O)$R^{20}$, —S(=O)$_nR^{20}$, and —S(=O)$_2NR^{22}R^{23}$; $R^8$ is chosen from H, $C_{1-6}$alkyl optionally substituted by 1-6 $R^{19}$, halogen, —$NR^{22}R^{23}$, and —$OR^{20}$; and $R^9$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{21}$, —$NR^{24}$S(=O)$_2NR^{22}R^{23}$, —$OR^{20}$, —OC(=O)$R^{20}$, —OC(=O)$NR^{22}R^{23}$, —S(=O)$_nR^{20}$, and —S(=O)$_2NR^{22}R^{23}$.

Embodiment 227

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, halogen, —CN, —C(=O)$R^{20}$, —C(=O)$OR^{20}$, —C(=O)$NR^{22}R^{23}$, —$NO_2$, —$NR^{22}R^{23}$, —$NR^{24}$C(=O)$R^{20}$, —$NR^{24}$S(=O)$_2R^{21}$, —$OR^{20}$, —OC(=O)$R^{20}$, —S(=)$_nR^{20}$, and —S(=O)$_2NR^{22}R^{23}$; $R^8$ is chosen from H, $C_{1-6}$alkyl optionally substituted by 1-6 $R^{19}$, and halogen; and $R^9$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}$C(=O)$R^{20}$, —$NR^{24}$C(=O)$NR^{22}R^{23}$, —$NR^{24}$S(=O)$_2R^{20}$, —$NR^{24}$S(=O)$_2NR^{22}R^{23}$, —$OR^{20}$, —OC(=O)$R^{20}$, —S(=)$_nR^{20}$ and —S(=O)$_2NR^{22}R^{23}$.

Embodiment 228

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, halogen, —$NR^{22}R^{23}$, —$NR^{24}$C(=O)$R^{20}$, —$NR^{24}$S(=O)$_2R^{21}$, —$OR^{20}$ and —OC(=O)$R^{20}$; $R^8$ is chosen from H, $C_{1-6}$alkyl optionally substituted by 1-6 $R^{19}$, and halogen; and $R^9$ is chosen from H, $C_{1-6}$alkyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=)$OR^{20}$, —C(=O)$NR^{22}R^{23}$, —$NO_2$, —$NR^{22}R^{23}$, —$NR^{24}$C(=O)$R^{20}$, —$NR^{24}$S(=O)$_2R^{21}$, —$OR^{20}$, —OC(=O)$R^{20}$, —S(=O)$_nR^{20}$, and —S(=O)$_2NR^{22}R^{23}$.

Embodiment 229

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{3-10}$-cycloalkyl optionally substituted by 1-6 $R^{19}$, halogen, —$NR^{22}R^{23}$, and —$OR^{20}$; $R^8$ is chosen from H and halogen; and $R^9$ is chosen from H, $C_{1-6}$alkyl optionally substituted by 1-6 $R^{19}$, $C_{2-6}$alkynyl optionally substituted by 1-6 $R^{19}$, $C_{6-10}$aryl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —C(=O)$R^{20}$, —C(=O)$OR^{20}$, —C(=O)$NR^{22}R^{23}$, —$NO_2$, —$NR^{22}R^{23}$, —$NR^{24}$C(=O)$R^{20}$, —$NR^{24}$S(=O)$_2R^{21}$, —$OR^{20}$, —OC(=O)$R^{20}$, and —S(=O)$_nR^{20}$.

Embodiment 230

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{3-10}$-cycloalkyl optionally substituted by 1-6 $R^{19}$, halogen, —$NR^{22}R^{23}$, and —$OR^{20}$; $R^8$ is chosen from H and halogen; and $R^9$ is chosen from H, $C_{1-6}$alkyl optionally substituted by 1-6 $R^{19}$, $C_{2-6}$alkynyl optionally substituted by 1-6 $R^{19}$, $C_{6-10}$aryl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —$NR^{22}R^{23}$, —$OR^{20}$, and —$S(=O)_nR^{20}$.

Embodiment 231

The compound of any of Embodiments 1-156, wherein $R^7$ is chosen from H, $C_{1-6}$alkyl optionally substituted by 1-3 $R^{19}$, $C_{2-6}$alkenyl optionally substituted by 1-3 $R^{19}$, $C_{3-10}$-cycloalkyl optionally substituted by 1-3 $R^{19}$, halogen, —$NR^{22}R^{23}$, and —$OR^{20}$; $R^8$ is chosen from H and halogen; and $R^9$ is chosen from H, $C_{2-6}$alkynyl optionally substituted by 1-3 $R^{19}$, $C_{6-10}$aryl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —$NR^{22}R^{23}$, —$OR^{20}$, and —$S(=O)_nR^{20}$.

Embodiment 232

The compound of any of Embodiments 1-156, wherein $R^7$ is chosen from H, $C_{1-6}$alkyl optionally substituted by 1-3 $R^{19}$, $C_{2-6}$alkenyl optionally substituted by 1-3 $R^{19}$, $C_{3-6}$cycloalkyl optionally substituted by 1-3 $R^{19}$, halogen, —$NR^{22}R^{23}$, and —$OR^{20}$; $R^8$ is chosen from H and halogen; and $R^9$ is chosen from H, $C_{2-6}$alkynyl optionally substituted by 1-3 $R^{19}$, $C_{6-10}$aryl optionally substituted by 1-3 $R^{19}$, 3-6 membered heterocycloalkyl optionally substituted by 1-3 $R^{19}$, 5-9 membered heteroaryl optionally substituted by 1-3 $R^{19}$, halogen, —$NR^{22}R^{23}$, —$OR^{20}$, and —$S(=O)_nR^{20}$.

Embodiment 233

The compound of any of Embodiments 1-156, wherein $R^7$ is chosen from H, $C_{1-6}$alkyl optionally substituted by 1-3 $R^{19}$, $C_{2-6}$alkenyl optionally substituted by 1-3 $R^{19}$, $C_{3-6}$cycloalkyl optionally substituted by 1-3 $R^{19}$, halogen, —$NR^{22}R^{23}$, and —$OR^{20}$; $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$S(=O)_nR^{20}$.

Embodiment 234

The compound of any of Embodiments 1-156 or 200-233, wherein $R^8$ is H.

Embodiment 235

The compound of any of Embodiments 1-156, wherein $R^7$ is chosen from H, $C_{1-6}$alkyl optionally substituted by 1-6 $R^{19}$, $C_{2-6}$alkenyl optionally substituted by 1-6 $R^{19}$, $C_{3-10}$-cycloalkyl optionally substituted by 1-6 $R^{19}$, halogen, —$NR^{22}R^{23}$, and —$OR^{20}$; $R^8$ is chosen from H and halogen; and $R^9$ is chosen from H, $C_{1-6}$alkyl, $C_{2-6}$alkynyl optionally substituted by 1-6 $R^{19}$, $C_{6-10}$aryl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —$NR^{22}R^{23}$, —$OR^{20}$, and —$SR^{20}$.

Embodiment 236

The compound of any of Embodiments 1-156, wherein $R^7$ is chosen from H, $C_{1-6}$alkyl, $C_{3-6}$cycloalkyl, halogen, —$NR^{22}R^{23}$, and —$OR^{20}$; $R^8$ is chosen from H and halogen; and $R^9$ is chosen from H, $C_{2-6}$alkynyl, $C_{6-10}$aryl, 3-10 membered heterocycloalkyl, 5-10 membered heteroaryl, halogen, —$NR^{22}R^{23}$, —$OR^{20}$, and —$SR^{20}$.

Embodiment 237

The compound of any of Embodiments 1-156, wherein $R^7$ is chosen from H, $C_{3-6}$cycloalkyl, and —$OR^{20}$; $R^8$ is chosen from H and halogen; and $R^9$ is chosen from H, $C_{2-6}$alkynyl optionally substituted by 1-3 $R^{19}$, $C_{6-10}$aryl optionally substituted by 1-3 $R^{19}$, 3-6 membered heterocycloalkyl optionally substituted by 1-3 $R^{19}$, 5-9 membered heteroaryl optionally substituted by 1-3 $R^{19}$, halogen, —$NR^{22}R^{23}$, —$OR^{20}$, and —$SR^{20}$.

Embodiment 238

The compound of any of Embodiments 1-156, wherein $R^7$ is chosen from H, $C_{3-6}$cycloalkyl, and —$OR^{20}$; $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

Embodiment 239

The compound of any of Embodiments 1-156, wherein $R^7$ is chosen from H, $C_{3-6}$cycloalkyl, and —O($C_{1-6}$alkyl); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

Embodiment 240

The compound of any of Embodiments 1-156, wherein $R^7$ is chosen from H, $C_{3-6}$cycloalkyl, and —$OR^{20}$; $R^8$ is H; and $R^9$ is H.

Embodiment 241

The compound of any of Embodiments 1-156, wherein $R^7$ is chosen from H, $C_{3-6}$cycloalkyl, and —O($C_{1-6}$alkyl); $R^8$ is H; and $R^9$ is H.

Embodiment 242

The compound of any of Embodiments 1-156, wherein $R^7$ is chosen from H, cyclopropyl, and —O($C_{1-6}$alkyl); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

Embodiment 243

The compound of any of Embodiments 1-156, wherein $R^7$ is chosen from H, cyclopropyl, and —$OR^{20}$; $R^8$ is H; and $R^9$ is H.

Embodiment 244

The compound of any of Embodiments 1-156, wherein $R^7$ is chosen from H, cyclopropyl, and —O($C_{1-6}$alkyl); $R^8$ is H; and $R^9$ is H.

Embodiment 245

The compound of any of Embodiments 1-156, wherein $R^7$ is chosen from H, cyclopropyl, and —O($CH_3$); $R^8$ is H; and $R^9$ is H.

Embodiment 246

The compound of any of Embodiments 1-156, wherein $R^7$ is H; $R^8$ is H; and $R^9$ is H.

Embodiment 247

The compound of any of Embodiments 1-156, wherein $R^7$ is cyclopropyl; $R^8$ is H; and $R^9$ is H.

Embodiment 248

The compound of any of Embodiments 1-156, wherein $R^7$ is —O($CH_3$); $R^8$ is H; and $R^9$ is H.

Embodiment 249

The compound of any of Embodiments 1-156, wherein $R^7$ is chosen from H, cyclopropyl, and —O($C_{1-6}$alkyl); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

Embodiment 250

The compound of any of Embodiments 1-156, wherein $R^7$ is chosen from H, $C_{3-6}$cycloalkyl, and —O($CH_3$); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

Embodiment 300

The compound of any of Embodiments 1, 2, 4-156, or 200-250, wherein $R^2$, $R^{13}$, $R^{14}$, and $R^{15}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{20}$, —C(=O)$OR^{20}$, —C(=O)$NR^{22}R^{23}$, —C(=O)C(=O)$R^{20}$, —C(=$NR^{25}$)$R^{20}$, —C(=$NR^{25}$)$NR^{22}R^{23}$, —C(=NOH)$NR^{22}R^{23}$, —C(=$NOR^{26}$)$R^{20}$, —C(=$NNR^{22}R^{23}$)$R^{20}$, —C(=$NNR^{24}$C(=O)$R^{21}$)$R^{20}$, —C(=$NNR^{24}$C(=O)$OR^{21}$)$R^{20}$, —C(=S)$NR^{22}R^{23}$, —NC, —$NO_2$, —$NR^{22}R^{23}$, —$NR^{24}NR^{22}R^{23}$, —N=$NR^{24}$, —$NR^{24}OR^{26}$, —$NR^{24}$C(=O)$R^{20}$, —$NR^2$C(=O)C(=O)$R^{20}$, —$NR^{24}$C(=O)$OR^{21}$, —$NR^{24}$C(=O)C(=O)$OR^{21}$, —$NR^{24}$C(=O)$NR^{22}R^{23}$, —$NR^{24}$C(=O)$NR^{24}$C(=O)$R^{20}$, —$NR^{24}$C(=O)$NR^{24}$C(=O)$OR^{20}$, —$NR^{24}$C(=$NR^{25}$)$NR^{22}R^{23}$, —$NR^{24}$C(=O)C(=O)$NR^{22}R^{23}$, —$NR^{24}$C(=S)$R^{20}$, —$NR^{24}$C(=S)$OR^{20}$, —$NR^{24}$C(=S)$NR^{22}R^{23}$, —$NR^{24}$S(=O)$_2R^{21}$, —$NR^{24}$S(=O)$_2NR^{22}R^{23}$, —$NR^{24}$P(=O)$R^{78}R^{78}$, —$NR^{24}$P(=O)$NR^{22}R^{23}$)($NR^{22}R^{23}$), —$NR^{24}$P(=)($OR^{20}$)($OR^{20}$), —$NR^{24}$P(=O)($SR^{20}$)($SR^{20}$), —$OR^{20}$, —OCN, —OC(=O)$R^{20}$, —OC(=O)$NR^{22}R^{23}$, —OC(=O)$OR^{20}$, —OC(=$NR^{25}$)$NR^{22}R^{23}$, —OS(=O)$R^{20}$, —OS(=O)$_2R^{20}$, —OS(=O)$_2OR^{20}$, —OS(=O)$_2NR^{22}R^{23}$, —OP(=O)$R^{78}R^{78}$, —OP(=O)($NR^{22}R^{23}$)($NR^{22}R^{23}$), —OP(=O)($OR^{20}$)($OR^{20}$), —OP(=O)($SR^{20}$)($SR^{20}$), —Si($R^{24}$)$_3$, —SCN, —S(=O)$_nR^{20}$, —S(=O)$_2OR^{20}$, —$SO_3R^{27}$, —S(=O)$_2NR^{22}R^{23}$, —S(=O)$NR^{22}R^{23}$, —SP(=O)$R^{78}R^{78}$, —SP(=O)($NR^{22}R^{23}$)($NR^{22}R^{23}$), —SP(=O)($OR^{20}$)($R^{20}$), —SP(=O)($SR^{20}$)($SR^{20}$), —P(=O)$R^{78}R^{78}$, —P(=O)($NR^{22}R^{23}$)($NR^{22}R^{23}$), —P(=O)($OR^{20}$)($OR^{20}$), and —P(=O)($SR^{20}$)($SR^{20}$); or either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 301

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{20}$, —C(=O)$OR^{20}$, —C(=O)$NR^{22}R^{23}$, —NC, —$NO_2$, —$NR^{22}R^{23}$, —$NR^{24}NR^{22}R^{23}$, —N=$NR^{24}$, —$NR^{24}OR^{26}$, —$NR^{24}$C(=O)$R^{20}$, —$NR^{24}$C(=O)$OR^{21}$, —$NR^{24}$C(=O)$NR^{22}R^{23}$, —$NR^{24}$S(=O)$_2R^{21}$, —$NR^{24}$S(=O)$_2NR^{22}R^{23}$, —$NR^{24}$P(=O)$R^{78}R^{78}$, —$NR^{24}$P(=O)($NR^{22}R^{23}$)($NR^{22}R^{23}$), —$NR^{24}$P(=O)($OR^{20}$)($OR^{20}$), —$OR^{20}$, —OCN, —OC(=O)$R^{20}$, —OC(=O)$NR^{22}R^{23}$, —OC(=O)$OR^{20}$, —OS(=O)$R^{20}$, —OS(=O)$_2R^{20}$, —OS(=O)$_2OR^{20}$, —OS(=O)$_2NR^{22}R^{23}$, —OP(=O)$R^{78}R^{78}$, —OP(=O)($NR^{22}R^{23}$)($NR^{22}R^{23}$), —OP(=O)($OR^{20}$)($OR^{20}$), —SCN, —S(=O)$_nR^{20}$, —S(=O)$_2OR^{20}$, —$SO_3R^{27}$, —S(=O)$_2NR^{22}R^{23}$, —S(=O)$NR^{22}R^{23}$, —P(=O)$R^{78}R^{78}$, —P(=O)($NR^{22}R^{23}$)($NR^{22}R^{23}$), and —P(=O)($OR^{20}$)($OR^{20}$); or either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 302

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$, 5-15 membered heteroaryl optionally substituted by 1-6 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}NR^{22}R^{23}$, —N═NR, —$NR^{24}OR^{26}$, —$NR^{24}$C(═O)$R^{20}$, —$NR^{24}$C(═)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$NR^{24}$P(═O)$R^{78}R^{78}$, —$NR^{24}$P(═O)($NR^{22}R^{23}$)($N^{22}R^{23}$), —$NR^{24}$P(═O)($OR^{20}$)($OR^{20}$), —$OR^{20}$, —OCN, —OC(═O)$R^{20}$, —OC(═O)$NR^{22}R^{23}$, —OC(═O)$OR^{20}$, —OS(═O)$R^{20}$, —OS(═O)$_2R^{20}$, —OS(═O)$_2OR^{20}$, —OS(═O)$_2NR^{22}R^{23}$, —OP(═O)$R^{78}R^{78}$, —OP(═O)($NR^{22}R^{23}$)($NR^{22}R^{23}$), —OP(═O)($OR^{20}$)($OR^{20}$), —SCN, —S(═O)$_nR^{20}$, —S(═O)$_2OR^{20}$, —$SO_3R^{27}$, —S(═O)$_2NR^{22}R^{23}$, —S(═O)$NR^{22}R^{23}$, —P(═O)$R^{78}R^{78}$, —P(═O)($NR^{22}R^{23}$)($NR^{22}R^{23}$), and —P(═O)($OR^{20}$)($OR^{20}$); or either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 303

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$, 5-15 membered heteroaryl optionally substituted by 1-6 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}$C(═O)$R^{20}$, —$NR^{24}$C(═)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —OC(═O)$NR^{22}R^{23}$, —OC(═O)$OR^{20}$, —S(═O)$_nR^{20}$, —S(═O)$_2OR^{20}$, —$SO_3R^{27}$, —S(═O)$_2NR^{22}R^{23}$, —S(═O)$NR^{22}R^{23}$, —P(═O)$R^{78}R^{78}$, —P(═O)($NR^{22}R^{23}$)($NR^{22}R^{23}$), and —P(═O)($OR^{20}$)($OR^{20}$); or either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 304

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-11}$aryl optionally substituted by 1-3 $R^{19}$, $C_{7-16}$arylalkyl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$, 5-15 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}$C(═O)

$R^{20}$, —$NR^{24}$C(═)$OR^{21}$, —$NR^{24}$C(═O)$NR^{22}R^{23}$, —$NR^{24}$S(═O)$_2R^{20}$, —$NR^{24}$S(═O)$_2NR^{22}R^{23}$, —$OR^{20}$, —OC(═O)$R^{20}$, —OC(═O)$NR^{22}R^{23}$, —OC(═O)$OR^{20}$, —S(═O)$_nR^{20}$, —S(═O)$_2OR^{20}$, —$SO_3R^{27}$, —S(═O)$_2NR^{22}R^{23}$, —S(═O)$NR^{22}R^{23}$, —P(═O)$R^{78}R^{78}$, —P(═O)($NR^{22}R^{23}$)($NR^{22}R^{23}$), and —P(═O)($OR^{20}$)($OR^{20}$); or either or both of $R^{12}$ and $R^{13}$, and/or $R^{14}$ and $R^{15}$, can, together with the atoms linking them, form a $C_{6-11}$aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 305

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —OC(═O)$NR^{22}R^{23}$, —OC(═O)$OR^{20}$, —S(═O)$_nR^{20}$, —S(═O)$_2OR^{20}$, —$SO_3R^{27}$, —S(═O)$_2NR^{22}R^{23}$, —S(═O)$NR^{22}R^{23}$, —P(═O)$R^{78}R^{78}$, —P(═O)($NR^{22}R^{23}$)($NR^{22}R^{23}$), and —P(═O)($OR^{20}$)($OR^{20}$); or either or both of $R^{12}$ and $R^{13}$, and/or $R^{14}$ and $R^{15}$, can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 306

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-7}$ cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —OC(═O)$NR^{22}R^{23}$, —OC(═O)$OR^{20}$, —S(═O)$_nR^{20}$, —S(═O)$_2R^{20}$, —$SO_3R^{27}$, —S(═O)$_2NR^{22}R^{23}$, —S(═O)$NR^{22}R^{23}$, —P(O)$R^{78}R^{78}$, —P(═O)($NR^{22}R^{23}$)($NR^{22}R^{23}$), and —P(═O)($OR^{20}$)($OR^{20}$); or either or both of $R^{12}$ and $R^{13}$, and/or $R^{14}$ and $R^{15}$, can, together with the atoms linking them, form a $C_{6-10}$aryl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 307

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(═O)$R^{20}$, —C(═O)$N^{22}R^{23}$, —$NO_2$, —$NR^{22}R^{23}$, —$NR^{24}$C(═O)$R^{20}$, —$NR^{24}$S(═O)$_2R^{21}$, —$OR^{20}$, —S(═O)$_nR^{20}$, and —S(═O)$_2NR^{22}R^{23}$; or either or both of $R^{12}$ and $R^{13}$, and/or $R^{14}$ and $R^{15}$, can, together with the atoms linking them, form a $C_{6-11}$ aryl optionally substituted by 1-3 $R^{19}$, $C_{3-11}$cycloalkyl optionally substituted by 1-3 $R^{19}$, 3-15 membered heterocycloalkyl optionally substituted by 1-3 $R^{19}$ or a 5-15 membered heteroaryl optionally substituted by 1-3 $R^{19}$.

Embodiment 308

The compound of any of Embodiments 1, 2, 4-156, or 200-250, wherein $R^{12}$, $R^{13}$, $R^{14}$, and $R^{15}$ are independently chosen from H, $C_{1-6}$alkyl optionally substituted by 1-3 $R^{19}$, phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$NR^{22}R^{23}$, —$NO_2$, —$NR^{22}R^{23}$, —$NR^{24}$C(═O)$R^{20}$, —$NR^{24}$S(═O)$_2R^{21}$, —$OR^{20}$, —S(═O)$_nR^{20}$, and —S(═O)$_2NR^{22}R^{23}$; or either or both of $R^{12}$ and $R^{13}$, and/or $R^{14}$ and $R^{15}$, can, together with the atoms linking them, form a phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

Embodiment 309

The compound of any of Embodiments 1, 2, 4-156, or 200-250, wherein $R^{12}$, $R^{14}$, and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$, 5-15 membered heteroaryl optionally substituted by 1-6 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}NR^{22}R^{23}$, —N═$NR^{24}$, —$NR^{24}OR^{26}$, —$NR^2$C(═O)$R^{20}$, —$NR^{24}$C(═O)C(═O)$R^{20}$, —$NR^{24}$C(═O)$OR^{21}$, —$NR^{24}$C(═O)C(═O)$OR^{21}$, —$NR^{24}$C(═O)$NR^{22}R^{23}$, —$NR^{24}$C(═O)$NR^{24}$C(═O)$R^{20}$, $NR^4$C(═O)$NR^{24}$C(═O)$OR^{20}$, —$NR^{24}$C(═$NR^{25}$)$NR^{22}R^{23}$, —$NR^{24}$C(═O)C(═O)$NR^{22}R^{23}$, —$NR^{24}$C(═S)$R^{20}$, —$NR^{24}$C(═S)$OR^{20}$, —$NR^{24}$C(═S)$NR^{22}R^{23}$, —$NR^{24}$S(═O)$_2R^{21}$, —$NR^{24}$S(═O)$_2NR^{22}R^{23}$, —$NR^{24}$P(═O)$R^{78}R^{78}$, —$NR^{24}$P(═O)($NR^{22}R^{23}$)($NR^{22}R^{23}$), —$NR^{24}$P(═O)($OR^{20}$)($OR^{20}$), —$NR^{24}$P(═O)($SR^{20}$)($SR^{20}$), —$OR^{20}$, —OCN, —OC(═O)$R^{20}$, —OC(═O)$NR^{22}R^{23}$, —OC(═)$OR^{20}$, —Si($R^{24}$)$_3$, —SCN, —S(═O)$_nR^{20}$, —S(═O)$_2OR^{20}$, —$SO_3R^{27}$, —S(═O)$_2NR^{22}R^{23}$, and —S(═O)$NR^{22}R^{23}$; or either or both of $R^{12}$ and $R^{13}$, and/or $R^{14}$ and $R^{15}$, can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 310

The compound of any of Embodiments 1, 2, 4-156, or 200-250, wherein $R^{12}$, $R^{14}$, and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}NR^{22}R^{23}$, —N═$NR^{24}$, —$NR^{24}OR^{26}$, —$NR^{24}$C(═O)$R^{20}$, —$NR^{24}$C(═O)C(═O)$R^{20}$, —$NR^{24}$C(═O)$OR^{21}$, —$NR^{24}$C(═O)C(═O)$OR^{21}$, —$NR^{24}$C(═O)$NR^{22}R^{23}$, —$NR^{24}$C(═O)$NR^{24}$C(═O)$R^{20}$, —$NR^{24}$C(═O)$NR^{24}$C(═O)$OR^{20}$, —$NR^{24}$C(═$NR^{25}$)$NR^{22}R^{23}$, —$NR^{24}$C(═O)C(═O)$NR^{22}R^{23}$, —$NR^{24}$C(═S)$R^{20}$, —$NR^{24}$C(═S)$OR^{20}$, —$NR^{24}$C(═S)$NR^{22}R^{23}$, —$NR^{24}$S(═O)$_2R^{21}$, —$NR^{24}$S(═O)$_2NR^{22}R^{23}$, —$NR^{24}$P(═O)$R^{78}R^{78}$, —$NR^{24}$P(═O)$NR^{22}R^{23}$)($NR^{22}$)($NR^{23}$), —$NR^{24}$P(═)($OR^{20}$)($OR^{20}$), —$NR^{24}$P(═O)($SR^{20}$)($SR^{20}$), —$OR^{20}$, —OCN, —OC(═O)$R^{20}$, —OC(═O)$NR^{22}R^{23}$, —OC(═O)$OR^{20}$, —Si($R^{24}$)$_3$, —SCN, —S(═O)$_nR^{20}$, —S(═O)$_2R^{20}$, —$SO_3R^{27}$, —S(═O)$_2NR^{22}R^{23}$, and —S(═O)$NR^{22}R^{23}$; or $R^{12}$ and $R^{13}$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 311

The compound of any of Embodiments 1, 2, 4-156, or 200-250, wherein $R^{12}$, $R^{14}$, and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═O)C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OCN, —OC(═O)$R^{20}$, —OC(═O)$NR^{22}R^{23}$, —OC(═O)$OR^{20}$, —SCN, —S(═O)$_nR^{20}$, and —S(═O)$_2NR^{22}R^{23}$; or $R^{12}$ and $R^{13}$ can, together with the atoms linking them, form a $C_6$10aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 312

The compound of any of Embodiments 1, 2, 4-156, or 200-250, wherein $R^{12}$, $R^{14}$, and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-3 $R^{19}$, phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═)$OR^{21}$, —$NR^2$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; or $R^{12}$ and $R^{13}$ can, together with the atoms linking them, form a phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-10 membered heteroaryl optionally substituted by 1-6 $R^{19}$.

Embodiment 313

The compound of any of Embodiments 1, 2, 4-156, or 200-250, wherein $R^{12}$, $R^{14}$, and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-3 $R^{19}$, phenyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

Embodiment 314

The compound of any of Embodiments 1, 2, 4-156, or 200-250, wherein $R^{12}$ and $R^{14}$ are H; $R^{15}$ is chosen from H, $C_{1-6}$alkyl optionally substituted by 1-3 $R^{19}$, and halogen; $R^{13}$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(═O)$R^{20}$, —C(═O)$OR^{20}$, —C(═O)$NR^{22}R^{23}$, —NC, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═O)C(═O)$R^{20}$, —$NR^{24}$C(═)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OCN, —OC(═O)$R^{20}$, —OC(═O)$NR^{22}R^{23}$, —OC(═O)$OR^{20}$, —SCN, —S(═O)$_nR^{20}$, and —S(═O)$_2NR^{22}R^{23}$; or $R^{12}$ and $R^{13}$ can, together with the atoms linking them, form a $C_6$10aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 315

The compound of any of Embodiments 1, 2, 4-156, or 200-250, wherein $R^{12}$ and $R^{14}$ are H; $R^{15}$ is chosen from H, $C_{1-6}$alkyl optionally substituted by 1-3 $R^{19}$, and halogen; $R^{13}$ is chosen from H, $C_{1-6}$alkyl optionally substituted by 1-3 $R^{19}$, phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; or $R^{12}$ and $R^{13}$ can, together with the atoms linking them, form a phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-10 membered heteroaryl optionally substituted by 1-6 $R^{19}$.

Embodiment 316

The compound of any of Embodiments 1, 2, 4-156, or 200-250, wherein $R^{12}$ and $R^{14}$ are H; $R^{15}$ is chosen from H and halogen; $R^{13}$ is chosen from H, $C_{1-6}$alkyl optionally substituted by 1-3 $R^{19}$, phenyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}NR^{22}R^{23}$, —$NR^2OR^{26}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

Embodiment 317

The compound of any of Embodiments 1, 2, 4-156, or 200-250, wherein $R^{14}$ is H; $R^{12}$ and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-3 $R^{19}$, phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═)$OR^{21}$, —$NR^2$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; or $R^{12}$ and $R^{13}$ can, together with the atoms linking them, form a phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-10 membered heteroaryl optionally substituted by 1-6 $R^{19}$.

Embodiment 318

The compound of any of Embodiments 1, 2, 4-156, or 200-250, wherein $R^{14}$ is H; $R^{12}$ and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-3 $R^{19}$, phenyl optionally substituted by 1-3 $R^{19}$, 5-6 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}NR^{22}R^{23}$, —$NR^{24}OR^{26}$, —$NR^{24}$C(═O)$R^{20}$, —$NR^{24}$C(═O)$OR^{21}$, —$NR^{24}$C(═O)$NR^{22}R^{23}$, —$NR^{24}$S(═O)$_2R^{21}$, —$NR^{24}$S(═O)$_2NR^{22}R^{23}$, —$OR^{20}$, —OC(═O)$R^{20}$, —S(═O)$_nR^{20}$, and —S(═O)$_2NR^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

Embodiment 319

The compound of any of Embodiments 1, 2, 4-156, or 200-250, wherein $R^{14}$ is H; $R^{12}$ and $R^{15}$ are independently chosen from H and halogen; $R^{13}$ is chosen from H, $C_{1-6}$alkyl optionally substituted by 1-3 $R^{19}$, halogen, —CN, —C(=O)$R^{20}$, —C(=O)O$R^{20}$, —C(=O)N$R^{22}R^{23}$, —$NO_2$, —N$R^{22}R^{23}$, —N$R^{24}$N$R^{22}R^{23}$, —N$R^{24}$O$R^{26}$, —N$R^{24}$C(=O)$R^{20}$, —N$R^{24}$C(=)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —S(=O)$_n$$R^{20}$ and —S(=O)$_2$N$R^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

Embodiment 320

The compound of any of Embodiments 1, 2, 4-156, or 200-250, wherein $R^{14}$ is H; $R^{12}$ and $R^{15}$ are independently chosen from H and halogen; $R^{13}$ is chosen from H, $C_{1-6}$alkyl optionally substituted by 1-3 $R^{19}$, halogen, —CN, —C(=O)N$R^{22}R^{23}$, —$NO_2$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{2}$, —S(=O)$_n$$R^{20}$, and —S(=O)$_2$N$R^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

Embodiment 321

The compound of any of Embodiments 1, 2, 4-156, or 200-250, wherein $R^{14}$ is H; $R^{12}$ and $R^{15}$ are independently chosen from H and halogen; $R^{13}$ is chosen from H, $C_{1-6}$alkyl optionally substituted by 1-3 $R^{19}$, halogen, —C(=O)N$R^{22}R^{23}$, —$NO_2$, —N$R^{22}R^{23}$, —N$R^{24}$C(=O)$R^{20}$, —N$R^{24}$C(=)O$R^{21}$, —N$R^{24}$C(=O)N$R^{22}R^{23}$, —N$R^{24}$S(=O)$_2R^{21}$, and —N$R^{24}$S(=O)$_2$N$R^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

Embodiment 322

The compound of any of Embodiments 1, 2, 4-156, or 200-250, wherein $R^{14}$ is H; $R^{12}$ and $R^{15}$ are independently chosen from H and halogen; $R^{13}$ is chosen from H, $C_{1-6}$alkyl optionally substituted by 1-3 $R^{19}$, halogen, —C(=O)N$R^{22}R^{23}$, —$NO_2$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, and —N$R^{24}$S(=O)$_2$N$R^{22}R^{23}$; or $R^{12}$ and $R^{13}$ can, together with the atoms linking them, form a phenyl optionally substituted by 1-3 $R^{19}$ or a 5-6 membered heteroaryl optionally substituted by 1-6 $R^{19}$.

Embodiment 323

The compound of any of Embodiments 1, 2, 4-156, or 200-250, wherein $R^{14}$ is H; $R^{12}$ and $R^{15}$ are independently chosen from H and halogen; $R^{13}$ is chosen from H, $C_{1-6}$alkyl optionally substituted by 1-3 $R^{19}$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, and —N$R^{24}$S(=O)$_2$N$R^{22}R^{23}$; or $R^{12}$ and $R^{13}$ can, together with the atoms linking them, form a phenyl optionally substituted by 1-3 $R^{19}$ or a 5-6 membered heteroaryl optionally substituted by 1-6 $R^{19}$.

Embodiment 324

The compound of any of Embodiments 1, 2, 4-156, or 200-250, wherein $R^{14}$ is H; $R^{12}$ and $R^{15}$ are independently chosen from H and halogen; $R^{13}$ is chosen from H, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, and —N$R^{24}$S(=O)$_2$N$R^{22}R^{23}$; or $R^{12}$ and $R^{13}$ can, together with the atoms linking them, form a 5-6 membered heteroaryl optionally substituted by 1-6 $R^{19}$.

Embodiment 325

The compound of any of Embodiments 1, 2, 4-156, or 200-250, wherein $R^{14}$ is H; $R^{12}$ and $R^{15}$ are independently chosen from H and halogen; $R^{13}$ is chosen from H, —N$R^{22}R^{23}$, and —N$R^{24}$C(=O)$R^{20}$; or $R^{12}$ and $R^{13}$ can, together with the atoms linking them, form a 5-6 membered heteroaryl optionally substituted by 1-6 $R^{19}$.

Embodiment 326

The compound of any of Embodiments 1, 2, 4-156, or 200-250, wherein $R^{14}$ is H; $R^{12}$ and $R^{15}$ are independently chosen from H and halogen; $R^{13}$ is chosen from H, —N$R^{22}R^{23}$, and —N$R^{24}$C(=O)$R^{20}$; or $R^{12}$ and $R^{13}$ can, together with the atoms linking them, form a 5-6 membered heteroaryl optionally substituted by 1-3 $R^{19}$.

Embodiment 327

The compound of any of Embodiments 1, 2, 4-156, or 200-250, wherein $R^{12}$ and $R^{14}$ are H; $R^{15}$ is chosen from H and halogen; $R^{13}$ is chosen from H, —N$R^{22}R^{23}$, and —N$R^{24}$C(=O)$R^{20}$; or $R^{12}$ and $R^{13}$ can, together with the atoms linking them, form a 5-6 membered heteroaryl optionally substituted by 1-3 $R^{19}$.

Embodiment 328

The compound of any of Embodiments 1, 2, 4-156, or 200-250, wherein $R^{14}$ and $R^{15}$ are H; $R^{12}$ is chosen from H and halogen; $R^{13}$ is chosen from H, —N$R^{22}R^{23}$, and —N$R^{24}$C(=O)$R^{20}$; or $R^{12}$ and $R^{13}$ can, together with the atoms linking them, form a 5-6 membered heteroaryl optionally substituted by 1-3 $R^{19}$.

Embodiment 329

The compound of any of Embodiments 1, 2, 4-156, or 200-250, wherein $R^{14}$ is H; $R^{12}$ and $R^{15}$ are independently chosen from H and halogen; $R^{13}$ is chosen from H, —N$R^{22}R^{23}$, and —N$R^{24}$C(=O)$R^{20}$; or $R^{12}$ and $R^{13}$ can, together with the atoms linking them, form a 5 membered heteroaryl optionally substituted by 1-3 $R^{19}$.

Embodiment 330

The compound of any of Embodiments 1, 2, 4-156, or 200-250, wherein $R^{12}$ and $R^{14}$ are H; $R^{15}$ is chosen from H and halogen; $R^{13}$ is chosen from H, —N$R^{22}R^{23}$, and —$NR^{24}C(=O)R^{20}$; or $R^{12}$ and $R^{13}$ can, together with the atoms linking them, form a 5 membered heteroaryl optionally substituted by 1-3 $R^{19}$.

Embodiment 331

The compound of any of Embodiments 1, 2, 4-156, or 200-250, wherein $R^{14}$ and $R^{15}$ are H; $R^{12}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1-3 $R^{19}$.

Embodiment 332

The compound of any of Embodiments 1, 2, 4-156, or 200-250, wherein $R^{14}$ is H; $R^{12}$ and $R^{15}$ are independently chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1-2 $R^{19}$.

Embodiment 333

The compound of any of Embodiments 1, 2, 4-156, or 200-250, wherein $R^{12}$ and $R^{14}$ are H; $R^{15}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1-2 $R^{19}$.

Embodiment 334

The compound of any of Embodiments 1, 2, 4-156, or 200-250, wherein $R^{14}$ and $R^{15}$ are H; $R^{12}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1-2 $R^{19}$.

Embodiment 335

The compound of any of Embodiments 1, 2, 4-156, or 200-250, wherein $R^{14}$ is H; $R^{12}$ and $R^{15}$ are independently chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1 $R^{19}$.

Embodiment 336

The compound of any of Embodiments 1, 2, 4-156, or 200-250, wherein $R^{12}$ and $R^{14}$ are H; $R^{15}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1 $R^{19}$.

Embodiment 337

The compound of any of Embodiments 1, 2, 4-156, or 200-250, wherein $R^{14}$ and $R^{15}$ are H; $R^{12}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a 5 membered heteroaryl optionally substituted by 1 $R^{19}$.

Embodiment 338

The compound of any of Embodiments 1, 2, 4-156, or 200-250, wherein $R^{14}$ is H; $R^{12}$ and $R^{15}$ are independently chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a pyrrolyl ring optionally substituted by 1 $R^{19}$.

Embodiment 339

The compound of any of Embodiments 1, 2, 4-156, or 200-250, wherein $R^{12}$ and $R^{14}$ are H; $R^{15}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a pyrrolyl ring optionally substituted by 1 $R^{19}$.

Embodiment 340

The compound of any of Embodiments 1, 2, 4-156, or 200-250, wherein $R^{14}$ and $R^{15}$ are H; $R^{12}$ is chosen from H and halogen; $R^{13}$ is chosen from H, —$NR^{22}R^{23}$, and —$NR^{24}C(=O)R^{20}$; or $R^{12}$ and $R^{13}$ can, together with the atoms linking them, form a pyrrolyl ring optionally substituted by 1 $R^{19}$.

Embodiment 341

The compound of any of Embodiments 300-340, wherein $R^{14}$ is H.

Embodiment 342

The compound of any of Embodiments 300-341, wherein $R^{15}$ is H.

Embodiment 343

The compound of any of Embodiments 300-342, wherein $R^{12}$ is H.

Embodiment 344

The compound of any of Embodiments 300-343, wherein $R^{13}$ is H.

Embodiment 345

The compound of any of Embodiments 300-340, wherein $R^{14}$ and $R^{15}$ are H.

Embodiment 346

The compound of any of Embodiments 300-340, wherein $R^{12}$ are $R^{15}$ are H.

Embodiment 347

The compound of any of Embodiments 300-340, wherein $R^{12}$, $R^{14}$ and $R^{15}$ are H.

Embodiment 348

The compound of any of Embodiments 300-340, wherein $R^{12}$ are $R^{14}$ are H.

Embodiment 349

The compound of any of Embodiments 1, 2, 4-156, 200-250, or 300-340, wherein $R^{12}$, $R^{13}$, $R^{14}$, and $R^{15}$ are H.

Embodiment 350

The compound of any of Embodiments 300-342, wherein $R^{12}$ and $R^{13}$, together with the atoms linking them, form a 5 membered heteroaryl optionally substituted by 1-2 $R^{19}$.

Embodiment 351

The compound of any of Embodiments 300-342, wherein $R^{12}$ and $R^{13}$, together with the atoms linking them, form a 5 membered heteroaryl optionally substituted by 1 $R^{19}$.

Embodiment 352

The compound of any of Embodiments 300-342, wherein $R^{12}$ and $R^{13}$, together with the atoms linking them, form a pyrrolyl ring optionally substituted by 1 $R^{19}$.

Embodiment 353

The compound of any of Embodiments 300-342, wherein $R^{12}$ and $R^{13}$, together with the atoms linking them, form a pyrrolyl ring.

Embodiment 354

The compound of any of Embodiments 1, 2, 4-156, or 200-250, wherein $R^{12}$, $R^{14}$, and $R^{15}$ are H, and $R^{13}$ is chosen from H, $C_{7-16}$arylalkyl optionally substituted by 1-6 $R^{19}$, 5-15 membered heteroaryl optionally substituted by 1-6 $R^{19}$, halogen, —$NR^{22}R^{23}$, and —$NR^{24}C(=O)R^{20}$; or $R^{12}$ and $R^{13}$ can, together with the atoms linking them, form a $C_{6-11}$aryl optionally substituted by 1-6 $R^{19}$, 3-15 membered heterocycloalkyl optionally substituted by 1-6 $R^{19}$, or a 5-15 membered heteroaryl optionally substituted by 1-6 $R^{19}$.

Embodiment 355

The compound of any of Embodiments 1, 2, 4-156, or 200-250, wherein $R^{12}$, $R^{14}$, and $R^{15}$ are H, and $R^{13}$ is chosen from H, $C_{7-16}$arylalkyl optionally substituted by 1-6 $R^{19}$, 5-10 membered heteroaryl optionally substituted by 1-6 $R^{19}$, halogen, —$NR^{22}R^{23}$, and —$NR^{24}C(=O)R^{20}$; or $R^{12}$ and $R^{13}$ can, together with the atoms linking them, form a $C_{6-11}$aryl optionally substituted by 1-6 $R^{19}$, 5-10 membered heterocycloalkyl optionally substituted by 1-6 $R^{19}$, or a 5-10 membered heteroaryl optionally substituted by 1-6 $R^{19}$.

Embodiment 356

The compound of any of Embodiments 1, 2, 4-156, or 200-250, wherein $R^{12}$, $R^{14}$, and $R^{15}$ are H, and $R^{13}$ is chosen from H, $C_{7-16}$arylalkyl optionally substituted by 1-3 $R^{19}$, 5-10 membered heteroaryl optionally substituted by 1-3 $R^{19}$, halogen, —$NR^{22}R^{23}$, and —$NR^{24}C(=O)R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

Embodiment 357

The compound of any of Embodiments 1, 2, 4-156, or 200-250, wherein $R^{12}$, $R^{14}$, and $R^{15}$ are H, and $R^{13}$ is chosen from H, halogen, —$NR^{22}R^{23}$, and —$NR^{24}C(=O)R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

Embodiment 358

The compound of any of Embodiments 1, 2, 4-156, or 200-250, wherein $R^{12}$, $R^{14}$, and $R^{15}$ are H, and $R^{13}$ is chosen from H, halogen, —$NR^{22}R^{23}$, and —$NR^{24}C(=O)R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 or 2 nitrogen atoms, or a 5-10 membered heteroaryl optionally substituted by 1-3 $R^{19}$ in which the heteroaryl contains carbon atoms and 1 or 2 nitrogen atoms.

Embodiment 359

The compound of any of Embodiments 1, 2, 4-156, or 200-250, wherein $R^{12}$, $R^{14}$, and $R^{15}$ are H, and $R^{13}$ is chosen from H, halogen, —$NR^{22}R^{23}$, and —$NR^{24}C(=O)R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 nitrogen atom, or a 5-10 membered heteroaryl optionally substituted by 1-3 $R^{19}$ in which the heteroaryl contains carbon atoms and 1 nitrogen atom.

Embodiment 360

The compound of any of Embodiments 1, 2, 4-156, or 200-250, wherein $R^{12}$, $R^{14}$, and $R^{15}$ are H, and $R^{13}$ is chosen from H, —$NR^{22}R^{23}$, and —$NR^{24}C(=O)R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

Embodiment 361

The compound of any of Embodiments 1, 2, 4-156, or 200-250, wherein $R^{12}$, $R^{14}$, and $R^{15}$ are H, and $R^{13}$ is chosen from H, —$NR^{22}R^{23}$, and —$NR^{24}C(=O)R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 or 2 nitrogen atoms, or a 5-10 membered heteroaryl optionally substituted by 1-3 $R^{19}$ in which the heteroaryl contains carbon atoms and 1 or 2 nitrogen atoms.

Embodiment 362

The compound of any of Embodiments 1, 2, 4-156, or 200-250, wherein $R^{12}$, $R^{14}$, and $R^{15}$ are H, and $R^{13}$ is chosen from H, —$NR^{22}R^{23}$, and $NR^{24}C(=O)R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 nitrogen atom, or a 5-10 membered heteroaryl optionally substituted by 1-3 $R^{19}$ in which the heteroaryl contains carbon atoms and 1 nitrogen atom.

Embodiment 363

The compound of any of Embodiments 1, 2, 4-156, or 200-250, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

Embodiment 364

The compound of any of Embodiments 1, 2, 4-156, or 200-250, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 or 2 nitrogen atoms, or a 5-10 membered heteroaryl optionally substituted by 1-3 $R^{19}$ in which the heteroaryl contains carbon atoms and 1 or 2 nitrogen atoms.

Embodiment 365

The compound of any of Embodiments 1, 2, 4-156, or 200-250, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 nitrogen atom, or a 5-10 membered heteroaryl optionally substituted by 1-3 $R^{19}$ in which the heteroaryl contains carbon atoms and 1 nitrogen atom.

Embodiment 366

The compound of any of Embodiments 1, 2, 4-156, or 200-250, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a 5-10 membered heteroaryl optionally substituted by 1-3 $R^{19}$.

Embodiment 367

The compound of any of Embodiments 1, 2, 4-156, or 200-250, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a 5-10 membered heteroaryl optionally substituted by 1-3 $R^{19}$ in which the heteroaryl contains carbon atoms and 1 or 2 nitrogen atoms.

Embodiment 368

The compound of any of Embodiments 1, 2, 4-156, or 200-250, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a 5-10 membered heteroaryl optionally substituted by 1-3 $R^{19}$ in which the heteroaryl contains carbon atoms and 1 nitrogen atom.

Embodiment 369

The compound of any of Embodiments 1, 2, 4-156, or 200-250, wherein $R^{12}$, $R^{14}$, and $R^{15}$ are H, and $R^{13}$ is chosen from H and —$NHR^{23}$; or $R^{12}$ and $R^{13}$ can, together with the atoms linking them, form a 5-10 membered heteroaryl optionally substituted by 1-3 $R^{19}$.

Embodiment 370

The compound of any of Embodiments 1, 2, 4-156, or 200-250, wherein $R^{12}$, $R^{14}$, and $R^{15}$ are H, and $R^{13}$ is chosen from H and —$NHR^{23}$; or $R^{12}$ and $R^{13}$ can, together with the atoms linking them, form a 5-10 membered heteroaryl optionally substituted by 1-3 $R^{19}$ in which the heteroaryl contains carbon atoms and 1 or 2 nitrogen atoms.

Embodiment 371

The compound of any of Embodiments 1, 2, 4-156, or 200-250, wherein $R^{12}$, $R^{14}$, and $R^{15}$ are H, and $R^{13}$ is chosen from H and —$NHR^{23}$; or $R^{12}$ and $R^{13}$ can, together with the atoms linking them, form a 5-10 membered heteroaryl optionally substituted by 1-3 $R^{19}$ in which the heteroaryl contains carbon atoms and 1 nitrogen atom.

Embodiment 400

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(═O)$R^{20}$, —C(═O)$OR^{20}$, —C(═O)$NR^{22}R^{23}$, —C(═O)C(═O)$R^{20}$, —C(═$NR^{25}$)$R^{20}$, —C(═$NR^{25}$)$NR^{22}R^{23}$, —C(═NOH)$NR^{22}R^{23}$, —C(═$NOR^{26}$)$R^{20}$, —C(═$NNR^{22}R^{23}$)$R^{20}$, —C(═$NNR^{24}$C(═O)$R^{21}$)$R^{20}$, —C(═$NNR^{24}$C(═)$OR^{21}$)$R^{20}$, —C(═S)$NR^{22}R^{23}$, —NC, —$NO_2$, —$NR^{22}R^{23}$, —$NR^{24}NR^{22}R^{23}$, —N═$NR^{24}$, —$NR^{240}R^{26}$, —$NR^{24}$C(═O)$R^{20}$, —$NR^{24}$C(═O)C(═O)$R^{20}$, —$NR^{24}$C(═O)$OR^{21}$, —$NR^{24}$C(═O)C(═O)$OR^{21}$, —$NR^{24}$C(═O)$NR^{22}R^{23}$, —$NR^{24}$C(═O)$NR^{24}$C(═O)$R^{20}$, —$NR^{24}$C(═O)$NR^{24}$C(═O)$OR^{20}$, —$NR^{24}$C(═$NR^{25}$)$NR^{22}R^{23}$, —$NR^{24}$C(═O)C(═O)$NR^{22}$, —$NR^{24}$C(═S)$R^{20}$, —$NR^{24}$C(═S)$OR^{20}$, —$NR^{24}$C(═S)$NR^{22}R^{23}$, —$NR^{24}$S(═O)$_2R^{21}$, —$NR^{24}$S(═O)$_2NR^{22}R^{23}$, —$NR^{24}$P(═O)$R^{78}R^{78}$, —$NR^{24}$P(═O)($NR^{22}R^{23}$)($NR^{22}R^{23}$), —$NR^{24}$P(═O)($OR^{20}$)($OR^{20}$), —$NR^{24}$P(═O)($SR^{20}$)($SR^{20}$), —$OR^{20}$, —OCN, —OC(═O)$R^{20}$, —OC(═O)$NR^{22}R^{23}$, —OC(═O)$OR^{20}$, —OC(═$NR^{25}$)$NR^{22}R^{23}$, —OS(═O)$R^{20}$, —OS(═O)$_2R^{20}$, —OS(═O)$_2OR^{20}$, —OS(═O)$_2NR^{22}R^{23}$, —OP(═O)$R^7R^7$, —OP(═O)($NR^{22}R^{23}$)($NR^{22}R^{22}R^{23}$), —OP(═O)($OR^{20}$)($OR^{20}$), —OP(═O)($SR^{20}$)($SR^{20}$), —Si($R^{24}$)$_3$, —SCN, —S(═O)$_nR^{20}$, —S(═O)$_2R^{20}$, —$SO_3R^{27}$, —S(═O)$_2NR^{22}R^{23}$, —S(═O)$NR^{22}R^{23}$, —SP(═O)$R^{78}R^{78}$, —SP(═O)($NR^{22}R^{23}$)($NR^{22}R^{23}$), —SP(═O)($OR^{20}$)($R^{20}$), —SP(═O)($SR^{20}$)($SR^{20}$), —P(═O)$R^{78}R^{78}$, —P(═O)($NR^{22}R^{23}$)($NR^{22}R^{23}$), —P(═O)($OR^{20}$)($OR^{20}$), and —P(═O)($SR^{20}$)($SR^{20}$); or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 401

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(=O)$R^{20}$, —C(=O)O$R^{20}$, —C(=O)N$R^{22}R^{23}$, —C(=O)C(=O)$R^{20}$, —NC, —$NO_2$, —N$R^{22}R^{23}$, —N$R^{24}$N$R^{22}R^{23}$, —N=N$R^{24}$, —N$R^{24}$O$R^{26}$, —N$R^{24}$C(=O)$R^{20}$, —N$R^{24}$C(=O)C(=O)$R^{20}$, —N$R^{24}$C(=)O$R^{21}$, —N$R^2$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=O)C(=O)N$R^{22}R^{23}$, —N$R^{24}$S(=O)$_2R^{21}$, —N$R^{24}$S(=O)$_2$N$R^{22}R^{23}$, —N$R^{24}$P(=O)$R^{78}R^{78}$, —N$R^{24}$P(=O)(N$R^{22}R^{23}$)(N$R^{22}R^{23}$), —N$R^{24}$P(=O)(O$R^{20}$)(O$R^{20}$), —N$R^{24}$P(=O)(S$R^{20}$)(S$R^{20}$), —O$R^{20}$, —OCN, —OC(=O)$R^{20}$, —OC(=O)N$R^{22}R^{23}$, —OC(=O)O$R^{20}$, —OC(=N$R^{25}$)N$R^{22}R^{23}$, —OS(=O)$R^{20}$, —OS(=O)$_2R^{20}$, —OS(=O)$_2$O$R^{20}$, —OS(=O)$_2$N$R^{22}R^{23}$, —OP(=O)$R^{78}R^{78}$, —OP(=O)(N$R^{22}R^{23}$)(N$R^{22}R^{23}$)(N$R^2$), —OP(=O)(O$R^{20}$)(O$R^{20}$), —OP(=O)(S$R^2$)(S$R^{20}$), —Si($R^{24}$)$_3$, —SCN, —S(=O)$_nR^{20}$, —S(=O)$_2$O$R^{20}$, —$SO_3R^{27}$, —S(=O)$_2$N$R^{22}R^{23}$, —S(=O)N$R^{22}R^{23}$, —SP(=O)$R^{78}R^{78}$, —SP(=O)(N$R^{22}R^{23}$)(N$R^{22}R^{23}$), —SP(=O)(O$R^{20}$)(O$R^{20}$), —SP(=O)(S$R^{20}$)(S$R^{20}$), —P(=O)$R^{78}R^{78}$, —P(=O)(N$R^{22}R^{23}$)(N$R^{22}R^{23}$), —P(=O)(O$R^{20}$)(O$R^{20}$), and —P(=O)(S$R^{20}$)(S$R^{20}$); or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 402

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$, 5-15 membered heteroaryl optionally substituted by 1-6 $R^{19}$, halogen, —CN, —C(=O)$R^{20}$, —C(=O)O$R^{20}$, —C(=O)N$R^{22}R^{23}$, —NC, —$NO_2$, —N$R^{22}R^{23}$, —N$R^{24}$N$R^{22}R^{23}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=O)C(=O)N$R^{22}R^{23}$, —N$R^{24}$S(=O)$_2R^{21}$, —N$R^{24}$S(=O)$_2$N$R^{22}R^{23}$, —O$R^{20}$, —OCN, —OC(=O)$R^{20}$, —OC(=O)N$R^{22}R^{23}$, —OC(=O)O$R^{20}$, —OS(=O)$R^{20}$, —OS(=O)$_2R^{20}$, —OS(=O)$_2$O$R^{20}$, —OS(=O)$_2$N$R^{22}R^{23}$, —Si($R^{24}$)$_3$, —SCN, —S(=O)$_nR^{20}$, —S(=O)$_2$O$R^{20}$, —$SO_3R^{27}$, and —S(=O)$_2$N$R^{22}R^{23}$; or any of $R^a$ and $R^b$, $R^a$ and $R^e$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^f$, $R^f$ and $R^h$, and $R^g$ and $R^h$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 403

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)O$R^{20}$, —C(=O)N$R^{22}R^{23}$, —NC, —$NO_2$, —N$R^{22}R^{23}$, —N$R^{24}$N$R^{22}R^{23}$, —N$R^{24}$O$R^{26}$, —N$R^{24}$C(=O)$R^{20}$, —N$R^{24}$C(=O)C(=O)$R^{20}$, —N$R^{24}$C(=O)O$R^{21}$, —N$R^{24}$C(=O)C(=O)O$R^{21}$, —N$R^{24}$C(=O)N$R^{22}R^{23}$, —N$R^{24}$C(=O)N$R^{24}$C(=O)$R^{20}$, —N$R^{24}$C(=O)N$R^{24}$C(=O)O$R^{20}$, —N$R^{24}$C(=O)C(=O)N$R^{22}R^{23}$, —N$R^{24}$S(=O)$_2R^{21}$, —N$R^{24}$S(=O)$_2$N$R^{22}R^{23}$, —O$R^{20}$, —OCN, —OC(=O)$R^{20}$, —OC(=O)N$R^{22}R^{23}$, —OC(=O)O$R^{20}$, —OS(=O)$R^{20}$, —OS(=O)$_2R^{20}$, —OS(=O)$_2R^{20}$, —OS(=O)$_2$N$R^{22}R^{23}$, —Si($R^{24}$)$_3$, —SCN, —S(=O)$_nR^{20}$, —S(=O)$_2R^{20}$, —$SO_3R^{27}$, and —S(=O)$_2$N$R^{22}R^{23}$; or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 404

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)O$R^{20}$, —C(=O)N$R^{22}R^{23}$, —NC, —$NO_2$, —N$R^{22}R^{23}$, —N$R^{24}$C(=O)$R^{20}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —OC(=O)O$R^{20}$, —$S(=O)_nR^{20}$, and —$S(=O)_2NR^{22}R^{23}$; or any of $R^a$ and $R^b$, $R^a$ and $R^e$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 405

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —$C(=O)R^{20}$, —$C(=O)OR^{20}$, —$C(=O)NR^{22}R^{23}$, —NC, —$NO_2$, —$NR^{22}R^{23}$, —$NR^{24}C(=O)R^{20}$, —$NR^{24}C(=O)NR^{22}R^{23}$, —$NR^{24}S(=O)_2R^{21}$, —$NR^{24}S(=O)_2NR^{22}R^{23}$, —$OR^{20}$, —$OC(=O)R^{20}$, —$OC(=O)NR^{22}R^{23}$, —$OC(=O)OR^{20}$, —$S(=O)_nR^{20}$, and —$S(=O)_2NR^{22}R^{23}$; or any of $R^a$ and $R^b$, $R^a$ and $R^e$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 406

The compound of any of Embodiments 1, 3-156, 200-250, or 300-371, wherein $R^a$, $R^b$, $R^e$, $R^d$, $R^e$, $R^f$, $R^g$, and $R^h$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, 5-10 membered heteroaryl optionally substituted by 1-3 $R^{19}$, halogen, —CN, —$C(=O)R^{20}$, —$C(=O)OR^{20}$, —$C(=O)NR^{22}R^{23}$, —$NO_2$, —$NR^{22}R^{23}$, —$NR^{24}C(=O)R^{20}$, —$NR^{24}C(=O)NR^{22}R^{23}$, —$NR^{24}S(=O)_2R^{21}$, —$NR^{24}S(=O)_2NR^{22}R^{23}$, —$OR^{20}$, —$OC(=O)R^{20}$, —$OC(=O)NR^{22}R^{23}$, —$OC(=O)OR^{20}$, —$S(=)_nR^{20}$, and —$S(=O)_2NR^{22}R^{23}$.

Embodiment 407

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, $C_{7-11}$arylalkyl optionally substituted by 1-3 $R^{19}$, halogen, —CN, —$C(=O)R^{20}$, —$C(=O)OR^{20}$, —$C(=O)NR^{22}R^{23}$, —$NO_2$, —$NR^{22}R^{23}$, —$NR^{24}C(=O)R^{20}$, —$NR^{24}S(=O)_2R^{21}$, —$OR^{20}$, —$OC(=O)R^{20}$, —$OC(=O)OR^{20}$, —$S(=)_nR^{20}$, and —$S(=O)_2NR^{22}R^{23}$.

Embodiment 408

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, $C_{7-11}$arylalkyl optionally substituted by 1-3 $R^{19}$, halogen, —$NO_2$, —$NR^{22}R^{23}$, —$NR^{24}C(=O)R^{20}$, and —$NR^{24}S(=O)_2R^{21}$.

Embodiment 409

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, $C_{7-11}$arylalkyl optionally substituted by 1-3 $R^{19}$, —$NR^{22}R^{23}$, —$NR^{24}C(=O)R^{20}$, and —$NR^{24}S(=O)_2R^{21}$.

Embodiment 410

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, $C_{7-11}$arylalkyl optionally substituted by 1-3 $R^{19}$, —$NR^{22}R^{23}$, and —$NR^{24}C(=O)R^{20}$.

Embodiment 411

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, and $C_{7-11}$arylalkyl optionally substituted by 1-3 $R^{19}$.

Embodiment 412

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, and benzyl optionally substituted by 1-3 $R^{19}$.

Embodiment 413

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1 $R^{19}$, and benzyl optionally substituted by 1 $R^{19}$.

Embodiment 414

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, $C_{1-6}$alkyl optionally substituted by 1 $R^{19}$, and benzyl.

Embodiment 415

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, methyl optionally substituted by 1 $R^{19}$, and benzyl optionally substituted by 1 $R^{19}$.

Embodiment 416

The compound of any of Embodiments 1, 3-156, 200-250, or 300-371, wherein $R^a$, $R^b$, $R^c$, $R^d$, $R^e$, $R^f$, $R^g$, and $R^h$ are independently chosen from H, methyl optionally substituted by 1 $R^{19}$, and benzyl.

Embodiment 417

The compound of any of Embodiments 400-416, wherein at least three of $R^a$, $R^b$, $R^c$, $R^d$, $R^e$, $R^f$, $R^g$, and $R^h$ are H.

Embodiment 418

The compound of any of Embodiments 400-416, wherein at least four of $R^a$, $R^b$, $R^c$, $R^d$, $R^e$, $R^f$, $R^g$, and $R^h$ are H.

Embodiment 419

The compound of any of Embodiments 400-416, wherein at least five of $R^a$, $R^b$, $R^c$, $R^d$, $R^e$, $R^f$, $R^g$, and $R^h$ are H.

Embodiment 420

The compound of any of Embodiments 400-416, wherein at least six of $R^a$, $R^b$, $R^c$, $R^d$, $R^e$, $R^f$, $R^g$, and $R^h$ are H.

Embodiment 421

The compound of any of Embodiments 400-416, wherein at least seven of $R^a$, $R^b$, $R^e$, $R^d$, $R^e$, $R^f$, $R^g$, and $R^h$ are H.

Embodiment 422

The compound of any of Embodiments 400-416, wherein $R^a$, $R^b$ $R^c$, $R^e$, $R^f$, $R^g$, and $R^h$ are H.

Embodiment 423

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(═O)$R^{20}$, —C(═O)O$R^{20}$, —C(═O)N$R^{22}R^{23}$, —C(═O)C(═O)$R^{20}$, —C(═N$R^{25}$)$R^{20}$, —C(═N$R^{25}$)N$R^{22}R^{23}$, —C(═NOH)N$R^{22}R^{23}$, —C(═NO$R^{26}$)$R^{20}$, —C(═NN$R^{22}R^{23}$)$R^{20}$, —C(═NN$R^{24}$C(═O)$R^{21}$)$R^{20}$, —C(═NN$R^{24}$C(═O)O$R^{21}$)$R^{20}$, —C(═S)N$R^{22}R^{23}$, —NC, —$NO_2$, —N$R^{22}R^{23}$, —N$R^{24}$N$R^{22}R^{23}$, —N═N$R^{24}$, —N$R^{24}$O$R^{26}$, —N$R^{24}$C(═O)$R^{20}$, —N$R^{24}$C(═O)C(═O)$R^{20}$, —N$R^{24}$C(═O)O$R^{21}$, —N$R^{24}$C(═O)C(═O)O$R^{21}$, —N$R^{24}$C(═O)N$R^{22}R^{23}$, —N$R^{24}$C(═O)N$R^{24}$C(═O)$R^{20}$, —N$R^{24}$C(═O)N$R^{24}$C(═O)O$R^{20}$, —N$R^{24}$C(═N$R^{25}$)N$R^{22}R^{23}$, —N$R^{24}$C(═O)C(═O)N$R^{22}R^{23}$, —N$R^{24}$C(═S)$R^{20}$, —N$R^{24}$C(═S)O$R^{20}$, —N$R^{24}$C(═S)N$R^{22}R^{23}$, —N$R^{24}$S(═O)$_2R^{21}$, —N$R^{24}$S(═O)$_2$N$R^{22}R^{23}$, —N$R^{24}$P(═O)$R^{78}R^{78}$, —N$R^{24}$P(═O)(N$R^{22}R^{23}$)(N$R^{22}R^{23}$), —N$R^{24}$P(═O)(O$R^{20}$)(O$R^{20}$), —N$R^{24}$P(═O)(S$R^{20}$)(S$R^{20}$), —O$R^{20}$, —OCN, —OC(═O)$R^{20}$, —OC(═O)N$R^{22}R^{23}$, —OC(═O)O$R^{20}$, —OC(═N$R^{25}$)N$R^{22}R^{23}$, —OS(═O)$R^{20}$, —OS(═O)$_2R^{20}$, —OS(═O)$_2$O$R^{20}$, —OS(═O)$_2$N$R^{22}R^{23}$, —OP(═O)$R^{78}R^{78}$, —OP(═O)(N$R^{22}R^{23}$)(N$R^{22}R^{23}$), —OP(═O)(O$R^{20}$)(O$R^{20}$), —OP(═O)(S$R^{20}$)(S$R^{20}$), —Si($R^{24}$)$^3$, —SCN, —S(═O)$_n$$R^{20}$, —S(═O)$_2R^{20}$, —$SO_3R^{27}$, —S(═O)$_2$N$R^{22}R^{23}$, —S(═O)N$R^{22}R^{23}$, —SP(═O)$R^{78}R^{78}$, —SP(═O)(N$R^{22}R^{23}$)(N$R^{22}R^{23}$), —SP(═O)(O$R^{20}$)($R^{20}$), —SP(═O)(S$R^{20}$)(S$R^{20}$), —P(═O)$R^{78}R^{78}$, —P(═O)(N$R^{22}R^{23}$)(N$R^{22}R^{23}$), —P(═O)(O$R^{20}$)(O$R^{20}$), and —P(═O)(S$R^{20}$)(S$R^{20}$); or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 424

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6 $R^{19}$, $C_{4-17}$cycloalkylalkyl optionally substituted by 1-6 $R^{19}$, 3-15 membered heterocycloalkyl optionally substituted by 1-6 $R^{19}$, 4-21 membered heterocycloalkylalkyl optionally substituted by 1-6 $R^{19}$, 5-15 membered heteroaryl optionally substituted by 1-6 $R^{19}$, 6-21 membered heteroarylalkyl optionally substituted by 1-6 $R^{19}$, halogen, —CN, —C(═O)$R^{20}$, —C(═O)O$R^{20}$, —C(═O)N$R^{22}R^{23}$, —C(═O)C(═O)$R^{20}$, —NC, —$NO_2$, —N$R^{22}R^{23}$, —N$R^{24}$N$R^{22}R^{23}$, —N═N$R^{24}$, —N$R^{24}$O$R^{26}$, —N$R^{24}$C(═O)$R^{20}$, —N$R^{24}$C(═O)C(═O)$R^{20}$, —N$R^{24}$C(═O)O$R^{21}$, —N$R^{24}$C(═O)C(═O)O$R^{21}$, —N$R^{24}$C(═O)N$R^{22}R^{23}$, —N$R^{24}$C(═O)N$R^{24}$C(═O)$R^{20}$, —N$R^{24}$C(═O)N$R^{24}$C(═O)O$R^{20}$, —N$R^{24}$C(═O)C(═O)N$R^{22}R^{23}$, —N$R^{24}$S(═O)$_2R^{21}$, —N$R^{24}$S(═O)$_2$N$R^{22}R^{23}$, —N$R^{24}$P(═O)$R^{78}R^{78}$, —N$R^{24}$P(═O)(N$R^{22}R^{23}$)(N$R^{22}R^{23}$), —N$R^{24}$P(═O)(O$R^{20}$)(O$R^{20}$), —N$R^{24}$P(═O)(S$R^{20}$)(S$R^{20}$), —O$R^{20}$, —OCN, —OC(═O)$R^{20}$, —OC(═O)N$R^{22}R^{23}$, —OC(═O)O$R^{20}$, —OC(═N$R^{25}$)N$R^{22}R^{23}$, —OS(═O)$R^{20}$, —OS(═O)$_2R^{20}$, —OS(═O)$_2$O$R^{20}$, —OS(═O)$_2$N$R^{22}R^{23}$, —OP(═O)$R^{78}R^{78}$, —OP(═O)(N$R^{22}R^{23}$)(N$R^{22}R^{23}$), —OP(═O)(O$R^{20}$)(O$R^{20}$), —OP(═O)(S$R^{20}$)(S$R^{20}$), —Si($R^{24}$)$_3$, —SCN, —S(═O)$_n$$R^{20}$, —S(═O)$_2$O$R^{20}$, —$SO_3R^{27}$, —S(═O)$_2$N$R^{22}R^{23}$, —S(═O)N$R^{22}R^{23}$, —SP(═O)$R^{78}R^{78}$, —SP(═O)(N$R^{22}R^{23}$)(N$R^{22}R^{23}$), —SP(═O)(O$R^{20}$)(O$R^{20}$), —SP(═O)(S$R^{20}$)(S$R^{20}$), —P(═O)$R^{78}R^{78}$, —P(═O)(N$R^{22}R^{23}$)(N$R^{22}R^{23}$), —P(═O)(O$R^{20}$)(O$R^{20}$), and —P(═O)(SR(S$R^{20}$); or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 425

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-11}$aryl optionally substituted by 1-6 $R^{19}$, $C_{7-16}$arylalkyl optionally substituted by 1-6 $R^{19}$, $C_{3-11}$cycloalkyl optionally substituted by 1-6

$R^{19}$, 3-15 membered heterocycloalkyl optionally substituted by 1-6 $R^{19}$, 5-15 membered heteroaryl optionally substituted by 1-6 $R^{19}$, halogen, —CN, —C(═O)$R^{20}$, —C(═O)O$R^{20}$, —C(═O)N$R^{22}R^{23}$, —NC, —$NO_2$, —N$R^{22}R^{23}$, —N$R^{24}$N$R^{22}R^{23}$, —N$R^{24}$O$R^{26}$, —N$R^{24}$C(═O)$R^{20}$, —N$R^{24}$C(═O)C(═O)$R^{20}$, —N$R^{24}$C(═O)O$R^{21}$, —N$R^{24}$C(═O)C(═O)O$R^{21}$, —N$R^{24}$C(═O)N$R^{22}R^{23}$, —N$R^{24}$C(═O)N$R^{24}$C(═O)$R^{20}$, —N$R^{24}$C(═O)N$R^{24}$C(═O)O$R^{20}$, —N$R^{24}$C(═O)C(═O)N$R^{22}R^{23}$, —N$R^{24}$S(═O)$_2R^{21}$, —N$R^{24}$S(═O)$_2$N$R^{22}R^{23}$, —O$R^{20}$, —OCN, —OC(═O)$R^{20}$, —OC(═O)N$R^{22}R^{23}$, —OC(═O)O$R^{20}$, —OS(═O)$R^{20}$, —OS(═O)$_2R^{20}$, —OS(═O)$_2$O$R^{20}$, —OS(═O)$_2$N$R^{22}R^{23}$, —Si$(R^{24})_3$, —SCN, —S(═O)$_nR^{20}$, —S(═O)$_2$O$R^{20}$, —$SO_3R^{27}$, and —S(═O)$_2$N$R^{22}R^{23}$; or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-11}$aryl optionally substituted by 1-6 $R^{19}$, $C_{3-11}$cycloalkyl optionally substituted by 1-6 $R^{19}$, 3-15 membered heterocycloalkyl optionally substituted by 1-6 $R^{19}$ or a 5-15 membered heteroaryl optionally substituted by 1-6 $R^{19}$.

Embodiment 426

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(═O)$R^{20}$, —C(═O)O$R^{20}$, —C(═O)N$R^{22}R^{23}$, —NC, —$NO_2$, —N$R^{22}R^{23}$, —N$R^{24}$N$R^{22}R^{23}$, —N$R^{24}$O$R^{26}$, —N$R^{24}$C(═O)$R^{20}$, —N$R^{24}$C(═O)C(═O)$R^{20}$, —N$R^{24}$C(═O)O$R^{21}$, —N$R^{24}$C(═O)C(═O)O$R^{21}$, —N$R^{24}$C(═O)N$R^{22}R^{23}$, —N$R^{24}$C(═O)N$R^{24}$C(═O)$R^{20}$, —N$R^{24}$C(═O)N$R^{24}$C(═O)O$R^{20}$, —N$R^{24}$C(═O)C(═O)N$R^{22}R^{23}$, —N$R^{24}$S(═O)$_2R^{21}$, —N$R^{24}$S(═O)$_2$N$R^{22}R^{23}$, —O$R^{20}$, —OCN, —OC(═O)$R^{20}$, —OC(═O)N$R^{22}R^{23}$, —OC(═O)O$R^{20}$, —OS(═O)$R^{20}$, —OS(═O)$_2R^{20}$, —OS(═O)$_2$O$R^{20}$, —OS(═O)$_2$N$R^{22}R^{23}$, —Si$(R^{24})_3$, —SCN, —S(═O)$_nR^{20}$, —S(═O)$_2$O$R^{20}$, —$SO_3R^{27}$, and —S(═O)$_2$N$R^{22}R^{23}$; or any of $R^a$ and $R^b$, $R^a$ and $R^e$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 427

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{7-11}$arylalkyl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(═O)$R^{20}$, —C(═O)O$R^{20}$, —C(═O)N$R^{22}R^{23}$, —NC, —$NO_2$, —N$R^{22}R^{23}$, —N$R^{24}$C(═O)$R^{20}$, —N$R^{24}$C(═O)N$R^{22}R^{23}$, —N$R^{24}$S(═O)$_2R^{21}$, —N$R^{24}$S(═O)$_2$N$R^{22}R^{23}$, —O$R^{20}$, —OC(═O)$R^{20}$, —OC(═O)N$R^{22}R^{23}$, —OC(═O)O$R^{20}$, —S(═O)$_nR^{20}$, and —S(═O)$_2$N$R^{22}R^{23}$; or any of $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$ or a 5-10 membered heteroaryl optionally substituted by 1-6 $R^{19}$.

Embodiment 428

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{2-6}$alkenyl optionally substituted by 1-3 $R^{19}$, $C_{2-6}$alkynyl optionally substituted by 1-3 $R^{19}$, $C_{6-10}$aryl optionally substituted by 1-3 $R^{19}$, $C_{7-11}$arylalkyl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$, 5-10 membered heteroaryl optionally substituted by 1-3 $R^{19}$, halogen, —CN, —C(═O)$R^{20}$, —C(═O)O$R^{20}$, —C(═O)N$R^{22}R^{23}$, —NC, —$NO_2$, —N$R^{22}R^{23}$, —N$R^{24}$C(═O)$R^{20}$, —N$R^{24}$C(═O)N$R^{22}R^{23}$, —N$R^{24}$S(═O)$_2R^{21}$, —N$R^{24}$S(═O)$_2$N$R^{22}R^{23}$, —O$R^{20}$, —OC(═O)$R^{20}$, —OC(═O)N$R^{22}R^{23}$, —OC(═O)O$R^{20}$, —S(═O)$_nR^{20}$, and —S(═O)$_2$N$R^{22}R^{23}$; or any of $R^a$ and $R^b$, $R^a$ and $R^e$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-10}$aryl optionally substituted by 1-3 $R^{19}$, $C_{3-10}$cycloalkyl optionally substituted by 1-3 $R^{19}$, 3-10 membered heterocycloalkyl optionally substituted by 1-3 $R^{19}$ or a 5-10 membered heteroaryl optionally substituted by 1-3 $R^{19}$.

Embodiment 429

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, 5-10 membered heteroaryl optionally substituted by 1-3 $R^{19}$, halogen, —CN, —C(═O)$R^{20}$, —C(═O)O$R^{20}$, —C(═O)N$R^{22}R^{23}$, —$NO_2$, —N$R^{22}R^{23}$, —N$R^{24}$C(═O)$R^{20}$, —N$R^{24}$C(═O)N$R^{22}R^{23}$, —N$R^{24}$S(═O)$_2R^{21}$, —N$R^{24}$S(═O)$_2$N$R^{22}R^{23}$, —O$R^{20}$, —OC(═O)$R^{20}$, —OC(═O)N$R^{22}R^{23}$, —OC(═O)O$R^{20}$, —S(═O)$_nR^{20}$, and —S(═O)$_2$N$R^{22}R^{23}$.

Embodiment 430

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{7-11}$arylalkyl optionally substituted by 1-3 $R^{19}$, halogen, —CN, —C(═O)$R^{20}$, —C(═O)O$R^{20}$, —C(═O)N$R^{22}R^{23}$, —$NO_2$, —N$R^{22}R^{23}$, —N$R^{24}$C(═O)$R^{20}$, —N$R^{24}$S(═O)$_2R^{21}$, —O$R^{20}$, —OC(═O)$R^{20}$, —OC(═O)O$R^{20}$, —S(═O)$_nR^{20}$, and —S(═O)$_2$N$R^{22}R^{23}$.

Embodiment 431

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{7-11}$arylalkyl optionally substituted by 1-3 $R^{19}$, halogen, —$NO_2$, —$NR^{22}R^{23}$, —$NR^{24}C(=O)R^{20}$, and —$NR^{24}S(=O)_2R^{21}$.

Embodiment 432

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{7-11}$arylalkyl optionally substituted by 1-3 $R^{19}$, —$NR^{22}R^{23}$, —$NR^{24}C(=O)R^{20}$, and —$NR^{24}S(=O)_2R^{21}$.

Embodiment 433

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{7-11}$arylalkyl optionally substituted by 1-3 $R^{19}$, —$NR^{22}R^{23}$, and —$NR^{24}C(=O)R^{20}$.

Embodiment 434

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, and $C_{7-11}$arylalkyl optionally substituted by 1-3 $R^{19}$.

Embodiment 435

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, and benzyl optionally substituted by 1-3 $R^{19}$.

Embodiment 436

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1 $R^{19}$, and benzyl optionally substituted by 1 $R^{19}$.

Embodiment 437

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, $C_{1-6}$alkyl optionally substituted by 1 $R^{19}$, and benzyl.

Embodiment 438

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, methyl optionally substituted by 1 $R^{19}$, and benzyl optionally substituted by 1 $R^{19}$.

Embodiment 439

The compound of any of Embodiments 1, 3-156, 200-250, or 300-371, wherein $R^a$, $R^b$, $R^c$, $R^e$, $R^f$, $R^g$, and $R^h$ are H; and $R^d$ is chosen from H, methyl optionally substituted by 1 $R^{19}$, and benzyl.

Embodiment 440

The compound of any of Embodiments 1, 3-156, 200-250, or 300-371, wherein $R^a$, $R^b$, $R^c$, $R^d$, $R^e$, $R^f$, $R^g$, and $R^h$ are H.

Embodiment 500

The compound of any of Embodiments 1-156, 200-250, 300-371, or 400-440, wherein $R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —$C(=O)R^{30}$, —$C(=O)OR^{30}$, —$C(=O)NR^{32}R^{33}$, —$C(=O)C(=O)R^{30}$, —$C(=NR^{35})R^{30}$, —$C(=NR^{35})NR^{32}R^{33}$, —$C(=NOH)NR^{32}R^{33}$, —$C(=NOR^{36})R^{30}$, —$C(=NNR^{32}R^{33})R^{30}$, —$C(=NNR^{34}C(=O)R^{31})R^{30}$, —$C(=NNR^{34}C(=O)OR^{31})R^{30}$, —$C(=S)NR^{32}R^{33}$, —NC, —$NO_2$, —$NR^{32}R^{33}$, —$NR^{34}NR^{32}R^{33}$, —$N=NR^{34}$, =$NR^{30}$, =$NOR^{30}$, —$NR^{34}OR^{36}$, —$NR^{34}C(=O)R^{30}$, —$NR^{34}C(=O)C(=O)R^{30}$, —$NR^{34}C(=O)OR^{31}$, —$NR^{34}C(=O)C(=O)OR^{31}$, —$NR^{34}C(=O)NR^{32}R^{33}$, —$NR^{34}C(=O)NR^{34}C(=O)R^{30}$, —$NR^{34}C(=O)NR^{34}C(=O)OR^{30}$, —$NR^{34}C(=NR^{35})NR^{32}R^{33}$, —$NR^{34}C(=O)C(=O)NR^{32}R^{33}$, —$NR^{34}C(=S)R^{30}$, —$NR^{34}C(=S)OR^{30}$, —$NR^{34}C(=S)NR^{32}R^{33}$, —$NR^{34}S(=O)_2R^{31}$, —$NR^{34}S(=O)_2NR^{32}R^{33}$, —$NR^{34}P(=O)R^{78}R^{78}$, —$NR^{34}P(=O)(NR^{32}R^{33})(NR^{32}R^{33})$, —$NR^{34}P(=O)(OR^{30})(OR^{30})$, —$NR^{34}P(=O)(SR^{30})(SR^{3})$, —$OR^{30}$, =O, —OCN, —$OC(=O)R^{30}$, —$OC(=O)NR^{32}R^{33}$, —$OC(=O)OR^{30}$, —$OC(=NR^{35})NR^{32}R^{33}$, —$OS(=O)R^{30}$, —$OS(=O)_2R^{30}$, —$OS(=O)_2OR^{30}$, —$OS(=O)_2NR^{32}R^{33}$, —$OP(=O)R^{78}R^{78}$, —$OP(=O)(NR^{32}R^{33})(NR^{32}R^{33})$, —$OP(=O)(OR^{30})$, —$OP(=O)(SR^{30})(SR^{30})$, —$Si(R^{34})_3$, —SCN, =S, —$S(=O)_nR^{30}$, —$S(=O)_2OR^{30}$, —$SO_3R^{37}$, —$S(=O)_2NR^{32}R^{33}$, —$S(=O)NR^{32}R^{33}$, —$SP(=O)R^{78}R^{78}$, —$SP(=O)(NR^{32}R^{33})(NR^{32}R^{33})$, —$SP(=O)(OR^{30})(OR^{30})$, —$SP(=O)(SR^{30})(SR^{30})$, —$P(=O)R^{78}R^{78}$, —$P(=O)(NR^{32}R^{33})(NR^{32}R^{33})$, —$P(=O)(OR^{30})(OR^{30})$, and —$P(=O)(SR^{30})(SR^{30})$.

Embodiment 501

The compound of any of Embodiments 1-156, 200-250, 300-371, or 400-440, wherein $R^{19}$ at each occurrence is independently chosen from $C_{1-6}$alkyl optionally substituted by 1-6 $R^{39}$, $C_{2-6}$alkenyl optionally substituted by 1-6 $R^{39}$, $C_{2-6}$alkynyl optionally substituted by 1-6 $R^{39}$, $C_{6-11}$aryl optionally substituted by 1-6 $R^{39}$, $C_{7-16}$arylalkyl optionally substituted by 1-6 $R^{39}$, $C_{3-11}$cycloalkyl optionally substituted by 1-6 $R^{39}$, $C_{4-17}$cycloalkylalkyl optionally substituted by 1-6 $R^{39}$, 3-15 membered heterocycloalkyl optionally substituted by 1-6 $R^{39}$, 4-21 membered heterocycloalkylalkyl optionally substituted by 1-6 $R^{39}$, 5-15 membered heteroaryl optionally substituted by 1-6 $R^{39}$, 6-21 membered heteroarylalkyl optionally substituted by 1-6 $R^{39}$, halogen, —CN, —$C(=O)R^{30}$, —$C(=)OR^{30}$, —$C(=O)NR^{32}R^{33}$, —$C(=O)C(=O)R^{30}$, —$C(=NR^{35})R^{30}$, —$C(=NR^{35})NR^{32}R^{33}$, —$C(=NOH)NR^{32}R^{33}$, —$C(=NOR^{36})R^{3}$, —C(=NNR$^{32}$R$^{33}$)R$^{30}$, —C(=NNR$^{34}$C(=O)R$^{31}$)R$^{30}$, —C(=NNR$^{34}$C(=O)OR$^{31}$)R$^{30}$, —C(=S)NR$^{32}$R$^{33}$, —NC, —NO$_2$, —NR$^{32}$R$^{33}$, —NR$^{34}$NR$^{32}$R$^{33}$, —N=NR$^{34}$, =NR$^{30}$, =NOR$^{30}$, —NR$^{34}$OR$^{36}$, —NR$^{34}$C(=O)R$^{30}$, —NR$^{34}$C(=O)C(=O)R$^{30}$, —NR$^{34}$C(=O)OR$^{31}$, —NR$^{34}$C(=O)C(=O)OR$^{31}$, —NR$^{34}$C(=O)NR$^{32}$R$^{33}$, —NR$^{34}$C(=O)NR$^{34}$C(=O)R$^{30}$, —NR$^{34}$C(=O)NR$^{34}$C(=O)OR$^{30}$, —NR$^{34}$C(=NR$^{35}$)NR$^{32}$R$^{33}$, —NR$^{34}$C(=O)C(=O)NR$^{32}$R$^{30}$, —NR$^{34}$C(=S)R$^{30}$, —NR$^{34}$C(=S)OR$^{30}$, —NR$^{34}$C(=S)NR$^{32}$R$^{33}$, —NR$^{34}$S(=O)$_2$R$^{31}$, —NR$^{34}$S(=O)$_2$NR$^{32}$R$^{33}$, —NR$^{34}$P(=O)R$^{78}$R$^{78}$, —NR$^{34}$P(=O)(NR$^{32}$R$^{33}$)(NR$^{32}$R$^{33}$), —NR$^{34}$P(=O)(OR$^{30}$)(OR$^{30}$), —NR$^{34}$P(=O)(SR$^{30}$)(SR$^{3}$), —OR$^{30}$, =O, —OCN, —OC(=O)R$^{3}$, —OC(=O)NR$^{32}$R$^{33}$, —OC(=O)OR$^{30}$, —OC(=NR$^{35}$)NR$^{32}$R$^{33}$, —OS(=O)R$^{30}$, —OS(=O)$_2$R$^{30}$, —OS(=O)$_2$OR$^{30}$, —OS(=O)$_2$NR$^{32}$R$^{33}$, —OP(=O)R$^{78}$R$^{78}$, —OP(=O)(NR$^{32}$R$^{33}$)(NR$^{32}$R$^{33}$), —OP(=O)(OR$^{30}$)(OR$^{30}$), —OP(=O)(SR$^{30}$)(SR$^{30}$), —Si(R$^{34}$)$_3$, —SCN, =S, —S(=O)$_n$R$^{30}$, —S(=O)$_2$OR$^{30}$, —SO$_3$R$^{37}$, —S(=O)$_2$NR$^{32}$R$^{33}$, —S(=O)NR$^{32}$R$^{33}$, —SP(=O)R$^{78}$R$^{78}$, —SP(=O)(NR$^{32}$R$^{33}$)(NR$^{32}$R$^{33}$), —SP(=O)(OR$^{30}$)(OR$^{30}$), —SP(=O)(SR$^{30}$)(SR$^{30}$), —P(=O)R$^{78}$R$^{78}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$)(SR).

Embodiment 502

The compound of any of Embodiments 1-156, 200-250, 300-371, or 400-440, wherein R$^{19}$ at each occurrence is independently chosen from C$_{1-6}$alkyl optionally substituted by 1-6 R$^{39}$, C$_{2-6}$alkenyl optionally substituted by 1-6 R$^{39}$, C$_{2-6}$alkynyl optionally substituted by 1-6 R$^{39}$, C$_{6-11}$aryl optionally substituted by 1-6 R$^{39}$, C$_{7-16}$arylalkyl optionally substituted by 1-6 R$^{39}$, C$_{3-11}$cycloalkyl optionally substituted by 1-6 R$^{39}$, C$_{4-17}$cycloalkylalkyl optionally substituted by 1-6 R$^{39}$, 3-15 membered heterocycloalkyl optionally substituted by 1-6 R$^{39}$, 4-21 membered heterocycloalkylalkyl optionally substituted by 1-6 R$^{39}$, 5-15 membered heteroaryl optionally substituted by 1-6 R$^{39}$, 6-21 membered heteroarylalkyl optionally substituted by 1-6 R$^{39}$, halogen, —CN, —C(=O)R$^{30}$, —C(=)OR$^{30}$, —C(=O)NR$^{32}$R$^{33}$, —C(=)C(=)R$^{30}$, —NC, —NO$_2$, —NR$^{32}$R$^{33}$, —NR$^{34}$NR$^{32}$R$^{33}$, —NR$^{34}$OR$^{36}$, —NR$^{34}$C(=O)R$^{30}$, —NR$^{34}$C(=O)C(=O)R$^{30}$, —NR$^{34}$C(=O)OR$^{31}$, —NR$^{34}$C(=O)C(=O)OR$^{31}$, —NR$^{34}$C(=O)NR$^{32}$R$^{33}$, —NR$^{34}$C(=O)NR$^{34}$C(=O)R$^{30}$, —NR$^{34}$C(=O)NR$^{34}$C(=O)OR$^{30}$, —NR$^{34}$C(=NR$^{35}$)NR$^{32}$R$^{33}$, —NR$^{34}$C(=O)C(=O)NR$^{32}$R$^{33}$, —NR$^{34}$S(=O)$_2$R$^{31}$, —NR$^{34}$S(=O)$_2$NR$^{32}$R$^{33}$, —OR$^{30}$, =O, —OCN, —OC(=O)R$^{30}$, —OC(=O)NR$^{32}$R$^{33}$, —OC(=O)OR$^{30}$, —OC(=NR$^{35}$)NR$^{32}$R$^{33}$, —Si(R$^{34}$)$_3$, —SCN, =S, —S(=O)$_n$R$^{30}$, —S(=O)$_2$OR$^{30}$, —SO$_3$R$^{37}$, —S(=O)$_2$NR$^{32}$R$^{33}$, —S(=O)NR$^{32}$R$^{33}$, —P(=O)R$^{78}$R$^{78}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$).

Embodiment 503

The compound of any of Embodiments 1-156, 200-250, 300-371, or 400-440, wherein R$^{19}$ at each occurrence is independently chosen from C$_{1-6}$alkyl optionally substituted by 1-3 R$^{39}$, C$_{2-6}$alkenyl optionally substituted by 1-3 R$^{39}$, C$_{2-6}$alkynyl optionally substituted by 1-3 R$^{39}$, C$_{6-11}$aryl optionally substituted by 1-3 R$^{39}$, C$_{7-16}$arylalkyl optionally substituted by 1-3 R$^{39}$, C$_{3-11}$cycloalkyl optionally substituted by 1-3 R$^{39}$, C$_{4-17}$cycloalkylalkyl optionally substituted by 1-3 R$^{39}$, 3-15 membered heterocycloalkyl optionally substituted by 1-3 R$^{39}$, 4-21 membered heterocycloalkylalkyl optionally substituted by 1-3 R$^{39}$, 5-15 membered heteroaryl optionally substituted by 1-3 R$^{39}$, 6-21 membered heteroarylalkyl optionally substituted by 1-3 R$^{39}$, halogen, —CN, —C(=O)R$^{30}$, —C(=)OR$^{30}$, —C(=O)NR$^{32}$R$^{33}$, —C(=O)C(=O)R$^{30}$, —NC, —NO$_2$, —NR$^{32}$R$^{33}$, —NR$^{34}$NR$^{32}$R$^{33}$, —NR$^{34}$OR$^{36}$, —NR$^{34}$C(=O)R$^{30}$, —NR$^{34}$C(=O)C(=O)R$^{30}$, —NR$^{34}$C(=O)OR$^{31}$, —NR$^{34}$C(=O)C(=O)OR$^{31}$, —NR$^{34}$C(=O)NR$^{32}$R$^{33}$, —NR$^{34}$C(=O)NR$^{34}$C(=O)R$^{30}$, —NR$^{34}$C(=O)NR$^{34}$C(=O)OR$^{3}$, —NR$^{34}$C(=NR$^{35}$)NR$^{32}$R$^{33}$, —NR$^{34}$C(=O)C(=O)NR$^{32}$R$^{33}$, —NR$^{34}$S(=O)$_2$R$^{31}$, —NR$^{34}$S(=O)$_2$NR$^{32}$R$^{33}$, —OR$^{30}$, =O, —OCN, —OC(=O)R$^{30}$, —OC(=O)NR$^{32}$R$^{33}$, —OC(=O)OR$^{30}$, —OC(=NR$^{35}$)NR$^{32}$R$^{33}$, —Si(R$^{34}$)$_3$, —SCN, =S, —S(=O)$_n$R$^{30}$, —S(=O)$_2$OR$^{30}$, —SO$_3$R$^{37}$, —S(=O)$_2$NR$^{32}$R$^{33}$, —S(=O)NR$^{32}$R$^{33}$, —P(=O)R$^{78}$R$^{78}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$).

Embodiment 504

The compound of any of Embodiments 1-156, 200-250, 300-371, or 400-440, wherein R$^{19}$ at each occurrence is independently chosen from C$_{1-6}$alkyl optionally substituted by 1-3 R$^{39}$, C$_{2-6}$alkenyl optionally substituted by 1-3 R$^{39}$, C$_{2-6}$alkynyl optionally substituted by 1-3 R$^{39}$, C$_{6-10}$aryl optionally substituted by 1-3 R$^{39}$, C$_{7-11}$arylalkyl optionally substituted by 1-3 R$^{39}$, C$_{3-10}$cycloalkyl optionally substituted by 1-3 R$^{39}$, 3-10 membered heterocycloalkyl optionally substituted by 1-3 R$^{39}$, 5-10 membered heteroaryl optionally substituted by 1-3 R$^{39}$, halogen, —CN, —C(=O)R$^{30}$, —C(=)OR$^{30}$, —C(=O)NR$^{32}$R$^{33}$, —C(=O)C(=O)R$^{30}$, —NC, —NO$_2$, —NR$^{32}$R$^{33}$, —NR$^{34}$NR$^{32}$R$^{33}$, —NR$^{34}$OR$^{36}$, —NR$^{34}$C(=O)R$^{30}$, —NR$^{34}$C(=O)C(=O)R$^{30}$, —NR$^{34}$C(=O)OR$^{31}$, —NR$^{34}$=O)C(=O)OR$^{31}$, —NR$^{34}$C(=O)NR$^{32}$R$^{33}$, —NR$^{34}$C(=O)NR$^{34}$C(=O)R$^{30}$, —NR$^{34}$C(=O)NR$^{34}$C(=O)OR$^{30}$, —NR$^{34}$C(=NR$^{35}$)NR$^{32}$R$^{33}$, —NR$^{34}$C(=O)C(=O)NR$^{32}$R$^{33}$, —NR$^{34}$S(=O)$_2$R$^{31}$, —NR$^{34}$S(=O)$_2$NR$^{32}$R$^{33}$, —OR$^{30}$, =O, —OCN, —OC(=O)R$^{30}$, —OC(=O)NR$^{32}$R$^{33}$, —OC(=O)OR$^{30}$, —OC(=NR$^{35}$)NR$^{32}$R$^{33}$, —Si(R$^{34}$)$_3$, —SCN, =S, —S(=O)$_n$R$^{30}$, —S(=O)$_2$OR$^{30}$, —SO$_3$R$^{37}$, —S(=O)$_2$NR$^{32}$R$^{33}$, —S(=O)NR$^{32}$R$^{33}$, —P(=O)R$^{78}$R$^{78}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$).

Embodiment 505

The compound of any of Embodiments 1-156, 200-250, 300-371, or 400-440, wherein R$^{19}$ at each occurrence is independently chosen from C$_{1-6}$alkyl optionally substituted by 1-3 R$^{39}$, C$_{2-6}$alkenyl optionally substituted by 1-3 R$^{39}$, C$_{2-6}$alkynyl optionally substituted by 1-3 R$^{39}$, C$_{6-10}$aryl optionally substituted by 1-3 R$^{39}$, C$_{7-11}$arylalkyl optionally substituted by 1-3 R$^{39}$, C$_{3-10}$cycloalkyl optionally substituted by 1-3 R$^{39}$, 3-10 membered heterocycloalkyl optionally substituted by 1-3 R$^{39}$, 5-10 membered heteroaryl optionally substituted by 1-3 R$^{39}$, halogen, —CN, —C(=O)R$^{30}$, —C(=O)OR$^{30}$, —C(=O)NR$^{32}$R$^{33}$, —NO$_2$, —NR$^{32}$R$^{33}$, —NR$^{34}$C(=O)R$^{30}$, —NR$^{34}$C(=O)OR$^{31}$, —NR$^{34}$C(=O)NR$^{32}$R$^{33}$, —NR$^{34}$S(=O)$_2$R$^{31}$, —NR$^{34}$S(=O)$_2$NR$^{32}$R$^{33}$, —OR$^{30}$, =O, —OC(=O)R$^{3}$, —OC(=O)NR$^{32}$R$^{33}$, —Si(R$^{34}$)$_3$, =S, —S(=O)$_n$R$^{30}$, —S(=O)$_2$OR$^{3}$, —SO$_3$R$^{37}$, —S(=O)$_2$NR$^{32}$R$^{33}$, —S(=O)NR$^{32}$R$^{33}$, —P(=O)R$^{78}$R$^{78}$, —P(=O)(NR$^{32}$R$^{33}$)(NR$^{32}$R$^{33}$), —P(=O)(OR$^{30}$)(OR$^{30}$), and —P(=O)(SR$^{30}$)(SR$^{30}$).

Embodiment 506

The compound of any of Embodiments 1-156, 200-250, 300-371, or 400-440, wherein R$^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{2-6}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, —CN, —C(═O)$R^3$, —C(═O)$OR^{30}$, —C(═O)$NR^{32}R^{33}$, —$NO_2$, —$NR^{32}R^{33}$, —$NR^{34}$C(═O)$R^{30}$, —$NR^{34}$C(═O)$OR^{31}$, —$NR^{34}$C(═O)$NR^{32}R^{33}$, —$NR^{34}S(═O)_2R^{31}$, —$NR^{34}S(═O)_2NR^{32}R^{33}$, —$OR^{30}$, ═O, —OC(═O)$R^3$, —OC(═O)$NR^{32}R^{33}$, —$Si(R^{34})_3$, ═S, —$S(═O)_nR^3$, —$S(═O)_2NR^{32}R^{33}$, and —S(═O)$NR^{32}R^{33}$.

Embodiment 507

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-10}$cycloalkyl optionally substituted by 1-3 $R^{39}$, 3-10 membered heterocycloalkyl optionally substituted by 1-3 $R^{39}$, 5-10 membered heteroaryl optionally substituted by 1-3 $R^{39}$, halogen, —CN, —C(═O)$R^{30}$, —C(═O)$OR^{30}$, —C(═O)$NR^{32}R^{33}$, —$NO_2$, —$NR^{32}R^{33}$, —$NR^{34}$C(═O)$R^{30}$, —$NR^{34}$C(═O)$NR^{32}R^{33}$, —$NR^{34}S(═O)_2R^{31}$, —$NR^{34}S(═O)_2NR^{32}R^{33}$, —OR, ═O, —OC(═O)$R^{30}$, —OC(═O)$NR^{32}R^{33}$, —$Si(R^{34})_3$, ═S, —$S(═O)_nR^{30}$, and —$S(═O)_2NR^{32}R^{33}$.

Embodiment 508

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)$R^3$, —C(═O)$OR^3$, —C(═O)$NR^{32}R^{33}$, —$NO_2$, —$NR^{32}R^{33}$, —$NR^{34}$C(═O)$R^{30}$, —$NR^{34}$C(═O)$NR^{32}R^{33}$, —$NR^{34}S(═O)_2R^{31}$, —$NR^{34}S(═O)_2NR^{32}R^{33}$, —$OR^{30}$, ═O, —OC(═O)$R^{30}$, —OC(═O)$NR^{32}R^{33}$, —$Si(R^{34})_3$, ═S, —$S(═O)_nR^{30}$, and —$S(═O)_2NR^{32}R^{33}$.

Embodiment 509

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)$R^3$, —C(═O)$OR^{30}$, —C(═O)$NR^{32}R^{33}$, —$NO_2$, —$NR^{32}R^{33}$, —$NR^{34}$C(═O)$R^{30}$, —$NR^{34}S(═O)_2R^{31}$, —$OR^{30}$, ═O, —OC(═O)$R^{30}$, —OC(═O)$NR^{32}R^{33}$, —$Si(R^{34})_3$, —$S(═O)_nR^{30}$, and —$S(═O)_2NR^{32}R^{33}$.

Embodiment 510

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)$R^{30}$, —C(═O)$NR^{32}R^{33}$, —$NR^{32}R^{33}$, —$NR^{34}$C(═O)$R^{30}$, —$NR^{34}S(═O)_2R^{31}$, —$OR^{30}$, ═O, —$S(═O)_nR^{30}$, and —$S(═O)_2NR^{32}R^{33}$.

Embodiment 511

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)$R^{30}$, —C(═O)$NR^{32}R^{33}$, —$NR^{32}R^{33}$, —$NR^{34}$C(═O)$R^{30}$, —$OR^{30}$, and ═O.

Embodiment 512

The compound of any of Embodiments 1-156, 200-250, 300-371, or 400-440, wherein $R^{19}$ at each occurrence is independently chosen from $C_{1-6}$alkyl, $C_{6-10}$aryl, $C_{7-11}$arylalkyl, $C_{3-6}$cycloalkyl, 3-6 membered heterocycloalkyl, 5-6 membered heteroaryl, halogen, —CN, —C(═O)$R^{30}$, —C(═O)$NR^{32}R^{33}$, —$NR^{32}R^{33}$, —$NR^{34}$C(═O)$R^{30}$, —$OR^{30}$, and ═O.

Embodiment 513

The compound of any of Embodiments 1-156, 200-250, 300-371, or 400-440, wherein $R^{19}$ at each occurrence is independently chosen from $C_{1-6}$alkyl, $C_{6-10}$aryl, $C_{7-11}$arylalkyl, $C_{3-6}$cycloalkyl, 3-6 membered heterocycloalkyl, 5-6 membered heteroaryl, halogen, —C(═O)$R^{30}$, —C(═O)$OR^{30}$, —C(═O)$NR^{32}R^{33}$, —$NR^{32}R^{33}$, and $OR^{30}$.

Embodiment 514

The compound of any of Embodiments 1-156, 200-250, 300-371, or 400-440, wherein $R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —C(═O)$NR^{32}R^{33}$, —$NO_2$, —$NR^{32}R^{33}$, and —$OR^{30}$.

Embodiment 515

The compound of any of Embodiments 1-156, 200-250, 300-371, or 400-440, wherein $R^{19}$ at each occurrence is independently chosen from $C_{1-6}$alkyl optionally substituted by 1-13 $R^{39}$.

Embodiment 516

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{6-10}$aryl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —C(═O)OR$^{30}$, —NR$^{32}$R$^{33}$, and —OR$^{30}$.

Embodiment 517

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, phenyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —C(═O)OR$^{30}$, —NR$^{32}$R$^{33}$, and —OR$^{3}$.

Embodiment 518

The compound of any of Embodiments 1-156, 200-250, 300-371, or 400-440, wherein $R^{19}$ at each occurrence is independently chosen from $C_{1-6}$alkyl, phenyl optionally substituted by 1-3 $R^{39}$, $C_{3-6}$cycloalkyl, 3-6 membered heterocycloalkyl optionally substituted by 1-3 $R^{39}$, 5-6 membered heteroaryl, halogen, —C(═O)OR$^{30}$, —NR$^{32}$R$^{33}$, and —OR$^{30}$.

Embodiment 519

The compound of any of Embodiments 1-156, 200-250, 300-371, or 400-440, wherein $R^{19}$ at each occurrence is independently chosen from $C_{1-6}$alkyl, phenyl optionally substituted by 1 $R^{39}$, $C_{3-6}$cycloalkyl, 3-6 membered heterocycloalkyl optionally substituted by 1 $R^{39}$, 5-6 membered heteroaryl, halogen, —C(═O)OR$^{30}$, —NR$^{32}$R$^{33}$, and —OR$^{30}$.

Embodiment 520

The compound of any of Embodiments 1-156, 200-250, 300-371, or 400-440, wherein $R^{19}$ at each occurrence is independently chosen from $C_{1-6}$alkyl, phenyl, $C_{3-6}$cycloalkyl, 3-6 membered heterocycloalkyl, 5-6 membered heteroaryl, halogen, —C(═O)OR$^{30}$, —NR$^{32}$R$^{33}$, and —OR$^{30}$.

Embodiment 521

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)R$^{30}$, —C(═O)OR$^{30}$, —C(═O)NR$^{32}$R$^{33}$, —NO$_2$, —NR$^{32}$R$^{33}$, —NR$^{34}$C(═O)R$^{30}$, —NR$^{34}$C(═O)NR$^{32}$R$^{33}$, —NR$^{34}$S(═O)$_2$R$^{31}$, —NR$^{34}$S(═O)$_2$NR$^{32}$R$^{33}$, —OR$^{30}$, ═O, —OC(═O)R$^{3}$, —OC(═O)NR$^{32}$R$^{33}$, —Si(R$^{34}$)$_3$, ═S, —S(═O)$_n$R$^{30}$, and —S(═O)$_2$NR$^{32}$R$^{33}$.

Embodiment 522

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)OR$^{30}$, —C(═O)NR$^{32}$R$^{33}$, —NR$^{32}$R$^{33}$, —NR$^{34}$C(═O)R$^{30}$, —NR$^{34}$S(═O)$_2$R$^{31}$, —OR$^{30}$, ═O, —OC(═O)R$^{3}$, —S(═O)$_n$R$^{30}$, and —S(═O)$_2$NR$^{32}$R$^{33}$.

Embodiment 523

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, —CN, —C(═O)OR$^{30}$, —C(═O)NR$^{32}$R$^{33}$, —NR$^{32}$R$^{33}$, —NR$^{34}$S(═O)$_2$R$^{31}$, —OR$^{30}$, and ═O.

Embodiment 524

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, —CN, —C(═O)OR$^{30}$, —C(═O)NR$^{32}$R$^{33}$, —NR$^{32}$R$^{33}$, —NR$^{34}$S(═O)$_2$R$^{31}$, and —OR$^{30}$.

Embodiment 525

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, benzyl optionally substituted by 1-3 $R^{39}$, cyclopropyl optionally substituted by 1-3 $R^{39}$, 6 membered heterocycloalkyl optionally substituted by 1-3 $R^{39}$, 5 membered heteroaryl optionally substituted by 1-3 $R^{39}$, —CN, —C(═O)OR$^{30}$, —C(═O)NR$^{32}$R$^{33}$, —NR$^{32}$R$^{33}$, —NR$^{34}$S(═O)$_2$R$^{31}$, —OR$^{30}$, and ═O.

Embodiment 526

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, benzyl optionally substituted by 1-3 $R^{39}$, cyclopropyl optionally substituted by 1-3 $R^{39}$, 6 membered heterocycloalkyl optionally substituted by 1-3 $R^{39}$, 5 membered heteroaryl optionally substituted by 1-3 $R^{39}$, —CN, —C(=O)OR$^{30}$, —C(=O)NR$^{32}$R$^{33}$, —NR$^{32}$R$^{33}$, —NR$^{34}$S(=O)$_2$R$^{31}$, and —OR$^{30}$.

Embodiment 527

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, benzyl optionally substituted by 1-3 $R^{39}$, cyclopropyl optionally substituted by 1-3 $R^{39}$, morpholinyl optionally substituted by 1-3 $R^{39}$, pyrazolyl optionally substituted by 1-3 $R^{39}$, —CN, —C(=O)OR$^{30}$, —C(=O)NR$^{32}$R$^{33}$, —NR$^{32}$R$^{33}$, —NR$^{34}$S(=O)$_2$R$^{31}$, —OR$^{30}$, and =O.

Embodiment 528

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl optionally substituted by 1-3 $R^{39}$, benzyl optionally substituted by 1-3 $R^{39}$, cyclopropyl optionally substituted by 1-3 $R^{39}$, morpholinyl optionally substituted by 1-3 $R^{39}$, pyrazolyl optionally substituted by 1-3 $R^{39}$, —CN, —C(=O)OR$^{30}$, —C(=O)NR$^{32}$R$^{33}$, —NR$^{32}$R$^{33}$, —NR$^{34}$S(=O)$_2$R$^{31}$, and —OR$^{30}$.

Embodiment 529

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl, $C_{7-11}$arylalkyl optionally substituted by 1-3 $R^{39}$, $C_{3-6}$cycloalkyl, 3-6 membered heterocycloalkyl, 5-6 membered heteroaryl, —CN, —C(=O)OR$^{30}$, —C(=O)NR$^{32}$R$^{33}$, —NR$^{32}$R$^{33}$, —NR$^{34}$S(=O)$_2$R$^{31}$, —OR$^{30}$, and =O.

Embodiment 530

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl, $C_{7-11}$arylalkyl optionally substituted by 1-3 $R^{39}$, $C_{3-6}$cycloalkyl, 3-6 membered heterocycloalkyl, 5-6 membered heteroaryl, —CN, —C(=O)OR$^{30}$, —C(=O)NR$^{32}$R$^{33}$, —NR$^{32}$R$^{33}$, —NR$^{34}$S(=O)$_2$R$^{31}$, and —OR$^{30}$.

Embodiment 531

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl, benzyl optionally substituted by 1-3 $R^{39}$, $C_{3-6}$cycloalkyl, 3-6 membered heterocycloalkyl, 5-6 membered heteroaryl, —CN, —C(=O)OR$^{30}$, —C(=O)NR$^{32}$R$^{33}$, —NR$^{32}$R$^{33}$, —NR$^{34}$S(=O)$_2$R$^{31}$, —OR$^{30}$, and =O.

Embodiment 532

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl, benzyl optionally substituted by 1-3 $R^{39}$, $C_{3-6}$cycloalkyl, 3-6 membered heterocycloalkyl, 5-6 membered heteroaryl, —CN, —C(=O)OR$^{30}$, —C(=O)NR$^{32}$R$^{33}$, —NR$^{32}$R$^{33}$, —NR$^{34}$S(=O)$_2$R$^{31}$, and —OR$^{30}$.

Embodiment 533

The compound of any of Embodiments 1-156, 200-250, 300-371, or 400-440, wherein $R^{19}$ at each occurrence is independently chosen from $C_{1-6}$alkyl optionally substituted by 1-3 $R^{39}$, $C_{2-6}$alkynyl, benzyl optionally substituted by 1-3 $R^{39}$, cyclopropyl, morpholinyl, pyrazolyl, —CN, —C(=O)OR$^{30}$, —C(=O)NR$^{32}$R$^{33}$, —NR$^{32}$R$^{33}$, —NR$^{34}$S(=O)$_2$R$^{31}$, —OR$^{30}$, and =O.

Embodiment 600

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-6 $R^{49}$, $C_{2-6}$alkenyl optionally substituted by 1-6 $R^{49}$, $C_{2-6}$alkynyl optionally substituted by 1-6 $R^{49}$, $C_{6-11}$aryl optionally substituted by 1-6 $R^{49}$, $C_{7-16}$arylalkyl optionally substituted by 1-6 $R^{49}$, $C_{3-11}$cycloalkyl optionally substituted by 1-6 $R^{49}$, $C_{4-17}$cycloalkylalkyl optionally substituted by 1-6 $R^{49}$, 3-15 membered heterocycloalkyl optionally substituted by 1-6 $R^{49}$, 4-21 membered heterocycloalkylalkyl optionally substituted by 1-6 $R^{49}$, 5-15 membered heteroaryl optionally substituted by 1-6 $R^{49}$, and 6-21 membered heteroarylalkyl optionally substituted by 1-6 $R^{49}$.

Embodiment 601

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-6 $R^{49}$, $C_{2-6}$alkenyl optionally substituted by 1-6 $R^{49}$, $C_{2-6}$alkynyl optionally substituted by 1-6 $R^{49}$, $C_{6-10}$aryl optionally substituted by 1-6 $R^{49}$, $C_{7-11}$arylalkyl optionally substituted by 1-6 $R^{49}$, $C_{3-10}$cycloalkyl optionally substituted by 1-6 $R^{49}$, 3-10 membered heterocycloalkyl optionally substituted by 1-6 $R^{49}$, and 5-10 membered heteroaryl optionally substituted by 1-6 $R^{49}$.

Embodiment 602

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{2-6}$alkenyl optionally substituted by 1-3 $R^{49}$, $C_{2-6}$alkynyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 603

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 604

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 605

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 606

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, and $C_{3-6}$cycloalkyl optionally substituted by 1-3 $R^{49}$.

Embodiment 607

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl, 3-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 608

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, and $C_{3-6}$cycloalkyl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 609

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl, 3-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 610

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-6 $R^{49}$.

Embodiment 611

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 612

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 613

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{6-10}$aryl optionally substituted by 1-3 $R^{49}$, benzyl optionally substituted by 1-3 $R^{49}$, $C_{3-6}$cycloalkyl optionally substituted by 1-3 $R^{49}$, and 5-6 membered heteroaryl optionally substituted by 1-3 $R^{49}$.

Embodiment 614

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl optionally substituted by 1-3 $R^{49}$, and 5-6 membered heteroaryl optionally substituted by 1-3 $R^{49}$.

Embodiment 615

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, and cyclopropyl optionally substituted by 1-3 $R^{49}$.

Embodiment 616

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, cyclopropyl, thienyl, and pyrazinyl.

Embodiment 617

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl, benzyl optionally substituted by 1-3 $R^{49}$, cyclopropyl, thienyl, and pyrazinyl.

Embodiment 618

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl optionally substituted by 1-3 $R^{49}$, cyclopropyl, 5 membered heterocycloalkyl, and 5 membered heteroaryl.

Embodiment 619

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl optionally substituted by 1-3 $R^{49}$, cyclopropyl, 5 membered heterocycloalkyl, and 5 membered heteroaryl.

Embodiment 620

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl optionally substituted by 1 $R^{49}$, $C_{3-6}$cycloalkyl, 5-6 membered heterocycloalkyl, and 5-6 membered heteroaryl.

Embodiment 621

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl optionally substituted by 1 $R^{49}$, $C_{3-6}$cycloalkyl, 5-6 membered heterocycloalkyl, and 5-6 membered heteroaryl.

Embodiment 622

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl, $C_{3-6}$cycloalkyl, 5-6 membered heterocycloalkyl, and 5-6 membered heteroaryl.

Embodiment 623

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl, $C_{3-6}$cycloalkyl, 5-6 membered heterocycloalkyl, and 5-6 membered heteroaryl.

Embodiment 624

The compound of any of Embodiments 1-156, 200-250, 300-371, 400-440, or 500-533, wherein $R^{2}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl, phenyl, cyclopropyl, 5 membered heterocycloalkyl, and 5 membered heteroaryl.

Embodiment 625

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, phenyl, cyclopropyl, 5 membered heterocycloalkyl, and 5 membered heteroaryl.

Embodiment 626

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 627

The compound of any of Embodiments 1-156, 200-250, 300-371, 400-440, or 500-533, wherein $R^{20}$ at each occurrence is independently chosen from H, $C_{6-10}$aryl optionally substituted by 1-3 $R^{49}$, benzyl optionally substituted by 1-3 $R^{49}$, cyclopropyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 628

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, cyclopropyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 629

The compound of any of Embodiments 1-156, 200-250, 300-371, 400-440, or 500-533, wherein $R^{20}$ at each occurrence is independently chosen from H, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 630

The compound of any of Embodiments 1-156, 200-250, 300-371, 400-440, or 500-533, wherein $R^{20}$ at each occurrence is independently chosen from H, $C_{1-6}$alkyl, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 631

The compound of any of Embodiments 1-156, 200-250, 300-371, 400-440, or 500-533, wherein $R^{20}$ at each occurrence is independently chosen from H, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 632

The compound of any of Embodiments 1-156, 200-250, 300-371, 400-440, or 500-533, wherein $R^{20}$ at each occurrence is independently chosen from H, $C_{1-6}$alkyl, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 633

The compound of any of Embodiments 1-156, 200-250, 300-371, 400-440, or 500-533, wherein $R^{20}$ at each occurrence is independently chosen from H, phenyl optionally substituted by 1-3 $R^{49}$, benzyl optionally substituted by 1-3 $R^{49}$, and cyclopropyl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 634

The compound of any of Embodiments 1-156, 200-250, 300-371, 400-440, or 500-533, wherein $R^{20}$ at each occurrence is independently chosen from H, $C_{1-6}$alkyl, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 635

The compound of any of Embodiments 1-156, 200-250, 300-371, 400-440, or 500-533, wherein $R^{20}$ at each occurrence is independently chosen from H, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 636

The compound of any of Embodiments 1-156, 200-250, 300-371, 400-440, or 500-533, wherein $R^{20}$ at each occurrence is independently chosen from H, $C_{1-6}$alkyl, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 637

The compound of any of Embodiments 1-156, 200-250, 300-371, 400-440, or 500-533, wherein $R^{20}$ at each occurrence is independently chosen from H, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 638

The compound of any of Embodiments 1-156, 200-250, 300-371, 400-440, or 500-533, wherein $R^{20}$ at each occurrence is independently chosen from H, $C_{1-6}$alkyl, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 639

The compound of any of Embodiments 1-156, 200-250, 300-371, 400-440, or 500-533, wherein $R^{20}$ at each occurrence is independently chosen from H, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl optionally substituted by 1-3 $R^{49}$.

Embodiment 640

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 641

The compound of any of Embodiments 1-156, 200-250, 300-371, 400-440, or 500-533, wherein $R^{20}$ at each occurrence is independently chosen from H, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 642

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, and $C_{3-6}$cycloalkyl optionally substituted by 1-3 $R^{49}$; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl.

Embodiment 643

The compound of any of Embodiments 1-156, 200-250, 300-371, 400-440, or 500-533, wherein $R^{20}$ at each occurrence is independently chosen from H, phenyl optionally substituted by 1-3 $R^{49}$, $C_{3-6}$cycloalkyl optionally substituted by 1-3 $R^{49}$, 5-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl.

Embodiment 644

The compound of any of Embodiments 1-156, 200-250, 300-371, 400-440, or 500-533, wherein $R^{20}$ at each occurrence is independently chosen from H, $C_{1-6}$alkyl, phenyl optionally substituted by 1-3 $R^{49}$, benzyl optionally substituted by 1-3 $R^{49}$, and $C_{3-6}$cycloalkyl; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl.

Embodiment 645

The compound of any of Embodiments 1-156, 200-250, 300-371, 400-440, or 500-533, wherein $R^{20}$ at each occurrence is independently chosen from H, phenyl optionally substituted by 1-3 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 646

The compound of any of Embodiments 1-156, 200-250, 300-371, 400-440, or 500-533, wherein $R^{20}$ at each occurrence is independently chosen from H, $C_{1-6}$alkyl, phenyl optionally substituted by 1-3 $R^{49}$, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 647

The compound of any of Embodiments 1-156, 200-250, 300-371, 400-440, or 500-533, wherein $R^{20}$ at each occurrence is independently chosen from H, phenyl optionally substituted by 1-3 $R^{49}$, benzyl optionally substituted by 1-3 $R^{49}$, $C_{3-6}$cycloalkyl, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 648

The compound of any of Embodiments 1-156, 200-250, 300-371, 400-440, or 500-533, wherein $R^{20}$ at each occurrence is independently chosen from H, $C_{1-6}$alkyl, phenyl, benzyl optionally substituted by 1-3 $R^{49}$, $C_{3-6}$cycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 649

The compound of any of Embodiments 1-156, 200-250, 300-371, 400-440, or 500-533, wherein $R^{20}$ at each occurrence is independently chosen from H, $C_{1-6}$alkyl, phenyl, benzyl optionally substituted by 1-3 $R^{49}$, cyclopropyl, thienyl, and pyrazinyl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 650

The compound of any of Embodiments 1-156, 200-250, 300-371, 400-440, or 500-533, wherein $R^{20}$ at each occurrence is independently chosen from H, $C_{1-6}$alkyl, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 651

The compound of any of Embodiments 1-156, 200-250, 300-371, 400-440, or 500-533, wherein $R^{20}$ at each occurrence is independently chosen from H, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 652

The compound of any of Embodiments 1-156, 200-250, 300-371, 400-440, or 500-533, wherein $R^{20}$ at each occurrence is independently chosen from H, $C_{1-6}$alkyl, phenyl, cyclopropyl, 5 membered heterocycloalkyl, and 5 membered heteroaryl; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is independently chosen from H and $C_{1-6}$alkyl.

Embodiment 653

The compound of any of Embodiments 1-156, 200-250, 300-371, 400-440, or 500-533, wherein $R^{20}$ at each occurrence is independently chosen from H, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

Embodiment 654

The compound of any of Embodiments 1-156, 200-250, 300-371, 400-440, or 500-533, wherein $R^{20}$ at each occurrence is independently chosen from H, $C_{1-6}$alkyl optionally substituted by 1-3 $R^{49}$, $C_{6-10}$aryl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 655

The compound of any of Embodiments 1-156, 200-250, 300-371, 400-440, or 500-533, wherein $R^{20}$ at each occurrence is independently chosen from H, $C_{6-10}$aryl optionally substituted by 1-3 $R^{49}$, benzyl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 656

The compound of any of Embodiments 1-156, 200-250, 300-371, 400-440, or 500-533, wherein $R^{20}$ at each occurrence is independently chosen from H, phenyl optionally substituted by 1-3 $R^{49}$, benzyl optionally substituted by 1-3 $R^{49}$, $C_{3-6}$cycloalkyl optionally substituted by 1-3 $R^{49}$, and 5-6 membered heteroaryl optionally substituted by 1-3 $R^{49}$; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 657

The compound of any of Embodiments 1-156, 200-250, 300-371, 400-440, or 500-533, wherein $R^{20}$ at each occurrence is independently chosen from H, phenyl optionally substituted by 1-3 $R^{49}$, benzyl optionally substituted by 1-3 $R^{49}$, $C_{3-6}$cycloalkyl, and 5-6 membered heteroaryl; $R^{21}$, $R^{24}$, $R^{25}$, $R^{26}$, $R^{27}$, $R^{3}$, $R^{31}$, $R^{34}$, $R^{3}$, $R^{36}$ and $R^{37}$ at each occurrence is H.

Embodiment 658

The compound of any of Embodiments 1-156, 200-250, 300-371, 400-440, or 500-533, wherein $R^{20}$ at each occurrence is independently chosen from H, phenyl, benzyl optionally substituted by 1-3 $R^{49}$, $C_{3-6}$cycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 659

The compound of any of Embodiments 1-156, 200-250, 300-371, 400-440, or 500-533, wherein $R^{20}$ at each occurrence is independently chosen from H, phenyl optionally substituted by 1-3 $R^{49}$, benzyl optionally substituted by 1-3 $R^{49}$, cyclopropyl optionally substituted by 1-3 $R^{49}$; $R^{21}$, $R^{24}$, $R^{25}$, $R^{26}$, $R^{27}$, $R^{3}$, $R^{31}$, $R^{34}$, $R^{35}$, $R^{36}$ and $R^{37}$ at each occurrence is H.

Embodiment 660

The compound of any of Embodiments 1-156, 200-250, 300-371, 400-440, or 500-533, wherein $R^{20}$ at each occurrence is independently chosen from H, phenyl optionally substituted by 1-3 $R^{49}$, benzyl optionally substituted by 1-3 $R^{49}$, and cyclopropyl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 661

The compound of any of Embodiments 1-156, 200-250, 300-371, 400-440, or 500-533, wherein $R^{20}$ at each occurrence is independently chosen from H, phenyl, benzyl optionally substituted by 1-3 $R^{49}$, cyclopropyl, thienyl, and pyrazinyl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 662

The compound of any of Embodiments 1-156, 200-250, 300-371, 400-440, or 500-533, wherein $R^{20}$ at each occurrence is independently chosen from H, $C_{1-6}$alkyl, phenyl optionally substituted by 1 $R^{49}$, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 663

The compound of any of Embodiments 1-156, 200-250, 300-371, 400-440, or 500-533, wherein $R^{20}$ at each occurrence is independently chosen from H, phenyl optionally substituted by 1 $R^{49}$, $C_{3-6}$cycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 664

The compound of any of Embodiments 1-156, 200-250, 300-371, 400-440, or 500-533, wherein $R^{20}$ at each occurrence is independently chosen from H, $C_{1-6}$alkyl, phenyl, $C_{3-6}$cycloalkyl, 5-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 665

The compound of any of Embodiments 1-156, 200-250, 300-371, 400-440, or 500-533, wherein $R^{20}$ at each occurrence is independently chosen from H, phenyl, $C_{3-6}$cycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 666

The compound of any of Embodiments 1-156, 200-250, 300-371, 400-440, or 500-533, wherein $R^{20}$ at each occurrence is independently chosen from H, $C_{1-6}$alkyl, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 667

The compound of any of Embodiments 1-156, 200-250, 300-371, 400-440, or 500-533, wherein $R^{20}$ at each occurrence is independently chosen from H, phenyl, cyclopropyl, 5 membered heterocycloalkyl, and 5 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 668

The compound of any of Embodiments 1-156, 200-250, 300-371, 400-440, or 500-533, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

Embodiment 700

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$.

Embodiment 701

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$, $C_{2-6}$alkenyl optionally substituted by 1-3 $R^{49}$, $C_{2-6}$alkynyl optionally substituted by 1-3 $R^{49}$, $C_{6-11}$aryl optionally substituted by 1-3 $R^{49}$, $C_{7-16}$arylalkyl optionally substituted by 1-3 $R^{49}$, $C_{3-11}$cycloalkyl optionally substituted by 1-3 $R^{49}$, $C_{4-17}$cycloalkylalkyl optionally substituted by 1-3 $R^{49}$, 3-15 membered heterocycloalkyl optionally substituted by 1-3 $R^{49}$, 4-21 membered heterocycloalkylalkyl optionally substituted by 1-3 $R^{49}$, 5-15 membered heteroaryl optionally substituted by 1-3 $R^{49}$, and 6-21 membered heteroarylalkyl optionally substituted by 1-3 $R^{49}$.

Embodiment 702

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$, $C_{2-6}$alkenyl optionally substituted by 1-3 $R^{49}$, $C_{2-6}$alkynyl optionally substituted by 1-3 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 703

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$, $C_{6-10}$aryl optionally substituted by 1-3 $R^{49}$, $C_{7-11}$arylalkyl optionally substituted by 1-3 $R^{49}$, $C_{3-10}$cycloalkyl optionally substituted by 1-3 $R^{49}$, 3-10 membered heterocycloalkyl optionally substituted by 1-3 $R^{49}$, and 5-10 membered heteroaryl optionally substituted by 1-3 $R^{49}$.

Embodiment 704

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$, phenyl optionally substituted by 1-3 $R^{49}$, benzyl optionally substituted by 1-3 $R^{49}$, $C_{3-6}$cycloalkyl optionally substituted by 1-3 $R^{49}$, 3-6 membered heterocycloalkyl optionally substituted by 1-3 $R^{49}$, and 5-6 membered heteroaryl optionally substituted by 1-3 $R^{49}$.

Embodiment 705

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$, phenyl optionally substituted by 1-3 $R^{49}$, benzyl, $C_{3-6}$cycloalkyl, 3-6 membered heterocycloalkyl, and 5-6 membered heteroaryl.

Embodiment 706

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$ and 3-6 membered heterocycloalkyl optionally substituted by 1-3 $R^{49}$.

Embodiment 707

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$ and 5-6 membered heterocycloalkyl optionally substituted by 1-3 $R^{49}$.

Embodiment 708

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$ and 5-6 membered heterocycloalkyl.

Embodiment 709

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$ and 5 membered heterocycloalkyl optionally substituted by 1-6 $R^{49}$.

Embodiment 710

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$ and 5 membered heterocycloalkyl.

Embodiment 711

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-6 $R^{49}$ and pyrrolidinyl.

Embodiment 712

The compound of any of Embodiments 1-156, 200-250, 300-371, 400-440, 500-533, or 600-668, wherein $R^{28}$ at each occurrence is independently chosen from $C_{1-6}$alkyl optionally substituted by 1-3 $R^{49}$ and 5 membered heterocycloalkyl.

Embodiment 713

The compound of any of Embodiments 1-156, 200-250, 300-371, 400-440, 500-533, or 600-668, wherein $R^{28}$ at each occurrence is $C_{1-6}$alkyl optionally substituted by 1-6 $R^{49}$.

Embodiment 714

The compound of any of Embodiments 1-156, 200-250, 300-371, 400-440, 500-533, or 600-668, wherein $R^{28}$ at each occurrence is $C_{1-6}$alkyl optionally substituted by 1-3 $R^{49}$.

Embodiment 750

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 751

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-11}$aryl optionally substituted by 1-3 $R^{59}$, $C_{7-16}$arylalkyl optionally substituted by 1-3 $R^{59}$, $C_{3-11}$cycloalkyl optionally substituted by 1-3 $R^{59}$, $C_{4-17}$cycloalkylalkyl optionally substituted by 1-3 $R^{59}$, 3-15 membered heterocycloalkyl optionally substituted by 1-3 $R^{59}$, 4-21 membered heterocycloalkylalkyl optionally substituted by 1-3 $R^{59}$, 5-15 membered heteroaryl optionally substituted by 1-3 $R^{59}$, and 6-21 membered heteroarylalkyl optionally substituted by 1-3 $R^{59}$; or any $R^{22}$ and $R^{23}$ and/or $R^{32}$ and $R^{33}$ may form, together with the nitrogen atom to which they are attached, a 3-15 membered heterocycloalkyl optionally substituted by 1-3 $R^{69}$ or a 5-15 membered heteroaryl optionally substituted by 1-3 $R^{69}$.

Embodiment 752

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; or any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 753

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$.

Embodiment 754

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$.

Embodiment 755

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, $C_{6-10}$aryl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$.

Embodiment 756

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl optionally substituted by 1-3 $R^{59}$, 3-6 membered heterocycloalkyl optionally substituted by 1-3 $R^{59}$, and 5-10 membered heteroaryl optionally substituted by 1-3 $R^{59}$.

Embodiment 757

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl optionally substituted by 1-3 $R^{59}$, 4-5 membered heterocycloalkyl optionally substituted by 1-3 $R^{59}$, and 5-9 membered heteroaryl optionally substituted by 1-3 $R^{59}$.

Embodiment 758

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 3-6 membered heterocycloalkyl, and 5-10 membered heteroaryl optionally substituted by 1-3 $R^{59}$.

Embodiment 759

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 4-5 membered heterocycloalkyl, and 5-9 membered heteroaryl optionally substituted by 1-3 $R^{59}$.

Embodiment 760

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, and 5-6 membered heteroaryl optionally substituted by 1-3 $R^{59}$.

Embodiment 761

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, and 6 membered heteroaryl optionally substituted by 1-3 $R^{59}$.

Embodiment 762

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1 $R^{59}$, and 6 membered heteroaryl optionally substituted by 1 $R^{59}$.

Embodiment 763

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$ cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; $R^{23}$ and $R^{33}$ at each occurrence is independently chosen from H and $C_{1-6}$alkyl; or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 764

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-11}$aryl optionally substituted by 1-3 $R^{59}$, $C_{7-16}$arylalkyl optionally substituted by 1-3 $R^{59}$, $C_{3-11}$cycloalkyl optionally substituted by 1-3 $R^{59}$, $C_{4-17}$cycloalkylalkyl optionally substituted by 1-3 $R^{59}$, 3-15 membered heterocycloalkyl optionally substituted by 1-3 $R^{59}$, 4-21 membered heterocycloalkylalkyl optionally substituted by 1-3 $R^{59}$, 5-15 membered heteroaryl optionally substituted by 1-3 $R^{59}$, and 6-21 membered heteroarylalkyl optionally substituted by 1-3 $R^{59}$; $R^{23}$ and $R^{33}$ at each occurrence is independently chosen from H and $C_{1-6}$alkyl; or any $R^{22}$ and $R^{23}$ and/or $R^{32}$ and $R^{33}$ may form, together with the nitrogen atom to which they are attached, a 3-15 membered heterocycloalkyl optionally substituted by 1-3 $R^{69}$ or a 5-15 membered heteroaryl optionally substituted by 1-3 $R^{69}$.

Embodiment 765

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl optionally substituted by 1-3 $R^{59}$, $C_{6-10}$aryl optionally substituted by 1-3 $R^{59}$, bezyl optionally substituted by 1-3 $R^{59}$, $C_{3-10}$cycloalkyl optionally substituted by 1-3 $R^{59}$, 3-6 membered heterocycloalkyl optionally substituted by 1-3 $R^{59}$, and 5-10 membered heteroaryl optionally substituted by 1-3 $R^{59}$; $R^{23}$ and $R^{33}$ at each occurrence is independently chosen from H and $C_{1-6}$alkyl.

Embodiment 766

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl optionally substituted by 1-3 $R^{59}$, phenyl optionally substituted by 1-3 $R^{59}$, $C_{3-10}$cycloalkyl optionally substituted by 1-3 $R^{59}$, 3-6 membered heterocycloalkyl optionally substituted by 1-3 $R^{59}$, and 5-10 membered heteroaryl optionally substituted by 1-3 $R^{59}$; $R^{23}$ and $R^{33}$ at each occurrence are independently chosen from H and $C_{1-6}$alkyl.

Embodiment 767

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl optionally substituted by 1-3 $R^{59}$, phenyl optionally substituted by 1-3 $R^{59}$, benzyl optionally substituted by 1-3 $R^{59}$, $C_{3-10}$cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$ and $R^{33}$ at each occurrence are independently chosen from H and $C_{1-6}$alkyl.

Embodiment 768

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl optionally substituted by 1-3 $R^{59}$, 4-5 membered heterocycloalkyl optionally substituted by 1-3 $R^{59}$, and 5-9 membered heteroaryl optionally substituted by 1-3 $R^{59}$; $R^{23}$, $R^{32}$ and $R^{33}$ at each occurrence is independently chosen from H and $C_{1-6}$alkyl.

Embodiment 769

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl, phenyl, benzyl, $C_{3-6}$cycloalkyl, 3-6 membered heterocycloalkyl, and 5-6 membered heteroaryl; $R^{23}$ and $R^{33}$ at each occurrence are independently chosen from H and $C_{1-6}$alkyl.

Embodiment 770

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 3-6 membered heterocycloalkyl, and 5-10 membered heteroaryl optionally substituted by 1-3 $R^{59}$; $R^{23}$, $R^{32}$ and $R^{33}$ at each occurrence is independently chosen from H and $C_{1-6}$alkyl optionally substituted by 1-3 $R^{59}$.

Embodiment 771

The compound of any of Embodiments 1-156, 200-250, 300-371, 400-440, 500-533, 600-668, or 700-714, wherein $R^{22}$ and $R^{32}$ at each occurrence are independently chosen from H, $C_{1-6}$alkyl optionally substituted by 1-3 $R^{59}$, phenyl optionally substituted by 1-3 $R^{59}$, benzyl, $C_{3-10}$cycloalkyl, 4-5 membered heterocycloalkyl, and 5-9 membered heteroaryl optionally substituted by 1-3 $R^{59}$; $R^{23}$ and $R^{33}$ at each occurrence is independently chosen from H and $C_{1-6}$alkyl optionally substituted by 1-3 $R^{59}$.

Embodiment 772

The compound of any of Embodiments 1-156, 200-250, 300-371, 400-440, 500-533, 600-668, or 700-714, wherein $R^{22}$ at each occurrence is independently chosen from H, $C_{6-10}$aryl optionally substituted by 1-3 $R^{59}$, and 5-10 membered heteroaryl optionally substituted by 1-3 $R^{59}$; $R^{23}$, $R^{32}$ and $R^{33}$ at each occurrence is independently chosen from H and $C_{1-6}$alkyl.

Embodiment 773

The compound of any of Embodiments 1-156, 200-250, 300-371, 400-440, 500-533, 600-668, or 700-714, wherein $R^{22}$ at each occurrence is independently chosen from H, phenyl optionally substituted by 1-3 $R^{59}$, and 5-6 membered heteroaryl optionally substituted by 1-3 $R^{59}$; $R^{23}$, $R^{32}$ and $R^{33}$ at each occurrence is independently chosen from H and $C_{1-6}$alkyl.

Embodiment 774

The compound of any of Embodiments 1-156, 200-250, 300-371, 400-440, 500-533, 600-668, or 700-714, wherein $R^{22}$ and $R^{32}$ at each occurrence are independently chosen from H, phenyl optionally substituted by 1-3 $R^{59}$, benzyl, and 6 membered heteroaryl optionally substituted by 1-3 $R^{59}$; $R^{23}$ and $R^{33}$ at each occurrence is independently chosen from H and $C_{1-6}$alkyl.

Embodiment 775

The compound of any of Embodiments 1-156, 200-250, 300-371, 400-440, 500-533, 600-668, or 700-714, wherein $R^{22}$ at each occurrence is independently chosen from H, phenyl optionally substituted by 1 $R^{59}$, and 6 membered heteroaryl optionally substituted by 1 $R^{59}$; $R^{23}$, $R^{32}$ and $R^{33}$ at each occurrence is independently chosen from H and $C_{1-6}$alkyl.

Embodiment 776

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$; $R^{23}$, $R^{32}$ and $R^{33}$ at each occurrence is H; or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 777

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-11}$aryl optionally substituted by 1-3 $R^{59}$, $C_{7-16}$arylalkyl optionally substituted by 1-3 $R^{59}$, $C_{3-11}$cycloalkyl optionally substituted by 1-3 $R^{59}$, $C_{4-17}$cycloalkylalkyl optionally substituted by 1-3 $R^{59}$, 3-15 membered heterocycloalkyl optionally substituted by 1-3 $R^{59}$, 4-21 membered heterocycloalkylalkyl optionally substituted by 1-3 $R^{59}$, 5-15 membered heteroaryl optionally substituted by 1-3 $R^{59}$, and 6-21 membered heteroarylalkyl optionally substituted by 1-3 $R^{59}$; $R^{23}$, $R^{32}$ and $R^{33}$ at each occurrence is H; or any $R^{22}$ and $R^{23}$ and/or $R^{32}$ and $R^{33}$ may form, together with the nitrogen atom to which they are attached, a 3-15 membered heterocycloalkyl optionally substituted by 1-3 $R^{69}$ or a 5-15 membered heteroaryl optionally substituted by 1-3 $R^{69}$.

Embodiment 778

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, $C_{2-6}$alkenyl optionally substituted by 1-3 $R^{59}$, $C_{2-6}$alkynyl optionally substituted by 1-3 $R^{59}$, $C_{6-10}$aryl optionally substituted by 1-3 $R^{59}$, $C_{7-11}$arylalkyl optionally substituted by 1-3 $R^{59}$, $C_{3-10}$-cycloalkyl optionally substituted by 1-3 $R^{59}$, 3-10 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is H; or any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 779

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl optionally substituted by 1-3 $R^{59}$, 3-6 membered heterocycloalkyl optionally substituted by 1-3 $R^{59}$, and 5-10 membered heteroaryl optionally substituted by 1-3 $R^{59}$; $R^{23}$, $R^{32}$ and $R^{33}$ at each occurrence is H.

Embodiment 780

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 3-6 membered heterocycloalkyl, and 5-10 membered heteroaryl optionally substituted by 1-3 $R^{59}$; $R^{23}$, $R^{32}$ and $R^{33}$ at each occurrence is H; or any $R^{22}$ and $R^{23}$ and/or $R^{32}$ and $R^{33}$ may form, together with the nitrogen atom to which they are attached, a 3-10 membered heterocycloalkyl optionally substituted by 1-3 $R^{69}$ or a 5-10 membered heteroaryl optionally substituted by 1-3 $R^{69}$.

Embodiment 781

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 3-6 membered heterocycloalkyl, and 5-10 membered heteroaryl optionally substituted by 1-3 $R^{59}$; $R^{23}$, $R^{32}$ and $R^{33}$ at each occurrence is H.

Embodiment 782

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 4-5 membered heterocycloalkyl, and 5-10 membered heteroaryl optionally substituted by 1-3 $R^{59}$; $R^{23}$, $R^{32}$ and $R^{33}$ at each occurrence is H.

Embodiment 783

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 4-5 membered heterocycloalkyl optionally substituted by 1-3 $R^{59}$, and 5-9 membered heteroaryl optionally substituted by 1-3 $R^{59}$; $R^{23}$, $R^{32}$ and $R^{33}$ at each occurrence is H.

Embodiment 784

The compound of any of Embodiments 1-156, 200-250, 300-371, 400-440, 500-533, 600-668, or 700-714, wherein $R^{22}$ at each occurrence is independently chosen from H, $C_{1-6}$alkyl optionally substituted by 1-3 $R^{59}$, phenyl optionally substituted by 1-3 $R^{59}$, $C_{3-10}$cycloalkyl, 4-5 membered heterocycloalkyl, and 5-9 membered heteroaryl optionally substituted by 1-3 $R^{59}$; $R^{23}$, $R^{32}$ and $R^{33}$ at each occurrence is H.

Embodiment 785

The compound of any of Embodiments 1-156, 200-250, 300-371, 400-440, 500-533, 600-668, or 700-714, wherein $R^{22}$ at each occurrence is independently chosen from H, $C_{6-10}$aryl optionally substituted by 1-3 $R^{59}$, and 5-10 membered heteroaryl optionally substituted by 1-3 $R^{59}$; $R^{23}$, $R^{32}$ and $R^{33}$ at each occurrence is H.

Embodiment 786

The compound of any of Embodiments 1-156, 200-250, 300-371, 400-440, 500-533, 600-668, or 700-714, wherein $R^{22}$ at each occurrence is independently chosen from H, phenyl optionally substituted by 1-3 $R^{59}$, and 5-6 membered heteroaryl optionally substituted by 1-3 $R^{59}$; $R^{23}$, $R^{32}$ and $R^{33}$ at each occurrence is H.

Embodiment 787

The compound of any of Embodiments 1-156, 200-250, 300-371, 400-440, 500-533, 600-668, or 700-714, wherein $R^{22}$ at each occurrence is independently chosen from H, phenyl optionally substituted by 1-3 $R^{59}$, and 6 membered heteroaryl optionally substituted by 1-3 $R^{59}$; $R^{23}$, $R^{32}$ and $R^{33}$ at each occurrence is H.

Embodiment 788

The compound of any of Embodiments 1-156, 200-250, 300-371, 400-440, 500-533, 600-668, or 700-714, wherein $R^{22}$ at each occurrence is independently chosen from H, phenyl optionally substituted by 1 $R^{59}$, and 6 membered heteroaryl optionally substituted by 1 $R^{59}$; $R^{23}$, $R^{32}$ and $R^{33}$ at each occurrence is H.

Embodiment 789

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H and $C_{1-6}$alkyl.

Embodiment 790

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is H.

Embodiment 791

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H and $C_{1-6}$alkyl optionally substituted by 1-13 $R^{59}$; or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$.

Embodiment 792

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H and $C_{1-6}$alkyl optionally substituted by 1-6

$R^{59}$; or any $R^{22}$ and $R^{23}$ and/or $R^{32}$ and $R^{33}$ may form, together with the nitrogen atom to which they are attached, a 3-15 membered heterocycloalkyl optionally substituted by 1-6 $R^{69}$ or a 5-15 membered heteroaryl optionally substituted by 1-6 $R^{69}$.

Embodiment 793

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H and $C_{1-6}$alkyl optionally substituted by 1-6 $R^{59}$; or any $R^{22}$ and $R^{23}$ and/or $R^{32}$ and $R^{33}$ may form, together with the nitrogen atom to which they are attached, a 3-10 membered heterocycloalkyl optionally substituted by 1-6 $R^{69}$ or a 5-10 membered heteroaryl optionally substituted by 1-6 $R^{69}$.

Embodiment 794

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H and $C_{1-6}$alkyl optionally substituted by 1-6 $R^{59}$; or any $R^{22}$ and $R^{23}$ and/or $R^{32}$ and $R^{33}$ may form, together with the nitrogen atom to which they are attached, a 3-6 membered heterocycloalkyl optionally substituted by 1-6 $R^{69}$ or a 5-6 membered heteroaryl optionally substituted by 1-6 $R^{69}$.

Embodiment 795

The compound of any of Embodiments 1-156, 200-250, 300-371, 400-440, 500-533, 600-668, or 700-714, wherein $R^{22}$, $R^{23}$, $R^{32}$ and $R^{33}$ at each occurrence is independently chosen from H and $C_{1-6}$alkyl optionally; or any $R^{22}$ and $R^{23}$ and/or $R^{32}$ and $R^{33}$ may form, together with the nitrogen atom to which they are attached, a 3-6 membered heterocycloalkyl or a 5-6 membered heteroaryl.

Embodiment 800

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-6 $R^{79}$, $C_{2-6}$alkenyl optionally substituted by 1-6 $R^{79}$, $C_{2-6}$alkynyl optionally substituted by 1-6 $R^{79}$, $C_{6-11}$aryl optionally substituted by 1-6 $R^{79}$, $C_{7-16}$arylalkyl optionally substituted by 1-6 $R^{79}$, $C_{3-11}$cycloalkyl optionally substituted by 1-6 $R^{79}$, $C_{4-17}$cycloalkylalkyl optionally substituted by 1-6 $R^{79}$, 3-15 membered heterocycloalkyl optionally substituted by 1-6 $R^{79}$, 4-21 membered heterocycloalkylalkyl optionally substituted by 1-6 $R^{79}$, 5-15 membered heteroaryl optionally substituted by 1-6 $R^{79}$, 6-21 membered heteroarylalkyl optionally substituted by 1-6 $R^{79}$, halogen, —CN, —C(═O)$R^{70}$, —C(═O)O$R^{70}$, —C(═O)N$R^{72}R^{73}$, —(═O)C(═O)$R^{70}$, —C(═N$R^{75}$)$R^{70}$, —C(═N$R^{75}$)N$R^{72}R^{73}$, —C(═NOH)N$R^{72}R^{73}$, —C(═NO$R^{76}$)$R^{70}$, —C(═NN$R^{72}R^{73}$)$R^{70}$, —C(═NN$R^{74}$C(═O)$R^{71}$)$R^{70}$, —C(═NN$R^{74}$C(═O)O$R^{71}$)$R^{70}$, —C(═S)N$R^{72}R^{73}$, —NC, —$NO_2$, —N$R^{72}R^{73}$, —N$R^{74}$N$R^{72}R^{73}$, —N═N$R^{74}$, ═N$R^{70}$, ═NO$R^{70}$, —N$R^{74}$O$R^{76}$, —N$R^{74}$C(═O)$R^{70}$, —N$R^{74}$C(═O)C(═O)$R^{70}$, —N$R^{74}$C(═O)O$R^{71}$, —N$R^{74}$C(═O)C(═O)O$R^{71}$, —N$R^{74}$C(═O)N$R^{72}R^{73}$, —N$R^{74}$C(═O)N$R^{74}$C(═O)$R^{70}$, —N$R^{74}$C(═O)N$R^{74}$C(═O)O$R^{70}$, —N$R^{74}$C(═N$R^{75}$)N$R^{72}R^{73}$, —N$R^{74}$C(═O)C(═O)N$R^{72}R^{73}$, —N$R^{74}$C(═S)$R^{70}$, —N$R^{74}$C(═S)O$R^{70}$, —N$R^{74}$C(═S)N$R^{72}R^{73}$, —N$R^{74}$S(═O)$_2R^{71}$, —N$R^{74}$S(═O)$_2$N$R^{72}R^{73}$, —N$R^{74}$P(═O)$R^{78}R^{78}$, —N$R^{74}$P(═O)(N$R^{72}R^{73}$)(N$R^{72}R^{73}$), —N$R^{74}$P(═)(O$R^{70}$)(O$R^{70}$), —N$R^{74}$P(═O)(S$R^{70}$)(S$R^{70}$), —O$R^{70}$, ═O, —OCN, —OC(═O)$R^{70}$, —OC(═O)N$R^{72}R^{73}$, —OC(═O)O$R^{70}$, —OC(═N$R^{75}$)N$R^{72}R^{73}$, —OS(═O)$R^{70}$, —OS(═O)$_2R^{70}$, —OS(═O)$_2$O$R^{70}$, —OS(═O)$_2$N$R^{72}R^{73}$, —OP(═O)$R^{78}R^{78}$, —OP(═O)(N$R^{72}R^{73}$)(N$R^{72}R^{73}$), —OP(═O)(O$R^{70}$)(O$R^{70}$), —OP(═O)(S$R^{70}$)(S$R^{70}$), —Si($R^{74}$)$_3$, —SCN, ═S, —S(═O)$_n R^{70}$, —S(═O)$_2$O$R^{70}$, —SO$_3R^{77}$, —S(═O)$_2$N$R^{72}R^{73}$, —S(═O)N$R^{72}R^{73}$, —SP(═O)$R^{78}R^{78}$, —SP(═O)(N$R^{72}R^{73}$)(N$R^{72}R^{73}$), —SP(═O)(O$R^{70}$)(O$R^{70}$), —SP(═O)(S$R^{70}$)(S$R^{70}$), —P(═O)$R^{78}R^{78}$, —P(═O)(N$R^{72}R^{73}$)(N$R^{72}R^{73}$), —P(═O)(O$R^{70}$)(O$R^{70}$), and —P(═O)(S$R^{70}$)(S$R^{70}$).

Embodiment 801

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-6 $R^{79}$, $C_{6-11}$aryl optionally substituted by 1-6 $R^{79}$, $C_{7-16}$arylalkyl optionally substituted by 1-6 $R^{79}$, $C_{3-11}$cycloalkyl optionally substituted by 1-6 $R^{79}$, 3-15 membered heterocycloalkyl optionally substituted by 1-6 $R^{79}$, 5-15 membered heteroaryl optionally substituted by 1-6 $R^{79}$, halogen, —CN, —C(═O)$R^{70}$, —C(═O)O$R^{70}$, —C(═O)N$R^{72}R^{73}$, —NC, —$NO_2$, —N$R^{72}R^{73}$, —N$R^{74}$N$R^{72}R^{73}$, —N$R^{74}$O$R^{76}$, —N$R^{74}$C(═O)$R^{70}$, —N$R^{74}$C(═O)O$R^{71}$, —N$R^{74}$C(═O)N$R^{72}R^{73}$, —N$R^{74}$C(═O)N$R^{74}$C(═O)$R^{70}$, —N$R^{74}$S(═O)$_2R^{71}$, —N$R^{74}$S(═O)$_2$N$R^{72}R^{73}$, —O$R^{70}$, ═O, —OCN, —OC(═O)$R^{70}$, —OC(═O)N$R^{72}R^{73}$, —OC(═O)O$R^{70}$, —Si($R^{74}$)$_3$, —SCN, ═S, —S(═O)$_n R^{70}$, and —S(═O)$_2$N$R^{72}R^{73}$.

Embodiment 802

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-6 $R^{79}$, $C_{6-10}$aryl optionally substituted by 1-6 $R^{79}$, $C_{7-11}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, 5-10 membered heteroaryl optionally substituted by 1-6 $R^{79}$, halogen, —CN, —C(═O)$R^{70}$, —C(═O)O$R^{70}$, —C(═O)N$R^{72}R^{73}$, —$NO_2$, —N$R^{72}R^{73}$, —N$R^{74}$C(═O)$R^{70}$, —N$R^{74}$C(═O)O$R^{71}$, —N$R^{74}$C(═O)N$R^{72}R^{73}$, —N$R^{74}$C(═O)N$R^{74}$C(═O)$R^{70}$, —N$R^{74}$S(═O)$_2R^{71}$, —N$R^{74}$S(═O)$_2$N$R^{72}R^{73}$, —O$R^{70}$, ═O, —OC(═O)$R^{70}$, —OC(═O)N$R^{72}R^{73}$, —OC(═O)O$R^{70}$, —Si($R^{74}$)$_3$, —S(═O)$_n R^{70}$, and —S(═O)$_2$N$R^{72}R^{73}$.

Embodiment 803

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$, $C_{6-10}$aryl optionally substituted by 1-3 $R^{79}$, $C_{7-11}$arylalkyl optionally substituted by 1-3 $R^{79}$, $C_{3-10}$cycloalkyl optionally substituted by 1-3 $R^{79}$, 3-10 membered heterocycloalkyl optionally substituted by 1-3 $R^{79}$, 5-10 membered heteroaryl optionally substituted by 1-3 $R^{79}$, halogen, —CN, —C(═O)$R^{70}$, —C(═O)O$R^{70}$, —C(═O)N$R^{72}R^{73}$, —$NO_2$, —N$R^{72}R^{73}$, —N$R^{74}$C(═O)$R^{70}$, —N$R^{74}$C(═O)O$R^{71}$, —N$R^{74}$C(═O)N$R^{72}R^{73}$, —N$R^{74}$C(═O)N$R^{74}$C(═O)$R^{70}$, —N$R^{74}$S(═O)$_2R^{71}$, —N$R^{74}$S(═O)$_2$N$R^{72}R^{73}$, —O$R^{70}$, ═O, —OC(═O)$R^{70}$, —OC(═O)N$R^{72}R^{73}$, —OC(═O)O$R^{70}$, —Si($R^{74}$)$_3$, —S(═O)$_n R^{70}$, and —S(═O)$_2$N$R^{72}R^{73}$.

Embodiment 804

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, benzyl optionally substituted by 1-3 $R^{79}$, $C_{3-6}$cycloalkyl optionally substituted by 1-3 $R^{79}$, 3-6 membered heterocycloalkyl optionally substituted by 1-3 $R^{79}$, 5-6 membered heteroaryl optionally substituted by 1-3 $R^{79}$, halogen, —CN, —C(═O)$R^{70}$, —C(═O)O$R^{70}$, —C(═O)N$R^{72}R^{73}$, —$NO_2$, —N$R^{72}R^{73}$, —N$R^{74}$C(═O)$R^{70}$, —N$R^{74}$C(═)O$R^{71}$, —N$R^{74}$C(═O)N$R^{72}R^{73}$, —N$R^{74}$C(═O)N$R^{74}$C(═O)$R^{70}$, —N$R^{74}$S(═O)$_2R^{71}$, —N$R^{74}$S(═O)$_2$N$R^{72}R^{73}$, —O$R^{70}$, ═O, —OC(═O)$R^{70}$, —OC(═O)N$R^{72}R^{73}$, —OC(═O)O$R^{70}$, —Si($R^{74}$)$_3$, —S(═O)$_n R^{70}$, and —S(═O)$_2$N$R^{72}R^{73}$.

Embodiment 805

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, benzyl optionally substituted by 1-3 $R^{79}$, $C_{3-6}$cycloalkyl optionally substituted by 1-3 $R^{79}$, 3-6 membered heterocycloalkyl optionally substituted by 1-3 $R^{79}$, 5-6 membered heteroaryl optionally substituted by 1-3 $R^{79}$, halogen, —CN, —C(═O)$R^{70}$, —C(═O)O$R^{70}$, —C(═O)N$R^{72}R^{73}$, —$NO_2$, —N$R^{72}R^{73}$, —N$R^{74}$C(═O)$R^{70}$, —N$R^{74}$S(═O)$_2R^{71}$, —O$R^{70}$, —OC(═O)$R^{70}$, —OC(═O)N$R^{72}R^{73}$, —S(═O)$_n R^{70}$, and —S(═O)$_2$N$R^{72}R^{73}$.

Embodiment 806

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, benzyl optionally substituted by 1-3 $R^{79}$, $C_{3-6}$cycloalkyl optionally substituted by 1-3 $R^{79}$, 3-6 membered heterocycloalkyl optionally substituted by 1-3 $R^{79}$, 5-6 membered heteroaryl optionally substituted by 1-3 $R^{79}$, halogen, —CN, —C(═O)N$R^{72}R^{73}$, —N$R^{72}R^{73}$, —O$R^{70}$, and —S(═O)$_n R^{70}$.

Embodiment 807

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, benzyl optionally substituted by 1-3 $R^{79}$, $C_{3-6}$cycloalkyl, 3-6 membered heterocycloalkyl, 5-6 membered heteroaryl, halogen, —CN, —C(═O)N$R^{72}R^{73}$, —N$R^{72}R^{73}$, —O$R^{70}$, and —S(═O)$_n R^{70}$.

Embodiment 808

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, benzyl optionally substituted by 1-3 $R^{79}$, cyclopropyl, 5-6 membered heterocycloalkyl, 5-6 membered heteroaryl, halogen, —CN, —C(═O)N$R^{72}R^{73}$, —N$R^{72}R^{73}$, —O$R^{70}$, and —S(═O)$_n R^{70}$.

Embodiment 809

The compound of any of Embodiments 800-808, wherein $R^{39}$ at each occurrence is independently chosen from $C_{1-6}$alkyl optionally substituted by 1-3 $R^{79}$, benzyl optionally substituted by 1-3 $R^{79}$, and 5-6 membered heteroaryl.

Embodiment 810

The compound of any of Embodiments 800-808, wherein $R^{39}$ at each occurrence is independently chosen from $C_{1-6}$alkyl optionally substituted by 1-3 $R^{79}$, benzyl optionally substituted by 1-3 $R^{79}$, and 6 membered heteroaryl.

Embodiment 811

The compound of any of Embodiments 800-810, wherein $R^{49}$ at each occurrence is independently chosen from $C_{1-6}$alkyl optionally substituted by 1-3 $R^{79}$, phenyl optionally substituted by 1-3 $R^{79}$, 5-6 membered heterocycloalkyl, 5-6 membered heteroaryl, halogen, —C(═O)N$R^{72}R^{73}$, and —N$R^{72}R^{73}$.

Embodiment 812

The compound of any of Embodiments 800-810, wherein $R^{49}$ at each occurrence is independently chosen from $C_{1-6}$alkyl optionally substituted by 1-3 $R^{79}$, phenyl optionally substituted by 1-3 $R^{79}$, 5-6 membered heterocycloalkyl, 6 membered heteroaryl, halogen, —C(═O)N$R^{72}R^{73}$, and —N$R^{72}R^{73}$.

Embodiment 813

The compound of any of Embodiments 800-812, wherein $R^{59}$ at each occurrence is independently chosen from $C_{1-6}$alkyl optionally substituted by 1-3 $R^{79}$, phenyl optionally substituted by 1-3 $R^{79}$, cyclopropyl, 5-6 membered heterocycloalkyl, 5-6 membered heteroaryl, halogen, —CN, —N$R^{72}R^{73}$, —O$R^{70}$, and —S(═O)$R^{70}$.

Embodiment 814

The compound of any of Embodiments 800-812, wherein $R^{59}$ at each occurrence is independently chosen from $C_{1-6}$alkyl optionally substituted by 1-3 $R^{79}$, phenyl optionally substituted by 1-3 $R^{79}$, cyclopropyl, 6 membered heterocycloalkyl, 5-6 membered heteroaryl, halogen, —CN, —N$R^{72}R^{73}$, —O$R^{70}$, and —S(═O)$_n R^{70}$.

Embodiment 815

The compound of any of Embodiments 800-814, wherein $R^{69}$ at each occurrence is independently chosen from $C_{1-6}$alkyl optionally substituted by 1-3 $R^{79}$.

Embodiment 816

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently chosen from $C_{1-6}$alkyl optionally substituted by 1-3 $R^{79}$.

Embodiment 817

The compound of any of Embodiments 1-156, 200-250, 300-371, 400-440, 500-533, 600-668, 700-714, or 750-795, wherein $R^{39}$, $R^{49}$, $R^{59}$ and $R^{69}$ at each occurrence is independently $C_{1-6}$alkyl.

Embodiment 850

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$.

Embodiment 851

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-6 $R^{89}$, $C_{2-6}$alkenyl optionally substituted by 1-6 $R^{89}$, $C_{2-6}$alkynyl optionally substituted by 1-6 $R^{89}$, $C_{6-10}$aryl optionally substituted by 1-6 $R^{89}$, $C_{7-11}$arylalkyl optionally substituted by 1-6 $R^{89}$, $C_{3-10}$cycloalkyl optionally substituted by 1-6 $R^{89}$, 3-10 membered heterocycloalkyl optionally substituted by 1-6 $R^{89}$, and 5-10 membered heteroaryl optionally substituted by 1-6 $R^{89}$.

Embodiment 852

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

Embodiment 853

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, phenyl optionally substituted by 1-3 $R^{89}$, benzyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$.

Embodiment 854

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl, phenyl, benzyl, $C_{3-10}$cycloalkyl, 3-10 membered heterocycloalkyl, and 5-10 membered heteroaryl.

Embodiment 855

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl optionally substituted by 1-3 $R^{89}$, phenyl optionally substituted by 1-3 $R^{89}$, benzyl optionally substituted by 1-3 $R^{89}$, $C_{5-6}$cycloalkyl optionally substituted by 1-3 $R^{89}$, 5-6 membered heterocycloalkyl optionally substituted by 1-3 $R^{89}$, and 5-6 membered heteroaryl optionally substituted by 1-3 $R^{89}$.

Embodiment 856

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 857

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl, phenyl, $C_{5-6}$cycloalkyl, 5-6 membered heterocycloalkyl, and 5-6 membered heteroaryl.

Embodiment 858

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H, $C_{1-6}$alkyl, phenyl, benzyl, $C_{5-6}$cycloalkyl, 5-6 membered heterocycloalkyl optionally substituted by 1 $R^{89}$, and 5-6 membered heteroaryl.

Embodiment 859

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H and $C_{1-6}$alkyl optionally substituted by 1-3 $R^{89}$.

Embodiment 860

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is independently chosen from H and $C_{1-6}$alkyl.

Embodiment 861

The compound of any of Embodiments 1-156, 200-250, 300-371, 400-440, 500-533, 600-668, 700-714, 750-795, or 800-817, wherein $R^{70}$, $R^{71}$, $R^{74}$, $R^{75}$, $R^{76}$ and $R^{77}$ at each occurrence is H.

Embodiment 862

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, and 6-21 membered heteroarylalkyl optionally substituted by 1-27 $R^{99}$; or any $R^{72}$ and $R^{73}$ may form, together with the nitrogen atom to which they are attached, a 3-15 membered heterocycloalkyl optionally substituted by 1-28 $R^{109}$ or a 5-15 membered heteroaryl optionally substituted by 1-15 $R^{109}$.

Embodiment 863

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-6 $R^{99}$, $C_{2-6}$alkenyl optionally substituted by 1-6 $R^{99}$, $C_{2-6}$alkynyl optionally substituted by 1-6 $R^{99}$, $C_{6-11}$aryl optionally substituted by 1-6 $R^{99}$, $C_{7-16}$arylalkyl optionally substituted by 1-6 $R^{99}$, $C_{3-11}$cycloalkyl optionally substituted by 1-6 $R^{99}$, $C_{4-17}$cycloalkylalkyl optionally substituted by 1-6 $R^{99}$, 3-15 membered heterocycloalkyl optionally substituted by 1-6 $R^{99}$, 4-21 membered heterocycloalkylalkyl optionally substituted by 1-6 $R^{99}$, 5-15 membered heteroaryl optionally substituted by 1-6 $R^{99}$, and 6-21 membered heteroarylalkyl optionally substituted by 1-6 $R^{99}$; or any $R^{72}$ and $R^{73}$ may form, together with the nitrogen atom to which they are attached, a 3-15 membered heterocycloalkyl optionally substituted by 1-6 $R^{109}$ or a 5-15 membered heteroaryl optionally substituted by 1-6 $R^{109}$.

Embodiment 864

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, $C_{3-10}$cycloalkyl optionally substituted by 1-3 $R^{99}$, 3-10 membered heterocycloalkyl optionally substituted by 1-3 $R^{99}$, and 5-10 membered heteroaryl optionally substituted by 1-3 $R^{99}$; or any $R^{72}$ and $R^{73}$ may form, together with the nitrogen atom to which they are attached, a 3-15 membered heterocycloalkyl optionally substituted by 1-3 $R^{109}$ or a 5-15 membered heteroaryl optionally substituted by 1-3 $R^{109}$.

Embodiment 865

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, $C_{3-10}$cycloalkyl optionally substituted by 1-3 $R^{99}$, 3-10 membered heterocycloalkyl optionally substituted by 1-3 $R^{99}$, and 5-10 membered heteroaryl optionally substituted by 1-3 $R^{99}$.

Embodiment 866

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, $C_{3-6}$cycloalkyl optionally substituted by 1-3 $R^{99}$, 3-6 membered heterocycloalkyl optionally substituted by 1-3 $R^{99}$, and 5-6 membered heteroaryl optionally substituted by 1-3 $R^{99}$; or any $R^{72}$ and $R^{73}$ may form, together with the nitrogen atom to which they are attached, a 3-10 membered heterocycloalkyl optionally substituted by 1-3 $R^{109}$ or a 5-10 membered heteroaryl optionally substituted by 1-3 $R^{109}$.

Embodiment 867

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, $C_{5-6}$cycloalkyl optionally substituted by 1-3 $R^{99}$, 5-6 membered heterocycloalkyl optionally substituted by 1-3 $R^{99}$, and 5-6 membered heteroaryl optionally substituted by 1-3 $R^{99}$.

Embodiment 868

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, benzyl optionally substituted by 1-3 $R^{99}$, 5-6 membered heterocycloalkyl optionally substituted by 1-3 $R^{99}$, and 5-6 membered heteroaryl optionally substituted by 1-3 $R^{99}$.

Embodiment 869

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl; or any $R^{72}$ and $R^{73}$ may form, together with the nitrogen atom to which they are attached, a 5-6 membered heterocycloalkyl or a 5-6 membered heteroaryl.

Embodiment 870

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 871

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl optionally substituted by 1-3 $R^{99}$, phenyl optionally substituted by 1-3 $R^{99}$, and benzyl optionally substituted by 1-3 $R^{99}$.

Embodiment 872

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H and $C_{1-6}$alkyl optionally substituted by 1-3 $R^{99}$.

Embodiment 873

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H, $C_{1-6}$alkyl, phenyl, and benzyl.

Embodiment 874

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is independently chosen from H and $C_{1-6}$alkyl.

Embodiment 875

The compound of any of Embodiments 1-156, 200-250, 300-371, 400-440, 500-533, 600-668, 700-714, 750-795, 800-817, or 850-861, wherein $R^{72}$ and $R^{73}$ at each occurrence is H.

Embodiment 876

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$; or any two $R^{78}$ attached to the same phosphorus atom can, together with the phosphorus atom linking them, form a 3-10 membered heterocycloalkyl optionally substituted by 1-6 $R^{89}$.

Embodiment 877

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-11}$aryl optionally substituted by 1-3 $R^{89}$, $C_{7-16}$arylalkyl optionally substituted by 1-3 $R^{89}$, $C_{3-11}$cycloalkyl optionally substituted by 1-3 $R^{89}$, $C_{4-17}$cycloalkylalkyl optionally substituted by 1-3 $R^{89}$, 3-15 membered heterocycloalkyl optionally substituted by 1-3 $R^{89}$, 4-21 membered heterocycloalkylalkyl optionally substituted by 1-3 $R^{89}$, 5-15 membered heteroaryl optionally substituted by 1-3 $R^{89}$, and 6-21 membered heteroarylalkyl optionally substituted by 1-3 $R^{89}$; or any two $R^{78}$ attached to the same phosphorus atom can, together with the phosphorus atom linking them, form a 3-10 membered heterocycloalkyl optionally substituted by 1-6 $R^{89}$.

Embodiment 878

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-3 $R^{89}$, $C_{2-6}$alkenyl optionally substituted by 1-3 $R^{89}$, $C_{2-6}$alkynyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$; or any two $R^{78}$ attached to the same phosphorus atom can, together with the phosphorus atom linking them, form a 3-6 membered heterocycloalkyl optionally substituted by 1-3 $R^{89}$.

Embodiment 879

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-3 $R^{89}$, $C_{6-10}$aryl optionally substituted by 1-3 $R^{89}$, $C_{7-11}$arylalkyl optionally substituted by 1-3 $R^{89}$, $C_{3-10}$cycloalkyl optionally substituted by 1-3 $R^{89}$, 3-10 membered heterocycloalkyl optionally substituted by 1-3 $R^{89}$, and 5-10 membered heteroaryl optionally substituted by 1-3 $R^{89}$; or any two $R^{78}$ attached to the same phosphorus atom can, together with the phosphorus atom linking them, form a 3-6 membered heterocycloalkyl optionally substituted by 1-3 $R^{89}$.

Embodiment 880

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-3 $R^{89}$, phenyl optionally substituted by 1-3 $R^{89}$, benzyl optionally substituted by 1-3 $R^{89}$, $C_{3-6}$cycloalkyl optionally substituted by 1-3 $R^{89}$, 3-6 membered heterocycloalkyl optionally substituted by 1-3 $R^{89}$, and 5-6 membered heteroaryl optionally substituted by 1-3 $R^{89}$; or any two $R^{78}$ attached to the same phosphorus atom can, together with the phosphorus atom linking them, form a 3-6 membered heterocycloalkyl optionally substituted by 1-3 $R^{89}$.

Embodiment 881

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl, phenyl, benzyl, $C_{3-6}$cycloalkyl, 3-6 membered heterocycloalkyl, and 5-6 membered heteroaryl; or any two $R^{78}$ attached to the same phosphorus atom can, together with the phosphorus atom linking them, form a 6 membered heterocycloalkyl optionally substituted by 1-3 $R^{89}$.

Embodiment 882

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-3 $R^{89}$, phenyl, and benzyl.

Embodiment 883

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl optionally substituted by 1-3 $R^{89}$, phenyl optionally substituted by 1-3 $R^{89}$, and benzyl optionally substituted by 1-3 $R^{89}$; or any two $R^{78}$ attached to the same phosphorus atom can, together with the phosphorus atom linking them, form a 6 membered heterocycloalkyl optionally substituted by 1-3 $R^{89}$.

Embodiment 884

The compound of any of Embodiments 1-156, 200-250, 300-371, 400-440, 500-533, 600-668, 700-714, 750-795, 800-817, or 850-875, wherein $R^{78}$ at each occurrence is independently chosen from $C_{1-6}$alkyl, phenyl, and benzyl; or any two $R^{78}$ attached to the same phosphorus atom can, together with the phosphorus atom linking them, form an azaphosphinane ring optionally substituted by 1-3 $C_{1-6}$alkyl.

Embodiment 885

The compound of any of Embodiments 1-156, 200-250, 300-371, 400-440, 500-533, 600-668, 700-714, 750-795, 800-817, or 850-875, wherein $R^{78}$ at each occurrence is $C_{1-6}$alkyl optionally substituted by 1-3 $R^{89}$; or any two $R^{78}$ attached to the same phosphorus atom can, together with the phosphorus atom linking them, form an azaphosphinane ring optionally substituted by 1-3 $R^{89}$.

Embodiment 886

The compound of any of Embodiments 1-156, 200-250, 300-371, 400-440, 500-533, 600-668, 700-714, 750-795, 800-817, or 850-875, wherein $R^{78}$ at each occurrence is $C_{1-6}$alkyl.

Embodiment 900

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-6 $R^{119}$, $C_{2-6}$alkenyl optionally substituted by 1-6 $R^{119}$, $C_{2-6}$alkynyl optionally substituted by 1-6 $R^{119}$, $C_{6-11}$aryl optionally substituted by 1-6 $R^{119}$, $C_{7-16}$arylalkyl optionally substituted by 1-6 $R^{119}$, $C_{3-11}$cycloalkyl optionally substituted by 1-6 $R^{119}$, $C_{4-17}$cycloalkylalkyl optionally substituted by 1-6 $R^{119}$, 3-15 membered heterocycloalkyl optionally substituted by 1-6 $R^{119}$, 4-21 membered heterocycloalkylalkyl optionally substituted by 1-6 $R^{119}$, 5-15 membered heteroaryl optionally substituted by 1-6 $R^{19}$, 6-21 membered heteroarylalkyl optionally substituted by 1-6 $R^{119}$, halogen, —CN, —C(=O)$R^{110}$, —C(=O)O$R^{110}$, —C(=O)N$R^{112}R^{113}$, —C(=O)C(=O)$R^{110}$, —C(=N$R^{115}$)$R^{110}$, —C(=N$R^{115}$)N$R^{112}R^{113}$, —C(=NOH)N$R^{112}R^{113}$, —C(=NO$R^{116}$)$R^{110}$, —C(=NN$R^{112}R^{113}$)$R^{110}$, —C(=NN$R^{114}$C(=O)$R^{111}$)$R^{110}$, —C(=NN$R^{114}$C(=O)O$R^{111}$)$R^{110}$, —C(=S)N$R^{112}R^{113}$, —NC, —$NO_2$, —N$R^{112}R^{113}$, —N$R^{114}$N$R^{112}R^{113}$, —N=N$R^{114}$, =N$R^{110}$, =NO$R^{110}$, —N$R^{114}$O$R^{116}$, —N$R^{114}$C(=O)$R^{110}$, —N$R^{114}$C(=O)C(=O)$R^{110}$, —N$R^{114}$C(=O)O$R^{111}$, —N$R^{114}$C(=O)C(=O)O$R^{111}$, —N$R^{114}$C(=O)N$R^{112}R^{113}$, —N$R^{114}$C(=O)N$R^{114}$C(=O)$R^{110}$, —N$R^{14}$C(=O)N$R^{114}$C(=O)O$R^{110}$, —N$R^{14}$C(=N$R^{115}$)N$R^{112}R^{113}$, —N$R^{114}$C(=O)C(=O)N$R^{112}R^{113}$, —N$R^{114}$C(=S)$R^{110}$, —N$R^{114}$C(=S)O$R^{110}$, —N$R^{114}$C(=S)N$R^{112}R^{113}$, —N$R^{114}$S(=O)$_2R^{11}$, —N$R^{114}$S(=O)$_2$N$R^{112}R^{113}$, —N$R^{114}$P(=O)$R^{118}R^{118}$, —N$R^{114}$P(=O)(N$R^{112}R^{113}$)(N$R^{112}R^{113}$), —N$R^{114}$P(=O)(O$R^{110}$)(O$R^{110}$)—N$R^{114}$P(=O)(S$R^{110}$)(S$R^{110}$), —O$R^{110}$, =O, —OCN, —OC(=O)$R^{110}$, —OC(=O)N$R^{112}R^{113}$, —OC(=O)O$R^{110}$, —OC(=N$R^{115}$)N$R^{112}R^{113}$, —OS(=O)$R^{110}$, —OS(=O)$_2$R, —OS(=O)$_2$O$R^{110}$, —OS(=O)$_2$N$R^{112}R^{113}$, —OP(=O)$R^{118}R^{118}$, —OP(=O)(N$R^{112}R^{113}$)(N$R^{112}R^{113}$), —OP(=O)(O$R^{110}$)(O$R^{110}$), —OP(=O)(S$R^{110}$)(S$R^{110}$), —Si($R^{114}$)$_3$, —SCN, =S, —S(=O)$_n R^{110}$, —S(=O)$_2$O$R^{110}$, —$SO_3R^{1111}$, —S(=O)$_2$N$R^{112}R^{113}$, —S(=O)N$R^{112}R^{113}$, —SP(=O)$R^{118}R^{118}$, —SP(=O)(N$R^{112}R^{113}$)(N$R^{112}R^{113}$), —SP(=O)(O$R^{110}$)(O$R^{110}$), —SP(=O)(S$R^{110}$)(S$R^{110}$), —P(=O)$R^{118}R^{118}$, —P(=O)(N$R^{112}R^{113}$)(N$R^{112}R^{113}$), —P(=O)(O$R^{110}$)(O$R^{110}$), and —P(=O)(S$R^{110}$)(S$R^{110}$).

Embodiment 901

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-6 $R^{119}$, $C_{6-11}$aryl optionally substituted by 1-6 $R^{119}$, $C_{7-16}$arylalkyl optionally substituted by 1-6 $R^{119}$, $C_{3-11}$cycloalkyl optionally substituted by 1-6 $R^{119}$, 3-15 membered heterocycloalkyl optionally substituted by 1-6 $R^{119}$, 5-15 membered heteroaryl optionally substituted by 1-6 $R^{119}$, halogen, —CN, —C(=O)$R^{110}$, —C(=O)O$R^{110}$, —C(=O)N$R^{112}R^{113}$, —NC, —$NO_2$, —N$R^{112}R^{113}$, —N$R^{114}$N$R^{112}R^{113}$, —N$R^{114}$O$R^{116}$, —N$R^{114}$C(=O)$R^{110}$, —N$R^{114}$C(=O)O$R^{111}$, —N$R^{114}$C(=O)N$R^{112}R^{113}$, —N$R^{114}$C(=O)N$R^{114}$C(=O)$R^{110}$, —N$R^{114}$S(=O)$_2R^{111}$, —N$R^{114}$S(=O)$_2$N$R^{112}R^{113}$, —O$R^{110}$, =O, —OCN, —OC(=O)$R^{110}$, —OC(=O)N$R^{112}R^{113}$, —OC(=O)O$R^{110}$, —Si($R^{114}$)$_3$, —SCN, =S, —S(=O)$_n R^{110}$, and —S(=O)$_2$N$R^{112}R^{113}$.

Embodiment 902

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-6 $R^{119}$, $C_{6-10}$aryl optionally substituted by 1-6 $R^{119}$, $C_{7-11}$arylalkyl optionally substituted by 1-6 $R^{119}$, $C_{3-10}$cycloalkyl optionally substituted by 1-6 $R^{119}$, 3-10 membered heterocycloalkyl optionally substituted by 1-6 $R^{119}$, 5-10 membered heteroaryl optionally substituted by 1-6 $R^{119}$, halogen, —CN, —C(═O)$R^{110}$, —C(═O)$OR^{110}$, —C(═O)$NR^{112}R^{113}$, —$NO_2$, —$NR^{112}R^{113}$, —$NR^{114}$C(═O)$R^{110}$, —$NR^{114}$C(═O)$OR^{111}$, —$NR^{114}$C(═O)$NR^{112}R^{113}$, —$NR^{114}$C(═O)$NR^{114}$C(═O)$R^{110}$, —$NR^{114}$S(═O)$_2R^{111}$, —$NR^{114}$S(═O)$_2NR^{112}R^{113}$, —$OR^{110}$, ═O, —OC(═O)$R^{110}$, —OC(═O)$NR^{112}R^{113}$, —OC(═O)$OR^{110}$, —Si($R^{114}$)$_3$, —S(═O)$_n R^{110}$, and —S(═O)$_2NR^{112}R^{113}$.

Embodiment 903

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-3 $R^{119}$, $C_{6-10}$aryl optionally substituted by 1-3 $R^{119}$, $C_{7-11}$arylalkyl optionally substituted by 1-3 $R^{119}$, $C_{3-10}$cycloalkyl optionally substituted by 1-3 $R^{119}$, 3-10 membered heterocycloalkyl optionally substituted by 1-3 $R^{119}$, 5-10 membered heteroaryl optionally substituted by 1-3 $R^{119}$, halogen, —CN, —C(═O)$R^{110}$, —C(═O)$OR^{110}$, —C(═O)$NR^{112}R^{113}$, —$NO_2$, —$NR^{112}R^{113}$, —$NR^{114}$C(═O)$R^{110}$, —$NR^{114}$C(═O)$OR^{111}$, —$NR^{114}$C(═O)$NR^{112}R^{113}$, —$NR^{114}$C(═O)$NR^{114}$C(═O)$R^{110}$, —$NR^{114}$S(═O)$_2R^{111}$, —$NR^{114}$S(═O)$_2NR^{112}R^{113}$, —$OR^{110}$, ═O, —OC(═O)$R^{110}$, —OC(═O)$NR^{112}R^{113}$, —OC(═)$OR^{110}$, —Si($R^{114}$)$_3$, —S(═O)$_n R^{110}$, and —S(═O)$_2NR^{112}R^{113}$.

Embodiment 904

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-3 $R^{119}$, phenyl optionally substituted by 1-3 $R^{119}$, benzyl optionally substituted by 1-3 $R^{119}$, $C_{3-6}$cycloalkyl optionally substituted by 1-3 $R^{119}$, 3-6 membered heterocycloalkyl optionally substituted by 1-3 $R^{119}$, 5-6 membered heteroaryl optionally substituted by 1-3 $R^{119}$, halogen, —CN, —C(═O)$R^{11}$, —C(═O)$OR^{110}$, —C(═O)$NR^{112}R^{113}$, —$NO_2$, —$NR^{112}R^{113}$, —$NR^{114}$C(═O)$R^{110}$, —$NR^{114}$C(═O)$OR^{111}$, —$NR^{114}$C(═O)$NR^{112}R^{113}$, —$NR^{114}$C(═O)$NR^{114}$C(═O)$R^{110}$, —$NR^{114}$S(═O)$_2R^{111}$, —$NR^{114}$S(═O)$_2NR^{112}R^{113}$, —$OR^{10}$, ═O, —OC(═O)$R^{110}$, —OC(═O)$NR^{112}R^{113}$, —OC(═O)$OR^{110}$, —Si($R^{114}$)$_3$, —S(═)$_n R^{110}$, and —S(═O)$_2NR^{112}R^{113}$.

Embodiment 905

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-3 $R^{119}$, phenyl optionally substituted by 1-3 $R^{119}$, benzyl optionally substituted by 1-3 $R^{119}$, $C_{3-6}$cycloalkyl optionally substituted by 1-3 $R^{119}$, 3-6 membered heterocycloalkyl optionally substituted by 1-3 $R^{119}$, 5-6 membered heteroaryl optionally substituted by 1-3 $R^{119}$, halogen, —CN, —C(═O)$R^{11}$, —C(═O)$OR^{110}$, —C(═O)$NR^{112}R^{113}$, —$NO_2$, —$NR^{112}R^{113}$, —$NR^{114}$C(═O)$R^{111}$, —$NR^{114}$S(═O)$_2R^{111}$, —$OR^{110}$, —OC(═O)$R^{110}$, —OC(═O)$NR^{112}R^{113}$, —S(═O)$_n R^{110}$, and —S(═O)$_2NR^{112}R^{113}$.

Embodiment 906

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl, phenyl, benzyl, $C_{3-6}$cycloalkyl, 3-6 membered heterocycloalkyl, 5-6 membered heteroaryl, halogen, —CN, —C(═O)$R^{110}$, —C(═O)$OR^{110}$, —C(═O)$NR^{112}R^{113}$, —$NO_2$, —$NR^{112}R^{113}$, —$NR^{114}$C(═O)$R^{110}$, —$NR^{114}$S(═O)$_2R^{111}$, —$OR^{110}$, —OC(═O)$R^{110}$, —OC(═O)$NR^{112}R^{113}$, —S(═O)$_n R^{110}$, and —S(═O)$_2NR^{112}R^{113}$.

Embodiment 907

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl, phenyl, benzyl, halogen, —CN, —C(═O)$OR^{110}$, —C(═O)$NR^{112}R^{113}$, —$NO_2$, —$NR^{112}R^{113}$, —$OR^{110}$, and —S(═O)$_n R^{110}$.

Embodiment 908

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-3 $R^{119}$, phenyl optionally substituted by 1-3 $R^{119}$, benzyl optionally substituted by 1-3 $R^{119}$, halogen, —CN, —C(═O)$OR^{110}$, —C(═O)$NR^{112}R^{113}$, —$NO_2$, —$NR^{112}R^{113}$, —$OR^{110}$, and —S(═O)$_n R^{110}$.

Embodiment 909

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl, phenyl, benzyl, halogen, —$NR^{112}R^{113}$ and —$OR^{110}$.

Embodiment 910

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl, halogen, —$NR^{12}R^{113}$, and —$OR^{110}$.

Embodiment 911

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-3 $R^{119}$ and halogen.

Embodiment 912

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently chosen from $C_{1-6}$alkyl optionally substituted by 1-3 $R^{119}$.

Embodiment 913

The compound of any of Embodiments 1-156, 200-250, 300-371, 400-440, 500-533, 600-668, 700-714, 750-795, 800-817, or 850-886, wherein $R^{79}$, $R^{89}$, $R^{99}$ and $R^{109}$ at each occurrence is independently $C_{1-6}$alkyl.

Embodiment 914

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{114}$, $R^{115}$, $R^{116}$ and $R^{117}$ at each occurrence is independently chosen from H, $C_{1-6}$alkyl optionally substituted by 1-13 $R^{129}$, $C_{2-6}$alkenyl optionally substituted by 1-11 $R^{129}$, $C_{2-6}$alkynyl optionally substituted by 1-9 $R^{129}$, $C_{6-11}$aryl optionally substituted by 1-11 $R^{129}$, $C_{7-16}$arylalkyl optionally substituted by 1-19 $R^{129}$, $C_{3-11}$cycloalkyl optionally substituted by 1-21 $R^{129}$, $C_{4-17}$cycloalkylalkyl optionally substituted by 1-32 $R^{129}$, 3-15 membered heterocycloalkyl optionally substituted by 1-28 $R^{129}$, 4-21 membered heterocycloalkylalkyl optionally substituted by 1-40 $R^{129}$, 5-15 membered heteroaryl optionally substituted by 1-15 $R^{129}$, and 6-21 membered heteroarylalkyl optionally substituted by 1-27 $R^{129}$.

Embodiment 915

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{4}$, $R^{115}$, $R^{116}$ and $R^{117}$ at each occurrence is independently chosen from H, $C_{1-6}$alkyl optionally substituted by 1-6 $R^{129}$, $C_{2-6}$alkenyl optionally substituted by 1-6 $R^{129}$, $C_{2-6}$alkynyl optionally substituted by 1-6 $R^{129}$, $C_{6-10}$aryl optionally substituted by 1-6 $R^{129}$, $C_{7-11}$arylalkyl optionally substituted by 1-6 $R^{129}$, $C_{3-10}$cycloalkyl optionally substituted by 1-6 $R^{129}$, 3-10 membered heterocycloalkyl optionally substituted by 1-6 $R^{129}$, and 5-10 membered heteroaryl optionally substituted by 1-6 $R^{129}$.

Embodiment 916

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{114}$, $R^{115}$, $R^{116}$ and $R^{117}$ at each occurrence is independently chosen from H, $C_{1-6}$alkyl optionally substituted by 1-3 $R^{129}$, $C_{2-6}$alkenyl optionally substituted by 1-3 $R^{129}$, $C_{2-6}$alkynyl optionally substituted by 1-3 $R^{129}$, $C_{6-10}$aryl optionally substituted by 1-3 $R^{129}$, $C_{7-11}$arylalkyl optionally substituted by 1-3 $R^{129}$, $C_{3-10}$cycloalkyl optionally substituted by 1-3 $R^{129}$, 3-10 membered heterocycloalkyl optionally substituted by 1-3 $R^{129}$, and 5-10 membered heteroaryl optionally substituted by 1-3 $R^{129}$.

Embodiment 917

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{4}$, $R^{115}$, $R^{116}$ and $R^{117}$ at each occurrence is independently chosen from H, $C_{1-6}$alkyl optionally substituted by 1-3 $R^{129}$, phenyl optionally substituted by 1-3 $R^{129}$, benzyl optionally substituted by 1-3 $R^{129}$, $C_{3-10}$cycloalkyl optionally substituted by 1-3 $R^{129}$, 3-10 membered heterocycloalkyl optionally substituted by 1-3 $R^{129}$, and 5-10 membered heteroaryl optionally substituted by 1-3 $R^{129}$.

Embodiment 918

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{114}$, $R^{115}$, $R^{116}$ and $R^{117}$ at each occurrence is independently chosen from H, $C_{1-6}$alkyl, phenyl, benzyl, $C_{3-10}$cycloalkyl, 3-10 membered heterocycloalkyl, and 5-10 membered heteroaryl.

Embodiment 919

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{114}$, $R^{115}$, $R^{116}$ and $R^{117}$ at each occurrence is independently chosen from H, $C_{1-6}$alkyl optionally substituted by 1-3 $R^{129}$, phenyl optionally substituted by 1-3 $R^{129}$, benzyl optionally substituted by 1-3 $R^{129}$, $C_{5-6}$cycloalkyl optionally substituted by 1-3 $R^{129}$, 5-6 membered heterocycloalkyl optionally substituted by 1-3 $R^{129}$, and 5-6 membered heteroaryl optionally substituted by 1-3 $R^{129}$.

Embodiment 920

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{114}$, $R^{115}$, $R^{116}$ and $R^{117}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 921

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{4}$, $R^{115}$, $R^{116}$ and $R^{117}$ at each occurrence is independently chosen from H, $C_{1-6}$alkyl, phenyl, $C_{5-6}$cycloalkyl, 5-6 membered heterocycloalkyl, and 5-6 membered heteroaryl.

Embodiment 922

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{4}$, $R^{115}$, $R^{116}$ and $R^{117}$ at each occurrence is independently chosen from H, $C_{1-6}$alkyl, phenyl, benzyl, $C_{5-6}$cycloalkyl, 5-6 membered heterocycloalkyl optionally substituted by 1 $R^{129}$, and 5-6 membered heteroaryl.

Embodiment 923

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{4}$, $R^{115}$, $R^{116}$ and $R^{117}$ at each occurrence is independently chosen from H and $C_{1-6}$alkyl optionally substituted by 1-3 $R^{129}$.

Embodiment 924

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^{114}$, $R^{115}$, $R^{116}$ and $R^{117}$ at each occurrence is independently chosen from H and $C_{1-6}$alkyl.

Embodiment 925

The compound of any of Embodiments 1-156, 200-250, 300-371, 400-440, 500-533, 600-668, 700-714, 750-795, 800-817, 850-886, or 900-913, wherein $R^{110}$, $R^{111}$, $R^4$, $R^{115}$, $R^{116}$ and $R^{117}$ at each occurrence is H.

Embodiment 926

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$aryl optionally substituted by 1-11 $R^{139}$, $C_{7-16}$arylalkyl optionally substituted by 1-19 $R^{139}$, $C_{3-11}$ optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, and 6-21 membered heteroarylalkyl optionally substituted by 1-27 $R^{139}$; or any $R^{112}$ and $R^{113}$ may form, together with the nitrogen atom to which they are attached, a 3-15 membered heterocycloalkyl optionally substituted by 1-28 $R^{149}$ or a 5-15 membered heteroaryl optionally substituted by 1-15 $R^{149}$.

Embodiment 927

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-6 $R^{139}$, $C_{2-6}$alkenyl optionally substituted by 1-6 $R^{139}$, $C_{2-6}$alkynyl optionally substituted by 1-6 $R^{39}$, $C_{6-11}$aryl optionally substituted by 1-6 $R^{139}$, $C_{7-16}$arylalkyl optionally substituted by 1-6 $R^{139}$, $C_{3-11}$cycloalkyl optionally substituted by 1-6 $R^{139}$, $C_{4-17}$cycloalkylalkyl optionally substituted by 1-6 $R^{139}$, 3-15 membered heterocycloalkyl optionally substituted by 1-6 $R^{139}$, 4-21 membered heterocycloalkylalkyl optionally substituted by 1-6 $R^{139}$, 5-15 membered heteroaryl optionally substituted by 1-6 $R^{139}$, and 6-21 membered heteroarylalkyl optionally substituted by 1-6 $R^{139}$; or any $R^2$ and $R^{113}$ may form, together with the nitrogen atom to which they are attached, a 3-15 membered heterocycloalkyl optionally substituted by 1-6 $R^{149}$ or a 5-15 membered heteroaryl optionally substituted by 1-6 $R^{149}$.

Embodiment 928

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-3 $R^{139}$, phenyl optionally substituted by 1-3 $R^{139}$, benzyl optionally substituted by 1-3 $R^{139}$, $C_{3-10}$cycloalkyl optionally substituted by 1-3 $R^{139}$, 3-10 membered heterocycloalkyl optionally substituted by 1-3 $R^{139}$, and 5-10 membered heteroaryl optionally substituted by 1-3 $R^{139}$; or any $R^{112}$ and $R^{113}$ may form, together with the nitrogen atom to which they are attached, a 3-15 membered heterocycloalkyl optionally substituted by 1-3 $R^{149}$ or a 5-15 membered heteroaryl optionally substituted by 1-3 $R^{149}$.

Embodiment 929

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-3 $R^{139}$, phenyl optionally substituted by 1-3 $R^{139}$, benzyl optionally substituted by 1-3 $R^{139}$, $C_{3-10}$cycloalkyl optionally substituted by 1-3 $R^{139}$, 3-10 membered heterocycloalkyl optionally substituted by 1-3 $R^{139}$, and 5-10 membered heteroaryl optionally substituted by 1-3 $R^{139}$.

Embodiment 930

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-3 $R^{139}$, phenyl optionally substituted by 1-3 $R^{139}$, benzyl optionally substituted by 1-3 $R^{139}$, $C_{3-6}$cycloalkyl optionally substituted by 1-3 $R^{139}$, 3-6 membered heterocycloalkyl optionally substituted by 1-3 $R^{139}$, and 5-6 membered heteroaryl optionally substituted by 1-3 $R^{139}$; or any $R^{112}$ and $R^{113}$ may form, together with the nitrogen atom to which they are attached, a 3-10 membered heterocycloalkyl optionally substituted by 1-3 $R^{149}$ or a 5-10 membered heteroaryl optionally substituted by 1-3 $R^{149}$.

Embodiment 931

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-3 $R^{139}$, phenyl optionally substituted by 1-3 $R^{139}$, benzyl optionally substituted by 1-3 $R^{139}$, $C_{5-6}$cycloalkyl optionally substituted by 1-3 $R^{139}$, 5-6 membered heterocycloalkyl optionally substituted by 1-3 $R^{139}$, and 5-6 membered heteroaryl optionally substituted by 1-3 $R^{139}$.

Embodiment 932

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-3 $R^{139}$, phenyl optionally substituted by 1-3 $R^{139}$, benzyl optionally substituted by 1-3 $R^{139}$, 5-6 membered heterocycloalkyl optionally substituted by 1-3 $R^{139}$, and 5-6 membered heteroaryl optionally substituted by 1-3 $R^{139}$.

Embodiment 933

The compound of any of Embodiments 1-156, 200-250, 300-371, 400-440, 500-533, 600-668, 700-714, 750-795, 800-817, 850-886, or 900-925, wherein $R^{112}$ and $R^{113}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl; or any $R^{112}$ and $R^{113}$ may form, together with the nitrogen atom to which they are attached, a 5-6 membered heterocycloalkyl or a 5-6 membered heteroaryl.

Embodiment 934

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 935

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H, $C_{1-6}$alkyl optionally substituted by 1-3 $R^{139}$, phenyl optionally substituted by 1-3 $R^{139}$, and benzyl optionally substituted by 1-3 $R^{139}$.

Embodiment 936

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H and $C_{1-6}$alkyl optionally substituted by 1-3 $R^{139}$.

Embodiment 937

The compound of any of Embodiments 1-156, 200-250, 300-371, 400-440, 500-533, 600-668, 700-714, 750-795, 800-817, 850-886, or 900-925, wherein $R^{112}$ and $R^{113}$ at each occurrence is independently chosen from H, $C_{1-6}$alkyl, phenyl, and benzyl.

Embodiment 938

The compound of any of Embodiments 1-156, 200-250, 300-371, 400-440, 500-533, 600-668, 700-714, 750-795, 800-817, 850-886, or 900-925, wherein $R^{12}$ and $R^{113}$ at each occurrence is independently chosen from H and $C_{1-6}$alkyl.

Embodiment 939

The compound of any of Embodiments 1-156, 200-250, 300-371, 400-440, 500-533, 600-668, 700-714, 750-795, 800-817, 850-886, or 900-925, wherein $R^{112}$ and $R^{113}$ at each occurrence is H.

Embodiment 940

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-13 $R^{129}$, $C_{2-6}$alkenyl optionally substituted by 1-11 $R^{129}$, $C_{2-6}$alkynyl optionally substituted by 1-9 $R^{129}$, $C_{6-11}$aryl optionally substituted by 1-11 $R^{129}$, $C_{7-16}$arylalkyl optionally substituted by 1-19 $R^{129}$, $C_{3-11}$cycloalkyl optionally substituted by 1-21 $R^{129}$, $C_{4-17}$cycloalkylalkyl optionally substituted by 1-32 $R^{129}$, 3-15 membered heterocycloalkyl optionally substituted by 1-28 $R^{129}$, 4-21 membered heterocycloalkylalkyl optionally substituted by 1-40 $R^{129}$, 5-15 membered heteroaryl optionally substituted by 1-15 $R^{129}$, and 6-21 membered heteroarylalkyl optionally substituted by 1-27 $R^{129}$.

Embodiment 941

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-3 $R^{129}$, $C_{2-6}$alkenyl optionally substituted by 1-3 $R^{129}$, $C_{2-6}$alkynyl optionally substituted by 1-3 $R^{129}$, $C_{6-11}$aryl optionally substituted by 1-3 $R^{129}$, $C_{7-16}$arylalkyl optionally substituted by 1-3 $R^{129}$, $C_{3-11}$ cycloalkyl optionally substituted by 1-3 $R^{129}$, $C_{4-17}$cycloalkylalkyl optionally substituted by 1-3 $R^{129}$, 3-15 membered heterocycloalkyl optionally substituted by 1-3 $R^{129}$, 4-21 membered heterocycloalkylalkyl optionally substituted by 1-3 $R^{129}$, 5-15 membered heteroaryl optionally substituted by 1-3 $R^{129}$, and 6-21 membered heteroarylalkyl optionally substituted by 1-3 $R^{129}$.

Embodiment 942

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-3 $R^{129}$, $C_{2-6}$alkenyl optionally substituted by 1-3 $R^{129}$, $C_{2-6}$alkynyl optionally substituted by 1-3 $R^{129}$, $C_{6-10}$aryl optionally substituted by 1-3 $R^{129}$, $C_{7-11}$arylalkyl optionally substituted by 1-3 $R^{129}$, $C_{3-10}$cycloalkyl optionally substituted by 1-3 $R^{129}$, 3-10 membered heterocycloalkyl optionally substituted by 1-3 $R^{129}$, and 5-10 membered heteroaryl optionally substituted by 1-3 $R^{129}$.

Embodiment 943

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-3 $R^{129}$, $C_{6-10}$aryl optionally substituted by 1-3 $R^{129}$, $C_{7-11}$arylalkyl optionally substituted by 1-3 $R^{129}$, $C_{3-10}$cycloalkyl optionally substituted by 1-3 $R^{129}$, 3-10 membered heterocycloalkyl optionally substituted by 1-3 $R^{129}$, and 5-10 membered heteroaryl optionally substituted by 1-3 $R^{129}$.

Embodiment 944

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-3 $R^{129}$, phenyl optionally substituted by 1-3 $R^{129}$, benzyl optionally substituted by 1-3 $R^{129}$, $C_{3-6}$cycloalkyl optionally substituted by 1-3 $R^{129}$, 3-6 membered heterocycloalkyl optionally substituted by 1-3 $R^{129}$, and 5-6 membered heteroaryl optionally substituted by 1-3 $R^{129}$.

Embodiment 945

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl, phenyl, benzyl, $C_{3-6}$cycloalkyl, 3-6 membered heterocycloalkyl, and 5-6 membered heteroaryl.

Embodiment 946

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-3 $R^{129}$, phenyl, and benzyl.

Embodiment 947

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl optionally substituted by 1-3 $R^{129}$, phenyl optionally substituted by 1-3 $R^{129}$, and benzyl optionally substituted by 1-3 $R^{129}$.

Embodiment 948

The compound of any of Embodiments 1-156, 200-250, 300-371, 400-440, 500-533, 600-668, 700-714, 750-795, 800-817, 850-886, or 900-939, wherein $R^{118}$ at each occurrence is independently chosen from $C_{1-6}$alkyl, phenyl, and benzyl.

Embodiment 949

The compound of any of Embodiments 1-156, 200-250, 300-371, 400-440, 500-533, 600-668, 700-714, 750-795, 800-817, 850-886, or 900-939, wherein $R^{118}$ at each occurrence is $C_{1-6}$alkyl optionally substituted by 1-3 $R^{129}$.

Embodiment 950

The compound of any of Embodiments 1-156, 200-250, 300-371, 400-440, 500-533, 600-668, 700-714, 750-795, 800-817, 850-886, or 900-939, wherein $R^{118}$ at each occurrence is $C_{1-6}$alkyl.

Embodiment 951

The compound of any of Embodiments 1-156, 200-250, 300-371, 400-440, 500-533, 600-668, 700-714, 750-795, 800-817, 850-886, or 900-950, wherein $R^{119}$, $R^{129}$, —$R^{139}$ and $R^{149}$ at each occurrence is independently chosen from $C_{1-6}$alkyl optionally substituted by 1-6 $R^{159}$, $C_{2-6}$alkenyl optionally substituted by 1-6 $R^{159}$, $C_{2-6}$alkynyl optionally substituted by 1-6 $R^{159}$, $C_{6-11}$aryl optionally substituted by 1-6 $R^{159}$, $C_{7-16}$arylalkyl optionally substituted by 1-6 $R^{159}$, $C_{3-11}$cycloalkyl optionally substituted by 1-6 $R^{159}$, $C_{4-17}$cycloalkylalkyl optionally substituted by 1-6 $R^{159}$, 3-15 membered heterocycloalkyl optionally substituted by 1-6 $R^{159}$, 4-21 membered heterocycloalkylalkyl optionally substituted by 1-6 $R^{159}$, 5-15 membered heteroaryl optionally substituted by 1-6 $R^{159}$, 6-21 membered heteroarylalkyl optionally substituted by 1-6 $R^{159}$, halogen, —CN, —C(═O)$R^{150}$, —C(═O)O$R^{150}$, —C(═O)N$R^{152}R^{153}$, —(═O)C(═O)$R^{150}$, —C(═N$R^{155}$)$R^{150}$, —C(═N$R^{155}$)N$R^{152}R^{153}$, —C(═NOH)N$R^{152}R^{153}$, —C(═NO$R^{156}$)$R^{150}$, —C(═NN$R^{152}R^{153}$)$R^{150}$, —C(═NN$R^{154}$C(═O)$R^{151}$)$R^{150}$, —C(═NN$R^{154}$C(═O)O$R^{151}$)$R^{150}$, —C(═S)N$R^{152}R^{153}$, —NC, —$NO_2$, —N$R^{152}R^{153}$, —N$R^{154}$N$R^{152}R^{153}$, —N═N$R^{154}$, ═N$R^{150}$, ═NO$R^{150}$, —N$R^{154}$O$R^{156}$, —N$R^{154}$C(═O)$R^{150}$, —N$R^{154}$C(═O)C(═O)$R^{150}$, —N$R^{154}$C(═O)O$R^{151}$, —N$R^{154}$C(═O)C(═O)O$R^{151}$, —N$R^{154}$C(═O)N$R^{152}R^{153}$, —N$R^{154}$C(═O)N$R^{154}$C(═O)$R^{150}$, —N$R^{154}$C(═O)N$R^{154}$C(═O)O$R^{150}$, —N$R^{154}$C(═N$R^{155}$)N$R^{152}R^{153}$, —N$R^{154}$C(═O)C(═O)N$R^{152}R^{153}$, —N$R^{154}$C(═S)$R^{150}$, —N$R^{154}$C(═S)O$R^{150}$, —N$R^{154}$C(═S)N$R^{152}R^{153}$, —N$R^{154}$S(═O)$_2R^{151}$, —N$R^{154}$S(═O)$_2$N$R^{152}R^{15}$, —N$R^{154}$P(═O)$R^{158}R^{15}$, —N$R^{154}$P(═O)(N$R^{152}R^{153}$)(N$R^{152}R^{153}$), —N$R^{154}$P(═O)(O$R^{150}$)(O$R^{150}$), —N$R^{154}$P(═O)(S$R^{150}$)(S$R^{150}$), —O$R^{150}$, ═O, —OCN, —OC(═O)$R^{150}$, —OC(═O)N$R^{152}R^{153}$, —OC(═O)O$R^{150}$, —OC(═N$R^{155}$)N$R^{152}R^{153}$, —OS(═O)$R^{150}$, —OS(═O)$_2R^{150}$, —OS(═O)$_2$O$R^{150}$, —OS(═O)$_2$N$R^{152}R^{153}$, —OP(═O)$R^{158}R^{158}$, —OP(═O)(N$R^{152}R^{153}$)(N$R^{152}R^{153}$), —OP(═O)(O$R^{150}$)(O$R^{150}$), —OP(═O)(S$R^{150}$)(S$R^{150}$), —Si($R^{154}$)$_3$, —SCN, ═S, —S(═O)$_n$R, —S(═O)$_2$O$R^{150}$, —SO$_3R^{1515}$, —S(═O)$_2$N$R^{152}R^{153}$, —S(═O)N$R^{152}R^{153}$, —SP(═O)$R^{158}R^{158}$, —SP(═O)(N$R^{152}R^{153}$)(N$R^{152}R^{153}$), —SP(═O)(O$R^{150}$)(O$R^{150}$), —SP(═O)(S$R^{150}$)(S$R^{150}$), —P(═O)$R^{158}R^{158}$, —P(═O)(N$R^{152}R^{153}$)(N$R^{152}R^{153}$), —P(═O)(O$R^{150}$)(O$R^{150}$), and —P(═O)(S$R^{150}$)(S$R^{150}$).

Embodiment 952

The compound of any of Embodiments 1-156, 200-250, 300-371, 400-440, 500-533, 600-668, 700-714, 750-795, 800-817, 850-886, or 900-950, wherein $R^{119}$, $R^{129}$, —$R^{139}$ and $R^{149}$ at each occurrence is independently chosen from $C_{1-6}$alkyl optionally substituted by 1-6 $R^{159}$, $C_{6-11}$aryl optionally substituted by 1-6 $R^{159}$, $C_{7-16}$arylalkyl optionally substituted by 1-6 $R^{159}$, $C_{3-11}$cycloalkyl optionally substituted by 1-6 $R^{159}$, 3-15 membered heterocycloalkyl optionally substituted by 1-6 $R^{159}$, 5-15 membered heteroaryl optionally substituted by 1-6 $R^{159}$, halogen, —CN, —C(═O)$R^{150}$, —C(═O)O$R^{150}$, —C(═O)N$R^{152}R^{153}$, —NC, —$NO_2$, —N$R^{152}R^{153}$, —N$R^{154}$N$R^{152}R^{153}$, —N$R^{154}$O$R^{156}$, —N$R^{154}$C(═O)$R^{150}$, —N$R^{154}$C(═O)O$R^{151}$, —N$R^{154}$C(═O)N$R^{152}R^{153}$, —N$R^{154}$C(═O)N$R^{154}$C(═O)$R^{150}$, —N$R^{154}$S(═O)$_2R^{151}$, —N$R^{154}$S(═O)N$R^{152}R^{153}$, —O$R^{150}$, ═O, —OCN, —OC(═O)$R^{150}$, —OC(═O)N$R^{152}R^{153}$, —OC(═O)O$R^{150}$, —Si($R^{154}$)$_3$, —SCN, ═S, —S(═)$_n R^{150}$, and —S(═O)$_2$N$R^{152}R^{153}$.

Embodiment 953

The compound of any of Embodiments 1-156, 200-250, 300-371, 400-440, 500-533, 600-668, 700-714, 750-795, 800-817, 850-886, or 900-950, wherein $R^{119}$, $R^{129}$, —$R^{139}$ and $R^{149}$ at each occurrence is independently chosen from $C_{1-6}$alkyl optionally substituted by 1-6 $R^{159}$, $C_{6-10}$aryl optionally substituted by 1-6 $R^{159}$, $C_{7-11}$arylalkyl optionally substituted by 1-6 $R^{159}$, $C_{3-10}$cycloalkyl optionally substituted by 1-6 $R^{159}$, 3-10 membered heterocycloalkyl optionally substituted by 1-6 $R^{159}$, 5-10 membered heteroaryl optionally substituted by 1-6 $R^{159}$, halogen, —CN, —C(═O)$R^{150}$, —C(═O)O$R^{150}$, —C(═O)N$R^{152}R^{153}$, —$NO_2$, —N$R^{152}R^{153}$, —N$R^{154}$C(═O)$R^{150}$, —N$R^{154}$C(═O)O$R^{151}$, —N$R^{154}$C(═O)N$R^{152}R^{153}$, —N$R^{154C}$(═O)N$R^{154}$C(═O)$R^{150}$, —N$R^{154}$S(═O)$_2R^{151}$, —N$R^{154}$S(═O)$_2$N$R^{152}R^{153}$, —O$R^{150}$, ═O, —OC(═O)$R^{150}$, —OC(═O)N$R^{152}R^{153}$, —OC(═O)O$R^{150}$, —Si($R^{154}$)$^3$, —S(═O)$_n R^{150}$, and —S(═O)$_2$N$R^{152}R^{153}$.

Embodiment 954

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl optionally substituted by 1-3 $R^{159}$, $C_{6-10}$aryl optionally substituted by 1-3 $R^{159}$, $C_{7-11}$arylalkyl optionally substituted by 1-3 $R^{159}$, $C_{3-10}$cycloalkyl optionally substituted by 1-3 $R^{159}$, 3-10 membered heterocycloalkyl optionally substituted by 1-3 $R^{159}$, 5-10 membered heteroaryl optionally substituted by 1-3 $R^{159}$, halogen, —CN, $-C(=O)R^{150}$, $-C(=O)OR^{150}$, $-C(=O)NR^{152}R^{153}$, $-NO_2$, $-NR^{152}R^{153}$, $-NR^{154}C(=O)R^{150}$, $-NR^{154}C(=O)OR^{151}$, $-NR^{154}C(=O)NR^{152}R^{153}$, $-NR^{154}C(=O)NR^{154}C(=O)R^{150}$, $-NR^{154}S(=O)_2R^{151}$, $-NR^{154}S(=O)_2NR^{152}R^{153}$, $-OR^{150}$, $=O$, $-OC(=O)R^{150}$, $-OC(=O)NR^{152}R^{153}$, $-OC(=O)OR$, $-Si(R^{154})_3$, $-S(=O)_nR^{150}$, and $-S(=O)_2NR^{152}R^{153}$.

Embodiment 955

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl optionally substituted by 1-3 $R^{159}$, phenyl optionally substituted by 1-3 $R^{159}$, benzyl optionally substituted by 1-3 $R^{159}$, $C_{3-6}$cycloalkyl optionally substituted by 1-3 $R^{159}$, 3-6 membered heterocycloalkyl optionally substituted by 1-3 $R^{159}$, 5-6 membered heteroaryl optionally substituted by 1-3 $R^{159}$, halogen, $-CN$, $-C(=O)R^{150}$, $-C(=O)OR^{150}$, $-C(=O)NR^{152}R^{153}$, $-NO_2$, $-NR^{152}R^{153}$, $-NR^{154}C(=O)R^{150}$, $-NR^{154}C(=O)OR^{151}$, $-NR^{154}C(=O)NR^{152}R^{153}$, $-NR^{154}C(=O)NR^{154}C(=O)R^{150}$, $-NR^{154}S(=O)_2R^{151}$, $-NR^{154}S(=O)_2NR^{152}R^{153}$, $-OR^{150}$, $=O$, $-OC(=O)R^{150}$, $-OC(=O)NR^{152}R^{153}$, $-OC(=O)OR^{150}$, $-Si(R^{154})_3$, $-S(=O)_nR^{150}$, and $-S(=O)_2NR^{152}R^{153}$.

Embodiment 956

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl optionally substituted by 1-3 $R^{159}$, phenyl optionally substituted by 1-3 $R^{159}$, benzyl optionally substituted by 1-3 $R^{159}$, $C_{3-6}$cycloalkyl optionally substituted by 1-3 $R^{159}$, 3-6 membered heterocycloalkyl optionally substituted by 1-3 $R^{159}$, 5-6 membered heteroaryl optionally substituted by 1-3 $R^{159}$, halogen, $-CN$, $-C(=O)R^{150}$, $-C(=)OR^{150}$, $-C(=O)NR^{152}R^{153}$, $-NO_2$, $-NR^{152}R^{153}$, $-NR^{154}C(=O)R^{150}$, $-NR^{154}S(=O)_2R^{151}$, $-OR^{150}$, $-OC(=O)R^{150}$, $-OC(=O)NR^{152}R^{153}$, $-S(=O)_nR^{150}$, and $-S(=O)_2NR^{152}R^{153}$.

Embodiment 957

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl, phenyl, benzyl, $C_{3-6}$cycloalkyl, 3-6 membered heterocycloalkyl, 5-6 membered heteroaryl, halogen, $-CN$, $-C(=O)R^{50}$, $-C(=O)OR^{150}$, $-C(=O)NR^{152}R^{153}$, $-NO_2$, $-NR^{152}R^{15}$, $-NR^{154}C(=O)R^{150}$, $-NR^{154}S(=O)_2R^{151}$, $-OR^{150}$, $-OC(=O)R^{150}$, $-OC(=O)NR^{152}R^{153}$, $-S(=O)_nR^{150}$, and $-S(=O)_2NR^{152}R^{153}$.

Embodiment 958

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl, phenyl, benzyl, halogen, $-CN$, $-C(=O)OR^{5}$, $-C(=O)NR^{152}R^{153}$, $-NO_2$, $-NR^{152}R^{153}$, $-OR^{150}$, and $-S(=O)_nR^{15}$.

Embodiment 959

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl optionally substituted by 1-3 $R^{159}$, phenyl optionally substituted by 1-3 $R^{159}$, benzyl optionally substituted by 1-3 $R^{159}$, halogen, $-CN$, $-C(=O)OR^{150}$, $-C(=O)NR^{152}R^{153}$, $-NO_2$, $-NR^{152}R^{153}$, $-OR^{150}$, and $-S(=O)_nR^{150}$.

Embodiment 960

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl, phenyl, benzyl, halogen, $-NR^{152}R^{153}$, and $-OR^{150}$.

Embodiment 961

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl, halogen, $-NR^{152}R^{153}$, and $-OR^{150}$.

Embodiment 962

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl optionally substituted by 1-3 $R^{159}$ and halogen.

Embodiment 963

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently chosen from $C_{1-6}$alkyl optionally substituted by 1-3 $R^{159}$.

Embodiment 964

The compound of any of Embodiments 1-156, 200-250, 300-371, 400-440, 500-533, 600-668, 700-714, 750-795, 800-817, 850-886, or 900-950, wherein $R^{119}$, $R^{129}$, $R^{139}$ and $R^{149}$ at each occurrence is independently $C_{1-6}$alkyl.

Embodiment 965

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{5}$, $R^{156}$ and $R^{157}$ at each occurrence is independently chosen from H, $C_{1-6}$alkyl optionally substituted by 1-13 $R^{169}$, $C_{2-6}$alkenyl optionally substituted by 1-11 $R^{169}$, $C_{2-6}$alkynyl optionally substituted by 1-9 $R^{169}$, $C_{6-11}$aryl optionally substituted by 1-11 $R^{169}$, $C_{7-16}$arylalkyl optionally substituted by 1-19 $R^{169}$, $C_{3-11}$cycloalkyl optionally substituted by 1-21 $R^{169}$, $C_{4-17}$cycloalkylalkyl optionally substituted by 1-32 $R^{169}$, 3-15 membered heterocycloalkyl optionally substituted by 1-28 $R^{169}$, 4-21 membered heterocycloalkylalkyl optionally substituted by 1-40 $R^{169}$, 5-15 membered heteroaryl optionally substituted by 1-15 $R^{169}$, and 6-21 membered heteroarylalkyl optionally substituted by 1-27 $R^{169}$.

Embodiment 966

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H, $C_{1-6}$alkyl optionally substituted by 1-6 $R^{169}$, $C_{2-6}$alkenyl optionally substituted by 1-6 $R^{169}$, $C_{2-6}$alkynyl optionally substituted by 1-6 $R^{169}$, $C_{6-10}$aryl optionally substituted by 1-6 $R^{169}$, $C_{7-11}$arylalkyl optionally substituted by 1-6 $R^{169}$, $C_{3-10}$cycloalkyl optionally substituted by 1-6 $R^{169}$, 3-10 membered heterocycloalkyl optionally substituted by 1-6 $R^{169}$, and 5-10 membered heteroaryl optionally substituted by 1-6 $R^{169}$.

Embodiment 967

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H, $C_{1-6}$alkyl optionally substituted by 1-3 $R^{169}$, $C_{2-6}$alkenyl optionally substituted by 1-3 $R^{169}$, $C_{2-6}$alkynyl optionally substituted by 1-3 $R^{169}$, $C_{6-10}$aryl optionally substituted by 1-3 $R^{169}$, $C_{7-11}$arylalkyl optionally substituted by 1-3 $R^{169}$, $C_{3-10}$cycloalkyl optionally substituted by 1-3 $R^{169}$, 3-10 membered heterocycloalkyl optionally substituted by 1-3 $R^{169}$, and 5-10 membered heteroaryl optionally substituted by 1-3 $R^{169}$.

Embodiment 968

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H, $C_{1-6}$alkyl optionally substituted by 1-3 $R^{169}$, phenyl optionally substituted by 1-3 $R^{169}$, benzyl optionally substituted by 1-3 $R^{169}$, $C_{3-10}$cycloalkyl optionally substituted by 1-3 $R^{169}$, 3-10 membered heterocycloalkyl optionally substituted by 1-3 $R^{169}$, and 5-10 membered heteroaryl optionally substituted by 1-3 $R^{69}$.

Embodiment 969

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}R^{156}$ and $R^{157}$ at each occurrence is independently chosen from H, $C_{1-6}$alkyl, phenyl, benzyl, $C_{3-10}$cycloalkyl, 3-10 membered heterocycloalkyl, and 5-10 membered heteroaryl.

Embodiment 970

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{54}$, $R^{15}$, $R^{156}$ and $R^{157}$ at each occurrence is independently chosen from H, $C_{1-6}$alkyl optionally substituted by 1-3 $R^{169}$, phenyl optionally substituted by 1-3 $R^{169}$, benzyl optionally substituted by 1-3 $R^{169}$, $C_{5-6}$cycloalkyl optionally substituted by 1-3 $R^{169}$, 5-6 membered heterocycloalkyl optionally substituted by 1-3 $R^{169}$, and 5-6 membered heteroaryl optionally substituted by 1-3 $R^{169}$.

Embodiment 971

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 972

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H, $C_{1-6}$alkyl, phenyl, $C_{5-6}$cycloalkyl, 5-6 membered heterocycloalkyl, and 5-6 membered heteroaryl.

Embodiment 973

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H, $C_{1-6}$alkyl, phenyl, benzyl, $C_{5-6}$cycloalkyl, 5-6 membered heterocycloalkyl optionally substituted by 1 $R^{169}$, and 5-6 membered heteroaryl.

Embodiment 974

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is independently chosen from H and $C_{1-6}$alkyl optionally substituted by 1-3 $R^{169}$.

Embodiment 975

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}R^{156}$ and $R^{157}$ at each occurrence is independently chosen from H and $C_{1-6}$alkyl.

Embodiment 976

The compound of any of Embodiments 1-156, 200-250, 300-371, 400-440, 500-533, 600-668, 700-714, 750-795, 800-817, 850-886, or 900-964, wherein $R^{150}$, $R^{151}$, $R^{154}$, $R^{155}$, $R^{156}$ and $R^{157}$ at each occurrence is H.

Embodiment 977

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, and 6-21 membered heteroarylalkyl optionally substituted by 1-27 $R^{179}$; or any $R^{152}$ and $R^{153}$ may form, together with the nitrogen atom to which they are attached, a 3-15 membered heterocycloalkyl optionally substituted by 1-28 $R^{189}$ or a 5-15 membered heteroaryl optionally substituted by 1-15 $R^{189}$.

Embodiment 978

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-6 $R^{179}$, $C_{2-6}$alkenyl optionally substituted by 1-6 $R^{179}$, $C_{2-6}$alkynyl optionally substituted by 1-6 $R^{179}$, $C_{6-11}$aryl optionally substituted by 1-6 $R^{179}$, $C_{7-16}$arylalkyl optionally substituted by 1-6 $R^{179}$, $C_{3-11}$cycloalkyl optionally substituted by 1-6 $R^{179}$, $C_{4-17}$cycloalkylalkyl optionally substituted by 1-6 $R^{179}$, 3-15 membered heterocycloalkyl optionally substituted by 1-6 $R^{179}$, 4-21 membered heterocycloalkylalkyl optionally substituted by 1-6 $R^{179}$, 5-15 membered heteroaryl optionally substituted by 1-6 $R^{179}$, and 6-21 membered heteroarylalkyl optionally substituted by 1-6 $R^{179}$; or any $R^{152}$ and $R^{153}$ may form, together with the nitrogen atom to which they are attached, a 3-15 membered heterocycloalkyl optionally substituted by 1-6 $R^{189}$ or a 5-15 membered heteroaryl optionally substituted by 1-6 $R^{189}$.

Embodiment 979

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-3 $R^{179}$, phenyl optionally substituted by 1-3 $R^{179}$, benzyl optionally substituted by 1-3 $R^{179}$, $C_{3-10}$cycloalkyl optionally substituted by 1-3 $R^{179}$, 3-10 membered heterocycloalkyl optionally substituted by 1-3 $R^{179}$, and 5-10 membered heteroaryl optionally substituted by 1-3 $R^{179}$; or any $R^{152}$ and $R^{153}$ may form, together with the nitrogen atom to which they are attached, a 3-15 membered heterocycloalkyl optionally substituted by 1-3 $R^{189}$ or a 5-15 membered heteroaryl optionally substituted by 1-3 $R^{189}$.

Embodiment 980

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-3 $R^{179}$, phenyl optionally substituted by 1-3 $R^{179}$, benzyl optionally substituted by 1-3 $R^{179}$, $C_{3-10}$cycloalkyl optionally substituted by 1-3 $R^{179}$, 3-10 membered heterocycloalkyl optionally substituted by 1-3 $R^{179}$, and 5-10 membered heteroaryl optionally substituted by 1-3 $R^{179}$.

Embodiment 981

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-3 $R^{179}$, phenyl optionally substituted by 1-3 $R^{179}$, benzyl optionally substituted by 1-3 $R^{179}$, $C_{3-6}$cycloalkyl optionally substituted by 1-3 $R^{179}$, 3-6 membered heterocycloalkyl optionally substituted by 1-3 $R^{179}$, and 5-6 membered heteroaryl optionally substituted by 1-3 $R^{179}$; or any $R^{152}$ and $R^{153}$ may form, together with the nitrogen atom to which they are attached, a 3-10 membered heterocycloalkyl optionally substituted by 1-3 $R^{189}$ or a 5-10 membered heteroaryl optionally substituted by 1-3 $R^{189}$.

Embodiment 982

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-3 $R^{179}$, phenyl optionally substituted by 1-3 $R^{179}$, benzyl optionally substituted by 1-3 $R^{179}$, $C_{5-6}$cycloalkyl optionally substituted by 1-3 $R^{179}$, 5-6 membered heterocycloalkyl optionally substituted by 1-3 $R^{179}$, and 5-6 membered heteroaryl optionally substituted by 1-3 $R^{179}$.

Embodiment 983

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-3 $R^{179}$, phenyl optionally substituted by 1-3 $R^{179}$, benzyl optionally substituted by 1-3 $R^{179}$, 5-6 membered heterocycloalkyl optionally substituted by 1-3 $R^{179}$, and 5-6 membered heteroaryl optionally substituted by 1-3 $R^{179}$.

Embodiment 984

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl; or any $R^{152}$ and $R^{153}$ may form, together with the nitrogen atom to which they are attached, a 5-6 membered heterocycloalkyl or a 5-6 membered heteroaryl.

Embodiment 985

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 986

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl optionally substituted by 1-3 $R^{179}$, phenyl optionally substituted by 1-3 $R^{179}$, and benzyl optionally substituted by 1-3 $R^{179}$.

Embodiment 987

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H and $C_{1-6}$alkyl optionally substituted by 1-3 $R^{179}$.

Embodiment 988

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H, $C_{1-6}$alkyl, phenyl, and benzyl.

Embodiment 989

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is independently chosen from H and $C_{1-6}$alkyl.

Embodiment 990

The compound of any of Embodiments 1-156, 200-250, 300-371, 400-440, 500-533, 600-668, 700-714, 750-795, 800-817, 850-886, or 900-976, wherein $R^{152}$ and $R^{153}$ at each occurrence is H.

Embodiment 991

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-13 $R^{169}$, $C_{2-6}$alkenyl optionally substituted by 1-11 $R^{169}$, $C_{2-6}$alkynyl optionally substituted by 1-9 $R^{169}$, $C_{6-11}$aryl optionally substituted by 1-11 $R^{169}$, $C_{7-16}$arylalkyl optionally substituted by 1-19 $R^{169}$, $C_{3-11}$cycloalkyl optionally substituted by 1-21 $R^{169}$, $C_{4-17}$cycloalkylalkyl optionally substituted by 1-32 $R^{169}$, 3-15 membered heterocycloalkyl optionally substituted by 1-28 $R^{169}$, 4-21 membered heterocycloalkylalkyl optionally substituted by 1-40 $R^{169}$, 5-15 membered heteroaryl optionally substituted by 1-15 $R^{169}$, and 6-21 membered heteroarylalkyl optionally substituted by 1-27 $R^{169}$.

Embodiment 992

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-3 $R^{169}$, $C_{2-6}$alkenyl optionally substituted by 1-3 $R^{169}$, $C_{2-6}$alkynyl optionally substituted by 1-3 $R^{169}$, $C_{6-11}$aryl optionally substituted by 1-3 $R^{169}$, $C_{7-16}$arylalkyl optionally substituted by 1-3 $R^{169}$, $C_{3-11}$cycloalkyl optionally substituted by 1-3 $R^{169}$, $C_{4-17}$cycloalkylalkyl optionally substituted by 1-3 $R^{169}$, 3-15 membered heterocycloalkyl optionally substituted by 1-3 $R^{169}$, 4-21 membered heterocycloalkylalkyl optionally substituted by 1-3 $R^{169}$, 5-15 membered heteroaryl optionally substituted by 1-3 $R^{169}$, and 6-21 membered heteroarylalkyl optionally substituted by 1-3 $R^{169}$.

Embodiment 993

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-3 $R^{169}$, $C_{2-6}$alkenyl optionally substituted by 1-3 $R^{169}$, $C_{2-6}$alkynyl optionally substituted by 1-3 $R^{169}$, $C_{6-10}$aryl optionally substituted by 1-3 $R^{169}$, $C_{7-11}$arylalkyl optionally substituted by 1-3 $R^{169}$, $C_{3-10}$cycloalkyl optionally substituted by 1-3 $R^{169}$, 3-10 membered heterocycloalkyl optionally substituted by 1-3 $R^{169}$, and 5-10 membered heteroaryl optionally substituted by 1-3 $R^{169}$.

Embodiment 994

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-3 $R^{169}$, $C_{6-10}$aryl optionally substituted by 1-3 $R^{169}$, $C_{7-11}$arylalkyl optionally substituted by 1-3 $R^{169}$, $C_{3-10}$cycloalkyl optionally substituted by 1-3 $R^{169}$, 3-10 membered heterocycloalkyl optionally substituted by 1-3 $R^{169}$, and 5-10 membered heteroaryl optionally substituted by 1-3 $R^{169}$.

Embodiment 995

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-3 $R^{169}$, phenyl optionally substituted by 1-3 $R^{169}$, benzyl optionally substituted by 1-3 $R^{169}$, $C_{3-6}$cycloalkyl optionally substituted by 1-3 $R^{169}$, 3-6 membered heterocycloalkyl optionally substituted by 1-3 $R^{169}$, and 5-6 membered heteroaryl optionally substituted by 1-3 $R^{169}$.

Embodiment 996

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl, phenyl, benzyl, $C_{3-6}$cycloalkyl, 3-6 membered heterocycloalkyl, and 5-6 membered heteroaryl.

Embodiment 997

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-3 $R^{169}$, phenyl, and benzyl.

Embodiment 998

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl optionally substituted by 1-3 $R^{169}$, phenyl optionally substituted by 1-3 $R^{169}$, and benzyl optionally substituted by 1-3 $R^{169}$.

Embodiment 999

The compound of any of Embodiments 1-156, 200-250, 300-371, 400-440, 500-533, 600-668, 700-714, 750-795, 800-817, 850-886, or 900-990, wherein $R^{158}$ at each occurrence is independently chosen from $C_{1-6}$alkyl, phenyl, and benzyl.

Embodiment 1000

The compound of any of Embodiments 1-156, 200-250, 300-371, 400-440, 500-533, 600-668, 700-714, 750-795, 800-817, 850-886, or 900-990, wherein $R^{158}$ at each occurrence is $C_{1-6}$alkyl optionally substituted by 1-3 $R^{169}$.

Embodiment 1001

The compound of any of Embodiments 1-156, 200-250, 300-371, 400-440, 500-533, 600-668, 700-714, 750-795, 800-817, 850-886, or 900-990, wherein $R^{158}$ at each occurrence is $C_{1-6}$alkyl.

Embodiment 1002

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-6 $R^{199}$, $C_{2-6}$alkenyl optionally substituted by 1-6 $R^{199}$, $C_{2-6}$alkynyl optionally substituted by 1-6 $R^{199}$, $C_{6-11}$aryl optionally substituted by 1-6 $R^{199}$, $C_{7-16}$arylalkyl optionally substituted by 1-6 $R^{199}$, $C_{3-11}$cycloalkyl optionally substituted by 1-6 $R^{199}$, $C_{4-17}$cycloalkylalkyl optionally substituted by 1-6 $R^{199}$, 3-15 membered heterocycloalkyl optionally substituted by 1-6 $R^{199}$, 4-21 membered heterocycloalkylalkyl optionally substituted by 1-6 $R^{199}$, 5-15 membered heteroaryl optionally substituted by 1-6 $R^{199}$, 6-21 membered heteroarylalkyl optionally substituted by 1-6 $R^{199}$, halogen, —CN, —C(═O)$R^{190}$, —C(═)O$R^{190}$, —C(═O)N$R^{192}R^{193}$, —(═O)C(═O)$R^{190}$, —C(═N$R^{195}$)$R^{190}$, —C(═N$R^{195}$)N$R^{192}R^{193}$, —C(═NOH)N$R^{192}R^{193}$, —C(═NO$R^{196}$)$R^{190}$, —C(═NN$R^{192}R^{193}$)$R^{190}$, —C(═NN$R^{194}$C(═O)$R^{191}$)$R^{190}$, —C(═NN$R^{194}$C(═O)O$R^{191}$)$R^{190}$, —C(═S)N$R^{192}R^{193}$, —NC, —$NO_2$, —N$R^{192}R^{193}$, —N$R^{194}$N$R^{192}R^{193}$, —N═N$R^{194}$, ═N$R^{190}$, ═NO$R^{190}$, —N$R^{194}$O$R^{196}$, —N$R^{194}$C(═O)$R^{190}$, —N$R^{194}$C(═O)C(═O)$R^{190}$, —N$R^{194}$C(═O)OR, —N$R^{194}$C(═O)C(═O)O$R^{191}$, —N$R^{194}$C(═O)N$R^{192}R^{193}$, —N$R^{194}$C(═O)N$R^{194}$C(═O)$R^{190}$, —N$R^{194}$C(═O)N$R^{194}$C(═O)O$R^{190}$, —N$R^{194}$C(═N$R^{195}$)N$R^{192}R^{193}$, —N$R^{194}$C(═O)C(═O)N$R^{192}R^{193}$, —N$R^{194}$C(═S)$R^{190}$, —N$R^{194}$C(═S)O$R^{190}$, —N$R^{194}$C(═S)N$R^{192}R^{193}$, —N$R^{194}$S(═O)$_2R^{19}$, —N$R^{194}$S(═O)$_2$N$R^{192}R^{193}$, —N$R^{194}$P(═O)$R^{198}R^{198}$, —N$R^{194}$P(═O)(N$R^{192}R^{193}$)(N$R^{192}R^{193}$), —N$R^{194}$P(═)(O$R^{190}$)(O$R^{190}$), —N$R^{194}$P(═O)(S$R^{190}$)(S$R^{190}$), —O$R^{190}$, ═O, —OCN, —OC(═O)$R^{190}$, —OC(═O)N$R^{192}R^{193}$, —OC(═O)O$R^{190}$, —OC(═N$R^{195}$)N$R^{192}R^{193}$, —OS(═O)$R^{190}$, —OS(═O)$_2R^{190}$, —OS(═O)$_2$O$R^{190}$, —OS(═O)$_2$N$R^{192}R^{193}$, —OP(═O)$R^{198}R^{198}$, —OP(═O)(N$R^{192}R^{193}$)(N$R^{192}R^{193}$), —OP(═O)(O$R^{190}$)(O$R^{190}$), —OP(═O)(S$R^{190}$)(S$R^{190}$), —Si($R^{194}$)$_3$, —SCN, ═S, —S(═O)$_nR^{190}$, —S(═O)$_2$O$R^{190}$, —$SO_3$R, —S(═O)$_2$N$R^{192}R^{193}$, —S(═O)N$R^{192}R^{193}$, —SP(═O)$R^{198}R^{198}$, —SP(═O)(N$R^{192}R^{193}$)(N$R^{192}R^{193}$), —SP(═O)(O$R^{190}$)(O$R^{190}$), —SP(═O)(S$R^{190}$)(S$R^{190}$), —P(═O)$R^{198}R^{198}$, —P(═O)(N$R^{192}R^{193}$)(N$R^{192}R^{193}$), —P(═O)(O$R^{190}$)(O$R^{190}$), and —P(═O)(S$R^{190}$)(S$R^{190}$).

Embodiment 1003

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-6 $R^{199}$, $C_{6-11}$aryl optionally substituted by 1-6 $R^{199}$, $C_{7-16}$arylalkyl optionally substituted by 1-6 $R^{199}$, $C_{3-11}$cycloalkyl optionally substituted by 1-6 $R^{199}$, 3-15 membered heterocycloalkyl optionally substituted by 1-6 $R^{199}$, 5-15 membered heteroaryl optionally substituted by 1-6 $R^{199}$, halogen, —CN, —C(═O)$R^{190}$, —C(═O)O$R^{190}$, —C(═O)N$R^{192}R^{193}$, —NC, —$NO_2$, —N$R^{192}R^{193}$, —N$R^{194}$N$R^{192}R^{193}$, —N$R^{194}$O$R^{196}$, —N$R^{194}$C(═O)$R^{190}$, —N$R^{194}$C(═O)O$R^{191}$, —N$R^{194}$C(═O)N$R^{192}R^{193}$, —N$R^{194}$C(═O)N$R^{194}$C(═O)$R^{190}$, —N$R^{194}$S(═O)$_2R^{191}$, —N$R^{194}$S(═O)$_2$N$R^{192}R^{193}$, —O$R^{190}$, ═O, —OCN, —OC(═O)$R^{190}$, —OC(═O)N$R^{192}R^{193}$, —OC(═O)O$R^{190}$, —Si($R^{194}$)$_3$, —SCN, ═S, —S(═O)$_nR^{190}$, and —S(═O)$_2$N$R^{192}R^{193}$.

Embodiment 1004

The compound of any of Embodiments 1-156, 200-250, 300-371, 400-440, 500-533, 600-668, 700-714, 750-795, 800-817, 850-886, or 900-1001, wherein $R^{159}$, $R^{169}$, $R^{179}$ and $R^{189}$ at each occurrence is independently chosen from $C_{1-6}$alkyl optionally substituted by 1-6 $R^{199}$, $C_{6-10}$aryl optionally substituted by 1-6 $R^{199}$, $C_{7-11}$arylalkyl optionally substituted by 1-6 $R^{199}$, $C_{3-10}$cycloalkyl optionally substituted by 1-6 $R^{199}$, 3-10 membered heterocycloalkyl optionally substituted by 1-6 $R^{199}$, 5-10 membered heteroaryl optionally substituted by 1-6 $R^{199}$, halogen, —CN, —C(═O)$R^{190}$, —C(═O)O$R^{190}$, —C(═O)N$R^{192}R^{193}$, —$NO_2$, —N$R^{192}R^{193}$, —N$R^{194}$C(═O)$R^{190}$, —N$R^{194}$C(═O)OR, —N$R^{194}$C(═O)N$R^{192}R^{193}$, —N$R^{194}$C(═O)N$R^{194}$C(═O)$R^{190}$, —N$R^{194}$S(═O)$_2R^{191}$, —N$R^{194}$S(═O)$_2$N$R^{192}R^{193}$, —O$R^{190}$, ═O, —OC(═O)$R^{190}$, —OC(═O)N$R^{192}R^{193}$, —OC(═O)O$R^{190}$, —Si($R^{194}$)$_3$, —S(═O)$_nR^{190}$, and —S(═O)$_2$N$R^{192}R^{193}$.

Embodiment 1005

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-3 $R^{199}$, $C_{6-10}$aryl optionally substituted by 1-3 $R^{199}$, $C_{7-11}$arylalkyl optionally substituted by 1-3 $R^{199}$, $C_{3-10}$cycloalkyl optionally substituted by 1-3 $R^{199}$, 3-10 membered heterocycloalkyl optionally substituted by 1-3 $R^{199}$, 5-10 membered heteroaryl optionally substituted by 1-3 $R^{199}$, halogen, —CN, —C(═O)$R^{190}$, —C(═O)O$R^{190}$, —C(═O)N$R^{192}R^{193}$, —$NO_2$, —N$R^{192}R^{193}$, —N$R^{194}$C(═O)$R^{190}$, —N$R^{194}$C(═O)O$R^{191}$, —N$R^{194}$C(═O)N$R^{192}R^{193}$, —N$R^{194}$C(═O)N$R^{194}$C(═O)$R^{190}$, —N$R^{194}$S(═O)$_2R^{191}$, —N$R^{194}$S(═O)$_2$N$R^{192}R^{193}$, —O$R^{190}$, ═O, —OC(═O)$R^{190}$, —OC(═O)N$R^{192}R^{193}$, —OC(═O)O$R^{190}$, —Si($R^{194}$)$_3$, —S(═O)$_nR^{190}$, and —S(═O)$_2$N$R^{192}R^{193}$.

Embodiment 1006

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-3 $R^{199}$, phenyl optionally substituted by 1-3 $R^{199}$, benzyl optionally substituted by 1-3 $R^{199}$, $C_{3-6}$cycloalkyl optionally substituted by 1-3 $R^{199}$, 3-6 membered heterocycloalkyl optionally substituted by 1-3 $R^{199}$, 5-6 membered heteroaryl optionally substituted by 1-3 $R^{199}$, halogen, —CN, —C(═O)$R^{190}$, —C(═O)$OR^{190}$, —C(═O)$NR^{192}R^{193}$, —$NO_2$, —$NR^{192}R^{193}$, —$NR^{194}C$(═O)$R^{190}$, —$NR^{194}C$(═O)$OR^{191}$, —$NR^{194}C$(═O)$NR^{192}R^{193}$, —$NR^{194}C$(═O)$NR^{194}C$(═O)$R^{190}$, —$NR^{194}S$(═O)$_2R^{191}$, —$NR^{194}S$(═O)$_2NR^{192}R^{193}$, —$OR^{190}$, ═O, —OC(═O)$R^{190}$, —OC(═O)$NR^{192}R$, —OC(═O)$OR^{190}$, —Si$(R^{194})_3$, —S(═O)$_nR^{190}$, and —S(═O)$_2NR^{192}R^{193}$.

Embodiment 1007

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-3 $R^{199}$, phenyl optionally substituted by 1-3 $R^{199}$, benzyl optionally substituted by 1-3 $R^{199}$, $C_{3-6}$cycloalkyl optionally substituted by 1-3 $R^{199}$, 3-6 membered heterocycloalkyl optionally substituted by 1-3 $R^{199}$, 5-6 membered heteroaryl optionally substituted by 1-3 $R^{199}$, halogen, —CN, —C(═O)$R^{190}$, —C(═O)$OR^{190}$, —C(═O)$NR^{192}R^{193}$, —$NO_2$, —$NR^{192}R^{193}$, —$NR^{194}C$(═O)$R^{190}$, —$NR^{194}S$(═O)$_2R^{191}$, —$OR^{190}$, —OC(═O)$R^{190}$, —OC(═O)$NR^{192}R^{193}$, —S(═O)$_nR^{190}$, and —S(═O)$_2NR^{192}R^{193}$.

Embodiment 1008

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl, phenyl, benzyl, $C_{3-6}$cycloalkyl, 3-6 membered heterocycloalkyl, 5-6 membered heteroaryl, halogen, —CN, —C(═O)$R^{190}$, —C(═O)$OR^{190}$, —C(═O)$NR^{192}R^{9}$, —$NO_2$, —$NR^{192}R^{193}$, —$NR^{194}C$(═O)$R^{190}$, —$NR^{194}S$(═O)$_2R^{191}$, —$OR^{190}$, —OC(═O)$R^{190}$, —OC(═O)$NR^{192}R^{193}$, —S(═O)$_nR^{190}$, and —S(═O)$_2NR^{192}R^{193}$.

Embodiment 1009

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl, phenyl, benzyl, halogen, —CN, —C(═O)$OR^{190}$, —C(═O)$NR^{192}R^{193}$, —$NO_2$, —$NR^{192}R^{193}$, —$OR^{190}$, and —S(═O)$_nR^{190}$.

Embodiment 1010

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-3 $R^{199}$, phenyl optionally substituted by 1-3 $R^{199}$, benzyl optionally substituted by 1-3 $R^{199}$, halogen, —CN, —C(═O)$OR^{190}$, —C(═O)$NR^{192}R^{193}$, —$NO_2$, —$NR^{192}R^{193}$, —$OR^{190}$, and —S(═O)$_nR^{190}$.

Embodiment 1011

The compound of any of Embodiments 1-156, 200-250, 300-371, 400-440, 500-533, 600-668, 700-714, 750-795, 800-817, 850-886, or 900-1001, wherein $R^{159}$, $R^{169}$, $R^{179}$ and $R^{189}$ at each occurrence is independently chosen from $C_{1-6}$alkyl, phenyl, benzyl, halogen, —$NR^{192}R^{193}$, and —$OR^{190}$.

Embodiment 1012

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl, halogen, —$NR^{192}R^{193}$, and —$OR^{190}$.

Embodiment 1013

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-3 $R^{199}$ and halogen.

Embodiment 1014

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently chosen from $C_{1-6}$alkyl optionally substituted by 1-3 $R^{199}$.

Embodiment 1015

The compound of any of Embodiments 1-156, 200-250, 300-371, 400-440, 500-533, 600-668, 700-714, 750-795, 800-817, 850-886, or 900-1001, wherein $R^{59}$, $R^{169}$, $R^{179}$ and $R^{189}$ at each occurrence is independently $C_{1-6}$alkyl.

Embodiment 1016

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl optionally substituted by 1-13 $R^{209}$, $C_{2-6}$alkenyl optionally substituted by 1-11 $R^{209}$, $C_{2-6}$alkynyl optionally substituted by 1-9 $R^{209}$, $C_{6-11}$aryl optionally substituted by 1-11 $R^{209}$, $C_{7-16}$arylalkyl optionally substituted by 1-19 $R^{209}$, $C_{3-11}$cycloalkyl optionally substituted by 1-21 $R^{209}$, $C_{4-17}$cycloalkylalkyl optionally substituted by 1-32 $R^{209}$, 3-15 membered heterocycloalkyl optionally substituted by 1-28 $R^{209}$, 4-21 membered heterocycloalkylalkyl optionally substituted by 1-40 $R^{209}$, 5-15 membered heteroaryl optionally substituted by 1-15 $R^{209}$, and 6-21 membered heteroarylalkyl optionally substituted by 1-27 $R^{209}$.

Embodiment 1017

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl optionally substituted by 1-6 $R^{209}$, $C_{2-6}$alkenyl optionally substituted by 1-6 $R^{209}$, $C_{2-6}$alkynyl optionally substituted by 1-6 $R^{209}$, $C_{6-10}$aryl optionally substituted by 1-6 $R^{209}$, $C_{7-11}$arylalkyl optionally substituted by 1-6 $R^{209}$, $C_{3-10}$cycloalkyl optionally substituted by 1-6

$R^{209}$, 3-10 membered heterocycloalkyl optionally substituted by 1-6 $R^{209}$, and 5-10 membered heteroaryl optionally substituted by 1-6 $R^{209}$.

Embodiment 1018

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl optionally substituted by 1-3 $R^{209}$, $C_{2-6}$alkenyl optionally substituted by 1-3 $R^{209}$, $C_{2-6}$alkynyl optionally substituted by 1-3 $R^{209}$, $C_{6-10}$aryl optionally substituted by 1-3 $R^{209}$, $C_{7-11}$-arylalkyl optionally substituted by 1-3 $R^{209}$, $C_{3-10}$cycloalkyl optionally substituted by 1-3 $R^{209}$, 3-10 membered heterocycloalkyl optionally substituted by 1-3 $R^{209}$, and 5-10 membered heteroaryl optionally substituted by 1-3 $R^{209}$.

Embodiment 1019

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl optionally substituted by 1-3 $R^{209}$, phenyl optionally substituted by 1-3 $R^{209}$, benzyl optionally substituted by 1-3 $R^{209}$, $C_{3-10}$cycloalkyl optionally substituted by 1-3 $R^{209}$, 3-10 membered heterocycloalkyl optionally substituted by 1-3 $R^{209}$, and 5-10 membered heteroaryl optionally substituted by 1-3 $R^{209}$.

Embodiment 1020

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl, phenyl, benzyl, $C_{3-10}$cycloalkyl, 3-10 membered heterocycloalkyl, and 5-10 membered heteroaryl.

Embodiment 1021

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl optionally substituted by 1-3 $R^{209}$, phenyl optionally substituted by 1-3 $R^{209}$, benzyl optionally substituted by 1-3 $R^{209}$, $C_{5-6}$cycloalkyl optionally substituted by 1-3 $R^{209}$, 5-6 membered heterocycloalkyl optionally substituted by 1-3 $R^{209}$, and 5-6 membered heteroaryl optionally substituted by 1-3 $R^{209}$.

Embodiment 1022

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 1023

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl, phenyl, $C_{5-6}$cycloalkyl, 5-6 membered heterocycloalkyl, and 5-6 membered heteroaryl.

Embodiment 1024

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H, $C_{1-6}$alkyl, phenyl, benzyl, $C_{5-6}$cycloalkyl, 5-6 membered heterocycloalkyl optionally substituted by 1 $R^{209}$, and 5-6 membered heteroaryl.

Embodiment 1025

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H and $C_{1-6}$alkyl optionally substituted by 1-3 $R^{209}$.

Embodiment 1026

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is independently chosen from H and $C_{1-6}$alkyl.

Embodiment 1027

The compound of any of Embodiments 1-156, 200-250, 300-371, 400-440, 500-533, 600-668, 700-714, 750-795, 800-817, 850-886, or 900-1015, wherein $R^{190}$, $R^{191}$, $R^{194}$, $R^{195}$, $R^{196}$ and $R^{197}$ at each occurrence is H.

Embodiment 1028

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, and 6-21 membered heteroarylalkyl optionally substituted by 1-27 $R^{219}$; or any $R^{192}$ and $R^{193}$ may form, together with the nitrogen atom to which they are attached, a 3-15 membered heterocycloalkyl optionally substituted by 1-28 $R^{229}$ or a 5-15 membered heteroaryl optionally substituted by 1-15 $R^{229}$.

Embodiment 1029

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-6 $R^{219}$, $C_{2-6}$alkenyl optionally substituted by 1-6 $R^{219}$, $C_{2-6}$alkynyl optionally substituted by 1-6 $R^{219}$, $C_{6-11}$aryl optionally substituted by 1-6 $R^{219}$, $C_{7-16}$arylalkyl optionally substituted by 1-6 $R^{219}$, $C_{3-11}$cycloalkyl optionally substituted by 1-6 $R^{219}$, $C_{4-17}$cycloalkylalkyl optionally substituted by 1-6 $R^{219}$, 3-15 membered heterocycloalkyl optionally substituted by 1-6 $R^{219}$, 4-21 membered heterocycloalkylalkyl optionally substituted by 1-6 $R^{219}$, 5-15 membered heteroaryl optionally substituted by 1-6 $R^{219}$, and 6-21 membered heteroarylalkyl optionally substituted by 1-6 $R^{219}$; or any $R^{192}$ and $R^{193}$ may form, together with the nitrogen atom to which they are attached, a 3-15 membered heterocycloalkyl optionally substituted by 1-6 $R^{229}$ or a 5-15 membered heteroaryl optionally substituted by 1-6 $R^{229}$.

Embodiment 1030

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-3 $R^{219}$, phenyl optionally substituted by 1-3 $R^{219}$, benzyl optionally substituted by 1-3 $R^{219}$, $C_{3-10}$cycloalkyl optionally substituted by 1-3 $R^{219}$, 3-10 membered heterocycloalkyl optionally substituted by 1-3 $R^{219}$, and 5-10 membered heteroaryl optionally substituted by 1-3 $R^{219}$; or any $R^{192}$ and $R^{193}$ may form, together with the nitrogen atom to which they are attached, a 3-15 membered heterocycloalkyl optionally substituted by 1-3 $R^{229}$ or a 5-15 membered heteroaryl optionally substituted by 1-3 $R^{229}$.

Embodiment 1031

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-3 $R^{219}$, phenyl optionally substituted by 1-3 $R^{219}$, benzyl optionally substituted by 1-3 $R^{219}$, $C_{3-10}$cycloalkyl optionally substituted by 1-3 $R^{219}$, 3-10 membered heterocycloalkyl optionally substituted by 1-3 $R^{219}$, and 5-10 membered heteroaryl optionally substituted by 1-3 $R^{219}$.

Embodiment 1032

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-3 $R^{219}$, phenyl optionally substituted by 1-3 $R^{219}$, benzyl optionally substituted by 1-3 $R^{219}$, $C_{3-6}$cycloalkyl optionally substituted by 1-3 $R^{219}$, 3-6 membered heterocycloalkyl optionally substituted by 1-3 $R^{219}$, and 5-6 membered heteroaryl optionally substituted by 1-3 $R^{219}$; or any $R^{192}$ and $R^{193}$ may form, together with the nitrogen atom to which they are attached, a 3-10 membered heterocycloalkyl optionally substituted by 1-3 $R^{229}$ or a 5-10 membered heteroaryl optionally substituted by 1-3 $R^{229}$.

Embodiment 1033

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-3 $R^{219}$, phenyl optionally substituted by 1-3 $R^{219}$, benzyl optionally substituted by 1-3 $R^{219}$, $C_{5-6}$cycloalkyl optionally substituted by 1-3 $R^{219}$, 5-6 membered heterocycloalkyl optionally substituted by 1-3 $R^{219}$, and 5-6 membered heteroaryl optionally substituted by 1-3 $R^{219}$.

Embodiment 1034

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-3 $R^{219}$, phenyl optionally substituted by 1-3 $R^{219}$, benzyl optionally substituted by 1-3 $R^{219}$, 5-6 membered heterocycloalkyl optionally substituted by 1-3 $R^{219}$, and 5-6 membered heteroaryl optionally substituted by 1-3 $R^{219}$.

Embodiment 1035

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl; or any $R^{192}$ and $R^{193}$ may form, together with the nitrogen atom to which they are attached, a 5-6 membered heterocycloalkyl or a 5-6 membered heteroaryl.

Embodiment 1036

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl, phenyl, benzyl, $C_{5-6}$cycloalkyl, 5-6 membered heterocycloalkyl, and 5-6 membered heteroaryl.

Embodiment 1037

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl optionally substituted by 1-3 $R^{219}$, phenyl optionally substituted by 1-3 $R^{219}$, and benzyl optionally substituted by 1-3 $R^{219}$.

Embodiment 1038

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H and $C_{1-6}$alkyl optionally substituted by 1-3 $R^{219}$.

Embodiment 1039

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H, $C_{1-6}$alkyl, phenyl, and benzyl.

Embodiment 1040

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is independently chosen from H and $C_{1-6}$alkyl.

Embodiment 1041

The compound of any of Embodiments 1-156, 200-250, 300-371, 400-440, 500-533, 600-668, 700-714, 750-795, 800-817, 850-886, or 900-1027, wherein $R^{192}$ and $R^{193}$ at each occurrence is H.

Embodiment 1042

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-13 $R^{209}$, $C_{2-6}$alkenyl optionally substituted by 1-11 $R^{209}$, $C_{2-6}$alkynyl optionally substituted by 1-9 $R^{209}$, $C_{6-11}$aryl optionally substituted by 1-11 $R^{209}$, $C_{7-16}$arylalkyl optionally substituted by 1-19 $R^{209}$, $C_{3-11}$cycloalkyl optionally substituted by 1-21 $R^{209}$, $C_{4-17}$cycloalkylalkyl optionally substituted by 1-32 $R^{209}$, 3-15 membered heterocycloalkyl optionally substituted by 1-28 $R^{209}$, 4-21 membered heterocycloalkylalkyl optionally substituted by 1-40 $R^{209}$, 5-15 membered heteroaryl optionally substituted by 1-15 $R^{209}$, and 6-21 membered heteroarylalkyl optionally substituted by 1-27 $R^{209}$.

Embodiment 1043

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-3 $R^{209}$, $C_{2-6}$alkenyl optionally substituted by 1-3 $R^{209}$, $C_{2-6}$alkynyl optionally substituted by 1-3 $R^{209}$, $C_{6-11}$aryl optionally substituted by 1-3 $R^{209}$, $C_{7-16}$arylalkyl optionally substituted by 1-3 $R^{209}$, $C_{3-11}$cycloalkyl optionally substituted by 1-3 $R^{209}$, $C_{4-17}$cycloalkylalkyl optionally substituted by 1-3 $R^{209}$, 3-15 membered heterocycloalkyl optionally substituted by 1-3 $R^{209}$, 4-21 membered heterocycloalkylalkyl optionally substituted by 1-3 $R^{209}$, 5-15 membered heteroaryl optionally substituted by 1-3 $R^{209}$, and 6-21 membered heteroarylalkyl optionally substituted by 1-3 $R^{209}$.

Embodiment 1044

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-3 $R^{209}$, $C_{2-6}$alkenyl optionally substituted by 1-3 $R^{209}$, $C_{2-6}$alkynyl optionally substituted by 1-3 $R^{209}$, $C_{6-10}$aryl optionally substituted by 1-3 $R^{209}$, $C_{7-11}$arylalkyl optionally substituted by 1-3 $R^{209}$, $C_{3-10}$cycloalkyl optionally substituted by 1-3 $R^{209}$, 3-10 membered heterocycloalkyl optionally substituted by 1-3 $R^{209}$, and 5-10 membered heteroaryl optionally substituted by 1-3 $R^{209}$.

Embodiment 1045

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-3 $R^{209}$, $C_{6-10}$aryl optionally substituted by 1-3 $R^{209}$, $C_{7-11}$arylalkyl optionally substituted by 1-3 $R^{209}$, $C_{3-10}$ cycloalkyl optionally substituted by 1-3 $R^{209}$, 3-10 membered heterocycloalkyl optionally substituted by 1-3 $R^{209}$, and 5-10 membered heteroaryl optionally substituted by 1-3 $R^{209}$.

Embodiment 1046

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-3 $R^{209}$, phenyl optionally substituted by 1-3 $R^{209}$, benzyl optionally substituted by 1-3 $R^{209}$, $C_{3-6}$cycloalkyl optionally substituted by 1-3 $R^{209}$, 3-6 membered heterocycloalkyl optionally substituted by 1-3 $R^{209}$, and 5-6 membered heteroaryl optionally substituted by 1-3 $R^{209}$.

Embodiment 1047

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl, phenyl, benzyl, $C_{3-6}$cycloalkyl, 3-6 membered heterocycloalkyl, and 5-6 membered heteroaryl.

Embodiment 1048

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-3 $R^{209}$, phenyl, and benzyl.

Embodiment 1049

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl optionally substituted by 1-3 $R^{209}$, phenyl optionally substituted by 1-3 $R^{209}$, and benzyl optionally substituted by 1-3 $R^{209}$.

Embodiment 1050

The compound of any of Embodiments 1-156, 200-250, 300-371, 400-440, 500-533, 600-668, 700-714, 750-795, 800-817, 850-886, or 900-1041, wherein $R^{198}$ at each occurrence is independently chosen from $C_{1-6}$alkyl, phenyl, and benzyl.

Embodiment 1051

The compound of any of Embodiments 1-156, 200-250, 300-371, 400-440, 500-533, 600-668, 700-714, 750-795, 800-817, 850-886, or 900-1041, wherein $R^{198}$ at each occurrence is $C_{1-6}$alkyl optionally substituted by 1-3 $R^{209}$.

Embodiment 1052

The compound of any of Embodiments 1-156, 200-250, 300-371, 400-440, 500-533, 600-668, 700-714, 750-795, 800-817, 850-886, or 900-1041, wherein $R^{198}$ at each occurrence is $C_{1-6}$alkyl.

Embodiment 1053

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, —C(═O)$R^{230}$, —C(═O)O$R^{230}$, —C(═O)N$R^{230}R^{230}$, —C(═O)C(═O)$R^{230}$, —C(═N$R^{230}$)$R^{230}$, —C(═N$R^{230}$)N$R^{230}R^{230}$, —C(═NOH)N$R^{230}R^{230}$, —C(═NO$R^{230}$)$R^{230}$, —C(═NN$R^{230}R^{230}$)$R^{230}$, —C(═N$NR^{230}$C(═O)$R^{230}$)$R^{230}$, —C(═N$NR^{230}$C(═O)O$R^{230}$)$R^{230}$, —C(═S)N$R^{230}R^{230}$, —NC, —$NO_2$, —N$R^{230}R^{230}$, —N$R^{230}$N$R^{230}R^{230}$, —N═N$R^{230}$, ═N$R^{230}$, ═NO$R^{230}$, —N$R^{230}$O$R^{230}$, —N$R^{230}$C(═O)$R^{230}$, —N$R^{230}$C(═O)C(═O)$R^{230}$, —N$R^{230}$C(═O)O$R^{230}$, —N$R^{230}$C(═O)C(═O)O$R^{230}$, —N$R^{230}$C(═O)N$R^{230}R^{230}$, —N$R^{230}$C(═O)N$R^{230}$C(═O)$R^{230}$, —N$R^{230}$C(═O)N$R^{230}$C(═O)O$R^{230}$, —N$R^{230}$C(═N$R^{230}$)N$R^{230}R^{230}$, —N$R^{230}$C(O)C(═O)N$R^{230}R^{230}$, —N$R^{230}$C(═S)$R^{230}$, —N$R^{230}$C(═S)O$R^{230}$, —N$R^{230}$C(═S)N$R^{230}R^{230}$, —N$R^{230}$S(═O)$_2R^{230}$, —N$R^{230}$S(═O)$_2$N$^{230}R^{230}$, —N$R^{230}$P(═O)$R^{231}R^{231}$, —N$R^{230}$P(═O)(N$R^{230}R^{230}$)(N$R^{230}R^{230}$), —N$R^{230}$P(═O)(O$R^{230}$)(O$R^{230}$), —N$R^{230}$P(═)(S$R^{230}$)(S$R^{230}$), —O$R^{230}$, ═O, —OCN, —OC(═O)$R^{230}$, —OC(═O)N$R^{230}R^{230}$, —OC(═)O$R^{230}$, —OC(═N$R^{230}$)N$R^{230}R^{230}$, —OS(═O)$R^{230}$, —OS(═O)$_2R^{230}$, —OS(═O)$_2$O$R^{230}$, —OS(═O)$_2$N$R^{230}R^{230}$, —OP(═O)$R^{231}R^{231}$, —OP(═O)(N$R^{230}R^{230}$)(N$R^{230}R^{230}$), —OP(═)(O$R^{230}$)(O$R^{230}$), —OP(═O)(S$R^{230}$)(S$R^{230}$), —Si($R^{230}$)$_3$, —SCN, ═S, —S(═O)$_nR^{230}$, —S(═O)$_2R^{230}$, —SO$_3R^{230}$, —S(═O)$_2$N$R^{230}R^{230}$, —S(═O)N$R^{230}R^{230}$, —SP(═O)$R^{231}R^{231}$, —SP(═O)(N$R^{230}R^{230}$)(N$R^{230}R^{230}$), —SP(═O)(O$R^{230}$)(O$R^{230}$), —SP(═O)(S$R^{230}$)(S$R^{230}$), —P(═O)$R^{231}R^{231}$, —P(═O)(N$R^{230}R^{230}$)(N$R^{230}R^{230}$), —P(═O)(O$R^{230}$)(O$R^{230}$), and —P(═O)(S$R^{230}$)(S$R^{230}$).

Embodiment 1054

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-6 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-15 membered heterocycloalkylalkyl, 5-15 membered heteroaryl, 6-15 membered heteroarylalkyl, halogen, —CN, —C(═O)$R^{230}$, —C(═O)O$R^{230}$, —C(═O)N$R^{230}R^{230}$, —C(═O)C(═O)$R^{230}$, —NC, —$NO_2$, —N$R^{230}R^{230}$, —N$R^{230}$N$R^{230}R^{230}$, —N$R^{230}$O$R^{230}$, —N$R^{230}$C(═O)$R^{230}$, —N$R^{230}$C(═O)C(═O)$R^{230}$, —N$R^{230}$C(═O)O$R^{230}$, —N$R^{230}$C(═O)C(═O)O$R^{230}$, —N$R^{230}$C(═O)N$R^{230}R^{230}$, —N$R^{230}$C(═O)N$R^{230}$C(═O)$R^{230}$, —N$R^{230}$C(═O)N$R^{230}$C(═O)O$R^{230}$, —N$R^{230}$C(═O)C(═O)N$R^{230}R^{230}$, —N$R^{230}$S(═O)$_2R^{230}$, —N$R^{230}$S(═O)$_2$N$R^{230}R^{230}$, —N$R^{230}$P(═O)$R^{231}R^{231}$, —N$R^{230}$P(═O)(N$R^{230}R^{230}$)(N$R^{230}R^{230}$), —N$R^{230}$P(═O)(O$R^{230}$)(O$R^{230}$), —O$R^{230}$, ═O, —OCN, —OC(═O)$R^{230}$, —OC(═O)N$R^{230}R^{230}$, —OC(═O)O$R^{230}$, —OS(═O)$R^{230}$, —OS(═O)$_2R^{230}$, —OS(═O)$_2R^{230}$, —OS(═O)$_2$N$R^{230}R^{230}$, —OP(═O)$R^{231}R^{231}$, —OP(═O)(N$R^{230}R^{230}$)(N$R^{230}R^{230}$), —OP(═O)(O$R^{230}$)(O$R^{230}$), —Si($R^{230}$)$_3$, —SCN, ═S, —S(═O)$_nR^{230}$, —S(═O)$_2$O$R^{230}$, —SO$_3R^{230}$, —S(═O)$_2$N$R^{230}R^{230}$, —S(═O)N$R^{230}R^{230}$, —P(═O)$R^{231}R^{231}$, —P(═O)(N$R^{230}R^{230}$)(N$R^{230}R^{230}$), and —P(═O)(O$R^{230}$)(O$R^{230}$).

Embodiment 1055

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-3 halogen, $C_{2-6}$alkenyl, $C_{2-6}$alkynyl, $C_{6-10}$aryl, $C_{7-11}$arylalkyl, $C_{3-10}$cycloalkyl, $C_{4-17}$cycloalkylalkyl, 3-10 membered heterocycloalkyl, 4-10 membered heterocycloalkylalkyl, 5-10 membered heteroaryl, 6-10 membered heteroarylalkyl, halogen, —CN, —C(═O)$R^{230}$, —C(═O)O$R^{230}$, —C(═O)N$R^{230}R^{230}$, —NC, —$NO_2$, —N$R^{230}R^{230}$, —N$R^{230}$O$R^{230}$, —N$R^{230}$C(═O)$R^{230}$, —N$R^{230}$C(═O)O$R^{230}$, —N$R^{230}$C(═O)N$R^{230}R^{230}$, —N$R^{230}$C(═O)N$R^{230}$C(═O)$R^{230}$, —N$R^{230}$S(═O)$_2R^{230}$, —N$R^{230}$S(═O)$_2$N$R^{230}R^{230}$, —N$R^{230}$P(═O)$R^{231}R^{231}$, —N$R^{230}$P(═O)(N$R^{230}R^{230}$)(N$R^{230}R^{230}$), —N$R^{230}$P(═O)(O$R^{230}$)(O$R^{230}$), —O$R^{230}$, ═O, —OCN, —OC(═O)$R^{230}$, —OC(═O)N$R^{230}R^{230}$, —OS(═O)$_2$N$R^{230}R^{230}$, —OP(═O)$R^{231}R^{231}$, —OP(═O)(N$R^{230}R^{230}$)(N$R^{230}R^{230}$), —SCN, ═S, —S(═O)$_nR^{230}$, —S(═O)$_2$N$R^{230230}$, —S(═O)N$R^{230}R^{230}$, —P(═O)$R^{231}R^{231}$, and —P(═O)(N$R^{230}R^{230}$)(N$R^{230}R^{230}$).

Embodiment 1056

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-3 halogen, $C_{2-6}$alkenyl, $C_{2-6}$alkynyl, $C_{6-10}$aryl, $C_{7-11}$arylalkyl, $C_{3-10}$cycloalkyl, 3-10 membered heterocycloalkyl, 5-10 membered heteroaryl, halogen, —CN, —C(═O)$R^{230}$, —C(═O)O$R^{230}$, —C(═O)N$R^{230}R^{230}$, —$NO_2$, —N$R^{230}R^{230}$, —N$R^{230}$O$R^{230}$, —N$R^{230}$C(═O)$R^{230}$, —N$R^{230}$C(═O)N$R^{230}R^{230}$, —N$R^{230}$S(═O)$_2R^{230}$, —N$R^{230}$S(═O)$_2$N$R^{230}R^{230}$, —O$R^{230}$, ═O, —OCN, —OC(═O)$R^{230}$, —S(═O)$_nR^{230}$, —S(═O)$_2$N$R^{230}R^{230}$, and —S(═O)N$R^{230}R^{230}$.

Embodiment 1057

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-3 halogen, $C_{2-6}$alkenyl, $C_{2-6}$alkynyl, phenyl, benzyl, $C_{3-6}$cycloalkyl, 3-6 membered heterocycloalkyl, 5-6 membered heteroaryl, halogen, —CN, —C(═O)$R^{230}$, —C(═O)O$R^{230}$, —C(═O)N$R^{230}R^{230}$, —$NO_2$, —N$R^{230}R^{230}$, —N$R^{230}$C(═O)$R^{230}$, —N$R^{230}$C(═O)N$R^{230}R^{230}$, —N$R^{230}$S(═O)$_2R^{230}$, —N$R^{230}$S(═O)$_2$N$R^{230}R^{230}$, —O$R^{230}$, ═O, —S(═O)$_nR^{230}$, and —S(═O)$_2$N$R^{230}R^{230}$.

Embodiment 1058

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-3 halogen, $C_{2-6}$alkenyl, $C_{2-6}$alkynyl, phenyl, benzyl, $C_{3-6}$cycloalkyl, 3-6 membered heterocycloalkyl, 5-6 membered heteroaryl, halogen, —CN, —C(═O)$R^{230}$, —C(═O)O$R^{230}$, —C(═O)N$R^{230}R^{230}$, —N$R^{230}R^{230}$, —N$R^{230}$C(═O)$R^{230}$, —N$R^{230}$S(═O)$_2R^{230}$, —O$R^{230}$, ═O, —S(═O)$_n R^{230}$, and —S(═O)$_2$N$R^{230}R^{230}$.

Embodiment 1059

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-3 halogen, phenyl, benzyl, $C_{3-6}$cycloalkyl, 3-6 membered heterocycloalkyl, 5-6 membered heteroaryl, halogen, —CN, —C(═O)$R^{230}$, —C(═O)O$R^{230}$, —C(═O)N$R^{230}R^{230}$, —N$R^{230}R^{230}$, —O$R^{230}$, ═O, —S(═O)$_n R^{230}$, and —S(═O)$_2$N$R^{230}R^{230}$.

Embodiment 1060

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl optionally substituted by 1-3 halogen, halogen, and —N$R^2$30$R^{230}$.

Embodiment 1061

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl, halogen, and —N$R^{230}R^{230}$.

Embodiment 1062

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is independently chosen from $C_{1-6}$alkyl and —N$R^{230}R^{230}$.

Embodiment 1063

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is —N$R^{230}R^{230}$.

Embodiment 1064

The compound of any of Embodiments 1-156, 200-250, 300-371, 400-440, 500-533, 600-668, 700-714, 750-795, 800-817, 850-886, or 900-1052, wherein $R^{199}$, $R^{209}$, $R^{219}$ and $R^{229}$ at each occurrence is $C_{1-6}$alkyl.

Embodiment 1065

The compound of any of Embodiments 1-156, 200-250, 300-371, 400-440, 500-533, 600-668, 700-714, 750-795, 800-817, 850-886, or 900-1052, wherein $R^{199}$ at each occurrence is independently chosen from $C_{1-6}$alkyl and —N$R^{230}R^{230}$; $R^{209}$, $R^{219}$ and $R^{229}$ at each occurrence is $C_{1-6}$alkyl.

Embodiment 1066

The compound of any of Embodiments 1-156, 200-250, 300-371, 400-440, 500-533, 600-668, 700-714, 750-795, 800-817, 850-886, or 900-1052, wherein $R^{199}$ at each occurrence is independently chosen from $C_{1-6}$alkyl and —N$R^{230}R^{230}$; $R^{209}$, $R^{219}$ and $R^{229}$ at each occurrence is —N$R^{230}R^{230}$.

Embodiment 1067

The compound of any of Embodiments 1-156, 200-250, 300-371, 400-440, 500-533, 600-668, 700-714, 750-795, 800-817, 850-886, or 900-1052, wherein $R^{199}$ at each occurrence is —N$R^{230}R^{230}$; $R^{209}$, $R^{219}$ and $R^{229}$ at each occurrence is $C_{1-6}$alkyl.

Embodiment 1068

The compound of any of Embodiments 1-156, 200-250, 300-371, 400-440, 500-533, 600-668, 700-714, 750-795, 800-817, 850-886, or 900-1067, wherein $R^{230}$ at each occurrence is independently chosen from H, $C_{1-6}$alkyl and $C_{1-6}$-haloalkyl.

Embodiment 1069

The compound of any of Embodiments 1-156, 200-250, 300-371, 400-440, 500-533, 600-668, 700-714, 750-795, 800-817, 850-886, or 900-1067, wherein $R^{230}$ at each occurrence is independently chosen from H and $C_{1-6}$alkyl.

Embodiment 1070

The compound of any of Embodiments 1-156, 200-250, 300-371, 400-440, 500-533, 600-668, 700-714, 750-795, 800-817, 850-886, or 900-1067, wherein $R^{230}$ at each occurrence is $C_{1-6}$alkyl.

Embodiment 1071

The compound of any of Embodiments 1-156, 200-250, 300-371, 400-440, 500-533, 600-668, 700-714, 750-795, 800-817, 850-886, or 900-1067, wherein $R^{230}$ at each occurrence is H.

Embodiment 1072

The compound of any of Embodiments 1-156, 200-250, 300-371, 400-440, 500-533, 600-668, 700-714, 750-795, 800-817, 850-886, or 900-1071, wherein $R^{231}$ at each occurrence is independently chosen from $C_{1-6}$alkyl and $C_{1-6}$-haloalkyl.

Embodiment 1073

The compound of any of Embodiments 1-156, 200-250, 300-371, 400-440, 500-533, 600-668, 700-714, 750-795, 800-817, 850-886, or 900-1071, wherein $R^{231}$ at each occurrence is $C_{1-6}$alkyl.

Embodiment 1074

The compound of any of Embodiments 1-156, 200-250, 300-371, 400-440, 500-533, 600-668, 700-714, 750-795, 800-817, 850-886, or 900-1071, wherein $R^{231}$ at each occurrence is $C_{1-6}$-haloalkyl.

Embodiment 1075

The compound of any of Embodiments 1-156, 200-250, 300-371, 400-440, 500-533, 600-668, 700-714, 750-795, 800-817, 850-886, or 900-1074, wherein n at each occurrence is independently chosen from 0, 1, and 2.

Embodiment 1076

The compound of any of Embodiments 1-156, 200-250, 300-371, 400-440, 500-533, 600-668, 700-714, 750-795, 800-817, 850-886, or 900-1074, wherein n at each occurrence is independently chosen from 0 and 2.

Embodiment 1077

The compound of any of Embodiments 1-156, 200-250, 300-371, 400-440, 500-533, 600-668, 700-714, 750-795, 800-817, 850-886, or 900-1074, wherein n at each occurrence is independently chosen from 1 and 2.

Embodiment 1078

The compound of any of Embodiments 1-156, 200-250, 300-371, 400-440, 500-533, 600-668, 700-714, 750-795, 800-817, 850-886, or 900-1074, wherein n at each occurrence is independently chosen from 0 and 1.

Embodiment 1079

The compound of any of Embodiments 1-156, 200-250, 300-371, 400-440, 500-533, 600-668, 700-714, 750-795, 800-817, 850-886, or 900-1074, wherein n at each occurrence is 0.

Embodiment 1080

The compound of any of Embodiments 1-156, 200-250, 300-371, 400-440, 500-533, 600-668, 700-714, 750-795, 800-817, 850-886, or 900-1074, wherein n at each occurrence is 1.

Embodiment 1081

The compound of any of Embodiments 1-156, 200-250, 300-371, 400-440, 500-533, 600-668, 700-714, 750-795, 800-817, 850-886, or 900-1074, wherein n at each occurrence is 2.

The above Embodiments include salts of acidic and basic compounds of formula (I). Preferably, the salts are pharmaceutically acceptable. Pharmaceutically acceptable acid addition salts of basic compounds of formula (I) include, but are not limited to, salts derived from inorganic acids such as hydrochloric, nitric, phosphoric, sulfuric, hydrobromic, hydriodic, and phosphorus, as well as the salts derived from organic acids, such as aliphatic mono- and dicarboxylic acids, phenyl-substituted alkanoic acids, hydroxy alkanoic acids, alkanedioic acids, aromatic acids, and aliphatic and aromatic sulfonic acids. Such salts thus include, but are not limited to, sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, and methanesulfonate. See, for example, Berge et al., "Pharmaceutical Salts," J. of Pharmaceutical Science, 1977; 66:1-19.

Acid addition salts may be prepared by contacting a compound of formula (I) with a sufficient amount of the desired acid to produce the salt in the conventional manner. The free base form of the compound of formula (I) may be regenerated by contacting the salt form with a base and isolating the free base in the conventional manner.

Pharmaceutically acceptable base salts of acidic compounds of formula (I) are formed with metals or amines, such as alkali and alkaline earth metal hydroxides, or of organic amines. Examples of metals used as cations include, but are not limited to, sodium, potassium, magnesium, and calcium. Examples of suitable amines include, but are not limited to, N,N'-dibenzylethylenediamine, chloroprocaine, choline, diethanolamine, ethylenediamine (ethane-1,2-diamine), N-methylglucamine, and procaine. See, for example, Berge et al., "Pharmaceutical Salts," J. of Pharmaceutical Science, 1977; 66:1-19.

Base salts may be prepared by contacting a compound of formula (I) with a sufficient amount of the desired base to produce the salt in the conventional manner. The acid form of the compound of formula (I) may be regenerated by contacting the salt form with an acid and isolating the acid in a conventional manner.

Some compounds of the present application may exist as stereoisomers, including enantiomers, diastereomers, and geometric isomers. Geometric isomers include compounds of the present application that have alkenyl groups, which may exist as entgegen or zusammen conformations, in which case all geometric forms thereof, both entgegen and zusammen, cis and trans, and mixtures thereof, are within the scope of the present application. Some compounds of the present application have cycloalkyl groups, which may be substituted at more than one carbon atom, in which case all geometric forms thereof, both cis and trans, and mixtures thereof, are within the scope of the present application. All of these forms, including (R), (S), epimers, diastereomers, cis, trans, syn, anti, (E), (Z), tautomers, and mixtures thereof, are included in the compounds of the present application.

The compounds of the present application may be in any physical form, including amorphous or crystalline solids in any polymorphic form, in any state of purity. Crystalline polymorphic forms include unsolvated forms as well as solvated forms, such as hydrated forms.

III. Pharmaceutical Compositions

The present application further provides pharmaceutical compositions comprising a compound of any of the above Embodiments (e.g., a compound of formula (I) or a pharmaceutically acceptable salt thereof), together with a pharmaceutically acceptable excipient. For preparing a pharmaceutical composition from a compound of the present application, pharmaceutically acceptable excipients can be either solid or liquid. An excipient can be one or more substances which may act as, e.g., a carrier, diluent, flavoring agent, binder, preservative, tablet disintegrating agent, or an encapsulating material. The pharmaceutical composition may contain two or more compounds of the present application (e.g., two different salt forms of a compound of formula (I), may be used together in the same pharmaceutical composition). Preferably, the pharmaceutical composition contains a therapeutically effective amount of a compound of formula (I) or a pharmaceutically acceptable salt form thereof. In one embodiment, the composition contains an amount of a compound of formula (I) or a pharmaceutically acceptable salt form thereof effective to treat an atypical protein kinase C (aPKC)-dependent disorder or condition. Preferably, a compound of the present application will cause a decrease in symptoms or disease indicia associated with an aPKC-dependent disorder as measured quantitatively or qualitatively. The composition may also contain, in addition to a compound of formula (I) or a pharmaceutically acceptable salt form thereof and a pharmaceutically acceptable excipient, another therapeutic compound, such as a compound useful in the treatment of cancer.

A compound of the present application can be formulated as a pharmaceutical composition in any delivery form, such as a syrup, an elixir, a suspension, a powder, a granule, a tablet, a capsule, a lozenge, a troche, an aqueous solution, a cream, an ointment, a lotion, a gel, an emulsion, etc. Solid form preparations include powders, tablets, pills, capsules, cachets, suppositories, and dispersible granules. Preferably, the pharmaceutical composition is a tablet or capsule. In one embodiment, the pharmaceutical composition is a tablet. In another embodiment, the pharmaceutical composition is a capsule.

In powders, the excipient may be a finely divided solid in a mixture with a finely divided active component (i.e., compound of the present application). In tablets, the active component may be mixed with an excipient having the necessary binding properties in suitable proportions and compacted in the shape and size desired. Suitable excipients include magnesium carbonate, magnesium stearate, talc, sugar, lactose, pectin, dextrin, starch, gelatin, tragacanth, methylcellulose, sodium carboxymethylcellulose, low melting wax, cocoa butter, and the like.

The pharmaceutical composition preferably contains from 1% to 95% (w/w) of the active compound (i.e., compound of the present application). More preferably, the pharmaceutical composition contains from 5% to 70% (w/w) of the active compound.

For preparing suppositories, a low melting wax, such as a mixture of fatty acid glycerides or cocoa butter, may be melted and the active component dispersed homogeneously therein, as by stirring. The molten homogeneous mixture may then be poured into convenient sized molds, allowed to cool, and thereby to solidify.

Liquid form preparations include solutions, suspensions, and emulsions. Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In practice, compositions can be administered, for example, by intravenous infusion, orally, topically, intraperitoneally, intravesically or intrathecally. The formulations of compounds can be presented in unit-dose or multi-dose sealed containers, such as ampoules and vials. Injection solutions and suspensions can be prepared from sterile powders, granules, and tablets of the kind previously described.

A compound of the present application, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

Pharmaceutically acceptable excipients are determined in part by the particular composition being administered, as well as by the particular method used to administer the composition. Accordingly, there is a wide variety of suitable formulations of pharmaceutical compositions of the present application (see, e.g., *Remington: The Science and Practice of Pharmacy,* 20th ed., Gennaro et al. Eds., Lippincott Williams and Wilkins, 2000).

The quantity of active component in a pharmaceutical composition may be varied or adjusted from, e.g., 1 mg to 1,000 mg, 5 mg to 500 mg, 10 mg to 300 mg, or 25 mg to 250 mg, according to the particular application and the desired size of the dosage form.

The dose administered to a subject is preferably sufficient to induce a beneficial therapeutic response in the subject over time. The beneficial dose can vary from subject to subject depending upon, e.g., the subject's condition, body weight, surface area, and side effect susceptibility. Administration can be accomplished via single or divided doses.

IV. Method of Treatment

In another aspect, the present application provides a method of treating an aPKC-dependent disorder or condition in a subject comprising: administering to the subject a compound of formula (I) as defined in any of the above Embodiments or a pharmaceutically acceptable salt form thereof. In another aspect, the present application provides a compound of formula (I) as defined in any of the above Embodiments or a pharmaceutically acceptable salt form thereof for use in treating an aPKC-dependent disorder or condition in a subject. In another aspect, the present application provides a compound of formula (I) as defined in any of the above Embodiments or a pharmaceutically acceptable salt form thereof for use in the preparation of a medicament for treating an aPKC-dependent disorder or condition in a subject. Preferably, the compound is administered to the subject as a pharmaceutical composition comprising a pharmaceutically acceptable excipient. Preferably, the compound is administered to the subject in a pharmaceutically acceptable amount. In one embodiment, the aPKC-dependent condition or disorder is cancer. In another embodiment, the aPKC-dependent condition is selected from non-small cell lung cancer (NSCLC), squamous cell carcinoma (e.g., oesophageal squamous cell carcinoma), leukaemia, prostate cancer, non-Hodgkin's lymphoma (e.g., follicular lymphoma), endometrial cancer, lung cancer and breast cancer.

The aPKC-dependent disorder or condition can be treated prophylactically, acutely, or chronically using compounds of the present application, depending on the nature of the disorder or condition. Typically, the subject in each of these methods is human, although other mammals can also benefit from the administration of a compound of the present application.

In another embodiment, the present application provides a method of treating a proliferative disorder in a subject, comprising administering to the subject a compound of formula (I) as defined in any of the above Embodiments or a pharmaceutically acceptable salt form thereof.

In another aspect, the present application provides a compound of formula (I) as defined in any of the above Embodiments or a pharmaceutically acceptable salt form thereof for use in treating a proliferative disorder in a subject. In another aspect, the present application provides a compound of formula (I) as defined in any of the above Embodiments or a pharmaceutically acceptable salt form thereof for use in the preparation of a medicament for treating a proliferative disorder in a subject. Preferably, the compound is administered to the subject in a pharmaceutical composition comprising a pharmaceutically acceptable excipient. Preferably, the compound is administered to the subject in a pharmaceutically acceptable amount. In certain embodiments, the proliferative disorder is aPKC-dependent. In certain embodiments, the proliferative disorder is cancer. In certain embodiments, the proliferative disorder is selected from non-small cell lung cancer (NSCLC), squamous cell carcinoma (e.g., oesophageal squamous cell carcinoma), leukaemia, prostate cancer, non-Hodgkin's lymphoma (e.g., follicular lymphoma), endometrial cancer, lung cancer and breast cancer.

The proliferative disorder can be treated prophylactically, acutely, or chronically using a compound of the present application, depending on the nature of the disorder or condition. Typically, the subject in each of these methods is human, although other mammals can also benefit from the administration of a compound of the present application.

In therapeutic applications, the compounds of the present application can be prepared and administered in a wide variety of oral and parenteral dosage forms. Thus, the compounds of the present application can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present application can be administered transdermally. In another embodiment, the compounds of the present application are delivered orally. The compounds can also be delivered rectally, bucally or by insufflation.

Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired. A typical dose is about 1 mg to about 1,000 mg per day, such as about 5 mg to about 500 mg per day. In certain embodiments, the dose is about 10 mg to about 300 mg per day, such as about 25 mg to about 250 mg per day.

V. Chemistry

Abbreviations

For convenience, the following common abbreviations are used herein:

LCMS for Liquid Chromatography-Mass Spectrometry.
HPLC for High Pressure Liquid Chromatography.
NMR for Nuclear Magnetic Resonance.
RT for Retention Time.
MI for Molecular Ion
h for hours
min for minutes
$AlCl_3$ for aluminium chloride
$BBr_3$ for boron tribromide
Boc for tert-butoxycarbonyl
cataCXium C for trans-Bis(acetato)bis[o-(di-o-tolylphosphino)benzyl]dipalladium(II).
$Cs_2CO_3$ for cesium carbonate
CuI for copper(I)iodide
DAST for diethylaminosulfur trifluoride
DBU for 1,8-diazabicyclo(5.4.0)undec-7-ene
DMAP for 4-(dimethylamino) pyridine
DCE for 1,1-dichloroethane or ethylidene chloride
DCM for dichloromethane or methylene chloride
DEA for diethanolamine
DIPEA for N,N,-di-isopropyethylamine, Hunig's base
DMA for N,N-dimethylacetamide
DMF for N,N-dimethylformamide
DMSO for dimethylsulfoxide.
$Et_3N$ for triethylamine
EtOH for ethyl alcohol, ethanol
Ex for example
HCl for hydrochloric acid
$H_2SO_4$ for sulfuric acid
Int for intermediate
KOH for potassium hydroxide
MW for microwave
mCPBA for meta-Chloroperoxybenzoic acid
MeOH for methyl alcohol, methanol
$Mo(CO)_6$ for Molybdenum hexacarbonyl
MP-$BH_4$ for macroporous triethylammonium methyl polystyrene borohydride
NaOH for sodium hydroxide
$Na_2CO_3$ for sodium carbonate
$Na_2SO_4$ for sodium sulphate
NaOAc for sodium acetate
NaOtBu for sodium t-butoxide
NMP for 1-methyl-2-pyrrolidinone
NMM for N-methylmorpholine
$Pd(dba)_2$ for Bis(dibenzylideneacetone)palladium
$Pd(OAc)_2$ for Palladium diacetate
$Pd(Ph_3)_4$ for tetrakis(triphenylphosphine)palladium
$Pd(PPh_3)_2Cl_2$ for Bis(triphenylphosphine)palladium(II) dichloride
$POCl_3$ for phosphorus oxychloride
$PPh_3$ for triphenylphosphine
PS-TsCl for polystyrene sulfonyl chloride
PS-$PPh_3$-Pd for polystyrene triphenylphosphine-Pd(0)
SCX-2 for a silica-based sorbent with a chemically bonded propylsulfonic acid functional group
TBAF for Tetra-n-butylammonium fluoride
TBDMS for tert-butyldimethylsilyl
TCA for trichloroacetic acid
TFA for trifluoroacetic acid
THF for tetrahydrofuran
TMS azide for trimethylsilyl azide
Xantphos for 4,5-Bis(diphenylphosphino)-9,9-dimethylxanthene
XPhos for 2-Dicyclohexylphosphino-2',4',6'-triisopropylbiphenyl LCMS Methods Samples analysed by High Performance Liquid Chromatography-Mass Spectrometry employed the following conditions. Unless otherwise noted, Method X was utilized.

Method 1

Method 1 employed Gilson 306 pumps, Gilson 811C mixer, Gilson 806 manometric module, and Gilson UV/VIS 152 detector at 254 nm wavelength. The mass spectrometer was a Finnigan AQA and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 2

Method 2 employed Waters 515 pumps, a Waters 2525 mixer and a Waters 2996 diode array detector. The detection was performed between 210 nm and 650 nm. The mass spectrometer was a Waters micromass ZQ and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 3

Method 3 employed Waters 515 pumps, a Waters 2525 mixer and a Waters 2487 UV detector (single wavelength 254 nm). The mass spectrometer was a Waters micromass ZQ and the column used was a Waters SunFire, 5 μm pore size, C18 of dimensions 50×4.60 mm. The injection volume was 10 μl. The mobile phase consisted of a mixture of water and acetonitrile containing 0.1% formic acid. The eluent flow rate was 1.5 mL/min, using 95% water: 5% acetonitrile, changed linearly to 5% water: 95% acetonitrile over 5.5 minutes and then maintained at this mixture for 2 minutes.

Method 4

Method 4 employed Waters 515 pumps, a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 μl of a solution (around 1 mg/ml). The flow rate was 1.5 mL/min and the mobile phases of water pH 10 0.03% ammonium hydroxide) (3 ml/101) and acetonitrile 0.03% ammonium hydroxide (3 ml/101). The elution was started at 95% water: 5% acetonitrile ramping up to 5% water:95% acetonitrile over 5.50 minutes. The eluent level was returned to the starting conditions of 95% water: 5% acetonitrile over 6 seconds. These conditions were held for 1.4 minutes to allow equilibration of the column before the next sample was injected. The run lasted 7 minutes in total.

Method 5

Method 5 employed Waters 515 pumps, a Waters 2525 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 μL of a solution (around 1 mg/mL). The flow rate was 1.5 mL/min and the mobile phases of water and methanol contained 0.1% formic acid. The elution was started at 85% water:15% methanol ramping up to 15% water:85% methanol over 4.5 minutes, these conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 6

Method 6 employed Waters 515 pumps, a Waters 2545 mixer with valves directing to the different columns and a Waters 2996 diode array detector. The detection was done between 210 nm and 650 nm. The mass spectrometer used was a Waters 3100 which detected masses between 100 and 700 g/mol. The column used was a XBridge, 5 micron pore size, C18, 50×4.60 mm. The injection volume was 10 μL of a solution (around 1 mg/mL). The flow rate was 1.5 mL/min and the mobile phases of water pH 10 0.03% ammonium hydroxide) (3 ml/101) and methanol 0.03% ammonium hydroxide (3 ml/101). The elution was started at 85% water: 15% methanol ramping up to 15% water:85% methanol over 4.5 minutes. These conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 7

Method 7 employed Waters 515 pumps, a Waters 2545 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 μL of a solution (around 1 mg/mL). The flow rate was 1.5 mL/min and the mobile phases of water and methanol contained 0.1% formic acid. The elution was started at 85% water:15% methanol ramping up to 15% water:85% methanol over 4.5 minutes., these conditions were held for 1 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 8

Method 8 employed Waters 515 pumps, a Waters 2525 mixer with valves directing to the different columns and a Waters 2487 UV detector. The detection was done between at 254 nm. The mass spectrometer used was a Waters micromass ZQ which detected masses between 100 and 700 g/mol. The column used was a SunFire, 5 micron pore size, C18 column of dimensions 50×4.60 mm was used. The injection volume was 10 μL of a solution (around 1 mg/mL). The flow rate was 1.5 mL/min and the mobile phases of water and methanol contained 0.1% formic acid. The elution was started at 85% water:15% methanol ramping up to 15% water:85% methanol over 3 minutes., these conditions were held for 2.5 minute before the eluent level was returned to the starting conditions of 85% water:15% methanol over 6 seconds. These conditions were held for 1.4 minutes to allow equilibration of the column before the next sample was injected. The run lasted 7 minutes in total.

Method 9

Method 9 employed Waters 515 pumps, a Waters 2545 mixer with valves directing to the different columns and a Waters 2487 UV detector. The detection was done between at 254 nm. The mass spectrometer used was a Waters micromass ZQ which detected masses between 100 and 700 g/mol. The column used was a XBridge, 5 micron pore size, C18, 50×4.60 mm. The injection volume was 10 μL of a solution (around 1 mg/mL). The flow rate was 1.5 mL/min and the mobile phases of water pH 10 0.03% ammonium hydroxide) (3 ml/101) and methanol 0.03% ammonium hydroxide (3 ml/101). The elution was started at 85% water:15% methanol ramping up to 15% water:85% methanol over 4.5 minutes. These conditions were held for 1 minute before the eluent level was returned to the starting conditions of 85% water: 15% methanol over 6 seconds. These conditions were held for 1.4 minutes to allow equilibration of the column before the next sample was injected. The run lasted 7 minutes in total.

Method 10

LCMS results were obtained on either of two instruments. LCMS analysis was performed on a Waters Aquity Ultra Performance LC with a 2.1 mm×50 mm Waters Aquity UPLC BEH C18 1.7 μm column. The target column temperature was 45° C., with a run time of two (2) minutes, a flow rate of 0.600 mL/min, and a solvent mixture of 5% (0.1% formic acid/water):95% (acetonitrile/0.1% formic acid). The mass spectrometry data was acquired on a Micromass LC-ZQ 2000 quadrupole mass spectrometer. Alternatively, LCMS analysis was performed on a Bruker Esquire 200 ion trap.

Preparative HPLC Methods

Samples purified by Mass Spectrometry directed High Performance Liquid Chromatography employed the following conditions.

Method A

Method A employed Waters 515 pumps, a Waters 2525 mixer and a Waters 2487 UV detector (single wavelength 254 nm). The mass spectrometer was a Waters micromass ZQ and the column used was a Waters SunFire, 5 μm pore size, C18 of dimensions 50×19 mm. The injection volume was up to 500 μL of solution at a maximum concentration of 50 mg/mL. The mobile phase consisted of a mixture of water and acetonitrile containing 0.1% formic acid. The eluent flow rate was 25 mL/min using 95% water, 5% acetonitrile, changing linearly over 5.3 minutes to 95% acetonitrile, 5% water, and maintaining for 0.5 minutes.

Method B

Method B employed Waters 515 pumps a Waters 2545 mixer with valves directing to the different columns and a Waters 2996 diode array detector. The detection was performed between 210 nm and 650 nm. The mass spectrometer used was a Waters 3100 which detected masses between 100 and 700 g/mol. The column used was a XBridge, 5 micron pore size, C18, 50×19 mm. The injection volume was chosen by the user and can be up to 500 L of the solution (max 50 mg/mL). The flow rate was 25 mL/min and the mobile phases of water pH 10 0.03% ammonium hydroxide (3 ml/101) and acetonitrile 0.03% ammonium hydroxide (3 ml/101). The elution was started at 95% water:5% acetonitrile ramping up to 5% water:95% acetonitrile over 5.30 minutes. The eluent level was returned to the starting conditions of 95% water: 5% acetonitrile over 0.6 minutes. These conditions were held for 1.4 minutes to allow equilibration of the column before the next sample was injected. The run lasted 7 minutes in total.

Analytical HPLC Methods

Method X

Method X employs gradient elution (0 to 100%) acetonitrile (containing 0.1% trifluoroacetic acid):water (containing 0.1% trifluoroacetic acid) over five minutes on a 4.6×75 mm (2.5 micron) Zorbax XDB-C8 column at 2.5 ml/min on an Agilent 1100 series HPLC.

Synthesis

Several methods for the chemical synthesis of 4-substituted-2-(pyridin-4-yl)-azaquinazoline compounds (for convenience, collectively referred to herein as “4PAZ compounds”) of the present application are described herein. These and/or other well known methods may be modified and/or adapted in known ways in order to facilitate the synthesis of additional compounds within the scope of the present application.

[F-001]

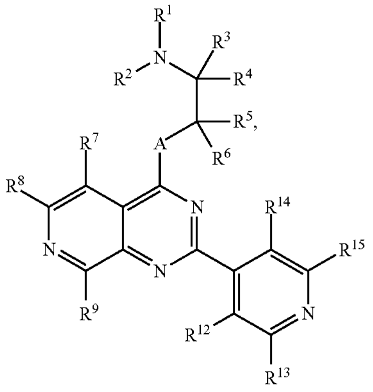

[F-002]

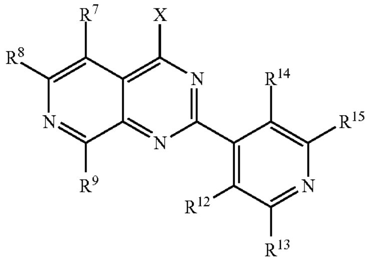

[F-003]

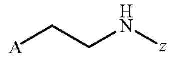

In one approach, 4PAZ compounds of general formula [F-001](where A=NH or N alkyl) are prepared by reacting a compound of formula [F-002](where X is a halogen such as chlorine or a sulfonate) with a compound of formula [F-003] (where A is NH or NH2 and Z on the terminal nitrogen is H, alkyl or a suitable nitrogen protecting group, such as Boc, Alloc, Cbz or Fmoc) in a suitable solvent such as DMF in the presence of a suitable base such as triethylamine. The reaction is suitably conducted at an elevated temperature for example 40° C. Where Z is a suitable nitrogen protecting group, such as Boc, Alloc, Cbz or Fmoc, compounds of formula [F-001] are prepared by a suitable deprotection reaction. For example: where Z is a Boc protecting group reaction with an acid such as TFA in a suitable solvent such as DCM. The reaction is suitably conducted at ambient temperature. In one approach, compounds of formula [F-001](where A=O) are prepared by reacting a compound of formula [F-002](where X is a halogen such as chlorine or sulfonate) with a compound of formula [F-003](where A is OH and Z on the terminal nitrogen is H, alkyl or a suitable nitrogen protecting group, such as Boc, Alloc, Cbz or Fmoc) in a suitable solvent such as DMA in the presence of a suitable base such as sodium hydride. The reaction is suitably conducted at ambient temperature. Where Z is a suitable nitrogen protecting group, such as Boc, Alloc, Cbz or Fmoc, compounds of formula [F-001] are prepared by a suitable deprotection reaction. For example: where Z is a Boc protecting group reaction with an acid such as TFA in a suitable solvent such as DCM. The reaction is suitably conducted at ambient temperature.

[F-004]

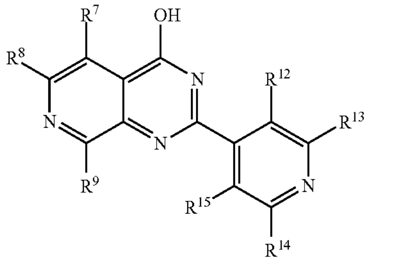

In one approach, compounds of formula [F-002](where X is a halogen such as chlorine) are prepared by reacting a compound of formula [F-004] with a suitable halogenating agent such as phosphorous oxychloride. The reaction is suitably conducted at elevated temperature such as 125° C. Compounds of formula [F-002](where X is a sulfonate) are prepared by reacting a compound of formula [F-004] with a suitably substituted sulfonyl chloride in a suitable solvent such as DMA in the presence of a suitable base such as triethylamine and a catalytic amount of DMAP. The reaction is suitably conducted at ambient temperature.

[F-005]

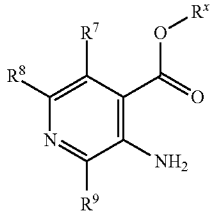

[F-006]

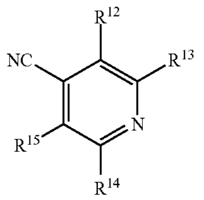

In one approach, compounds of formula [F-004] are prepared by reacting a compound of formula [F-005](where Rx is an alkyl group such as methyl or ethyl) with a compound of formula [F-006] in a suitable solvent in a dry non-aprotic solvent such as dioxane or THF in the presence of a hindered alkoxide base such as potassium-tert-pentylate 1.7M in toluene or potassium-tert-butoxide. The reaction is suitably conducted at ambient temperature.

In one approach, compounds of formula [F-004] are prepared by reacting a compound of formula [F-007] with a compound of formula [F-006] in a suitable solvent in a protic solvent such as methanol in the presence of a base such as sodium methoxide. The reaction is suitably conducted first at ambient temperature then at reflux overnight.

[F-007]

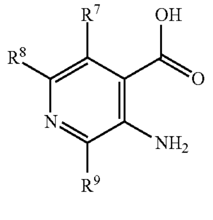

-continued

[F-006]

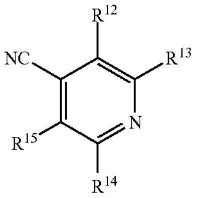

An example of a method as described above is illustrated in the following scheme.

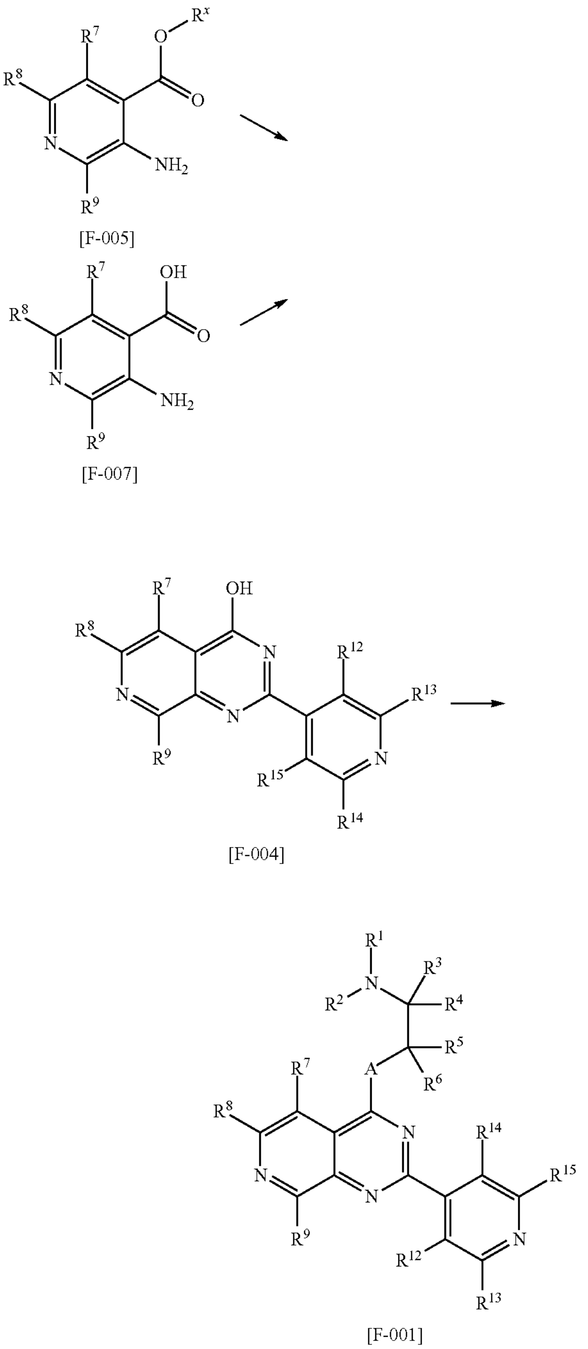

[F-005]

[F-007]

[F-004]

[F-001]

General Synthesis of 4-substituted-1-yl-2-pyridin-4-yl-pyrido[3,4-d]pyrimidine Derivatives of General Formula [F-001] Scheme A1

Substituted 2-Pyridin-4-yl-pyrido[3,4-d]pyrimidin-4-ol derivatives of general formula [F-001] were prepared by the reaction of a 2-amino-pyridyl derivative of general formula [F-005] with a 4-cyanopyridyl derivative of general formula [F-006] in the presence of a base such as sodium methoxide in a polar aprotic solvent such as methanol. The reaction is suitably conducted at elevated temperature to yield the cyclised 2-Pyridin-4-yl-pyrido[3,4-d]pyrimidin-4-ol product of general formula [F-004]. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with a chlorinatation agent such as phosphorous oxychloride to yield 4-chloro-1-yl-2-pyridin-4-yl-pyrido[3,4-d]pyrimidine derivatives of general formula [F-008] which were reacted with primary or secondary amino derivative of general formula [F-003], in a polar aprotic solvent such as DMA, DMF, NMP in the presence of a tertiary amine base such as Et3N, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP [method B]. The intermediate 6,7-substituted-(2,4,6-triiso-propyl-benzenesulfonic acid)-2-pyridin-4-yl-thieno[3,2-d]pyrimidin-4-yl ester was then reacted with a primary or secondary amino derivative, of general formula [F-003], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC Scheme A1

Method A

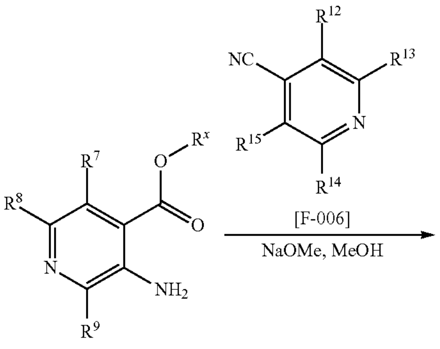

[F-005]

-continued

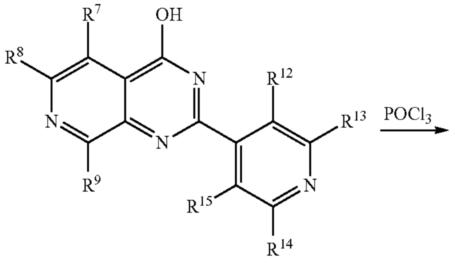

[F-004]

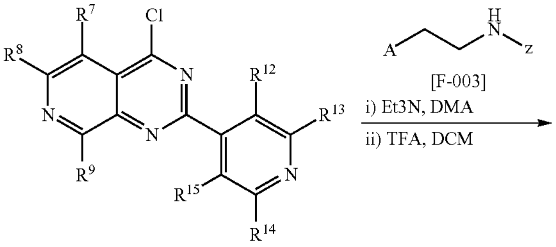

[F-008]

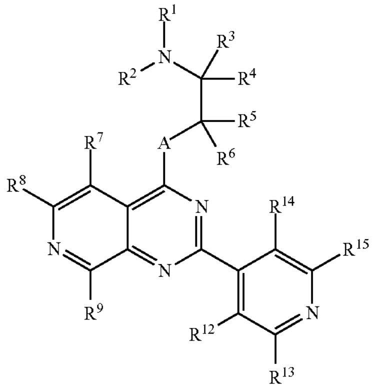

[F-001]

Method B

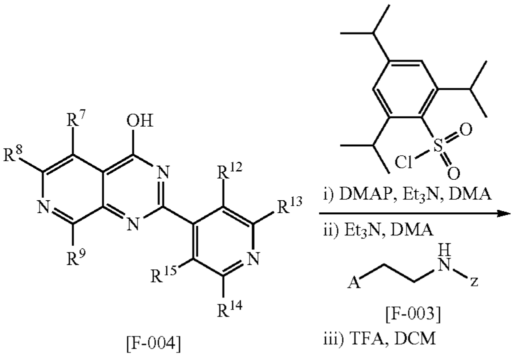

[F-004]

-continued

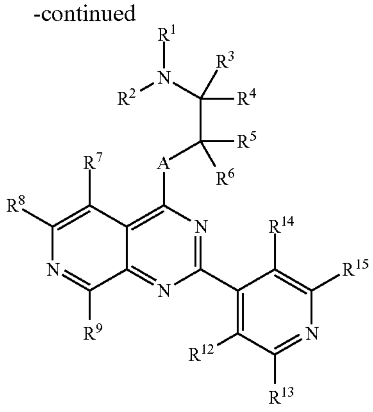

[F-001]

Synthesis of 4-Piperazin-1-yl-2-pyridin-4-yl-pyrido [3,4-d]pyrimidine [1] Method A

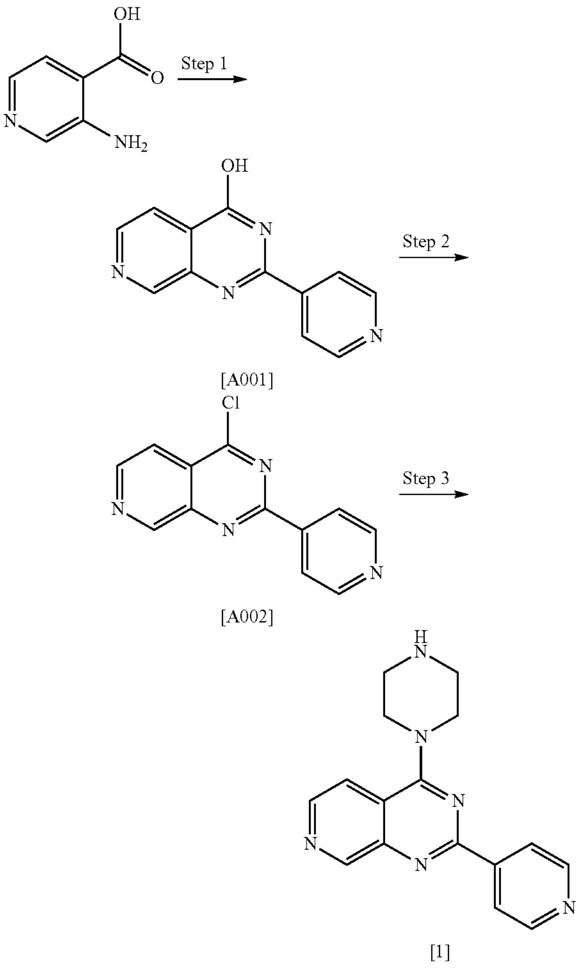

[A001]

[A002]

[1]

Synthesis of 2-Pyridin-4-yl-pyrido[3,4-d]pyrimidin-4-ol [A001]

A mixture of 4-Cyanopyridine (8.25 g, 79.2 mmol), sodium methoxide (891 mg, 16.5 mmol) and methanol (400 mL) was stirred at room temperature for 60 minutes. 3-Amino-isonicotinic acid (9.12 g, 66.0 mmol) was added and the mixture heated to reflux for 3 days. After cooling to room temperature the solid precipitate was collected by filtration then dried in the vacuum oven to yield the title compound as an off-white solid (6.02 g): (1H, 300 MHz, d6-dmso) 13.10 (1H, br s), 9.16 (1H, s), 8.80 (2H, dd), 8.70 (1H, d), 8.10 (2H, dd), 8.00 (1H, dd)

Synthesis of 4-Chloro-2-pyridin-4-yl-pyrido[3,4-d]pyrimidine [A002]

2-Pyridin-4-yl-pyrido[3,4-d]pyrimidin-4-ol [A001](4 g, 17.8 mmol) in $POCl_3$ (50 mL, 538 mmol) was heated to 110° C. for 3 hours. The reaction mixture was concentrated under vacuum, quenched with saturated $NaHCO_3$ solution, extracted into DCM, washed with water then brine, passed through a phase separator cartridge and evaporated to yield the title compound [A002] (2.6 g) as a yellow/brown solid which was used without further purification: LCMS method: 1, RT: 4.09 min, MI 243 [M+H].

Synthesis of 1-[2-(pyridin-4-yl)pyrido[3,4-d]pyrimidin-4-yl]piperazine [1]

A solution of 4-Chloro-2-pyridin-4-yl-pyrido[3,4-d]pyrimidine [A002](100 mg, 0.43 mmol), piperazine (172 mg, 2 mmol) in anhydrous DMA (5 mL) was stirred at room temperature for 3 days. The reaction mixture was partitioned between NaOH (2M aqueous solution) and ethyl acetate. The organic layer was further washed with water then brine, dried ($MgSO_4$), passed through a phase separator cartridge and evaporated to yield the crude material, which was purified by preparative HPLC (method A) to yield the title compound (1.87 mg). LCMS method: 1, RT: 3.49 min, MI 293 [M+H]; 1H-NMR (300 MHz; DMSO-d6): 9.26 (1H, s), 8.76 (2H, d), 8.58 (1H, d), 8.32 (2H, d), 8.24 (1H, s), 7.92 (1H, d), 3.96 (4H, br tr), 2.99 (4H, br tr)

Synthesis of (5-Methoxy-2-pyridin-4-yl-pyrido[3,4-d]pyrimidin-4-yl)-(R)-pyrrolidin-3-yl-amine [2]method B

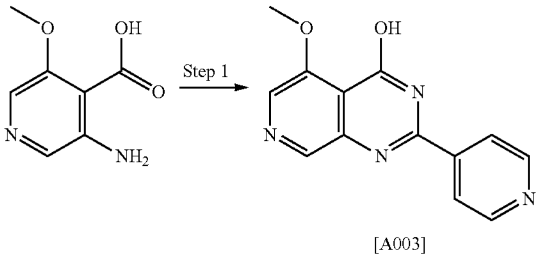

[A003]

Synthesis of 5-Methoxy-2-pyridin-4-yl-3H-pyrido [3,4-d]pyrimidin-4-one [A003]

To a stirred solution of 2-chloro-4-pyridinecarbonitrile (1 g, 9.6 mmol) in MeOH (20 mL) was added 0.5 M NaOMe (2 mmol, 4 mL) followed by 3-Amino-5-methoxy-isonicotinic acid (1.35 g, 8 mmol). The RM was heated at 75° C. over night. The RM was left to cool and a solid ppt formed which was collected by filtration, washed with cold MeOH and dried in a vac oven to give the title compound as a pale brown solid (610 mg, 30% yield). LCMS method: 1, RT: 3.82 min, MI 255.09 [M+H].

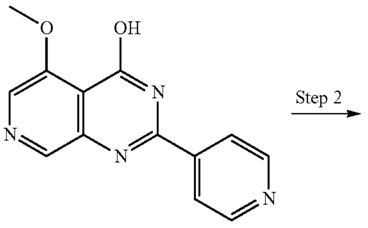

[A003]

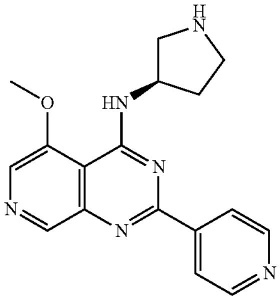

[2]

Synthesis of (5-Methoxy-2-pyridin-4-yl-pyrido[3,4-d]pyrimidin-4-yl)-(R)-pyrrolidin-3-yl-amine [2]

5-methoxy-2-pyridin-4-yl-pyrido[3,4-d]pyrimidin-4-[A003](0.157 mmol, 0.04 g), 2,4,6-triisopropylbenzenesulfonyl chloride (0.173 mmol, 0.052 g), were dissolved in anhydrous DMA (2 mL), and $Et_3N$ (0.314 mmol, 0.045 mL), and DMAP (5 mg) were added sequentially. The mixture was stirred at room temperature for 1 hour and (R)-3-amino-pyrrolidine-1-carboxylic acid tert-butyl ester (0.236 mmol, 0.044 g) was added. The mixture was stirred at room temperature overnight. The solvent was then removed under reduced pressure and the residue was stirred in trifluoro-acetic acid (1 mL) at room temperature for 3 h. The solution was poured on to an SCX-2 cartridge (5 g), washed with methanol (10 mL) and then washed with ammonia (2N in methanol, 20 mL). The ammonia washes were concentrated in vacuo to a brown residue that was purified by preparative HPLC (method A) to yield the title compound (0.016 g). LCMS method: 1, RT: 1.47 min, MI 323 [M+H]; 1H-NMR 300 MHz (1H d6-dmso) 8.81 (1H, s), 8.76 (2H, dd), 8.35 (1H, s), 8.32 (2H, dd), 8.23 (1H, d), 6.42 (1H, s), 4.98 (1H, m), 4.14 (3H, s), 3.19-3.07 (2H, m), 2.41-2.29 (2H, m), 2.07-1.95 (2H, m).

Synthesis of 2-(3-Fluoro-pyridin-4-yl)-pyrido[3,4-d]pyrimidin-4-ol [A004]

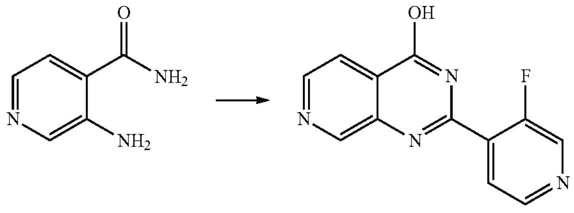

[A004]

2-(3-Fluoro-pyridin-4-yl)-pyrido[3,4-d]pyrimidin-4-ol [A004]

3-Amino-2-chloro-isonicotinamide (0.5 g, 3.64 mmol), 3-Fluoroisonicotinaldehyde (0.54 g, 4.37 mmol), NaHSO3 (0.75 g, 7.29 mmol) and DMA (5 mL) were added successively to a microwave vial. The vial was sealed then heated at 160° C. for 6 min. Water (10 mL) was added and the resulting solid was filtered and used without further purification. LCMS method: 1, RT: 3.07 min, MI 243 [M+H]

Synthesis of 8-Chloro-2-pyridin-4-yl-3H-pyrido[3,4-d]pyrimidin-4-one [A005]

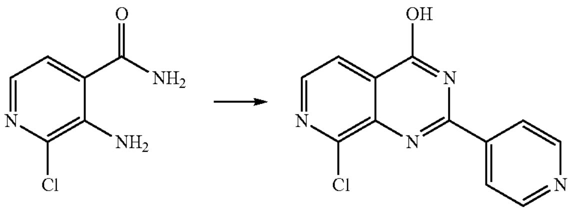

[A005]

8-Chloro-2-pyridin-4-yl-3H-pyrido[3,4-d]pyrimidin-4-one [A005]

A solution of 3-Amino-2-chloro-isonicotinamide (0.5 g, 2.91 mmol) and 4-Pyridinecarboxaldehyde (0.35 g, 3.32 mmol) in DMA (10 mL) was heated under microwave (100° C., 2 h). Sodium hydrogen sulfite (0.606 g, 5.83 mmol) was then added and the mixture was heated under microwave (150° C., 1 h). Water was then added to the mixture and the resulting solid (0.34 g, 45%) was collected, washed with water and then by MeOH. LCMS method: 1, RT: 3.89 min, MI 258 [M+H]

Synthesis of 8-Chloro-2-Pyridin-4-Yl-3H-Pyrido[3,4-d]Pyrimidin-4-One [A005]

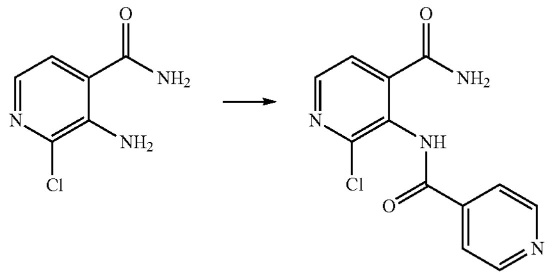

[A006]

Synthesis of 2-Chloro-3-[(pyridine-4-carbonyl)-amino]-isonicotinamide [A006]

To a suspension of 3-Amino-2-chloro-isonicotinamide (0.5 g, 2.913 mmol) and $K_2CO_3$ (1 g, 7.28 mmol) in refluxing $Et_2O$ (25 mL), Isonicotinoyl chloride hydrochloride (0.622 g, 3.5 mmol) was added portionwise. The mixture was stirred under reflux for 4 h. The solvent was removed under reduced pressure and water (50 mL) was added. The resulting solid was filtered, washed with $H_2O$ and then collected, dried with an azeotrope with toluene, to yield the title compound (0.78 g, 96%) which was used without further purification. LCMS method: 1, RT: 2.55 min, MI 277 [M+H]

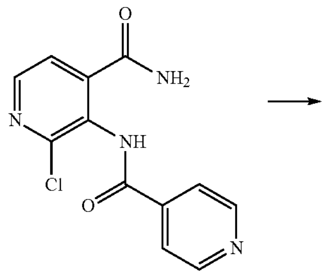

[A006]

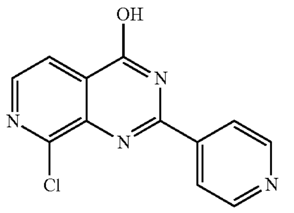

[A005]

Synthesis of 8-Chloro-2-pyridin-4-yl-3H-pyrido[3,4-d]pyrimidin-4-one [A004]

To a solution of 2-Chloro-3-[(pyridine-4-carbonyl)-amino]-isonicotinamide [A006](0.2 g, 0.723 mmol) in MeOH (20 mL) was added a solution of cesium carbonate (0.47 g, 1.44 mmol) in $H_2O$ (2 mL). The mixture was stirred at room temperature overnight. The MeOH was removed under reduced pressure and water (10 mL) was added. Acetic acid was added slowly and the resulting solid was collected, dried with a toluene azeotrope to yield the title compound which was used without further purification. LCMS method: 1, RT: 3.43 min, MI 259 [M+H]

Synthesis of 6-Chloro-2-pyridin-4-yl-3H-pyrido[3,4-d]pyrimidin-4-one [A007]

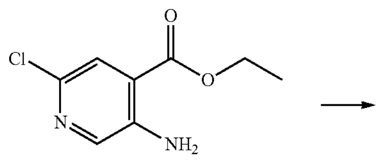

-continued

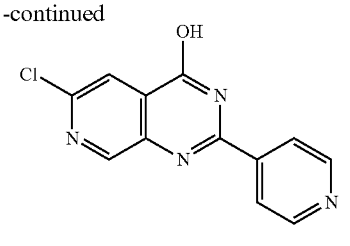

[A007]

6-Chloro-2-pyridin-4-yl-3H-pyrido[3,4-d]pyrimidin-4-one [A007]

A solution of potassium pentoxide (2.6 mL, 5.1 mmol, 25% soln in Toluene) was added dropwise (~0.5 mL/min) to a solution of 5-Amino-2-chloro-isonicotinic acid ethyl ester (0.4 g, 2 mmol) and 4-cyanopyridine (0.25 g, 2.4 mmol) in anhydrous THF (5 mL) cooled in an ice bath. The reaction was allowed to warm to RT and left to stir at room temperature overnight. Water (9 mL) was added and the mixture was stirred at RT for 20 mins. Acetic acid (~1 mL) was then added and the mixture was left to stir at RT and the resulting yellow precipitate was filtered and the siolid washed with deionised water (2×3 mL). To give the title compound (0.43 g, 83% yield). LCMS method: 1, RT: 2.21 min, MI 259 [M+H]

Synthesis of 2-(3-Fluoro-pyridin-4-yl)-5-methoxy-pyrido[3,4-d]pyrimidin-4-ol [A008]

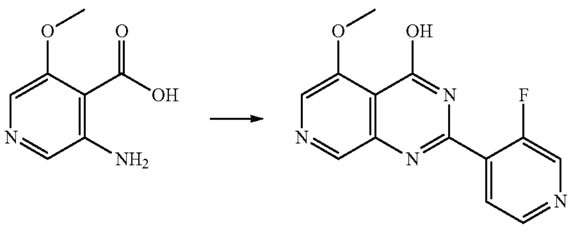

[A008]

2-(3-Fluoro-pyridin-4-yl)-5-methoxy-pyrido[3,4-d]pyrimidin-4-ol [A008]

To a stirred solution of 3-Fluoroisonicotinonitrile (0.088 g, 0.71 mmol) in MeOH (5 mL) was added NaOMe (0.008 g, 0.15 mmol). After 1 hr 3-amino-5-methoxy-isonicotinic acid (0.1 g, 0.54 mmol) was added and the RM heated to 85° C. for 18 hr. The solution became yellow in colour. The reaction mixture was allowed to cool to RT and the white solid was collected by filtration and washed with MeOH to yield the title compound (0.07 g, 43% yield). LCMS method: 1, RT: 1.19 min, MI 271.24 [M+H]

The following compounds were synthesised according to the general synthesis shown in scheme [A1]:

| Ex | Pre-cursor | Meth-od | Amine [F-003] | Analysis LCMS | NMR | Name |
|---|---|---|---|---|---|---|
| 3 | [A001] | A | 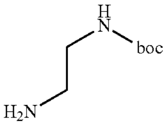 | Method 1: RT: 2.2 min, MI: 267 [M + H] | | N-(2-aminoethyl)-2-(pyridin-4-yl)pyrido[3,4-d]pyrimidin-4-amine |
| 4 | [A001 | A | 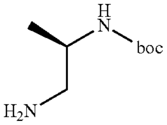 | Method 1: RT: 2.45 min, MI, 281 [M + H] | | N-[(2R)-2-aminopropyl]-2-(pyridin-4-yl)pyrido[3,4-d]pyrimidin-4-amine |
| 5 | [A001] | A | 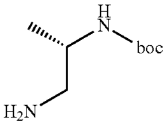 | Method 1: RT: 2.52 min, MI, 281 [M + H] | | N-[(2S)-2-aminopropyl]-2-(pyridin-4-yl)pyrido[3,4-d]pyrimidin-4-amine |
| 6 | [A001] | B | 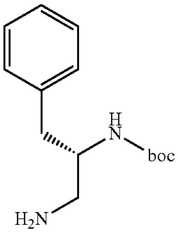 | Method 1: RT: 2.51 min, MI, 357 [M + H] | (1H, 300 MHz, d6-dmso); 9.15 ppm (1H, d), 8.70 ppm (2H, d), 8.62 ppm (2H, d), 8.20 ppm (1H, d), 8.12 ppm (2H, d), 7.35-7.26 ppm (5H, m), 3.86 ppm, (1H, d), 3.35 ppm (2H, m), 2.27 ppm (2H, m) | N-[(2S)-2-amino-3-phenylpropyl]-2-(pyridin-4-yl)pyrido[3,4-d]pyrimidin-4-amine |
| 7 | [A001] | B | 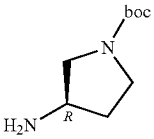 | Method 1: RT: 0.88 min, MI, 293 [M + H] | (1H, 300 MHz, d6-dmso), 9.18 (1H, s), 8.94-8.90 (1H, m), 8.76 (2H, dd), 8.65 (1H, d), 8.35 (2H, dd), 4.94-4.85 (1H, m), 3.87-3.74 (3H, m), 3.19-3.07 (2H, m), 2.30-2.18 (2H, m), 2.02-1.92 (2H, m) | (3R)-N-[2-(pyridin-4-yl)pyrido[3,4-d]pyrimidin-4-yl]pyrrolidin-3-amine |
| 8 | [A004] | B | 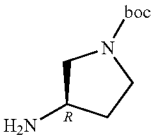 | Method 1: RT: 0.5 min, MI, 311 [M + H] | (1H, 300 MHz, d6-dmso), 9.47 (1H, brd), 9.15 (1H, s), 8.71 (1H, d), 8.66 (1H, d), 8.57 (1H, d), 8.47 (1H, s), 8.39 (1H, d), 8.08 (1H, dd), 4.92 (1H, br s), 3.46 (1H, dd), 3.34-3.22 (2H, m), 2.30-2.20 (1H, m), 2.18-2.08 (1H, m) | (3R)-N-[2-(3-fluoropyridin-4-yl)pyrido[3,4-d]pyrimidin-4-yl]pyrrolidin-3-amine |
| 9 | [A003] | B | 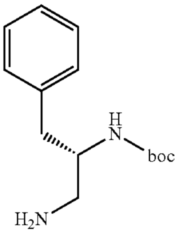 | Method 1: RT: 2.92 min, MI, 387 [M + H] | (1H, 300 MHz, d6-dmso); 8.72 (1H, s), 8.68 (2H, d), 8.28 (1H, s), 8.00 (2H, d), 7.39-7.30 (5H, m), 4.00 (3H, s), 3.96-3.91 (1H, m), 3.59 (2H, br s), 3.00 (1H, dd), 2.79 (1H, dd) | N-[(2S)-2-amino-3-phenylpropyl]-5-methoxy-2-(pyridin-4-yl)pyrido[3,4-d]pyrimidin-4-amine |
| 10 | [A004] | B | 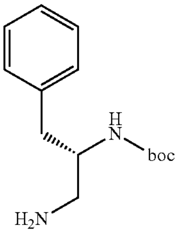 | Method 1: RT: ,2.95 min MI, 375 [M + H] | (1H, 300 MHz, d6-dmso), 9.12 (1H, s), 8.69 (1H, d), 8.53 (1H, d), 8.46 (1H, S), 8.21 (1H, d), 7.83 (1H, dd), 7.28-7.19 (5H, m), 3.81 (1H, dd), 3.66-3.49 (2H, m), 2.90 (1H, dd), 2.80 (1H, dd), | N-[(2S)-2-amino-3-phenylpropyl]-2-(3-fluoropyridin-4-yl)pyrido[3,4-d]pyrimidin-4-amine |

-continued

| | Pre- | Meth- | Amine | Analysis | | |
|---|---|---|---|---|---|---|
| Ex | cursor | od | [F-003] | LCMS | NMR | Name |
| 11 | [A005] | B | 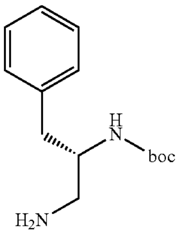 | Method 1: RT: 2.98 min, MI: 392 [M + H] | (1H, 300 MHz, d6-dmso), 8.70 (2H, d), 8.40 (1H, d), 8.36 (1H, br s), 7.98 (2H, d), 7.43-7.32 (5H, m), 3.97 (1H, d), 3.69-3.54 (2H, m), 3.06 (1H, dd), 2.84 (1H, dd) | N-[(2S)-2-amino-3-phenylpropyl]-8-chloro-2-(pyridin-4-yl)pyrido[3,4-d]pyrimidin-4-amine |
| 12 | [A007] | A | 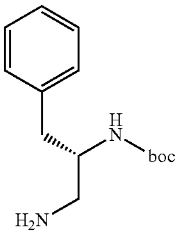 | Method 1: RT: 6.51 min, MI: 391 [M + H] | (1H, 300 MHz, d6-dmso) 9.06 s), 8.69 (2H, dd), 7.98 (2H, dd), 7.87 (1H, s), 7.42-7.27 (5H, m), 4.54 (1H, dd), 4.37 (1H, d), 3.58-3.48 (1H, m), 3.04-2.93 (3H, m), 2.85-2.59 (3H, m) | N-[(2S)-2-amino-3-phenylpropyl]-6-chloro-2-(pyridin-4-yl)pyrido[3,4-d]pyrimidin-4-amine |
| 13 | [A007] | A | 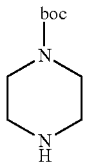 | Method 1: RT: 4.35 min, MI: 327 [M + H] | (300 MHz, 1H, d6-dmso) 9.20 (1H, s), 8.79 (2H, d), 8.35 (2H, d), 8.13 (1H, s), 6.61 (1H, s), 4.15 (4H, br s), 3.33 (4H, br s) | 1-[6-chloro-2-(pyridin-4-yl)pyrido[3,4-d]pyrimidin-4-yl]piperazine |
| 14 | [A007] | A | 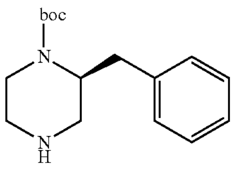 | Method 1: RT: 2.91 min, MI: 443.9 [M + H] | (300 MHz, 1H, d6-dmso) 9.06 (1H, s), 8.69 (2H, dd), 7.98 (2H, dd), 7.87 (1H, s), 7.41-7.29 (5H, m), 4.54 (1H, dd), 4.37 (1H, d), 3.53 (1H, dt), 3.03-2.93 (3H, m), 2.85-2.57 (3H, m) | (3S)-3-benzyl-1-[6-chloro-2-(pyridin-4-yl)pyrido[3,4-d]pyrimidin-4-yl]piperazine |
| 15 | [A001] | A | 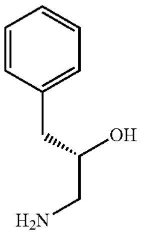 [SMILES: NC[C@@H](O)Cc1ccccc1] | Method 1: RT: 4.30 min, MI: 358 [M + H] | (300 MHz, 1H, d4-MeOH) 8.55 (d, 1H), 8.22 (dd, 2H), 8.03 (dd, 1H), 7.76 (m, 5H), 4.28 (m, 1H), 4.09 (1H, dd), 3.58 (1H, dd), 2.96 (1H, dd), 2.88 (1H, dd) | (2S)-1-phenyl-3-{[2-(pyridin-4-yl)pyrido[3,4-d]pyrimidin-4-yl]amino}propan-2-ol |
| 16 | [A001] | A | 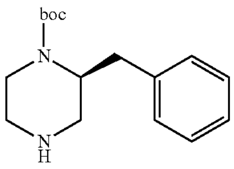 | Method 1: RT: 2.44 min, MI: 383 [M + H] | (1H, 300 MHz, $CDCl_3$): 9.34 (s, 1H), 8.73 (d, 2H), 8.46 (d, 1H), 8.21 (d, 2H), 7.49 (d, 1H), 7.33 (m, 3H), 7.25 (d, 2H), 4.58 (d, 1H), 4.48 (d, 1H), 3.46 (t, 1H), 3.02 (m, 4H), 2.76 (m, 2H) | (3S)-3-benzyl-1-[2-(pyridin-4-yl)pyrido[3,4-d]pyrimidin-4-yl]piperazine |
| 17 | [A001] | A | 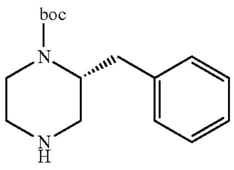 | Method 1: RT: 2.45 min, MI: 383 [M + H] | (1H, 300 MHz, $CDCl_3$): 9.34 (s, 1H), 8.73 (d, 2H), 8.46 (d, 1H), 8.21 (d, 2H), 7.49 (d, 1H), 7.33 (m, 3H), 7.25 (d, 2H), 4.58 (d, 1H), 4.48 (d, 1H), 3.46 (t, 1H), 3.02 (m, 4H), 2.76 (m, 2H) | (3R)-3-benzyl-1-[2-(pyridin-4-yl)pyrido[3,4-d]pyrimidin-4-yl]piperazine |

-continued

| Ex | Pre-cursor | Meth-od | Amine [F-003] | Analysis LCMS | NMR | Name |
|---|---|---|---|---|---|---|
| 18 | [A001] | A | 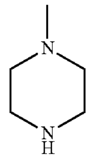 | Method 1: RT: 3.99 min, MI: 307 [M + H] | (1H, 300 MHz, d6-dmso) 9.26 (1H, s), 8.75 (2H, dd), 8.58 (1H, d), 8.31 (2H, dd), 7.91 (1H, d), 3.98-3.96 (4H, m), 2.55-2.52 (4H, m), 2.25 (3H, s) | 1-methyl-4-[2-(pyridin-4-yl)pyrido[3,4-d]pyrimidin-4-yl]piperazine |
| 19 | [A001] | A | 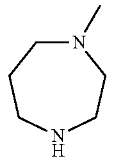 | Method 1: RT: 4.00 min, MI: 321 [M + H] | (1H, 300 MHz, d6-dmso) 9.19 (1H, s), 8.75 (2H, dd), 8.52 (1H, d), 8.29 (2H, dd), 7.98 (1H, d), 4.13-4.06 (4H, m), 2.85-2.83 (2H, m), 2.55-2.51 (2H, m), 2.26 (3H, s), 2.10-2.03 (2H, m) | 1-methyl-4-[2-(pyridin-4-yl)pyrido[3,4-d]pyrimidin-4-yl]-1,4-diazepane |
| 20 | [A001] | A | 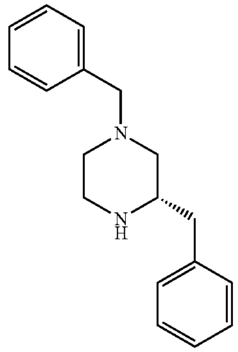 [SMILES: c1ccc(C[C@H]2CN(Cc3ccccc3)CCN2)cc1] | Method 1: RT: 4.29 min, MI: 473 [M + H] | (1H, 300 MHz, $CDCl_3$): 9.31 (s, 1H), 8.75 (d, 2H), 8.47 (d, 1H), 8.30 (d, 2H), 7.49 (d, 1H), 7.36 (m, 5H), 7.02 (m, 5H), 5.02 (s, 1H), 4.30 (d, 1H), 3.90 (td, 1H), 3.62 (d, 1H), 3.45 (d, 1H), 3.26 (m, 2H), 3.04 (d, 1H), 2.92 (d, 1H), 2.35 (m, 2H) | (2S)-2,4-dibenzyl-1-[2-(pyridin-4-yl)pyrido[3,4-d]pyrimidin-4-yl]piperazine |
| 21 | [A001] | A | 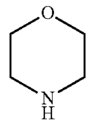 | Method 1: RT: 2.86 min, MI: 294 [M + H] | (1H, 300 MHz, d6-dmso) 9.28 (1H, s), 8.76 (2H, d), 8.59 (1H, d), 8.33 (2H, d), 7.97 (1H, d), 4.02-3.99 (4H, t), 3.83-3.80 (4H, t) | 4-[2-(pyridin-4-yl)pyrido[3,4-d]pyrimidin-4-yl]morpholine |
| 22 | [A001] | A | 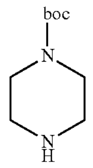 | Method 1: RT: 4.76 min, MI: 349 [M + H] | (1H, 300 MHz, d6-dmso) 9.28 (1H, s), 8.77 (2H, dd), 8.60 (1H, d), 8.34 (2H, dd), 7.97 (1H, d), 4.03-4.00 (4H, m), 3.61 (4H, br s), 1.43 (9H, s) | tert-butyl 4-[2-(pyridin-4-yl)pyrido[3,4-d]pyrimidin-4-yl]piperazine-1-carboxylate |
| 23 | [A001] | A | 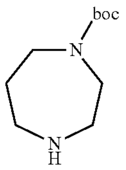 | Method 1: RT: 4.18 min, MI: 407 [M + H] | (1H, 300 MHz, d6-dmso) 9.22 (1H, s), 8.76 (2H, dd), 8.56 (1H, d), 8.30 (2H, dd), 8.08-8.03 (1H, m), 4.28-4.22 (2H, m), 4.15-4.10 (2H, m), 3.72-3.65 (2H, m), 3.42 (2H, br s), 2.09-1.97 (2H, m), 1.11 (4H, s), 0.93 (5H, s) | tert-butyl 4-[2-(pyridin-4-yl)pyrido[3,4-d]pyrimidin-4-yl]-1,4-diazepane-1-carboxylate |
| 24 | [A001] | A | 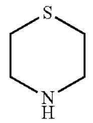 | Method 1: RT: 3.8 min, MI: 310 [M + H] | (1H, 300 MHz, d6-dmso) 9.29 (1H, s), 8.76 (2H, dd), 8.60 (1H, d), 8.32 (2H, dd), 7.87 (1H, d), 4.23-4.20 (4H, m), 2.93-2.89 (4H, m) | 4-[2-(pyridin-4-yl)pyrido[3,4-d]pyrimidin-4-yl]thiomorpholine |

-continued

| Ex | Pre-cursor | Meth-od | Amine [F-003] | Analysis LCMS | NMR | Name |
|---|---|---|---|---|---|---|
| 25 | [A001] | A | 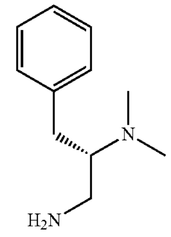 [A009] | Method 1: RT: 2.34 min, MI: 385 [M + H] | (1H, 300 MHz, d6-dmso) 9.13 (1H, s), 8.67 (2H, dd), 8.61 (1H, d), 8.15 (1H, d), 7.99 (2H, d), 7.37-7.26 (5H, m), 3.76 (2H, br s), 3.33-3.13 (1H, m), 3.07-2.88 (2H, m), 2.35 (6H, br s) | N,N-Dimethyl[(2S)-1-phenyl-3-{[2-(pyridin-4-yl)pyrido[3,4-d]pyrimidin-4-yl]amino}propan-2-yl]amine |
| 26 | [A001] | A | 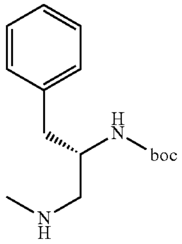 [A013] | Method 1: RT: 2.44 min, MI: 371 [M + H] | (1H, 300 MHz, d6-dmso) 9.15 (1H, s), 8.77-8.75 (2H, m), 8.64 (1H, d), 8.30-8.28 (2H, m), 8.24 (1H, d), 7.32-7.29 (2H, m), 7.20-7.15 (2H, m), 7.09-7.04 (1H, m), 5.08-4.99 (1H, m), 3.11-2.87 (4H, m), 2.38 (3H, s). | N-[(2S)-2-amino-3-phenylpropyl]-N-methyl-2-(pyridin-4-yl)pyrido[3,4-d]pyrimidin-4-amine |
| 27 | [A001] | A | 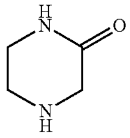 | Method 1: RT: 2.21 min, MI: 307 [M + H] | 1H NMR (d6-DMSO, 300 MHz) 9.28 (1H, s), 8.77 (2H, d), 8.61 (1H, d), 8.34 (2H, d), 8.31 (1H, s), 8.03 (1H, d), 4.51 (2H, s), 4.18 (2H, t), 3.53-3.43 (2H, m). | 4-[2-(pyridin-4-yl)pyrido[3,4-d]pyrimidin-4-yl]piperazin-2-one |
| 28 | [A001] | A | 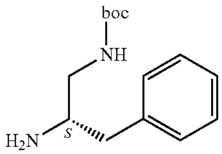 | Method 1: RT: 2.44 min, MI: 357 [M + H] | — | N-[(2S)-1-amino-3-phenylpropan-2-yl]-2-(pyridin-4-yl)pyrido[3,4-d]pyrimidin-4-amine |
| 29 | [A001] | A | 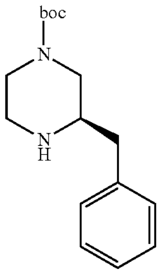 | Method 1: RT: 2.12 min, MI: 383.18 [M + H] | (1H, 300 MHz, $CDCl_3$): 9.27 (s, 1H), 8.75 (d, 2H), 8.47 (d, 1H), 8.29 (d, 2H), 7.45 (d, 1H), 7.11 (m, 5H), 5.05 (m, 1H), 4.28 (d, 1H), 3.83 (dt, 1H), 3.23 (m, 3H), 3.09 (m, 2H), 3.01 (dt, 1H). | (2R)-2-benzyl-1-[2-(pyridin-4-yl)pyrido[3,4-d]pyrimidin-4-yl]piperazine |
| 30 | [A003] | B | 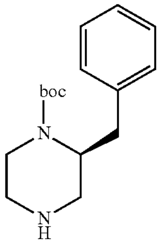 | Method 1: RT: 2.71 min, MI: 413.17 [M + H] | (1H, 500 MHz, d6-dmso) 8.77 (s, 1H), 8.69 (d, 2H), 8.22 (s, 1H), 8.03 (d, 2H), 7.34 (m, 3H), 7.27 (d, 2H), 4.27 (m, 1H), 4.02 (m, 1H), 3.90 (s, 3H), 3.22 (t, 1H), 2.99 (m, 2H), 2.83 (t, 1H), 2.72 (dd, 1H), 2.63 (t, 1H), 2.62 (dd, 1H). | (3S)-3-benzyl-1-[5-methoxy-2-(pyridin-4-yl)pyrido[3,4-d]pyrimidin-4-yl]piperazine |

-continued

| Ex | Pre-cursor | Meth-od | Amine [F-003] | Analysis LCMS | NMR | Name |
|---|---|---|---|---|---|---|
| 31 | [A003] | B | 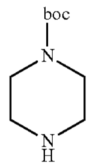 | Method 1: RT: 1.261 min, MI: 323.07 [M + H] | (1H, 300 MHz, d6-dmso) 8.86 (1H, t), 8.78-8.76 (2H, m), 8.36 (1H, s), 8.32-8.30 (2H, m), 4.08 (3H, s), 3.75 (4H, m), 3.03 (4H, m). | 1-[5-methoxy-2-(pyridin-4-yl)pyrido[3,4-d]pyrimidin-4-yl]piperazine |
| 32 | [A005] | B | 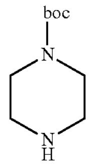 | Method 1: RT: 1.39 min, MI: 327 [M + H] | (1H, 300 MHz, d6-dmso): 8.79 (d, 2H), 8.32-8.37 (m, 3H), 7.92 (d, 1H), 3.94 (brs, 4H), 2.95 (brs, 4H). | 1-[8-chloro-2-(pyridin-4-yl)pyrido[3,4-d]pyrimidin-4-yl]piperazine |
| 33 | [A001] | A | 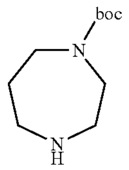 | Method 1: RT: 3.92 min, MI: 307 [M + H] | (1H, 300 MHz, d6-dmso) 9.21 (1H, s), 8.77-8.75 (2H, m), 8.54 (1H, d), 8.32-8.30 (2H, m), 8.00 (1H, d), 4.14-4.07 (4H, m), 3.15-3.12 (2H, m), 2.85-2.81 (2H, m), 2.04-1.97 (2H, m). | 1-[2-(pyridin-4-yl)pyrido[3,4-d]pyrimidin-4-yl]-1,4-diazepane |
| 34 | [A001] | A | 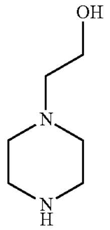 | Method 1: RT: 4.04 min, MI: 337 [M + H] | (1H, 300 MHz, d6-dmso) 9.27 (1H, s), 8.78-8.76 (2H, m), 8.60 (1H, d), 8.34-8.32 (2H, m), 7.94 (1H, d), 4.50 (1H, br m), 4.00 (4H, br m), 3.60-3.54 (2H, m), 2.67 (4H, br m), 2.49-2.46 (2H, m). | 2-{4-[2-(pyridin-4-yl)pyrido[3,4-d]pyrimidin-4-yl]piperazin-1-yl}ethan-1-ol |
| 35 | [A001] | A | 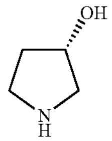 | Method 1: RT: 2.35 min, MI: 294 [M + H] | (1H, 300 MHz, d6-dmso) 9.19 (1H, s), 8.77-8.74 (2H, m), 8.56 (1H, d), 8.34-8.32 (2H, m), 8.17 (1H, br m), 5.18 (1H, d), 4.49 (1H, br m), 4.08 (3H, br m), 3.88 (1H, br d), 2.05 (2H, br m). | (3S)-1-[2-(pyridin-4-yl)pyrido[3,4-d]pyrimidin-4-yl]pyrrolidin-3-ol |
| 36 | [A001] | A | 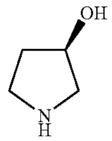 | Method 1: RT: 2.39 min, MI: 294 [M + H] | (1H, 300 MHz, d6-dmso) 9.19 (1H, s), 8.77-8.74 (2H, m), 8.56 (1H, d), 8.34-8.32 (2H, m), 8.17 (1H, br m), 5.18 (1H, d), 4.49 (1H, br m), 4.08 (3H, br m), 3.88 (1H, br d), 2.05 (2H, br m). | (3R)-1-[2-(pyridin-4-yl)pyrido[3,4-d]pyrimidin-4-yl]pyrrolidin-3-ol |
| 37 | [A003] | B | 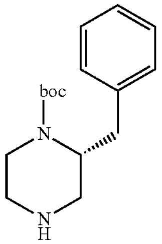 | Method 1: RT: 2.74 min, MI: 413.17 [M + H] | (1H, 500 MHz, d6-dmso): 8.79 (s, 1H), 8.70 (d, 2H), 8.23 (s, 1H), 8.05 (d, 2H), 7.33 (m, 3H), 7.27 (d, 2H), 3.21 (t, 1H), 3.17 (d, 2H), 3.00 (d, 1H), 2.92 (m, 1H), 2.82 (t, 1H), 2.76 (dd, 1H), 2.68 (d, 1H), 2.61 (dd, 1H). | (3R)-3-benzyl-1-[5-methoxy-2-(pyridin-4-yl)pyrido[3,4-d]pyrimidin-4-yl]piperazine |

-continued

| Ex | Pre-cursor | Meth-od | Amine [F-003] | Analysis | | Name |
|---|---|---|---|---|---|---|
| | | | | LCMS | NMR | |
| 38 | [A001] | A | 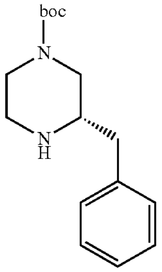 | Method 1: RT: 2.06 min, MI: 383.17 [M + H] | (1H, 500 MHz, $CDCl_3$): 9.29 (s, 1H), 8.75 (d, 2H), 8.47 (d, 1H), 8.28 (d, 2H), 7.45 (d, 1H), 7.09 (m, 5H), 5.04 (m, 1H), 4.25 (d, 1H), 3.83 (t, 1H), 3.28 (m, 2H), 3.22 (d, 1H), 3.09 (m, 2H), 3.02 (t, 1H). | (2S)-2-benzyl-1-[2-(pyridin-4-yl)pyrido[3,4-d]pyrimidin-4-yl]piperazine |
| 39 | [A001] | A | 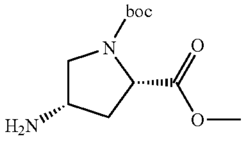 [A015] | Method 1: RT: 1.04 min, MI: 351.25 [M + H] | (1H, 300 MHz, d4-MeOH): 9.20 (s, 1H), 8.71 (dd, 2H), 8.59 (d, 1H), 8.48 (dd, 2H), 8.08 (d, 1H), 4.98 (m, 1H), 4.99 (m, 1H), 4.02 (dd, 1H), 3.74 (s, 3H), 3.42 (dd, 1H), 3.25 (dd, 1H), 2.78 (m, 2H), 2.21 (m, 1H). | methyl (2S,4S)-4-{[2-(pyridin-4-yl)pyrido[3,4-d]pyrimidin-4-yl]amino}pyrrolidine-2-carboxylate |
| 40 | [A001] | A | 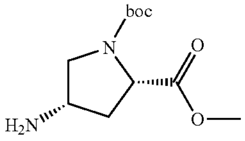 [A015] | Method 1: RT: 0.52 min, MI: 463 [M + H] | (1H, 300 MHz, d4-MeOH): 9.21 (s, 1H), 8.71 (ss, 2H), 8.60 (d, 1H), 8.50 (dd, 2H), 8.09 (d, 1H), 4.99 (m, 1H), 4.29 (m, 1H), 3.86 (m, 2H), 3.73 (s, 3H), 3.47 (dd, 1H), 3.14 (m, 2H), 2.89 (dd, 1H), 2.74 (m, 1H), 2.49 (m, 1H), 2.12 (m, 1H), 1.88 (m, 1H). | methyl (2S,4S)-4-[(2S,4S)-4-{[2-(pyridin-4-yl)pyrido[3,4-d]pyrimidin-4-yl]amino}pyrrolidine-2-amido]pyrrolidine-2-carboxylate |
| 41 | [A003] | A | 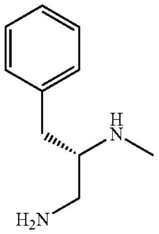 | Method 1: RT: 5.14 min, MI: 401 [M + H] | (1H, 300 MHz, d6-dmso) 8.77 (s, 1H), 8.72-8.70 (2H, m), 8.33 (1H, s), 8.20 (1H, s), 8.12-8.10 (2H, m), 7.33-7.23 (5H, m), 4.12 (3H, s), 3.86-3.78 (1H, m), 3.62-3.53 (1H, m), 3.18-3.11 (1H, m), 2.98-2.92 (1H, m)2.71-2.64 (1H, m), 2.45 (3H, s). | [(2S)-1-{[5-methoxy-2-(pyridin-4-yl)pyrido[3,4-d]pyrimidin-4-yl]amino}-3-phenylpropan-2-yl](methyl)amine |
| 42 | [A001] | A | 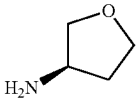 | Method 1: RT: 3.0 min, MI: 294 [M + H] | (1H, 300 MHz, d6-dmso) 9.21 (1H, s), 8.81-8.77 (3H, m), 8.67 (1H, d), 8.37-8.33 (3H, m), 6.57 (2H, s), 5.00-4.90 (1H, m), 4.14-4.09 (1H, m), 4.01-3.94 (1H, m), 3.86-3.79 (2H, m), 2.42-2.33 (1H, m), 2.20-2.09 (1H, m). | N-[(3R)-oxolan-3-yl]-2-(pyridin-4-yl)pyrido[3,4-d]pyrimidin-4-amine |
| 43 | [A003] | B | 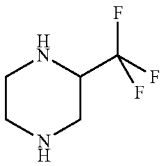 | Method 1: RT: 3.41 min, MI: 391.13 [M + H] | (1H, 300 MHz, $CDCl_3$): 9.01 (s, 1H), 8.76 (d, 2H), 8.31 (d, 2H), 8.22 (s, 1H), 4.42 (d, 1H), 4.15-4.04 (m, 1H), 4.07 (s, 3H), 3.62 (br m, 1H), 3.33-3.12 (m, 3H), 3.00 (t, 1H). | 1-[5-methoxy-2-(pyridin-4-yl)pyrido[3,4-d]pyrimidin-4-yl]-3-(trifluoromethyl)piperazine |
| 44 | [A003] | B | 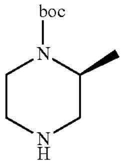 | 3jdf138qc, 96%, 337.23, 1.37 min, + [M + H] LC-MS17QC | (1H, 300 MHz, $CDCl_3$): 8.95 (s, 1H), 8.74 (d, 2H), 8.31 (d, 2H), 8.16 (s, 1H), 4.20 (t, 2H), 4.05 (s, 3H), 3.16 (m, 2H), 2.99 (m, 2H), 2.81 (t, 1H), 1.14 (d, 3H). | (3S)-1-[5-methoxy-2-(pyridin-4-yl)pyrido[3,4-d]pyrimidin-4-yl]-3-methylpiperazine |

-continued

| | Pre- | Meth- | Amine | Analysis | | |
|---|---|---|---|---|---|---|
| Ex | cursor | od | [F-003] | LCMS | NMR | Name |
| 45 | [A003] | B | 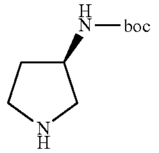 | Method RT: 1.52 min, MI: 323 [M + H] | (1H, 300 MHz, d6-dmso) 8.80 (1H, s), 8.78-8.75 (2H, m), 8.34 (1H, s), 8.32-8.30 (2H, m), 4.07 (3H, s), 3.94 (2H, br s), 3.82 (1H, br s), 3.72 (1H, br s), 2.15 (1H, br s), 1.10 (1H, br s). | (3R)-1-[5-methoxy-2-(pyridin-4-yl)pyrido[3,4-d]pyrimidin-4-yl]pyrrolidin-3-amine |
| 46 | [A003] | B | 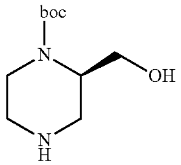 | Method 1: RT: 1.32 min, MI: 353.2 [M + H] | (1H, 300 MHz, d6-dmso): 8.84 (s, 1H), 8.76 (d, 2H), 8.34 (s, 1H), 8.29 (d, 2H), 4.87 (bs, 1H), 4.28 (dd, 2H), 4.06 (s, 3H), 3.43 (m, 1H), 3.07 (m, 3H), 2.82 (m, 3H). | [(2R)-4-[5-methoxy-2-(pyridin-4-yl)pyrido[3,4-d]pyrimidin-4-yl]piperazin-2-yl]methanol |
| 47 | [A003] | B | 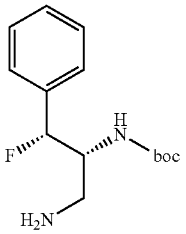 [A018] | Method 1: RT: 2.79 min, MI: 405.22 [M + H] | (1H, 300 MHz, $CDCl_3$): 8.90 (s, 1H), 8.72 (d, 2H), 8.22 (d, 2H), 8.14 (s, 1H), 7.40 (m, 5H), 5.43 (dd, 1H), 4.18 (m, 1H), 4.10 (s, 3H), 3.53 (m, 2H). | N-[(2R,3R)-2-amino-3-fluoro-3-phenylpropyl]-5-methoxy-2-(pyridin-4-yl)pyrido[3,4-d]pyrimidin-4-amine |
| 48 | [A003] | B | 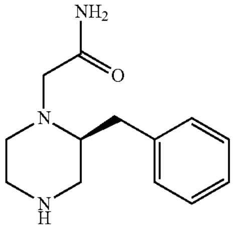 [SMILES: NC(=O)CN1CCNC[C@@H]1Cc1ccccc1] | Method 1: RT: 3.76 min, MI: 470.24 [M + H] | (1H, 300 MHz, $CDCl_3$): 8.94 (s, 1H), 8.70 (d, 2H), 8.12 (d, 2H), 8.05 (s, 1H), 7.28 (m, 2H), 7.08 (m, 3H), 4.04 (d, 1H), 3.84 (m, 4H), 3.65 (m, 1H), 3.56 (d, 1H), 3.29 (m, 1H), 3.06 (m, 3H), 2.89 (m, 1H), 2.66 (dt, 1H), 2.53 (dd, 1H). | 2-[(2S)-2-benzyl-4-[5-methoxy-2-(pyridin-4-yl)pyrido[3,4-d]pyrimidin-4-yl]piperazin-1-yl]acetamide |
| 49 | [A003] | A | 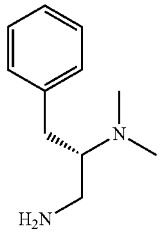 [A009] | Method 1: RT: 5.71 min, MI: 415 [M + H] | (1H, 300 MHz, d4-MeOH) 8.63 (1H, s), 8.58-8.56 (2H, m), 8.10 (1H, s), 8.06-8.04 (2H, m), 7.31-7.19 (5H, m), 4.06 (3H, m), 3.98-3.91 (1H, m), 3.71-3.63 (1H, m), 3.59-3.47 (1H, m), 3.20-3.14 (1H, m), 2.67-2.60 (7H, m). | [(2S)-1-{[5-methoxy-2-(pyridin-4-yl)pyrido[3,4-d]pyrimidin-4-yl]amino}-3-phenylpropan-2-yl]dimethylamine |
| 50 | [A003] | B | 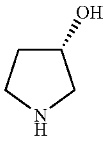 | Method 1: RT: 3.69 min, MI: 324.19 [M + H] | (1H, 300 MHz, $CDCl_3$) 8.92 (1H, s), 8.74-8.72 (2H, m), 8.36-8.34 (2H, m), 8.16 (1H, m), 4.62 (1H, br s), 4.26-4.16 (1H, m), 4.07 (3H, m), 3.82-3.75 (1H, m), 3.63 (1H, d), 2.12-2.20 (1H, m), 1.22-1.21 (2H, m). | (3S)-1-[5-methoxy-2-(pyridin-4-yl)pyrido[3,4-d]pyrimidin-4-yl]pyrrolidin-3-ol |
| 51 | [A003] | B | 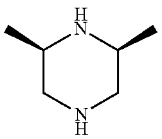 | Method 1: RT: 0.63 min, MI: 351 [M + H] | (1H, 300 MHz, $CDCl_3$): 8.97 (s, 1H), 8.78 (d, 2H), 8.31 (d, 2H), 8.19 (s, 1H), 4.23 (m, 2H), 4.07 (s, 3H), 3.08 (m, 2H), 2.75 (t, 2H), 1.16 (m, 6H). | 1-[5-methoxy-2-(pyridin-4-yl)pyrido[3,4-d]pyrimidin-4-yl]-3,5-cis-dimethylpiperazine |

-continued

| Ex | Pre-cursor | Meth-od | Amine [F-003] | Analysis | | |
|---|---|---|---|---|---|---|
| | | | | LCMS | NMR | Name |
| 52 | [A003] | B | 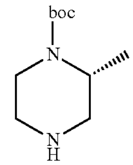 | Method 1: RT: 4.03 min, MI: 337.37 [M + H] | (1H, 300 MHz, $CDCl_3$): 8.98 (s, 1H), 8.77 (d, 2H), 8.32 (d, 2H), 8.19 (s, 1H), 4.22 (t, 2H), 4.07 (s, 3H), 3.19 (m, 2H), 3.05 (m, 2H), 2.82 (m, 1H), 1.15 (d, 3H). | (3R)-1-[5-methoxy-2-(pyridin-4-yl)pyrido[3,4-d]pyrimidin-4-yl]-3-methylpiperazine |
| 53 | [A003] | B | 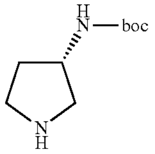 | | 1H NMR (300 MHz, $d_6$-DMSO) 8.78-8.73 (3H, m), 8.30-8.28 (3H, m), 4.05 (3H, s), 3.92 (4H, m), 3.36 (3H, m) | (3S)-1-[5-methoxy-2-(pyridin-4-yl)pyrido[3,4-d]pyrimidin-4-yl]pyrrolidin-3-amine |
| 54 | [A003] | B | 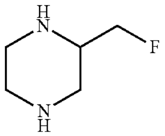 [A024] | Method 1: RT: 1.48 min, MI: 355.15 [M + H] | (1H, 300 MHz, $CDCl_3$) 9.02 (1H, s), 8.80-8.78 (2H, m), 8.35-8.33 (2H, m), 8.22 (1H, m), 4.59-4.57 (1H, m), 4.44-4.41 (1H, m), 4.28 (1H, d), 4.22-4.16 (1H, m), 4.10 (3H, s), 3.25-3.20 (1H, m), 3.12-3.03 (1H, m). | 3-(fluoromethyl)-1-[5-methoxy-2-(pyridin-4-yl)pyrido[3,4-d]pyrimidin-4-yl]piperazine |
| 55 | [A001] | A | 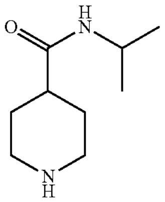 | Method 1: RT: 4.22 min, MI: 377.43 [M + H] | (1H, 300 MHz, d6-dmso) 9.25 (1H, s), 8.75 (2H, dd), 8.58 (1H, d), 8.31 (2H, dd), 7.89 (1H, d), 7.74 (1H, d), 4.58 (2H, d), 3.86-3.79 (1H, m), 3.33 (3H, m), 1.94-1.78 (4H, m), 1.03 (6H, d). | N-(propan-2-yl)-1-[2-(pyridin-4-yl)pyrido[3,4-d]pyrimidin-4-yl]piperidine-4-carboxamide |
| 56 | [A001] | A | 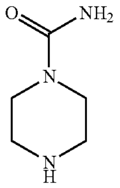 | Method 1: RT: 2.42 min, MI: 336.18 [M + H] | (1H, 300 MHz, d6-dmso) 9.27 (1H, s), 8.76 (2H, dd), 8.60 (1H, d), 8.33 (2H, dd), 7.98 (1H, d), 6.11 (2H, s), 4.02-3.99 (4H, m), 3.60-3.56 (4H, m). | 4-[2-(pyridin-4-yl)pyrido[3,4-d]pyrimidin-4-yl]piperazine-1-carboxamide |
| 57 | [A001] | A | 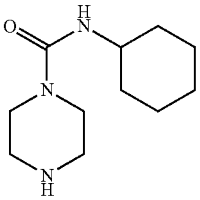 [SMILES: O=C(NC1CCCCC1)N1CCNCC1] | Method 1: RT: 4.8 min, MI: 418.47 [M + H] | (1H, 300 MHz, d6-dmso) 9.25 (1H, s), 8.76 (2H, d), 8.58 (1H, d), 8.31 (2H, d), 7.96 (1H, d), 6.27 (1H, d), 4.00 (4H, m), 3.57 (4H, m), 3.47-3.38 (1H, m), 1.77-1.66 (4H, m), 1.56 (1H, d, br), 1.25-1.04 (5H, m). | N-cyclohexyl-4-[2-(pyridin-4-yl)pyrido[3,4-d]pyrimidin-4-yl]piperazine-1-carboxamide |
| 58 | [A003] | B | 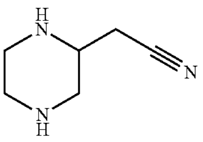 [A028] | Method 1: RT: 0.64 min, MI: 362.18 [M + H] | (1H, 300 MHz, $CDCl_3$) 9.03 (1H, s), 8.81-7.79 (2H, m), 8.36-8.34 (1H, m), 8.24 (1H, s), 4.38-4.34 (1H, m), 4.16-4.12 (4H, m), 3.42-3.33 (1H, m), 3.28-3.19 (2H, m), 3.09-3.02 (2H, m), 2.60-2.58 (2H, m). | 2-{4-[5-methoxy-2-(pyridin-4-yl)pyrido[3,4-d]pyrimidin-4-yl]piperazin-2-yl}acetonitrile |
| 59 | [A001] | A | 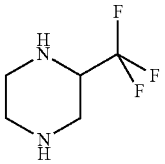 | Method 1: RT: 3.3 min, MI: 361 [M + H] | (1H, 300 MHz, d6-dmso) 9.31 (1H, s), 8.80-8.78 (2H, m), 8.63 (1H, d), 8.32-8.30 (2H, m), 7.97 (1H, d), 4.54 (1H, d), 4.25 (1H, d), 3.78-3.56 (3H, m), 3.18-3.06 (2H, m), 2.96-2.90 (2H, m). | 1-[2-(pyridin-4-yl)pyrido[3,4-d]pyrimidin-4-yl]-3-(trifluoromethyl)piperazine |

-continued

| Ex | Precursor | Method | Amine [F-003] | Analysis LCMS | Analysis NMR | Name |
|---|---|---|---|---|---|---|
| 60 | [A005] | B | 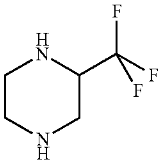 | Method 1: RT: 4.43 min, MI: 395 [M + H] | | 1-[8-chloro-2-(pyridin-4-yl)pyrido[3,4-d]pyrimidin-4-yl]-3-(trifluoromethyl)piperazine |
| 61 | [A001] | A | 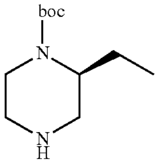 | Method 1: RT: 1.30 min, MI: 321 [M + H] | (1H, 300 MHz, d6-dmso) 9.33 (s, 1H), 8.78 (d, 2H), 8.65 (d, 1H), 8.33 (d, 2H), 8.01 (d, 1H), 4.55-4.66 (m, 1H), 3.73 (t, 1H), 3.28-3.47 (m, 4H), 1.66-1.75 (m, 2H), 1.04 (t, 3H). | (3S)-3-ethyl-1-[2-(pyridin-4-yl)pyrido[3,4-d]pyrimidin-4-yl]piperazine |
| 62 | [A001] | A | 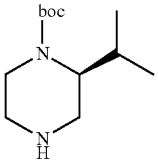 | Method 1: RT: 1.76 min, MI: 335 [M + H] | (1H, 300 MHz, d6-dmso) 9.21-9.25 (m, 1H), 8.71-8.77 (m, 2H), 8.54-8.60 (m, 1H), 8.22-8.29 (m, 2H), 7.82-7.89 (m, 1H), 4.44-4.62 (m, 2H), 3.31-3.44 (m, 2H), 3.01-3.15 (m, 2H), 2.90 (t, 1H), 2.73 (brs, 1H), 1.68-1.79 (m, 1H), 1.00 (d, 6H). | (3S)-3-(propan-2-yl)-1-[2-(pyridin-4-yl)pyrido[3,4-d]pyrimidin-4-yl]piperazine |
| 63 | [A008] | B | 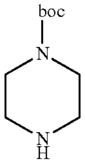 | Method 1: RT: 2.19 min, MI: 341.14 [M + H] | (1H, 300 MHz, d4-MeOH) 8.89 (1H, s), 8.61 (1H, d), 8.54 (1H, d), 8.43 (1H, s), 8.35 (1H, s), 8.20 (1H, dd), 4.16 (3H, s), 3.94 (4H, m), 3.36 (4H, m). | 1-[2-(3-fluoropyridin-4-yl)-5-methoxypyrido[3,4-d]pyrimidin-4-yl]piperazine |
| 64 | [A001] | A | 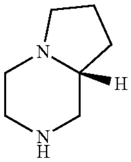 | Method 1: RT: 0.66 min, MI: 333 [M + H] | (1H, 300 MHz, d6-dmso) 9.27 (1H, s), 8.78-8.76 (2H, m), 8.59 (1H, d), 8.33-8.31 (2H, m), 7.94 (1H, d), 4.67 (2H, dd), 3.47-3.39 (1H, m), 3.18-3.10 (2H, m), 3.08-3.04 (1H, m), 2.41-2.33 (1H, m), 2.21-2.09 (2H, m), 1.94-1.83 (1H, m), 1.80-1.65 (2H, m), 1.48-1.35 (1H, m). | 4-{4-[(8aR)-octahydropyrrolo[1,2-a]piperazin-2-yl]pyrido[3,4-d]pyrimidin-2-yl}pyridine |
| 65 | [A004] | B | 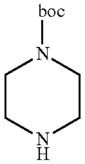 | Method 1: RT: 1.89 min, MI: 311.15 [M + H] | (1H, 300 MHz, d6-dmso) 9.28 (1H, s), 8.73 (1H, d), 8.65 (1H, d), 8.60 (1H, d), 8.13 (1H, dd), 8.00 (1H, d), 4.06 (4H, m), 3.22 (4H, m), 2.97 (1H, s, br). | 1-[2-(3-fluoropyridin-4-yl)pyrido[3,4-d]pyrimidin-4-yl]piperazine |
| 66 | [A004] | B | 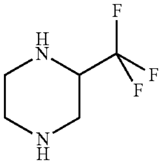 | Method 1: RT: 4.02 min, MI: 379.15 [M + H] | (1H, 300 MHz, d6-dmso) 9.27 (1H, s), 8.73 (1H, d), 8.64 (1H, d), 8.60 (1H, d), 8.11 (1H, dd), 7.97 (1H, dd), 4.53 (1H, dd), 4.21 (1H, d), 3.75 (1H, m), 3.66 (1H, td), 3.51 (1H, dd), 3.15 (1H, d), 3.03 (1H, d), 2.88 (1H, t). | 1-[2-(3-fluoropyridin-4-yl)pyrido[3,4-d]pyrimidin-4-yl]-3-(trifluoromethyl)piperazine |
| 67 | [A001] | A | 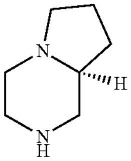 | Method 1: RT: 4.32 min, MI: 333.18 [M + H] | (1H, 300 MHz, d6-dmso) 9.27 (1H, s), 8.78-8.76 (2H, m), 8.59 (1H, d), 8.33-8.31 (2H, m), 7.94 (1H, d), 4.64 (1H, dd), 3.46 (1H, br t), 3.20-3.03 (3H, m), 2.41 (1H, br m), 2.18 (2H, br m), 1.94-1.04 (1H, br m), 1.78-1.68 (2H, br m), 1.49-1.36 (1H, m). | 4-{4-[(3aS)-octahydo-1H-pyrrolo[3,2-c]pyridin-5-yl]pyrido[3,4-d]pyrimidin-2-yl}pyridine |

-continued

| Ex | Precursor | Method | Amine [F-003] | Analysis LCMS | Analysis NMR | Name |
|---|---|---|---|---|---|---|
| 68 | [A005] | B | 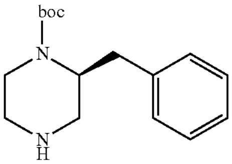 | Method 1: RT: 3.05 min, MI: 417 [M + H] | (1H, 300 MHz, d6-dmso) 7.79 (d, 2H), 7.53 (brs, 1H), 7.39 (d, 1H), 7.26 (d, 2H), 6.83 (d, 1H), 6.57-6.67 (m, 5H), 3.83 (dd, 1H), 3.04 (t, 1H), 2.82-2.93 (m, 1H), 2.68 (d, 1H), 2.59 (d, 1H), 2.35 (dd, 1H), 2.14 (dd, 1H). | (3S)-3-benzyl-1-[8-chloro-2-(pyridin-4-yl)pyrido[3,4-d]pyrimidin-4-yl]piperazine |
| 69 | [A001] | A | 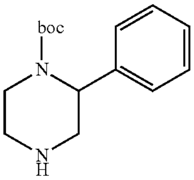 | Method 1: RT: 2.32 min, MI: 369 [M + H] | (1H, 300 MHz, d6-dmso) 9.23 (s, 1H), 8.74 (d, 2H), 8.56 (d, 1H), 8.26 (d, 2H), 7.89 (d, 1H), 7.51 (d, 2H), 7.25-7.40 (m, 3H), 4.51 (dd, 2H), 3.95 (d, 1H), 3.34-3.46 (m, 1H), 3.13-3.24 (m, 2H), 2.97-3.03 (m, 1H). | 3-phenyl-1-[2-(pyridin-4-yl)pyrido[3,4-d]pyrimidin-4-yl]piperazine |
| 70 | [A003] | B | 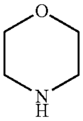 | Method 1: RT: 2.47 min, MI: 324.18 [M + H]; | (1H, 300 MHz, $CDCl_3$) 9.00 (1H, s), 8.76 (2H, d), 8.33 (2H, d), 8.20 (1H, s), 4.08 (3H, s), 3.89 (4H, t), 3.77 (4H, t). | 4-[5-methoxy-2-(pyridin-4-yl)pyrido[3,4-d]pyrimidin-4-yl]morpholine |
| 71 | [A001] | A | 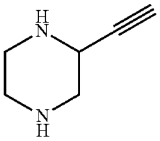 [A030] | Method 1: RT: 2.72 min, MI: 317.26 [M + H] | (1H, 300 MHz, d4-MeOH) 9.24 (1H, s), 8.69 (2H, dd), 8.54 (1H, d), 8.42 (2H, dd), 7.97 (1H, dd), 4.20 (1H, dd), 4.07-3.92 (4H, m), 3.36-3.29 (1H, m), 3.00-2.94 (1H, m), 2.80 (1H, d), 2.65 (1H, s, br). | 3-ethynyl-1-[2-(pyridin-4-yl)pyrido[3,4-d]pyrimidin-4-yl]piperazine |
| 72 | [A003] | B | 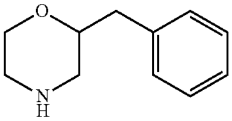 [A034] | Method 1: RT: 5.36 min, MI: 414.22 [M + H] | (1H, 300 MHz, d6-dmso) 8.82 (1H, s), 8.71 (2H, dd), 8.27 (1H, s), 8.10 (2H, dd), 7.34-7.28 (5H, m), 4.27 (1H, d), 4.04 (1H, d), 3.95-3.91 (1H, m), 3.91 (3H, s), 3.81-3.73 (1H, m), 3.59-3.52 (1H, m), 3.38-3.33 (1H, m), 3.04-2.96 (1H, dd), 2.91-2.75 (2H, m). | 2-benzyl-4-[5-methoxy-2-(pyridin-4-yl)pyrido[3,4-d]pyrimidin-4-yl]morpholine |
| 73 | [A005] | B | 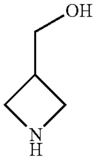 | Method 1: RT: 3.33 min, MI: 330 [M + H] | | {1-[8-chloro-2-(pyridin-4-yl)pyrido[3,4-d]pyrimidin-4-yl]azetidin-3-yl}methanol |
| 74 | [A003] | B | 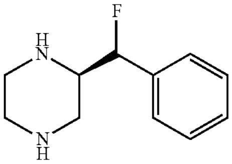 [A036] | Method 1: RT: 1.88 min, MI: 431.18 [M + H] | | (3R)-3-[fluoro(phenyl)methyl]-1-[5-methoxy-2-(pyridin-4-yl)pyrido[3,4-d]pyrimidin-4-yl]piperazine |
| 75 | [A005] | B | 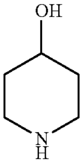 | Method 1: RT: 3.73 min, MI: 342 [M + H] | (1H, 300 MHz, d6-dmso) 8.78 (d, 2H), 8.35 (d, 1H), 8.33 (d, 2H), 7.89 (d, 1H), 4.88 (d, 1H), 4.21-4.27 (m, 2H), 3.85-3.91 (m, 1H), 3.64-3.72 (m, 2H), 1.93-1.99 (m, 2H), 1.57-1.65 (m, 2H). | 1-[8-chloro-2-(pyridin-4-yl)pyrido[3,4-d]pyrimidin-4-yl]piperidin-4-ol |

-continued

| Ex | Pre-cursor | Meth-od | Amine [F-003] | Analysis LCMS | NMR | Name |
|---|---|---|---|---|---|---|
| 76 | [A003] | B | 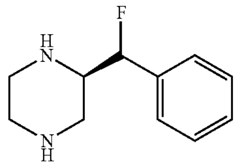 [A036] | Method 1: RT: 2.08 min, MI: 431.14 [M + H] | (1H, 500 MHz, d6-dmso) 8.81 (1H, s), 8.71 (2H, d), 8.28 (1H, s), 8.10 (2H, d), 7.46-7.45 (5H, m), 5.51 (1H, dd), 4.41 (1H, d, br), 4.02 (1H, m, br), 3.98 (3H, s), 3.20 (2H, t, br), 3.08 (1H, d), 2.99 (1H, d), 2.68 (1H, t). | (3R)-3-[fluoro(phenyl)methyl]-1-[5-methoxy-2-(pyridin-4-yl)pyrido[3,4-d]pyrimidin-4-yl]piperazine |
| 77 | [A003] | B | 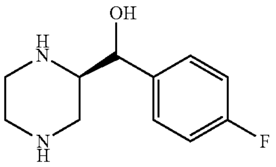 [A043] | Method 1: RT: 2.08 min, MI: 447.08 [M + H] (3:1 mixture of diastereomers) | (1H, 500 MHz, d6-dmso) 8.79 (0.25H, s), 8.77 (0.75H, s), 8.70 (2H, dd), 8.27 (0.25H, s), 8.22 (0.75H, s), 8.11 (0.75H, d), 8.08 (0.25H, d), 7.99 (1H, d, br), 7.43 (2H, t, br), 7.23 (1.5H, t), 7.20 (0.5H, t), 5.65 (0.75H, d), 5.54 (0.25H, d), 4.54 (0.25H, t), 4.43 (0.75H, t), 3.99 (0.75H, s), 3.93 (2.25H, s), 3.22 (0.75H, t), 3.14 (0.25H, t), 3.94-2.92 (2H, m), 2.85 (1H, t), 2.74 (1H, m), 2.65 (1H, t). | (4-fluorophenyl)[(2R)-4-[5-methoxy-2-(pyridin-4-yl)pyrido[3,4-d]pyrimidin-4-yl]piperazin-2-yl]methanol |

Synthesis of (S)—$N^2$,$N^2$-Dimethyl-3-phenyl-propane-1,2-diamine [A009]

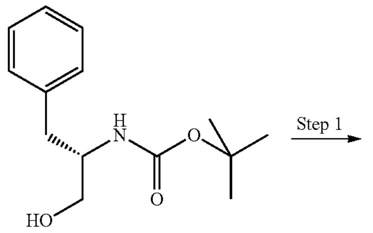

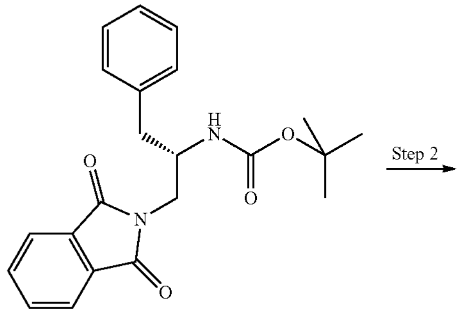

[A010]

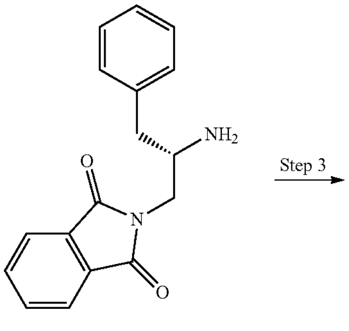

[A011]

-continued

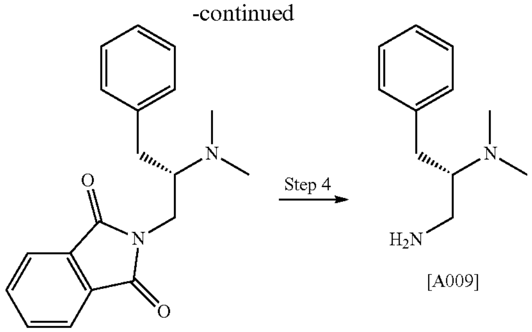

[A012]

[A009]

Synthesis of [(S)-1-(1,3-Dioxo-1,3-dihydro-isoindol-2-ylmethyl)-2-phenyl-ethyl]-carbamic acid tert-butyl ester [A010]

A mixture of Boc-L-phenylalaninol (25 g, 99.5 mmol), triphenylphosphine (31.3 g, 119.4 mmol), phthalimide (16.1 mg, 109.5 mmol) and THF (300 mL) was chilled to 0° C. A solution of diisopropyl azodicarboxylate (19.5 mL, 99.5 mmol) in THF (100 mL) was added over 15 mins. The resulting pale yellow solution was allowed to return to room temperature over night. The reaction mixture was concentrated to approximately 100 mL then partitioned between ethyl acetate and water. A white precipitate formed which was collected by filtration. The organic layer was washed with more water (×1) then brine (×1), dried ($MgSO_4$), filtered and evaporated to yield the title compound as a second white solid and this was material was used in further reactions, without further analysis.

Synthesis of ((S)-1-Aminomethyl-2-phenyl-ethyl)-carbamic acid tert-butyl ester [A011]

A mixture of [(S)-1-(1,3-Dioxo-1,3-dihydro-isoindol-2-ylmethyl)-2-phenyl-ethyl]-carbamic acid tert-butyl ester [A010](2 g, 5.25 mmol), 4M HCl in dioxane (5 mL, 20 mmol) and methanol (50 mL) was stirred at room temperature. The reaction mixture was loaded straight on to a methanol conditioned SCX-2 cartridge. The cartridge was washed with methanol (2col cols) and then eluted with 2N ammonia in methanol (2CV). LCMS analysis showed the target material to be predominantly in the methanol wash but also partially in the NH3 elution. The collected fractions were left to stand for a 3 days. After this time, needle like crystals started to form in the methanol fraction. The crystals were collected by filtration and dried in the vac oven to yield the title compound [A011] (400 mg): NMR: (1H, 300 MHz, d6-DMSO) 8.08 (2H, br s), 7.04 (4H, s), 7.35-7.29 (4H, m), 7.26-7.17 (1H, m), 3.83-3.66 (2H, m), 3.61 (1H, dd), 3.06 (1H, dd), 2.86 (1H, dd); LCMS method: 1, RT: 2.50 min, MI 281 [M+H]

Synthesis of 2-((S)-2-Dimethylamino-3-phenyl-propyl)-isoindole-1,3-dione [A012]

A mixture of 2-((S)-2-Amino-3-phenyl-propyl)-isoindole-1,3-dione [A011](200 mg, 0.71 mmol), formaldehyde (2 mL, xs) and formic acid (2 mL, xs) was heated to 100° C. for 2 hours. The reaction mixture was concentrated under vacuum then partioned between 2M $K_2CO_3$ and DCM. The organic layer was washed with water then brine, passed through a phase separator and evaporated to yield the title compound [A012] (200 mg) which was used without further purification: LCMS method: 1, RT: 2.42 min, MI 309 [M+H]

Synthesis of (S)—$N^2$,$N^2$-Dimethyl-3-phenyl-propane-1,2-diamine [A009]

A solution of 2-((S)-2-Dimethylamino-3-phenyl-propyl)-isoindole-1,3-dione [A012] (350 mg), hydrazine monohydrate (66.1 ul, 1.36 mmol) and methanol (50 mL) was stirred at room temperature for 20 hours. The solvent was removed under vacuum to yield a white solid. This was then partitioned between 10% citric acid and isopropanol. The aqueous layer was filtered, basified with 2M NaOH, extracted into isoropanol, washed with brine, passed through a phase separator and evaporated to yield title compound [A009] (93 mg): LCMS method: 1, RT: 0.53 min, MI 179 [M+H]

Synthesis of ((S)-1-Methylaminomethyl-2-phenyl-ethyl)-carbamic acid tert-butyl ester [A013]

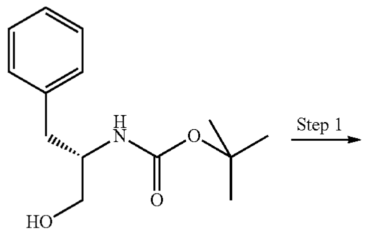

-continued

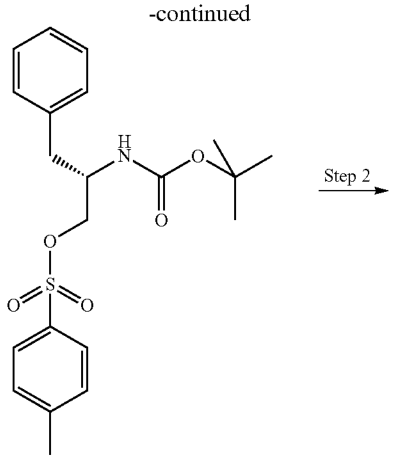

[A014]

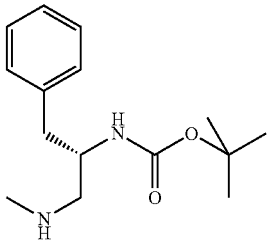

[A013]

Synthesis of Synthesis of Toluene-4-sulfonicacid (S)-2-tert-butoxycarbonylamino-3-phenyl-propyl ester [A014]

To a solution of Boc-L-phenylalaninol (0.5 g, 1.989 mmol) in DCM (10 mL) at 0° C. was added triethylamine (0.83 mL, 5.968 mmol). The reaction mixture was stirred at this temperature for 5 minutes. para-Toluenesufonyl chloride (2.188 mmol, 0.42 g) was added dropwise as a solution in DCM (5 mL), and the reaction mixture was allowed to warm up to room temperature slowly. The reaction mixture stirred at room temperature for 4 hours. The reaction mixture was diluted with DCM (20 mL) and washed with water. Layers separated and the organic layer dried over anhydrous magnesium sulphate. The DCM was evaporated to dryness under reduced pressure to afford the title compound [A014] as a clear oil (0.8 g). No further purification was carried out and the crude product was used immediately in the next step.

Synthesis of ((S)-1-Methylaminomethyl-2-phenyl-ethyl)-carbamic acid tert-butyl ester [A013]

Toluene-4-sulfonicacid(S)-2-tert-butoxycarbonylamino-3-phenyl-propyl ester [A014](0.80 g, 1.973 mmol) was dissolved in THF (10 mL) and methyl amine (2N in THF, 10 mL) was added in one portion. The reaction mixture was stirred at 60° C. overnight. The mixture was diluted with ethyl acetate and washed with brine. The layers were separated and the ethyl acetate dried over anhydrous magnesium sulphate. The solvent was removed under reduced pressure to afford the title compound [A013] as a clear oil. No further purification was carried out at this stage. Crude material was used directly in subsequent reactions without further purification.

Synthesis of (2S,4S)-4-Amino-2-hydroxymethyl-pyrrolidine-1-carboxylic acid tert-butyl ester [A015]

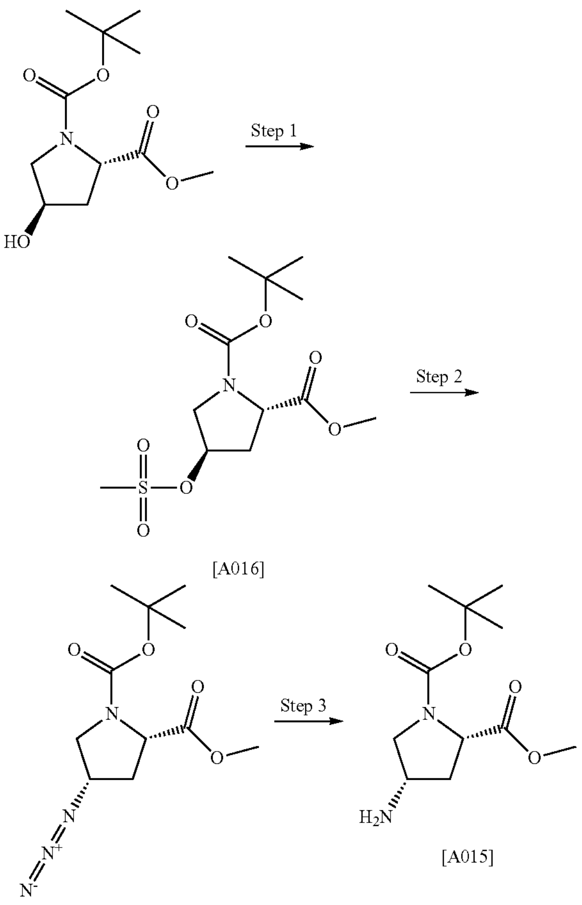

[A016]

[A017]

[A015]

Synthesis of (2S,4R)-4-Methanesulfonyloxy-pyrrolidine-1,2-dicarboxylic acid 1-tert-butyl ester 2-methyl ester [A016]

N-Boc-trans-4-hydroxy-L-proline methyl ester (12.28 mmol, 3 g), was dissolved in DCM (30 mL) and triethylamine (13.45 mmol, 1.87 mL) was added. The reaction was cooled to 0° C. and methanesulfonyl chloride (24.46 mmol, 1.89 mL) was added dropwise over 5 minutes. The reaction mixture was allowed to stir at this temperature for 45 minutes and then warmed to room temperature for 2 hours. Brine was added and the layers were separated, the aqueous was extracted with dichloromethane (x2). The organics were washed with brine (x1), dried with $MgSO_4$, filtered and evaporated to yield the title compound as a clear oil (3.95 g): NMR (1H, 300 MHz, $CDCl_3$): 5.22 (m, 1H), 4.39 (m, 1H), 3.74 (s, 3H), 3.73 (m, 2H), 3.65 (s, 3H), 3.07 (s, 3H), 2.51 (m, 1H), 2.22 (m, 2H), 1.41 (d, 9H)

Step 2: Synthesis of (2S,4S)-4-Azido-pyrrolidine-1,2-dicarboxylic acid 1-tert-butyl ester 2-methyl ester [A017]

(2S,4R)-4-Methanesulfonyloxy-pyrrolidine-1,2-dicarboxylic acid 1-tert-butyl ester 2-methyl ester [A016](12.28 mmol, 3.95 g), was dissolved in anhydrous DMF (20 mL) and sodium azide (61.14 mmol, 3.97 g) was added in one portion. The reaction was heated to 80° C. for 3 hours. Upon cooling the reaction mixture was quenched with water and extracted with ethyl acetate (x3). The organics were washed with brine, dried with $MgSO_4$, filtered and evaporated to a colourless oil. Purified by flash column chromatography using 0 to 40% EtOAc/cyclohexane to yield the title compound [A017] (2.24 g): NMR (1H, 300 MHz, $CDCl_3$): 4.36 (m, 1H), 4.13 (m, 1H), 3.74 (s, 3H), 3.67 (m, 1H), 3.48 (dt, 1H), 2.47 (m, 1H), 2.14 (m, 2H), 1.43 (d, 9H)

Synthesis of (2S,4S)-4-Amino-2-hydroxymethyl-pyrrolidine-1-carboxylic acid tert-butyl ester [A015]

Water (5 mL) was added to a stirred solution of (2S,4S)-4-azido-pyrrolidine-1,2-dicarboxylic acid 1-tert-butyl ester 2-methyl ester [A017](4.44 mmol, 1.2 g) and triphenylphosphine (9.32 mmol 2.45 g), in toluene (40 mL) and the reaction was heated to 60° C. overnight. Upon cooling water was added and the layers separated. The aqueous was basified with 2M NaOH added and extracted twice with ethyl acetate, the organics combined, dried over anhydrous $MgSO_4$, filtered and concentrated in vacuo to give the title compound (200 mg): NMR (1H, 300 MHz, $CDCl_3$): 4.20 (m, 1H), 3.71 (s, 3H), 3.62 (m, 1H), 3.50 (m, 1H), 3.22 (m, 1H), 2.43 (m, 1H), 1.78 (m, 1H), 1.43 (d, 9H)

Synthesis of ((1R,2R)-1-Aminomethyl-2-fluoro-2-phenyl-ethyl)-carbamic acid tert-butyl ester [A018]

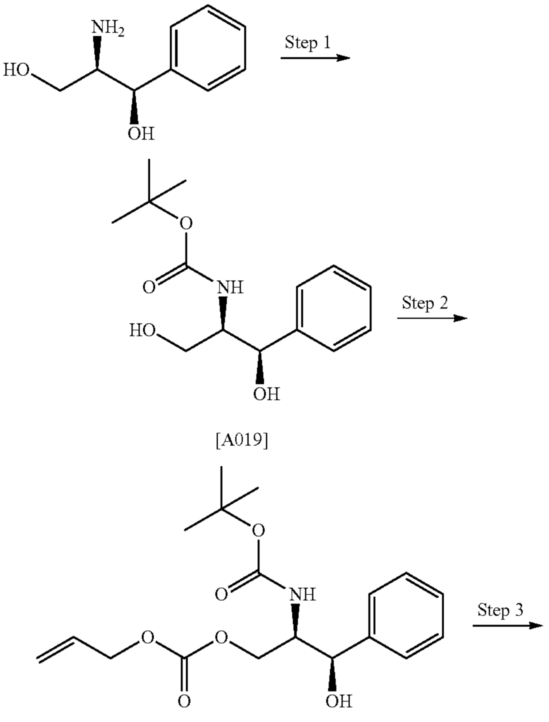

[A019]

[A020]

-continued

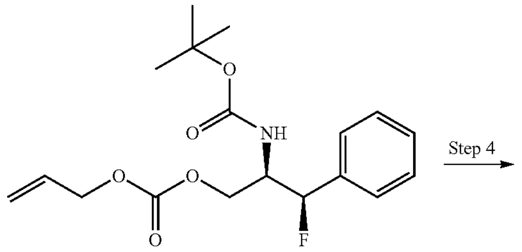

[A021]

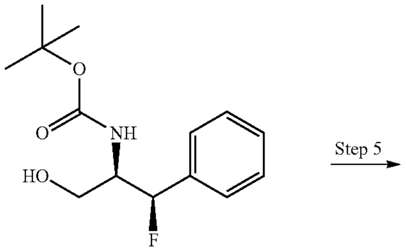

[A022]

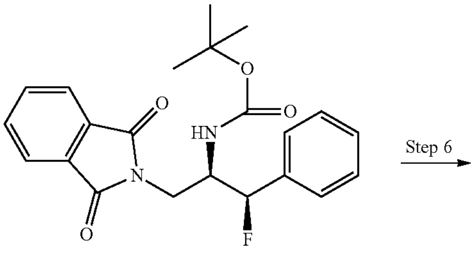

[A023]

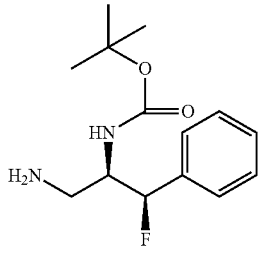

[A018]

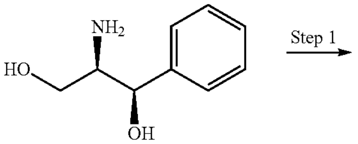

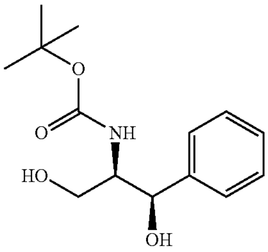

[A019]

Synthesis of ((1R,2R)-2-Hydroxy-1-hydroxymethyl-2-phenyl-ethyl)-carbamic acid tert-butyl ester [A019]

(1R,2R)-(−)-2-Amino-1-phenyl-propane-1,3-diol (5.98 mmol, 1.0 g) was dissolved in methanol (10 mL) and cooled to 0° C. A solution of di-tert-butyl dicarbonate in methanol (4 mL) was added and the reaction was warmed to room temperature and stirred for 2 hours. The solvent was removed in vacuo and the product was purified by flash chromatography eluting with 0 to 70% EtOAc/cyclohexane to yield the title compound [A019] (1.20 g): NMR (1H, 300 MHz, $CDCl_3$): 7.29 (m, 5H), 5.19 (m, 1H), 4.96 (m, 1H), 3.35 (m, 1H), 2.66 (m, 1H), 1.33 (s, 9H); LCMS method: 1, RT: 4.35 min, MI: no trace.

Synthesis of ((1R,2R)-2-Hydroxy-1-hydroxymethyl-2-phenyl-ethyl)-carbamic acid tert-butyl ester [A020]

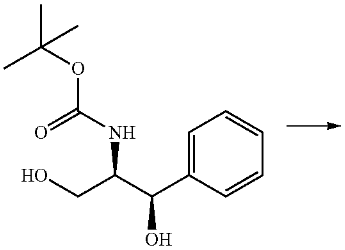

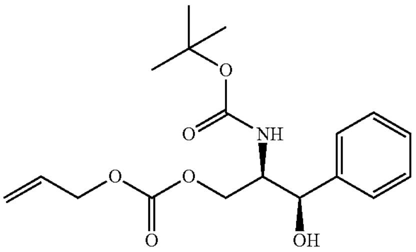

Allyl chloroformate (11.222 mmol, 1.35 g) was added dropwise to a stirred solution of ((1R,2R)-2-Hydroxy-1-hydroxymethyl-2-phenyl-ethyl)-carbamic acid tert-butyl ester [A019](1.20 g, 4.48 mmol) and pyridine (15.711 mmol, 1.27 mL) in DCM (50 mL) at 0° C. The reaction was allowed to warm to room temperature and stirred for an hour. Water was added and the layers separated. The aqueous was extracted twice with DCM. The organics were combined, washed with brine, dried over anhydrous MgSO4, filtered and concentrated in vacuo. The crude product was purified by flash chromatography using 0 to 100% EtOAc/cyclohexane to yield the title compound [A020] (0.93 g): NMR (1H, 300 MHz, $CDCl_3$): 7.28 (m, 5H), 5.91 (m, 1H), 5.34 (d, 1H), 5.27 (d, 1H), 4.99 (m, 1H), 4.84 (t, 1H), 4.61 (d, 2H), 4.27 (dd, 1H), 4.07 (dd, 1H), 4.01 (m, 1H), 3.09 (bs, 1H), 1.33 (s, 9H); LCMS: LC-MS17QC 94% 352+[M+H] 5.17 min Synthesis of Carbonic acid allyl ester (2R,3R)-2-tert-butoxycarbonylamino-3-phenyl-3-(tetrahydro-pyran-2-yloxy)-propyl ester [A021]

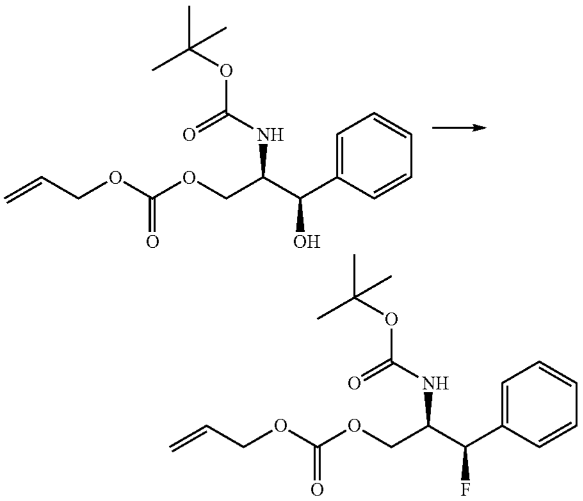

A solution of ((1R,2R)-2-Hydroxy-1-hydroxymethyl-2-phenyl-ethyl)-carbamic acid tert-butyl ester [A020](1.42 mmol, 0.50 g) and DIPEA (4.97 mmol 0.865 mL) in DCM (20 mL) was added dropwise to a solution of (diethylamino) sulfur trifluoride (DAST) (4.97 mmol, 0.610 mL) at −78° C. under nitrogen. The reaction was slowly warmed to room temperature and stirred for 2 hours. Water was added then extracted twice with DCM. The organics were combined, washed with brine, dried over anhydrous $MgSO_4$, filtered and concentrated in vacuo to yield the title compound [A021] which was used directly in the next step without further purification: LCMS method: 1, RT: 3.27 min, MI not seen.

Synthesis of ((1R,2R)-2-Fluoro-1-hydroxymethyl-2-phenyl-ethyl)-carbamic acid tert-butyl ester [A022]

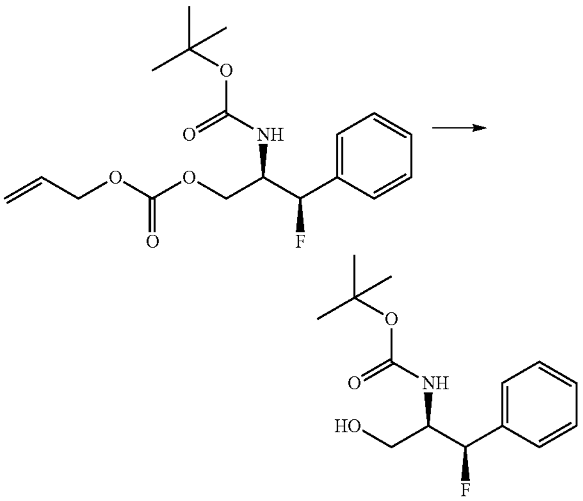

To a solution of carbonic acid allyl ester (2R,3R)-2-tert-butoxycarbonylamino-3-fluoro-3-phenyl-propyl ester [A021](2.0 mmol, 0.71 g) in anhydrous THF (15 mL) under nitrogen, was added tetrakis(triphenylphosphine)palladium (0) (0.08 mmol 0.093 g) and morpholine (3.014 mmol, 0.26 mL). The reaction was stirred at rt for 1 h under a nitrogen atmosphere. Brine was added and the mixture extracted twice with ethyl acetate. The organics were combined, dried over $MgSO_4$, filtered and concentrated in vacuo. The product was purified by flash chromatography using 0 to 10% MeOH/DCM to yield the title compound [A022] (0.19 g): NMR (1H, 300 MHz, $CDCl_3$): 7.32 (m, 5H), 5.68 (d, 1H), 5.11 (m, 1H), 3.99 (m, 1H), 3.86 (m, 1H), 3.67 (m, 1H), 1.39 (s, 9H)

Synthesis of [(1R,2R)-1-(1,3-Dioxo-1,3-dihydro-isoindol-2-ylmethyl)-2-fluoro-2-phenyl-ethyl]-carbamic acid tert-butyl ester [A023]

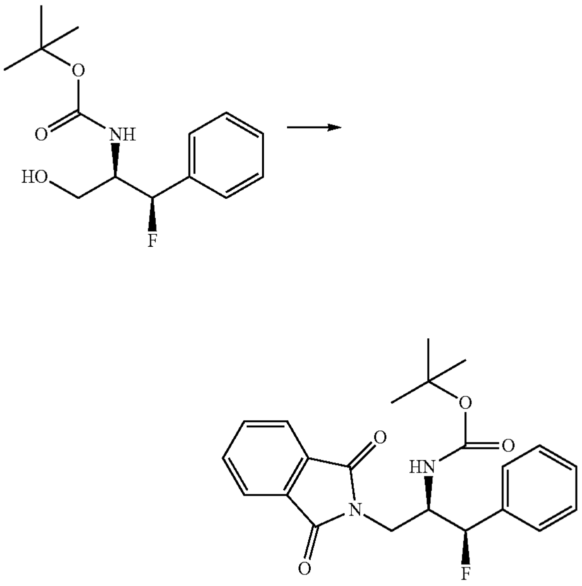

A solution of ((1R,2R)-2-Fluoro-1-hydroxymethyl-2-phenyl-ethyl)-carbamic acid tert-butyl ester [A022](0.705 mmol, 0.19 g), triphenylphosphine (0.988 mmol, 0.259 g) and phthalimide (0.988 mmol, 0.145 g) was cooled to 0° C. and diisopropyl azodicarboxylate (DIAD) (0.988 mmol, 0.193 mL) was added dropwise. The reaction was allowed to warm to room temperature and stirred for 1 hour. The solvent was removed in vacuo and the residue was dissolved in DCM. 2M NaOH (aqueous solution) was added and the layers separated using a phase separator. The organic was concentrated in vacuo. The product was purified by flash chromatography using 0 to 30% EtOAc/cyclohexane to yield the title compound [A023] (0.28 g): 1LCMS1; 98%, 399.15+[M+H]+, 5.45 min; NMR (1H, 300 MHz, $CDCl_3$): 7.80 (m, 2H), 7.65 (m, 2H), 7.40 (m, 4H), 7.31 (m, 1H), 5.72 (dd, 1H), 5.06 (d, 1 h), 4.47 (m, 1H), 3.83 (dd, 1H), 3.57 (dd, 1H), 1.20 (s, 9H)

Synthesis of ((1R,2R)-1-Aminomethyl-2-fluoro-2-phenyl-ethyl)-carbamic acid tert-butyl ester [A018]

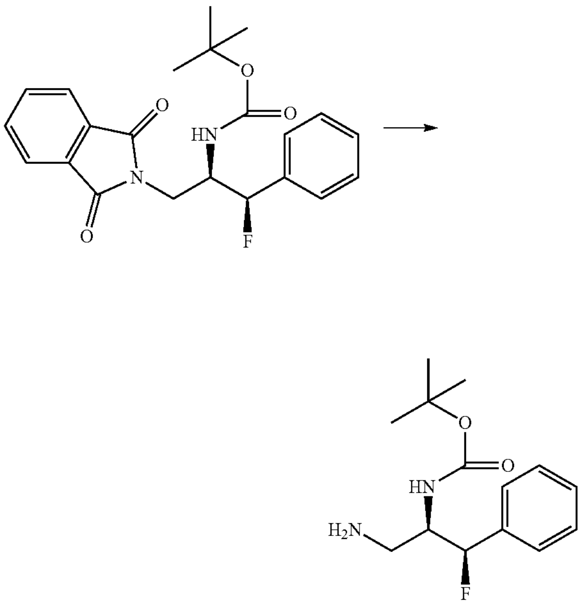

[(1R,2R)-1-(1,3-Dioxo-1,3-dihydro-isoindol-2-ylmethyl)-2-fluoro-2-phenyl-ethyl]-carbamic acid tert-butyl ester [A023](0.705 mmol, 0.28 g) was dissolved in methanol (5 mL) and Hydrazine monohydrate (0.916 mmol, 0.045 mL) was added. The reaction was stirred at room temperature for 1 hour then at 60° C. overnight. Upon cooling the solvent was removed in vacuo and the residue dissolved in DCM. 2M NaOH (aqueous solution) was added and the mixture extracted twice. The organics were combined, dried over anhydrous $MgSO_4$, filtered and concentrated in vacuo. The product was purified using an SCX-2 cartridge, applying the crude material as a DCM solution and washing with methanol and DCM. The material was then washed off the SCX-2 cartridge by washing with ammonia (2N in methanol) and the ammonia washes concentrated in vacuo to yield the title compound [A018] (0.12 g): NMR (1H, 300 MHz, $CDCl_3$): 7.34 (m, 5H), 5.62 (d, 1H), 5.19 (d, 1H), 3.89 (m, 1H), 2.83 (m, 2H), 1.40 (s, 9H) Synthesis of 2-Fluoromethyl-piperazine [A024]

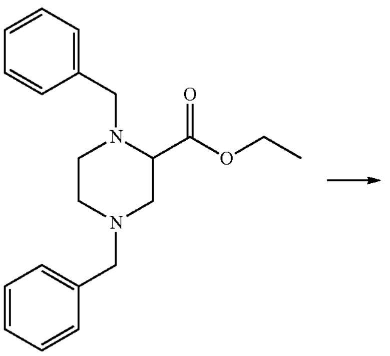

[A025]

-continued

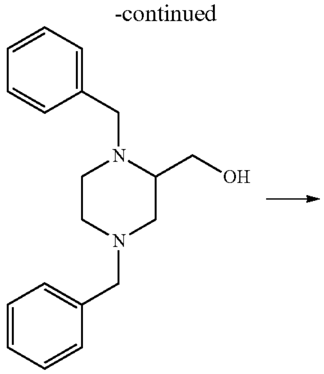

[A026]

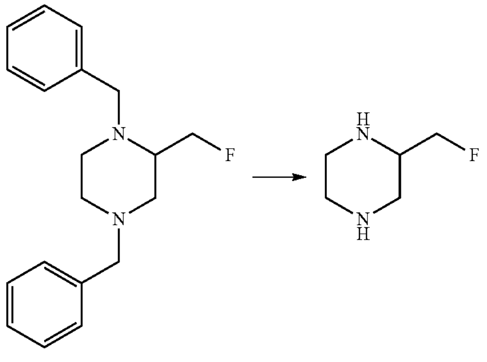

[A027] [A024]

(1,4-Dibenzyl-piperazin-2-yl)-methanol [A026]

A solution of 1,4-Dibenzyl-piperazine-2-carboxylic acid ethyl ester [A025](3.7 g, 10.9 mmol) in THF (10 mL) was added dropwise to a suspension of $LiAlH_4$ (2.24 g, 59 mmol) in THF (20 mL) at 0° C. The reaction was warmed to room temperature and stirred overnight. The reaction was diluted with ether, cooled to 0° C. and quenched with water (2.25 mL) and 2M NaOH (4.5 ml) and water (4.5 mL). The suspension was stirred for 15 mins and anhydrous MgSO4 was added and stirred for a further 15 mins. The white solid was filtered off (celite) and the solvent removed in vacuo. The product was purified by flash chromatography using 0 to 100% EtOAc/cyclohexane to give the title compound [A026](3.03 g, 94% yield). LCMS method: 1, RT: 2.16 min, MI 297.23 [M+H]; NMR (1H, 300 MHz, $CDCl_3$): 3.43 (m, 3H), 2.63 (m, 3H), 2.95 (m, 1H), 3.49 (m, 3H), 3.61 (d, 1H), 4.04 (dd, 2H), 7.31 (m, 10H)

1,4-Dibenzyl-2-fluoromethyl-piperazine [A027]

(1,4-Dibenzyl-piperazin-2-yl)-methanol [A026](1.09 g, 3.6 mmol) in DCM (5 mL) was added dropwise to a stirred solution of DAST (0.9 mL, 7.35 mmol) in DCM (10 mL) at 0° C. The reaction was warmed to room temperature and stirred overnight. Aqueous 2M NaOH (10 mL) was added the layers separated by phase seperator. The solvent was removed in vacuo and the product was purified by flash chromatography using 0 to 30% EtOAc/cyclohexane to give the title compound [A027](0.42 g, 38% yield). LCMS method: 1, RT: 5.88 min, MI 299.38 [M+H]; NMR (1H, 300 MHz, $CDCl_3$): 2.28 (m, 3H), 2.50 (m, 2H), 2.70 (m, 2H), 2.83 (m, 1H), 3.49 (m, 3H), 4.11 (d, 1H), 4.53 (ddd, 1H), 4.68 (ddd, 1H), 7.25 (m, 10H)

2-Fluoromethyl-piperazine [A024]

1,4-Dibenzyl-2-fluoromethyl-piperazine [A027](0.32 g, 1.07 mmol) was dissolved in DCE (10 mL) and 1-Chloroethyl chloroformate (0.35 mL, 3.21 mmol) was added. The reaction was heated to reflux overnight. Upon cooling the solvent was removed in vacuo and the intermediate dicarabamate was purified by flash chromatography eluting with 0 to 50% EtOAc/cyclohexane. The residue was dissolved in methanol (10 mL) and heated to reflux for 1 hour. The solvent was removed in vacuo to give the title compound [A024] which was used in the next step and used without further purification Synthesis of Piperazin-2-yl-acetonitrile [A028]

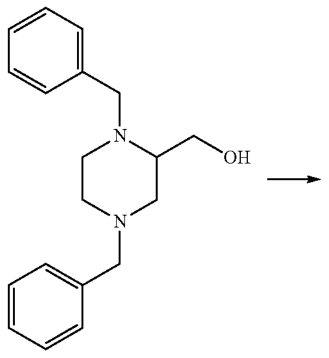

[A026]

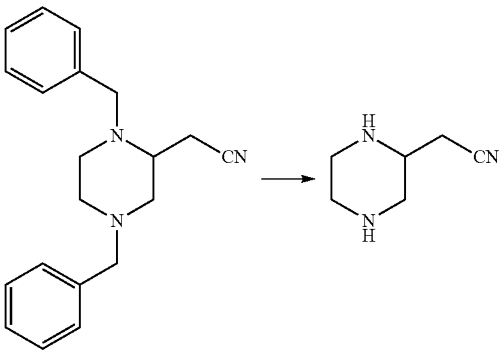

[A029] [A028]

(1,4-Dibenzyl-piperazin-2-yl)-acetonitrile [A029]

A solution of (1,4-Dibenzyl-piperazin-2-yl)-methanol [A026](1 g, 3.37 mmol) in DCM (10 mL) was added dropwise to a solution of thionyl chloride (0.32 mL, 4.4 mmol) in DCM (5 mL) and the reaction was stirred at room temperature overnight. The solvent was removed in vacuo and water was added. The aqueous was extracted with ether then bascified with saturated Na2CO3. This was extracted twice with DCM, dried over anhydrous MgSO4, filtered and concentrated in vacuo and used crude in the next step and used without further purification.

To a refluxing solution of KCN (0.244 g, 3.7 mmol) in water (10 mL) was added 1,4-Dibenzyl-2-chloromethyl-piperazine (0.91 g, 2.9 mmol) in ethanol (10 mL) dropwise. The reaction was heated to reflux for 3 hours. Upon cooling the solvent was removed in vacuo and the residue was taken up in DCM, washed with water, dried over MgSO4, filtered and concentrated in vacuo. The product was purified by flash chromatography using 0 to 40% EtOAc/cyclohexane, to give the title compound [A029](0.52 g, 59% yield). LCMS method: 1, RT: 2.87 min, MI 306.26 [M+H]; NMR (1H, 300 MHz, $CDCl_3$): 2.43 (m, 3H), 2.58 (m, 4H), 2.87 (dd, 1H), 3.00 (m, 1H), 3.48 (m, 3H), 3.80 (d, 1H), 7.28 (m, 10H).

Piperazin-2-yl-acetonitrile [A028]

(1,4-Dibenzyl-piperazin-2-yl)-acetonitrile [A029](0.52 g, 1.7 mmol) was dissolved in DCE (10 mL) and 1-Chloroethyl chloroformate (0.55 mL, 5.1 mmol) was added. The reaction was heated to reflux for 2 days. Upon cooling the solvent was removed in vacuo and the intermediate dicarabamate was purified by flash chromatography eluting with 0 to 40% EtOAc/cyclohexane. The residue was dissolved in methanol (10 ml) and heated to reflux for an hour. The solvent was removed in vacuo to give clean product. NMR (1H, 300 MHz, d6-dmso): 3.16 (m, 3H), 3.03 (t, 1H), 3.49 (m, 4H), 3.89 (m, 1H), 10.06 (m, 2H)

Synthesis of 2-Ethynyl-piperazine [A030]

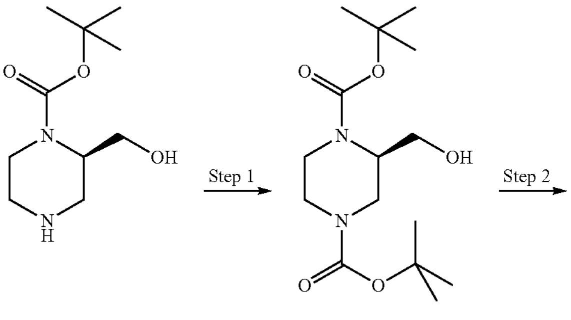

[A031]

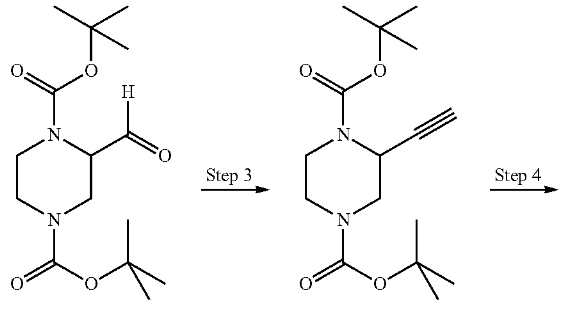

[A032] [A033]

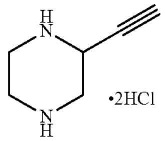

[A030]

Synthesis of (R)-2-Hydroxymethyl-piperazine-1,4-dicarboxylic acid di-tert-butyl ester [A031]

To a stirred solution of (R)-1-Boc-2-Hydroxymethyl-piperazine (1 g, 4.62 mmol) and $Na_2CO_3$ (990 mg, 9.25 mmol) in a mixture of dioxane (8 ml) and water (2 ml) at 0

OC was added Di-tert-butyl dicarbonate and the reaction mixture warmed to room temperature. After 18 hours all solvents were removed in vacuo and the resulting residue partitioned between DCM and water. The DCM phase was passed through phase separation cartridge and evaporated to provide a white solid. Purification by column chromatography (0-50% EtOAc:cyclohexane) gave the title compound [A031] as a white solid (1.26 g, 86%). 1H-NMR (1H, 300 MHz, $CDCl_3$): 4.17 (2H, s, br), 3.93 (1H, s, br), 3.84 (1H, d, br), 3.59 (2H, s, br), 2.95 (3H, s, br), 1.46 (18H, s).

Synthesis of 2-Formyl-piperazine-1,4-dicarboxylic acid di-tert-butyl ester [A032]

A solution of oxalyl chloride (165 μl, 1.90 mmol) in DCM (5 ml) was cooled to −78° C. DMSO (270 μl, 3.79 mmol) was added dropwise and the reaction mixture stirred for 15 mins. A solution of (R)-2-Hydroxymethyl-piperazine-1,4-dicarboxylic acid di-tert-butyl ester [A031](500 mg, 0.58 mmol) in DCM (1 ml) was added dropwise and the reaction mixture stirred for 1 hour. Triethylamine (1.1 ml, 7.90 mmol) was added and the reaction mixture warmed to room temperature. Saturated $NaHCO_3$ was added, the layers separated and the organic phase collected and evaporated to give the title compound [A032] as a white powder (480 mg, 97%). 1H-NMR (1H, 300 MHz, $CDCl_3$): 9.58 (1H, s), 4.63-4.45 (2H, m, br), 3.95-3.79 (2H, m, br), 3.15-3.11 (2H, m, br), 2.88 (1H, d, br), 1.44 (18H, s).

Synthesis of 2-Ethynyl-piperazine-1,4-dicarboxylic acid di-tert-butyl ester [A033]

To a stirred solution of 2-Formyl-piperazine-1,4-dicarboxylic acid di-tert-butyl ester [A032](480 mg, 0.530 mmol) and $K_2CO_3$ (425 mg, 3.06 mmol) in MeOH (20 ml) was added Dimethyl (1-diazo-2-oxopropyl)phosphonate (350 mg, 1.83 mmol). After 18 hours the solvent was removed in vacuo and the resulting residue partitioned (DCM:water). The organic phase was separated and concentrated to provide the title compound [A033] as a white solid (430 mg, 91%). 1H-NMR (1H, 300 MHz, $CDCl_3$): 4.88 (1H, s, br), 4.25-4.01 (2H, m, br), 3.80 (1H, d, br), 3.18 (1H, t, br), 3.02-2.74 (2H, m), 2.23 (1H, d), 1.47 (18H, s).

Synthesis of 2-Ethynyl-piperazine [A030]

2-Ethynyl-piperazine-1,4-dicarboxylic acid di-tert-butyl ester [A033](430 mg, 1.39 mmol) was stirred in 4N HCl: dioxane (1 ml) for 4 hours. A pale yellow solid (226 mg, 89%) was collected by filtration and washed with $Et_2O$ then dried in a vacuum oven at 40 OC to yield the title compound [A030]: 1H-NMR (1H, 300 MHz, d6-dmso): 4.57 (1H, dt), 4.04 (1H, d), 3.63 (1H, dd), 3.42-3.23 (5H, m).

Synthesis of 2-Benzyl-morpholine [A034]

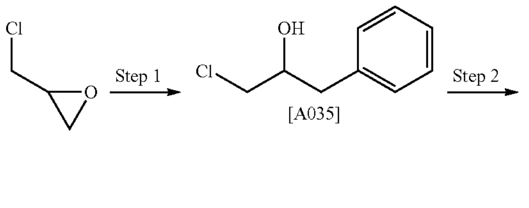

[A035]

-continued

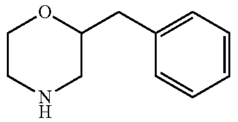

[A034]

Synthesis of 1-Chloro-3-phenyl-propan-2-ol [A035]

To a stirred solution of Phenyl magnesium bromide (3M in $Et_2O$, 4.4 ml, 13 mmol) in $Et_2O$ (14 ml) at 0° C. was added CuI (210 mg, 1.08 mmol). Epichlorohydrin (1 g, 10.8 mmol) in $Et_2O$ (14 ml) was then added and the reaction mixture allowed to warm to room temperature then stirred for 2 hours. Sat. $NH_4Cl$ was added and the solution diluted with water then extracted with EtOAc (×2). The combined organics were washed with brine, dried over $MgSO_4$ and concentrated. Purification by column chromatography (0-20% $Et_2O$:cyclohexane) provided the title compound [A035] as a colourless oil (1.66 g, 90%). 1H-NMR (1H, 300 MHz, $CDCl_3$): 7.36-7.22 (5H, m), 4.11-4.01 (1H, m), 3.59 (1H, dd), 3.50 (1H, dd), 2.90 (2H, d), 2.18 (1H, d).

Synthesis of 2-Benzyl-morpholine [A034]

To a stirred solution of NaOH (1.63 g, 40.8 mmol) in water 3.5 ml) was added 1-Chloro-3-phenyl-propan-2-ol [A035](1.16 g, 6.8 mmol) in MeOH (7 ml). After 5 min 2-Aminoethane hydrogen sulphate (3.84 g, 27.2 mmol) was added and the reaction mixture stirred at 40 OC for 2 hours. NaOH (powdered, 1.63 g, 40.8 mmol) and PhMe (18 ml) were then added and the reaction heated to 65° C. for 18 hours. Dilution with water (10 ml), was followed by extraction with PhMe (×2). The combined organics were washed (water then brine), dried and concentrated. Purification by column chromatography (0-10% MeOH:DCM) provided the title compound as a colourless oil (360 mg, 30%). 1H-NMR (1H, 300 MHz, $CDCl_3$): 7.31-7.19 (5H, m), 3.86 (1H, dd), 3.70-3.54 (2H, m), 2.92-2.77 (4H, m), 2.67-2.55 (2H, m).

Synthesis of (R)-2-(Fluoro-phenyl-methyl)-piperazine [A036]

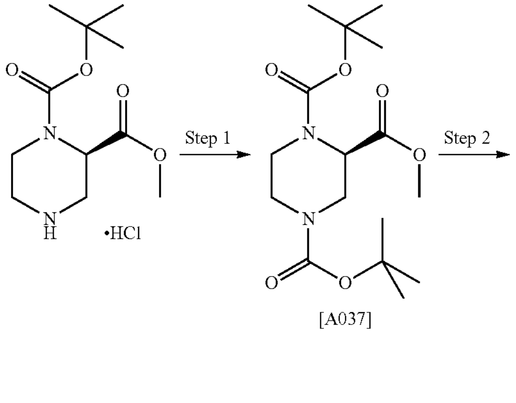

[A037]

-continued

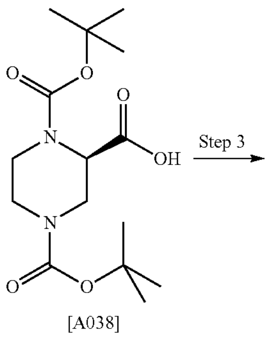

[A038]

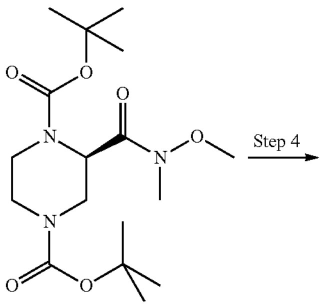

[A039]

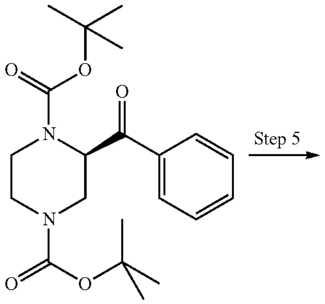

[A040]

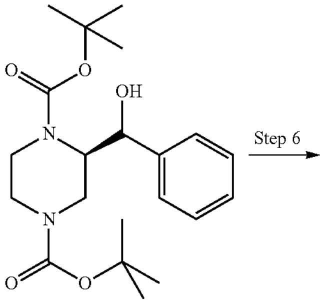

[A041]

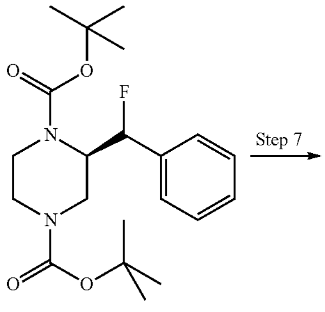

[A042]

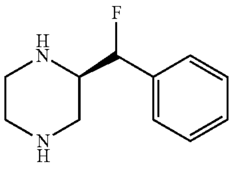

[A036]

Synthesis of (R)-Piperazine-1,2,4-tricarboxylic acid 1,4-di-tert-butyl ester 2-methyl ester [A037]

To a stirred suspension of (R)-1-N-Boc-piperazine-2-carboxylic acid methyl ester hydrochloride (2 g, 7.12 mmol) and $Na_2CO_3$ (2.26 g, 21.4 mmol) in dioxane (16 ml) and water (4 ml) at 0° C. was added Di-tert-butyl-dicarbonate (1.55 g, 7.12 mmol). After 18 hours all solvents were removed in vacuo and the resulting residue partitioned between DCM and water. The organic phase was collected and evaporated to give a colourless oil. Purification by column chromatography (0-30% EtOAc:cyclohexane) gave the title compound [A037] as a white powder (2.33 g, 95%). 1H-NMR (1H, 300 MHz, $CDCl_3$): 5.30 (1H, s), 4.72 (1H, s, br), 4.54 (1H, t, br), 4.08-3.80 (1H, m), 3.73 (3H, s), 3.27-2.73 (3H, m), 1.44 (18H, s).

Synthesis of (R)-Piperazine-1,2,4-tricarboxylic acid 1,4-di-tert-butyl ester [A038]

(R)-Piperazine-1,2,4-tricarboxylic acid 1,4-di-tert-butyl ester 2-methyl ester [A037](2.33 g, 6.77 mmol) and KOH (1.14 g, 20.3 mmol) were heated to reflux in EtOH (50 ml) for 18 hours. Having cooled to room temperature, solvents were removed in vacuo and the residue purified by column chromatography (0-10% MeOH:DCM; 0.1% TEA) to provide the title compound [A038] as a pale orange foam (2.1 g, 94%). 1H-NMR (1H, 300 MHz, $CDCl_3$): 4.66-4.50 (2H, m, br), 3.96-3.74 (2H, m, br), 3.47 (1H, s), 3.23 (1H, s, br), 2.85 (1H, s, br), 1.42 (18H, s).

Synthesis of (R)-2-(Methoxy-methyl-carbamoyl)-piperazine-1,4-dicarboxylic acid di-tert-butyl ester [A039]

(R)-Piperazine-1,2,4-tricarboxylic acid 1,4-di-tert-butyl ester [A038](2.10 g, 6.36 mmol), O-(7-Azabenzotriazol-1-yl)-N,N,N',N'-tetramethyluronium hexafluorophosphate (2.9 g, 7.63 mmol), N,O-Dimethylhydroxylamine hydrochloride (750 mg, 7.63 mmol) and TEA (2.2 ml, 15.3 mmol) were stirred in DMA for 18 hours. The reaction mixture was then partitioned between EtOAc and NaOH (1M), and the aqueous phase re-extracted with EtOAc. The combined organics were dried over $MgSO_4$ and concentrated. Purification by column chromatography (0-50% EtOAc:cyclohexane) gave the title compound [A039] as a viscous pale yellow oil (2.15 g, 91%). 1H-NMR (1H, 300 MHz, $CDCl_3$): 5.30 (1H, s), 4.86-4.71 (1H, m), 4.47-4.32 (1H, m), 4.06-3.75 (2H, m), 3.85 (3H, s), 3.18 (3H, s), 3.18-2.85 (2H, m), 1.45 (9H, s), 1.42 (9H, s). LCMS method: 1, RT: 3.46 min, MI 374.26 [M+H].

Synthesis of (R)-2-Benzoyl-Piperazine-1,4-Dicarboxylic Acid Di-Tert-Butyl Ester [A040]

To a stirred solution of (R)-2-(Methoxy-methyl-carbamoyl)-piperazine-1,4-dicarboxylic acid di-tert-butyl ester [A039](500 mg, 1.34 mmol) in THF at 0° C. was added Phenylmagnesium chloride solution (3.4 ml, 6.7 mmol, 2.0 M in THF) and the reaction mixture allowed to warm to room temperature. Having stirred for 4 hours the solution was quenched (1N NaOH) and solvents removed in vacuo. The residue was partitioned between DCM and Rochelles salt (10% aq.) and the organic phase separated and aqueous re-extracted with DCM. The combined organics were then dried ($MgSO_4$) and concentrated. Purification by column chromatography (0-50% EtOAc:cyclohexane) provided the title compound [A040] as a white solid (416 mg, 80%). 1H-NMR (1H, 300 MHz, $CDCl_3$): 7.89 (2H, s, br), 7.57 (1H, s, br), 7.47 (2H, s, br), 5.53 (0.6H, s, br), 5.35 (0.4H, s, br), 4.53-4.38 (1H, m, br), 4.06 (0.6H, m, br), 3.87-3.80 (1.4H, m, br), 3.67-3.53 (1H, m, br), 3.41-3.29 (1H, m, br), 2.94-2.81 (1H, m, br), 1.55-1.12 (19H, m, br); LCMS method: 1, RT: 3.75 min, MI 391.32 [M+H]

Synthesis of (R)-2-(Hydroxy-phenyl-methyl)-piperazine-1,4-dicarboxylic acid di-tert-butyl ester [A041]

To a stirred suspension of (R)-2-Benzoyl-piperazine-1,4-dicarboxylic acid di-tert-butyl ester [A040](220 mg, 0.553 mmol) in MeOH (4 ml) was added sodium borohydride (41 mg, 1.11 mmol). After 2 hours the reaction mixture was partitioned between EtOAc and water, the organic phase separated and concentrated in vacuo to give the title compound [A041] as a white crystalline solid (210 mg, 97%). 1H-NMR (1H, 300 MHz, $CDCl_3$): 7.43-7.26 (5H, m), 4.74 (1H, s, br), 4.31-3.65 (4H, m), 3.25-2.81 (3H, m), 1.55-1.46 (18H, m), 1.13 (1H, s, br); LCMS method: 1, RT: 3.86 min, MI 393.32 [M+H]

Synthesis of (R)-2-(Fluoro-phenyl-methyl)-piperazine-1,4-dicarboxylic acid di-tert-butyl ester [A042]

To a stirred solution of (R)-2-(Hydroxy-phenyl-methyl)-piperazine-1,4-dicarboxylic acid di-tert-butyl ester [A041] (210 mg, 0.535 mmol) in $CHCl_3$ (3 ml) at 0 OC was added (Diethylamino)sulfur trifluoride (330 µl, 2.68 mmol). After 2 hours the reaction mixture was quenched with ice, basified with $NaHCO_3$ (to pH8), then the product extracted into DCM, which was evaporated to give a colourless oil. Purification was achieved by column chromatography (0-50% EtOAc:cyclohexane) to provide the title compound [A042] as a white solid (85 mg, 40%). 1H-NMR (1H, 300 MHz, $CDCl_3$): 7.34 (5H, m, br), 5.53 (1H, d, br), 4.38-3.84 (4H, m, br), 3.08-2.84 (3H, m, br), 1.49 (9H, s, br), 1.25 (9H, s, br); LCMS method: 1, RT: 3.68 min, MI 295.21 [M+H]

Synthesis of (R)-2-(Fluoro-phenyl-methyl)-piperazine [A036]

(R)-2-(Fluoro-phenyl-methyl)-piperazine-1,4-dicarboxylic acid di-tert-butyl ester [A042](85 mg, 0.215 mmol) was stirred in 4N HCl:dioxane (2 ml). After 2 hours the solution was dissolved in MeOH and loaded onto an SCX cartridge which was washed with MeOH followed by 2N $NH_3$:MeOH. Evaporation provided the title compound [A036] as a yellow gum (35 mg, 83%). 1H-NMR (1H, 300 MHz, d4-MeOH): 7.49-7.43 (5H, m), 5.25 (1H, d), 3.85 (1H, dd), 3.79-3.726 (1H, m), 3.20-3.14 (2H, m), 3.00-2.82 (3H, m).

Synthesis of (4-Fluoro-phenyl)-(R)-piperazin-2-yl-methanol [A043]

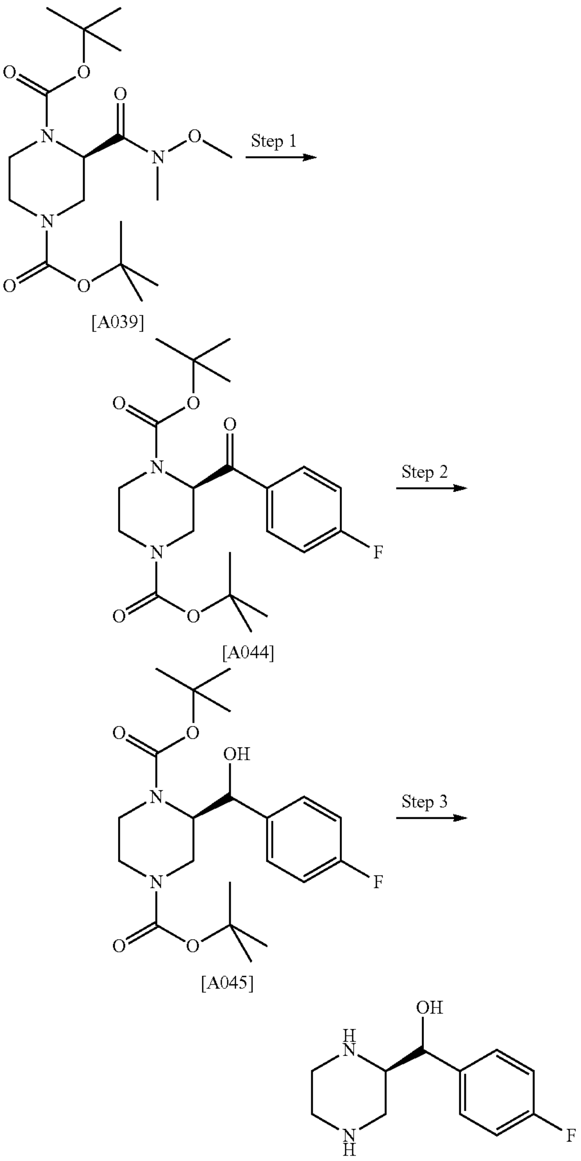

[A039]

[A044]

[A045]

[A043]

Synthesis of (R)-2-(4-Fluoro-benzoyl)-piperazine-1,4-dicarboxylic acid di-tert-butyl ester [A044]

To a stirred solution of (R)-2-(Methoxy-methyl-carbamoyl)-piperazine-1,4-dicarboxylic acid di-tert-butyl ester [A043](1.15 g, 3.08 mmol) in THF (24 ml) was added 4-Fluorophenylmagnesium bromide solution (2.0M in $Et_2O$, 7.7 ml, 15.4 mmol) and the reaction mixture allowed to warm to room temperature. Having stirred for 4 hours the reaction was quenched (1N NaOH) and solvents removed in vacuo. The residue was partitioned between DCM and Rochelles salt (10% aq). The organic phase was separated and aqueous phase re-extracted with DCM. Evaporation of the combined organics followed by purification by column chromatography (0-50% EtOAc:cyclohexane) gave the title compound [A044] as a pale yellow oil (800 mg, 64%). 1H-NMR (1H, 300 MHz, $CDCl_3$): 7.94 (2H, s, br), 7.15 (2H, s, br), 5.47 (1H, m, br), 4.48-4.32 (1H, m, br), 4.07-4.03 (1H, m, br), 3.91-3.76 (1H, m, br), 3.61-3.51 (1H, m, br), 3.43-3.31 (1H, m, br), 3.18-3.24 (1H, m, br), 1.56-1.17 (18H, m, br); LCMS method: 1, RT: 3.79 min, MI 409.32 [M+H]

Synthesis of (R)-2-[(4-Fluoro-phenyl)-hydroxy-methyl]-piperazine-1,4-dicarboxylic acid di-tert-butyl ester [A045]

To a stirred solution of (R)-2-(4-Fluoro-benzoyl)-piperazine-1,4-dicarboxylic acid di-tert-butyl ester [A044](520 mg, 1.28 mmol) in MeOH (8 ml) was added sodium borohydride at 0 OC and the reaction mixture allowed to warm to room temperature. After 2 hours the reaction mixture was partitioned between EtOAc and water, the organic phase separated and concentrated in vacuo to give a pale yellow oil. Purification by column chromatography (0-50% EtOAc: cyclohexane) provided the title compound [A045] as a white crystalline solid (330 mg, 63%). 1H-NMR (1H, 300 MHz, $CDCl_3$): 7.41-7.08 (5H, m), 4.74 (1H, m), 4.27-3.93 (3H, m), 3.64 (1H, m), 3.23-2.84 (1H, m), 1.45 (18H, m), 1.18 (1H, s, br).

Synthesis of (4-Fluoro-phenyl)-(R)-piperazin-2-yl-methanol [A043]

(R)-2-[(4-Fluoro-phenyl)-hydroxy-methyl]-piperazine-1,4-dicarboxylic acid di-tert-butyl ester [A045](330 mg, 0.808 mmol) was stirred in 4N HCl:dioxane (2 ml). After 2 hours the solution was dissolved in MeOH and loaded onto an SCX cartridge which was washed with MeOH followed by 2N $NH_3$:MeOH. Evaporation provided the title compound [A043] as a yellow gum which was used without further purification (170 mg, 100%).

Synthesis of N—[(S)-1-Benzyl-2-(2-pyridin-4-yl-pyrido[3,4-d]pyrimidin-4-ylamino)-ethyl]-formamide [78]

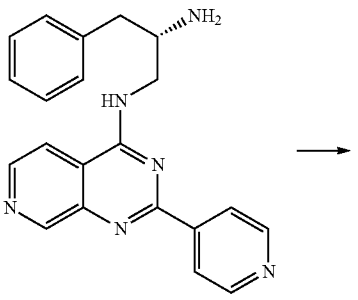

[6]

-continued

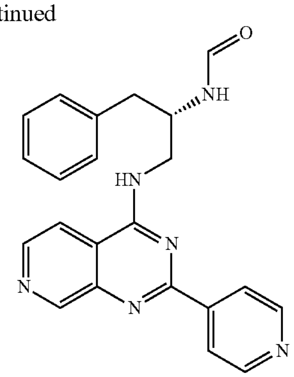

[78]

A mixture of (S)-3-Phenyl-N[1]-(2-pyridin-4-yl-pyrido[3,4-d]pyrimidin-4-yl)-propane-1,2-diamine [6](70 mg, 0.21 mmol) and ethylformate (1.5 mL, 18.6 mmol) was heated in the microwave at 100° C. for 1 hour. The reaction mixture was concentrated under vacuum, redissolved in methanol then loaded onto a methanol conditioned SCX-2 cartridge (5 g). The cartridge was washed with methanol (2ColVols) then eluted with 2N NH3 in methanol (2CV). The ammonia washes were evaporated to yield the title compound [78]: LCMS method: 1, RT: 3.87 min, MI 385 [M+H]; NMR: (1H, 300 MHz, d6-dmso) 9.17 (1H, s), 8.90-8.87 (1H, br t), 8.73 (2H, d), 8.63 (1H, d), 8.25 (2H, dd), 8.14 (1H, d), 8.04 (1H, br d), 7.97 (1H, br s), 7.327.20 (5H, m), 4.55-4.46 (1H, m), 3.98-3.90 (1H, m), 3.70-3.62 (1H, m), 3.00-2.93 (1H, dd), 2.85-2.77 (1H, dd)

Synthesis of N—[(S)-1-Benzyl-2-(2-pyridin-4-yl-pyrido[3,4-d]pyrimidin-4-ylamino)-ethyl]-acetamide [79]

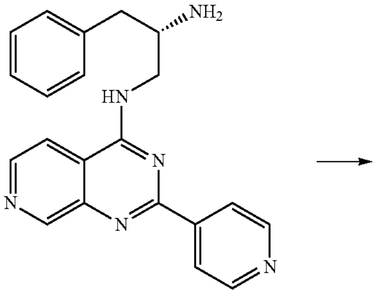

[6]

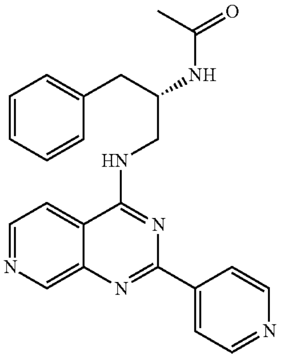

[79]

To a stirred solution of (S)-3-Phenyl-N[1]-(2-pyridin-4-yl-pyrido[3,4-d]pyrimidin-4-yl)-propane-1,2-diamine [6](70 mg, 0.21 mmol), DIPEA (73 ul, 0.42 mmol) and anhydrous DCM (5 mL) at room temperature was added acetic anhydride (29 μl, 0.31 mmol). The reaction mixture was concentrated under vacuum then redissolved in methanol plus formic acid (2 drops) and loaded onto a methanol conditioned SCX-2 cartridge (5 g). The cartridge was washed with methanol (2CV) then eluted with 2N $NH_3$ in methanol (2CV). The ammonia washes were evaporated to yield the title compound [79]: LCMS method: 1, RT: 3.92 min, MI 399 [M+H]; NMR: (1H, 300 MHz, d6-dmso) 9.17 (1H, s), 8.85 (1H, br t), 8.72 (2H, dd), 8.63 (1H, d), 7.85 (1H, dd), 7.30-7.17 (5H, m), 4.43-4.33 (1H, m), 4.01-3.92 (1H, m), 3.63-3.55 (1H, m), 2.90 (1H, dd), 2.80 (1H, dd), 1.70 (3H, s)

Synthesis of methyl[(2S)-1-phenyl-3-{[2-(pyridin-4-yl)pyrido[3,4-d]pyrimidin-4-yl]amino}propan-2-yl]amine [80]

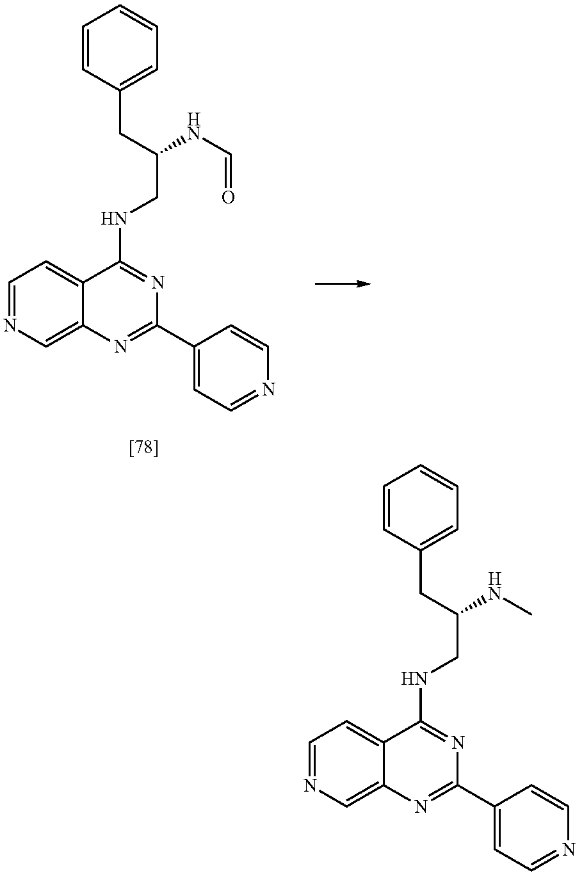

[78]

[80]

A stirred suspension of lithium aluminium hydride (19 mg, 0.5 mmol) in anhydrous THF (2.5 mL) was chilled to 0° C. N—[(S)-1-Benzyl-2-(2-pyridin-4-yl-pyrido[3,4-d]pyrimidin-4-ylamino)-ethyl]-formamide [78](40 mg, 0.1 mmol) in THF (2.5 mL) was added over five minutes. The reaction mixture was allowed to warm to room temperature and stirred for 18 h. A further portion of lithium aluminium hydride (10.5 mg, 0.28 mmol) was added to the reaction mixture and stirring continued at room temperature for 18 hours. Another portion of lithium aluminium hydride (30 mg, 0.79 mmol) was added to the reaction mixture and stirring continued at room temperature for a further 18 hours. This procedure was repeated on a second batch of N—[(S)-1-Benzyl-2-(2-pyridin-4-yl-pyrido[3,4-d]pyrimidin-4-ylamino)-ethyl]-formamide [78](40 mg, 0.234 mmol) and the crude reaction mixture combined and diluted with ether (20 mL), cooled to 0° C. and quenched by drop-wise addition of water (approx 150 μL), NaOH (approx 300 μL of a 2M solution) and water (approx 300 μL of a 2M solution) again. $MgSO_4$ was added and the mixture filtered and concentrated by rotary evaporation. The crude residue was purified by preparative HPLC (method A). The appropriate fractions were combined, the solvent evaporated and the residue was dissolved in MeOD resulting in precipitation of an impurity which was removed by filtration to give the title compound [80] (2.5 mg). LCMS method: 1, RT: 2.39 min, MI 371 [M+H]. $^1$H NMR (1H, 300 MHz, d6-dmso) 9.13 (1H, s), 8.64-8.62 (2H, m), 8.54 (1H, d), 8.21-8.19 (2H, m), 7.99 (1H, d), 7.32-7.21 (5H, m), 3.97-3.91 (1H, m), 3.78-3.71 (1H, m), 3.29-3.22 (1H, m), 3.05-2.99 (1H, m), 2.77-2.70 (1H, m).

Synthesis of (2S)-2-benzyl-4-[5-methoxy-2-(pyridin-4-yl)pyrido[3,4-d]pyrimidin-4-yl]-1-methylpiperazine; formic acid [81]

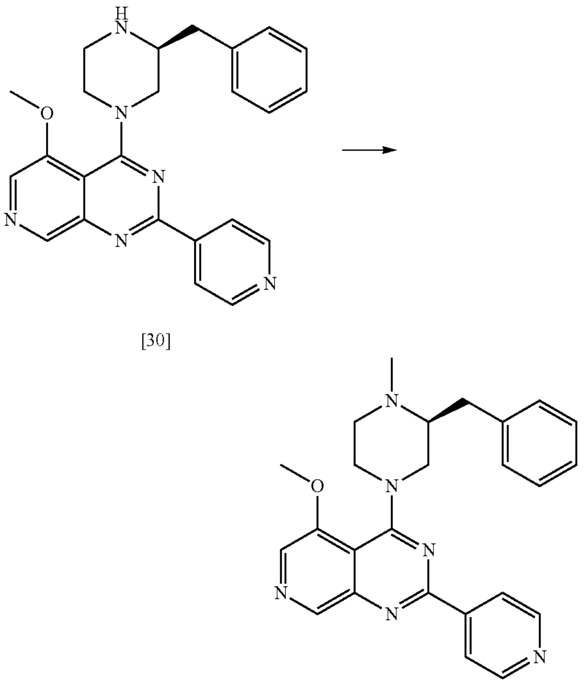

[30]

[81]

A stirred solution of 4-((S)-3-Benzyl-piperazin-1-yl)-5-methoxy-2-pyridin-4-yl-pyrido[3,4-d]pyrimidine [30] in $CH_2Cl_2$ (2 mL) was prepared. Paraformaldehyde (55 mg), acetic acid (6 mL, 0.121 mmol) and $CNBH_3$ (180 mg of MP-$CNBH_3$ with 2 mmol/g loading, 0.360 mmol) were added and the reaction was shaken at room temperature overnight. The resin was filtered off and the product was loaded onto a CSX cartridge, washing with methanol and eluting with ammonia in methanol. The ammonia fraction was concentrated and the residue purified then by prep LCMS. The appropriate fractions were combined and concentrated to give the title compound [81]. LCMS method: 1, RT: 2.74 min, MI 427.22 [M+H]; $^{1}$H NMR (1H, 300 MHz, $CDCl_3$) 8.95 (s, 1H), 8.73-8.71 (d, 2H), 8.29 (s, 1H), 8.13-8.11 (d, 2H), 8.06 (s, 1H), 7.37-7.35 (m, 3H), 7.22-7.19 (m, 2H), 4.28 (d, 1H), 4.07 (d, 1H), 3.82 (s, 3H), 3.72-3.63 (m, 1H), 3.34 (dd, 1H), 3.23-3.15 (m, 2H), 2.76-2.69 (m, 1H), 2.63 (s, 3H), 2.60-2.51 (m, 2H).

Synthesis of 2-{[(2S)-1-phenyl-3-{[2-(pyridin-4-yl)pyrido[3,4-d]pyrimidin-4-yl]amino}propan-2-yl]amino}acetamide [82]

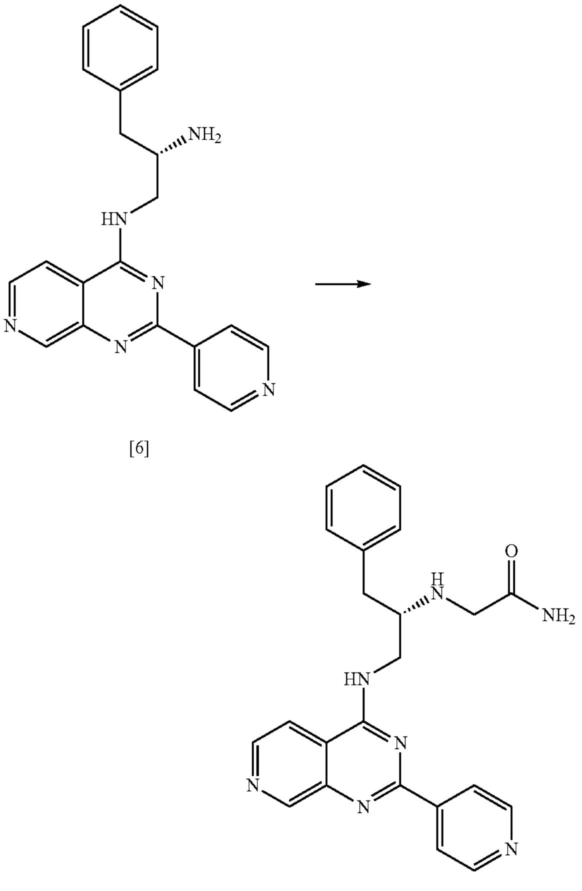

[6]

[82]

A mixture of N-[(2S)-2-amino-3-phenylpropyl]-2-(pyridin-4-yl)pyrido[3,4-d]pyrimidin-4-amine [6](100 mg, 0.28 mmol), 2-Bromoacetamide (38.5 mg, 0.28 mmol), and potassium carbonate (77.5 mg, 0.56 mmol) in DMF (5 mL) was stirred at room temperature for 3 days. A further portion of 2-Bromoacetamide (38.5 mg, 0.28 mmol) was added and the reaction mixture stirred for a further 24 h. The solvent was removed by rotary evaporation and the residue dissolved in methanol (2 mL), filtered then purified by preparative HPLC (method B). The appropriate fractions were combined, evaporated, triturated with diethyl ether and dried in the vac oven to give the title compound [82]: LCMS method: 1, RT: 4.49 min, MI 414 [M+H]; $^{1}$H NMR (1H, 300 MHz, d6-dmso) 9.16 (1H, s), 9.00 (1H, br m), 8.72-8.70 (2H, m), 8.64-8.62 (1H, m), 8.23-8.21 (1H, m), 8.10-8.08 (2H, m), 7.32-7.26 (5H, m), 7.03 (1H, br s), 3.89-3.81 (1H, m), 3.53-3.45 (1H, m).

Synthesis of N-(1-phenyl-3-{[2-(pyridin-4-yl)pyrido[3,4-d]pyrimidin-4-yl]amino}propan-2-yl)methanesulfonamide [83]

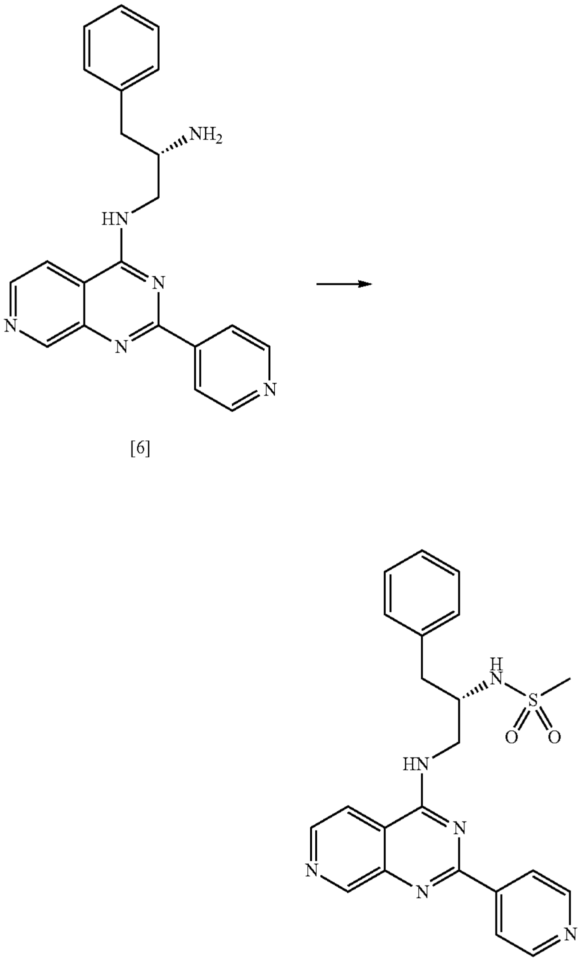

[6]

[83]

To a solution of N-[(2S)-2-amino-3-phenylpropyl]-2-(pyridin-4-yl)pyrido[3,4-d]pyrimidin-4-amine [6](100 mg, 0.28 mmol) and DIPEA (98 mL, 0.56 mmol) in $CH_2Cl_2$ (10 mL) at room temperature was added methane sulfonyl chloride (22 mL, 0.28 mmol). The reaction mixture was stirred at room temperature for 30 min, diluted with water and the organic phase separated, dried over $MgSO_4$ and purified by column chromatography on silica, eluting with $CH_2Cl_2$ containing 0-10% Methanol. The appropriate fractions were combined and concentrated to give the title compound [83]: LCMS method: 1, RT: 4.04 min, MI 435 [M+H]; $^{1}$H NMR (1H, 300 MHz, d6-dmso) 9.18 (1H, s), 8.92 (1H, br t), 8.73-8.71 (2H, m), 8.65 (1H, d), 8.22-8.20 (2H, m), 8.16 (1H, d), 7.39 (1H, br s), 7.33-7.31 (4H, m), 7.30-7.24 (1H, m), 3.93-3.88 (2H, m), 3.69-3.61 (1H, m), 2.99-2.92 (1H, m), 2.83-2.76 (1H, m), 2.35 (3H, s).

Synthesis of (1-phenyl-3-{[2-(pyridin-4-yl)pyrido[3,4-d]pyrimidin-4-yl]amino}propan-2-yl)urea [84]

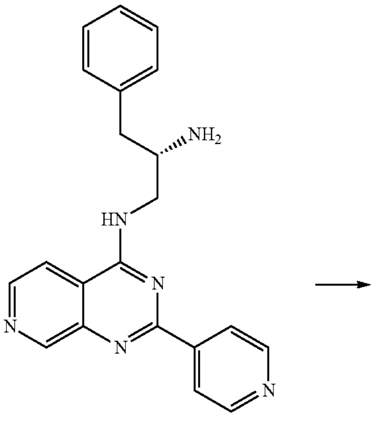

[6]

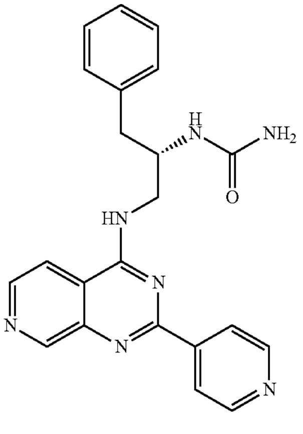

[84]

A mixture of N-[(2S)-2-amino-3-phenylpropyl]-2-(pyridin-4-yl)pyrido[3,4-d]pyrimidin-4-amine [6](100 mg, 0.28 mmol), potassium cyanate (227 mg, 2.8 mmol), and acetic acid (4 mL) in water (4 mL) was stirred at 50° C. for 3 hours. A further portion of potassium cyanate (227 mg, 2.8 mmol) was added and the reaction mixture heated in a sealed tube in the microwave at 100° C. for 30 min. The reaction mixture was concentrated under vacuum then partitioned between ethyl acetate and water. The target material was found to partially precipitate on the internal surface of the separating funnel. This solid was collected and combined with the organic layer which was evaporated to dryness then dissolved in DMSO/Methanol (1 mL), the target material started to precipitate, water (2 mL) was added and the solid was collected by filtration then dried in the vac oven to give (the title compound [84]: LCMS method: 1, RT: 4.54 min, MI 398 [M+H]; $^{1}H$ NMR (1H, 300 MHz, d6-dmso) 9.18 (1H, s), 8.99 (1H, br t), 8.74-8.72 (2H, m), 8.64 (1H, d), 8.28-8.25 (2H, m), 8.12 (1H, d), 7.32-7.19 (5H, m), 6.05 (1H, d), 5.48 (2H, s), 4.29-4.23 (1H, m), 3.88-3.80 (1H, m), 3.69-3.60 (1H, m), 2.94-2.88 (1H, m), 2.83-2.76 (1H, m).

Synthesis of 3-ethyl-1-(1-phenyl-3-{[2-(pyridin-4-yl)pyrido[3,4-d]pyrimidin-4-yl]amino}propan-2-yl) urea [85]

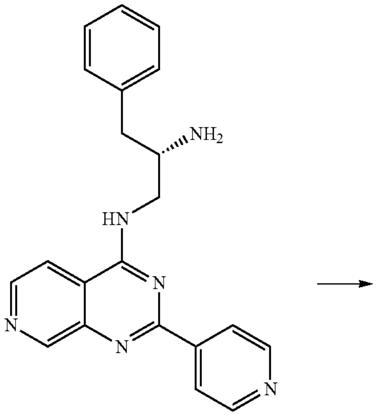

[6]

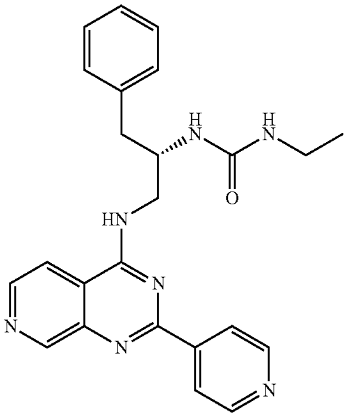

[85]

A solution of N-[(2S)-2-amino-3-phenylpropyl]-2-(pyridin-4-yl)pyrido[3,4-d]pyrimidin-4-amine [6](100 mg, 0.28 mmol) and ethyl isocyanate (19 mg, 0.27 mmol) in $CH_2Cl_2$ (5 mL) was stirred at room temperature for 1 h. The reaction mixture was concentrated by rotary evaporation and the residue purified by column chromatography on silica, eluting with $CH_2Cl_2$ containing 0-10% MeOH. The appropriate fractions were combined, evaporated and the residue triturated with diethyl ether then dried in the vacuum oven to give the title compound [85]. LCMS method: 1, RT: 4.20 min, MI 428 [M+H]; $^{1}H$ NMR (1H, 300 MHz, d6-dmso) 9.17 (1H, s), 8.94 (1H, br t), 8.74-8.72 (2H, m), 8.64 (1H, d), 8.28-8.24 (2H, m), 8.13 (1H, d), 7.32-7.20 (5H, m), 5.86 (1H, d), 5.79 (1H, t), 4.29-4.22 (1H, m), 3.90-3.83 (1H, m), 3.70-3.61 (1H, m), 2.94-2.77 (2H, m), 0.84 (3H, t).

Synthesis of (3aR)-5-[5-methoxy-2-(pyridin-4-yl) pyrido[3,4-d]pyrimidin-4-yl]-hexahydro-1H-[1,3] oxazolo[3,4-a]piperazin-1-one [86]

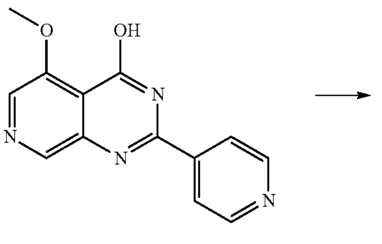

[A003]

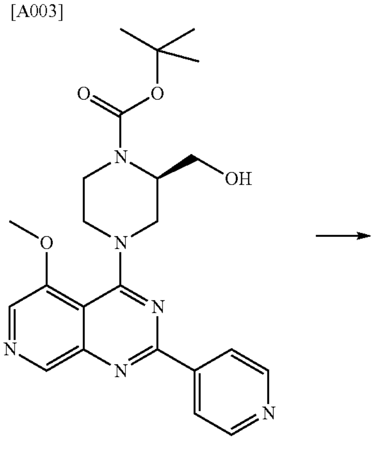

[A046]

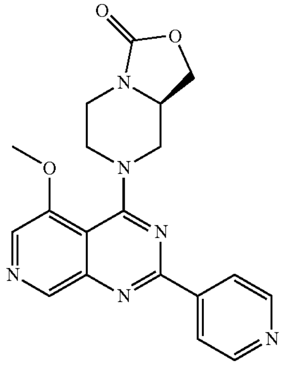

[86]

(R)-2-Benzyl-4-(5-methoxy-2-pyridin-4-yl-pyrido[3, 4-d]pyrimidin-4-yl)-piperazine-1-carboxylic acid tert-butyl ester [A046]

To a solution of 2-Pyridin-4-yl-pyrido[2,3-d]pyrimidin-4-ol [A003](0.2 g, 0.78 mmol) in DMA 93 mL), 2,4,6-Triisopropylbenzenesulfonyl chloride (0.26 g, 0.86 mmol), $Et_3N$ (0.22 mL, 1.57 mmol) and DMAP (10 mg) were added successively. The mixture was stirred at rt for 2 h and (R)-2-Hydroxymethyl-piperazine-1-carboxylic acid tert-butyl ester (0.2 g, 0.94 mmol) was added. The reaction was stirred overnight and the solvent was removed under reduced pressure. The product was purified by flash chromatography using 0 to 8% MeOH/DCM to give the title compound [A046](0.14 g, 39% yield). LCMS method: 1, RT: 4.41 min, MI 453.27 [M+H].

(3aR)-5-[5-methoxy-2-(pyridin-4-yl)pyrido[3,4-d] pyrimidin-4-yl]-hexahydro-1H-[1,3]oxazolo[3,4-a] piperazin-1-one [86]

A solution of (R)-2-Hydroxymethyl-4-(5-methoxy-2-pyridin-4-yl-pyrido[3,4-d]pyrimidin-4-yl)-piperazine-1-carboxylic acid tert-butyl ester [A046](20 mg, 0.044 mmol) in $CH_2Cl_2$ was added drop-wise to a stirred solution of DAST (11 mL, 0.088 mmol) in $CH_2Cl_2$ (3 mL) at 0° C. The reaction mixture was warmed to room temperature and stirred overnight. Aqueous $NaHCO_3$ was added the organic phase separated, loaded onto a SCX cartridge, washed with MeOH and eluted with ammonia in methanol. The product was purified purified by preparative HPLC (method A). The appropriate fractions were combined and concentrated to give the title compound [86]: LCMS method: 1, RT: 2.95 min, MI 379 [M+H]; $^1$H, NMR (1H, 300 MHz, $CDCl_3$): 9.03 (s, 1H), 8.60 (d, 2H), 8.29 (d, 2H), 8.24 (s, 1H), 4.50 (m, 2H), 4.18 (d, 1H), 4.09 (m, 4H), 3.97 (dd, 1H), 3.31 (td, 1H), 3.16 (td, 1H), 3.10 (dd, 1H).

Example [87]: Synthesis of 2-{4-[5-methoxy-2-(pyridin-4-yl)pyrido[3,4-d]pyrimidin-4-yl]piperazin-1-yl}acetonitrile [87]

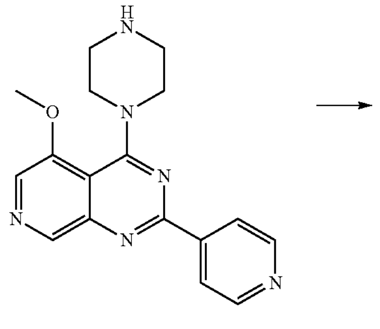

[31]

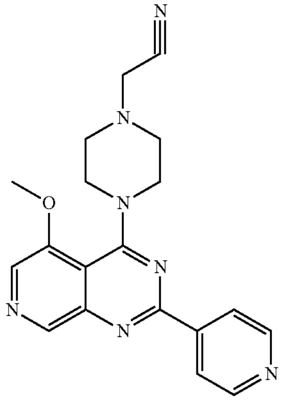

[87]

To a stirred mixture of 1-[5-methoxy-2-(pyridin-4-yl) pyrido[3,4-d]pyrimidin-4-yl]piperazine [31](90 mg, 0.28 mmol) and $NEt_3$ (78 mL, 0.56 mmol) in DMA (2 mL) was added Chloroacetonitrile (26 mL, 0.42 mmol) and the mixture was stirred at room temperature overnight. The crude reaction mixture was diluted with water and extracted with $CH_2Cl_2$ (2×5 mL), the organic extracts were combined washed with sat $NaHCO_3$ (2×10 mL) brine (10 mL) dried $MgSO_4$ filtered and evaporated to give a brown oil which was purified by SXC-2 ion exchange (1 g) to give the title compound [87] as a pale yellow solid (0.085 g, 90% yield). LCMS method: 1, RT: 4.90 min, MI 362 [M+H]; $^1$H NMR (1H, 300 MHz, $CDCl_3$): 9.02 (1H, s), 8.97-8.77 (2H, m), 8.36-8.34 (2H, m), 8.22 (s, 1H), 4.11 (3H, s), 3.81 (4H, br t), 3.65 (2H, s), 2.83 (4H, br t).

General Synthesis of 2-Substituted-Piperazine Derivatives of General Formula [F-008b] Scheme A2

2-substituted piperazine derivatives of general formula [F-008b] were prepared by the reaction of (R)-1,1-Dioxo-tetrahydro-2-oxa-1λ$^6$-thia-5,7a-diaza-indene-5-carboxylic acid tert-butyl ester [A049] with a phenol in the presence of a strong base such as sodium hydride or potassium cyanide in a polar aprotic solvent such as DMF to give the 2-substituted piperazine derivatives of general formula [F-008a]. After reaction work up, typically by a liquid-liquid extraction or purification by acidic ion exchange catch-release resin, followed by chromatographic purification. The N-Boc derivatives of general formula [F-008a] were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC to give the 2-substituted-piperazine derivatives of general formula [F-008b].

Scheme A2

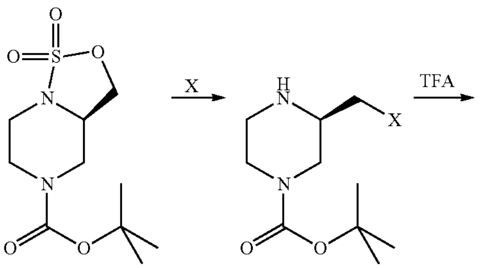

[A049] [F-008a]

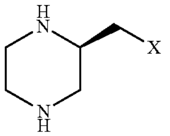

[F-008b]

Synthesis of (R)-2-Phenoxymethyl-piperazine [A047]

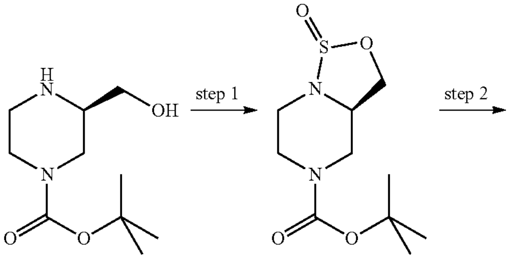

[A048]

-continued

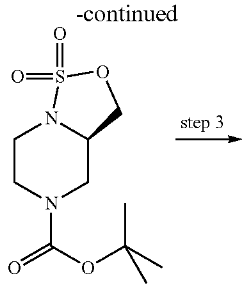

[A049]

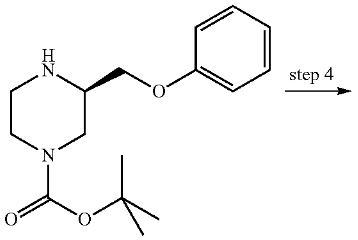

[A050]

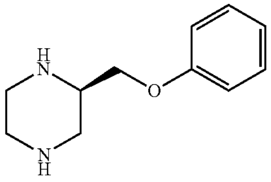

[A047]

(R)-1-Oxo-tetrahydro-2-oxa-1λ$^4$-thia-5,7a-diaza-indene-5-carboxylic acid tert-butyl ester [A048]

A solution of (R)-3-Hydroxymethyl-piperazine-1-carboxylic acid tert-butyl ester (5.00 g, 23.118 mmol) in $CH_2Cl_2$ (330 mL) was prepared and cooled to 0° C. Imidazole (6.295 g, 92.472 mmol) and triethylamine (7.06 mL, 50.860 mmol) were added followed drop-wise addition of thionyl chloride (1.94 mL, 26.586 mmol) as a solution in $CH_2Cl_2$ (20 mL) over 20 min. The reaction mixture was allowed to warm to room temperature (ice bath not removed) and the reaction mixture stirred at room temperature for 3 days. The reaction mixture was diluted with water (250 mL) and the organic phase separated. The aqueous phase was extracted with $CH_2Cl_2$ (3×50 mL) and the combined organic portions dried over $MgSO_4$, filtered and concentrated by rotary evaporation. The residue was purified by chromatography on silica, eluting with cyclohexane containing 0-50% EtOAc. The appropriate fractions were combined and concentrated to give the title compound [A048](5.196 g, 86%) as a pale yellow oil that solidified on standing. $^1$H NMR (1H, 400 MHz, d6-dmso) 4.81 (1H, dd), 4.58 (1H, dd), 4.44 (1H, dd), 4.28 (1H, br d), 4.12 (1H, br d), 4.02 (1H, br d), 3.93-3.87 (2H, m), 3.67-3.56 (2H, m), 3.46-3.34 (2H, m), 3.14-3.06 (1H, d), 3.01-2.69 (4H, br m), 2.55 (1H, dt), 1.42 (s, 9H), 1.41 (s, 9H).

(R)-1,1-Dioxo-tetrahydro-2-oxa-1λ$^6$-thia-5,7a-diaza-indene-5-carboxylic acid tert-butyl ester [A049]

A stirred solution of (R)-1-Oxo-tetrahydro-2-oxa-1λ$^4$-thia-5,7a-diaza-indene-5-carboxylic acid tert-butyl ester [A048](2.99 g, 11.409 mmol) in anhydrous MeCN (25 mL) was prepared under nitrogen and cooled to 0° C. Sodium (meta)periodate (2.464 g, 11.523 mmol) was added followed by ruthenium (III) chloride hydrate (24 mg, 0.114 mmol) (reaction mixture turns brown) and water (25 mL). The reaction mixture was stirred at 0° C. for 10 min and then removed from ice bath and stirred at room temperature for 10 min. TLC shows complete conversion to a new, slightly more polar spot. The reaction mixture was diluted with sat. $NaHCO_3$ (aq) (100 mL) and extracted with $CH_2Cl_2$ (3×40 mL). The combined organic extracts were dried and concentrated by rotary evaporation. The residue was purified by chromatography on silica, eluting with cyclohexane containing 0-50% EtOAc to give the title compound [A049] (1.72 g, 54%) as a pale yellow solid. $^1H$ NMR (1H, 500 MHz, $CDCl_3$) 4.63 (1H, dd), 4.25-4.07 (3H, overlapping t and broad m), 3.67-3.61 (1H, m), 3.45 (1H, br. d, J=11.2 Hz), 3.13 (1H, br. s), 2.98-2.94 (2H, br. m), 1.47 (9H, s).

(R)-3-Phenoxymethyl-piperazine-1-carboxylic acid tert-butyl ester [A050]

A solution of (R)-1,1-Dioxo-tetrahydro-2-oxa-1λ$^6$-thia-5,7a-diaza-indene-5-carboxylic acid tert-butyl ester [A049] (200 mg, 0.719 mmol) in anhydrous DMF (5 mL) was prepared under nitrogen. Sodium phenolate (88 mg, 0.754 mmol) was added and the reaction mixture heated to 50° C. overnight. A further 0.25 equivalents of sodium phenolate was added and heating continued for a further 5 hours. The reaction mixture was cooled to room temperature and 2 mL of 2M HCl (aq) was added. The mixture was stirred at room temperature for 1 hour. The reaction mixture was loaded onto a 10 g SCX cartridge, washing with methanol and eluting with 7N ammonia in MeOH. The ammonia fractions were combined and concentrated under reduced pressure. The residue was purified by chromatography on silica, eluting with $CH_2Cl_2$ containing 0-10% MeOH. The appropriate fractions were combined and concentrated to give the title compound [A00?](75 mg, 36%) as a colourless oil. LCMS method: 1, RT: 2.85 min, MI 293 [M+H]; $^1H$ NMR (1H, 500 MHz, $CDCl_3$) 7.31-7.24 (2H, m), 6.97 (1H, t), 6.91 (2H, d), 4.05 (1H, br s), 3.97-3.95 (2H, m), 3.88-3.85 (1H, m), 3.09 (1H, br s), 3.04-3.01 (1H, br m), 2.96-2.91 (1H, br m), 2.83-2.74 (1H, br m), 2.74 (1H, br s), 2.14 (1H, br s) 1.48 (9H, s).

(R)-2-Phenoxymethyl-piperazine [A047]

A solution of (R)-3-Phenoxymethyl-piperazine-1-carboxylic acid tert-butyl ester [A050](98 mg, 0.332 mmol) in anhydrous dioxane (1 mL) was prepared and 4M HCl in dioxane (5 mL) was added. The reaction mixture was stirred at room temperature for 2 hours. The reaction mixture was concentrated by rotary evaporation to give a pale pink solid. The product was dissolved in MeOH and loaded onto a SCX cartridge, washing with MeOH and eluting with 7N ammonia in MeOH. The ammonia fraction was concentrated by rotary evaporation to give the title compound [A047](58 mg, 91%) as a pale oil that crystalised on standing. LCMS method: 1, RT: 0.56 min, MI 193 [M+H]; $^1H$ NMR (1H, 500 MHz, $CDCl_3$) 7.30-7.27 (2H, m), 6.97-6.94 (1H, m), 6.91-6.90 (2H, m), 3.92-3.90 (1H, m), 3.83-3.83 (1H, m), 3.17-3.12 (1H, m), 3.07-3.03 (2H, m), 2.99-2.96 (1H, m), 2.92-2.87 (1H, m), 2.84-2.79 (1H, m) 2.63 (1H, dd).

Synthesis of (R)-2-(2-Fluoro-phenoxymethyl)-piperazine [A051]

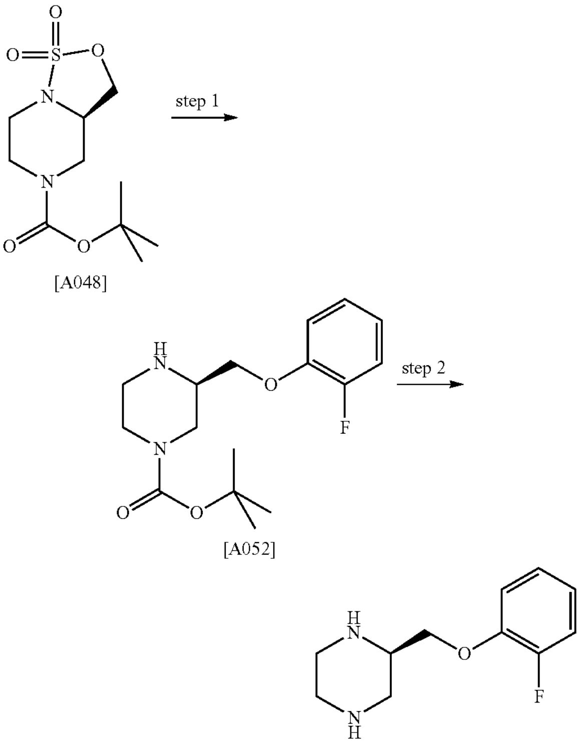

[A048]

[A052]

[A051]

(R)-3-(2-Fluoro-phenoxymethyl)-piperazine-1-carboxylic acid tert-butyl ester [A052]

A suspension of sodium hydride (69 mg, 1.726 mmol) in anhydrous DMF (5 mL) was prepared and 2-fluorophenol (0.15 mL, 1.726 mmol) added dropwise. The reaction mixture was stirred at room temperature for 10 min then (R)-1,1-Dioxo-tetrahydro-2-oxa-1λ$^6$-thia-5,7a-diaza-indene-5-carboxylic acid tert-butyl ester [A051](400 mg, 1.438 mmol) was added. The reaction mixture was heated to 50° C. overnight. The reaction mixture was cooled to room temperature and 2M HCl (aq) (1.4 mL, 2.875 mmol) was added. The reaction mixture was stirred at room temperature for 1.5 h. The reaction mixture was loaded onto a SCX cartridge, washing with methanol and eluting with 7N ammonia in MeOH. The ammonia fractions were combined and concentrated by rotary evaporation. The residue was purified by chromatography on silica, eluting with $CH_2Cl_2$ containing 0-10% MeOH. The appropriate fractions were combined and concentrated to give the title compound [A052](318 mg, 71%) as a colourless oil. LCMS method: 1, RT: 2.92 min, MI 311 [M+H]; $^1H$ NMR (1H, 500 MHz, $CDCl_3$) 7.10-7.04 (2H, m), 6.99-6.91 (2H, m), 4.04-3.89 (4H, m and overlapping br s), 3.14-3.11 (1H, m), 3.03 (1H, br d), 2.96 (1H, br t), 2.83-2.79 (1H, m), 2.75 (1H, br s), 2.23 (1H, br s), 1.48 (9H, s).

(R)-2-(2-Fluoro-phenoxymethyl)-piperazine [A051]

Following the procedure described in scheme A2, (R)-3-(2-Fluoro-phenoxymethyl)-piperazine-1-carboxylic acid tert-butyl ester [A052](310 mg, 1.00 mmol) was treated with 4M HCl in dioxane (2 mL) to give the title compound [A051](196 mg, 93%) as a pale yellow oil. LCMS method: 1, RT: 0.75 min, MI 211 [M+H]; LCMS method 1LCMS5, RT: 0.75 min, MI: 211 [M+1]. $^1$H NMR (1H, 500 MHz, $CDCl_3$) 7.10-7.03 (2H, m), 6.98-6.89 (2H, m), 4.00-3.97 (1H, m), 3.91-3.88 (1H, m), 3.23-3.18 (1H, m), 3.08-3.03 (2H, m), 3.00-2.98 (1H, m), 2.94-2.89 (1H, m), 2.85-2.80 (1H, m), 2.66-2.61 (1H, m).

Synthesis of (R)-2-(4-Fluoro-phenoxymethyl)-piperazine [A053]

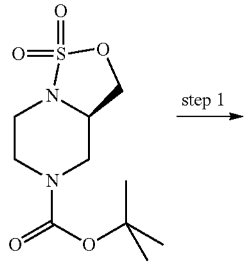

[A048]

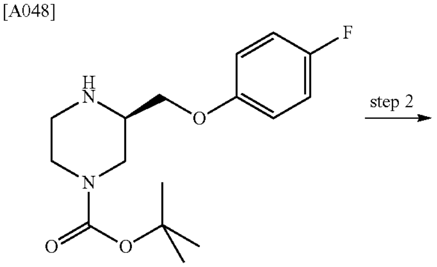

[A054]

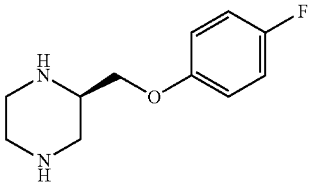

[A053]

(R)-3-(4-Fluoro-phenoxymethyl)-piperazine-1-carboxylic acid tert-butyl ester [A054]

Following the procedure described in Scheme A2 step 1, (R)-1,1-Dioxo-tetrahydro-2-oxa-1λ$^6$-thia-5,7a-diaza-indene-5-carboxylic acid tert-butyl ester [A048](400 mg, 1.438 mmol) was reacted with 4-fluorophenol (193 mg, 1.726 mmol) to give the title compound [A054](100 mg, 22%) as a colourless oil. LCMS method: 1, RT: 3.00 min, MI 311 [M+H]. $^1$H NMR (1H, 500 MHz, $CDCl_3$) 6.99-6.96 (2H, m), 6.85-6.83 (2H, m), 4.06 (1H, br s), 3.95 (1H, br s), 3.95-3.90 (1H, m), 3.84-3.80 (1H, m), 3.10-3.05 (1H, m), 3.03 (1H, br d), 2.93 (1H, br t), 2.83-2.78 (1H, m), 2.72 (1H, br s), 2.10 (1H, br s), 1.48 (9H, s).

(R)-2-(4-Fluoro-phenoxymethyl)-piperazine [A053]

Following the procedure described in example Scheme A2, step 4, (R)-3-(4-Fluoro-phenoxymethyl)-piperazine-1-carboxylic acid tert-butyl ester [A054](100 mg, 0.322 mmol) was treated with 4M HCl in dioxane (2 mL) to give the title compound [A053](68 mg, 100%) as a colourless oil that solidified on standing. LCMS method: 1, RT: 0.59 min, MI 211 [M+H]; $^1$H NMR (1H, 500 MHz, $CDCl_3$) 6.99-6.95 (2H, m), 6.85-6.82 (2H, m), 3.88-3.86 (1H, m), 3.81-3.78 (1H, m), 3.15-3.10 (1H, m), 3.05-3.02 (2H, m), 2.98-2.96 (1H, m), 2.91-2.86 (1H, m), 2.83-2.78 (1H, m), 2.63-2.58 (1H, m).

Synthesis of (S)-Piperazin-2-yl-acetonitrile [A055]

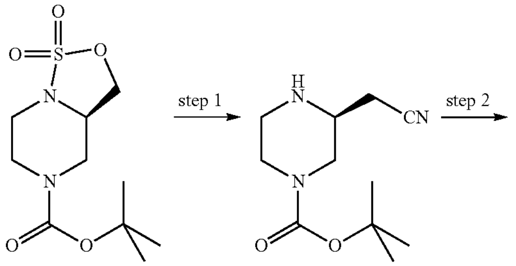

[A048] [A056]

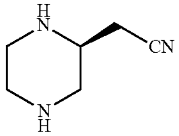

[A055]

(S)-3-Cyanomethyl-piperazine-1-carboxylic acid tert-butyl ester [A056]

Following the procedure described in Scheme A1, step 3, (R)-1,1-Dioxo-tetrahydro-2-oxa-1λ$^6$-thia-5,7a-diaza-indene-5-carboxylic acid tert-butyl ester [A048](1.52 g, 5.46 mmol) was reacted with KCN (356 mg, 5.46 mmol) to give the title compound [A056](850 mg, 69%). $^1$H NMR (1H, 500 MHz, $CDCl_3$) 3.95 (1H, br s), 3.84 (1H, br d), 3.03-2.92 (3H, m), 2.82-2.75 (1H, m), 2.70 (1H, br s), 2.51-2.41 (2H, m), 1.49 (9H, s). LCMS method: 1, RT: 1.39 min, MI 226 [M+H].

(S)-Piperazin-2-yl-acetonitrile [A055]

Following the procedure described in example Scheme A2, step 4, (S)-3-Cyanomethyl-piperazine-1-carboxylic acid tert-butyl ester [A056](800 mg, 3.55 mmol) was treated with 4M HCl in dioxane to give the title compound [A055](434 mg, 98%) as a pale orange solid. LCMS method: 1, RT: 0.49 min, MI 126 [M+H]; $^1$H NMR (1H, 500 MHz, $CDCl_3$) 3.06-2.99 (3H, m), 2.93-2.90 (1H, m), 2.87-2.82 (1H, m), 2.77-2.72 (1H, m), 2.56-2.51 (1H, m), 2.44-2.42 (2H, m).

Synthesis of Phenyl-(S)-piperidin-3-yl-amine [A057]

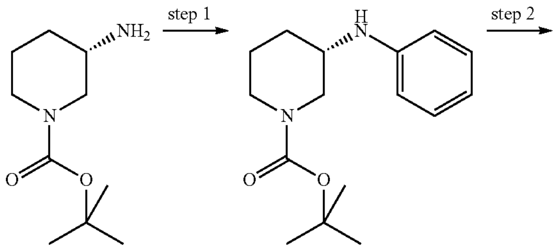

[A058]

-continued

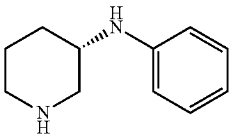

[A057]

(S)-3-Phenylamino-piperidine-1-carboxylic acid tert-butyl ester [A058]

A solution of (S)-3-Amino-piperidine-1-carboxylic acid tert-butyl ester (500 mg, 2.497 mmol), Pd2(dba)3 (95 mg, 0.104 mmol) and 2-Dicyclohexylphosphino-2'-(N,N-dimethylamino)biphenyl (61 mg, 0.156 mmol) in toluene (5 mL) was prepared under nitrogen. The solvent was degasses and sodium tert-butoxide (280 mg, 2.912 mmol) was added followed by bromobenzene (0.22 mL, 2.080 mmol). The reaction mixture was heated to 100° C. for 24 h. The reaction mixture was cooled to room temperature and concentrated by rotary evaporation. The residue was filtered through a plug of silica, eluting with $CH_2Cl_2$. The eluent was concentrated by rotary evaporation. The crude residue was purified by chromatography on silica, eluting with cyclohexane containing 5-50% EtOAc. The appropriate fractions were combined and concentrated to give the title compound [A058](535 mg, 78%) as a pale yellow oil that solidified on standing. LCMS method: 1, RT: 5.51 min, MI 227 [M+H]; $^1H$ NMR (1H, 500 MHz, $CDCl_3$) 7.20-7.17 (2H, m), 6.71 (1H, t), 6.64 (2H, d), 4.02 (1H, br s), 3.74-3.70 (1H, m), 3.63 (1H, br s), 3.39 (1H, br m), 3.09 (1H, br m), 2.89 (1H, br s), 2.02-1.99 (1H, m), 1.78-1.73 (1H, m), 1.59-1.51 (2H, m), 1.46 (9H, s).

Phenyl-(S)-piperidin-3-yl-amine [A057]

Following the procedure described in Scheme A2, step 4, (S)-3-phenylamino-piperidine-1-carboxylic acid tert-butyl ester [A058](138 mg, 0.5 mmol) was treated with 4 HCl in dioxane (2 mL) to give the title compound [A057](85 mg, 97%) as a pale yellow oil. LCMS method: 1, RT: 0.96 min, MI 177 [M+H].

General Synthesis of 8-Substituted-1-Yl-2-Pyridin-4-Yl-Pyrido[3,4-d]Pyrimidine Derivatives of General Formula [F-011] Scheme A3

4-Substituted 8-Chloro-2-pyridin-4-yl-pyrido[3,4-d]pyrimidin derivatives of general formula [F-010] were prepared by the reaction of a 8-Chloro-2-pyridin-4-yl-pyrido[3,4-d]pyrimidin-4-ol derivative of general formula [F-009] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-8-Chloro-2-pyridin-4-yl-pyrido[3,4-d]pyrimidini-4-yl ester was then reacted with a primary or secondary amino derivative, of general formula [F-003], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the crude reaction product was purified by normal phase chromatography or reverse phase preparative HPLC. The 4-Substituted 8-Chloro-2-pyridin-4-yl-pyrido[3,4-d]pyrimidin derivatives of general formula [F-010] were reacted in a Suzuki type reaction utilising a suitable boronic acid or boronic ester, of general formula [F-012], a palladium catalyst such as $Pd(PPh_3)_4$ or $Pd(PPh_3)_2Cl_2$a base such as $Et_3N$, KOH, $Na_2CO_3$ or NaOH in a polar solvent such as EtOH, THF, DMA or dioxane at high temperature either by heating thermally or using a microwave reactor. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase chromatography or reverse phase preparative HPLC.

Scheme A3

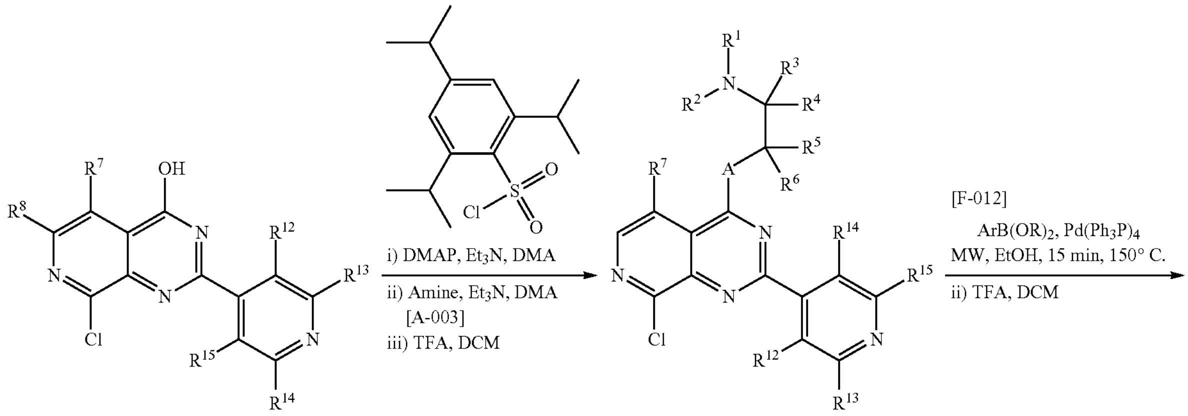

[F009]

[F-010]

-continued

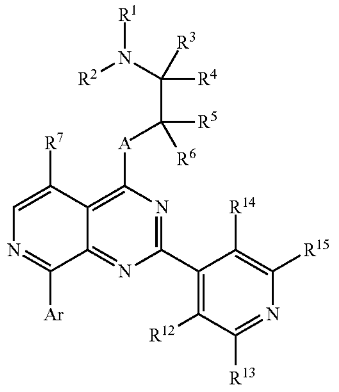

[F-011]

Synthesis of N-{3-[4-((S)-2-Amino-3-phenyl-propylamino)-2-pyridin-4-yl-pyrido[3,4-d]pyrimidin-8-yl]-phenyl}-methanesulfonamide [88]

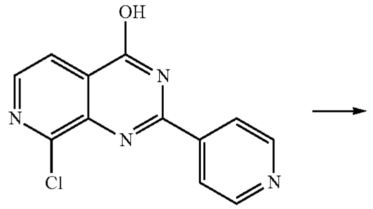

[A005]

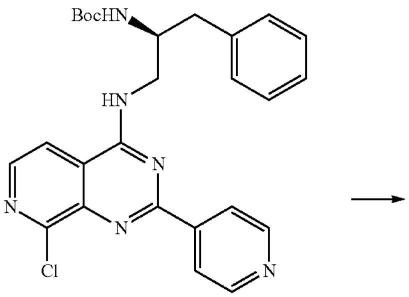

[A059]

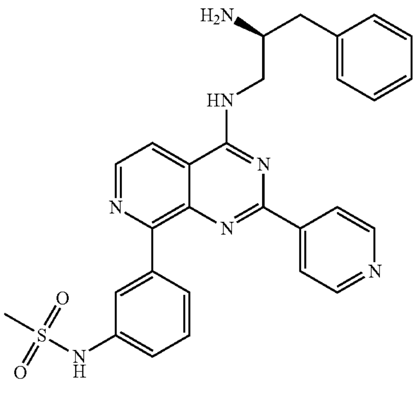

[88]

[(S)-1-Benzyl-2-(8-chloro-2-pyridin-4-yl-pyrido[3,4-d]pyrimidin-4-ylamino)-ethyl]-carbamic acid tert-butyl ester [A059]

To a solution of 2-Pyridin-4-yl-pyrido[2,3-d]pyrimidin-4-ol [A005](1 g, 3.8 mmol) in DMA (15 mL), 2,4,6-Triisopropylbenzenesulfonyl chloride (1.3 g, 4.25 mmol), $Et_3N$ (1.1 mL, 7.73 mmol) and DMAP (0.1 g) were added successively. The mixture was stirred at rt for 1 h then ((S)-2-Amino-1-benzyl-ethyl)-carbamic acid tert-butyl ester (1.16 g, 4.64 mmol) was added. The reaction was stirred overnight and the solvent was removed under reduced pressure and the crude mixture was purified by flash chromatography (SP1 [eluent: DCM/MeOH: 1/0 then 95/5 then 9/1]) to give the title compound: LCMS method: 1, RT: 5.76 min, MI 492 [M+H]

N-{3-[4-((S)-2-Amino-3-phenyl-propylamino)-2-pyridin-4-yl-pyrido[3,4-d]pyrimidin-8-yl]-phenyl}-methanesulfonamide [88]

A microwave vial was charged with [(S)-1-Benzyl-2-(8-chloro-2-pyridin-4-yl-pyrido[3,4-d]pyrimidin-4-ylamino)-ethyl]-carbamic acid tert-butyl ester [A059](0.07 g, 0.142 mmol), 3-(methanesulfonylamino)phenylboronic acid pinacol ester (0.06 g, 0.2 mmol), $Pd(Ph3P)_4$ (0.017 g, 0.014 mmol), aq K3PO4 (0.5M, 0.57 mL, 0.28 mmol) and DMA (1 mL). The vial was heated under microwave irradiations (150° C., 10 min). The solvent was removed under reduced pressure. The crude was purified by Column chromatography (Eluent: DCM/MeOH: 1:0 to 9/1). The purified compound was solubilised in DCM (2 mL) and TFA (0.5 mL) was added. The solution was stirred 3 h and then was poured onto SCX2 column, washed with MeOH and the expected product was released using a solution MeOH/NH3 2M which was used without further purification to give the title compound [88]: LCMS method: 1, RT: 3.01 min, MI 526 [M+H]; NMR 1H (1H, 300 MHz, d6-dmso) 8.70 (d, 2H), 8.68 (d, 1H), 8.25 (d, 2H), 8.14 (d, 1H), 8.04 (d, 2H), 7.37-7.24 (m, 7H), 3.91-3.86 (m, 1H), 3.46-3.33 (m, 2H), 3.10 (s, 3H), 2.77-2.69 (m, 2H).

The following compounds were synthesised according to the general synthesis shown in scheme [A3]:

| Ex | SM | Boronic acid | Analysis | | Name |
|---|---|---|---|---|---|
| 89 | [A059] | 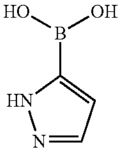 | Method 1: RT: 3.01 min, MI: 423 [M + H] | (1H, 300 MHz, d6-dmso) 8.76 ppm (2H, dd), 8.67 ppm (1H, d), 8.29 ppm (1H, s), 8.15 ppm (1H, d), 8.08 ppm (2H, dd), 7.71 ppm (1H, d), 7.61 ppm (1H, d), 7.41-7.30 ppm (5H, m), 3.97 ppm, (1H, d), 3.58 ppm (2H, br s), 3.35 ppm (2H, m), 2.97-2.80 ppm (2H, m) | N-[(2S)-2-amino-3-phenylpropyl]-8-(1H-pyrazol-5-yl)-2-(pyridin-4-yl)pyrido[3,4-d]pyrimidin-4-amine |
| 90 | [A059] | 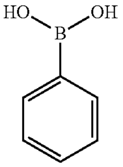 | Method 1: RT: 3.62 min, MI: 433 [M + H] | (1H, 300 MHz, d6-dmso) 9.47 ppm (1H, br s), 8.70 ppm (1H, d), 8.67 ppm (2H, dd), 8.42 ppm (1H, br s), 8.18-8.14 ppm (3H, m), 7.90 ppm (2H, dd), 7.57-7.46 ppm (3H, m), 7.42-7.31 ppm (5H, m), 3.99 ppm (1H, d), 3.67-3.51 ppm (2H, m), 3.01 ppm (1H, dd), 2.83 ppm (1H, dd) | N-[(2S)-2-amino-3-phenylpropyl]-8-phenyl-2-(pyridin-4-yl)pyrido[3,4-d]pyrimidin-4-amine |
| 91 | [A059] | 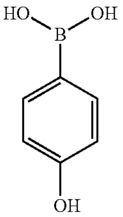 | Method 1: RT: 2.93 min, MI: 449 [M + H] | (1H, 300 MHz, d6-dmso), 8.85-8.85 ppm (1H, br s), 8.70 ppm (2H, d), 8.62 ppm (1H, d), 8.12 ppm (2H, d), 8.04 ppm (1H, d), 8.00 ppm (2H, d), 7.39-7.27 ppm (5H, m), 6.91 ppm (2H, d), 3.97-3.86 ppm (1H, m), 3.54-3.44 ppm (2H, m), 2.83 ppm (2H, br s) | 4-(4-{[(2S)-2-amino-3-phenylpropyl]-amino}-2-(pyridin-4-yl)pyrido[3,4-d]pyrimidin-8-yl)phenol |
| 92 | [A059] | 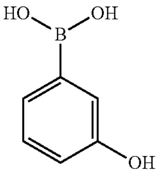 | Method 1: RT: 3.00 min, MI: 449 [M + H] | (1H, 300 MHz, d6-dmso), 8.73-8.69 ppm (3H, t), 8.16 ppm (1H, d), 8.04 ppm (2H, d), 7.64-7.62 ppm (2H, m), 7.36-7.23 ppm (5H, m), 6.88 ppm (1H, dd), 3.88 ppm (1H, d), 3.46-3.30 ppm (2H, m), 2.77-2.74 ppm (2H, m) | 3-(4-{[(2S)-2-amino-3-phenylpropyl]-amino}-2-(pyridin-4-yl)pyrido[3,4-d]pyrimidin-8-yl)phenol |
| 93 | [A059] | 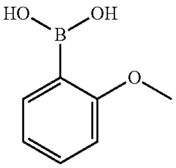 | Method 1: RT: 3.16 min, MI: 463 [M + H] | (1H, 300 MHz, d6-dmso), 8.65-8.63 ppm (3H, t), 8.19 ppm (1H, d), 7.87 ppm (2H, d), 7.48 ppm (1H, dt), 7.36-7.24 ppm (5H, m), 7.17 ppm (1H, d), 7.07 ppm (1H, t), 3.92-3.84 ppm (1H, dd), 3.61 ppm (3H, s), 3.44-3.29 ppm (2H, m), 2.77-2.75 ppm (2H, m) | N-[(2S)-2-amino-3-phenylpropyl]-8-(2-methoxyphenyl)-2-(pyridin-4-yl)pyrido[3,4-d]pyrimidin-4-amine |
| 94 | [A059] | 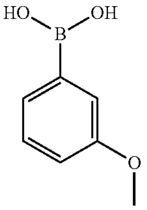 | Method 1: RT: 3.54 min, MI: 463 [M + H] | (1H, 300 MHz, d6-dmso), 8.70 ppm (3H, d), 8.18 ppm (1H, d), 8.02 ppm (2H, d), 7.80-7.76 ppm (2H, m), 7.45 ppm (1H, t), 7.34-7.24 ppm (5H, m), 7.07 ppm (1H, dd), 3.88 ppm (1H, d), 3.83 ppm (3H, s), 3.43-3.33 ppm (2H, m), 2.77-2.73 ppm (2H, m) | N-[(2S)-2-amino-3-phenylpropyl]-8-(3-methoxyphenyl)-2-(pyridin-4-yl)pyrido[3,4-d]pyrimidin-4-amine |
| 95 | [A059] | 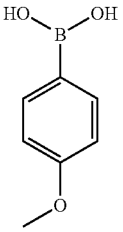 | Method 1: RT: 3.56 min, MI: 463 [M + H] | (1H, 300 MHz, d6-dmso), 8.70 ppm (2H, d), 8.65 ppm (1H, d), 8.24 (2H, d), 8.10 ppm (1H, d), 8.04 ppm (2H, d), 7.36-7.23 ppm (5H, m), 7.09 ppm (2H, d), 3.89-3.84 ppm (1H, m), 3.85 ppm (3H, s), 3.44-3.30 ppm (2H, m), 2.74 ppm (2H, t) | N-[(2S)-2-amino-3-phenylpropyl]-8-(4-methoxyphenyl)-2-(pyridin-4-yl)pyrido[3,4-d]pyrimidin-4-amine |

-continued

| Ex | SM | Boronic acid | Analysis | | Name |
|---|---|---|---|---|---|
| 96 | [A059] | 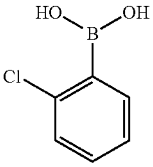 | Method 1: RT: 3.46 min, MI: 467 [M + H] | (1H, 300 MHz, d6-dmso) 8.69 ppm (2H, d), 8.63 ppm (2H, dd), 8.28 ppm (1H, d), 8.19-8.16 ppm (1H, m), 8.01 ppm (1H, d), 7.84 ppm (2H, dd), 7.64-7.60 ppm (1H, m), 7.36-7.23 ppm (5H, m), 3.92-3.84 ppm (1H, m), 3.44-3.25 ppm (2H, m), 2.76-2.74 ppm (2H, m) | N-[(2S)-2-amino-3-phenylpropyl]-8-(2-chlorophenyl)-2-(pyridin-4-yl)pyrido[3,4-d]pyrimidin-4-amine |
| 97 | [A059] | 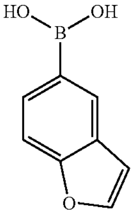 [SMILES: OB(O)c1ccc2occc2c1] | Method 1: RT: 3.69 min, MI: 473 [M + H] | (1H, 300 MHz, d6-dmso): 8.68 (d, 3H), 8.48 (d, 1H), 8.18-8.15 (m, 2H), 8.06 (d. 1H), 8.01 (d, 1H), 7.73 (d, 1H), 7.36-7.26 (m, 5H), 7.10 (d, 1H), 3.88 (d, 1H), 3.45-3.37 (m, 2H), 2.77-2.73 (m, 2H). | N-[(2S)-2-amino-3-phenylpropyl]-8-(1-benzofuran-5-yl)-2-(pyridin-4-yl)pyrido[3,4-d]pyrimidin-4-amine |
| 98 | [A059] | 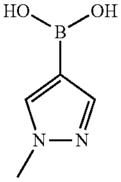 | Method 1: RT: 2.98 min, MI: 437 [M + H] | (1H, 300 MHz, d6-dmso) 8.77 (s, 1H), 8.75 (d, 2H), 8.54 (d, 1H), 8.44 (s, 1H), 8.12 (d, 2H), 7.97 (d, 1H), 7.36-7.27 (m, 5H), 3.99 (s, 3H), 3.87 (d, 1H), 3.43-3.35 (m, 2H), 2.77-2.74 (m, 2H). | N-[(2S)-2-amino-3-phenylpropyl]-8-(1-methyl-1H-pyrazol-4-yl)-2-(pyridin-4-yl)pyrido[3,4-d]pyrimidin-4-amine |
| 99 | [A059] | 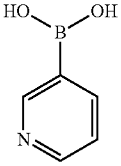 | Method 1: RT: 2.58 min, MI: 434 [M + H] | (1H, 300 MHz, d6-dmso): 9.33 (d, 1H), 8.73-8.66 (m, 3H), 8.51 (td, 1H), 8.21 (d, 1H), 7.98 (d, 2H), 7.57 (dd, 1H), 7.37-7.27 (m, 5H), 3.92-3.84 (m, 1H), 3.47-3.38 (m, 2H), 2.78-2.76 (m, 2H). | N-[(2S)-2-amino-3-phenylpropyl]-8-(pyridin-3-yl)-2-(pyridin-4-yl)pyrido[3,4-d]pyrimidin-4-amine |
| 100 | [A059] | 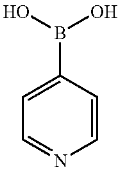 | Method 1: RT: 2.41 min, MI: 434 [M + H] | (1H, 300 MHz, d6-dmso): 8.77-2.75 (m, 3H), 8.71 (d, 2H), 8.28 (d, 1H), 8.15 (d, 2H), 8.02 (d, 2H), 7.36-7.26 (m, 5H), 3.91-3.86 (m, 1H), 3.46-3.36 (m, 2H), 2.78-2.73 (m, 2H). | N-[(2S)-2-amino-3-phenylpropyl]-2,8-bis(pyridin-4-yl)pyrido[3,4-d]pyrimidin-4-amine |
| 101 | [A059] | 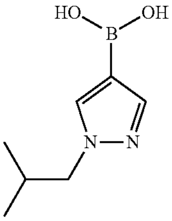 | Method 1: RT: 3.90 min, MI: 479 [M + H] | (1H, 300 MHz, d6-dmso): 8.75-8.73 (m, 3H), 8.54 (d, 1H), 8.49 (s, 1H), 8.11 (d, 2H), 7.98 (d, 1H), 7.35-7.25 (m, 5H), 4.07 (d, 2H), 3.88-3.84 (m, 1H), 3.43-3.36 (m, 2H), 2.74-2.70 (m, 2H), 2.23-2.14 (m, 1H), 0.91 (d, 6H). | N-[(2S)-2-amino-3-phenylpropyl]-8-[1-(2-methylpropyl)-1H-pyrazol-4-yl]-2-(pyridin-4-yl)pyrido[3,4-d]pyrimidin-4-amine |
| 102 | [A059] | 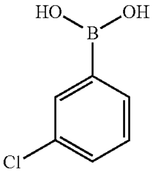 | Method 1: RT: 4.05 min, MI: 466 [M + H] | | N-[(2S)-2-amino-3-phenylpropyl]-8-(3-chlorophenyl)-2-(pyridin-4-yl)pyrido[3,4-d]pyrimidin-4-amine |

-continued

| Ex | SM | Boronic acid | Analysis | Name |
|---|---|---|---|---|
| 103 | [A059] | 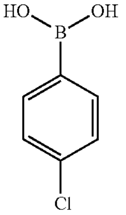 | Method 1: RT: 4.08 min, MI: 467 [M + H] (1H, 300 MHz, d6-dmso) 8.72-8.62 (m, 3H), 8.35 (s, 1H), 8.23 (d, 2H), 8.19 (d, 1H), 7.94 (d, 2H), 7.62 (d, 2H), 7.39-7.32 (m, 5H), 4.02-3.94 (m, 1H), 3.59-3.50 (m, 2H), 3.00-2.92 (m, 1H), 2.85-2.80 (m, 1H). | N-[(2S)-2-amino-3-phenylpropyl]-8-(4-chlorophenyl)-2-(pyridin-4-yl)pyrido[3,4-d]pyrimidin-4-amine |
| 104 | [A059] | 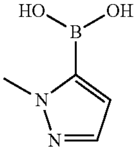 | Method 1: RT: 2.72 min, MI: 437 [M + H] (1H, 300 MHz, d6-dmso): 8.72 (d, 2H), 8.72 (d, 1H), 8.22 (d, 1H), 8.04 (d, 2H), 7.61 (d, 1H), 7.35-7.23 (m, 5H), 7.09 (d, 1H), 4.02 (s, 3H), 3.90-3.85 (m, 1H), 3.44-3.33 (m, 2H), 2.75-2.71 (m, 2H). | N-[(2S)-2-amino-3-phenylpropyl]-8-(1-methyl-1H-pyrazol-5-yl)-2-(pyridin-4-yl)pyrido[3,4-d]pyrimidin-4-amine |
| 105 | [A059] | 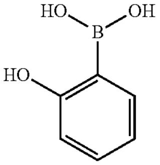 | (1H, 300 MHz, d6-dmso): 8.68-8.74 (m, 3H), 8.38 (d, 1H), 8.35 (s, 1H), 8.22 (d, 1H), 7.96 (d, 2H), 7.32-7.40 (m, 6H), 6.98-7.04 (m, 2H), 3.98 (d, 1H), 3.50-3.58 (m, 2H), 2.95 (dd, 1H), 2.85 (dd, 1H). | 2-(4-{[(2S)-2-amino-3-phenylpropyl]amino}-2-(pyridin-4-yl)pyrido[3,4-d]pyrimidin-8-yl)phenol |
| 106 | [A059] | 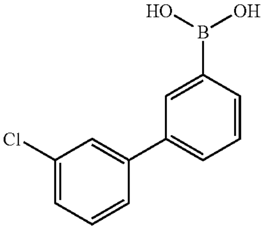 [SMILES: OB(O)c1cccc(-c2cccc(Cl)c2)c1] | Method 1: RT: 4.74 min, MI: 543 [M + H] (1H, 300 MHz, d6-dmso): 8.75 (d, 1H), 8.66 (d, 2H), 8.52 (s, 1H), 8.26-8.18 (m, 2H), 7.99 (d, 2H), 7.83 (d, 1H), 7.80 (s, 1H), 7.72 (d, 1H), 7.67 (t, 1H), 7.52 (t, 1H), 7.46 (d, 1H), 7.38-7.30 (m, 5H), 4.00-3.92 (m, 1H), 3.58-3.52 (m, 2H), 2.91-2.86 (m, 2H). | N-[(2S)-2-amino-3-phenylpropyl]-8-[3-(3-chlorophenyl)-phenyl]-2-(pyridin-4-yl)pyrido[3,4-d]pyrimidin-4-amine |
| 107 | [A059] | | Method 1: RT: 4.73 min, MI: 543 [M + H] (1H, 300 MHz, d6-dmso): 8.74 (d, 1H), 8.70 (d, 2H), 8.34 )d, 2H), 8.27 (d, 2H), 8.18 (d, 1H), 8.01 (d, 2H), 7.88 (d, 2H), 7.83 (d, 2H), 7.57 (d, 2H), 7.40-7.31 (m, 5H), 3.99-3.93 (m, 1H), 3.60-3.53 (m, 2H), 2.89-2.82 (m, 2H). | N-[(2S)-2-amino-3-phenylpropyl]-8-[4-(4-chlorophenyl)-phenyl]-2-(pyridin-4-yl)pyrido[3,4-d]pyrimidin-4-amine |
| 108 | [A059] | 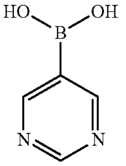 | Method 1: RT: 2.83 min, MI: 435 [M + H] (1H, 300 MHz, d6-dmso): 9.50 (s, 2H), 9.27 (s, 1H), 8.71 (d, 1H), 8.69 (d, 2H), 8.22 (d, 1H), 7.93 (d, 2H), 7.37-7.28 (m, 5H), 3.92-3.85 (m, 1H), 3.47-3.38 (m, 2H), 2.79-2.76 (m, 2H). | N-[(2S)-2-amino-3-phenylpropyl]-2-(pyridin-4-yl)-8-(pyrimidin-5-yl)pyrido[3,4-d]pyrimidin-4-amine |
| 109 | [A059] | 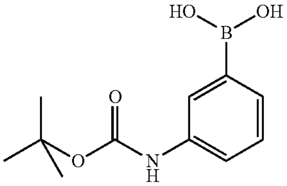 | Method 1: RT: 2.43 min, MI: 448 [M + H] (1H, 300 MHz, d6-dmso): 8.69 (d, 2H), 8.65 (d, 1H), 8.13 (d, 1H), 8.04 (d, 2H), 7.38-7.26 (m, 7H), 7.17 (t, 1H), 6.68 (d, 1H), 5.16 (brs, 2H), 3.91-3.85 (m, 1H), 3.45-3.35 (m, 2H), 2.77-2.75 (m, 2H). | N-[(2S)-2-amino-3-phenylpropyl]-8-(3-aminophenyl)-2-(pyridin-4-yl)pyrido[3,4-d]pyrimidin-4-amine |
| 110 | [A059] | 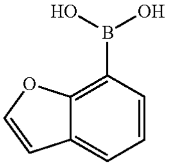 [SMILES: OB(O)c1cccc2ccoc12] | Method 1: RT: 4.07 min, MI: 473 [M + H] (1H, 300 MHz, d6-dmso): 8.78 (d, 2H), 8.72 (d, 1H), 8.53 (s, 1H), 8.16 (d, 3H), 7.90 (d, 1H), 7.71 (d, 1H), 7.43 (t, 1H), 7.36-7.26 (m, 6H), 3.92-3.84 (m, 1H), 3.52-3.45 (m, 2H), 2.83-2.79 (m, 2H). | N-[(2S)-2-amino-3-phenylpropyl]-8-(1-benzofuran-7-yl)-2-(pyridin-4-yl)pyrido[3,4-d]pyrimidin-4-amine |

-continued

| Ex | SM | Boronic acid | Analysis | Name |
|---|---|---|---|---|
| 111 | [A059] | 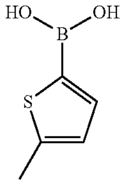 | Method 1: RT: 1.81 min, MI: 453 [M + H]<br>(1H, d6-DMSO, 500 MHz) 8.67 (d, 2H), 8.30-8.16 (m, 1H), 8.01 (d, 2H), 7.36-7.24 (m, 7H), 6.82 (d, 1H), 3.86-3.73 (m, 1H), 2.75-2.72 (m, 2H). | N-[(2S)-2-amino-3-phenylpropyl]-8-(5-methylthiophen-2-yl)-2-(pyridin-4-yl)pyrido[3,4-d]pyrimidin-4-amine |
| 112 | [A059] | 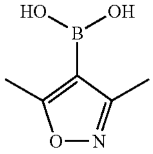 | Method 1: RT: 3.02 min, MI: 452 [M + H] | N-[(2S)-2-amino-3-phenylpropyl]-8-(dimethyl-1,2-oxazol-4-yl)-2-(pyridin-4-yl)pyrido[3,4-d]pyrimidin-4-amine |
| 113 | [A059] | 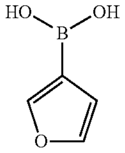 | Method 1: RT: 3.42 min, MI: 426 [M + H] C<br>(1H, 300 MHz, d6-dmso): 8.99 (d, 1H), 8.71 (d, 2H), 8.58 (d, 1H), 8.44 (s, 1H), 8.03 (d, 1H), 7.96 (d, 2H), 7.82 (t, 1H), 7.39-7.29 (m, 5H), 4.00-3.94 (m, 1H), 3.68-3.48 (m, 2H), 303 (dd, 1H), 2.84 (dd, 1H). | N-[(2S)-2-amino-3-phenylpropyl]-8-(furan-3-yl)-2-(pyridin-4-yl)pyrido[3,4-d]pyrimidin-4-amine |
| 114 | [A059] | 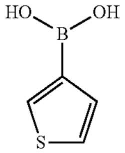 | Method 1: RT: 3.55 min, MI: 439 [M + H]<br>(1H, 300 MHz, d6-dmso): 8.96 (d, 1H), 8.74 (d, 2H), 8.63 (d, 1H), 8.13-8.09 (m, 4H), 7.64 (d, (dd, 1H), 7.36-7.25 (m, 5H), 3.92-3.85 (m, 1H), 3.45-3.36 (m, 2H), 2.76-2.71 (m, 2H). | N-[(2S)-2-amino-3-phenylpropyl]-2-(pyridin-4-yl)-8-(thiophen-3-yl)pyrido[3,4-d]pyrimidin-4-amine |
| 115 | [A059] | 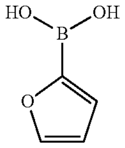 | Method 1: RT: 3.26 min, MI: 423 [M + H]<br>(1H, 300 MHz, d6-dmso): 8.76 (d, 2H), 8.61 (d, 1H), 8.12-8.06 (m, 3H), 7.95 (s, 1H), 7.36-7.26 (m, 5H), 6.80-6.78 (m, 1H), 3.92-3.85 (m, 1H), 3.46-3.39 (m, 2H), 2.78-2.75 (m, 2H). | N-[(2S)-2-amino-3-phenylpropyl]-8-(furan-2-yl)-2-(pyridin-4-yl)pyrido[3,4-d]pyrimidin-4-amine |
| 116 | [A059] | 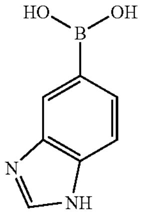 [SMILES: OB(O)c1ccc2[nH]cnc2c1] | Method 1: RT: 2.23 min, MI: 473 [M + H] | N-[(2S)-2-amino-3-phenylpropyl]-8-(1H-1,3-benzodiazol-5-yl)-2-(pyridin-4-yl)pyrido[3,4-d]pyrimidin-4-amine |
| 117 | [A059] | 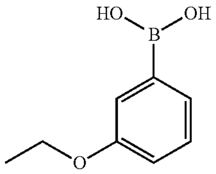 | Method 1: RT: 3.72 min, MI: 477 [M + H] | N-[(2S)-2-amino-3-phenylpropyl]-8-(3-ethoxyphenyl)-2-(pyridin-4-yl)pyrido[3,4-d]pyrimidin-4-amine |
| 118 | [A059] | 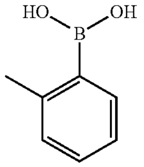 | | N-[(2S)-2-amino-3-phenylpropyl]-8-(2-methylphenyl)-2-(pyridin-4-yl)pyrido[3,4-d]pyrimidin-4-amine |

-continued

| Ex | SM | Boronic acid | Analysis | Name |
|---|---|---|---|---|
| 119 | [A059] | 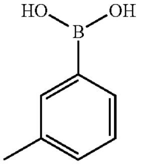 | | N-[(2S)-2-amino-3-phenylpropyl]-8-(3-methylphenyl)-2-(pyridin-4-yl)pyrirido[3,4-d]pyrimidin-4-amine |
| 120 | [A059] | 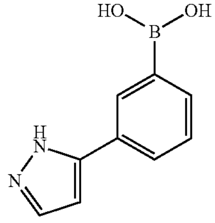 [SMILES: OB(O)c1cccc(-c2ccn[nH]2)c1] | Method 1: RT: 3.55 min, MI: 499 [M + H] (1H, 300 MHz, d6-dmso): 8.87 (brs, 1H), 8.70 (d, 1H), 8.67 (d, 2H), 8.18 (d, 1H), 8.14-8.09 (m, 3H), 7.91 (d, 1H), 7.77 (brs, 1H), 7.56 (t, 1H), 7.36-7.26 (m, 5H), 6.74 (d, 1H), 3.94-3.85 (m, 1H), 3.44-3.39 (m, 2H), 2.77-2.74 (m, 2H). | N-[(2S)-2-amino-3-phenylpropyl]-8-[3-(1H-pyrazol-5-yl)phenyl]-2-(pyridin-4-yl)pyrido[3,4-d]pyrimidin-4-amine |
| 121 | [A059] | 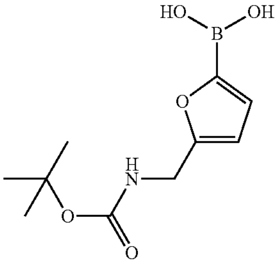 [SMILES: CC(C)(C)OC(=O)NCc1ccc(B(O)O)o1] | | N-[(2S)-2-amino-3-phenylpropyl]-8-[5-(aminomethyl)-furan-2-yl]-2-(pyridin-4-yl)pyrido[3,4-d]pyrimidin-4-amine |

General synthesis of 8-substituted-1-yl-2-pyridin-4-yl-pyrido[3,4-d]pyrimidine derivatives of General Formula [F011] Scheme A4

8-substituted-1-yl-2-pyridin-4-yl-pyrido[3,4-d]pyrimidine derivatives of general formula [F011] were prepared by reaction of a 4-Substituted 8-Chloro-2-pyridin-4-yl-pyrido [3,4-d]pyrimidin derivatives of general formula [F-010] in a Stille type reaction utilising a suitable stannane of general formula [F013], a palladium catalyst such as $Pd(PPh_3)_4$ or $Pd(PPh_3)_2Cl_2$ a base such as $K_3PO_4$, in a polar solvent such as DMA or dioxane at high temperature either by heating thermally or using a microwave reactor. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase chromatography or reverse phase preparative HPLC.

Scheme A4

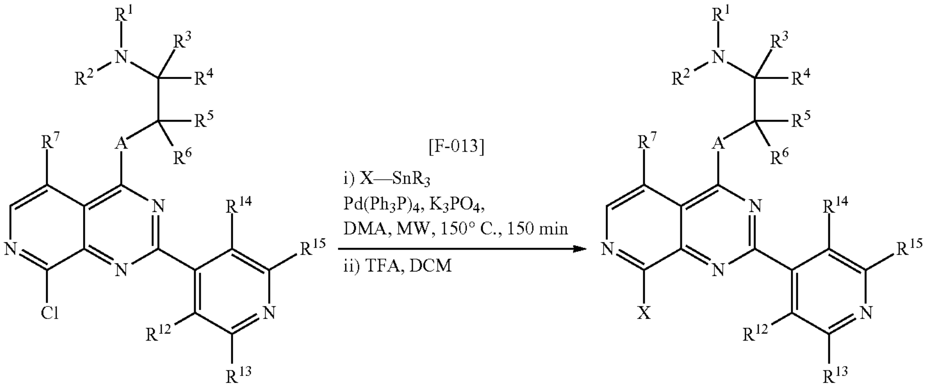

[F-010] [F-011]

Synthesis of (R)-3-Phenyl-N[1]-(2-pyridin-4-yl-8-pyridin-2-yl-pyrido[3,4-d]pyrimidin-4-yl)-propane-1,2-diamine [122]

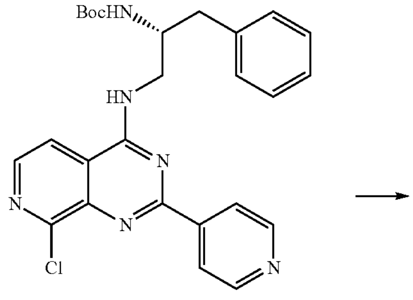

[A059]

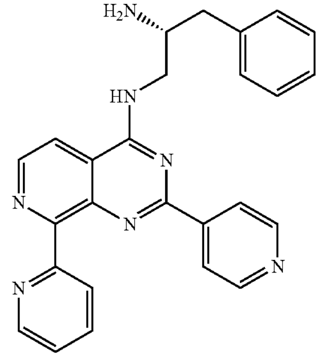

[122]

(R)-3-Phenyl-N[1]-(2-pyridin-4-yl-8-pyridin-2-yl-pyrido[3,4-d]pyrimidin-4-yl)-propane-1,2-diamine [122]

A microwave vial was charged with [(S)-1-Benzyl-2-(8-chloro-2-pyridin-4-yl-pyrido[3,4-d]pyrimidin-4-ylamino)-ethyl]-carbamic acid tert-butyl ester [A059](0.07 g, 0.142 mmol), 2-(Tributylstannyl)pyridine (0.068 g, 0.185 mmol), $Pd(Ph_3P)_4$ (0.016 g, 0.014 mmol), LiCl (0.018 g, 0.428 mmol) and DMA (1.5 mL). The mixture was heated under microwave irradiation (150° C., 10 min) and the solvent was removed under reduced pressure. The crude was purified by Column chromatography (Eluent: DCM/MeOH: 1:0 to 9:1). The purified compound was solubilised in DCM and 0.5 mL of TFA was added. The solution was stirred 3 h and then was poured on a SCX column, washed with MeOH and the expected product was released using a solution MeOH/NH3 2M, the basic solvent was concentrated under reduced pressure to yield the title compound as a yellow solid which was used without further purification: LCMS method: 1, RT: 2.34 min, MI 434 [M+H]; $^1$H NMR (1H, 500 MHz, $CDCl_3$); 8.70-8.76 (m, 2H), 8.63 (d, 2H), 8.42 (brs, 1H), 8.27 (d, 1H), 7.96 (dd, 1H), 7.93 (m, 1H), 7.81 (d, 2H), 7.50 (td, 1H), 7.32-7.52 (m, 5H), 4.00 (d, 1H), 3.51-3.60 (m, 2H), 3.01 (dd, 1H), 2.83 (dd, 1H).

General synthesis of 8-substituted-1-yl-2-pyridin-4-yl-pyrido[3,4-d]Pyrimidine Derivatives of General Formula [F-014] Scheme A5

8-substituted-1-yl-2-pyridin-4-yl-pyrido[3,4-d]pyrimidine derivatives of general formula [F-014] were prepared by reaction of a 4-Substituted 8-Chloro-2-pyridin-4-yl-pyrido[3,4-d]pyrimidin derivatives of general formula [F-010] in a Buchwald type reaction utilising a suitable amine, of general formula [F-015], a palladium catalyst such as $Pd(dba)_2$ or $Pd(OAc)_2$, a ligand such as Xantphos and a base such as NaOtBu or $Cs_2CO_3$ in a polar solvent such as dioxane or a combination of dioxane and DMA at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

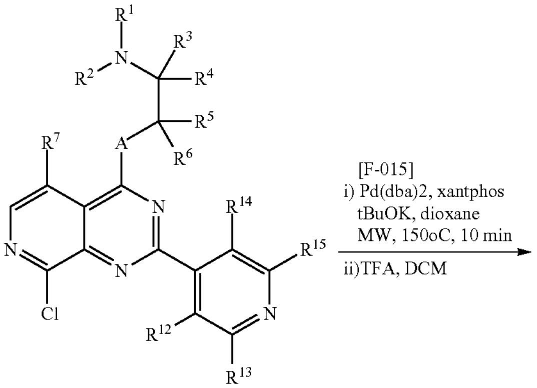

[F-010]

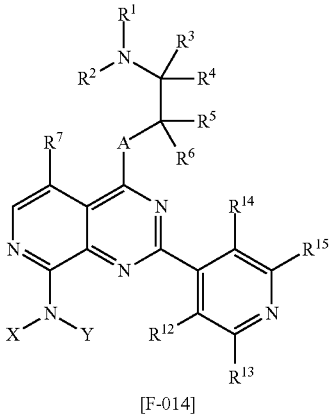

[F-014]

Synthesis of N[4]—((R)-2-Amino-3-phenyl-propyl)-N[8]-phenyl-2-pyridin-4-yl-pyrido[3,4-d]pyrimidine-4,8-diamine [123]

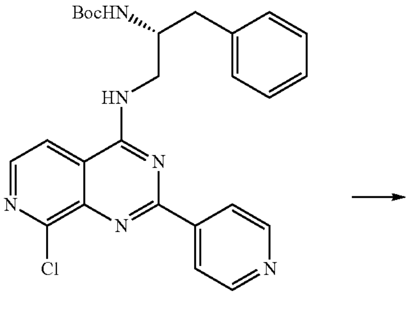

[A059]

-continued

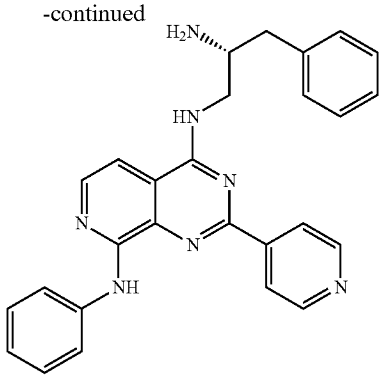

[123]

N4—((R)-2-Amino-3-phenyl-propyl)-N8-phenyl-2-pyridin-4-yl-pyrido[3,4-d]pyrimidine-4,8-diamine [123]

In a microwave vial, [(S)-1-Benzyl-2-(8-chloro-2-pyridin-4-yl-pyrido[3,4-d]pyrimidin-4-ylamino)-ethyl]-carbamic acid tert-butyl ester [A059](0.05 g 0.1 mmol) Aniline (0.015 g, 0.15 mmol), $Pd(dba)_2$ (0.003 g, 0.005 mmol), Xantphos (0.006 g, 0.01 mmol), Sodium tert butoxide (0.02 g, 0.2 mmol) and dioxane (1.3 mL) were added successively. The microwave vial was heated under microwaves (150° C., 10 min). The solvent was then removed under reduced pressure, DCM (2 mL) and TFA (0.5 mL) were added successively and the solution was stirred 3 h. The solution was poured on a SCX2 column and was washed with MeOH. The compound was released using a 2M NH3/MeOH solution, and then was concentrated under reduce pressure. The crude was purified by preparative HPLC (method A) to yield the title compound [123]: LCMS method: 1, RT: 3.53 min, MI 448 [M+H]; NMR (1H, 300 MHz, d6-dmso): peaks might be underneath solvent peaks at 2.5 and 3.3 ppm. 9.35 (s, 1H), 8.71 (d, 2H), 8.35 (d, 2H), 8.03-8.08 (m, 3H), 7.46 (d, 1H), 7.27-7.38 (m, 7H), 7.02 (t, 1H), 3.86 (d, 1H), 2.70-2.78 (m, 2H).

The following compounds were synthesised according to the general synthesis shown in scheme [A5]:

General synthesis of 8-substituted-1-yl-2-pyridin-4-yl-pyrido[3,4-d]pyrimidine derivatives of General Formula [F-014] Scheme A6

8-substituted-1-yl-2-pyridin-4-yl-pyrido[3,4-d]pyrimidine derivatives of general formula [F-014] were prepared by reaction of a 4-Substituted 8-Chloro-2-pyridin-4-yl-pyrido[3,4-d]pyrimidin derivative of general formula [F-010] in a nucleophilic aromatic substitution type reaction utilising a suitable amine [method A], thiol [method B] or phenol [method C] of general formula [F-015], and a base such as NaH in a polar aprotic solvent such as DMA or DMF at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme A6

Method A

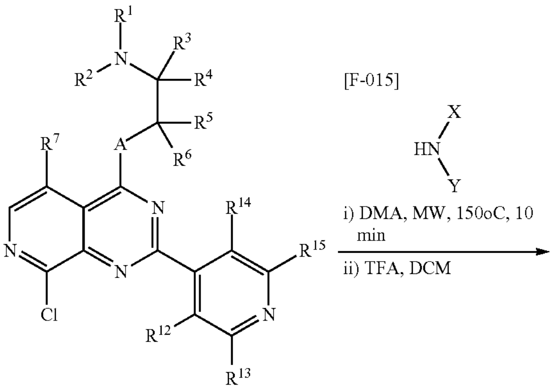

[F-010]

| Ex | SM | Amine | | Analysis | Name |
|---|---|---|---|---|---|
| 1124 | [A059] | 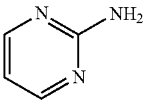 | Method 1: RT: 2.16 min, MI: 450 [M + H] | (1H, 300 MHz, d6-dmso): 8.70 (d, 2H), 8.64 (d, 2H), 8.34 (s, 1H), 8.25 (d, 1H), 8.04 (d, 2H), 7.70 (d, 1H), 7.40-7.33 (m, 5H), 7.10 (t, 1H), 3.97-3.92 (m, 1H), 3.58-3.50 (m, 2H), 2.99-2.93 (m, 1H), 2.87-2.80 (m, 1H). | 4-N-[(2S)-2-amino-3-phenylpropyl]-2-(pyridin-4-yl)-8-N-(pyrimidin-2-yl)pyrido[3,4-d]pyrimidine-4,8-diamine |
| 125 | [A059] | 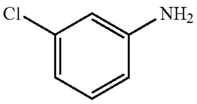 | Method 1: RT: 2.16 min, MI: 482 [M + H] | | 4-N-[(2S)-2-amino-3-phenylpropyl]-8-N-(3-chlorophenyl)-2-(pyridin-4-yl)pyrido[3,4-d]pyrimidine-4,8-diamine |
| 126 | [A059] | 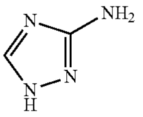 | Method 1: RT: 2.69 min, MI: 439 [M + H] | | 4-N-[(2S)-2-amino-3-phenylpropyl]-2-(pyridin-4-yl)-8-N-(1H-1,2,4-triazol-3-yl)pyrido[3,4-d]pyrimidine-4,8-diamine |

-continued

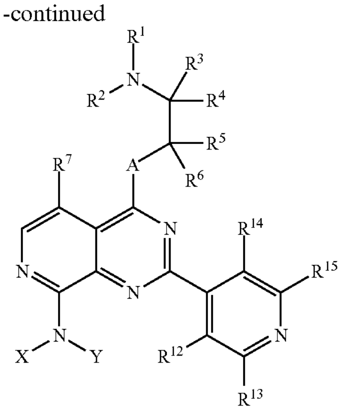

[F-014]

Method B

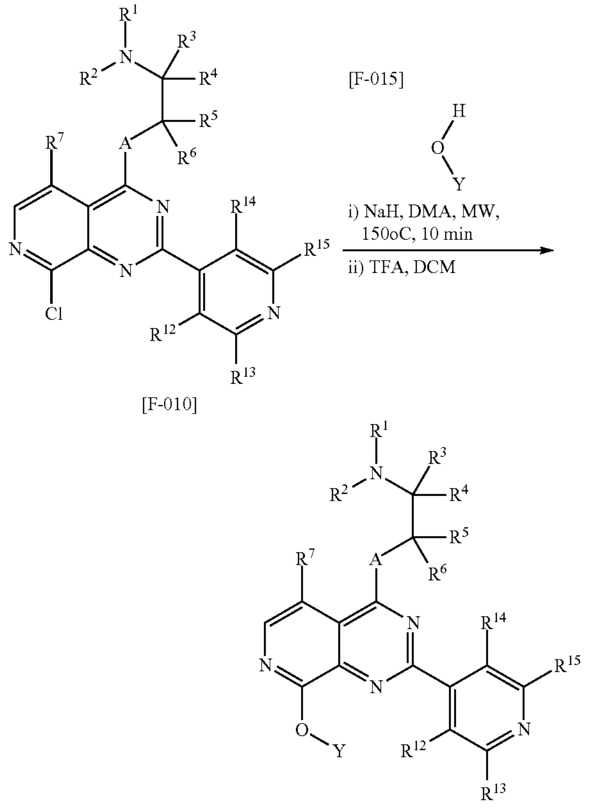

[F-015]

[F-010]

[F-014]

Method C

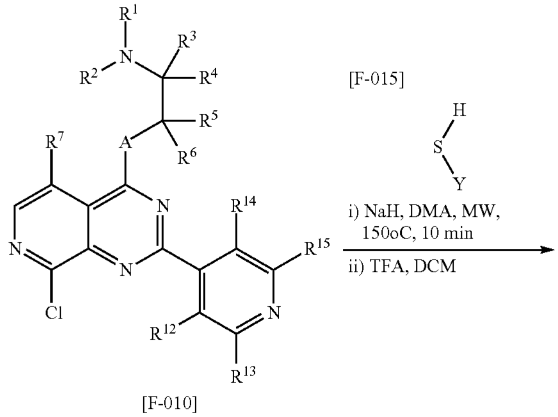

[F-015]

[F-010]

-continued

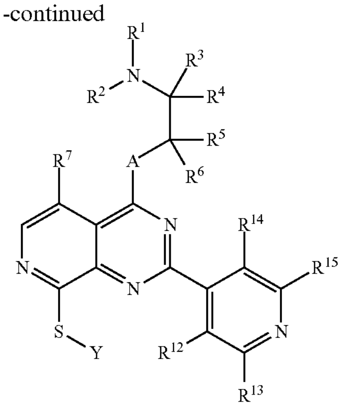

[F-014]

Synthesis of (R)—N-[8-(4-Methyl-piperazin-1-yl)-2-pyridin-4-yl-pyrido[3,4-d]pyrimidin-4-yl]-3-phenyl-propane-1,2-diamine [127]

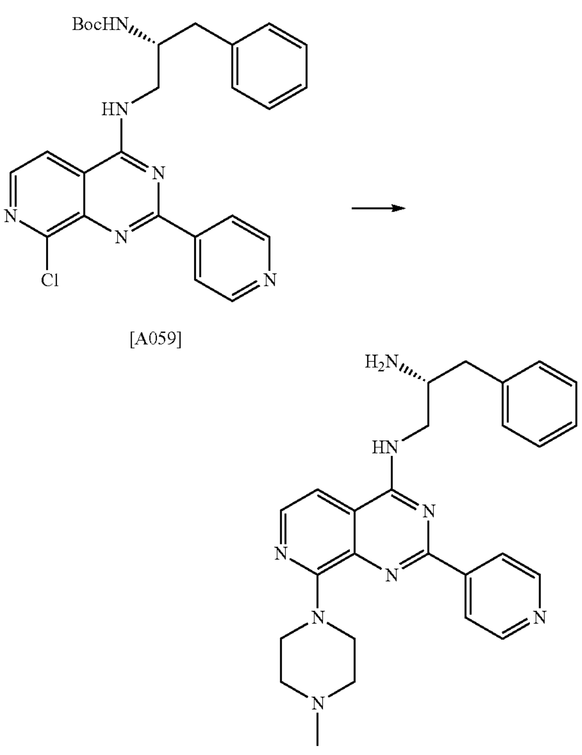

[A059]

[127]

(R)—$N^1$-[8-(4-Methyl-piperazin-1-yl)-2-pyridin-4-yl-pyrido[3,4-d]pyrimidin-4-yl]-3-phenyl-propane-1,2-diamine [127]

A microwave vial was charged with [(S)-1-Benzyl-2-(8-chloro-2-pyridin-4-yl-pyrido[3,4-d]pyrimidin-4-ylamino)-ethyl]-carbamic acid tert-butyl ester [A059](0.07 g, 0.142 mmol), N-methylpiperazine (0.031 mL, 0.285 mmol) and DMA (2 mL). The solution was heated under microwaves (150° C., 10 min). 2 other equivalent of N-methylpiperazine (0.031 mL, 0.285 mmol) was added and the vial was heated again under microwaves (150° C., 10 min). The solvent was removed under reduced pressure and DCM (2 mL) and TFA (0.5 mL) were added successively. The solution was stirred 3 h and then was poured on a SCX-2 column, washed with MeOH and the expected product was released using a solution MeOH/NH3 2M. The crude was then purified by preparative HPLC (method A) to yield the title compound [127]: LCMS method: 1, RT: 1.55 min, MI 455 [M+H]; NMR (1H, 300 MHz, d6-dmso): 9.17 (brs, 1H), 8.86 (d, 2H), 8.30 (s, 3H), 8.10 (d, 1H), 7.86 (d, 2H), 7.48 (d, 1H), 7.35-7.41 (m, 5H), 3.83-4.04 (m, 5H), 3.66-3.76 (m, 1H), 3.54-3.64 (m, 1H), 3.12 (dd, 1H), 2.86 (dd, 1H), 2.67-2.72 (m, 4H), 2.53 (s, 3H).

Synthesis of (R)-3-Phenyl-N1-(8-phenylsulfanyl-2-pyridin-4-yl-pyrido[3,4-d]pyrimidin-4-yl)-propane-1,2-diamine [128]

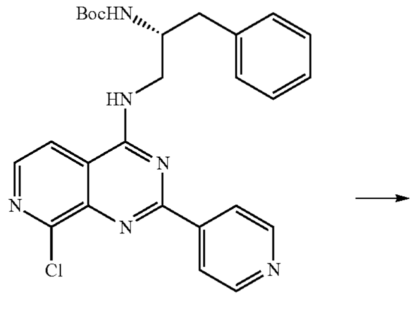

[A059]

-continued

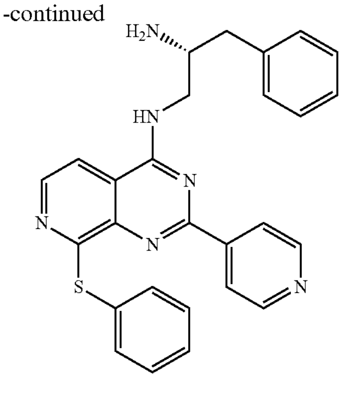

[128]

(R)-3-Phenyl-N1-(8-phenylsulfanyl-2-pyridin-4-yl-pyrido[3,4-d]pyrimidin-4-yl)-propane-1,2-diamine [128]

To a suspension of NaH (60% in mineral oil, 0.008 g, 0.2 mmol) in DMF (2 mL), Thiophenol (0.02 g, 0.185 mmol) was added. The mixture was stirred 1 h and [(S)-1-Benzyl-2-(8-chloro-2-pyridin-4-yl-pyrido[3,4-d]pyrimidin-4-ylamino)-ethyl]-carbamic acid tert-butyl ester [A059](0.07 g, 0.142 mmol) was added. The mixture was stirred over-night and water (0.3 mL) was added. The solvent were removed under reduced pressure and DCM (2 mL) and TFA (0.5 mL) were added successively. The solution was stirred 3 h and then was poured on a SCX-2 column, washed with MeOH and the expected product was released using a solution MeOH/NH3 2M. The crude was then purified by preparative HPLC (method A). To yield the title compound [128]: LCMS method: 1, RT: 4.06 min, MI 465 [M+H]; NMR (1H, 300 MHz, d6-dmso): 9.38 (brs, 1H), 8.72 (d, 2H), 8.23 (s, 3H), 8.03 (d, 2H), 7.89 (d, 1H), 7.58-7.61 (m, 2H), 7.36-7.47 (m, 6H), 3.98 (d, 1H), 3.56-3.73 (m, 2H), 3.05 (dd, 1H), 2.87 (dd, 1H).

The following compounds were synthesised according to the general synthesis shown in scheme [A6]:

| Ex | Meth-od | SM | Nuc | Analysis | | Name |
|---|---|---|---|---|---|---|
| 129 | B | [A059] | 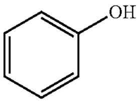 | Method 1: RT: 3.39 min, MI: 449 [M + H] | (1H, 300 MHz, d6-dmso): 9.43 (brs, 1H), 8.68 (d, 2H), 8.29 (s, 2H), 8.03 (d, 1H), 7.99 (d, 2H), 7.85 (d, 1H), 7.36-7.48 (m, 6H), 7.21-7.28 (m, 3H), 4.00 (d, 1H), 3.58-3.55 (m, 2H), 3.06 (dd, 1H), 2.81-2.93 (m, 1H), | N-[(2S)-2-amino-3-phenylpropyl]-8-phenoxy-2-(pyridin-4-yl)pyrido[3,4-d]pyrimidin-4-amine |
| 130 | C | [A059] | 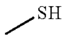 | Method 1: RT: 3.43 min, MI: 403 [M + H] | (1H, 300 MHz, d6-dmso): 9.58 (brs, 1H), 8.69 (d, 2H), 8.42 (d, 1H), 8.32 (s, 2H), 7.94 (d, 2H), 7.81 (d, 1H), 7.36-7.45 (m, 5H), 3.99 (d, 1H), 3.59-3.70 (m, 2H), 3.07 (dd, 1H), 2.81 (dd, 1H), 2.53 (s, 3H). | N-[(2S)-2-amino-3-phenylpropyl]-8-(methylsulfanyl)-2-(pyridin-4-yl)pyrido[3,4-d]pyrimidin-4-amine |

Synthesis of 4-(4-{[(2S)-2-amino-3-phenylpropyl]amino}-2-(pyridin-4-yl)pyrido[3,4-d]pyrimidin-8-yl)-2-methylbut-3-yn-2-ol [131]

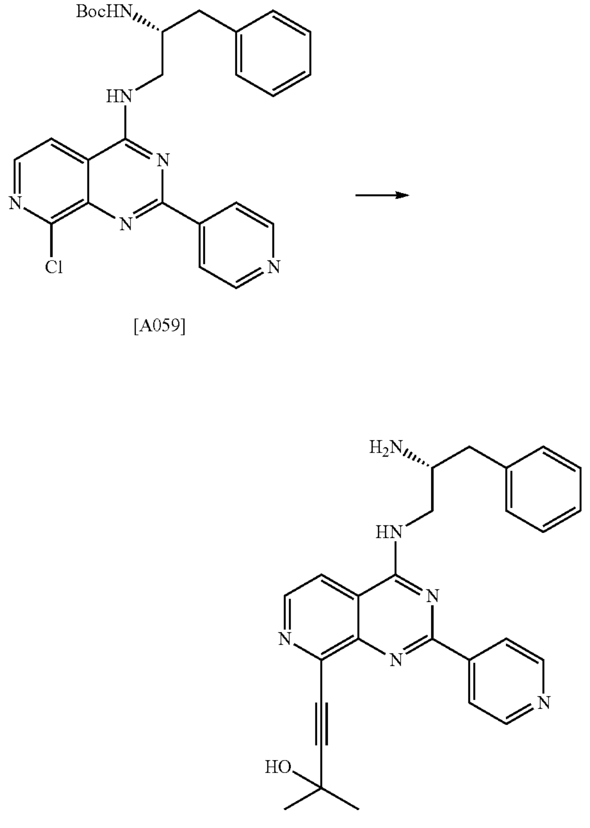

[A059]

[131]

4-(4-{[(2S)-2-amino-3-phenylpropyl]amino}-2-(pyridin-4-yl)pyrido[3,4-d]pyrimidin-8-yl)-2-methylbut-3-yn-2-ol [131]

A microwave vial was charged with [(S)-1-Benzyl-2-(8-chloro-2-pyridin-4-yl-pyrido[3,4-d]pyrimidin-4-ylamino)-ethyl]-carbamic acid tert-butyl ester [A059](0.05 g, 0.1 mmol), $Pd(PPh_3)_2Cl_2$ (0.007 g, 0.01 mmol), CuI (0.002 g, 0.1 mmol), 2-methyl-3-butyn-2-ol (0.035 g, 0.037 mmol), Triphenylphosphine (0.005 g, 0.02 mmol), Triethylamine (0.2 mL) and DMF (0.8 mL). The vial was heated under microwave (150° C., 10 min). The solvent was removed under reduced pressure and DCM (2 mL) and TFA (1 mL) were added and the mixture was stirred 3 h. The solution was poured on a SCX2 column and was washed with MeOH. The compound was released using a 2M NH3/MeOH solution, and then was concentrated under reduce pressure. The crude was purified by preparative HPLC (method A) to yield the title compound [131]: LCMS method: 1, RT: 3.12 min, MI 439 [M+H]; NMR (1H, 300 MHz, d6-dmso): 8.71 (d, 2H), 8.56 (d, 1H), 8.31 (brs, 1H), 8.15 (d, 1H), 8.08 (d, 2H), 7.41-7.31 (m, 5H), 3.97-3.92 (m, 1H), 3.59-3.50 (m, 2H), 2.99-2.90 (m, 1H), 2.86-2.79 (m, 1H), 1.59 (s, 6H).

General Synthesis of Substituted 5-Substituted-1-Yl-2-Pyridin-4-Yl-Pyrido[3,4-d]Pyrimidine Derivatives of General Formula [F-001] Scheme A7

2-Pyridin-4-yl-pyrido[3,4-d]pyrimidin-4-ol derivatives of general formula [F-004] were prepared by coupling of a ortho-halo-isonicotinic acid derivative of general formula [F-016] with an appropriately substituted 4-carbamimidoyl-pyridines of general formula [F-018] with a suitable coupling agent such as O-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula [F-017] were then cyclised to displace the relevant halogen group to yield the desired 2-Pyridin-4-yl-pyrido[3,4-d]pyrimidin-4-ol derivatives of general formula [F-004]. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with a chlorinatation agent such as phosphorous oxychloride and the intermediate 4-chloro derivative was then reacted with primary or secondary amino derivative of general formula [F-015], in a polar aprotic solvent such as DMA, DMF, NMP in the presence of a tertiary amine base such as $Et_3N$, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP [method B]. The intermediate 6,7-substituted-(2,4,6-triiso-propyl-benzenesulfonic acid)-2-pyridin-4-yl-thieno[3,2-d]pyrimidin-4-yl ester was then reacted with a primary or secondary amino derivative, of general formula [F-015], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme A7
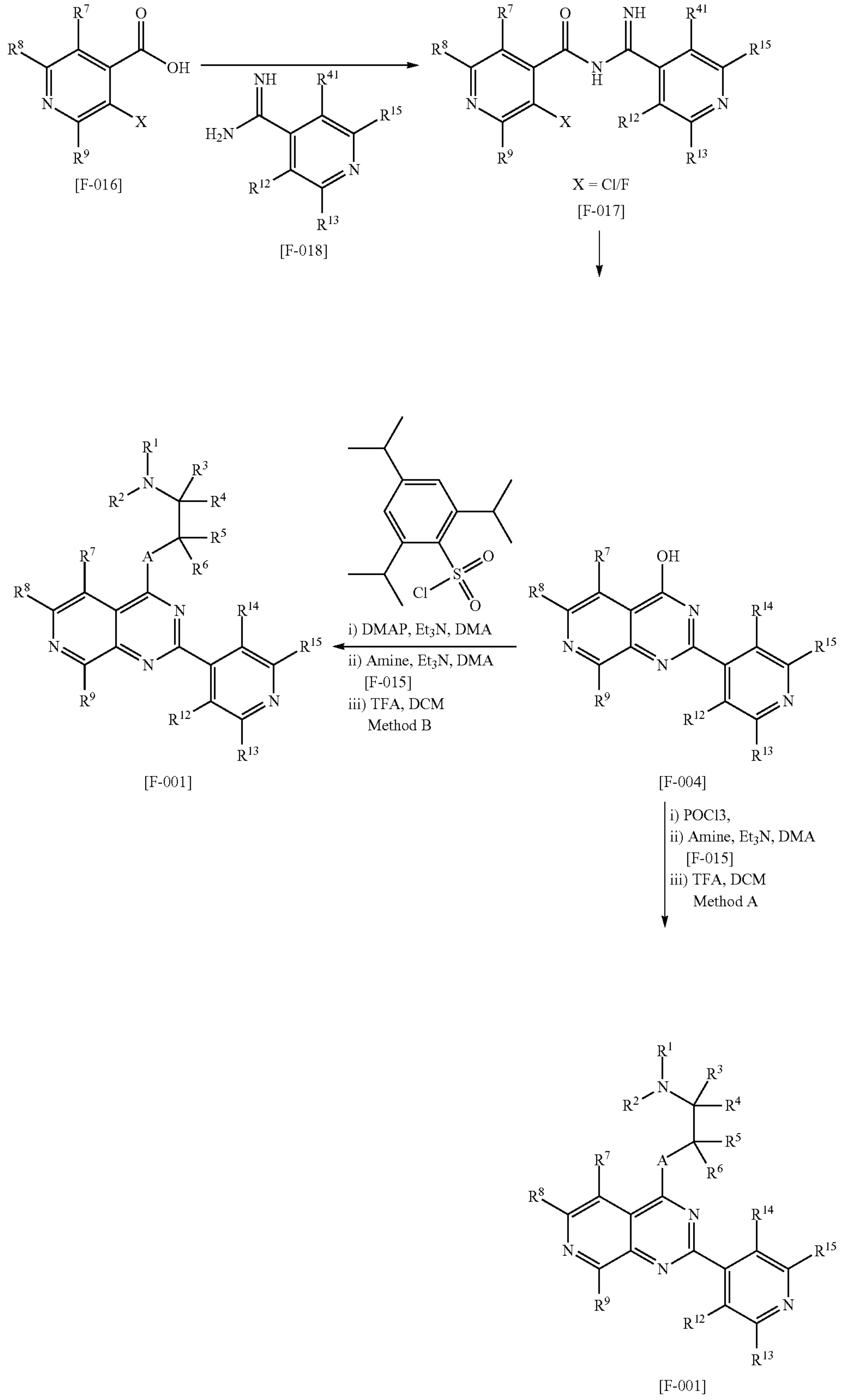
[F-016] [F-018] [F-017] [F-004] [F-001] [F-001]

Synthesis of 5-Chloro-4-piperazin-1-yl-2-pyridin-4-yl-pyrido[3,4-d]pyrimidine [132]

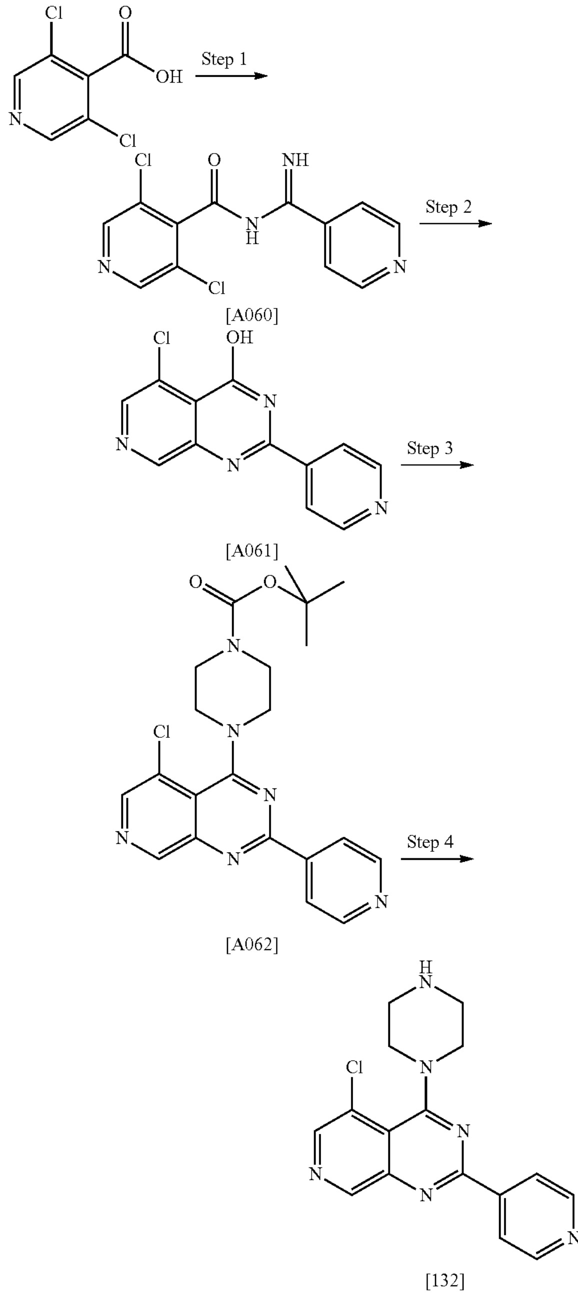

[A060]

[A061]

[A062]

[132]

Synthesis of 3,5-Dichloro-N-(imino-pyridin-4-yl-methyl)-isonicotinamide [A060]

3,5-Dichloro-isonicotinic acid (10.4 mmol, 1.997 g), was dissolved in anhydrous DMF (50 mL) at room temperature and HATU (10.4 mmol, 3.95 g), added in one portion and the mixture stirred for 5 mins. Then DIPEA (28.6 mmol, 5.0 mL) was added in one portion and reaction stirred for 40 minutes. Pyridine-4-carboximidamide hydrochloride (9.52 mmol, 1.5 g) was added in one portion and reaction stirred at room temperature for 18 hours.

The reaction mixture was then poured into water (~250 mL in total including rinses of reaction vessel) in a conical flask. The resultant mixture was stirred at room temperature for 90 minutes and the precipitate formed was filtered, washed with water (×2) and ether (×2). Then the solid was dried in vac oven for 4 hrs to yield the title compound [A060] (2.359 g), as a pale brown powder. LCMS method: 1, RT: 3.31 min, MI 295 [M+H].

Synthesis of 5-Chloro-2-pyridin-4-yl-3H-pyrido[3,4-d]pyrimidin-4-one [A061]

In a 25 mL Biotage microwave vessel, under nitrogen, was added 3,5-Dichloro-N-(imino-pyridin-4-yl-methyl)-isonicotinamide [A060](1.5 mmol, 0.443 g), cesium carbonate (3.0 mmol, 0.978 g) and N,N'-Dibenzylethylenediamine (0.3 mmol, 0.071 mL). The mixture was stirred in anhydrous DMA (10 mL), vigorously and iron (III) chloride (0.15 mmol, 0.024 g) added in one portion. Then the mixture was heated in the microwave at 120° C. for 90 mins. The reaction was allowed to cool to room temperature and acetic acid (12.0 mmol, 0.69 mL), added dropwise over about 5 minutes and the resulting mixture diluted with MeOH (10 mL) and stirred at RT for 30 mins. The mixture was added to a 10 g SCX-2 cartridge and washed with methanol (~25-30 mL). The cartridge was then washed with ammonia (2N in MeOH, 40 mL) and the ammonia washes concentrated in vacuo to yield 5-Chloro-2-pyridin-4-yl-3H-pyrido[3,4-d]pyrimidin-4-one (130 mg). The non-basic methanol washes of the SCX-2 cartridge were left standing overnight, forming a precipitate. This was filtered, washed with methanol (×1), and dried in a vacuum oven overnight to yield the title compound [A061] (13 mg) as an off-white solid. LCMS method: 1, RT: 2.12 min, MI 259 [M+H].

Synthesis of 4-(5-Chloro-2-pyridin-4-yl-pyrido[3,4-d]pyrimidin-4-yl)-piperazine-1-carboxylic acid tert-butyl ester [A062]

5-Chloro-2-pyridin-4-yl-3H-pyrido[3,4-d]pyrimidin-4-one [A061](0.553 mmol, 0.143 g), was suspended in anhydrous DCM (14 mL) at RT under nitrogen and triethylamine (1.38 mmol, 0.193 mL), DMAP (approximately 0.005 g) and 2,4,6-triisopropylbenzene sulfonyl chloride (0.663 mmol, 0.201 g) were added sequentially. The reaction was stirred at room temperature as an off-white suspension for 2 hrs. Slowly the mixture becomes a pale green suspension, that was left stirring overnight. Then pyridine (4 mL) was added and the reaction vessel sonicated for 5 minutes to try to improve the dissolution causing the reaction to change colour from green to brown suspension. The resultant mixture was stirred at room temperature for 1 hour. Boc-piperazine (0.608 mmol, 0.113 g) was added in one portion and the mixture left stirring for 18 hours.

The reaction was diluted with water and extracted with DCM (×3). Combined organics washed with brine (×1), dried ($MgSO_4$), filtered and concentrated in vacuo. To yield the title compound [A062] which was used in the next reaction without further purification: LCMS method: 1, RT: 5.69 min, MI 427 [M+H].

Synthesis of 5-Chloro-4-piperazin-1-yl-2-pyridin-4-yl-pyrido[3,4-d]pyrimidine [132]

To a solution of 4-(5-Chloro-2-pyridin-4-yl-pyrido[3,4-d]pyrimidin-4-yl)-piperazine-1-carboxylic acid tert-butyl ester [A062](0.47 mmol, 0.201 g), in anhydrous DCM (8 mL), at room temperature was added HCl (4.0N in dioxane, 2 mL) to yield an orange suspension that was stirred at room temperature for 3 hours. The mixture was then concentrated in vacuo, redissolved in DCM/MeOH (1:1, 6 mL total) and added to an SCX-2 10 g cartridge. The cartridge was washed with DCM and MeOH (~35 mL total ~2:3 ratio respectively). Then the cartridge was washed with ammonia in methanol (2N, 40 mL) and the ammonia washes were concentrated in vacuo to yield 92 mg brown oil. The crude material was purified by column chromatography (SP1 4 g VWR column with 0-20% MeOH/DCM 15 volumes) to yield the title compound [138] (0.044 g) as an orangey-yellow foam. LCMS method: 1, RT: 1.60 min, MI 327 [M+H]; NMR: (1H, 300 MHz, d6-dmso); 9.15 (1H, s), 8.77 (2H, d), 8.61 (1H, s), 8.29 (2H, d), 3.69 (4H, br s), 2.85 (4H, br s)

Synthesis of 5,8-Dichloro-2-pyridin-4-yl-3H-pyrido [3,4-d]pyrimidin-4-one [A063]

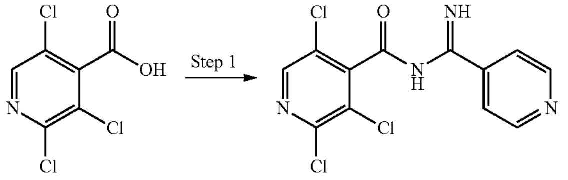

[A064]

2,3,5-Trichloro-N-(imino-pyridin-4-yl-methyl)-isonicotinamide [A064] was prepared by reaction of 2,3,5-Trichloro-isonicotinic acid, pyridine-4-carboximidamide hydrochloride, HATU, DIPEA and DMF at room temperature to give the title compound. LCMS method: 1, RT: 4.37 min, MI 330 [M+H]; NMR: (1H, 300 MHz, d6-dmso); 10.24 (1H, br s), 10.14 (1H, br s), 8.75 (2H, d), 8.60 (1H, s), 7.89 (2H, d).

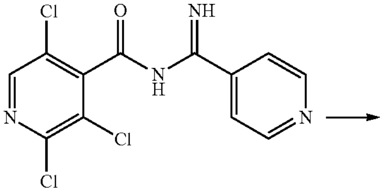

[A064]

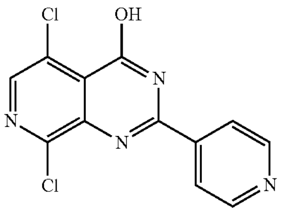

[A063]

5,8-Dichloro-2-pyridin-4-yl-3H-pyrido[3,4-d]pyrimidin-4-one [A063] was prepared by reaction of 2,3,5-Trichloro-N-(imino-pyridin-4-yl-methyl)-isonicotinamide [A064], $FeCl_3$, $Ce_2CO_3$, HCl (4N in dioxane) and DMA in a in wave for 2 hrs at 120° C. The reaction mixture was cooled and water (0.5 mL) was added followed by MeOH (2 mL) and HCl (4 eq wrt carbonate, 2.4 mmol, 0.6 mL 4N HCl in dioxane) and the mixture was stirred for 10 mins. The yellow precipitate was collected by filtration and the solid was washed with MeOH (2×, 2 mL) then dried in vac oven to give the title compound as a yellow solid (51 mg, 56% yield): LCMS method: 1, RT: 4.80 min, MI 293 [M+H]; NMR: (1H, 300 MHz, d6-dmso); 13.36 (1H, br s), 8.92 (2H, d), 8.49 (1H, s), 8.14 (2H, br d).

Synthesis of 3-Bromo-5-fluoro-N-(imino-pyridin-4-yl-methyl)-isonicotinamide [A065]

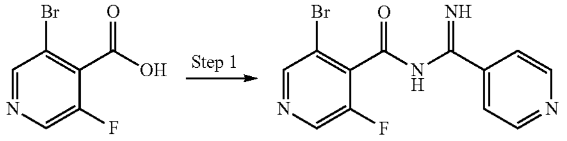

[A066]

2-Bromo-5-fluoro-N-(imino-pyridin-4-yl-methyl)-isonicotinamide [A066] was prepare by reaction of 3-Bromo-4-carboxy-5-fluoro-pyridinium; chloride, pyridine-4-carboximidamide hydrochloride, HATU, DIPEA and DMF at room temperature to give the title compound. LCMS method: 1, RT: 3.20 min, MI 325 [M+H].

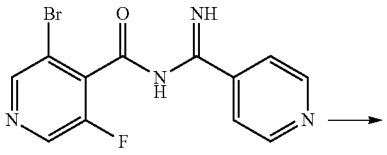

[A066]

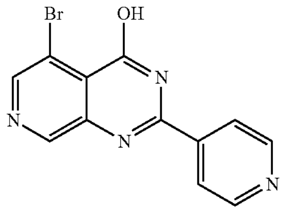

[A065]

2-Bromo-5-fluoro-N-(imino-pyridin-4-yl-methyl)-isonicotinamide [A066](0.05 g, 0.155 mmol), DMA (0.5 mL), $K_2CO_3$ (0.022 g, 0.16 mmol), DIPEA (0.28 mL, 0.16 mmol) and DBA (0.024 mL, 0.16 mmol) was heated at 150° C. in wave for 45 mins. The crude reaction mixture was evapourated under reduced pressure and the crude material was purified by column chromatography (SP1 4 g VWR column in 0.5% Et3N/DCM/0-20% MeOH) to yield the title compound [A065](0.044 g, 80% yield) as an orangey-yellow foam: LCMS method: 1, RT: 11.57 min, MI 304 [M+H].

The following compounds were synthesised according to the general synthesis shown in scheme [A7]:

| Ex | SM | Method | Amine [F-015] | | Analysis | Name |
|---|---|---|---|---|---|---|
| 133 | [A065] | A | 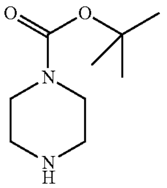 | Method 1: RT: 1.77 min, MI: 373 [M + H] | (1H, 500 MHz, d6-dmso), d6-dmso) 9.17 (1H, s), 8.77 (2H, dd), 8.72 (1H, s), 8.29 (2H, dd), 3.78-3.61 (4H, m), 2.94 (2H, br s), 2.82-2.71 (2H, m) | 1-[5-bromo-2-(pyridin-4-yl)pyrido[3,4-d]pyrimidin-4-yl]piperazine |
| 134 | [A063] | A | 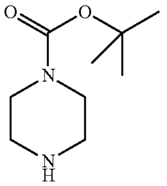 | Method 1: RT: 5.02 min, MI: 361 [M + H] | (1H, 500 MHz, d6-dmso) 8.79 (2H, dd), 8.41 (1H, s), 8.30 (2H, dd), 3.74 (4H, br s), 2.98-2.75 (4H, m) | 1-[5,8-dichloro-2-(pyridin-4-yl)pyrido[3,4-d]pyrimidin-4-yl]piperazine |

General Synthesis of Substituted 5-Substituted-1-Yl-2-Pyridin-4-Yl-Pyrido[3,4-d]Pyrimidine Derivatives of General Formula [F-001] Scheme A8

Ortho-halo-isonicotinic acid derivatives of general formula [F-020] were prepared by reaction of a dihalo isoinicotinic acid derivative of general formula [F-019] with a grindard reagent of general formula [F-021] in a polar aprotic solvent such as THF or $Et_2O$. 2-Pyridin-4-yl-pyrido[3,4-d]pyrimidin-4-ol derivatives of general formula [F-004] were prepared by coupling of a ortho-halo-isonicotinic acid derivative of general formula [F-020] with an appropriately substituted 4-carbamimidoyl-pyridines of general formula [F-018] with a suitable coupling agent such as 0-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula [F-022] were cyclised to displace the relevant halogen group to yield the desired-Pyridin-4-yl-pyrido[3,4-d]pyrimidin-4-ol derivatives of general formula [F-004]. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivative of general formula [F-004] with a chlorinatation agent such as phosphorous oxychloride and the intermediate 4-chloro derivative was then reacted with primary or secondary amino derivative of general formula [F-015], in a polar aprotic solvent such as DMA, DMF, NMP in the presence of a tertiary amine base such as $Et_3N$, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP [method B]. The intermediate 6,7-substituted-(2,4,6-triisopropyl-benzenesulfonic acid)-2-pyridin-4-yl-thieno[3,2-d]pyrimidin-4-yl ester was then reacted with a primary or secondary amino derivative, of general formula [F-015], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme A8

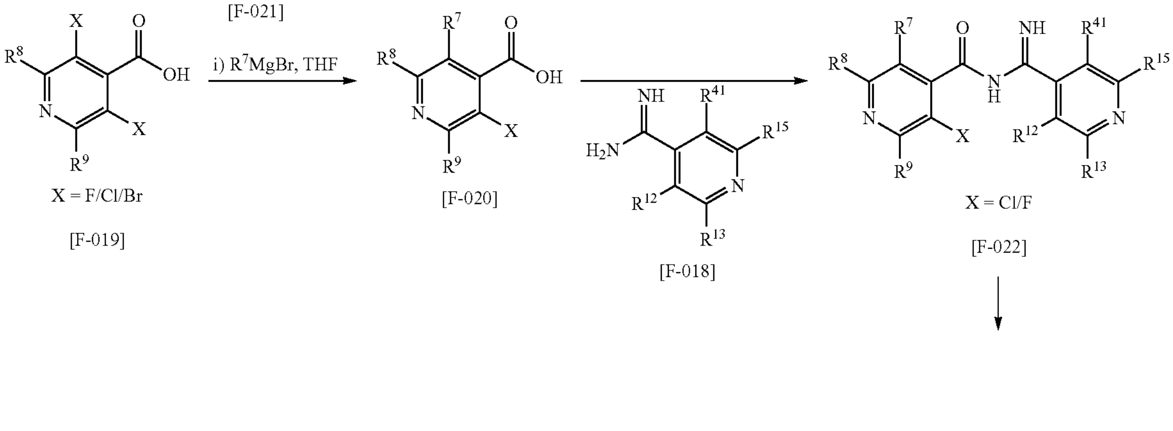

-continued
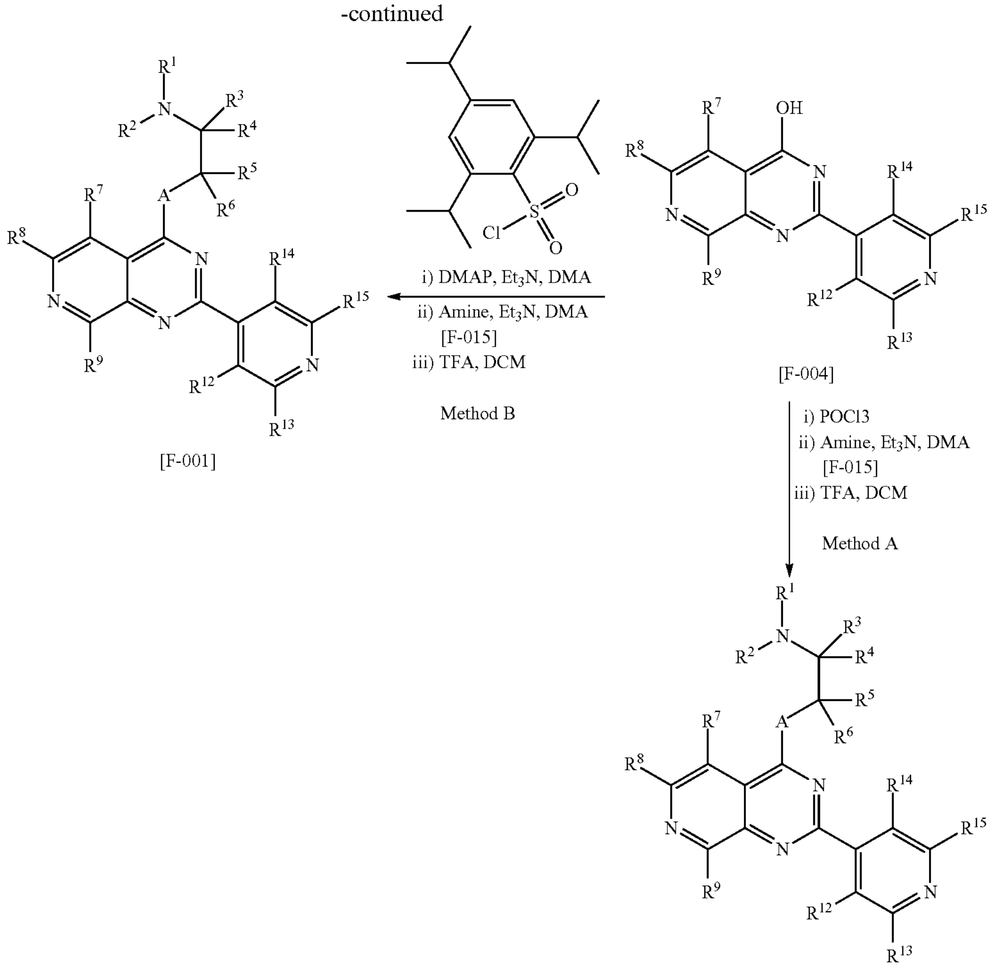
[F-001] [F-004] [F-001]
Synthesis of 5-Butyl-4-piperazin-1-yl-2-pyridin-4-yl-pyrido[3,4-d]pyrimidine [135]
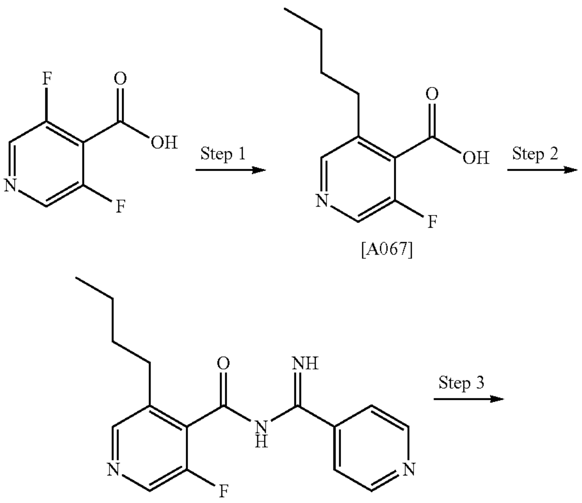
[A067] [A068]
-continued
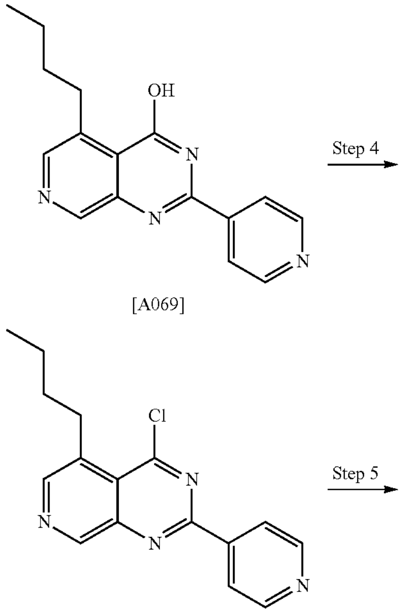
[A069] [A070]

-continued

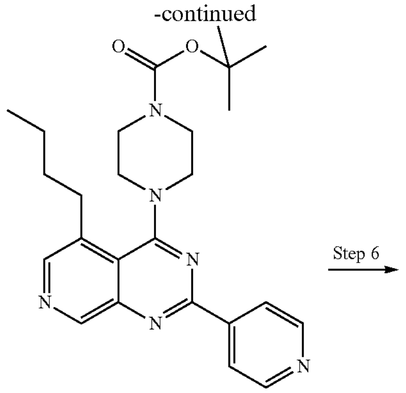

[A071]

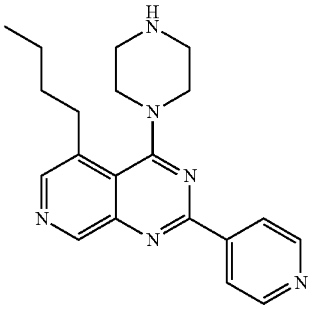

[135]

Synthesis of 3-Butyl-5-fluoro-isonicotinic acid [A067]

3,5-Difluoro-isonicotinic acid (0.557 g, 3.5 mmol) was suspended in anhydrous THF (8 mL) at 0° C., under an atmosphere of nitrogen. To this was added butyl magnesium chloride (2.0 M in diethyl ether, 5.25 mL, 10.5 mmol) dropwise over 10 minutes. The suspension slowly changed form during the slow addition with preliminary agglomeration of solid then the solid started to dissolve slowly, achieving full solution around completion of addition of reagent. The reaction mixture was allowed to warm to room temperature and stirred over 72 hours to form a thick yellow suspension. Diluted with water and transferred into a single neck flask and concentrated in vacuo. The yellow solid was diluted with water (10 mL) and EtOAc (10 mL). The pH was adjusted pH-2, by dropwise addition of HCl (conc.) and extracted with EtOAc (×3—some of the yellow colour goes into organics). Combined organics were washed with brine (×1), dried ($MgSO_4$) and concentrated in vacuo to yield the title compound [A067] as an orange gum/solid (0.402 g) that solidifies slowly: NMR: (1H, 300 MHz, d6-dmso); 8.52 (1H, s), 8.42 (1H, s), 2.67 (2H, t), 1.58-1.48 (2H, m), 1.35-1.22 (2H, m), 0.87 (3H, t); LCMS method: 1, RT: 1.22 min, MI 198 [M+H].

Synthesis of 3-Butyl-5-fluoro-N-(imino-pyridin-4-yl-methyl)-isonicotinamide [A068]

3-Butyl-5-fluoro-isonicotinic acid [A067](2.05 mmol, 0.402 g) was dissolved in anhydrous DMF (8 mL) and diisopropylethylamine (DIPEA) (5.95 mmol, 1.04 mL) was added and the mixture stirred at room temperature for 5 minutes. Then O-(7-Azabenzotriazol-1-yl)-N,N,N',N'-tetramethyluronium hexafluorophosphate (HATU) (2.05 mmol, 0.78 g) was added in one portion and the resultant mixture stirred for 1 hour. pyridine-4-carboximidamide hydrochloride (1.95 mmol, 0.307 g) was then added portionwise over 5 minutes to the reaction. The resultant solution was stirred at room temperature for 18 hours. The reaction mixture was poured into water (85 mL) and stirred for 30 minutes and then extracted with EtOAc (×3). The combined organics washed with water (×4), brine (×1), dried ($MgSO_4$), filtered and concentrated in vacuo to yield the title compound [A068] (480 mg) as a brown solid. The material was used crude in next reaction: NMR: (1H, 300 MHz, d6-dmso); 10.28 (1H, br s), 9.93 (1H, br s), 8.74 (2H, d), 8.45 (1H, s), 8.37 (1H, s), 7.90 (2H, d), 2.72-2.66 (2H, m), 1.58-1.48 (2H, m), 1.28-1.15 (2H, m), 0.79 (3H, t); LCMS method: 1, RT: 3.90 min, MI 301 [M+H].

Synthesis of 5-Butyl-2-pyridin-4-yl-3H-pyrido[3,4-d]pyrimidin-4-one [A069]

3-butyl-5-fluoro-N-(imino-pyridin-4-yl-methyl)-isonicotinamide [A068] was placed into 25 mL Biotage microwave vessel in solution in anhydrous DMA (5 mL) and heated at 150° C. in the microwave for 45 mins. The reaction mixture was filtered material through an SCX-2 25 g cartridge. The cartridge was washed with methanol (50 mL). Then the cartridge was washed with ammonia (2N, 40 mL) and the ammonia washes concentrated in vacuo to yield the title compound [A069] (390 mg) as a pale brown solid: NMR: (1H, 300 MHz, d6-dmso); 8.95 (1H, s), 8.79 (2H, dd), 8.46 (1H, s), 8.10 (2H, dd), 3.21 (2H, t), 1.63-1.50 (2H, m), 1.43-1.27 (2H, m), 0.91 (3H, t)—also shows one equivalent of DMA; LCMS method: 1, RT: 3.29 min, MI 281 [M+H].

Synthesis of 5-Butyl-4-chloro-2-pyridin-4-yl-pyrido[3,4-d]pyrimidine [A070]

5-Butyl-2-pyridin-4-yl-3H-pyrido[3,4-d]pyrimidin-4-one [A069](1.35 mmol, 0.378 g) was suspended in anhydrous 1,2-dichloroethane (DCE) (10 mL) and phosphorus oxychloride ($POCl_3$) (1.4 mmol, 0.131 mL) was added dropwise over 2-3 minutes. Finally DIPEA (2.0 mmol, 0.348 mL) was added and the mixture stirred at RT under nitrogen overnight. The brown solid slowly to change appearance after $POCl_3$ addition, then darkens further on addition of DIPEA to become a dark brown apparent solution. The reaction was left stirring at room temperature overnight under nitrogen. After 20 hours $POCl_3$ (65 μL) was added and stirred at room temperature overnight. The crude mixture was concentrated in vacuo, then azeotroped with toluene (×2) to dryness. The residue was diluted with sodium carbonate (aq. soln., 2N, 20 mL) and extracted with DCM (×2), EtOAc (×1). Combined organics washed with brine (×1), dried ($MgSO_4$), filtered through a pad of silica and concentrated in vacuo to yield the title compound [A070] (180 mg) as a of a pale brown solid which was used in the next reaction without further purification: LCMS method: 1, RT: 5.66 min, MI 299 [M+H].

Synthesis of 4-(5-Butyl-2-pyridin-4-yl-pyrido[3,4-d]pyrimidin-4-yl)-piperazine-1-carboxylic acid tert-butyl ester [A071]

5-Butyl-4-chloro-2-pyridin-4-yl-pyrido[3,4-d]pyrimidine [A070](0.615 mmol, 0.180 g), was dissolved in anhydrous DCM (5 mL), under nitrogen at room temperature and treated with triethylamine (0.868 mmol, 0.121 mL) and N-Boc-piperazine (0.682 mmol, 0.127 g) in one portion. The resulting mixture was stirred at room temperature for 2 hours. Then sodium carbonate (1N aq. soln, 20 mL) was added and extracted with DCM (×2) and EtOAc (×1). Combined organics washed with brine (×1), dried ($MgSO_4$), filtered and concentrated in vacuo to a dark brown solid, which was purified by column chromatography (SP1 on 25 g VWR cartridge in 0-10% MeOH/DCM, 15 col vols) to yield the title compound [A071] as a brown gum (0.092 g) which was used in the next reaction without further purification: NMR: (1H, 300 MHz, d6-dmso); 9.24 (1H, s), 8.79 (2H, d), 8.49 (1H, s), 8.36 (2H, d), 3.77-3.48 (8H, m), 3.19-3.07 (2H, m), 1.64-1.23 (4H, m), 1.48 (9H, s), 0.96-0.87 (3H, t)

Synthesis of 5-Butyl-4-piperazin-1-yl-2-pyridin-4-yl-pyrido[3,4-d]pyrimidine [135]

4-(5-Butyl-2-pyridin-4-yl-pyrido[3,4-d]pyrimidin-4-yl)-piperazine-1-carboxylic acid tert-butyl ester [A071](0.20 mmol, 0.09 g) was dissolved in anhydrous DCM (4 mL) and treated with hydrogen chloride (4N in dioxane, 4 mL) at room temperature and stirred for 2 hours. The reaction was diluted with methanol and poured onto SCX-2 cartridge (5 g), washing with MeOH/DCM (20 mL). The cartridge was then washed with ammonia (2N, 20 mL) and the ammonia washes concentrated in vacuo to yield a brown gum (0.059 g). The residue was purified by column chromatography (SP1 4 g column, in a gradient 5-20% MeOH/DCM 15col vols) to yield the title compound [133] as an orangey-brown gum (0.020 g); NMR: (1H, 300 MHz, d6-dmso); 9.09 (1H, s), 8.76 (2H, d), 8.51 (1H, s), 8.31 (2H, d), 3.73-3.58 (2H, br s), 3.50-3.37 (2H, br s), 3.07 (2H, t), 2.90-2.79 (4H, br s), 1.51-1.38 (2H, m), 1.28-1.15 µm (2H, m), 0.84 (3H, t); LCMS method: 1, RT: 2.58 min, MI 349 [M+H].

The following compounds were synthesised according to the general synthesis shown in scheme [A8]:

General synthesis of substituted 5-substituted-1-yl-2-pyridin-4-yl-pyrido[3,4-d]pyrimidine derivatives of general formula [F-001] Scheme A9

5-Substituted 2-Pyridin-4-yl-pyrido[3,4-d]pyrimidin-4-ol derivatives of general formula [F-004] were prepared by reaction of a 5-halo substituted 2-Pyridin-4-yl-pyrido[3,4-d]pyrimidin-4-ol derivatives of general formula [F-024] (prepared in scheme A7) in a palladium catalysed cross coupling reaction with a boronic acid or boronate ester derivative of general formula [F-023] in the presence of a palladium catalyst such as $Pd(PPh_3)_4$ or $Pd(OAc)_2$, and a base such as $K_2CO_3$ or $Cs_2CO_3$ in a polar solvent such as dioxane or a combination of dioxane and DMA at high temperature either by heating thermally or using a microwave reactor, or a palladium catalysed cross coupling reaction of a 5-halo substituted 2-Pyridin-4-yl-pyrido[3,4-d]pyrimidin-4-ol derivatives of general formula [F-024] (prepared in scheme A7) with a fluoroborate derivative of general formula [F-025] in the presence of a catalyst such as $Pd(PPh_3)_4$ or $Pd(OAc)_2$, a ligand such as RuPhos and a base such as $K_2CO_3$ or $Cs_2CO_3$ in a polar solvent such as dioxane or a combination of dioxane and DMA at high temperature either by heating thermally or using a microwave reactor. 5-substituted-1-yl-2-pyridin-4-yl-pyrido[3,4-d]pyrimidine derivatives of general formula [F-001] were prepared by the reaction of a 5-substituted 2-Pyridin-4-yl-pyrido[3,4-d]pyrimidin-4-ol derivatives of general formula [F-004] with a chlorinatation agent such as phosphorous oxychloride and the intermediated 4-chloro derivative was then reacted with primary or secondary amino derivative of general formula [F-015], in a polar aprotic solvent such as DMA, DMF, NMP in the presence of a tertiary amine base such as $Et_3N$, DIPEA or NMM at ambient temperature [method A]. After reaction work up, typically by a liquid-liquid extraction or purification by acidic ion exchange catch-release, the N-Boc deriva-

| Ex | SM [F-019] | Grig-nard [F-021] | Amine [F-015] | Analysis | | Name |
|---|---|---|---|---|---|---|
| 136 | 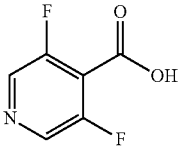 [SMILES: O=C(O)c1c(F)cncc1F] | EtMgBr | 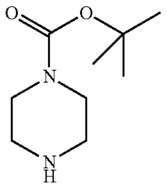 | Method 1: RT: 1.64 min, MI: 321 [M + H] | (1H, 300 MHz, d6-dmso), 9.08 (1H, s), 8.76 (2H, dd), 8.54 (1H, s), 8.30 (2H, dd), 3.72-3.58 (2H, br s), 3.55-3.45 (2H, br s), 3.10 (2H, dd), 2.89-2.77 (4H, br s), 1.17 (3H, t) | 1-[5-ethyl-2-(pyridin-4-yl)pyrido[3,4-d]pyrimidin-4-yl]piperazine |
| 137 | 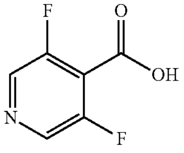 [SMILES: O=C(O)c1c(F)cncc1F] | EtMgBr | 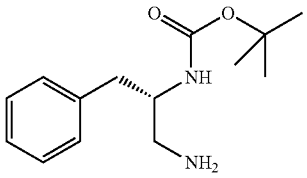 | Method 1: RT: 2.90 min, MI: 385 [M + H] | (1H, 300 MHz, d6-dmso) 9.02 (1H, s), 8.72 (2H, dd), 8.42 (1H, s), 8.16 (2H, dd), 7.35-7.24 (5H, m), 3.91 (1H, dd), 3.43 (1H, dd), 3.37-3.29 (1H, m), 3.21 (2H, dd), 2.83-2.70 (2H, m), 1.33 (3H, t) | N-[(2S)-2-amino-3-phenylpropyl]-5-ethyl-2-(pyridin-4-yl)pyrido[3,4-d]pyrimidin-4-amine |
| 138 | 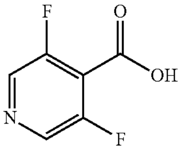 [SMILES: O=C(O)c1c(F)cncc1F] | MeMgBr | 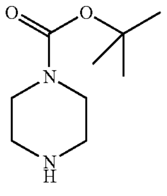 | Method 1: RT: 3.93 min, MI: 307 [M + H] | (1H, 300 MHz, d6-dmso) 9.06 (1H, s), 8.76 (2H, dd), 8.43 (1H, s), 8.30 (2H, dd), 3.57 (4H, br s), 2.84 (4H, br s), 2.65 (3H, s) | 1-[5-methyl-2-(pyridin-4-yl)pyrido[3,4-d]pyrimidin-4-yl]piperazine |

tives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-1-yl-2-pyridin-4-yl-pyrido[3,4-d]pyrimidine derivatives of general formula [F-001] were prepared by the reaction of a 2-Pyridin-4-yl-pyrido[3,4-d]pyrimidin-4-ol derivatives of general formula [F-004] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP [method B]. The intermediate 6,7-substituted-(2,4,6-triisopropyl-benzenesulfonic acid)-2-pyridin-4-yl-thieno[3,2-d]pyrimidin-4-yl ester was then reacted with a primary or secondary amino derivative, of general formula [F-015], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC Scheme A9

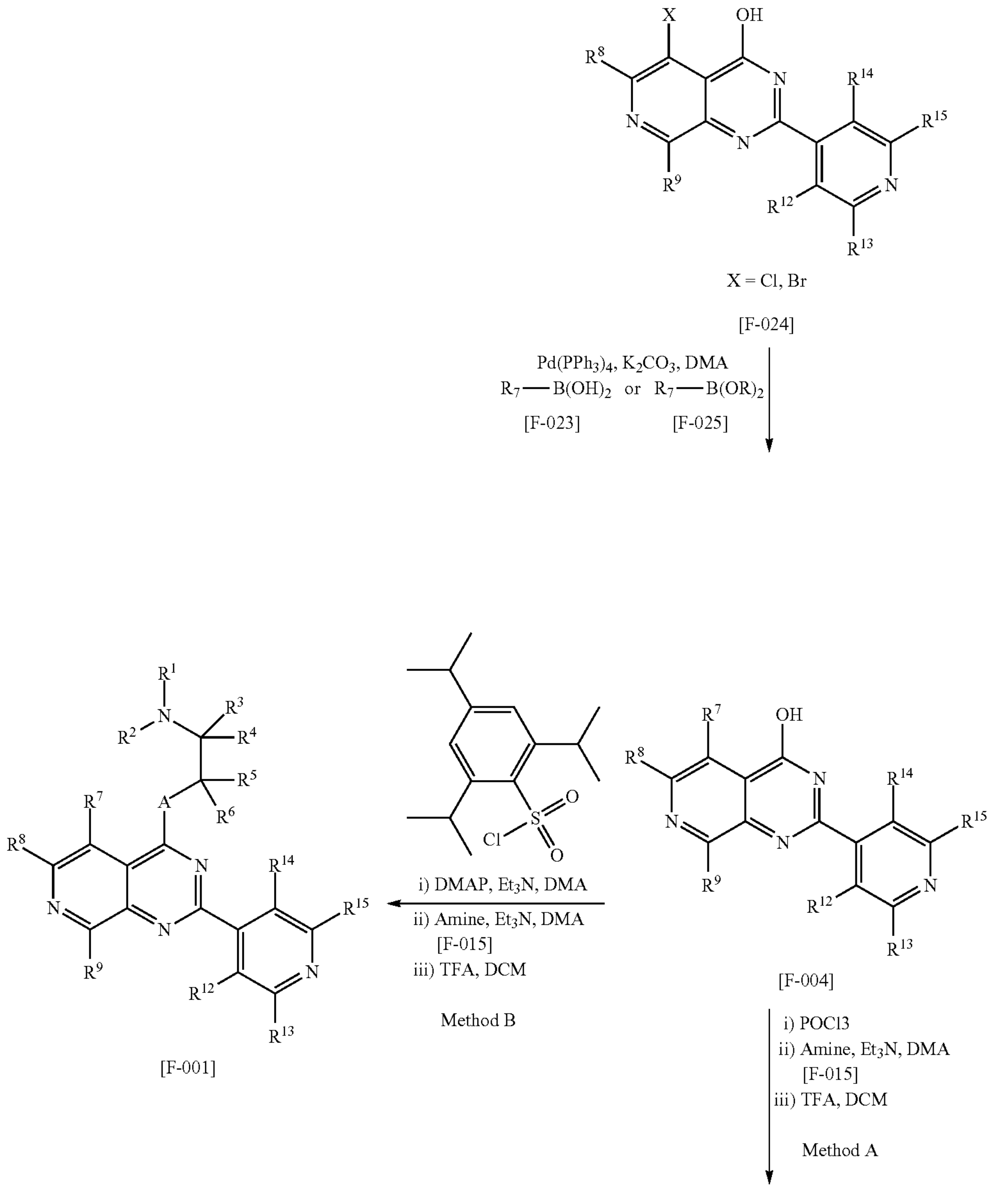

-continued

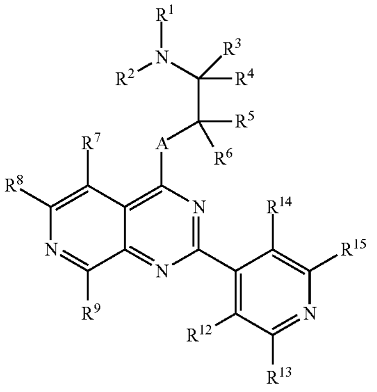

[F-001]

Synthesis of 1-[5-cyclopropyl-2-(pyridin-4-yl) pyrido[3,4-d]pyrimidin-4-yl]piperazine [139]

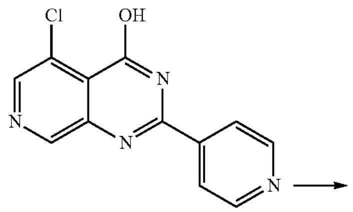

[A061]

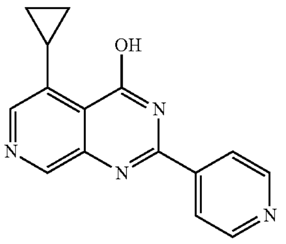

[A072]

5-Cyclopropyl-2-pyridin-4-yl-3H-pyrido[3,4-d]pyrimidin-4-one [A060]

5-Chloro-2-pyridin-4-yl-3H-pyrido[3,4-d]pyrimidin-4-one [A061](0.670 mmol, 0.173 g), potassium carbonate (2.01 mmol, 0.278 g) and cyclopropyl boronic acid (1.34 mmol, 0.115 g) was suspended in anhydrous DMA (3 mL) and then subjected to vacuum/argon balloon sparge (×3). Then tetrakis(triphenylphosphine)palladium (0.067 mmol, 0.077 g) was added in one portion and the reaction vessel sealed and heated in a microwave at 150° C. for 1 hr. The reaction was cooled to room temperature, under nitrogen. Potassium carbonate (2.0 mmol, 0.278 g) and cyclopropyl boronic acid (1.34 mmol, 0.115 g) were added and the reaction mixture subjected to vacuum/argon balloon sparge (×3). Then tetrakis(triphenylphosphine)palladium (0.067 mmol, 0.077 g) was added in one portion and the reaction vessel sealed and heated in a microwave at 180° C. for 1 hr. The reaction was cooled to room temperature under air and left standing over 48 hours. The reaction mixture was then poured on to an SCX-2 cartridge (10 g) and washed with methanol (~40 mL total). Then the cartridge was washed with ammonia (2N in MeOH, ~40 mL) and the ammonia washes concentrated in vacuo to yield the title compound [A072] (78 mg) as a yellow solid which was taken through to next reaction without purification.

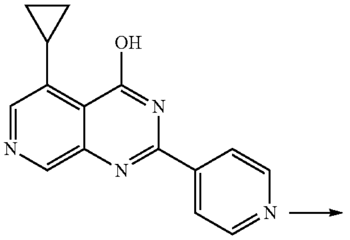

[A072]

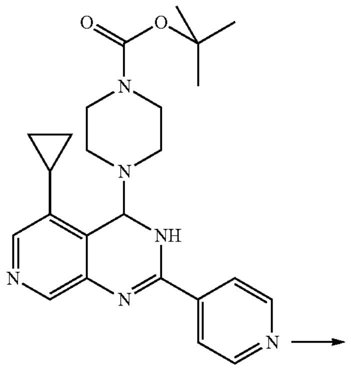

[A073]

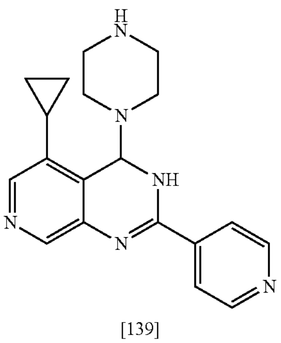

[139]

4-(5-Cyclopropyl-2-pyridin-4-yl-pyrido[3,4-d]pyrimidin-4-yl)-piperazine-1-carboxylic acid tert-butyl ester [A073]

A mixture of 5-Cyclopropyl-2-pyridin-4-yl-3H-pyrido[3,4-d]pyrimidin-4-one [A072](0.08 g, 0.3 mmol), DIPEA (0.16 mL, 0.9 mmol), 2,4,6-triisopropylbenzene sulfonyl chloride (0.11 g, 0.36 mmol), DMAP (3 mg) and DMA (2 mL) was stirred at room temperature under nitrogen and left to stir at at RT for 2 hrs. Boc-piperazine (0.062 g, 0.33 mmol) was added and the mixture was left to stir at RT overnight. Water was added and the mixture was extracted with EtOAc (×4). The extracts were combined washed with water (×4), brine, dried (MgSO4) and concentrated in vacuo. The crude reaction product was purified by flash column chromatography (SP1, EtOAc:cyclohexane elution) to yield the title compound [A073]: method: 1, RT: 5.57 min, MI 433 [M+H].

1-[5-cyclopropyl-2-(pyridin-4-yl)pyrido[3,4-d]pyrimidin-4-yl]piperazine [139]

A mixture of 4-(5-Cyclopropyl-2-pyridin-4-yl-pyrido[3,4-d]pyrimidin-4-yl)-piperazine-1-carboxylic acid tert-butyl ester [A073](0.9 g, 0.2 mmol) in DCM (3 mL) and 4N HCl dioxane (1 mL) was stirred at RT overnight. The crude reaction mixture was evapourated under reduced pressure then dissolved in MeOH and washed onto SCX-2 (5 g) cartridge and washed with MeOH/DCM (1:1, ~4 mL) then MeOH (10 mL). Then eluted with ammonia (2N in MeOH, 15 mL). The Ammonia eluent was concentrated in vacuo and the crude product was purified by normal phase chromatography (SiO2, SP1 in MeOH (0-15%)/CHCl3) to give the title compound [139](30 mg, 43% yield): LCMS method: 1, RT: 1.65 min, MI 333 [M+H]; NMR: (1H, 300 MHz, d6-dmso); 8.99 (1H, s), 8.76 (2H, dd), 8.30 (2H, dd), 8.09 (1H, s), 3.87-3.54 (4H, m), 2.87 (4H, br s), 2.63-2.57 (1H, m), 1.24 (2H, ddd), 1.01 (2H, ddd)

-continued

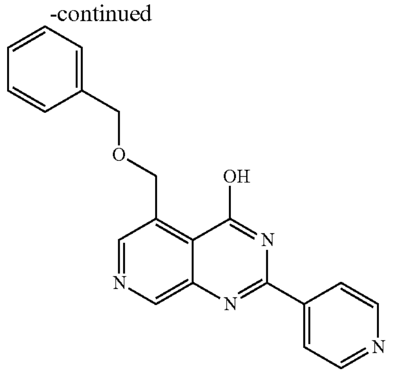

[A074]

5-Benzyloxymethyl-2-pyridin-4-yl-3H-pyrido[3,4-d]pyrimidin-4-one [A074]

A mixture of 5-Chloro-2-pyridin-4-yl-3H-pyrido[3,4-d]pyrimidin-4-one [A061](0.1 g, 0.4 mmol), Potassium benzyloxymethyltrifluoroborate (0.1 g, 0.45 mmol), cesium carbonate (0.4 g, 1.2 mmol) and RuPhos (12 mg, 0.028 mmol) were placed in Biotage 5 mL vessel and suspended in dioxane (1.8 mL) and water (0.2 mL). The mixture was subjected to spurging with vacuum/argon (×3) then the $Pd(OAc)_2$ (3 mg, 0.014 mmol) was added and the vessel sealed and heated at 104° C. overnight. DMA (1 mL) was added and the mixture was heated in wave at 150° C. for 1 hr. The RM was cooled and acetic acid (0.57 mL) was added and the mixture and stirred for 10 mins. Then flushed down SCX-2 cartridge (10 g) washing with MeOH (30-40 mL). Then washed with ammonia (2N in MeOH, 40 mL). Ammonia washes concentrated in vacuo to yield the title compound [A074] which was used without further purification: method: 1, RT: 3.31 min, MI 345 [M+H].

The following compounds were synthesised according to the general synthesis shown in scheme [A9]:

| Ex | SM | Method | Amine | Analysis | | Name |
|---|---|---|---|---|---|---|
| 140 | [A074] | B | 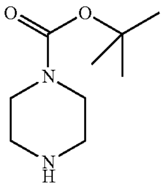 | Method 1: RT: 4.78 min, MI: 413 [M + H] | (1H, 500 MHz, d6-dmso), d6-dmso) 9.18 (1H, s), 8.77 (2H, d), 8.69 (1H, s), 8.31 (2H, dd), 7.33-7.25 (5H, m), 4.99 (2H, s), 4.54 (2H, s), 3.51 (4H, br s), 2.79 (4H, t) | 1-{5-[(benzyloxy)methyl]-2-(pyridin-4-yl)pyrido[3,4-d]pyrimidin-4-yl}piperazine |

Synthesis of 5-Benzyloxymethyl-2-pyridin-4-yl-3H-pyrido[3,4-d]pyrimidin-4-one [A074]

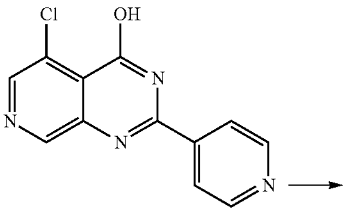

[A061]

Synthesis of 5-Chloro-4-piperazin-1-yl-8-(1H-pyrazol-3-yl)-2-pyridin-4-yl-pyrido[3,4-d]pyrimidine [141]

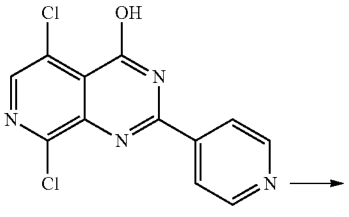

[A063]

-continued

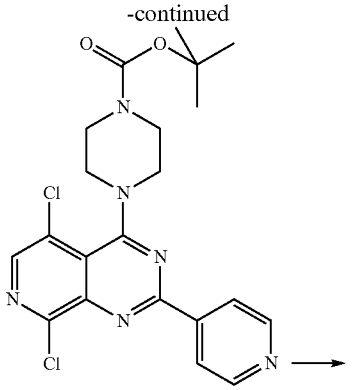

[A075]

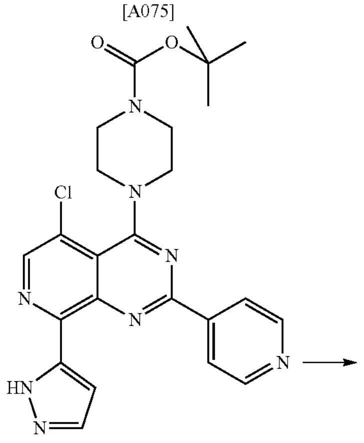

[A076]

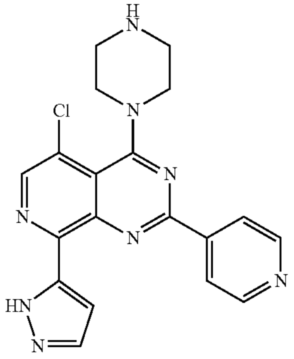

[141]

4-(5,8-Dichloro-2-pyridin-4-yl-pyrido[3,4-d]pyrimidin-4-yl)-piperazine-1-carboxylic acid tert-butyl ester [A075]

A mixture of 5,8-Dichloro-2-pyridin-4-yl-3H-pyrido[3,4-d]pyrimidin-4-one [A063](0.43 g, 1.47 mmol) $Et_3N$ (0.51 mL, 3.6 mmol), DCM (10 mL), pyridine (2 mL) was sonicated for 2 mins. Then DMAP (5 mg) was added followed by 2,4,6-triisopropylbenzene sulfonyl chloride (0.53 g, 1.77 mmol). The reaction mixture was left to stir at RT overnight. The dark brown solution was diluted with water and extracted with DCM (×3) and EtOAc (×1). Combined organics washed with brine (×1). Brine re-extracted with EtOAc (×1). Combined organics dried (MgSO4), filtered and concentrated in vacuo. The crude material was purified by normal phase chromatography ($SiO_2$, [SP1 (25 g vwr cartridge, 0-10% MeOH/DCM]) to give the title compound [A075](0.19 g, 28% yield): LCMS method: 1, RT: 4.17 min, MI 461 [M+H]; NMR: (1H, 300 MHz, d6-dmso); 8.81 (2H, d), 8.45 (1H, s), 8.33 (2H, d), 3.76 (4H, br s), 3.33 (4H, br s), 1.40 (9H, br s).

4-[5-Chloro-8-(1H-pyrazol-3-yl)-2-pyridin-4-yl-pyrido[3,4-d]pyrimidin-4-yl]-piperazine-1-carboxylic acid tert-butyl ester [A076]

A mixture of 4-(5,8-Dichloro-2-pyridin-4-yl-pyrido[3,4-d]pyrimidin-4-yl)-piperazine-1-carboxylic acid tert-butyl ester [A075](0.07 g, 0.15 mmol), potassium phosphate tribasic [$K_3PO_4$ 212.27 g/mol 21.2 g in 100 mL deionised water](0.3 mL, 0.3 mmol), tetrakis(triphenylphosphine)palladium (17 mg, 0.015 mmol), 1H-Pyrazole-5-boronic acid (24 mg, 0.21 mmol) and DMA (1 mL) were heated in μwave at 150° C. for 30 min. Acetic acid (0.52 mL) was added and the mixture was left to stir at rt for 20 mins and then the crude product was loaded onto an SCX cartridge and the cartridge was washed with methanol then the product was eluted with 2M ammonia/methanol. The eluent was concentrated under reduced pressure and the crude reaction mixture was purified by normal phase chromatography ($SiO_2$, ethyl acetate: cyclohexane elution) to give the title compound [A076]: LCMS method: 1, RT: 5.62 min, MI 493 [M+H].

Chloro-4-piperazin-1-yl-8-(1H-pyrazol-3-yl)-2-pyridin-4-yl-pyrido[3,4-d]pyrimidine [141]

A mixture of 4-[5-Chloro-8-(1H-pyrazol-3-yl)-2-pyridin-4-yl-pyrido[3,4-d]pyrimidin-4-yl]-piperazine-1-carboxylic acid tert-butyl ester [A076] and HCl dioxane (4N, 1 mL) was stirred at rt for 48 hours. The crude reaction mixture was evapourated under reduced pressure and the crude product loaded onto a SCX-2 cartridge (1 g) and washed with methanol. The product was released from the cartridge using a solution of 2M ammonia/methanol. The ammonia/methanol eluent was concentrated under reduced pressure and the crude product was purified by preparative HPLC (method A) to yield to the title compound: LCMS: method: 1, RT: 1.98 min, MI 393 [M+H]; NMR: (1H, 300 MHz, d6-dmso); 8.76-8.75 (3H, m), 8.50 (1H, s), 8.17 (2H, dd), 7.90 (1H, d), 6.67 μm (1H, dd), 3.76 (4H, br s), 2.93 (2H, br s), 2.80 (2H, br s)

Synthesis of 5-chloro-N,N-dimethyl-4-(piperazin-1-yl)-2-(pyridin-4-yl)pyrido[3,4-d]pyrimidin-8-amine [142]

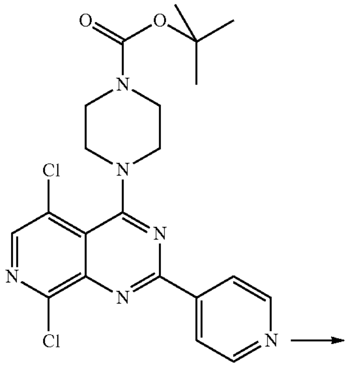

[A075]

-continued

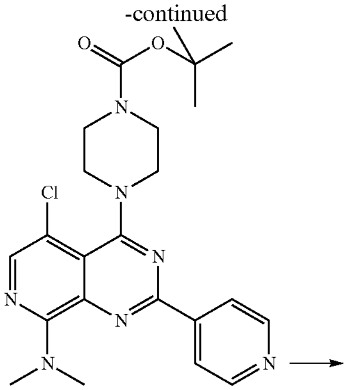

[A077]

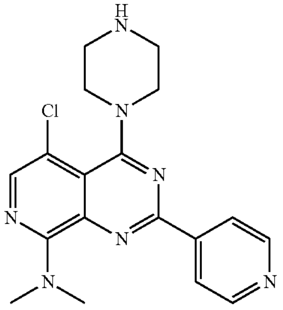

[142]

4-(5-Chloro-8-dimethylamino-2-pyridin-4-yl-pyrido[3,4-d]pyrimidin-4-yl)-piperazine-1-carboxylic acid tert-butyl ester [A077]

4-[5-Chloro-8-(1H-pyrazol-3-yl)-2-pyridin-4-yl-pyrido[3,4-d]pyrimidin-4-yl]-piperazine-1-carboxylic acid tert-butyl ester [A075](0.046 g, 0.1 mmol), DMF (2 mL) and dimethylamine in ethanol (0.5 mL) was warmed to 50° C. in a sealed vessel and left to stir for 24 h. The crude reaction mixture was evapourated under reduced pressure to yield the title compound [A077] which was used in the next step without further purification: LCMS: method: 1, RT: 4.41 min, MI 470 [M+H].

5-chloro-N,N-dimethyl-4-(piperazin-1-yl)-2-(pyridin-4-yl)pyrido[3,4-d]pyrimidin-8-amine [142]

A mixture of 4-(5-Chloro-8-dimethylamino-2-pyridin-4-yl-pyrido[3,4-d]pyrimidin-4-yl)-piperazine-1-carboxylic acid tert-butyl ester [A077](0.1 g, 0.22 mmol), DCM (3 mL) and HCl (1 mL of a 4N solution in dioxane) was stirred at RT for 2 h. The crude reaction mixture was evaporated under reduced pressure then the crude product was loaded onto an SCX cartridge and the cartridge was washed with methanol then the product was eluted with 2M ammonia/methanol. The eluent was concentrated under reduced pressure and the crude reaction mixture was purified by normal phase chromatography ($SiO_2$, SP1 on 4 g cartridge in 0-15% MeOH/DCM) to give the title compound: LCMS: method: 1, RT: 5.40 min, MI 370 [M+H]; NMR: (1H, 300 MHz, d6-dmso); 8.73 (2H, dd), 8.22 (2H, dd), 7.97 (1H, s), 3.76-3.68 (2H, m), 3.56-3.49 (2H, m), 3.16 (3H, s), 3.15 (3H, s), 2.95-2.87 (2H, m), 2.86.2-77 (2H, m)

Synthesis of 5-Isopropenyl-4-piperazin-1-yl-2-pyridin-4-yl-pyrido[3,4-d]pyrimidine [143]

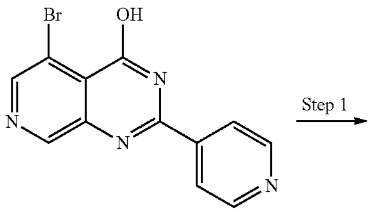

[A065]

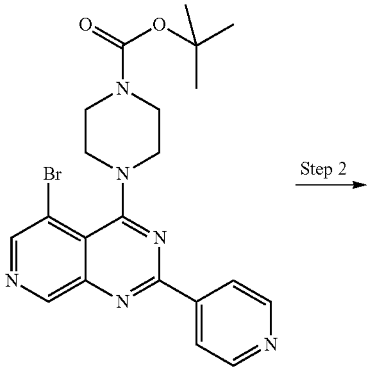

[A078]

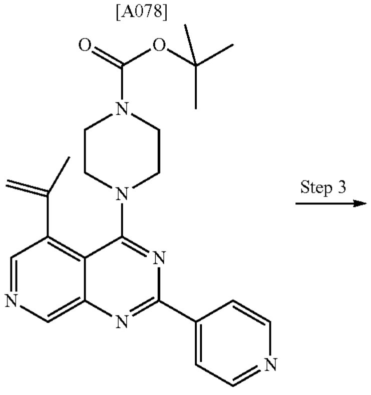

[A079]

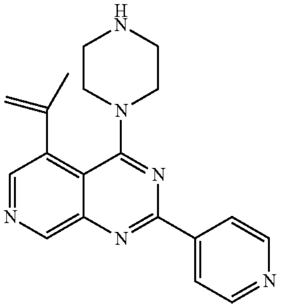

[143]

Step 1: Synthesis of 4-(5-Bromo-2-pyridin-4-yl-pyrido[3,4-d]pyrimidin-4-yl)-piperazine-1-carboxylic acid tert-butyl ester [A078]

A mixture of 5-Bromo-2-pyridin-4-yl-3H-pyrido[3,4-d]pyrimidin-4-one [A065](0.74 g, 2.45 mmol) in DMF (15 mL), DIPEA (1.3 mL, 7.3 mmol) and DMAP (5 mg) was stirred at rt for 10 min. 2,4,6-triisopropylbenzene sulfonyl chloride (0.89 g, 2.94 mmol) was added and the mixture was left to stir at rt for 80 mins at RT, then boc-piperazine (0.5 g, 2.94 mmol) was added in one portion and the rm was left to stir at rt over night. Water (30 mL) was added and the mixture was stirred at RT for 20 mins. The resultant solid was collected by filtration and the crude product was purified by column chromatography (SP1 (25 g cartridge) in 0-10% MeOH/DCM (~20 vols, 4 vols at 10% MeOH/DCM)) to yield the title compound [A078](0.69 g, 60% yield): LCMS: method: 1, RT: 5.83 min, MI 473 [M+H]; NMR: (1H, 300 MHz, d6-dmso); 9.22 (1H, s), 8.78 (3H, m), 8.32 (2H, d), 3.79 (4H, br s), 3.61 (4H, br s), 1.41 (9H, br s).

Step 2: Synthesis of 4-(5-Isopropenyl-2-pyridin-4-yl-pyrido[3,4-d]pyrimidin-4-yl)-piperazine-1-carboxylic acid tert-butyl ester [A079]

4-(5-Bromo-2-pyridin-4-yl-pyrido[3,4-d]pyrimidin-4-yl)-piperazine-1-carboxylic acid tert-butyl ester [A078](0.2 mmol, 0.094 g), potassium phosphate (tribasic) (0.60 mmol, 0.127 g), and Isopropenylboronic acid pinacol ester (0.30 mmol, 0.057 mL) were suspended in anhydrous dioxane (2 mL), in a 5 mL Biotage vessel under nitrogen. The vessel was subjected to vacuum/argon (balloon) sparge (×3) and then dichloro[1,1'-bis(diphenylphosphino)ferrocene]palladium (II) dichloromethane adduct (0.01 mmol, 0.008 g) added and the reaction sealed and warmed to 96° C. for 18 hours. The reaction mixture was cooled to room temperature under air, silica for chromatography added (1 g) and the mixture concentrated in vacuo to a brown powder. This was dry loaded onto a silica cartridge and purified by chromatography (SP1 0-10% MeOH/DCM 15 col vols) to yield 4-(5-Isopropenyl-2-pyridin-4-yl-pyrido[3,4-d]pyrimidin-4-yl)-piperazine-1-carboxylic acid tert-butyl ester [A079] (85 mg) as a 85 mg brown glass: NMR: (1H, 500 MHz, $CDCl_3$); 9.31 (1H, s), 8.79 (2H, d), 8.50 (1H, s), 8.36 (2H, d), 5.40 (1H, s), 5.32 (1H, s), 3.58 (8H, br s), 2.21 (3H, s), 1.24 (9H, s); LCMS: method: 1, RT: 5.66 min, MI 433 [M+H].

Step 3: Synthesis of 5-Isopropenyl-4-piperazin-1-yl-2-pyridin-4-yl-pyrido[3,4-d]pyrimidine To a solution of 4-(5-Isopropenyl-2-pyridin-4-yl-pyrido[3,4-d]pyrimidin-4-yl)-piperazine-1-carboxylic acid tert-butyl ester [A079](0.105 mmol 0.045 g), in DCM (2 mL) at room temperature was added hydrogen chloride (4N in dioxane, 1 mL), to obtain a thick yellowy-brown suspension, that was stirred overnight. The reaction mixture was then concentrated in vacuo, the residue redissolved in MeOH and washed onto SCX-2 cartridge. The cartridge was washed with DCM and MeOH (1:1, 20 mL total). Then the SCX-2 was washed with ammonia (2N in MeOH, 15 mL). The combined ammonia washes were concentrated to an orangey-brown solid, which was purified by column chromatography (SP1 4 g cartridge, 0-20% MeOH/DCM, 15 col vols) to yield 5-Isopropenyl-4-piperazin-1-yl-2-pyridin-4-yl-pyrido[3,4-d]pyrimidine [143] (0.011 g) as a yellow glass: NMR: (1H, 500 MHz, d4-MeOH) 9.15 (1H, s), 8.76 (2H, dd), 8.49 (1H, s), 8.31 (2H, dd), 5.40 (1H, s), 5.20 (1H, s), 3.56 (4H, br s), 2.79 (4H, t), 2.17 (3H, s); LCMS: method: 1, RT: 1.88 min, MI 333 [M+H]. LC-MS.

Example 151. 5-Methoxy-4-piperidin-1-yl-2-pyridin-4-yl-pyrido[3,4-d]pyrimidine 151a) 3-tert-Butoxycarbonylamino-pyrrolidine-1,3-dicarboxylic acid 1-(9H-fluoren-9-ylmethyl) ester: 3-tert-Butoxycarbonylamino-pyrrolidine-3-carboxylic acid (1.50 g, 6.50 mmol) was added to a solution of Sodium carbonate (1.65 g, 15.6 mmol) in Water (16.7 mL, 926 mmol) and 1,4-Dioxane (9 mL, 100 mmol). The resulting solution was stirred and cooled in an ice bath. To the stirring reaction solution was added a solution of 9-Fluorenylmethyl chloroformate (1.76 g, 6.82 mmol) in 1,4-Dioxane (13 mL, 160 mmol). The mixture was stirred at room temperature for 2 h, poured into Water (300 mL) and extracted twice with ether. The aqueous phase was cooled in an ice bath and slowly treated with 3 M of Hydrogen Chloride in Water (7.80 mL, 23.4 mmol) to neutralize. The resulting mix was extracted with EtOAc (2×), the combined organics dried over Na2SO4, filtered, and concentrated. The residue was pumped under high vacuum for 4 h, leaving 3.12 g (106%) of foam, which was used for subsequent step without further manipulation.

151b) 3-tert-Butoxycarbonylamino-3-carbamoyl-pyrrolidine-1-carboxylic acid 9H-fluoren-9-ylmethyl ester: At rt Di-tert-Butyldicarbonate (655 mg, 3.00 mmol) was added to a mixture of 3-tert-Butoxycarbonylamino-pyrrolidine-1,3-dicarboxylic acid 1-(9H-fluoren-9-ylmethyl) ester (905 mg, 2.00 mmol) and Pyridine (0.324 mL, 4.00 mmol) in 1,4-Dioxane (5 mL, 60 mmol). After 15 minutes, Ammonium Bicarbonate (0.474 g, 6.00 mmol) was added, and the reaction mixture was stirred for 72 h. Added water (10 mL) to resulting solid mass and swirled. Filtered off solid and rinsed liberally with water. After air drying, dried resulting solid under high vacuum at rt. Obtained 1.12 g (124%) of tannish solid. Proceeded and used this tannish solid for subsequent step without further manipulation.

151c) (3-Carbamoyl-pyrrolidin-3-yl)-carbamic acid tert-butyl ester 3-tert-Butoxycarbonylamino-3-carbamoyl-pyrrolidine-1-carboxylic acid 9H-fluoren-9-ylmethyl ester (410 mg, 0.91 mmol) was suspended in Methanol (5 mL, 100 mmol), then at rt added Piperidine (1 mL, 10 mmol) neat. After 16 hours concentrated reaction under reduced pressure, then pumped on residue under high vacuum overnight (to remove as much piperidine as possible), and used crude directly for subsequent reaction.

151d): 5-Methoxy-2-pyridin-4-yl-pyrido[3,4-d]pyrimidin-4-ol (127 mg, 0.501 mmol), Triethylamine (216 uL, 1.55 mmol), 2,4,6-Triisopropylbenzenesulfonyl Chloride (167 mg, 0.552 mmol), and 4-Dimethylaminopyridine (6.9 mg, 0.057 mmol) in N,N-Dimethylformamide (2.0 mL, 26 mmol) were stirred at room temperature for 1 h. Gradual dissolution of starting material was observed, intermediate sulfonate observed by hplc. (3-Carbamoyl-pyrrolidin-3-yl)-carbamic acid tert-butyl ester (126 mg, 0.550 mmol) was then added as a solution in N,N-Dimethylformamide and the reaction was stirred at room temperature. After 45 minutes concentrated reaction under reduced pressure, then partitioned residue between EtOAc and water. Took organic and washed with 3 mL of 1N HCl. Took aqueous solution, added small amount of DMSO and purified over two runs with preparative reverse phase HPLC. Combined purest fractions of each major product and lyophylized. Obtained 32 mg (14%) of yellow lyophilate of front running material [3-Carbamoyl-1-(5-methoxy-2-pyridin-4-yl-pyrido[3,4-d]pyrimidin-4-yl)-pyrrolidin-3-yl]-carbamic acid tert-butyl ester (LC/MS: M+H=466.2). Also obtained 35 mg (22%) of side product 5-Methoxy-4-piperidin-1-yl-2-pyridin-4-yl-pyrido[3,4-d]pyrimidine (LC/MS: M+H=322.1), which was generated from piperidine left over from preparation of starting material (3-Carbamoyl-pyrrolidin-3-yl)-carbamic acid tert-butyl ester. Proceeded on with [3-Carbamoyl-1-(5-methoxy- 2-pyridin-4-yl-pyrido[3,4-d]pyrimidin-4-yl)-pyrrolidin-3-yl]-carbamic acid tert-butyl ester for subsequent reaction without further manipulation.

Example 152. 3-Amino-1-(5-methoxy-2-pyridin-4-yl-pyrido[3,4-d]pyrimidin-4-yl)-pyrrolidine-3-carboxylic acid amide Added a solution of Trifluoroacetic Acid (1 mL, 10 mmol) in Methylene chloride (2 mL, 30 mmol) to [3-Carbamoyl-1-(5-methoxy-2-pyridin-4-yl-pyrido[3,4-d]pyrimidin-4-yl)-pyrrolidin-3-yl]-carbamic acid tert-butyl ester (30 mg, 0.06 mmol) at rt. After 30 minutes concentrated reaction mixture under reduced pressure, then to residue triturate with Et2O to get a solid. Filtered solid and washed liberally with Et2O. Obtained with 17 mg of title compound as a solid (LC/MS: +H=366.1).

Example 153. 3-Amino-1-(5-methoxy-2-pyridin-4-yl-pyrido[3,4-d]pyrimidin-4-yl)-pyrrolidine-3-carboxylic acid phenylamide 153a) 3-tert-Butoxycarbonylamino-3-phenylcarbamoyl-pyrrolidine-1-carboxylic acid-9H-fluoren-9-ylmethyl ester: N-(3-Dimethylaminopropyl)-N'-ethylcarbodiimide hydrochloride (575 mg, 3.00 mmol) was added to a mixture of 3-tert-Butoxycarbonylamino-pyrrolidine-1,3-dicarboxylic acid 1-(9H-fluoren-9-ylmethyl) ester (905 mg, 2.00 mmol), 1-Hydroxybenzotriazole (2.70E2 mg, 2.00 mmol) and Aniline (228 uL, 2.50 mmol) in Tetrahydrofuran (25 mL, 310 mmol). After 10 minutes added N,N-Dimethylformamide (10 mL, 100 mmol) to facilitate dissolution. After 1.5 hour concentrated reaction mixture under reduced pressure. The residue was partitioned between EtOAc (2×) and saturated aqueous NaHCO3. The combined organic phases were dried over Na2SO4, filtered, and concentrated under reduced pressure to yield 0.97 g (92%) of foam (LC/MS: M+H=528.1), which was used for subsequent step without further manipulation.

153b) (3-Phenylcarbamoyl-pyrrolidin-3-yl)-carbamic acid tert-butyl ester: 3-tert-Butoxycarbonylamino-3-phenylcarbamoyl-pyrrolidine-1-carboxylic acid 9H-fluoren-9-ylmethyl ester (960 mg, 1.8 mmol) was combined with Methanol (10 mL, 200 mmol), then at room temperature added Piperidine (2 mL, 20 mmol) neat and the reaction was stirred for 72 h. Concentrated reaction mixture under reduced pressure and Obtained a solid mass. Triturated entire sample with Et2O, filtered and rinsed solid liberally with Et2O. After air drying there remained 0.55 g (99%) of tannish solid. Proceeded and used this material in subsequent reaction without further manipulation.

153c) [1-(5-Methoxy-2-pyridin-4-yl-pyrido[3,4-d]pyrimidin-4-yl)-3-phenylcarbamoyl-pyrrolidin-3-yl]-carbamic acid tert-butyl ester: 5-Methoxy-2-pyridin-4-yl-pyrido[3,4-d]pyrimidin-4-ol (254 mg, 1.00 mmol), Triethylamine (431 uL, 3.10 mmol), 2,4,6-Triisopropylbenzenesulfonyl Chloride (334 mg, 1.10 mmol), and 4-Dimethylaminopyridine (14 mg, 0.11 mmol) in N,N-Dimethylformamide (4.0 mL, 52 mmol) were stirred at room temperature for 1 hour. (3-Phenylcarbamoyl-pyrrolidin-3-yl)-carbamic acid tert-butyl ester (335 mg, 1.10 mmol) was added neat and the reaction was stirred at room temperature overnight. The reaction was then concentrated under reduced pressure and partitioned residue between EtOAc and water. Had to filter before separating layers, as precipiated solid causing some problems between layers. The organic phase was dried over Na2SO4, filtered, and concentrated under reduced pressure to give 500 mg of crude product. Dissolved crude in DMSO (3.6 mL), filtered, and purified via preparative reverse phase HPLC. Took purest fractions and basified with saturated aqueous NaHCO3. Solid which crashed from the solution was filtered, and rinsed with water. After air drying there remained 50 mg (9%) off white solid. (LC/MS: M+H=542.1). Proceeded and used material for subsequent step without further manipulation.

153d) At rt dissolved [1-(5-Methoxy-2-pyridin-4-yl-pyrido[3,4-d]pyrimidin-4-yl)-3-phenylcarbamoyl-pyrrolidin-3-yl]-carbamic acid tert-butyl ester (50.0 mg, 0.0923 mmol) in Methylene chloride (2.0 mL, 31 mmol) then added Trifluoroacetic Acid (1.0 mL, 13 mmol) neat. After 2.5 h concentrated reaction under reduced pressure, dissolved residue in 0.80 mL DMSO, filtered, and purified via preparative reverse phase HPLC. Combined and lyophilized purest fractions. Obtained 32 mg (78%) of title compound as a yellow lyophilate (LC/MS: M+H=442.1).

Example 154. 4-Amino-1-(5-methoxy-2-pyridin-4-yl-pyrido[3,4-d]pyrimidin-4-yl)-piperidine-4-carboxylic acid [(S)-1-(4-chloro-phenyl)-3-hydroxy-propyl]-amide 154a) 4-tert-Butoxycarbonylamino-1-(5-methoxy-2-pyridin-4-yl-pyrido[3,4-d]pyrimidin-4-yl)-piperidine-4-carboxylic acid methyl ester: 5-Methoxy-2-pyridin-4-yl-pyrido[3,4-d]pyrimidin-4-ol (254 mg, 1.00 mmol), Triethylamine (0.432 mL, 3.10 mmol), 2,4,6-Triisopropylbenzenesulfonyl Chloride (334 mg, 1.10 mmol), and 4-Dimethylaminopyridine (14 mg, 0.11 mmol) were combined in N,N-Dimethylformamide (2.0 mL, 26 mmol), and stirred at room temperature. After 45 minutes 4-tert-Butoxycarbonylamino-piperidine-4-carboxylic acid methyl ester (284 mg, 1.10 mmol; Supplier=Oakwood) was added neat and stirred overnight. The reaction mixture was concentrated under reduced pressure and the residue partitioned between CH2Cl2 and water. The organic phase was dried over Na2SO4, filtered, and concentrated under reduced pressure. Resulting 380 mg (77%) of residue was used for subsequent steps without further manipulation.

154b) 4-tert-Butoxycarbonylamino-1-(5-methoxy-2-pyridin-4-yl-pyrido[3,4-d]pyrimidin-4-yl)-piperidine-4-carboxylic acid: Combined a solution of Lithium hydroxide (180 mg, 7.5 mmol) in water (3 mL, 200 mmol) to a solution of 4-tert-Butoxycarbonylamino-1-(5-methoxy-2-pyridin-4-yl-pyrido[3,4-d]pyrimidin-4-yl)-piperidine-4-carboxylic acid methyl ester (370 mg, 0.75 mmol) in Methanol (10 mL, 200 mmol) at rt and let homogeneous solution stir at rt for 16 hours. After cooling, treated reaction mixture with 1 M of Hydrogen Chloride in Water (7.5 mL, 7.5 mmol), then concentrated off most of MeOH, leaving mostly aqueous as solvent. Filtered resulting solid, then took aqueous filtrate and concentrated. Obtained 292 mg. Added 2.5 mL of DMSO, filtered, then purified via preparative reverse phase HPLC, lyopylized purest fractions to yield 45 mg (12%) of desired product as a yellow lyophilate, which was used for subsequent steps without further manipulation.

154c) [4-[(S)-1-(4-Chloro-phenyl)-3-hydroxy-propylcarbamoyl]-1-(5-methoxy-2-pyridin-4-yl-pyrido[3,4-d]pyrimidin-4-yl)-piperidin-4-yl]-carbamic acid tert-butyl ester: 4-tert-Butoxycarbonylamino-1-(5-methoxy-2-pyridin-4-yl-pyrido[3,4-d]pyrimidin-4-yl)-piperidine-4-carboxylic acid (30.0 mg, 0.0624 mmol) was combined with N,N-Dimethylformamide (1 mL, 10 mmol), then 1-Hydroxybenzotriazole (8.44 mg, 0.0624 mmol) and (S)-3-Amino-3-(4-chlorophenyl)-propan-1-ol; hydrochloride (27.7 mg, 0.125 mmol;

Supplier=Oakwood) were added followed by N-(3-Dimethylaminopropyl)-N'-ethylcarbodiimide hydrochloride (35.9 mg, 0.187 mmol). After 3 hours concentrated reaction under reduced pressure, then partitioned residue between EtOAc and water. The organic was then washed with saturated aqueous NaHCO3, dried over Na2SO4, filtered and concentrated. The crude residue was used for the subsequent step without further manipulation 154d) At rt dissolved [4-[(S)-1-(4-Chloro-phenyl)-3-hydroxy-propylcarbamoyl]-1-(5-methoxy-2-pyridin-4-yl-pyrido[3,4-d]pyrimidin-4-yl)-piperidin-4-yl]-carbamic acid tert-butyl ester (70 mg, 0.1 mmol) in Methylene chloride (2.0 mL) then added Trifluoroacetic Acid (1.0 mL, 13 mmol) neat. After 2 hours concentrated reaction under reduced pressure, dissolved residue in 1 mL DMSO, filtered, and purified via preparative reverse phase HPLC. Combined purest fractions and lyophylized overnight. Obtained 15 mg (20%) of title compound as a yellow lyophilate (LC/MS: M+H=548.1).

Example 155. 4-(5-Methoxy-2-pyridin-4-yl-pyrido[3,4-d]pyrimidin-4-yl)-piperazine-2-carboxylic acid methyl ester 155a) 4-(5-Methoxy-2-pyridin-4-yl-pyrido[3,4-d]pyrimidin-4-yl)-piperazine-1,2-dicarboxylic acid 1-tert-butyl ester 2-methyl ester: 5-Methoxy-2-pyridin-4-yl-pyrido[3,4-d]pyrimidin-4-ol (508 mg, 2.00 mmol), Triethylamine (863 uL, 6.19 mmol), 2,4,6-Triisopropylbenzenesulfonyl Chloride (668 mg, 2.20 mmol), and 4-Dimethylaminopyridine (28 mg, 0.23 mmol) in N,N-Dimethylformamide (10 mL) were stirred at room temperature for 2 hours. Gradual dissolution of starting material was observed and a considerable darkening of the solution. Piperazine-1,2-dicarboxylic acid 1-tert-butyl ester 2-methyl ester (536 mg, 2.20 mmol) was added and the reaction was stirred at room temperature for two hours. Water was added, and the resulting solid product was collected by filtration, washed with water, and dried. Obtained 448 mg (47%) tan colored solid product, which was used for subsequent steps without further manipulation).

155b) At room temperature (rt) dissolved 4-(5-Methoxy-2-pyridin-4-yl-pyrido[3,4-d]pyrimidin-4-yl)-piperazine-1,2-dicarboxylic acid 1-tert-butyl ester 2-methyl ester (50 mg, 0.1 mmol) in Methylene chloride (2.0 mL) then added Trifluoroacetic Acid (1.0 mL, 13 mmol) neat. After 2.5 hours concentrated reaction solution under reduced pressure, then dissolved residue in 1 mL of DMSO and purified via preparative reverse phase HPLC. Combined desired fractions and lyophylized overnight. Obtained 23 mg (60%) of title compound as a yellow lyophilate (LC/MS: M+H=381.1).

Example 156. 4-(5-Methoxy-2-pyridin-4-yl-pyrido[3,4-d]pyrimidin-4-yl)-piperazine-2-carboxylic acid phenylamide 156a) 4-(5-Methoxy-2-pyridin-4-yl-pyrido[3,4-d]pyrimidin-4-yl)-2-phenylcarbamoyl-piperazine-1-carboxylic acid tert-butyl ester: At rt 4-(5-Methoxy-2-pyridin-4-yl-pyrido[3,4-d]pyrimidin-4-yl)-piperazine-1,2-dicarboxylic acid 1-tert-butyl ester (77.0 mg, 0.165 mmol) was combined with N,N-Dimethylformamide (3 mL), then 1-Hydroxybenzotriazole (22.3 mg, 0.165 mmol), 4-Methylmorpholine (36.3 uL, 0.330 mmol) and Aniline (22.6 uL, 0.247 mmol) were added followed by N-(3-Dimethylaminopropyl)-N'-ethylcarbodiimide hydrochloride (94.9 mg, 0.495 mmol). After two hours the reaction mixture was concentrated under reduced pressure, and the resulting residue partitioned between EtOAc and saturated aqueous NaHCO3. The organic phase was dried over Na2SO4, filtered and concentrated. The crude residue was dissolved in 0.95 mL of DMSO, filtered, and purified via preparative reverse phase HPLC. The desired fractions were combined and lyophilized to yield 42 mg (47%) of desired product as a yellow lyophilate (LC/MS: M+H=542.2).

156b) Trifluoroacetic Acid (1 mL, 10 mmol) and Methylene chloride (2 mL, 30 mmol) were combined with 4-(5-Methoxy-2-pyridin-4-yl-pyrido[3,4-d]pyrimidin-4-yl)-2-phenylcarbamoyl-piperazine-1-carboxylic acid tert-butyl ester (42.0 mg, 0.0775 mmol) at rt. After 1.5 h the reaction solution was concentrated under reduced pressure, after which the resulting residue was dissolved in 1.3 mL of DMSO, filtered, and purified via preparative reverse phase HPLC. The desired fractions were combined and lyophylized overnight to yield 29 mg (85%) of title compound as a yellow lypohilate (LC/MS: M+H=442.1).

Example 157. 4-(5-Methoxy-2-pyridin-4-yl-pyrido[3,4-d]pyrimidin-4-yl)-piperazine-2-carboxylic acid benzylamide 157a) 2-Benzylcarbamoyl-4-(5-methoxy-2-pyridin-4-yl-pyrido[3,4-d]pyrimidin-4-yl)-piperazine-1-carboxylic acid tert-butyl ester: At room temperature 4-(5-Methoxy-2-pyridin-4-yl-pyrido[3,4-d]pyrimidin-4-yl)-piperazine-1,2-dicarboxylic acid 1-tert-butyl ester (77.0 mg, 0.165 mmol) was combined with N,N-Dimethylformamide (3 mL), then 1-Hydroxybenzotriazole (22.3 mg, 0.165 mmol), 4-Methylmorpholine (36.3 uL, 0.330 mmol) and Benzylamine (27.0 uL, 0.247 mmol) were added followed by N-(3-Dimethylaminopropyl)-N'-ethylcarbodiimide hydrochloride (94.9 mg, 0.495 mmol). After 1.5 h the reaction mixture was concentrated under reduced pressure and the resulting residue partitioned between EtOAc and saturated aqueous NaHCO3. The organic phase was dried over Na2SO4, filtered and concentrated. The crude residue was dissolved in 0.85 mL of DMSO, filtered, then purified via preparative reverse phase HPLC. The desired fractions were combined and lyophilized to yield 48 mg (52%) of desired product as a yellow lyophilate (LC/MS: M+H=556.2).

157b) A solution of Trifluoroacetic Acid (1 mL, 10 mmol) and Methylene chloride (2 mL, 30 mmol) was combined with 2-Benzylcarbamoyl-4-(5-methoxy-2-pyridin-4-yl-pyrido[3,4-d]pyrimidin-4-yl)-piperazine-1-carboxylic acid tert-butyl ester (47.0 mg, 0.0846 mmol) at rt. After 1.5 h concentrated mixture under reduced pressure, then dissolved residue in 1.15 mL of DMSO, filtered, and purified via preparative reverse phase HPLC. The desired fractions were combined and lyophilized to yield 38 mg (99%) of title compound as a yellow lypohilate (LC/MS: M+H=456.1).

Example 158. 4-(5-Methoxy-2-pyridin-4-yl-pyrido[3,4-d]pyrimidin-4-yl)-piperazine-2-carboxylic acid phenethyl-amide 158a) 4-(5-Methoxy-2-pyridin-4-yl-pyrido[3,4-d]pyrimidin-4-yl)-2-phenethylcarbamoyl-piperazine-1-carboxylic acid tert-butyl ester: At rt 4-(5-Methoxy-2-pyridin-4-yl-pyrido[3,4-d]pyrimidin-4-yl)-piperazine-1,2-dicarboxylic acid 1-tert-butyl ester (77.0 mg, 0.165 mmol) was combined with N,N-Dimethylformamide (3 mL, 30 mmol), then 1-Hydroxybenzotriazole (22.3 mg, 0.165 mmol), 4-Methylmorpholine (36.3 uL, 0.330 mmol) and Phenethylamine (31.1 uL, 0.248 mmol) were added followed by N-(3-Dimethylaminopropyl)-N'-ethylcarbodiimide hydrochloride (94.9 mg, 0.495 mmol). After 16 h the reaction mixture was concentrated under reduced pressure and the resulting residue partitioned between EtOAc and saturated aqueous NaHCO3. The organic phase was dried over Na2SO4, filtered and concentrated. The crude residue was dissolved in 0.9 mL of DMSO, filtered, then purified via preparative reverse phase HPLC. The desired fractions were combined and lyophilized to yield 53 mg (56%) of desired product as a yellow lyophilate (LC/MS: M+H=570.2).

158b) A solution of Trifluoroacetic Acid (1 mL, 10 mmol) and Methylene chloride (2 mL) was combined with 4-(5-Methoxy-2-pyridin-4-yl-pyrido[3,4-d]pyrimidin-4-yl)-2-phenethylcarbamoyl-piperazine-1-carboxylic acid tert-butyl ester (48.2 mg, 0.0846 mmol) at rt. After 1.5 h concentrated mixture under reduced pressure, then dissolved residue in 1.2 mL of DMSO, filtered, and purified via preparative reverse phase HPLC. The desired fractions were combined and lyophilized to yield 38 mg (96%) of title compound as a yellow lyophilate (LC/MS: M+H=470.2).

Synthesis of 4-(2-Pyridin-4-yl-pyrido[3,4-d]pyrimidin-4-yl)-piperazine-1-carboxylic acid tert-butyl ester [A080]

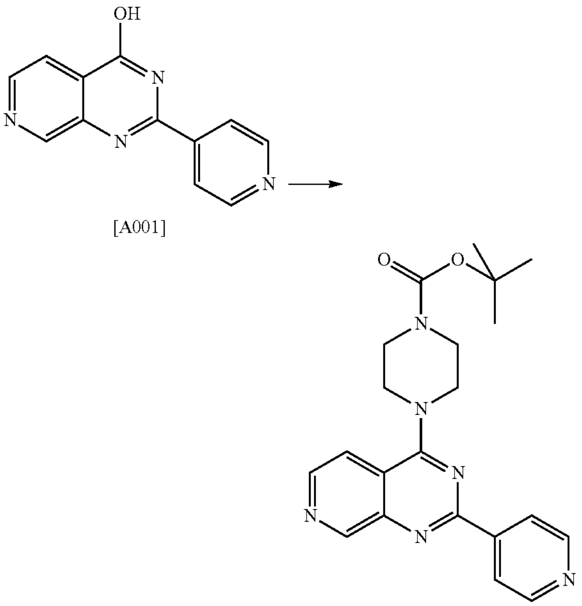

[A001]

[A080]

A mixture of 2-Pyridin-4-yl-3H-pyrido[3,4-d]pyrimidin-4-one [A001](1.0 g, 4.5 mmol), DMF (30 mL) and DIPEA (2.35 mL, 13.5 mmol) was stirred at room temperature under nitrogen. DMAP (5 mg) was added followed by 2,4,6-triisopropylbenzene sulfonyl chloride (1.64 g, 5.4 mmol) and the mixture was left to stir for two hours. 1-Boc piperazine (0.83 g, 4.5 mmol) was added and the mixture left to stir at room temperature over night. Water (50 mL) was added and the mixture left to stir for 20 min, filtered and washed with water (×3). The solid was dissolved in DCM (50 mL) and dried (MgSO4), filtered and evaporated under reduced pressure to give the title compound (1.2 g, 68% yield) which was used crude in the next step without further purification.

Synthesis of 4-(8-Propyl-2-pyridin-4-yl-pyrido[3,4-d]pyrimidin-4-yl)-piperazine-1-carboxylic acid tert-butyl ester [A081] and 4-(8-Methyl-2-pyridin-4-yl-pyrido[3,4-d]pyrimidin-4-yl)-piperazine-1-carboxylic acid tert-butyl ester [A082]

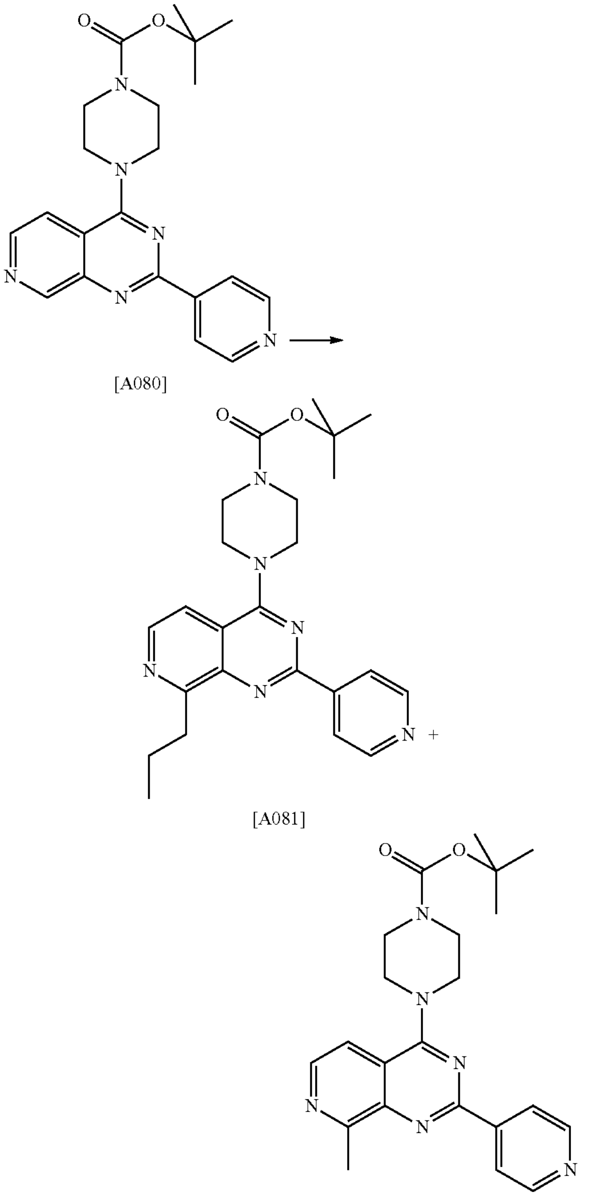

[A080]

[A081]

+

[A082]

To a solution of 4-(2-Pyridin-4-yl-pyrido[3,4-d]pyrimidin-4-yl)-piperazine-1-carboxylic acid tert-butyl ester [A080](0.196 g, 0.5 mmol), butyraldehyde (0.090 mL, 1.0 mmol), conc sulphuric acid (0.054 mL, 1.0 mmol) and iron sulphate heptahydrate (0.04 g, 0.15 mmol) in DMSO (5 mL) was added hydrogen peroxide (35% solution in water, 0.146 mL, 1.5 mmol) dropwise over 2 min. The reaction mixture was left to stir at room temperature overnight then water (5 mL) was added and the mixture was basified by addition of NaOH (1N) dropwise to pH ~7-8. The mixture was then extracted with DCM (×3) the organics were combined and washed with water (×1), brine (×1), dried (MgSO4), filtered and evaporated under reduced pressure. The crude residue was purified by column chromatography (SiO2 column, ISCO eluting with 50-90% EtOAc/cHex on 120 g column) to give: 4-(8-Propyl-2-pyridin-4-yl-pyrido[3,4-d]pyrimidin-4-yl)-piperazine-1-carboxylic acid tert-butyl ester (46 mg): LCMS: method: 5, RT: 5.79 min, MI 435 [M+H]; $^1$H NMR (1H, CDCl3, 500 MHz), 8.77 (2H, dd), 8.50 (1H, d), 8.38 (2H, dd), 7.46 (1H, d), 3.91-3.89 (4H, m), 3.71-3.69 (4H, m), 3.49 (2H, dd), 2.00-1.92 (2H, dq), 1.51 (9H, s), 1.09 (3H, t) and 4-(8-Methyl-2-pyridin-4-yl-pyrido[3,4-d]pyrimidin-4-yl)-piperazine-1-carboxylic acid tert-butyl ester (44 mg) as a colourless glass: LCMS: method: 5, RT: 5.11 min, MI 407 [M+H]; $^1$H NMR (CDCl3, 500 MHz) 8.78 (2H, dd), 8.46 (1H, d), 8.39 (2H, dd), 7.47 (1H, d), 3.91-3.89 (4H, m), 3.71-3.69 (4H, m), 3.09 (3H, s), 1.51 (9H, s).

Example 159. 4-Piperazin-1-yl-8-propyl-2-pyridin-4-yl-pyrido[3,4-d]pyrimidine A mixture of 4-(8-Propyl-2-pyridin-4-yl-pyrido[3,4-d]pyrimidin-4-yl)-piperazine-1-carboxylic acid [A081](0.046 g, 0.105 mmol), DCM (3 mL) and HCl (4N in dioxane, 1 mL) was stirred at room temperature for 90 min. The mixture was evaporated under reduced pressure then the crude product was dissolved in methanol and added to SCX-2 cartridge (10 g), washed with DCM/MeOH (1:1 10 mL) and MeOH (20 mL), then eluted with ammonia (7N in methanol, 30 mL). The Ammonia washes were evaporated under reduced pressure to give the title compound (34 mg, 75% yield) as a yellow solid: LCMS: method: 5, RT: 2.0 min, MI 335 [M+H]; $^1$H NMR (d6-dmso, 500 MHz), 8.76 (2H, dd), 8.45 (1H, d), 8.32 (2H, dd), 7.71 (1H, d), 3.89 (4H, t), 3.37 (2H, t), 2.95 (4H, t), 1.86 (2H, dq), 0.99 (3H, t).

Example 160. 8-Methyl-4-piperazin-1-yl-2-pyridin-4-yl-pyrido[3,4-d]pyrimidine A mixture of 4-(8-Methyl-2-pyridin-4-yl-pyrido[3,4-d]pyrimidin-4-yl)-piperazine-1-carboxylic acid [A082](0.045 g, 0.11 mmol), DCM (3 mL) and HCl (4N in dioxane, 1 mL) was stirred at room temperature for 90 min. The mixture was evaporated under reduced pressure then the crude product was dissolved in methanol and added to SCX-2 cartridge (10 g), washed with DCM/MeOH (1:1 10 mL) and MeOH (20 mL), then eluted with ammonia (7N in methanol, 30 mL). The Ammonia washes were evaporated under reduced pressure to give the title compound (29 mg, 75% yield) as a brown gum: LCMS: method: 5, RT: 2.17 min, MI 307 [M+H]; $^1$H NMR (d6-dmso, 500 MHz), 8.76 (2H, dd), 8.40 (1H, d), 8.33 (2H, dd), 7.70 (1H, d), 3.88 (4H, t), 2.94-2.92 (4H, m), 2.93 (3H, s)

General synthesis of substituted 2-amino pyridyl substituted 2-(2-amino-pyridin-4-yl)-pyrido[3,4-d]pyrimidin-4-yl amine derivatives of general formula [G-003] Scheme B1

2-(2-chloro-pyridin-4-yl)-pyrido[3,4-d]pyrimidin-4-yl amine derivatives of general formula [G-002] were prepared by the reaction of a 2-(2-chloro-pyridin-4-yl)-pyrido[3,4-d]pyrimidin-4-ol derivative of general formula [G-001] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as $Et_3N$, DIPEA or NMM at ambient temperature. The 2-(2-chloro-pyridin-4-yl)-pyrido[3,4-d]pyrimidin-4-yl amine derivatives of general formula [G-002] was involved in a Buchwald type reaction utilising a suitable amine, of general formula [G-005], a palladium catalyst such as $Pd(dba)_2$ or $Pd(OAc)_2$, a ligand such as Xantphos and a base such as NaOtBu or $Cs_2CO_3$ in a polar solvent such as dioxane or a combination of dioxane and DMA at high temperature either by heating thermally or using a microwave reactor, to yield substituted 2-amino pyridyl substituted 2-(2-amino-pyridin-4-yl)-pyrido[3,4-d]pyrimidin-4-yl amine derivatives of general formula [G-003]. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme B1

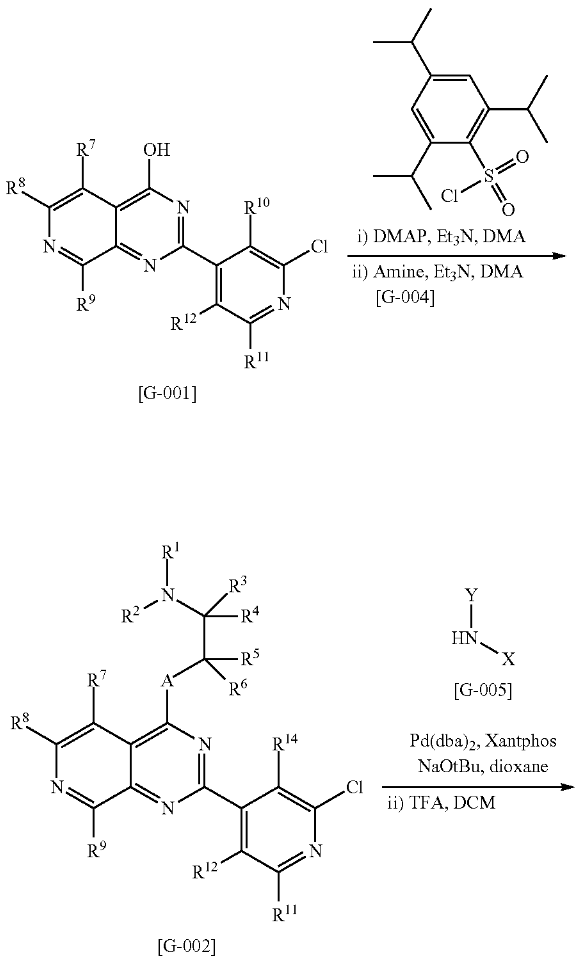

-continued

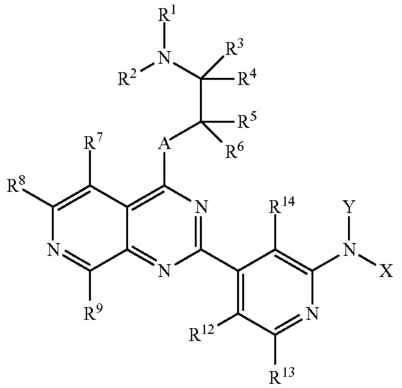

[G-003]

Synthesis of [4-(5-Methoxy-4-piperazin-1-yl-pyrido[3,4-d]pyrimidin-2-yl)-pyridin-2-yl]-phenyl-amine [200]

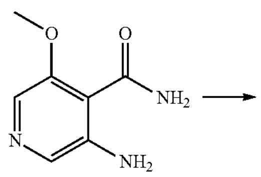

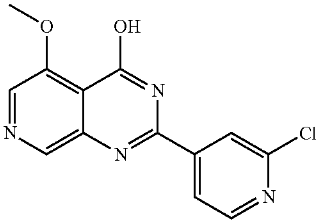

[B001]

2-(2-Chloro-pyridin-4-yl)-5-methoxy-pyrido[3,4-d]pyrimidin-4-ol [B001]

To a solution of 2-chloro-4-pyridinecarbonitrile (0.97 g, 7.03 mmol) in MeOH (35 mL) at RT, under nitrogen, was added NaOMe (0.08 g, 1.46 mmol) and left to stir for 60 mins. Then a solution of 3-Amino-5-methoxy-isonicotinic acid (1 g, 5.86 mmol) in MeOH (15 mL) was added to the dark brown mixture dropwise over 5-10 mins (via syringe). The solution was stirred at rt for 2 h and then overnight at 85° C. After cooling down, the solid was filtered and, washed with methanol and used without further purification to yield the title compound [B001](0.97 g 57% yield: LCMS: method: 5, RT: 6.32 min, MI 287.34 [M+H].

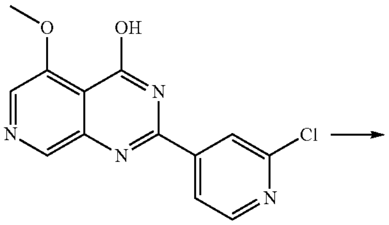

[B001]

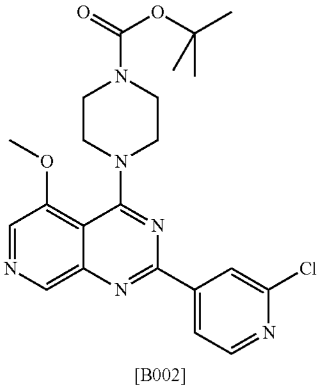

[B002]

4-[2-(2-Chloro-pyridin-4-yl)-5-methoxy-pyrido[3,4-d]pyrimidin-4-yl]-piperazine-1-carboxylic acid tert-butyl ester [B002]

A mixture of 2-(2-chloro-pyridin-4-yl)-5-methoxy-pyrido[3,4-d]pyrimidin-4-ol [B001](0.58 g, 2 mmol), anhydrous DMA (5 mL), triethylamine (0.58 mL, 4 mmol) and DMAP (20 mg, 0.16 mmol) was sonicated for 10 min then stirred at room temperature for 10 min. 2,4,6-Triisopropyl-benzene-sulfonyl chloride (0.67 g, 2.2 mmol) was added and the mixture was sonicated for 5 min then left to stir at room temperature for 2 hours. During this time the material went into solution to form a viscous solution. A solution of Boc piperazine (0.56 g, 3 mmol) in anhydrous DMA (1 mL) was added and the reaction mixture was left to stir at room temperature overnight. Water (20 mL) was added and the reaction mixture was extracted with DCM (2×30 mL), the extracts were combined and washed with water (20 mL), saturated bicarbonate solution (2×20 mL) and water (20 mL), dried ($MgSO_4$) filtered and evaporated under reduced pressure to give a pale yellow oil, which was purified by flash column chromatography (SP1, 50 g $SiO_2$ cartridge 100% EtOAc up to 95% EtOAc: 5% MeOH gradient) to give the title compound [B002] as a colourless solid (0.22 g 24% yield). LCMS: method: 5, RT: 10.86 min, MI 457 [M+H]; NMR: (1H, 500 MHz, $CDCl_3$); 9.0 (1H, s), 8.53 (1H, d), 8.35 (1H, s), 8.28 (1H, 1H, d), 8.23 (1H, s), 3.70 (4H, br s), 3.64 (4H, br s), 1.50 (9H, s)

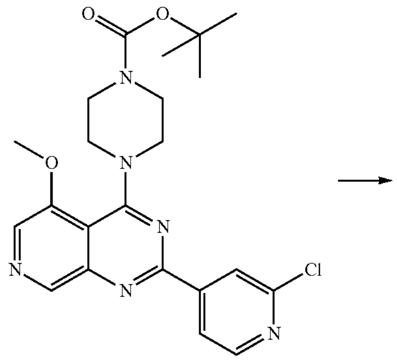

[B002]

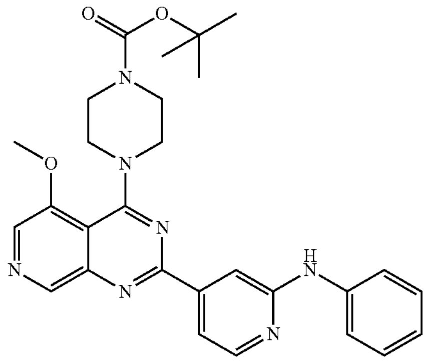

[B003]

4-[5-Methoxy-2-(2-phenylamino-pyridin-4-yl)-pyrido[3,4-d]pyrimidin-4-yl]-piperazine-1-carboxylic acid tert-butyl ester [B003]

A mixture of 4-[2-(2-Chloro-pyridin-4-yl)-5-methoxy-pyrido[3,4-d]pyrimidin-4-yl]-piperazine-1-carboxylic acid tert-butyl ester [B002](0.100 g, 0.22 mmol), $Pd(dba)_2$ (10 mg, 0.013 mmol), Xantphos (17.5 mg, 0.025 mmol), NaOtBu (43 mg, 0.440 mmol) and anhydrous dioxane (4 ml) was added to a microwave vial. Aniline was then added the vial was sealed and heated at 150° C. for 20 min. Water (10 mL) was added and the reaction mixture was extracted with DCM (2×10 mL), the extracts were combined and washed with water (10 mL), saturated bicarbonate (2×10 mL) and water (10 mL), dried with MgSO4 filtered and evaporated to give a pale yellow oil, which was purified by flash column chromatography (SP1, 25 g SiO2 cartridge 100% EtOAc up to 95% EtOAc: 5% MeOH gradient) to give the title compound [B003] as a colourless solid (0.04 g 36% yield). LCMS: method: 5, RT: 7.80 min, MI 514 [M+H]; NMR: (1H, 500 MHz, $CDCl_3$); 8.93 (1H, s), 8.65 (1H, d), 8.41 (1H, s), 7.39 (1H, d), 7.58 (5H, m), 6.55 (1H, br s), 3.63 (4H, m), 3.57 (4H, m), 1.49 (9H, s).

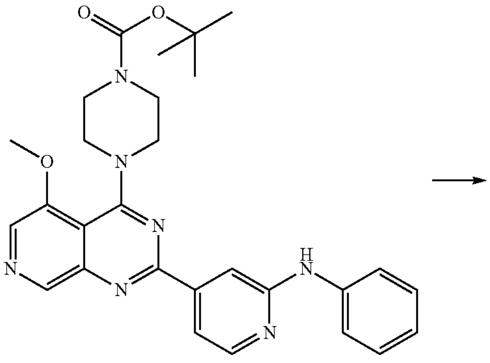

[B003]

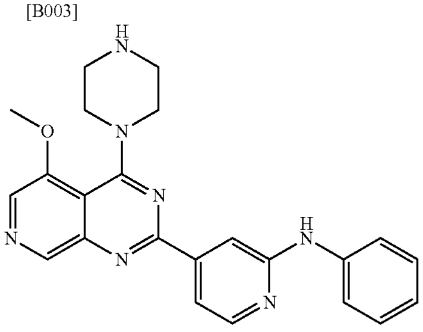

[200]

[4-(5-Methoxy-4-piperazin-1-yl-pyrido[3,4-d]pyrimidin-2-yl)-pyridin-2-yl]-phenyl-amine To a mixture of 4-[5-Methoxy-2-(2-phenylamino-pyridin-4-yl)-pyrido[3,4-d]pyrimidin-4-yl]-piperazine-1-carboxylic acid tert-butyl ester [B003](0.040 g, 0.080 mmol) in DCM (1 ml) was added TFA (1 ml) and the mixture was left to stir at room temperature for 2 hours. After completion the crude reaction mixture was diluted with DCM (5 mL) and poured onto a 1 g SCX-2 cartridge and washed with DCM and MeOH before eluting with 2N NH3/MeOH which was evaporated to give a pale yellow oil, which was evaporated in a genevac to give a pale yellow solid (25 mg). LCMS: method: 5, RT: 3.12 min, MI: 414.22 [M+H]; NMR: (1H, 500 MHz, d6-dmso); 9.32 (1H, br s), 8.8 (1H, s), 8.29 (2H, m), 7.88 (1H, s), 7.76 (2H, d), 7.64 (1H, d), 7.29 (2H, m), 6.88 (2H, m), 4.04 (3H, s), 3.64 (4H, m), 2.88 (4H, m).

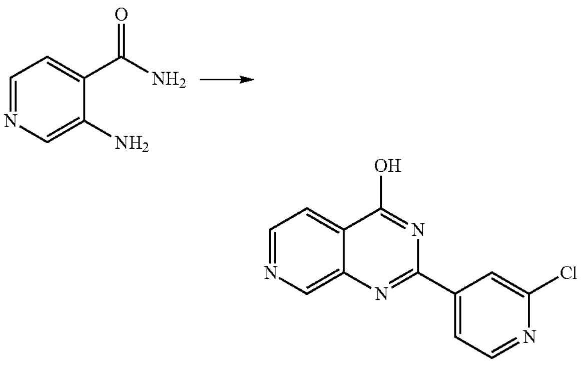

[B004]

2-(2-Chloro-pyridin-4-yl)-pyrido[3,4-d]pyrimidin-4-ol [B004]

To a solution of 2-chloro-4-pyridinecarbonitrile (2.18 g, 15.77 mmol) in dry THF (20 mL) was added 3-Amino-isonicotinic acid methyl ester (2 g, 13.1 mmol) followed by Potassium tert-pentoxide (15.5 mL, 26.3 mmol 1.7M in toluene). The reaction was stirred overnight at RT. The precipitate was collected by filtration to yield the title compound which was used without further purification: LCMS: method: 5, RT: 4.05 min, MI 259 [M+H].

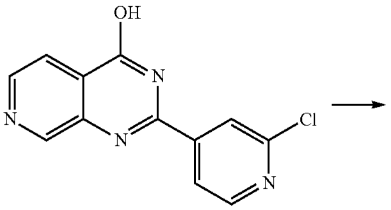

[B004]

-continued

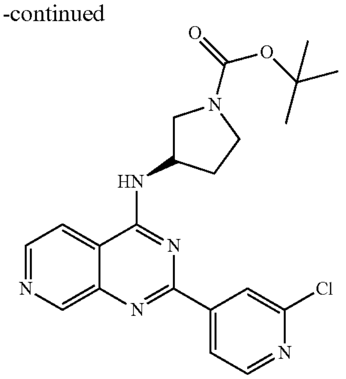

[B005]

(R)-3-[2-(2-Chloro-pyridin-4-yl)-pyrido[3,4-d]pyrimidin-4-ylamino]-pyrrolidine-1-carboxylic acid tert-butyl ester [B005]

A mixture of 2-(2-Chloro-pyridin-4-yl)-pyrido[3,4-d]pyrimidin-4-ol [B003](1 g, 3.86 mmol), anhydrous DMA (10 mL), triethylamine (1.1 mL, 7.73 mmol), 2,4,6-Triisopropylbenzenesulfonyl chloride (1.29 g, 3.25 mmol), and DMAP (47 mg, 0.386 mmol) was stirred at room temperature for 1 h and (R)-3-Amino-pyrrolidine-1-carboxylic acid tert-butyl ester (940 mg, 5.02 mmol) was added. The reaction mixture was stirred overnight and the solvent was evaporated under reduced pressure. DCM and $Et_2O$ were added and the resulting solid was collected and used without further purification in the next step. LCMS: method: 5, RT 6.19 min, MI 427 [M+H].

The following compounds were synthesised according to the general synthesis shown in scheme [B1](Example 1):

| Ex | SM [G-002] | Amine | Aniline | Analysis LCMS | Analysis NMR | Name |
|---|---|---|---|---|---|---|
| 201 | [B003] | 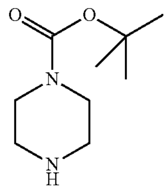 | 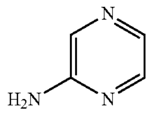 | Method 1: RT: 1.91 min, MI: 416.17 [M + H] | (1H, 300 MHz, $CDCl_3$) 10.22 (1H, m), 9.16 (1H, m), 8.82 (1H, m), 7.72 (1H, m), 8.43 (1H, m), 8.33 (1H, m), 8.30 (1H, m), 8.26 (1H, m), 7.85 (1H, m), 4.10 (3H, s), 3.71 (4H, m), 2.96 (4H, m) | [4-(5-Methoxy-4-piperazin-1-yl-pyrido[3,4-d]pyrimidin-2-yl)-pyridin-2-yl]-pyrazin-2-yl-amine |
| 202 | [B003] | 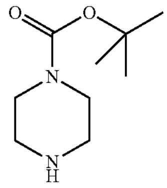 | 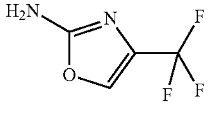 | Method 1: RT: 3.27 min, MI: 473.2 [M + H] | (1H, 500 MHz, d6-dmso) 9.35 (1H, s), 9.10 (1H, s), 8.91 (1H, s), 8.53 (1H, m), 8.46 (1H, d), 8.42 (1H, s), 7.99 (1H, dd), 4.09 (3H, s), 3.93 (4H, m, br), 3.27 (4H, m, br) | [4-5-Methoxy-4-piperazin-1-yl-pyrido[3,4-d]pyrimidin-2-yl)-pyridin-2-yl]-(4-trifluoro-methyl-oxazol-2-yl)-amine |
| 203 | [B003] | 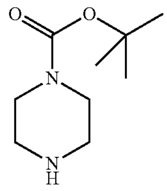 | 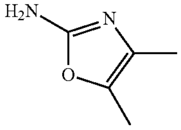 | Method 1: RT: 2.40 min, MI: 433.1 [M + H] | (1H, 500 MHz, d6-dmso) 10.55 (1H, s), 9.14 (1H, s), 8.81 (1H, s), 8.34 (1H, d), 8.31 (1H, s), 7.84 (1H, d), 4.06 (3H, s), 3.68 (4H, m), 2.90 (4H, m), 2.19 (3H, s), 2.01 (3H, s) | (4,5-Dimethyl-oxazol-2-yl)-[4-(5-methoxy-4-piperazin-1-yl-pyrido[3,4-d]pyrimidin-2-yl)-pyridin-2-yl]-amine |

-continued

| | SM | | | Analysis | | |
|---|---|---|---|---|---|---|
| Ex | [G-002] | Amine | Aniline | LCMS | NMR | Name |
| 204 | [B003] | 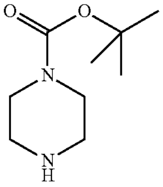 | 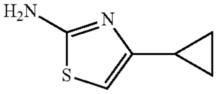 | Method 1: RT: 3.73 min, MI: 461.20 [M + H] | (1H, 500 MHz, d6-dmso) 9.68 (1H, s, br), 9.56 (2H, s, br), 8.96 (1H, s), 8.46 (1H, d), 8.42 (1H, s), 8.23 (1H, s), 7.88 (1H, dd), 4.10 (3H, s), 3.96 (4H, m), 3.32 (1H, m), 3.27 (4H, m), 0.86 (2H, m), 0.80 (2H, m) | (4-Cyclopropyl-thiazol-2-yl)-[4-(5-methoxy-4-piperazin-1-yl-pyrido[3,4-d]pyrimidin-2-yl)-pyridin-2-yl]-amine |
| 205 | [B003] | 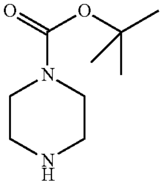 | 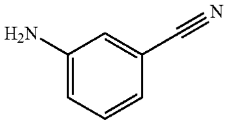 | Method 1: RT: 3.47 min, MI: 439.2 [M + H] | (1H, 300 MHz, d6-dmso) 9.82 (1H, s), 9.10 (1H, s, br), 8.89 (1H, s), 8.41 (2H, s, br), 8.40 (1H, s), 7.97 (1H, s), 7.89 (1H, d), 7.78 (1H, d), 7.48 (1H, t), 7.32 (1H, d), 4.09 (3H, s), 3.90 (4H, m), 3.31 (4H, m) | 3-[4-(5-Methoxy-4-piperazin-1-yl-pyrido[3,4-d]pyrimidin-2-yl)-pyridin-2-ylamino]-benzonitrile |
| 206 | [B003] | 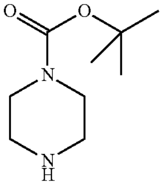 | 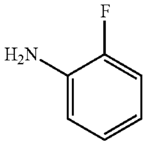 | Method 1: RT: 2.69 min, MI: 482.03 [M + H] | (1H, 300 MHz, d6-dmso) 8.95 (1H, s), 8.79 (1H, s), 8.31 (1H, s), 8.23 (1H, d), 8.20 (1H, dt), 8.01 (1H, s), 7.68 (1H, dd), 7.21 (1H, ddd), 7.14 (1H, td), 7.01-6.99 (1H, m), 4.06 (3H, s), 3.65 (4H, m, br), 2.87 (4H, m, br) | (2-Fluoro-phenyl)-[4-(5-methoxy-4-piperazin-l-yl-pyrido[3,4-d]pyrimidin-2-yl)-pyridin-2-yl]-amine |
| 207 | [B003] | 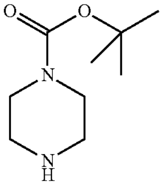 | 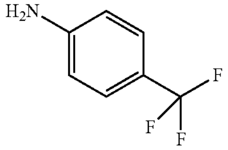 [SMILES: Nc1ccc(C(F)(F)F)cc1] | | (1H, 300 MHz, d6-dmso) 9.83 (1H, s), 8.85 (1H, s), 8.38 (1H, d), 8.36 (1H, s), 7.98 (2H, s), 7.96 (1H, s), 7.76 (1H, d), 7.61 (2H, d), 4.07 (3H, s), 3.79 (4H, m, br), 3.11 (4H, m, br) | [4-(5-Methoxy-4-piperazin-1-yl-pyrido[3,4-d]pyrimidin-2-yl)-pyridin-2-yl]-(4-trifluoro-methyl-phenyl)-amine |
| 208 | [B003] | 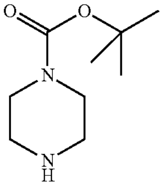 | 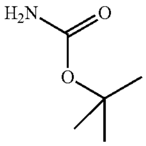 | Method 1: RT: 3.51 min, MI: 338.2 [M + H] | (1H, 300 MHz, d6-dmso) 8.78 (1H, s), 8.30 (1H, s), 8.27 (1H, s), 8.04 (1H, d), 7.47 (1H, s), 7.41 (1H, d), 6.10 (2H, s, br), 4.06 (3H, s), 3.66 (4H, m, br), 2.95 (4H, m, br) | 4-(5-Methoxy-4-piperazin-1-yl-pyrido[3,4-d]pyrimidin-2-yl)-pyridin-2-ylamine |
| 209 | [B003] | 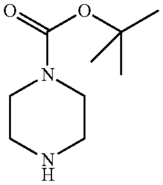 | 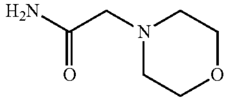 | Method 1: RT: 1.80 min, MI: 465.2 [M + H] | (1H, 300 MHz, d6-dmso) 10.11 (1H, s), 9.10 (1H, s), 8.88 (1H, s), 8.47 (1H, d), 8.37 (1H, s), 8.05 (1H, d), 4.08 (3H, s), 3.80 (4H, m, br), 3.64 (4H, t, br), 3.23 (2H, s), 3.15 (4H, m, br), 2.55 (4H, m, br) | N-[4-(5-Methoxy-4-piperazin-1-yl-pyrido[3,4-d]pyrimidin-2-yl)-pyridin-2-yl]-2-morpholin-4-yl-acetamide |
| 210 | [B003] | 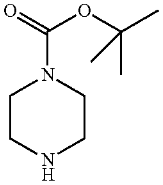 | 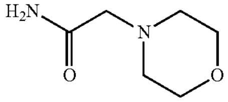 | Method 1: RT: 1.51 min, MI: 463.2 [M + H] | (1H, 300 MHz, d6-dmso) 9.19 (1H, s), 8.79 (1H, s), 8.41 (1H, d), 8.21 (1H, s), 8.10 (1H, d), 4.11 (3H, s), 3.77 (4H, m), 3.19 (2H, s), 3.01 (4H, m), 2.59 (4H, m), 1.73-1.69 (4H, m), 1.52 (2H, m) | N-[4-(5-Methoxy-4-piperazin-1-yl-pyrido[3,4-d]pyrimidin-2-yl)-pyridin-2-yl]-2-piperidin-1-yl-acetamide |

-continued

| | SM | | | Analysis | | |
|---|---|---|---|---|---|---|
| Ex | [G-002] | Amine | Aniline | LCMS | NMR | Name |
| 211 | [B003] | 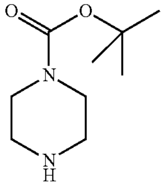 | 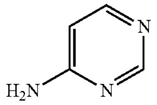 | Method 1: RT: 2.05 min, MI: 416.14 [M + H] | (1H, 300 MHz, d6-dmso) 10.42 (1H, s), 8.85 (1H, s), 8.75 (2H, s), 8.45 (2H, d), 8.35 (1H, s), 8.22 (1H, s), 7.90 (1H, dd), 4.08 (3H, s), 3.73 (4H, m), 2.98 (4H, m) | [4-(5-Methoxy-4-piperazin-1-yl-pyrido[3,4-d]pyrimidin-2-yl)-pyridin-2-yl]-pyrimidin-4-yl-amine |
| 212 | [B003] | 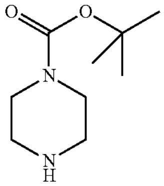 | 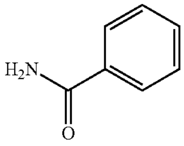 | Method 1: RT: 2.69 min, MI: 442.13 | (1H, 300 MHz, d6-dmso) 9.17 (1H, s), 8.85 (1H, s), 8.54 (1H, d), 8.33 (1H, s), 8.22 (1H, s), 8.09-8.05 (3H, m), 7.62-7.59 (1H, m), 7.54-7.51 (2H, m) | N-[4-(5-Methoxy-4-piperazin-1-yl-pyrido[3,4-d]pyrimidin-2-yl)-pyridin-2-yl]-benzamide |
| 213 | [B003] | 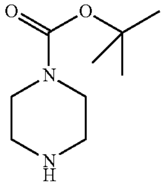 | 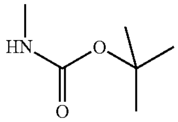 | Method 1: RT: 3.98 min, MI: 352.3 [M + H] | (1H, 300 MHz, d6-dmso) 8.80 (1H, s), 8.31 (1H, s), 8.11 (1H, d), 7.47 (1H, s), 7.39 (1H, d), 6.72 (1H, d), 4.05 (3H, s), 3.71 (4H, m), 3.03 (4H, m), 2.81 (3H, d) | [4-(5-Methoxy-4-piperazin-1-yl-pyrido[3,4-d]pyrimidin-2-yl)-pyridin-2-yl]-methyl-amine |
| 214 | [B003] | 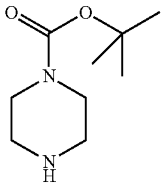 | 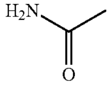 | Method 1: RT: 2.33 min MI: 380.18 [M + H] | (1H, 300 MHz, d6-dmso) 10.58 (1H, s), 9.05 (1H, s), 8.81 (1H, s), 8.43 (1H, d), 8.29 (1H, s), 7.97 (1H, d), 4.05 (3H, s), 3.63 (4H, m), 3.15 (1H, d, br), 2.87 (4H, m), 2.12 (3H, s) | N-[4-(5-Methoxy-4-piperazin-1-yl-pyrido[3,4-d]pyrimidin-2-yl)-pyridin-2-yl]-acetamide |
| 215 | [B003] | 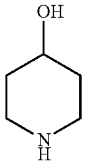 | 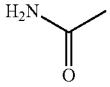 | Method 1: RT: 3.87 min, MI: 395.11 [M + H] | (1H, 300 MHz, d6-dmso) 10.58 (1H, s), 9.05 (1H, s), 8.81 (1H, s), 8.43 (1H, d), 8.32 (1H, s), 7.98 (1H, dd), 4.79 (1H, d), 4.06 (3H, s), 4.00 (1H, m, br), 3.81 (1H, m, br), 3.39 (3H, m, br), 2.12 (3H, s), 1.89 (2H, d, br), 1.56 (2H, m, br). | N-{4-[4-(4-Hydroxy-piperidin-1-yl)-5-methoxy-pyrido[3,4-d]pyrimidin-2-yl]-pyridin-2-yl}-acetamide |
| 216 | [B003] | 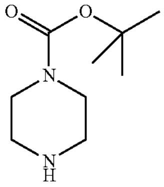 | 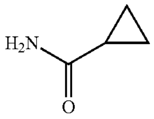 | Method 1: RT: 2.66 min, MI: 406.13 [M + H] | (1H, 300 MHz, d6-dmso) 8.28 (1H, s), 8.01 (1H, s), 7.61 (1H, d), 7.42 (1H, s), 7.26 (1H, dd), 3.32 (3H, s), 2.99 (4H, m), 2.27 (4H, m), 1.13 (1H, m), 0.22 (2H, m), 0.12 (2H, m) | Cyclopropane-carboxylic acid [4-(5-methoxy-4-piperazin-1-yl-pyrido[3,4-d]pyrimidin-2-yl)-pyridin-2-yl]-amide |
| 217 | [B003] | 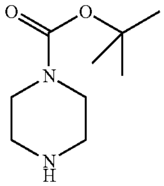 | 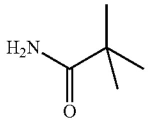 | Method 1: RT: 3.13 min, MI: 422.2 [M + H] | (1H, 300 MHz, d6-dmso) 9.89 (1H, s), 9.03 (1H, s), 8.84 (1H, s), 8.46 (1H, d), 8.33 (1H, s), 8.01 (1H, dd), 4.06 (3H, s), 3.68 (4H, m, br), 2.95 (4H, m, br), 1.27 (9H, s) | N-[4-(5-Methoxy-4-piperazin-1-yl-pyrido[3,4-d]pyrimidin-2-yl)-pyridin-2-yl]-2,2-dimethyl-propionamide |

-continued

| | SM | | | Analysis | | |
|---|---|---|---|---|---|---|
| Ex | [G-002] | Amine | Aniline | LCMS | NMR | Name |
| 218 | [B003] | 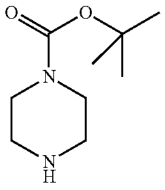 | 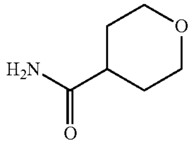 | Method 1: RT: 2.82 min, MI: 450.20 [M + H] | (1H, 300 MHz, d6-dmso) 10.59 (1H, s), 9.10 (1H, s), 8.87 (1H, s), 8.46 (1H, d), 8.36 (1H, s), 8.01 (1H, dd), 4.07 (3H, s), 3.90 (2H, dd, br), 3.78 (4H, m, br), 3.35 (2H, m), 3.13 (4H, m, br), 2.79 (1H, m), 1.74-1.66 (4H, m) | Tetrahydro-pyran-4-carboxylic acid[4-(5-methoxy-4-piperazin-1-yl-pyrido[3,4-d]pyrimidin-2-yl)-pyridin-2-yl]-amide |
| 219 | [B003] | 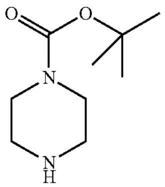 | 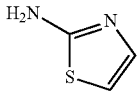 | Method 1: RT: 3.12 min, MI: 241.09 [M + H] | (1H, 300 MHz, d6-dmso) 8.84 (1H, s), 8.43 (1H, d), 8.35 (1H, s), 8.15 (1H, s), 7.82 (1H, dd), 7.40 (1H, d), 7.01 (1H, s), 4.07 (3H, s), 3.75 (4H, m), 3.04 (4H, m) | [4-(5-Methoxy-4-piperazin-1-yl-pyrido[3,4-d]pyrimidin-2-yl)-pyridin-2-yl]-thiazol-2-yl-amine |
| 220 | [B003] | 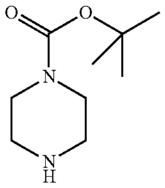 | 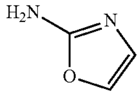 | Method 1: RT: 2.28 min, MI: 405.10 [M + H] | (1H, 500 MHz, d6-dmso) 10.82 (1H, s), 9.04 (1H, s), 8.84 (1H, s), 8.38 (1H, d), 8.34 (1H, s), 7.87 (1H, d), 7.74 (1H, s), 7.09 (1H, s), 4.07 (3H, s), 3.74 (4H, m), 3.01 (4H, m) | [4-(5-Methoxy-4-piperazin-1-yl-pyrido[3,4-d]pyrimidin-2-yl)-pyridin-2-yl]-oxazol-2-yl-amine |
| 221 | [B003] | 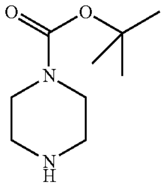 | 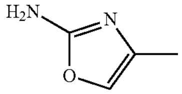 | Method 1: RT: 2.44 min, MI: 419.18 [M + H] | (1H, 500 MHz, d6-dmso) 10.77 (1H, s), 9.19 (1H, s), 8.91 (1H, s), 8.40 (1H, s), 8.39 (1H, d), 7.88 (1H, d), 7.44 (1H, s), 4.09 (3H, s), 3.92 (4H, m), 3.29 (4H, m), 2.10 (3H, s) | [4-(5-Methoxy-4-piperazin-1-yl-pyrido[3,4-d]pyrimidin-2-yl)-pyridin-2-yl]-(4-methyl -oxazol-2-yl)-amine |
| 222 | [B003] | 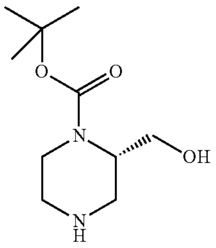 | 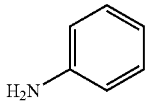 | Method 1: RT: 2.38 min, MI: 444.2 [M + H] | (1H, 500 MHz, d6-dmso) 9.39 (1H, s), 8.88 (1H, s), 8.39 (1H, s), 8.31 (1H, d), 7.94 (1H, s), 7.75 (2H, d), 7.68 (1H, d), 7.27 (2H, t), 6.89 (1H, t), 4.30 (2H, m), 4.09 (3H, s), 3.70 (2H, m), 3.48-3.36 (5H, m) | {(S)-4-[5-Methoxy-2-(2-phenylamino-pyridin-4-yl)-pyrido[3,4-d]pyrimidin-4-yl]-piperazin-2-yl}-methanol |
| 223 | [B003] | 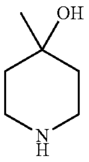 | 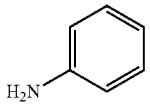 | Method 5: RT: 4.34 min, MI: 443.19 [M + H] | (1H, 500 MHz, d6-dmso) 9.29 (1H, s), 8.78 (1H, s), 8.30 (1H, s), 8.28 (1H, d), 7.89 (1H, d), 7.73 (2H, d), 7.65 (1H, dd), 7.27 (2H, t), 6.88 (1H, t), 4.47 (1H, s), 4.06 (3H, s), 3.94 (2H, m, br), 3.53 (2H, m), 1.64 (4H, m), 1.19 (3H, s) | 1-[5-Methoxy-2-(2-phenylamino-pyridin-4-yl)-pyrido[3,4-d]pyrimidin-4-yl]-4-methyl-piperidin-4-ol |
| 224 | [B003] | 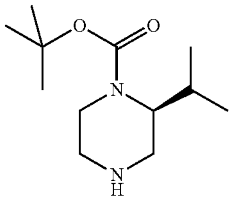 | 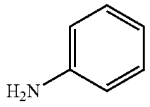 | Method 5: RT: 2.87 min, MI: 456.23 [M + H] | (1H, 500 MHz, d6-dmso) 9.30 (1H, s), 8.81 (1H, s), 8.32 (1H, s), 8.29 (1H, d), 7.88 (1H, s), 7.74 (2H, d), 7.64 (1H, dd), 7.27 (2H, t), 6.89 (1H, t), 4.24-4.12 (2H, m), 4.06 (3H, s), 3.15-3.06 (2H, m), 2.82 (2H, m), 2.59 (1H, m), 1.66 (1H, m), 0.96 (6H, dd) | {4-[4-((S)-3-Isopropyl-piperazin-1-yl)-5-methoxy-pyrido[3,4-d]pyrimidin-2-yl]-pyridin-2-yl}-phenyl-amine |

-continued

| Ex | SM [G-002] | Amine | Aniline | Analysis LCMS | NMR | Name |
|---|---|---|---|---|---|---|
| 225 | [B003] | 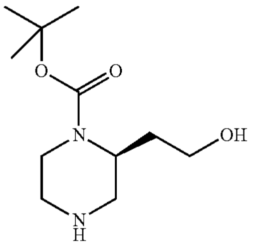 | 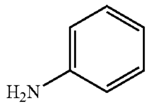 | Method 5: RT: 2.49 min, MI: 458.18 [M + H]] | (1H, 500 MHz, d6-dmso) 9.30 (1H, s), 8.82 (1H, s), 8.34 (1H, s), 8.29 (1H, d), 7.90 (1H, s), 7.73 (2H, d), 7.67 (1H, dd), 7.27 (2H, t), 6.89 (1H, t), 4.21 (2H, m, br), 4.06 (3H, s), 3.58 (2H, t), 3.22 (1H, t, br), 3.16-3.14 (2H, m), 2.95 (2H, m), 1.63 (2H, m) | 2-{(S)-4-[5-Methoxy-2-(2-phenylamino-pyridin-4-yl)-pyrido[3,4-d]pyrimidin-4-yl]-piperazin-2-yl}-ethanol |
| 226 | [B003] | 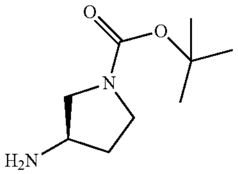 | 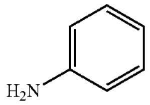 | Method 5: RT: 2.11 min, MI: 457.20 [M + H] | (1H, 500 MHz, d6-dmso) 8.90 (1H, s, br), 8.75 (1H, s), 8.32 (1H, s), 8.19 (1H, d), 8.07 (1H, d), 7.78 (1H, s), 7.55 (1H, d), 7.47 (2H, d), 6.72 (2H, d), 4.76-4.70 (1H, m), 4.12 (3H, s), 3.29 (1H, dd), 3.10-3.02 (1H, m), 2.93-2.87 (1H, m), 2.83 (6H, s), 2.32-2.23 (1H, m), 1.90-1.76 (1H, m) | N-{4-[5-Methoxy-4-((R)-pyrrolidin-3-ylamino)-pyrido[3,4-d]pyrimidin-2-yl]-pyridin-2-yl}-N',N'-dimethyl-benzene-1,4-diamine |
| 227 | [B003] | 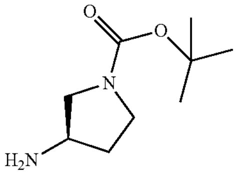 | 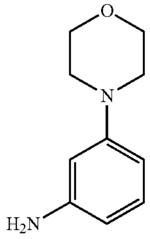 [SMILES: Nc1cccc(N2CCOCC2)c1] | Method 5: RT: 2.53 min, MI: 499.26 [M + H] | (1H, 500 MHz, d6-dmso) 9.23 (1H, s, br), 8.75 (1H, s), 8.32 (1H, s), 8.28 (1H, d), 8.09 (1H, d), 7.90 (1H, s), 7.65 (1H,d), 7.36 (1H, s), 7.22 (1H, s), 7.12 (1H, t), 6.53 (1H, dd), 4.81-4.75 (1H, m), 4.12 (3H, s), 3.75 (4H, m), 3.37-3.31 (1H, dd), 3.08 (4H, m), 2.95-2.90 (1H, m), 2.35-2.26 (1H, m), 1.88-1.82 (1H, m) | {5-Methoxy-2-[2-(3-morpholin-4-yl-phenylamino)-pyridin-4-yl]-pyrido[3,4-d]pyrimidin-4-yl}-(R)-pyrrolidin-3-yl-amine |
| 228 | [B003] | 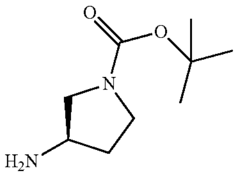 | 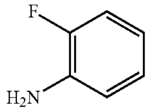 | Method 5: RT: 2.63 min, MI: 432.14 [M + H] | (1H, 500 MHz, d6-dmso) 9.00 (1H, s), 8.76 (1H, s), 8.33 (1H, s), 8.26 (1H, d), 8.16 (1H, t), 8.10 (1H, d), 8.01 (1H, s), 7.71 (1H, d), 7.23 (1H, t), 7.14 (1H, t), 7.01 (1H, t), 4.82-4.74 (1H, m), 4.13 (3H, s), 3.37-3.31 (1H, m), 3.12-3.04 (1H, m), 2.97-2.89 (1H, m), 2.35-2.25 (1H, m), 1.89-1.82 (1H, m) | {2-[2-(2-Fluoro-phenylamino)-pyridin-4-yl]-5-methoxy-pyrido[3,4-d]pyrimidin-4-yl}-(R)-pyrrolidin-3-yl-amine |
| 229 | [B003] | 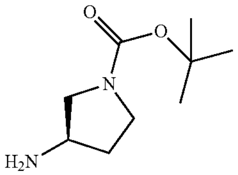 | 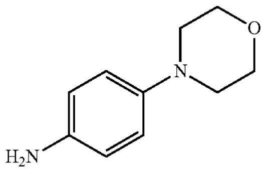 [SMILES: Nc1ccc(N2CCOCC2)cc1] | Method 5: RT: 2.34 min, MI: 499.25 [M + H] | (1H, 500 MHz, d6-dmso) 9.06 (1H, s), 8.76 (1H, s), 8.33 (1H, s), 8.22 (1H, d), 8.09 (1H, d), 7.83 (1H, s), 7.60 (1H, s), 7.58 (2H, d), 6.90 (2H, d), 4.81-4.74 (1H, m), 4.13 (3H, s), 3.73 (4H, t), 3.02 (4H, t), 2.96-2.93 (2H, m), 2.33-2.25 (1H, m), 1.89-1.82 (1H, m) | {5-Methoxy-2-[2-(4-morpholin-4-yl-phenylamino)-pyridin-4-yl]-pyrido [3,4-d] pyrimidin-4-yl}-(R)-pyrrolidin-3-yl-amine |

-continued

| Ex | SM [G-002] | Amine | Aniline | Analysis LCMS | NMR | Name |
|---|---|---|---|---|---|---|
| 230 | [B003] | 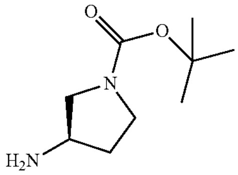 | 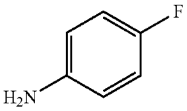 | Method 5: RT: 2.48 min, MI: 432.14 [M + H] | (1H, 300 MHz, d6-dmso) 9.46 (1H, s), 8.78 (1H, s), 8.35 (1H, s), 8.32 (1H, s), 8.27 (1H, d), 8.15 (1H, d), 7.89 (1H, s), 7.75 (2H, dd), 7.67 (1H, d), 7.11 (2H, t), 4.88-4.84 (1H, m), 4.14 (3H, s), 3.49-3.44 (1H, m), 3.21-3.16 (1H, m), 3.07-3.02 (1H, m), 2.35-2.32 (1H, m), 1.99-1.94 (1H, m) | {2-[2-(4-Fluoro-phenylamino)-pyridin-4-yl]-5-methoxy-pyrido[3,4-d]pyrimidin-4-yl}-(R)-pyrrolidin-3-yl-amine |
| 231 | [B003] | 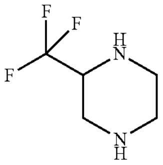 | 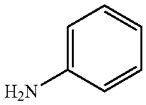 | Method 5: RT: 5.08 min, MI: 482.2 [M + H] | (1H, 300 MHz, d6-dmso) 9.34 (1H, s), 8.85 (1H, s), 8.36 (1H, s), 8.31 (1H, d), 7.89 (1H, s), 7.74 (2H, d), 7.64 (1H, dd), 7.28 (1H, d), 7.24 (1H, s), 6.89 (1H, t), 4.23 (1H, d), 4.07 (3H, s), 3.71-3.62 (1H, m), 3.22 (2H, dd), 3.08 (2H, d), 2.89-2.81 (1H, m) | {4-[5-Methoxy-4-(3-trifluoro-methyl-piperazin-1-yl)-pyrido[3,4-d]pyrimidin-2-yl]-pyridin-2-yl}-phenyl-amine |
| 232 | [B003] | 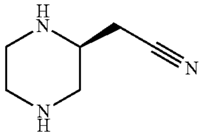 | 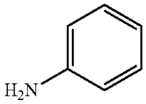 | Method 5: RT: 2.68 min, MI: 453.17 [M + H] | (1H, 300 MHz, d6-dmso) 9.28 (1H, s), 8.82 (1H, s), 8.33 (1H, s), 8.29 (1H, d), 7.89 (1H, s), 7.75 (2H, d), 7.67 (1H, d), 7.27 (2H, t), 6.89 (1H, t), 4.18 (1H, dd), 4.07 (3H, s), 3.29 (1H, m), 3.12-3.02 (3H, m), 2.93 (1H, t), 2.82 (1H, t), 2.71 (2H, d) | {(S)-4-[5-Methoxy-2-(2-phenylamino-pyridin-4-yl)-pyrido[3,4-d]pyrimidin-4-yl]-piperazin-2-yl}-acetonitrile |
| 233 | [B003] | 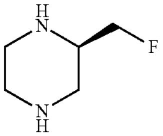 | 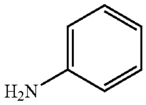 | Method 5: RT: 2.43 min, MI: 446.18 [M + H] | (1H, 300 MHz, d6-dmso) 9.30 (1H, s), 8.81 (1H, s), 8.33 (1H, s), 8.29 (1H, d), 7.88 (1H, s), 7.73 (2H, d), 7.65 (1H, d), 7.27 (1H, t), 6.89 (1H, t), 4.49 (1H, dd), 4.39 (1H, dd), 4.15 (2H, t, br), 4.06 (3H, s), 3.15-3.11 (2H, m), 3.04 (1H, dd), 2.97 (1H, dd), 2.83 (1H, t, br), 2.60 (1H, m, br) | {4-[4-((R)-3-Fluoromethyl-piperazin-1-yl)-5-methoxy-pyrido[3,4-d]pyrimidin-2-yl]-pyridin-2-yl}-phenyl-amine |
| 234 | [B003] | 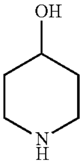 | 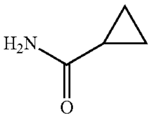 | Method 5: RT: 4.39 min, MI: 421.20 [M + H] | (1H, 500 MHz, d6-dmso) 10.89 (1H, s), 9.06 (1H, s), 8.80 (1H, s), 8.44 (1H, d), 8.31 (1H, s), 7.98 (1H, d), 4.79 (1H, d), 4.06 (1H, s), 3.99 (2H, d, br), 3.80 (1H, m), 3.38 (1H, m), 2.04 (1H, m), 1.89 (2H, d, br), 1.56 (2H, d, br), 0.86-0.81 (4H, m) | Cyclopropane-carboxylic acid {4-[4-(4-hydroxy-piperidin-1-yl)-5-methoxy-pyrido[3,4-d]pyrimidin-2-yl]-pyridin-2-yl}-amide |
| 235 | [B003] | 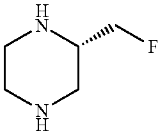 | 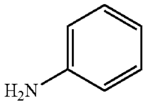 | Method 5: RT: 2.43 min, MI: 446.18 [M + H] | (1H, 500 MHz, d6-dmso) 9.30 (1H, s), 8.81 (1H, s), 8.33 (1H, s), 8.29 (1H, d), 7.89 (1H, s), 7.73 (2H, d), 7.65 (1H, d), 7.27 (2H, t), 6.89 (1H, t), 4.49 (1H, d, br), 4.39 (1H, d, br), 4.15 (2H, t, br), 4.06 (3H, s), 3.13 (2H, m, br), 3.03 (1H, d, br), 2.97 (1H, t, br), 2.83 (1H, t, br) | {4-[4-((S)-3-Fluoromethyl-piperazin-1-yl)-5-methoxy-pyrido[3,4-d]pyrimidin-2-yl]-pyridin-2-yl}-phenyl-amine |

-continued

| Ex | SM [G-002] | Amine | Aniline | Analysis LCMS | NMR | Name |
|---|---|---|---|---|---|---|
| 236 | [B003] | 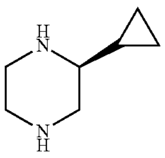 | 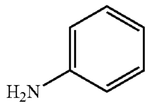 | Method 5: RT: 5.50 min, MI: 454.40 [M + H] | (1H, 500 MHz, d6-dmso) 9.31 (1H, s), 8.80 (1H, s), 8.32 (1H, s), 8.30 (1H, d), 7.88 (1H, s), 7.73 (2H, d), 7.63 (1H, dd), 7.27 (2H, t), 6.89 (1H, t), 4.20 (1H, d, br), 4.09 (1H, d, br), 4.04 (3H, s), 3.12 (1H, t), 3.00 (1H, d), 2.93 (1H, t), 2.73 (1H, t), 2.05 (1H, t), 0.76 (1H, m), 0.42 (2H, d, br), 0.28 (2H, m) | {4-[4-((S)-3-Cyclopropyl-piperazin-1-yl)-5-methoxy-pyrido[3,4-d]pyrimidin-2-yl]-pyridin-2-yl}-phenyl-amine |
| 237 | [B003] | 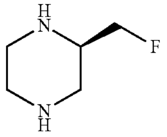 | 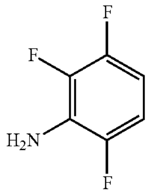 | Method 5: RT: 3.15 min, MI: 500.18 [M + H] | (1H, 500 MHz, d6-dmso) 9.02 (1H, s), 8.82 (1H, s), 8.33 (1H, s), 8.18 (1H, d), 7.84 (1H, s), 7.68 (1H, dd), 7.30 (1H, m), 7.19 (1H, m), 4.48 (1H, d), 4.39 (1H, d), 4.18 (1H, d, br), 4.12 (1H, m), 4.06 (3H, s), 3.13 (2H, m), 2.98 (2H, m), 2.84 (1H, t, br) | {4-[4-((R)-3-Fluoromethyl-piperazin-1-yl)-5-methoxy-pyrido[3,4-d]pyrimidin-2-yl]-pyridin-2-yl}-(2,3,6-trifluoro-phenyl)-amine |
| 238 | [B003] | 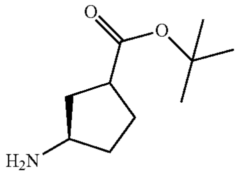 | 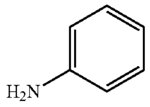 | Method 5: RT: 2.41 min, MI: 414 [M + H] | (1H, 300 MHz, d6-dmso) 2.03 (m, 1H), water peak very broad!!, 4.13 (s, 3H), 4.87 (brs, 1H), 6.89 (t, 1H), 7.27 (t, 2H), 7.68 (d, 1H), 7.76 (d, 2H), 7.93 (s, 1H), 8.30 (d, 1H), 8.35 (s, 1H), 8.79 (s, 1H), 9.44 (s, 1H) | [5-Methoxy-2-(2-phenylamino-pyridin-4-yl)-pyrido[3,4-d]pyrimidin-4-yl]-(R)-pyrrolidin-3-yl-amine |
| 239 | [B003] | 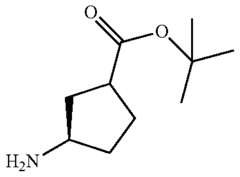 | 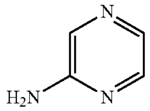 | Method 5: RT: 2.10 min, MI: 416 [M + H] | (1H, 300 MHz, d6-dmso) large water peak . . . 4.84 (brs, 1H), 6.60 (brs, 1H), 7.90 (d, 1H), 8.12 (d, 2H), 8.26 (d, 1H), 8.36 (s, 1H), 8.44 (d, 1H), 8.78 (d, 1H), 8.81 (s, 1H), 9.11 (s, 1H), 10.30 (s, 1H) | {5-Methoxy-2-[2-(pyrazin-2-ylamino)-pyridin-4-yl]-pyrido[3,4-d]pyrimidin-4-yl}-(R)-pyrrolidin-3-yl-amine |
| 240 | [B003] | 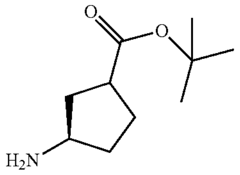 | 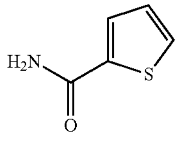 | Method 5: RT: 3.23 min, MI: 448 [M + H] | (1H, 300 MHz, d6-dmso) 1.92-2.05 (m, 2H), huge water peak, 3.81 (s, 3H), 4.87 (brs, 1H), 7.22 (dd, 1H), 7.91 (d, 1H), 8.11 (d, 1H), 8.19 (d, 1H), 8.26-8.29 (m, 2H), 8.37 (s, 1H), 8.55 (d, 1H), 8.83 (s, 1H), 9.16 (s, 1H), 11.07 (br s, 1H) | Thiophene-2-carboxylic acid {4-[5-methoxy-4-((R)-pyrrolidin-3-ylamino)-pyrido[3,4-d]pyrimidin-2-yl]-pyridin-2-yl}-amide |
| 241 | [B003] | 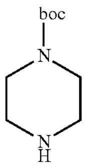 | 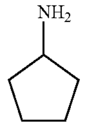 | Method 5: RT: 2.05 min, MI: 406.20 [M + H] | (1H, 300 MHz, d6-dmso) 8.84 (1H, s), 8.36 (1H, s), 8.09 (1H, d), 7.52 (1H, s), 7.37 (1H, dd), 6.79 (1H, s), 4.18 (1H, m), 4.07 (3H, s), 3.87 (4H, m, br), 3.27 (4H, m, br), 1.92 (2H, m, br), 1.69 (2H, m, br), 1.55-1.45 (4H, m). | Cyclopentyl-[4-(5-methoxy-4-piperazin-1-yl-pyrido[3,4-d]pyrimidin-2-yl)-pyridin-2-yl]-amine |

-continued

| | SM | | | Analysis | | |
|---|---|---|---|---|---|---|
| Ex | [G-002] | Amine | Aniline | LCMS | NMR | Name |
| 242 | [B003] | 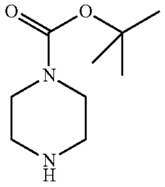 | 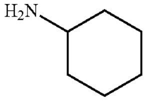 | Method 5: RT: 2.18 min, MI: 420.23 [M + H] | (1H, 500 MHz, d6-dmso) 8.79 (1H, s), 8.31 (1H, s), 8.06 (1H, d), 7.49 (1H, s), 7.34 (1H, dd), 6.62 (1H, d), 4.06 (3H, s), 3.74 (1H, m), 3.70 (4H, m), 3.01 (4H, m), 1.93 (2H, d, br), 1.71 (2H, m), 1.58 (1H, m), 1.33-1.28 (2H, m), 1.20-1.16 (3H, m) | Cyclohexyl-[4-(5-methoxy-4-piperazin-1-yl-pyrido[3,4-d]pyrimidin-2-yl)-pyridin-2-yl]-amine |
| 243 | [B003] | 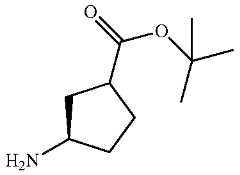 | 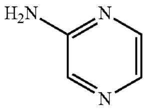 | Method 5: RT: 1.84 min, MI: 386.0 [M + H] | (1H, 500 MHz, d6-dmso): 10.32 (1H, s), 9.20 (1H, s), 9.15 (1H, d), 8.79 (1H, d), 8.66 (1H, d), 8.35-8.44 (2H, m), 8.29 (1H, s), 8.10 (1H, s), 7.92 (1H, d), 4.95 (1H, br s), 3.58 (1H, dd), 3.26 (3H, m), 2.35 (1H, m), 2.17 (1H, m). | {2-[2-(Pyrazin-2-ylamino)-pyridin-4-yl]-pyrido[3,4-d]pyrimidin-4-yl}-(R)-pyrrolidin-3-yl-amine |

Synthesis of {1-[5-Methoxy-2-(2-phenylamino-pyridin-4-yl)-pyrido[3,4-d]pyrimidin-4-yl]-piperidin-4-yl}-methanol [244]

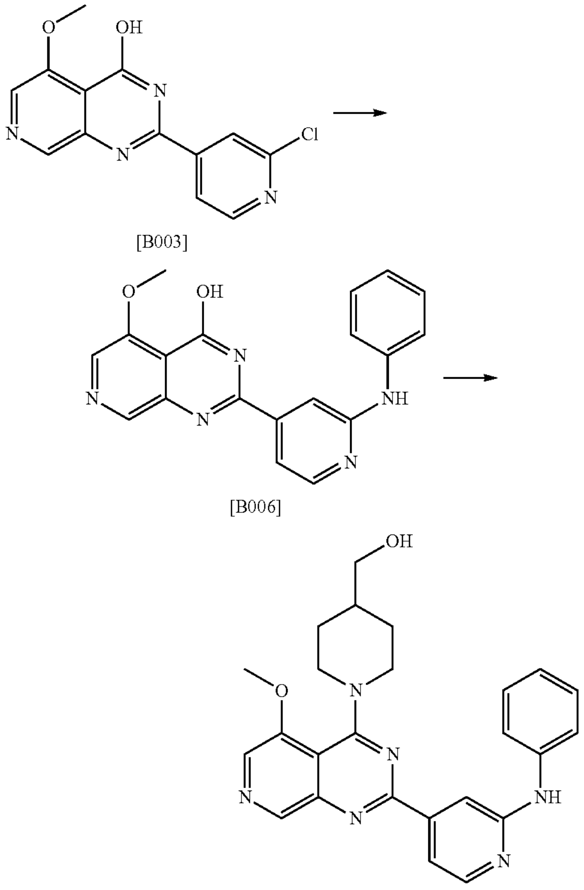

[B003]

[B006]

[244]

5-Methoxy-2-(2-phenylamino-pyridin-4-yl)-pyrido[3,4-d]pyrimidin-4-ol [B006]

A mixture of 4 2-(2-Chloro-pyridin-4-yl)-5-methoxy-pyrido[3,4-d]pyrimidin-4-ol [B003](0.100 g, 0.346 mmol), $Pd(OAc)_2$ (4 mg, 0.018 mmol), Xantphos (21 mg, 0.035 mmol), cesium carbonate (225 mg, 0.695 mmol) and anhydrous dioxane (1 ml) was heated at 900 overnight. Water (5 mL) was added and the reaction mixture triturated for 30 min after which a yellow solid was collected by filtration and washed with water (20 ml) and DCM (20 ml) to give the title compound as a yellow solid (0.07 g, 59% yield) which was used without further purification in the next step. LCMS method: 1, RT: 2.23 min, MI 346.24 [M+H]; NMR: (1H, 300 MHz, d6-dmso); 9.30 (1H, s), 8.60 (1H, s), 8.25 (1H, d), 7.71 (2H, d), 7.65 (1H, s), 7.45 (1H, dd), 7.26 (2H, t), 6.89 (1H, t), 3.96 (3H, s).

{1-[5-Methoxy-2-(2-phenylamino-pyridin-4-yl)-pyrido[3,4-d]pyrimidin-4-yl]-piperidin-4-yl}-methanol [244]

5-Methoxy-2-(2-phenylamino-pyridin-4-yl)-pyrido[3,4-d]pyrimidin-4-ol [B003](70 mg, 0.203 mmol), TEA (84 μl, 0.609 mmol) and DMAP (25 mg, 0.203 mmol) were sonicated in DMF (1.5 ml) for 30 min. 2,4,6-Triisopropylbenzenesulfonyl chloride (74 mg, 0.243 mmol) was then added and the reaction mixture stirred at room temperature for 3 hr. 4-Piperidinemethanol (28 mg, 0.243 mmol) was then added and the reaction mixture stirred at room temperature overnight. The solvent was evaporated under reduced pressure to give a pale yellow solid, which was purified by flash column chromatography (SP1, 12 g $SiO_2$ cartridge 100% DCM up to 95% DCM: 5% MeOH gradient) to give the title compound as a yellow solid (38 mg, 42% yield). LCMS method: 1, RT: 5.26 min, MI 443.35 [M+H]; NMR: (1H, 300 MHz, d6-dmso); 9.30 (1H, s), 8.79 (1H, s), 8.31 (1H, s), 8.28 (1H, d), 7.89 (1H, s), 7.74 (2H, d), 7.65 (1H, d), 7.27 (2H, t), 6.88 (1H, t), 4.52 (1H, t), 4.30 (2H, d, br), 4.07 (3H, s), 3.16 (1H, d), 3.11 (2H, t, br), 1.83 (2H, d, br), 1.72 (1H, s, br), 1.33 (2H, q, br), 1.13 (2H, dd)

Synthesis of 2-{3-[5-Methoxy-2-(2-phenylamino-pyridin-4-yl)-pyrido[3,4-d]pyrimidin-4-ylamino]-R-pyrrolidin-1-yl}-acetamide [245]

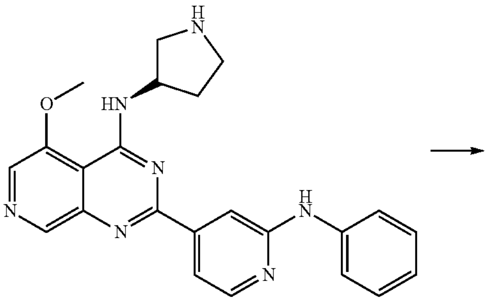

[238]

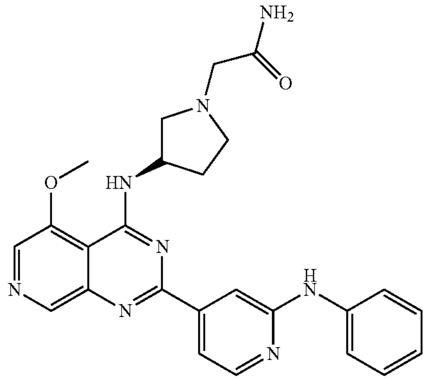

[245]

To a mixture of [5-Methoxy-2-(2-phenylamino-pyridin-4-yl)-pyrido[3,4-d]pyrimidin-4-yl]-(R)-pyrrolidin-3-yl-amine [238](50 mg, 0.121 mmol) and $K_2CO_3$ (50 mg, 0.363 mmol) in DMF (1 mL) was added 2-bromoacetamide (17 mg, 0.121 mmol). The reaction mixture was heated at 80° C. for 4 hr. Water (10 mL) was added and the reaction mixture was extracted with EtOAc (2×10 mL), the extracts were combined and washed with brine (20 mL), dried ($MgSO_4$) filtered and evaporated under reduced pressure to give a pale yellow oil, which was diluted with MeOH (5 mL) and poured onto a 1 g SCX-2 cartridge and washed with MeOH before eluting with 2N NH3/MeOH which was evaporated. The resulting oil was triturated in $Et_2O$ to give the title compound as a white solid (12 mg, 17% yield). LCMS method: 1, RT: 2.17 min, MI 471 [M+H]; NMR: (1H, 300 MHz, d6-dmso); 9.32 (1H, s), 8.78 (1H, s), 8.35 (1H, s), 8.31 (1H, d), 8.23 (1H, d), 7.76 (2H, d), 7.70 (1H, d), 7.28 (2H, t), 7.13 (1H, s), 6.90 (1H, t), 4.82 (1H, s), 4.15 (3H, s), 3.10 (2H, d), 3.00 (1H, m), 2.89 (1H, m), 2.81 (1H, m), 2.57 (1H, m), 2.40 (1H, m), 1.88 (1H, m).

General synthesis of 5-chloro substituted 2-amino pyridyl substituted 2-(2-amino-pyridin-4-yl)-pyrido[3,4-d]pyrimidin-4-yl amine derivatives of general formula [G-008] Scheme B2

5-chloro 2-(2-chloro-pyridin-4-yl)-pyrido[3,4-d]pyrimidin-4-yl amine derivatives of general formula [G-007] were prepared by the reaction of a 5-chloro 2-(2-chloro-pyridin-4-yl)-pyrido[3,4-d]pyrimidin-4-ol derivative of general formula [G-006] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as $Et_3N$, DIPEA or NMM at ambient temperature. 5-chloro 2-(2-chloro-pyridin-4-yl)-pyrido[3,4-d]pyrimidin-4-yl amine derivatives of general formula [G-007] was involved in a Buchwald type reaction utilising a suitable amine, of general formula [G-005], a palladium catalyst such as $Pd(dba)_2$ or $Pd(OAc)_2$, a ligand such as Xantphos and a base such as NaOtBu or $Cs_2CO_3$ in a polar solvent such as dioxane or a combination of dioxane and DMA at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme B2

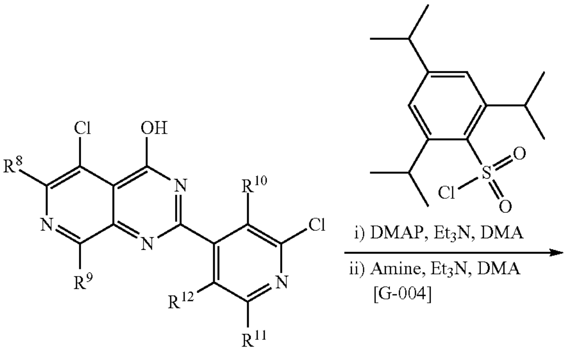

[G-006]

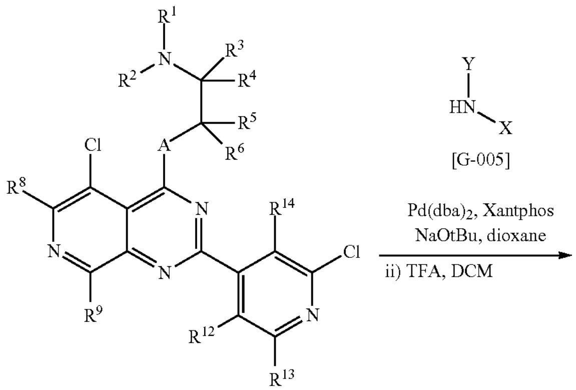

[G-005]

[G-007]

-continued

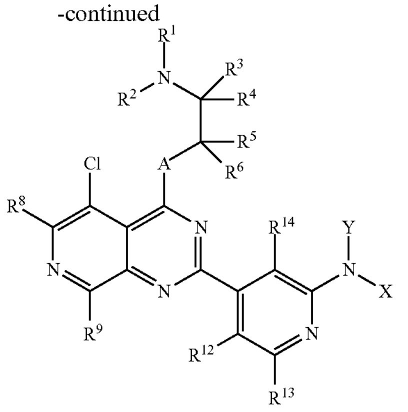

[G-008]

Synthesis of [4-(5-Chloro-4-piperazin-1-yl-pyrido[3,4-d]pyrimidin-2-yl)-pyridin-2-yl]-phenyl-amine [246]

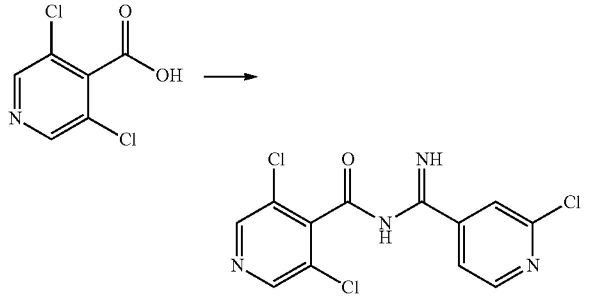

[B007]

3,5-Dichloro-N-[(2-chloro-pyridin-4-yl)-imino-methyl]-isonicotinamide [B007]

A mixture of 3,5-dichloropyridine-4-carboxylic acid (15 g, 78.12 mmol), DIPEA (37.5 mL, 214 mmol) in DMF (400 mL) was stirred at room temperature then HATU (29.7 g, 78.12 mmol) was added in one portion and the mixture was left to stir for 45 min. 2-Chloro-isonicotinamide (14.25 g, 74.2 mmol) was added and the mixture left to stir for a further 2 hours. The crude reaction mixture was then poured onto water (800 mL) and left to stir overnight. The crude reaction mixture was filtered and the solid washed with water, then dried in in a vacuum oven over night to give the title compound (22 g, 85% yield) as an off white solid: LCMS method: 1, RT: 4.89 min, MI 330 [M+H]; NMR: (1H, 300 MHz, d6-dmso); 10.25 (1H, br s), 10.10 (1H, br s), 8.70 (2H, s), 8.57 (1H, s), 7.99 (1H, s), 7.88 (1H, s).

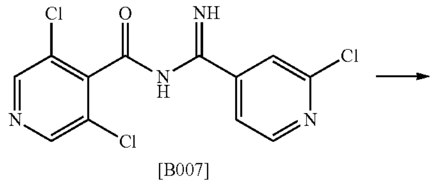

[B007]

-continued

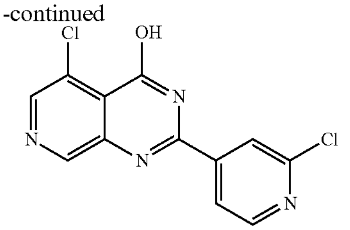

[B008]

5-Chloro-2-(2-chloro-pyridin-4-yl)-pyrido[3,4-d]pyrimidin-4-ol [B008]

3,5-Dichloro-N-[(2-chloro-pyridin-4-yl)-imino-methyl]-isonicotinamide [B007](10 g, 30.34 mmol) cesium carbonate (19.8 g, 60.69 mmol) and DMA (180 mL) were stirred at room temperature. The mixture was flushed with nitrogen then iron(III) chloride (0.98 g, 6.07 mmol) was added and the mixture heated at 140 C overnight under an atmosphere of nitrogen. The crude reaction mixture was cooled then poured onto a mixture of ice water, the mixture was then acidified by the addition of glacial acetic acid, and the mixture was then left to stir at room temperature for 2 hours. The solid precipitate was collected by filtration, washed with water then dried in a vacuum oven over night to give the title compound (5.26 g, 59% yield) as a pale brown solid: LCMS method: 1, RT: 4.83 min, MI 293 [M+H];

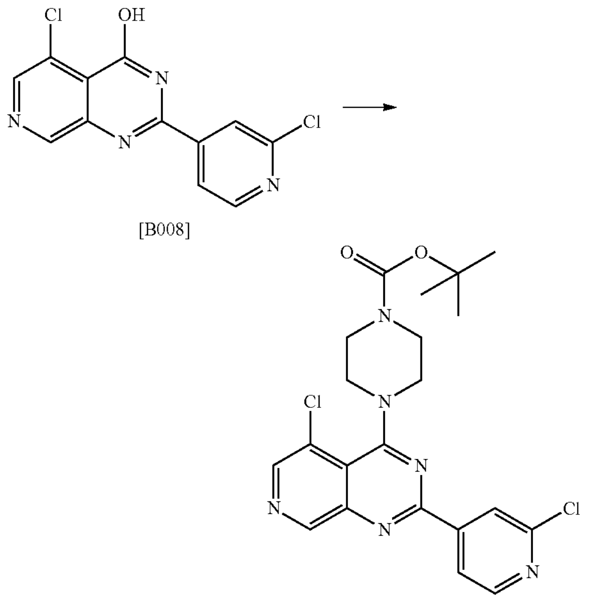

[B008]

[B009]

4-[5-Chloro-2-(2-chloro-pyridin-4-yl)-pyrido[3,4-d]pyrimidin-4-yl]-piperazine-1-carboxylic acid tert-butyl ester [B009]

A mixture of 5-Chloro-2-(2-chloro-pyridin-4-yl)-pyrido[3,4-d]pyrimidin-4-ol [B008](1.05 g, 3.58 mmol), anhydrous DMF (40 mL), triethylamine (1.5 mL, 10.7 mmol) and DMAP (440 mg, 3.58 mmol) was sonicated for 45 min. 2,4,6-Triisopropyl-benzenesulfonyl chloride (1.3 g, 4.3 mmol) was added and the reaction mixture left to stir at room temperature for 2 hr. During this time the material went into solution to form a viscous solution. 1-Boc-piperazine (0.800 g, 4.3 mmol) was added and the reaction mixture was left to stir at room temperature overnight. The solvent was evaporated under reduced pressure and residue triturated in DCM to give brown solid, which was purified by flash column chromatography (SP1, 20 g $SiO_2$ cartridge 100% DCM up to 95% DCM: 5% MeOH gradient) to give the title compound [B009] as a beige solid (1.1 g, 67% yield). LCMS method: 1, RT: 5.50 min, MI: 461 [M+H]; NMR: (1H, 300 MHz, d6-dmso); 9.20 (1H, s), 8.67 (1H, s), 8.62 (1H, d), 8.33 (1H, d), 8.32 (1H, s), 7.94 (1H, s), 3.72 (4H, m, br), 3.53 (4H, m, br), 1.41 (9H, s).

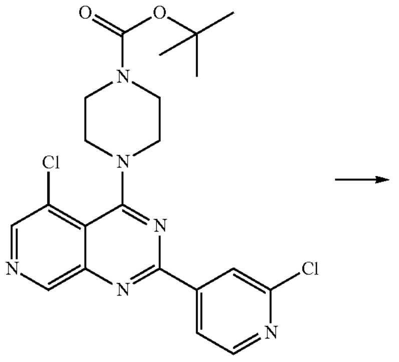

[B009]

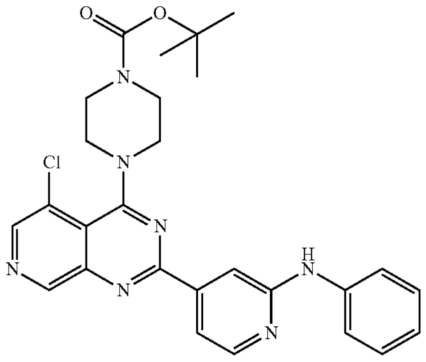

[B010]

4-[5-Chloro-2-(2-phenylamino-pyridin-4-yl)-pyrido [3,4-d]pyrimidin-4-yl]-piperazine-1-carboxylic acid tert-butyl ester [B010]

A mixture of 4-[5-Chloro-2-(2-chloro-pyridin-4-yl)-pyrido[3,4-d]pyrimidin-4-yl]-piperazine-1-carboxylic acid tert-butyl ester [B009](0.150 g, 0.325 mmol), Aniline (61 μL, 0.650 mml), $Pd(OAc)_2$ (4 mg, 0.017 mmol), Xantphos (19 mg, 0.033 mmol), cesium carbonate (212 mg, 0.650 mmol) and anhydrous dioxane (1 ml) was heated at 900 overnight. Solvent evaporated under reduced pressure and residue purified by flash column chromatography (SP1, 20 g $SiO_2$ cartridge 100% DCM up to 97% DCM: 3% MeOH gradient) to give the title compound [B010] as a beige solid (65 mg, 39% yield). LCMS method: 1, RT: 4.34 min, MI: 518.31 [M+H].

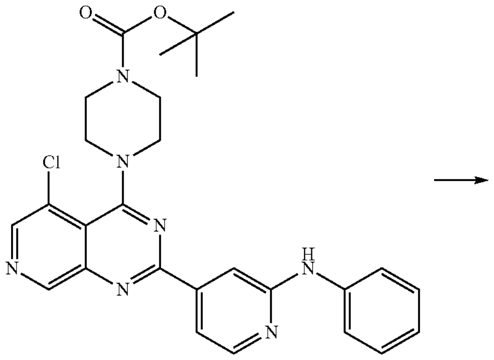

[B010]

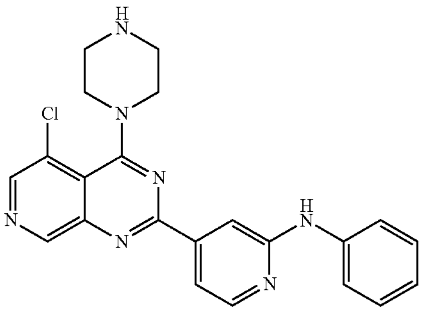

[246]

[4-(5-Chloro-4-piperazin-1-yl-pyrido[3,4-d]pyrimidin-2-yl)-pyridin-2-yl]-phenyl-amine [246]

A mixture of 4-[5-Chloro-2-(2-phenylamino-pyridin-4-yl)-pyrido[3,4-d]pyrimidin-4-yl]-piperazine-1-carboxylic acid tert-butyl ester [B010](60 mg, 0.125 mmol) in 4N HCl in dioxane (1 mL) was stirred at room temperature for 2 hours. After completion solvent was evaporated in vacuo and residue diluted with MeOH (5 mL) and poured onto a 1 g SCX-2 cartridge and washed with DCM and MeOH before eluting with 2N NH3/MeOH which was evaporated evaporated under reduced pressure. The residue purified by flash column chromatography (SP1, 20 g $SiO_2$ cartridge 100% DCM up to 90% DCM: 10% MeOH gradient) to give the title compound [246] as a yellow solid (23 mg, 44% yield). LCMS method: 1, RT: 5.48 min, MI: 418.29 [M+H]; NMR: (1H, 300 MHz, d6-dmso); 9.33 (1H, s), 9.12 (1H, s), 8.60 (1H, s), 8.32 (1H, d), 7.89 (1H, s), 7.74 (2H, d), 7.65 (1H, dd), 7.27 (2H, t), 6.89 (1H, t), 3.68 (4H, m), 3.15 (1H, d), 2.86 (4H, m).

The following compounds were synthesised according to the general synthesis shown in scheme [B2]

| Ex | Amine | Aniline | Analysis<br>LCMS | <br>NMR | <br>Name |
|---|---|---|---|---|---|
| 247 | 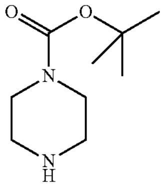 | 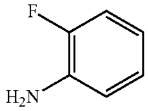 | Method 5:<br>RT: 3.18<br>min, MI:<br>436 [M + H] | (1H, 500 MHz, d6-dmso)<br>8.99 (1H, s), 8.60 (1H, s),<br>8.29 (1H, d), 8.19 (1H, m),<br>8.02 (1H, d), 7.69 (1H, d),<br>7.22 (1H, m), 7.14 (1H, m),<br>7.00 (1H, m), 3.68 (4H,<br>br s), 2.86 (4H, br s) | [4-(5-Chloro-4-<br>piperazin-1-yl-<br>pyrido[3,4-<br>d]pyrimidin-2-<br>yl)-pyridin-2-yl]-<br>(2-fluoro-<br>phenyl)-amine |
| 248 | 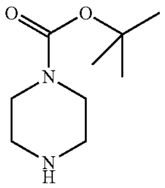 | 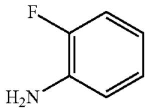 | Method 5:<br>RT: 3.37<br>min, MI:<br>511 [M + H] | (1H, 500 MHz, d6-dmso)<br>8.97 (1H, s), 8.74 (1H s),<br>8.41 (1H, s), 8.29 (1H, d),<br>8.22 (1H, t), 8.04 (1H, s),<br>7.72 (1H, d), 7.31 (1H, m),<br>7.22 (1H, m), 7.14 (1H, m),<br>7.09 (2H, m), 7 (1H, m),<br>3.54 (4H, s), 2.83 (4H, s). | (2-Fluoro-<br>phenyl)-{2-[2-<br>(2-fluoro-<br>phenylamino)-<br>pyridin-4-yl]-4-<br>piperazin-1-yl-<br>pyrido[3,4-<br>d]pyrimidin-5-<br>yl}-amine |
| 249 | 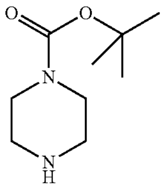 | 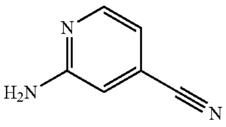 | Method 5:<br>RT: 2.58<br>min, MI:<br>444 [M + H] | (1H, 500 MHz, d6-dmso)<br>10.51 (1H, s), 9.25 (1H, s),<br>8.70 (1H, s), 8.65 (1H, s),<br>8.50 (2H, dd), 7.91 (1H, d),<br>7.31 (1H, d), 3.91 (4H,<br>br s), 3.33 (4H, br s) | 4-{5-(4-Cyano-<br>pyridin-2-<br>ylamino)-2-[2-<br>(4-cyano-<br>pyridin-2-<br>ylamino)-<br>pyridin-4-yl]-<br>pyrido[3,4-<br>d]pyrimidin-4-<br>yl}-piperazine |
| 250 | 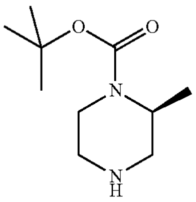 | 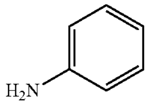 | Method 5:<br>RT: 2.80<br>min, MI:<br>432.15<br>[M + H] | (1H, 500 MHz, d6-dmso)<br>9.33 (1H, s), 9.12 (1H, s),<br>8.59 (1H, s), 8.31 (1H, d),<br>7.89 (1H, s), 7.73 (2H, d),<br>7.64 (1H, d), 7.27 (2H, t),<br>6.90 (1H, t), 4.09 (2H, m,<br>br), 3.31 (2H, m, br),<br>3.16 (1H, d), 2.88 (2H,<br>m, br), 1.01 (3H, s) | {4-[5-Chloro-4<br>((S)-3-methyl-<br>piperazin-1-yl)<br>pyrido[3,4-<br>d]pyrimidin-2-<br>yl]-pyridin-2-<br>yl}-phenyl-<br>amine |
| 251 | 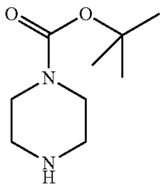 | 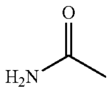 | Method 5:<br>RT: 2.64<br>min, MI:<br>384.08<br>[M + H] | (1H, 500 MHz, d6-dmso)<br>10.64 (1H, s), 9.20 (1H, s),<br>9.09 (1H, s), 8.64 (1H, s),<br>8.47 (1H, d), 8.00 (1H, d),<br>3.77 (4H, m), 3.05<br>(4H, m), 2.13 (3H, s) | N-[4-(5-Chloro-<br>4-piperazin-1-yl-<br>pyrido[3,4-<br>d]pyrimidin-2-<br>yl)-pyridin-2-yl]-<br>acetamide |
| 252 | 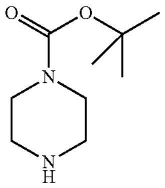 | 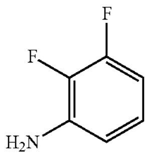 | Method 5:<br>RT: 3.60<br>min, MI:<br>454<br>[M + H] | (1H, 300 MHz, d6-dmso)<br>9.26 (1H, bs), 9.19 (1H, s),<br>8.66 (1H, s), 8.35 (1H, d),<br>8.09 (2H, m), 7.75 (1H, dd),<br>7.14 (1H, m), 7.04 (1H, m),<br>3.79 (4H, s), 3.08 (4H, s) | [4-(5-Chloro-4-<br>piperazin-1-yl-<br>pyrido[3,4-<br>d]pyrimidin-2-<br>yl)-pyridin-2-yl]-<br>(2,3-difluoro-<br>phenyl)-amine |
| 253 | 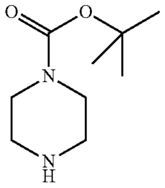 | 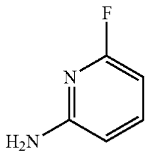 | Method 5:<br>RT: 2.69<br>min, MI:<br>437<br>[M + H] | (1H, 500 MHz, d6-dmso)<br>10.15 (1H, s), 9.16 (1H, s),<br>8.69 (1H, s), 8.63 (1H, s),<br>8.38 (1H, s), 7.82 (2H, s),<br>7.72 (1H, s), 6.58 (1H, s),<br>3.88 (4H, s), 3.25 (4H, s) | [4-(5-Chloro-4-<br>piperazin-1-yl-<br>pyrido[3,4-<br>d]pyrimidin-2-<br>yl)-pyridin-2-yl]-<br>(6-fluoro-<br>pyridin-2-yl)-<br>amine |

-continued

| | | | Analysis | | |
|---|---|---|---|---|---|
| Ex | Amine | Aniline | LCMS | NMR | Name |
| 254 | 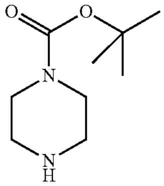 | 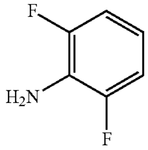 | Method 5: RT: 2.17 min, MI: 454 [M + H] | (1H, 300 MHz, d6-dmso) 9.24 (1H, s), 8.85 (1H, s), 8.71 (1H, s), 8.20 (1H, d), 7.82 (1H, s), 7.69 (1H, dd), 7.17 (2H, m), 3.87 (4H, s), 3.31 (4H, s) | [4-(5-Chloro-4-piperazin-1-yl-pyrido[3,4-d]pyrimidin-2-yl)-pyridin-2-yl]-(2,6-difluoro-phenyl)-amine |
| 255 | 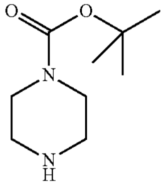 | 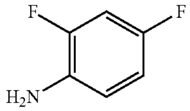 | Method 5: RT: 3.29 min, MI: 454 [M + H] | (1H, 300 MHz, d6-dmso) 9.15 (1H, s), 8.98 (1H, s), 8.62 (1H, s), 8.27 (1H, d), 8.20 (1H, s), 8.13 (1H, m), 7.97 (1H, s), 7.70 (1H, dd), 7.30 (1H, m), 7.06 (1H, m), 3.72 (4H, s), 2.93 (4H, s) | [4-(5-Chloro-4-piperazin-1-yl-pyrido[3,4-d]pyrimidin-2-yl)-pyridin-2-yl]-(2,4-difluoro-phenyl)-amine |
| 256 | 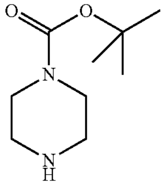 | 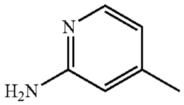 | Method 5: RT: 2.24 min, MI: 433 [M + H] | (1H, 300 MHz, d6-dmso) 9.83 (1H, s), 9.16 (1H, s), 8.79 (1H, s), 8.61 (1H, s), 8.38 (1H, d), 8.13 (1H, d), 7.78 (1H, dd), 7.64 (1H, s), 6.76 (1H, d), 3.71 (4H, s), 2.88 (4H, s), 2.29 (3H, s) | [4-(5-Chloro-4-piperazin-1-yl-pyrido[3,4-d]pyrimidin-2-yl)-pyridin-2-yl]-(4-methyl-pyridin-2-yl)-amine |
| 257 | 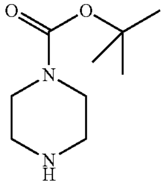 | 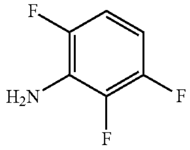 | Method 5: RT: 3.42 min, MI: 472 [M + H] | (1H, 500 MHz, d6-dmso) 9.19 (1H, s), 9.08 (1H, s), 8.65 (1H, s), 8.22 (1H, d), 7.88 (1H, s), 7.71 (1H, d), 7.35-7.29 (1H, m), 7.23-7.14 (1H, m), 3.79 (4H, s), 3.12 (4H, s). | [4-(5-Chloro-4-piperazin-1-yl-pyrido[3,4-d]pyrimidin-2-yl)-pyridin-2-yl]-(2,3,6-trifluoro-phenyl)-amine |
| 258 | 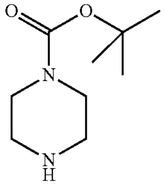 | 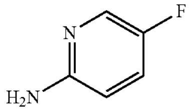 | Method 5: RT: 5.38 min, MI: 437 [M + H] | (1H, 500 MHz, d6-dmso) 10.02 (1H, s), 9.25 (1H, s), 8.72 (1H, s), 8.69 (1H, s), 8.41 (1H, d), 8.28 (1H, d), 7.93 (1H, dd), 7.82 (1H, dd), 7.69 (1H, m), 3.89 (4H, s), 3.27 (4H, s) | [4-(5-Chloro-4-piperazin-1-yl-pyrido[3,4-d]pyrimidin-2-yl)-pyridin-2-yl]-(5-fluoro-pyridin-2-yl)-amine |
| 259 | 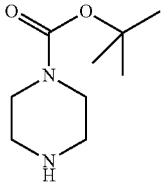 | 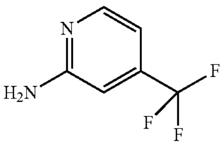 [SMILES: Nc1cc(C(F)(F)F)ccn1] | Method 5: RT: 5.92 min, MI: 487 [M + H] | (1H, 500 MHz, d6-dmso) 10.40 (1H, s), 9.21 (1H, s), 8.72 (1H, s), 8.66 (1H, s), 8.52 (1H, d), 8.47 (1H, d), 8.32 (1H, s), 7.88 (1H, d), 7.23 (1H, d), 3.81 (4H, s), 3.07 (4H, s) | [4-(5-Chloro-4-piperazin-1-yl-pyrido[3,4-d]pyrimidin-2-yl)-pyridin-2-yl]-(4-trifluoromethyl-pyridin-2-yl)-amine |
| 260 | 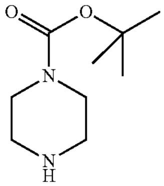 | 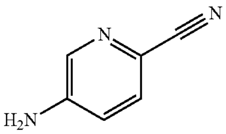 | Method 5: RT: 5.32 min, MI: 444 [M + H] | (1H, 500 MHz, d6-dmso) 10.25 (1H, s), 9.19 (1H, s), 8.94 (1H, s), 8.66 (1H, s), 8.58 (1H, dd), 8.48 (1H, d), 8.03 (1H, s), 7.93 (1H, d), 7.89 (1H, d), 3.80 (4H, s), 3.08 (4H, s) | 5-[4-(5-Chloro-4-piperazin-1-yl-pyrido[3,4-d]pyrimidin-2-yl)-pyridin-2-ylamino]-pyridine-2-carbonitrile |

-continued

| Ex | Amine | Aniline | Analysis LCMS | NMR | Name |
|---|---|---|---|---|---|
| 261 | 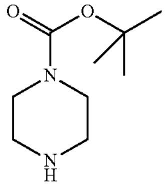 | 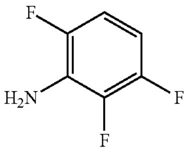 | Method 5: RT: 5.27 min, MI: 583 [M + H] | (1H, 500 MHz, d6-dmso) 9.05 (1H, s), 8.74 (1H, s), 8.37 (1H, s), 8.23 (1H, s), 8.21 (1H, s), 7.88 (1H, s), 7.72 (1H, dd), 7.37-7.17 (4H, m), 3.62 (4H, s), 2.88 (4H, s) | {4-Piperazin-1-yl-2-[2-(2,3,6-trifluoro-phenylamino)-pyridin-4-yl]-pyrido[3,4-d]pyrimidin-5-yl}-(2,3,6-trifluoro-phenyl)-amine |
| 262 | 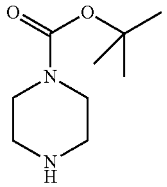 | 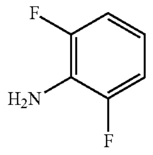 | Method 5: RT: 3.37 min, MI: 511 [M + H] | (1H, 500 MHz, d6-dmso) 8.97 (1H, s), 8.74 (1H, s), 8.41 (1H, s), 8.29 (1H, d), 8.22 (1H, t), 8.04 (1H, s), 7.72 (1H, d), 7.31 (1H, m), 7.22 (1H, m), 7.14 (1H, m), 7.09 (2H, m), 7 (1H, m), 3.54 (4H, m), 2.83 (4H, s) | (2,6-Difluoro-phenyl)-{2-[2-(2,6-difluoro-phenylamino)-pyridin-4-yl]-4-piperazin-1-yl-pyrido[3,4-d]pyrimidin-5-yl}-amine |

General synthesis of substituted 2-amino pyridyl substituted 2-(2-amino-pyridin-4-yl)-pyrido[3,4-d]pyrimidin-4-yl amine derivatives of general formula [G-003] Scheme B3

5-chloro 2-(2-chloro-pyridin-4-yl)-pyrido[3,4-d]pyrimidin-4-yl amine derivatives of general formula [G-007] were prepared by the reaction of a 5-chloro 2-(2-chloro-pyridin-4-yl)-pyrido[3,4-d]pyrimidin-4-ol derivative of general formula [G-006] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as $Et_3N$, DIPEA or NMM at ambient temperature. 5-chloro 2-(2-chloro-pyridin-4-yl)-pyrido[3,4-d]pyrimidin-4-yl amine derivatives of general formula [G-007] was involved in a Buchwald type reaction utilising a suitable amine, of general formula [G-005], a palladium catalyst such as $Pd(dba)_2$ or $Pd(OAc)_2$, a ligand such as Xantphos and a base such as NaOtBu or $Cs_2CO_3$ in a polar solvent such as dioxane or a combination of dioxane and DMA at high temperature either by heating thermally or using a microwave reactor. The 5-chlotro 2-amino-pyridyl substituted 2-(2-amino-pyridin-4-yl)-pyrido[3,4-d]pyrimidin-4-yl amine derivatives of general formula [G-008]. were reacted in a Suzuki type reaction utilising a suitable boronic acid or boronic ester, of general formula [G-009], a palladium catalyst such as $Pd(PPh_3)_4$ or $Pd(PPh_3)_2Cl_2$ a base such as $Et_3N$, KOH, $Na_2CO_3$ or NaOH in a polar solvent such as EtOH, THF, DMA or dioxane at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme B3

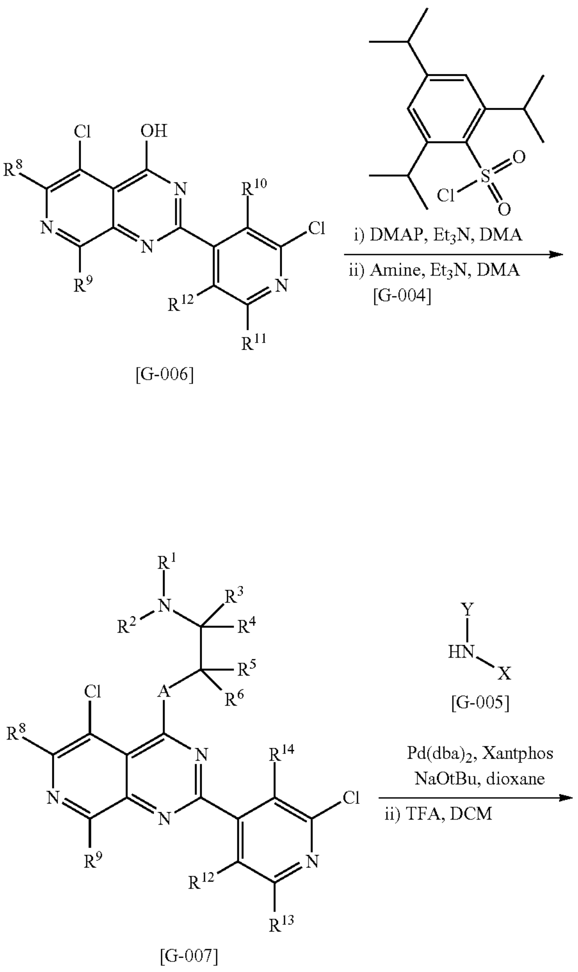

-continued

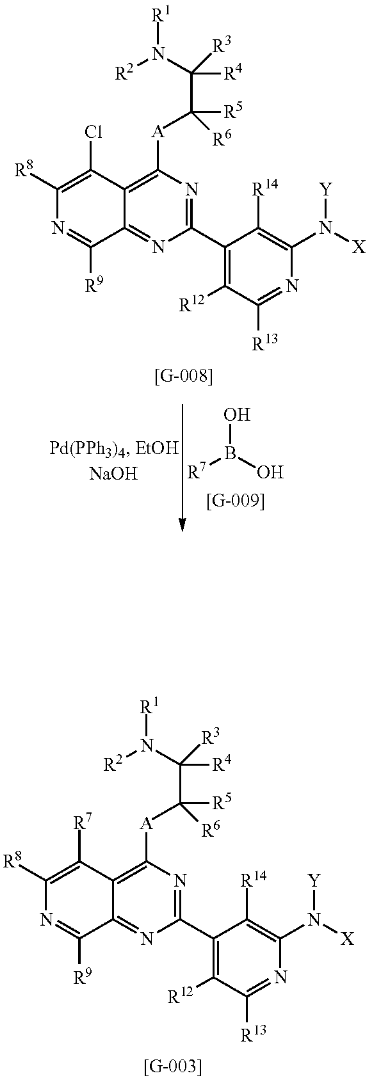

[G-008]

[G-009]

[G-003]

Synthesis of [4-(5-Cyclopropyl-4-piperazin-1-yl-pyrido[3,4-d]pyrimidin-2-yl)-pyridin-2-yl]-(2-fluoro-phenyl)-amine [263]

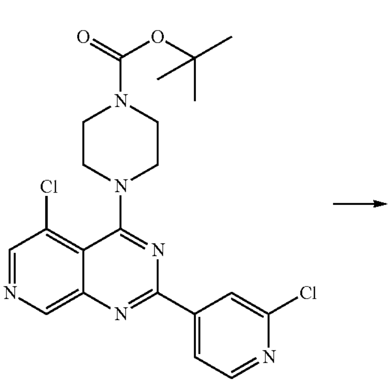

[B009]

-continued

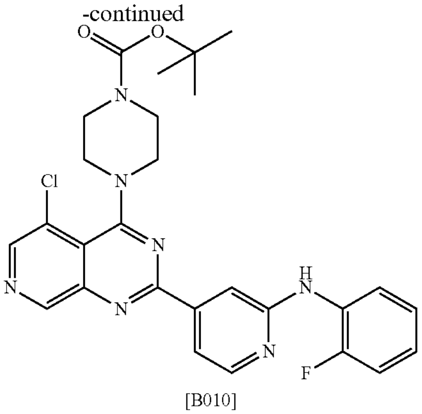

[B010]

4-{5-Chloro-2-[2-(2-fluoro-phenylamino)-pyridin-4-yl]-pyrido[3,4-d]pyrimidin-4-yl}-piperazine-1-carboxylic acid tert-butyl ester [B010]

A mixture of 4-[5-Chloro-2-(2-chloro-pyridin-4-yl)-pyrido[3,4-d]pyrimidin-4-yl]-piperazine-1-carboxylic acid tert-butyl ester [B009](3 g, 6.48 mmol), 2-fluoroaniline (654 µL, 6.48 mml), $Pd(OAc)_2$ (79 mg, 0.324 mmol), Xantphos (375 mg, 0.648 mmol), ceasium carbonate (4.11 g, 12.6 mmol) and anhydrous dioxane (20 ml) was heated at 900 overnight. Solvent was evaporated under reduced pressure and residue purified by flash column chromatography (ISCO, 120 g $SiO_2$ cartridge 100% cyclohexane up to 70% cyclohexane: 30% Ethylacetate gradient) to give the title compound [B010] as a yellow solid (1.2 g, 52% yield). LCMS method: 5, RT: 4.19 min, MI 516.57 [M+H].

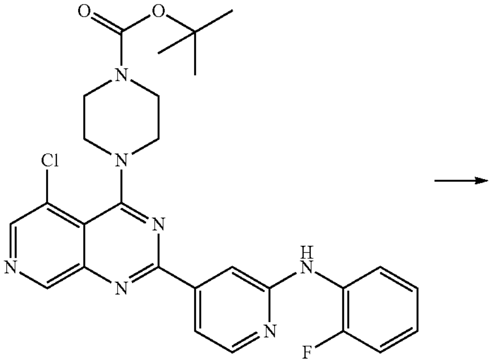

[B010]

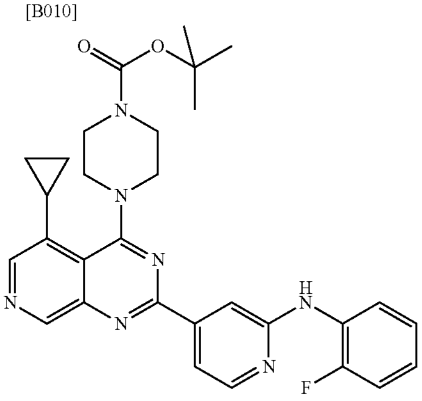

[B011]

4-{5-Cyclopropyl-2-[2-(2-fluoro-phenylamino)-pyridin-4-yl]-pyrido[3,4-d]pyrimidin-4-yl}-piperazine-1-carboxylic acid tert-butyl ester [B011]

A mixture of 4-{5-Chloro-2-[2-(2-fluoro-phenylamino)-pyridin-4-yl]-pyrido[3,4-d]pyrimidin-4-yl}-piperazine-1-carboxylic acid tert-butyl ester [B010](1.8 g, 3.36 mmol), $Pd(dppf)Cl_2.CH_2Cl_2$ (137 mg, 0.168 mmol), $K_3PO_4$ (2.14 g, 10.075 mmol), cyclopropyl boronic acid (578 mg, 6.72 mmol) and anhydrous dioxane (30 ml) plus few drops of DMA was added to a microwave vial. Solvent was evaporated under reduced pressure and residue purified by flash column chromatography (ISCO, 40 g $SiO_2$ cartridge 100% cyclohexane up to 70% cyclohexane: 30% Ethylacetate gradient) to give the title compound [B011] as a yellow solid (950 mg, 52% yield). LCMS method: 5, RT: 4.72 min, MI 542 [M+H].

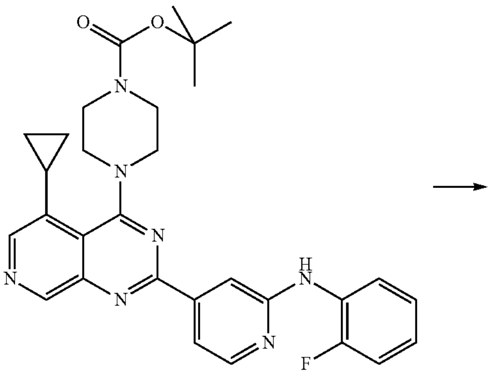

[B011]

-continued

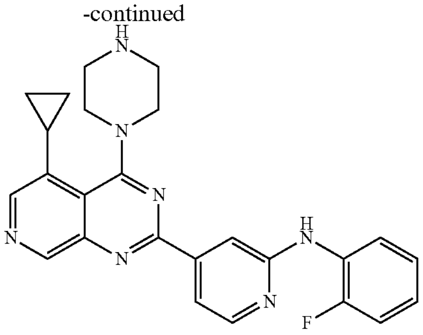

[263]

[4-(5-Cyclopropyl-4-piperazin-1-yl-pyrido[3,4-d]pyrimidin-2-yl)-pyridin-2-yl]-(2-fluoro-phenyl)-amine [263]

A mixture of 4-{5-Cyclopropyl-2-[2-(2-fluoro-phenylamino)-pyridin-4-yl]-pyrido[3,4-d]pyrimidin-4-yl}-piperazine-1-carboxylic acid tert-butyl ester [B011](300 mg, 0.554 mmol) in 4N HCl in dioxane (1.5 mL) was stirred at room temperature for 2 hours. Solvent was evaporated under reduced pressure and residue purified by reverse phase flash column chromatography (ISCO, 24 g $SiO_2$ cartridge, 100% $H_2O$:0.1% formic acid up to 20% $H_2O$:0.1% formic acid: 80% MeOH: 0.1% formic acid gradient) The residue was diluted with MeOH (5 mL) and poured onto a 1 g SCX-2 cartridge and washed with DCM and MeOH before eluting with 2N NH3/MeOH which was evaporated under reduced pressure to give the title compound [263] as a yellow solid (110 mg, 45% yield). LCMS method: 1, RT: 4.03 min, MI 442 [M+H]; NMR: (1H, 500 MHz, d6-dmso); 8.95 (1H, s), 8.27 (1H, d), 8.21 (1H, m), 8.08 (1H, s), 8.03 (1H, s), 7.70-7.69 (1H, dd), 7.23 (1H, m), 7.14 (1H, m), 6.99 (1H, m), 3.78-3.62 (4H, m), 2.84 (4H, s), 2.61 (1H, m), 1.25-1.24 (2H, m), 1.02-1.01 (2H, m).

The following compounds were synthesised according to the general synthesis shown in scheme [B3]

| | | | Analysis | | |
|---|---|---|---|---|---|
| Ex | Amine | Aniline | LCMS | NMR | Name |
| 264 | 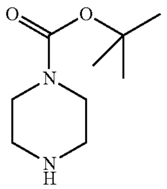 | 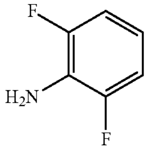 | Method 5: RT: 3.01 min, MI: 460 [M + H] | (1H, 500 MHz, d6-dmso) 8.95 (1H, s), 8.14 (1H, d), 8.08 (1H, s), 7.79 (1H, s), 7.64 (1H, d), 7.26 (1H, m), 7.15 (2H, m), 3.68 (4H, br s), 2.83 (4H, s), 2.61 (1H, m), 1.23 (2H, m), 1.02 (2H, m) | [4-(5-Cyclopropyl-4-piperazin-1-yl-pyrido[3,4-d]pyrimidin-2-yl)-pyridin-2-yl]-(2,6-difluoro-phenyl)-amine |
| 265 | 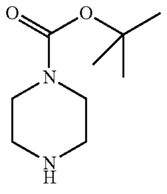 | 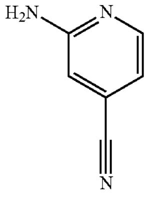 | Method 5: RT: 2.62 min, MI: 450 [M + H] | (1H, 500 MHz, d6-dmso) 10.39 (1H, s), 9.05 (1H, s), 8.36 (1H, s), 8.48 (2H, dd), 8.35 (1H, s), 7.91 (1H, d), 7.31 (1H, d), 3.91 (4H, s), 3.33 (4H, s), 2.67 (1H, s), 1.24-1.26 (2H, m), 1.07-1.09 (2H, m). | 2-[4-(5-Cyclopropyl-4-piperazin-1-yl-pyrido[3,4-d]pyrimidin-2-yl)-pyridin-2-ylamino]-isonicotinonitrile |

-continued

| | | | Analysis | | |
|---|---|---|---|---|---|
| Ex | Amine | Aniline | LCMS | NMR | Name |
| 266 | 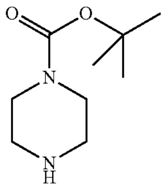 | 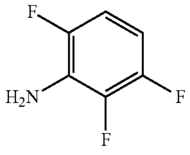 | Method 5: RT: 2.60 min, MI: 478 [M + H] | (1H, 500 MHz, d6-dmso) 9.04 (1H, s), 9.00 (1H, s), 8.21 (1H, d, 8.13 (1H, s), 7.88 (1H, s), 7.72 (1H, dd), 7.32 (1H, m), 7.20 (1H, m), 3.76 (4H, s), 3.02 (4H, s), 2.63 (1H, m), 1.25 (2 H, m), 1.05 (2H, m) | [4-(5-Cyclopropyl-4-piperazin-1-yl-pyrido[3,4-d]pyrimidin-2-yl)-pyridin-2-yl]-(2,3,6-trifluoro-phenyl)-amine |
| 267 | 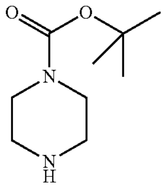 | 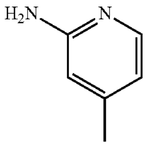 | Method 5: RT: 9.34 min, MI: 439 [M + H] | (1H, 300 MHz, d6-dmso) 9.80 (1H, s), 8.99 (1H, s), 8.78 (1H, s), 8.38 (1H, d), 8.10 (2H, m), 7.79 (1H, d), 7.66 (1H, s), 6.74 (1H, d), 3.73 (4H, bs), 2.92 (4H, s), 2.63 (1H, m), 2.29 (3H, s), 1.27 (2H, m), 1.04 (2H, m) | [4-(5-Cyclopropyl-4-piperazin-1-yl-pyrido[3,4-d]pyrimidin-2-yl)-pyridin-2-yl]-(4-methyl-pyridin-2-yl)-amine |
| 268 | 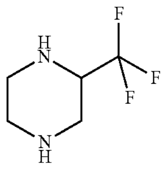 | 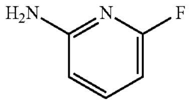 | Method 5: RT: 4.80 min, MI: 511 [M + H] | (1H, 500 MHz, d6-dmso) 10.19 (1H, s), 9.02 (1H, s), 8.72 (1H, s), 8.43 (1H, d), 7.86 (2H, m), 7.74 (1H, d), 7.62-7.53 (1H, m), 6.60 (1H, dd), 4.05 (1H, m), 3.61 (2H, m), 3.05 (4H, s), 2.63 (1H, t), 1.29 (2H, m), 1.08 (2H, m) | {4-[5-Cyclopropyl-4-(3-trifluoromethyl-piperazin-1-yl)-pyrido[3,4-d]pyrimidin-2-yl]-pyridin-2-yl}-(6-fluoro-pyridin-2-yl)-amine |
| 269 | 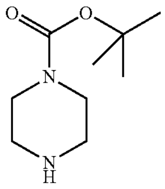 | 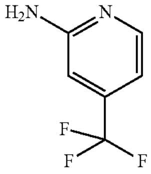 | Method 5: RT: 3.21 min, MI: 493 [M + H] | (1H, 500 MHz, d6-dmso) 10.39 (s, 1H), 9.08 (s, 1H), 8.73 (s, 1H), 8.53 (d, 1H), 8.47 (d, 1H), 8.33 (s, 1H), 8.19 (s, 1H), 7.90 (d, 1H), 7.23 (d, 1H), 3.93 (s, 4H), 3.32 (s, 4H), 2.69 (m, 1H), 1.27 (m, 2H), 1.078 (m, 2H) | [4-(5-Cyclopropyl-4-piperazin-1-yl-pyrido[3,4-d]pyrimidin-2-yl)-pyridin-2-yl]-(4-trifluoromethyl-pyridin-2-yl)-amine |
| 270 | 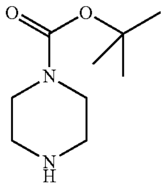 | 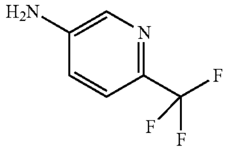 [SMILES: Nc1ccc(C(F)(F)F)nc1] | Method 5: RT: 5.71 min, MI: 493 [M + H] | (1H, 500 MHz, d6-dmso) 10.11 (s, 1H), 9.06 (s, 1H), 8.96 (d, 1H), 8.62 (dd, 1H), 8.46 (d, 1H), 8.18 (s, 1H), 8.05 (s, 1H), 7.87 (dd, 1H), 7.82 (d, 1H), 3.85 (s, 4H), 3.28 (s, 4H), 2.68 (m, 1H), 1.27 (m, 2H), 1.08 (m, 2H) | [4-(5-Cyclopropyl-4-piperazin-1-yl-pyrido[3,4-d]pyrimidin-2-yl)-pyridin-2-yl]-(6-trifluoromethyl-pyridin-3-yl)-amine |
| 271 | 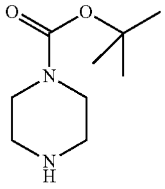 | 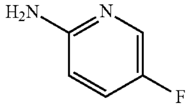 | Method 5: RT: 5.25 min, MI: 433 [M + H] | (1H, 500 MHz, d6-dmso) 9.99 (1H, s), 9.07 (1H, s), 8.71 (1H, s), 8.40 (1H, d), 8.27 (1H, d), 8.18 (1H, s), 7.94 (1H, dd), 7.83 (1H, dd), 7.68 (1H, m), 3.93 (4H, s), 3.27 (4H, s), 2.70 (1H, m), 1.26 (2H, m), 1.07 (2H, m) | [4-(5-Cyclopropyl-4-piperazin-1-yl-pyrido[3,4-d]pyrimidin-2-yl)-pyridin-2-yl]-(5-fluoro-pyridin-2-yl)-amine |

General synthesis of 5-cyclopropyl substituted 2-amino pyridyl substituted 2-(2-amino-pyridin-4-yl)-pyrido[3,4-d]pyrimidin-4-yl amine derivatives of general formula [G-012]

Scheme B4

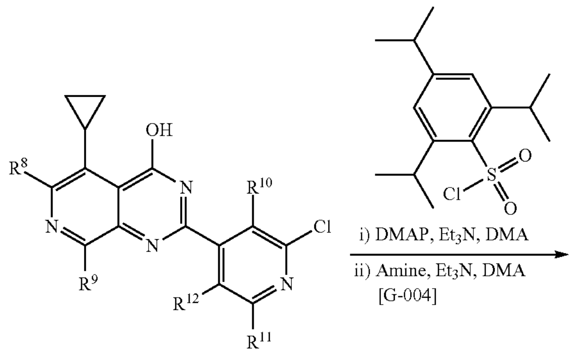

[G-010]

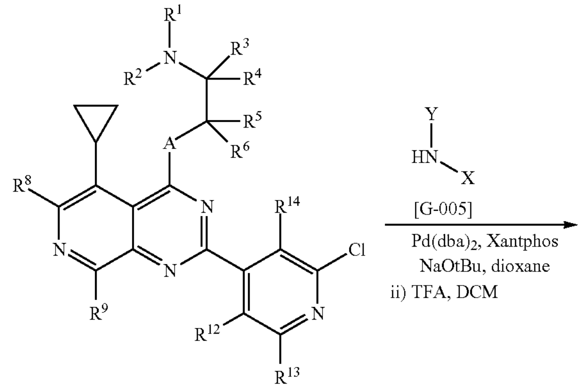

[G-011]

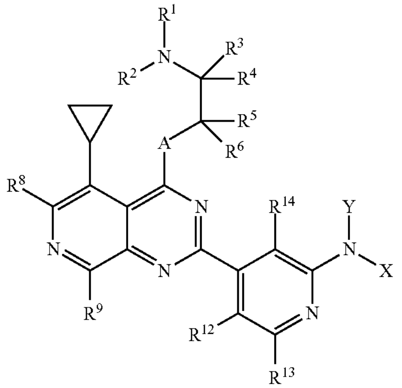

[G-012]

5-cyclopropyl 2-(2-chloro-pyridin-4-yl)-pyrido[3,4-d]pyrimidin-4-yl amine derivatives of general formula [G-011] were prepared by the reaction of a 5-cyclopropylo 2-(2-chloro-pyridin-4-yl)-pyrido[3,4-d]pyrimidin-4-ol derivative of general formula [G-010] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-2-(2-chloro-pyridin-4-yl)-pyrido[3,4-d]pyrimidin-4-yl ester was then reacted with a primary or secondary amino derivative, of general formula [G-004], in a polar aprotic solvent such as DMA, DMF, NMP in the presence of a tertiary amine base such as $Et_3N$, DIPEA or NMM at ambient temperature. 5-cyclopropyl 2-(2-chloro-pyridin-4-yl)-pyrido[3,4-d]pyrimidin-4-yl amine derivatives of general formula [G-011] was involved in a Buchwald type reaction utilising a suitable amine, of general formula [G-005], a palladium catalyst such as $Pd(dba)_2$ or $Pd(OAc)_2$, a ligand such as Xantphos and a base such as NaOtBu or $Cs_2CO_3$ in a polar solvent such as dioxane or a combination of dioxane and DMA at high temperature either by heating thermally or using a microwave reactor. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Synthesis of [4-(5-Cyclopropyl-4-piperazin-1-yl-pyrido[3,4-d]pyrimidin-2-yl)-pyridin-2-yl]-(4,5-dimethyl-oxazol-2-yl)-amine [272]

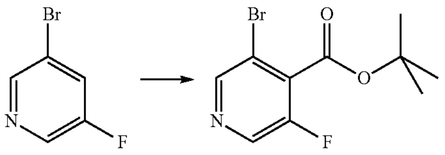

[B012]

Synthesis of 3-Bromo-5-fluoro-isonicotinic acid tert-butyl ester [B012]

To a solution of LDA (2M, 72 mL, 144 mmol) in THF (100 mL) cooled to approximately −70° C. was added dropwise via cannula a solution of 3-bromo-5-fluoropyridine (21.12 g, 120 mmol) in anhydrous THF (50 mL) pre-cooled to −70° C. The rate of addition was controlled such that the internal temperature did not rise above −65° C. The dark red-brown solution was stirred for 1 hour. Di-tert-butyldicarbonate (52.4 g, 240 mmol) in THF (50 mL) was cooled to −10° C. in a methanol/ice bath then added dropwise via cannula to the dark red-brown solution. The mixture was stirred for 2 hours then allowed to warm to room temperature and stirred for another 1 hour. Saturated aqueous ammonium chloride (100 mL) was added slowly and then water (200 mL) and EtOAc (200 mL) and the mixture was vigorously stirred for 45 minutes. The mixture was transferred to a separatory funnel and the layers were separated. The aqueous layer was extracted with EtOAc (200 mL). The THF and EtOAc layers were combined, dried over magnesium sulfate, filtered and evaporated. The recovered dark red-brown oil was purified by column chromatography (Cyclohexane/AcOEt: 1/0 to 97/3). Fractions containing desired material were concentrated in vacuo to yield the title compound [B012] as a pale yellow oil (14 g, 85%). LCMS method: 1, RT: 5.44 min, MI: 277 [M+H]; NMR: (1H, 300 MHz, d6-dmso); 8.56 (s, 1H), 8.43 (s, 1H), 1.62 (s, 9H).

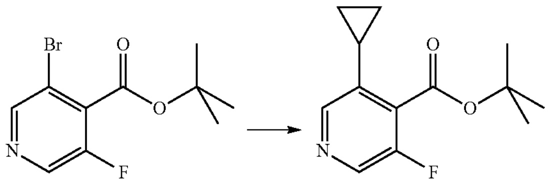

[B012] [B013]

Synthesis of 3-Cyclopropyl-5-fluoro-isonicotinic acid tert-butyl ester [B013]

A solution containing 3-Bromo-5-fluoro-isonicotinic acid tert-butyl ester [B012](5.52 g, 20 mmol), potassium phosphate tribasic (12.74 g, 60 mmol) and cyclopropyl boronic acid (2.58 g, 30 mmol), in anhydrous dioxane (100 mL) was subjected to vacuum/argon balloon (three times). Dichloro [1,1'-bis(diphenylphosphino)ferrocene]palladium (II) dichloromethane adduct (0.408 g, 0.5 mmol) was added and the reaction heated at 96° C. overnight under positive pressure of nitrogen. The mixture was cooled to room temperature and was filtered through a pad of 200 g silica and washed with EtOAc (1 L). The filtrate was concentrated in vacuo and the crude was purified by column chromatography (Cyclohexane/AcOEt: 98:2 to 96:4). The combined fractions were concentrated under reduced pressure to yield the title compound [B013] as a colourless oil (3.42 g, 72%). LCMS method: 1, RT: 5.36 min, MI: 238 [M+H].

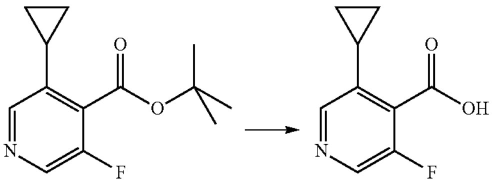

[B013] [B014]

Synthesis of 3-Cyclopropyl-5-fluoro-isonicotinic acid [B014]

In a microwave vial, 3-cyclopropyl-5-fluoro-isonicotinic acid tert-butyl ester [B013](1.186 g, 5 mmol) was dissolved in anhydrous methanol and then heated in microwave at 140° C. for 1 hr. The reaction was concentrated in vacuo to give the title compound [B014] 0.84 g (92%) as a white crystalline solid. LCMS method: 1, RT: 1.51 min, MI: 182 [M+H].

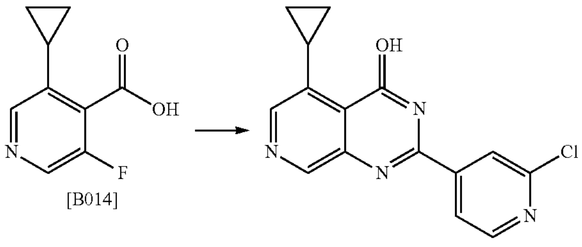

[B014] [B015]

Synthesis of 2-(2-Chloro-pyridin-4-yl)-5-cyclopropyl-pyrido[3,4-d]pyrimidin-4-ol [B015]

A mixture of 3-Cyclopropyl-5-fluoro-isonicotinic acid [B014](5 g, 27.6 mmol) and HATU (10.5 g, 82.86 mmol) was stirred in DMF (35 mL) and DIPEA (14.5 mL, 82.86 mmol) was added. The mixture was left to stir at rt for 1 hour then 2-Chloro-isonicotinamidine hydrochloride (5.3 g, 27.52 mmol) was added in one portion and the mixture was left to stir at rt for 18 hours. The crude reaction mixture was poured onto water (180 mL) and left to stir for stirred for 2 hours and then the beige solid was collected by filtration, washed with water and dried in a vacuum oven to give N-[(2-Chloro-pyridin-4-yl)-imino-methyl]-3-cyclopropyl-5-fluoro-isonicotinamide (6.60 g, 75% yield) which was used in the next step without further purification: LCMS method: 1, RT: 3.45 min, MI: 319 [M+H]; NMR: (1H, 300 MHz, d6-dmso); 10.25 (s, br, 1H), 9.92 (s, br, 1H), 8.59 (d, 1H), 8.42 (s, 1H), 8.11 (s, 1H), 8.00 (s, 1H), 7.92 (dd, 1H), 2.01 (m, 1H), 0.98 (m, 2H), 0.85 (m, 2H).

A mixture of N-[(2-Chloro-pyridin-4-yl)-imino-methyl]-3-cyclopropyl-5-fluoro-isonicotinamide (6.60 g, 20.70 mmol) and Cs2CO3 (6.7 g, 20.7 mmol) and DMA (90 mL) was heated at 90° C. overnight. The reaction mixture was poured into ice/water (100 ml), then acidified by the drop-wise addition of glacial acetic acid and the mixture was left to stir at 0 OC for 1 hour. The beige precipitate was collected by filtration and washed with water then dried in a vacuum oven to give the title compound [B015](4.8 g, 78% yield). LCMS method: 1, RT: 3.90 min, MI: 299 [M+H]; NMR: (1H, 300 MHz, d6-dmso); 12.92 (s, 1H), 8.88 (s, 1H), 8.66 (d, 1H), 8.25 (dd, 2H), 8.16 (dd, 1H), 3.39 (m, 1H), 1.11 (m, 2H), 0.94 (m, 2H).

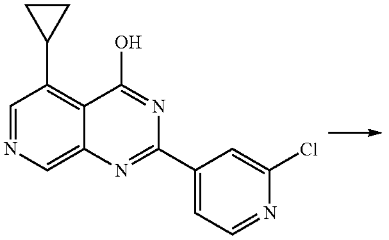

[B015]

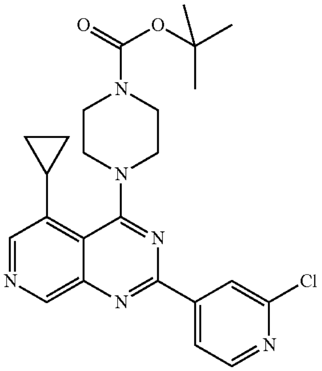

[B016]

4-[2-(2-Chloro-pyridin-4-yl)-5-cyclopropyl-pyrido[3,4-d]pyrimidin-4-yl]-piperazine-1-carboxylic acid tert-butyl ester [B016]

A mixture of 2-(2-Chloro-pyridin-4-yl)-5-cyclopropyl-pyrido[3,4-d]pyrimidin-4-ol [B015](280 mg, 0.937 mmol), anhydrous DMF (9 mL), triethylamine (0.390 mL, 2.81 mmol) and DMAP (115 mg, 0.937 mmol) was sonicated for 10 min then stirred at room temperature for 10 min. 2,4,6-Triisopropyl-benzenesulfonyl chloride (340 mg, 1.12 mmol) was added and the mixture was sonicated for 5 min then left to stir at room temperature for 2 hours. During this time the material went into solution to form a viscous solution. 1-Boc-piperazine (190 mg, 1.03 mmol) was added and the reaction mixture was left to stir at room temperature overnight. Solvent was evaporated under reduced pressure and residue purified by flash column chromatography (SP1, 20 g $SiO_2$ cartridge 100% DCM up to 95% DCM: 5% MeOH gradient) to give the title compound [B016] as a yellow solid (276 mg, 63% yield). LCMS method: 5, RT: 5.16 min, MI: 467 [M+H]; NMR: (1H, 500 MHz, d6-dmso); 9.02 (1H, s), 8.61 (1H, dd), 8.34 (2H, m), 8.15 (1H, s), 3.68-3.83 (4H, very broad s), 3.51 (4H, br s), 2.59 (1H, m), 1.24 (2H, m), 1.16 (2H, m).

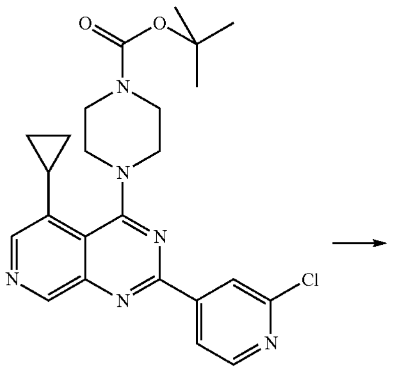

[B016]

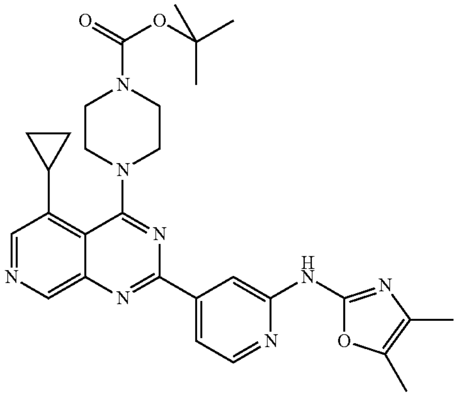

[B017]

4-{5-Cyclopropyl-2-[2-(4,5-dimethyl-oxazol-2-ylamino)-pyridin-4-yl]-pyrido[3,4-d]pyrimidin-4-yl}-piperazine-1-carboxylic acid tert-butyl ester [B017]

A mixture of 4-[2-(2-Chloro-pyridin-4-yl)-5-cyclopropyl-pyrido[3,4-d]pyrimidin-4-yl]-piperazine-1-carboxylic acid tert-butyl ester [B016](280 mg, 0.591 mmol), 4,5-dimethyl-oxazol-2-ylamine (132 mg, 1.18 mml), $Pd(OAc)_2$ (7 mg, 0.030 mmol), Xantphos (35 mg, 0.060 mmol), ceasium carbonate (384 mg, 1.18 mmol) and anhydrous dioxane (1.5 ml) was heated at 900 overnight. Solvent was evaporated under reduced pressure and residue purified by flash column chromatography (SP1, 20 g $SiO_2$ cartridge 100% DCM up to 96% DCM: 4% MeOH gradient) to give the title compound [B017] as a beige solid (61 mg, 19% yield). LCMS method: 5, RT: 4.07 min, MI: 543 [M+H].

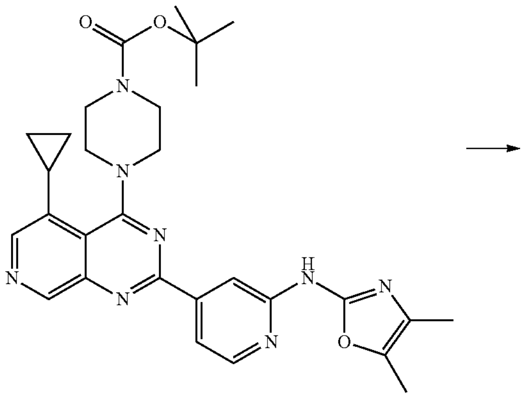

[B017]

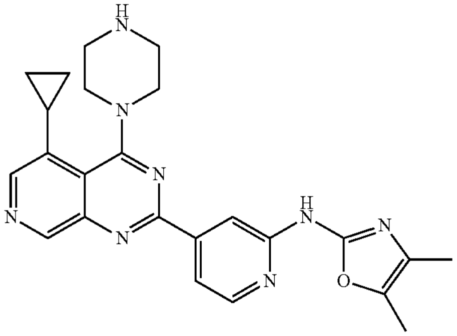

[272]

[4-(5-Cyclopropyl-4-piperazin-1-yl-pyrido[3,4-d]pyrimidin-2-yl)-pyridin-2-yl]-(4,5-dimethyl-oxazol-2-yl)-amine [272]

A mixture of 4-{5-Cyclopropyl-2-[2-(4,5-dimethyl-oxazol-2-ylamino)-pyridin-4-yl]-pyrido[3,4-d]pyrimidin-4-yl}-piperazine-1-carboxylic acid tert-butyl ester [B017](60 mg, 0.112 mmol) in 4N HCl in dioxane (1 mL) was stirred at room temperature for 2 hours. After completion solvent was evaporated under reduced pressure and residue diluted with MeOH (5 mL) and poured onto a 1 g SCX-2 cartridge and washed with DCM and MeOH before eluting with 2N NH3/MeOH which was evaporated under reduced pressure. The residue was then purified by flash column chromatography (SP1, 10 g $SiO_2$ cartridge 100% DCM up to 90% DCM: 10% MeOH gradient) to give the title compound [272] as a yellow solid (22 mg, 44% yield). LCMS method: 5, RT: 2.70 min, MI: 443 [M+H]; NMR: (1H, 500 MHz, d6-dmso); 10.61 (1H, s), 9.17 (1H, s), 9.05 (1H, s), 8.38 (1H, d), 8.16 (1H, s), 7.87 (1H, d), 3.94 (1H, s, br), 3.26 (4H, m, br), 2.69 (2H, m), 2.19 (3H, s), 2.04 (3H, s), 1.25-1.22 (3H, m), 1.06-1.05 (2H, m).

The following compounds were synthesised according to the general synthesis shown in scheme [B4]

| | | | Analysis | | |
|---|---|---|---|---|---|
| Ex | Amine | Aniline | LCMS | NMR | Name |
| 273 | 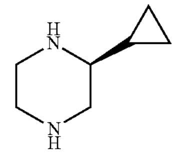 | 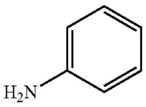 | Method 5: RT: 1.91 min, MI: 416.17 [M + H] | (1H, 500 MHz, d6-dmso) 8.98 (1H, s), 8.93 (1H, s), 8.32 (1H, d), 8.13 (1H, s), 7.92 (1H, s), 7.71-7.67 (3H, m), 7.29 (2H, t), 6.93 (1H, t), 4.28 (1H, d), 4.16 (1H, d), 3.28 (1H, t), 3.05 (1H, dd), 2.78 (1H, t), 2.63 (1H, m), 2.17 (1H, m), 1.25 (2H, m), 1.02-0.95 (2H, m), 0.77 (1H, m), 0.43 (2H, dd), 0.29-0.25 (2H, m) | {4-[5-Cyclopropyl-4-((S)-3-cyclopropyl-piperazin-1-yl)-pyrido[3,4-d]pyrimidin-2-yl]-pyridin-2-yl}-phenyl-amine |
| 274 | 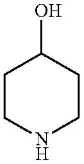 | 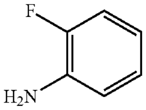 | Method 5: RT: 4.93 min, MI: 457 [M + H] | (1H, 500 MHz, d6-dmso) 8.97 (1H, s), 8.95 (1H, s), 8.26 (1H, d), 8.20 (1H, t), 8.08 (1H, s), 8.04 (1H, s), 7.70 (1H, dd), 7.22 (1H, dd), 7.14 (1H, t), 7.00 (1H, m), 4.07 (2H, m, br), 3.78 (1H, m, br), 3.54-3.40 (2H, m, br), 3.15 (1H, d), 2.59 (1H, m, br), 1.86 (2H, d, br), 1.25 (2H, d, br), 1.02 (2H, m, br). | 1-{5-Cyclopropyl-2-[2-(2-fluoro-phenylamino)-pyridin-4-yl]-pyrido[3,4-d]pyrimidin-4-yl}-piperidin-4-ol |
| 275 | 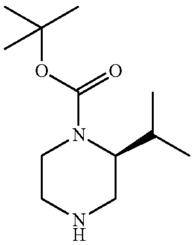 | 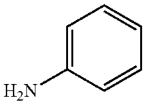 | Method 5: RT: 3.24 min, MI: 466 [M + H] | (1H, 400 MHz, d6-dmso 90° C.) 8.98 (1H, s), 8.91 (1H, s), 8.31 (1H, d), 8.12 (1H, s), 7.92 (1H, s), 7.71-7.68 (3H, m), 7.29 (2H, t), 6.93 (1H, t), 4.31 (1H, d), 4.20 (1H, d), 3.70 (1H, s, br), 3.29 (1H, t), 3.22 (2H, s), 3.05 (1H, dd), 2.81 (1H, t), 2.68-1.63 (1H, m), 1.65 (1H, m), 1.27-1.25 (2H, m), 1.03 (1H, m), 0.96 (6H, dd) | {4-[5-Cyclopropyl-4-((S)-3-isopropyl-piperazin-1-yl)-pyrido[3,4-d]pyrimidin-2-yl]-pyridin-2-yl}-phenyl-amine |
| 276 | 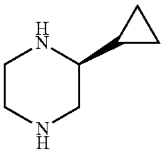 | 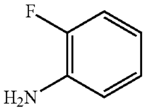 | Method 5: RT: 2.48 min, MI: 482.25 [M + H] | (1H, 400 MHz, d6-dmso 90° C.) 8.97 (1H, s), 8.53 (1H, s), 8.29 (1H, dd), 8.13 (1H, s), 8.07 (1H, td), 7.95 (1H, s), 7.71 (1H, dd), 7.23 (1H, dd), 7.21-7.14 (1H, m), 7.07-7.04 (1H, m), 4.28 (1H, d), 4.14 (1H, d), 3.27 (1H, t), 3.22 (1H, s), 3.04 (1H, m), 2.77 (1H, t), 2.62 (1H, m), 2.16 (1H, t), 1.24 (1H, m), 1.02-0.95 (2H, m), 0.78 (1H, m), 0.42 (2H, dd), 0.29-0.24 (2H, m) | {4-[5-Cyclopropyl-4-((S)-3-cyclopropyl-piperazin-1-yl)-pyrido[3,4-d]pyrimidin-2-yl]-pyridin-2-yl}-(2-fluoro-phenyl)-amine |
| 277 | 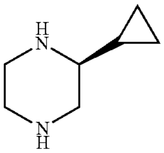 | 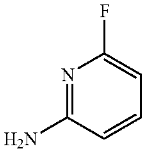 | Method 5: RT: 3.20 min, MI: 483 [M + H] | (1H, 400 MHz, d6-dmso 90° C.) 9.75 (1H, s), 8.99 (1H, s), 8.69 (1H, s), 8.41 (1H, d), 8.14 (1H, s), 7.86 (1H, dd), 7.82 (1H, qd), 7.70 (1H, dd), 6.55 (1H, dd), 4.29 (1H, d), 4.20 (1H, d), 3.30 (1H, t), 3.09-3.05 (1H, m), 2.80 (1H, t), 2.68-2.63 (1H, m), 2.16 (1H, t), 1.26-1.24 (2H, m), 1.03-0.95 (2H, m), 0.81-0.75 (1H, m), 0.42-0.40 (2H, m), 0.28-0.24 (2H, m) | {4-[5-Cyclopropyl-4-((S)-3-cyclopropyl-piperazin-1-yl)-pyrido[3,4-d]pyrimidin-2-yl]-pyridin-2-yl}-(6-fluoro-pyridin-2-yl)-amine |
| 278 | 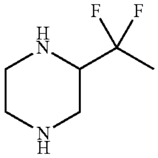 | 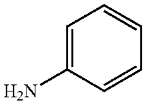 | Method 5: RT: 5.65 min, MI: 488 [M + H] | (1H, 500 MHz, d6-dmso) 9.52 (1H, s, br), 9.18 (1H, s, br), 8.51 (1H, s), 8.30 (1H, s), 8.09 (1H, s), 7.94 (2H, d, br), 7.86 (1H, s), 7.46 (2H, m, br), 7.09 (1H, t, br), 4.27 (2H, m, br), 3.34 (2H, m, br), 3.09 (2H, m, br), 2.82 (1H, m, br), 1.88-1.81 (3H, m, br), 1.48 (1H, s, br), 1.38 (3H, m, br), 1.24-1.19 (2H, m, br) | (4-{5-Cyclopropyl-4-[3-(1,1-difluoro-ethyl)-piperazin-1-yl]-pyrido[3,4-d]pyrimidin-2-yl}-pyridin-2-yl)-phenyl-amine |
| 279 | 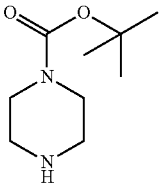 | 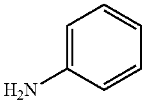 | Method 5: RT: 5.48 min, MI: 424 [M + H] | (1H, 500 MHz, d6-dmso) 9.10 (1H, s), 8.35 (1H, d), 8.04 (1h, s), 8.00 (1H, s), 7.79 (1H, d), 7.44 (2H, d), 7.36 (2H, t), 7.06 (1H, t), 6.77 (1H, s), 3.76 (4H, m, br), 3.01 (4H, m), 2.68 (1H, m), 1.26 (2H, m), 0.99 (2H, m) | [4-(5-Cyclopropyl-4-piperazin-1-yl-pyrido[3,4-d]pyrimidin-2-yl)-pyridin-2-yl]-phenyl-amine |

-continued

| | | | Analysis | | |
|---|---|---|---|---|---|
| Ex | Amine | Aniline | LCMS | NMR | Name |
| 280 | 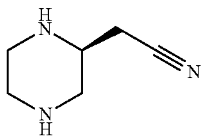 | 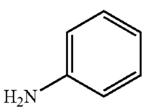 | Method 5: RT: 3.26 min, MI: 463 [M + H] | (1H, 500 MHz, d6-dmso) 9.28 (1H, s), 8.98 (1H, s), 8.31 (1H, d), 8.11 (1H, s), 7.91 (1H, s), 7.75 (2H, d), 7.69 (1H, d), 7.27 (1H, t), 6.89 (1H, t), 4.12 (2H, m, br), 3.20 (1H, m, br), 2.94 (3H, m, br), 2.71 (4H, m, br), 1.25 (2H, m, br), 1.03 (2H, m, br) | {(S)-4-[5-Cyclopropyl-2-(2-phenylamino-pyridin-4-yl)-pyrido[3,4-d]pyrimidin-4-yl]-piperazin-2-yl}-acetonitrile |

Synthesis of Cyclopentyl-[4-(5-cyclopropyl-4-piperazin-1-yl-pyrido[3,4-d]pyrimidin-2-yl)-pyridin-2-yl]-amine [281]

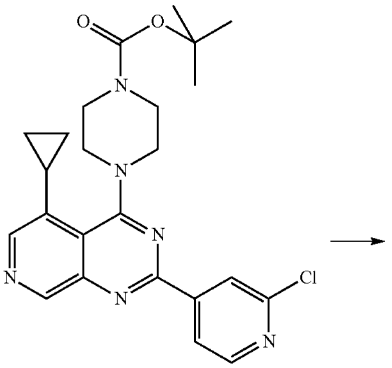

[B016]

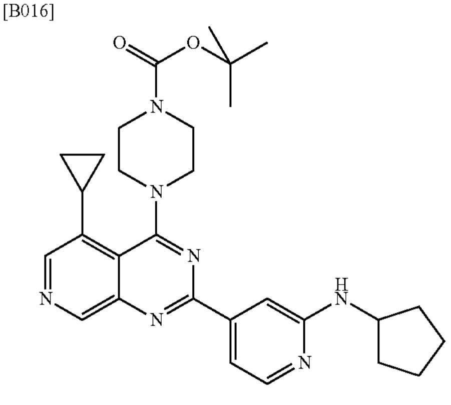

[B018]

4-[2-(2-Cyclopentylamino-pyridin-4-yl)-5-cyclopropyl-pyrido[3,4-d]pyrimidin-4-yl]-piperazine-1-carboxylic acid tert-butyl ester [B018]

A mixture of 4-[2-(2-Chloro-pyridin-4-yl)-5-cyclopropyl-pyrido[3,4-d]pyrimidin-4-yl]-piperazine-1-carboxylic acid tert-butyl ester [B016][prepared according to the general synthesis shown in Scheme B4](170 mg, 0.364 mmol), cyclopentylamine (73 μL, 0.728 mmol), $Pd(t-Bu_3P)_2$ (38 mg, 0.073 mmol), sodium tert-butoxide (54 mg, 0.546 mmol) and anhydrous dioxane (2 ml) was heated at 110° C. overnight. Solvent was evaporated under reduced pressure and residue purified by flash column chromatography (SP1, 20 g $SiO_2$ cartridge 100% DCM up to 96% DCM: 4% MeOH gradient) to give the title compound [B018] as a yellow solid (92 mg, 48% yield). LCMS: method: 5, RT: 4.19 min, MI 516.57 [M+H].

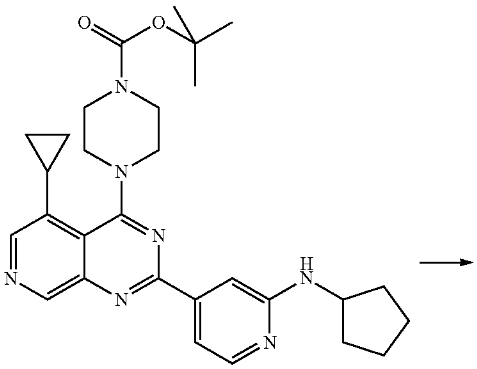

[B018]

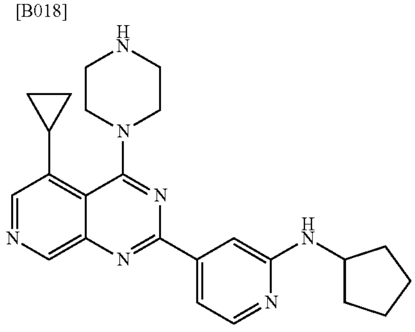

[281]

Cyclopentyl-[4-(5-cyclopropyl-4-piperazin-1-yl-pyrido[3,4-d]pyrimidin-2-yl)-pyridin-2-yl]-amine [281]

A mixture of 4-[2-(2-Cyclopentylamino-pyridin-4-yl)-5-cyclopropyl-pyrido[3,4-d]pyrimidin-4-yl]-piperazine-1-carboxylic acid tert-butyl ester [B018](90 mg, 0.178 mmol) in 4N HCl in dioxane (2 mL) was stirred at room temperature for 2 hours. Solvent was evaporated under reduced pressure and residue diluted with MeOH (5 mL) and poured onto a 1 g SCX-2 cartridge and washed with DCM and MeOH before eluting with 2N NH3/MeOH which was evaporated under reduced pressure. The residue was then purified by flash column chromatography (SP1, 10 g $SiO_2$ cartridge 100% DCM up to 95% DCM: 5% MeOH gradient) to give the title compound [281] as a yellow solid to give the title compound as a yellow solid (26 mg, 37% yield). LCMS: method: 5, RT: 2.22 min, MI 416.25 [M+H]; NMR: (1H, 500 MHz, d6-dmso); 8.95 (1H, s), 8.10 (2H, d), 8.08 (1H, s), 7.51 (1H, s), 7.38 (1H, dd), 6.75 (1H, d), 4.17 (1H, m), 3.84-3.65 (4H, m), 3.11 (4H, m), 2.91 (1H, m), 2.62 (2H, m), 1.98-1.92 (2H, m), 1.69 (2H, m), 1.55 (2H, m), 1.46 (2H, m), 1.24-1.22 (2H, m), 1.03 (2H, m).

The following compounds were synthesised according to the general synthesis shown in scheme [B4]

8.69 (d, J=5.4 Hz, 1H), 8.61 (d, J=4.6 Hz, 1H), 8.37-8.29 (m, 3H), 4.94 (br s, 1H), 3.88-3.71 (m, 1H), 3.55-3.29 (m, 3H), 2.37-2.25 (m, 1H), 2.19-2.04 (m, 1H), 1.46-1.39 (m, 9H). MS=427, 429 (MH)+.

303c) A tube was charged with (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol), 2-Amino-benzamide (35.0 mg, 0.257 mmol), Palladium Acetate (5.0 mg, 0.022 mmol), 4,5-Bis-(di-tert-butyl-phosphanyl)-9,9-dimethyl-9H-xanthene (12.0 mg, 0.0241 mmol), Cesium Carbonate (115.0 mg, 0.3530 mmol) and 1,4-Dioxane (1 mL, 10 mmol) under an atmosphere of Nitrogen. The tube was carefully evacuated and backflushed with nitrogen once. The tube was sealed and heated at 100° C. and stirred overnight. The mixture was cooled to room temperature, diluted with dichloromethane (10 mL), filtered through a plug of diatomaceous earth and evaporated to a dark resin. To the residue was added Trifluoroacetic acid (0.5 mL) and dichloromethane (0.5 mL). The mixture was stirred for 1 hour and the volatiles were evaporated. The residue was purified via reverse phase chromatography using a Gilson apparatus (10%→0% Acetonitrile:Water w/TFA modifier). 2-Amino-N-{4-[4-((R)-pyrrolidin-3-ylamino)-pyrido[3,4-d]pyrimidin-2-yl]-pyridin-2-yl}-benzamide as the trifluoroacetic acid salt was isolated as a yellow lyophilate (0.009 g, 9%). $^1$HNMR (400 MHz, d6-DMSO, δ, ppm): 9.28 (s, 1H), 9.15 (s, 1H), 8.88 (br s, 2H), 8.75-8.70 (m, 2H), 8.55 (d, J=5.1 Hz, 1H), 8.27 (d, J=5.4 Hz, 1H), 8.13 (d, J=4.3 Hz, 1H), 7.77 (d, J=8.4 Hz, 1H), 7.24 (t, J=8.4 Hz,

| | | | Analysis | | |
|---|---|---|---|---|---|
| Ex | Amine 1 | Amine 2 | LCMS | NMR | Name |
| 282 | 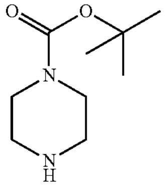 | 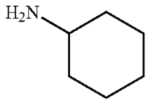 | Method 5: RT: 2.43 min, MI: 430.28 [M + H] | (1H, 500 MHz, d6-dmso) 8.93 (1H, s), 8.07 (1H, d), 8.06 (1H, s), 7.50 (1H, s), 7.35 (1H, dd), 6.63 (1H, d), 3.76-3.58 (4H, m, br), 2.87 (4H, m, br), 2.67 (2H, m), 1.94 (2H, d, br), 1.72 (2H, dt, br), 1.59 (1H, d, br), 1.37-1.17 (7H, m), 1.02 (2H, m) | Cyclohexyl-[4-(5-cyclopropyl-4-piperazin-1-yl-pyrido[3,4-d]pyrimidin-2-yl)-pyridin-2-yl]-amine |
| 283 | 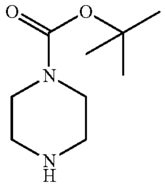 | 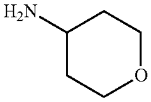 | Method 5: RT: 1.93 min, MI: 432.23 [M + H] | (1H, 500 MHz, d6-dmso) 8.94 (1H, s), 8.10 (1H, d), 8.07 (1H, s), 7.53 (1H, s), 7.40 (1H, d), 6.77 (1H, d), 4.09-3.97 (2H, m), 3.88-3.86 (2H, m), 3.75-3.57 (4H, m), 3.41 (2H, t), 3.15 (1H, d), 2.93 (4H, m), 2.62 (1H, m), 1.90 (2H, d, br), 1.48-1.40 (2H, m), 1.28-1.23 (2H, m), 1.03 (2H, m) | [4-(5-Cyclopropyl-4-piperazin-1-yl-pyrido[3,4-d]pyrimidin-2-yl)-pyridin-2-yl]-(tetrahydro-pyran-4-yl)-amine |
| 284 | 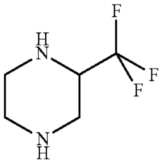 | 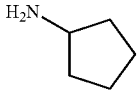 | Method 5: RT: 3.75 min, MI: 484.21 [M + H] | (1H, 400 MHz, d4-MeOH 50° C.) 9.01 (1H, s), 8.09 (1H, s), 8.07 (1H, d), 7.59 (1H, s), 7.54 (1H, dd), 4.16-4.07 (1H, m), 3.71-3.66 (1H, m), 3.13-3.07 (1H, m), 2.75-2.68 (1H, m), 2.13-2.05 (2H, m), 1.82-1.76 (2H, m), 1.69-1.65 (2H, m), 1.60-1.52 (2H, m), 1.28-1.23 (3H, m), 1.06-0.96 (2H, m) | Cyclopentyl-{4-[5-cyclopropyl-4-(3-trifluoromethyl-piperazin-1-yl)-pyrido[3,4-d]pyrimidin-2-yl]-pyridin-2-yl]-amine |
| 285 | 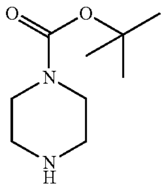 | 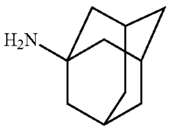 | Method 5: RT: 3.05 min, MI: 482.25 [M + H] | (1H, 500 MHz, d6-dmso) 8.92 (1H, s), 8.05 (2H, m), 7.55 (1H, s), 7.33 (1H, d), 6.36 (1H, s), 3.80-3.52 (4H, m), 2.85 (4H, m, br), 2.62-2.60 (1H, m), 2.10 (6H, m, br), 2.05 (3H, m, br), 1.66 (6H, m, br), 1.24-1.23 (2H, m, br), 1.18-1.16 (1H, m), 1.10-1.08 (1H, m), 1.03-1.00 (2H, m) | Adamantan-1-yl-[4-(5-cyclopropyl-4-piperazin-1-yl-pyrido[3,4-d]pyrimidin-2-yl)-pyridin-2-yl]-amine |

Example 303. 2-Amino-N-{4-[4-((R)-pyrrolidin-3-ylamino)-pyrido[3,4-d]pyrimidin-2-yl]-pyridin-2-yl}-benzamide 303a) 2-(2-Chloro-pyridin-4-yl)-pyrido[3,4-d]pyrimidin-4-ol was prepared from 2-Chloro-isonicotinonitrile (0.60 g, 4.3 mmol) and 3-Amino-isonicotinic acid (0.50 g, 3.6 mmol) in an analogous manner to Example 1a. Product isolated as a tan solid (0.479 g, 51%). $^1$HNMR (400 MHz, d6-DMSO, δ, ppm): 13.13 (br s, 1H), 9.19 (s, 1H), 8.74 (d, J=4.2 Hz, 1H), 8.66 (d, J=5.1 Hz, 1H), 8.24 (s, 1H), 8.15 (d, J=5.1 Hz, 1H), 8.02 (d, J=4.8 Hz, 1H). MS=259, 261 (MH)+.

303b) (R)-3-[2-(2-Chloro-pyridin-4-yl)-pyrido[3,4-d]pyrimidin-4-ylamino]-pyrrolidine-1-carboxylic acid tert-butyl ester was prepared from 2-(2-Chloro-pyridin-4-yl)-pyrido[3,4-d]pyrimidin-4-ol (1.50 g, 5.80 mmol) and (R)-3-Amino-pyrrolidine-1-carboxylic acid tert-butyl ester (1.1 mL, 6.6 mmol) in an analogous manner to [B016]. Product was isolated as a yellow foam (2.15 g, 87%). $^1$HNMR (400 MHz, d6-DMSO, δ, ppm): 9.22 (s, 1H), 8.76 (d, J=5.7 Hz, 1H), 1H), 6.80 (d, J=8.6 Hz, 1H), 6.60 (t, J=7.2 Hz, 1H), 4.93 (br s, 1H), 3.80-3.70 (m, 1H), 3.52-3.35 (m, 3H), 2.53-2.40 (m, 2H), 2.32-2.24 (m, 1H). MS=427 (MH)+.

Example 304. 4-{4-[4-((R)-Pyrrolidin-3-ylamino)-pyrido[3,4-d]pyrimidin-2-yl]-pyridin-2-ylamino}-benzamide 4-{4-[4-((R)-Pyrrolidin-3-ylamino)-pyrido[3,4-d]pyrimidin-2-yl]-pyridin-2-ylamino}-benzamide was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 4-Amino-benzamide (35.0 mg, 0.257 mmol) in an analogous manner to Example 303c. Product was isolated as the trifluoroacetic acid salt as a yellow lyophilate (0.008 g, 8%). $^{1}$HNMR (400 MHz, d6-DMSO, δ, ppm): 9.67 (s, 1H), 9.24 (s, 1H), 8.87 (br s, 2H), 8.74-8.69 (m, 1H), 8.40 (d, J=5.2 Hz, 1H), 8.26 (d, J=5.7 Hz, 1H), 8.02 (s, 1H), 7.84-7.74 (m, 6H), 7.13 (br s, 1H), 4.95 (br s, 1H), 3.80-3.30 (m, 3H), 2.52-2.38 (m, 2H), 2.31-2.22 (m, 1H). MS=427 (MH)+.

Example 305. 4-Amino-N-{4-[4-((R)-pyrrolidin-3-ylamino)-pyrido[3,4-d]pyrimidin-2-yl]-pyridin-2-yl}-benzamide 4-Amino-N-{4-[4-((R)-pyrrolidin-3-ylamino)-pyrido[3,4-d]pyrimidin-2-yl]-pyridin-2-yl}-benzamide was a byproduct from Example 304 isolated as the trifluoroacetic acid salt as an orange-brown lyophilate (0.012 g, 12%). $^{1}$HNMR (400 MHz, d6-DMSO, δ, ppm): 10.41 (s, 1H), 9.28 (s, 1H), 9.23 (s, 1H), 8.87 (br s, 2H), 8.75-8.70 (m, 2H), 8.54-8.50 (m, 1H), 8.27 (d, J=5.2 Hz, 1H), 8.10 (d, J=4.8 Hz, 1H), 7.85 (d, J=8.1 Hz, 2H), 6.61 (d, J=7.7 Hz, 2H), 4.95-4.88 (m, 1H), 3.82-3.30 (m, 3H), 2.55-2.40 (m, 2H), 2.33-2.25 (m, 1H). MS=427 (MH)+.

Example 306. {4-[(1S,4S)-4-(2,5-Diaza-bicyclo[2.2.1]hept-2-yl)-pyrido[3,4-d]pyrimidin-2-yl]-pyridin-2-yl}-phenyl-amine 306a) (1S,4S)-5-[2-(2-Chloro-pyridin-4-yl)-pyrido[3,4-d]pyrimidin-4-yl]-2,5-diaza-bicyclo[2.2.1]heptane-2-carboxylic acid tert-butyl ester was prepared from 2-(2-Chloro-pyridin-4-yl)-pyrido[3,4-d]pyrimidin-4-ol (250.0 mg, 0.9665 mmol) and (1S,4S)-2,5-Diaza-bicyclo[2.2.1]heptane-2-carboxylic acid tert-butyl ester (215.0 mg, 1.084 mmol) in an analogous manner to Example 301b. Product isolated as a yellow resin (0.110 g, 26%). $^{1}$HNMR (400 MHz, d6-DMSO, δ, ppm): 9.22 (s, 1H), 8.62-8.55 (m, 2H), 8.37-8.32 (m, 2H), 8.07-8.03 (m, 1H), 5.53 (d, J=18.5 Hz, 1H), 4.62 (d, J=18.5 Hz, 1H), 4.33 (br s, 1H), 3.92 (br s, 1H), 3.62-3.44 (m, 2H), 2.08-2.00 (m, 2H), 1.45-1.30 (m, 9H). MS=439, 441 (MH)+.

306b) {4-[(1S,4S)-4-(2,5-Diaza-bicyclo[2.2.1]hept-2-yl)-pyrido[3,4-d]pyrimidin-2-yl]-pyridin-2-yl}-phenyl-amine was prepared from (1S,4S)-5-[2-(2-Chloro-pyridin-4-yl)-pyrido[3,4-d]pyrimidin-4-yl]-2,5-diaza-bicyclo[2.2.1]heptane-2-carboxylic acid tert-butyl ester (115.0 mg, 0.2620 mmol) and Aniline (27.0 μL, 0.296 mmol) in an analogous manner to Example 303c. Product isolated as the trifluoroacetic acid salt as a yellow lyophilate (0.133 g, 128%). $^{1}$HNMR (400 MHz, d6-DMSO, δ, ppm): 9.49 (br s, 1H), 9.28 (s, 1H), 9.23 (br s, 1H), 8.65 (d, J=5.4 Hz, 1H), 8.45 (br s, 1H), 8.33-8.29 (m, 1H), 8.03 (d, J=5.6 Hz, 1H), 7.99 (s, 1H), 7.76-7.70 (m, 3H), 7.32 (t, J=7.4 Hz, 2H), 7.00-6.93 (m, 1H), 5.49 (s, 1H), 4.62 (s, 1H), 4.44 (d, J=10.8 Hz, 1H), 4.12 (d, J=11.1 Hz, 1H), 3.61-3.41 (m, 2H), 2.34 (d, J=10.4 Hz, 1H), 2.07 (d, J=10.9 Hz, 1H). MS=396 (MH)+.

Example 307. Pyrazine-2-carboxylic acid {4-[4-((R)-pyrrolidin-3-ylamino)-pyrido[3,4-d]pyrimidin-2-yl]-pyridin-2-yl}-amide Pyrazine-2-carboxylic acid {4-[4-((R)-pyrrolidin-3-ylamino)-pyrido[3,4-d]pyrimidin-2-yl]-pyridin-2-yl}-amide was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and Pyrazine-2-carboxylic acid amide (32.0 mg, 0.260 mmol) in an analogous manner to Example 303c. Product isolated as the trifluoroacetic acid salt as a pale yellow lyophilate (0.099 g, 100%). $^{1}$HNMR (400 MHz, d6-DMSO, δ, ppm): 10.50 (s, 1H), 9.40 (s, 1H), 9.34 (s, 1H), 9.30 (s, 1H), 9.02-8.86 (m, 4H), 8.77 (d, J=4.4 Hz, 1H), 8.74 (d, J=5.4 Hz, 1H), 8.60 (d, J=5.0 Hz, 1H), 8.28 (d, J=5.5 Hz, 1H), 8.21 (d, J=5.1 Hz, 1H), 4.98-4.90 (m, 1H), 3.84-3.74 (m, 2H), 3.54-3.38 (m, 3H), 2.53-2.42 (m, 1H), 2.35-2.25 (m, 1H). MS=414 (MH)+.

Example 308. 3-{4-[4-((R)-Pyrrolidin-3-ylamino)-pyrido[3,4-d]pyrimidin-2-yl]-pyridin-2-ylamino}-benzamide 3-{4-[4-((R)-Pyrrolidin-3-ylamino)-pyrido[3,4-d]pyrimidin-2-yl]-pyridin-2-ylamino}-benzamide was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 3-Amino-benzamide (35.0 mg, 0.257 mmol) in an analogous manner to Example 303c. Product isolated as the bis-trifluoroacetic acid salt as yellow lyophilate (0.005 g, 5%). $^{1}$HNMR (400 MHz, d6-DMSO, δ, ppm): 9.49 (s, 1H), 9.24 (s, 1H), 8.85 (br s, 1H), 8.72 (d, J=5.1 Hz, 1H), 8.70-8.67 (m, 1H), 8.36 (d, J=5.4 Hz, 1H), 8.24 (d, J=5.0 Hz, 1H), 8.18 (s, 1H), 7.99 (s, 1H), 7.95-7.88 (m, 2H), 7.77 (d, J=4.5 Hz, 1H), 7.41 (d, J=7.2 Hz, 1H), 7.37 (d, J=8.1 Hz, 1H), 7.34-7.29 (m, 1H), 4.99-4.91 (m, 1H), 3.76-3.69 (m, 1H), 3.51-3.45 (m, 1H), 3.43-3.34 (m, 3H), 2.50-2.38 (m, 2H), 2.31-2.22 (m, 1H). MS=427 (MH)+.

Example 309. 3-Amino-N-{4-[4-((R)-pyrrolidin-3-ylamino)-pyrido[3,4-d]pyrimidin-2-yl]-pyridin-2-yl}-benzamide 3-Amino-N-{4-[4-((R)-pyrrolidin-3-ylamino)-pyrido[3,4-d]pyrimidin-2-yl]-pyridin-2-yl}-benzamide was a byproduct from Example 309 isolated as a free base as an off-white solid (0.007 g, 7%). $^{1}$HNMR (400 MHz, d6-DMSO, δ, ppm): 10.53 (s, 1H), 9.21 (s, 2H), 8.66 (d, J=5.3 Hz, 1H), 8.54 (br s, 1H), 8.53 (d, J=4.5 Hz, 1H), 8.35-8.30 (m, 1H), 8.12 (d, J=4.8 Hz, 1H), 7.24-7.19 (m, 2H), 7.15 (t, J=7.5 Hz, 1H), 6.77 (d, J=7.7 Hz, 1H), 5.31 (s, 2H), 4.77 (br s, 1H), 3.24 (br s, 1H), 3.05-2.80 (m, 3H), 2.23 (br s, 1H), 1.90 (br s, 1H). MS=427 (MH)+.

Example 310. 2-(4-{4-[4-((R)-Pyrrolidin-3-ylamino)-pyrido[3,4-d]pyrimidin-2-yl]-pyridin-2-ylamino}-phenoxy)-acetamide 310a) To a stirred suspension of 4-Nitrophenol (2.00 g, 14.4 mmol) and Potassium carbonate (3.0 g, 22 mmol) in Acetone (20 mL, 300 mmol) was added Ethyl bromoacetate (1.60 mL, 14.4 mmol). The mixture was heated at 30° C. overnight. The mixture was cooled to room temperature, diluted with ether (50 mL) and filtered through a plug of diatomaceous earth and evaporated. (4-Nitro-phenoxy)-acetic acid ethyl ester was isolated as an off-white solid (3.20 g, 99%). $^1$HNMR (400 MHz, CDCl3, δ, ppm): 8.22 (d, J=7.8 Hz, 2H), 6.98 (d, J=7.8 Hz, 2H), 4.72 (s, 2H), 4.29 (q, J=7.1 Hz, 2H), 1.31 (t, J=7.1 Hz, 3H). MS=226 (MH)+.

310b) A Paar bottle (500 mL) was charged with 10% Palladium on Carbon (50% Wet)(5:45:50, Palladium:carbon black:Water, 3.0 g, 1.4 mmol) followed by a solution of (4-Nitro-phenoxy)-acetic acid ethyl ester (3.20 g, 14.2 mmol) in 2:1 Ethyl acetate:Methanol(2:1, Ethyl acetate: Methanol, 75 mL, 510 mmol). The mixture was degassed and charged with Hydrogen (50 psi). The mixture was shaken on a Paar apparatus until adsorption of Hydrogen ceased. The mixture was degassed and backflushed with nitrogen. The mixture was filtered through a plug of diatomaceous earth and evaporated. (4-Amino-phenoxy)-acetic acid ethyl ester was isolated as a tan solid (2.65 g, 96%). $^1$HNMR (400 MHz, CDCl3, δ, ppm): 6.77 (d, J=7.9 Hz, 1H), 6.63 (d, J=7.8 Hz, 1H), 4.54 (s, 2H), 4.26 (q, J=7.1 Hz, 2H), 3.40 (br s, 2H), 1.29 (t, J=7.1 Hz, 3H). MS=196 (MH)+.

310c) (R)-3-{2-[2-(4-Ethoxycarbonylmethoxy-phenylamino)-pyridin-4-yl]-pyrido[3, 4-d]pyrimidin-4-ylamino}-pyrrolidine-1-carboxylic acid tert-butyl ester was prepared from (R)-3-[2-(2-Chloro-pyridin-4-yl)-pyrido[3,4-d]pyrimidin-4-ylamino]-pyrrolidine-1-carboxylic acid tert-butyl ester (200.0 mg, 0.4685 mmol) and (4-Amino-phenoxy)-acetic acid ethyl ester (100.0 mg, 0.5122 mmol) in an analogous manner to Example 303c. The orange residue was suspended in Methanol (1 mL, 20 mmol) and Water (1 mL, 60 mmol) and Lithium hydroxide monohydrate (25.0 mg, 0.596 mmol) was added. The mixture was stirred at room temperature overnight. The volatiles were evaporated to yield an orange solid. The orange solid was suspended in 1,4-Dioxane (5 mL, 60 mmol). Pyridine (0.1 mL, 1 mmol) was added followed by Di-tert-Butyldicarbonate (105.0 mg, 0.4811 mmol) and Ammonium Carbonate (70.0 mg, 0.728 mmol). The mixture was stirred at room temperature for overnight. The mixture was diluted with dichloromethane (25 mL) and filtered through a plug of diatomaceous earth and the filtrate was evaporated. The solid was dissolved in dichloromethane (1 mL) and trifluoroacetic acid (0.5 mL) was added. The mixture was stirred for 1 hour at room temperature then the volatiles were evaporated. The residue was purified via reverse phase chromatography using a Gilson apparatus (5%-30% Acetonitrile:Water w/ 0.1% TFA modifier). 2-(4-{4-[4-((R)-Pyrrolidin-3-ylamino)-pyrido[3, 4-d]pyrimidin-2-yl]-pyridin-2-ylamino}-phenoxy)-acetamide was isolated as the trifluoroacetic acid salt as an orange-yellow lyophilate (0.118 g, 55%). $^1$HNMR (400 MHz, d6-DMSO, δ, ppm): 9.62 (br s, 1H), 9.24 (s, 1H), 8.98 (br s, 2H), 8.76 (d, J=4.5 Hz, 1H), 8.73 (d, J=5.3 Hz, 1H), 8.27 (d, J=5.6 Hz, 1H), 8.21 (d, J=5.3 Hz, 1H), 7.96 (s, 1H), 7.74 (d, J=5.5 Hz, 1H), 7.57 (d, J=8.1 Hz, 2H), 7.54 (s, 1H), 7.42 (s, 1H), 6.99 (d, J=8.4 Hz, 2H), 4.96-4.86 (m, 1H), 4.43 (s, 2H), 3.74-3.64 (m, 1H), 3.54-3.34 (m, 3H), 2.45-2.35 (m, 1H), 2.31-2.21 (m, 1H). MS=457 (MH)+.

Example 311. 2-(3-{4-[4-((R)-Pyrrolidin-3-ylamino)-pyrido[3,4-d]pyrimidin-2-yl]-pyridin-2-ylamino}-phenoxy)-acetamide 311a) (3-Nitro-phenoxy)-acetic acid ethyl ester was prepared from m-Nitrophenol (2.00 g, 14.4 mmol) and Ethyl bromoacetate (1.60 mL, 14.4 mmol) in an analogous manner to Example 310a. Product isolated as a yellow oil (3.20 g, 99%). $^1$HNMR (400 MHz, CDCl3, δ, ppm): 7.88 (d, J=8.1 Hz, 1H), 7.73 (s, 1H), 7.46 (t, J=8.3 Hz, 1H), 7.27 (d, J=8.5 Hz, 1H), 4.71 (s, 2H), 4.30 (q, J=7.1 Hz, 2H), 1.32 (t, J=7.1 Hz, 3H). LC/MS=248 (M+Na)+.

311b) (3-Amino-phenoxy)-acetic acid ethyl ester was prepared from (3-Nitro-phenoxy)-acetic acid ethyl ester (3.20 g, 14.2 mmol) in an analogous manner to Example 310b. Product isolated as an orange oil (2.60 g, 94%). $^1$HNMR (400 MHz, CDCl3, δ, ppm): 7.05 (t, J=7.8 Hz, 1H), 6.35-6.26 (m, 3H), 4.57 (s, 2H), 4.27 (q, J=7.2 Hz, 2H), 3.67 (br s, 2H), 1.30 (t, J=7.1 Hz, 3H). MS=196 (MH)+.

311c) 2-(3-{4-[4-((R)-Pyrrolidin-3-ylamino)-pyrido[3,4-d]pyrimidin-2-yl]-pyridin-2-ylamino}-phenoxy)-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (200.0 mg, 0.4685 mmol) and (3-Amino-phenoxy)-acetic acid ethyl ester (100.0 mg, 0.5122 mmol) in an analogous manner to Example 310c. Product isolated as the trifluoroacetic acid salt as a yellow lyophilate (0.011 g, 5%). $^1$HNMR (400 MHz, d6-DMSO, δ, ppm): 9.40 (br s, 1H), 9.23 (s, 1H), 8.85 (br s, 2H), 8.72 (d, J=5.3 Hz, 1H), 8.69 D, J=5.1 Hz, 1H), 8.35 (d, J=4.8 Hz, 1H), 8.26 (d, J=5.3 Hz, 1H), 7.98 (s, 1H), 7.75 (d, J=5.2 Hz, 1H), 7.55 (s, 1H), 7.52 (s, 1H), 7.39 (s, 1H), 7.28 (d, J=7.9 Hz, 1H), 7.20 (t, J=7.9 Hz, 1H), 6.51 (d, J=8.3 Hz, 1H), 4.98-4.90 (m, 1H), 4.41 (s, 2H), 3.76-3.70 (m, 1H), 3.52-3.33 (m, 3H), 2.45-2.38 (m, 1H), 2.30-2.23 (m, 1H). MS=457 (MH)+.

Example 313. 2-(4-{4-[4-((R)-Pyrrolidin-3-ylamino)-pyrido[3,4-d]pyrimidin-2-yl]-pyridin-2-ylamino}-phenyl)-acetamide 313a) To a stirred suspension of [A]4-Nitrophenylacetic Acid (1.0 g, 5.5 mmol) and Pyridine (0.27 mL, 3.3 mmol) in 1,4-Dioxane (10 mL, 100 mmol) was added Di-tert-Butyldicarbonate (1.3 g, 6.1 mmol). The mixture was stirred for 10 minutes at room temperature then Ammonium Carbonate (0.80 g, 8.3 mmol) was added. The mixture was stirred at room temperature overnight. The volatiles were evaporated to a leave an off-white solid. The solid was triturated with methanol, filtered and rinsed with methanol. The methanolic filtrate was evaporated. 2-(4-Nitro-phenyl)-acetamide was isolated as an off-white solid (0.65 g, 65%). $^1$HNMR (400 MHz, d6-DMSO, 6, ppm):8.18 (d, J=7.9 Hz, 2H), 7.59 (br s, 1H), 7.54 (d, J=7.9 Hz, 2H), 7.01 (br s, 1H), 3.55 (s, 2H). LC/MS=181 (MH)+.

313b) 2-(4-Amino-phenyl)-acetamide was prepared from 2-(4-Nitro-phenyl)-acetamide (0.65 g, 3.6 mmol) in an analogous manner to Example 310b. Product isolated as a pale yellow solid (0.57 g, 99%). $^1$HNMR (400 MHz, d6-DMSO, δ, ppm): 7.25 (br s, 1H), 6.89 (d, J=8.1 Hz, 2H), 6.74 (br s, 1H), 6.47 (d, J=8.2 Hz, 2H), 4.89 (br s, 2H), 3.14 (s, 2H). MS=151 (MH)+.

313c). 2-(4-{4-[4-((R)-Pyrrolidin-3-ylamino)-pyrido[3,4-d]pyrimidin-2-yl]-pyridin-2-ylamino}-phenyl)-acetamide was prepared from [A](R)-3-[2-(2-Chloro-pyridin-4-yl)-pyrido[3,4-d]pyrimidin-4-ylamino]-pyrrolidine-1-carboxylic acid tert-butyl ester (200.0 mg, 0.4685 mmol) and 2-(4-Amino-phenyl)-acetamide (85.0 mg, 0.566 mmol) in an analogous manner to Example 303c. Product isolated as the trifluoroacetic acid salt as a yellow lyophilate (0.029 g, 14%). $^1$HNMR (400 MHz, d6-DMSO, δ, ppm): 9.36 (br s, 1H), 9.23 (s, 1H), 8.85 (br s, 2H), 8.72 (d, J=5.6 Hz, 1H), 8.70-8.67 (m, 1H), 8.30 (d, J=5.1 Hz, 1H), 8.25 (d, J=5.5 Hz, 1H), 7.96 (s, 1H), 7.72 (d, J=5.2 Hz, 1H), 7.63 (d, J=7.4 Hz, 2H), 7.42 (br s, 1H), 7.20 (d, J=8.3 Hz, 2H), 6.86 (br s, 1H), 4.96-4.87 (m, 1H), 3.75-3.65 (m, 1H), 3.51-3.30 (m, 5H), 2.46-2.36 (m, 1H), 2.31-2.21 (m, 1H). MS=441 (MH)+.

Example 314. 2-(4-Amino-phenyl)-N-{4-[4-((R)-pyrrolidin-3-ylamino)-pyrido[3,4-d]pyrimidin-2-yl]-pyridin-2-yl}-acetamide 2-(4-Amino-phenyl)-N-{4-[4-((R)-pyrrolidin-3-ylamino)-pyrido[34-d]pyrimidin-2-yl]-pyridin-2-yl}-acetamide was a byproduct from Example 313. Product isolated as the trifluoroacetic acid salt as a yellow lyophilate (0.018 g, 8%). $^1$HNMR (400 MHz, d6-DMSO, δ, ppm): 10.84 (s, 1H), 9.24 (s, 1H), 9.12 (s, 1H), 8.94 (br s, 2H), 8.71 (d, J=5.5 Hz, 2H), 8.50 (d, J=5.2 Hz, 1H), 8.26 (d, J=5.7 Hz, 1H), 8.09 (d, J=4.6 Hz, 1H), 7.34 (d, J=8.0 Hz, 2H), 7.08 (d, J=7.5 Hz, 2H), 4.95-4.87 (m, 1H), 3.77-3.65 (m, 3H), 3.51-3.33 (m, 3H), 2.47-2.36 (m, 1H), 2.31-2.21 (m, 1H). MS=441 (MH)+.

Example 316. 2-(3-{4-[4-((R)-Pyrrolidin-3-ylamino)-pyrido[3,4-d]pyrimidin-2-yl]-pyridin-2-ylamino}-phenyl)-acetamide 316a) 2-(3-Nitro-phenyl)-acetamide was prepared from (3-Nitro-phenyl)-acetic acid (1.0 g, 5.5 mmol) in an analogous manner to Example 13a. Product isolated as a crude off-white solid (1.2 g, 50%). $^1$HNMR (400 MHz, d6-DMSO, δ, ppm): 8.15 (s, 1H), 8.10 (d, J=8.2 Hz, 1H), 7.71 (d, J=7.7 Hz, 1H), 7.63-7.54 (m, 2H), 7.01 (br s, 1H), 3.56 (s, 2H). MS=181 (MH)+.

316b) 2-(3-Amino-phenyl)-acetamide was prepared from 2-(3-Nitro-phenyl)-acetamide (1.2 g, 6.7 mmol) in an analogous manner to Example 10b. Product isolated as an off-white solid (1.0 g, 70%). $^1$HNMR (400 MHz, d6-DMSO, δ, ppm): 7.32 (br s, 1H), 6.90 (t, J=7.7 Hz, 1H), 6.79 (br s, 1H), 6.46 (s, 1H), 6.42-6.37 (m, 2H), 4.97 (br s, 2H), 3.18 (s, 2H). MS=151 (MH)+.

316c) 2-(3-{4-[4-((R)-Pyrrolidin-3-ylamino)-pyrido[3,4-d]pyrimidin-2-yl]-pyridin-2-ylamino}-phenyl)-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (200.0 mg, 0.4685 mmol) and 2-(3-Amino-phenyl)-acetamide (85.0 mg, 0.566 mmol) in an analogous manner to Example 303c. Product isolated as the trifluoroacetic acid salt as a yellow lyophilate (0.055 g, 26%). $^1$HNMR (400 MHz, d6-DMSO, δ, ppm): 9.50 (br s, 1H), 9.24 (s, 1H), 8.91 (br s, 2H), 8.72 (d, J=5.5 Hz, 1H), 8.31 (d, J=5.4 Hz, 1H), 8.26 (d, J=5.7 Hz, 1H), 7.99 (s, 1H), 7.75 (d, J=5.4 HZ, 1H), 7.66 (d, J=8.6 Hz, 1H), 7.54 (s, 1H), 7.48 (br s, 1H), 7.25 (t, J=7.7 Hz, 1H), 6.93-6.86 (m, 2H), 4.97-4.87 (m, 1H), 3.76-3.66 (m, 1H), 3.54-3.34 (m, 5H), 2.46-2.36 (m, 1H), 2.31-2.21 (m, 1H). MS=441 (MH)+.

Example 317. 2-(3-Amino-phenyl)-N-{4-[4-((R)-pyrrolidin-3-ylamino)-pyrido[3,4-d]pyrimidin-2-yl]-pyridin-2-yl}-acetamide 2-(3-Amino-phenyl)-N-{4-[4-((R)-pyrrolidin-3-ylamino)-pyrido[34-d]pyrimidin-2-yl]-pyridin-2-yl}-acetamide was a byproduct from Example 16. Product isolated as the trifluoroacetic acid salt as a pale yellow lyophilate (0.047 g, 23%). $^1$HNMR (400 MHz, d6-DMSO, δ, ppm): 10.90 (s, 1H), 9.24 (s, 1H), 9.14 (s, 1H), 8.94 (br s, 2H), 8.75-8.70 (m, 2H), 8.51 (d, J=5.1 Hz, 1H), 8.26 (d, J=5.5 Hz, 1H), 8.10 (dd, J=5.1, 1.1 Hz, 1H), 7.28 (t, J=7.8 Hz, 1H), 7.10-7.02 (m, 3H), 6.94 (d, J=6.6 Hz, 1H), 6.40-4.00 (m, 3H), 3.76 (s, 2H), 3.75-3.65 (m, 1H), 3.52-3.32 (m, 3H), 2.47-2.36 (m, 1H), 2.31-2.21 (m, 1H). MS=441 (MH)+.

Example 318. {2-[2-(5-Phenyl-pyridin-2-ylamino)-pyridin-4-yl]-pyrido[3,4-d]pyrimidin-4-yl}-(R)-pyrrolidin-3-yl-amine 2-[2-(5-Phenyl-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 5-Phenyl-pyridin-2-ylamine (36.0 mg, 0.212 mmol) in an analogous manner to Example 303c. Product isolated as the trifluoroacetic acid salt as a yellow lyophilate (0.098 g, 97%). $^1$HNMR (400 MHz, d6-DMSO, δ, ppm): 9.28 (s, 1H), 8.92 (br s, 2H), 8.78-8.74 (m, 2H), 8.66-8.63 (m, 2H), 8.49 (d, J=5.8 Hz, 1H), 8.29 (d, J=5.2 Hz, 1H), 8.24-8.18 (m, 1H), 8.04-8.01 (m, 1H), 7.80-7.71 (m, 3H), 7.55-7.49 (m, 2H), 7.44-7.39 (m, 1H), 5.00-4.92 (m, 1H), 3.80-3.71 (m, 1H), 3.55-3.35 (m, 3H), 2.48-2.40 (m, 1H), 2.34-2.25 (m, 1H). MS=461 (MH)+.

Example 319. {2-[2-(6-Morpholin-4-yl-pyridin-3-ylamino)-pyridin-4-yl]-pyrido[3,4-d]pyrimidin-4-yl}-(R)-pyrrolidin-3-yl-amine {2-[2-(6-Morpholin-4-yl-pyridin-3-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 6-Morpholin-4-yl-pyridin-3-ylamine (39.0 mg, 0.218 mmol) in an analogous manner to Example 303c. Product isolated as the trifluoroacetic acid salt as an orange-brown lyophilate (0.082 g, 80%). $^1$HNMR (400 MHz, d6-DMSO, δ, ppm): 9.71 (br s, 1H), 9.24 (s, 1H), 9.01 (br s, 2H), 8.77 (d, J=5.5 Hz, 1H), 8.73 (d, J=5.5 Hz, 1H), 8.62 (br s, 1H), 8.29-8.24 (m, 2H), 8.01-7.95 (m, 2H), 7.78 (dd, J=5.5, 1.3 Hz, 1H), 7.15 (d, J=9.2 Hz, 1H), 4.98-4.90 (m, 1H), 3.78-3.67 (m, 5H), 3.55-3.34 (m, 8H), 2.46-2.36 (m, 1H), 2.31-2.21 (m, 1H). MS=470 (MH)+.

Example 320. (2-{2-[6-(4-Methyl-piperazin-1-yl)-pyridin-3-ylamino]-pyridin-4-yl}-pyrido[3,4-d]pyrimidin-4-yl)-(R)-pyrrolidin-3-yl-amine (2-{2-[6-(4-Methyl-piperazin-1-yl)-pyridin-3-ylamino]-pyridin-4-yl}-pyrido[3,4-d]pyrimidin-4-yl)-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 6-(4-Methyl-piperazin-1-yl)-pyridin-3-ylamine (41.0 mg, 0.213 mmol) in an analogous manner to Example 303c. Product isolated as the trifluoroacetic acid salt as a brown lyophilate (0.094 g, 90%). $^1$HNMR (400 MHz, d6-DMSO, δ, ppm): 9.86 (br s, 1H), 9.45 (br s, 1H), 9.22 (s, 1H), 9.04 (br s, 2H), 8.76 (d, J=5.4 Hz, 1H), 8.72 (d, J=5.6 Hz, 1H), 8.51 (d, J=2.7 Hz, 1H), 8.27 (d, J=5.8 Hz, 1H), 8.24 (d, J=5.6 Hz, 1H), 8.02 (dd, J=9.0, 2.6 Hz, 1H), 7.93 (s, 1H), 7.73 (dd, J=5.4, 1.2 Hz, 1H), 7.02 (d, J=9.2 Hz, 1H), 4.99-4.90 (m, 1H), 4.38-4.25 (m, 2H), 3.78-3.68 (m, 1H), 3.59-3.34 (m, 5H), 3.18-3.02 (m, 4H), 2.87 (s, 3H), 2.47-2.36 (m, 1H), 2.31-2.22 (m, 1H). MS=483 (MH)+.

Example 321. 2-{4-[4-((R)-Pyrrolidin-3-ylamino)-pyrido[3,4-d]pyrimidin-2-yl]-pyridin-2-ylamino}-isonicotinonitrile 2-{4-[4-((R)-Pyrrolidin-3-ylamino)-pyrido[3,4-d]pyrimidin-2-yl]-pyridin-2-ylamino}-isonicotinonitrile was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 2-Amino-isonicotinonitrile (25.0 mg, 0.210 mmol) in an analogous manner to Example 303c. Product isolated as the trifluoroacetic acid salt as a pale yellow lyophilate (0.012 g, 13%).

Example 322. {2-[2-(4-Imidazol-1-ylmethyl-phenylamino)-pyridin-4-yl]-pyrido[3,4-d]pyrimidin-4-yl}-(R)-pyrrolidin-3-yl-amine {2-[2-(4-Imidazol-1-ylmethyl-phenylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 4-Imidazol-1-ylmethyl-phenylamine (37.0 mg, 0.214 mmol) in an analogous manner to Example 303c. Product isolated as the trifluoroacetic acid salt as a yellow lyophilate (0.097 g, 95%). $^1$HNMR (400 MHz, d6-DMSO, δ, ppm): 9.56 (s, 1H), 9.24 (t, J=1.4 Hz, 1H), 9.22 (s, 1H), 9.06 (br s, 2H), 8.77 (d, J=5.4 Hz, 1H), 8.71 (d, J=5.5 Hz, 1H), 8.33 (d, J=5.5 Hz, 1H), 8.27 (d, J=5.8 Hz, 1H), 7.97 (s, 1H), 7.83-7.76 (m, 4H), 7.70 (t, J=1.7 Hz, 1H), 7.38 (d, J=8.7 Hz, 2H), 5.36 (s, 2H), 5.01-4.92 (m, 1H), 3.78-3.69 (m, 1H), 3.55-3.34 (m, 3H), 2.47-2.36 (m, 1H), 2.31-2.22 (m, 1H). MS=464 (MH)+.

Example 323. 2-(3-{4-[5-Methoxy-4-((R)-pyrrolidin-3-ylamino)-pyrido[3,4-d]pyrimidin-2-yl]-pyridin-2-ylamino}-phenoxy)-acetamide 2-(3-{4-[5-Methoxy-4-((R)-pyrrolidin-3-ylamino)-pyrido[3,4-d]pyrimidin-2-yl]-pyridin-2-ylamino}-phenoxy)-acetamide was prepared from R)-3-[2-(2-Chloro-pyridin-4-yl)-5-methoxy-pyrido[3,4-d]pyrimidin-4-ylamino]-pyrrolidine-1-carboxylic acid tert-butyl ester (150.0 mg, 0.3283 mmol) and (3-Amino-phenoxy)-acetic acid ethyl ester (75.0 mg, 0.384 mmol) in an analogous manner to Example 303c and Example 10c and Example 1c. Product isolated as the trifluoroacetic acid salt as a yellow lyophilate (0.082 g, 41%). $^1$HNMR (400 MHz, d6-DMSO, δ, ppm): 9.42 (s, 1H), 8.94 (br s, 1H), 8.89-8.80 (m, 2H), 8.41 (s, 1H), 8.34 (d, J=5.2 Hz, 1H), 8.16 (d, J=6.2 Hz, 1H), 7.95 (s, 1H), 7.72 (dd, J=5.4, 1.3 Hz, 1H), 7.54 (t, J=2.1 Hz, 1H), 7.52 (s, 1H), 7.38 (s, 1H), 7.30-7.25 (m, 1H), 7.20 (t, J=8.2 Hz, 1H), 6.51 (dd, J=7.8, 1.7 Hz, 1H), 5.05-4.95 (m, 1H), 4.41 (s, 2H), 4.16 (m, 3H), 3.73-3.64 (m, 1H), 3.52-3.30 (m, 3H), 2.53-2.45 (m, 1H), 2.27-2.16 (m, 1H). MS=487 (MH)+.

Example 324. 2-(3-{4-[5-Methoxy-4-((R)-pyrrolidin-3-ylamino)-pyrido[3,4-d]pyrimidin-2-yl]-pyridin-2-ylamino}-phenyl)-acetamide 2-(3-{4-[5-Methoxy-4-((R)-pyrrolidin-3-ylamino)-pyrido[3,4-d]pyrimidin-2-yl]-pyridin-2-ylamino}-phenyl)-acetamide was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (150.0 mg, 0.3283 mmol) and 2-(3-Amino-phenyl)-acetamide (60.0 mg, 0.400 mmol) in an analogous manner to Example 303c. Product isolated as the trifluoroacetic acid salt as a yellow lyophilate (0.043 g, 22%). $^1$HNMR (400 MHz, d6-DMSO, δ, ppm): 9.36 (s, 1H), 9.00-8.77 (m, 3H), 8.40 (s, 1H), 8.31 (d, J=5.4 Hz, 1H), 8.15 (d, J=6.2 Hz, 1H), 7.94 (s, 1H), 7.72-7.65 (m, 2H), 7.56 (s, 1H), 7.46 (s, 1H), 7.22 (t, J=7.7 Hz, 1H), 6.90-6.83 (m, 2H), 5.05-4.95 (m, 1H), 4.16 (s, 3H), 3.73-3.63 (m, 1H), 3.50-3.23 (m, 5H), 2.55-2.45 (m, 1H), 2.26-2.16 (m, 1H). MS=471 (MH)+.

Example 325. 2-(3-Amino-phenyl)-N-{4-[5-methoxy-4-((R)-pyrrolidin-3-ylamino)-pyrido[3,4-d]pyrimidin-2-yl]-pyridin-2-yl}-acetamide 2-(3-Amino-phenyl)-N-{4-[5-methoxy-4-((R)-pyrrolidin-3-ylamino)-pyrido[3,4-d]pyrimidin-2-yl]-pyridin-2-yl}-acetamide was a byproduct from Example 24. Product isolated as the trifluoroacetic acid salt as a yellow lyophilate (0.033 g, 17%). $^1$HNMR (400 MHz, d6-DMSO, δ, ppm): 10.84 (s, 1H), 9.11 (s, 1H), 9.00-8.78 (m, 3H), 8.50 (d, J=5.5 Hz, 1H), 8.40 (s, 1H), 8.15 (d, J=5.9 Hz, 1H), 8.06 (dd, J=5.2, 1.4 Hz, 1H), 7.25-7.10 (m, 1H), 7.00-6.65 (m, 3H), 5.00-4.01 (m, 1H), 4.15 (s, 3H), 3.80-3.28 (m, 8H), 2.55-2.45 (m, 1H), 2.26-2.16 (m, 1H). MS=471 (MH)+

Example 326. 2-(4-{4-[5-Methoxy-4-((R)-pyrrolidin-3-ylamino)-pyrido[3,4-d]pyrimidin-2-yl]-pyridin-2-ylamino}-phenyl)-acetamide 2-(4-{4-[5-Methoxy-4-((R)-pyrrolidin-3-ylamino)-pyrido[3,4-d]pyrimidin-2-yl]-pyridin-2-ylamino}-phenyl)-acetamide was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (150.0 mg, 0.3283 mmol) and 2-(4-Amino-phenyl)-acetamide (60.0 mg, 0.400 mmol) in an analogous manner to Example 303c. Product isolated as the trifluoroacetic acid salt as a yellow lyophilate (0.072 g, 37%). $^1$HNMR (400 MHz, d6-DMSO, δ, ppm): 9.29 (s, 1H), 9.10-8.80 (m, 3H), 8.40 (s, 1H), 8.31 (d, J=5.3 Hz, 1H), 8.15 (d, J=6.1 Hz, 1H), 7.92 (s, 1H), 7.68 (dd, J=5.3, 1.3 Hz, 1H), 7.63 (d, J=8.5 Hz, 2H), 7.43-7.39 (m, 1H), 7.18 (d, J=8.5 Hz, 2H), 6.84 (s, 1H), 5.05-4.95 (m, 1H), 4.16 (s, 3H), 3.72-3.63 (m, 1H), 3.50-3.20 (m, 5H), 2.54-2.45 (m, 1H), 2.26-2.16 (m, 1H). MS=471 (MH)+.

Example 327. 2-(4-Amino-phenyl)-N-{4-[5-methoxy-4-((R)-pyrrolidin-3-ylamino)-pyrido[3,4-d]pyrimidin-2-yl]-pyridin-2-yl}-acetamide 2-(4-Amino-phenyl)-N-{4-[5-methoxy-4-((R)-pyrrolidin-3-ylamino)-pyrido[3,4-d]pyrimidin-2-yl]-pyridin-2-yl}-acetamide was a byproduct from Example 26. Product isolated as the trifluoroacetic acid salt was isolated as a yellow lyophilate (0.025 g, 13%). $^1$HNMR (400 MHz, d6-DMSO, δ, ppm): 10.81 (s, 1H), 9.09 (s, 1H), 9.02-8.83 (m, 3H), 8.49 (dd, J=5.2, 0.70 Hz, 1H), 8.40 (s, 1H), 8.16 (d, J=6.0 Hz, 1H), 8.05 (dd, J=5.2, 1.5 Hz, 1H), 7.28 (d, J=7.8 Hz, 2H), 7.00-6.93 (m, 2H), 5.01-4.91 (m, 1H), 4.15 (s, 3H), 3.72-3.61 (m, 3H), 3.47-3.28 (m, 3H), 2.54-2.44 (m, 1H), 2.26-2.16 (m, 1H). MS=471 (MH)+.

Example 328. 1-{4-[4-((R)-Pyrrolidin-3-ylamino)-pyrido[3,4-d]pyrimidin-2-yl]-pyridin-2-yl}-1H-pyrrolo[2,3-b]pyridine-4-carbonitrile 1-{4-[4-((R)-Pyrrolidin-3-ylamino)-pyrido[3,4-d]pyrimidin-2-yl]-pyridin-2-yl}-1H-pyrrolo[2,3-b]pyridine-4-carbonitrile was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 1H-Pyrrolo[2,3-b]pyridine-4-carbonitrile (30.0 mg, 0.210 mmol) in an analogous manner to Example 303c. Product isolated as the trifluoroacetic acid salt as an off-white lyophilate (0.068 g, 71%). $^1$HNMR (400 MHz, d6-DMSO, δ, ppm): 9.83 (s, 1H), 9.31 (s, 1H), 8.89 (br s, 2H), 8.79-8.75 (m, 4H), 8.72 (d, J=4.9 Hz, 1H), 8.37 (d, J=5.2 Hz, 1H), 8.30 (d, J=5.6 Hz, 1H), 7.87 (d, J=4.9 Hz, 1H), 7.04 (d, J=3.9 Hz, 1H), 5.00-4.91 (m, 1H), 3.83-3.74 (m, 1H), 3.57-3.39 (m, 3H), 2.54-2.44 (m, 1H), 2.37-2.30 (m, 1H). MS=434 (MH)+.

Example 329. {5-Methoxy-2-[2-(5-phenyl-pyridin-2-ylamino)-pyridin-4-yl]-pyrido[3,4-d]pyrimidin-4-yl}-(R)-pyrrolidin-3-yl-amine {5-Methoxy-2-[2-(5-phenyl-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (75.0 mg, 0.164 mmol) and 5-Phenyl-pyridin-2-ylamine (31.0 mg, 0.182 mmol) in an analogous manner to Example 303c. Product isolated as the trifluoroacetic acid salt as a yellow lyophilate (0.043 g, 43%). $^1$HNMR (400 MHz, d6-DMSO, δ, ppm): 9.04-8.85 (m, 3H), 8.66-8.61 (m, 2H), 8.48 (d, J=5.5 Hz, 1H), 8.44 (s, 1H), 8.23-8.15 (m, 2H), 8.00-7.95 (m, 1H), 7.82-7.75 (m, 1H), 7.74-7.71 (m, 2H), 7.51 (t, J=7.6 Hz, 2H), 7.41 (t, J=7.1 Hz, 1H), 5.07-5.00 (m, 1H), 4.18 (s, 3H), 3.76-3.66 (m, 1H), 3.54-3.30 (m, 3H), 2.55-2.45 (m, 1H), 2.30-2.20 (m, 1H). MS=491 (MH)+.

Example 330. {5-Methoxy-2-[2-(6-morpholin-4-yl-pyridin-3-ylamino)-pyridin-4-yl]-pyrido[3,4-d]pyrimidin-4-yl}-(R)-pyrrolidin-3-yl-amine {5-Methoxy-2-[2-(6-morpholin-4-yl-pyridin-3-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (75.0 mg, 0.164 mmol) and 6-Morpholin-4-yl-pyridin-3-ylamine (33.0 mg, 0.184 mmol) in an analogous manner to Example 303c. Product isolated as the trifluoroacetic acid salt as a tan lyophilate (0.033 g, 33%) $^1$HNMR (400 MHz, d6-DMSO, δ, ppm): 9.02-8.82 (m, 3H), 8.60-8.52 (m, 1H), 8.41 (s, 1H), 8.26 (d, J=4.8 Hz, 1H), 8.17 (d, J=4.4 Hz, 1H), 8.00-7.95 (m, 1H), 7.89 (s, 1H), 7.72-7.68 (m, 1H), 7.10-6.98 (m, 1H), 5.05-4.95 (m, 1H), 4.16 (s, 3H), 3.76-3.63 (m, 5H), 3.50-3.29 (m, 7H), 2.54-2.45 (m, 1H), 2.26-2.16 (m, 1H). MS=500 (MH)+.

Example 331. (5-Methoxy-2-{2-[6-(4-methyl-piperazin-1-yl)-pyridin-3-ylamino]-pyridin-4-yl}-pyrido[3,4-d]pyrimidin-4-yl)-(R)-pyrrolidin-3-yl-amine (5-Methoxy-2-{2-[6-(4-methyl-piperazin-1-yl)-pyridin-3-ylamino]-pyridin-4-yl}-pyrido[3,4-d]pyrimidin-4-yl)-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (75.0 mg, 0.164 mmol) and 6-(4-Methyl-piperazin-1-yl)-pyridin-3-ylamine (35.0 mg, 0.182 mmol) in an analogous manner to Example 303c. Product isolated as the bis-trifluoroacetic acid salt as a brown lyophilate (0.036 g, 29%). $^1$HNMR (400 MHz, d6-DMSO, δ, ppm): 9.69 (br s, 1H), 9.26 (br s, 1H), 9.06-8.81 (m, 3H), 8.51 (d, J=2.6 Hz, 1H), 8.40 (s, 1H), 8.25 (d, J=5.5 Hz, 1H), 8.16 (d, J=6.0 Hz, 1H), 8.04 (dd, J=9.1, 2.6 Hz, 1H), 7.86 (s, 1H), 7.67 (d, J=5.3 Hz, 1H), 6.98 (d, J=9.0 Hz, 1H), 5.04-4.98 (m, 1H), 4.32-4.26 (m, 2H), 4.16 (s, 3H), 3.71-3.65 (m, 1H), 3.55-3.50 (m, 2H), 3.50-3.30 (m, 3H), 3.16-3.01 (m, 4H), 2.86 (d, J=4.3 Hz, 3H), 2.53-2.43 (m, 1H), 2.26-2.16 (m, 1H). MS=513 (MH)+.

Example 332. 2-{4-[5-Methoxy-4-((R)-pyrrolidin-3-ylamino)-pyrido[3,4-d]pyrimidin-2-yl]-pyridin-2-ylamino}-isonicotinonitrile 2-{4-[5-Methoxy-4-((R)-pyrrolidin-3-ylamino)-pyrido[3,4-d]pyrimidin-2-yl]-pyridin-2-ylamino}-isonicotinonitrile was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (75.0 mg, 0.164 mmol) and 2-Amino-isonicotinonitrile (22.0 mg, 0.185 mmol) in an analogous manner to Example 303c. Product isolated as the trifluoroacetic acid salt as a yellow lyophilate (0.014 g, 15%). $^1$HNMR (400 MHz, d6-DMSO, δ, ppm): 10.42 (s, 1H), 8.98-8.80 (m, 3H), 8.60 (s, 1H), 8.51 (d, J=5.1 Hz, 1H), 8.48 (d, J=5.3 Hz, 1H), 8.42 (s, 1H), 8.34 (s, 1H), 8.16 (d, J=5.8 Hz, 1H), 7.92 (dd, J=5.2, 1.3 Hz, 1H), 7.32 (dd, J=5.0, 1.3 Hz, 1H), 5.03-4.95 (m, 1H), 4.17 (s, 3H), 3.75-3.66 (m, 1H), 3.50-3.30 (m, 3H), 2.55-2.45 (m, 1H), 2.28-2.18 (m, 1H). MS=440 (MH)+.

Example 333. {2-[2-(4-Imidazol-1-ylmethyl-phenylamino)-pyridin-4-yl]-5-methoxy-pyrido[3,4-d]pyrimidin-4-yl}-(R)-pyrrolidin-3-yl-amine {2-[2-(4-Imidazol-1-ylmethyl-phenylamino)-pyridin-4-yl]-5-methoxy-pyrido[3,4-d]pyrimidin-4-yl}-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (75.0 mg, 0.164 mmol) and 4-Imidazol-1-ylmethyl-phenylamine (32.0 mg, 0.185 mmol) in an analogous manner to Example 303c. Product isolated as the trifluoroacetic acid salt as a yellow-orange lyophilate (0.037 g, 37%). $^1$HNMR (400 MHz, d6-DMSO, δ, ppm): 9.53 (s, 1H), 9.24-9.22 (m, 1H), 9.18-8.92 (m, 2H), 8.82 (s, 1H), 8.40 (s, 1H), 8.33 (d, J=5.3 Hz, 1H), 8.18 (d, J=6.3 Hz, 1H), 7.94 (s, 1H), 7.81 (d, J=8.6 Hz, 2H), 7.78 (t, J=1.7 Hz, 1H), 7.74 (dd, J=5.2, 1.3 Hz, 1H), 7.70 (t, J=1.7 Hz, 1H), 7.37 (d, J=8.7 Hz, 2H), 5.36 (s, 2H), 5.08-4.99 (m, 1H), 4.16 (s, 3H), 3.74-3.64 (m, 1H), 3.52-3.29 (m, 3H), 2.53-2.43 (m, 1H), 2.26-2.16 (m, 1H). MS=494 (MH)+.

Example 334. 2-Phenyl-N-{4-[4-((R)-pyrrolidin-3-ylamino)-pyrido[3,4-d]pyrimidin-2-yl]-pyridin-2-yl}-acetamide 2-Phenyl-N-{4-[4-((R)-pyrrolidin-3-ylamino)-pyrido[3,4-d]pyrimidin-2-yl]-pyridin-2-yl}-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and Benzeneacetamide (27.0 mg, 0.200 mmol) in an analogous manner to Example 303c. Product isolated as the trifluoroacetic acid salt as a tan lyophilate (0.036 g, 38%). $^1$HNMR (400 MHz, d6-DMSO, δ, ppm): 10.89 (s, 1H), 9.25 (s, 1H), 9.14 (s, 1H), 8.90 (br s, 2H), 8.73-8.69 (m, 2H), 8.50 (dd, J=5.2, 0.6 Hz, 1H), 8.25 (d, J=5.2 Hz, 1H), 8.09 (dd, J=5.2, 1.4 Hz, 1H), 7.41-7.24

(m, 5H), 4.93-4.85 (m, 1H), 3.79 (s, 2H), 3.75-3.65 (m, 1H), 3.51-3.33 (m, 3H), 2.47-2.37 (m, 1H), 2.31-2.21 (m, 1H). MS=426 (MH)+.

Example 335. 2-(4-Methoxy-phenyl)-N-{4-[4-((R)-pyrrolidin-3-ylamino)-pyrido[3,4-d]pyrimidin-2-yl]-pyridin-2-yl}-acetamide 2-(4-Methoxy-phenyl)-N-{4-[4-((R)-pyrrolidin-3-ylamino)-pyrido[3,4-d]pyrimidin-2-yl]-pyridin-2-yl}-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 4-Methoxyphenylacetamide (33.0 mg, 0.200 mmol) in an analogous manner to Example 303c. Product isolated as the trifluoroacetic acid salt as a yellow lyophilate (0.021 g, 21%). $^1$HNMR (400 MHz, d6-DMSO, δ, ppm): 10.81 (s, 1H), 9.24 (s, 1H), 9.13 (s, 1H), 8.88 (br s, 2H), 8.71 (d, J=5.6 Hz, 1H), 8.69 (d, J=4.8 Hz, 1H), 8.49 (d, J=5.2 Hz, 1H), 8.25 (d, J=5.3 Hz, 1H), 8.08 (dd, J=5.1, 1.5 Hz, 1H), 7.30 (d, J=8.7 Hz, 2H), 6.91 (d, J=8.7 Hz, 2H), 4.93-4.85 (m, 1H), 3.75-3.65 (m, 6H), 3.49-3.34 (m, 3H), 2.47-2.37 (m, 1H), 2.31-2.21 (m, 1H). MS=456 (MH)+.

Example 336. 2-(2-Methoxy-phenyl)-N-{4-[4-((R)-pyrrolidin-3-ylamino)-pyrido[3,4-d]pyrimidin-2-yl]-pyridin-2-yl}-acetamide 336a) 2-(2-Methoxy-phenyl)-acetamide was prepared from 2-Methoxybenzeneacetic acid (1.0 g, 6.0 mmol) in an analogous manner to Example 13a. Product isolated as a white solid (0.64 g, 64%). $^1$HNMR (400 MHz, d6-DMSO, δ, ppm): 7.24-7.18 (m, 2H), 7.15 (dd, J=7.5, 1.6 Hz, 1H), 6.95 (d, J=7.7 Hz, 1H), 6.90-6.84 (m, 1H), 6.81 (br s, 1H), 3.75 (s, 3H), 3.35 (s, 2H). MS=166 (MH)+.

336b) 2-(2-Methoxy-phenyl)-N-{4-[4-((R)-pyrrolidin-3-ylamino)-pyrido[3,4-d]pyrimidin-2-yl]-pyridin-2-yl}-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol;) and 2-(2-Methoxy-phenyl)-acetamide (32.0 mg, 0.194 mmol) in an analogous manner to Example 303c. Product isolated as the trifluoroacetic acid salt as a tan lyophilate (0.048 g, 48%). $^1$HNMR (400 MHz, d6-DMSO, δ, ppm): 10.66 (s, 1H), 9.24 (s, 1H), 9.12 (s, 1H), 8.84 (br s, 2H), 8.71 (d, J=5.7 Hz, 1H), 8.69-8.65 (m, 1H), 8.50 (d, J=5.2 Hz, 1H), 8.25 (d, J=5.3 Hz, 1H), 8.08 (dd, J=5.3, 1.3 Hz, 1H), 7.30-7.23 (m, 2H), 7.01 (d, J=7.8 Hz, 1H), 6.95-6.90 (m, 1H), 4.93-4.85 (m, 1H), 3.80-3.74 (m, 5H), 3.72-3.63 (m, 1H), 3.49-3.30 (m, 3H), 2.45-2.37 (m, 1H), 2.30-2.20 (m, 1H). MS=456 (MH)+.

Example 337. 2-(3-Methoxy-phenyl)-N-{4-[4-((R)-pyrrolidin-3-ylamino)-pyrido[3,4-d]pyrimidin-2-yl]-pyridin-2-yl}-acetamide 2-(3-Methoxy-phenyl)-N-{4-[4-((R)-pyrrolidin-3-ylamino)-pyrido[3,4-d]pyrimidin-2-yl]-pyridin-2-yl}-acetamide (R)-3-[2-(2-Chloro-pyridin-4-yl)-pyrido[3,4-d]pyrimidin-4-ylamino]-pyrrolidine-1-carboxylic acid tert-butyl ester (75.0 mg, 0.176 mmol) and 2-(3-Methoxy-phenyl)-acetamide (32.0 mg, 0.194 mmol) in an analogous manner to Example 303c. Product isolated as the trifluoroacetic acid salt as a tan lyophilate (0.099 g). $^1$HNMR (400 MHz, d6-DMSO, δ, ppm): 10.86 (s, 1H), 9.25 (s, 1H), 9.13 (s, 1H), 8.89 (br s, 2H), 8.73-8.68 (m, 2H), 8.50 (d, J=5.2 Hz, 1H), 8.25 (d, J=5.2 Hz, 1H), 8.09 (dd, J=5.2, 1.5 Hz, 1H), 7.26 (t, J=7.8 Hz, 1H), 6.98-6.94 (m, 2H), 6.86-6.82 (m, 1H), 4.94-4.85 (m, 1H), 3.77-3.65 (m, 6H), 3.51-3.34 (m, 3H), 2.47-2.37 (m, 1H), 2.31-2.21 (m, 1H). MS=456 (MH)+.

Example 338. {2-[2-(4-Methyl-pyridin-2-ylamino)-pyridin-4-yl]-pyrido[3,4-d]pyrimidin-4-yl}-(R)-pyrrolidin-3-yl-amine {2-[2-(4-Methyl-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 4-Methyl-pyridin-2-ylamine (31.0 mg, 0.287 mmol) in an analogous manner to Example 303c. Product isolated as the trifluoroacetic acid salt as a pale yellow lyophilate (0.107 g). $^1$HNMR=31550651 (400 MHz, d6-DMSO, δ, ppm): 9.28-9.27 (m, 1H), 8.99 (br s, 2H), 8.84-8.79 (m, 1H), 8.77-8.74 (m, 1H), 8.55 (d, J=5.4 Hz, 1H), 8.42-8.36 (m, 1H), 8.31-8.26 (m, 2H), 8.18-8.14 (m, 1H), 7.27 (s, 1H), 7.16-7.12 (m, 1H), 5.04-4.94 (m, 1H), 3.78-3.68 (m, 1H), 3.54-3.34 (m, 3H), 2.48 (s, 3H), 2.46-2.36 (m, 1H), 2.32-2.22 (m, 1H). MS=399 (MH)+.

Example 339. {2-[2-(4-Chloro-pyridin-2-ylamino)-pyridin-4-yl]-pyrido[3,4-d]pyrimidin-4-yl}-(R)-pyrrolidin-3-yl-amine {2-[2-(4-Chloro-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (105.0 mg, 0.2460 mmol) and 4-Chloro-pyridin-2-ylamine (37.0 mg, 0.288 mmol) in an analogous manner to Example 303c. Product isolated as the trifluoroacetic acid salt as a pale yellow lyophilate (0.124 g, 96%). $^1$HNMR (400 MHz, d6-DMSO, δ, ppm): 10.43 (br s, 1H), 9.26 (s, 1H), 8.90 (br s, 2H), 8.75-8.70 (m, 2H), 8.64 (s, 1H), 8.46 (d, J=5.6 Hz, 1H), 8.30-8.25 (m, 2H), 8.01 (s, 1H), 7.95 (d, J=5.4 Hz, 1H), 7.07 (d, J=5.3 Hz, 1H), 4.97-4.89 (m, 1H), 3.80-3.70 (m, 1H), 3.53-3.35 (m, 3H), 2.49-2.39 (m, 1H), 2.34-2.24 (m, 1H). MS=419 (MH)+.

Example 340. [4-(5-Methoxy-4-piperazin-1-yl-pyrido[3,4-d]pyrimidin-2-yl)-pyridin-2-yl]-pyrazin-2-yl-amine

[4-(5-Methoxy-4-piperazin-1-yl-pyrido[3,4-d]pyrimidin-2-yl)-pyridin-2-yl]-pyrazin-2-yl-amine was prepared from 4-[2-(2-Chloro-pyridin-4-yl)-5-methoxy-pyrido[3,4-d]pyrimidin-4-yl]-piperazine-1-carboxylic acid tert-butyl ester (352.0 mg, 0.7704 mmol) and 2-Aminopyrazine (81 mg, 0.85 mmol) in an analogous manner to Example 303c. Product was isolated as the free base as an off-white solid (0.050 g, 16%). $^1$HNMR (400 MHz, d6-DMSO, δ, ppm): 10.22 (s, 1H), 9.17 (d, J=1.4 Hz, 1H), 8.83 (s, 1H), 8.72 (s, 1H), 8.43 (d, J=5.2 Hz, 1H), 8.33 (s, 1H), 8.28 (dd, J=1.6, 2.6 Hz, 1H), 8.12 (d, J=2.7 Hz, 1H), 7.86 (dd, J=1.3, 5.2 Hz, 1H), 4.07 (s, 3H), 3.70-3.65 (m, 4H), 2.90-2.85 (m, 4H). MS=416 (MH)+.

Example 341. 6-{4-[4-((R)-Pyrrolidin-3-ylamino)-pyrido[3,4-d]pyrimidin-2-yl]-pyridin-2-ylamino}-nicotinonitrile 6-{4-[4-((R)-Pyrrolidin-3-ylamino)-pyrido[3,4-d]pyrimidin-2-yl]-pyridin-2-ylamino}-nicotinonitrile was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 6-Amino-nicotinonitrile (33.0 mg, 0.277 mmol) in an analogous manner to Example 303c. Product isolated as the trifluoroacetic acid salt as a pale yellow lyophilate (0.016 g, 13%). $^1$HNMR (400 MHz, d6-DMSO, δ, ppm): 10.60 (s, 1H), 9.26 (s, 1H), 8.92-8.80 (m, 3H), 8.75-8.72 (m, 2H), 8.69 (d, J=4.6 Hz, 1H), 8.48 (d, J=5.3 Hz, 1H), 8.28 (d, J=5.2 Hz, 1H), 8.10 (dd, J=8.9, 2.3 Hz, 1H), 8.00 (dd, J=5.2, 1.3 Hz, 1H), 7.90 (d, J=8.9 Hz, 1H), 4.94-4.89 (m, 1H), 3.78-3.70 (m, 1H), 3.51-3.35 (m, 3H), 2.46-2.40 (m, 1H), 2.35-2.25 (m, 1H). MS=410 (MH)+.

Example 342. 2-[4-(4-Piperazin-1-yl-pyrido[3,4-d]pyrimidin-2-yl)-pyridin-2-ylamino]-isonicotinonitrile 342a) 4-[2-(2-Chloro-pyridin-4-yl)-pyrido[3,4-d]pyrimidin-4-yl]-piperazine-1-carboxylic acid tert-butyl ester was prepared from 2-(2-Chloro-pyridin-4-yl)-pyrido[3,4-d]pyrimidin-4-ol (500.0 mg, 1.933 mmol) and tert-Butyl 1-Piperazinecarboxylate (432.0 mg, 2.320 mmol) in an analogous manner to [B016]. Product isolated as a yellow foam (0.817 g, 99%). $^1$HNMR (400 MHz, d6-DMSO, δ, ppm): 9.30 (s, 1H), 8.64-8.60 (m, 2H), 8.38-8.35 (m, 2H), 8.01-7.98 (m, 1H), 4.06-4.01 (m, 4H), 3.67-3.62 (m, 4H), 3.32 (s, 3H), 1.45 (s, 9H). MS=427 (MH)+.

342b) 2-[4-(4-Piperazin-1-yl-pyrido[3,4-d]pyrimidin-2-yl)-pyridin-2-ylamino]-isonicotinonitrile was prepared from 4-[2-(2-Chloro-pyridin-4-yl)-pyrido[3,4-d]pyrimidin-4-yl]-piperazine-1-carboxylic acid tert-butyl ester (100.0 mg, 0.2342 mmol) and 2-Amino-isonicotinonitrile (31.0 mg, 0.260 mmol) in an analogous manner to Example 303c. Product isolated as the trifluoroacetic acid salt as a pale yellow lyophilate (0.015 g, 12%). $^1$HNMR (400 MHz, d6-DMSO, δ, ppm): 10.44 (s, 1H), 9.36 (s, 1H), 8.90 (br s, 2H), 8.69-8.66 (m, 2H), 8.53-8.48 (m, 2H), 8.36 (s, 1H), 8.04 (d, J=5.7 Hz, 1H), 7.95 (dd, J=5.3, 1.3 Hz, 1H), 7.33 (dd, J=5.1, 1.3 Hz, 1H), 4.18-4.13 (m, 4H), 3.42-3.37 (m, 4H). MS=410 (MH)+.

Example 343. {2-[2-(4-Morpholin-4-yl-pyridin-2-ylamino)-pyridin-4-yl]-pyrido[3,4-d]pyrimidin-4-yl}-(R)-pyrrolidin-3-yl-amine {2-[2-(4-Morpholin-4-yl-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 4-Morpholin-4-yl-pyridin-2-ylamine (47.0 mg, 0.262 mmol)[prepared as described in WO2006/040520] in an analogous manner to Example 303c. Product isolated the free base as a pale yellow solid (0.016 g, 14%). $^1$HNMR (400 MHz, d6-DMSO, δ, ppm): 9.51 (s, 1H), 9.17 (s, 1H), 8.86 (s, 1H), 8.67-8.52 (m, 2H), 8.35-8.27 (m, 2H), 7.95 (d, J=6.0 Hz, 1H), 7.81-7.78 (m, 1H), 7.30-7.27 (m, 1H), 6.52-6.47 (m, 1H), 4.97-4.75 (m, 1H), 3.77-3.72 (m, 4H), 3.35-3.30 (m, 1H), 3.26-3.22 (m, 4H), 3.06-2.98 (m, 1H), 2.92-2.84 (m, 2H), 2.31-2.21 (m, 1H), 1.93-1.83 (m, 1H). MS=470 (MH)+.

Example 344. 6-{4-[5-Methoxy-4-((R)-pyrrolidin-3-ylamino)-pyrido[3,4-d]pyrimidin-2-yl]-pyridin-2-ylamino}-nicotinonitrile 344a) 2-(2-Chloro-pyridin-4-yl)-5-methoxy-pyrido[3,4-d]pyrimidin-4-ol was prepared from 2-Chloro-isonicotinonitrile (0.96 g, 6.9 mmol) and 3-Amino-5-methoxy-isonicotinic acid (0.97 g, 5.8 mmol) in an analogous manner to example 1501a. Product isolated as a tan solid (0.774 g, 46%). $^1$HNMR (400 MHz, d1-TFA, δ, ppm): 9.24 (s, 1H), 9.11 (d, J=6.2 Hz, 1H), 8.93 (s, 1H), 8.85 (d, J=6.0 Hz, 1H), 8.71 (s, 1H), 4.36 (s, 3H). MS=289 (MH)+.

344b) R)-3-[2-(2-Chloro-pyridin-4-yl)-5-methoxy-pyrido[3,4-d]pyrimidin-4-ylamino]-pyrrolidine-1-carboxylic acid tert-butyl ester was prepared from 2-(2-Chloro-pyridin-4-yl)-5-methoxy-pyrido[3,4-d]pyrimidin-4-ol (0.50 g, 1.7 mmol) and (R)-3-Amino-pyrrolidine-1-carboxylic acid tert-butyl ester (0.32 mL, 1.9 mmol) in an analogous manner to [B016]. Product isolated as a light brown solid (0.50 g, 63%). $^1$HNMR (400 MHz, d6-DMSO, δ, ppm): 8.84 (s, 1H), 8.61 (d, J=5.0 Hz, 1H), 8.39 (s, 1H), 8.36-8.32 (m, 2H), 8.24-8.17 (m, 1H), 5.09-4.92 (m, 1H), 4.14 (s, 3H), 3.86-3.72 (m, 1H), 3.55-3.32 (m, 3H), 2.37-2.25 (m, 1H), 2.21-2.07 (m, 1H), 1.45-1.38 (m, 9H). MS=457 (MH)+.

344c) 6-{4-[5-Methoxy-4-((R)-pyrrolidin-3-ylamino)-pyrido[3,4-d]pyrimidin-2-yl]-pyridin-2-ylamino}-nicotinonitrile was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (160.0 mg, 0.3502 mmol) and 6-Amino-nicotinonitrile (50.0 mg, 0.420 mmol) in an analogous manner to Example 303c. Product isolated as the trifluoroacetic acid salt as a pale yellow lyophilate (0.043 g, 22%). $^1$HNMR (400 MHz, d6-DMSO, δ, ppm): 10.60 (s, 1H), 9.00-8.80 (m, 4H), 8.72 (d, J=2.2 Hz, 1H), 8.48 (d, J=5.3 Hz, 1H), 8.42 (s, 1H), 8.15 (d, J=5.8 Hz, 1H), 8.10 (dd, J=8.9, 2.4 Hz, 1H), 7.97 (dd, J=5.3, 1.5 Hz, 1H), 7.90 (d, J=9.0 Hz, 1H), 5.01-4.93 (m, 1H), 4.17 (s, 3H), 3.75-3.65 (m, 1H), 3.52-3.30 (m, 3H), 2.55-2.45 (m, 1H), 2.29-2.19 (m, 1H). MS=440 (MH)+.

Example 345. {2-[2-(5-Methyl-pyridin-2-ylamino)-pyridin-4-yl]-pyrido[3,4-d]pyrimidin-4-yl}-(R)-pyrrolidin-3-yl-amine {2-[2-(5-Methyl-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 5-Methyl-pyridin-2-ylamine (30.0 mg, 0.277 mmol) in an analogous manner to Example 303c. Product isolated as the trifluoroacetic acid salt as a pale yellow lyophilate (0.033 g, 27%). $^1$HNMR (400 MHz, d6-DMSO, δ, ppm): 9.27 (s, 1H), 8.93 (br s, 2H), 8.81-8.77 (m, 1H), 8.76 (d, J=5.6 Hz, 1H), 8.52-8.45 (m, 2H), 8.29 (d, J=5.5 Hz, 1H), 8.20 (s, 1H), 8.08 (br s, 1H), 7.87 (br s, 1H), 7.49 (br s, 1H), 5.00-4.90 (m, 1H), 3.79-3.69 (m, 1H), 3.55-3.35 (m, 3H), 2.47-2.37 (m, 1H), 2.34-2.24 (m, 4H). MS=399 (MH)+.

Example 346. {2-[2-(5-Chloro-pyridin-2-ylamino)-pyridin-4-yl]-pyrido[3,4-d]pyrimidin-4-yl}-(R)-pyrrolidin-3-yl-amine {2-[2-(5-Chloro-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 2-Amino-5-chloropyridine (36.0 mg, 0.280 mmol) in an analogous manner to Example 303c. Product isolated as the trifluoroacetic acid salt as a yellow lyophilate (0.081 g, 65%). $^1$HNMR (400 MHz, d6-DMSO, δ, ppm): 10.36 (br s, 1H), 9.26 (s, 1H), 8.89 (br s, 2H), 8.74 (d, J=5.6 Hz, 1H), 8.71 (d, J=4.8 Hz, 1H), 8.67 (s, 1H), 8.42 (d, J=5.5 Hz, 1H), 8.34-8.32 (m, 1H), 8.27 (d, J=5.1 Hz, 1H), 7.93 (d, J=5.5 Hz, 1H), 7.88-7.82 (m, 2H), 4.97-4.87 (m, 1H), 3.79-3.70 (m, 1H), 3.55-3.35 (m, 3H), 2.50-2.40 (m, 1H), 2.34-2.24 (m, 1H). MS=419 (MH)+.

Example 347. 2-[2-(Pyrimidin-4-ylamino)-pyridin-4-yl]-pyrido[3,4-d]pyrimidin-4-yl}-(R)-pyrrolidin-3-yl-amine {2-[2-(Pyrimidin-4-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and Pyrimidin-4-ylamine (27.0 mg, 0.284 mmol) in an analogous manner to Example 303c. Product isolated as the trifluoroacetic acid salt as an off-white lyophilate (0.033 g, 28%). $^1$HNMR (400 MHz, d6-DMSO, δ, ppm): 11.07 (br s, 1H), 9.26 (s, 1H), 9.07 (br s, 2H), 8.95 (s, 1H), 8.87 (d, J=5.3 Hz, 1H), 8.84 (s, 1H), 8.73 (d, J=5.6 Hz, 1H), 8.56-8.53 (m, 2H), 8.35 (d, J=5.5 Hz, 1H), 8.10 (d, J=5.2, 1.2 Hz, 1H), 7.97-7.90 (m, 1H), 5.00-4.92 (m, 1H), 3.79-3.69 (m, 1H), 3.55-3.35 (m, 3H), 2.49-2.39 (m, 1H), 2.35-2.25 (m, 1H). MS=386 (MH)+.

Example 348. 2-(3-Cyano-phenyl)-N-{4-[4-((R)-pyrrolidin-3-ylamino)-pyrido[3,4-d]pyrimidin-2-yl]-pyridin-2-yl}-acetamide 348a) 2-(3-Cyano-phenyl)-acetamide was prepared from (3-Cyano-phenyl)-acetic acid (1.0 g, 6.2 mmol) in an analogous manner to Example 313a. Product isolated as an off-white solid (0.50 g, 50%). $^1$HNMR (400 MHz, d6-DMSO, δ, ppm): 7.72-7.69 (m, 2H), 7.61-7.58 (m, 1H), 7.56-7.50 (m, 2H), 6.97 (br s, 1H), 3.47 (s, 2H). MS=161 (MH)+.

348b) 2-(3-Cyano-phenyl)-N-{4-[4-((R)-pyrrolidin-3-ylamino)-pyrido[3,4-d]pyrimidin-2-yl]-pyridin-2-yl}-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 2-(3-Cyano-phenyl)-acetamide (45.0 mg, 0.281 mmol) in an analogous manner to Example 303c and Example 1c. Product isolated as the trifluoroacetic acid salt as a pale yellow lyophilate (0.125 g, 94%). $^1$HNMR (400 MHz, d6-DMSO, δ, ppm): 10.97 (s, 1H), 9.24 (s, 1H), 9.12 (s, 1H), 8.90 (br s, 2H), 8.73-8.69 (m, 2H), 8.51 (dd, J=5.1, 0.5 Hz, 1H), 8.25 (dd, J=5.6, 0.7 Hz, 1H), 8.10 (dd, J=5.2, 1.5 Hz, 1H), 7.84-7.82 (m, 1H), 7.78-7.75 (m, 1H), 7.74-7.70 (m, 1H), 7.58 (t, J=7.8 Hz, 1H), 4.94-4.85 (m, 1H), 3.90 (s, 2H), 3.74-3.64 (m, 1H), 3.51-3.33 (m, 3H), 2.47-2.37 (m, 1H), 2.30-2.20 (m, 1H). MS=451 (MH)+.

Example 349. 2-(4-Cyano-phenyl)-N-{4-[4-((R)-pyrrolidin-3-ylamino)-pyrido[3,4-d]pyrimidin-2-yl]-pyridin-2-yl}-acetamide 349a) 2-(4-Cyano-phenyl)-acetamide was prepared from (4-Cyano-phenyl)-acetic acid (1.0 g, 6.2 mmol) in an analogous manner to Example 313a. Product isolated as an off-white solid (0.71 g, 71%). $^1$HNMR (400 MHz, d6-DMSO, δ, ppm): 7.77 (d, J=8.3 Hz, 2H), 7.55 (br s, 1H), 7.45 (d, J=8.3 Hz, 2H), 6.98 (br s, 1H), 3.49 (s, 2H). MS=161 (MH)+.

349b) 2-(4-Cyano-phenyl)-N-{4-[4-((R)-pyrrolidin-3-ylamino)-pyrido[3,4-d]pyrimidin-2-yl]-pyridin-2-yl}-acetamide was prepared from (R)-3-[2-(2-Chloro-pyridin-4-yl)-pyrido[3,4-d]pyrimidin-4-ylamino]-pyrrolidine-1-carboxylic acid tert-butyl ester (120.0 mg, 0.2811 mmol) and 2-(4-Cyano-phenyl)-acetamide (45.0 mg, 0.281 mmol) in an analogous manner to Example 303c and Example 1c. Product isolated as the trifluoroacetic acid salt as a pale orange lyophilate (0.148 g, 93%). $^1$HNMR (400 MHz, d6-DMSO, δ, ppm): 10.98 (s, 1H), 9.23 (s, 1H), 9.12 (s, 1H), 8.87 (br s, 2H), 8.73-8.68 (m, 2H), 8.51 (dd, J=5.1, 0.6 Hz, 1H), 8.25 (dd, J=5.7, 0.6 Hz, 1H), 8.10 (dd, J=5.1, 1.4 Hz, 1H), 7.83 (d, J=8.4 Hz, 2H), 7.58 (d, J=8.4 Hz, 2H), 4.93-4.84 (m, 1H), 3.92 (s, 2H), 3.73-3.64 (m, 1H), 3.51-3.32 (m, 3H), 2.47-2.36 (m, 1H), 2.30-2.21 (m, 1H). MS=451 (MH)+.

Example 350. (R)-Pyrrolidin-3-yl-{2-[2-(4-trifluoromethyl-pyridin-2-ylamino)-pyridin-4-yl]-pyrido[3,4-d]pyrimidin-4-yl}-amine (R)-Pyrrolidin-3-yl-{2-[2-(4-trifluoromethyl-pyridin-2-ylamino)-pyridin-4-yl]-pyrido[3,4-d]pyrimidin-4-yl}-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 4-Trifluoromethyl-pyridin-2-ylamine (46.0 mg, 0.284 mmol) in an analogous manner to Example 303c and Example 1c. Product isolated as the trifluoroacetic acid salt as a pale yellow lyophilate (0.127 g, 95%). $^1$HNMR (400 MHz, d6-DMSO, δ, ppm): 10.57 (s, 1H), 9.26 (d, J=0.4 Hz, 1H), 8.94 (br s, 2H), 8.75-8.72 (m, 2H), 8.69 (s, 1H), 8.56 (d, J=5.1 Hz, 1H), 8.47 (d, J=5.4 Hz, 1H), 8.28 (dd, J=5.7, 0.6 Hz, 1H), 8.26 (s, 1H), 7.97 (dd, J=5.4, 1.5 Hz, 1H), 7.25 (dd, J=5.9, 1.0 Hz, 1H), 4.99-4.90 (m, 1H), 3.80-3.71 (m, 1H), 3.55-3.35 (m, 3H), 2.48-2.40 (m, 1H), 2.34-2.24 (m, 1H). MS=453 (MH)+.

Example 351. (R)-Pyrrolidin-3-yl-{2-[2-(5-trifluoromethyl-pyridin-2-ylamino)-pyridin-4-yl]-pyrido[3,4-d]pyrimidin-4-yl}-amine (R)-Pyrrolidin-3-yl-{2-[2-(5-trifluoromethyl-pyridin-2-ylamino)-pyridin-4-yl]-pyrido[3,4-d]pyrimidin-4-yl}-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 5-Trifluoromethyl-pyridin-2-ylamine (46.0 mg, 0.284 mmol) in an analogous manner to Example 303c and Example 1c. Product isolated as a trifluoroacetic acid salt as a pale yellow lyophilate (0.102 g, 76%). $^1$HNMR (400 MHz, d6-DMSO, δ, ppm): 10.64 (s, 1H), 9.27 (d, J=0.6 Hz, 1H), 8.94 (br s, 2H), 8.75-7.73 (m, 3H), 8.66-8.63 (m, 1H), 8.48 (dd, J=5.2, 0.3 Hz, 1H), 8.28 (dd, J=5.6, 0.7 Hz, 1H), 8.08 (dd, J=9.1, 2.5 Hz, 1H), 8.03-7.98 (m, 2H), 4.99-4.90 (m, 1H), 3.80-3.70 (m, 1H), 3.55-3.35 (m, 3H), 2.50-2.40 (m, 1H), 2.34-2.24 (m, 1H). MS=453 (MH)+.

Example 352. 2-[4-(5-Methoxy-4-piperazin-1-yl-pyrido[3,4-d]pyrimidin-2-yl)-pyridin-2-ylamino]-isonicotinonitrile 352a) 4-[2-(2-Chloro-pyridin-4-yl)-5-methoxy-pyrido[3,4-d]pyrimidin-4-yl]-piperazine-1-carboxylic acid tert-butyl ester was prepared from 2-(2-Chloro-pyridin-4-yl)-5-methoxy-pyrido[3,4-d]pyrimidin-4-ol (2.0 g, 6.9 mmol) and tert-Butyl 1-Piperazinecarboxylate (1.5 g, 8.3 mmol; Supplier=Aldrich) in an analogous manner to [B016]. Product isolated as an off-white solid (1.35 g, 43%). $^1$HNMR (400 MHz, d6-DMSO, δ, ppm): 8.88 (s, 1H), 8.61 (dd, J=4.9, 0.8 Hz, 1H), 8.39 (s, 1H), 8.34-8.31 (m, 2H), 4.09 (s, 3H), 3.72-3.67 (m, 4H), 3.57-3.52 (m, 4H), 1.44 (s, 9H). MS=457, 459 (MH)+.

352b) 2-[4-(5-Methoxy-4-piperazin-1-yl-pyrido[3,4-d]pyrimidin-2-yl)-pyridin-2-ylamino]-isonicotinonitrile was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-Amino-isonicotinonitrile (31.0 mg, 0.260 mmol) in an analogous manner to Example 303c and Example 1c. Product isolated as the trifluoroacetic acid salt as a pale yellow lyophilate (0.105 g, 86%). $^1$HNMR (400 MHz, d6-DMSO, δ, ppm): 10.49 (s, 1H), 8.93 (s, 1H), 8.88 (br s, 2H), 8.64 (s, 1H), 8.51 (dd, J=5.1, 0.6 Hz, 1H), 8.48 (d, J=5.5 Hz, 1H), 8.43 (s, 1H), 8.34 (s, 1H), 7.92 (dd, J=5.4, 1.4 Hz, 1H), 7.34 (dd, J=5.0, 1.3 Hz, 1H), 4.11 (s, 3H), 3.93-3.88 (m, 4H), 3.37-3.30 (m, 4H). MS=440 (MH)+.

Example 353. 6-[4-(5-Methoxy-4-piperazin-1-yl-yl-pyrido[3,4-d]pyrimidin-2-yl)-pyridin-2-ylamino]-nicotinonitrile 6-[4-(5-Methoxy-4-piperazin-1-yl-pyrido[3,4-d]pyrimidin-2-yl)-pyridin-2-ylamino]-nicotinonitrile was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Amino-nicotinonitrile (31.0 mg, 0.260 mmol) in an analogous manner to Example 303c and Example 1c. Product isolated as the trifluoroacetic acid salt as pale yellow lyophilate (0.109 g, 89%). $^1$HNMR (400 MHz, d6-DMSO, δ, ppm): 10.64 (s, 1H), 8.93 (s, 1H), 8.90-8.82 (m, 3H), 8.72 (d, J=2.2 Hz, 1H), 8.49 (d, J=5.4 Hz, 1H), 8.43 (s, 1H), 8.11 (dd, J=8.9, 2.4 Hz, 1H), 7.96 (dd, J=5.2, 1.4 Hz, 1H), 7.92 (d, J=8.9 Hz, 1H), 4.11 (s, 3H), 3.93-3.88 (m, 4H), 3.37-3.31 (m, 4H). MS=440 (MH)+.

Example 354. {4-[5-Methoxy-4-(4-morpholin-4-yl-piperidin-1-yl)-pyrido[3,4-d]pyrimidin-2-yl]-pyridin-2-yl}-phenyl-amine 354a) 2-(2-Chloro-pyridin-4-yl)-5-methoxy-4-(4-morpholin-4-yl-piperidin-1-yl)-pyrido[3,4-d]pyrimidine was prepared from 2-(2-Chloro-pyridin-4-yl)-5-methoxy-pyrido[3,4-d]pyrimidin-4-ol (190.0 mg, 0.6581 mmol) and 4-Piperidin-4-yl-morpholine (134.0 mg, 0.7871 mmol) in an analogous manner to [B016]. Product isolated as a red-orange solid (0.146 g, 50%). $^1$HNMR (400 MHz, d6-DMSO, δ, ppm): 8.84 (s, 1H), 8.60 (dd, J=4.9, 0.6 Hz, 1H), 8.36 (s, 1H), 8.32-8.29 (m, 2H), 4.28 (d, J=11.6 Hz, 2H), 4.08 (s, 3H), 3.60-3.55 (m, 4H), 3.15 (t, J=11.6 Hz, 2H), 2.53-2.46 (m, 5H), 1.96 (d, J=11.3 Hz, 2H), 1.61-1.49 (m, 2H). (400 MHz, CDCl3, δ, ppm): 8.97 (s, 1H), 8.52 (d, J=4.9 Hz, 1H), 8.37 (s, 1H), 8.28 (dd, J=5.2, 1.3 Hz, 1H), 8.21 (s, 1H), 4.36 (d, J=13.2 Hz, 2H), 4.09 (s, 3H), 3.77-3.73 (m, 4H), 3.18-3.09 (m, 2H), 2.63-2.58 (m, 4H), 2.53-2.43 (m, 1H), 2.06 (d, J=12.7 Hz, 2H), 1.74-1.63 (m, 2H). MS=441, 443 (MH)+.

354b) {4-[5-Methoxy-4-(4-morpholin-4-yl-piperidin-1-yl)-pyrido[3,4-d]pyrimidin-2-yl]-pyridin-2-yl}-phenyl-amine was prepared from 2-(2-Chloro-pyridin-4-yl)-5-methoxy-4-(4-morpholin-4-yl-piperidin-1-yl)-pyrido[3,4-d]pyrimidine (80.0 mg, 0.181 mmol) and Aniline (18.6 μL, 0.204 mmol) in an analogous manner to Example 303c and Example 1501c. Product isolated as the trifluoroacetic acid salt as a yellow lyophilate (0.108 g, 97%). $^1$HNMR (400 MHz, d6-DMSO, δ, ppm): 9.74 (br s, 1H), 9.46 (br s, 1H), 8.87 (s, 1H), 8.39 (s, 1H), 8.31 (d, J=5.4 Hz, 1H), 7.94 (s, 1H), 7.75-7.73 (m, 2H), 7.70 (dd, J=5.3, 1.3 Hz, 1H), 7.31 (t, J=7.6 Hz, 2H), 6.95 (t, J=7.2 Hz, 1H), 4.42 (d, J=12.6 Hz, 2H), 4.12 (s, 3H), 4.04 (d, J=11.7 Hz, 2H), 3.67 (t, J=12.1 Hz, 2H), 3.62-3.54 (m, 1H), 3.51 (d, J=12.1 Hz, 2H), 3.22-3.10 (m, 4H), 2.25 (d, J=10.4 Hz, 2H), 1.85-1.72 (m, 2H). MS=498 (MH)+.

Example 355. 2-(4-Cyano-phenyl)-N-[4-(5-methoxy-4-piperazin-1-yl-pyrido[3,4-d]pyrimidin-2-yl)-pyridin-2-yl]-acetamide 2-(4-Cyano-phenyl)-N-[4-(5-methoxy-4-piperazin-1-yl-pyrido[3,4-d]pyrimidin-2-yl)-pyridin-2-yl]-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(4-Cyano-phenyl)-acetamide (45.0 mg, 0.281 mmol) in an analogous manner to Example 303c and Example 1c. Product isolated as the trifluoroacetic acid salt as a pale orange lyophilate (0.102 g, 78%). $^1$HNMR (400 MHz, d6-DMSO, δ, ppm): 10.99 (s, 1H), 9.08 (s, 1H), 8.90 (s, 1H), 8.83 (br s, 2H), 8.51 (dd, J=5.2, 0.6 Hz, 1H), 8.41 (s, 1H), 8.06 (dd, J=5.1, 1.5 Hz, 1H), 7.83 (d, J=8.4 Hz, 2H), 7.58 (d, J=8.4 Hz, 2H), 4.09 (s, 3H), 3.92 (s, 2H), 3.87-3.83 (m, 4H), 3.31 (br s, 4H). MS=481 (MH)+.

Example 356. 2-(3-Cyano-phenyl)-N-[4-(5-methoxy-4-piperazin-1-yl-pyrido[3,4-d]pyrimidin-2-yl)-pyridin-2-yl]-acetamide 2-(3-Cyano-phenyl)-N-[4-(5-methoxy-4-piperazin-1-yl-pyrido[3,4-d]pyrimidin-2-yl)-pyridin-2-yl]-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(3-Cyano-phenyl)-acetamide (45.0 mg, 0.281 mmol) in an analogous manner to Example 303c and Example 1501c. Product isolated as a pale yellow lyophilate (0.125 g, 96%). $^1$HNMR (400 MHz, d6-DMSO, δ, ppm): 10.97 (s, 1H), 9.07 (s, 1H), 8.91 (s, 1H), 8.87 (br s, 2H), 8.52 (dd, J=5.1, 0.4 Hz, 1H), 8.41 (s, 1H), 8.06 (dd, J=5.2, 1.4 Hz, 1H), 7.84-7.82 (m, 1H), 7.78-7.74 (m, 1H), 7.73-7.70 (m, 1H), 7.57 (t, J=7.7 Hz, 1H), 4.09 (s, 3H), 3.89 (s, 2H), 3.87-3.83 (m, 4H), 3.31 (br s, 4H). MS=481 (MH)+.

Example 357. {2-[2-(5-Morpholin-4-yl-pyridin-2-ylamino)-pyridin-4-yl]-pyrido[3,4-d]pyrimidin-4-yl}-(R)-pyrrolidin-3-yl-amine {2-[2-(5-Morpholin-4-yl-pyridin-2-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (100.0 mg, 0.2342 mmol) and 5-Morpholin-4-yl-pyridin-2-ylamine (48.0 mg, 0.268 mmol) [prepared as described in Toogood, P. L.; et. al. *J. Med. Chem.* 2005, 48(7), 2388-2406.] in an analogous manner to Example 303c and Example 1501c. Product isolated as the trifluoroacetic acid salt as an orange lyophilate (0.103 g, 60%). $^1$HNMR (400 MHz, d6-DMSO, δ, ppm): 9.27 (s, 1H), 8.93 (br s, 2H), 8.83-8.79 (m, 1H), 8.76 (d, J=5.5 Hz, 1H), 8.14 (d, J=5.9 Hz, 1H), 8.40 (s, 1H), 8.26 (d, J=5.5 Hz, 1H), 8.07-8.01 (m, 1H), 7.94 (d, J=2.9 Hz, 1H), 7.87-7.86 (m, 1H), 7.49-7.40 (m, 1H), 5.00-4.91 (m, 1H), 3.81-3.77 (m, 4H), 3.76-3.69 (m, 1H), 3.55-3.36 (m, 3H), 3.17-3.13 (m, 4H), 2.47-2.37 (m, 1H), 2.33-2.23 (m, 1H). MS=470 (MH)+.

Example 358. {2-[2-(2-Methoxy-4-morpholin-4-yl-phenylamino)-pyridin-4-yl]-pyrido[3,4-d]pyrimidin-4-yl}-(R)-pyrrolidin-3-yl-amine {2-[2-(2-Methoxy-4-morpholin-4-yl-phenylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (115.0 mg, 0.2694 mmol) and 2-Methoxy-4-morpholin-4-yl-phenylamine (58.0 mg, 0.278 mmol) [prepared as described in WO2008/051547] in an analogous manner to Example 303c and Example 1501c. Product isolated as the trifluoroacetic acid salt as an orange-brown lyophilate (0.155 g, 93%). $^1$HNMR (400 MHz, d6-DMSO, δ, ppm): 10.25 (br s, 1H), 9.27 (s, 1H), 9.08 (br s, 2H), 8.87 (d, J=5.1 Hz, 1H), 8.77 (d, J=5.6 Hz, 1H), 8.30 (d, J=5.3 Hz, 1H), 8.16 (s, 1H), 7.98 (d, J=6.5 Hz, 1H), 7.81 (dd, J=6.6, 1.3 Hz, 1H), 7.31 (d, J=8.5 Hz, 1H), 6.76 (d, J=2.3 Hz, 1H), 6.64 (dd, J=8.8, 2.4 Hz, 1H), 4.94-4.85 (m, 1H), 3.82 (s, 3H), 3.80-3.75 (m, 4H), 3.73-3.63 (m, 1H), 3.55-3.33 (m, 3H), 3.25-3.20 (m, 4H), 2.43-2.34 (m, 1H), 2.31-2.22 (m, 1H). MS=499 (MH)+.

Example 359. (2-Methoxy-4-morpholin-4-yl-phenyl)-[4-(5-methoxy-4-piperazin-1-yl-pyrido[3,4-d]pyrimidin-2-yl)-pyridin-2-yl]-amine (2-Methoxy-4-morpholin-4-yl-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (115.0 mg, 0.2517 mmol) and 2-Methoxy-4-morpholin-4-yl-phenylamine (55.0 mg, 0.264 mmol) in an analogous manner to Example 303c and Example 1501c. Product isolated as the trifluoroacetic acid salt as an orange-brown lyophilate (0.150 g, 92%). $^1$HNMR (400 MHz, d6-DMSO, δ, ppm): 10.25 (br s, 1H), 9.05 (br s, 2H), 8.93 (s, 1H), 8.47 (s, 1H), 8.13 (s, 1H), 8.00 (d, J=6.6 Hz, 1H), 7.76 (dd, J=6.5, 1.3 Hz, 1H), 7.31 (d, J=8.5 Hz, 1H), 6.76 (d, J=2.4 Hz, 1H), 6.64 (dd, J=8.7, 2.4 Hz, 1H), 4.11 (s, 3H), 3.91-3.86 (m, 4H), 3.81 (s, 3H), 3.80-3.76 (m, 4H), 3.32 (br s, 4H), 3.25-3.21 (m, 4H). MS=529 (MH)+.

Example 360. {5-Methoxy-2-[2-(2-methoxy-4-morpholin-4-yl-phenylamino)-pyridin-4-yl]-pyrido[3,4-d]pyrimidin-4-yl}-(R)-pyrrolidin-3-yl-amine {5-Methoxy-2-[2-(2-methoxy-4-morpholin-4-yl-phenylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (100.0 mg, 0.2188 mmol) and 2-Methoxy-4-morpholin-4-yl-phenylamine (55.0 mg, 0.264 mmol) in an analogous manner to Example 303c and Example 1501c. Product isolated as the trifluoroacetic acid salt as an orange-brown lyophilate (0.057 g, 40%). $^1$HNMR (400 MHz, d6-DMSO, δ, ppm): 10.13 (br s, 1H), 9.21-9.00 (m, 2H), 8.86 (s, 1H), 8.46 (s, 1H), 8.26 (d, J=6.2 Hz, 1H), 8.10 (s, 1H), 7.99 (d, J=6.4 Hz, 1H), 7.74 (dd, J=6.4, 1.2 Hz, 1H), 7.33 (d, J=8.2 Hz, 1H), 6.76 (d, J=2.4 Hz, 1H), 6.63 (dd, J=8.7, 2.4 Hz, 1H), 5.01-4.91 (m, 1H), 4.17 (s, 3H), 3.81 (s, 3H), 3.80-3.75 (m, 4H), 3.69-3.59 (m, 1H), 3.53-3.40 (m, 2H), 3.37-3.26 (m, 1H), 3.25-3.20 (m, 4H), 2.51-2.41 (m, 1H), 2.26-2.16 (m, 1H). MS=529 (MH)+.

Example 361. (5-Methoxy-2-{2-[4-(tetrahydro-pyran-4-yl)-phenylamino]-pyridin-4-yl}-pyrido[3,4-d]pyrimidin-4-yl)-(R)-pyrrolidin-3-yl-amine (5-Methoxy-2-{2-[4-(tetrahydro-pyran-4-yl)-phenylamino]-pyridin-4-yl}-pyrido[3,4-d]pyrimidin-4-yl)-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (100.0 mg, 0.2188 mmol) and 4-(Tetrahydro-pyran-4-yl)-phenylamine (43.0 mg, 0.243 mmol) in an analogous manner to Example 303c and Example 1501c. Product isolated as the trifluoroacetic salt as a yellow lyophilate (0.109 g, 81%). $^1$HNMR (400 MHz, d6-DMSO, δ, ppm): 9.41 (br s, 1H), 8.99 (br s, 1H), 8.88 (br s, 1H), 8.83 (s, 1H), 8.41 (s, 1H), 8.28 (d, J=5.5 Hz, 1H), 8.16 (d, J=6.2 Hz, 1H), 7.93 (s, 1H), 7.69 (dd, J=5.5, 1.2 Hz, 1H), 7.64 d, J=8.5 Hz, 2H), 7.20 (d, J=8.5 Hz, 2H), 5.05-4.95 (m, 1H), 4.16 (s, 3H), 3.98-3.92 (m, 2H), 3.72-3.63 (m, 1H), 3.50-3.28 (m, 5H), 2.76-2.68 (m, 1H), 2.50-2.43 (m, 1H), 2.27-2.17 (m, 1H), 1.73-1.60 (m, 4H). MS=498 (MH)+.

Example 362. [4-(5-Methoxy-4-piperazin-1-yl-pyrido[3,4-d]pyrimidin-2-yl)-pyridin-2-yl]-[4-(tetrahydro-pyran-4-yl)-phenyl]-amine

[4-(5-Methoxy-4-piperazin-1-yl-pyrido[3,4-d]pyrimidin-2-yl)-pyridin-2-yl]-[4-(tetrahydro-pyran-4-yl)-phenyl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-(Tetrahydro-pyran-4-yl)-phenylamine (43.0 mg, 0.243 mmol) in an analogous manner to Example 303c and Example 1501c. Product isolated as the trifluoroacetic acid salt as a yellow lyophilate (0.099 g, 74%). $^1$HNMR (400 MHz, d6-DMSO, δ, ppm): 9.43 (br s, 1H), 8.95-8.83 (m, 3H), 8.42 (s, 1H), 8.28 (d, J=5.5 Hz, 1H), 7.93 (s, 1H), 7.68 (dd, J=5.4, 1.2 Hz, 1H), 7.64 (d, J=8.4 Hz, 2H), 7.20 (d, J=8.5 Hz, 2H), 4.10 (s, 3H), 3.98-3.92 (m, 2H), 3.90-3.85 (m, 4H), 3.44 (ddd, J=11.2, 11.2, 3.0 Hz, 2H), 3.35-3.29 (m, 4H), 2.76-2.68 (m, 1H), 1.72-1.60 (m, 4H). MS=498 (MH)+.

Example 363. [4-(5-Methoxy-4-piperazin-1-yl-pyrido[3,4-d]pyrimidin-2-yl)-pyridin-2-yl]-(4-methyl-pyridin-2-yl)-amine

[4-(5-Methoxy-4-piperazin-1-yl-pyrido[3,4-d]pyrimidin-2-yl)-pyridin-2-yl]-(4-methyl-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-Methyl-pyridin-2-ylamine (27.0 mg, 0.250 mmol) in an analogous manner to Example 303c and Example 1501c. Product isolated as the trifluoroacetic acid salt as a yellow lyophilate (0.100 g, 84%). $^1$HNMR (400 MHz, d6-DMSO, δ, ppm): 11.72 (br s, 1H), 9.03-8.90 (m, 3H), 8.55 (d, J=5.5 Hz, 1H), 8.46 (s, 1H), 8.37 (s, 1H), 8.27 (d, J=6.1 Hz, 1H), 8.12 (d, J=5.2 Hz, 1H), 7.27 (s, 1H), 7.14 (d, J=4.5 Hz, 1H), 4.12 (s, 3H), 3.94-3.88 (m, 4H), 3.37-3.30 (m, 4H), 2.47 (s, 3H). MS=429 (MH)+.

Example 364. [4-(5-Methoxy-4-piperazin-1-yl-pyrido[3,4-d]pyrimidin-2-yl)-pyridin-2-yl]-(5-methyl-pyridin-2-yl)-amine

[4-(5-Methoxy-4-piperazin-1-yl-pyrido[3,4-d]pyrimidin-2-yl)-pyridin-2-yl]-(5-methyl-pyridin-2-yl)-amine was prepared from 4-[2-(2-Chloro-pyridin-4-yl)-5-methoxy-pyrido

[3,4-d]pyrimidin-4-yl]-piperazine-1-carboxylic acid tert-butyl ester (110.0 mg, 0.2407 mmol) and 5-Methyl-pyridin-2-ylamine (27.0 mg, 0.250 mmol) in an analogous manner to Example 303c and Example 1501c. Product isolated as the trifluoroacetic acid salt as a yellow lyophilate (0.122 g, 93%). $^1$HNMR (400 MHz, d6-DMSO, δ, ppm): 11.73 (br s, 1H), 8.98 (br s, 2H), 8.94 (s, 1H), 8.54 (d, J=5.7 Hz, 1H), 8.46 (s, 1H), 8.37 (s, 1H), 8.22 (s, 1H), 8.12-8.08 (m, 1H), 8.00-7.94 (m, 1H), 7.42 (d, J=7.6 Hz, 1H), 4.12 (s, 3H), 3.94-3.88 (m, 4H), 3.37-3.30 (m, 4H), 2.34 (s, 3H). MS=429 (MH)+.

Example 365. (4-Chloro-pyridin-2-yl)-[4-(5-methoxy-4-piperazin-1-yl-pyrido[3,4-d]pyrimidin-2-yl)-pyridin-2-yl]-amine (4-Chloro-pyridin-2-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-Chloro-pyridin-2-ylamine (32.0 mg, 0.249 mmol) in an analogous manner to Example 303c and Example 1501c. Product isolated as the trifluoroacetic acid as a yellow lyophilate (0.107 g, 86%). $^1$HNMR (400 MHz, d6-DMSO, δ, ppm): 10.56 (br s, 1H), 9.00-8.85 (m, 3H), 8.63 (s, 1H), 8.46 (d, J=5.4 Hz, 1H), 8.43 (s, 1H), 8.29 (d, J=5.6 Hz, 1H), 7.99 (s, 1H), 7.92 (dd, J=5.4, 1.2 Hz, 1H), 7.10 (dd, J=5.6, 1.8 Hz, 1H), 4.10 (s, 1H), 3.94-3.88 (m, 4H), 3.37-3.29 (m, 4H). MS=449 (MH)+.

Example 366. (5-Chloro-pyridin-2-yl)-[4-(5-methoxy-4-piperazin-1-yl-pyrido[3,4-d]pyrimidin-2-yl)-pyridin-2-yl]-amine (5-Chloro-pyridin-2-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (110.0 mg, 0.2407 mmol) and 2-Amino-5-chloropyridine (32.0 mg, 0.249 mmol) in an analogous manner to Example 303c and Example 1501c. Product isolated as the trifluoroacetic acid salt as a yellow lyophilate (0.134 g, 98%). $^1$HNMR (400 MHz, d6-DMSO, δ, ppm): 10.45 (br s, 1H), 8.93 (s, 1H), 8.87 (br s, 2H), 8.67 (s, 1H), 8.44-8.41 (m, 2H), 8.34-8.32 (s, 1H), 7.90 (d, J=5.4 Hz, 1H), 7.88-7.81 (m, 2H), 4.10 (s, 3H), 3.94-3.87 (m, 4H), 3.37-3.30 (m, 4H). MS=449 (MH)+.

Example 367. [4-(5-Methoxy-4-piperazin-1-yl-pyrido[3,4-d]pyrimidin-2-yl)-pyridin-2-yl]-(4-trifluoromethyl-pyridin-2-yl)-amine

[4-(5-Methoxy-4-piperazin-1-yl-pyrido[3,4-d]pyrimidin-2-yl)-pyridin-2-yl]-(4-trifluoromethyl-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-Trifluoromethyl-pyridin-2-ylamine (40.0 mg, 0.247 mmol) in an analogous manner to Example 303c and Example 1501c. Product isolated as the trifluoroacetic acid salt as a yellow solid (0.116 g, 88%). $^1$HNMR (400 MHz, d6-DMSO, δ, ppm): 10.49 (br s, 1H), 8.93 (s, 1H), 8.87 (br s, 2H), 8.70 (s, 1H), 8.54 (d, J=5.3 Hz, 1H), 8.47 (d, J=5.3 Hz, 1H), 8.42 (s, 1H), 8.30 (s, 1H), 7.91 (dd, J=5.3, 1.3 Hz, 1H), 7.25 (d, J=4.4 Hz, 1H), 4.11 (s, 3H), 3.94-3.88 (m, 4H), 3.37-3.30 (m, 4H). MS=483 (MH)+.

Example 368. [4-(5-Methoxy-4-piperazin-1-yl-pyrido[3,4-d]pyrimidin-2-yl)-pyridin-2-yl]-(5-trifluoromethyl-pyridin-2-yl)-amine

[4-(5-Methoxy-4-piperazin-1-yl-pyrido[3,4-d]pyrimidin-2-yl)-pyridin-2-yl]-(5-trifluoromethyl-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 5-Trifluoromethyl-pyridin-2-ylamine (40.0 mg, 0.247 mmol) in an analogous manner to Example 303c and Example 1501c. Product isolated as the trifluoroacetic acid salt as a yellow lyophilate (0.116 g, 88%). $^1$HNMR (400 MHz, d6-DMSO, δ, ppm): 10.56 (br s, 1H), 8.94 (s, 1H), 8.88 (br s, 2H), 8.78 (s, 1H), 8.64 (s, 1H), 8.47 (d, J=5.3 Hz, 1H), 8.43 (s, 1H), 8.07 (dd, J=9.0, 2.3 Hz, 1H), 8.01 (d, J=9.0 Hz, 1H), 7.94 (dd, J=5.3, 1.3 Hz, 1H), 4.11 (s, 3H), 3.94-3.88 (m, 4H), 3.37-3.30 (m, 4H). MS=483 (MH)+.

Example 369. 2-(4-Chloro-phenyl)-N-[4-(5-methoxy-4-piperazin-1-yl-pyrido[3,4-d]pyrimidin-2-yl)-pyridin-2-yl]-acetamide 369a) 2-(4-Chloro-phenyl)-acetamide was prepared from (4-Chloro-phenyl)-acetic acid (1.0 g, 5.9 mmol) in an analogous manner to Example 313a. Product isolated as a white solid (0.97 g, 97%). $^1$HNMR (400 MHz, d6-DMSO, δ, ppm): 7.47 (br s, 1H), 7.35 (d, J=8.5 Hz, 2H), 7.27 (d, J=8.5 Hz, 2H), 6.90 (br s, 1H), 3.37 (s, 2H). MS=170, 172 (MH)+.

369b) 2-(4-Chloro-phenyl)-N-[4-(5-methoxy-4-piperazin-1-yl-pyrido[3,4-d]pyrimidin-2-yl)-pyridin-2-yl]-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(4-Chloro-phenyl)-acetamide (42.0 mg, 0.248 mmol) in an analogous manner to Example 303c and Example 1501c. Product isolated as the trifluoroacetic acid salt as a pale yellow lyophilate (0.101 g, 76%). $^1$HNMR (400 MHz, d6-DMSO, δ, ppm): 10.92 (s, 1H), 9.08 (s, 1H), 8.91 (s, 1H), 8.85 (br s, 2H), 8.51 (dd, J=5.1, 0.5 Hz, 1H), 8.41 (s, 1H), 8.05 (dd, J=5.1, 1.5 Hz, 1H), 7.43-7.37 (m, 4H), 4.09 (s, 3H), 3.88-3.83 (m, 4H), 3.79 (s, 2H), 3.35-3.28 (m, 4H). MS=490 (MH)+.

Example 370. 2-(3-Chloro-phenyl)-N-[4-(5-methoxy-4-piperazin-1-yl-pyrido[3,4-d]pyrimidin-2-yl)-pyridin-2-yl]-acetamide 370a) 2-(3-Chloro-phenyl)-acetamide was prepared from (3-Chloro-phenyl)-acetic acid (1.0 g, 5.9 mmol) in an analogous manner to Example 313a. Product isolated as a white solid (0.82 g, 82%). $^1$HNMR (400 MHz, d6-DMSO, δ, ppm): 7.50 (br s, 1H), 7.35-7.27 (m, 3H), 7.23-7.19 (m, 1H), 6.93 (br s, 1H), 3.39 (s, 2H). MS=170, 172 (MH)+.

370b) 2-(3-Chloro-phenyl)-N-[4-(5-methoxy-4-piperazin-1-yl-pyrido[3,4-d]pyrimidin-2-yl)-pyridin-2-yl]-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(3-Chloro-phenyl)-acetamide (42.0 mg, 0.248 mmol) in an analogous manner to Example 303c and Example 1501c. Product isolated as the trifluoroacetic acid salt as a yellow lyophilate (0.103 g, 77%). $^1$HNMR (400 MHz, d6-DMSO, δ, ppm): 10.94 (s, 1H), 9.08 (s, 1H), 8.91 (s, 1H), 8.88 (br s, 2H), 8.51 (dd, J=5.0, 0.5 Hz, 1H), 8.41 (s, 1H), 8.06 (dd, J=5.1, 1.5 Hz, 1H), 7.47-7.45 (m, 1H), 7.41-7.32

(m, 3H), 4.09 (s, 3H), 3.88-3.83 (m, 4H), 3.81 (s, 2H), 3.35-3.29 (m, 4H). MS=490 (MH)+.

Example 371. N-[4-(5-Methoxy-4-piperazin-1-yl-yl-pyrido[3,4-d]pyrimidin-2-yl)-pyridin-2-yl]-2-phenyl-acetamide N-[4-(5-Methoxy-4-piperazin-1-yl-pyrido[3,4-d]pyrimidin-2-yl)-pyridin-2-yl]-2-phenyl-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and Benzeneacetamide (34.0 mg, 0.252 mmol) in an analogous manner to Example 303c and Example 1501c. Product isolated as the trifluoroacetic acid salt as a pale yellow lyophilate (0.120 g, 96%). $^1$HNMR (400 MHz, d6-DMSO, δ, ppm): 10.90 (s, 1H), 9.09 (s, 1H), 8.91 (s, 1H), 8.87 (br s, 2H), 8.51 (d, J=5.2 Hz, 1H), 8.41 (s, 1H), 8.05 (dd, J=5.0, 1.3 Hz, 1H), 7.40-7.32 (m, 4H), 7.29-7.23 (m, 1H), 4.09 (s, 3H), 3.88-3.83 (m, 4H), 3.78 (s, 2H), 3.35-3.28 (m, 4H). MS=456 (MH)+.

Example 372. 2-(3-Methoxy-phenyl)-N-[4-(5-methoxy-4-piperazin-1-yl-pyrido[3,4-d]pyrimidin-2-yl)-pyridin-2-yl]-acetamide 2-(3-Methoxy-phenyl)-N-[4-(5-methoxy-4-piperazin-1-yl-pyrido[3,4-d]pyrimidin-2-yl)-pyridin-2-yl]-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(3-Methoxy-phenyl)-acetamide (43.0 mg, 0.260 mmol) in an analogous manner to Example 303c and Example 1501c. Product isolated as the trifluoroacetic acid salt as a yellow lyophilate (0.056 g, 42%). $^1$HNMR (400 MHz, d6-DMSO, δ, ppm): 10.87 (s, 1H), 9.09 (s, 1H), 8.91 (s, 1H), 8.87 (br s, 2H), 8.51 (dd, J=5.1, 0.6 Hz, 1H), 8.41 (s, 1H), 8.05 (dd, J=5.1, 1.4 Hz, 1H), 7.25 (t, J=7.8 Hz, 1H), 6.97-6.93 (m, 2H), 6.86-6.82 (m, 1H), 4.09 (s, 3H), 3.88-3.83 (m, 4H), 3.78 (s, 3H), 3.74 (s, 2H), 3.35-3.29 (m, 4H). MS=486 (MH)+.

Example 373. N-[4-(5-Methoxy-4-piperazin-1-yl-pyrido[3,4-d]pyrimidin-2-yl)-pyridin-2-yl]-2-(3-trifluoromethyl-phenyl)-acetamide 373a) 2-(3-Trifluoromethyl-phenyl)-acetamide was prepared from (3-Trifluoromethyl-phenyl)-acetic acid (1.0 g, 4.9 mmol) in an analogous manner to Example 313a. Product isolated as white solid (0.88 g, 88%). $^1$HNMR (400 MHz, d6-DMSO, δ, ppm): 7.63-7.51 (m, 5H), 6.96 (br s, 1H), 3.50 (s, 2H). MS=204 (MH)+.

373b) N-[4-(5-Methoxy-4-piperazin-1-yl-pyrido[3,4-d]pyrimidin-2-yl)-pyridin-2-yl]-2-(3-trifluoromethyl-phenyl)-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(3-Trifluoromethyl-phenyl)-acetamide (53.0 mg, 0.261 mmol) in an analogous manner to Example 303c and Example 1501c. Product isolated as the trifluoroacetic acid salt as a yellow lyophilate (0.037 g, 26%). $^1$HNMR (400 MHz, d6-DMSO, δ, ppm): 10.98 (s, 1H), 9.07 (s, 1H), 8.91 (s, 1H), 8.87 (br s, 2H), 8.52 (dd, J=5.1, 0.4 Hz, 1H), 8.41 (s, 1H), 8.06 (dd, J=5.1, 1.4 Hz, 1H), 7.75 (s, 1H), 7.70-7.57 (m, 3H), 4.09 (s, 3H), 3.92 (s, 2H), 3.88-3.83 (m, 4H), 3.35-3.28 (m, 4H). MS=524 (MH)+.

Example 374. 2-(4-Methoxy-phenyl)-N-[4-(5-methoxy-4-piperazin-1-yl-pyrido[3,4-d]pyrimidin-2-yl)-pyridin-2-yl]-acetamide 2-(4-Methoxy-phenyl)-N-[4-(5-methoxy-4-piperazin-1-yl-pyrido[3,4-d]pyrimidin-2-yl)-pyridin-2-yl]-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-Methoxyphenylacetamide (43.0 mg, 0.260 mmol) in an analogous manner to Example 303c and Example 1501c. Product isolated as the trifluoroacetic acid salt as a yellow lyophilate (0.067 g, 50%). $^1$HNMR (400 MHz, d6-DMSO, δ, ppm): 10.83 (s, 1H), 9.08 (s, 1H), 8.91 (s, 1H), 8.85 (br s, 2H), 8.50 (dd, J=5.1, 0.6 Hz, 1H), 8.41 (s, 1H), 8.04 (dd, J=5.1, 1.4 Hz, 1H), 7.29 (d, J=8.8 Hz, 2H), 6.90 (d, J=8.8 Hz, 2H), 4.09 (s, 3H), 3.88-3.83 (m, 4H), 3.73 (s, 3H), 3.69 (s, 2H), 3.35-3.29 (m, 4H). MS=486 (MH)+.

Example 375. [4-(5-Methoxy-4-piperazin-1-yl-pyrido[3,4-d]pyrimidin-2-yl)-pyridin-2-yl]-(6-morpholin-4-yl-pyridin-3-yl)-amine

[4-(5-Methoxy-4-piperazin-1-yl-pyrido[3,4-d]pyrimidin-2-yl)-pyridin-2-yl]-(6-morpholin-4-yl-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (106.0 mg, 0.2320 mmol) and 6-Morpholin-4-yl-pyridin-3-ylamine (48.0 mg, 0.268 mmol) in an analogous manner to Example 303c and Example 1501c. Product isolated as the bis-trifluoroacetic acid salt as a yellow lyophilate (0.148 g, 87%). $^1$HNMR (400 MHz, d6-DMSO, δ, ppm): 9.52 (br s, 1H), 8.98-8.85 (m, 3H), 8.59 (br s, 1H), 8.43 (s, 1H), 8.26 (d, J=5.3 Hz, 1H), 8.01-7.96 (m, 1H), 7.90 (s, 1H), 7.70 (d, J=5.2 Hz, 1H), 7.09 (br s, 1H), 4.10 (s, 3H), 3.90-3.85 (m, 4H), 3.77-3.72 (m, 4H), 3.48-3.42 (m, 4H), 3.36-3.29 (m, 4H). MS=500 (MH)+.

Example 376. {2-[2-(Pyridin-3-ylamino)-pyridin-4-yl]-pyrido[3,4-d]pyrimidin-4-yl}-(R)-pyrrolidin-3-yl-amine {2-[2-(Pyridin-3-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-pyrido[3,4-d]pyrimidin-4-ylamino]-pyrrolidine-1-carboxylic acid tert-butyl ester (103.0 mg, 0.2413 mmol) and 3-aminopyridine (27.0 mg, 0.287 mmol) in an analogous manner to Example 303c and Example 1501c. Product isolated as the bis-trifluoroacetic acid salt as a pale yellow lyophilate (0.141 g, 95%). $^1$HNMR (400 MHz, d6-DMSO, δ, ppm): 10.25 (br s, 1H), 9.39 (s, 1H), 9.24 (d, J=0.6 Hz, 1H), 8.97 (br s, 2H), 8.76 (d, J=5.5 Hz, 1H), 8.73 (d, J=5.6 Hz, 1H), 8.51-8.45 (m, 2H), 8.38 (d, J=5.2 Hz, 1H), 8.28 (dd, J=5.6, 0.7 Hz, 1H), 8.07 (s, 1H), 7.93 (dd, J=5.3, 1.2 Hz, 1H), 7.81 (dd, J=8.2, 5.34 Hz, 1H), 5.02-4.93 (m, 1H), 3.78-3.69 (m, 1H), 3.55-3.34 (m, 3H), 2.47-2.37 (m, 1H), 2.32-2.22 (m, 1H). MS=385 (MH)+.

Example 377. {5-Methoxy-2-[2-(pyridin-3-ylamino)-pyridin-4-yl]-pyrido[3,4-d]pyrimidin-4-yl}-(R)-pyrrolidin-3-yl-amine {5-Methoxy-2-[2-(pyridin-3-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (107.0 mg, 0.2342 mmol)

and 3-aminopyridine (25.0 mg, 0.266 mmol) in an analogous manner to Example 303c and Example 1501c. Product Isolated as the Bis-Trifluoroacetic Acid Salt as a Pale Yellow Lyophilate (0.063 g, 41%). $^1$HNMR (400 MHz, d6-DMSO, δ, ppm): 10.15 (br s, 1H), 9.31 (s, 1H), 9.05 (br s, 1H), 8.92 (br s, 1H), 8.84 (s, 1H), 8.48-8.41 (m, 3H), 8.34 (d, J=5.0 Hz, 1H), 8.20 (d, J=6.3 Hz, 1H), 8.03 (s, 1H), 7.87 (d, J=5.3 Hz, 1H), 7.74-7.71 (m, 1H), 5.09-5.00 (m, 1H), 4.17 (s, 3H), 3.74-3.65 (m, 1H), 3.52-3.29 (m, 3H), 2.54-2.44 (m, 1H), 2.27-2.17 (m, 1H). MS=415 (MH)+.

Example 378. [4-(5-Methoxy-4-piperazin-1-yl-pyrido[3,4-d]pyrimidin-2-yl)-pyridin-2-yl]-pyridin-3-yl-amine

[4-(5-Methoxy-4-piperazin-1-yl-pyrido[3,4-d]pyrimidin-2-yl)-pyridin-2-yl]-pyridin-3-yl-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 3-aminopyridine (25.0 mg, 0.266 mmol) in an analogous manner to Example 303c and Example 1501c. Product isolated as the bis trifluoroacetic acid salt as a yellow lyophilate (0.123 g, 87%). $^1$HNMR (400 MHz, d6-DMSO, δ, ppm): 10.17 (br s, 1H), 9.33 (s, 1H), 9.02-8.88 (m, 3H), 8.49-8.42 (m, 3H), 8.34 (d, J=4.6 Hz, 1H), 8.03 (s, 1H), 7.87 (dd, J=5.2, 1.3 Hz, 1H), 7.74 (dd, J=8.3, 5.2 Hz, 1H), 4.11 (s, 3H), 3.92-3.86 (m, 4H), 3.37-3.30 (m, 4H). MS=415 (MH)+.

Example 379. 2-[4-(5-Methoxy-4-piperazin-1-yl-yl-pyrido[3,4-d]pyrimidin-2-yl)-pyridin-2-ylamino]-isonicotinamide 2-[4-(5-Methoxy-4-piperazin-1-yl-pyrido[3,4-d]pyrimidin-2-yl)-pyridin-2-ylamino]-isonicotinamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-Amino-isonicotinamide (36.0 mg, 0.262 mmol) in an analogous manner to Example 303c and Example 1501c. Product isolated as the trifluoroacetic acid salt as a yellow lyophilate (0.004 g, 2%). $^1$HNMR (400 MHz, d6-DMSO, δ, ppm): 8.94 (s, 1H), 8.86 (br s, 2H), 8.69 (s, 1H), 8.46 (d, J=5.5 Hz, 1H), 8.44 (s, 1H), 8.41 (d, J=5.3 Hz, 1H), 8.19 (br s, 1H), 8.09 (br s, 1H), 7.95-7.91 (m, 1H), 7.71 (br s, 1H), 7.36-7.33 (m, 1H), 4.11 (s, 3H), 3.93-3.89 (m, 4H), 3.37-3.30 (m, 4H). MS=458 (MH)+.

Example 380. 6-[4-(5-Methoxy-4-piperazin-1-yl-yl-pyrido[3,4-d]pyrimidin-2-yl)-pyridin-2-ylamino]-nicotinamide 6-[4-(5-Methoxy-4-piperazin-1-yl-pyrido[3,4-d]pyrimidin-2-yl)-pyridin-2-ylamino]-nicotinamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Amino-nicotinamide (36.0 mg, 0.262 mmol) in an analogous manner to Example 303c and Example 1501c. Product isolated as the trifluoroacetic acid salt as a pale yellow lyophilate (0.047 g, 37%). $^1$HNMR (400 MHz, d6-DMSO, δ, ppm): 9.08 (br s, 2H), 8.94 (s, 1H), 8.83 (s, 1H), 8.72 (s, 1H), 8.50 (d, J=5.4 Hz, 1H), 8.45 (s, 1H), 8.26 (br s, 1H), 8.10-7.99 (m, 2H), 7.72 (br s, 1H), 7.47 (br s, 1H), 4.11 (s, 3H), 3.96-3.92 (m, 4H), 3.36-3.29 (m, 4H). MS=458 (MH)+.

Example 382. (3-Methoxy-4-morpholin-4-yl-phenyl)-[4-(5-methoxy-4-piperazin-1-yl-pyrido[3,4-d]pyrimidin-2-yl)-pyridin-2-yl]-amine (3-Methoxy-4-morpholin-4-yl-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (110.0 mg, 0.2407 mmol) and 3-Methoxy-4-morpholin-4-yl-phenylamine (55.0 mg, 0.264 mmol) [prepared as described in WO2008/051547] in an analogous manner to Example 303c and Example 1501c. Product isolated as the trifluoroacetic acid salt as an orange lyophilate (0.147 g, 95%). $^1$HNMR (400 MHz, d6-DMSO, δ, ppm): 9.71 (br s, 1H), 9.12-8.95 (m, 2H), 8.91 (s, 1H), 8.43 (s, 1H), 8.25 (d, J=5.3 Hz, 1H), 7.99 (s, 1H), 7.72 (d, J=4.9 Hz, 1H), 7.44 (br s, 1H), 7.25 (d, J=7.5 Hz, 1H), 7.06 (br s, 1H), 4.11 (s, 3H), 3.92-3.86 (m, 4H), 3.84 (s, 3H), 3.82-3.76 (m, 4H), 3.35-3.29 (m, 4H), 3.17-3.00 (m, 4H). MS=529 (MH)+.

Example 383. [4-(5-Methoxy-4-piperazin-1-yl-pyrido[3,4-d]pyrimidin-2-yl)-pyridin-2-yl]-(2-methyl-4-morpholin-4-yl-phenyl)-amine

[4-(5-Methoxy-4-piperazin-1-yl-pyrido[3,4-d]pyrimidin-2-yl)-pyridin-2-yl]-(2-methyl-4-morpholin-4-yl-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-Methyl-4-morpholin-4-yl-phenylamine (50.0 mg, 0.260 mmol)[prepared as described in WO2008/051547] in an analogous manner to Example 303c and Example 1501c. Product isolated as the trifluoroacetic acid salt as an orange lyophilate (0.125 g, 91%). $^1$HNMR (400 MHz, d6-DMSO, δ, ppm): 10.06 (br s, 1H), 9.07-8.95 (m, 2H), 8.92 (s, 1H), 8.46 (s, 1H), 8.01 (d, J=5.9 Hz, 1H), 7.74 (dd, J=6.3, 1.1 Hz, 1H), 7.27 (d, J=8.7 Hz, 1H), 7.00 (d, J=2.5 Hz, 1H), 6.92 (dd, J=8.8, 2.7 Hz, 1H), 4.11 (s, 3H), 3.89-3.84 (m, 4H), 3.79-3.75 (m, 4H), 3.34-3.27 (m, 4H), 3.20-3.16 (m, 4H), 2.20 (s, 3H). MS=513 (MH)+.

Example 384. 5-[4-(5-Methoxy-4-piperazin-1-yl-pyrido[3,4-d]pyrimidin-2-yl)-pyridin-2-ylamino]-pyridine-2-carbonitrile 5-[4-(5-Methoxy-4-piperazin-1-yl-pyrido[3,4-d]pyrimidin-2-yl)-pyridin-2-ylamino]-pyridine-2-carbonitrile was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 5-Amino-pyridine-2-carbonitrile (32.0 mg, 0.269 mmol) in an analogous manner to Example 303c and Example 1501c. Product isolated as the trifluoroacetic acid salt as a yellow lyophilate (0.093 g, 76%). $^1$HNMR (400 MHz, d6-DMSO, δ, ppm): 10.24 (s, 1H), 8.95 (d, J=2.4 Hz, 1H), 8.91 (s, 1H), 8.88 (br s, 2H), 8.56 (dd, J=8.7, 2.6 Hz, 1H), 8.47 (d, J=5.4 Hz, 1H), 8.43 (s, 1H), 8.05 (s, 1H), 7.93 (d, J=8.6 Hz, 1H), 7.90 (dd, J=5.4, 1.4 Hz, 1H), 4.11 (s, 3H), 3.91-3.87 (m, 4H), 3.36-3.30 (m, 4H). MS=440 (MH)+.

Example 385. {5-Methoxy-2-[2-(pyrimidin-5-ylamino)-pyridin-4-yl]-pyrido[3,4-d]pyrimidin-4-yl}-(R)-pyrrolidin-3-yl-amine {5-Methoxy-2-[2-(pyrimidin-5-ylamino)-pyridin-4-yl]-pyrido[3,4-d]pyrimidin-4-yl}-(R)-pyrrolidin-3-yl-amine was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (108.0 mg, 0.2364 mmol) and Pyrimidin-5-ylamine (25.0 mg, 0.263 mmol) in an analogous manner to Example 303c and Example 1501c. Product isolated as the trifluoroacetic acid salt as a yellow lyophilate (0.029 g, 22%). $^1$HNMR (400 MHz, d6-DMSO, δ, ppm): 9.77 (s, 1H), 9.22-9.21 (m, 2H), 9.00-8.80 (m, 3H), 8.74 (s, 1H), 8.43-8.40 (m, 2H), 8.18 (d, J=6.3 Hz, 1H), 7.99 (s, 1H), 7.83 (dd, J=5.3, 1.4 Hz, 1H), 5.08-4.98 (m, 1H), 4.17 (s, 3H), 3.74-3.64 (m, 1H), 3.50-3.30 (m, 3H), 2.52-2.44 (m, 1H), 2.28-2.18 (m, 1H). MS=416 (MH)+.

Example 386. [4-(5-Methoxy-4-piperazin-1-yl-pyrido[3,4-d]pyrimidin-2-yl)-pyridin-2-yl]-pyrimidin-5-yl-amine

[4-(5-Methoxy-4-piperazin-1-yl-pyrido[3,4-d]pyrimidin-2-yl)-pyridin-2-yl]-pyrimidin-5-yl-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and Pyrimidin-5-ylamine (25.0 mg, 0.263 mmol) in an analogous manner to Example 303c and Example 1501c. Product isolated as the trifluoroacetic acid salt as a yellow lyophilate (0.073 g, 62%). $^1$HNMR (400 MHz, d6-DMSO, δ, ppm): 9.79 (s, 1H), 9.22-9.21 (m, 2H), 8.98-8.95 (m, 3H), 8.74 (s, 1H), 8.43-8.40 (m, 2H), 7.99 (s, 1H), 7.82 (dd, J=5.3, 1.4 Hz, 1H), 4.11 (s, 3H), 3.92-3.86 (m, 4H), 3.37-3.29 (m, 4H). MS=416 (MH)+.

Example 387. [4-(5-Methoxy-4-piperazin-1-yl-pyrido[3,4-d]pyrimidin-2-yl)-pyridin-2-yl]-pyridin-2-yl-amine

[4-(5-Methoxy-4-piperazin-1-yl-pyrido[3,4-d]pyrimidin-2-yl)-pyridin-2-yl]-pyridin-2-yl-amine was prepared from 4-[2-(2-Chloro-pyridin-4-yl)-5-methoxy-pyrido[3,4-d]pyrimidin-4-yl]-piperazine-1-carboxylic acid tert-butyl ester (102.0 mg, 0.2232 mmol) and 2-Pyridinamine (25.0 mg, 0.266 mmol) in an analogous manner to Example 303c and Example 1501c. Product isolated as the trifluoroacetic acid salt as a yellow lyophilate (0.056 g, 47%). $^1$HNMR (400 MHz, d6-DMSO, δ, ppm): 11.54 (br s, 1H), 9.05-8.90 (m, 3H), 8.53 (d, J=4.9 Hz, 1H), 8.50-8.45 (m, 2H), 8.39 (d, J=5.2 Hz, 1H), 8.11-8.00 (m, 2H), 7.54 (s, 1H), 7.21 (s, 1H), 4.12 (s, 3H), 3.94-3.89 (m, 4H), 3.37-3.30 (m, 4H). MS=415 (MH)+.

Example 388. 2-[4-(5-Methoxy-4-morpholin-4-yl-pyrido[3,4-d]pyrimidin-2-yl)-pyridin-2-ylamino]-isonicotinonitrile 388a) 2-(2-Chloro-pyridin-4-yl)-5-methoxy-4-morpholin-4-yl-pyrido[3,4-d]pyrimidine was prepared from 2-(2-Chloro-pyridin-4-yl)-5-methoxy-pyrido[3,4-d]pyrimidin-4-ol (0.25 g, 0.86 mmol) and Morpholine (0.10 mL, 1.1 mmol) in an analogous manner to [B016]. Product isolated as a tan solid (0.269 g, 87%). $^1$HNMR (400 MHz, d6-DMSO, δ, ppm): 8.87 (s, 1H), 8.60 (dd, J=5.0, 0.9 Hz, 1H), 8.38 (s, 1H), 8.33-8.30 (m, 2H), 4.08 (s, 3H), 3.81-3.71 (m, 8H). MS=358 (MH)+.

388b) 2-[4-(5-Methoxy-4-morpholin-4-yl-pyrido[3,4-d]pyrimidin-2-yl)-pyridin-2-ylamino]-isonicotinonitrile was prepared from 2-(2-Chloro-pyridin-4-yl)-5-methoxy-4-morpholin-4-yl-pyrido[3,4-d]pyrimidine (100.0 mg, 0.2795 mmol) and 2-Amino-isonicotinonitrile (40.0 mg, 0.336 mmol) in an analogous manner to Example 303c and Example 1501c. Product isolated as the trifluoroacetic acid salt as a yellow lyophilate (0.014 g, 9%). $^1$HNMR (400 MHz, d6-DMSO, δ, ppm): 10.63 (br s, 1H), 8.87 (s, 1H), 8.58 (s, 1H), 8.51 (d, J=5.0 Hz, 1H), 8.47 (d, J=5.4 Hz, 1H), 8.37 (s, 1H), 8.29 (s, 1H), 7.92 (d, J=5.4 Hz, 1H), 7.35 (d, J=4.9 Hz, 1H), 4.09 (s, 3H), 3.82-3.74 (m, 8H). MS=441 (MH)+.

Example 389. 2-(3-Cyano-phenyl)-N-[4-(5-methoxy-4-morpholin-4-yl-pyrido[3,4-d]pyrimidin-2-yl)-pyridin-2-yl]-acetamide 2-(3-Cyano-phenyl)-N-[4-(5-methoxy-4-morpholin-4-yl-pyrido[3,4-d]pyrimidin-2-yl)-pyridin-2-yl]-acetamide was prepared from 2-(2-Chloro-pyridin-4-yl)-5-methoxy-4-morpholin-4-yl-pyrido[3,4-d]pyrimidine (110.0 mg, 0.3074 mmol) and 2-(3-Cyano-phenyl)-acetamide (54.0 mg, 0.337 mmol) in an analogous manner to Example 303c and Example 1501c. Product isolated as the trifluoroacetic acid salt as a yellow lyophilate (0.082 g, 44%). $^1$HNMR (400 MHz, d6-DMSO, δ, ppm): 10.96 (s, 1H), 9.03 (s, 1H), 8.85 (s, 1H), 8.49 (dd, J=5.1, 0.6 Hz, 1H), 8.35 (s, 1H), 8.04 (dd, J=5.1, 1.5 Hz, 1H), 7.84-7.82 (m, 1H), 7.77-7.74 (m, 1H), 7.73-7.70 (m, 1H), 7.57 (t, J=7.8 Hz, 1H), 4.07 (s, 3H), 3.89 (s, 2H), 3.79-3.69 (m, 8H). MS=482 (MH)+.

Example 390. [4-(5-Methoxy-4-piperazin-1-yl-pyrido[3,4-d]pyrimidin-2-yl)-pyridin-2-yl]-(3,4,5-trimethoxy-phenyl)-amine 4-(5-Methoxy-4-piperazin-1-yl-pyrido[3,4-d]pyrimidin-2-yl)-pyridin-2-yl]-(3,4,5-trimethoxy-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (106.0 mg, 0.2320 mmol) and 3,4,5-Trimethoxyaniline (48.0 mg, 0.262 mmol) in an analogous manner to Example 303c and Example 1501c. Product isolated as the trifluoroacetic acid salt as an orange lyophilate (0.074 g, 52%). $^1$HNMR (400 MHz, d6-DMSO, δ, ppm): 9.45 (br s, 1H), 8.98-8.84 (m, 3H), 8.42 (s, 1H), 8.30 (d, J=5.4 Hz, 1H), 7.94 (s, 1H), 7.70 (d, J=5.6 Hz, 1H), 7.13-7.10 (m, 2H), 4.10 (s, 3H), 3.90-3.85 (m, 4H), 3.79 (s, 6H), 3.64 (s, 3H), 3.36-3.29 (m, 4H). MS=504 (MH)+.

Example 391. N-[4-(5-Methoxy-4-piperazin-1-yl-yl-pyrido[3,4-d]pyrimidin-2-yl)-pyridin-2-yl]-2-(4-trifluoromethyl-phenyl)-acetamide 391a) 2-(4-Trifluoromethyl-phenyl)-acetamide was prepared from (4-Trifluoromethyl-phenyl)-acetic acid (1.0 g, 4.9 mmol) in an analogous manner to Example 313a. Product isolated as a white solid (0.92 g, 92%). $^1$HNMR (400 MHz, d6-DMSO, δ, ppm): 7.66 (d, J=8.1 Hz, 2H), 7.54 (br s, 1H), 7.47 (d, J=8.0 Hz, 2H), 6.96 (br s, 1H), 3.49 (s, 2H). MS=204 (MH)+.

391b) N-[4-(5-Methoxy-4-piperazin-1-yl-pyrido[3,4-d]pyrimidin-2-yl)-pyridin-2-yl]-2-(4-trifluoromethyl-phenyl)-acetamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-(4-Trifluoromethyl-phenyl)-acetamide (54.0 mg, 0.266 mmol) in an analogous manner to Example 303c and Example 1501c. Product isolated as the trifluoroacetic acid salt as a yellow lyophilate (0.051 g, 36%). $^1$HNMR (400 MHz, d6-DMSO, δ, ppm): 10.99 (s, 1H), 9.08 (s, 1H), 8.91 (s, 1H), 8.84 (br s, 2H), 8.52 (dd, J=5.1, 0.5 Hz, 1H), 8.41 (s, 1H), 8.06 (dd, J=5.1, 1.4 Hz, 1H), 7.72 (d, J=8.1 Hz, 2H), 7.60 (d, J=8.0 Hz, 2H), 4.09 (s, 3H), 3.92 (s, 2H), 3.87-3.83 (m, 4H), 3.34-3.28 (m, 4H). MS=524 (MH)+.

Example 392. [4-(5-Methoxy-4-piperazin-1-yl-pyrido[3,4-d]pyrimidin-2-yl)-pyridin-2-yl]-(6-phenyl-pyridin-3-yl)-amine

[4-(5-Methoxy-4-piperazin-1-yl-pyrido[3,4-d]pyrimidin-2-yl)-pyridin-2-yl]-(6-phenyl-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Phenyl-pyridin-3-ylamine (45.0 mg, 0.264 mmol) in an analogous manner to Example 303c and Example 1501c. Product isolated as the trifluoroacetic acid salt as a yellow lyophilate (0.086 g, 65%). $^1$HNMR (400 MHz, d6-DMSO, δ, ppm): 9.82 (s, 1H), 9.01 (d, J=2.3 Hz, 1H), 8.95-8.85 (m, 3H), 8.46-8.40 (m, 3H), 8.06-7.95 (m, 4H), 7.80 (dd, J=5.3, 1.3 Hz, 1H), 7.49 (t, J=7.4 Hz, 2H), 7.42-7.37 (m, 1H), 4.11 (s, 3H), 3.92-3.87 (m, 4H), 3.37-3.30 (m, 4H). MS=491 (MH)+.

Example 393. [4-(5-Methoxy-4-piperazin-1-yl-pyrido[3,4-d]pyrimidin-2-yl)-pyridin-2-yl]-(6-methyl-pyridin-3-yl)-amine

[4-(5-Methoxy-4-piperazin-1-yl-pyrido[3,4-d]pyrimidin-2-yl)-pyridin-2-yl]-(6-methyl-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Methyl-pyridin-3-ylamine (29.0 mg, 0.268 mmol) in an analogous manner to Example 303c and Example 1501c. Product isolated as the trifluoroacetic acid salt as a yellow lyophilate (0.068 g, 56%). $^1$HNMR (400 MHz, d6-DMSO, δ, ppm): 10.22 (s, 1H), 9.34 (s, 1H), 8.96 (br s, 2H), 8.91 (s, 1H), 8.46 (d, J=5.4 Hz, 1H), 8.43 (s, 1H), 8.38 (dd, J=8.8, 2.4 Hz, 1H), 8.02 (s, 1H), 7.88 (dd, J=5.3, 1.4 Hz, 1H), 7.73 (d, J=8.8 Hz, 1H), 4.11 (s, 3H), 3.91-3.87 (m, 4H), 3.36-3.30 (m, 4H), 2.61 (s, 3H). MS=429 (MH)+.

Example 394. [4-(5-Methoxy-4-piperazin-1-yl-pyrido[3,4-d]pyrimidin-2-yl)-pyridin-2-yl]-(6-methoxy-pyridin-3-yl)-amine

[4-(5-Methoxy-4-piperazin-1-yl-pyrido[3,4-d]pyrimidin-2-yl)-pyridin-2-yl]-(6-methoxy-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 5-Amino-2-methoxypyridine (33.0 mg, 0.266 mmol) in an analogous manner to Example 303c and Example 1501c. Product isolated as the trifluoroacetic acid salt as an orange lyophilate (0.091 g, 74%). $^1$HNMR (400 MHz, d6-DMSO, δ, ppm): 9.43 (s, 1H), 9.00-8.85 (m, 3H), 8.48 (d, J=2.8 Hz, 1H), 8.42 (s, 1H), 8.26 (d, J=5.4 Hz, 1H), 8.06 (dd, J=8.8, 2.7 Hz, 1H), 7.89 (s, 1H), 7.69 (dd, J=5.3, 1.1 Hz, 1H), 6.83 (d, J=8.8 Hz, 1H), 4.10 (s, 3H), 3.90-3.86 (m, 4H), 3.84 (s, 3H), 3.35-3.29 (m, 4H). MS=445 (MH)+.

Example 395. [4-(5-Methoxy-4-piperazin-1-yl-pyrido[3,4-d]pyrimidin-2-yl)-pyridin-2-yl]-(6-trifluoromethyl-pyridin-3-yl)-amine

[4-(5-Methoxy-4-piperazin-1-yl-pyrido[3,4-d]pyrimidin-2-yl)-pyridin-2-yl]-(6-trifluoromethyl-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Trifluoromethyl-pyridin-3-ylamine (43.0 mg, 0.265 mmol) in an analogous manner to Example 303c and Example 1501c. Product isolated as the trifluoroacetic acid salt as an orange lyophilate (0.084 g, 64%). $^1$HNMR (400 MHz, d6-DMSO, δ, ppm): 10.09 (s, 1H), 8.96 (d, J=2.5 Hz, 1H), 8.94-8.84 (m, 3H), 8.61 (dd, J=8.7, 2.3 Hz, 1H), 8.46-8.42 (m, 2H), 8.04 (s, 1H), 7.86 (dd, J=5.3, 1.3 Hz, 1H), 7.81 (d, J=8.9 Hz, 1H), 4.11 (s, 3H), 3.93-3.86 (m, 4H), 3.37-3.30 (m, 4H). MS=483 (MH)+.

Example 396. N-{4-[5-Methoxy-4-((R)-pyrrolidin-3-ylamino)-pyrido[3,4-d]pyrimidin-2-yl]-pyridin-2-yl}-2-pyridin-3-yl-acetamide N-{4-[5-Methoxy-4-((R)-pyrrolidin-3-ylamino)-pyrido[3,4-d]pyrimidin-2-yl]-pyridin-2-yl}-2-pyridin-3-yl-acetamide was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (100.0 mg, 0.2188 mmol) and 2-Pyridin-3-yl-acetamide (35.0 mg, 0.257 mmol) in an analogous manner to Example 303c and Example 1501c. Product isolated as the trifluoroacetic acid salt as a yellow lyophilate (0.008 g, 6%). $^1$HNMR (400 MHz, d6-DMSO, δ, ppm): 10.99 (s, 1H), 9.09 (s, 1H), 8.95-8.75 (m, 3H), 8.64 (s, 1H), 8.56 (d, J=4.7 Hz, 1H), 8.51 (d, J=5.1 Hz, 1H), 8.40 (s, 1H), 8.15 (d, J=6.1 Hz, 1H), 8.07 (dd, J=5.2, 1.4 Hz, 1H), 7.93 (d, J=7.7 Hz, 1H), 7.54-7.48 (m, 1H), 4.98-4.90 (m, 1H), 4.15 (s, 3H), 3.49 (s, 2H), 3.70-3.60 (m, 1H), 3.48-3.28 (m, 3H), 2.53-2.43 (m, 1H), 2.25-2.15 (m, 1H). MS=457 (MH)+.

Example 397. 2-{4-[5-Methoxy-4-(4-methyl-piperazin-1-yl)-pyrido[3,4-d]pyrimidin-2-yl]-pyridin-2-ylamino}-isonicotinonitrile 397a) 2-(2-Chloro-pyridin-4-yl)-5-methoxy-4-(4-methyl-piperazin-1-yl)-pyrido[3,4-d]pyrimidine was prepared from 2-(2-Chloro-pyridin-4-yl)-5-methoxy-pyrido[3,4-d]pyrimidin-4-ol (0.25 g, 0.86 mmol) and 1-Methylpiperazine (0.12 mL, 1.0 mmol) in an analogous manner to [B016]. Product isolated as tan needles (0.283 g, 88%). $^1$HNMR (400 MHz, d6-DMSO, δ, ppm): 8.85 (s, 1H), 8.60 (d, J=5.1 Hz, 1H), 8.37 (s, 1H), 8.33-8.29 (m, 2H), 4.07 (s, 3H), 3.75-3.70 (m, 4H), 2.52-2.48 (m, 4H), 2.24 (s, 3H). MS=371, 373 (MH)+.

397b) 2-{4-[5-Methoxy-4-(4-methyl-piperazin-1-yl)-pyrido[3,4-d]pyrimidin-2-yl]-pyridin-2-ylamino}-isonicotinonitrile was prepared from 2-(2-Chloro-pyridin-4-yl)-5-methoxy-4-(4-methyl-piperazin-1-yl)-pyrido[3,4-d]pyrimidine (100.0 mg, 0.2697 mmol) and 2-Amino-isonicotinonitrile (39.0 mg, 0.327 mmol) in an analogous manner to Example 303c and Example 1501c. Product isolated as the trifluoroacetic acid salt as a yellow lyophilate (0.123 g, 80%). $^1$HNMR (400 MHz, d6-DMSO, δ, ppm): 10.46 (s, 1H), 9.83 (s, 1H), 8.94 (s, 1H), 8.64 (s, 1H), 8.51 (dd, J=5.0, 0.6 Hz, 1H), 8.49 (d, J=5.3 Hz, 1H), 8.44 (s, 1H), 8.35 (s, 1H), 7.93 (dd, J=5.3, 1.4 Hz, 1H), 7.33 (dd, J=5.1, 1.4 Hz, 1H), 4.43 (d, J=13.4, 2H), 4.12 (s, 3H), 3.60 (d, J=11.8 Hz, 2H), 3.46 (t, J=12.9 Hz, 2H), 3.30-3.20 (m, 2H), 2.97-2.85 (m, 3H). MS=454 (MH)+.

Example 398. 2-(3-Chloro-phenyl)-N-{4-[5-methoxy-4-(4-methyl-piperazin-1-yl)-pyrido[3,4-d]pyrimidin-2-yl]-pyridin-2-yl}-acetamide 2-(3-Chloro-phenyl)-N-{4-[5-methoxy-4-(4-methyl-piperazin-1-yl)-pyrido[3,4-d]pyrimidin-2-yl]-pyridin-2-yl}-acetamide was prepared from 2-(2-Chloro-pyridin-4-yl)-5-methoxy-4-(4-methyl-piperazin-1-yl)-pyrido[3,4-d] pyrimidine (100.0 mg, 0.2697 mmol) and 2-(3-Chloro-phenyl)-acetamide (55.1 mg, 0.325 mmol) in an analogous manner to Example 303c and Example 1501c. Product isolated as the trifluoroacetic acid salt as an orange lyophilate (0.050 g, 29%). $^1$HNMR (400 MHz, d6-DMSO, δ, ppm): 10.94 (s, 1H), 9.89 (br s, 1H), 9.09 (s, 1H), 8.92 (s, 1H), 8.52 (dd, J=5.1, 0.6 Hz, 1H), 8.42 (s, 1H), 8.07 (dd, J=5.2, 1.5 Hz, 1H), 7.47-7.75 (m, 1H), 7.41-7.32 (m, 3H), 4.37 (d, J=13.9 Hz, 2H), 4.11 (s, 3H), 3.81 (s, 2H), 3.59 (d, J=11.8 Hz, 2H), 3.41 (t, J=13.1 Hz, 2H), 3.29-3.17 (m, 2H), 2.89 (s, 3H). MS=504, 506 (MH)+.

Example 399. N-[4-(5-Methoxy-4-piperazin-1-yl-pyrido[3,4-d]pyrimidin-2-yl)-pyridin-2-yl]-2-pyridin-3-yl-acetamide N-[4-(5-Methoxy-4-piperazin-1-yl-pyrido[3,4-d]pyrimidin-2-yl)-pyridin-2-yl]-2-pyridin-3-yl-acetamide was prepared from 4-[2-(2-Chloro-pyridin-4-yl)-5-methoxy-pyrido [3,4-d]pyrimidin-4-yl]-piperazine-1-carboxylic acid tert-butyl ester (100.0 mg, 0.2188 mmol) and 2-Pyridin-3-yl-acetamide (36.0 mg, 0.264 mmol), in an analogous manner to Example 303c and Example 1501c. Product isolated as the trifluoroacetic acid salt as a yellow lyophilate (0.115 g, 91%). HNMR (400 MHz, d6-DMSO, δ, ppm): 11.03 (s, 1H), 9.07 (s, 1H), 8.92-8.83 (m, 3H), 8.71 (d, J=1.5 Hz, 1H), 8.64 (dd, J=5.1, 1.2 Hz, 1H), 8.52 (dd, J=5.1, 0.6 Hz, 1H), 8.41 (s, 1H), 8.11-8.05 (m, 2H), 7.68-7.63 (m, 1H), 4.09 (s, 3H), 3.96 (s, 2H), 3.87-3.82 (m, 4H), 3.34-3.28 (m, 4H). MS=457 (MH)+.

Example 400. N-[4-(5-Methoxy-4-piperazin-1-yl-pyrido[3,4-d]pyrimidin-2-yl)-pyridin-2-yl]-2-pyridin-4-yl-acetamide N-[4-(5-Methoxy-4-piperazin-1-yl-pyrido[3,4-d]pyrimidin-2-yl)-pyridin-2-yl]-2-pyridin-4-yl-acetamide was prepared from 4-[2-(2-Chloro-pyridin-4-yl)-5-methoxy-pyrido [3,4-d]pyrimidin-4-yl]-piperazine-1-carboxylic acid tert-butyl ester (100.0 mg, 0.2188 mmol) and 2-Pyridin-4-yl-acetamide (35.0 mg, 0.257 mmol) in an analogous manner to Example 303c and Example 1501c. Product isolated as the trifluoroacetic acid salt as an orange lyophilate resin (0.113 g, 90%). $^1$HNMR (400 MHz, d6-DMSO, δ, ppm): 11.06 (s, 1H), 9.07 (s, 1H), 8.90 (s, 1H), 8.86 (br s, 2H), 8.71 (s, 2H), 8.53 (dd, J=5.1, 0.6 Hz, 1H), 8.41 (s, 1H), 8.08 (dd. J=5.2, 1.5 Hz, 1H), 7.71 (br s, 2H), 4.09 (s, 3H), 4.03 (s, 2H), 3.87-3.83 (m, 4H), 3.34-3.28 (m, 4H). MS=457 (MH)+.

Example 401. [4-(5-Methoxy-4-piperazin-1-yl-pyrido[3,4-d]pyrimidin-2-yl)-pyridin-2-yl]-(4-methoxy-pyridin-2-yl)-amine

[4-(5-Methoxy-4-piperazin-1-yl-pyrido[3,4-d]pyrimidin-2-yl)-pyridin-2-yl]-(4-methoxy-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-Methoxy-pyridin-2-ylamine (33.0 mg, 0.266 mmol) in an analogous manner to Example 303c and Example 1501c. Product isolated as the trifluoroacetic acid salt as a yellow lyophilate (0.098 g, 79%). $^1$HNMR (400 MHz, d6-DMSO, δ, ppm): 9.00-8.90 (m, 3H), 8.55 (d, J=5.4 Hz, 1H), 8.45 (s, 1H), 8.31 (s, 1H), 8.24 (d, J=6.9 Hz, 1H), 8.12-8.08 (m, 1H), 6.92 (br s, 2H), 4.11 (s, 3H), 4.00 (s, 3H), 3.93-3.88 (m, 4H), 3.37-3.30 (m, 4H). MS=445 (MH)+.

Example 402. 2-{4-[4-(4-Hydroxy-piperidin-1-yl)-5-methoxy-pyrido[3,4-d]pyrimidin-2-yl]-pyridin-2-ylamino}-isonicotinonitrile 402a) 1-[2-(2-Chloro-pyridin-4-yl)-5-methoxy-pyrido[3,4-d]pyrimidin-4-yl]-piperidin-4-ol was prepared from 2-(2-Chloro-pyridin-4-yl)-5-methoxy-pyrido[3,4-d]pyrimidin-4-ol (0.40 g, 1.4 mmol) and Piperidin-4-ol (0.17 g, 1.7 mmol) in an analogous manner to [B016]. Product isolated as an orange solid (0.317 g, 62%). $^1$HNMR (400 MHz, d6-DMSO, δ, ppm): 8.84 (s, 1H), 8.60 (dd, J=4.9, 0.7 Hz, 1H), 8.36 (s, 1H), 8.32-8.29 (m, 2H), 4.81 (d, J=4.1 Hz, 1H), 4.08 (s, 3H), 4.05-3.97 (m, 2H), 3.85-3.77 (m, 1H), 3.45-3.37 (m, 2H), 1.96-1.88 (m, 2H), 1.61-1.51 (m, 2H). MS=372, 374 (MH)+.

402b) 2-{4-[4-(4-Hydroxy-piperidin-1-yl)-5-methoxy-pyrido[3,4-d]pyrimidin-2-yl]-pyridin-2-ylamino}-isonicotinonitrile was prepared from 1-[2-(2-Chloro-pyridin-4-yl)-5-methoxy-pyrido[3,4-d]pyrimidin-4-yl]-piperidin-4-ol (100.0 mg, 0.2689 mmol) and 2-Amino-isonicotinonitrile (39.0 mg, 0.327 mmol) in an analogous manner to Example 303c and Example 1501c. Product isolated as the trifluoroacetic acid salt as a yellow lyophilate (0.082 g, 53%). $^1$HNMR (400 MHz, d6-DMSO, δ, ppm): 10.76 (br s, 1H), 8.84 (s, 1H), 8.58 (s, 1H), 8.52 (d, J=5.2 Hz, 1H), 8.47 (d, J=5.6 Hz, 1H), 8.36 (s, 1H), 8.23 (s, 1H), 7.93 (d, J=5.6 Hz, 1H), 7.37 (d, J=4.3 Hz, 1H), 4.09 (s, 3H), 4.08-4.00 (m, 2H), 3.87-3.80 (m, 1H), 3.50-3.40 (m, 2H), 1.97-1.89 (m, 2H), 1.64-1.54 (m, 2H). MS=455 (MH)+.

Example 403. 2-(3-Cyano-phenyl)-N-{4-[4-(4-hydroxy-piperidin-1-yl)-5-methoxy-pyrido[3,4-d]pyrimidin-2-yl]-pyridin-2-yl}-acetamide 2-(3-Cyano-phenyl)-N-{4-[4-(4-hydroxy-piperidin-1-yl)-5-methoxy-pyrido[3,4-d]pyrimidin-2-yl]-pyridin-2-yl}-acetamide was prepared from 1-[2-(2-Chloro-pyridin-4-yl)-5-methoxy-pyrido[3,4-d]pyrimidin-4-yl]-piperidin-4-ol (100.0 mg, 0.2689 mmol) and 2-(3-Cyano-phenyl)-acetamide (52.0 mg, 0.325 mmol) in an analogous manner to Example 303c and Example 1501c. Product isolated as the trifluoroacetic acid salt as a yellow lyophilate (0.072 g, 43%). $^1$HNMR (400 MHz, d6-DMSO, δ, ppm): 10.95 (s, 1H), 9.03 (s, 1H), 8.82 (s, 1H), 8.49 (dd, J=5.2, 0.6 Hz, 1H), 8.34 (s, 1H), 8.03 (dd, J=5.2, 1.6 Hz, 1H), 7.84-7.82 (m, 1H), 7.77-7.74 (m, 1H), 7.73-7.70 (m, 1H), 7.57 (t, J=7.8 Hz, 1H), 4.07 (s, 3H), 4.03-3.95 (m, 2H), 3.89 (s, 2H), 3.85-3.77 (m, 1H), 3.45-3.36 (m, 2H), 1.94-1.86 (m, 2H), 1.60-1.50 (m, 2H). MS=496 (MH)+.

Example 404. 2-(3-Cyano-phenyl)-N-{4-[5-methoxy-4-(4-methyl-piperazin-1-yl)-pyrido[3,4-d]pyrimidin-2-yl]-pyridin-2-yl}-acetamide 2-(3-Cyano-phenyl)-N-{4-[5-methoxy-4-(4-methyl-piperazin-1-yl)-pyrido[3,4-d]pyrimidin-2-yl]-pyridin-2-yl}-acetamide was prepared from 2-(2-Chloro-pyridin-4-yl)-5-methoxy-4-(4-methyl-piperazin-1-yl)-pyrido[3,4-d] pyrimidine (100.0 mg, 0.2697 mmol) and 2-(3-Cyano-phenyl)-acetamide (52.0 mg, 0.325 mmol) in an analogous manner to Example 303c and Example 1501c. Product isolated as the trifluoroacetic acid salt as a yellow lyophilate (0.044 g, 26%). $^1$HNMR (400 MHz, d6-DMSO, δ, ppm): 10.97 (s, 1H), 9.79 (br s, 1H), 9.08 (s, 1H), 8.92 (s, 1H), 8.52

(dd, J=5.1, 0.6 Hz, 1H), 8.42 (s, 1H), 8.08 (dd, J=5.1, 1.5 Hz, 1H), 7.84-7.82 (m, 1H), 7.78-7.75 (m, 1H), 7.73-7.70 (m, 1H), 7.58 (t, J=7.8 Hz, 1H), 4.37 (d, J=13.9 Hz, 2H), 4.11 (s, 3H), 3.89 (s, 2H), 3.59 (d, J=11.0 Hz, 2H), 3.45-3.35 (m, 2H), 3.28-3.18 (m, 2H), 2.91-2.87 (m, 3H). MS=495 (MH)+.

Example 405. (6-Chloro-pyridin-3-yl)-[4-(5-methoxy-4-piperazin-1-yl-pyrido[3,4-d]pyrimidin-2-yl)-pyridin-2-yl]-amine (6-Chloro-pyridin-3-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Chloro-pyridin-3-ylamine (34.0 mg, 0.264 mmol) in an analogous manner to Example 303c and Example 1501c. Product isolated as the free base as a yellow solid (0.010 g, 9%). MP=206-208° C. $^1$HNMR (400 MHz, d6-DMSO, δ, ppm): 9.71 (s, 1H), 8.81 (s, 1H), 8.74 (d, J=2.8 Hz, 1H), 8.37-8.32 (m, 3H), 7.92 (s, 1H), 7.75 (dd, J=5.4, 1.1 Hz, 1H), 7.42 (d, J=8.7 Hz, 1H), 4.07 (s, 3H), 3.68-3.63 (m, 4H), 2.90-2.85 (m, 4H). MS=449, 451 (MH)+.

Example 406. (R)—N-{4-[5-Methoxy-4-((R)-pyrrolidin-3-ylamino)-pyrido[3,4-d]pyrimidin-2-yl]-pyridin-2-yl}-2-phenyl-propionamide 406a) (R)-2-Phenyl-propionamide was prepared from (R)-2-Phenyl-propionic acid (0.941 g, 6.27 mmol) in an analogous manner to Example 313a. Product isolated as a white solid (0.457 g, 48%). $^1$HNMR (400 MHz, d6-DMSO, δ, ppm): 7.35 (s, 1H), 7.33-7.18 (m, 5H), 6.79 (s, 1H), 3.55 (q, J=7.0 Hz, 1H), 1.30 (d, J=7.0 Hz, 3H). MS=150 (MH)+.

406b) (R)—N-{4-[5-Methoxy-4-((R)-pyrrolidin-3-ylamino)-pyrido[3,4-d]pyrimidin-2-yl]-pyridin-2-yl}-2-phenyl-propionamide was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (100.0 mg, 0.2188 mmol) and (R)-2-Phenyl-propionamide (45.0 mg, 0.302 mmol) in an analogous manner to Example 303c and Example 4501c. Product isolated as the trifluoroacetic acid salt as a yellow lyophilate (0.100 g, 78%). $^1$HNMR (400 MHz, d6-DMSO, δ, ppm): 10.79 (s, 1H), 9.12 (s, 1H), 8.97-8.77 (m, 3H), 8.47 (dd, J=5.3, 0.6 Hz, 1H), 8.41 (s, 1H), 8.15 (d, J=6.0 Hz, 1H), 8.03 (dd, J=5.2, 1.5 Hz, 1H), 7.47-7.43 (m, 2H), 7.37-7.32 (m, 2H), 7.27-7.22 (m, 1H), 5.00-4.90 (m, 1H), 4.16 (s, 3H), 4.09 (q, J=6.9 Hz, 1H), 3.72-3.62 (m, 1H), 3.50-3.30 (m, 3H), 2.53-2.47 (m, 1H), 2.27-2.17 (m, 1H), 1.46 (d, J=7.0, 3H). MS=470 (MH)+.

Example 407. (S)—N-{4-[5-Methoxy-4-((R)-pyrrolidin-3-ylamino)-pyrido[3,4-d]pyrimidin-2-yl]-pyridin-2-yl}-2-phenyl-propionamide 407a) (S)-2-Phenyl-propionamide was prepared from (S)-2-Phenyl-propionic acid (1.25 g, 8.32 mmol) in an analogous manner to Example 313a. Product isolated as a white solid. $^1$HNMR (400 MHz, d6-DMSO, δ, ppm): 7.35 (s, 1H), 7.33-7.18 (m, 5H), 6.79 (s, 1H), 3.55 (q, J=7.1 Hz, 1H), 1.30 (d, J=7.1 Hz, 3H).

407b) (S)—N-{4-[5-Methoxy-4-((R)-pyrrolidin-3-ylamino)-pyrido[3,4-d]pyrimidin-2-yl]-pyridin-2-yl}-2-phenyl-propionamide was prepared from (R)-3-[2-(2-Chloro-pyridin-4-yl)-5-methoxy-pyrido[3,4-d]pyrimidin-4-ylamino]-pyrrolidine-1-carboxylic acid tert-butyl ester (100.0 mg, 0.2188 mmol) and (S)-2-Phenyl-propionamide (45.0 mg, 0.302 mmol) in an analogous manner to Example 303c and Example 1501c. Product isolated as the trifluoroacetic acid salt as a yellow lyophilate (0.100 g, 78%). $^1$HNMR (400 MHz, d6-DMSO, δ, ppm): 10.79 (s, 1H), 9.12 (s, 1H), 8.99-8.79 (m, 3H), 8.47 (dd, J=5.2, 0.6 Hz, 1H), 8.41 (s, 1H), 8.15 (d, J=5.9 Hz, 1H), 8.04 (dd, J=5.2, 1.5 Hz, 1H), 7.47-7.43 (m, 2H), 7.37-7.32 (m, 2H), 7.27-7.22 (m, 1H), 5.00-4.90 (m, 1H), 4.16 (s, 3H), 4.09 (q, J=6.8 Hz, 1H), 3.72-3.62 (m, 1H), 3.50-3.30 (m, 3H), 2.53-2.47 (m, 1H), 2.27-2.17 (m, 1H), 1.46 (d, J=7.0 Hz, 3H). MS=470 (MH)+.

Example 408. (R)—N-[4-(5-Methoxy-4-piperazin-1-yl-pyrido[3,4-d]pyrimidin-2-yl)-pyridin-2-yl]-2-phenyl-propionamide (R)—N-[4-(5-Methoxy-4-piperazin-1-yl-pyrido[3,4-d]pyrimidin-2-yl)-pyridin-2-yl]-2-phenyl-propionamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and (R)-2-Phenyl-propionamide (45.0 mg, 0.302 mmol) in an analogous manner to Example 303c and Example 1501c. Product isolated as the trifluoroacetic acid salt as a yellow lyophilate (0.115 g, 89%). $^1$HNMR (400 MHz, d6-DMSO, δ, ppm): 10.82 (s, 1H), 9.11 (s, 1H), 8.93 (s, 1H), 8.88 (br s, 2H), 8.48 (dd, J=5.1, 0.7 Hz, 1H), 8.42 (s, 1H), 8.04 (dd, J=5.1, 1.4 Hz, 1H), 7.46-7.43 (m, 2H), 7.37-7.33 (m, 2H), 7.27-7.22 (m, 1H), 4.12-4.05 (m, 4H), 3.90-3.86 (m, 4H), 3.36-3.29 (m, 4H), 1.45 (d, J=7.0 Hz, 3H). MS=470 (MH)+.

Example 409. (S)—N-[4-(5-Methoxy-4-piperazin-1-yl-pyrido[3,4-d]pyrimidin-2-yl)-pyridin-2-yl]-2-phenyl-propionamide (S)—N-[4-(5-Methoxy-4-piperazin-1-yl-pyrido[3,4-d]pyrimidin-2-yl)-pyridin-2-yl]-2-phenyl-propionamide was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and (S)-2-Phenyl-propionamide (45.0 mg, 0.302 mmol) in an analogous manner to Example 303c and Example 1501c. Product isolated as the trifluoroacetic acid salt as a yellow lyophilate (0.104 g, 81%). $^1$HNMR (400 MHz, d6-DMSO, δ, ppm): 10.81 (s, 1H), 9.11 (s, 1H), 8.93 (s, 1H), 8.88 (br s, 2H), 8.48 (dd, J=5.1, 0.5 Hz, 1H), 8.42 (s, 1H), 8.04 (d, J=5.1, 1.4 Hz, 1H), 7.47-7.41 (m, 2H), 7.37-7.32 (m, 2H), 7.27-7.22 (m, 1H), 4.12-4.05 (m, 4H), 3.89-3.84 (m, 4H), 3.36-3.29 (m, 4H), 1.45 (d, J=7.0 Hz, 3H). MS=470 (MH)+.

Example 410. [4-(5-Methoxy-4-piperazin-1-yl-pyrido[3,4-d]pyrimidin-2-yl)-pyridin-2-yl]-(3-methyl-pyridin-2-yl)-amine

[4-(5-Methoxy-4-piperazin-1-yl-pyrido[3,4-d]pyrimidin-2-yl)-pyridin-2-yl]-(3-methyl-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (90.0 mg, 0.197 mmol) and 3-Methyl-pyridin-2-ylamine (30.0 mg, 0.277 mmol) in an analogous manner to Example 303c and Example 1501c. Product isolated as the free base as a yellow foam (0.062 g, 73%). $^1$HNMR (400 MHz, d6-DMSO, δ, ppm): 8.97 (s, 1H), 8.81 (s, 1H), 8.52 (s, 1H), 8.35 (dd, J=5.2, 0.5 Hz, 1H), 8.32 (s, 1H), 8.15 (dd, J=4.7, 1.4 Hz, 1H), 7.80 (dd, J=5.2, 1.4 Hz, 1H), 7.59-7.55 (m, 1H), 6.94 (dd, J=7.3, 5.0 Hz, 1H), 4.07 (s, 3H), 3.68-3.64 (m, 4H), 2.90-2.85 (m, 4H), 2.32 (s, 3H). MS=429 (MH)+.

Example 411. (3-Fluoro-pyridin-2-yl)-[4-(5-methoxy-4-piperazin-1-yl-pyrido[3,4-d]pyrimidin-2-yl)-pyridin-2-yl]-amine (3-Fluoro-pyridin-2-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (90.0 mg, 0.197 mmol) and 3-Fluoro-pyridin-2-ylamine (31.0 mg, 0.276 mmol) in an analogous manner to Example 303c and Example 1501c. Product isolated as the bis-trifluoroacetic acid salt as a yellow lyophilate (0.110 g, 84%). $^1$HNMR (400 MHz, d6-DMSO, δ, ppm): 10.34 (br s, 1H), 8.97-8.79 (m, 4H), 8.48-8.44 (m, 2H), 8.27 (d, J=4.8 Hz, 1H), 8.04 (dd, J=5.6, 1.2 Hz, 1H), 7.86-7.80 (m, 1H), 7.21-7.16 (m, 1H), 4.11 (s, 3H), 3.94-3.88 (m, 4H), 3.37-3.30 (m, 4H). MS=433 (MH)+.

Example 412. [4-(5-Methoxy-4-piperazin-1-yl-pyrido[3,4-d]pyrimidin-2-yl)-pyridin-2-yl]-(6-piperazin-1-ylpyridin-3-yl)-amine 4-(5-Methoxy-4-piperazin-1-yl-pyrido[3,4-d]pyrimidin-2-yl)-pyridin-2-yl]-(6-piperazin-1-yl-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (106 mg, 0.232 mmol) and 4-(5-Amino-pyridin-2-yl)-piperazine-1-carboxylic acid tert-butyl ester (73.0 mg, 0.262 mmol) in an analogous manner to Example 303c and Example 1501c. Product isolated as the bis-trifluoroacetic acid salt as a brown lyophilate (0.107 g, 63%). $^1$HNMR (400 MHz, d6-DMSO, δ, ppm): 9.28 (s, 1H), 8.95-8.85 (m, 3H), 8.73 (br s, 2H), 8.51 (d, J=2.8 Hz, 1H), 8.42 (s, 1H), 8.25 (d, J=5.4 Hz, 1H), 8.03 (dd, J=9.1, 2.8 Hz, 1H), 7.59 (s, 1H), 7.66 (dd, J=5.4, 1.2 Hz, 1H), 6.97 (d, J=9.2 Hz, 1H), 4.10 (s, 3H), 3.90-3.85 (m, 4H), 3.65-3.60 (m, 4H), 3.36-3.29 (m, 4H), 3.25-3.19 (m, 4H). MS=499 (MH)+.

Example 413. [4-(5-Methoxy-4-piperazin-1-yl-pyrido[3,4-d]pyrimidin-2-yl)-pyridin-2-yl]-[2-methyl-4-(4-methyl-piperazin-1-yl)-phenyl]-amine

[4-(5-Methoxy-4-piperazin-1-yl-pyrido[3,4-d]pyrimidin-2-yl)-pyridin-2-yl]-[2-methyl-4-(4-methyl-piperazin-1-yl)-phenyl]-amine was prepared from 4-[2-(2-Chloro-pyridin-4-yl)-5-methoxy-pyrido[3,4-d]pyrimidin-4-yl]-piperazine-1-carboxylic acid tert-butyl ester (102.0 mg, 0.2232 mmol) and 2-Methyl-4-(4-methyl-piperazin-1-yl)-phenylamine (54.0 mg, 0.263 mmol)[prepared as described in WO2008/051547] in an analogous manner to Example 303c and Example 1501c. Product isolated as the bis-trifluoroacetic acid salt as a brown lyophilate (0.128 g, 75%). $^1$HNMR (400 MHz, d6-DMSO, δ, ppm): 10.00-9.30 (m, 2H), 9.07 (br s, 2H), 8.90 (s, 1H), 8.44 (s, 1H), 8.06 (d, J=5.9 Hz, 1H), 7.95 (s, 1H), 7.70 (d, J=5.7 Hz, 1H), 7.34 (d, J=8.7 Hz, 1H), 7.02 (d, J=2.3 Hz, 1H), 6.94 (dd, J=8.7, 2.4 Hz, 1H), 4.11 (s, 3H), 3.95-3.80 (m, 6H), 3.55 (d, J=11.5 Hz, 2H), 3.35-3.28 (m, 4H), 3.23-3.12 (m, 2H), 2.99 (t, J=13.8 Hz, 2H), 2.89 (s, 3H), 2.21 (s, 3H). MS=526 (MH)+.

Example 414. [4-(5-Methoxy-4-piperazin-1-yl-pyrido[3,4-d]pyrimidin-2-yl)-pyridin-2-yl]-(1-piperidin-4-yl-1H-pyrazol-4-yl)-amine

[4-(5-Methoxy-4-piperazin-1-yl-pyrido[3,4-d]pyrimidin-2-yl)-pyridin-2-yl]-(1-piperidin-4-yl-1H-pyrazol-4-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-(4-Amino-pyrazol-1-yl)-piperidine-1-carboxylic acid tert-butyl ester (70.0 mg, 0.263 mmol) in an analogous manner to Example 303c and Example 1501c. Product isolated as the bis-trifluoroacetic acid salt as a brown lyophilate (0.123 g, 78%). $^1$HNMR (400 MHz, d6-DMSO, δ, ppm): 9.40 (br s, 1H), 9.00 (br s, 2H), 8.90 (s, 1H), 8.75-8.65 (m, 1H), 8.50-8.37 (m, 2H), 8.25 (d, J=5.6 Hz, 1H), 8.10 (s, 1H), 7.84 (s, 1H), 7.62 (d, J=5.5 Hz, 1H), 7.55 (s, 1H), 4.54-4.44 (m, 1H), 4.10 (s, 3H), 3.90-3.85 (m, 4H), 3.47-3.40 (m, 2H), 3.36-3.30 (m, 4H), 3.15-3.02 (m, 2H), 2.23-2.06 (m, 4H). MS=487 (MH)+.

Example 415. [4-(5-Methoxy-4-piperazin-1-yl-pyrido[3,4-d]pyrimidin-2-yl)-pyridin-2-yl]-(6-methyl-pyridin-2-yl)-amine

[4-(5-Methoxy-4-piperazin-1-yl-pyrido[3,4-d]pyrimidin-2-yl)-pyridin-2-yl]-(6-methyl-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Methyl-pyridin-2-ylamine (30.0 mg, 0.277 mmol) in an analogous manner to Example 303c and Example 1501c. Product isolated as the trifluoroacetic acid salt as a yellow lyophilate (0.095 g, 80%). $^1$HNMR (400 MHz, d6-DMSO, δ, ppm): 8.96-8.87 (m, 3H), 8.56 (br s, 1H), 8.53 (d, J=5.6 Hz, 1H), 8.45 (s, 1H), 8.05-8.00 (m, 1H), 7.85 (br s, 1H), 7.45-7.39 (m, 1H), 7.04-6.99 (m, 1H), 4.11 (s, 3H), 3.93-3.88 (m, 4H), 3.37-3.30 (m, 4H). MS=429 (MH)+.

Example 416. [4-(5-Methoxy-4-piperazin-1-yl-pyrido[3,4-d]pyrimidin-2-yl)-pyridin-2-yl]-(5-methyl-pyridin-3-yl)-amine

[4-(5-Methoxy-4-piperazin-1-yl-pyrido[3,4-d]pyrimidin-2-yl)-pyridin-2-yl]-(5-methyl-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (104.0 mg, 0.2276 mmol) and 5-Methyl-pyridin-3-ylamine (30.0 mg, 0.277 mmol) in an analogous manner to Example 303c and Example 1501c. Product isolated as the trifluoroacetic acid salt as a pale yellow lyophilate (0.123 g, 99%). $^1$HNMR (400 MHz, d6-DMSO, δ, ppm): 10.13 (br s, 1H), 9.17 (br s, 1H), 8.95-8.85 (m, 3H), 8.46 (d, J=5.4 Hz, 1H), 8.43 (s, 1H), 8.30 (s, 1H), 8.24 (s, 1H), 8.02 (s, 1H), 7.87 (dd, J=5.4, 1.3 Hz, 1H), 4.11 (s, 3H), 3.91-3.86 (m, 4H), 3.36-3.30 (m, 4H), 2.43 (s, 3H). MS=429 (MH)+.

Example 417. (5-Chloro-pyridin-3-yl)-[4-(5-methoxy-4-piperazin-1-yl-pyrido[3,4-d]pyrimidin-2-yl)-pyridin-2-yl]-amine (5-Chloro-pyridin-3-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 5-Chloro-pyridin-3-ylamine (35.0 mg, 0.272 mmol) in an analogous manner to Example 303c and Example 1501c. Product isolated as the trifluoroacetic acid salt as a pale yellow lyophilate (0.112 g, 90%). $^1$HNMR (400 MHz, d6-DMSO, δ, ppm): 9.88 (s, 1H), 8.91 (s, 1H), 8.84 (br s, 2H), 8.69 (d, J=2.3 Hz, 1H), 8.64 (t, J=2.2 Hz, 1H), 8.45-8.42 (m, 2H), 8.13 (d, J=2.2 Hz, 1H), 7.99 (s, 1H), 7.82 (dd, J=5.3, 1.3 Hz, 1H), 4.11 (s, 3H), 3.91-3.86 (m, 4H), 3.36-3.30 (m, 4H). MS=406, 408 (MH)+.

Example 418. (2-Fluoro-4-morpholin-4-yl-phenyl)-[4-(5-methoxy-4-piperazin-1-yl-pyrido[3,4-d]pyrimidin-2-yl)-pyridin-2-yl]-amine 418a) 2-Fluoro-4-morpholin-4-yl-phenylamine was prepared from 4-(3-Fluoro-4-nitro-phenyl)-morpholine (0.52 g, 2.3 mmol) [prepared as described in Quan, M. L.; et. al. J. Med. Chem. 2005, 48, 1729-1744.] in an analogous manner to Example 10b. Product isolated as a pale pink solid (0.40 g, 88%). $^1$HNMR 400 MHz, d6-DMSO, δ, ppm): 6.71-6.63 (m, 2H), 6.53 (dd, J=8.5, 2.3 Hz, 1H), 4.56 (br s, 2H), 3.71-3.67 (m, 4H), 2.93-2.89 (m, 4H). MS=197 (MH)+.

418b) (2-Fluoro-4-morpholin-4-yl-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (105.0 mg, 0.2298 mmol) and 2-Fluoro-4-morpholin-4-yl-phenylamine (52.0 mg, 0.265 mmol) in an analogous manner to Example 303c and Example 1501c. Product isolated as the bis-trifluoroacetic acid salt as an orange lyophilate (0.120 g, 70%). $^1$HNMR (400 MHz, d6-DMSO, δ, ppm): 9.27 (br s, 1H), 8.96-8.89 (m, 3H), 8.43 (s, 1H), 8.16 (d, J=5.7 Hz, 1H), 7.94 (s, 1H), 7.70 (dd, J=5.6, 1.1 Hz, 1H), 7.61 (t, J=9.2 Hz, 1H), 6.93 (dd, J=14.1, 2.5 Hz, 1H), 6.82 (dd, J=8.9, 2.3 Hz, 1H), 4.10 (s, 3H), 3.90-3.85 (m, 4H), 3.77-3.73 (m, 4H), 3.34-3.28 (m, 4H), 3.17-3.08 (m, 4H). MS=517 (MH)+.

Example 419. 3-Fluoro-4-[4-(5-methoxy-4-piperazin-1-yl-pyrido[3,4-d]pyrimidin-2-yl)-pyridin-2-ylamino]-benzonitrile 3-Fluoro-4-[4-(5-methoxy-4-piperazin-1-yl-pyrido[3,4-d]pyrimidin-2-yl)-pyridin-2-ylamino]-benzonitrile was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 4-Amino-3-fluoro-benzonitrile (36.0 mg, 0.264 mmol) in an analogous manner to Example 303c and Example 1501c. Product isolated as the free base as a yellow solid (0.019 g, 19%). $^1$HNMR (400 MHz, d6-DMSO, δ, ppm): 9.58 (d, J=2.5 Hz, 1H), 8.91 (s, 1H), 8.85-8.70 (m, 2H), 8.45 (m, 2H), 8.30 (s, 1H), 7.89 (dd, J=5.3, 1.3 Hz, 1H), 7.83 (dd, J=11.7, 1.9 Hz, 1H), 7.66-7.62 (m, 1H), 4.10 (s, 3H), 3.91-3.87 (m, 4H), 3.33-3.30 (m, 4H). MS=457 (MH)+.

Example 420. 4-Fluoro-3-[4-(5-methoxy-4-piperazin-1-yl-pyrido[3,4-d]pyrimidin-2-yl)-pyridin-2-ylamino]-benzonitrile 420a) A 100 mL round bottom flask equipped with a large magnetic stir bar, reflux condenser and nitrogen inlet adapter was charged with 4-Fluoro-3-nitro-benzonitrile (1.0 g, 6.0 mmol), Ammonium chloride (1.6 g, 30 mmol), Ethanol (20 mL, 300 mmol) and Water (10 mL, 600 mmol). To the suspension was added powdered Iron (1.1 g, 20 mmol). The suspension was stirred vigorously to allow iron to disperse into the suspension without clinging to the stir bar. The mixture was kept under an atmosphere of Nitrogen. An induction period (~20 minutes) was observed before the reaction began to darken to a rusty brown color and maintain a mild exotherm from 23° C. to 26° C. over the course of three hours. After 3 hours, the reaction was complete by HPLC. The reaction was filtered through a plug of diatomaceous earth. The filter pad was rinsed with methanol (~100 mL). The filtrate was evaporated to dryness. The solid was triturated with dichloromethane (~100 mL) and filtered. The filtrate was evaporated. 3-Amino-4-fluoro-benzonitrile was isolated as a brown solid (0.78 g, 95%). $^1$HNMR (400 MHz, d6-DMSO, δ, ppm): 7.19 (dd, J=11.5, 8.3 Hz, 1H), 7.09 (dd, J=8.3, 2.1 Hz, 1H), 6.96 (ddd, J=8.3, 4.3, 2.1 Hz, 1H), 5.69 (br s, 2H). MS=137 (MH)+.

420b) 4-Fluoro-3-[4-(5-methoxy-4-piperazin-1-yl-pyrido[3,4-d]pyrimidin-2-yl)-pyridin-2-ylamino]-benzonitrile was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 3-Amino-4-fluoro-benzonitrile (36.0 mg, 0.264 mmol) in an analogous manner to Example 303c and Example 1501c. Product isolated as the bis-trifluoroacetic acid salt as a yellow lyophilate (0.096 g) $^1$HNMR (400 MHz, d6-DMSO, δ, ppm): 9.41 (d, J=2.0 Hz, 1H), 8.99-8.85 (m, 1H), 8.93-8.84 (m, 3H), 8.44-8.41 (m, 2H), 8.22 (s, 1H), 7.84 (dd, J=5.3, 1.4 Hz, 1H), 7.53-7.46 (m, 2H), 4.11 (s, 3H), 3.92-3.87 (m, 4H), 3.36-3.30 (m, 4H). MS=457 (MH)+.

Example 421. (2,6-Difluoro-phenyl)-[4-(5-methoxy-4-piperazin-1-yl-pyrido[3,4-d]pyrimidin-2-yl)-pyridin-2-yl]-amine (2,6-Difluoro-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,6-Difluoro-phenylamine (30.0 μL, 0.279 mmol) in an analogous manner to Example 303c and Example 1501c. Product isolated as the bis-trifluoroacetic acid salt as a yellow lyophilate (0.132 g, 88%). $^1$HNMR (400 MHz, d6-DMSO, δ, ppm): 8.91-8.80 (m, 4H), 8.41 (s, 1H), 8.18 (d, J=5.6 Hz, 1H), 7.82 (s, 1H), 7.69-7.66 (m, 1H), 7.33-7.25 (m, 1H), 7.21-7.12 (m, 2H), 4.10 (s, 3H), 3.89-3.84 (m, 4H), 3.35-3.27 (m, 4H). MS=450 (MH)+.

Example 422. (2-Fluoro-6-methyl-phenyl)-[4-(5-methoxy-4-piperazin-1-yl-pyrido[3,4-d]pyrimidin-2-yl)-pyridin-2-yl]-amine (2-Fluoro-6-methyl-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-Fluoro-6-methyl-phenylamine (33.0 mg, 0.264 mmol) in an analogous manner to Example 303c and Example 1501c. Product isolated as the bis-trifluoroacetic acid salt as a yellow lyophilate (0.099 g, 67%). $^1$HNMR (400 MHz, d6-DMSO, δ, ppm): 8.98-8.83 (m, 4H), 8.42 (s, 1H), 8.14 (d, J=5.5 Hz, 1H), 7.75 (br s, 1H), 7.65 (d, J=5.3 Hz, 1H), 7.26-7.10 (m, 3H), 4.10 (s, 3H), 3.88-3.82 (m, 4H), 3.36-3.27 (m, 4H), 2.25 (s, 3H). MS=446 (MH)+.

Example 423. [4-(5-Methoxy-4-piperazin-1-yl-pyrido[3,4-d]pyrimidin-2-yl)-pyridin-2-yl]-pyrimidin-2-yl-amine

[4-(5-Methoxy-4-piperazin-1-yl-pyrido[3,4-d]pyrimidin-2-yl)-pyridin-2-yl]-pyrimidin-2-yl-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2-amino-pyrimidine (25.0 mg, 0.263 mmol) in an analogous manner to Example 303c and Example 1501c. Product isolated as the free base as a yellow solid (0.009 g, 10%). MP=200-203° C. $^1$HNMR (400 MHz, d6-DMSO, δ, ppm): 9.94 (s, 1H), 9.31 (s, 1H), 8.39 (s, 1H), 8.59 (d, J=4.8 Hz, 2H), 8.44-8.41 (m, 1H), 8.33 (s, 1H), 7.90 (dd, J=5.2, 1.5 Hz, 1H), 7.00 (t, J=4.8 Hz, 1H), 4.07 (s, 3H), 3.71-3.66 (m, 4H), 2.92-2.87 (m, 4H). MS=416 (MH)+.

Example 424. [4-(5-Methoxy-4-piperazin-1-yl-pyrido[3,4-d]pyrimidin-2-yl)-pyridin-2-yl]-(5-methoxy-pyridin-3-yl)-amine

[4-(5-Methoxy-4-piperazin-1-yl-pyrido[3,4-d]pyrimidin-2-yl)-pyridin-2-yl]-(5-methoxy-pyridin-3-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (108.0 mg, 0.2364 mmol) and 5-Methoxy-pyridin-3-ylamine (33.0 mg, 0.266 mmol) in an analogous manner to Example 303c and Example 1501c. Product isolated as the trifluoroacetic acid salt as a yellow lyophilate (0.104 g, 99%). $^1$HNMR (400 MHz, d6-DMSO, δ, ppm): 9.84 (s, 1H), 8.91 (s, 1H), 8.85 (br s, 2H), 8.62 (s, 1H), 8.44-8.41 (m, 2H), 8.10 (t, J=2.2 Hz, 1H), 7.99 (s, 2H), 7.81 (d, J=5.3 Hz, 1H), 4.11 (s, 3H), 3.91-3.86 (m, 7H), 3.36-3.30 (m, 4H). MS=445 (MH)+.

Example 425. (S)-1-[5-Methoxy-2-(2-phenylamino-pyridin-4-yl)-pyrido[3,4-d]pyrimidin-4-yl]-piperidin-3-ol 425a) (S)-1-[2-(2-Chloro-pyridin-4-yl)-5-methoxy-pyrido[3,4-d]pyrimidin-4-yl]-piperidin-3-ol was prepared from 2-(2-Chloro-pyridin-4-yl)-5-methoxy-pyrido[3,4-d]pyrimidin-4-ol (1000.0 mg, 3.4639 mmol) and (S)-Piperidin-3-ol; hydrochloride (570.0 mg, 4.142 mmol) in an analogous manner to [B016]. Product isolated as a yellow foam (0.747 g, 58%). $^1$HNMR (400 MHz, d6-DMSO, δ, ppm): 8.83 (s, 1H), 8.60 (dd, J=5.0, 0.6 Hz, 1H), 8.35 (s, 1H), 8.32-8.29 (m, 2H), 4.88 (d, J=3.9 Hz, 1H), 4.14-4.05 (m, 4H), 3.95-3.89 (m, 1H), 3.69-3.61 (m, 1H), 3.48-3.38 (m, 1H), 3.09 (dd, J=12.4, 8.3 Hz, 1H), 1.96-1.84 (m, 2H), 1.62-1.40 (m, 2H). MS=372, 374 (MH)+.

425b) (S)-1-[5-Methoxy-2-(2-phenylamino-pyridin-4-yl)-pyrido[3,4-d]pyrimidin-4-yl]-piperidin-3-ol was prepared from (S)-1-[2-(2-Chloro-pyridin-4-yl)-5-methoxy-pyrido[3,4-d]pyrimidin-4-yl]-piperidin-3-ol (101.0 mg, 0.2716 mmol) and Aniline (30.0 μL, 0.329 mmol) in an analogous manner to Example 303c and Example 1501c. Product isolated as the trifluoroacetic acid salt as a yellow lyophilate (0.102 g, 69%). $^1$HNMR (400 MHz, d6-DMSO, δ, ppm): 9.60 (br s, 1H), 8.81 (s, 1H), 8.35 (s, 1H), 8.27 (d, J=5.6 Hz, 1H), 7.94 (s, 1H), 7.72-7.68 (m, 3H), 7.33 (t, J=7.7 Hz, 2H), 6.99 (t, J=6.8 Hz, 1H), 4.11-4.04 (m, 5H), 3.97-3.90 (m, 1H), 3.70-3.62 (m, 1H), 3.49-3.40 (m, 1H), 3.11 (dd, J=12.8, 8.3 Hz, 1H), 1.98-1.85 (m, 2H), 1.65-1.43 (m, 2H). MS=429 (MH)+.

Example 426. 2-{4-[4-((S)-3-Hydroxy-piperidin-1-yl)-5-methoxy-pyrido[3,4-d]pyrimidin-2-yl]-pyridin-2-ylamino}-isonicotinonitrile 2-{4-[4-((S)-3-Hydroxy-piperidin-1-yl)-5-methoxy-pyrido[3,4-d]pyrimidin-2-yl]-pyridin-2-ylamino}-isonicotinonitrile was prepared from (S)-1-[2-(2-Chloro-pyridin-4-yl)-5-methoxy-pyrido[3,4-d]pyrimidin-4-yl]-piperidin-3-ol (109.0 mg, 0.2932 mmol) and 2-Amino-isonicotinonitrile (39.0 mg, 0.327 mmol) in an analogous manner to Example 303c and Example 1501c. Product isolated as the trifluoroacetic acid salt as a yellow lyophilate (0.121 g, 72%). $^1$HNMR (400 MHz, d6-DMSO, δ, ppm): 10.60 (br s, 1H), 8.83 (s, 1H), 8.61 (s, 1H), 8.52 (d, J=5.2 Hz, 1H), 8.46 (d, J=5.4 Hz, 1H), 8.35 (s, 1H), 8.26 (s, 1H), 7.91 (d, J=5.1 Hz, 1H), 7.34 (d, J=4.9 Hz, 1H), 4.15-4.05 (m, 5H), 4.00-3.92 (m, 1H), 3.70-3.62 (m, 1H), 3.52-3.40 (m, 1H), 3.11 (dd, J=12.7, 8.3 Hz, 1H), 1.98-1.87 (m, 2H), 1.67-1.43 (m, 2H). MS=455 (MH)+.

Example 427. 1-[5-Methoxy-2-(2-phenylamino-pyridin-4-yl)-pyrido[3,4-d]pyrimidin-4-yl]-piperidin-4-ol 1-[5-Methoxy-2-(2-phenylamino-pyridin-4-yl)-pyrido[3,4-d]pyrimidin-4-yl]-piperidin-4-ol was prepared from 1-[2-(2-Chloro-pyridin-4-yl)-5-methoxy-pyrido[3,4-d]pyrimidin-4-yl]-piperidin-4-ol (104.0 mg, 0.2797 mmol) and Aniline (30.0 μL, 0.329 mmol) in an analogous manner to Example 303c and Example 1501c. Product isolated as the trifluoroacetic acid salt as a yellow lyophilate (0.093 g, 61%). $^1$HNMR (400 MHz, d6-DMSO, δ, ppm): 9.66 (br s, 1H), 8.82 (s, 1H), 8.36 (s, 1H), 8.25 (d, J=5.6 Hz, 1H), 7.96 (s, 1H), 7.72-7.67 (m, 3H), 7.34 (t, J=7.8 Hz, 2H), 7.02 (t, J=7.2 Hz, 1H), 4.08 (s, 3H), 4.05-3.97 (m, 2H), 3.87-3.79 (m, 1H), 3.47-3.39 (m, 2H), 1.96-1.88 (m, 2H), 1.63-1.52 (m, 2H). MS=429 (MH)+.

Example 428. (R)-1-[5-Methoxy-2-(2-phenylamino-pyridin-4-yl)-pyrido[3,4-d]pyrimidin-4-yl]-piperidin-3-ol 428a) (R)-1-[2-(2-Chloro-pyridin-4-yl)-5-methoxy-pyrido[3,4-d]pyrimidin-4-yl]-piperidin-3-ol was prepared from 2-(2-Chloro-pyridin-4-yl)-5-methoxy-pyrido[3,4-d]pyrimidin-4-ol (1000.0 mg, 3.4639 mmol) and (R)-Piperidin-3-ol; hydrochloride (570.0 mg, 4.142 mmol) in an analogous manner to [B016]. Product isolated as a tan solid (0.561 g, 44%). $^1$HNMR (400 MHz, d6-DMSO, δ, ppm): 8.83 (s, 1H), 8.60 (dd, J=5.0, 0.5 Hz, 1H), 8.35 (s, 1H), 8.32-8.29 (m, 2H), 4.88 (d, J=3.9 Hz, 1H), 4.15-4.05 (m, 4H), 3.95-3.88 (m, 1H), 3.70-3.60 (m, 1H), 3.47-3.37 (m, 1H), 3.09 (dd, J=12.7, 8.3 Hz, 1H), 1.96-1.84 (m, 2H), 1.60-1.40 (m, 2H). MS=372, 374 (MH)+.

Example 429. 2-{4-[4-((R)-3-Hydroxy-piperidin-1-yl)-5-methoxy-pyrido[3,4-d]pyrimidin-2-yl]-pyridin-2-ylamino}-isonicotinonitrile 2-{4-[4-((R)-3-Hydroxy-piperidin-1-yl)-5-methoxy-pyrido[3,4-d]pyrimidin-2-yl]-pyridin-2-ylamino}-isonicotinonitrile was prepared from (R)-1-[2-(2-Chloro-pyridin-4-yl)-5-methoxy-pyrido[3,4-d]pyrimidin-4-yl]-piperidin-3-ol (105.0 mg, 0.2824 mmol) and 2-Amino-isonicotinonitrile (39.0 mg, 0.327 mmol) in an analogous manner to Example 303c and Example 1501c. Product isolated as the trifluoroacetic acid salt as a yellow lyophilate (0.013 g, 8%). $^1$HNMR (400 MHz, d6-DMSO, δ, ppm): 10.60 (br s, 1H), 8.83 (s, 1H), 8.61 (s, 1H), 8.52 (d, J=5.1 Hz, 1H), 8.46 (d, J=5.7 Hz, 1H), 8.35 (s, 1H), 8.26 (s, 1H), 7.91 (d, J=5.4 Hz, 1H), 7.34 (d, J=5.3 Hz, 1H), 4.14-4.04 (m, 4H), 4.00-3.92 (m, 1H), 3.70-3.62 (m, 1H), 3.51-3.41 (m, 1H), 3.12 (dd, J=12.9, 8.2 Hz, 1H), 1.98-1.88 (m, 2H), 1.65-1.43 (m, 2H). MS=455 (MH)+.

Example 430. [5-Methoxy-2-(2-phenylamino-pyridin-4-yl)-pyrido[3,4-d]pyrimidin-4-yl]-(S)-1-pyrrolidin-2-ylmethyl-amine 430a) (S)-2-{[2-(2-Chloro-pyridin-4-yl)-5-methoxy-pyrido[3,4-d]pyrimidin-4-ylamino]-methyl}-pyrrolidine-1-carboxylic acid tert-butyl ester was prepared from 2-(2-Chloro-pyridin-4-yl)-5-methoxy-pyrido[3,4-d]pyrimidin-4-ol (1000.0 mg, 3.4639 mmol) and (S)-2-Aminomethyl-pyrrolidine-1-carboxylic acid tert-butyl ester (840.0 mg, 4.194 mmol) in an analogous manner to [B016]. Product isolated as a yellow foam (0.817 g, 50%). $^1$HNMR (400 MHz, d6-DMSO, δ, ppm): 8.87-8.25 (m, 6H), 4.30-4.22 (m, 1H), 4.14 (s, 3H), 4.01-3.91 (m, 1H), 3.72-3.50 (m, 1H), 3.37-3.27 (m, 1H), 2.03-1.78 (m, 5H), 1.45-1.10 (m, 9H). MS=471, 473 (MH)+.

430b) [5-Methoxy-2-(2-phenylamino-pyridin-4-yl)-pyrido[3,4-d]pyrimidin-4-yl]-(S)-1-pyrrolidin-2-ylmethyl-amine was prepared from (S)-2-{[2-(2-Chloro-pyridin-4-yl)-5-methoxy-pyrido[3,4-d]pyrimidin-4-ylamino]-methyl}-pyrrolidine-1-carboxylic acid tert-butyl ester (108.0 mg, 0.2293 mmol) and Aniline (25.0 µL, 0.274 mmol) in an analogous manner to Example 303c and Example 1501c. Product isolated as the trifluoroacetic acid salt as a yellow lyophilate (0.109 g, 87%). $^1$HNMR (400 MHz, d6-DMSO, δ, ppm): 9.42 (br s, 1H), 8.97 (br s, 1H), 8.82 (s, 1H), 8.64 (t, J=5.7 Hz, 1H), 8.54 (br s, 1H), 8.40 (s, 1H), 8.31 (d, J=5.4 Hz, 1H), 7.94 (s, 1H), 7.75-7.70 (m, 3H), 7.31 (t, J=7.7 Hz, 2H), 6.95 (t, J=7.4 Hz, 1H), 4.15 (s, 3H), 4.12-3.85 (m, 3H), 3.34-3.14 (m, 2H), 2.20-1.74 (m, 4H). MS=428 (MH)+.

Example 431. [5-Methoxy-2-(2-phenylamino-pyridin-4-yl)-pyrido[3,4-d]pyrimidin-4-yl]-(R)-1-pyrrolidin-2-ylmethyl-amine 431a) (R)-2-{[2-(2-Chloro-pyridin-4-yl)-5-methoxy-pyrido[3,4-d]pyrimidin-4-ylamino]-methyl}-pyrrolidine-1-carboxylic acid tert-butyl ester was prepared from 2-(2-Chloro-pyridin-4-yl)-5-methoxy-pyrido[3,4-d]pyrimidin-4-ol (1000.0 mg, 3.4639 mmol) and (R)-2-Aminomethyl-pyrrolidine-1-carboxylic acid tert-butyl ester (840.0 mg, 4.194 mmol) in an analogous manner to [B016]. Product isolated as a yellow foam (0.869 g, 53%). $^1$HNMR (400 MHz, d6-DMSO, δ, ppm): 8.86-8.25 (m, 6H), 4.31-4.21 (m, 1H), 4.14 (s, 3H), 4.00-3.90 (m, 1H), 3.72-3.50 (m, 1H), 3.36-3.28 (m, 1H), 2.02-1.78 (m, 5H), 1.45-1.10 (m, 9H). LC/MS=471, 473 (MH)+.

431b) [5-Methoxy-2-(2-phenylamino-pyridin-4-yl)-pyrido[3,4-d]pyrimidin-4-yl]-(R)-1-pyrrolidin-2-ylmethyl-amine was prepared from (R)-2-{[2-(2-Chloro-pyridin-4-yl)-5-methoxy-pyrido[3,4-d]pyrimidin-4-ylamino]-methyl}-pyrrolidine-1-carboxylic acid tert-butyl ester (105.0 mg, 0.2230 mmol) and Aniline (25.0 µL, 0.274 mmol) in an analogous manner to Example 303c and Example 1501c. Product isolated as the trifluoroacetic acid salt as a yellow lyophilate (0.117 g, 97%). $^1$HNMR (400 MHz, d6-DMSO, δ, ppm): 9.42 (br s, 1H), 8.97 (br s, 1H), 8.82 (s, 1H), 8.64 (t, J=5.9 Hz, 1H), 8.53 (br s, 1H), 8.40 (s, 1H), 8.31 (d, J=5.4 Hz, 1H), 7.94 (s, 1H), 7.75-7.70 (m, 3H), 7.31 (t, J=7.5 Hz, 2H), 6.95 (t, J=7.4 Hz, 1H), 4.15 (s, 3H), 4.12-3.85 (m, 3H), 3.34-3.15 (m, 2H), 2.20-1.74 (m, 4H). MS=428 (MH)+.

Example 432. 2-{4-[5-Methoxy-2-(2-phenylamino-pyridin-4-yl)-pyrido[3,4-d]pyrimidin-4-yl]-piperazin-1-yl}-ethanol 432a) 2-{4-[2-(2-Chloro-pyridin-4-yl)-5-methoxy-pyrido[3,4-d]pyrimidin-4-yl]-piperazin-1-yl}-ethanol was prepared from 2-(2-Chloro-pyridin-4-yl)-5-methoxy-pyrido[3,4-d]pyrimidin-4-ol (1000.0 mg, 3.4639 mmol) and 2-Piperazin-1-yl-ethanol (550.0 mg, 4.225 mmol) in an analogous manner to Example 303c and Example 1501c. Product isolated as a yellow solid (0.414 g, 30%). $^1$HNMR (400 MHz, d6-DMSO, δ, ppm): 8.84 (s, 1H), 8.60 (dd, J=5.1, 0.7 Hz, 1H), 8.36 (s, 1H), 8.32-8.29 (m, 2H), 4.46 (t, J=5.4 Hz, 1H), 4.07 (s, 3H), 3.75-3.70 (m, 4H), 3.58-3.52 (m, 2H), 2.63-2.58 (m, 4H), 2.46 (t, J=6.2 Hz, 2H). LC/MS=401, 403 (MH)+.

Example 433. {1-[5-Methoxy-2-(2-phenylamino-pyridin-4-yl)-pyrido[3,4-d]pyrimidin-4-yl]-azetidin-3-yl}-methanol 433a) {1-[2-(2-Chloro-pyridin-4-yl)-5-methoxy-pyrido[3,4-d]pyrimidin-4-yl]-azetidin-3-yl}-methanol was prepared from 2-(2-Chloro-pyridin-4-yl)-5-methoxy-pyrido[3,4-d]pyrimidin-4-ol (1000.0 mg, 3.4639 mmol) and Azetidin-3-yl-methanol; hydrochloride (550.0 mg, 4.450 mmol) in an analogous manner to [B016]. Product isolated as a tan solid (0.925 g, 75%). $^1$HNMR (400 MHz, d6-DMSO, δ, ppm): 8.80 (s, 1H), 8.59 (dd, J=4.8, 1.1 Hz, 1H), 8.33-8.29 (m, 3H), 4.83 (t. J=5.5 Hz, 1H), 4.60-4.53 (m, 1H), 4.41-4.34 (m, 1H), 4.27-4.21 (m, 1H), 4.16-4.10 (m, 1H), 4.06 (s, 3H), 3.59 (t, J=5.7 Hz, 2H), 2.85-2.75 (m, 1H). MS=358, 360 (MH)+.

433b) {1-[5-Methoxy-2-(2-phenylamino-pyridin-4-yl)-pyrido[3,4-d]pyrimidin-4-yl]-azetidin-3-yl}-methanol was prepared from {1-[2-(2-Chloro-pyridin-4-yl)-5-methoxy-pyrido[3,4-d]pyrimidin-4-yl]-azetidin-3-yl}-methanol (114.0 mg, 0.3186 mmol) and Aniline (31.0 µL, 0.340 mmol) in an analogous manner to Example 303c and Example 1501c. Product isolated as the trifluoroacetic acid salt as a yellow lyophilate (0.117 g, 69%). $^1$HNMR (400 MHz, d6-DMSO, δ, ppm): 9.65 (br s, 1H), 8.79 (s, 1H), 8.33 (s, 1H), 8.25 (d, J=5.5 Hz, 1H), 7.97 (s, 1H), 7.72-7.67 (m, 3H), 7.34 (t, J=7.8 Hz, 2H), 7.01 (t, J=7.3 Hz, 1H), 4.61-4.11 (m, 4H), 4.07 (s, 3H), 3.60 (d, J=6.2 Hz, 2H), 2.87-2.76 (m, 1H). MS=415 (MH)+.

Example 434. {(R)-4-[5-Methoxy-2-(2-phenylamino-pyridin-4-yl)-pyrido[3,4-d]pyrimidin-4-yl]-piperazin-2-yl}-methanol 434a) (R)-4-[2-(2-Chloro-pyridin-4-yl)-5-methoxy-pyrido[3,4-d]pyrimidin-4-yl]-2-hydroxymethyl-piperazine-1-carboxylic acid tert-butyl ester was prepared from 2-(2-Chloro-pyridin-4-yl)-5-methoxy-pyrido[3,4-d]pyrimidin-4-ol (1.00 g, 3.46 mmol) and (R)-2-Hydroxymethyl-piperazine-1-carboxylic acid tert-butyl ester (0.90 g, 4.2 mmol) in an analogous manner to [B016]. Product isolated as an off-white solid (1.23 g, 72%). $^1$HNMR (400 MHz, d6-DMSO, δ, ppm): 8.86 (s, 1H), 8.60 (d, J=5.4 Hz, 1H), 8.38 (s, 1H), 8.36-8.32 (m, 2H), 4.78 (t, J=5.2 Hz, 1H), 4.48 (d, J=12.7 Hz, 1H), 4.17-4.11 (m, 1H), 4.09 (s, 3H), 4.06-3.99 (m, 1H), 3.88-3.80 (m, 1H), 3.47-3.35 (m, 3H), 3.29-3.21 (m, 2H), 1.42 (s, 9H). LC/MS=487, 489 (MH)+.

434b) {(R)-4-[5-Methoxy-2-(2-phenylamino-pyridin-4-yl)-pyrido[3,4-d]pyrimidin-4-yl]-piperazin-2-yl}-methanol was prepared from (R)-4-[2-(2-Chloro-pyridin-4-yl)-5-methoxy-pyrido[3,4-d]pyrimidin-4-yl]-2-hydroxymethyl-piperazine-1-carboxylic acid tert-butyl ester (104.0 mg, 0.2136 mmol) and Aniline (23.0 µL, 0.252 mmol) in an analogous manner to Example 303c and Example 1501c. Product isolated as the free base as a yellow foam (0.033 g, 34%). $^1$HNMR (400 MHz, d6-DMSO, δ, ppm): 9.31 (s, 1H), 8.81 (s, 1H), 8.33 (s, 1H), 8.30 (d, J=5.3 Hz, 1H), 7.89 (s, 1H), 7.77-7.73 (m, 2H), 7.66 (dd, J=5.3, 1.3 Hz, 1H), 7.30-7.25 (m, 2H), 6.92-6.87 (m, 1H), 4.71 (t, J=5.5 Hz, 1H), 4.24-4.15 (m, 2H), 4.07 (s, 3H), 3.44-3.36 (m, 2H), 3.16-3.02 (m, 2H), 2.88-2.78 (m, 3H). MS=444 (MH)+.

Example 435. (R)-7-[5-Methoxy-2-(2-phenylamino-pyridin-4-yl)-pyrido[3,4-d]pyrimidin-4-yl]-hexahydro-oxazolo[3,4-a]pyrazin-3-one (R)-7-[5-Methoxy-2-(2-phenylamino-pyridin-4-yl)-pyrido[3,4-d]pyrimidin-4-yl]-hexahydro-oxazolo[3,4-a] pyrazin-3-one was a byproduct from Example 434. Product isolated as the free base as a yellow foam (0.023 g, 23%). $^1$HNMR (400 MHz, d6-DMSO, δ, ppm): 9.31 (s, 1H), 8.87 (s, 1H), 8.38 (s, 1H), 8.32 (d, J=5.2 Hz, 1H), 7.91 (s, 1H), 7.77-7.74 (m, 2H), 7.69 (dd, J=5.3, 1.4 Hz, 1H), 7.31-7.26 (m, 2H), 6.93-6.88 (m, 1H), 4.50-4.39 (m, 2H), 4.29 (d, J=13.1 Hz, 1H), 4.12-4.03 (m, 6H), 3.77 (dd, J=13.2, 2.1 Hz, 1H), 3.17-3.06 (m, 2H). MS=470 (MH)+.

Example 436. (±)-cis-1-[5-Methoxy-2-(2-phenylamino-pyridin-4-yl)-pyrido[3,4-d]pyrimidin-4-yl]-piperidine-3,4-diol 436a) To a solution of 3,6-Dihydro-2H-pyridine-1-carboxylic acid benzyl ester (1.16 g, 5.34 mmol) [prepared as described in Solares, F. L.; et. al. *Tetrahedron* 2006, 62, 3284-3291] in Acetone (4 mL,) and Water (4 mL,) was added N-Methylmorpholine N-oxide (0.88 g, 7.5 mmol) followed by 2.5 wt % (w/v) OsO4 in t-BuOH(2.5:97.5, Osmium tetraoxide:tert-Butyl alcohol, 0.8 mL, 0.06 mmol). The mixture was stirred at room temperature for 1 hour. Reaction was complete by LC/MS. Saturated aqueous sodium thiosulfate (50 mL) was added and mixture was stirred for 5 minutes then extracted with ethyl acetate (3×50 mL). The combined organic layers were dried over sodium sulfate, filtered and evaporated to a red-brown oil. The recovered oil was purified via chromatography using an ISCO apparatus (silica gel column (24 g) and 2:1 Ethyl Acetate:Hexane). (±)-cis-3,4-Dihydroxy-piperidine-1-carboxylic acid benzyl ester was isolated as a pale yellow oil (1.13 g, 84%). $^1$HNMR (400 MHz, d6-DMSO, δ, ppm): 7.43-7.27 (m, 5H), 5.05 (s, 2H), 4.66 (d, J=4.1 Hz, 1H), 4.55 (d, J=3.7 Hz, 1H), 3.75-3.64 (m, 1H), 3.51-3.18 (m, 5H), 1.69-1.60 (m, 1H), 1.52-1.43 (m, 1H). MS=274 (M+Na)+.

436b) A Paar bottle (500 mL) was charged with 10% Palladium on Carbon (50% Wet)(5:45:50, Palladium:carbon black:Water, 1.0 g, 0.47 mmol) followed by a solution of (±)-cis-3,4-Dihydroxy-piperidine-1-carboxylic acid benzyl ester (1.13 g, 4.50 mmol) in 2:1 Ethyl Acetate:Methanol (50 mL). The reaction mixture was degassed and charged with Hydrogen (50 psi). The mixture was shaken on a Paar apparatus for 4 hours. The reaction mixture was degassed and kept under an atmosphere of Nitrogen. The mixture was filtered through a plug of diatomaceous earth and rinsed with dichloromethane. The filtrate was evaporated. (±)-cis-Piperidine-3,4-diol was isolated as a pale yellow oil (0.569 g, 100%). $^1$HNMR (400 MHz, d6-DMSO, δ, ppm): 4.11 (br s, 3H), 3.57-3.53 (m, 1H), 3.46-3.42 (m, 1H), 2.79-2.67 (m, 2H), 2.57-2.49 (m, 1H), 2.47-2.37 (m, 1H), 1.61-1.51 (m, 1H), 1.47-1.39 (m, 1H). MS=118 (MH)+.

436c) (±)-cis-1-[2-(2-Chloro-pyridin-4-yl)-5-methoxy-pyrido[3,4-d]pyrimidin-4-yl]-piperidine-3,4-diol was prepared from 2-(2-Chloro-pyridin-4-yl)-5-methoxy-pyrido[3,4-d]pyrimidin-4-ol (1.00 g, 3.46 mmol) and (±)-cis-Piperidine-3,4-diol (0.56 g, 4.8 mmol) in analogous manner to [B016]. Product isolated as a pale yellow solid (0.927 g, 69%). $^1$HNMR (400 MHz, d6-DMSO, δ, ppm): 8.82 (s, 1H), 8.60 (dd, J=5.0, 0.5 Hz, 1H), 8.35 (s, 1H), 8.32-8.29 (m, 2H), 4.65-4.61 (m, 2H), 4.07 (s, 3H), 3.94 (br s, 1H), 3.83-3.74 (m, 2H), 3.65-3.53 (m, 3H), 1.94-1.85 (m, 1H), 1.73-1.65 (m, 1H). MS=388, 390 (MH)+.

436d) (1)-cis-1-[5-Methoxy-2-(2-phenylamino-pyridin-4-yl)-pyrido[3,4-d]pyrimidin-4-yl]-piperidine-3,4-diol was prepared from (1)-cis-1-[2-(2-Chloro-pyridin-4-yl)-5-methoxy-pyrido[3,4-d]pyrimidin-4-yl]-piperidine-3,4-diol (100.0 mg, 0.2578 mmol) and Aniline (29.0 μL, 0.318 mmol) in an analogous manner to Example 303c. Product isolated as the free base as a yellow solid (0.039 g, 34%). MP=241-243° C. $^1$HNMR (400 MHz, d6-DMSO, δ, ppm): 9.32 (s, 1H), 8.79 (s, 1H), 8.32-8.29 (m, 2H), 7.90 (s, 1H), 7.77-7.74 (m, 2H), 7.67 (dd, J=5.3, 1.3 Hz, 1H), 7.30-7.25 (m, 2H), 6.92-6.87 (m, 1H), 4.64-4.60 (m, 2H), 4.07 (s, 3H), 3.98-3.88 (m, 1H), 3.85-3.72 (m, 2H), 3.66-3.53 (m, 3H), 1.97-1.87 (m, 1H), 1.76-1.66 (m, 1H). MS=445 (MH)+.

Example 437. (±)-trans-1-[5-Methoxy-2-(2-phenylamino-pyridin-4-yl)-pyrido[3,4-d]pyrimidin-4-yl]-piperidine-3,4-diol 437a) (±)-trans-Piperidine-3,4-diol was prepared from (1)-trans-3,4-Dihydroxy-piperidine-1-carboxylic acid benzyl ester (1.0 g, 4.0 mmol) [prepared as described in Solares, F. L.; et. al. *Tetrahedron* 2006, 62, 3284-3291] in an analogous manner to Example 436a. Product isolated as a pale yellow oil (0.451 g, 97%). $^1$HNMR (400 MHz, d6-DMSO, δ, ppm): 4.59 (br s, 2H), 4.09 (br s, 1H), 3.20-3.13 (m, 1H), 3.11-3.04 (m, 1H), 2.88 (ddd, J=4.4, 12.1, 1.2 Hz, 1H), 2.77 (dddd, J=12.6, 4.1, 4.1, 1.2 Hz, 1H), 2.35 (dddd, J=14.1, 11.3, 2.9 Hz, 1H), 2.15 (dd, J=12.2, 9.1 Hz, 1H), 1.71 (dddd, J=12.6, 3.8, 3.8, 3.8 Hz, 1H), 1.25-1.15 (m, 1H). MS=118 (MH)+.

437b) (±)-trans-1-[2-(2-Chloro-pyridin-4-yl)-5-methoxy-pyrido[3,4-d]pyrimidin-4-yl]-piperidine-3,4-diol was prepared from 2-(2-Chloro-pyridin-4-yl)-5-methoxy-pyrido[3,4-d]pyrimidin-4-ol (1.00 g, 3.46 mmol) and (±)-trans-Piperidine-3,4-diol (0.46 g, 3.9 mmol) in an analogous manner to [B016]. Product isolated as a tan solid (0.700 g, 52%). MP=213-216° C. $^1$HNMR (400 MHz, d6-DMSO, δ, ppm): 8.83 (s, 1H), 8.61 (dd, J=5.0, 0.6 Hz, 1H), 8.36 (s, 1H), 8.32-8.29 (m, 2H), 5.00 (d, J=4.1 Hz, 1H), 4.94 (d, J=4.2 Hz, 1H), 4.11-4.03 (m, 4H), 4.00-3.90 (m, 1H), 3.59-3.47 (m, 2H), 3.44-3.37 (m, 1H), 3.16 (dd, J=13.1, 7.9 Hz, 1H), 2.07-1.99 (m, 1H), 1.54-1.44 (m, 1H). MS=388, 390 (MH)+.

437c) desired (1)-trans-1-[5-Methoxy-2-(2-phenylamino-pyridin-4-yl)-pyrido[3,4-d]pyrimidin-4-yl]-piperidine-3,4-diol was prepared from (±)-trans-1-[2-(2-Chloro-pyridin-4-yl)-5-methoxy-pyrido[3,4-d]pyrimidin-4-yl]-piperidine-3,4-diol (100.0 mg, 0.2578 mmol) and Aniline (29.0 μL, 0.318 mmol) in an analogous manner to Example 303c and Example 1501c. Product isolated as the free base as tan foam (0.1126 g, 98%). $^1$HNMR (400 MHz, d6-DMSO, δ, ppm): 9.32 (s, 1H), 8.80 (s, 1H), 8.33 (s, 1H), 8.30 (d, J=5.4 Hz, 1H), 7.90 (s, 1H), 7.77-7.74 (m, 2H), 7.67 (dd, J=5.3, 1.3 Hz, 1H), 7.40-7.36 (m, 1H), 7.30-7.25 (m, 2H), 6.92-6.87 (m, 1H), 5.00 (d, J=4.1 Hz, 1H), 4.94 (d, J=4.2 Hz, 1H), 4.10-4.04 (m, 4H), 3.98 (d, J=13.4 Hz, 1H), 3.55-3.46 (m, 1H), 3.40 (dddd, J=7.7, 7.7, 4.2, 4.2 Hz, 1H), 3.13 (dd, J=13.0, 7.7 Hz, 1H), 2.09-2.00 (m, 1H), 1.57-1.46 (m, 1H). MS=445 (MH)+.

Example 438. 4-[5-Methoxy-2-(2-phenylamino-pyridin-4-yl)-pyrido[3,4-d]pyrimidin-4-yl]-piperazin-2-one 438a) 4-[2-(2-Chloro-pyridin-4-yl)-5-methoxy-pyrido[3,4-d]pyrimidin-4-yl]-piperazin-2-one was prepared from 2-(2-Chloro-pyridin-4-yl)-5-methoxy-pyrido[3,4-d]pyrimidin-4-ol (1.0 g, 3.5 mmol) and Piperazin-2-one (0.42 g, 4.2 mmol) in an analogous manner to [B016]. Product isolated as a tan solid (1.12 g, 87%). $^1$HNMR (400 MHz, d6-DMSO, δ, ppm): 8.89 (s, 1H), 8.63-8.60 (m, 1H), 8.41 (s, 1H), 8.34-8.32 (m, 2H), 8.15 (s, 1H), 4.23 (s, 2H), 4.10 (s, 3H), 3.95-3.90 (m, 2H), 3.43-3.39 (m, 2H). LC/MS=371, 373 (MH)+.

438b) 4-[5-Methoxy-2-(2-phenylamino-pyridin-4-yl)-pyrido[3,4-d]pyrimidin-4-yl]-piperazin-2-one was prepared from 4-[2-(2-Chloro-pyridin-4-yl)-5-methoxy-pyrido[3,4-d]pyrimidin-4-yl]-piperazin-2-one (100.0 mg, 0.2697 mmol) and Aniline (30.0 μL, 0.329 mmol) in an analogous manner to Example 303c and Example 1501c. Product isolated as the trifluoroacetic acid salt as a yellow lyophilate (0.022 g, 19%). $^1$HNMR (400 MHz, d6-DMSO, δ, ppm): 9.66 (br s, 1H), 8.87 (s, 1H), 8.40 (s, 1H), 8.27 (d, J=5.5 Hz, 1H), 8.18 (s, 1H), 7.97 (s, 1H), 7.74-7.69 (m, 3H), 7.34 (t, J=7.7 Hz, 2H), 7.00 (t, J=7.0 Hz, 1H), 4.23 (s, 2H), 4.10 (s, 3H), 3.92-3.87 (m, 2H), 3.46-3.41 (m, 2H). MS=428 (MH)+.

Example 439. (2,3-Difluoro-phenyl)-[4-(5-methoxy-4-piperazin-1-yl-pyrido[3,4-d]pyrimidin-2-yl)-pyridin-2-yl]-amine (2,3-Difluoro-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,3-Difluoro-phenylamine (27.0 μL, 0.266 mmol) in an analogous manner to Example 303c and Example 1501c. Product isolated as the bis-trifluoroacetic acid salt as a yellow lyophilate (0.125 g, 84%). $^1$HNMR (400 MHz, d6-DMSO, δ, ppm): 9.24 (s, 1H), 8.91 (s, 1H), 8.86 (br s, 2H), 8.42 (s, 1H), 8.33 (d, J=5.4 Hz, 1H), 8.10 (s, 1H), 8.07-8.03 (m, 1H), 7.78 (dd, J=5.3, 1.4 Hz, 1H), 7.19-7.11 (m, 1H), 7.06-6.98 (m, 1H), 4.10 (s, 3H), 3.91-3.86 (m, 4H), 3.36-3.29 (m, 4H). MS=450 (MH)+.

Example 440. (2,5-Difluoro-phenyl)-[4-(5-methoxy-4-piperazin-1-yl-pyrido[3,4-d]pyrimidin-2-yl)-pyridin-2-yl]-amine (2,5-Difluoro-phenyl)-[4-(5-methoxy-4-piperazin-1-yl-pyrido[3,4-d]pyrimidin-2-yl)-pyridin-2-yl]-amine was prepared 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,5-Difluoro-phenylamine (27.0 μL, 0.268 mmol) in an analogous manner to Example 303c and Example 1501c. Product isolated as the bis-trifluoroacetic acid salt as a yellow lyophilate (0.036 g, 24%). $^1$HNMR (400 MHz, d6-DMSO, δ, ppm): 9.25 (s, 1H), 8.91 (s, 1H), 8.89 (br s, 2H), 8.45-8.38 (m, 3H), 8.21 (s, 1H), 7.81 (dd, J=5.3, 1.4 Hz, 1H), 7.31-7.24 (m, 1H), 6.80-6.74 (m, 1H), 4.11 (s, 3H), 3.92-3.87 (m, 4H), 3.36-3.30 (m, 4H). MS=450 (MH)+.

Example 441. [4-(5-Methoxy-4-piperazin-1-yl-pyrido[3,4-d]pyrimidin-2-yl)-pyridin-2-yl]-(2,4,6-trifluoro-phenyl)-amine

[4-(5-Methoxy-4-piperazin-1-yl-pyrido[3,4-d]pyrimidin-2-yl)-pyridin-2-yl]-(2,4,6-trifluoro-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,4,6-Trifluoro-phenylamine (39.0 mg, 0.265 mmol) in an analogous manner to Example 303c and Example 1501c. Product isolated as the bis-trifluoroacetic acid salt as a yellow lyophilate (0.092 g, 60%). $^1$HNMR (400 MHz, d6-DMSO, δ, ppm): 8.93 (br s, 2H), 8.90 (s, 1H), 8.82 (s, 1H), 8.42 (s, 1H), 8.17 (dd, J=5.4, 0.5 Hz, 1H), 7.83 (s, 1H), 7.68 (dd, J=5.3, 1.4 Hz, 1H), 7.34-7.23 (m, 2H), 4.10 (s, 3H), 3.90-3.84 (m, 4H), 3.35-3.29 (m, 4H). MS=468 (MH)+.

Example 442. ((R)-4-{2-[2-(2,6-Difluoro-phenylamino)-pyridin-4-yl]-5-methoxy-pyrido[3,4-d]pyrimidin-4-yl}-piperazin-2-yl)-methanol ((R)-4-{2-[2-(2,6-Difluoro-phenylamino)-pyridin-4-yl]-5-methoxy-pyrido[3,4-d]pyrimidin-4-yl}-piperazin-2-yl)-methanol was prepared from (R)-4-[2-(2-Chloro-pyridin-4-yl)-5-methoxy-pyrido[3,4-d]pyrimidin-4-yl]-2-hydroxymethyl-piperazine-1-carboxylic acid tert-butyl ester (100.0 mg, 0.2054 mmol) and 2,6-Difluoro-phenylamine (32.0 mg, 0.248 mmol) in an analogous manner to Example 303c and Example 1501c. Product isolated as the free base as a tan foam (0.066 g, 66%). $^1$HNMR (400 MHz, d6-DMSO, δ, ppm): 8.80 (s, 1H), 8.76 (s, 1H), 8.32 (s, 1H), 8.15 (d, J=5.3 Hz, 1H), 7.77 (s, 1H), 7.64 (d, J-5.2, 1.3 Hz, 1H), 7.31-7.10 (m, 3H), 4.70 (t, J=5.5 Hz, 1H), 4.21-4.12 (m, 2H), 4.06 (s, 3H), 3.42-3.35 (m, 2H), 3.15-3.00 (m, 2H), 2.86-2.77 (m, 3H). MS=480 (MH)+.

Example 443. 3-Hydroxymethyl-1-[5-methoxy-2-(2-phenylamino-pyridin-4-yl)-pyrido[3,4-d]pyrimidin-4-yl]-piperidin-4-ol 443a) To a cooled solution of 4-Oxo-piperidine-3-carboxylic acid ethyl ester; hydrochloride (5.0 g, 24 mmol) and Sodium bicarbonate (4.40 g, 52.4 mmol) in Water (50 mL) at 5° C. was added Benzyl chloroformate (3.40 mL, 23.8 mmol) dropwise. The mixture was stirred at room temperature overnight. Saturated aqueous sodium carbonate (10 mL) was added and stirred for 30 minutes. The reaction mixture was extracted dichloromethane (3×30 mL). The combined organic layer was dried over magnesium sulfate, filtered and evaporated. The crude material was purified via chromatography using an ISCO apparatus (silica gel column 120 g and 10%→50% Ethyl Acetate:hexane). 4-Oxo-piperidine-1,3-dicarboxylic acid 1-benzyl ester 3-ethyl ester was isolated as a clear oil (7.30 g, 100%). $^1$HNMR (400 MHz, CDCl3, δ, ppm): 12.07 (s, 1H), 7.43-7.29 (m, 5H), 5.20-5.15 (m, 2H), 4.24 (q, J=7.2 Hz, 2H), 4.14 (br s, 2H), 3.65 (t, J=5.9 Hz, 2H), 2.39 (br s, 2H), 1.31 (t, J=7.2 Hz, 3H). MS=328 (M+Na)+.

443b) Sodium borohydride (4.5 g, 120 mmol) was added in 0.5 g portions over 1 hour to a stirred solution of 4-Oxo-piperidine-1,3-dicarboxylic acid 1-benzyl ester 3-ethyl ester (3.0 g, 9.8 mmol) in Methanol (30 mL) under an atmosphere of Nitrogen at room temperature. Gas evolution and exotherm was noted during each addition. The slow portionwise addition kept reaction temperatures below 25° C. during the course of additions. The mixture was stirred for 1 hour at room temperature then slowly warmed. The reaction was refluxed for 4 hours, cooled to room temperature and stirred overnight. A 1:1 mixture of water: methanol (100 mL) was added dropwise to the reaction over 1 hour. No exotherm or gas evolution was noted. The mixture was stirred for 4 hours. The methanol was evaporated under reduced pressure. Methanol (50 mL) was added and the white suspension was heated at reflux for 30 minutes. The methanol was evaporated under reduced pressure. This was repeated twice. The mixture was evaporated to a white oily solid. The solid was triturated with dichloromethane (3×50 mL) and decanted. The combined organic was dried over magnesium sulfate, filtered and evaporated. 4-Hydroxy-3-hydroxymethyl-piperidine-1-carboxylic acid benzyl ester was isolated as a clear oil (0.655 g, 25%). $^1$HNMR (400 MHz, d6-DMSO, δ, ppm): 7.41-7.28 (m, 5H), 5.13-5.00 (m, 2H), 4.70-4.56 (m, 1H), 4.50-4.39 (m, 1H), 4.09-3.60 (m, 3H), 3.47-2.58 (m, 4H), 1.80-1.20 (m, 3H). MS=288 (M+Na)+.

443c) 3-Hydroxymethyl-piperidin-4-ol was prepared from 4-Hydroxy-3-hydroxymethyl-piperidine-1-carboxylic acid benzyl ester (0.655 g, 2.47 mmol) in an analogous manner to Example 436b. Product isolated as a viscous oil (0.324 g, 100%). $^1$HNMR (400 MHz, d6-DMSO, δ, ppm): 4.60-3.18 (m, 7H), 3.3-2.78 (m, 1H), 2.70-2.56 (m, 1H), 2.43-2.10 (m, 1H), 1.74-1.18 (m, 3H).

443d) 1-[2-(2-Chloro-pyridin-4-yl)-5-methoxy-pyrido[3,4-d]pyrimidin-4-yl]-3-hydroxymethyl-piperidin-4-ol was prepared from 2-(2-Chloro-pyridin-4-yl)-5-methoxy-pyrido[3,4-d]pyrimidin-4-ol (0.70 g, 2.4 mmol) and 3-Hydroxymethyl-piperidin-4-ol (0.324 g, 2.47 mmol) in an analogous manner to [B016]. Product isolated as a pale yellow foam (0.342 g, 35%). $^1$HNMR (400 MHz, d6-DMSO, δ, ppm): 8.83 (d, J=5.4 Hz, 1H), 8.61-5.85 (m, 1H), 8.35 (d, J=6.2 Hz, 1H), 8.33-8.29 (m, 2H), 4.78-4.69 (m, 1H), 4.58-4.46 (m, 1H), 4.36-3.70 (m, 6H), 3.56-3.12 (m, 4H), 2.02-1.45 (m, 3H). MS=402, 404 (MH)+.

443e) 3-Hydroxymethyl-1-[5-methoxy-2-(2-phenylamino-pyridin-4-yl)-pyrido[3,4-d]pyrimidin-4-yl]-piperidin-4-ol was prepared from 1-[2-(2-Chloro-pyridin-4-yl)-5-methoxy-pyrido[3,4-d]pyrimidin-4-yl]-3-hydroxymethyl-piperidin-4-ol (100.0 mg, 0.2488 mmol) and Aniline (28.0 μL, 0.307 mmol) in an analogous manner to Example 303c and Example 1501c. Product was isolated as the free base as a mixture of enantiomers as a yellow foam (0.071 g, 62%). $^1$HNMR (400 MHz, d6-DMSO, δ, ppm): 9.31 (d, J=3.0 Hz, 1H), 8.80 (d, J=4.5 Hz, 1H), 8.34-8.29 (m, 2H), 7.90 (s, 1H), 7.75 (d, J=7.7 H, 2H), 7.68 (dd, J=5.3, 1.2 Hz, 1H), 7.31-7.25 (m, 2H), 6.92-6.87 (m, 1H), 4.79-4.69 (m, 1H), 4.55-4.43 (m, 1H), 4.30-3.70 (m, 6H), 3.56-3.25 (m, 3H), 3.19-2.91 (m, 1H), 2.04-1.50 (m, 3H). MS=459 (MH)+.

Example 444. [4-(5-Methoxy-4-piperazin-1-yl-pyrido[3,4-d]pyrimidin-2-yl)-pyridin-2-yl]-(2,3,6-trifluoro-phenyl)-amine

[4-(5-Methoxy-4-piperazin-1-yl-pyrido[3,4-d]pyrimidin-2-yl)-pyridin-2-yl]-(2,3,6-trifluoro-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (121.0 mg, 0.2648 mmol) and 2,3,6-Trifluoro-phenylamine (33.9 μL, 0.320 mmol) in an analogous manner to Example 303c and Example 1501c. Product isolated as the bis-trifluoroacetic acid salt as a yellow lyophilate (0.155 g, 84%). $^1$HNMR (400 MHz, d6-DMSO, δ, ppm): 9.07 (s, 1H), 8.94-8.84 (m, 3H), 8.42 (s, 1H), 8.21 (d, J=5.3 Hz, 1H), 7.89 (s, 1H), 7.72 (dd, J=5.3, 1.4 Hz, 1H), 7.33 (dddd, J=9.7, 9.7, 9.7, 4.9 Hz, 1H), 7.21 (dddd, J=9.6, 4.7, 4.7, 2.2 Hz, 1H), 4.10 (s, 3H), 3.91-3.84 (m, 4H), 3.36-3.28 (m, 4H). MS=468 (MH)+.

Example 445. [4-(5-Methoxy-4-piperazin-1-yl-pyrido[3,4-d]pyrimidin-2-yl)-pyridin-2-yl]-(2-trifluoromethyl-phenyl)-amine

[4-(5-Methoxy-4-piperazin-1-yl-pyrido[3,4-d]pyrimidin-2-yl)-pyridin-2-yl]-(2-trifluoromethyl-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (124.0 mg, 0.2714 mmol) and 2-(trifluoromethyl)-Benzenamine (40.0 μL, 0.318 mmol) in an analogous manner to Example 303c and Example 1501c. Product isolated as the bis-trifluoroacetic acid salt as a yellow lyophilate (0.134 g, 69%). $^1$HNMR (400 MHz, d6-DMSO, δ, ppm): 9.00-8.85 (m, 4H), 8.42 (d, J=2.3 Hz, 1H), 8.19 (dd, J=5.4, 1.4 Hz, 1H), 7.99 (s, 1H), 7.80-7.66 (m, 4H), 7.44-7.37 (m, 1H), 4.11 (s, 3H), 3.90-3.84 (m, 4H), 3.35-3.28 (m, 4H). MS=482 (MH)+.

Example 446. [4-(5-Methoxy-4-piperazin-1-yl-pyrido[3,4-d]pyrimidin-2-yl)-pyridin-2-yl]-(3-trifluoromethyl-phenyl)-amine

[4-(5-Methoxy-4-piperazin-1-yl-pyrido[3,4-d]pyrimidin-2-yl)-pyridin-2-yl]-(3-trifluoromethyl-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (140.0 mg, 0.3064 mmol) and 3-(trifluoromethyl)-Benzenamine (46.2 μL, 0.370 mmol) in an analogous manner to Example 303c and Example 1501c. Product isolated as the trifluoroacetic acid salt as a yellow lyophilate (0.179 g, 98%). $^1$HNMR (400 MHz, d6-DMSO, δ, ppm): 9.76 (s, 1H), 8.93-8.83 (m, 3H), 8.42 (s, 1H), 8.41 (d, J=5.4 Hz, 1H), 8.34 (s, 1H), 7.97 (s, 1H), 7.92 (d, J=8.3 Hz, 1H), 7.78 (dd, J=5.3, 1.3 Hz, 1H), 7.52 (t, J=7.9 Hz, 1H), 7.23 (d, J=7.6 Hz, 1H), 4.11 (s, 3H), 3.91-3.86 (m, 4H), 3.36-3.30 (m, 4H). MS=482 (MH)+.

Example 447. (6-Fluoro-pyridin-2-yl)-[4-(5-methoxy-4-piperazin-1-yl-pyrido[3,4-d]pyrimidin-2-yl)-pyridin-2-yl]-amine (6-Fluoro-pyridin-2-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Fluoro-pyridin-2-ylamine (30.0 mg, 0.268 mmol) in an analogous manner to Example 303c and Example 1501c. Product isolated as the free base as an off-white solid (0.003 g, 2%). $^1$HNMR (400 MHz, d6-DMSO, δ, ppm): 10.15 (s, 1H), 8.81 (s, 1H), 8.74 (s, 1H), 8.40 (d, J=5.1 Hz, 1H), 8.32 (s, 1H), 7.88-7.81 (m, 2H), 7.75 (dd, J=8.1, 2.6 Hz, 1H), 6.59 (dd, J=7.7, 2.3 Hz, 1H), 4.07 (s, 3H), 3.71-3.66 (m, 4H), 2.90-2.85 (m, 4H). MS=433 (MH)+.

Example 448. [4-(5-Methoxy-4-piperazin-1-yl-pyrido[3,4-d]pyrimidin-2-yl)-pyridin-2-yl]-(6-methoxy-pyridin-2-yl)-amine

[4-(5-Methoxy-4-piperazin-1-yl-pyrido[3,4-d]pyrimidin-2-yl)-pyridin-2-yl]-(6-methoxy-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (124.0 mg, 0.2714 mmol) and 6-Methoxy-pyridin-2-ylamine (40.0 mg, 0.322 mmol) in an analogous manner to Example 303c and Example 1501c. Product isolated as the free base as an off-white solid (0.098 g, 80%).

MP=189-191° C. $^1$HNMR (400 MHz, d6-DMSO, δ, ppm): 9.79 (s, 1H), 9.04 (s, 1H), 8.73 (s, 1H), 8.37 (d, J=5.2 Hz, 1H), 8.31 (s, 1H), 7.79 (dd, J=5.2, 1.4 Hz, 1H), 7.58 (t, J=7.9 Hz, 1H), 7.16 (d, J=7.8 Hz, 1H), 6.30 (d, J=7.7 Hz, 1H), 4.07 (s, 3H), 4.04 (s, 3H), 3.67-3.62 (m, 4H), 2.89-2.84 (m, 4H). MS=445 (MH)+.

Example 449. [4-(5-Methoxy-4-piperazin-1-yl-pyrido[3,4-d]pyrimidin-2-yl)-pyridin-2-yl]-(6-trifluoromethyl-pyridin-2-yl)-amine

[4-(5-Methoxy-4-piperazin-1-yl-pyrido[3,4-d]pyrimidin-2-yl)-pyridin-2-yl]-(6-trifluoromethyl-pyridin-2-yl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 6-Trifluoromethyl-pyridin-2-ylamine (43.0 mg, 0.265 mmol) in an analogous manner to Example 303c and Example 1501c. Product isolated as the free base as off-white solid (0.005 g, 5%). $^1$HNMR (400 MHz, d6-DMSO, δ, ppm): 10.34 (s, 1H), 8.80-8.78 (m, 2H), 8.42 (d, J=4.7 Hz, 1H), 8.32 (s, 1H), 8.08 (d, J=8.1 Hz, 1H), 7.94 (t, J=8.1 Hz, 1H), 7.89 (dd, J=5.1, 1.3 Hz, 1H), 7.36 (d, J=7.4 Hz, 1H), 4.07 (s, 3H), 3.68-3.63 (m, 4H), 2.90-2.85 (m, 4H). MS=483 (MH)+.

Example 450. (2-Fluoro-pyridin-3-yl)-[4-(5-methoxy-4-piperazin-1-yl-pyrido[3,4-d]pyrimidin-2-yl)-pyridin-2-yl]-amine (2-Fluoro-pyridin-3-yl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (124.0 mg, 0.2714 mmol) and 2-Fluoro-pyridin-3-ylamine (40.0 mg, 0.357 mmol) in an analogous manner to Example 303c and Example 1501c. Product isolated as the bis-trifluoroacetic acid salt as a yellow lyophilate (0.156 g, 86%). $^1$HNMR (400 MHz, d6-DMSO, δ, ppm): 9.26 (s, 1H), 8.91 (br s, 3H), 8.86 (ddd, J=10.0, 8.0, 1.7 Hz, 1H), 8.42 (s, 1H), 8.36 (dd, J=5.5 Hz, 1H), 8.19 (s, 1H), 7.81 (dd, J=5.3, 1.3 Hz, 1H), 7.77 (ddd, J=4.6, 1.5, 1.5 Hz, 1H), 7.32 (ddd, J=7.9, 4.8, 0.9 Hz, 1H), 4.11 (s, 3H), 3.93-3.87 (m, 4H), 3.36-3.30 (m, 4H). MS=433 (MH)+.

Example 451. (2-Fluoro-3-methyl-phenyl)-[4-(5-methoxy-4-piperazin-1-yl-pyrido[3,4-d]pyrimidin-2-yl)-pyridin-2-yl]-amine (2-Fluoro-3-methyl-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (111.0 mg, 0.2429 mmol) and 2-Fluoro-3-methyl-phenylamine (36.0 mg, 0.288 mmol) in an analogous manner to Example 303c and Example 1501c. Product isolated as the tris-trifluoroacetic acid salt as a yellow lyophilate (0.146 g, 76%). $^1$HNMR (400 MHz, d6-DMSO, δ, ppm): 9.04 (br s, 1H), 8.90 (s, 1H), 8.87 (br s, 2H), 8.42 (s, 1H), 8.28 (d, J=5.3 Hz, 1H), 8.06 (s, 1H), 7.98 (t, J=7.8 Hz, 1H), 7.73 (dd, J=5.3, 1.3 Hz, 1H), 7.05 (t, J=7.8 Hz, 1H), 6.93 (t, J=7.2 Hz, 1H), 4.10 (s, 3H), 3.91-3.86 (m, 4H), 3.35-3.29 (m, 4H), 2.28 (d, J=1.8 Hz, 3H). MS=446 (MH)+.

Example 452. (2-Fluoro-3-trifluoromethyl-phenyl)-[4-(5-methoxy-4-piperazin-1-yl-pyrido[3,4-d]pyrimidin-2-yl)-pyridin-2-yl]-amine (2-Fluoro-3-trifluoromethyl-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (102.0 mg, 0.2232 mmol) and 2-Fluoro-3-trifluoromethyl-phenylamine (48.0 mg, 0.268 mmol) in an analogous manner to Example 303c and Example 1501c. Product isolated as the bis-trifluoroacetic acid salt as a yellow lyophilate (0.050 g, 30%). $^1$HNMR (400 MHz, d6-DMSO, δ, ppm): 9.32 (s, 1H), 8.91 (s, 1H), 8.85 (br s, 2H), 8.63 (ddd, J=7.8, 7.8, 2.3 Hz, 1H), 8.42 (s, 1H), 8.35 (d, J=5.3 Hz, 1H), 8.14 (s, 1H), 7.81 (dd, J=5.3, 1.4 Hz, 1H), 7.39-7.30 (m, 2H), 4.11 (s, 3H), 3.92-3.86 (m, 4H), 3.36-3.29 (m, 4H). MS=500 (MH)+.

Example 453. 2,4-Difluoro-phenyl)-[4-(5-methoxy-4-piperazin-1-yl-pyrido[3,4-d]pyrimidin-2-yl)-pyridin-2-yl]-amine (2,4-Difluoro-phenyl)-[4-(5-methoxy-4-piperazin-1-yl-pyrido[3,4-d]pyrimidin-2-yl)-pyridin-2-yl]-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,4-Difluoro-phenylamine (27.0 μL, 0.265 mmol) in an analogous manner to Example 303c and Example 1501c. Product isolated as the bis-trifluoroacetic acid salt as a yellow lyophilate (0.059 g, 39%). $^1$HNMR (400 MHz, d6-DMSO, δ, ppm): 9.03 (s, 1H), 8.90 (s, 1H), 8.87 (br s, 2H), 8.42 (s, 1H), 8.27 (d, J=5.3 Hz, 1H), 8.10 (ddd, J=9.3, 9.3, 6.3 Hz, 1H), 8.00 (s, 1H), 7.72 (dd, J=5.4, 1.3 Hz, 1H), 7.31 (ddd, J=11.5, 9.0, 2.9 Hz, 1H), 7.11-7.04 (m, 1H), 4.10 (s, 3H), 3.90-3.85 (m, 4H), 3.35-3.29 (m, 4H). MS=450 (MH)+.

Example 454. [4-(5-Methoxy-4-piperazin-1-yl-pyrido[3,4-d]pyrimidin-2-yl)-pyridin-2-yl]-(2,3,4-trifluoro-phenyl)-amine

[4-(5-Methoxy-4-piperazin-1-yl-pyrido[3,4-d]pyrimidin-2-yl)-pyridin-2-yl]-(2,3,4-trifluoro-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,3,4-Trifluoro-phenylamine (28.0 μL, 0.265 mmol) in an analogous manner to Example 303c and Example 1501c. Product isolated as the bis-trifluoroacetic acid salt as a yellow lyophilate (0.104 g, 68%). $^1$HNMR (400 MHz, d6-DMSO, δ, ppm): 9.21 (s, 1H), 8.95-8.85 (m, 3H), 8.42 (s, 1H), 8.30 (d, J=5.3 Hz, 1H), 8.04 (s, 1H), 7.99-7.91 (m, 1H), 7.77 (dd, J=5.3, 1.3 Hz, 1H), 7.33-7.24 (m, 1H), 4.10 (s, 1H), 3.91-3.86 (m, 4H), 3.36-3.29 (m, 4H). MS=468 (MH)+.

Example 455. [4-(5-Methoxy-4-piperazin-1-yl-pyrido[3,4-d]pyrimidin-2-yl)-pyridin-2-yl]-(2,4,5-trifluoro-phenyl)-amine

[4-(5-Methoxy-4-piperazin-1-yl-pyrido[3,4-d]pyrimidin-2-yl)-pyridin-2-yl]-(2,4,5-trifluoro-phenyl)-amine was prepared from 4-[2-(2-Chloro-pyridin-4-yl)-5-methoxy-pyrido[3,4-d]pyrimidin-4-yl]-piperazine-1-carboxylic acid tert-butyl ester (100.0 mg, 0.2188 mmol) and 2,4,5-Trifluoro-phenylamine (39.0 mg, 0.265 mmol) in an analogous manner to Example 303c and Example 1501c. Product isolated as the bis-trifluoroacetic acid salt as a yellow lyophilate (0.027 g, 17%). $^1$HNMR (400 MHz, d6-DMSO, δ, ppm): 9.21 (s, 1H), 8.91 (s, 1H), 8.86 (br s, 2H), 8.54 (ddd, J=13.6, 8.5, 8.5 Hz, 1H), 8.42 (s, 1H), 8.36 (d, J=5.4 Hz, 1H), 8.14 (s, 1H), 7.79 (dd, J=5.3, 1.4 Hz, 1H), 7.60 (ddd, J=10.9, 10.9, 7.7 Hz, 1H), 4.10 (s, 3H), 3.91-3.86 (m, 4H), 3.36-3.29 (m, 4H). MS=468 (MH)+.

Example 456. (3S,4S)-1-[5-Methoxy-2-(2-phenylamino-pyridin-4-yl)-pyrido[3,4-d]pyrimidin-4-yl]-piperidine-3,4-diol or (3R,4R)-1-[5-Methoxy-2-(2-phenylamino-pyridin-4-yl)-pyrido[3,4-d]pyrimidin-4-yl]-piperidine-3,4-diol (3S,4S)- or (3R,4R)-1-[5-Methoxy-2-(2-phenylamino-pyridin-4-yl)-pyrido[3,4-d]pyrimidin-4-yl]-piperidine-3,4-diol was prepared from (1)-trans-1-[5-Methoxy-2-(2-phenylamino-pyridin-4-yl)-pyrido[3,4-d]pyrimidin-4-yl]-piperidine-3,4-diol (67.52 mg) via super critical fluid chiral chromatography using Chiralcel OJ-H (10×250 mm) column using 30% MeOH (w/ 0.1% diethylamine modifier): 70% CO2 eluent at 6.0 mL/min over 4 injections of 150 μL, T=35° C., P=120 bar, UV=220 nm. Product isolated as the initial peak as a yellow solid (0.0166 g, 24%). Purity: >99% ee @100% purity. RT: 8.6 min, $^1$HNMR (400 MHz, d6-DMSO, δ, ppm): 9.31 (s, 1H), 8.80 (s, 1H), 8.33 (s, 1H), 8.31 (d, J=5.4 Hz, 1H), 7.90 (s, 1H), 7.77-7.74 (m, 2H), 7.67 (dd, J=5.3, 1.3 Hz, 1H), 7.30-7.25 (m, 2H), 6.92-6.87 (m, 1H), 5.01-4.98 (m, 1H), 4.94 (d, J=4.1 Hz, 1H), 4.11-3.94 (m, 5H), 3.55-3.38 (m, 3H), 3.16-3.10 (m, 1H), 2.08-2.00 (m, 1H), 1.57-1.47 (m, 1H). MS=445 (MH)+.

Example 457. (3R,4R)-1-[5-Methoxy-2-(2-phenylamino-pyridin-4-yl)-pyrido[3,4-d]pyrimidin-4-yl]-piperidine-3,4-diol or (3S,4S)-1-[5-Methoxy-2-(2-phenylamino-pyridin-4-yl)-pyrido[3,4-d]pyrimidin-4-yl]-piperidine-3,4-diol (3R,4R)- or (3S,4S)-1-[5-Methoxy-2-(2-phenylamino-pyridin-4-yl)-pyrido[3,4-d]pyrimidin-4-yl]-piperidine-3,4-diol was prepared from (±)-trans-1-[5-Methoxy-2-(2-phenylamino-pyridin-4-yl)-pyrido[3,4-d]pyrimidin-4-yl]-piperidine-3,4-diol (67.52 mg) via super critical fluid chiral chromatography using Chiralcel OJ-H (10×250 mm) column using 30% MeOH (w/ 0.1% diethylamine modifier): 70% CO2 eluent at 6.0 mL/min over 4 injections of 150 μL, T=35° C., P=120 bar, UV=220 nm. Product isolated as the secondary peak as a yellow solid (0.0209 g, 31%). Purity: >97.6% ee @98% purity. RT: 12.98 min. $^1$HNMR (400 MHz, d6-DMSO, δ, ppm): 9.32 (s, 1H), 8.80 (s, 1H), 8.33 (s, 1H), 8.31 (d, J=5.2 Hz, 1H), 7.90 (s, 1H), 7.77-7.74 (m, 2H), 7.67 (dd, J=5.4, 1.3 Hz, 1H), 7.30-7.25 (m, 2H), 6.92-6.87 (m, 1H), 5.02-4.98 (m, 2H), 4.11-3.93 (m, 5H), 3.55-3.37 (m, 3H), 3.16-3.10 (m, 1H), 2.08-2.00 (m, 1H), 1.57-1.47 (m, 1H). MS=445 (MH)+.

Example 458. 3-[5-Methoxy-2-(2-phenylamino-pyridin-4-yl)-pyrido[3,4-d]pyrimidin-4-ylamino]-propionamide 458a) 3-[2-(2-Chloro-pyridin-4-yl)-5-methoxy-pyrido[3,4-d]pyrimidin-4-ylamino]-propionamide was prepared from 2-(2-Chloro-pyridin-4-yl)-5-methoxy-pyrido[3,4-d]pyrimidin-4-ol (1.00 g, 3.46 mmol) and 3-Amino-propionamide; hydrochloride (0.52 g, 4.2 mmol) in an analogous manner to [B016]. Product isolated as a tan solid (0.303 g, 24%). $^1$HNMR (400 MHz, d6-DMSO, δ, ppm): 8.93 (t, J=5.5 Hz, 1H), 8.79 (s, 1H), 8.61-8.58 (m, 1H), 8.35 (s, 1H), 8.34-8.32 (m, 2H), 7.50 (br s, 1H), 7.00 (br s, 1H), 4.11 (s, 3H), 3.94-3.87 (m, 2H), 2.57-2.52 (m, 2H). MS=359, 361 (MH)+.

458b) 3-[5-Methoxy-2-(2-phenylamino-pyridin-4-yl)-pyrido[3,4-d]pyrimidin-4-ylamino]-propionamide was prepared from 3-[2-(2-Chloro-pyridin-4-yl)-5-methoxy-pyrido[3,4-d]pyrimidin-4-ylamino]-propionamide (100.0 mg, 0.2787 mmol) and Aniline (30.0 μL, 0.329 mmol) in an analogous manner to Example 303c and Example 1501c. Product isolated as the trifluoroacetic acid salt as a yellow lyophilate (0.043 g, 28%). $^1$HNMR (400 MHz, d6-DMSO, δ, ppm): 9.55 (br s, 1H), 8.88 (t, J=5.4 Hz, 1H), 8.77 (s, 1H), 8.34 (s, 1H), 8.26 (d, J=5.4 Hz, 1H), 7.96 (s, 1H), 7.74-7.69 (m, 3H), 7.50 (s, 1H), 7.33 (t, J=7.9 Hz, 2H), 7.04-6.95 (m, 2H), 4.12 (s, 3H), 3.95-3.89 (m, 2H), 2.58-2.53 (m, 2H). MS=416 (MH)+.

Example 459. [4-(5-Methoxy-4-piperidin-1-yl-pyrido[3,4-d]pyrimidin-2-yl)-pyridin-2-yl]-phenyl-amine 459a) 2-(2-Chloro-pyridin-4-yl)-5-methoxy-4-piperidin-1-yl-pyrido[3,4-d]pyrimidine was prepared from 2-(2-Chloro-pyridin-4-yl)-5-methoxy-pyrido[3,4-d]pyrimidin-4-ol (1.0 g, 3.5 mmol) and Piperidine (0.41 mL, 4.2 mmol) in an analogous manner to [B016]. Product isolated as a yellow-orange solid (0.61 g, 49%). $^1$HNMR (400 MHz, d6-DMSO, δ, ppm): 8.83 (s, 1H), 8.59 (d, J=5.0 Hz, 1H), 8.35 (s, 1H), 8.31-8.28 (m, 2H), 4.08 (s, 3H), 3.71-3.65 (m, 4H), 1.75-1.65 (m, 6H). MS=356, 358 (MH)+.

459b) [4-(5-Methoxy-4-piperidin-1-yl-pyrido[3,4-d]pyrimidin-2-yl)-pyridin-2-yl]-phenyl-amine was prepared from 2-(2-Chloro-pyridin-4-yl)-5-methoxy-4-piperidin-1-yl-pyrido[3,4-d]pyrimidine (100.0 mg, 0.2810 mmol) and Aniline (31.0 μL, 0.340 mmol) in an analogous manner to Example 303c and Example 1501c. Product isolated as the free base as a yellow solid (0.075 g, 64%). MP=221-223° C. $^1$HNMR (400 MHz, d6-DMSO, δ, ppm): 9.31 (s, 1H), 8.80 (s, 1H), 8.32 (s, 1H), 8.30 (d, J=5.2 Hz, 1H), 7.90 (s, 1H), 7.77-7.73 (m, 2H), 7.66 (dd, J=5.2, 1.3 Hz, 1H), 7.30-7.25 (m, 2H), 6.92-6.87 (m, 1H), 4.08 (s, 3H), 3.70-3.65 (m, 4H), 1.75-1.67 (m, 6H). MS=413 (MH)+.

Example 460. {4-[4-(4,4-Difluoro-piperidin-1-yl)-5-methoxy-pyrido[3,4-d]pyrimidin-2-yl]-pyridin-2-yl}-phenyl-amine 460a) 2-(2-Chloro-pyridin-4-yl)-4-(4,4-difluoro-piperidin-1-yl)-5-methoxy-pyrido[3,4-d]pyrimidine was prepared from 2-(2-Chloro-pyridin-4-yl)-5-methoxy-pyrido[3,4-d]pyrimidin-4-ol (1.0 g, 3.5 mmol) and 4,4-Difluoro-piperidine; hydrochloride (0.66 g, 4.2 mmol) in an analogous manner to [B016]. Product isolated as an orange solid (0.806 g, 59%). $^1$HNMR (400 MHz, d6-DMSO, δ, ppm): 8.90 (s, 1H), 8.61 (dd, J=4.9, 0.8 Hz, 1H), 8.41 (s, 1H), 8.34-8.31 (m, 2H), 4.10 (s, 3H), 3.84-3.79 (m, 4H), 2.26-2.14 (m, 4H). MS=392, 394 (MH)+.

460b) {4-[4-(4,4-Difluoro-piperidin-1-yl)-5-methoxy-pyrido[3,4-d]pyrimidin-2-yl]-pyridin-2-yl}-phenyl-amine was prepared from 2-(2-Chloro-pyridin-4-yl)-4-(4,4-difluoro-piperidin-1-yl)-5-methoxy-pyrido[3,4-d]pyrimidine (100.0 mg, 0.2552 mmol) and Aniline (28.0 μL, 0.307 mmol) in an analogous manner to Example 303c and Example 1501c. Product isolated as the free base as an orange solid (0.027 g, 23%). $^1$HNMR (400 MHz, d6-DMSO, δ, ppm): 9.32 (s, 1H), 8.87 (s, 1H), 8.38 (s, 1H), 8.32 (d, J=5.2 Hz, 1H), 7.92 (s, 1H), 7.78-7.74 (m, 2H), 7.68 (dd, J=5.3, 1.4 Hz, 1H), 7.31-7.25 (m, 2H), 6.93-6.88 (m, 1H), 4.10 (s, 3H), 3.82-3.78 (m, 4H), 2.27-2.15 (m, 4H). MS=449 (MH)+.

Example 461. 1-[5-Methoxy-2-(2-phenylamino-pyridin-4-yl)-pyrido[3,4-d]pyrimidin-4-yl]-piperidine-4-carbonitrile 461a) 1-[2-(2-Chloro-pyridin-4-yl)-5-methoxy-pyrido[3,4-d]pyrimidin-4-yl]-piperidine-4-carbonitrile was prepared from 2-(2-Chloro-pyridin-4-yl)-5-methoxy-pyrido[3,4-d]pyrimidin-4-ol (1.0 g, 3.5 mmol) and Piperidine-4-carbonitrile (0.46 g, 4.2 mmol) in an analogous manner to [B016]. Product isolated as an orange solid (0.80 g, 61%). $^1$HNMR (400 MHz, d6-DMSO, δ, ppm): 8.87 (s, 1H), 8.61 (dd, J=5.0, 0.7 Hz, 1H), 8.39 (s, 1H), 8.34-8.31 (m, 2H), 4.10 (s, 3H), 3.96-3.88 (m, 2H), 3.57-3.49 (m, 2H), 3.25-3.17 (m, 1H), 2.14-2.05 (m, 2H), 1.96-1.86 (m, 2H). MS=381, 383 (MH)+.

461b) 1-[5-Methoxy-2-(2-phenylamino-pyridin-4-yl)-pyrido[3,4-d]pyrimidin-4-yl]-piperidine-4-carbonitrile was prepared from 1-[2-(2-Chloro-pyridin-4-yl)-5-methoxy-pyrido[3,4-d]pyrimidin-4-yl]-piperidine-4-carbonitrile (100.0 mg, 0.2626 mmol) and Aniline (29.0 μL, 0.318 mmol) in an analogous manner to Example 303c and Example 1501c. Product isolated as the free base as a yellow solid (0.090 g, 77%). MP=242-244° C. $^1$HNMR (400 MHz, d6-DMSO, δ, ppm): 9.32 (s, 1H), 8.84 (s, 1H), 8.36 (s, 1H), 8.31 (d, J=5.2 Hz, 1H), 7.91 (s, 1H), 7.77-7.74 (m, 2H), 7.67 (dd, J=5.4, 1.4 Hz, 1H), 7.31-7.26 (m, 2H), 6.93-6.88 (m, 1H), 4.09 (s, 3H), 3.96-3.88 (m, 2H), 3.56-3.48 (m, 2H), 3.26-3.19 (m, 1H), 2.15-2.06 (m, 2H), 1.98-1.88 (m, 2H). MS=438 (MH)+.

Example 462. {4-[4-(4-Fluoro-piperidin-1-yl)-5-methoxy-pyrido[3,4-d]pyrimidin-2-yl]-pyridin-2-yl}-phenyl-amine 462a) 2-(2-Chloro-pyridin-4-yl)-4-(4-fluoro-piperidin-1-yl)-5-methoxy-pyrido[3,4-d]pyrimidine was prepared from 2-(2-Chloro-pyridin-4-yl)-5-methoxy-pyrido[3,4-d]pyrimidin-4-ol (1.0 g, 3.5 mmol) and 4-Fluoro-piperidine; hydrochloride (0.58 g, 4.2 mmol) in an analogous manner to [B016]. Product isolated as an orange solid (0.61 g, 47%). $^1$HNMR (400 MHz, d6-DMSO, δ, ppm): 8.87 (s, 1H), 8.61 (dd, J=4.9, 0.7 Hz, 1H), 8.38 (s, 1H), 8.33-8.30 (m, 2H), 5.08-4.90 (m, 1H), 4.09 (s, 3H), 3.83-3.68 (m, 4H), 2.16-2.00 (m, 2H), 1.97-1.85 (m, 2H). MS=374, 376 (MH)+.

462b) {4-[4-(4-Fluoro-piperidin-1-yl)-5-methoxy-pyrido[3,4-d]pyrimidin-2-yl]-pyridin-2-yl}-phenyl-amine was prepared from 2-(2-Chloro-pyridin-4-yl)-4-(4-fluoro-piperidin-1-yl)-5-methoxy-pyrido[3,4-d]pyrimidine (100.0 mg, 0.2675 mmol) and Aniline (30.0 μL, 0.329 mmol) in an analogous manner to Example 303c and Example 1501c. Product isolated as the free base as a yellow solid (0.057 g, 49%). MP=202-205° C. $^1$HNMR (400 MHz, d6-DMSO, δ, ppm): 9.32 (s, 1H), 8.83 (s, 1H), 8.35 (s, 1H), 8.31 (d, J=5.3 Hz, 1H), 7.91 (s, 1H), 7.77-7.74 (m, 2H), 7.67 (dd, J=5.3, 1.3 Hz, 1H), 7.31-7.25 (m, 2H), 6.92-6.87 (m, 1H), 5.10-4.90 (m, 1H), 4.09 (s, 3H), 3.84-3.67 (m, 4H), 2.17-2.02 (m, 2H), 1.98-1.85 (m, 2H). MS=431 (MH)+.

Example 463. (3R,4S)-1-[5-Methoxy-2-(2-phenylamino-pyridin-4-yl)-pyrido[3,4-d]pyrimidin-4-yl]-piperidine-3,4-diol or (3S,4R)-1-[5-Methoxy-2-(2-phenylamino-pyridin-4-yl)-pyrido[3,4-d]pyrimidin-4-yl]-piperidine-3,4-diol (3R,4S)- or (3S,4R)-1-[5-Methoxy-2-(2-phenylamino-pyridin-4-yl)-pyrido[3,4-d]pyrimidin-4-yl]-piperidine-3,4-diol was prepared from (±)-cis-1-[5-Methoxy-2-(2-phenylamino-pyridin-4-yl)-pyrido[3,4-d]pyrimidin-4-yl]-piperidine-3,4-diol via super critical fluid chiral chromatography was performed using a Chiralpak AD-H (10×250 mm) column using 40% MeoH (w/ 0.1% diethylamine modifier):60% CO2 eluent at 6.0 mL/min over 2 injections of 400 μL, T=35° C., P=120 bar, UV=220 nm. Product isolated as the initial peak as a yellow solid (0.0254 g, 38%). Purity: >99% ee @100% purity. RT: 9.4 min. $^1$HNMR (400 MHz, d6-DMSO, δ, ppm): 9.32 (s, 1H), 8.79 (s, 1H), 8.32-8.29 (m, 2H), 7.90 (s, 1H), 7.77-7.73 (m, 2H), 7.67 (dd, J=5.3, 1.4 Hz, 1H), 7.30-7.25 (m, 2H), 6.92-6.87 (m, 1H), 4.63 (br s, 2H), 4.07 (s, 3H), 4.00-3.88 (m, 1H), 3.84-3.72 (m, 2H), 3.65-3.52 (m, 3H), 1.97-1.88 (m, 1H), 1.75-1.68 (m, 1H). MS=445 (MH)+.

Example 464. (3S,4R)-1-[5-Methoxy-2-(2-phenylamino-pyridin-4-yl)-pyrido[3,4-d]pyrimidin-4-yl]-piperidine-3,4-diol or (3R,4S)-1-[5-Methoxy-2-(2-phenylamino-pyridin-4-yl)-pyrido[3,4-d]pyrimidin-4-yl]-piperidine-3,4-diol (3S,4R)- or (3R,4S)-1-[5-Methoxy-2-(2-phenylamino-pyridin-4-yl)-pyrido[3,4-d]pyrimidin-4-yl]-piperidine-3,4-diol was prepared from (±)-cis-1-[5-Methoxy-2-(2-phenylamino-pyridin-4-yl)-pyrido[3,4-d]pyrimidin-4-yl]-piperidine-3,4-diol via super critical fluid chiral chromatography was performed using a Chiralpak AD-H (10×250 mm) column using 40% MeOH (w/ 0.1% diethylamine modifier):60% CO2 eluent at 6.0 mL/min over 2 injections of 400 μL, T=35° C., P=120 bar, UV=220 nm. Product isolated as the secondary peak as a yellow solid (0.0255 g, 38%). Purity: >99% ee @100% Purity. RT: 8.6 min. $^1$HNMR (400 MHz, d6-DMSO, δ, ppm): 9.32 (s, 1H), 8.79 (s, 1H), 8.32-8.29 (m, 2H), 7.90 (s, 1H), 7.77-7.74 (m, 2H), 7.67 (dd, J=5.2, 1.3 Hz, 1H), 7.30-7.25 (m, 2H), 6.92-6.87 (m, 1H), 4.64 (br s, 2H), 4.07 (s, 3H), 3.99-3.73 (m, 3H), 3.65-3.54 (m, 3H), 1.97-1.87 (m, 1H), 1.76-1.66 (m, 1H). MS=445 (MH)+.

Example 465. {(R)-1-[5-Methoxy-2-(2-phenylamino-pyridin-4-yl)-pyrido[3,4-d]pyrimidin-4-yl]-pyrrolidin-3-yl}-methanol 465a) {(R)-1-[2-(2-Chloro-pyridin-4-yl)-5-methoxy-pyrido[3,4-d]pyrimidin-4-yl]-pyrrolidin-3-yl}-methanol was prepared from 2-(2-Chloro-pyridin-4-yl)-5-methoxy-pyrido[3,4-d]pyrimidin-4-ol (0.50 g, 1.7 mmol) and (R)-3-Hydroxymethyl-pyrrolidine-1-carboxylic acid tert-butyl ester (0.42 g, 2.1 mmol) [deprotected with 1:1 trifluoroacetic acid:methylene chloride before addition] in an analogous manner to [B016]. Product isolated as a yellow foam (0.186 g, 28%). $^1$HNMR (400 MHz, d6-DMSO, δ, ppm): 8.78 (s, 1H), 8.59 (dd, J=5.0, 0.6 Hz, 1H), 8.34 (s, 1H), 8.32-8.29 (m, 2H), 4.72 (br s, 1H), 4.07 (s, 3H), 3.90-3.37 (m, 6H), 2.37 (br s, 1H), 1.99 (br s, 1H), 1.68 (br s, 1H). MS=372, 374 (MH)+.

465b) {(R)-1-[5-Methoxy-2-(2-phenylamino-pyridin-4-yl)-pyrido[3,4-d]pyrimidin-4-yl]-pyrrolidin-3-yl}-methanol was prepared from {(R)-1-[2-(2-Chloro-pyridin-4-yl)-5-methoxy-pyrido[3,4-d]pyrimidin-4-yl]-pyrrolidin-3-yl}-methanol (186.0 mg, 0.5002 mmol) and Aniline (55.0 μL, 0.604 mmol) in an analogous manner to Example 303c and Example 1501c. Product isolated as the free base as a yellow solid (0.091 g, 42%). MP=208-209° C. $^1$HNMR (400 MHz, d6-DMSO, δ, ppm): 9.31 (s, 1H), 8.75 (s, 1H), 8.30 (s, 1H), 8.29 (d, J=5.2 Hz, 1H), 7.90 (s, 1H), 7.78-7.74 (m, 2H), 7.68 (dd, J=5.3, 1.3 Hz, 1H), 7.30-7.25 (m, 2H), 6.91-6.86 (m, 1H), 4.73 (br s, 1H), 4.07 (s, 3H), 3.88-3.35 (m, 6H), 2.37 (br s, 1H), 2.00 (br s, 1H), 1.70 (br s, 1H). MS=429 (MH)+.

Example 466. {(S)-1-[5-Methoxy-2-(2-phenylamino-pyridin-4-yl)-pyrido[3,4-d]pyrimidin-4-yl]-pyrrolidin-3-yl}-methanol 466a) desired {(S)-1-[2-(2-Chloro-pyridin-4-yl)-5-methoxy-pyrido[3,4-d]pyrimidin-4-yl]-pyrrolidin-3-yl}-methanol was prepared from 2-(2-Chloro-pyridin-4-yl)-5-methoxy-pyrido[3,4-d]pyrimidin-4-ol (0.50 g, 1.7 mmol) and (S)-3-Hydroxymethyl-pyrrolidine-1-carboxylic acid tert-butyl ester (0.42 g, 2.1 mmol) [deprotected with 1:1 trifluoroacetic acid:methylene chloride before addition] in an analogous manner to [B016]. Product isolated as a yellow resin (0.185 g, 29%). $^1$HNMR (400 MHz, d6-DMSO, δ, ppm): 8.78 (s, 1H), 8.59 (d, J=5.0 Hz, 1H), 8.34 (s, 1H), 8.32-8.29 (m, 2H), 4.72 (br s, 1H), 4.07 (s, 3H), 3.90-3.35 (m, 6H), 2.42 (br s, 1H), 1.99 (br s, 1H), 1.70 (br s, 1H). MS=372, 374 (MH)+.

466b) {(S)-1-[5-Methoxy-2-(2-phenylamino-pyridin-4-yl)-pyrido[3,4-d]pyrimidin-4-yl]-pyrrolidin-3-yl}-methanol was prepared from {(S)-1-[2-(2-Chloro-pyridin-4-yl)-5-methoxy-pyrido[3,4-d]pyrimidin-4-yl]-pyrrolidin-3-yl}-methanol (185.0 mg, 0.4976 mmol) and Aniline (55.0 μL, 0.604 mmol) in an analogous manner to Example 303c and Example 1501c. Product isolated as the free base as a yellow foam (0.093 g, 43%). MP=210-211° C. $^1$HNMR (400 MHz, d6-DMSO, δ, ppm): 9.31 (s, 1H), 8.75 (s, 1H), 8.30 (s, 1H), 8.29 (d, J=5.3 Hz, 1H), 7.90 (s, 1H), 7.78-7.74 (m, 2H), 7.68 (dd, J=5.3, 1.4 Hz, 1H), 7.30-7.25 (m, 2H), 6.92-6.86 (m, 1H), 4.73 (br s, 1H), 4.07 (s, 1H), 3.88-3.35 (m, 6H), 2.37 (br s, 1H), 2.00 (br s, 1H), 1.71 (br s, 1H). MS=429 (MH)+.

Example 467. (meso)-cis-1-[5-Methoxy-2-(2-phenylamino-pyridin-4-yl)-pyrido[3,4-d]pyrimidin-4-yl]-azepane-4,5-diol 467a) To a round bottom flask equipped a stir bar and a reflux condenser containing But-3-enylamine (0.58 g, 8.1 mmol) and Tetrahydrofuran (50 mL) was added 4-Bromo-but-1-ene (1.0 g, 7.4 mmol) and the mixture was heated at 60° C. for 18 hours. The mixture was cooled to room temperature. Triethylamine (1.1 mL, 8.1 mmol) was added followed Di-tert-Butyldicarbonate (1.8 g, 8.1 mmol). The suspension was stirred at room temperature for 1 hour. The suspension was filtered through a plug of diatomaceous earth and the filtrate was evaporated to a yellow suspension. To the residue was added methanol (40 mL) followed by 1N aqueous Sodium hydroxide (5 mL). The mixture was stirred for 1 hour. The resulting suspension was filtered through a plug of diatomaceous earth. The filtrate was evaporated. The residue was purified via chromatography using an ISCO apparatus (silica gel column 24 g 0%-5% Ethyl Acetate: Hexane). Di-but-3-enyl-carbamic acid tert-butyl ester was isolated as clear oil (0.304 g, 18%). $^1$HNMR (400 MHz, CDCl3, δ, ppm): 5.83-5.70 (m, 2H), 5.10-4.99 (m, 4H), 3.23 (br s, 4H), 2.31-2.24 (m, 4H), 1.46 (s, 9H). MS=248 (M+Na)+.

467b) To a solution of Di-but-3-enyl-carbamic acid tert-butyl ester (0.30 g, 1.3 mmol) in dry Toluene (30 mL) under an atmosphere of Nitrogen was added (1,3-Bis-(2,4,6-trimethylphenyl)-2-imidazolidinylidene)dichloro(o-isopropoxyphenylmethylene)ruthenium (45.0 mg, 0.0717 mmol). The mixture was heated at 50° C. for 5 hours. The mixture was cooled to room temperature and stirred overnight. The volatiles were evaporated. The residue was triturated with hexane (30 mL) and the suspension was filtered through a plug of diatomaceous earth. The filtrate was evaporated. The residue was purified via chromatography using an ISCO apparatus (silica gel column 24 g with 0%→5% Ethyl Acetate:Hexane). 2,3,6,7-Tetrahydro-azepine-1-carboxylic acid tert-butyl ester was isolated as a clear oil (0.166 g, 63%). $^1$HNMR (400 MHz, CDCl3, δ, ppm): 5.79-5.66 (m, 2H), 3.50-3.38 (m, 4H), 2.28 (br s, 4H), 1.47 (s, 9H). MS=220 (M+Na)+.

467c) (meso)-cis-4,5-Dihydroxy-azepane-1-carboxylic acid tert-butyl ester was prepared from 2,3,6,7-Tetrahydro-azepine-1-carboxylic acid tert-butyl ester (0.166 g, 0.841 mmol) in an analogous manner to Example 436a. Product isolated as an off-white solid (0.151 g, 77%). $^1$HNMR (400 MHz, d6-DMSO, δ, ppm): 4.48 (d, J=4.3 Hz, 2H), 3.67-3.60 (m, 2H), 3.45-3.32 (m, 2H), 3.19-3.05 (m, 2H), 1.84-1.73 (m, 2H), 1.64-1.52 (m, 2H), 1.38 (s, 9H). MS=254 (M+Na)+.

467d) (meso)-cis-1-[2-(2-Chloro-pyridin-4-yl)-5-methoxy-pyrido[3,4-d]pyrimidin-4-yl]-azepane-4,5-diol was prepared from 2-(2-Chloro-pyridin-4-yl)-5-methoxy-pyrido[3,4-d]pyrimidin-4-ol (0.20 g, 0.69 mmol), and (meso)-cis-4,5-Dihydroxy-azepane-1-carboxylic acid tert-butyl ester (0.15 g, 0.65 mmol) [deprotected with 1:1 trifluoroacetic acid:methylene chloride before addition] in an analogous manner to [B016]. Product isolated as an orange resin (0.115 g, 44%). $^1$HNMR (400 MHz, d6-DMSO, δ, ppm): 8.77 (s, 1H), 8.59 (dd, J=4.8, 1.0 Hz, 1H), 8.32-8.28 (m, 3H), 4.45-4.42 (m, 2H), 4.04 (s, 3H), 3.88-3.60 (m, 6H), 2.10-2.00 (m, 2H), 1.86-1.77 (m, 2H). MS=402, 404 (MH)+.

467e) (meso)-cis-1-[5-Methoxy-2-(2-phenylamino-pyridin-4-yl)-pyrido[3,4-d]pyrimidin-4-yl]-azepane-4,5-diol was prepared from (meso)-cis-1-[2-(2-Chloro-pyridin-4-yl)-5-methoxy-pyrido[3,4-d]pyrimidin-4-yl]-azepane-4,5-diol (115.0 mg, 0.2862 mmol) and Aniline (33.0 μL, 0.362 mmol) in an analogous manner to Example 303c and Example 1501c. Product isolated as the free base as a yellow foam (0.033 g, 25%). $^1$HNMR (400 MHz, d6-DMSO, δ, ppm): 9.29 (s, 1H), 8.74 (s, 1H), 8.29 (d, J=5.2 Hz, 1H), 8.26 (s, 1H), 7.90 (s, 1H), 7.77-7.74 (m, 2H), 7.67 (dd, J=5.3, 1.3 Hz, 1H), 7.30-7.25 (m, 2H), 6.92-6.87 (m, 1H), 4.45 (d, J=4.2 Hz, 2H), 4.05 (s, 3H), 3.87-3.60 (m, 6H), 2.12-2.02 (m, 2H), 1.87-1.78 (m, 2H). MS=459 (MH)+.

Example 468. 1-{2-[2-(6-Fluoro-pyridin-2-ylamino)-pyridin-4-yl]-5-methoxy-pyrido[3,4-d]pyrimidin-4-yl}-piperidin-4-ol 1-{2-[2-(6-Fluoro-pyridin-2-ylamino)-pyridin-4-yl]-5-methoxy-pyrido[3,4-d]pyrimidin-4-yl}-piperidin-4-ol was prepared from 1-[2-(2-Chloro-pyridin-4-yl)-5-methoxy-pyrido[3,4-d]pyrimidin-4-yl]-piperidin-4-ol (90.0 mg, 0.242 mmol) and 6-Fluoro-pyridin-2-ylamine (33.0 mg, 0.294 mmol) in an analogous manner to Example 303c and Example 1501c. Product isolated as the free base as a yellow foam (0.048 g, 35%). $^1$HNMR (400 MHz, d6-DMSO, δ, ppm): 10.43 (br s, 1H), 8.83 (s, 1H), 8.71 (s, 1H), 8.43 (d, J=5.3 Hz, 1H), 8.36 (s, 1H), 7.92-7.85 (m, 2H), 7.69-7.65 (m, 1H), 6.65 (dd, J=7.9, 2.2 Hz, 1H), 4.11-4.01 (m, 5H), 3.87-3.80 (m, 1H), 3.51-3.42 (m, 2H), 1.97-1.89 (m, 2H), 1.64-1.54 (m, 2H). MS=448 (MH)+.

Example 469. 1-{5-Methoxy-2-[2-(6-methoxy-pyridin-2-ylamino)-pyridin-4-yl]-pyrido[3,4-d]pyrimidin-4-yl}-piperidin-4-ol 1-{5-Methoxy-2-[2-(6-methoxy-pyridin-2-ylamino)-pyridin-4-yl]-pyrido[3,4-d]pyrimidin-4-yl}-piperidin-4-ol was prepared from 1-[2-(2-Chloro-pyridin-4-yl)-5-methoxy-pyrido[3,4-d]pyrimidin-4-yl]-piperidin-4-ol (90.0 mg, 0.242 mmol) and 6-Methoxy-pyridin-2-ylamine (36.0 mg, 0.290 mmol) in an analogous manner to Example 303c and Example 1501c. Product isolated as the free base as a yellow foam (0.031 g, 27%). $^1$HNMR (400 MHz, d6-DMSO, δ, ppm): 10.45 (br s, 1H), 8.86 (s, 1H), 8.78 (s, 1H), 8.43 (d, J=5.6 Hz, 1H), 8.36 (s, 1H), 7.90 (d, J=6.0 Hz, 1H), 7.69 (t, J=7.9 Hz, 1H), 7.05 (d, J=8.0 Hz, 1H), 6.44 (d, J=8.0 Hz, 1H), 4.10-3.98 (m, 8H), 3.87-3.80 (m, 1H), 3.48-3.39 (m, 2H), 1.97-1.89 (m, 2H), 1.63-1.53 (m, 2H). MS=460 (MH)+.

Example 470. ((S)-1-{2-[2-(6-Fluoro-pyridin-2-ylamino)-pyridin-4-yl]-5-methoxy-pyrido[3,4-d]pyrimidin-4-yl}-pyrrolidin-3-yl)-methanol ((S)-1-{2-[2-(6-Fluoro-pyridin-2-ylamino)-pyridin-4-yl]-5-methoxy-pyrido[3,4-d]pyrimidin-4-yl}-pyrrolidin-3-yl)-methanol was prepared from {(S)-1-[2-(2-Chloro-pyridin-4-yl)-5-methoxy-pyrido[3,4-d]pyrimidin-4-yl]-pyrrolidin-3-yl}-methanol (90.0 mg, 0.242 mmol) and 6-Fluoro-pyridin-2-ylamine (40.0 mg, 0.357 mmol) in an analogous manner to Example 303c and Example 1501c. Product isolated as the trifluoroacetic acid salt as a yellow lyophilate (0.026 g, 19%). $^1$HNMR (400 MHz, d6-DMSO, δ, ppm): 10.43 (br s, 1H), 8.79 (s, 1H), 8.68 (s, 1H), 8.43 (d, J=5.5 Hz, 1H), 8.37 (s, 1H), 7.92-7.85 (m, 2H), 7.68 (d, J=7.9 Hz, 1H), 6.65 (d, J=8.0 Hz, 1H), 4.09 (s, 3H), 3.92-3.40 (m, 6H), 2.45-2.30 (m, 1H), 2.08-1.98 (m, 1H), 1.80-1.65 (m, 1H). MS=448 (MH)+.

Example 471. ((S)-1-{5-Methoxy-2-[2-(6-methoxy-pyridin-2-ylamino)-pyridin-4-yl]-pyrido[3,4-d]pyrimidin-4-yl}-pyrrolidin-3-yl)-methanol ((S)-1-{5-Methoxy-2-[2-(6-methoxy-pyridin-2-ylamino)-pyridin-4-yl]-pyrido[3,4-d]pyrimidin-4-yl}-pyrrolidin-3-yl)-methanol was prepared from {(S)-1-[2-(2-Chloro-pyridin-4-yl)-5-methoxy-pyrido[3,4-d]pyrimidin-4-yl]-pyrrolidin-3-yl}-methanol (90.0 mg, 0.242 mmol) and 6-Methoxy-pyridin-2-ylamine (45.0 mg, 0.362 mmol) in an analogous manner to Example 303c and Example 1501c. Product isolated as the trifluoroacetic acid salt as a yellow lyophilate (0.044 g, 31%). $^1$HNMR (400 MHz, d6-DMSO, δ, ppm): 10.44 (br s, 1H), 8.86 (s, 1H), 8.73 (s, 1H), 8.43 (d, J=5.6 Hz, 1H), 8.36 (s, 1H), 7.91 (d, J=5.0 Hz, 1H), 7.68 (t, J=8.2 Hz, 1H), 7.03 (d, J=8.0 Hz, 1H), 6.44 (d, J=7.8 Hz, 1H), 4.08 (s, 3H), 4.04 (s, 3H), 3.90-3.35 (m, 6H), 2.45-2.30 (m, 1H), 2.05-1.95 (m, 1H), 1.77-1.64 (m, 1H). MS=460 (MH)+.

Example 473. 2-(4-Cyano-phenyl)-N-[4-(5-cyclopropyl-4-piperazin-1-yl-pyrido[3,4-d]pyrimidin-2-yl)-pyridin-2-yl]-acetamide 2-(4-Cyano-phenyl)-N-[4-(5-cyclopropyl-4-piperazin-1-yl-pyrido[3,4-d]pyrimidin-2-yl)-pyridin-2-yl]-acetamide was prepared from 4-[2-(2-Chloro-pyridin-4-yl)-5-cyclopropyl-pyrido[3,4-d]pyrimidin-4-yl]-piperazine-1-carboxylic acid tert-butyl ester (100.0 mg, 0.2141 mmol) and 2-(4-Cyano-phenyl)-acetamide (50.0 mg, 0.312 mmol) in an analogous manner to Example 303c and Example 1501c. Product isolated as the free base as a tan solid (0.094 g, 89%). MP=200-203° C. $^1$HNMR (400 MHz, d6-DMSO, δ, ppm): 9.05 (s, 1H), 8.97 (s, 1H), 8.49 (dd, J=5.1, 0.6 Hz, 1H), 8.09 (s, 1H), 8.04 (dd, J=5.2, 1.4 Hz, 1H), 7.84-7.81 (m, 2H), 7.60-7.57 (m, 2H), 3.91 (s, 2H), 3.85-3.45 (m, 4H), 2.83 (m, 4H), 2.63-2.55 (m, 1H), 1.28-1.22 (m, 2H), 1.04-0.99 (m, 2H). LC/MS=491 (MH)+.

Example 474. [4-(5-Cyclopropyl-4-piperazin-1-yl-pyrido[3,4-d]pyrimidin-2-yl)-pyridin-2-yl]-(2-methyl-4-morpholin-4-yl-phenyl)-amine

[4-(5-Cyclopropyl-4-piperazin-1-yl-pyrido[3,4-d]pyridin-2-yl)-pyridin-2-yl]-(2-methyl-4-morpholin-4-yl-phenyl)-amine was prepared from 4-[2-(2-Chloro-pyridin-4-yl)-5-cyclopropyl-pyrido[3,4-d]pyrimidin-4-yl]-piperazine-1-carboxylic acid tert-butyl ester (100.0 mg, 0.2141 mmol) and 2-Methyl-4-morpholin-4-yl-phenylamine (61.0 mg, 0.317 mmol) in an analogous manner to Example 303c and Example 1501c. Product isolated as the free base as an orange-brown solid (0.085 g, 75%). MP=214-220° C. $^1$HNMR (400 MHz, d6-DMSO, δ, ppm): 8.93 (s, 1H), 8.23 (s, 1H), 8.14 (d, J=5.3 Hz, 1H), 8.07 (s, 1H), 7.58 (s, 1H), 7.52 (dd, J=5.2, 1.3 Hz, 1H), 7.28 (d, J=8.6 Hz, 1H), 6.86 (d, J=2.7 Hz, 1H), 6.79 (dd, J=8.6, 2.8 Hz, 1H), 3.80-3.50 (m, 8H), 3.10-3.06 (m, 4H), 2.81 (br s, 4H), 2.64-2.56 (m, 1H), 2.19 (s, 3H), 1.27-1.21 (m, 2H), 1.04-0.99 (m, 2H). LC/MS=523 (MH)+.

Example 475. [4-(5-Cyclopropyl-4-piperazin-1-yl-pyrido[3,4-d]pyrimidin-2-yl)-pyridin-2-yl]-(6-morpholin-4-yl-pyridin-3-yl)-amine

[4-(5-Cyclopropyl-4-piperazin-1-yl-pyrido[3,4-d]pyrimidin-2-yl)-pyridin-2-yl]-(6-morpholin-4-yl-pyridin-3-yl)-amine was prepared from 4-[2-(2-Chloro-pyridin-4-yl)-5-cyclopropyl-pyrido[3,4-d]pyrimidin-4-yl]-piperazine-1-carboxylic acid tert-butyl ester (107.0 mg, 0.2291 mmol) and 6-Morpholin-4-yl-pyridin-3-ylamine (57.0 mg, 0.318 mmol) in an analogous manner to Example 303c and Example 1501c. Product isolated as the free base as a yellow solid (0.103 g, 87%). MP=217-219° C. $^1$HNMR (400 MHz, d6-DMSO, δ, ppm): 9.08 (s, 1H), 8.96 (s, 1H), 8.45 (d, J=2.6 Hz, 1H), 8.24 (d, J=5.4 Hz, 1H), 8.09 (s, 1H), 7.99 (dd, J=9.1, 2.7 Hz, 1H), 7.81 (s, 1H), 7.62 (dd, J=5.3, 1.3 Hz, 1H), 6.85 (d, J=9.1 Hz, 1H), 3.90-3.50 (m, 8H), 3.37-3.34 (m, 4H), 2.86 (br s, 4H), 2.66-2.58 (m, 1H), 1.29-1.23 (m, 2H), 1.05-1.00 (m, 2H). LC/MS=510 (MH)+.

Example 476. [4-(5-Cyclopropyl-4-piperazin-1-yl-pyrido[3,4-d]pyrimidin-2-yl)-pyridin-2-yl]-pyridin-3-yl-amine

[4-(5-Cyclopropyl-4-piperazin-1-yl-pyrido[3,4-d]pyrimidin-2-yl)-pyridin-2-yl]-pyridin-3-yl-amine was prepared from 4-[2-(2-Chloro-pyridin-4-yl)-5-cyclopropyl-pyrido[3,4-d]pyrimidin-4-yl]-piperazine-1-carboxylic acid tert-butyl ester (100.0 mg, 0.2141 mmol) and 3-aminopyridine (30.0 mg, 0.319 mmol) in an analogous manner to Example 303c and Example 1501c. Product isolated as the free base as a pale yellow solid (0.067 g, 74%). MP=226-228° C. $^1$HNMR (400 MHz, d6-DMSO, δ, ppm): 9.55 (s, 1H), 8.98 (s, 1H), 8.87 (d, J=2.5 Hz, 1H), 8.35 (d, J=5.4 Hz, 1H), 8.32-8.28 (m, 1H), 8.12-8.09 (m, 2H), 7.95 (s, 1H), 7.75 (dd, J=5.3, 1.2 Hz, 1H), 7.30 (dd, J=8.4, 4.7 Hz, 1H), 3.96-3.46 (m, 4H), 2.87 (br s, 4H), 2.66-2.58 (m, 1H), 1.30-1.23 (m, 2H), 1.06-1.01 (m, 2H). LC/MS=425.0 (MH)+.

Example 477. (2-Chloro-phenyl)-[4-(5-cyclopropyl-4-piperazin-1-yl-pyrido[3,4-d]pyrimidin-2-yl)-pyridin-2-yl]-amine (2-Chloro-phenyl)-[4-(5-cyclopropyl-4-piperazin-1-yl-pyrido[3,4-d]pyrimidin-2-yl)-pyridin-2-yl]-amine was prepared from 4-[2-(2-Chloro-pyridin-4-yl)-5-cyclopropyl-pyrido[3,4-d]pyrimidin-4-yl]-piperazine-1-carboxylic acid tert-butyl ester (100.0 mg, 0.2141 mmol) and o-Chloroaniline (52.0 uL, 0.315 mmol) in an analogous manner to Example 303c and Example 1501c. Product isolated as the free base as an orange foam (0.086 g, 88%). $^1$HNMR (400 MHz, d6-DMSO, δ, ppm): 8.97 (s, 1H), 8.68 (s, 1H), 8.26 (d, J=5.3 Hz, 1H), 8.09 (s, 1H), 8.04-8.00 (m, 2H), 7.72 (dd, J=5.3, 1.4 Hz, 1H), 7.48 (dd, J=8.0, 1.5 Hz, 1H), 7.34-7.29 (m, 1H), 7.09-7.04 (m, 1H), 3.96-3.46 (m, 4H), 2.86 (br s, 4H), 2.65-2.57 (m, 1H), 1.29-1.23 (m, 2H), 1.05-1.00 (m, 2H). LC/MS=458.0 (MH)+.

Example 478. [4-(5-Cyclopropyl-4-piperazin-1-yl-pyrido[3,4-d]pyrimidin-2-yl)-pyridin-2-yl]-(4-methyl-pyridin-3-yl)-amine

[4-(5-Cyclopropyl-4-piperazin-1-yl-pyrido[3,4-d]pyrimidin-2-yl)-pyridin-2-yl]-(4-methyl-pyridin-3-yl)-amine was prepared from 4-[2-(2-Chloro-pyridin-4-yl)-5-cyclopropyl-pyrido[3,4-d]pyrimidin-4-yl]-piperazine-1-carboxylic acid tert-butyl ester (100.0 mg, 0.2141 mmol) and 4-Methyl-pyridin-3-ylamine (34.0 mg, 0.314 mmol) in an analogous manner to Example 303c and Example 1501c. Product isolated as the free base as a pale yellow foam (0.070 g, 74%). $^1$HNMR (400 MHz, d6-DMSO, δ, ppm): 8.98 (s, 1H), 8.81 (s, 1H), 8.64 (s, 1H), 8.22 (d, J=5.4 Hz, 1H), 8.16 (d, J=4.9 Hz, 1H), 8.11 (s, 1H), 7.87 (s, 1H), 7.67 (dd, J=5.2, 1.3 Hz, 1H), 7.25 (d, J=4.9 Hz, 1H), 3.95-3.45 (m, 4H), 2.93 (br s, 4H), 2.65-2.59 (m, 1H), 2.28 (s, 3H), 1.29-1.23 (m, 2H), 1.06-1.01 (m, 2H). LC/MS=439.2 (MH)+.

Example 481. [4-(5-Cyclopropyl-4-piperazin-1-yl-pyrido[3,4-d]pyrimidin-2-yl)-pyridin-2-yl]-phenyl-amine 481a) 3-Bromo-5-fluoro-isonicotinic acid tert-butyl ester (1.9 g, 6.9 mmol), cyclopropyltrifluoroborate (1.18 g, 7.97 mmol), palladium acetate (81.3 mg, 0.36 mmol), butyl-ditricyclo[3.3.1.1(3,7)]decan-1-yl-phosphane (194.8 mg, 0.54 mmol), and cesium carbonate (7 g, 21.7 mmol) was heated at 85° C. in toluene (35 mL)/water (4 mL) overnight, under nitrogen. Cooled, partitioned between ether and water. Organic extracts dried ($MgSO_4$), filtered, solvent evaporated; product isolated by flash chromatography (ISCO, Silica gel, EtOAc/Hexanes 0-10%; 2nd fraction is product): 3-cyclopropyl-5-fluoro-isonicotinic acid tert-butyl ester (50% yield).

481b) 3-Cyclopropyl-5-fluoro-isonicotinic acid tert-butyl ester (700.0 mg, 2.95 mmol) was treated with trifluoroacetic acid (2.0 mL, 26.0 mmol) in methylene chloride (5 mL) at 25° C. overnight. Solvent was evaporated, and the crude residue was dried on high vacuum, and then used without further purification: 3-cyclopropyl-5-fluoro-isonicotinic acid; compound with trifluoro-acetic acid (quant.).

481c) 3-Cyclopropyl-5-fluoro-isonicotinic acid; compound with trifluoro-acetic acid (995 mg, 3.37 mmol) and 2-chloro-isonicotinamidine; hydrochloride (1.3 g, 6.7 mmol) were treated with N,N,N',N'-tetramethyl-O-(7-azabenzotriazol-1-yl)uronium hexafluorophosphate (1.35 g, 3.54 mmol) and N,N-diisopropylethylamine (3.5 mL, 20.2 mmol) in N,N-dimethylformamide (14 mL) at room temperature overnight. The reaction mixture was partitioned between DCM and water, organic layer washed extensively with water, dried ($MgSO_4$), solvent evaporated when a precipitate formed. Trituration from ether followed by filtration afforded N-[(2-chloro-pyridin-4-yl)-imino-methyl]-3-cyclopropyl-5-fluoro-isonicotinamide, which was used in the next step without further purification.

481d) N-[(2-Chloro-pyridin-4-yl)-imino-methyl]-3-cyclopropyl-5-fluoro-isonicotinamide (solid product from step c) and cesium carbonate (1.4 g, 4.2 mmol) were mixed in N,N-dimethylacetamide (17 mL). The reaction was microwaved on 300 watts, 120° C. for 20 minutes. Reaction mixture was diluted with ice/water and neutralized with AcOH to pH 5 at 0 OC, and the precipitate was collected by filtration, washed with water and dried: 2-(2-chloro-pyridin-4-yl)-5-cyclopropyl-3H-pyrido[3,4-d]pyrimidin-4-one (33% yield over 2 steps).

481e) A suspension of 2-(2-chloro-pyridin-4-yl)-5-cyclopropyl-3H-pyrido[3,4-d]pyrimidin-4-one (0.85 g, 2.8 mmol), triethylamine (1.3 mL, 9.3 mmol) and 4-dimethylaminopyridine (43.0 mg, 0.352 mmol) in N,N-dimethylformamide (10 mL, 100 mmol) was treated with 2,4,6-triisopropylbenzenesulfonyl chloride (0.98 g, 3.2 mmol) and the mixture was stirred at room temperature for 1 hour. tert-Butyl-1-piperazinecarboxylate (0.65 g, 3.5 mmol) was added and the mixture was stirred at room temperature overnight. Water (40 mL) was added and the mixture was stirred vigorously for 1 hour. The suspension was filtered, rinsed with water and dried. The solid was dissolved in DCM, the solution was dried ($MgSO_4$), filtered and the solvent was evaporated under vacuum. The product was isolated by flash chromatography (Isco, Silica Gel, 20%→100% Ethyl Acetate/Hexane): 4-[2-(2-chloro-pyridin-4-yl)-5-cyclopropyl-pyrido[3,4-d]pyrimidin-4-yl]-piperazine-1-carboxylic acid tert-butyl ester, tan solid (1.03 g).

481f) A reaction tube was charged with 4-[2-(2-chloro-pyridin-4-yl)-5-cyclopropyl-pyrido[3,4-d]pyrimidin-4-yl]-piperazine-1-carboxylic acid tert-butyl ester (200 mg, 0.428 mmol), aniline (43.9 μL, 0.482 mmol), palladium acetate (16 mg, 0.07 mmol), 9,9-dimethyl-4,5-bis(diphenylphosphino) xanthene (38.8 mg, 0.067 mmol), and cesium carbonate (366 mg, 1.125 mmol) in 1,4-dioxane (2 mL). The tube was evacuated and back-filled with nitrogen three times, and then flushed with argon, capped, and heated at 100° C. for 3 h. The reaction mixture was cooled to room temperature and partitioned between ether and water. The organic extracts were dried ($MgSO_4$), then the solvent was evaporated under reduced pressure. The product was used in the next step without further purification. The crude product obtained in step 1 was treated with trifluoroacetic acid (1.48 mL, 19.2 mmol) in methylene chloride (5.92 mL) at room temperature until reaction was complete (by hplc); approx. 1 h. The volatiles were evaporated under reduced pressure and the product was isolated by reverse phase chromatography (Gilson) followed by neutralization by cation-exchange column (Strata, from Phenomenex) filtration and releasing with methanolic ammonia: [4-(5-cyclopropyl-4-piperazin-1-yl-pyrido[3,4-d]pyrimidin-2-yl)-pyridin-2-yl]-phenyl-amine (133 mg, 73% yield over 2 steps); bright yellow solid; MP: 221-226 C; $^1$H-NMR ($CDCl_3$) δ: 9.11 (s, 1H), 8.36 (d, J=5.2 Hz, 1H), 8.04 (s, 1H), 8.00 (s, 1H), 7.80 (dd, J=5.2; 1.3 Hz, 1H), 7.45 (d, J=8.3 Hz, 2H), 7.37 (dd, J=8.4; 8.4 Hz, 2H), 7.07 (t, J=8.4 Hz, 1H), 6.68 (br s, 1H), 3.75 (br s, 4H), 3.01 (m, 4H), 269 (m, 1H), 1.59 (water and exchangeable NH), 1.26 (m, 2H), 1.00 (m, 2H); LC/MS (ESI+): 424.17 (M+H).

Example 482. 2-{4-[5-Cyclopropyl-4-(4-hydroxy-piperidin-1-yl)-pyrido[3,4-d]pyrimidin-2-yl]-pyridin-2-ylamino}-isonicotinonitrile This product was prepared from 2-(2-chloro-pyridin-4-yl)-5-cyclopropyl-3H-pyrido[3,4-d]pyrimidin-4-one according to a procedure similar to Example 481e,f: white solid; $^1$H NMR (dmso-d) δ: 10.40 (s, 1H), 8.98 (s, 1H), 8.64 (br s, 1H), 8.49 (dd, J=6.0; 0.4 Hz, 1H), 8.45 (d, J=5.2 Hz, 1H), 8.37 (br s, 1H), 8.10 (s, 1H), 7.88 (dd, J=5.2; 1.4 Hz, 1H), 7.30 (dd, J=6.0; 1.4 Hz, 1H), 7.81 (br s, 1H), 4.11 (m, 2H), 3.80 (br s, 1H), 3.50 (br s, 2H), 2.60 (br s, 1H), 1.90 (m, 2H), 1.52 (br s, 1H), 1.26 (m, 2H), 1.04 (m, 2H); LC/MS (ESI+): 465.2 (M+H).

Example 483. [4-(5-Cyclopropyl-4-piperazin-1-yl-pyrido[3,4-d]pyrimidin-2-yl)-pyridin-2-yl]-(6-fluoro-pyridin-2-yl)-amine This product was prepared from 2-(2-chloro-pyridin-4-yl)-5-cyclopropyl-3H-pyrido[3,4-d]pyrimidin-4-one according to a procedure similar to Example 481e,f: yellow lyophilate; $^1$H NMR (dmso-$d_6$) δ: 10.40 (s, 1H), 9.08 (s, 1H), 9.03 (br s, 2H), 8.81 (s, 1H), 8.45 (d, J=5.3 Hz, 1H), 8.20 (s, 1H), 7.92 (m, 1H), 7.86 (m, 1H), 7.69 (m, 1H), 6.65 (m, 1H), 3.97 (br s, 4H), 3.34 (br s, 4H), 2.69 (m, 1H), 1.27 (m, 2H), 1.09 (m, 2H); LC/MS (ESI+): 443.2 (M+H).

Example 484. [4-(5-Cyclopropyl-4-piperazin-1-yl-pyrido[3,4-d]pyrimidin-2-yl)-pyridin-2-yl]-(2-fluoro-phenyl)-amine This product was prepared from 4-[2-(2-chloro-pyridin-4-yl)-5-cyclopropyl-pyrido[3,4-d]pyrimidin-4-yl]-piperazine-1-carboxylic acid tert-butyl ester according to a procedure similar to Example 481f: off-white foam; $^1$H-NMR ($CDCl_3$) δ: 9.12 (s, 1H), 8.39 (d, J=5.3 Hz, 1H), 8.23 (m, 1H), 8.05 (s, 1H), 7.93 (s, 1H), 7.85 (m, 1H), 7.14 (m, 2H), 6.97 (m, 2H), 6.86 (br s, 1H), 3.76 (br s, 4H), 3.03 (m, 4H), 2.69 (m, 1H), 1.93 (br s, water and exch. protons), 1.27 (m, 2H), 1.01 (m, 2H); LC/MS (ESI+): 442.1 (M+H).

Example 485. (±)-2-{4-[5-Cyclopropyl-4-cis-3,4-dihydroxy-piperidin-1-yl)-pyrido[3,4-d]pyrimidin-2-yl]-pyridin-2-ylamino}-isonicotinonitrile This product was prepared from 2-(2-chloro-pyridin-4-yl)-5-cyclopropyl-3H-pyrido[3,4-d]pyrimidin-4-one according to a procedure similar to Example 481e,f: tan solid; $^1$H-NMR ($CDCl_3$) δ: 9.18 (s, 1H), 8.52 (s, 1H), 8.44 (d, J=5.2 Hz, 1H), 8.39 (m, 2H), 8.15 (m, 2H), 7.93 (m, 1H), 7.04 (m, 1H), 3.95 (m, 7H), 2.78 (br s, 1H), 2.60 (m, 1H), 1.87 (m, 2H), 1.63 (br s, water), 1.27 (m, 2H), 1.01 (m, 2H); LC/MS (ESI+): 481.0 (M+H).

Example 486. [4-(5-Cyclopropyl-4-piperazin-1-yl-pyrido[3,4-d]pyrimidin-2-yl)-pyridin-2-yl]-o-tolyl-amine This product was prepared from 4-[2-(2-chloro-pyridin-4-yl)-5-cyclopropyl-pyrido[3,4-d]pyrimidin-4-yl]-piperazine-1-carboxylic acid tert-butyl ester according to a procedure similar to Example 481f: yellow foam; $^1$H-NMR ($CDCl_3$) δ: 9.08 (s, 1H), 8.33 (d, J=5.2 Hz, 1H), 8.02 (s, 1H), 7.81 (s, 1H), 7.76 (m, 1H), 7.60 (m, 1H), 7.24 (m, 2H), 7.08 (m, 1H), 6.54 (br s, 1H), 3.72 (br s, 4H), 2.97 (m, 4H), 2.67 (m, 1H), 3.04 (s, 3H), 1.95 (br s, NH), 1.25 (m, 2H), 0.99 (m, 2H); LC/MS (ESI+): 438.1 (M+H).

Example 487. 2-{4-[5-Cyclopropyl-4-((3R,4S)-3,4-dihydroxy-piperidin-1-yl)-pyrido[3,4-d]pyrimidin-2-yl]-pyridin-2-ylamino}-isonicotinonitrile This product was obtained by separation of enantiomers (SCF chiral chromatography) of racemic Example 485.

Example 488. 2-{4-[5-Cyclopropyl-4-((3S,4R)-3,4-dihydroxy-piperidin-1-yl)-pyrido[3,4-d]pyrimidin-2-yl]-pyridin-2-ylamino}-isonicotinonitrile This product was obtained by separation of enantiomers (SCF chiral chromatography) of racemic Example 485. It is the optical antipode of Example 487.

Example 489. 4-(5-Methoxy-4-piperazin-1-yl-pyrido[3,4-d]pyrimidin-2-yl)-N-(1-phenylpyrazol-4-yl)pyridin-2-amine A tube was charged with 4-[2-(2-chloro-pyridin-4-yl)-5-methoxy-pyrido[3,4-d]pyrimidin-4-yl]-piperazine-1-carboxylic acid tert-butyl ester (131.4 mg, 0.2877 mmol), 1-phenyl-1H-pyrazol-4-ylamine (55.0 mg, 0.346 mmol), Palladium Acetate (7.9 mg, 0.035 mmol), 9,9-Dimethyl-4,5-bis(diphenylphosphino)xanthene (21.0 mg, 0.0364 mmol), cesium carbonate (144.6 mg, 0.4438 mmol) and 1,4-dioxane (1 mL). The tube was evacuated and back flushed with nitrogen. The tube was sealed and the reaction mixture was heated at 90° C. for 18 hours. The mixture was cooled to room temperature and diluted with water (10 mL). The suspension was stirred for 15 minutes, filtered, rinsed with water and dried by suction to yield a dark solid.

The dark solid was suspended in methylene chloride (3 mL) and stirred at room temperature. Trifluoroacetic Acid (1 mL, 20 mmol) was added dropwise and the mixture was stirred at room temperature for 1 hour. The volatiles were evaporated. The residue was purified via reverse phase chromatography using a Gilson apparatus with 5%→30% acetonitrile: water (w/ 0.1% TFA as modifier) solvent gradient. The desired fractions were combined, frozen and lyophilized. The recovered lyophilate was consistent for desired 4-(5-methoxy-4-piperazin-1-yl-pyrido[3,4-d]pyrimidin-2-yl)-N-(1-phenylpyrazol-4-yl)pyridin-2-amine (14 mg, 10%). $^1$H NMR (DMSO-$d_6$): δ-8.91 (bs, 1H), 8.71 (bs, 3H), 8.41 (s, 1H), 8.34 (d, 1H, J=5.43 Hz), 7.88 (s, 1H), 7.84 (s, 1H), 7.83 (dd, 2H, JJ=1.09, 8.69 Hz), 7.66 (dd, 1H, JJ=1.30, 5.65), 7.47-7.53 (m, 2H), 7.25-7.31 (m, 1H), 4.10 (s, 3H), 3.88 (bs, 4H), 3.33 (bs, 4H). LCMS (ESI+) 480.3 (M+H).

Example 490. (2,3-Dimethyl-2H-indazol-6-yl)-[4-(5-methoxy-4-piperazin-1-yl-pyrido[3, 4-d]pyrimidin-2-yl)-pyridin-2-yl]-amine A tube was charged with 4-[2-(2-chloro-pyridin-4-yl)-5-methoxy-pyrido[3,4-d]pyrimidin-4-yl]-piperazine-1-carboxylic acid tert-butyl ester (131.4 mg, 0.2877 mmol), 2,3-dimethyl-2H-indazol-6-ylamine (55.7 mg, 0.346 mmol), palladium acetate (7.9 mg, 0.035 mmol), 9,9-dimethyl-4,5-bis(diphenylphosphino)xanthene (21.0 mg, 0.0364 mmol), cesium carbonate (144.6 mg, 0.4438 mmol) and 1,4-dioxane (1 mL). The tube was evacuated and back flushed with nitrogen. The tube was sealed and the reaction mixture was heated at 90° C. for 18 hours. The mixture was cooled to room temperature and diluted with water (10 mL). The suspension was stirred for 15 minutes, filtered, rinsed with water and dried by suction to yield a dark solid.

The dark solid was suspended in methylene chloride (3 mL, 40 mmol) and stirred at room temperature. Trifluoroacetic Acid (1 mL, 20 mmol) was added dropwise and the mixture was stirred at room temperature for 1 hour. The volatiles were evaporated. The residue was purified via reverse phase chromatography using a Gilson apparatus with 5%-30% acetonitrile: water (w/0.1% TFA as modifier) solvent gradient. The desired fractions were combined, frozen and lyophilized. The recovered lyophilate was consistent for desired (2,3-dimethyl-2H-indazol-6-yl)-[4-(5-methoxy-4-piperazin-1-yl-pyrido[3, 4-d]pyrimidin-2-yl)-pyridin-2-yl]-amine (38 mg, 27%). $^1$H NMR (DMSO-$d_6$): δ-9.50 9 bs, 1H), 8.91 (bs, 3H), 8.42 (s, 1H), 8.36 (d, 1H, J=5.19 Hz), 8.24 (bs, 1H), 8.01 (bs, 1H), 7.72 (dd, 1H, J=1.20, 5.28 Hz), 7.58 (d, 1H, J=9.07 Hz), 7.06 (dd, 1H, JJ=1.65, 8.87 Hz), 4.10 (s, 3H), 3.99 (s, 3H0, 3.89 (bs, 4H), 3.33 (bs, 3H), 2.57 (s, 3H). LCMS (ESI+) 482.1 (M+H).

Example 491. [1-(2-Fluoro-phenyl)-1H-pyrazol-4-yl]-[4-(5-methoxy-4-piperazin-1-yl-pyrido[3, 4-d]pyrimidin-2-yl)-pyridin-2-yl]-amine A tube was charged with 4-[2-(2-chloro-pyridin-4-yl)-5-methoxy-pyrido[3,4-d]pyrimidin-4-yl]-piperazine-1-carboxylic acid tert-butyl ester (131.4 mg, 0.2877 mmol), 1-(2-fluoro-phenyl)-1H-pyrazol-4-ylamine (61.2 mg, 0.346 mmol), palladium acetate (7.9 mg, 0.035 mmol), 9,9-dimethyl-4,5-bis(diphenylphosphino)xanthene (21.0 mg, 0.0364 mmol), cesium carbonate (144.6 mg, 0.4438 mmol) and 1,4-dioxane (1 mL). The tube was evacuated and back-flushed with nitrogen. The tube was sealed and the reaction mixture was heated at 90° C. for 18 hours. The mixture was cooled to room temperature and diluted with water (10 mL). The suspension was stirred for 15 minutes, filtered, rinsed with water and dried by suction to yield a dark solid.

The dark solid was suspended in methylene chloride (3 mL) and stirred at room temperature. Trifluoroacetic Acid (1 mL, 20 mmol) was added dropwise and the mixture was stirred at room temperature for 1 hour. The volatiles were evaporated. The residue was purified via reverse phase chromatography using a Gilson apparatus with 5%-*30% acetonitrile: water (w/ 0.1% TFA as modifier) solvent gradient. The desired fractions were combined, frozen and lyophilized. The recovered lyophilate was consistent for desired [1-(2-fluoro-phenyl)-1H-pyrazol-4-yl]-[4-(5-methoxy-4-piperazin-1-yl-pyrido[3, 4-d]pyrimidin-2-yl)-pyridin-2-yl]-amine (12 mg, 8.4%) $^1$H NMR (DMSO-$d_6$): δ-9.51 (bs, 1H), 8.90 (bs, 3H), 8.59 (d, 1H, J=3.17 Hz), 8.41 (s, 1H), 8.33 (d, 1H, J=5.50 Hz), 7.83-7.88 (m, 3H), 7.69 (dd, 1H, J=1.33, 5.50 Hz), 7.33-7.51 (m, 3H), 4.10 (s, 3H), 3.88 (bs, 4H), 3.33 (bs, 4H). LCMS (ESI+) 490.1 (M+H). HPLC>95% pure (retaintion time=1.7 min. in G method).

Example 492. [4-(5-cyclopropyl-4-piperazin-1-yl-pyrido[3,4-d]pyrimidin-2-yl)-pyridin-2-yl]-(1-phenyl-1H-pyrazol-4-yl)-amine A tube was charged with 4-[2-(2-Chloro-pyridin-4-yl)-5-cyclopropyl-pyrido[3,4-d]pyrimidin-4-yl]-piperazine-1-carboxylic acid tert-butyl ester (403.0 mg, 0.8631 mmol), 1-Phenyl-1H-pyrazol-4-ylamine (165.0 mg, 1.036 mmol), Palladium Acetate (24 mg, 0.10 mmol), 9,9-Dimethyl-4,5-bis(diphenylphosphino)xanthene (63.1 mg, 0.109 mmol), Cesium Carbonate (433.8 mg, 1.331 mmol) and 1,4-Dioxane (4 mL). The tube was evacuated and backflushed with nitrogen. The tube was sealed and the reaction mixture was heated at 90° C. for 18 hours. The mixture was cooled to room temperature and diluted with water (10 mL). The suspension was stirred for 15 minutes, filtered, rinsed with water and dried by suction to yield a dark solid.

The dark solid was suspended in methylene chloride (8 mL) and stirred at room temperature. Trifluoroacetic Acid (4 mL, 50 mmol) was added dropwise and the mixture was stirred at room temperature for 1 hour. The volatiles were evaporated. The residue was purified via reverse phase chromatography using a Gilson apparatus with 5%-*30% acetonitrile: water (w/ 0.1% TFA as modifier) solvent gradient. The desired fractions were combined, frozen and lyophilized. The recovered lyophilate was consistent for desired [4-(5-cyclopropyl-4-piperazin-1-yl-pyrido[3,4-d]pyrimidin-2-yl)-pyridin-2-yl]-(1-phenyl-1H-pyrazol-4-yl)-amine (10 mg, 4%).

$^1$H NMR (DMSO-$d_6$): δ-9.40 (s, 1H), 8.97 (s, 1H), 8.7 (s, 1H), 8.35 (d, 1H, J=5.65 Hz), 8.09 (s, 1H), 7.78-7.85 (m, 4H), 7.63 (dd, 1H, J=1.42, 5.34 Hz), 7.49 (t, 2H, J=8.37 Hz), 7.27 (t, 1H, J=7.48 Hz), 3.52-3.88 (bm, 4H), 2.58-2.85 (bm, 5H), 1.20-1.32 (m, 2H), 1.00-1.06 (m, 2H). LCMS (ESI+) 490.19 (M+H). HPLC>95% pure (retaintion time=1.8 min. in G method).

Example 493. [4-(5-Cyclopropyl-4-piperazin-1-yl-pyrido[3,4-d]pyrimidin-2-yl)-pyridin-2-yl]-(2,3-dimethyl-2H-indazol-6-yl)-amine A tube was charged with 4-[2-(2-Chloro-pyridin-4-yl)-5-cyclopropyl-pyrido[3,4-d]pyrimidin-4-yl]-piperazine-1-carboxylic acid tert-butyl ester (241.2 mg, 0.5166 mmol), 2,3-Dimethyl-2H-indazol-6-ylamine (100.0 mg, 0.6203 mmol), Palladium Acetate (14 mg, 0.063 mmol), 9,9-Dimethyl-4,5-bis(diphenylphosphino)xanthene (37.8 mg, 0.0653 mmol), Cesium Carbonate (259.6 mg, 0.7968 mmol) and 1,4-Dioxane (2 mL). The tube was evacuated and back-flushed with nitrogen. The tube was sealed and the reaction mixture was heated at 90° C. for 18 hours. The mixture was cooled to room temperature and diluted with water (10 mL). The suspension was stirred for 15 minutes, filtered, rinsed with water and dried by suction to yield a brown solid. The dark solid was suspended in Methylene chloride (5 mL, 70 mmol) and stirred at room temperature. Trifluoroacetic Acid (2 mL, 30 mmol) was added dropwise and the mixture was stirred at room temperature for 1 hour. The volatiles were evaporated. The residue was purified via reverse phase chromatography using a Gilson apparatus with 5%→30% Acetonitrile: Water (w/0.1% TFA as modifier) solvent gradient. The desired fractions were combined, frozen and lyophilized. The recovered lyophilate was consistent with [4-(5-Cyclopropyl-4-piperazin-1-yl-pyrido[3,4-d]pyrimidin-2-yl)-pyridin-2-yl]-(2,3-dimethyl-2H-indazol-6-yl)-amine (60 mg, 24%). $^1$H NMR (DMSO-$d_6$): δ-9.32 (s, 1H), 8.96 (s, 1H), 8.35 (d, 1H, J=5.25 Hz), 8.28 (bs, 1H), 8.08 (s, 1H), 7.95 (bs, 1H), 7.68 (dd, 1H, J=1.36, 5.45 Hz), 7.52 (d, 1H, J=8.95 Hz), 7.04 (dd, 1H, J=1.56, 8.95 Hz), 3.97 (s, 3H), 2.53-2.70 (m, 5H), 2.45 (bs, 4H), 2.45 (s, 3H), 1.21-1.29 (m, 2H), 1.00-1.06 (m, 2H). LCMS (ESI+) 492.20 (M+H). HPLC>95% pure (retaintion time=1.7 min. in G method).

Example 494. Phenyl-[4-(4-piperazin-1-yl-pyrido[3, 4-d]pyrimidin-2-yl)-pyridin-2-yl]-amine Following a procedure similar to 303c, 4-[2-(2-Chloro-pyridin-4-yl)-pyrido[3,4-d]pyrimidin-4-yl]-piperazine-1-carboxylic acid tert-butyl ester (180 mg, 0.42 mmol), and Aniline (51.1 uL, 0.561 mmol) were converted to the title compound 35.28 mgs, 22% yield. LC/MS=384.2 (M+H)+

Example 495. [4-(5-cyclopropyl-4-piperazin-1-yl-pyrido[3,4-d]pyrimidin-2-yl)-pyridin-2-yl]-(2-fluoro-pyridin-3-yl)-amine A tube was charged with 4-[2-(2-chloro-pyridin-4-yl)-5-cyclopropyl-pyrido[3,4-d]pyrimidin-4-yl]-piperazine-1-carboxylic acid tert-butyl ester (100 mg, 0.214 mmol), 2-fluoro-pyridin-3-ylamine (46.2 mg, 0.412 mmol), palladium acetate (12.0 mg, 0.053 mmol), 9,9-dimethyl-4,5-bis (diphenylphosphino)xanthene (34.0 mg, 0.058 mmol), cesium carbonate (120 mg, 0.368 mmol) and 1,4-dioxane (0.7 mL, 8 mmol). The tube was evacuated and backflushed with nitrogen. The tube was sealed and the reaction mixture was heated at 100° C. for 3 h. The mixture was cooled to room temperature and diluted with dichloromethane (10 mL) and filtered through celite. The filtrate was evaporated to a dark resin.

The brown resin was dissolved in methylene chloride (0.7 mL, 10 mmol) and trifluoroacetic acid (0.7 mL, 9 mmol) was added. The mixture was stirred for 1 hour at room temperature and concentrated. The residue was purified via reverse phase chromatography using a Gilson apparatus. The desired fractions were loaded onto a SCX cartridge and rinsed with methanol and the product was released with 2M ammonia in methanol. The ammonia filtrate was evaporated and placed under high vacuum for 2 hours. The recovered yellow solid (35 mg, 37%) was consistent for the title compound. 1H NMR (300 MHz, DMSO-d6): 9.26 (s, 1H), 8.98 (s, 1H), 8.88 (t, J=9 Hz, 1H), 8.34 (d, J=5 Hz, 1H), 8.18 (s, 1H), 8.10 (s, 1H), 7.79 (d, J=5 Hz, 1H), 7.75 (d, J=4 Hz, 1H), 7.31 (m, 1H), 3.72 (m, 4H), 2.88 (br s, 4H), 2.62 (m, 1H), 1.26 (d, J=8 Hz, 2H), 1.04 (d, J=5 Hz, 2H), MS: 433 (M+H).

Example 496. [4-(5-Methoxy-4-piperazin-1-yl-pyrido[3,4-d]pyrimidin-2-yl)-pyridin-2-yl]-(5-methyl-isoxazol-3-yl)-amine 4-[2-(2-Chloro-pyridin-4-yl)-5-methoxy-pyrido[3,4-d]pyrimidin-4-yl]-piperazine-1-carboxylic acid tert-butyl ester (75 mg, 0.16 mmol), 5-methyl-isoxazol-3-ylamine (32.2 mg, 0.3283 mmol), bis(dibenzylideneacetone)palladium(0) (5 mg, 0.0085 mmol), XANTPHOS (10 mg, 0.171 mmol), and lithium hexamethylsilazide (55 mg, 0.328 mmol) were combined in tetrahydrofuran (3 mL), degassed with Argon and subjected to reaction in a microwave at 120 C for six hours. Additional palladium, isoxazole, and silazide were added and the microwave temperature was raised to 150 C for an additional six hours. The reaction was concentrated and purification was effected via reverse phase chromatography to afford the title compound (2 mg, 3%). MS: 419.23 (M+H).

Example 497. 2-[2-(3-Piperazin-1-yl-phenylamino)-pyridin-4-yl]-pyrido[3,4-d]pyrimidin-4-ol Following a procedure similar to Example 303c, 2-(2-Chloro-pyridin-4-yl)-pyrido[3,4-d]pyrimidin-4-ol (67 mg, 0.26 mmol) and 4-(3-Amino-phenyl)-piperazine-1-carboxylic acid tert-butyl ester (1.1 eq) were converted to the title compound isolated as the bis-TFA salt (21 mg, 13%). LC/MS: M+H+=400.

Example 498. 2-[2-(3-Piperazin-1-ylmethyl-phenylamino)-pyridin-4-yl]-pyrido[3,4-d]pyrimidin-4-ol Following a procedure similar to Example 303c, 2-(2-Chloro-pyridin-4-yl)-pyrido[3,4-d]pyrimidin-4-ol (143 mg, 0.56 mmol) and 4-(3-Amino-benzyl)-piperazine-1-carboxylic acid tert-butyl ester (1.1 eq) were converted to the title compound isolated as the bis TFA salt (51.4 mg, 14%). LC/MS: M+H+=414.

Example 499. 2-[2-(1-Piperidin-4-ylmethyl-1H-pyrazol-4-ylamino)-pyridin-4-yl]-pyrido[3, 4-d]pyrimidin-4-ol Following a procedure similar to Example 303c, 2-(2-Chloro-pyridin-4-yl)-pyrido[3,4-d]pyrimidin-4-ol (145 mg, 0.56 mmol) and 4-(4-Amino-pyrazol-1-ylmethyl)-piperidine-1-carboxylic acid tert-butyl ester (1.1 eq) were converted to the title compound isolated as the bis TFA salt (20.56 mg, 6%). LC/MS: M+H+=403.

Example 500. {5-Methoxy-2-[2-(3-piperazin-1-yl-phenylamino)-pyridin-4-yl]-pyrido[3,4-d]pyrimidin-4-yl}-methyl-amine Following a procedure similar to Example 303b, 2-(2-Chloro-pyridin-4-yl)-5-methoxy-pyrido[3,4-d]pyrimidin-4-ol (362 mgs, 1.25 mmol) and methylamine.HCl (1.1 eq) were converted to [2-(2-Chloro-pyridin-4-yl)-5-methoxy-pyrido[3,4-d]pyrimidin-4-yl]-methyl-amine (64% yield) which was converted using a procedure analogous to Example 497 to the title compound isolated as a bis TFA salt (14 mgs, 5% yield), LC/MS: M+H+=443.25

Example 501. (5-Methoxy-2-{2-[4-(2-pyrrolidin-1-yl-ethoxy)-phenylamino]-pyridin-4-yl}-pyrido[3,4-d]pyrimidin-4-yl)-methyl-amine Following a procedure analogous to Example 500, 4-(2-Pyrrolidin-1-yl-ethoxy)-phenylamine (44 mg, 0.21 mmol) was converted to the title compound isolated as the bis-TFA salt (6.35 mgs, 5% yield) LC/MS: M+H+=472.

Example 502. {5-Methoxy-2-[2-(3-piperidin-4-yl-phenylamino)-pyridin-4-yl]-pyrido[3,4-d]pyrimidin-4-yl}-methyl-amine Following a procedure analogous to Example 500, 4-(3-Amino-phenyl)-piperidine-1-carboxylic acid tert-butyl ester (0.1468 g, 0.5312 mmol) was converted to the title compound isolated as a bis-TFA salt (23.61 mgs, 7% yield). LC/MS: M+H+=442.

Example 503. [4-(5-Methoxy-pyrido[3,4-d]pyrimidin-2-yl)-pyridin-2-yl]-(3-piperazin-1-yl-phenyl)-amine 503a) 2-(2-Chloro-pyridin-4-yl)-5-methoxy-pyrido[3,4-d]pyrimidin-4-ol (208 mg, 0.720 mmol), 2,4,6-Triisopropylbenzenesulfonyl Chloride (221.1 mg, 0.7301 mmol), Triethylamine (0.31 mL, 2.2 mmol), and 4-Dimethylaminopyridine (8.8 mg, 0.072 mmol) in N,N-Dimethylformamide (2 mL, 30 mmol) were stirred at room temperature for 1 h, Hydrazine hydrate (0.05410 g, 1.081 mmol) was added and the reaction was stirred overnight. The product precipitated and was triturated from ether. Taking on without further purification.

503b) [2-(2-Chloro-pyridin-4-yl)-5-methoxy-pyrido[3,4-d]pyrimidin-4-yl]-hydrazine (0.218 g, 0.720 mmol) was treated with 1,4-Dioxane (5.0 mL, 65 mmol) and Water (0.6 mL, 30 mmol) and then Silver(I) Oxide (334 mg, 1.44 mmol) and stirred at room temperature. After 1.5 h, LC/MS indicated major product (M+H)+=273. Filtered off silver salts and concentrated and put on high vac. Purified by ISCO chomatography 12 g SiO2, gradient elution 0% to 100% EA/hexane over 13 minutes to give 2-(2-Chloro-pyridin-4-yl)-5-methoxy-pyrido[3,4-d]pyrimidine 503c) Using a procedure analogous to Example 497 to the title compound 2-(2-Chloro-pyridin-4-yl)-5-methoxy-pyrido[3,4-d]pyrimidine (31 mgs, 0.11 mmol) was converted to the title compound (6.37 mgs, 13% yield). LC/MS: M+H+=414.

The following compounds were synthesised according to the general synthesis shown in scheme [B4]

| Ex | Amine 1 | Amine 2 | Analysis LCMS | NMR | Name |
|---|---|---|---|---|---|
| 504 | 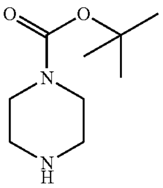 | 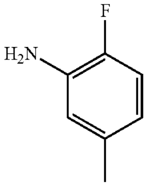 | method 5: RT: 2.87 min, MI: 456 [M + H] | 1H NMR (DMSO, 500 MHz) 9.04 (1H, s), 8.30 (1H, d), 8.17 (1H, s), 8.05 (1H, s), 7.94 (1H, d), 7.73 (1H, d), 7.13 (1H, d), 6.87 (1H, m), 3.90 (4H, very broad s), 3.31 (4H, 1H NMR (DMSO, 500 MHz) 9.04 (1H, s), 8.30 (1H, d), 8.17 (1H, s), 8.05 (1H, s), 7.94 (1H, d), 7.73 (1H, d), 7.13 (1H, d), 6.87 (1H, m), 3.90 (4H, very broad s), 3.31 (4H, broad s), 2.68 (1H, m), 2.29 (3H, s), 1.25 (2H, m), 1.06 (2H, m). | [4-(5-Cyclopropyl-4-piperazin-1-yl-pyrido[3,4-d]pyrimidin-2-yl)-pyridin-2-yl]-(2-fluoro-5-methyl-phenyl)-amine |
| 505 | 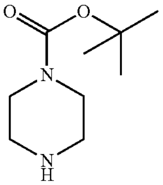 | 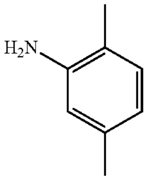 | method 5: RT: 2.20 min, MI: 452 [M + H] | 1H NMR (DMSO, 500 MHz) 9.07 (1H, s), 8.19 (1H, s), 8.14 (1H, d), 7.98 (1H, s), 7.73 (1H, d), 7.33 (1H, s), 7.22 (1H, d), 7.03 (1H, d), 3.89 (4H, very broad s), 3.30 (4H, 1H NMR (DMSO, 500 MHz) 9.07 (1H, s), 8.19 (1H, s), 8.14 (1H, d), 7.98 (1H, s), 7.73 (1H, d), 7.33 (1H, s), 7.22 (1H, d), 7.03 (1H, d), 3.89 (4H, very broad s), 3.30 (4H, broad s), 2.48 (1H, m), 2.29 (3H, s), 2.20 (3H, s), 1.25 (2H, m), 1.07 (2H, m) | [4-(5-Cyclopropyl-4-piperazin-1-yl-pyrido[3,4-d]pyrimidin-2-yl)-pyridin-2-yl]-(2,5-dimethyl-phenyl)-amine |
| 506 | 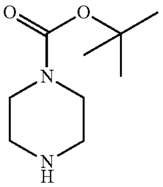 | 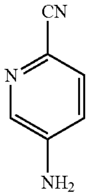 | method 5: RT: 5.19 min, MI: 450 [M + H] | NMR: (DMSO) 10.27 ppm (s, 1H), 9.06 ppm (s, 1H), 8.95 ppm (d, 1H), 8.58 ppm (dd, 1H), 8.48 ppm (d, 1H), 8.19 ppm (s, 1H), 8.06 ppm (s, 1H), 7.91 ppm (m, 2H), 3.85 ppm (s, 4H), 3.90 ppm (broad s, 4H), 2.68 ppm (m, 1H), 1.27 ppm (m, 2H), 1.09 ppm (m, 2H). A second set of piperazine 4H is suspected to be running under the DMSO water peak at 3.33 ppm. | 5-[4-(5-Cyclopropyl-4-piperazin-1-yl-pyrido[3,4-d]pyrimidin-2-yl)-pyridin-2-ylamino]-pyridine-2-carbonitrile |
| 507 | 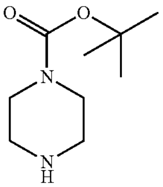 | 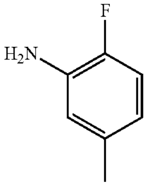 | method 5: RT: 2.10 min, MI: 426 [M + H] | 1H NMR (DMSO, 500 MHz) 9.08 (1H, s), 8.78 (1H, s), 8.47 (1H, d), 8.31 (1H, m), 8.19 (1H, s), 8.16 (1H, d), 7.94 (2H, dd), 3.93 (4H, very broad s), 3.31 (4H, br s), 2.68 (1H, m), 1.26-1.24 (2H, m), 1.08-1.05 (2H, m). | 4-(5-Cyclopropyl-4-piperazin-1-yl-pyrido[3,4-d]pyrimidin-2-yl)-pyridin-2-yl]-pyrazin-2-yl-amine |
| 508 | 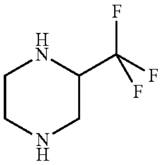 | 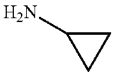 | method 5: RT 3.28 min, MI: 456.17 [M + H] | 1H NMR (DMSO, 500 MHz) 8.99 (1H, s), 8.15 (1H, d), 8.10 (1H, s), 7.64 (1H, s), 7.49 (1H, d), 6.98 (1H, s), 4.56-4.25 (1H, m, br), 3.95 (1H, d, br), 3.65 (s, br, 4H), 3.03 (4H, s, br), 1.28-1.22 (3H, m, br), 1.05-1.01 2H, m, br), 0.73 (2H, d, br), 0.47 (2H, s, br). | Cyclopropyl-{4-[5-cyclopropyl-4-(3-trifluoromethyl-piperazin-1-yl)-pyrido[3,4-d]pyrimidin-2-yl]-pyridin-2-yl}-amine |
| 509 | 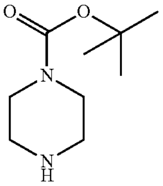 | 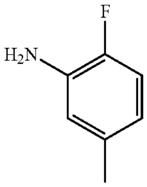 | method 5: RT 1.73 min:, MI: 418.19 [M + H] | 1H NMR (DMSO, 500 MHz) 8.99 (1H, s), 8.13 (1H, d), 8.12 (1H, s), 7.58 (1H, s), 7.45 (1H, d), 7.05 (1H, d), 4.43 (1H, m, br), 3.91-3.82 (2H, m), 3.80 (4H, m, br), 3.75-3.70 1H NMR (DMSO, 500 MHz) 8.99 (1H, s), 8.13 (1H, d), 8.12 (1H, s), 7.58 (1H, s), 7.45 (1H, d), 7.05 (1H, d), 4.43 (1H, m, br), 3.91-3.82 (2H, m), 3.80 (4H, m, br), 3.75-3.70 (1H, m), 3.54 (1H, dd), 3.20 (4H, m, br), 2.70-2.67 (1H, m), 2.21-2.14 (1H, m), | [4-(5-Cyclopropyl-4-piperazin-1-yl-pyrido[3,4-d]pyrimidin-2-yl)-pyridin-2-yl]-(R)-tetrahydro-furan-3-yl-amine |

-continued

| | | | Analysis | | |
|---|---|---|---|---|---|
| Ex | Amine 1 | Amine 2 | LCMS | NMR | Name |
| 510 | 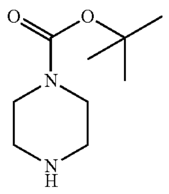 | 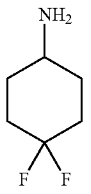 | method 5: RT: 2.37 min, MI: 466.20 [M + H] | 1H NMR (500 MHz, DMSO) 8.93 (1H, s), 8.11 (1H, d), 8.06 (1H, s), 7.54 (1H, s), 7.41 (1H, d), 6.80 (1H, d), 4.02-3.97 (1H, m, br), 3.79-3.54 (4H, m, br), 2.84 (4H, m, 2.62 1H NMR (500 MHz, DMSO) 8.93 (1H, s), 8.11 (1H, d), 8.06 (1H, s), 7.54 (1H, s), 7.41 (1H, d), 6.80 (1H, d), 4.02-3.97 (1H, m, br), 3.79-3.54 (4H, m, br), 2.84 (4H, m, 2.62-2.59 (1H, m), 2.10-1.89 (6H, m, br), 1.59-1.53 (2H, m, br), 1.26-1.22 (2H, m), 1 | [4-(5-Cyclopropyl-4-piperazin-1-yl-pyrido[3,4-d]pyrimidin-2-yl)-pyridin-2-yl]-(4,4-difluoro-cyclohexyl)-amine |
| 511 | 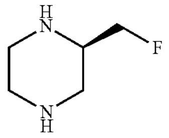 | 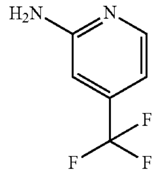 [SMILES: Nc1cc(C(F)(F)F)ccn1] | method 5: RT: 2.31 min, MI: 525 [M + H] | 1H NMR (DMSO, 500 MHz) 9.00 (1H, s), 8.68 (1H, s), 8.50 (1H, m), 8.45 (1H, m), 8.32 (1H, m), 8.11 (1H, s), 7.89 (1H, d), 7.85 (1H, m), 4.47 (1H, d), 4.38 (1H, d), 4.30 (1H, m), 4.16 (1H, m), 3.32 (1H, m), 3.22 (2H, m), 3.13 (2H, m), 2.62 (1H, m), 1.26-1.24 (2H, m), 1.05-1.03 (2H, m) | {4-[5-Cyclopropyl-4-((R)-3-fluorometh-yl-piperazin-1-yl)-pyrido[3,4-d]py-rimidin-2-yl]-pyridin-2-yl}-(4-trifluoromethyl-pyridin-2-yl)-amine |
| 512 | 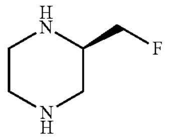 | 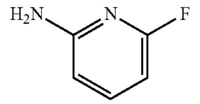 | method 5: RT: 2.31 min, MI: 525 [M + H] | 1H NMR (DMSO, 500 MHz) 9.00 (1H, s), 8.68 (1H, s), 8.50 (1H, m), 8.45 (1H, m), 8.32 (1H, m), 8.11 (1H, s), 7.89 (1H, d), 7.85 (1H, m), 4.47 (1H, d), 4.38 (1H, d), 4.30 (1H, m), 4.16 (1H, m), 3.32 (1H, m), 3.22 (2H, m), 3.13 (2H, m), 2.62 (1H, m), 1.26-1.24 (2H, m), 1.05-1.03 (2H, m) | {4-[5-Cyclopropyl-4-((R)-3-fluorometh-yl-piperazin-1-yl)-pyrido[3,4-d]py-rimidin-2-yl]-pyridin-2-yl}-(6-fluoro-pyridin-2-yl)-amine |
| 513 | 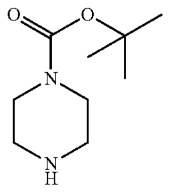 | 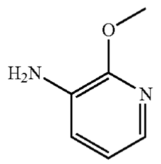 | 455.2 (M + H) | ($CDCl_3$) 9.12 (d, J = 1.6 Hz, 1H), 8.70 (dd, J = 8.0; 1.5 Hz, 1H), 8.40 (d, J = 4.4 Hz, 1H), 8.06 (s, 1H), 7.89 (s, 1H), 7.83 (dd, J = 5.2; 1.3 Hz, 1H), 7.75 (m, 1H), 7.19 (s, 1H), 6.92 (m, 1H), 4.07 (s, 3H), 3.77 (br s, 4H), 3.04 (m, 4H), 2.70 (m, 1H), 1.84 (exch. protos), 1.27 (m, 2H), 1.01 (m, 2H) | [4-(5-Cyclopropyl-4-piperazin-1-yl-pyrido[3,4-d]pyrimidin-2-yl)-pyridin-2-yl]-(2-methoxy-pyridin-3-yl)-amine |
| 514 | 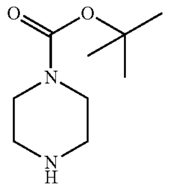 | 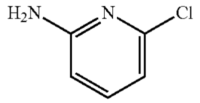 | 459.1 (M + H) | (dmso-d6) 10.24 (s, 1H), 8.98 (s, 1H), 8.75 (s, 1H), 8.41 (d, J = 5.2 Hz, 1H), 8.10 (s, 1H), 7.88 (m, 1H), 7.82 (m, 1H), 7.74 (m, 1H), 6.97 (d, J = 7.5 Hz, 1H), 3.75 (br m, 4H), 2.86 (br m, 4H), 2.62 (m, 1H), 1.25 (m, 2H), 1.03 (m, 2H) | (6-Chloro-pyridin-2-yl)-[4-(5-cyclo-propyl-4-piperazin-1-yl-pyrido[3,4-d]pyrimidin-2-yl)-pyridin-2-yl]-amine |
| 515 | 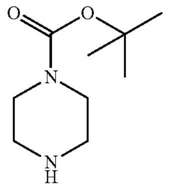 | 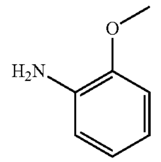 | 454.2 (MH)+ | | [4-(5-Cyclopropyl-4-piperazin-1-yl-pyrido[3,4-d]pyrimidin-2-yl)-pyridin-2-yl]-(2-methoxy-phenyl)-amine |
| 516 | 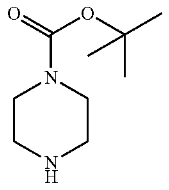 | 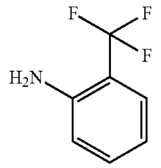 [SMILES: Nc1ccccc1C(F)(F)F] | 492.1 (MH)+ | | [4-(5-Cyclopropyl-4-piperazin-1-yl-pyrido[3,4-d]pyrimidin-2-yl)-pyridin-2-yl]-(2-trifluoromethyl-phenyl)-amine |

-continued

| Ex | Amine 1 | Amine 2 | Analysis LCMS | NMR | Name |
|---|---|---|---|---|---|
| 517 | 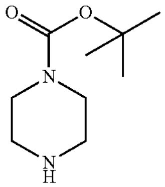 | 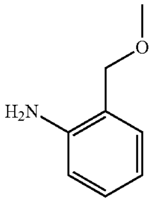 | 468.2 (M + H)+ | ($CDCl_3$) 9.11 (s, 1H), 8.37 (dd, J = 5.3; 0.4 Hz, 1H), 8.04 (s, 1H), 7.96 (s, 1H), 7.93 (d, J = 8.0 Hz, 1H), 7.79 (dd, J = 5.3; 1.3 Hz, 1H), 7.72 (br s, 1H), 7.35 (m, 1H), 7.27 (m, 1H), 7.01 (m, 1H), 4.57 (s, 2H), 3.75 (br s, 4H), 3.43 (s, 3H), 3.01 (m, 4H), 2.69 (m, 1H), 2.04 (br s, esch. protons), 1.26 (m, 2H), 1.00 (m, 2H) | [4-(5-Cyclopropyl-4-piperazin-1-yl-pyrido[3,4-d]pyrimidin-2-yl)-pyridin-2-yl]-(2-methoxymethyl-phenyl)-amine |
| 518 | 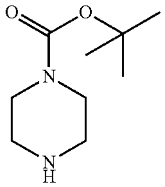 | 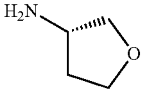 | method 5: RT: 2.27 min, MI: 418.17 M + H] | 1H NMR (500 MHz, DMSO) 8.93 (1H, s), 8.11 (1H, d), 8.06 (1H, s), 7.56 (1H, s), 7.43 (1H, dd), 7.01 (1H, d), 4.45-4.39 (1H, m), 3.90-3.53 (4H, s, br), 3.89 (1H, dd), 3.85 (1H, q), 3.75-3.70 (1H, m), 3.55 (1H, dd), 3.15 (2H, d), 2.85 (4H, s, br), 2.62-2.61 (1H, m), 2.20-2.16 (1H, m), 1.85-1.80 (1H, m), 1.26-1.22 (2H, m), 1.02-1.01 (2H, m) | [4-(5-Cyclopropyl-4-piperazin-1-yl-pyrido[3,4-d]pyrimidin-2-yl)-pyridin-2-yl]-(S)-tetrahydro-furan-3-yl-amine |
| 519 | 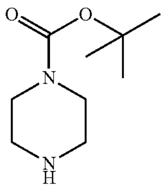 | 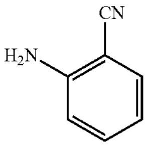 | 449.1 (M + H)+ | ($CDCl_3$) 9.14 (m, 2H), 8.42 (d, J = 1.4 Hz, 1H), 8.07 (s, 1H), 7.93 (d, J = 8.1 Hz, 1H), 7.84 (dd, J = 8.1; 5.9 Hz, 1H), 7.68 (m, 2H), 7.39 (m, 2H), 3.82 (m, 4H), 3.05 (m, 4H), 2.71 (m, 1H), 1.7 (br s, exch. H's), 1.28 (m, 2H), 1.02 (m, 2H) | 2-[4-(5-Cyclopropyl-4-piperazin-1-yl-pyrido[3,4-d]pyrimidin-2-yl)-pyridin-2-ylamino]-benzonitrile |
| 520 | 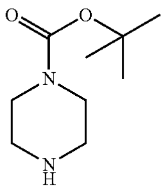 | 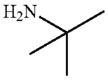 | method 5: RT: 3.73 min, MI: 404.30 [M + H] | 1H NMR (DMSO, 500 MHz) 8.92 (1H, s), 8.07 (2H, dd), 7.56 (1H, s), 7.35 (1H, s), 6.47 (1H, s), 3.75-3.54 (4H, m, br), 2.83 (4H, m, br), 2.62 (1H, m, br), 1.41 (9H, s), 1.24 (2H, m, br), 1.00 (2H, m, br). | tert-Butyl-[4-(5-cyclopropyl-4-piperazin-1-yl-pyrido[3,4-d]pyrimidin-2-yl)-pyrido-2-yl]-amine |
| 521 | 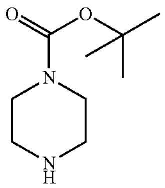 | 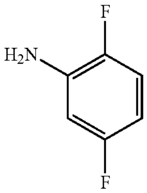 | method 5: RT: 3.90 min, MI: 460 [M + H] | 1H NMR (DMSO, 500 MHz) 9.25 (1H, s), 9.05 (1H, s), 8.97 (1H, s, br), 8.39 (1H, d), 8.24 (1H, s), 8.17 (1H, s), 7.78 (1H, d), 7.28 (1H, m), 6.76 (1H, m), 3.96-3.88 (4H, s, br), 3.31 (4H, s, br), 2.65 (1H, m), 1.28-1.25 (2H, m), 1.08-1.05 (2H, m) | [4-(5-Cyclopropyl-4-piperazin-1-yl-pyrido[3,4-d]pyrimidin-2-yl)-pyridin-2-yl]-(2,5-difluoro-phenyl)-amine |
| 522 | 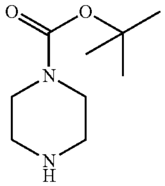 | 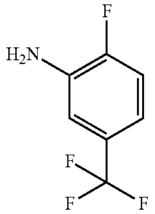 [SMILES: Nc1cc(C(F)(F)F)ccc1F] | method 5: RT: 4.02 min, MI: 510 [M + H] | 1H NMR (DMSO, 500 MHz) 9.37 (1H, s), 9.06 (1'H, s), 8.97 (1H, s, br), 8.41 (1H, d), 8.23 (1H, s), 8.18 (1H, s), 7.84 (1H, d), 7.47 (1H, m), 7.32 (1H, m), 3.96-3.88 (4H, s, br), 3.31 (4H, s, br), 2.65 (1H, m), 1.28-1.25 (2H, m), 1.08-1.05 (2H, m). | [4-(5-Cyclopropyl-4-piperazin-1-yl-pyrido[3,4-d]pyrimidin-2-yl)-pyridin-2-yl]-(2-fluoro-5-trifluoromethyl-phenyl)-amine |
| 523 | 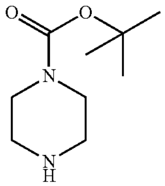 | 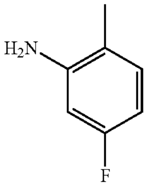 | method 5: RT: 3.80 min, MI: 466 [M + H] | 1H NMR (DMSO, 500 MHz) 9.05 (1H, s), 8.97 (1H, s, br), 8.28 (1H, d), 8.18 (1H, s), 8.05 (1H, s), 7.81 (1H, s), 7.75 (1H, d), 7.23 (1H, d), 6.81 (1H, d), 3.96-3.88 (4H, s, br), 3.31 (4H, s, br), 2.66 (1H, m), 2.27 (3H, s), 1.28-1.25 (2H, m), 1.08-1.05 (2H, m) | [4-(5-Cyclopropyl-4-piperazin-1-yl-pyrido[3,4-d]pyrimidin-2-yl)-pyridin-2-yl]-(5-fluoro-2-methyl-phenyl)-amine |

-continued

| Ex | Amine 1 | Amine 2 | Analysis LCMS | NMR | Name |
|---|---|---|---|---|---|
| 524 | 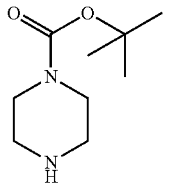 | 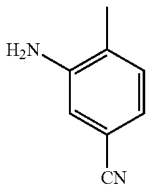 | | 1H NMR (DMSO, 500 MHz) 9.06 (1H, s), 8.96 (1H, s, br), 8.78 (1H, s), 8.36 (1H, s), 8.33 (1H, d), 8.18 (1H, s), 8.06 (1H, s), 7.78 (1H, d), 7.43 (1H, m), 3.96-3.88 (4H, s, br), 3.31 (4H, s, br), 2.68 (1H, m), 2.38 (3H, s), 1.28-1.25 (2H, m), 1.08-1.05 (2H, m) | 3-[4-(5-Cyclopropyl-4-piperaizn-1-yl-pyrido[3,4-d]pyrimidin-2-yl)-pyridin-2-ylamino]-4-methyl-benzonitrile |
| 525 | 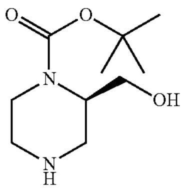 | 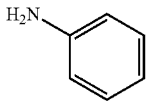 | method 5: RT: 3.20 min, MI: 480 [M + H] | 1H NMR (DMSO, 500 MHz) 9.30 (1H, s), 9.01 (1H, s), 8.32 (1H, d), 8.16 (1H, s), 7.91 (1H, s), 7.75 (1H, d), 7.70 (1H, d,), 7.28 (2H, m), 6.90 (1H, m), 4.43 (4H, m), 4.05 (2H, m), 3.67 (1H, m), 3.48 (1H, m), 3.21 (1H, m), 2.53 (1H, m), 1.28-1.25 (2H, m), 1.3-1.01 (2H, m) | 7-[5-Cyclopropyl-2-(2-phenylamino-pyri-din-4-yl)-pyrido[3,4-d]pyrimidin-4-yl]-hexahydro-oxazolo[3,4-a]pyrazin-3-one |
| 526 | 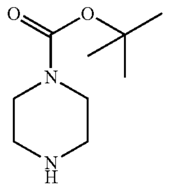 | 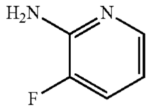 | method 5: RT: 2.33 min, MI: 443 [M + H] | 1H NMR (DMSO, 500 MHz) 11.53 (1H, s), 9.11 (1H, s), 8.92 (1H, s), 8.55 (1H, d), 8.30 (1H, d), 8.24 (1H, s), 8.21 (1H, dd), 7.98 (1H, m), 7.31 (1H, m), 4.01 (4H, s), 3.30 (4H, s), 2.68 (1H, m), 1.28 (2H, m), 1.10 (2H, m). | [4-(5-Cyclopropyl-4-piperazin-1-yl-pyrido[3,4-d]pyrimidin-2-yl)-pyridin-2-yl]-(3-fluoro-pyridin-2-yl)-amine |
| 527 | 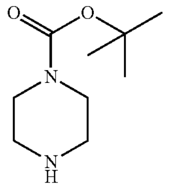 | 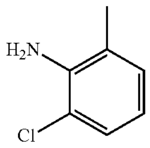 | method 5: RT: 5.3 min, MI: 472 [M + H] | 1H NMR (DMSO, 500 MHz, 1IGO538) 9.05 (1H, s), 9.02-8.90 (2H, broad s), 8.19 (1H, s), 8.14 (1H, d), 7.75 (1H, s), 7.69 (1H, d), 7.45 (1H, d), 7.34 (1H, d), 7.27 (1H, m), 3.89 (4H, s), 3.31 (4H, s), 2.67 (1H, m), 1.26 (2H, m), 1.07 (2H, m) | (2-Chloro-6-methyl-phenyl)-[4-(5-cyclopropyl-4-piperazin-1-yl-pyrido[3,4-d]pyrimidin-2-yl)-pyridin-2-yl]-amine |
| 528 | 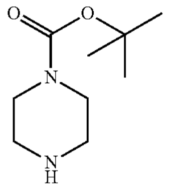 | 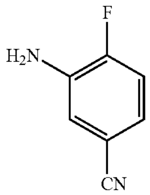 | method 5: RT: 3.68 min, MI: 467 [M + H] | 1H NMR (DMSO, 500 MHz, 1IGO539) 9.41 (1H, s), 9.05 (1H, s), 8.98 (1H, d), 8.43 (1H, d), 8.23 (1H, s), 8.18 (1H, s), 7.86 (1H, d), 7.49 (1H, m), 3.94 (4H, s), 3.33 (4H, s), 2.69 (1H, m), 1.26 (2H, m), 1.08 (2H, m). | 3-[4-(5-Cyclopropyl-4-piperazin-1-yl-pyrido[3,4-d]pyrimidin-2-yl)-pyridin-2-ylamino]-4-fluoro-benzonitrile |
| 529 | 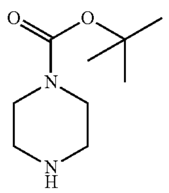 | 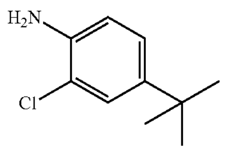 | method 5: RT: 4.21 min, MI: 514 [M + H] | 1H NMR (DMSO, 500 MHz, 1IGO541) 9.06 (1H, s), 9.01-8.90 (2H, broad s), 8.24 (1H, d), 8.19 (1H, s), 8.01 (1H, s), 7.84 (1H, d), 7.75 (1H, dd), 7.48 (1H, d), 7.39 (1H, dd), 3.91 (4H, s), 3.32 (4H, s), 2.68 (1H, m), 1.31 (9H, s), 1.24 (2H, m), 1.08 (2H, m). | (4-tert-Butyl-2-chloro-phenyl)-[4-(5-cyclopropyl-4-piperazin-1-yl-pyrido[3,4-d]pyrimidin-2-yl)-pyridin-2-yl]-amine |
| 530 | 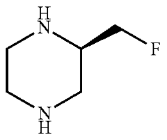 | 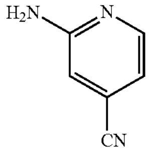 | method 5: RT: 2.13 min, MI: 482 [M + H] | 1H NMR (DMSO, 500 MHz) 10.00 (1H, s), 9.06 (1H, s), 8.61 (1H, s), 8.48 (2H, m), 8.31 (1H, s), 7.93 (1H, d), 7.26 (1H, d), 4.44 (2H, m), 4.06 (2H, m), 3.77 (1H, m), 3.35 (4H, m), 2.68 (1H, m), 1.28-1.25 (2H, m), 1.02-0.99 (2H, m) | 2-[4-[5-Cyclopropyl-4-((R)-3-fluoro methyl-piperazin-1-yl)-pyrido[3,4-d] pyrimidin-2-yl]-pyridin-2-ylamino}-isonicotinonitrile |

-continued

| | | | Analysis | | |
|---|---|---|---|---|---|
| Ex | Amine 1 | Amine 2 | LCMS | NMR | Name |
| 531 | 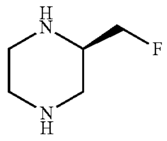 | 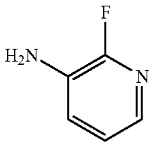 | method 5: RT: 2.54 min, MI: 475 [M + H] | 1H NMR (DMSO, 500 MHz) 9.22 (1H, s), 8.98 (1H, s), 8.86 (1H, m), 8.33 (1H, d), 8.15 (1H, s), 8.13 (1H, s), 8.11 (1H, s), 7.79 (1H, d), 7.74 (1H, d), 7.30 (1H, m), 4.50 (1H, d), 4.40 (1H, d), 4.17 (1H, m), 3.34 (2H, m), 3.21 (2H, m), 2.99 (2H, m), 2.53 (1H, m), 1.26-1.24 (2H, m), 1.05-1.03 (2H, m). | {4-[5-Cyclopropyl-4-((R)-3-fluorometh-yl-piperazin-1-yl)-pyrido[3,4-d]pyri-midin-2-yl]-pyridin-2-yl}-(2-fluoro-pyridin-3-yl)-amine |
| 532 | 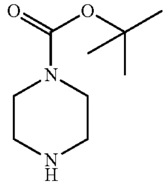 | 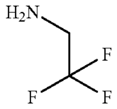 | method 5: RT: 2.75 min, MI: 430.26 [M + H] | 1H NMR (DMSO, 500 MHz) 8.94 (1H, s), 8.16 (1H, d), 8.07 (1H, s), 7.8 (1H, s), 7.54 (1H, dd), 7.40 (1H, t), 4.24-4.20 (2H, m), 3.86-3.51 (4H, m, br), 2.84 (4H, m, br), 2.63-2.57 (1H, m), 1.25-1.23 (2H, m), 1.02-1.01 (2H, m). | [4-(5-Cyclopropyl-4-piperazin-1-yl-pyrido[3,4-d]pyrimidin-2-yl)-pyridin-2-yl]-(2,2,2-trifluoro-ethyl)-amine |
| 533 | 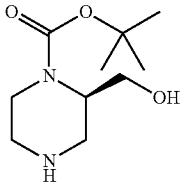 | 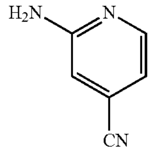 | method 5: RT: 2.99 min, MI: 506 [M + H] | 1H NMR (DMSO, 500 MHz) 10.00 (1H, s), 9.06 (1H, s), 8.61 (1H, s), 8.48 (2H, m), 8.31 (1H, s), 7.93 (1H, d), 7.26 (1H, d), 4.44 (2H, m), 4.06 (2H, m), 3.77 (1H, m), 3.35 (4H, m), 2.68 (1H, m), 1.28-1.25 (2H, m), 1.02-0.99 (2H, m) | 2-{4-[5-Cyclopropyl-4-(3-oxo-tetrahydro-oxazolo[3,4-a]pyrazin-7-yl)-py-rido[3,4-d]pyrimidin-2-yl]-pyridin-2-ylamino}-isonicotinonitrile |
| 534 | 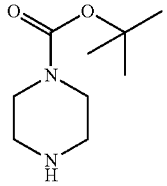 | 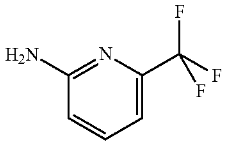 | method 5: RT: 3.4 min, MI: 493 [M + H] | | [4-(5-cyclopropyl-4-piperazin-1-yl-pyrido[3,4-d]pyrimidin-2-yl)-pyridin-2-yl]-(6-trifluoromethyl-pyridin-2-yl)-amine |
| 535 | 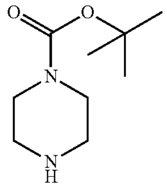 | 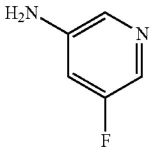 | method 5: RT: 3.81 min, MI: 443 [M + H] | 1H NMR (DMSO, 500 MHz, 1IGO528) 9.90 (1H, s), 8.98 (1H, s), 8.59 (1H, t), 8.48-8.44 (1H, td), 8.42 (1H, d), 8.20 (1H, s), 8.07 (1H, d), 7.98 (1H, s), 7.82 (1H, dd), 2.89 (4H, s), 2.63 (1H, m), 1.27 (2H, m), 1.40 (2H, m). | [4-(5-Cyclopropyl-4-piperazin-1-yl-pyrido[3,4-d]pyrimidin-2-yl)-pyridin-2-yl]-(5-fluoro-pyridin-3-yl)-amine |
| 536 | 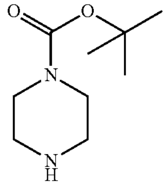 | 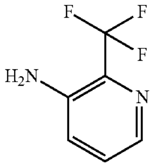 [SMILES: Nc1cccnc1C(F)(F)F] | method 5: RT: 3.31 min, MI: 493 [M + H] | 1H NMR (DMSO, 500 MHz, 1IGO529) 8.98 (1H, s), 8.83 (1H, s), 8.44 (1H, d), 8.28 (1H, d), 8.20 (1H, d), 8.10 (1H, s), 8.04 (1H, s), 7.75 (1H, d), 7.69-7.66 (1H, q), 3.42 (4H, broad s), 2.87 (1H, s), 2.62 (1H, m), 1.27 (2H, m), 1.04 (2H, m). | [4-(5-Cyclopropyl-4-piperazin-1-yl-pyrido[3,4-d]pyrimidin-2-yl)-pyridin-2-yl]-(2-trifluoromethyl-pyridin-3-yl)-amine |
| 537 | 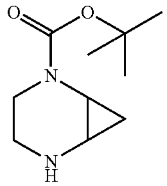 | 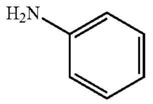 | 436.1 | | {4-[5-Cyclopropyl-4-(2,5-diaza-bicy-clo[4.1.0]hept-2-yl)-pyrido[3,4-d]py-rimidin-2-yl]-pyridin-2-yl}-phenyl-amine |

-continued

| | | | Analysis | | |
|---|---|---|---|---|---|
| Ex | Amine 1 | Amine 2 | LCMS | NMR | Name |
| 538 | 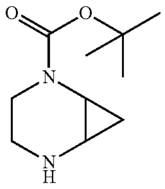 | 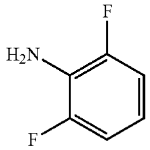 | 472.1 | | {4-[5-Cyclopropyl-4-(2,5-diaza-bicyclo[4.1.0]hept-2-yl)-pyrido[3,4-d]pyrimidin-2-yl]-pyridin-2-yl}-(2,6-difluoro-phenyl)-amine |
| 539 | 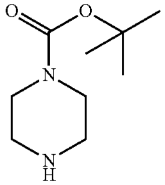 | 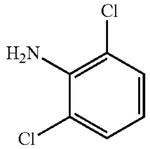 | 492.1 (MH)+ | | [4-(5-Cyclopropyl-4-piperazin-1-yl-pyrido[3,4-d]pyrimidin-2-yl)-pyridin-2-yl]-(2,6-dichloro-phenyl)-amine |
| 540 | 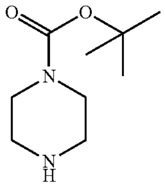 | 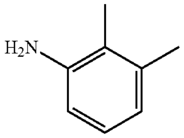 | 452.2 (MH)+ | | [4-(5-Cyclopropyl-4-piperazin-1-yl-pyrido[3,4-d]pyrimidin-2-yl)-pyridin-2-yl]-(2,3-dimethyl-phenyl)-amine |
| 541 | 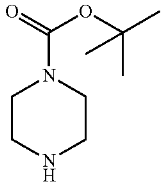 | 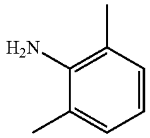 | 452.2 (MH)+ | | [4-(5-Cyclopropyl-4-piperazin-1-yl-pyrido[3,4-d]pyrimidin-2-yl)-pyridin-2-yl]-(2,6-dimethyl-phenyl)-amine |
| 542 | 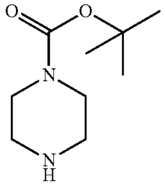 | 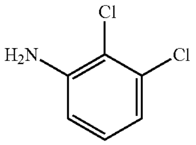 | 492.1 (MH)+ | | [4-(5-Cyclopropyl-4-piperazin-1-yl-pyrido[3,4-d]pyrimidin-2-yl)-pyridin-2-yl]-(2,3-dichloro-phenyl)-amine |
| 543 | 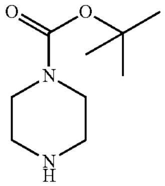 | 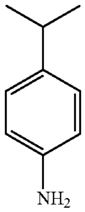 | 466.30 (M + H) | | [4-(5-Cyclopropyl-4-piperazin-1-yl-pyrido[3,4-d]pyrimidin-2-yl)-pyridin-2-yl]-(2,3-dichloro-phenyl)-amine |
| 544 | 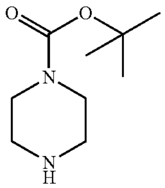 | 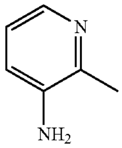 | 439.20 (M + H) | | [4-(5-Cyclopropyl-4-piperazin-1-yl-pyrido[3,4-d]pyrimidin-2-yl)-pyridin-2-yl]-(2-methyl-pyridin-3-yl)-amine |

-continued

| | | | Analysis | | |
|---|---|---|---|---|---|
| Ex | Amine 1 | Amine 2 | LCMS | NMR | Name |
| 545 | 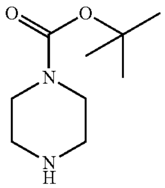 | 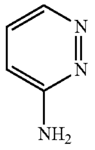 | 426.15 (M + H) | | [4-(5-Cyclopropyl-4-piperazin-1-yl-pyrido[3,4-d]pyrimidin-2-yl)-pyridin-2-yl]-pyridazin-3-yl-amine |
| 546 | 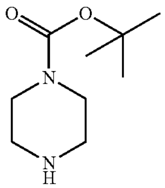 | 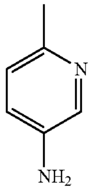 | 439.20 (M + H) | | [4-(5-Cyclopropyl-4-piperazin-1-yl-pyrido[3,4-d]pyrimidin-2-yl)-pyridin-2-yl]-(6-methyl-pyridin-3-yl)-amine |
| 547 | 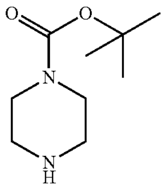 | 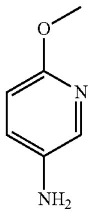 | 455.20 (M + H) | | [4-(5-Cyclopropyl-4-piperazin-1-yl-pyrido[3,4-d]pyrimidin-2-yl)-pyridin-2-yl]-(6-methoxy-pyridin-3-yl)-amine |
| 548 | 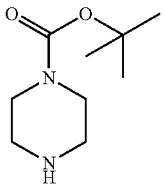 | 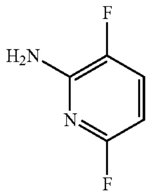 | 461.20 (M + H) | | [4-(5-Cyclopropyl-4-piperazin-1-yl-pyrido[3,4-d]pyrimidin-2-yl)-pyridin-2-yl]-(3,6-difluoro-pyridin-2-yl)-amine |
| 549 | 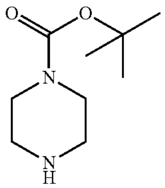 | 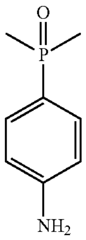 | 500.20 (M + H) | | [4-(5-Cyclopropyl-4-piperazin-1-yl-pyrido[3,4-d]pyrimidin-2-yl)-pyridin-2-yl]-[4-(dimethyl-phosphinoyl)-phenyl]-amine |
| 550 | 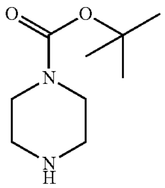 | 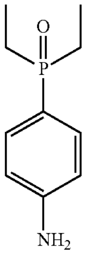 | 528.20 (M + H) | | [4-(5-Cyclopropyl-4-piperazin-1-yl-pyrido[3,4-d]pyrimidin-2-yl)-pyridin-2-yl]-[4-(diethyl-phosphinoyl)-phenyl]-amine |

-continued

| Ex | Amine 1 | Amine 2 | Analysis LCMS | NMR | Name |
|---|---|---|---|---|---|
| 551 | 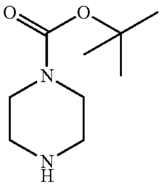 | 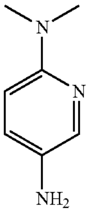 | 468.25 (M + H) | | $N^5$-[4-(5-Cyclopropyl-4-piperazin-1-yl-pyrido[3,4-d]pyrimidin-2-yl)-pyridin-2-yl]-$N^2$,$N^2$-dimethyl-pyridine-2,5-diamine |
| 552 | 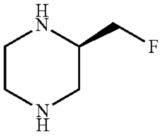 | 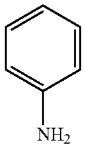 | method 5: RT: 2.16 min, MI: 456 [M + H] | 1H NMR (DMSO, 500 MHz) 9.30 (1H, s), 8.98 (1H, s), 8.31 (1H, d), 8.11 (1H, s), 7.90 (1H, s), 7.75 (1H, d), 7.66 (1H, d), 7.27 (2H, m), 6.89 (1H, m), 4.46 (1H, d), 4.38 (1H, d), 4.13 (2H, m), 3.34 (2H, m), 3.00 (3H, m), 2.68 (1H, m), 1.28-1.25 (2H, m), 1.08-1.05 (2H, m) | {4-[5-Cyclopropyl-4-((R)-3-fluoro-methyl-piperazin-1-yl)-pyrido[3,4-d]pyrimidin-2-yl]-pyridin-2-yl}-phenyl-amine |
| 553 | 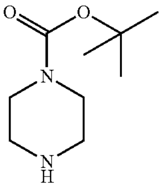 | 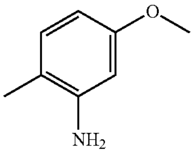 | method 5: RT: 3.74 min, MI: 468 [M + H] | 1H NMR (DMSO, 500 MHz) 9.05 (1H, s), 8.91 (1H, s, br), 8.19 (2H, dd), 7.97 (1H, s), 7.72 (1H, d), 7.26 (1H, s), 7.21 (1H, dd), 6.73 (1H, d), 3.99-3.88 (4H, s, br), 3.73 (3H, s), 3.30 (4H, s, br), 2.62 (1H, m, br), 2.19 (3H, s), 2.20 (3H, s), 1.25-1.23 (2H, m), 1.08-1.05 (2H, m). | [4-(5-Cyclopropyl-4-piperazin-1-yl-pyrido[3,4-d]pyrimidin-2-yl)-pyridin-2-yl]-(5-methoxy-2-methyl-phenyl)-amine |
| 554 | 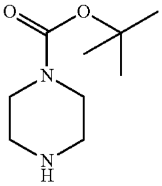 | 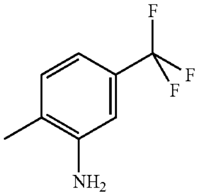 | method 5: RT: 2.92 min, MI: 405 [M + H] | 1H NMR (DMSO, 500 MHz) 9.05 (1H, s), 8.98 (1H, s, br), 8.28 (1H, dd), 8.22 (1H, s), 8.18 (1H, s), 8.06 (1H, s), 7.78 (1H, d), 7.49 (1H, d), 7.36 (1H, d), 3.96-3.88 (4H, s, br), 3.30 (4H, s, br), 2.68 (1H, m), 2.37 (3H, s), 1.26-1.23 (2H, m), 1.08-1.05 (2H, m) | [4-(5-Cyclopropyl-4-piperazin-1-yl-pyrido[3,4-d]pyrimidin-2-yl)-pyridin-2-yl]-(2-methyl-5-trifluoromethyl-phenyl)-amine |
| 555 | 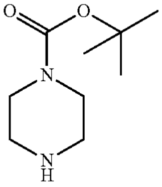 | 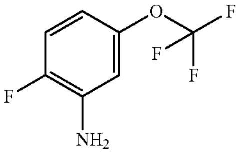 | method 5: RT: 3.30 min, MI: 526 [M + H] | 1H NMR (DMSO, 500 MHz) 9.32 (1H, s), 9.05 (1H, s), 8.92 (1H, s, br), 8.62 (1H, m), 8.40 (1H, d), 8.23 (1H, s), 8.18 (1H, s), 8.06 (1H, s), 7.83 (1H, d), 7.49 (1H, d), 7.36 (1H, m), 3.96-3.88 (4H, s, br), 3.33 (4H, s, br), 2.68 (1H, m), 1.26-1.23 (2H, m), 1.08-1.05 (2H, m). | [4-(5-Cyclopropyl-4-piperazin-1-yl-pyrido[3,4-d]pyrimidin-2-yl)-pyridin-2-yl]-(2-fluoro-5-trifluoromethoxy-phenyl)-amine |
| 556 | 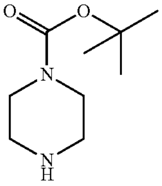 | 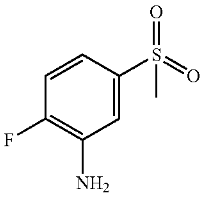 | method 5: RT: 2.35 min, MI: 520 [M + H] | 1H NMR (DMSO, 500 MHz) 9.44 (1H, s), 9.08 (1H, s), 9.04 (1H, s), 8.97 (1H, s, br), 8.43 (1H, dd), 8.24 (1H, s), 8.20 (1H, s), 7.87 (1H, d), 7.56 (1H, d), 3.96-3.88 (4H, s, br), 3.35 (4H, s, br), 3.24 (3H, s), 2.69 (1H, m), 1.28-1.25 (2H, m), 1.08-1.05 (2H, m). | [4-(5-Cyclopropyl-4-piperazin-1-yl-pyrido[3,4-d]pyrimidin-2-yl)-pyridin-2-yl]-(2-fluoro-5-methanesulfonyl-phenyl)-amine |
| 557 | 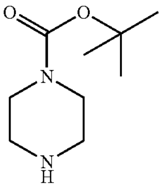 | 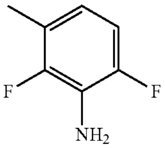 | method 5: RT: 2.37 min, MI: 474 [M + H] | H NMR (DMSO, 500 MHz) 9.05 (1H, s), 8.93 (1H, s, br), 8.83 (1H, s), 8.18 (1H, s), 7.82 (1H, s), 7.15 (1H, m), 7.06 (1H, m), 3.87 (4H, s, br), 3.31 (4H, s, br), 2.69 (1H, m), 2.24 (3H, s), 1.26-1.24 (2H, m), 1.07-1.05 (2H, m). | [4-(5-Cyclopropyl-4-piperazin-1-yl-pyrido[3,4-d]pyrimidin-2-yl)-pyridin-2-yl]-(2,6-difluoro-3-methyl-phenyl)-amine |

-continued

| Ex | Amine 1 | Amine 2 | Analysis LCMS | Analysis NMR | Analysis Name |
|---|---|---|---|---|---|
| 558 | 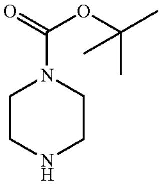 | 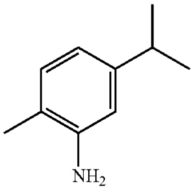 | method 5: RT: 4.08 min, MI: 480 [M + H] | 1H NMR (DMSO, 500 MHz) 9.02 (1H, s), 8.93 (1H, s, br), 8.17 (2H, dd), 7.90 (1H, s), 7.71 (1H, s), 7.38 (1H, s), 7.23 (1H, dd), 7.02 (1H, m), 4.02-3.88 (4H, s, br), 3.30 (4H, s, br), 2.87 (1H, m, br), 2.63-2.57 (1H, m), 2.20 (3H, s), 1.25-1.23 (2H, m), 1.20 (6H, m), 1.06-1.02 (2H, m) | [4-(5-Cyclopropyl-4-piperazin-1-yl-pyrido[3,4-d]pyrimidin-2-yl)-pyridin-2-yl]-(5-isopropyl-2-methyl-phenyl)-amine |
| 559 | 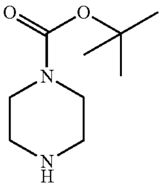 | 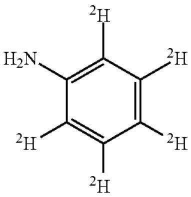 | method 5: RT: 2.01 min, MI: 429 [M + H] | 1H NMR (DMSO, 500 MHz) 9.45 (1H, s, br), 9.05 (1H, s), 8.90 (1H, s, br), 8.32 (1H, d), 8.18 (1H, s), 7.82 (1H, s), 7.15 (1H, m), 7.06 (1H, m), 3.87 (4H, s, br), 3.31 (4H, s, br), 2.69 (1H, m), 2.24 (3H, s), 1.26-1.24 (2H, m), 1.07-1.05 (2H, m). | [4-(5-Cyclopropyl-4-piperazin-1-yl-pyrido[3,4-d]pyrimidin-2-yl)-pyridin-2-yl]-pent-deuterio-phenyl-amine |
| 560 | 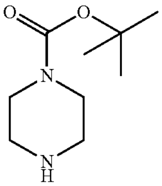 | 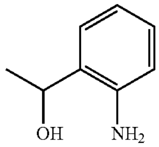 | 450.2 (M − OH)+ | ($CDCl_3$) 9.07 (s, 1H), 8.30 (d, J = 5.3 Hz, 1H), 8.00 (br s, 2H), 7.91 (s, 1H), 7.80 (d, J = 7.5 Hz, 1H), 7.75 (dd, J = 5.3; 1.2 Hz, 1H), 7.30 (m, 2H), 7.05 (m, 1H), 5.09 (q, J = 6.6 Hz, 1H), 3.73 (br s, 4H), 2.97 (m, 4H), 2.66 (m, 1H), 2.17 (br s, OH, exch. NH), 1.61 (d, J = 6.6 Hz, 3H), 1.24 (m, 2H), 0.98 (m, 2H) | 1-{2-[4-(5-Cyclopropyl-4-piperazin-1-yl-pyrido[3,4-d]pyimidin-2-yl)-pyridin-2-ylamino]-phenyl}-ethanol |
| 561 | 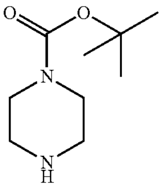 | 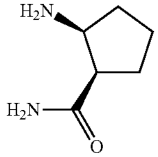 | 459.25 (M + H)+ | (dmso-d6; note: a minor rotamer also observed) 10.85 (s, 1H), 9.17 (br s, exch. 3H), 9.08 (s, 1H), 8.53 (d, J = 5.2 Hz, 1H), 8.19 (s, 1H), 8.10 (dd, J = 5.2; 1.4 Hz, 1H), 8.04 (br s, 3H), 4.19 (br s, large exch. H's signal), 3.91 (m, 4H), 3.35 (br s, 4H), 3.08 (m, 1H), 2.70 (m, 1H), 2.24 (m, 1H), 2.08 (m, 2H), 1.73 (m, 4H), 1.26 (m, 2H), 1.08 (m, 2H) | (1R, 2S)-2-Amino-cyclopentane-carboxylic acid [4-(5-cyclopropyl-4-piperazin-1-yl-pyrido[3,4-d]pyrimidin-2-yl)-pyridin-2-yl]-amide |
| 562 | 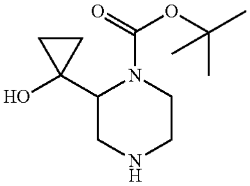 | — | 423.00 (M + H) | | 1-{4-[2-(2-Chloro-pyridin-4-yl)-5-cyclopropyl-pyrido[3,4-d]pyrimidin-4-yl]-piperazin-2-yl}-cyclopropanol |
| 563 | 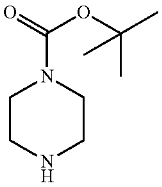 | 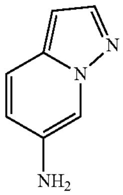 | 464.20 (M + H) | | [4-(5-Cyclopropyl-4-piperazin-1-yl-pyrido[3,4-d]pyrimidin-2-yl)-pyridin-2-yl]-pyrazolo[1,5-a]pyridin-6-yl-amine |
| 564 | 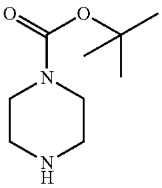 | 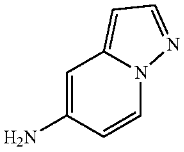 | 464.15 (M + H) | | [4-(5-Cyclopropyl-4-piperazin-1-yl-pyrido[3,4-d]pyrimidin-2-yl)-pyridin-2-yl]-pyrazolo[1,5-a]pyridin-5-yl-amine |

-continued

| | | | Analysis | | |
|---|---|---|---|---|---|
| Ex | Amine 1 | Amine 2 | LCMS | NMR | Name |
| 565 | 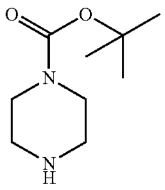 | 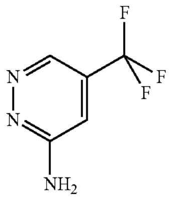 [SMILES: Nc1cc(C(F)(F)F)cnn1] | 494.10 (M + H) | | [4-(5-Cyclopropyl-4-piperazin-1-yl-pyrido[3,4-d]pyrimidin-2-yl)-pyridin-2-yl]-(5-trifluoromethyl-pyridazin-3-yl)-amine |
| 566 | 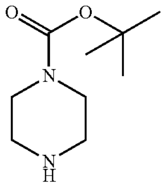 | 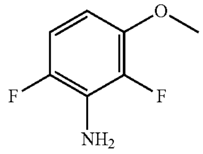 | 490 | (dmso-d6) 9.11 (br s, 3H, exch. H's), 9.07 (s, 1H), 8.20 (m, 2H), 7.88 (s, 1H), 7.73 (dd, J = 5.3; 1.4 Hz, 1H), 7.09 (m, 2H), 3.92 (br s, 4H), 3.87 (s, 3H), 3.33 (br s, 4H), 2.69 (m, 1H), 1.26 (m, 2H), 1.09 (m, 2H) | [4-(5-Cyclopropyl-4-piperazin-1-yl-pyrido[3,4-d]pyrimidin-2-yl)-pyridin-2-yl]-(2,6-difluoro-3-methoxy-phenyl)-amine |
| 567 | 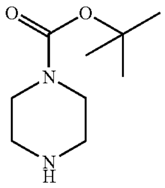 | 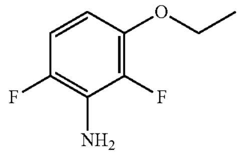 | 503.9 | (dmso-d6) 9.06 (s, 1H), 9.05 (br s, 3H, exch. H's), 8.20 (m, 2H), 7.87 (s, 1H), 7.72 (dd, J = 5.4; 1.3 Hz, 1H), 7.07 (m, 2H), 5.40 (br s, exch. H's), 4.12 (q, J = 7.0 Hz, 2H), 3.93 (br s, 4H), 3.33 (br s, 4H), 2.68 (m, 1H), 1.36 (t, J = 7.0 Hz, 3H), 1.26 (m, 2H), 1.09 (m, 2H) | [4-(5-Cyclopropyl-4-piperazin--1yl-pyrido[3,4-d]pyrimidin-2-yl)-pyridin-2-yl]-(3-ethoxy-2,6-difluoro-phenyl)-amine |
| 568 | 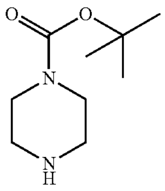 | 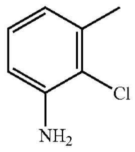 | method 5: RT: 3.46 min, MI: 472 [M + H] | 1H NMR (DMSO, 500 MHz), 9.06 (1H, s), 8.26 (1H, d), 8.18 (1H, s), 8.05 (1H, s), 7.84 (1H, d), 7.75 (1H, dd), 7.24 (1H, t), 7.11 (1H, s), 3.91 (4H, s), 3.32 (4H, s), 2.68 (1H, m), 2.39 (3H, s), 1.25 (2H, m), 1.08 (2H, m). | (2-Chloro-3-methyl-phenyl)-[4-(5-cylcopropyl-4-piperazin-1-yl-pyrido[3,4-d]pyrimidin-2-yl)-pyridin-2-yl]-amine |
| 569 | 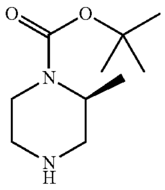 | 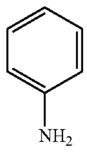 | method 5: RT: 4.22 min, MI: 438.28 [M + H] | 1H NMR (DMSO, 500 MHz) 9.59 (1H, br s), 9.05 (1H, s), 8.99 (1H, br s), 8.31 (1H, d), 8.18 (1H, s), 7.97 (1H, s), 7.73-7.69 (2H, m), 7.32 (2H, t), 6.77 (1H, t), 4.96 (4H, br s), 4.32 (1H, br s), 3.37 (2H, br s), 1.34-1.23 (5H, m), 1.07 (2H, br s). | {4-[5-Cycopropyl-4-((S)-3-methyl-piperazin-1-yl)-pyrido[3,4-d]pyrimidin-2-yl]-pyridin-2-yl}-phenyl-amine |
| 570 | 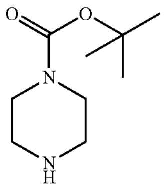 | 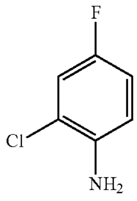 | method 5: RT: 5.57 min, MI: 476 [M + H] | 1H NMR (DMSO, 500 MHz),) 9.07 (1H, s), 8.25 (1H, d), 8.19 (1H, s), 8.01 (1H, s), 7.93 (1H, m), 7.76 (1H, d), 7.54 (1H, dd), 7.26 (1H, m), 3.92 (4H, s), 3.32 (4H, s), 2.68 (1H, m), 1.24 (2H, m), 1.09 (2H, m). | (2-Chloro-4-fluoro-phenyl)-[4-(5-cyclopropyl-4-piperazin-1-yl-pyrido[3,4-d]pyrimidin-2-yl)-pyridin-2-yl]-amine |
| 571 | 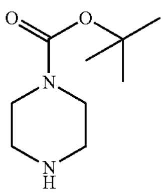 | 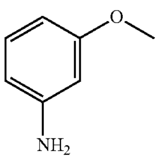 | method 5: RT: 5.27 min, MI: 454 [M + H] | 1H NMR (DMSO, 500 MHz,) 9.53 (1H, s), 9.06 (1H, s), 8.33 (1H, d), 8.19 (1H, s), 7.98 (1H, s), 7.74 (1H, dd), 7.46 (1H, s), 7.24 (2H, m), 6.56 (1H, d), 3.91 (4H, s), 3.76 (3H, s), 3.33 (4H, s), 2.69 (1H, m), 1.25 (2H, m), 1.08 (2H, m). | [4-(5-Cyclopropyl-4-piperazin-1-yl-pyrido[3,4-d]pyrimidin-2-yl)-pyridin-2-yl]-(3-methoxy-phenyl)-amine |

-continued

| | | | Analysis | | |
|---|---|---|---|---|---|
| Ex | Amine 1 | Amine 2 | LCMS | NMR | Name |
| 572 | 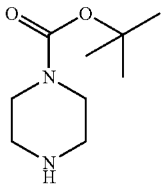 | 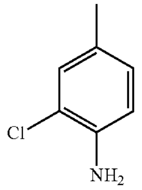 | method 5: RT: 5.77 min, MI: 472 [M + H] | 1H NMR (DMSO, 500 MHz,) 9.07 (1H, s), 8.22 (1H, d), 8.19 (1H, s), 8.03 (1H, s), 7.76 (1H, dd), 7.46 (1H, s), 7.74 (1H, d), 7.40 (1H, s), 7.20 (1H, d), 3.93 (4H, s), 3.32 (4H, s), 2.66 (1H, m), 2.33 (3H, s), 1.25 (2H, m), 1.08 (2H, m). | (2-Chloro-4-methyl-phenyl)-[4-(5-cyclopropyl-4-piperazin-1-yl-pyrido[3,4-d]pyrimidin-2-yl)-pyridin-2-yl]-amine |
| 573 | 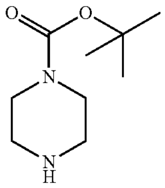 | 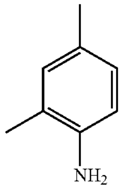 | 452.0 (MH)+ | | [4-(5-Cyclopropyl-4-piperazin-1-yl-pyrido[3,4-d]pyrimidin-2-yl)-pyridin-2-yl]-(2,4-dimethyl-phenyl)-amine |
| 574 | 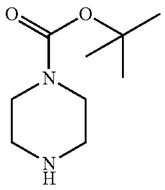 | 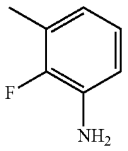 | 455.9 (MH)+ | | [4-(5-Cyclopropyl-4-piperazin-1-yl-pyrido[3,4-d]pyrimidin-2-yl)-pyridin-2-yl]-(2-fluoro-3-methyl-phenyl)-amine |
| 575 | 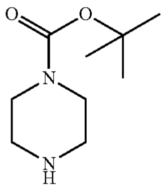 | 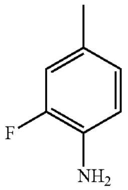 | 455.9 (MH)+ | | [4-(5-Cylcopropyl-4-piperazin-1-yl-pyrido[3,4-d]pyrimidin-2-yl)-pyridin-2-yl]-(2-fluoro-4-methyl-phenyl)-amine |
| 576 | 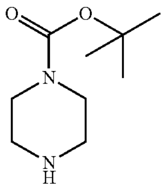 | 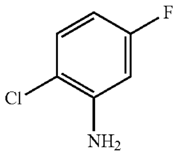 | method 5: RT: 4.02 min, MI: 476 [M + H] | 1H NMR (DMSO, 500 MHz,) 9.07 (1H, s), 8.87 (1H, s), 8.39 (1H, d), 8.23 (2H, m), 8.19 (1H, s), 7.85 (1H, dd), 7.51 (1H, m), 6.88 (1H, m), 3.93 (4H, s), 3.33 (4H, s), 2.69 (1H, m), 1.26 (2H, m), 1.08 (2H, m). | (2-Chloro-5-fluoro-phenyl)-[4-(5-cyclopropyl-4-piperazin-1-yl-pyrido[3,4-d]pyrimidin-2-yl)-pyridin-2-yl]-Amine |
| 577 | 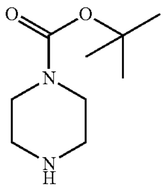 | 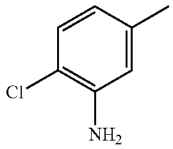 | method 5: RT: 3.48 min, MI: 472 [M + H] | 1H NMR (DMSO, 500 MHz,) 9.07 (1H, s), 8.28 (1H, d), 8.17 (1H, s), 8.05 (1H, s), 7.78 (2H, s), 7.41 (1H, dd), 6.98 (1H, d), 3.92 (4H, s), 3.32 (4H, s), 2.68 (1H, m), 2.32 (3H, s), 1.25 (2H, m), 1.08 (2H, m). | (2-Chloro-5-methyl-phenyl)-[4-(5-cyclopropyl-4-piperazin-1-yl-pyrido[3,4-d]pyrimidin-2-yl)-pyridin-2-yl]-Amine |
| 578 | 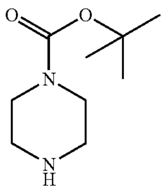 | 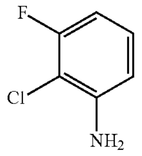 | method 5: RT: 5.25 min, MI: 476 [M + H] | 1H NMR (DMSO, 500 MHz,) 9.07 (1H, s), 8.33 (1H, d), 8.19 (1H, s), 8.14 (1H, s), 7.97 (1H, d), 7.82 (1H, dd), 7.37-7.32 (1H, m), 7.10-7.06 (1H, m), 3.93 (4H, s), 3.33 (4H, s). 2.69 (1H, m), 1.26 (2H, m), 1.09 (2H, m). | (2-Chloro-3-fluoro-phenyl)-[4-(5-cyclopropyl-4-piperazin-1-yl-pyrido[3,4-d]pyrimidin-2-yl)-pyridin-2-yl]-Amine |

-continued

| Ex | Amine 1 | Amine 2 | Analysis: LCMS | Analysis: NMR | Name |
|---|---|---|---|---|---|
| 579 | 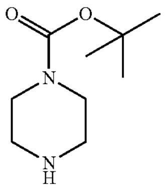 | 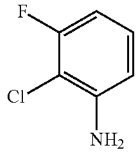 | 44 | | 5-Cyclopropyl-2-(6,7-dimethoxy-quinolin-4-yl)-4-piperazin-1-yl-pyrido[3,4-d]pyrimidine |
| 580 | 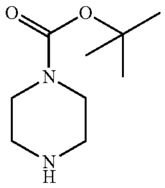 | 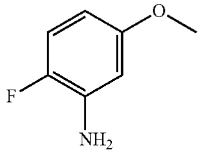 | 471.9 | ($CDCl_3$) 9.12 (s, 1H), 8.41 (dd, J = 5.3; 0.4 Hz, 1H), 8.05 (s, 1H), 7.98 (dd, J = 7.0; 3.1 Hz, 1H), 7.95 (s, 1H), 7.85 (dd, J = 5.3; 1.3 Hz, 1H), 7.02 (dd, J = 10.8; 8.9 Hz, 1H), 6.89 (m, 1H), 6.45 (m, 1H), 3.82 (s, 3H), 3.78 (br s, 4H), 3.03 (m ,4H), 2.70 (m, 1H), 1.87 (br s, exch. H's), 1.27 (m, 2H), 1.01 (m, 2H) | [4-(5-Cyclopropyl-4-piperazin-1-yl-pyrido[3,4-d]pyrimidin-2-yl)-pyridin-2-yl]-(2-fluoro-5-methoxy-phenyl)-amine |
| 581 | 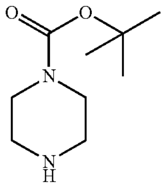 | 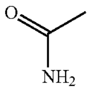 | 390.10 (M + H) | | N-[4-(5-Cycopropyl-4-piperazin-1-yl-pyrido[3,4-d]pyrimidin-2-yl)-pyridin-2-yl]-acetamide |
| 582 | 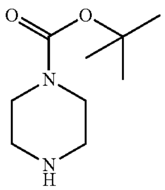 | 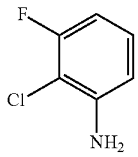 | 348.05 (M + H) | | 4-(5-Cyclopropyl-4-piperazin-1-yl-pyrido[3,4-d]pyrimidin-2-yl)-pyridin-2-ylamine |
| 583 | 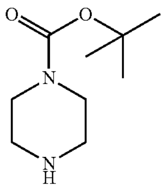 | 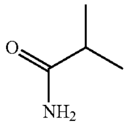 | 418.15 (M + H) | | N-[4-(5-Cyclopropyl-4-piperazin-1-yl-pyrido[3,4-d]pyrimidin-2-yl)-pyridin-2-yl]-isobutyramide |
| 584 | 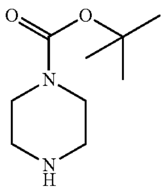 | 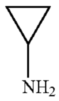 | 416.10 (M + H) | | Cyclopropane-carboxylic acid [4-(5-cyclopropyl-4-piperazin-1-yl-pyrido[3,4-d]pyrimidin-2-yl)-pyridin-2-yl]-amide |
| 585 | 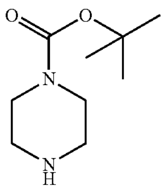 | 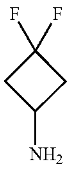 | 438 | | [4-(5-Cyclopropyl-4-piperazin-1-yl-pyrido[3,4-d]pyrimidin-2-yl)-pyridin-2-yl]-(3,3-difluorocyclo-butyl)-amine |

-continued

| Ex | Amine 1 | Amine 2 | Analysis LCMS | NMR | Name |
|---|---|---|---|---|---|
| 586 | 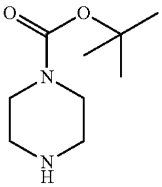 | 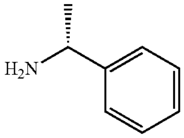 | 452.0 (M + H) | (dmso-d6) 9.14 (br s, exch. H's), 9.07 (s, 1H), 8.22 (s, 1H), 8.09 (d, J = 6.4 Hz, 1H), 8.02 (br s, 1H), 7.70 (d, J = 6.3 Hz, 1H), 7.47 (m, 2H), 7.40 (m, 2H), 7.30 (m, 1H), 5.10 (m, 1H), 3.90 (br s, 4H), 3.33 (br s, 4H), 2.66 (m, 1H), 1.58 (d, J = 6.7 Hz, 3H), 1.26 (m, 2H), 1.08 (m, 2H) | [4-(5-Cyclopropyl-4-piperazin-1-yl-pyrido[3,4-d]pyrimidin-2-yl)-pyridin-2-yl]-((R)-1-phenyl-ethyl)-amine |
| 587 | 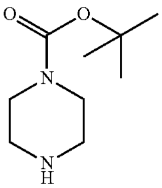 | 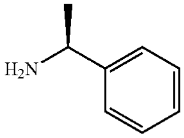 | 452.0 (M + H) | (dmso-d6) 9.12 (br s, exch. H's), 9.06 (s, 1H), 8.21 (s, 1H), 8.09 (d, J = 6.4 Hz, 1H), 7.98 (br s, 1H), 7.680 (d, J = 6.3 Hz, 1H), 7.47 (m, 2H), 7.39 (m, 2H), 7.29 (m, 1H), 5.10 (m, 1H), 3.89 (br s, 4H), 3.33 (br s, 4H), 2.65 (m, 1H), 1.57 (d, J = 6.7 Hz, 3H), 1.26 (m, 2H), 1.08 (m, 2H) | [4-(5-Cyclopropyl-4-piperazin-1-yl-pyrido[3,4-d]pyrimidin-2-yl)-pyridin-2-yl]-((S)-1-phenyl-ethyl)-amine |
| 588 | 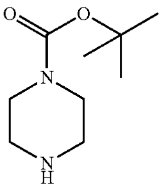 | 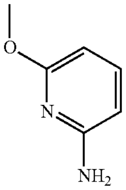 | 455.0 (M + H) | (CDCl3) 9.05 (s, 1H), 8.95 (s, 1H), 8.40 (dd, J = 5.2; 0.3 Hz, 1H), 8.05 (s, 1H), 7.89 (dd, J = 5.2; 1.4 Hz, 1H), 7.76 (s, 1H), 7.51 (m, 1H), 6.95 (d, J = 7.8 Hz, 1H), 6.33 (d, J = 7.8 Hz, 1H), 4.10 (s, 3H), 375 (br s, 4H), 3.03 (m, 4H), 2.71 (m, 1H), 1.96 (br s, exch. H's), 1.27 (m, 2H), 1.01 (m, 2H) | [4-(5-Cyclopropyl-4-piperazin-1-yl-pyrido[3,4-d]pyrimidin-2-yl)-pyridin-2-yl]-(6-methoxy-pyridin-2-yl)-amine |
| 589 | 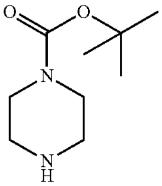 | 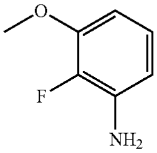 | 472.0 (MH)+ | | [4-(5-Cyclopropyl-4-piperazin-1-yl-pyrido[3,4-d]pyrimidin-2-yl)-pyridin-2-yl]-(2-fluoro-3-methoxy-phenyl)-amine |
| 590 | 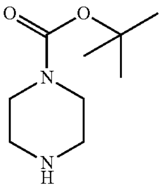 | 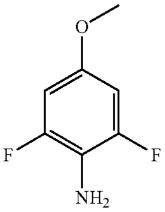 | 489.9 (MH)+ | | [4-(5-Cyclopropyl-4-piperazin-1-yl-pyrido[3,4-d]pyrimidin-2-yl)-pyridin-2-yl]-(2,6-difluoro-4-methoxy-phenyl)-amine |
| 591 | 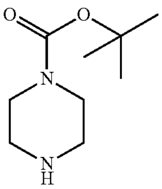 | 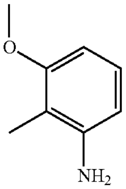 | 468.0 (MH)+ | | [4-(5-Cyclopropyl-4-piperazin-1-yl-pyrido[3,4-d]pyrimidin-2-yl)-pyridin-2-yl]-(3-methoxy-2-methyl-phenyl)-amine |
| 592 | 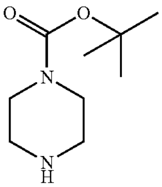 | 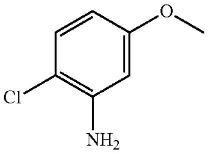 | method 5: RT: 2.59 min, MI: 488 [M + H] | 1H NMR (DMSO, 500 MHz,) 9.06 (1H, s), 8.32 (1H, d), 8.19 (1H, s), 8.12 (1H, s), 7.80 (1H, dd), 7.76 (1H, d), 7.41 (1H, d), 6.72 (1H, dd), 3.92 (4H, s), 3.77 (3H, s), 3.33 (4H, s), 2.68 (1H, m), 1.26 (2H, m), 1.08 (2H, m). | (2-Chloro-5-methoxy-phenyl)-[4-(5-cyclopropyl-4-piperazin-1-yl-pyrido[3,4-d]pyrimidin-2-yl)-pyridin-2-yl]-amine |

-continued

| | | | Analysis | | |
|---|---|---|---|---|---|
| Ex | Amine 1 | Amine 2 | LCMS | NMR | Name |
| 594 | 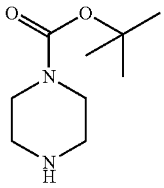 | 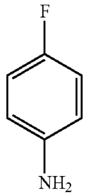 | method 5: RT: 2.19 min, MI: 442 [M + H] | 1H NMR (DMSO, 500 MHz), 9.55 (1H, s), 9.06 (1H, s), 8.31 (1H, d), 8.19 (1H, s), 7.93 (1H, s), 7.76-7.72 (3H, m), 7.16 (2H, t), 3.92 (4H, s), 3.33 (4H, s), 2.69 (1H, m), 1.25 (2H, m), 1.09 (2H, m). | [4-(5-Cyclopropyl-4-piperazin-1-yl-pyrido[3,4-d]pyrimidin-2-yl)-pyridin-2-yl]-(4-fluoro-phenyl)-amine |
| 595 | 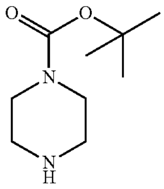 | 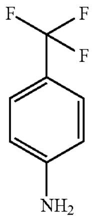 | method 5: RT: 3.33 min, MI: 492 [M + H] | 1H NMR (DMSO, 500 MHz,) 9.86 (1H, s), 9.07 (1H, s), 8.43 (1H, d), 8.19 (1H, s), 8.02 (1H, s), 7.99 (2H, d), 7.83 (1H, dd), 7.64 (2H, d), 3.94 (4H, s), 3.34 (4H, s), 2.69 (1H, m), 1.27 (2H, m), 1.08 (2H, m). | [4-(5-Cyclopropyl-4-piperazin-1-yl-pyrido[3,4-d]pyrimidin-2-yl)-pyridin-2-yl]-(4-trifluoromethyl-phenyl)-amine |
| 596 | 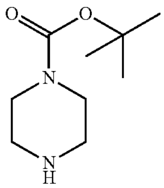 | 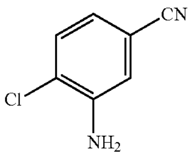 | method 5: RT: 2.9 min, MI: 483 [M + H] | 1H NMR (DMSO, 500 MHz,) 9.07 (2H, s), 8.71 (1H, d), 8.40 (1H, d), 8.24 (1H, s), 8.19 (1H, s), 7.88 (1H, dd), 7.72 (1H, d), 7.48 (1H, dd), 3.92 (4H, s), 3.34 (4H, s), 2.69 (1H, m), 1.25 (2H, m), 1.08 (2H, m). | [4-(5-Cyclopropyl-4-piperazin-1-yl-pyrido[3,4-d]pyrimidin-2-yl)-pyridin-2-yl]-(4-trifluoromethyl-phenyl)-amine |
| 597 | 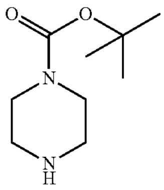 | 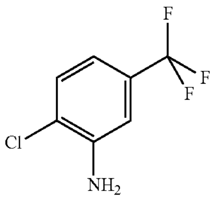 | method 5: RT: 3.41 min, MI: 526 [M + H] | 1H NMR (DMSO, 500 MHz,) 9.07 (1H, s), 9.02 (1H, s), 8.69 (1H, d), 8.39 (1H, d), 8.25 (1H, s), 8.19 (1H, s), 7.86 (1H, dd), 7.73 (1H, d), 7.36 (1H, dd), 3.94 (4H, s), 3.34 (4H, s), 2.69 (1H, m), 1.26 (2H, m), 1.08 (2H, m). | (2-Chloro-5-trifluoromethyl-phenyl)-[4-(5-cyclopropyl-4-piperazin-1-yl-pyrido[3,4-d]pyrimidin-2-yl)-pyridin-2-yl]-amine |
| 598 | 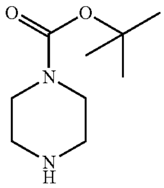 | 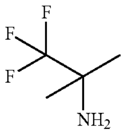 | method 5: RT: 5.48 min, MI: [M + H] | 1H NMR (500 MHz, DMSO) 8.93 (1H, s), 8.13 (1H, d), 8.06 (1H, s), 7.74 (1H, s), 7.51 (1H, d), 6.87 (1H, s), 3.77 (4H, m, br), 2.83 (4H, m, br), 2.62-2.61 (1H, m), 1.66 (6H, s), 1.25-1.23 (2H, m), 1.02-1.01 (2H, m). | [4-(5-Cyclopropyl-4-piperazin-1-yl-pyrido[3,4-d]pyrimidin-2-yl)-pyridin-2-yl]-(2,2,2-trifluoro-1,1-dimethyl-ethyl)-amine |
| 599 | 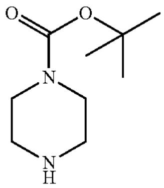 | 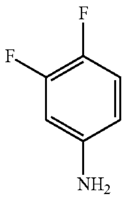 | method 5: RT: 2.85 min, MI: 460 [M + H] | 1H NMR (DMSO, 500 MHz,) 9.70 (1H, s), 9.06 (1H, s), 8.37 (1H, d), 8.18 (1H, s), 8.12-8.07 (1H, m), 7.94 (1H, s), 7.77 (1H, d), 7.37 (2H, m), 3.94 (4H, s), 3.34 (4H, s), 2.69 (1H, m), 1.27 (2H, m), 1.08 (2H, m). | [4-(5-Cyclopropyl-4-piperazin-1-yl-pyrido[3,4-d]pyrimidin-2-yl)-pyridin-2-yl]-(3,4-difluoro-phenyl)-amine |
| 600 | 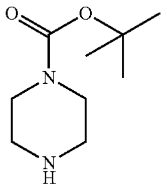 | 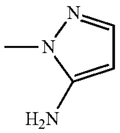 | 428 | (dmso-d6) 9.39 (s, 1H), 8.97 (s, 1H), 8.37 (s, 1H), 8.25 (d, J = 5.3 Hz, 1H), 8.09 (s, 1H), 7.63 (dd, J = 5.2; 1.4 Hz, 1H), 7.53 (d, J = 2.2 Hz, 1H), 6.34 (d, J = 2.2 Hz, 1H), 3.77 (s, 3H), 3.70 (br s, 4H), 3.30-3.32 (exch. H's), 2.85 (br s, 4H), 2.63 (m, 1H), 1.25 (m, 2H), 1.02 (m, 2H) | [4-(5-Cyclopropyl-4-piperazin-1-yl-pyrido[3,4-d]pyrimidin-2-yl)-pyridin-2-yl]-(1-methyl-1H-pyrazol-3-yl)-amine |

-continued

| Ex | Amine 1 | Amine 2 | Analysis LCMS | Analysis NMR | Analysis Name |
|---|---|---|---|---|---|
| 601 | 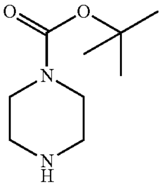 | 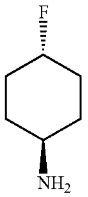 | method 5: RT: 2.29 min, MI: 448.35 [M + H] | 1H NMR (500 MHZ, DMSO) 9.16 (2H, s, br), 9.06 (1H, s), 8.21 (1H, s), 8.08 (1H, d), 8.05 (1H, s), 4.85 (1H, d), 3.96 (4H, m, br), 3.80 (1H, s, br), 3.37-3.32 (4H, m), 2.66-2.62 (1H, m), 2.02-1.98 (2H, m), 1.87-1.85 (2H, m), 1.73 (1H, t), 1.65-1.61 (3H, m), 1.27-1.23 (2H, m), 1.09-1.06 (2H, m). | [4-(5-Cyclopropyl-4-piperazin-1-yl-pyrido[3,4-d]pyrimidin-2-yl)-pyridin-2-yl]-(4-fluorocyclohexyl)-amine |
| 602 | 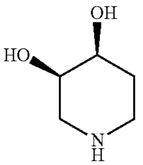 | 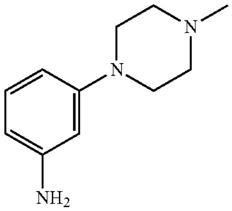 | 553.1 (M + H) | ($CDCl_3$) 9.07 (s, 1H), 8.32 (d, J = 5.2 Hz, 1H), 8.08 (br s, 1H), 8.02 (s, 1H), 7.79 (d, J = 5.2 Hz, 1H), 7.24 (dd, J = 8.4 Hz, 1H), 7.06 (br s, 1H), 6.98 (br s, 1H), 6.82 (br d, J = 7.08 Hz, 1H), 6.69 (dd, J = 8.4; 1.9 Hz, 1H), 3.95 (m, 5H), 3.55 (m, br s, 1H), 3.25 (br s, 5H), 2.60 (m, 5H), 2.34 (s, 3H), 1.91 (m, 1H), 1.7 br s (exch. H's), 1.24 (m, 2H), 0.97 (m, 2H) | (+/−)-(cis)-1-(5-Cylcopropyl-2-(2-[3-(4-methyl-piperazin-1-yl)-phenylamino]-pyridin-4-yl}-pyrido[3,4-d]pyrimidin-4-yl)-piperidine-3,4-diol |
| 603 | 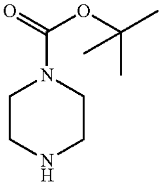 | 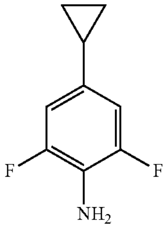 | 500.0 (MH)+ | | (4-Cyclopropyl-2,6-difluoro-phenyl)-[4-(5-cyclopropyl-4-piperazin-1-yl-pyrido[3,4-d]pyrimidin-2-yl)-pyridin-2-yl]-amine |
| 604 | 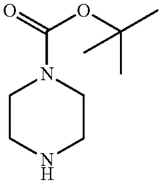 | 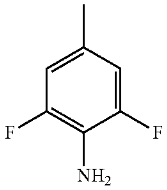 | 473.9 (MH)+ | | [4-(5-Cyclopropyl-4-piperazin-1-yl-pyrido[3,4-d]pyrimidin-2-yl)-pyridin-2-yl]-(2,6-difluoro-4-methyl-phenyl)-amine |
| 605 | 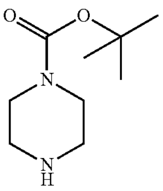 | 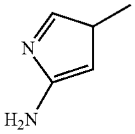 | 428.0 (M + H) | ($CDCl_3$) 9.13 (s, 1H), 8.37 (d, J = 5.4 Hz, 1H), 8.05 (s, 1H), 7.81 (s, 1H), 7.73 (dd, J = 5.4; 1.3 Hz, 1H), 7.47 (br s, 1H), 7.37 (d, J = 1.5 Hz, 1H), 7.26 (s, 1H, *"shoulder" under solvent's peak), 3.77 (br s, 4H), 3.71 (s, 3H), 3.03 (m, 4H), 2.70 (m, 1H), 2.93 (br s, exch. H's), 1.26 (m, 2H), 1.01 (m, 2H) | [4-(5-Cyclopropyl-4-piperazin-1-yl-pyrido[3,4-d]pyrimidin-2-yl)-pyridin-2-yl]-(1-methyl-1H-imidazol-4-yl)-amine |
| 606 | 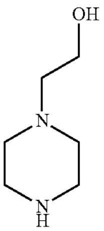 | 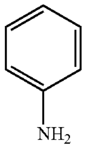 | 468.0 (M + H) | ($CDCl_3$) 9.11 (s, 1H), 8.34 (d, J = 5.2 Hz, 1H), 8.04 (s, 1H), 8.01 (s, 1H), 7.78 (dd, J = 5.2; 1.3 Hz, 1H), 7.45 (m, 2H), 7.35 (m, 2H), 7.17 (br s, 1H), 7.06 (m, 1H), 3.79 (br s, 4H), 3.68 (m, 2H), 3.14 (br s, exch. H's), 2.63 (m, 5H), 2.60 (m, 2H), 1.26 (m, 2H), 1.0 (m, 2H) | 2-{4-[5-Cyclopropyl-2-(2-phenylamino-pyridin-4-yl)-pyrido[3,4-d]pyrimidin-4-yl]-piperazin-1-yl}-ethanol |

-continued

| | | | Analysis | | |
|---|---|---|---|---|---|
| Ex | Amine 1 | Amine 2 | LCMS | NMR | Name |
| 607 | 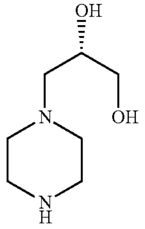 [SMILES: OC[C@@H](O)CN1CCNCC1] | 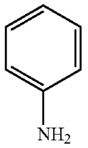 | 498.0 (M + H) | ($CDCl_3$) 9.11 (s, 1H), 8.35 (d, J = 5.2 Hz, 1H), 8.04 (s, 1H), 8.00 (s, 1H), 7.78 (dd, J = 5.3; 1.3 Hz, 1H), 7.45 (m, 2H), 7.35 (m, 2H), 7.06 (m, 1H), 6.98 (br s, 1H), 3.87 (m, 1H), 3.79 (m, 5H), 3.54 (d, J = 11.5; 4.4 Hz, 1H), 3.40-2.10 (br signal, —OH's), 2.78 (m, 2H), 2.64 (m, 2H), 2.58 (m, 2H), 2.40 (dd, J = 12.5 Hz,; 3.7 Hz, 1H), 1.25 (m, 2H), 1.00 (m, 2H) | (S)-3-{4-[5-Cyclopropyl-2-(2-phenylamino-pyridin-4-yl)-pyrido[3,4-d]pyrimidin-4-yl]-piperazin-1-yl}-propane-1,2-diol |
| 608 | 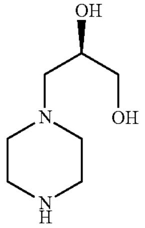 [SMILES: OC[C@H](O)CN1CCNCC1] | 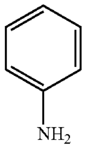 | 498.0 (M + H) | ($CDCl_3$) 9.11 (s, 1H), 8.35 (d, J = 5.2 Hz, 1H), 8.04 (s, 1H), 8.00 (s, 1H), 7.78 (dd, J = 5.3; 1.3 Hz, 1H), 7.45 (m, 2H), 7.35 (m, 2H), 7.09 (br s, 1H), 7.06 (m, 1H), 3.87 (m, 1H), 3.79 (m, 5H), 3.54 (d, J = 11.5; 4.4 Hz, 1H), 3.40-2.10 (br signal, —OH's), 2.78 (m, 2H), 2.64 (m, 2H), 2.58 (m, 2H), 2.40 (dd, J = 12.5 Hz; 3.7 Hz, 1H), 1.25 (m, 2H), 1.00 (m, 2H) | (R)-3-{4-[5-Cyclopropyl-2-(2-phenylamino-pyridin-4-yl)-pyrido[3,4-d]pyrimidin-4-yl]-piperazin-1-yl}-propane-1,2-diol |
| 609 | 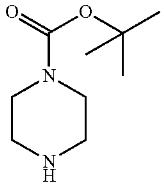 | 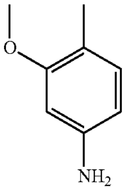 | 468.0 (MH)+ | | [4-(5-Cyclopropyl-4-piperazin-1-yl-pyrido[3,4-d]pyrimidin-2-yl)-pyridin-2-yl]-(3-methoxy-4-methyl-phenyl)-amine |
| 610 | 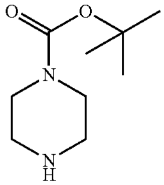 | 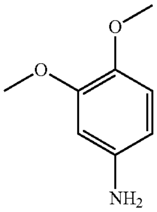 | 484.0 (MH)+ | | [4-(5-Cyclopropyl-4-piperazin-1-yl-pyrido[3,4-d]pyrimidin-2-yl)-pyridin-2-yl]-(3,4-dimethoxy-phenyl)-amine |
| 611 | 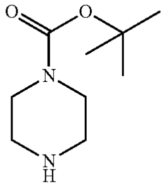 | 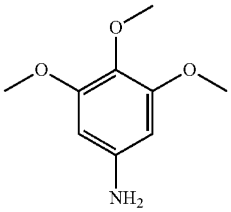 | 514.0 (MH)+ | | [4-(5-Cylcopropyl-4-piperazin-1-yl-pyrido[3,4-d]pyrimidin-2-yl)-pyridin-2-yl]-(3,4,5-trimethoxy-phenyl)-amine |
| 612 | 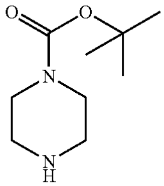 | 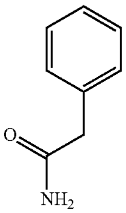 | 466.15 (M + H) | | N-[4-(5-Cyclopropyl-4-piperazin-1-yl-pyrido[3,4-d]pyrimidin-2-yl)-pyridin-2-yl]-2-phenyl-acetamide |

-continued

| | | | Analysis | | |
|---|---|---|---|---|---|
| Ex | Amine 1 | Amine 2 | LCMS | NMR | Name |
| 613 | 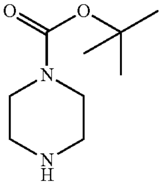 | 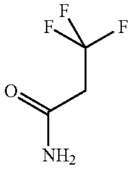 | 458.15 (M + H) | | N-[4-(5-Cyclopropyl-4-piperazin-1-yl-pyrido[3,4-d]pyrimidin-2-yl)-pyridin-2-yl]-3,3,3-trifluoro-propionamide |
| 614 | 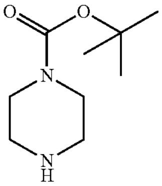 | 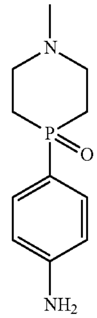 | 555.25 (M + H) | | [4-(5-Cyclopropyl-4-piperazin-1-yl-pyrido[3,4-d]pyrimidin-2-yl)-pyridin-2-yl]-[4-(1-methyl-4-oxo-4$\lambda^5$-[1,4]azaphos-phinan-4-yl)-phenyl]-amine |
| 615 | 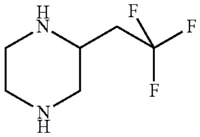 [SMILES: FC(F)(F)CC1CNCCN1] | — | 449.10 (M + H) | | 2-(2-Chloro-pyridin-4-yl)-5-cyclopropyl-4-[3-(2,2,2-trifluoro-ethyl)-piperazin-1-yl]-pyrido[3,4-d]pyrimidine |
| 616 | 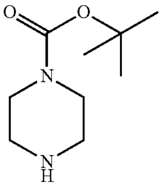 | 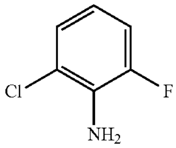 | method 5: RT: 3.25 min, MI: 476 [M + H] | 1H NMR (DMSO, 500 MHz) 9.05 (2H, bs), 8.93 (1H, bs), 8.21 (1H, d), 8.17 (1H, s), 7.88 (1H, s), 7.73 (1H, dd), 7.48 (1H, m), 7.25 (1H, m), 4.68 (4H, bs), 3.89 (4H, bs), 2.70 (1H, m), 1.28-1.25 (2H, m), 1.06-1.05 (2H, m). | (2-Chloro-6-fluoro-phenyl)-[4-(5-cyclopropyl-4-piperazin-1-yl-pyrido[3,4-d]pyrimidin-2-yl)-pyridin-2-yl]-amine |
| 617 | 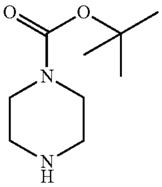 | 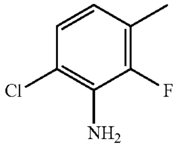 | method 5: RT: 3.36 min, MI: 490 [M + H] | 1H NMR (DMSO, 500 MHz) 9.04 (1H, s), 8.80 (1H, bs), 8.17 (1H, s), 8.15 (1H, d), 7.80 (1H, s), 7.67 (1H, d), 7.30 (1H, dd), 7.19 (1H, m), 3.91 (4H, bs), 3.31 (4H, bs), 2.68 (1H, m), 2.24 (3H, s), 1.23 (2H, m), 1.08-1.07 (2H, m). | (6-Chloro-2-fluoro-3-methyl-phenyl)-[4-(5-cylcopropyl-4-piperazin-1-yl-pyrido[3,4-d]pyrimidin-2-yl)-pyridin-2-yl]-amine |
| 618 | 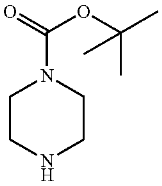 | 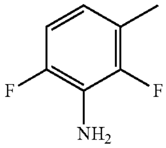 | method 5: RT: 2.62 min, MI: 494 [M + H] | 1H NMR (DMSO, 500 MHz) 9.05 (1H, s), 8.86 (1H, bs), 8.20 (1H, d), 8.17 (1H, s), 7.88 (1H, s), 7.73 (1H, dd), 7.47 (1H, m), 7.25 (1H, m), 3.89 (4H, bs), 3.31 (4H, bs), 2.68 (1H, m), 1.28-1.25 (2H, m), 1.08-1.07 (2H, m). | (3-Chloro-2,6-difluoro-phenyl)-[4-(5-cyclopropyl-4-piperazin-1-yl-pyrido[3,4-d]pyrimidin-2-yl)-pyridin-2-yl]-amine |
| 619 | 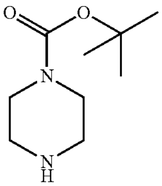 | 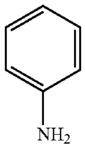 | method 5: RT: 3.04 min, MI: 438 [M + H] | NMR:- (1H, d6-dmso, 500 MHz) 9.30 (1H, s), 9.04 (1H, s), 8.69 (1H, s), 8.29 (1H, d), 7.90 (1H, s), 7.74 (2H, d), 7.65 (1H, dd), 7.27 (2H,tr), 6.89 (1H, tr), 4.26-4.20 (1H, m), 3.67 (2H, br s), 3.46 (2H, br s), 2.93 (2H, br s), 2.83 (2H, br s), 2.46-2.43 (2H, m partially hidden by large DMSO peak), 2.21-2.14 (2H, m), 2.10-2.03 (1H, m), 1.92-1.86 (1H, m). | [4-(5-Cyclobutyl-4-piperazin-1-yl-pyrido[3,4-d]pyrimidin-2-yl)-pyridin-2-yl]-phenyl-amine |

-continued

| Ex | Amine 1 | Amine 2 | Analysis LCMS | Analysis NMR | Name |
|---|---|---|---|---|---|
| 620 | 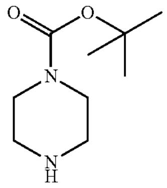 | 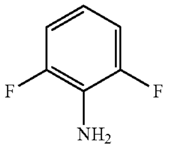 | method 5: RT: 3.39 min, MI: 474 [M + H] | NMR: (1H, d6-dmso, 500 MHz) 9.02 (1H, s), 8.75 (1H, s), 8.68 (1H, s), 8.14 (1H, d), 7.77 (1H, s), 7.63 (1H, dd), 7.29-7.23 (1H, m), 7.15 (2H, t), 4.22 (1H, dq), 3.63 (2H, br s), 3.50 (2H, br s), 2.90 (2H, br s), 2.78 (2H, br s), 2.44-2.42 (2H, m, partially obscured by DMSO peak), 2.20-2.12 (2H, m), 2.10-2.01 (1H, m), 1.91-1.86 (1H, m) | [4-(5-Cyclobutyl-4-piperazin-1-yl-pyrido[3,4-d]pyrimidin-2-yl)-pyridin-2-yl]-2,6-difluoro-phenyl)-amine |
| 621 | 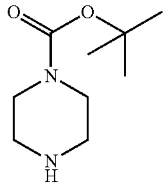 | 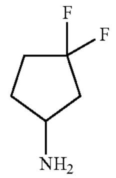 | method 5: RT: 2.24 min, MI: 452.37 [M + H] | 1H NMR (500 MHz, DMSO) 8.93 (1H, s), 8.13 (1H, d), 8.06 (1H, s), 7.53 (1H, s), 7.44 (1H, dd), 7.04 (1H, d), 4.42-4.38 (1H, m), 3.75-3.57 (4H, m, br), 2.84 (4H, m), 2.62-2.58 (2H, m), 2.27-1.97 (4H, m), 1.77-1.69 (1H, m),, 1.26-1.22 (2H, m), 1.01-1.00 (2H, m). | [4-(5-Cyclopropyl-4-piperazin-1-yl-pyrido[3,4-d]pyrimidin-2-yl)-pyridin-2-yl]-(3,3-difluoro-cyclopentyl)-amine |
| 622 | 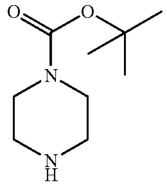 | 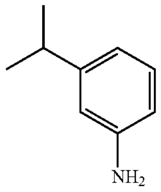 | 466.30 (M + H) | | [4-(5-Cyclopropyl-4-piperazin-1-yl-pyrido[3,4-d]pyrimidin-2-yl)-pyridin-2-yl]-(3-isopropyl-phenyl)-amine |
| 623 | 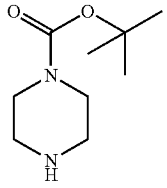 | 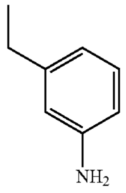 | 452.25 (M + H) | | [4-(5-Cyclopropyl-4-piperazin-1-yl-pyrido[3,4-d]pyrimidin-2-yl)-pyridin-2-yl]-(3-ethyl-phenyl)-amine |
| 624 | 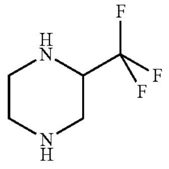 | — | 435.10 (M + H) | | 2-(2-Chloro-pyridin-4-yl)-5-cyclopropyl-4-(3-trifluoromethyl-piperazin-1-yl)-pyrido[3,4-d]pyrimidine |
| 625 | 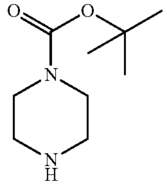 | 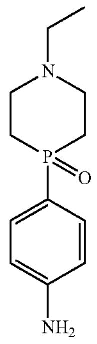 | 599.20 (M + H) | | [4-(5-Cyclopropyl-4-piperazin-1-yl-pyrido[3,4-d]pyrimidin-2-yl)-pyridin-2-yl]-[4-(1-ethyl-4-oxo-4λ$^5$-[1,4]azaphos-phinan-4-yl)-2-methoxy-phenyl]-amine |

-continued

| Ex | Amine 1 | Amine 2 | Analysis LCMS | NMR | Name |
|---|---|---|---|---|---|
| 626 | 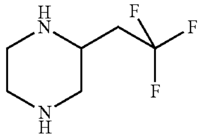 [SMILES: FC(F)(F)CC1CNCCN1] | 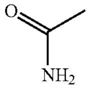 | 472.00 (M + H) | | N-(4-{5-Cyclopropyl-4-[3-(2,2,2-trifluoro-ethyl)-piperazin-1-yl]-pyrido[3,4-d]pyrimidin-2-yl}-pyridin-2-yl)-acetamide |
| 627 | 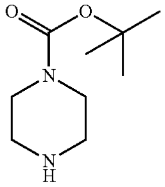 | 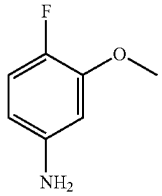 | method 5: RT: 0.48 min, MI: 472 [M + H] | 1H NMR (DMSO, 500 MHz,) 9.62 (1H, s), 9.06 (1H, s), 8.32 (1H, d), 8.19 (1H, s), 7.96 (1H, s), 7.74 (1H, d), 7.62 (1H, dd), 7.28 (1H, m), 7.17-7.13 (1H, m), 3.85 (7H, m), 3.34 (4H, s), 2.68 (1H, m), 1.27 (2H, m), 1.09 (2H, m). | [4-(5-Cyclopropyl-4-piperazin-1-yl-pyrido[3,4-d]pyrimidin-2-yl)-pyridin-2-yl]-(4-fluoro-3-methoxy-phenyl)-amine |
| 628 | 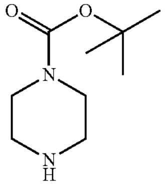 | 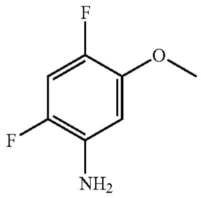 | method 5: RT: 2.37 min, MI: 490 [M + H] | 1H NMR (DMSO, 500 MHz, 1IGO570) 9.27 (1H, s), 9.06 (1H, s), 8.30 (1H, d), 8.18 (1H, s), 8.06 (1H, s), 7.96 (1H, t), 7.78 (1H, dd), 7.39 (1H, t), 3.96 (4H, s), 3.84 (3H, s), 3.33 (4H, s), 2.68 (1H, m), 1.27 (2H, m), 1.08 (2H, m). | [4-(5-Cyclopropyl-4-piperazin-1-yl-pyrido[3,4-d]pyrimidin-2-yl)-pyridin-2-yl]-(2,4-difluoro-5-methoxy-phenyl)-amine |
| 629 | 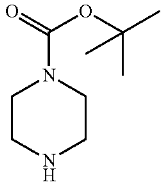 | 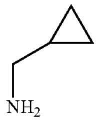 | method 5: RT: 2.16 min, MI: 402.22 [M + H] | 1H NMR (500 MHz, CDCl3) 9.07 (1H, s), 8.21 (1H, s), 8.04 (2H, d), 7.65 (1H, d), 4.10-3.74 (8H, m, br), 3.26 (2H, d), 2.66-2.62 (1H, m), 1.28-1.24 (2H, m), 1.15-1.13 (1H, m), 1.09-1.07 (2H, m), 0.57-0.56 (2H, m), 0.32-0.31 (2H, m). | Cyclopropylmethyl-[4-(5-cyclopropyl-4-piperazin-1-yl-pyrido[3,4-d]pyrimidin-2-yl)-pyridin-2-yl]-amine |
| 630 | 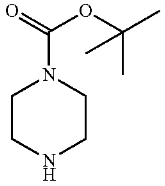 | 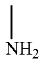 | method 5: RT: 1.61 min, MI: 362.19 [M + H] | 1H NMR (500 MHz, DMSO) 8.94 (1H, s), 8.12 ('1H, d), 8.06 (1H, s), 7.48 (1H, s), 7.41 (1H, dd), 6.72 (1H, d), 3.77-3.55 (4H, m), 2.85 (4H, m, br), 2.82 (3H, d), 2.63-2.59 (1H, m), 1.25-1.22 (2H, m), 1.02-1.00 (2H, m). | [4-(5-Cyclopropyl-4-piperazin-1-yl-pyrido[3,4-d]pyrimidin-2-yl)-pyridin-2-yl]-methyl-amine |
| 631 | 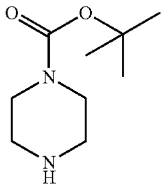 | 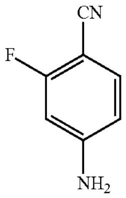 | method 5: RT: 3.04 min, MI: 467 [M + H] | 1H NMR (DMSO, 500 MHz,) 10.30 (1H, s), 9.06 (1H, s), 8.50 (1H, d), 8.23 (1H, dd), 8.19 (1H, s), 8.05 (1H, s), 7.92 (1H ,dd), 7.75 (1H, t), 7.52 (1H, dd), 3.94 (4H, s), 3.33 (4H, s), 2.68 (1H, m), 1.26 (2H, m), 1.09 (2H, m). | 4-[4-(5-Cyclopropyl-4-piperazin-1-yl-pyrido[3,4-d]pyrimidin-2-yl)-pyridin-2-ylamino]-2-fluoro-benzonitrile |
| 632 | 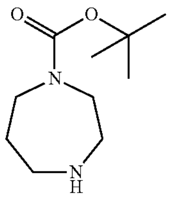 | 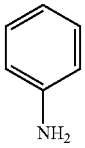 | method 5: RT: 1.96 min, MI: 438 [M + H] | 1H NMR (DMSO, 400 MHz, 90° C., 1IGO565_2) 8.99 (1H, s), 8.31 (1H, dd), 8.18 (1H, s), 7.95 (1H, s), 7.72 (1H, dd), 7.70-7.67 (2H, dd), 7.32 (2H, t), 6.97 (1H, t), 4.22 (2H, t), 4.05 (2H, t), 3.50 (2H, t), 3.20 (2H, t), 2.44 (1H, m), 2.11 (2H, quin), 1.27-1.23 (2H, m), 0.97-0.93 (2H, m). | [4-(5-Cyclopropyl-4-[1,4]diazepan-1-yl-pyrido[3,4-d]pyrimidin-2-yl)-pyridin-2-yl]-phenyl-amine |

-continued

| | | | Analysis | | |
|---|---|---|---|---|---|
| Ex | Amine 1 | Amine 2 | LCMS | NMR | Name |
| 633 | 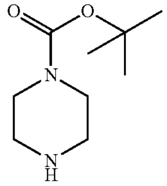 | 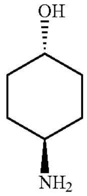 | method 5: RT: 2.02 min, MI: 446.23 [M + H] | 1H NMR (500 MHz, DMSO) 8.92 (1H, s), 8.08 (1H, d), 8.06 (1H, s), 7.49 (1H, s), 7.35 (1H, dd), 6.61 (1H, d), 4.53 (1H, d), 3.83-3.67 (5H, m, br), 3.51-3.42 (1H, m), 2.85 (4H, m), 2.61-2.60 (1H, m), 2.53 (2H, m), 1.97-1.95 (2H, m), 1.85-1.83 (2H, m), 1.24-1.20 (6H, m), 1.01-0.95 (6H, m). | 4-[4-(5-Cyclopropyl-4-piperazin-1-yl-pyrido[3,4-d]pyrimidin-2-yl)-pyridin-2-ylamino]-cyclohexanol |
| 634 | 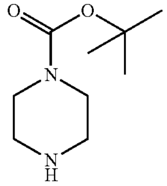 | 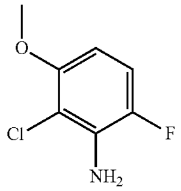 | method 5: RT: 2.29 min, MI: 506 [M + H] | 1H NMR (DMSO, 500 MHz) 9.06 (1H, s), 8.83 (1H, bs), 8.17 (1H, s), 8.16 (1H, d), 7.81 (1H, s), 7.67 (1H, dd), 7.25 (1H, t), 7.03 (1H, dd), 4.7 (4H, bs), 3.87 (3H, s), 3.31 (4H, m) 2.68 (1H, m), 1.26-1.23 (2H, m), 1.06-1.05 (2H, m). | (2-Choro-6-fluoro-3-methoxy-phenyl)-[4-(5-cyclopropyl-4-piperazin-1-yl-pyrido[3,4-d]pyrimidin-2-yl)-pyridin-2-yl]-amine |
| 635 | 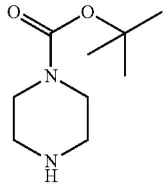 | 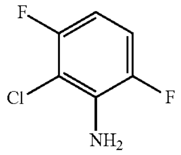 | method 5: RT: 2.53 min, MI: 494 [M + H] | 1H NMR (DMSO, 500 MHz) 9.05 (1H, s), 9.01 (1H, s), 8.86 (1H, bs), 8.18 (1H, s), 8.17 (1H, d), 7.87 (1H, s), 7.71 (1H, dd), 7.35 (1H, m), 3.89 (4H, bs), 3.31 (4H, m) 2.68 (1H, m), 2.35 (3H, s), 1.25-1.23 (2H, m), 1.08-1.06 (2H, m). | (2-Chloro-3,6-difluoro-phenyl)-[4-(5-cyclopropyl-4-piperaizn-1-yl-pyrido[3,4-d]pyrimidin-2-yl)-pyridin-2-yl]-amine |
| 636 | 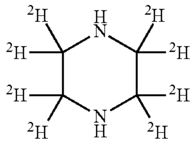 | 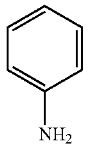 | method 5: RT: 1.36 min, MI: 432 [M + H] | 1H NMR (DMSO, 500 MHz) 9.05 (1H, s), 9.01 (1H, s), 8.86 (1H, bs), 8.18 (1H, s), 8.17 (1H, d), 7.87 (1H, s), 7.71 (1H, dd), 7.35 (1H, m), 3.89 (4H, bs), 3.31 (4H, m) 2.68 (1H, m), 2.35 (3H, s), 1.25-1.23 (2H, m), 1.08-1.06 (2H, m). | {4-[5-Cyclopropyl-4-(2,2,3,3,5,5,6,6-octadeuterio-piperazin-1-yl)-pyrido[3,4-d]pyrimidin-2-yl]-pyridin-2-yl}-phenyl-amine |
| 637 | 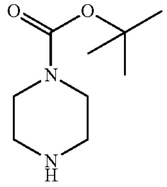 | 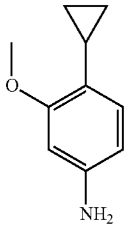 | 494.0 (MH)+ | | (4-Cyclopropyl-3-methoxy-phenyl)-[4-(5-cyclopropyl-4-piperazin-1-yl-pyrido[3,4-d]pyrimidin-2-yl)-pyridin-2-yl]-amine |
| 638 | 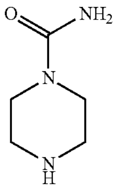 | 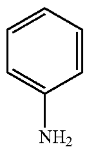 | 467.0 (M + H) | (dmso-d6) 9.61 (br s, 1H), 8.95 (s, 1H), 8.21 (d, J = 5.6 Hz, 1H), 8.09 (s, 1H), 7.92 (s, 1H), 7.67 (dd, J = 5.6; 1.1 Hz, 1H), 7.63 (d, J = 7.8 Hz, 2H), 7.29 (dd, J = 7.8; 8.0 Hz, 2H), 6.96 (t, J = 7.2 Hz, 1H), 6.06 (br s, 2H), 3.47-3.95 (br m, 4H), 3.47-3.37 (m, 5H), 2.55 (m, 1H), 1.21 (m, 2H), 0.99 (m, 2H) | 4-[5-Cyclopropyl-2-(2-phenylamino-pyridin-4-yl)-pyrido[3,4-d]pyrimidin-4-yl]-piperazine-1-carboxylic acidamide |
| 639 | 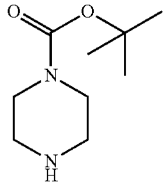 | 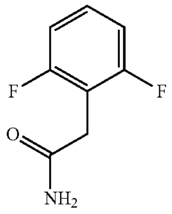 [SMILES: NC(=O)Cc1c(F)cccc1F] | 502 (M + H) | | N-[4-(5-Cyclopropyl-4-piperazin-1-yl-pyrido[3,4-d]pyrimidin-2-yl)-pyridin-2-yl]-2-(2,6-difluoro-phenyl)-acetamide |

-continued

| Ex | Amine 1 | Amine 2 | Analysis LCMS | NMR | Name |
|---|---|---|---|---|---|
| 640 | 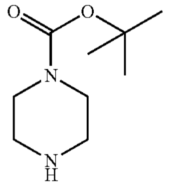 | 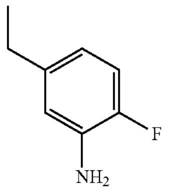 | 484.20 | | [4-(5-Cyclopropyl-4-piperazin-1-yl-pyrido[3,4-d]pyrimidin-2-yl)-pyridin-2-yl]-(2-fluoro-5-propyl-phenyl)-amine |
| 641 | 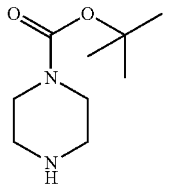 | 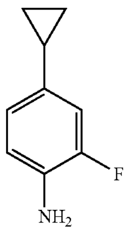 [SMILES: Nc1ccc(C2CC2)cc1F] | 482.15 | | (4-Cyclopropyl-2-fluoro-phenyl)-[4-(5-cyclopropyl-4-piperazin-1-yl-pyrido[3,4-d]pyrimidin-2-yl)-pyridin-2-yl]-amine |
| 642 | 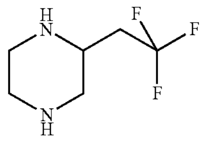 [SMILES: FC(F)(F)CC1CNCCN1] | 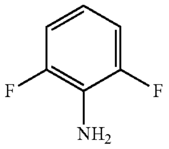 | 542.10 (M + H) | | (4-{5-Cyclopropyl-4-[3-(2,2,2-trifluoro-ethyl)-piperazin-1-yl]-pyrido[3,4-d]pyrimidin-2-yl}-pyridin-2-yl)-(2,6-difluoro-phenyl)-amine |
| 643 | 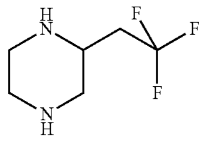 [SMILES: FC(F)(F)CC1CNCCN1] | 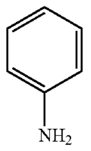 | 506.20 (M + H) | | (4-{5-Cyclopropyl-4-[3-(2,2,2-trifluoro-ethyl)-piperazin-1-yl]-pyrido[3,4-d]pyrimidin-2-yl}-pyridin-2-yl)-penyl-amine |
| 644 | 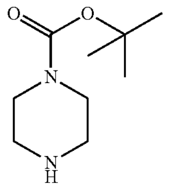 | 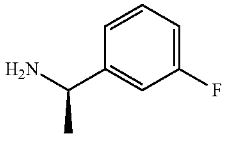 | 470 (M + H) | 1H NMR (500 MHz, DMSO) 8.92 (1H, s), 8.05 (1H, s), 8.04 (1H, d), 7.55 (1H, s), 7.40 (1H, dd), 7.35-7.29 (2H, m), 7.24 (1H, d), 7.21 (1H, d), 6.99 (1H, td), 5.08 (1H, t), 4.09-4.08 (1H, m), 3.78-3.51 (4H, m, br), 2.62-2.58 (1H, m), 1.44 (3H, d), 1.24-1.22 (2H, m), 1.01-1.00 (2H, m). | [4-(5-Cyclopropyl-4-piperazin-1-yl-pyrido[3,4-d]pyrimidin-2-yl)-pyridin-2-yl]-[(R)-1-(3-fluoro-phenyl)-ethyl]-amine |
| 645 | 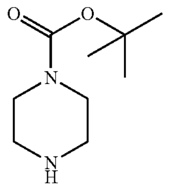 | 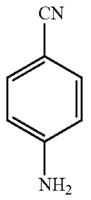 | method 5: RT: 3.83 min, MI: 449 [M + H] | 1H NMR (DMSO, 500 MHz,) 9.98 (1H, s), 9.05 (1H, s), 8.44 (1H, d), 8.18 (1H, s), 8.02 (1H, s), 7.97 (2H, d), 7.85 (1H, dd), 7.72 (2H, d), 3.92 (4H, s), 3.33 (4H, s), 2.68 (1H, m), 1.25 (2H, m), 1.07 (2H, m). | 4-[4-(5-Cyclopropyl-4-piperazin-1-yl-pyrido[3,4-d]pyrimidin-2-yl)-pyridin-2-yalmino]-benzonitrile |
| 646 | 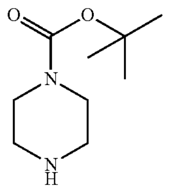 | 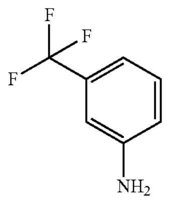 | method 5: RT: 4.3 min, MI: 492 [M + H] | 1H NMR (DMSO, 500 MHz,) 9.79 (1H, s), 9.06 (1H, s), 8.42 (1H, d), 8.34 (1H, s), 8.18 (1H, s), 7.99 (1H, s), 7.94 (1H, d), 7.80 (1H, dd), 7.52 (1H, t), 7.24 (1H, d), 3.92 (4H, s), 3.34 (4H, s), 2.69 (1H, m), 1.27 (2H, m), 1.09 (2H, m). | [4-(5-Cyclopropyl-4-piperazin-1-yl-pyrido[3,4-d]pyrimidin-2-yl)-pyridin-2-yl]-(3-trifluoromethyl-phenyl)-amine |

-continued

| Ex | Amine 1 | Amine 2 | Analysis<br>LCMS | <br>NMR | <br>Name |
|---|---|---|---|---|---|
| 649 | 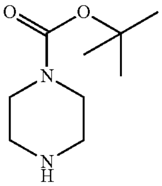 | 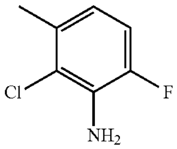 | method 5: RT: 2.44 min, MI: 490 [M + H] | 1H NMR (DMSO, 500 MHz) 9.04 (1H, s), 8.79 (1H, bs), 8.17 (1H, s), 8.15 (1H, d), 7.80 (1H, s), 7.66 (1H, dd), 7.27 (1H, dd), 7.20 (1H, t), 3.88 (4H, bs), 3.31 (4H, m) 2.68 (1H, m), 2.35 (3H, s), 1.26-1.23 (2H, m), 1.08-1.06 (2H, m). | (3-Chloro-2,6-difluoro-phenyl)-[4-(5-cylcopropyl-4-piperazin-1-yl-pyrido[3,4-d]pyrimidin-2-yl)-pyridin-2-yl]-amine |
| 650 | 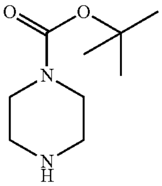 | 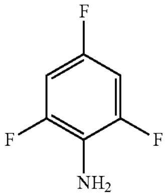 | method 5: RT: 3.26 min, MI: 478 [M + H] | 1H NMR (DMSO, 500 MHz,) 9.06 (1H, s), 8.85 (1H, s), 8.18 (2H, s), 7.84 (1H, s), 7.71 (1H, dd), 7.29 (2H, t), 3.90 (4H, s), 3.33 (4H, s), 2.69 (1H, m), 1.25 (2H, m), 1.08 (2H, m). | [4-(5-Cyclopropyl-4-piperazin-1-yl-pyrido[3,4-d]pyrimidin-2-yl)-pyridin-2-yl]-(2,4,6-trifluoro-phenyl)-amine |
| 651 | 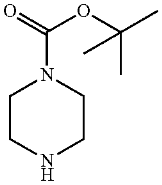 | 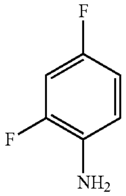 | method 5: RT: 3.22 min, MI: 460 [M + H] | 1H NMR (DMSO, 500 MHz, 1IGO581) 9.13 (1H, s), 9.06 (1H, s), 8.28 (1H, d), 8.18 (1H, s), 8.12-8.07 (1H, m), 8.02 (1H, s), 7.75 (1H, dd), 7.35-7.30 (1H, m), 7.11-7.06 (1H, m), 3.92 (4H, s), 3.33 (4H, s), 2.69 (1H, m), 1.26 (2H, m), 1.08 (2H, m). | [4-(5-Cyclopropyl-4-piperazin-1-yl-pyrido[3,4-d]pyrimidin-2-yl)-pyridin-2-yl]-(2,4-difluoro-phenyl)-amine |
| 652 | 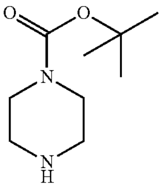 | 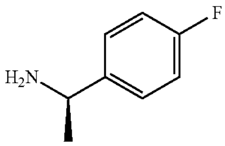 | method 5: RT: 2.71 min, MI: 470.37 [M + H] | 1H NMR (500 MHz, DMSO) 8.92 (1H, s), 8.05 (1H, s), 8.03 (1H, d), 7.63 (1H, s), 7.42 (2H, dd), 7.39 (1H, dd), 7.26 (1H, d), 7.15 (1H, t), 7.10 (2H, t), 5.06 (1H, 03.77-3.52 (4H, m), 2.83 (4H, m), 2.62-2.58 (1H, m), 1.43 (3H, s), 1.30 (1H, d), 1.24-1.22 (2H, m), 1.01-1.00 (2H, m). | 4-(5-Cyclopropyl-4-piperazin-1-yl-pyrido[3,4-d]pyrimidin-2-yl)-pyridin-2-yl]-[(R)-1(4-fluoro-phenyl)-ethyl]-amine |
| 653 | 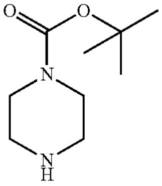 | 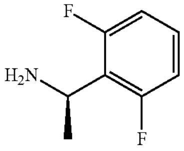 | method 5: RT: 5.46 min, MI: 488.35 [M + H] | 1H NMR (500 MHz, DMSO) 8.92 (1H, s), 8.06 (1H, s), 8.04 (1H, d), 7.61 (1H, d), 7.39 (1H, dd), 7.27 (1H, dt), 7.24 (1H, d), 7.00 (2H, t), 5.47 (1H, t), 3.78-3.54 (4H, m), 2.86 (4H, m), 2.63-2.62 (2H, m), 2.37-2.35 (1H, m), 1.55 (3H, d), 1.24-1.22 (2H, m), 1.01-1.00 (2H, m). | [4-(5-Cyclopropyl-4-piperazin-1-yl-pyrido[3,4-d]pyrimidin-2-yl)-pyridin-2-yl]-[(R)-1-(2,6-difluoro-phenyl)-ethyl]-amine |
| 654 | 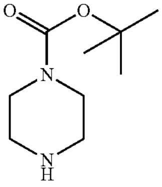 | 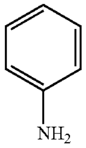 | method 5: RT: 2.31 min, MI: 442.34 [M + H] | 1H NMR (500 MHz, DMSO) 9.28 (1H, s), 8.93 (1H, s), 8.24 (1H, d), 8.11 (1H, s), 7.66 (1H, d), 7.62 (2H, d), 7.26 (2H, t), 6.89 (1H, t), 3.68 (4H, s, br), 3.15 (1H, d), 2.82 (4H, s, br), 2.59-2.57 (1H, m), 1.26-1.24 (2H, m), 1.03-1.02 (2H, m). | [4-(5-Cyclopropyl-4-piperazin-1-yl-pyrido[3,4-d]pyrimidin-2-yl)-5-fluoro-pyridin-2-yl]-phenyl-amine |
| 655 | 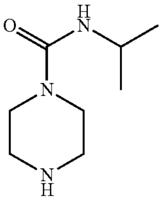 | 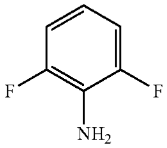 | 544 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid isopropylamide |

-continued

| | | | Analysis | | |
|---|---|---|---|---|---|
| Ex | Amine 1 | Amine 2 | LCMS | NMR | Name |
| 656 | 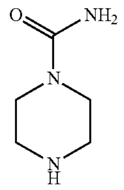 | 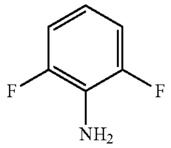 | 502 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid amide |
| 657 | 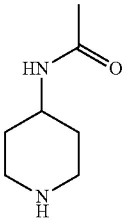 | 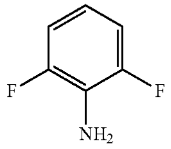 | 516 (M + H) | | N-(1-{5-Cyclopropyl-2-[2-(2,6-difluoro-phenylamino)-pyridin-4-yl]-pyrido[3,4-d]pyrimidin-4-yl}-piperidin-4-yl)-acetamide |
| 658 | 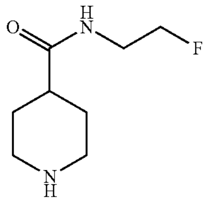 [SMILES: O=C(NCCF)C1CCNCC1] | 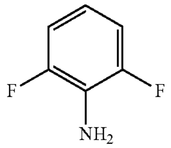 | 548 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid (2-fluoro-ethyl)-amide |
| 659 | 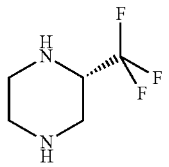 | 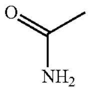 | 458 | | N-{4-[5-Cyclopropyl-4-((S)-3-trifluoromethyl-piperazin-1-yl)-pyrido[3,4-d]pyrimidine-2-yl]-pyridin-2-yl}-acetamide |
| 660 | 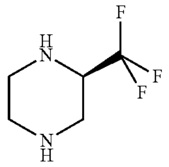 | — | 435 | | 2-(2-Chloro-pyridin-4-yl)-5-cyclopropyl-4-((R)-3-trifluoromethyl-piperazin-1-yl)-pyrido[3,4-d]pyrimidine |
| 661 | 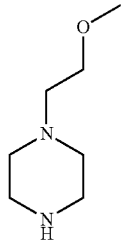 | 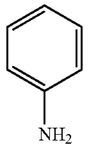 | 482 | | (4-{5-Cyclopropyl-4-[4-(2-methoxy-ethyl)-piperazin-1-yl]-pyrido[3,4-d]pyrimidin-2-yl}-pyridin-2-yl)-phenyl-amine |

-continued

| | | | Analysis | | |
|---|---|---|---|---|---|
| Ex | Amine 1 | Amine 2 | LCMS | NMR | Name |
| 662 | 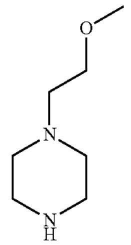 | 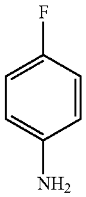 | 500 | | (4-{5-Cyclopropyl-4-[4-(2-methoxy-ethyl)-piperazin-1-yl]-pyrido[3,4-d]pyrimidin-2-yl}-pyridin-2-yl)-(4-fluoro-phenyl-amine |
| 663 | 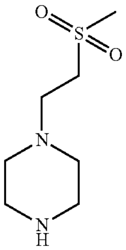 | 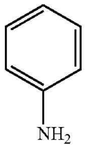 | 530 | | (4-{5-Cyclopropyl-4-{4-(2-methanesulfonyl-ethyl)-piperazin-1-yl]-pyrido[3,-d]pyrimidin-2-yl}-pyridin-2-yl)-phenyl-amine |
| 664 | 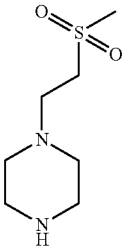 | 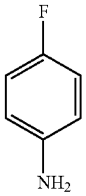 | 548 | | (4-{5-Cyclopropyl-4-[4-(2-methanesulfonyl-ethyl)-piperazin-1-yl]-pyrido[3,4-d]pyrimidin-2-yl}-pyridin-2-yl)-(4-fluoro-phenyl)-amine |
| 665 | 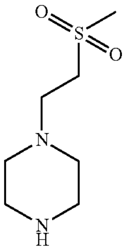 | 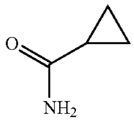 | 522 | | Cyclopropane-carboxylic acid (4-{5-cyclopropyl-4-[4-(2-methanesulfonyl-ethyl)-piperazin-1-yl]-pyrido[3,4-d]pyrimidin-2-yl}-pyridin-2-yl)-amide |
| 666 | 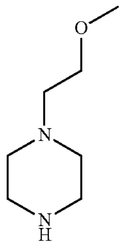 | 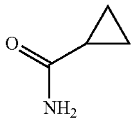 | 474 | | Cyclopropane-carboxylic acid (4-{5-cyclopropyl-4-[4-(2-methoxy-ethyl)-piperazin-1-yl]-pyrido[3,4-d]pyrimidin-2-yl}-pyridin-2-yl)-amide |
| 667 | 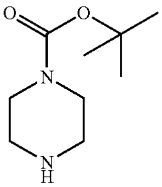 | 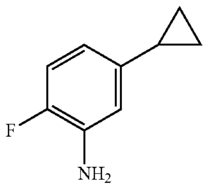 [SMILES: Nc1cc(C2CC2)ccc1F] | 482 | | (5-Cyclopropyl-2-fluoro-phenyl)-[4-(5-cyclopropyl-4-piperazin-1-yl-pyrido[3,4-d]pyrimidin-2-yl)-pyridin-2-yl]-amine |

-continued

| | | | Analysis | | |
|---|---|---|---|---|---|
| Ex | Amine 1 | Amine 2 | LCMS | NMR | Name |
| 668 | 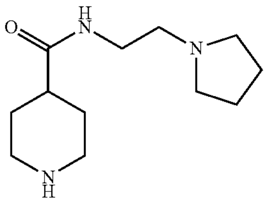 [SMILES: O=C(NCCN1CCCC1)C1CCNCC1] | 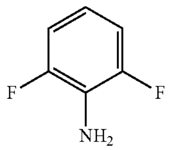 | 599 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid (2-pyrrolidin-1-yl-ethyl)-amide |
| 669 | 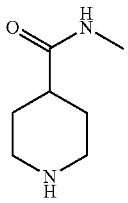 | 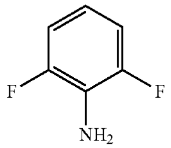 | 516 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid methylamide |
| 670 | 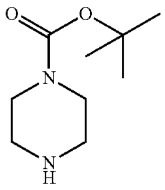 | 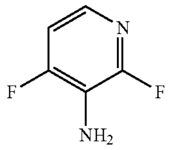 | 461.2 (MH)+ | | [4-(5-Cyclopropyl-4-piperazin-1-yl-pyrido[3,4-d]pyrimidin-2-yl)-pyridin-2-yl]-(2,4-difluoro-pyridin-3-yl)-amine |
| 671 | 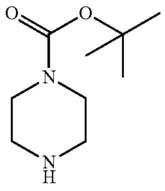 | 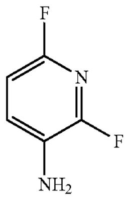 | 461.0 (MH)+ | | [4-(5-Cyclopropyl-4-piperazin-1-yl-pyrido[3,4-d]pyrimidin-2-yl)-pyridin-2-yl]-(2,6-difluoro-pyridin-3-yl)-amine |
| 672 | 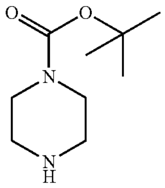 | 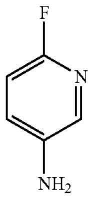 | 443.1 (MH)+ | | [4-(5-Cyclopropyl-4-piperazin-1-yl-pyrido[3,4-d]pyrimidin-2-yl)-pyridin-2-yl]-(6-fluoro-pyridin-3-yl)-amine |
| 673 | 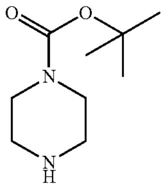 | 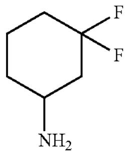 | method 5: RT: 2.41 min, MI: 466.32 [M + H] | 1H NMR (500 MHz, DMSO) 9.05 (1H, s), 8.19 (1H, s), 8.10 (1H, d), 7.91 (1H, s, br), 7.64 (1H, d, br), 3.98-3.80 (5H, m), 3.31 (4H, m, br), 2.67-2.62 (1H, m), 2.03-2.01 (2H, m), 1.94-1.79 (3H, m), 1.54-1.51 (1H, m), 1.35-1.32 (1H, m), 1.26-1.24 (2H, m), 1.07-1.06 (2H, m). | [4-(5-Cyclopropyl-4-piperazin-1-yl-pyrido[3,4-d]pyrimidin-2-yl)-pyridin-2-yl]-(3,3-difluoro-cyclohexyl)-amine |
| 674 | 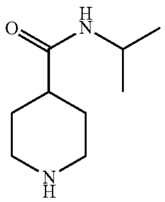 | 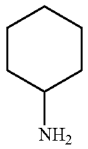 | 514 (M + H) | | 1-[2-(2-Cyclohexylamino-pyridin-4-yl)-5-cyclopropyl-pyrido[3,4-d]pyrimidin-4-yl]-piperidine-4-carboxylic acid isopropylamide |

-continued

| Ex | Amine 1 | Amine 2 | Analysis LCMS | Analysis NMR | Name |
|---|---|---|---|---|---|
| 675 | 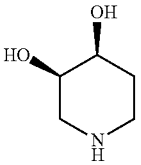 | 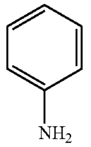 | 455.1 | (dmso-d6) 9.84 (br s, 1H), 8.98 (s, 1H), 8.26 (d, J = 5.7 Hz, 1H), 8.12 (s, 1H), 7.99 (s, 1H), 7.74 (dd, J = 5.7; 1.2 Hz, 1H), 7.67 (d, J = 7.8 Hz, 2H), 7.38 (app t, J = 8.00 Hz, 2H), 7.07 (app t, 6.8 Hz, 1H), 4.19 (large br s, exch. H's), 3.77 (br s, 4H), 3.70-3.47 (m, 2H), 3.47-3.25 (m, 1H), 3.13-1.78 (m, 1H), 1.68 (br s, 1H), 1.47-1.13 (m, 2H), 1.13-0.87 (m, 2H) | (+/−)-(cis)-1-[5-Cyclopropyl-2-(2-phenylamino-pyridin-4-yl-pyrido[3,4-d]pyrimidin-4-yl]-piperidine-3,4-diol |

The following compounds were synthesised according to the general synthesis shown in scheme [B4]

| Ex | Amine 1 | Amine 2 | Analysis LCMS | Analysis NMR | Name |
|---|---|---|---|---|---|
| 676 | 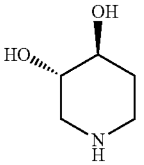 | 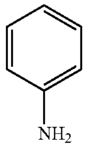 | 455.1 (M + H) | NMR (dmso-d6) 9.74 (br s, 1H), 8.98 (s, 1H), 8.27 (d, J = 5.6 Hz, 1H), 8.13 (s, 1H), 7.98 (s, 1H), 7.73 (d, J = 6.4 Hz, 1H), 7.68 (d, J = 8.0 Hz, 2H), 7.36 (app t, J = 8.0 Hz, 2H), 7.04 (app t, J = 7.2 Hz, 1H), 3.80 (large br s, exch. H's - overlapping other signals), 3.52 (br s, 2H), 3.40-3.35 (m, 2H), 2.23-1.83 (m, 2H), 1.55 (br s, 1H), 1.49 (br s, 1H), 1.35 (br s, 1H), 1.12-0.92 (m, 2H) | (+/−)-(trans)-1-[5-Cyclopropyl-2-(2-phenylamino-pyridin-4-yl)-pyrido[3,4-d]pyrimidin-4-yl]-piperidine-3,4-diol |
| 677 | 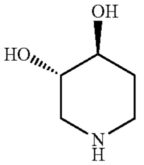 | 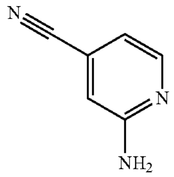 | 481.1 (M + H) | ($CDCl_3$) 10.39 (br s, 1H), 8.97 (br s, 1H), 8.65 (s, 1H), 8.50 (d, J = 4.8 Hz, 1H), 8.46 (d, J = 5.2 Hz, 1H), 8.35 (s, 1H), 8.10 (s, 1H), 7.89 (d, J = 4.9 Hz, 1H), 7.30 (d, J = 4.9 Hz, 1H), 5.25-4.65 (m, 2H), 4.40-3.70 (m, 4H), 3.52 (br s, 1H), 2.25-1.85 (m, 1H), 1.65-1.50 (m, 1H), 1.50-1.15 (m, 3H), 1.10-0.90 (m, 2H) | (+/−)-2-{4-[5-Cyclopropyl-4-((trans)-3,4-dihydroxy-piperidin-1-yl)-pyrido[3,4-d]pyrimidin-2-yl]-pyridin-2-ylamino}-isonicotinonitrile |
| 678 | 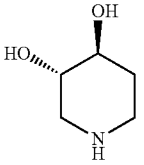 | 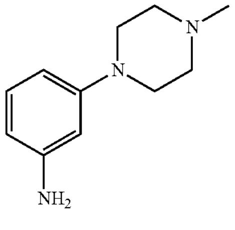 | 553.26 (M + H) | ($CDCl_3$) 9.16 (s, 1H), 8.94 (s, 1H), 8.30 (d, J = 5.3 Hz, 1H), 8.08 (s, 1H), 7.91 (s, 1H), 7.66 (dd, J = 5.2; 1.0 Hz, 1H), 7.34 (app t, J = 2.0 Hz, 1H), 7.22 (dd, J = 8.0; 1.1 Hz, 1H), 7.11 (app t, J = 8.1 Hz, 1H), 6.52 (dd, J = 8.2; 1.8 Hz, 1H), 5.28-4.67 (m, 2H), 4.28-3.71 (m, 2H), 3.50 (br s, 1H), 3.15-3.11 (m, 4H), 2.61-2.53 (m, 1H), 2.49-2.45 (m, 4H), 2.23 (s, 3H), 2.18-1.73 (m, 2H), 1.44-1.11 (m, 3H), 1.10-0.90 (m, 2H) | (+/−)-(trans)-1-(5-Cyclopropyl-2-{2-[3-(4-methyl-piperazin-1-yl)-phenylamino]-pyridin-4-yl}-pyrido[3,4d]pyrimidin-4-yl)-piperidine-3,4-diol |

-continued

| | | | Analysis | | |
|---|---|---|---|---|---|
| Ex | Amine 1 | Amine 2 | LCMS | NMR | Name |
| 679 | 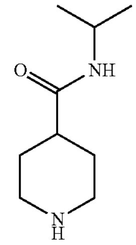 | 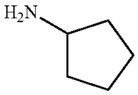 | 500 (M + H) | | 1-[2-(2-Cyclopentylamino-pyridin-4-yl)-5-cyclopropyl-pyrido[3,4-d]pyrimidin-4-yl]-piperidine-4-carboxylicacid isopropylamide |
| 680 | 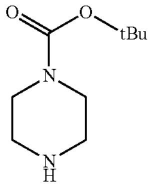 [SMILES: CC(C)(C)OC(=O)N1CCNCC1] | 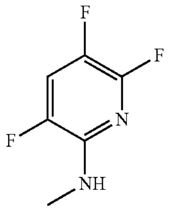 | 479.1 (M + H)+ | $^{1}$H NMR (400 MHz, DMSO-$d_6$) δ ppm 9.69 (s, 1 H) 8.98 (s, 1 H) 8.81 (s, 1 H) 8.40 (dd, J = 5.3, 0.8 Hz, 1 H) 8.21-8.30 (m, 1 H) 8.10 (s, 1 H) 7.92 (dd, J = 5.1, 1.4 Hz, 1 H) 3.77 (d, J = 11.3 Hz, 4 H) 2.85 (br. s., 4 H) 2.59-2.65 (m, 1 H) 1.21-1.31 (m, 3 H) 1.00-1.07 (m, 2 H) | 4-(5-Cyclopropyl-4-piperazin-1-yl-pyrido[3,4-d]pyrimidin-2-yl)-pyridin-2-yl]-(3,5,6-trifluoro-pyridin-2-yl)-amine |
| 681 | 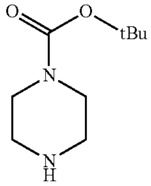 [SMILES: CC(C)(C)OC(=O)N1CCNCC1] | 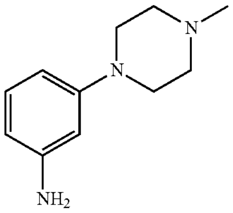 | 522.19 (M + H) | 1H NMR (400 MHz, DMSO-d6) 9.55 (1 H, s), 9.07 (1 H, s), 8.73-9.00 (2 H, m), 8.38 (1 H, d, J = 5.5 Hz), 8.19 (1 H, s), 7.99 (1 H, s), 7.87 (2 H, d, J = 8.5 Hz), 7.75 (1 H, dd, J = 5.3, 1.3 Hz), 7.60-7.69 (4 H, m), 7.45 (2 H, t, J = 7.7 Hz), 7.25-7.36 (1 H, m), 3.94 (4 H, br. s.), 3.34 (4 H, br. s.), 2.70 (1 H, br. s.), 1.21-1.31 (2 H, m), 1.09 (2 H, d, J = 3.5 Hz) | [4-(5-Cyclopropyl-4-piperazin-1-yl-pyrido[3,4-d]pyrimidin-2-yl)-pyridin-2-yl]-[3-(4-methyl-piperazin-1-yl)-phenyl]-amine |
| 682 | 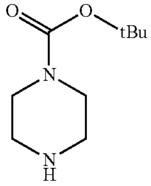 [SMILES: CC(C)(C)OC(=O)N1CCNCC1] | 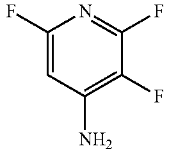 | 479.1 (M + H)+ | 1H NMR (400 MHz, DMSO-d6) 9.82 (1 H, s), 9.07 (1 H, s), 8.69-8.99 (2 H, m), 8.43 (1 H, d, J = 5.3 Hz), 8.19 (1 H, s), 8.03 (1 H, s), 7.88 (4 H, s), 7.82 (1 H, dd, J = 5.3, 1.3 Hz), 3.94 (4 H, br. s.), 3.34 (4 H, br. s.), 2.67-2.75 (1 H, m), 1.26 (2 H, d, J = 8.5 Hz), 1.09 (2 H, d, J = 5.5 Hz) | [4-(5-Cyclopropyl-4-piperazin-1-yl-pyrido[3,4-d]pyrimidin-2-yl)-pyridin-2-yl]-(2,3,6-trifluoro-pyridin-4-yl)-amine |
| 683 | 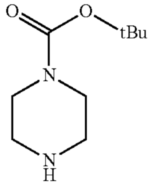 [SMILES: CC(C)(C)OC(=O)N1CCNCC1] | 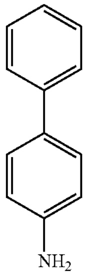 [SMILES: Nc1ccc(-c2ccccc2)cc1] | 500 (M + H) | | Biphenyl-4-yl-[4-(5-cyclopropyl-4-piperazin-1-yl-pyrido[3,4-d]pyrimidin-2-yl)-pyridin-2-yl]-amine |

-continued

| Ex | Amine 1 | Amine 2 | Analysis LCMS | Analysis NMR | Name |
|---|---|---|---|---|---|
| 684 | 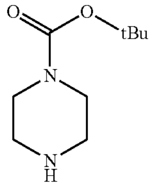 [SMILES: CC(C)(C)OC(=O)N1CCNCC1] | 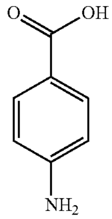 | 468 (M + H) | | 4-[4-(5-Cyclopropyl-4-piperazin-1-yl-pyrido[3,4-d]pyrimidin-2-yl)-pyridin-2-ylamino]-benzoic acid |
| 685 | 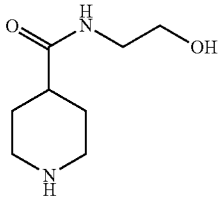 [SMILES: O=C(NCCO)C1CCNCC1] | 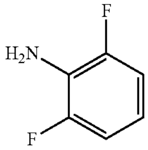 | 546 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid (2-hydroxy-ethyl)-amide |
| 686 | 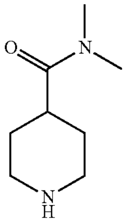 | 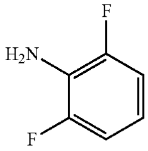 | 530 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid dimethylamide |
| 687 | 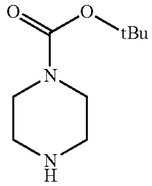 [SMILES: CC(C)(C)OC(=O)N1CCNCC1] | 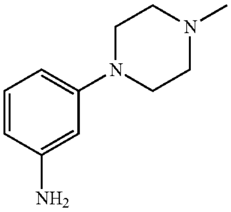 | 565.18 (M + H) | (dmso-d6) 9.99 (br s, 1H), 9.87 (s, 1H), 9.02 (s, 1H), 8.26 (d, J = 5.8 Hz, 1H), 8.16 (s, 1H), 8.02 (s, 1H), 7.76 (dd, J = 5.8; 1.4 Hz, 1H), 7.37 (s, 1H), 7.27 (app t, J = 8.1 Hz, 1H), 7.15 (d, J = 8.1 Hz, 1H), 6.75 (dd, J = 8.2; 1.6 Hz, 1H), 6.13 (br s, 1H), 4.56 (br s, exchangeable H's), 3.87-3.81 (m, 4H), 3.67 (br s, 2H), 3.60-3.50 (m, 7H), 3.19 (br s, 2H), 3.01 (app t, J = 12.2 Hz, 2H), 2.89 (s, 3H), 2.65-2.60 (m, 1H), 1.31-1.26 (m, 2H), 1.09-1.04 (m, 2H) | 4-(5-Cyclopropyl-2-{2-[3-(4-methyl-piperazin-1-yl)-phenylamino]-pyridin-4-yl}-pyrido[3,4-d]pyrimidin-4-yl)-piperazine-1-carboxylic acid amide |
| 688 | 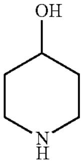 | 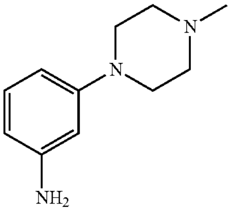 | 537.3 (M + H) | (dmso-d6) 9.17 (s, 1H), 8.96 (s, 1H), 8.30 (d, J = 5.3 Hz, 1H), 8.09 (s, 1H), 7.92 (s, 1H), 7.66 (dd, J = 5.3; 1.4 Hz, 1H), 7.34 (app t, J = 2.0 Hz, 1H), 7.22 (dd, J = 8.0; 1.2 Hz, 1H), 7.11 (app t, J = 8.0 Hz, 1H), 6.52 (dd, J = 8.2 Hz; 1.8 Hz, 1H), 4.82 (br s, 1H), 4.1-4.06 (m, 2H), 3.79 (br s, 1H), 3.51 (br s, 2H), 3.15-3.11 (m, 4H), 2.50 (br s, 1H), 2.50-2.45 (m, 4H), 2.23 (s, 3H), 1.91-1.87 (m, 2H), 1.54 (br s, 2H), 1.27-1.24 (m, 2H), 1.04-1.02 (m, 2H) | 1-(5-Cyclopropyl-2-{2-[3-(4-methyl-piperazin-1-yl)-phenylamino]-pyridin-4-yl}-pyrido[3,4-d]pyrimidin-4-yl)-piperidin-4-ol |

-continued

| | | | Analysis | | |
|---|---|---|---|---|---|
| Ex | Amine 1 | Amine 2 | LCMS | NMR | Name |
| 689 | 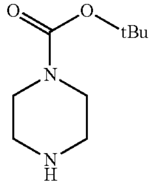 [SMILES: CC(C)(C)OC(=O)N1CCNCC1] | — | method 5: RT: 2.86 min, MI: 351.25 [M + H] | 1H NMR (500 MHz, DMSO) 8.98 (1H, s), 8.41 (1H, d), 8.26 (1H, d), 8.11 (1H, s), 7.95 (1H, d), 3.79-3.61 (4H, m), 2.83 (4H, m), 2.65-2.57 (1H, m), 1.26-1.24 (2H, m), 1.03-1.01 (2H, m). | 5-Cyclopropyl-2-(2-fluoro-pyridin-4-yl)-4-piperazin-1-yl-pyrido[3,4-d]pyrimidine |
| 690 | 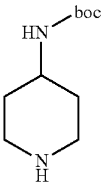 | 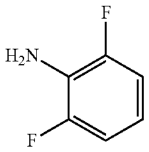 | 474 (M + H) | | {4-[4-(4-Amino-piperidin-1-yl)-5-cyclopropyl-pyrido[3,4-d]pyrimidin-2-yl]-pyridin-2-yl}-(2,6-difluoro-phenyl)-amine |
| 691 | 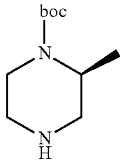 | 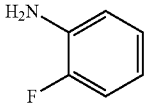 | method 5: RT: 2.43 min, MI: 456 [M + H] | 1H NMR (DMSO, 400 MHz, 1IG0596, 90° C.) 9.06 (1H, s), 8.32 (1H, dd), 8.22 (1H, s), 8.10-8.05 (1H, td), 7.98 (1H, s), 7.75 (1H, dd), 7.25-7.15 (2H, m), 7.09-7.03 (1H, m), 4.30 (2H, m), 3.55 (2H, m), 3.42 (1H, m), 3.36-3.23 (2H, m), 2.66 (1H, m), 1.32 (3H, d), 1.26 (2H, m), 1.05 (2H, m). | {4-[5-Cyclopropyl-4-((S)-3-methyl-piperazin-1-yl)-pyrido[3,4-d]pyrimidin-2-yl]-pyridin-2-yl}-(2-fluoro-phenyl)-amine |
| 692 | 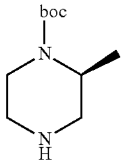 | 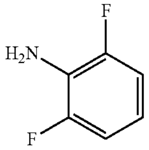 | method 5: RT: 2.42 min, MI: 474 [M + H] | 1H NMR (DMSO, 500 MHz, 1IG0593) 9.06 (1H, s), 8.22 (2H, m), 7.76 (1H, s), 7.71 (1H, dd), 7.32-7.25 (1H, m), 7.16 (2H, m), 2.67 (1H, m), 1.31 (3H, d), 1.26 (2H, m), 1.05 (2H, m). [methyl piperazine side chain peaks not integrated). | {4-[5-Cyclopropyl-4-((S)-3-methyl-piperazin-1-yl)-pyrido[3,4-d]pyrimidin-2-yl]-pyridin-2-yl}-(2,6-difluoro-phenyl)-amine |
| 693 | 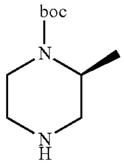 | 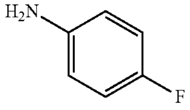 | method 5: RT: 2.27 min, MI: 456 [M + H] | 1H NMR (DMSO, 400 MHz, 1IG0594, 90° C.) 9.07 (1H, s), 8.32 (1H, dd), 8.22 (1H, s), 7.90 (1H, s), 7.70 (3H, m), 7.11 (2H, m), 4.34 (2H, m), 3.55 (2H, m), 3.43 (1H, m), 3.30 (2H, m), 2.67 (1H, m), 1.32 (3H, d), 1.24 (2H, m), 1.04 (2H, m). | {4-[5-Cyclopropyl-4-((S)-3-methyl-piperazin-1-yl)-pyrido[3,4-d]pyrimidin-2-yl]-pyridin-2-yl}-(4-fluoro-phenyl)-amine |
| 694 | 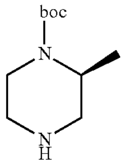 | 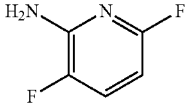 | method 5: RT: 2.65 min, MI: 475 [M + H] | 1H NMR (DMSO, 400 MHz, 1IG0595, 90° C.) 9.08 (1H, s), 8.94 (1H, m), 8.46 (1H, dd), 8.23 (1H, s), 8.00 (1H, dd), 7.83-7.77 (1H, m), 6.69-6.65 (1H, m), 4.36 (2H, m), 3.58 (2H, m), 3.46-3.27 (3H, m), 2.67 (1H, m), 1.31 (3H, d), 1.27 (2H, m), 1.05 (2H, m). | {4-[5-Cyclopropyl-4-((S)-3-methyl-piperazin-1-yl)-pyrido[3,4-d]pyrimidin-2-yl]-pyridin-2-yl}-(3,6-difluoro-pyridin-2-yl)-amine |

-continued

| | | | Analysis | | |
|---|---|---|---|---|---|
| Ex | Amine 1 | Amine 2 | LCMS | NMR | Name |
| 695 | 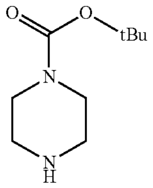 [SMILES: CC(C)(C)OC(=O)N1CCNCC1] | 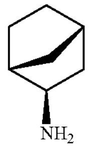 | 442 (M + H) | | (+/−)-(1RS,2RS,4SR)-Bicyclo[2.2.1]hept-2-yl-[4-(5-cyclopropyl-4-piperazin-1-yl-pyrido[3,4-d]pyrimidin-2-yl)-pyridin-2-yl]-amine |
| 696 | 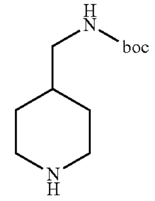 | 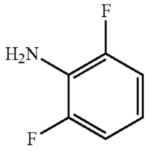 | 488 (M + H) | 1H NMR (400 MHz, DMSO-d6) 9.07 (1 H, s), 8.93 (2 H, br. s.), 8.22 (1 H, s), 8.07 (1 H, d, J = 6.3 Hz), 7.80-8.03 (1 H, m), 7.65 (1H, br. s.), 3.91-4.00 (2 H, m), 3.61- 3.65 (4 H, m), 3.27 -3.34 (4 H, m), 2.62- 2.67(1 H, m), 2.30 (1 H, br. s.), 1.85 (1 H, br. s.), 1.41-1.64 (4 H, m), 1.12-1.38 (6 H, m), 1.01-1.12 (2 H, m) | {4-[4-(4-Aminomethyl-piperidin-1-yl)-5-cyclopropyl-pyrido[3,4-d]pyrimidin-2-yl]-pyridin-2-yl}-(2,6-difluoro-phenyl)-amine |
| 697 | 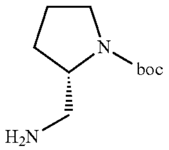 | 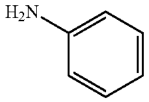 | 438.1 (MH)+ | | [5-Cyclopropyl-2-(2-phenylamino-pyridin-4-yl)-pyrido[3,4-d]pyrimidin-4-yl]-(S)-1-pyrrolidin-2-ylmethyl-amine |
| 698 | 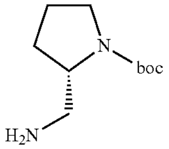 | 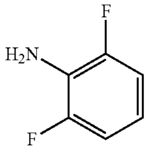 | 474.3 (MH)+ | | {5-Cyclopropyl-2-[2-(2,6-difluoro-phenylamino)-pyridin-4-yl]-pyrido[3,4-d]pyrimidin-4-yl}-(S)-1-pyrrolidin-2-ylmethyl-amine |
| 699 | 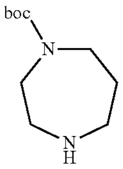 | 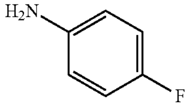 | method 5: RT: 2.19 min, MI: 456 [M + H] | 1H NMR (DMSO, 500 MHz) 9.49 (1H, s), 8.96 (1H, s), 8.30 (1H, d), 8.14 (1H, s), 7.91 (1H, s), 7.76 (2H, m), 7.71 (1H, dd), 7.17 (2H, m), 4.17 (2H, m), 4.01 (2H, m), 3.49 (2H, m), 3.16 (2H, m), 2.35 (1H, m), 2.06 (2H, m), 1.24 (2H, m), 0.97 (2H, m). | [4-(5-Cyclopropyl-4-[1,4]diazepan-1-yl-pyrido[3,4-d]pyrimidin-2-yl)-pyridin-2-yl]-(4-fluoro-phenyl)-amine |
| 700 | 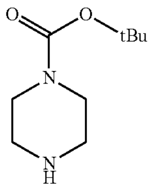 [SMILES: CC(C)(C)OC(=O)N1CCNCC1] | 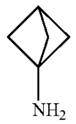 | method 5: RT: 2.59 min, MI: 414.29 [M + H] | 1H NMR (500 MHz, DMSO) 8.94 (1H, s), 8.18 (1H, d), 8.06 (1H, s), 7.58 (1H, s), 7.46 (1H, dd), 7.39 (1H, s), 3.74-3.63 (4H, m), 2.88 (4H, m), 2.62-2.60 (2H, m), 2.09 (6H, s), 1.24-1.22 (2H, m), 1.01-0.99 (4H, m). | Bicyclo[1.1.1]pent-1-yl-[4-(5-cyclopropyl-4-piperazin-1-yl-pyrido[3,4-d]pyrimidin-2-yl)-pyridin-2-yl]-amine |
| 701 | 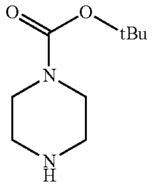 [SMILES: CC(C)(C)OC(=O)N1CCNCC1] | 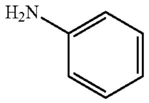 | method 5: RT: 3.76 min, MI: 442.33 [M + H] | 1H NMR (500 MHz, DMSO) 8.98 (1H, d), 8.94 (1H, s), 8.11 (1H, s), 8.06 (1H, d), 7.81 (2H, d), 7.42 (1H, t), 7.28 (2H, t), 6.95 (1H, t), 3.73 (4H, s, br), 2.82 (4H, s, br), 2.63-2.57 (1H, m), 1.27-1.25 (2H, m), 1.03-1.02 (2H, m). | [4-(5-Cyclopropyl-4-piperazin-1-yl-pyrido[3,4-d]pyrimidin-2-yl)-3-fluoro-pyridin-2-yl]-phenyl-amine |

-continued

| Ex | Amine 1 | Amine 2 | Analysis LCMS | NMR | Name |
|---|---|---|---|---|---|
| 702 | 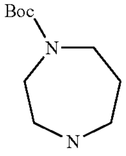 | 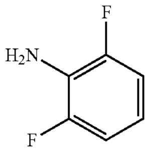 | method 5: RT: 2.35 min, MI: 474 [M + H] | 1H NMR (DMSO, 500 MHz) 9.04 (1H, s), 8.98 (1H, s), 8.18 (1H, d), 8.15 (1H, s), 7.84 (1H, s), 7.71 (1H, dd), 7.31 (1H, m), 7.19 (2H, t), 4.18 (2H, m), 4.01 (2H, m), 3.47 (2H, m), 3.16 (2H, m), 2.35 (1H, m), 2.06 (2H, m), 1.26 (2H, m), 0.98 (2H, m). | [4-(5-Cyclopropyl-4-[1,4]diazepan-1-yl-pyrido[3,4-d]pyrimidin-2-yl)-pyridin-2-yl]-(2,6-difluoro-phenyl)-amine |
| 703 | 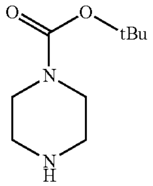 [SMILES: CC(C)(C)OC(=O)N1CCNCC1] | 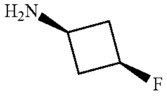 | method 5: RT: 2.19 min, MI: 420.29 [M + H] | 1H NMR (500 MHz, DMSO) 8.93 (1H, s), 8.11 (1H, d), 9.06 (1H, s), 7.48 (1H, s), 7.44 (1H, dd), 7.14 (1H, d), 5.34-5.20 (1H, m), 4.85 (1H, m, br), 3.77-3.56 (5H, m, br), 2.84 (4H, s), 2.62-2.59 (2H, m), 2.36-2.27 (2H, m), 1.26-1.23 (2H, m), 1.03-1.00 (2H, m). | (+/−)cis-[4-(5-Cyclopropyl-4-piperazin-1-yl-pyrido[3,4-d]pyrimidin-2-yl)-pyridin-2-yl]-(3-fluoro-cyclobutyl)-amine |
| 704 | 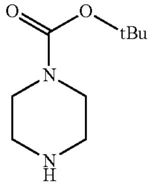 [SMILES: CC(C)(C)OC(=O)N1CCNCC1] | 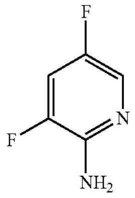 | 461.54 | $^1$H NMR (400 MHz, DMSO-$d_6$) δ ppm 9.39 (s, 1 H) 8.98 (s, 1 H) 8.67 (s, 1 H) 8.35 (d, J = 5.3 Hz, 1 H) 8.22 (d, J = 2.5 Hz, 1 H) 8.10 (s, 1 H) 7.94 (ddd, J = 10.7, 8.3, 2.6 Hz, 1 H) 7.84 (dd, J = 5.1, 1.4 Hz, 1 H) 3.58-3.86 (m, 4 H) 2.85 (br. s., 4 H) 2.73-52 (m, 1H) 1.22-1.31 (m, 2 H) 0.99-1.07 (m, 2 H) | [4-(5-Cyclopropyl-4-piperazin-1-yl-pyrido[3,4-d]pyrimidin-2-yl)-pyridin-2-yl]-(3,5-difluoro-pyridin-2-yl)-amine |
| 705 | 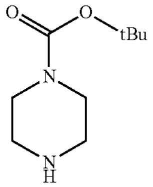 [SMILES: CC(C)(C)OC(=O)N1CCNCC1] | 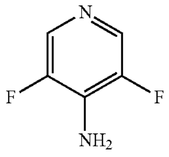 | 461.63 | | [4-(5-Cyclopropyl-4-piperazin-1-yl-pyrido[3,4-d]pyrimidin-2-yl)-pyridin-2-yl]-(3,5-difluoro-pyridin-4-yl)-amine |
| 706 | 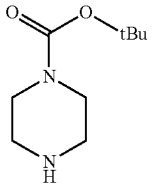 [SMILES: CC(C)(C)OC(=O)N1CCNCC1] | 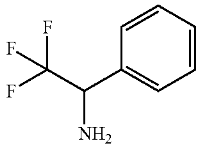 [SMILES: NC(c1ccccc1)C(F)(F)F] | 506.53 (M + H) | (dmso-d6) 9.05 (s, 1H), 8.99 (br s, 1H), 8.22-8.16 (m, 2H), 8.13 (d, J = 10.0 Hz, 1H), 7.89 (s, 1H), 7.65 (app d, J = 7.2 Hz, 2H), 7.61 (dd, J = 5.4; 1.4 Hz, 1H), 7.48-7.35 (m, 3H), 6.23 (quint, J = 9.2 Hz, 1H), 4.51 (br s, exch. H's), 3.91 (br s, 6H), 2.74-2.64 (m, 1H), 1.30-1.22 (m, 2H), 1.12-1.04 (m, 2H) | [4-(5-Cyclopropyl-4-piperazin-1-yl-pyrido[3,4-d]pyrimidin-2-yl)-pyridin-2-yl]-(2,2,2-trifluoro-1-phenyl-ethyl)-amine |
| 707 | 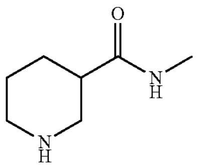 | 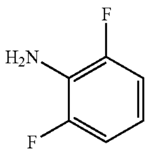 | 516 (M + H) | | 1-{5-Cyclopropyl-2-[2-(2,6-difluoro-phenylamino)-pyridin-4-yl]-pyrido[3,4-d]pyrimidin-4-yl}-piperidine-3-carboxylic acid methyl amide |

-continued

| Ex | Amine 1 | Amine 2 | Analysis LCMS | Analysis NMR | Name |
|---|---|---|---|---|---|
| 708 | 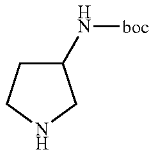 | 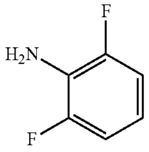 | 460 (M + H) | | {4-[4-(3-Amino-pyrrolidin-1-yl)-5-cyclopropyl-pyrido[3,4-d]pyrimidin-2-yl]-pyridin-2-yl}-(2,6-difluoro-phenyl)-amine |
| 709 | 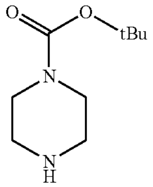 [SMILES: CC(C)(C)OC(=O)N1CCNCC1] | 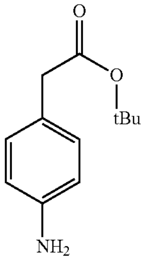 [SMILES: CC(C)(C)OC(=O)Cc1ccc(N)cc1] | 482 (M + H) | 1H NMR (400 MHz, DMSO-d6) 9.52 (1 H, br. s.), 9.06 (1 H, s), 8.76-9.04 (2 H, m), 8.31 (1 H, d, J = 5.3 Hz), 8.19 (1 H, s), 7.97 (1 H, s), 7.72 (1H, dd, J = 5.5, 1.3 Hz), 7.65 (2 H, d, J = 8.5 Hz), 7.21 (2 H, d, J = 8.5 Hz), 3.78-3.99 (4 H, m), 3.52 (2 H, s), 3.33 (4 H, br. s.), 2.65-2.78 (1 H, m), 1.19-1.34 (2 H, m), 0.99-1.14 (2 H, m) | {4-[4-(5-Cyclopropyl-4-piperazin-1-yl-pyrido[3,4-d]pyrimidin-2-yl)-pyridin-2-ylamino]-phenyl}-acetic acid |
| 710 | 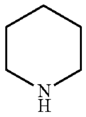 | 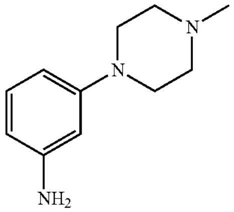 | 521.78 | ($CDCl_3$) 9.06 (s, 1H), 8.35 (d, J = 5.2 Hz, 1H), 8.07 (s, 1H), 8.01 (s, 1H), 7.79 (dd, J = 5.2; 1.3 Hz, 1H), 7.23 (app t, J = 8.0 Hz, 1H), 7.05-7.02 (m, 1H), 7.00-6.98 (m, 1H), 6.93 (dd, J = 8.0; 1.6 Hz, 1H), 6.65 (dd, J = 8.0; 2.0 Hz, 1H), 3.70 (br s, 4H), 3.28-3.24 (m, 4H), 2.66-2.62 (m, 1H), 2.61-2.56 (m, 4H), 2.35 (s, 3H), 1.69 br s, 6H), 1.26-1.18 (m, 2H), 1.00-0.95 (m, 2H) | [4-(5-Cyclopropyl-4-piperidin-1-yl-pyrido[3,4d]pyrimidin-2-yl)-pyridin-2-yl]-[3-(4-methyl-piperazin-1-yl)-phenyl]-amine |
| 711 | 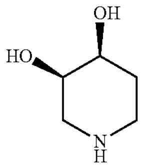 | 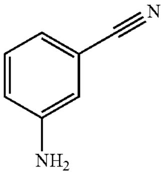 | 480.59 | | 3-{4-[5-Cyclopropyl-4-((3R,4S)-3,4-dihydroxy-piperidin-1-yl)-pyrido[3,4-d]pyrimidin-2-yl]-pyridin-2-ylamino}-benzonitrile |
| 712 | 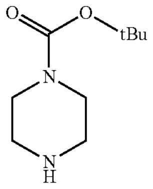 [SMILES: CC(C)(C)OC(=O)N1CCNCC1] | 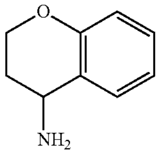 | 480 (M + H) | 1H NMR (400 MHz, DMSO-d6) 9.06 (1H, s), 8.88 (2 H, br. s.), 8.13-8.25 (2 H, m), 7.89 (1 H, br. s.), 7.63 (1 H, br. s.), 7.33 (1 H, d, J = 7.3 Hz), 7.23 (1 H, t, J = 7.5 Hz), 6.92 (1 H, t, J = 7.3 Hz), 6.86 (1H, d, J = 8.3 Hz), 5.21 (1 H, br. s.), 4.18-4.31 (3 H, m), 3.83-3.94 (4 H, m), 3.31 (4 H, br. s.), 2.64-2.72 (1 H, m), 2.13-2.26 (1 H, m), 2.00-2.13 (1 H, m), 1.20-1.33 (2 H, m), 1.01-1.12 (2 H, m) | Chroman-4-yl-[4-(5-cyclopropyl-4-piperazin-1-yl-pyrido[3,4-d]pyrimidin-2-yl)-pyridin-2-yl]-amine |

-continued

| | | | Analysis | | |
|---|---|---|---|---|---|
| Ex | Amine 1 | Amine 2 | LCMS | NMR | Name |
| 713 | 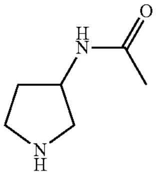 | 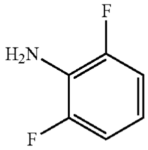 | 502 (M + H) | | N-(1-{5-Cyclopropyl-2-[2-(2,6-difluoro-phenylamino)-pyridin-4-yl]-pyrido[3,4-d]pyrimidin-4-yl}-pyrrolidin-3-yl)-acetamide |
| 714 | 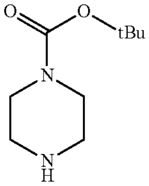 [SMILES: CC(C)(C)OC(=O)N1CCNCC1] | 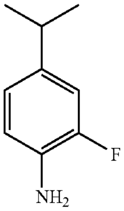 | 484.25 | | [4-(5-Cyclopropyl-4-piperazin-1-yl-pyrido[3,4-d]pyrimidin-2-yl)-pyridin-2-yl]-(2-fluoro-4-isopropyl-phenyl)-amine |
| 715 | 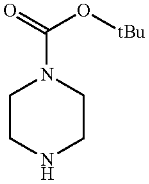 [SMILES: CC(C)(C)OC(=O)N1CCNCC1] | 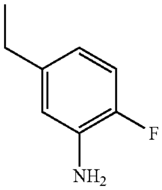 | 470 | | [4-(5-Cyclopropyl-4-piperazin-1-yl-pyrido[3,4-d]pyrimidin-2-yl)-pyridin-2-yl]-(5-ethyl-2-fluoro-phenyl)-amine |
| 716 | 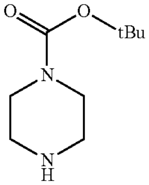 [SMILES: CC(C)(C)OC(=O)N1CCNCC1] | 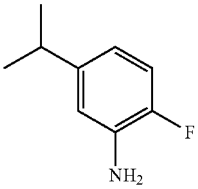 | 484.2 | | [4-(5-Cyclopropyl-4-piperazin-1-yl-pyrido[3,4-d]pyrimidin-2-yl)-pyridin-2-yl]-(2-fluoro-5-isopropyl-phenyl)-amine |
| 717 | 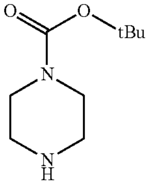 [SMILES: CC(C)(C)OC(=O)N1CCNCC1] | 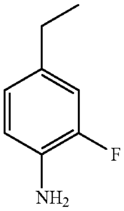 | 470.2 | | [4-(5-Cyclopropyl-4-piperazin-1-yl-pyrido[3,4-d]pyrimidin-2-yl)-pyridin-2-yl]-(4-ethyl-2-fluoro-phenyl)-amine |
| 718 | 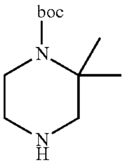 | 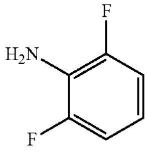 | 488 (M + H) | 1H NMR (500 MHz, DMSO) 8.92 (1H, s), 8.75 (1H, s), 8.15 (1H, d), 8.08 (1H, s), 7.74 (1H, s), 7.64 (1H, dd), 7.34-7.24 (1H, m), 7.16 (2H, t), 3.91-3.52 (4H, m, br), 2.85 (2H, s), 2.50-2.45 (1H, m), 1.23-1.22 (2H, m), 1.08-0.98 (6H, m), 0.78 (2H, s, br). | {4-[5-Cyclopropyl-4-(3,3-dimethyl-piperazin-1-yl)-pyrido[3,4-d]pyrimidin-2-yl]-pyridin-2-yl}-(2,6-difluoro-phenyl)-amine |
| 719 | 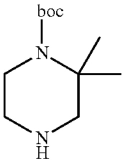 | 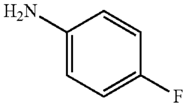 | 470 (M + H) | 1H NMR (500 MHz, DMSO) 9.32 (1H, s), 8.93 (1H, s), 8.28 (1H, d), 8.08 (1H, s), 7.85 (1H, s), 7.76-7.73 (2H, m), 7.66 (1H, d), 7.11 (2H, t), 3.95-3.55 (4H, m), 2.87 (2H, m, br), 2.53 (1H, m), 1.24-1.22 (2H, m), 1.06-0.78 (9H, m). | {4-[5-Cyclopropyl-4-(3,3-dimethyl-piperazin-1-yl)-pyrido[3,4-d]pyrimidin-2-yl]-pyridin-2-yl}-(4-fluoro-phenyl)-amine |

-continued

| | | | Analysis | | |
|---|---|---|---|---|---|
| Ex | Amine 1 | Amine 2 | LCMS | NMR | Name |
| 720 | 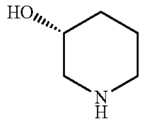 | 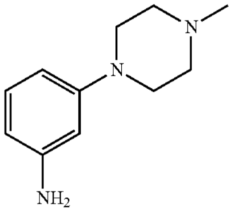 | 537.67 | | (R)-1-(5-Cyclopropyl-2-{2-[3-(4-methyl-piperazin-1-yl)-phenylamino]-pyridin-4-yl}-pyrido[3,4-d]pyrimidin-4-yl)-piperidin-3-ol |
| 721 | 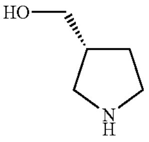 | 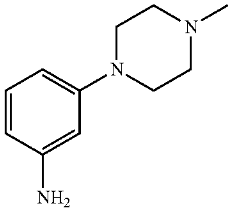 | 537.71 | | [(R)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-yl]-methanol |
| 722 | 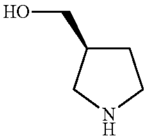 | 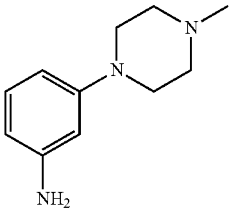 | 537.7 | | [(S)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-yl]-methanol |
| 723 | 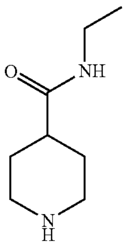 | 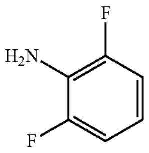 | 530 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid ethylamide |
| 724 | 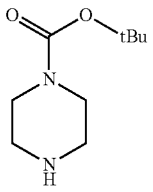 [SMILES: CC(C)(C)OC(=O)N1CCNCC1] | 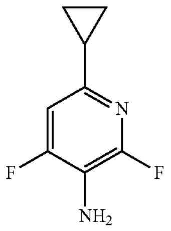 [SMILES: Nc1c(F)cc(C2CC2)nc1F] | 501.57 (MH)+ | | (6-Cyclopropyl-2,4-difluoro-pyridin-3-yl)-[4-(5-cyclopropyl-4-piperazin-1-yl-pyrido[3,4-d]pyrimidin-2-yl)-pyridin-2-yl]-amine; bis-trifluoroacetic salt |
| 725 | 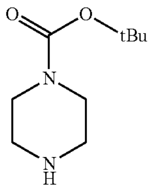 [SMILES: CC(C)(C)OC(=O)N1CCNCC1] | 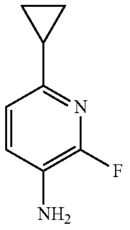 [SMILES: Nc1ccc(C2CC2)nc1F] | 483.61 (MH)+ | | (6-Cyclopropyl-2-fluoro-pyridin-3-yl)-[4-(5-cyclopropyl-4-piperazin-1-yl-pyrido[3,4-d]pyrimidin-2-yl)-pyridin-2-yl]-amine; bis-trifluoroacetic acid salt |

-continued

| | | | Analysis | | |
|---|---|---|---|---|---|
| Ex | Amine 1 | Amine 2 | LCMS | NMR | Name |
| 726 | 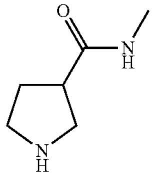 | 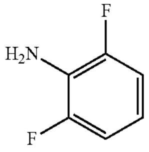 | 502 (M + H) | | 1-{5-Cyclopropyl-2-[2-(2,6-difluoro-phenylamino)-pyridin-4-yl]-pyrido[3,4-d]pyrimidin-4-yl}-pyrrolidine-3-carboxylic acid methylamide |
| 727 | 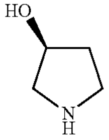 | 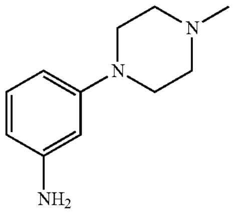 | 523.66 (M + H)+ | | (S)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-ol |
| 728 | 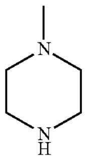 | 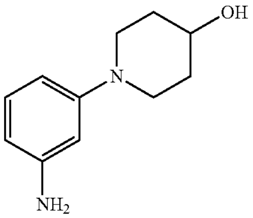 [SMILES: Nc1cccc(N2CCC(O)CC2)c1] | 537.73 (M + H)+ | | 1-(3-{4-[5-Cyclopropyl-4-(4-methyl-piperazin-1-yl)-pyrido[3,4-d]pyrimidin-2-yl]-pyridin-2-ylamino}-phenyl)-piperidin-4-ol |
| 729 | 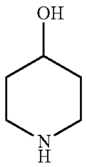 | 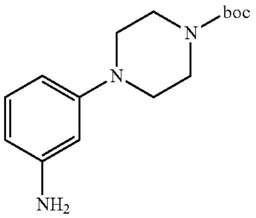 | 523.70 (M + H)+ | | 1-{5-Cyclopropyl-2-[2-(3-piperazin-1-yl-phenylamino)-pyridin-4-yl]-pyrido[3,4-d]pyrimidin-4-yl}-piperidin-4-ol |
| 730 | 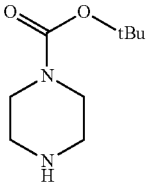 [SMILES: CC(C)(C)OC(=O)N1CCNCC1] | 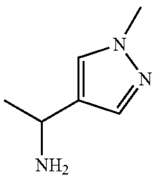 | 456 (M + H) | 1H NMR (400 MHz, DMSO-d6) 9.08 (4 H, s), 8.22(1 H, s), 8.08 (1 H, d, J = 6.5 Hz), 8.04 (1 H, br. s.), 7.75 (1 H, s), 7.70 (1 H, dd, J = 6.5, 1.3 Hz), 7.49 (1 H, s), 5.06 (1 H, br. s.), 3.6-3.9 (8 H, m), 3.32 (4 H, br. s.), 2.62-2.68 (1H, m), 1.55 (3 H, d, J = 6.8 Hz), 1.21-1.31 (2 H, m), 1.05-1.12 (2 H, m) | [4-(5-Cyclopropyl-4-piperazin-1-yl-pyrido[3,4-d]pyrimidin-2-yl)-pyridin-2-yl]-[1-(1-methyl-1H-pyrazol-4-yl)-ethyl]-amine |
| 731 | 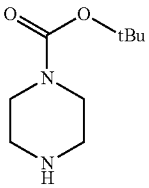 [SMILES: CC(C)(C)OC(=O)N1CCNCC1] | 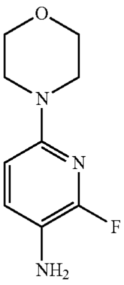 [SMILES: Nc1ccc(N2CCOCC2)nc1F] | 528.63 (MH)+ | | [4-(5-Cyclopropyl-4-piperazin-1-yl-pyrido[3,4-d]pyrimidin-2-yl)-pyridin-2-yl]-(2-fluoro-6-morpholin-4-yl-pyridin-3-yl)-amine |

-continued

| | | | Analysis | | |
|---|---|---|---|---|---|
| Ex | Amine 1 | Amine 2 | LCMS | NMR | Name |
| 732 | 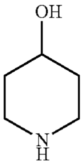 | 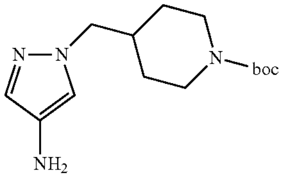 | 526 | | 1-{5-Cyclopropyl-2-[2-(1-piperidin-4-ylmethyl-1H-pyrazol-4-ylamino)-pyridin-4-yl]-pyrido[3,4-d]pyrimidin-4-yl}-piperidin-4-ol |
| 733 | 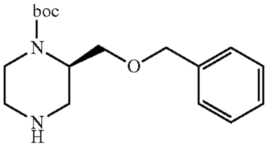 | — | 487.15 | | 4-((R)-3-Benzyloxymethyl-piperazin-1-yl)-2-(2-chloro-pyridin-4-yl)-5-cyclopropyl-pyrido[3,4-d]pyrimidine |
| 734 | 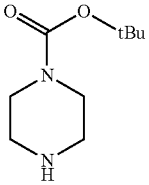 [SMILES: CC(C)(C)OC(=O)N1CCNCC1] | 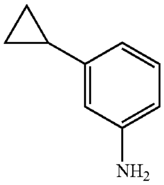 | 464.2 | | (3-Cyclopropyl-phenyl)-[4-(5-cyclopropyl-4-piperazin-1-yl-pyrido[3,4-d]pyrimidin-2-yl)-pyridin-2-yl]-amine |
| 735 | 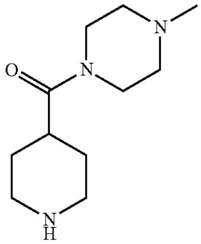 | 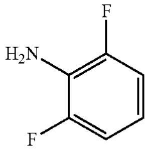 | 585 (M + H) | | (1-{5-Cyclopropyl-2-[2-(2,6-difluoro-phenylamino)-pyridin-4-yl]-pyrido[3,4-d]pyrimidin-4-yl}-piperidin-4-yl)-(4-methyl-piperazin-1-yl)-methanone |
| 736 | 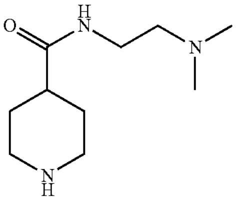 | 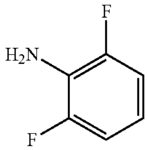 | 573 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid (2-dimethylamino-ethyl)-amide |
| 737 | 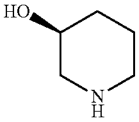 | 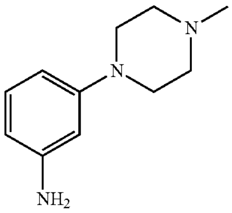 | 537.72 (M + H) | | (S)-1-(5-Cyclopropyl-2-{2-[3-(4-methyl-piperazin-1-yl)-phenylamino]-pyridin-4-yl}-pyrido[3,4-d]pyrimidin-4-yl)-piperidin-3-ol |
| 738 | 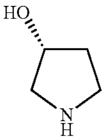 | 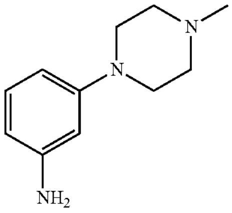 | 523.68 (M + H)+ | | (R)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-ol |

-continued

| | | | Analysis | | |
|---|---|---|---|---|---|
| Ex | Amine 1 | Amine 2 | LCMS | NMR | Name |
| 739 | 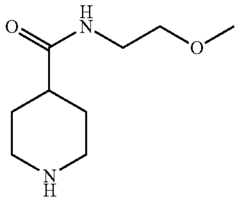 | 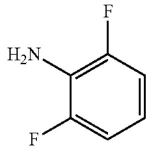 | 560 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid (2-methoxy-ethyl)-amide |
| 740 | 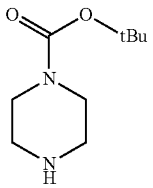 [SMILES: CC(C)(C)OC(=O)N1CCNCC1] | 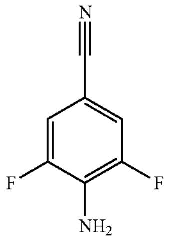 [SMILES: N#Cc1cc(F)c(N)c(F)c1] | 485 (M + H) | 1H NMR (400 MHz, DMSO-d6) 9.13 (1 H, s), 9.02-9.09 (1 H, m), 8.75 - 8.98 (2 H, m), 8.39 (1 H, br. s.), 8.17-8.31 (2 H, m), 7.74-8.06 (2 H, m), 3.84-4.04 (4 H, m), 3.36 (4 H, br. s.), 2.71 (1 H, br. s.), 1.19-1.33 (2 H, m), 1.04-1.16 (2 H, m) | 4-[4-(5-Cyclopropyl-4-piperazin-1-yl-pyrido[3,4-d]pyrimidin-2-yl)-pyridin-2-ylamino]-3,5-difluoro-benzonitrile |
| 741 | 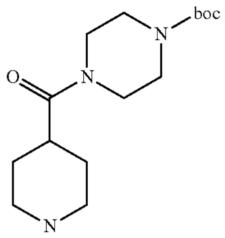 | 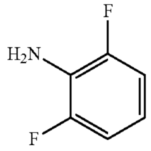 | 571 (M + H) | | (1-{5-Cyclopropyl-2-[2-(2,6-difluoro-phenylamino)-pyridin-4-yl]-pyrido[3,4-d]pyrimidin-4-yl}-piperidin-4-yl)-piperazin-1-yl-methanone |
| 742 | 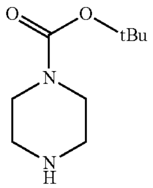 [SMILES: CC(C)(C)OC(=O)N1CCNCC1] | 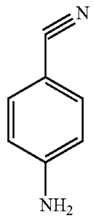 | 467 (M + H) | 1H NMR (400 MHz, DMSO-d6) 9.72 (1 H, s), 9.07 (1 H, s), 8.78-9.03 (2 H, m), 8.41 (1 H, d, J = 5.3 Hz), 8.19 (1 H, s), 8.01 (1 H, s), 7.69-7.89 (6 H, m), 7.14 (1 H, br. s.), 3.94 (4 H, br. s.), 3.34 (4 H, br. s.), 2.64-2.77 (1 H, m), 1.20-1.32 (2 H, m), 1.01-1.13 (2 H, m) | 4-[4-(5-Cyclopropyl-4-piperazin-1-yl-pyrido[3,4-d]pyrimidin-2-yl)-pyridin-2-ylamino]-benzamide |
| 743 | 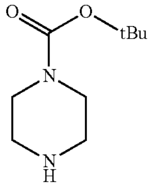 [SMILES: CC(C)(C)OC(=O)N1CCNCC1] | 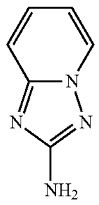 | 465.56 (MH)+ | | [4-(5-Cyclopropyl-4-piperazin-1-yl-pyrido[3,4-d]pyrimidin-2-yl)-pyridin-2-yl]-[1,2,4]triazolo[1,5-a]pyridin-2-yl-amine |
| 744 | 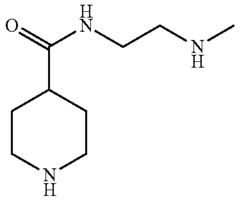 | 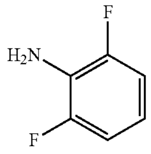 | 559 (M + H) | | 1-{5-Cyclopropyl-2-[2-(2,6-difluoro-phenylamino)-pyridin-4-yl]-pyrido[3,4-d]pyrimidin-4-yl}-piperidine-4-carboxylic acid (2-methylamino-ethyl)-amide |

-continued

| Ex | Amine 1 | Amine 2 | Analysis: LCMS | Analysis: NMR | Name |
|---|---|---|---|---|---|
| 745 | 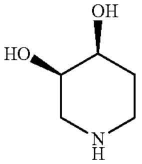 | 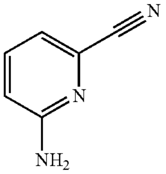 | 481.53 | | 6-{4-[5-Cyclopropyl-4-((cis)-3,4-dihydroxy-piperidin-1-yl)-pyrido[3,4-d]pyrimidin-2-yl]-pyridin-2-ylamino}-pyridine-2-carbonitrile |
| 746 | 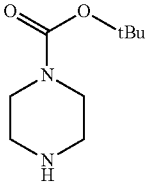 [SMILES: CC(C)(C)OC(=O)N1CCNCC1] | 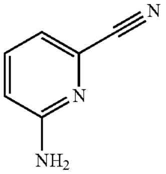 | 450.55 (M + H)+ | | 6-[4-(5-Cyclopropyl-4-piperazin-1-yl-pyrido[3,4-d]pyrimidin-2-yl)-pyridin-2-ylamino]-pyridine-2-carbonitrile |
| 747 | 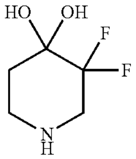 | 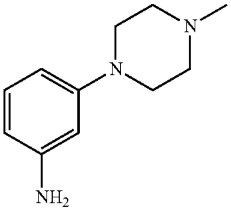 | 589.70 (M + H)+ | | 1-(5-Cyclopropyl-2-{2-[3-(4-methyl-piperazin-1-yl)-phenylamino]-pyridin-4-yl}-pyrido[3,4-d]pyrimidin-4-yl)-3,3-difluoro-piperidine-4,4-diol |
| 748 | 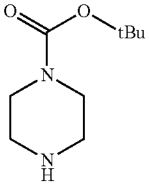 [SMILES: CC(C)(C)OC(=O)N1CCNCC1] | 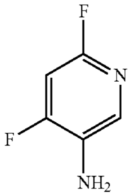 | 461.51 (MH)+ | | [4-(5-Cyclopropyl-4-piperazin-1-yl-pyrido[3,4-d]pyrimidin-2-yl)-pyridin-2-yl]-(4,6-difluoro-pyridin-3-yl)-amine |
| 749 | 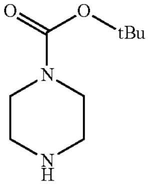 [SMILES: CC(C)(C)OC(=O)N1CCNCC1] | 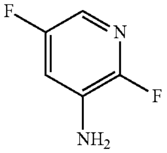 | 461.50 (MH)+ | | [4-(5-Cyclopropyl-4-piperazin-1-yl-pyrido[3,4-d]pyrimidin-2-yl)-pyridin-2-yl]-(2,5-difluoro-pyridin-3-yl)-amine |
| 750 | 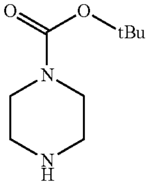 [SMILES: CC(C)(C)OC(=O)N1CCNCC1] | 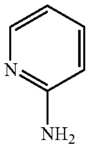 | 425.54 (M + H)+ | | [4-(5-Cyclopropyl-4-piperazin-1-yl-pyrido[3,4-d]pyrimidin-2-yl)-pyridin-2-yl]-pyridin-2-yl-amine |
| 751 | 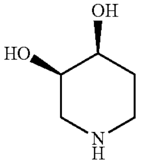 Or enantiomer | 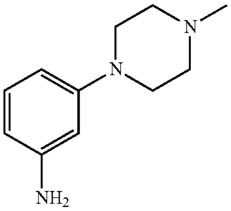 | 553.28 | ($CDCl_3$) 9.07 (s, 1H), 8.32 (d, J = 5.2 Hz, 1H), 8.08 (br s, 1H), 8.02 (s, 1H), 7.79 (d, J = 5.2 Hz, 1H), 7.24 (dd, J = 8.4 Hz, 1H)), 7.06 (br s, 1H), 6.98 (br s, 1H), 6.82 (br d, J = 7.08 Hz, 1H), 6.69 (dd, J = 8.4; 1.9 Hz, 1H), 3.95 (m, 5H), 3.55 (m, br s, 1H), 3.25 (br s, 5H), 2.60 (m, 5H), 2.34 (s, 3H), 1.91 (m, 1H), 1.7 br s (exch. H's), 1.24 (m, 2H), 0.97 (m, 2H) | (3R,4S or 3R,4S)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol Single enantiomer, unassigned |

-continued

| Ex | Amine 1 | Amine 2 | Analysis | | Name |
|---|---|---|---|---|---|
| | | | LCMS | NMR | |
| 752 | 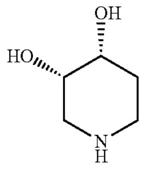 Or enantiomer | 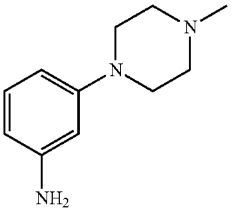 | 553.29 | ($CDCl_3$) 9.07 (s, 1H), 8.32 (d, J = 5.2 Hz, 1H), 8.08 (br s, 1H), 8.02 (s, 1H), 7.79 (d, J = 5.2 Hz, 1H), 7.24 (dd, J = 8.4 Hz, 1H)), 7.06 (br s, 1H), 6.98 (br s, 1H), 6.82 (br d, J = 7.08 Hz, 1H), 6.69 (dd, J = 8.4; 1.9 Hz, 1H), 3.95 (m, 5H), 3.55 (m, br s, 1H), 3.25 (br s, 5H), 2.60 (m, 5H), 2.34 (s, 3H), 1.91 (m, 1H), 1.7 br s (exch. H's), 1.24 (m, 2H), 0.97 (m, 2H) | (3R,4S or 3R,4S)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol Single enantiomer, unassigned |
| 753 | 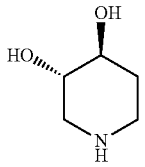 Or enantiomer | 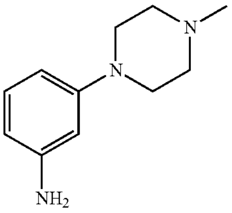 | 553.3 | ($CDCl_3$) 9.16 (s, 1H), 8.94 (s, 1H), 8.30 (d, J = 5.3 Hz, 1H), 8.08 (s, 1H), 7.91 (s, 1H), 7.66 (dd, J = 5.2; 1.0 Hz, 1H), 7.34 (app t, J = 2.0 Hz, 1H), 7.22 (dd, J = 8.0; 1.1 Hz, 1H), 7.11 (app t, J = 8.1 Hz, 1H), 6.52 (dd, J = 8.2; 1.8 Hz, 1H), 5.28-4.67 (m, 2H), 4.28-3.71 (m, 2H), 3.50 (br s, 1H), 3.15-3.11 (m, 4H), 2.61-2.53 (m, 1H), 2.49-2.45 (m, 4H), 2.23 (s, 3H), 2.18-1.73 (m, 2H), 1.44-1.11 (m, 3H), 1.10-0.90 (m, 2H) | (3S,4S or 3R,4R)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol Single enantiomer, unassigned |
| 754 | 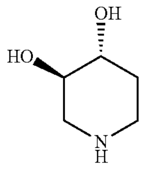 Or enantiomer | 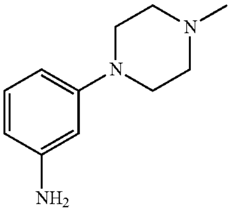 | 553.3 | ($CDCl_3$) 9.16 (s, 1H), 8.94 (s, 1H), 8.30 (d, J = 5.3 Hz, 1H), 8.08 (s, 1H), 7.91 (s, 1H), 7.66 (dd, J = 5.2; 1.0 Hz, 1H), 7.34 (app t, J = 2.0 Hz, 1H), 7.22 (dd, J = 8.0; 1.1 Hz, 1H), 7.11 (app t, J = 8.1 Hz, 1H), 6.52 (dd, J = 8.2; 1.8 Hz, 1H), 5.28-4.67 (m, 2H), 4.28-3.71 (m, 2H), 3.50 (br s, 1H), 3.15-3.11 (m, 4H), 2.61-2.53 (m, 1H), 2.49-2.45 (m, 4H), 2.23 (s, 3H), 2.18-1.73 (m, 2H), 1.44-1.11 (m, 3H), 1.10-0.90 (m, 2H) | (3S,4S or 3R,4R)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol Single enantiomer, unassigned |
| 755 | 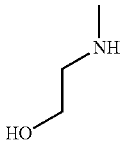 | 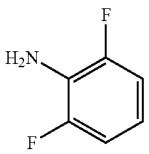 | 449 (M + H) | | {4-[5-Cyclopropyl-4-(2-methylamino-ethoxy)-pyrido[3,4-d]pyrimidin-2-yl]-pyridin-2-yl}-(2,6-difluoro-phenyl)-amine |
| 756 | 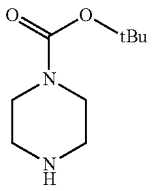 [SMILES: CC(C)(C)OC(=O)N1CCNCC1] | 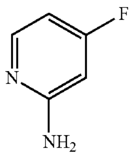 | 443 (M + H)+ | | [4-(5-Cyclopropyl-4-piperazin-1-yl-pyrido[3,4-d]pyrimidin-2-yl)-pyridin-2-yl]-(4-fluoro-pyridin-2-yl)-amine |

-continued

| | | | Analysis | | |
|---|---|---|---|---|---|
| Ex | Amine 1 | Amine 2 | LCMS | NMR | Name |
| 757 | 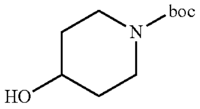 | 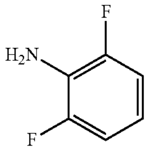 | 475 (M + H) | | {4-[5-Cyclopropyl-4-(piperidin-4-yloxy)-pyrido[3,4-d]pyrimidin-2-yl]-pyridin-2-yl}-(2,6-difluoro-phenyl)-amine |
| 758 | 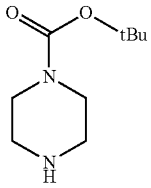 [SMILES: CC(C)(C)OC(=O)N1CCNCC1] | 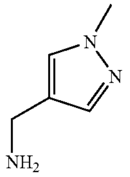 | 442 (M + H) | 1H NMR (400 MHz, DMSO-d6) 9.08 (1 H, s), 8.78-9.01 (2 H, m), 8.22 (1 H, s), 8.11 (1 H, d, J = 6.3 Hz), 7.90-8.05 (1 H, m), 7.76 (1 H, s), 7.68 (1 H, d, J = 6.8 Hz), 7.50 (1 H, s), 4.45 (2 H, br. s.), 3.88 (4 H, br. s.), 3.83 (3 H, s), 3.31 (4 H, br. s.), 2.63-2.70 (1 H, m), 1.19-1.34 (2 H, m), 1.02-1.15 (2 H, m) | [4-(5-Cyclopropyl-4-piperazin-1-yl-pyrido[3,4-d]pyrimidin-2-yl)-pyridin-2-yl]-(1-methyl-1H-pyrazol-4-ylmethyl)-amine |
| 759 | 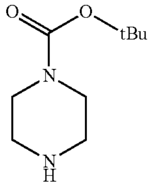 [SMILES: CC(C)(C)OC(=O)N1CCNCC1] | 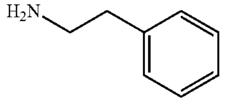 | method 5: RT: 2.56 min, MI: 452 [M + H] | 1H NMR (DMSO, 500 MHz) 8.99 (1H, s), 8.17 (4H, m), 7.55 (1H, m), 7.44 (1H, m), 7.28 (4H, m), 7.20 (1H, m), 6.89 (1H, m), 3.75 (4H, s), 3.56 (6H, m), 2.88 (2H, m), 2.66 (1H, m), 1.25 (2H, m), 1.03 (2H, m). | [4-(5-Cyclopropyl-4-piperazin-1-yl-pyrido[3,4-d]pyrimidin-2-yl)-pyridin-2-yl]-phenethyl-amine |
| 760 | 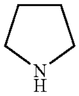 | 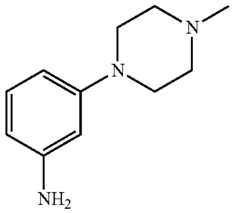 | 507.35 (M + H) | | [4-(5-Cyclopropyl-4-pyrrolidin-1-yl-pyrido[3,4-d]pyrimidin-2-yl)-pyridin-2-yl]-[3-(4-methyl-piperazin-1-yl)-phenyl]-amine |
| 761 | 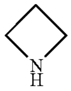 | 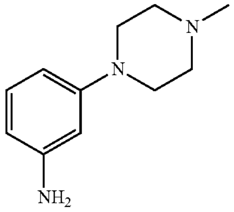 | 493.39 (M + H) | | [4-(4-Azetidin-1-yl-5-cyclopropyl-pyrido[3,4-d]pyrimidin-2-yl)-pyridin-2-yl]-[3-(4-methyl-piperazin-1-yl)-phenyl]-amine |
| 762 | 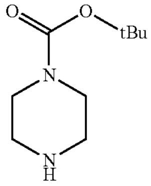 [SMILES: CC(C)(C)OC(=O)N1CCNCC1] | 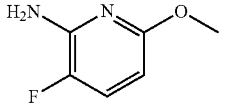 | method 5: RT: 3.12 min, MI: 473 [M + H] | | [4-(5-Cyclopropyl-4-piperazin-1-yl-pyrido[3,4-d]pyrimidin-2-yl)-pyridin-2-yl]-(3-fluoro-6-methoxy-pyridin-2-yl)-amine |
| 763 | 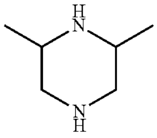 | 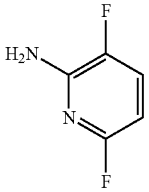 | method 5: RT: 3.03 min, MI: 489 [M + H] | | {4-[5-Cyclopropyl-4-(3,5-dimethyl-piperazin-1-yl)-pyrido[3,4-d]pyrimidin-2-yl]-pyridin-2-yl}-(3,6-difluoro-pyridin-2-yl)-amine |

-continued

| Ex | Amine 1 | Amine 2 | Analysis LCMS | Analysis NMR | Name |
|---|---|---|---|---|---|
| 764 | 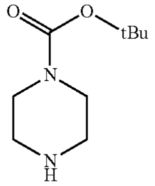 [SMILES: CC(C)(C)OC(=O)N1CCNCC1] | 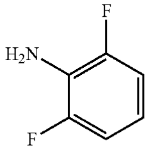 | method 5: RT: 4.20 min, MI: 478.39 [M + H] | 1H NMR (500 MHz, DMSO) 8.93 (1H, s), 8.75 (1H, s), 8.11 (1H, d), 8.10 (1H, s), 7.50 (1H, d), 7.26-7.23 (1H, m), 7.15 (2H, t), 4.09-4.08 (2H, m), 3.67 (4H, s, br), 2.80 (4H, s, br), 2.58-2.54 (1H, m), 1.26-1.24 (2H, m), 1.03-1.01 (2H, m). | [4-(5-Cyclopropyl-4-piperazin-1-yl-pyrido[3,4-d]pyrimidin-2-yl)-5-fluoro-pyridin-2-yl]-(2,6-difluoro-phenyl)-amine |
| 765 | 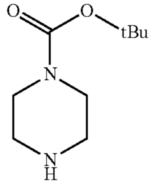 [SMILES: CC(C)(C)OC(=O)N1CCNCC1] | 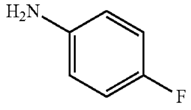 | method 5: RT: 4.58 min, MI: 460.40 [M + H] | 1H NMR (500 MHz, DMSO) 9.31 (1H, s), 8.94 (1H, s), 8.23 (1H, d), 8.18 (1H, s), 8.12 (1H, s), 7.67 (2H, dd), 7.58 (1H, 7.11 (2H, t), 3.69 (4H, s, br), 2.88 (4H, s, br), 2.60-2.56 (1H, m), 1.26-1.24 (2H, m), 1.03-1.02 (2H, m). | [4-(5-Cyclopropyl-4-piperazin-1-yl-pyrido[3,4-d]pyrimidin-2-yl)-5-fluoro-pyridin-2-yl]-(4-fluoro-phenyl)-amine |
| 766 | 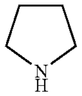 | 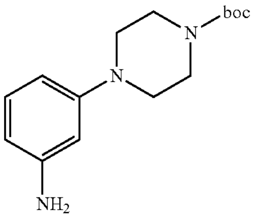 | 493.39 (M + H) | | [4-(5-Cyclopropyl-4-pyrrolidin-1-yl-pyrido[3,4-d]pyrimidin-2-yl)-pyridin-2-yl]-(3-piperazin-1-yl-phenyl)-amine |
| 767 | 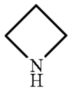 | 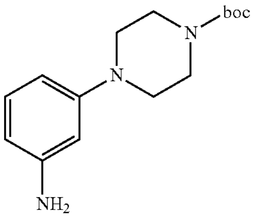 | 479.29 (M + H) | | [4-(4-Azetidin-1-yl-5-cyclopropyl-pyrido[3,4-d]pyrimidin-2-yl)-pyridin-2-yl]-(3-piperazin-1-yl-phenyl)-amine |
| 768 | 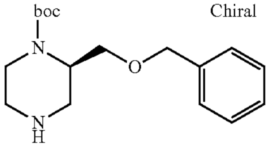 Chiral | 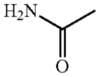 | 510.25 | | N-{4-[4-((R)-3-Benzyloxymethyl-piperazin-1-yl)-5-cyclopropyl-pyrido[3,4-d]pyrimidin-2-yl]-pyridin-2-yl}-acetamide |
| 769 | 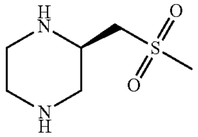 | 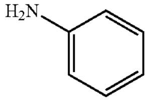 | 516 | | {4-[5-Cyclopropyl-4-((R)-3-methanesulfonyl-methyl-piperazin-1-yl)-pyrido[3,4-d]pyrimidin-2-yl]-pyridin-2-yl}-phenyl-amine |
| 770 | 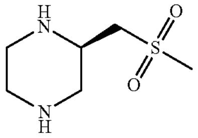 | 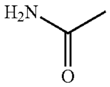 | 482 | | N-{4-[5-Cyclopropyl-4-((R)-3-methanesulfonyl-methyl-piperazin-1-yl)-pyrido[3,4-d]pyrimidin-2-yl]-pyridin-2-yl}-acetamide |

-continued

| Ex | Amine 1 | Amine 2 | Analysis LCMS | Analysis NMR | Name |
|---|---|---|---|---|---|
| 771 | 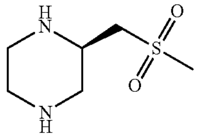 | 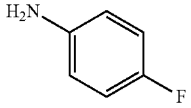 | 534.2 | | {4-[5-Cyclopropyl-4-((R)-3-methanesulfonyl-methyl-piperazin-1-yl)-pyrido[3,4-d]pyrimidin-2-yl]-pyridin-2-yl}-(4-fluoro-phenyl)-amine |
| 772 | 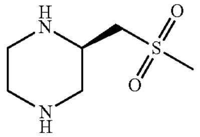 | 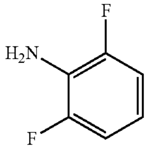 | 552.2 | | {4-[5-Cyclopropyl-4-((R)-3-methanesulfonyl-methyl-piperazin-1-yl)-pyrido[3,4-d]pyrimidin-2-yl]-pyridin-2-yl}-(2,6-difluoro-phenyl)-amine |
| 773 | 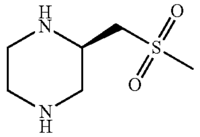 | 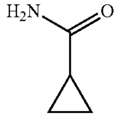 | 508.2 | | Cyclopropanecarboxylic acid {4-[5-cyclopropyl-4-((R)-3-methanesulfonyl-methyl-piperazin-1-yl)-pyrido[3,4-d]pyrimidin-2-yl]-pyridin-2-yl}-amide |
| 774 | 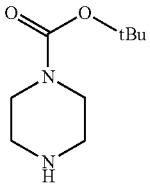 [SMILES: CC(C)(C)OC(=O)N1CCNCC1] | 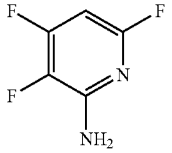 | 479 (M + H)+ | $^1$H NMR (400 MHz, DMSO-$d_6$) δ ppm 10.08 (s, 1 H) 8.96-9.02 (m, 1 H) 8.89-9.13 (m, 3 H) 8.43-8.53 (m, 1 H) 8.19 (s, 1 H) 8.00 (dd, J = 5.1, 1.4 Hz, 1 H) 7.01 (dt, J = 9.3, 3.0 Hz, 1 H) 3.77-4.13 (m, 4 H) 3.28-3.41 (m, 4 H) 2.63-2.74 (m, 1 H) 1.20-1.33 (m, 2 H) 1.04-1.13 (m, 2 H) | [4-(5-Cyclopropyl-4-piperazin-1-yl-pyrido[3,4-d]pyrimidin-2-yl)-pyridin-2-yl]-(3,4,6-trifluoro-pyridin-2-yl)-amine |
| 775 | 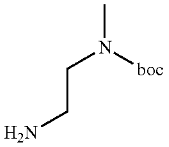 | 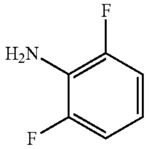 | 448 (M + H) | | N-{5-Cyclopropyl-2-[2-(2,6-difluoro-phenylamino)-pyridin-4-yl]-pyrido[3,4-d]pyrimidin-4-yl}-N'-methyl-ethane-1,2-diamine |
| 776 | 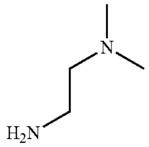 | 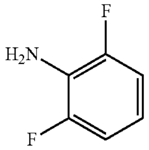 | 462 (M + H) | | N-{5-Cyclopropyl-2-[2-(2,6-difluoro-phenylamino)-pyridin-4-yl]-pyrido[3,4-d]pyrimidin-4-yl}-N',N'-dimethyl-ethane-1,2-diamine |
| 777 | 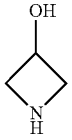 | 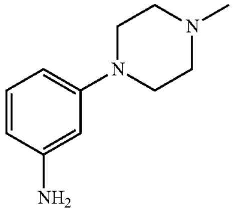 | 509.26 (M + H) | | 1-(5-Cyclopropyl-2-{2-[3-(4-methyl-piperazin-1-yl)-phenylamino]-pyridin-4-yl}-pyrido[3,4-d]pyrimidin-4-yl)-azetidin-3-ol |

-continued

| | | | Analysis | | |
|---|---|---|---|---|---|
| Ex | Amine 1 | Amine 2 | LCMS | NMR | Name |
| 778 | 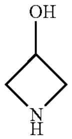 | 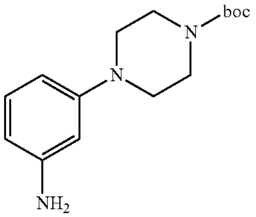 | 495.29 (M + H) | | 1-{5-Cyclopropyl-2-[2-(3-piperazin-1-yl-phenylamino)-pyridin-4-yl]-pyrido[3,4-d]pyrimidin-4-yl}-azetidin-3-ol |
| 779 | 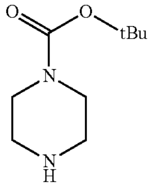 [SMILES: CC(C)(C)OC(=O)N1CCNCC1] | 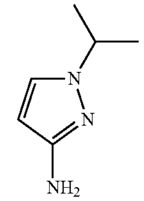 | 456.22 (M + H) | | [4-(5-Cyclopropyl-4-piperazin-1-yl-pyrido[3,4-d]pyrimidin-2-yl)-pyridin-2-yl]-(1-isopropyl-1H-pyrazol-3-yl)-amine |
| 780 | 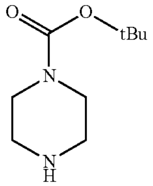 [SMILES: CC(C)(C)OC(=O)N1CCNCC1] | 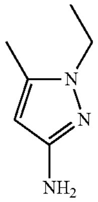 | 456.24 (M + H) | | [4-(5-Cyclopropyl-4-piperazin-1-yl-pyrido[3,4-d]pyrimidin-2-yl)-pyridin-2-yl]-(1-ethyl-5-methyl-1H-pyrazol-3-yl)-amine |
| 781 | 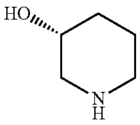 | 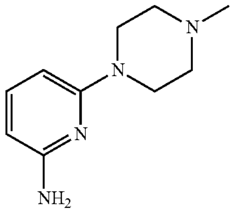 | 538.36 (M + H) | | (R)-1-(5-Cyclopropyl-2-{2-[6-(4-methyl-piperazin-1-yl)-pyridin-2-ylamino]-pyridin-4-yl}-pyrido[3,4-d]pyrimidin-4-yl)-piperidin-3-ol |
| 782 | 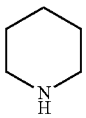 | 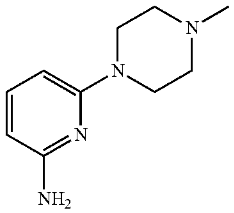 | 523.66 (M + H) | | [4-(5-Cyclopropyl-4-piperidin-1-yl-pyrido[3,4-d]pyrimidin-2-yl)-pyridin-2-yl]-[6-(4-methyl-piperazin-1-yl)-pyridin-2-yl]-amine |
| 783 | 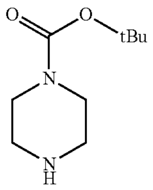 [SMILES: CC(C)(C)OC(=O)N1CCNCC1] | 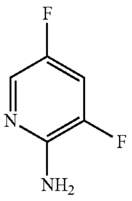 | 475.19 (MH)+ | | [4-(5-Cyclobutyl-4-piperazin-1-yl-pyrido[3,4-d]pyrimidin-2-yl)-pyridin-2-yl]-(3,5-difluoro-pyridin-2-yl)-amine |
| 784 | 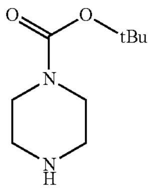 [SMILES: CC(C)(C)OC(=O)N1CCNCC1] | 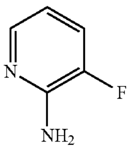 | 457.25 (MH)+ | | [4-(5-Cyclobutyl-4-piperazin-1-yl-pyrido[3,4-d]pyrimidin-2-yl)-pyridin-2-yl]-(3-fluoro-pyridin-2-yl)-amine |

-continued

| Ex | Amine 1 | Amine 2 | Analysis: LCMS | Analysis: NMR | Name |
|---|---|---|---|---|---|
| 785 | 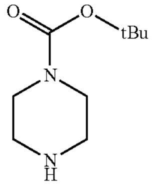 [SMILES: CC(C)(C)OC(=O)N1CCNCC1] | 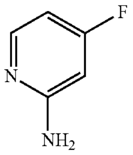 | 457.29 (M + H)+ | | [4-(5-Cyclobutyl-4-piperazin-1-yl-pyrido[3,4-d]pyrimidin-2-yl)-pyridin-2-yl]-(4-fluoro-pyridin-2-yl)-amine |
| 786 | 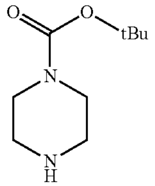 [SMILES: CC(C)(C)OC(=O)N1CCNCC1] | 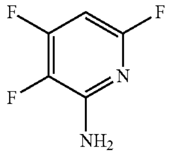 | 593.28 (M + H)+ | $^{1}H$ NMR (400 MHz, DMSO-$d_6$) δ ppm 10.09 (s, 1 H) 9.15 (s, 1 H) 8.79-8.96 (m, 3 H) 8.48 (d, J = 5.3 Hz, 1 H) 8.00 (dd, J = 5.1, 1.4 Hz, 1 H) 7.02 (dt, J = 9.5, 3.0 Hz, 1 H) 4.17-4.32 (m, 1 H) 3.81-3.92 (m, 4 H) 3.19-3.39 (m, 4 H) 1.86-2.44 (m, 6 H) | [4-(5-Cyclobutyl-4-piperazin-1-yl-pyrido[3,4-d]pyrimidin-2-yl)-pyridin-2-yl]-(3,4,6-trifluoro-pyridin-2-yl)-amine |
| 787 | 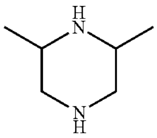 | 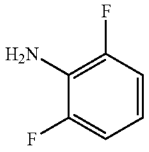 | method 5: RT: 3.09 min, MI: 488 [M + H] | | {4-[5-Cyclopropyl-4-(3,5-dimethyl-piperazin-1-yl)-pyrido[3,4-d]pyrimidin-2-yl]-pyridin-2-yl}-(2,6-difluoro-phenyl)-amine |
| 788 | 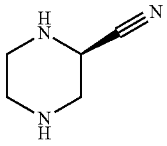 | 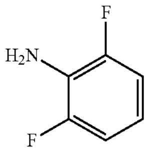 | method 5: RT: 4.07 min, MI: 485 [M + H] | | (R)-4-{5-Cyclopropyl-2-[2-(2,6-difluoro-phenylamino)-pyridin-4-yl]-pyrido[3,4-d]pyrimidin-4-yl}-piperazine-2-carbonitrile |
| 789 | 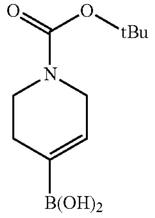 [SMILES: CC(C)(C)OC(=O)N1CC=C(B(O)O)CC1] | 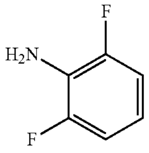 | 457 (M + H) | | {4-[5-Cyclopropyl-4-(1,2,3,6-tetrahydro-pyridin-4-yl)-pyrido[3,4-d]pyrimidin-2-yl]-pyridin-2-yl}-(2,6-difluoro-phenyl)-amine |
| 790 | 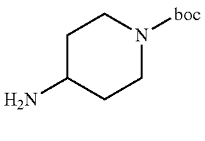 | 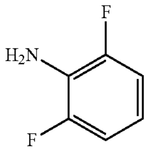 | 474 (M + H) | | {5-Cyclopropyl-2-[2-(2,6-difluoro-phenylamino)-pyridin-4-yl]-pyrido[3,4-d]pyrimidin-4-yl}-piperidin-4-yl-amine |
| 791 | 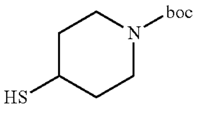 | 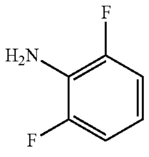 | 491 (M + H) | | {4-[5-Cyclopropyl-4-(piperidin-4-ylsulfanyl)-pyrido[3,4-d]pyrimidin-2-yl]-pyridin-2-yl}-(2,6-difluoro-phenyl)-amine |

-continued

| | | | Analysis | | |
|---|---|---|---|---|---|
| Ex | Amine 1 | Amine 2 | LCMS | NMR | Name |
| 792 | 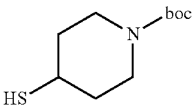 | 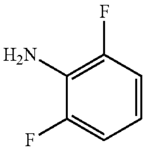 | 491 (M + H) | | {4-[5-Cyclopropyl-4-(piperidin-4-ylsulfanyl)-pyrido[3,4-d]pyrimidin-2-yl]-pyridin-2-yl}-(2,6-difluoro-phenyl)-amine |
| 793 | 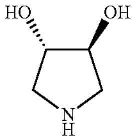 | 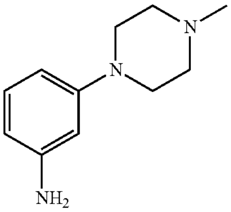 | 539.5 (M + H) | | (3S,4S)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidine-3,4-diol |
| 794 | 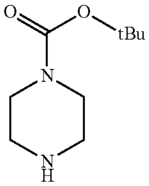 [SMILES: CC(C)(C)OC(=O)N1CCNCC1] | 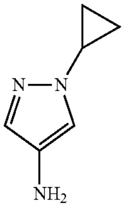 | 454.25 | | [4-(5-Cyclopropyl-4-piperazin-1-yl-pyrido[3,4-d]pyrimidin-2-yl)-pyridin-2-yl]-(1-cyclopropyl-1H-pyrazol-4-yl)-amine |
| 795 | 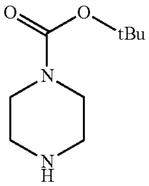 [SMILES: CC(C)(C)OC(=O)N1CCNCC1] | 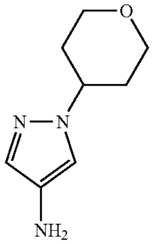 [SMILES: Nc1cnn(C2CCOCC2)c1] | 498.25 | | [4-(5-Cyclopropyl-4-piperazin-1-yl-pyrido[3,4-d]pyrimidin-2-yl)-pyridin-2-yl]-[1-(tetrahydro-pyran-4-yl)-1H-pyrazol-4-yl]-amine |
| 796 | 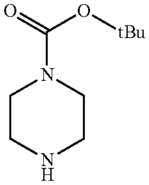 [SMILES: CC(C)(C)OC(=O)N1CCNCC1] | 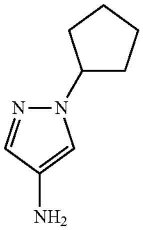 [SMILES: Nc1cnn(C2CCCC2)c1] | 482.2 | | (1-Cyclopentyl-1H-pyrazol-4-yl)-[4-(5-cyclopropyl-4-piperazin-1-yl-pyrido[3,4-d]pyrimidin-2-yl)-pyridin-2-yl]-amine |
| 797 | 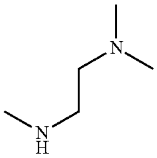 | 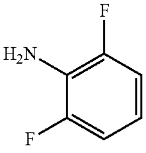 | 476 (M + H) | | N-{5-Cyclopropyl-2-[2-(2,6-difluoro-phenylamino)-pyridin-4-yl]-pyrido[3,4-d]pyrimidin-4-yl}-N,N',N'-trimethyl-ethane-1,2-diamine |

-continued

| Ex | Amine 1 | Amine 2 | Analysis LCMS | Analysis NMR | Name |
|---|---|---|---|---|---|
| 798 | 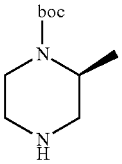 | 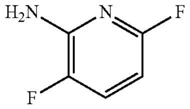 | method: 5, RT: 2.78 min, MI: 489 [M + H] | 1H NMR (DMSO, 500 MHz) 9.70 (1H, s), 9.17 (1H, s, br), 9.11 (1H, s), 8.69 (1H, s), 8.46 (1H, m), 7.98 (1H, m), 7.85 (1H, m), 6.71 (1H, m), 4.28 (1H, m), 4.26 (1H, m), 4.06 (1H, m), 3.91 (1H, m), 3.79 (1H, m), 3.65 (1H, m), 3.23 (1H, m), 3.06 (1H, m), 2.52 (3H, s), 2.16 (2H, m), 2.21 (2H, m), 2.09 (1H, m), 1.91 (1H, m). | {4-[5-Cyclobutyl-4-((S)-3-methyl-piperazin-1-yl)-pyrido[3,4-d]pyrimidin-2-yl]-pyridin-2-yl}-(3,6-difluoro-pyridin-2-yl)-amine |
| 799 | 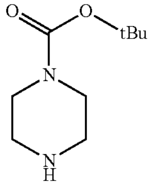 | 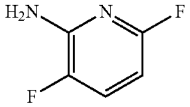 | method 5: RT: 2.72 min, MI: 475 [M + H] | 1H NMR (DMSO, 500 MHz) 9.70 (1 H, s), 9.14 (1H, s, br), 9.02 (1H, s), 8.80 (1H, d), 8.46 (1H, m), 7.97 (1H, m), 7.86 (1H, m), 6.71 (1H, m), 4.25 (1H, m), 3.86 (4H, m), 3.58 (4H, m), 2.80 (2H, m), 2.21 (2H, m), 2.08 (1H, m), 1.93 (1H, m). | [4-(5-Cyclobutyl-4-piperazin-1-yl-pyrido[3,4-d]pyrimidin-2-yl)-pyridin-2-yl]-(3,6-difluoro-pyridin-2-yl)-amine |
| 800 | 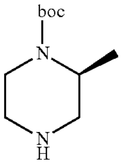 | 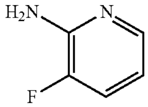 | method 5: RT: 1.62 min, MI: 457 [M + H] | | {4-[5-Cyclopropyl-4-((S)-3-methyl-piperazin-1-yl)-pyrido[3,4-d]pyrimidin-2-yl]-pyridin-2-yl}-(3-fluoro-pyridin-2-yl)-amine |
| 801 | 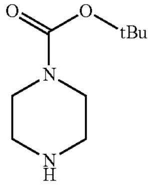 [SMILES: CC(C)(C)OC(=O)N1CCNCC1] | 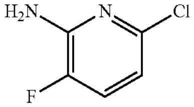 | method 5: RT: 2.59 min, MI: 477 [M + H] | | (6-Chloro-3-fluoro-pyridin-2-yl)-[4-(5-cyclopropyl-4-piperazin-1-yl-pyrido[3,4-d]pyrimidin-2-yl)-pyridin-2-yl]-amine |
| 802 | 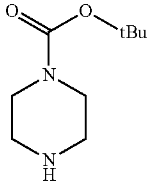 [SMILES: CC(C)(C)OC(=O)N1CCNCC1] | Chiral 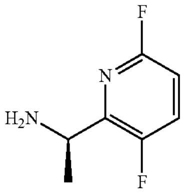 | method 5: RT: 2.57 min, MI: 489.49 [M + H] | 1H NMR (500 MHz, DMSO) 8.93 (1H, s), 8.06 (1H, s), 8.01 (1H, d), 7.92-7.84 (1H, m), 7.66 (1H, s), 7.39 (1H, d), , 7.33 (1H, d), 7.12-7.07 (1H, m), 5.42 (1H, t, br), 3.83-3.57 (4H, m, br), 3.16 (1H, s, br), 2.84 (4H, s, br), 2.61 (1H, m, br), 1.45 (3H, d), 1.25-1.22 (2H, m), 1.03-1.01 (2H, m). | [4-(5-Cyclopropyl-4-piperazin-1-yl-pyrido[3,4-d]pyrimidin-2-yl)-pyridin-2-yl]-[(R)-1-(3,6-difluoro-pyridin-2-yl)-ethyl]-amine |
| 803 | 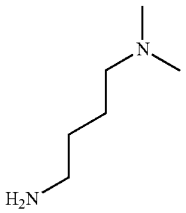 | 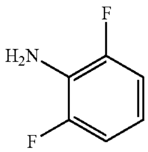 | 490 (M + H) | | N-{5-Cyclopropyl-2-[2-(2,6-difluoro-phenylamino)-pyridin-4-yl]-pyrido[3,4-d]pyrimidin-4-yl}-N',N'-dimethyl-butane-1,4-diamine |

-continued

| | | | Analysis | | |
|---|---|---|---|---|---|
| Ex | Amine 1 | Amine 2 | LCMS | NMR | Name |
| 804 | 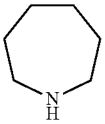 | 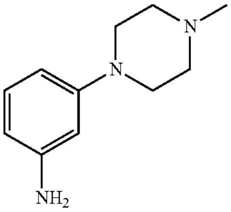 | 535.50 (M + H) | | [4-(4-Azepan-1-yl-5-cyclopropyl-pyrido[3,4-d]pyrimidin-2-yl)-pyridin-2-yl]-[3-(4-methyl-piperazin-1-yl)-phenyl]-amine |
| 805 | 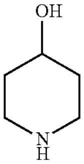 | 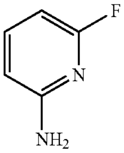 | 458.36 (M + H) | | 1-{5-Cyclopropyl-2-[2-(6-fluoro-pyridin-2-ylamino)-pyridin-4-yl]-pyrido[3,4-d]pyrimidin-4-yl}-piperidin-4-ol |
| 806 | 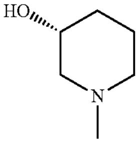 | 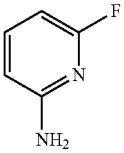 | 458.20 (M + H) | | (R)-1-{5-Cyclopropyl-2-[2-(6-fluoro-pyridin-2-ylamino)-pyridin-4-yl]-pyrido[3,4-d]pyrimidin-4-yl}-piperidin-3-ol |
| 807 | 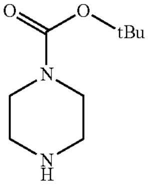 [SMILES: CC(C)(C)OC(=O)N1CCNCC1] | 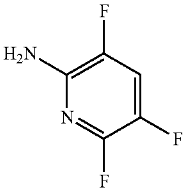 | method 5: RT: 2.88 min, MI: 493 [M + H] | 1H NMR (DMSO, 500 MHz) 9.74 (1H, s), 9.13 (1H, s, br), 8.80 (2H, dd), 8.42 (1H, d), 8.26 (1H, m), 7.94 (1H, d), 4.23 (1H, m), 3.84 (4H, m), 3.25 (4H, m), 2.38 (2H, m), 2.21 (2H, m), 2.10 (1H, m), 1.89 (1H, m). | [4-(5-Cyclobutyl-4-piperazin-1-yl-pyrido[3,4-d]pyrimidin-2-yl)-pyridin-2-yl]-(3,5,6-trifluoro-pyridin-2-yl)-amine |
| 808 | 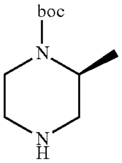 | 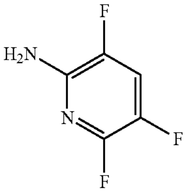 | method 5: RT: 2.90 min, MI: 506 [M + H] | 1H NMR (DMSO, 500 MHz) 9.76 (1H, s), 9.17 (1H, s, br), 9.11 (1H, s), 8.70 (1H, s), 8.44 (1H, m), 8.28 (1H, m), 7.95 (1H, m), 4.27 (1H, m), 4.26 (1H, m), 4.06 (1H, m), 3.91 (1H, m), 3.79 (1H, m), 3.65 (1H, m), 3.23 (1H, m), 3.06 (1H, m), 2.53 (3H, s), 2.16 (2H, m), 2.16 (2H, m), 2.07 (1H, m), 1.89 (1H, m). | {4-[5-Cyclobutyl-4-((S)-3-methyl-piperazin-1-yl)-pyrido[3,4-d]pyrimidin-2-yl]-pyridin-2-yl}-(3,5,6-trifluoro-pyridin-2-yl)-amine |
| 809 | 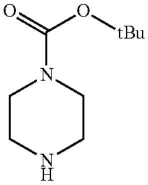 [SMILES: CC(C)(C)OC(=O)N1CCNCC1] | 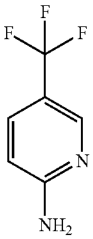 | 507.19 (MH)+ | | [4-(5-Cyclobutyl-4-piperazin-1-yl-pyrido[3,4-d]pyrimidin-2-yl)-pyridin-2-yl]-(5-trifluoromethyl-pyridin-2-yl)-amine |
| 810 | 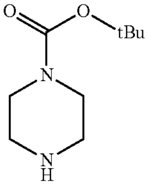 [SMILES: CC(C)(C)OC(=O)N1CCNCC1] | 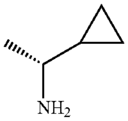 | 416.26 (M + H) | | ((R)-1-Cyclopropyl-ethyl)-[4-(5-cyclopropyl-4-piperazin-1-yl-pyrido[3,4-d]pyrimidin-2-yl)-pyridin-2-yl]-amine |

-continued

| | | | Analysis | | |
|---|---|---|---|---|---|
| Ex | Amine 1 | Amine 2 | LCMS | NMR | Name |
| 811 | 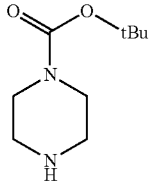 [SMILES: CC(C)(C)OC(=O)N1CCNCC1] | 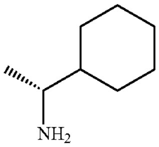 | 458.29 (M + H) | | ((R)-1-Cyclohexyl-ethyl)-[4-(5-cyclopropyl-4-piperazin-1-yl-pyrido[3,4-d]pyrimidin-2-yl)-pyridin-2-yl]-amine |
| 812 | 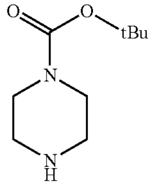 [SMILES: CC(C)(C)OC(=O)N1CCNCC1] | 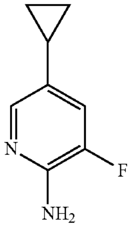 [SMILES: Nc1ncc(C2CC2)cc1F] | 483.21 (MH)+ | | (5-Cyclopropyl-3-fluoro-pyridin-2-yl)-[4-(5-cyclopropyl-4-piperazin-1-yl-pyrido[3,4-d]pyrimidin-2-yl)-pyridin-2-yl]-amine |
| 813 | 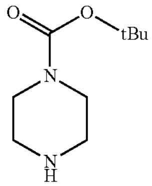 [SMILES: CC(C)(C)OC(=O)N1CCNCC1] | 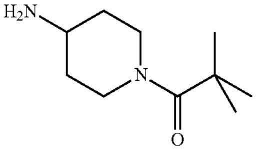 | method 5: RT: 2.60 min, MI: 515.51 [M + H] | 1H NMR (500 MHz, DMSO, 90° C.) 9.07 (1H, s), 8.23 (1H, s), 8.13 (1H, d), 7.76 (1H, s), 7.57 (1H, dd), 4.22-4.19 (2H, m), 4.11-4.06 (1H, m), 3.97 (4H, t, br), 3.35 (4H, t, br), 3.15-3.08 (2H, m), 2.70-2.66 (1H, m), 2.05-2.03 (2H, m), 1.52-1.42 (2H, m), 1.29-1.27 (2H, m), 1.26 (9H, s), 1.05-1.03 (2H, m). | 1-{4-[4-(5-Cyclopropyl-4-piperazin-1-yl-pyrido[3,4-d]pyrimidin-2-yl)-pyridin-2-ylamino]-piperidin-1-yl}-2,2-dimethyl-propan-1-one |
| 814 | 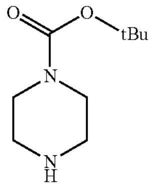 [SMILES: CC(C)(C)OC(=O)N1CCNCC1] | 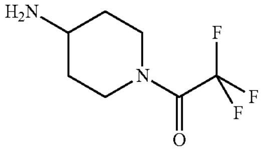 [SMILES: NC1CCN(C(=O)C(F)(F)F)CC1] | method 5: RT: 2.43 min, MI: 513.41 [M + H] | 1H NMR (500 MHz, DMSO, 90° C.) 9.07 (1H, s), 8.23 (1H, s), 8.10 (1H, d), 7.81 (1H, s), 7.58 (1H, dd), 3.97 (4H, t, br), 3.86-3.81 (1H, m), 3.34 (4H, t, br), 3.20 (2H, q), 3.01-2.98 (2H, m), 2.70-2.67 (1H, m), 2.61 (2H, t), 2.00-1.97 (2H, m), 1.66-1.57 (2H, m), 1.30-1.25 (2H, m), 1.05-1.03 (2H, m). | [4-(5-Cyclopropyl-4-piperazin-1-yl-pyrido[3,4-d]pyrimidin-2-yl)-pyridin-2-yl]-[1-(2,2,2-trifluoro-ethyl)-piperidin-4-yl]-amine |
| 815 | 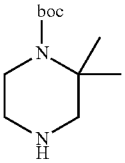 | 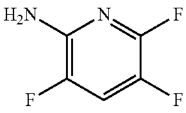 | method 5: RT: 3.71 min, MI: 507.41 [M + H] | 1H NMR (500 MHz, DMSO, 90° C.) 9.07 (1H, s), 8.71 (1H, s), 8.43 (1H, d), 8.26 (1H, s), 8.12 (1H, q), 7.98 (1H, dd), 4.02 (2H, t, br), 3.95 (2H, s), 3.38 (2H, t), 2.56-2.54 (1H, m), 1.31 (6H, s), 1.30-1.27 (2H, m), 1.02 (2H, dd). | {4-[5-Cyclopropyl-4-(3,3-dimethyl-piperazin-1-yl)-pyrido[3,4-d]pyrimidin-2-yl]-pyridin-2-yl}-(3,5,6-trifluoro-pyridin-2-yl)-amine |
| 816 | 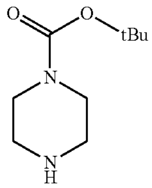 [SMILES: CC(C)(C)OC(=O)N1CCNCC1] | 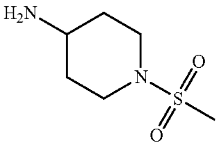 | method 5: RT: 2.06 min, MI: 509.44 [M + H] | 1H NMR (500 MHz, DMSO, 90° C.) 9.07 (1H, s), 8.22 (1H, s), 8.14 (1H, d), 7.74 (1H, s), 7.57 (1H, dd), 3.97 (4H, t, br), 3.65-3.60 (2H, m), 3.35 (4H, t, br), 3.04-2.97 (2H, m), 2.90 (3H, s), 2.71-2.65 (1H, m), 2.12-2.07 (2H, m), 1.68-1.59 (2H, m), 1.29-1.26 (2H, m), 1.05-1.03 (2H, m). | [4-(5-Cyclopropyl-4-piperazin-1-yl-pyrido[3,4-d]pyrimidin-2-yl)-pyridin-2-yl]-(1-methanesulfonyl-piperidin-4-yl)-amine |

-continued

| | | | Analysis | | |
|---|---|---|---|---|---|
| Ex | Amine 1 | Amine 2 | LCMS | NMR | Name |
| 817 | 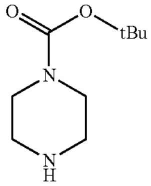 [SMILES: CC(C)(C)OC(=O)N1CCNCC1] | 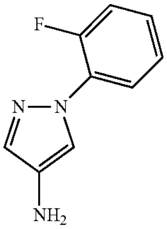 [SMILES: Nc1cnn(-c2ccccc2F)c1] | 508.05 | | [4-(5-Cyclopropyl-4-piperazin-1-yl-pyrido[3,4-d]pyrimidin-2-yl)-pyridin-2-yl]-[1-(2-fluoro-phenyl)-1H-pyrazol-4-yl]-amine |
| 818 | 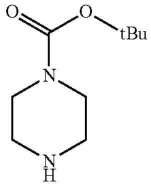 [SMILES: CC(C)(C)OC(=O)N1CCNCC1] | 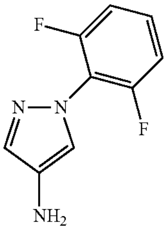 [SMILES: Nc1cnn(-c2c(F)cccc2F)c1] | 526.2 | | [4-(5-Cyclopropyl-4-piperazin-1-yl-pyrido[3,4-d]pyrimidin-2-yl)-pyridin-2-yl]-[1-(2,6-difluoro-phenyl)-1H-pyrazol-4-yl]-amine |
| 820 | 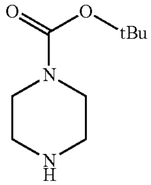 [SMILES: CC(C)(C)OC(=O)N1CCNCC1] | 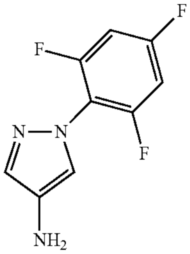 [SMILES: Nc1cnn(-c2c(F)cc(F)cc2F)c1] | 544.2 | | [4-(5-Cyclopropyl-4-piperazin-1-yl-pyrido[3,4-d]pyrimidin-2-yl)-pyridin-2-yl]-[1-(2,4,6-trifluoro-phenyl)-1H-pyrazol-4-yl]-amine |
| 821 | 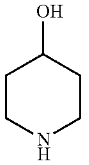 | 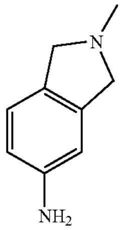 | 494.25 (M + H) | | 1-{5-Cyclopropyl-2-[2-(2-methyl-2,3-dihydro-1H-isoindol-5-ylamino)-pyridin-4-yl]-pyrido[3,4-d]pyrimidin-4-yl}-piperidin-4-ol |
| 822 | 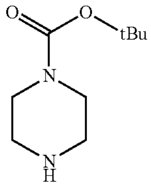 [SMILES: CC(C)(C)OC(=O)N1CCNCC1] | 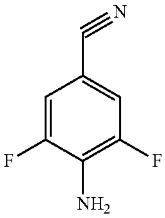 [SMILES: N#Cc1cc(F)c(N)c(F)c1] | 486 (M + H − NH3) | 1H NMR (400 MHz, DMSO-d6) 9.10 (1 H, s), 8.93 (3 H, d, J = 7.8 Hz), 8.45-8.51 (1 H, m), 8.22 (1H, s), 8.03 (1 H, dd, J = 7.7, 1.9 Hz), 7.97 (1 H, ddd, J = 10.6, 8.8, 2.9 Hz), 7.86 (1 H, dt, J = 8.5, 1.5 Hz), 4.00 (4 H, br. s.), 3.40 (4 H, br. s.), 2.65-2.78 (1 H, m), 1.26-1.36 (2 H, m), 1.07-1.16 (2 H, m) | 4-[4-(5-Cyclopropyl-4-piperazin-1-yl-pyrido[3,4-d]pyrimidin-2-yl)-pyridin-2-ylamino]-3,5-difluoro-benzamide |
| 823 | 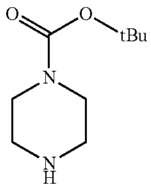 [SMILES: CC(C)(C)OC(=O)N1CCNCC1] | 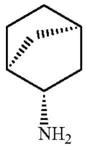 | 442 (M + H) | 1H NMR (400 MHz, DMSO-d6) 9.10 (1 H, s), 8.97 (2 H, br. s.), 8.25 (1 H, s), 8.08 (2 H, d, J = 6.3 Hz), 7.70 (1 H, d, J = 5.8 Hz), 4.19-4.47 (4 H, m), 3.66 (2 H, br. s.), 3.34 (4 H, br. s.), 2.65-2.76 (1 H, m), 2.32-2.39 (2 H, m), 1.85-1.96 (1H, m), 1.43-1.69 (4H, m), 1.05-1.41 (8 H, m) | (1S,2S,4R)-Bicyclo[2.2.1]hept-2-yl-[4-(5-cyclopropyl-4-piperazin-1-yl-pyrido[3,4-d]pyrimidin-2-yl)-pyridin-2-yl]-amine |

-continued

| | | | Analysis | | |
|---|---|---|---|---|---|
| Ex | Amine 1 | Amine 2 | LCMS | NMR | Name |
| 824 | 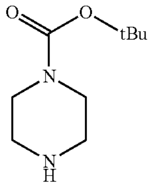 [SMILES: CC(C)(C)OC(=O)N1CCNCC1] | 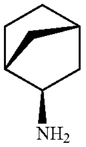 | 442 (M + H) | 1H NMR (400 MHz, DMSO-d6) 9.09 (1 H, s), 8.82-9.05 (2 H, m), 8.24 (1 H, s), 8.08 (2 H, d, J = 6.8 Hz), 7.63-7.74 (1 H, m), 4.02-4.30 (4 H, m), 3.63-3.67 (2 H, m), 3.34 (4 H, br. s.), 2.66-2.71 (1 H, m), 2.26-2.41 (2 H, m), 1.90 (1 H, m), 1.54 (4 H, br. s.), 1.06-1.42 (8 H, m) | (1R,2R,4S)-Bicyclo[2.2.1]hept-2-yl-[4-(5-cyclopropyl-4-piperazin-1-yl-pyrido[3,4-d]pyrimidin-2-yl)-pyridin-2-yl]-amine |
| 825 | 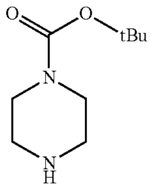 [SMILES: CC(C)(C)OC(=O)N1CCNCC1] | 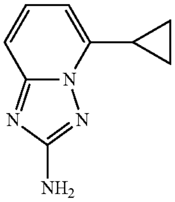 [SMILES: Nc1nc2cccc(C3CC3)n2n1] | 505.24 (MH)+ | | [4-(5-Cyclopropyl-4-piperazin-1-yl-pyrido[3,4-d]pyrimidin-2-yl)-pyridin-2-yl]-(5-cyclopropyl-[1,2,4]triazolo[1,5-a]pyridin-2-yl)-amine |
| 826 | 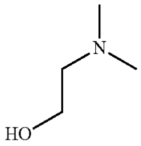 | 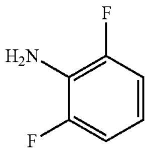 | 463 (M + H) | | {4-[5-Cyclopropyl-4-(2-dimethylamino-ethoxy)-pyrido[3,4-d]pyrimidin-2-yl]-pyridin-2-yl}-(2,6-difluoro-phenyl)-amine |
| 827 | 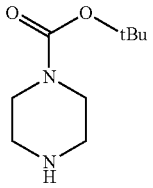 [SMILES: CC(C)(C)OC(=O)N1CCNCC1] | 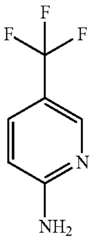 | 493.19 (MH)+ | | [4-(5-Cyclopropyl-4-piperazin-1-yl-pyrido[3,4-d]pyrimidin-2-yl)-pyridin-2-yl]-(5-trifluoromethyl-pyridin-2-yl)-amine |
| 828 | 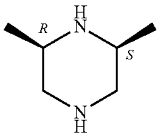 | 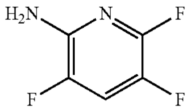 | method 5: RT: 2.69 min, MI: 507 [M + H] | 1H NMR (DMSO, 400 MHz, 90° C.) 9.08 (1H, s), 8.67 (1H, s), 8.43 (1H, dd), 8.23 (1H, s), 8.12 (1H, m), 7.97 (1H, m), 4.39 (2H, m), 3.23 (2H, m), 2.67 (1H, m), 1.34 (6H, m), 1.26 (2H, m), 1.15 (2H, m), 1.06 (2H, m). | {4-[5-Cyclopropyl-4-((3R,5S)-3,5-dimethyl-piperazin-1-yl)-pyrido[3,4-d]pyrimidin-2-yl]-pyridin-2-yl}-(3,5,6-trifluoro-pyridin-2-yl)-amine |
| 829 | 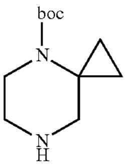 | 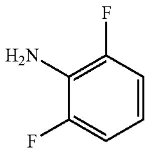 | method 5; RT: 3.32 min, MI: 486.42 [M + H] | 1H NMR (500 MHz, DMSO, 90° C.) 9.05 (1H, s), 8.23 (1H, s), 8.20 (1H, d), 7.76 (1H, s), 7.69 (1H, dd), 7.32-7.27 (2H, m), 7.14 (2H, t), 4.04 (2H, t), 3.96 (2H, s), 3.67-3.60 (1H, m), 3.42 (2H, t), 2.64-2.60 (1H, m), 1.28-1.24 (2H, m), 1.03-1.00 (4H, m), 0.82 (2H, t). | {4-[5-Cyclopropyl-4-(4,7-diaza-spiro[2.5]oct-7-yl)-pyrido[3,4-d]pyrimidin-2-yl]-pyridin-2-yl}-(2,6-difluoro-phenyl)-amine |

-continued

| Ex | Amine 1 | Amine 2 | Analysis LCMS | Analysis NMR | Name |
|---|---|---|---|---|---|
| 830 | 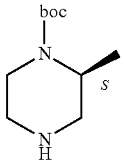 | 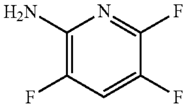 | method 5: RT: 2.66 min, MI: 493 [M + H] | 1H NMR (DMSO, 500 MHz) 9.81 (1H, s), 9.07 (1H, s), 8.43 (1H, d), 8.28 (1H, m), 8.20 (1H, s), 7.97 (1H, m), 4.25 (2H, m), 2.54 (1H, m), 1.23 (3H, m), 1.16 (2H, m), 1.09 (3H, m). (Piperazine aliphatic protons under the water peak at 3.33 ppm, therefore not integrated). | {4-[5-Cyclopropyl-4-((S)-3-methyl-piperazin-1-yl)-pyrido[3,4-d]pyrimidin-2-yl]-pyridin-2-yl}-(3,5,6-trifluoro-pyridin-2-yl)-amine |
| 831 | 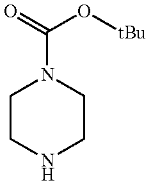 [SMILES: CC(C)(C)OC(=O)N1CCNCC1] | 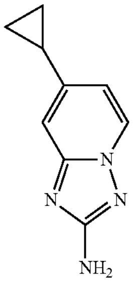 [SMILES: Nc1nc2cc(C3CC3)ccn2n1] | 505.27 (MH)+ | | [4-(5-Cyclopropyl-4-piperazin-1-yl-pyrido[3,4-d]pyrimidin-2-yl)-pyridin-2-yl]-(7-cyclopropyl-[1,2,4]triazolo[1,5-a]pyridin-2-yl)-amine |
| 832 | 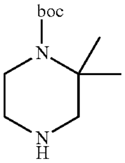 | 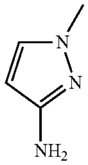 | 456.27 (M + H) | | {4-[5-Cyclopropyl-4-(3,3-dimethyl-piperazin-1-yl)-pyrido[3,4-d]pyrimidin-2-yl]-pyridin-2-yl}-(1-methyl-1H-pyrazol-3-yl)-amine |
| 833 | 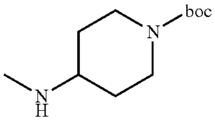 | 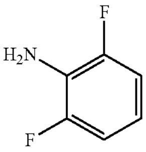 | 488 (M + H) | | {5-Cyclopropyl-2-[2-(2,6-difluoro-phenylamino)-pyridin-4-yl]-pyrido[3,4-d]pyrimidin-4-yl}-methyl-piperidin-4-yl-amine |
| 834 | 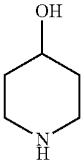 | 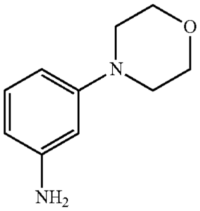 [SMILES: Nc1cccc(N2CCOCC2)c1] | 524.26 | | 1-{5-Cyclopropyl-2-[2-(3-morpholin-4-yl-phenylamino)-pyridin-4-yl]-pyrido[3,4-d]pyrimidin-4-yl}-piperidin-4-ol |
| 835 | 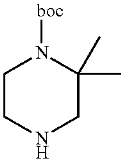 | 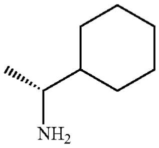 | 486.33 | | ((R)-1-Cyclohexyl-ethyl)-{4-[5-cyclopropyl-4-(3,3-dimethyl-piperazin-1-yl)-pyrido[3,4-d]pyrimidin-2-yl]-pyridin-2-yl}-amine |
| 836 | 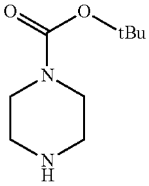 [SMILES: CC(C)(C)OC(=O)N1CCNCC1] | 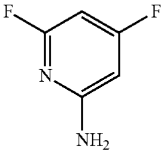 | 461.18 (MH)+ | | [4-(5-Cyclopropyl-4-piperazin-1-yl-pyrido[3,4-d]pyrimidin-2-yl)-pyridin-2-yl]-(4,6-difluoro-pyridin-2-yl)-amine |

-continued

| Ex | Amine 1 | Amine 2 | Analysis LCMS | Analysis NMR | Name |
|---|---|---|---|---|---|
| 837 | 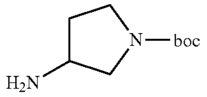 | 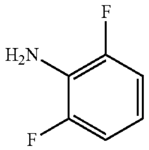 | 460 (M + H) | | {5-Cyclopropyl-2-[2-(2,6-difluoro-phenylamino)-pyridin-4-yl]-pyrido[3,4-d]pyrimidin-4-yl}-pyrrolidin-3-yl-amine |
| 838 | 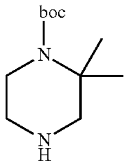 | 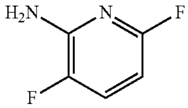 | method 5: RT: 3.52 min, MI: 489.41 [M + H] | 1H NMR (500 MHz, DMSO, 90° C.) 8.97 (1H, s), 8.90 (1H, s), 8.42 (1H, d), 8.14 (1H, s), 7.97 (1H, dd), 7.81-7.75 (1H, m), 6.67-6.63 (1H, m), 3.81 (2H, s, br), 3.68 (2H, s), 2.95 (2H, s), 1.25 (2H, dd), 0.99-0.96 (8H, m). | {4-[5-Cyclopropyl-4-(3,3-dimethyl-piperazin-1-yl)-pyrido[3,4-d]pyrimidin-2-yl]-pyridin-2-yl}-(3,6-difluoro-pyridin-2-yl)-amine |
| 839 | 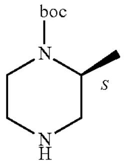 | 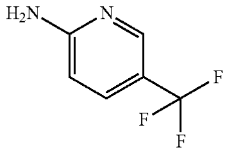 [SMILES: Nc1ccc(C(F)(F)F)cn1] | method 5: RT: 2.39 min, MI: 507 [M + H] | 1H NMR (DMSO, 500 MHz) 10.91 (1H, s), 9.09 (1H, s), 9.03 (1H, s), 8.78 (1H, s), 8.65 (1H, s), 8.49 (1H, d), 8.20 (1H, s), 8.09 (1H, dd), 7.99 (1H, dd), 7.92 (1H, m), 4.34 (2H, m), 3.71 (1H, m), 3.42 (4H, m), 3.06 (1H, m), 1.30 (5H, m), 1.08 (2H, m). | {4-[5-Cyclopropyl-4-((S)-3-methyl-piperazin-1-yl)-pyrido[3,4-d]pyrimidin-2-yl]-pyridin-2-yl}-(5-trifluoromethyl-pyridin-2-yl)-amine |
| 840 | 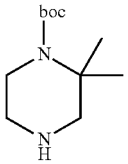 | 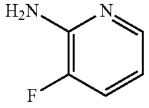 | method 5: RT: 2.50 min, MI: 471.42 [M + H] | 1H NMR (500 MHz, DMSO, 90° C.) 8.97 (2H, s), 8.64 (1H, s, br), 8.39 (1H, d d), 8.15 (1H, dd), 8.13 (1H, s), 7.89 (1H, dd), 7.65-7.60 (1H, m), 7.07-7.02 (1H, m), 3.79 (2H, t, br), 3.67 (2H, s), 2.95 (2H, s), 1.25 (2H, dd), 0.99-0.96 (8H, m). | {4-[5-Cyclopropyl-4-(3,3-dimethyl-piperazin-1-yl)-pyrido[3,4-d]pyrimidin-2-yl]-pyridin-2-yl}-(3-fluoro-pyridin-2-yl)-amine |
| 841 | 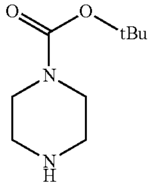 [SMILES: CC(C)(C)OC(=O)N1CCNCC1] | 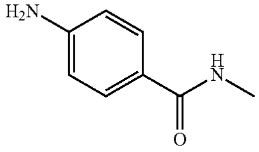 | method 5: RT: 3.13 min, MI: 481.47 [M + H] | 1H NMR (500 MHz, DMSO, 90° C.) 9.08 (1H, s), 8.40 (1H, dd), 8.23 (1H, s), 8.01 (1H, s), 7.85 (1H, s, br), 7.79-7.78 (5H, m), 3.99-3.97 (4H, m), 3.37-3.35 (4H, m), 2.82 (3H, s), 2.72-2.68 (1H, m), 1.29-1.27 (2H, m), 1.06-1.04 (2H, m). | -[4-(5-Cyclopropyl-4-piperazin-1-yl-pyrido[3,4-d]pyrimidin-2-yl)-pyridin-2-ylamino]-N-methyl-benzamide |
| 842 | 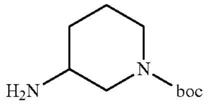 | 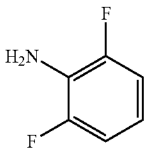 | 474 (M + H) | | {5-Cyclopropyl-2-[2-(2,6-difluoro-phenylamino)-pyridin-4-yl]-pyrido[3,4-d]pyrimidin-4-yl}-piperidin-3-yl-amine |
| 843 | 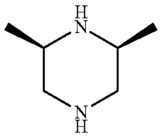 | 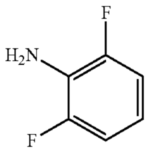 | method 5: RT: 2.36 min, MI: 488 [M + H] | 1H NMR (DMSO, 400 MHz, 90° C.) 9.06 (1H, s), 8.22 (2H, m), 7.74 (1H, s), 7.71 (1H, dd), 7.29 (1H, m), 7.13 (2H, t), 4.30 (2H, m), 3.53 (2H, m), 3.21 (2H, m), 2.66 (1H, m), 1.33 (6H, d), 1.93 (2H, m), 1.04 (2H, m). | {4-[5-Cyclopropyl-4-((3R,5S)-3,5-dimethyl-piperazin-1-yl)-pyrido[3,4-d]pyrimidin-2-yl]-pyridin-2-yl}-(2,6-difluoro-phenyl)-amine |

-continued

| Ex | Amine 1 | Amine 2 | Analysis LCMS | NMR | Name |
|---|---|---|---|---|---|
| 844 | 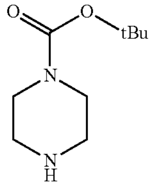 [SMILES: CC(C)(C)OC(=O)N1CCNCC1] | 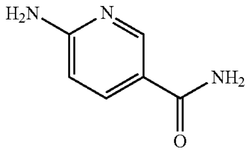 | | 1H NMR (500 MHz, DMSO) 9.09 (1H, s), 8.83 (1H, d), 8.64 (1H, s), 8.51 (1H, d), 8.29 (1H, dd), 8.21 (1H, s), 8.12 (1H, s), 8.07 (1H, d), 7.63 (1H, d), 7.54 (1H, s), 3.96 (4H, s, br), 3.34 (4H, s), 2.72-2.67 (1H, m), 1.27-1.24 (2H, m), 1.09-1.08 (2H, m). | 6-[4-(5-Cyclopropyl-4-piperazin-1-yl-pyrido[3,4-d]pyrimidin-2-yl)-pyridin-2-ylamino]-nicotinamide |
| 845 | 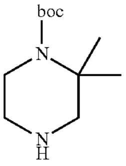 | 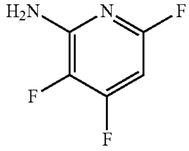 | method 5: RT: 3.87 min, MI: 507.41 [M + H] | 1H NMR (500 MH, DMSO) 10.07 (1H, s), 9.05 (1H, s), 8.85 (1H, s), 8.47 (1H, d), 8.20 (1H, s), 8.02 (1H, d), 7.01 (1H, dd), 3.91 (4H, s, br), 3.35 (2H, s, br), 2.55 (2H, s, br), 1.32-1.02 (13H, m). | {4-[5-Cyclopropyl-4-(3,3-dimethyl-piperazin-1-yl)-pyrido[3,4-d]pyrimidin-2-yl]-pyridin-2-yl}-(3,4,6-trifluoro-pyridin-2-yl)-amine |
| 846 | 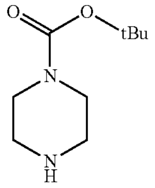 [SMILES: CC(C)(C)OC(=O)N1CCNCC1] | 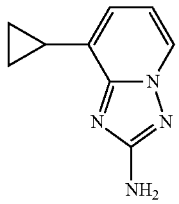 [SMILES: Nc1nc2c(C3CC3)cccn2n1] | 505.25 (MH)+ | | [4-(5-Cyclopropyl-4-piperazin-1-yl-pyrido[3,4-d]pyrimidin-2-yl)-pyridin-2-yl]-(8-cyclopropyl-[1,2,4]triazolo[1,5-a]pyridin-2-yl)-amine |

General synthesis of substituted substituted 2-morpholin-4-yl-pyrido[3,4-d]pyrimidine derivatives of general formula [H-006] Scheme C1

Amino-isonicotinamide derivatives of general formula [H-002] were prepared by reaction of a substituted amino-isonicotinamide derivative of general formula [H-001] with di-tert-butyl dicarbonate and ammonium carbonate in a polar aprotic solvent such as DMA, DMF, NMP with a base pyridine. Substituted 2-mercapto-3H-pyrido[3,4-d]pyrimidin-4-one derivatives of general formula [H-003] were prepared by cyclisation of a Amino-isonicotinamide derivatives of general formula [H-002] with carbon disulfide in a polar aprotic solvent such as DMA, DMF, NMP with a hindered base such as DBU. 2-Chloro-pyrido[3,4-d]pyrimidin-4-ol derivatives of general formula [H-004] were prepared by reaction of a Substituted 2-mercapto-3H-pyrido[3,4-d]pyrimidin-4-one derivatives of general formula [H-003] with thiophosgene in a polar aprotic solvent such as 1,4-dioxane. The 2-morpholin-4-yl-pyrido[3,4-d]pyrimidin-ol derivatives of general formula [H-005] were prepared by the reaction of a 2-Chloro-pyrido[3,4-d]pyrimidin-4-ol derivative of general formula [H-004] with a substituted morpholine derivative of general formula [H-007] in a polar aprotic solvent such as DMA, DMF, NMP at high temperature either by heating thermally or using a microwave reactor. 2-morpholin-4-yl-pyrido[3,4-d]pyrimidine derivatives of general formula [H-006] were prepared by the reaction of a 2-morpholin-4-yl-pyrido[3,4-d]pyrimidin-ol derivatives of general formula [H-005] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP. The intermediate 6,7-substituted-(2,4,6-triisopropyl-benzenesulfonic acid)-2-morphol-4-yl-pyrido[3,4-d]pyrimidin-4-yl ester was then reacted with a primary or secondary amino derivative, of general formula [H-008], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme C1

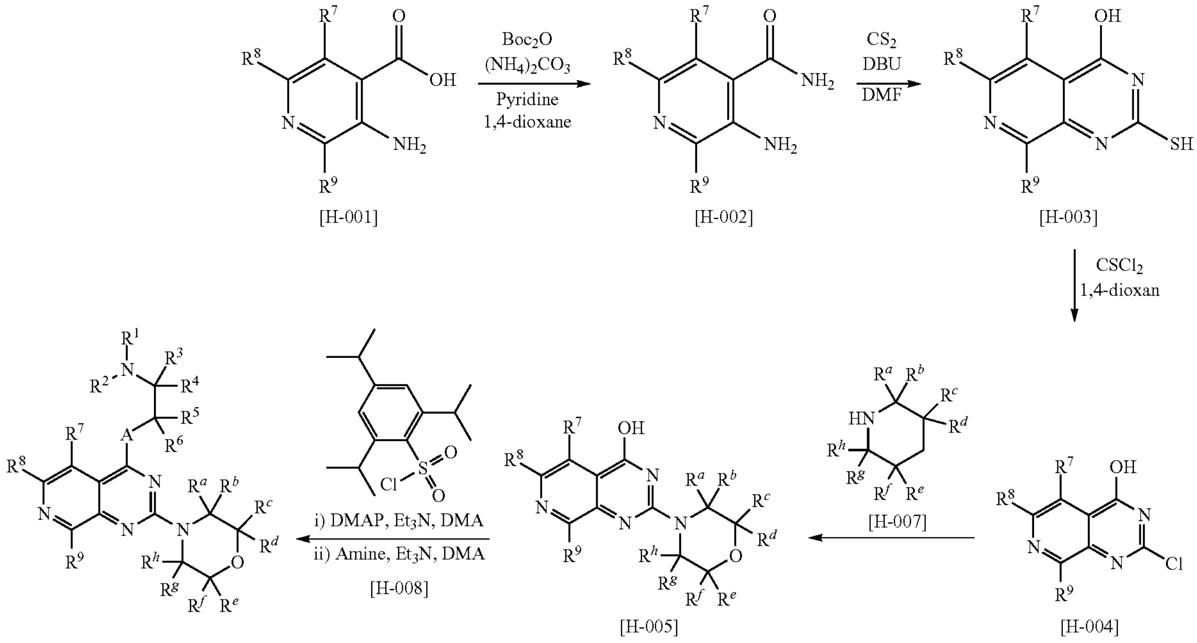

[H-001] [H-002] [H-003] [H-004] [H-005] [H-006]

Synthesis of 4-((S)-3-Benzyl-piperazin-1-yl)-2-morpholin-4-yl-pyrido[3,4-d]pyrimidine [1000]

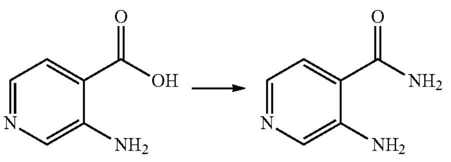

[C001]

3-Amino-isonicotinamide [C001]

A slurry of 3-aminoisonicotinic acid (1.00 g, 7.24 mmol) and CDI (1.76 g, 10.85 mmol) in DMF (15 mL) was heated to 40° C. for 0.5 h then cooled. Concentrated aqueous ammonia (50 mL) was added and the mixture was stirred for 15 min then extracted with ethyl acetate. Removal of the solvent gave a solid which was dissolved in EtOAc. The organic phase was washed with water and brine, dried over $MgSO_4$, filtered and then concentrated under reduced pressure to give the title compound [C001](780 mg, 79%) LCMS method: 5, RT: 0.54 min, MI 138 [M+H].

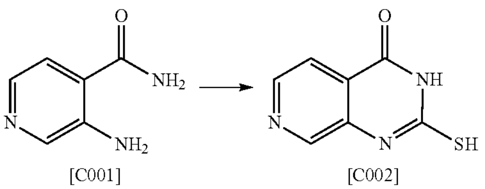

[C001] [C002]

2-Mercapto-3H-pyrido[3,4-d]pyrimidin-4-one hydrochloride [C002]

3-Amino-isonicotinamide [C001](5 g, 36.46 mmol) was dissolved in DMF (40 mL). Carbon disulfide (11 mL, 183 mmol) and DBU (10.9 mL, 73 mmol) were added and the reaction heated to 60° C. for 2 hours. 2M HCl (40 mL) was added and the precipitate was collected, washed with water and dried under vacuum, to yield the title compound [C002] as a white solid which was was used without further purification: LCMS method: 5, RT: 1.55 min, MI 180 [M+H].

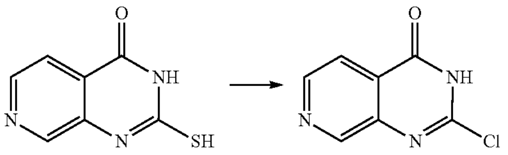

[C002] [C003]

2-Chloro-3H-pyrido[3,4-d]pyrimidin-4-one hydrochloride [C003]

To a mixture of 2-Mercapto-pyrido[3,4-d]pyrimidin-4-ol [C002](5.45 g, 30.41 mmol) in dioxine (100 mL) was added thiophosgene (3.5 mL, 45.6 mmol) dropwise and the mixture was heated at 100° C. for 3 h. The mixture was allowed to cool to room temperature and the resulting solid was diluted with $Et_2O$ (100 mL) and the precipitate was collected by filtration and the solid was washed with $Et_2O$ to yield the title compound which was used without further purification: LCMS method: 5, RT: 2.61 min, MI 182 [M+H].

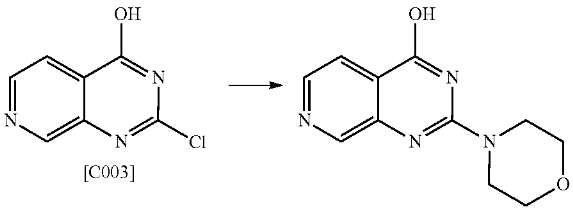

[C003]

[C004]

2-Morpholin-4-yl-pyrido[3,4-d]pyrimidin-4-ol [C004]

In a microwave vial, a solution of 2-Chloro-pyrido[3,4-d]pyrimidin-4-ol hydrochloride (300 mg, 1.38 mmol) and morpholine (0.22 mL, 2.48 mmol) in DMA (4 mL) was heated under microwave irradiation to 150° C. for 20 min. The solvent was removed under reduced pressure and the resulting solid was washed with ether and collected to give the title compound [C004] which was used without further purification. LCMS method: 5, RT: 2.20 min, MI 232 [M+H].

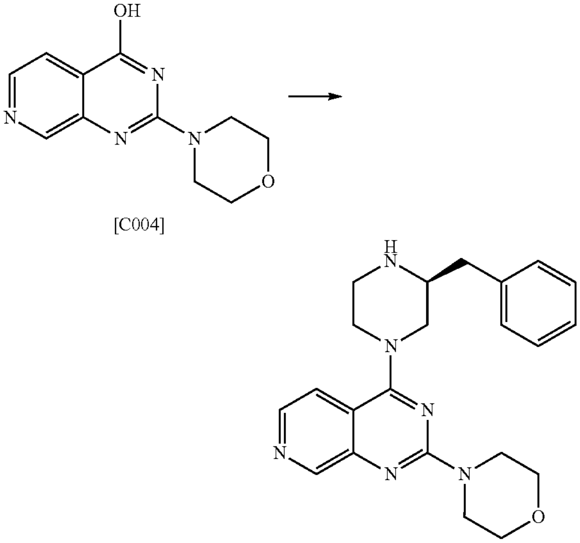

[C004]

[1000]

4-((S)-3-Benzyl-piperazin-1-yl)-2-morpholin-4-yl-pyrido[3,4-d]pyrimidine [1000]

To a solution of 2-Morpholin-4-yl-pyrido[3,4-d]pyrimidin-4-ol [C004](100 mg, 0.43 mmol) in DMA (3 mL), 2,4,6-Triisopropylbenzenesulfonyl chloride (143 mg, 0.47 mmol), $NEt_3$ (0.12 mL, 0.86 mmol) and DMAP (10 mg) were added successively. The mixture was stirred at rt for 1 h and (S)-1-Boc-2-benzylpiperazine (154 mg, 0.56 mmol) was added. The reaction was stirred overnight and the solvent was removed under reduced pressure. The mixture was purified by column chromatography on silica gel eluting with $CH_2Cl_2$ containing 0-10% MeOH. The appropriate fractions were combined and the solvent removed by rotary evaporation. The residue was dissolved in $CH_2Cl_2$ (2 mL) and TFA (0.5 mL) was added. The solution was stirred for 3 h and then loaded onto a SCX-2 cartridge, washing with MeOH (6 mL) and eluting with 2 M ammonia in MeOH. The solvent was removed from the ammonia fraction to give the title compound [1000]: LCMS method: 5, RT: 2.33 min, MI 391 [M+H]; NMR: (1H, 300 MHz, $CDCl_3$); 8.88 (1H, s), 8.10 (1H, d), 7.35-7.21 (7H, m), 4.31-4.21 (2H, m), 3.78-3.71 (8H, m), 3.39-3.30 (1H, m), 3.18-3.08 (2H, m), 2.98-2.90 (2H, m), 2.76 (2H, d).

Synthesis of 2-Chloro-5-methoxy-pyrido[3,4-d]pyrimidin-4-ol hydrochloride [C-005]

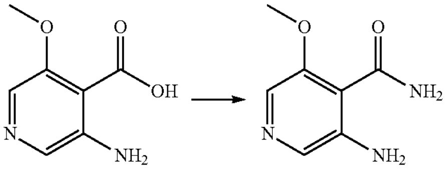

[C-006]

3-amino-5-methoxy-isonicotinamide [C-006]

A stirred suspension of 3-Amino-5-methoxy-isonicotinic acid (1.00 g, 5.947 mmol) in anhydrous dioxane (10 mL) was prepared under nitrogen at room temperature. Pyridine (0.53 mL, 6.542 mmol) was added followed by di-tert-butyl dicarbonate (1.43 g, 6.542 mmol) and ammonium carbonate (1.26 g, 13.083 mmol). The reaction mixture was stirred at room temperature for 5 hours then diluted with diethyl ether (50 mL) and the suspension stirred at room temperature for 18 hours. The suspension was filtered and the solid washed with diethyl ether (50 mL) then dissolved in methanol and filtered to remove the inorganic salts. The filtrate was concentrated by rotary evaporation to give the title compound [C-006](690 mg, 70%) as a cream coloured solid. LCMS method: 5, RT 1.27 min, MI 168 [M+H]; NMR: (1H, 300 MHz, d6-dmso) 7.77 (s, 1H), 7.65 (br. S, 1H), 7.58 (br. S, 1H), 7.57 (s, 1H), 6.30 (s, 2H), 3.85 (s, 3H).

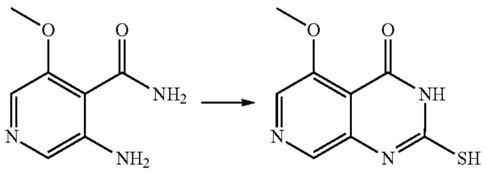

[C-006] [C-007]

2-Mercapto-5-methoxy-3H-pyrido[3,4-d]pyrimidin-4-one [C-007]

A suspension of 3-Amino-5-methoxy-isonicotinamide [C-006](1.10 g, 6.58 mmol) in anhydrous DMF (10 mL) was prepared under nitrogen. Carbon disulfide (1.97 mL, 32.90 mmol) was added followed by drop-wise addition of DBU (1.96 mL, 13.16 mmol) and the reaction mixture heated to 60° C. for 2.5 hours. The reaction mixture was cooled to room temperature and diluted with 2M HCl, the precipitate was filtered and washed with water. The precipitate was suspended in toluene (40 mL), the toluene was decanted and this was repeated once more. The precipitate was then suspended in toluene (30 mL) and concentrated by rotary evaporation to yield the title compound [C-007](1.05 g, 65%) as a yellow solid. LCMS method: 5, RT 2.33 min, MI 210 [M+H]; NMR: (1H, 500 MHz, d6-dmso) 12.71 (1H, s), 12.38 (1H, s), 8.30 (1H, s), 8.22 (1H, s), 3.95 (3H, s).

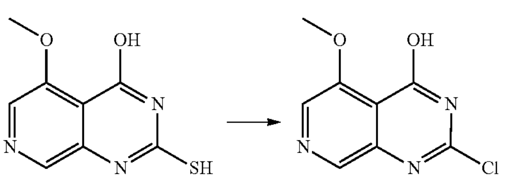

[C-007] [C-005]

2-Chloro-5-methoxy-pyrido[3,4-d]pyrimidin-4-ol hydrochloride [C-005]

A suspension of 2-Mercapto-5-methoxy-3H-pyrido[3,4-d]pyrimidin-4-one hydrochloride [C-007](1.145 g, 4.660 mmol) in anhydrous dioxane (20 mL) was prepared under nitrogen. Thiophosgene (0.54 mL, 6.990 mmol) was added drop-wise. The reaction mixture was stirred at room temperature for 10 min and then heated to 95° C. for 4 hours. A further portion of thiophosgene (0.09 mL, 1.165 mmol) was added and heating continued for a further 1.5 hours before stirring at room temperature overnight. The reaction mixture was diluted with diethyl ether and the precipitate was filtered, washed with diethyl ether and dried under vacuum to give the title compound [C-003](1.16 g, 100%) as a pale yellow solid. LCMS method: 5, RT 2.71 min, MI 212 [M+H]; NMR: (1H, 500 MHz, d6-dmso) 8.53 (1H, s), 8.40 (1H, s), 3.98 (3H, s).

Synthesis of [2-(2-Benzyl-morpholin-4-yl)-pyrido[3,4-d]pyrimidin-4-yl]-(R)-pyrrolidin-3-yl-amine [1001]

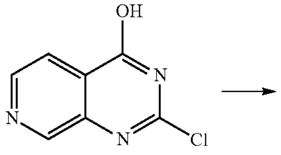

[C003]

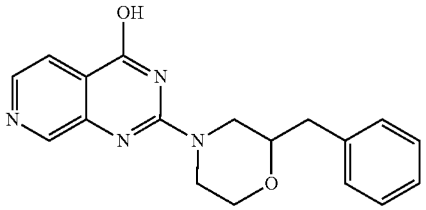

[C008]

2-(2-Benzyl-morpholin-4-yl)-pyrido[3,4-d]pyrimidin-4-ol [C008]

Following the procedure described in Scheme C1, 2-Chloro-pyrido[3,4-d]pyrimidin-4-ol hydrochloride (100 mg, 0.459 mmol) was reacted with 2-Benzyl-morpholine (146 mg, 0.825 mmol) to give the title compound [C008] (114 mg, 64%) following column chromatography on silica, eluting with $CH_2Cl_2$ containing 0-10% MeOH. LCMS method: 5, RT 2.37 min, MI 323.24 [M+H].

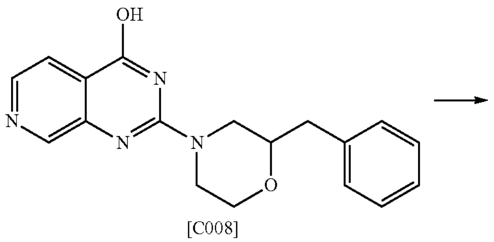

[C008]

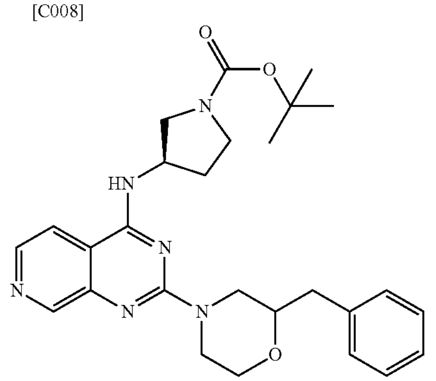

[C009]

(R)-3-[2-(2-Benzyl-morpholin-4-yl)-pyrido[3,4-d]pyrimidin-4-ylamino]-pyrrolidine-1-carboxylic acid tert-butyl ester [C009]

To a stirred solution of 2-(2-Benzyl-morpholin-4-yl)-pyrido[3,4-d]pyrimidin-4-ol [C008](70 mg, 0.21 mmol), $NEt_3$ (90 mL, 0.63 mmol) and DMAP (3 mg, 0.02 mmol) in DMA (1 mL) was added 2,4,6-triisopropylbenzenesulfonyl chloride (77 mg, 0.25 mmol). After 4 h (R)-(+)-1-Boc-3-aminopyrrolidine (43 mL, 0.25 mmol) was added and stirred overnight at RT. The reaction mixture was partitioned between $CH_2Cl_2$ and $H_2O$ and the organic phase separated and evaporated. The residue was purified by column chromatography on silica, eluting with CH2Cl2 containing 0-5% MeOH. The appropriate fractions were combined and evaporated to give the title compound [C009](43 mg, 33%) as an off-white solid. LCMS method: 5, RT 3.59 min, MI 491.33 [M+H].

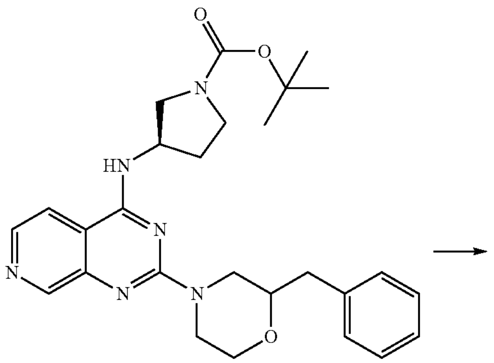

[C009]

-continued

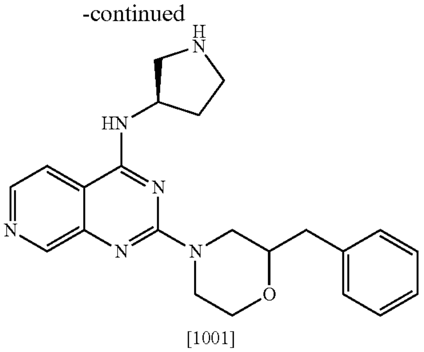

[1001]

[2-(2-Benzyl-morpholin-4-yl)-pyrido[3,4-d]pyrimidin-4-yl]-(R)-pyrrolidin-3-yl-amine [1001]

(R)-3-[2-(2-Benzyl-morpholin-4-yl)-pyrido[3,4-d]pyrimidin-4-ylamino]-pyrrolidine-1-carboxylic acid tert-butyl ester [C009](34 mg, 0.069 mmol) was stirred in 4N HCl in dioxane (2 mL) for 1 h. The reaction mixture was diluted with MeOH and loaded onto a SCX-cartridge, washing with MeOH and eluting with ammonia in methanol. The ammonia phase was evaporated to give the title compound [1001] (21 mg, 78%). LCMS method: 5, RT 1.97 min, MI 391.21 [M+H]; NMR: (1H, 300 MHz, d4-MeOD) 8.66 (1H, s), 8.14 (1H, dd), 7.83 (1H, ddd), 7.35-7.22 (5H, m), 4.66-4.59 (2H, m), 4.50-4.48 (1H, m), 3.98 (1H, dd), 3.71-3.55 (2H, m), 3.44-3.41 (1H, m), 3.16-3.07 (2H, m), 2.99-2.91 (1H, m), 2.85-2.74 (3H, m), 2.34-2.13 (3H, m).

General synthesis of substituted substituted 2-morpholin-4-yl-pyrido[3,4-d]pyrimidine derivatives of general formula [H-006] Scheme C2

The 2-morpholin-4-yl-pyrido[3,4-d]pyrimidin-4-yl derivatives of general formula [H-009] were prepared by the reaction of a 2-Chloro-pyrido[3,4-d]pyrimidin-4-ol derivative of general formula [H-004] with a chlorinatation agent such as phosphorous oxychloride and then reacted with primary or secondary amino derivative of general formula [H-008], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the 2-morpholin-4-yl-pyrido[3,4-d]pyrimidine derivatives of general formula [H-009] were reacted with a substituted morpholine derivative of general formula [H-007] in a polar aprotic solvent such as DMA, DMF, NMP at high temperature either by heating thermally or using a microwave reactor. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme C2

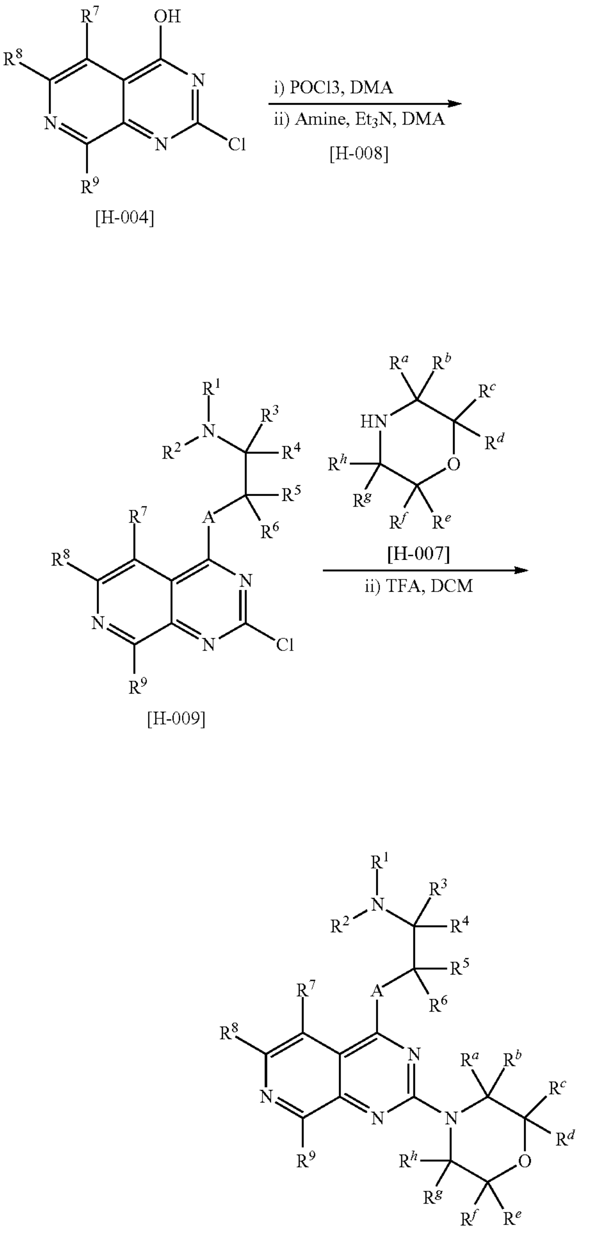

[H-004] [H-009] [H-006]

Synthesis of (S)—$N^1$-(5-Methoxy-2-morpholin-4-yl-pyrido[3,4-d]pyrimidin-4-yl)-3-phenyl-propane-1,2-diamine [1002]

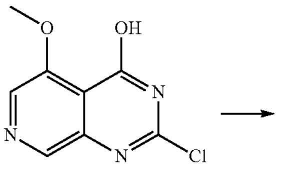

[C-005]

-continued

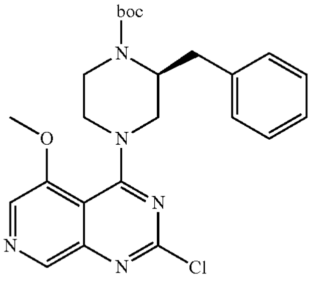

[C-010]

(S)-2-Benzyl-4-(2-chloro-5-methoxy-pyrido[3,4-d]pyrimidin-4-yl)-piperazine-1-carboxylic acid tert-butyl ester [C010]

A solution of 2-Chloro-5-methoxy-pyrido[3,4-d]pyrimidin-4-ol [C005](1.04 g, 4.911 mmol) in DCE (50 mL) was prepared under nitrogen. DIPEA (1.72 mL 9.822 mmol) and $POCl_3$ (0.46 mL, 4.911 mmol) were added and the reaction mixture stirred at room temperature for 2 hours. The reaction mixture was evapourated under reduced pressure and the residue used directly in the next step. A solution of 2,4-Dichloro-5-methoxy-pyrido[3,4-d]pyrimidine (280 mg of crude residue, 1.228 mmol assuming complete conversion) in DCM (15 mL) was prepared under nitrogen. Triethylamine (0.34 mL, 2.456 mmol) was added followed by (S)-2-Benzyl-piperazine-1-carboxylicacidtert-butylester (170 mg, 0.614 mmol). The reaction mixture was stirred at room temperature over night. The reaction mixture was evapourated under reduced pressure and the residue purified by chromatography on silica, eluting with DCM containing 0-10% MeOH to yield the title compound [C-010](110 mg, 19%): LCMS method: 5, RT 2.55 min, MI 263 [M+H]; NMR: (1H, 500 MHz, d6-dmso) 8.69 (1H, d, J=3.7 Hz), 8.39 (1H, d, J=3.7 Hz), 4.10 (3H, s), 3.63 (4H, broad s), 3.54 (4H, broad s), 1.47 (9H, s).

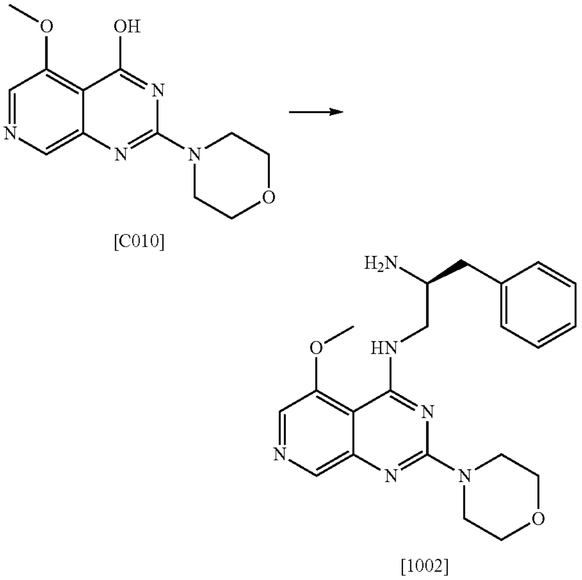

[C010]

[1002]

(S)—N[1]-(5-Methoxy-2-morpholin-4-yl-pyrido[3,4-d]pyrimidin-4-yl)-3-phenyl-propane-1,2-diamine [1002]

A solution of (S)-2-Benzyl-4-(2-chloro-5-methoxy-pyrido[3,4-d]pyrimidin-4-yl)-piperazine-1-carboxylic acid tert-butyl ester [C010](100 mg, 0.213 mmol) in anhydrous DMA (2 mL) was prepared. Morpholine (19 mg, 0.213 mmol) and DIPEA (0.04 mL, 0.213 mmol) were added and the mixture heated to 150° C. for 20 min in the microwave. The reaction mixture was evapourated under reduced pressure and the crude residue was purified by chromatography on silica eluting with DCM containing 0-10% MeOH. The product was stirred in 4M HCl in dioxane at room temperature for 1 hour and the reaction mixture was evapourated under reduced pressure and loaded onto an SCX cartridge, washing with methanol and eluting with 7N ammonia in methanol. The ammonia eluent was evapourated under reduced pressure to the title compound [1001](46 mg, 51%) as a yellow solid: LCMS method: 5, RT 2.51 min, MI 421 [M+H]; NMR: (1H, 500 MHz, d6-dmso) 8.34 (1H, s), 7.82 (1H, s), 7.35-7.32 (2H, m), 7.28-7.25 (3H, m), 4.0-3.97 (1H, m), 3.80 (4H, broad s), 3.62-3.61 (8H, broad m), 3.08-3.03 (1H, m), 2.98-2.91 (1H, m), 2.76-2.57 (6H, m).

Synthesis of 5-Methoxy-2-morpholin-4-yl-4-piperazin-1-yl-pyrido[3,4-d]pyrimidine [1003]

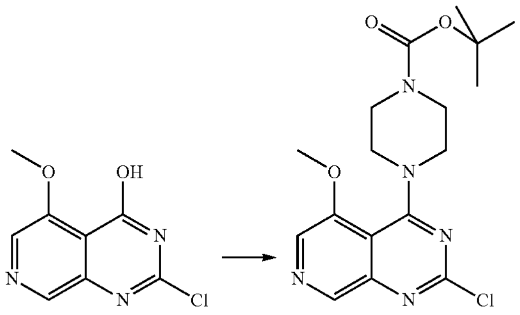

[C005] [C011]

4-(2-Chloro-5-methoxy-pyrido[3,4-d]pyrimidin-4-yl)-piperazine-1-carboxylic acid tert-butyl ester [C011]

A stirred suspension of 2-Chloro-5-methoxy-pyrido[3,4-d]pyrimidin-4-ol hydrochloride [C005](200 mg, 0.806 mmol) in DCE (10 mL) was prepared under nitrogen. DIPEA (0.31 mL, 1.773 mmol) was added followed by drop-wise addition of $POCl_3$ (0.08 mL, 0.887 mmol). The reaction mixture was stirred at room temperature for 2 hours. A further portion of DIPEA (0.31 mL, 1.773 mmol) and POCL3 (0.08 mL, 0.887 mmol) were added and stirring continued at room temperature for 3 hours. The reaction mixture was evapourated under reduced pressure and the residue partitioned between $CH_2Cl_2$ (30 mL) and sat. $NaHCO_3$ (aq) (30 mL). The organic phase was separated and the aqueous extracted with $CH_2Cl_2$ (2×10 mL). The combined organic portions were dried (phase separator) and evapourated under reduced pressure to give a crude residue containing 2,4-Dichloro-5-methoxy-pyrido[3,4-d]pyrimidine (assumed 185 mg, 100%) which was used without further purification. A solution containing crude 2,4-Dichloro-5-methoxy-pyrido[3,4-d]pyrimidine (assumed 185 mg, 0.806 mmol) in $CH_2Cl_2$ (10 mL) was prepared under nitrogen. Triethylamine (0.17 mL, 1.209 mmol) was added followed by piperazine-1-carboxylic acid tert-butyl ester (120 mg, 0.645 mmol) and the reaction mixture stirred at room temperature overnight. The reaction mixture was evapourated under reduced pressure and the residue purified by chromatography on silica eluting with $CH_2Cl_2$ containing 0-10% MeOH. The appropriate fractions were combined and concentrated to yield the title compound [1003](177 mg, 58%) as a yellow solid. LCMS method: 5, RT 5.44 min, MI 380 [M+H]; NMR: (1H, 500 MHz, d6-dmso) 8.65 (s, 1H), 8.34 (s, 1H), 4.06 (s, 3H), 3.59 (br. m, 4H), 3.49 (br. m, 4H), 1.42 (s, 9H).

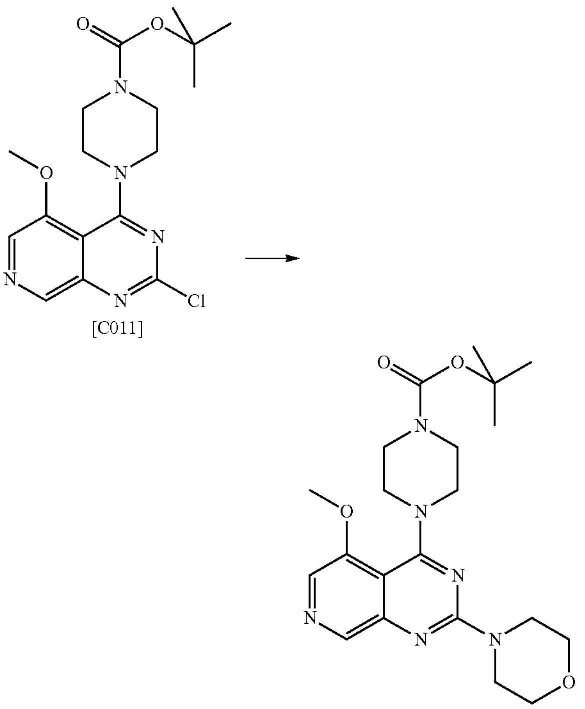

[C011]

[C012]

5-Methoxy-2-morpholin-4-yl-4-piperazin-1-yl-pyrido[3,4-d]pyrimidine [C012]

To a solution of 2,4-Dichloro-5-methoxy-pyrido[3,4-d]pyrimidine [C011](70 mg, 0.19 mmol) in DMA (2 mL) was added morpholine (20 mg, 0.228 mmol) and DIPEA (0.04 mL, 0.228 mmol). The reaction mixture was heated to 150° C. for 20 min in a microwave. The reaction mixture was concentrated under reduced pressure and the crude residue was purified by chromatography on silica (eluting with CH2C12 containing 0-10% MeOH) to give the title compound [C012] LCMS method: 5, RT 4.01 min, MI 431 [M+H].

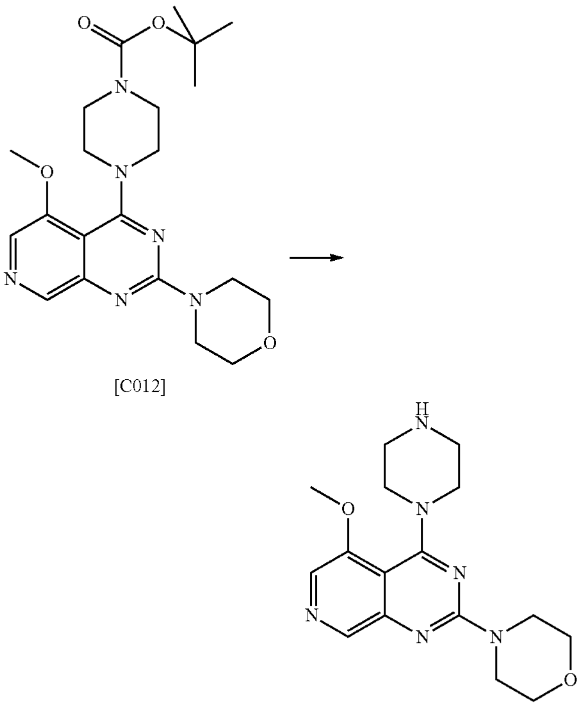

[C012]

[1003]

5-Methoxy-2-morpholin-4-yl-4-piperazin-1-yl-pyrido[3,4-d]pyrimidine [1003]

5-Methoxy-2-morpholin-4-yl-4-piperazin-1-yl-pyrido[3,4-d]pyrimidine [C012] was stirred in 4M HCl in dioxane (2 mL) at room temperature for 2 hours. The reaction mixture was diluted with methanol (to dissolved precipitate) and loaded onto a SCX cartridge, washing with methanol and eluting with 7M ammonia in methanol. The ammonia fraction was evapourated under reduced pressure and dried under vacuum to give the title compound [1003](48 mg, 83%): LCMS method: 5, RT 3.54 min, MI 331 [M+H]; NMR: (1H, 500 MHz, d6-dmso) 8.33 (1H, broad d, J=0.9 Hz), 7.88 (1H, s), 3.95 (3H, s), 3.73-3.71 (4H, m), 3.64-3.62 (4H, m), 3.38 (4H, broad m), 2.82-2.80 (4H, broad t, J=4.5 Hz).

The following intermediate compounds were synthesised according to the general synthesis shown in scheme [C2]

| | | | Analysis | | |
|---|---|---|---|---|---|
| Int | SM | Amine | LCMS | NMR | Name |
| [C013] | 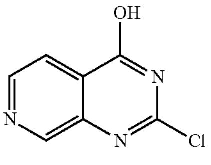 [C003] | 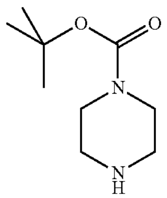 | Method 5: RT: 522 min, MI: 350 [M + H] | | 4-(2-Chloro-5-methoxy-pyrido[3,4-d]pyrimidin-4-yl)-piperazine-1-carboxylic acid tert-butyl ester |

-continued

| Int | SM | Amine | Analysis LCMS | Analysis NMR | Name |
|---|---|---|---|---|---|
| [C014] | 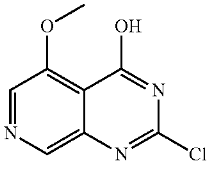 [C005] | 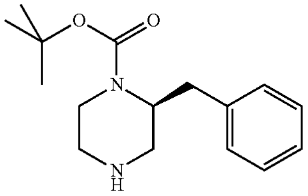 | Method 5: RT: 6.18 min, MI: 470 [M + H] | | (S)-2-Benzyl-4-(2-chloro-4-methoxy-pyrido[3,4-d]pyrimidin-4-yl)-piperazine-1-carboxylic acid tert-butyl ester |
| [C015] | 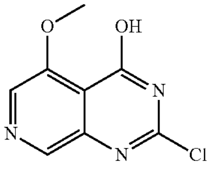 [C005] | 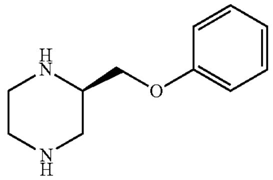 [SMILES: c1ccc(OC[C@H]2CNCCN2)cc1] | Method 5: RT: 2.99 min, MI: 386 [M + H] | (1H, 500 MHz, $CDCl_3$): 8.82 (1H, s), 8.18 (1H, s), 7.31-7.28 (2H, m), 6.98 (1H, t, J = 7.4), 6.90 (2H, d, J = 7.9 Hz), 4.27-4.24 (1H, br. d, J = 12.1 Hz), 4.15-4.10 (1H, m), 4.06 (3H, s), 4.03-4.00 (1H, m), 3.98-3.94 (1H, m), 3.39-3.34 (1H, br. s), 3.27-3.18 (2H, m), 3.11-3.02 (2H, m). | 2-Chloro-5-methoxy-4-((R)-3-phenoxymethyl-piperazin-1-yl)-pyrido[3,4-d]pyrimidine |
| [C016] | 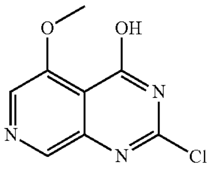 [C005] | 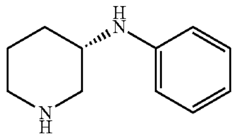 [SMILES: c1ccc(N[C@H]2CCCNC2)cc1] | Method 5: RT: 5.40 min, MI: 370 [M + H] | (1H, 500 MHz, d6-dmso): 8.61 (1H, s), 8.29 (1H, s), 7.06 (2H, t, J = 7.6 Hz), 6.77 (1H, br. d, J = 7.3 Hz), 6.51 (1H, t, J = 7.3 Hz), 5.61 (1H, d, J = 7.2 Hz), 4.48 (1H, br. s), 4.03 (3H, s), 3.85 (1H, br, d, J = 12.7 Hz), 3.46-3.40 (1H, br. m), 3.55-3.30 (1H, br. m), 2.83 (1H, t, J = 10.7 Hz), 1.99 (1H, br. s), 1.79-1.78 (1H, br. m), 1.57-1.49 (2H, br. m). | [(S)-1-(2-Chloro-5-methoxy-pyrido[3,4-d]pyrimidin-4-yl)-piperidin-3-yl]-phenyl-amine |
| [C017] | 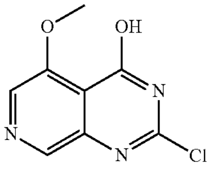 [C005] | 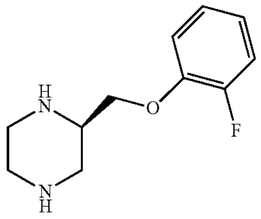 [SMILES: Fc1ccccc1OC[C@H]1CNCCN1] | Method 5: RT: 3.00 min, MI: 404 [M + H] | (1H, 500 MHz, d6-dmso) 8.62 (1H, s), 8.32 (1H, s), 7.21-7.16 (2H, m), 7.11 (1H, t, J = 7.9 Hz), 6.96-6.93 (1H, m), 4.15-4.13 (1H, br. m), 4.05-3.97 (3H, m), 4.02 (3H, s), 3.19-3.18 (1H, br. m), 3.12-3.03 (2H, m), 2.99-2.95 (1H, m), 2.84-2.79 (1H, br. m). | 2-Chloro-4-[(R)-3-(2-fluoro-phenoxymethyl)-piperazin-1-yl]-5-methoxy-pyrido[3,4-d]pyrimidine |

-continued

| | | | Analysis | | |
|---|---|---|---|---|---|
| Int | SM | Amine | LCMS | NMR | Name |
| [C018] | 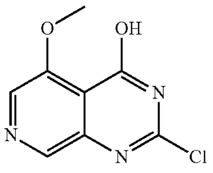 [C005] | 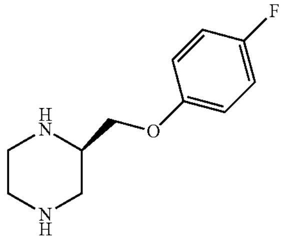 [SMILES: Fc1ccc(OC[C@H]2CNCCN2)cc1] | Method 5: RT: 3.13 min, MI: 404 [M + H] | (1H, 500 MHz, d6-dmso) 8.63 (1H, s), 8.34 (1H, s), 7.14-7.10 (2H, m), 6.98-6.95 (2H, m), 4.16-4.12 (1H, br m), 4.04 (3H, s), 4.04-3.99 (1H, br m), 3.93 (2H, d), 3.16-3.09 (3H, m), 2.98-2.94 (1H, m), 2.84-2.79 (1H, m). | 2-Chloro-4-[(R)-3-(4-fluoro-phenoxymethyl)-piperazin-1-yl]-5-methoxy-pyrido[3,4-d]pyrimidine |
| [C019] | 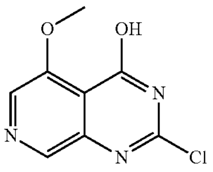 [C005] | 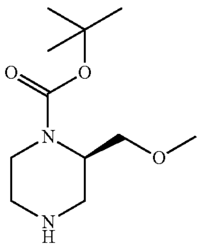 | Method 5: RT: 5.45 min, MI: 423 [M + H] | (1H, 500 MHz, d6-dmso) 8.64 (1H, s), 8.34 (1H, s), 4.26 (1H, br. s), 4.20 (1H, br. d, J = 13.2 Hz), 4.06 (3H, s), 3.92 (1H, br. d, J = 8 Hz), 3.82-3.80 (1H, br. m), 3.39-3.35 (1H, br. m), 3.31-3.24 (2H, m), 3.21-3.19 (2H, m), 3.10 (3H, br. s), 1.40 (9H, s). | (R)-4-(2-Chloro-5-methoxy-pyrido[3,4-d]pyrimidin-4-yl)-2-methoxymethyl-piperazine-1-carboxylic acid tert-butyl ester |
| [C020] | 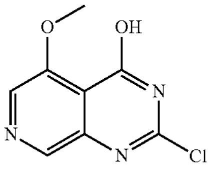 [C005] | 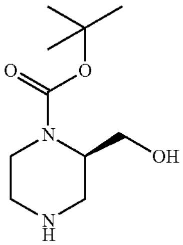 | Method 5: RT: 4.89 min, MI: 410 [M + H] | (1H, 500 MHz, d6-dmso) 1.40 (s, 9H), 3.17 (t, 1H), 3.22-3.33 (m, 1H), 3.33-3.39 (m, 2H), 3.72-3.82 (m, 1H), 3.87-3.92 (m, 1H), 4.05n (s, 3H), 4.02-4.10 (m, 1H), 4.18-4.24 (m, 1H), 4.76-4.78 (m, 1H), 8.33 (s, 1H), 8.63 (s, 1H). | (R)-4-(2-Chloro-5-methoxy-pyrido[3,4-d]pyrimidin-4-yl)-2-hydroxymethyl-piperazine-1-carboxylic acid tert-butyl ester |
| [C021] | 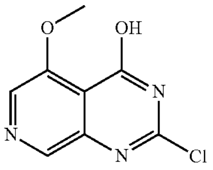 [C003] | 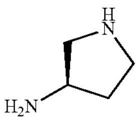 | Method 5: RT: 4.10 min, MI: 350 [M + H] | | (2-Chloro-5-methoxy-pyrido[3,4-d]pyrimidin-4-yl)-(R)-pyrrolidin-3-yl-amine |

The following compounds were synthesised according to the general synthesis shown in scheme [C2]

| | | | Analysis | | |
|---|---|---|---|---|---|
| Ex | Precursor | Amine | LCMS | NMR | Name |
| 1004 | 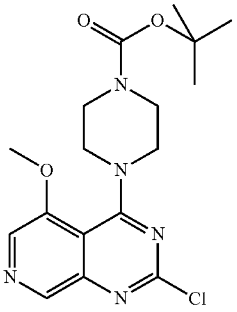 [C011] | 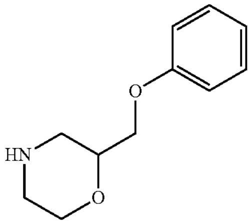 [SMILES: c1ccc(OCC2CNCCO2)cc1] | Method 5: RT: 2.74 min, MI: 437 [M + H] | (1H, 500 MHz, d6-dmso) 8.39 (1H, s), 7.94 (1H, s), 7.36-7.32 (2H, m), 7.03-6.97 (3H, m), 4.70 (1H, broad, d, J = 12.8 Hz), 4.53 (1H, broad d, J = 13.1 Hz), 4.16-4.10 (2H, m), 4.04-4.00 (1H, m), 4.00 (3H, s), 3.86-3.81 (1H, m), 3.63-3.57 (1H, m), 3.44-3.43 (4H, broad m), 3.20 (1H, d, J = 6 Hz), 3.11-3.06+ (1H, m), 2.99-2.94 (1H, m), 2.86 (4H, broad t, J = 4.7 Hz) | 5-Methoxy-2-(2-phenoxymethyl-morpholin-4-yl)-4-piperazin-1-yl-pyrido[3,4-d]pyrimidine |
| 1005 | 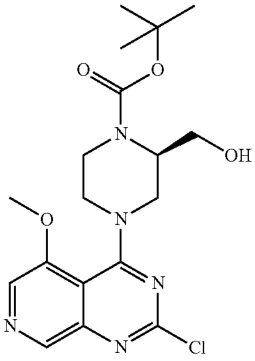 [C020] | 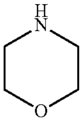 | Method 5: RT: 3.49 min, MI: 3.61 (M + H] | (1H, 500 MHz, d6-dmso) 8.34 (1H, s), 7.90 (1H, s), 4.66 (1H, br t, J = 5.1 Hz), 3.98-3.94 (1H, m), 3.95 (3H, s), 3.86 (1H, br d, J = 11.8 Hz), 3.74-3.73 (4H, m), 3.66-3.44 (4H, m), 3.40-3.33 (2H, m), 2.97-2.88 (2H, m), 2.81-2.75 (2H, m), 2.62-2.57 (1H, m). | [(R)-4-(5-Methoxy-2-morpholin-4-yl-pyrido[3,4-d]pyrimidin-4-yl)-piperazin-2-yl]-methanol |
| 1006 | 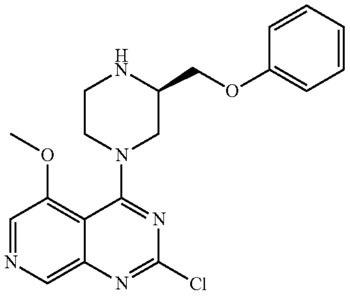 [C015] | 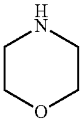 | Method 5: RT: 5.02 min, MI: 4.37 [M + H] | (1H, 500 MHz, d6-dmso) 8.34 (1H, s), 7.90 (1H, s), 7.30-7.27 (2H, m), 6.94-6.93 (3H, m), 4.90 (1H, br. d, J = 11.9 Hz), 3.96-3.90 (2H, m), 3.94 (3H, s), 3.84 (1H, br. d, J = 11.8 Hz), 3.72-3.70 (4H, m), 3.63-3.61 (4H, m), 3.19 (1H, br. s), 3.02-2.98 (2H, br. m), 2.81-2.74 (2H, br. m). | 5-Methoxy-2-morpholin-4-yl-4-((R)-3-phenoxymethyl-piperazin-1-yl)-pyrido[3,4-d]pyrimidine |
| 1007 | 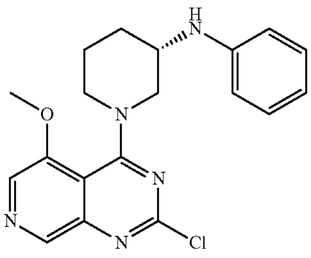 [C016] | 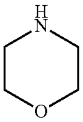 | Method 5: RT: 3.12 min, MI: 421 [M + H] | (1H, 500 MHz, $CDCl_3$) 8.54 (1H, s), 7.83 (1H, s), 7.17-7.14 (2H, m), 6.69 (1H, br. t, J = 7.3 Hz), 6.62 (2H, br. d, J = 7.5 Hz), 4.02-3.97 (1H, br. m), 4.00 (3H, s), 3.87-3.86 (4H, m), 3.77-3.75 (4H, m), 3.69 (1H, br. s), 3.59-3.55 (1H, br. m), 3.36-3.27 (2H, br. m), 2.04-1.97 (1H, br. m), 1.89-1.84 (1H, br. m), 1.71-1.65 (2H, br. m). | [(S)-1-(5-Methoxy-2-morpholine-4-yl-pyrido[3,4-d[pyrimidin-4-yl)-piperidin-3-yl]-phenyl-amine |

-continued

| Ex | Precursor | Amine | Analysis | | Name |
|---|---|---|---|---|---|
| | | | LCMS | NMR | |
| 1008 | 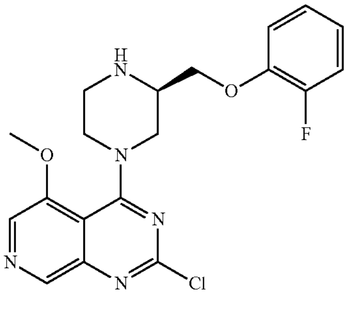 [C017] | 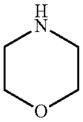 | Method 5: RT: 2.54 min, MI: 455 [M + H] | (1H, 500 MHz, d6-dmso): 8.33 (1H, s), 7.89 (1H, s), 7.22-7.16 (2H, m), 7.11 (1H, br. t, J = 7.5 Hz), 6.96-6.92 (1H, m), 4.14 (1H, br. d, J = 12.3 Hz), 4.05-4.02 (1H, m), 3.97-3.93 (1H, m), 3.93 (3H, s), 3.83-3.80 (1H, m), 3.72-3.70 (4H, m), 3.63-3.61 (4H, m), 3.20 (1H, br. s), 3.03-2.96 (2H, m), 2.78-2.73 (2H, m). | 4-[(R)-3-(2-Fluoro-phenxoymethyl)-piperazin-1-yl]-5-methoxy-2-morpholin-4-yl-pyrido[3,4-d]pyrimidine |
| 1009 | 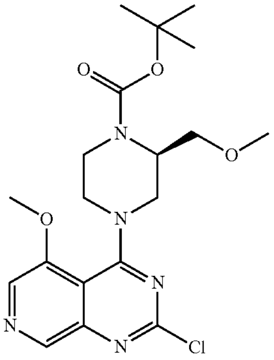 [C019] | 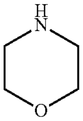 | Method 5: RT: 1.26 min, MI: 375 [M + H] | (1H, 500 MHz, d6-dmso): 8.34 (1H, s), 7.90 (1H, s), 3.95 (3H, s), 3.91 (1H, br. d, J = 12.4 Hz), 3.84 (1H, br. d, J = 12.5 Hz), 3.74-3.72 (4H, m), 3.66-3.64 (4H, m), 3.28 (2H, d, J = 5.9 Hz), 3.26 (3H, s), 2.98-2.93 (3H, m), 2.78-2.74 (1H, m), 2.66-2.61 (1H, m). | 5-Methoxy-4-((R)-3-methoxymethyl-piperazin-1-yl)-2-morpholin-4-yl-pyrido[3,4-d]pyrimidine |
| 1010 | 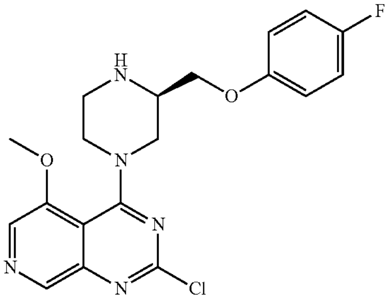 [C018] | 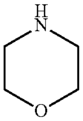 | Method 5: RT: 2.62 min, MI: 455 [M + H] | (1H, 500 MHz, d6-dmso): 8.35 (1H, s), 7.91 (1H, s), 7.14-7.10 (2H, m), 6.97-6.95 (2H, m), 4.07 (1H, br. d, J = 12.2 Hz), 3.95 (3H, s), 3.92-3.90 (2H, m), 3.84 (1H, br. d, J = 12.2 Hz), 3.73-3.71 (4H, m), 3.64-3.62 (4H, m), 3.17-3.16 (1H, br. m), 3.01-2.97 (2H, br. m), 2.80-2.73 (2H, br. m). | 4-[(R)-3-(4-Fluoro-phenoxymethyl)-piperazin-1-yl]-5-methoxy-2-morpholin-4-yl-pyrido[3,4-d]pyrimidine |
| 1011 | 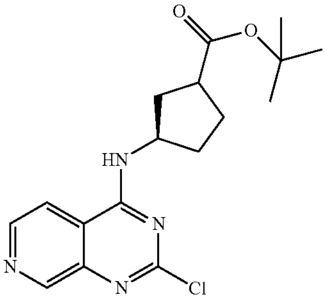 [C021] | 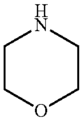 | Method 5: RT: 0.54 min, MI: 301 [M + H] | 1H NMR ($CDCl_3$, 500 MHz) 8.83 (s, 1H), 8.19 (d, 1H), 7.49 (d, 1H), 6.74 (d, 1H), 4.85-4.75 (m, 1H), 3.92-3.87 (m, 4H), 3.80-3.75 (m, 4H), 3.31-3.06 (m, 4H), 2.38-2.22 (m, 2H). | (2-Morpholin-4-yl-pyrido[3,4-d]pyrimidin-4-yl)-(R)-pyrrolidin-3-yl-amine |

Synthesis of [2-Morpholin-4-yl-8-(2H-pyrazol-3-yl)-pyrido[3,4-d]pyrimidin-4-yl]-(R)-pyrrolidin-3-yl-amine [1012]

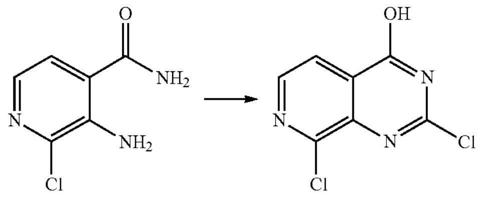

[C022]

2,8-Dichloro-pyrido[3,4-d]pyrimidin-4-ol [C022]

To a suspension of 3-Amino-2-chloro-isonicotinamide (2.00 g, 11.65 mmol) in dioxane (30 mL), thiophosgene (2.25 mL, 29.13 mmol) was added dropwise and the suspension was stirred 15 min. The reaction was then heated at 100° C. for 3 h then cooled down to room temperature and diluted with $Et_2O$. The resulting solid was collected and dried to give the title compound [C022](2.41 g, 96%) which was used without further purification. LCMS method: 5, RT 3.51 min, MI 216 [M+H].

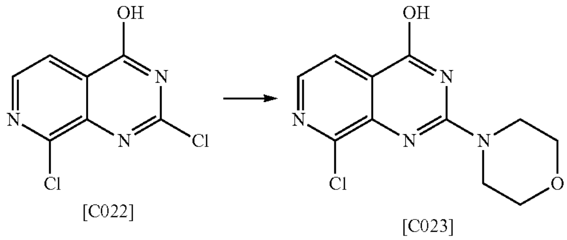

[C022] [C023]

8-Chloro-2-morpholin-4-yl-pyrido[3,4-d]pyrimidin-4-ol [C023]

To a solution of 2,8-Dichloro-pyrido[3,4-d]pyrimidin-4-ol [C022](200 mg, 0.926 mmol) in DMA (2 mL), morpholine (0.1 mL, 1.20 mmol) was added. The solution was stirred at room temperature for 30 min then heated to 40° C. for 3 h. The solvent was removed under reduced pressure, a minimum amount of $CH_2Cl_2$ was added to dissolve the crude residue and $Et_2O$ was added. The resulting solid was collected and dried to give the title compound [C022](200 mg, 80%) which was used without further purification. LCMS method: 5, RT 3.95 min, MI 267 [M+H].

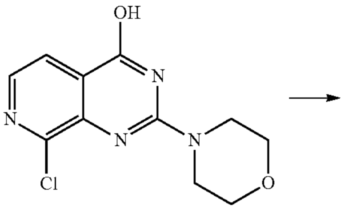

[C023]

-continued

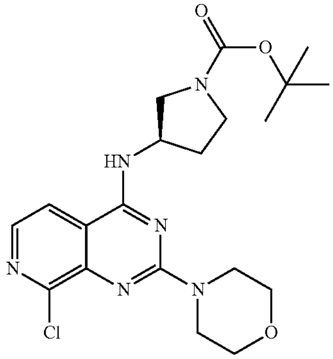

[C024]

(R)-3-(8-Chloro-2-morpholin-4-yl-pyrido[3,4-d]pyrimidin-4-ylamino)-pyrrolidine-1-carboxylic acid tert-butyl ester [C024]

To a solution of 8-Chloro-2-morpholin-4-yl-pyrido[3,4-d]pyrimidin-4-ol [C022](500 mg, 1.87 mmol) in DMA (10 mL), 2,4,6-Triisopropylbenzenesulfonyl chloride (690 mg, 2.25 mmol), $NEt_3$ (0.52 mL, 3.75 mmol) and DMAP (50 mg, 0.41 mmol) were added successively. The mixture was stirred at 40° C. for 1 h and then (R)-3-Amino-pyrrolidine-1-carboxylic acid tert-butyl ester (460 mg, 2.44 mmol). The reaction was stirred overnight at room temperature then the solvent was removed under reduced pressure. The mixture was purified by column chromatography on silica eluting with $CH_2Cl_2$ containing 0-10% MeOH. The appropriate fractions were combined and evapourated under reduced pressure to give the title compound [C023](310 mg, 38%). LCMS method: 5, RT 5.77 min, MI 435 [M+H].

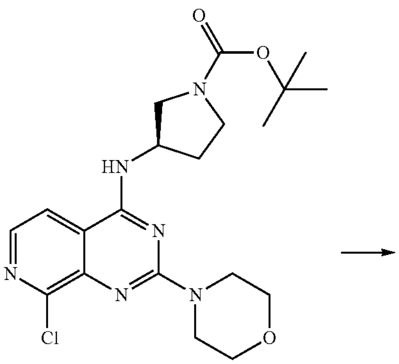

[C024]

-continued

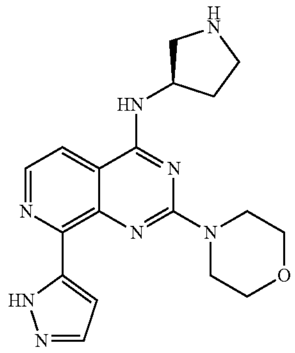

[1012]

[2-Morpholin-4-yl-8-(2H-pyrazol-3-yl)-pyrido[3,4-d]pyrimidin-4-yl]-(R)-pyrrolidin-3-yl-amine [1012]

A microwave vial was charged with (R)-3-(8-Chloro-2-morpholin-4-yl-pyrido[3,4-d]pyrimidin-4-ylamino)-pyrrolidine-1-carboxylic acid tert-butyl ester [C024](100 mg, 0.23 mmol), 1H-Pyrazole-5-boronic acid (38 mg, 0.35 mmol), $Pd(Ph_3P)_4$ (27 mg, 0.023 mmol), a solution of $K_3PO_4$ (0.92 mL of a 0.5M in $H_2O$, 0.46 mmol) and DMA (3.5 mL). The mixture was heated under microwave irradiation to 150° C. for 10 min. The solvent was removed under reduced pressure and the residue purified by chromatography on silica, eluting with $CH_2Cl_2$ containing 0-10% MeOH. The appropriate fractions were combined and the solvent evaporated under reduced pressure to give the Boc-protected intermediate which was dissolved in $CH_2Cl_2$ (2 mL) and TFA (0.5 mL) was added. The solution was stirred for 3 h and then loaded onto a SCX-2 cartridge, washing with MeOH and eluting with 2N ammonia in MeOH solution. The solvent was removed from the ammonia fraction under reduced pressure to yield the title compound [1012]: LCMS method: 5, RT 4.39 min, MI 367 [M+H]; NMR: (1H, 300 MHz, d6-dmso) 8.28 (d, 1H), 7.96 (d, 1H), 7.60 (d, 1H), 7.33 (d, 1H), 4.61-4.68 (m, 1H), 3.78-3.81 (m, 4H), 3.68-3.74 (m, 4H), 3.33-3.40 (m, 2H), 3.18-3.23 (m, 1H), 3.02-3.07 (m, 1H), 2.15-2.24 (m, 1H), 1.98-2.04 (m, 1H).

Synthesis of $N^4$—((S)-2-Amino-3-phenyl-propyl)-2-morpholin-4-yl-pyrido[3,4-d]pyrimidine-4,8-diamine [1013]

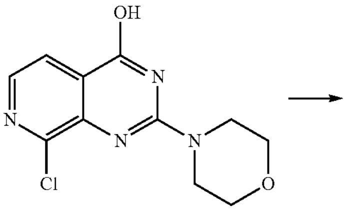

[C023]

-continued

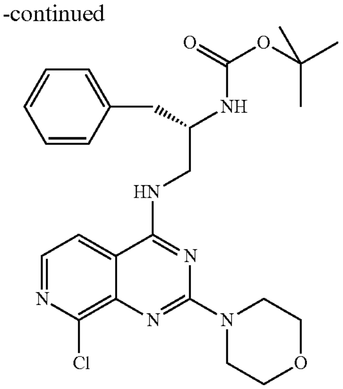

[C025]

[(S)-1-Benzyl-2-(8-chloro-2-morpholin-4-yl-pyrido[3,4-d]pyrimidin-4-ylamino)-ethyl]-carbamic acid tert-butyl ester [C025]

Following the procedure described above, 8-Chloro-2-morpholin-4-yl-pyrido[3,4-d]pyrimidin-4-o [C023]1 (500 mg, 1.87 mmol) was reacted with ((S)-1-Aminomethyl-2-phenyl-ethyl)-carbamic acid tert-butyl ester (600 mg, 2.44 mmol) to give the title compound [C024](350 mg, 38%). LCMS method: 5, RT 5.90 min, MI 499 [M+H].

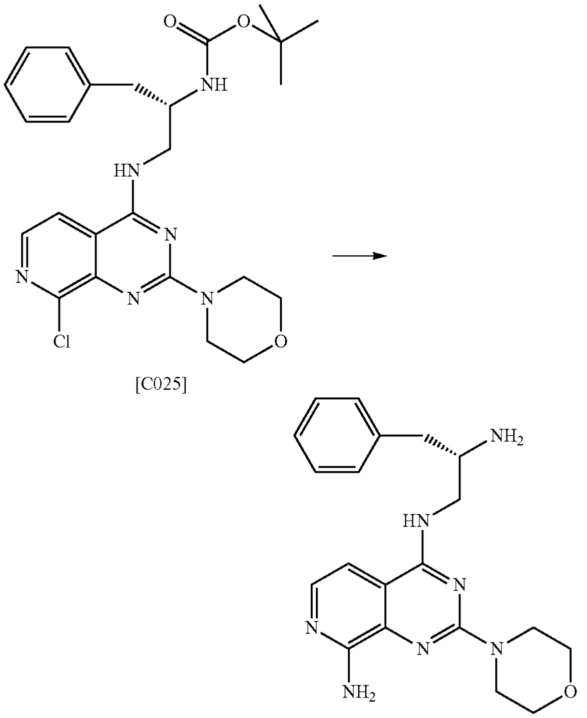

[C025]

[1013]

$N^4$—((S)-2-Amino-3-phenyl-propyl)-2-morpholin-4-yl-pyrido[3,4-d]pyrimidine-4,8-diamine A microwave vial was charged with [(S)-1-Benzyl-2-(8-chloro-2-morpholin-4-yl-pyrido[3,4-d]pyrimidin-4-ylamino)-ethyl]-carbamic acid tert-butyl ester [C025](100 mg, 0.20 mmol), EtOH (2 mL) and $NH_4OH$ (2 mL). The reaction mixture was heated under microwave irradiation to 150° C. for 1 h. This was repeated until reasonable conversion to the desired product was identified by LCMS analysis. The solvent was then removed under reduced pressure and the BOC protected compounds were diluted in $CH_2Cl_2$ (2 mL) and TFA (0.5 mL) was added. The solution was stirred for 3 h and then loaded onto a SCX-2 cartridge, washing with MeOH and eluting with 2M ammonia in MeOH solution. The solvent was removed from the ammonia fraction and the residue was purified by preparative HPLC (method A) to yield the title compound [1013] LCMS method: 5, RT 2.11 min, MI 380 [M+H]; NMR: (1H, 300 MHz, d6-dmso) 8.30-8.35 (m, 1H), 8.27 (br s, 1H), 7.49 (d, 1H), 7.22-7.33 (m, 4H), 6.97 (d, 1H), 6.34 (br s, 2H), 3.68-3.78 (m, 1H), 3.61-3.65 (m, 1H), 3.37-3.54 (m, 8H), 3.25-3.35 (m, 2H), 2.91 (dd, 1H), 2.73 (dd, 1H).

Synthesis of (S)—$N^1$-(2-Morpholin-4-yl-pyrido[3,4-d]pyrimidin-4-yl)-3-phenyl-propane-1,2-diamine [1014]

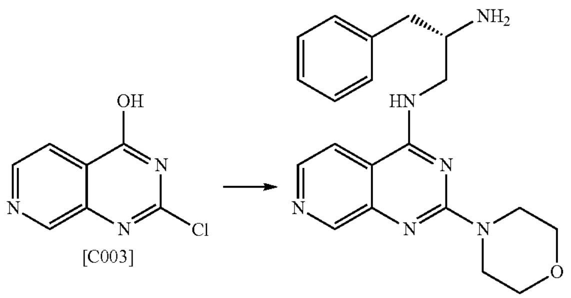

[C003]

[1014]

2-Chloro-pyrido[3,4-d]pyrimidin-4-ol [C003](1.50 g, 8.26 mmol) was suspended in DMA (30 mL). Triethylamine (2.3 mL, 16.52 mmol) was added and the reaction mixture stirred at room temperature. 2,4,6-Triisopropylbenzenesulfonyl chloride (2.75 g, 9.09 mmol) and DMAP (50 mg, 0.41 mmol) were both added and the mixture was stirred at room temperature for 6 hours. ((S)-1-Aminomethyl-2-phenyl-ethyl)-carbamic acid tert-butyl ester (3.10 g, 12.39 mmol) was added to the reaction mixture and stirring continued at room temperature for 18 hours. To the crude solution was added morpholine (1 mL) and the mixture sealed and heated under microwave irradiation to 150° C. for 20 min. The mixture was taken up in DCM and washed with water and brine. The layers were separated and the organic layer was dried over $MgSO_4$. The solvent was removed under reduced pressure and the crude mixture purified by flash column chromatography; eluting with a 5% methanol in $CH_2Cl_2$. The appropriate fractions were combined and concentrated and the residue stirred in 4M HCl in dioxane for 18 hours. The mixture was concentrated under reduced pressure and the residue loaded onto a SCX cartridge, washing with MeOH and eluting with 2M ammonia in methanol. The solvent was removed from the ammonia fraction under reduced pressure to give the title compound [1014](150 mg, 22%). LCMS method: 5, RT 1.79 min, MI 365 [M+H]; NMR: (1H, 300 MHz, d6-dmso) 8.73 (1H, br s), 8.64 (1H, s), 8.29 (2H, br s), 8.20 (1H, d), 8.00 (1H, d), 7.38-7.28 (5H, m), 3.90-3.83 (1H, m), 3.62-3.34 (10H overlapping br m), 3.13-3.07 (1H, m), 2.88-2.81 (1H, m).

General synthesis of substituted substituted 2-morpholin-4-yl-pyrido[3,4-d]pyrimidine derivatives of general formula [H-006] Scheme C3

3-halo-N-(imino-morpholin-4-yl-methyl)-isonicotinamide derivatives of general formula [H-011] were prepared by coupling of a ortho-halo-isonicotinic acid derivative of general formula [H-010] with an appropriately substituted 4-carbamimidoyl-morpholine of general formula [H-004] with a suitable coupling agent such as O-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula [H-011] were cyclised to displace the relevant halogen group to yield the desired morpholin-4-yl-pyrido[3,4-d]pyrimidin-4-ol derivatives of general formula [H-005]. The 2-morpholin-4-yl-pyrido[3,4-d]pyrimidin-4-yl derivatives of general formula [H-006] were prepared by the reaction of a morpholin-4-yl-pyrido[3,4-d]pyrimidin-4-ol derivatives of general formula [H-005] with a chlorinatation agent such as phosphorous oxychloride or a triflating agent such as N-Phenyl-bis(trifluoromethanesulfonimide and then reacted with primary or secondary amino derivative of general formula [H-008], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme C3

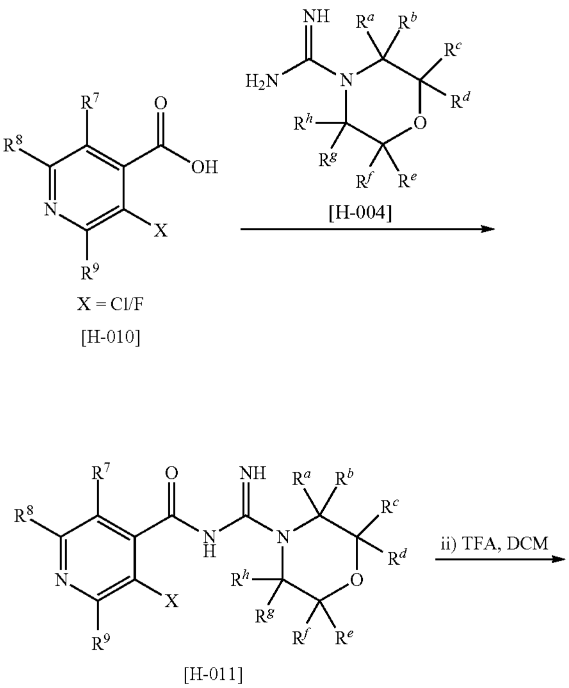

[H-010]

[H-004]

[H-011]

-continued

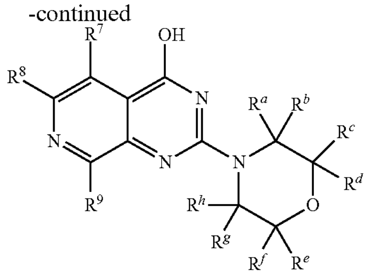

[H-005]

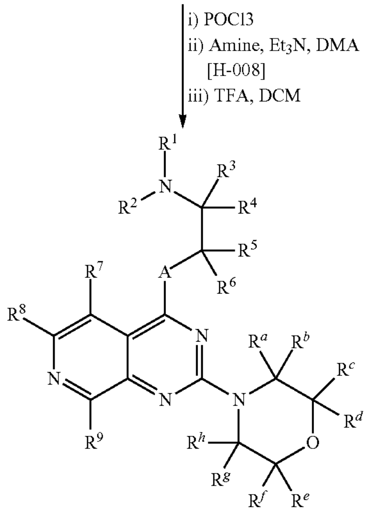

[H-006]

Synthesis of 5-Bromo-2-morpholin-4-yl-4-piperazin-1-yl-pyrido[3,4-d]pyrimidine [1015]

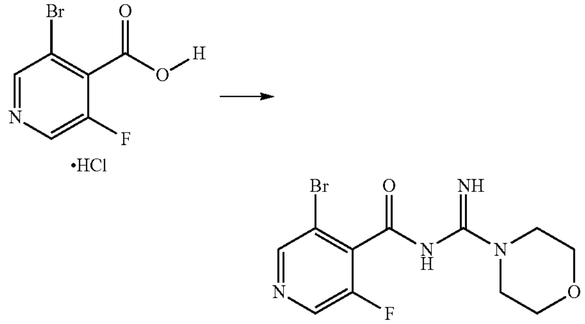

•HCl

[C026]

3-Bromo-5-fluoro-N-(imino-morpholin-4-yl-methyl)-isonicotinamide [C026]

A stirred solution of 3-Bromo-5-fluoro-isonicotinic acid hydrochloride (800 mg, 3.119 mmol) and DIPEA (1.91 mL, 10.917 mmol) in DMF (11 mL) was prepared. HATU (1.186 g, 3.119 mmol) was added and the reaction mixture stirred at room temperature for 1 hour, during which time reaction mixture turned slowly brown. 4-Morpholinylformamidine hydrobromide (655 mg, 3.119 mmol) was added and stirring continued at room temperature for 2 hours. The reaction mixture was diluted with water (30 mL) and stirred at room temperature for 10 mins. The reaction mixture was extracted with EtOAc (3x20 mL) and the combined organics dried and evapourated under reduced pressure to give the title compound [C026] a brown gum (1.15 g, 87%) which was used without purification in the next step: LCMS method: 5, RT 2.86 min, MI 331 [M+H].

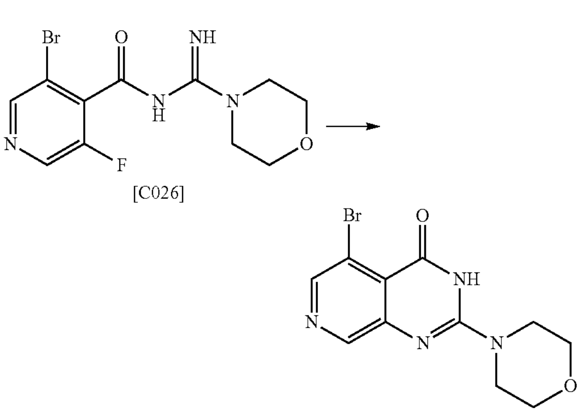

[C026]

[C027]

5-Bromo-2-morpholin-4-yl-3H-pyrido[3,4-d]pyrimidin-4-one [C027]

A solution of 3-Bromo-5-fluoro-N-(imino-morpholin-4-yl-methyl)-isonicotinamide [C025](crude product containing 1.03 g, 3.119 mmol starting material assuming 100% conversion) in anhydrous DMA (10 mL) was prepared and potassium carbonate (453 mg, 3.275 mmol) was added. The reaction mixture was heated to 150° C. for 1 hour in the microwave. The reaction mixture was poured into water (20 mL) and acidified with acetic acid. The resulting beige precipitate was filtered, washed with water and dried in the vac. oven over night to give the title compound [C027](400 mg, 41%): LCMS method: 5, RT 1.42 min, MI 313 [M+H].

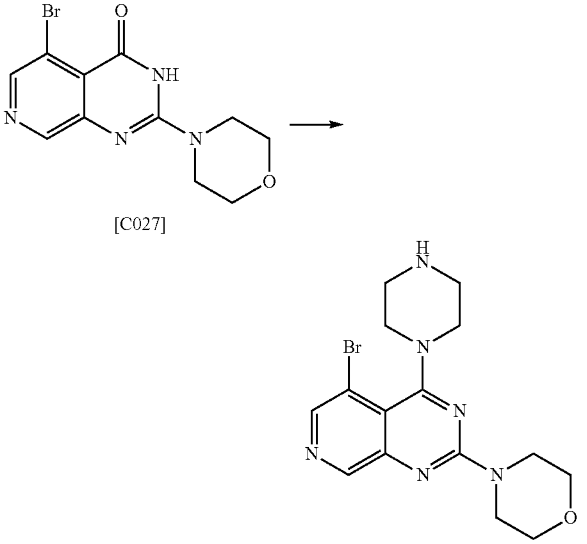

[C027]

[1015]

5-Bromo-2-morpholin-4-yl-4-piperazin-1-yl-pyrido[3,4-d]pyrimidine [1015]

A solution of 5-Bromo-2-morpholin-4-yl-3H-pyrido[3,4-d]pyrimidin-4-one (50 mg, 0.161 mmol) in anhydrous DMF (2 mL) was prepared under nitrogen. N-Phenyl-bis(trifluoromethanesulfonimide) (60 mg, 0.169 mmol) was added followed by DIPEA (0.06 mL, 0.354 mmol) and the reaction mixture stirred at room overnight. Piperazine-1-carboxylic acid tert-butyl ester (60 mg, 0.322 mmol) was added and stirring continued at room temperature overnight. The reaction mixture was concentrated under reduced pressure and the residue diluted with EtOAc (10 mL) and washed with water (3×5 mL). The organic phase was dried, filtered and concentrated by rotary evaporation. The residue was purified by chromatography on silica, eluting with cyclohexane containing 5-50% EtOAc. The appropriate fractions were combined and concentrated to give 4-(5-Bromo-2-morpholin-4-yl-pyrido[3,4-d]pyrimidin-4-yl)-piperazine-1-carboxylic acid tert-butyl ester [C027](35 mg, 45%) as a yellow solid. LCMS method: 5, RT 5.92 min, MI 479 [M+H]; NMR: (1H, 500 MHz, d6-dmso) 8.67 (1H, s), 8.29 (1H, s), 3.78-3.76 (4H, m), 3.66-3.62 (4H, m), 3.62 (2H, very broad s), 3.52-3.47 (4H, very broad m), 3.24 (2H, very broad s), 1.40 (9H, s).

The Boc protected intermediate [C026] was taken up in 4M HCl in dioxane (2 mL) and stirred at room temperature 2 hours. The reaction mixture was concentrated by rotary evaporation and the residue loaded onto a SCX-2 cartridge, washing with MeOH and eluting with 7N ammonia in MeOH. The ammonia fraction was concentrated under reduced pressure to give the title compound [1015](24 mg, 86%) as a yellow solid. LCMS method: 5, RT 2.24 min, MI 379 [M+H]; NMR: (1H, 500 MHz, $CDCl_3$) 8.76 (1H, s), 8.28 (s, 1H), 3.89-3.87 (4H, m), 3.78-3.76 (4H, m), 3.70 (2H, br. s), 3.33 (2H, br. s), 3.09 (2H, br. s), 3.00 (2H, br. s).

Synthesis of 5-Cyclopropyl-2-morpholin-4-yl-4-piperazin-1-yl-pyrido[3,4-d]pyrimidine

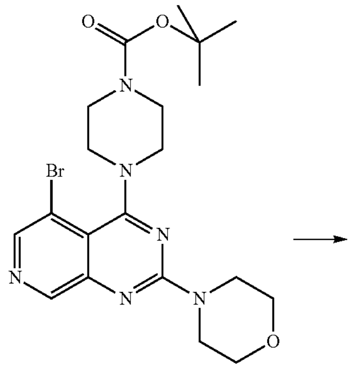

[C028]

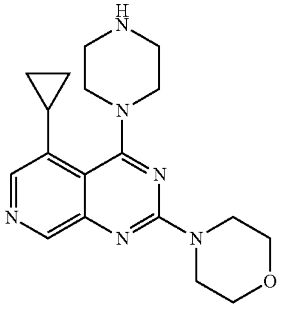

[1016]

A solution of 4-(5-Bromo-2-morpholin-4-yl-pyrido[3,4-d]pyrimidin-4-yl)-piperazine-1-carboxylic acid tert-butyl ester [C028](110 mg, 0.229 mmol) in anhydrous dioxane (2.5 mL) was prepared in a microwave vial. potassium phosphate (tribasic) (ground, 145 mg, 0.687 mmol) and cyclopropyl boronic acid (30 mg, 0.344 mmol) were added. The reaction mixture was purged with argon (vacuum/argon balloon) 3 times and then Dichloro[1,1'-bis(diphenylphosphino)ferrocene]palladium (II) dichloromethane adduct (9 mg, 0.011 mmol) was added and the vial sealed and heated to 95° C. for 5 hours. The reaction mixture was cooled to room temperature and allowed to stand overnight. The reaction mixture was evaporated onto silica and purified by chromatography on silica, eluting with $CH_2Cl_2$ containing 0-8% MeOH. The product was not purified with this solvent system and so the appropriate fractions were concentrated and purification repeated, eluting with cyclo-hexane containing 50-100% EtOAc. The appropriate fractions were combined and concentrated to give 4-(5-Cyclopropyl-2-morpholin-4-yl-pyrido[3,4-d]pyrimidin-4-yl)-piperazine-1-carboxylic acid tert-butyl ester (53 mg, 52%) as a yellow glassy solid. LCMS method: 5, RT 4.09 min, MI 441 [M+H]; NMR: (1H, 500 MHz, d6-dmso) 8.50 (1H, s), 7.68 (1H, s), 3.79-3.19 (8H, very broad set of signals), 3.79-3.74 (4H, m), 3.66-3.64 (4H, m), 2.62-2.59 (1H, m), 1.40 (9H, s), 1.18-1.14 (2H, m), 0.93-0.90 (2H, m). The Boc-protected intermediate was stirred in 4M HCl in dioxane (2 mL) at room temperature for 2 hours. The reaction mixture was concentrated by rotary evaporation and loaded onto a SCX cartridge, washing with MeOH and eluting with 7N ammonia in MeOH. The ammonia fraction was concentrated by rotary evaporation to give the title compound [1016](37 mg, 90%) as a pale yellow solid. LCMS method: 5, RT 4.41 min, MI 341 [M+H]; NMR: (1H, 500 MHz, d6-dmso) 8.48 (1H, s), 7.65 (1H, s), 3.75-3.73 (4H, m), 3.66-3.62 (overlapping 4H m and 2H very broad s), 3.19 (2H, very broad s), 2.80 (4H, br. m), 2.63-2.58 (1H, m), 1.17-1.14 (2H, m), 0.93-0.90 (2H, m).

Synthesis of 4-((S)-3-Benzyl-piperazin-1-yl)-5-cyclopropyl-2-morpholin-4-yl-pyrido[3,4-d]pyrimidine [1017]

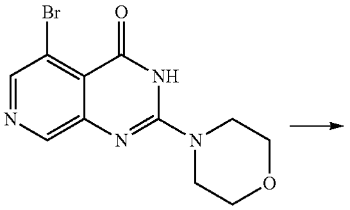

[C027]

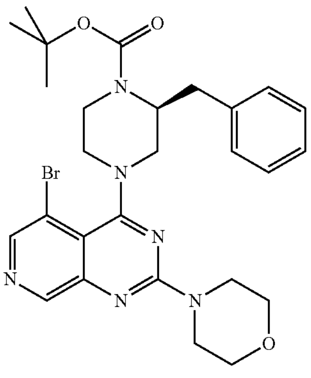

[C029]

(S)-2-Benzyl-4-(5-bromo-2-morpholin-4-yl-pyrido[3,4-d]pyrimidin-4-yl)-piperazine-1-carboxylic acid tert-butyl ester [C029]

Following the procedure described in Scheme C3,5-Bromo-2-morpholin-4-yl-3H-pyrido[3,4-d]pyrimidin-4-one [C027](200 mg, 0.64 mmol) was reacted with (S)-2-Benzyl-piperazine-1-carboxylicacidtert-butylester (355 mg, 1.28 mmol) to give (S)-2-Benzyl-4-(5-bromo-2-morpholin-4-yl-pyrido[3,4-d]pyrimidin-4-yl)-piperazine-1-carboxylic acid tert-butyl ester [C028](139 mg, 38%). LCMS method: 5, RT: 5.64 min, MI: 569/571 [M+1].

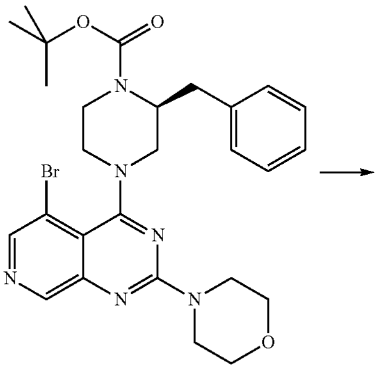

[C029]

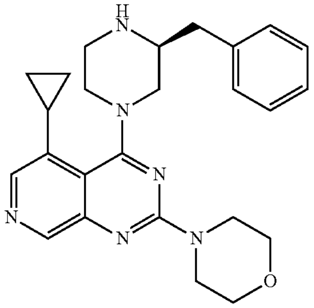

[1017]

4-((S)-3-Benzyl-piperazin-1-yl)-5-cyclopropyl-2-morpholin-4-yl-pyrido[3,4-d]pyrimidine Following the procedure described in Scheme C3, (S)-2-Benzyl-4-(5-bromo-2-morpholin-4-yl-pyrido[3,4-d]pyrimidin-4-yl)-piperazine-1-carboxylic acid tert-butyl ester [C029](135 mg, 0.24 mmol) was reacted with cyclopropyl boronic acid (31 mg, 0.36 mmol) to give 4-((S)-3-Benzyl-piperazin-1-yl)-5-cyclopropyl-2-morpholin-4-yl-pyrido[3,4-d]pyrimidine [1017](62 mg, 61%) s a yellow solid. LCMS method: 5, RT 2.74 min, MI 431 [M+H]; NMR: (1H, 500 MHz, $CDCl_3$) 8.66 (1H, s), 7.65 (1H, s), 7.33-7.19 (5H, m), 4.35-2.42 (18H, very broad overlapping multiplets), 1.16-1.08 (2H, br m), 0.90-0.82 (2H, br m).

Synthesis of [(S)-4-(5-Cyclopropyl-2-morpholin-4-yl-pyrido[3,4-d]pyrimidin-4-yl)-piperazin-2-yl]-acetonitrile [1018]

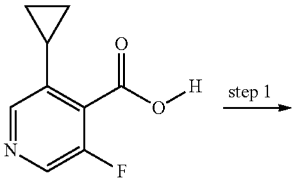

•TFA

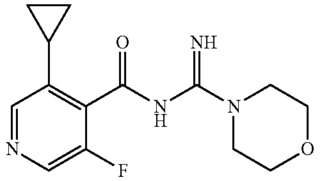

[C030]

3-Cyclopropyl-5-fluoro-N-(imino-morpholin-4-yl-methyl)-isonicotinamide [C030]

Following the procedure described in Scheme C3, trifluoro-acetate 4-carboxy-3-cyclopropyl-5-fluoro-pyridinium (1.51 g, 5.10 mmol) was reacted with 4-Morpholinylformamidine hydrobromide (1.56 g, 5.10 mmol) to give 3-Cyclopropyl-5-fluoro-N-(imino-morpholin-4-yl-methyl)-isonicotinamide [C029](1.23 g, 84%) which was used without purification in the next step. LCMS method: 5, RT 2.35 min, MI 293 [M+H].

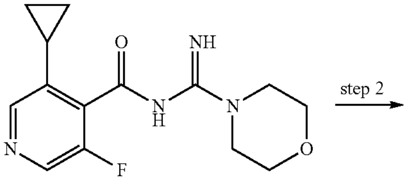

[C030]

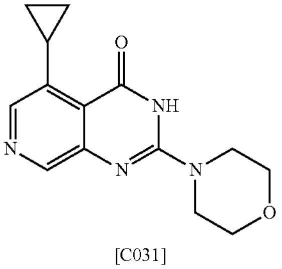

[C031]

Step 2: 5-Cyclopropyl-2-morpholin-4-yl-3H-pyrido[3,4-d]pyrimidin-4-one [C031]

Following the procedure described in Scheme C3,3-Cyclopropyl-5-fluoro-N-(imino-morpholin-4-yl-methyl)-isonicotinamide (1.26 g, 4.30 mmol) was treated with $K_2CO_3$ under microwave irradiation to 5-Cyclopropyl-2-morpholin-4-yl-3H-pyrido[3,4-d]pyrimidin-4-one [C030](402 mg, 34%). LCMS method: 5, RT 3.41 min, MI 273 [M+H].

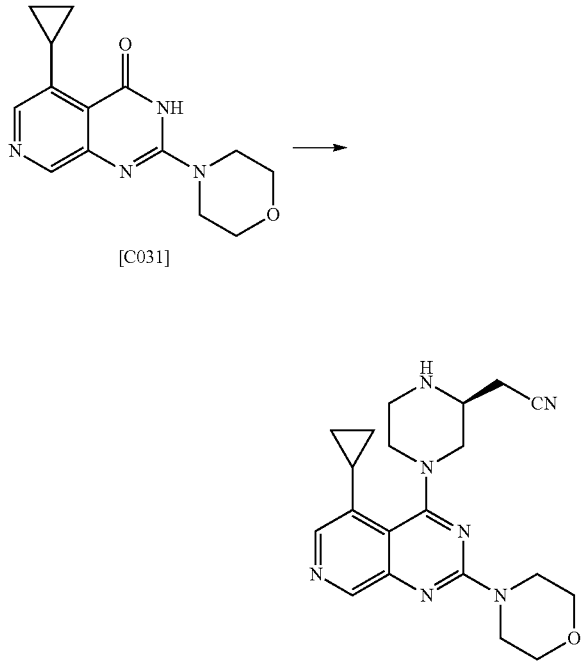

[C031]

[1018]

[(S)-4-(5-Cyclopropyl-2-morpholin-4-yl-pyrido[3,4-d]pyrimidin-4-yl)-piperazin-2-yl]-acetonitrile [1018]

A stirred solution of 5-Cyclopropyl-2-morpholin-4-yl-3H-pyrido[3,4-d]pyrimidin-4-one [C031](50 mg, 0.184 mmol) in DMF (5 mL) was prepared at room temperature under nitrogen. Triethylamine (0.03 mL, 0.193 mmol) was added followed by 2,4,6-triisopropylbenzenesulfonyl chloride (56 mg, 0.186 mmol). The reaction mixture was stirred at room temperature for 2 hours then (S)-Piperazin-2-yl-acetonitrile (23 mg, 0.184 mmol) was added. The reaction mixture was stirred at room temperature overnight. The reaction mixture was concentrated under reduced pressure and the residue purified by chromatography on silica, eluting with $CH_2Cl_2$ containing 0-10% MeOH. The appropriate fractions were combined and concentrated to give the title compound [1018](30 mg, 43%) as a yellow solid. LCMS method: 5, RT 5.76 min, MI 380 [M+H]; NMR: (1H, 500 MHz, $CDCl_3$) 8.69 (1H, s), 7.70 (1H, s), 4.46-4.29 (1H, br s), 3.95-3.93 (1H, br m), 3.88 (4H, t), 3.78 (4H, t), 3.32-3.27 (1H, m), 3.20-2.66 (5H, br m), 2.50 (2H, br s), 1.80 (1H, br s), 1.16 (2H, br s), 0.95 (2H, br s).

4PPAZ Compounds

Several methods for the chemical synthesis of 4-substituted-2-(1H-pyrrolo[2,3-b]pyridin-4-yl)-azaquinazoline compounds (for convenience, collectively referred to herein as "4PPAZ compounds") of the present application are described herein, of general formula [I-001]. These and/or other well known methods may be modified and/or adapted in known ways in order to facilitate the synthesis of additional compounds within the scope of the present application.

[I-001]

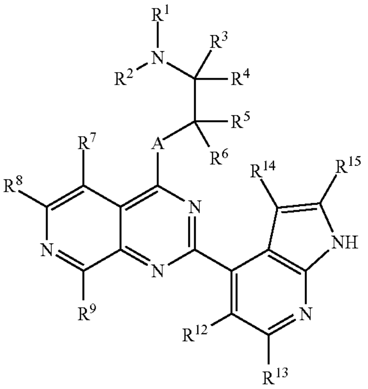

General synthesis of substituted substituted 4-substituted-2-(1H-pyrrolo[2,3-b]pyridin-4-yl)-azaquinazoline derivatives of general formula [I-001] Scheme D1

The 4-substituted-2-(1H-pyrrolo[2,3-b]pyridin-4-yl)-azaquinazoline derivatives of general formula [I-003] were prepared by the reaction of a 2-Chloro-pyrido[3,4-d]pyrimidine derivative of general formula [I-002], prepared in scheme C2, in a Suzuki type palladium catalysed cross coupling reaction with boronic acid or boronate ester derivative of general formula [I-004] a palladium catalyst such as $Pd(PPh_3)_4$, a base such as $K_2PO_4$ in a polar aprotic solvent such as DMA or DMF at elevated temperature either by heating thermally or using a microwave reactor, to yield 4PPAZ derivative of general formula [I-003]. After reaction work up, typically by a liquid-liquid extraction or purification by acidic ion exchange catch-release, the intermediate was purified by column chromatography. The intermediate arylsulphonate protected derivative of general formula [I-003] was then subjected to a deprotection reaction in the presence of a base such as sodium hydroxide in a polar protic solvent such as ethanol. After reaction work up, typically by a liquid-liquid extraction or purification by acidic ion exchange catch-release, the intermediate was purified by column chromatography and the N-Boc derivatives were deprotected under acidic conditions with a strong acid such as TFA, HCl in a solvent such as DCM, DCE or 1,4-dioxane or by catch and release sulfonic acidic resins such as polymer supported toluene sulfonic acid and the crude reaction product was purified by normal phase chromatography or reverse phase preparative HPLC.

Scheme D1

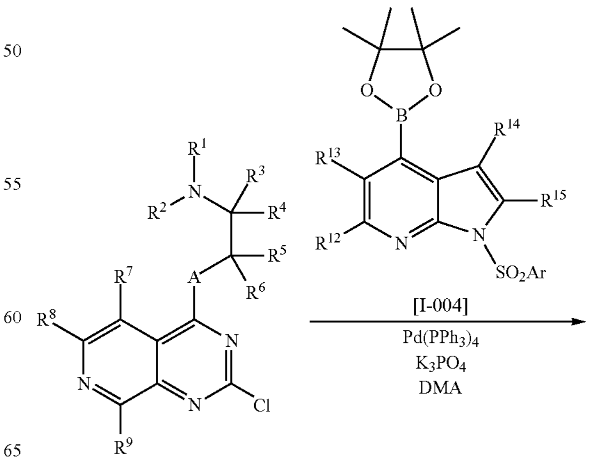

[I-002]

-continued

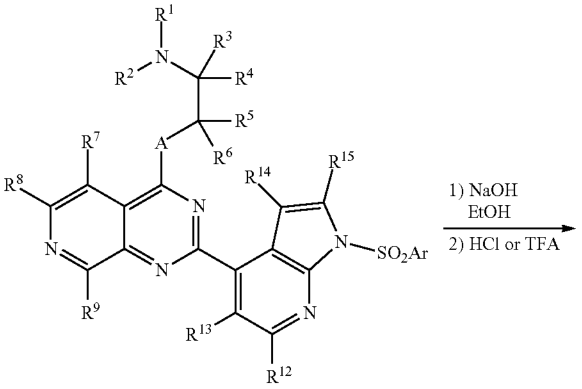

[I-003]

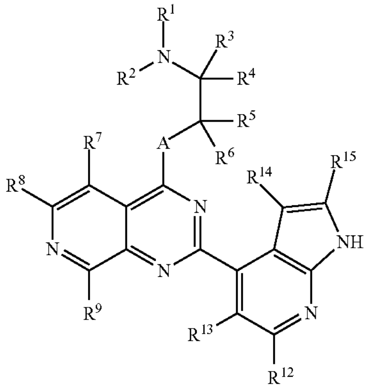

[I-001]

Synthesis of 5-Methoxy-4-piperazin-1-yl-2-(1H-pyrrolo[2,3-b]pyridin-4-yl)-pyrido[3,4-d]pyrimidine [1200]

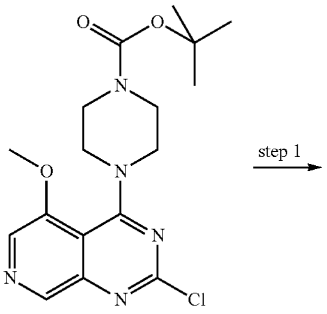

[C011]

-continued

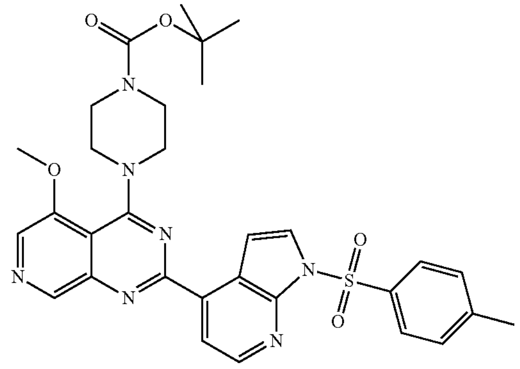

[D001]

4-{5-Methoxy-2-[1-(toluene-4-sulfonyl)-1H-pyrrolo[2,3-b]pyridin-4-yl]-pyrido[3,4-d]pyrimidin-4-yl}-piperazine-1-carboxylic acid tert-butyl ester [D001]

A solution of 4-(2-Chloro-5-methoxy-pyrido[3,4-d]pyrimidin-4-yl)-piperazine-1-carboxylic acid tert-butyl ester [C011 prepared in scheme C2](250 mg, 0.671 mmol) in DMA (7.5 mL) was prepared. 4-(4,4,5,5-Tetramethyl-[1,3,2]dioxaborolan-2-yl)-1-(toluene-4-sulfonyl)-1H-pyrrolo[2,3-b]pyridine [D002](374 mg, 0.940 mmol), $Pd(PPh_3)_4$(77 mg, 0.067 mmol) and $K_3PO_4$ (2.68 mL of a 0.5 M solution in water) were added. The reaction mixture was heated to 150° C. in the microwave for 10 min. The reaction mixture was concentrated by rotovap and purified by column chromatography on silica, eluting with cyclohexane containing 0-100% EtOAc. The appropriate fractions were combined and concentrated to give the title compound [D001]](115 mg, 28%) as a yellow solid. LCMS method: 5, RT 5.13 min, MI 616 [M+H]; NMR: (1H, 500 MHz, d6-dmso) 8.92 (s, 1H), 8.53 (d, 1H), 8.37 (s, 1H), 8.26 (d, 1H), 8.05 (d, 1H), 8.02 (d, 1H), 7.77 (d, 1H), 7.64-7.60 (m, 1H), 7.57-7.53 (m, 1H), 7.43 (d, 2H), 4.09 (s, 3H), 3.67 (br. m, 4H), 3.56 (br. m, 4H), 1.43 (s, 9H).

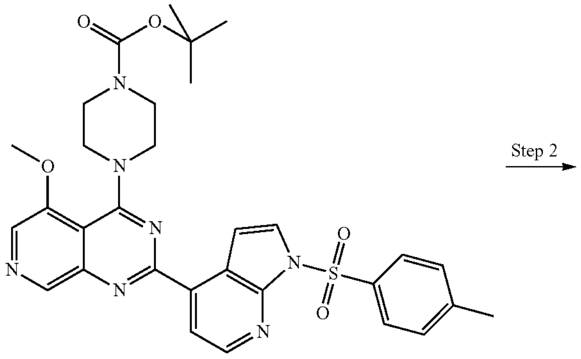

[D001]

-continued

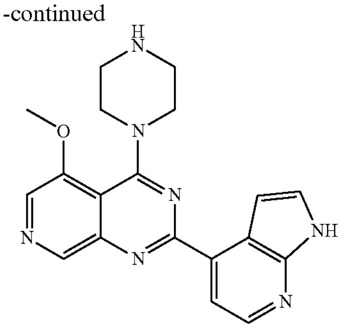

[1200]

5-Methoxy-4-piperazin-1-yl-2-(1H-pyrrolo[2,3-b]pyridin-4-yl)-pyrido[3,4-d]pyrimidine A solution of 4-{5-Methoxy-2-[1-(toluene-4-sulfonyl)-1H-pyrrolo[2,3-b]pyridin-4-yl]-pyrido[3,4-d]pyrimidin-4-yl}-piperazine-1-carboxylic acid tert-butyl ester [D001](100 mg, 0.162 mmol) in ethanol (4 mL) was prepared and NaOH (1 mL of a 5 M solution) was added. The reaction mixture was stirred at room temperature overnight. The reaction mixture was concentrated by rotary evaporation and the residue dissolved in DCM (10 mL) and water (10 mL). The pH was adjusted to approx 7 by addition of ammonium chloride and the mixture extracted with DCM (3×10 mL). The combined organic extracts were dried (phase separator) and concentrated by rotary evaporation. The residue was purified by column chromatography on silica, eluting with cyclohexane containing 75-100% EtOAc. The appropriate fractions were combined and concentrated to give intermediate 4-[5-Methoxy-2-(1H-pyrrolo[2,3-b]pyridin-4-yl)-pyrido[3,4-d]pyrimidin-4-yl]-piperazine-1-carboxylic acid tert-butyl ester which was stirred in 4M HCl in dioxane (2 mL) at room temperature for 1 hour. The reaction mixture was concentrated by rotary evaporation, loaded onto a SCX cartridge, washed with methanol and eluted with 7N ammonia in methanol. The ammonia fraction was concentrated by rotary evaporation to give the title compound [1200](29 mg, 49%) as a yellow solid. LCMS method: 5, RT 2.23 min, MI 362 [M+H]; NMR: (1H, 500 MHz, d6-dmso) 11.81 (1H, s), 8.89 (1H, s), 8.37 (1H, d, J=5.0 Hz), 8.31 (1H, s), 8.09 (1H, d, J=5.0 Hz), 7.63-7.62 (1H, m), 7.43 (1H, dd, J=3.3, 1.8 Hz), 4.07 (3H, s), 3.66-3.64 (4H, m), 2.91-2.89 (4H, m).

General Synthesis of Substituted Boronic Acid or Boronate Ester Derivative of General Formula [I-004] Scheme D2

The substituted boronic acid or boronate ester derivatives of general formula [I-004] were prepared by the reaction of a 4-Bromo-1H-pyrrolo[2,3-b]pyridine derivative of general formula [I-005] with an arylsuphonyl chloride derivative of general formula [I-008] with a base such as NaH in a polar aprotic solvent such as THF at low temperature. The 1-arylsulfonyl-4-bromo-1H-pyrrolo[2,3-b]pyridine derivative of general formula [I-006] was then reacted with a strong base such as LDA, in a polar aprotic solvent such as THF at low temperature and a alkyl halide derivative of general formula [I-009]. The C2 substituted 4-bromo-1H-pyrrolo[2,3-b]pyridine derivative of general formula [I-007] was then reacted in a palladium catalysed cross coupling reaction with a palladium catalyst such as $PdCl_2$ dppf, a boron agent such as bispinocolatodiboron, potassium acetate in a polar aprotic solvent such as dioxane at elevated temperature either by heating thermally or using a microwave reactor, to yield the substituted boronate ester derivative of general formula [I-004] which after reaction work up, typically by a liquid-liquid extraction was purified by column chromatography.

Scheme D2

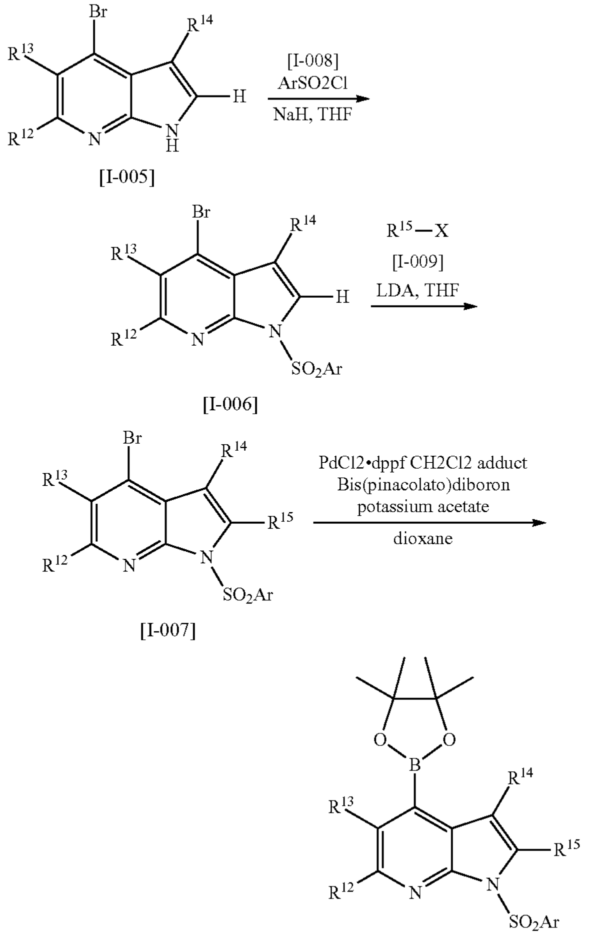

[I-005]

[I-006]

[I-007]

[I-004]

Synthesis of 4-(4,4,5,5-Tetramethyl-[1,3,2]dioxaborolan-2-yl)-1-(toluene-4-sulfonyl)-1H-pyrrolo[2,3-b]pyridine [D002]

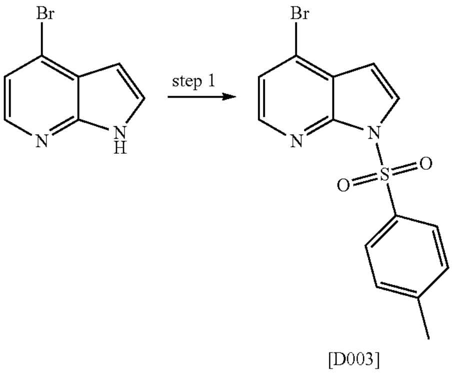

[D003]

4-Bromo-1-(toluene-4-sulfonyl)-1H-pyrrolo[2,3-b]pyridine [D003]

4-Bromo-7-azaindole (3 g, 15.22 mmol) was weighed into a round bottom flask and dissolved in THF (50 mL) under nitrogen. The reaction mixture was cooled to 0° C. and treated portionwise with sodium hydride (60% in mineral oil, 0.67 g, 16.75 mmol), the addition was accompanied by fizzing. After the addition the reaction mixture was allowed to stir for 30 minutes at room temperature and then treated with benzenesulfonyl chloride (2.14 mL, 16.75 mmol). The reaction mixture was allowed to warm to room temperature and stirred for 2 hours. The reaction mixture was evaporated under reduced pressure and dissolved in DCM 30 mL, the organics were washed with 2×30 mL portions of 2M sodium carbonate, dried with MgSO4, filtered and evaporated to an orange oil. Purified by flash column chromatography eluting with 1:9 ethyl acetate:cyclohexane to provide the title compound as an off white solid (92%). LCMS method: 5, RT 5.36 min, MI 337 [M+H]; NMR: (1H, 500 MHz, $CDCl_3$) 8.22 (d, 1H), 8.18 (d, 2H), 7.78 (d, 1H), 7.58 (t, 1H), 7.48 (t, 2H), 7.35 (d, 1H), 6.63 (d, 1H).

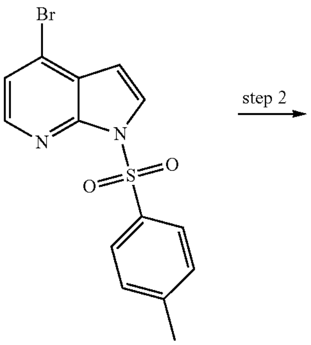

[D003]

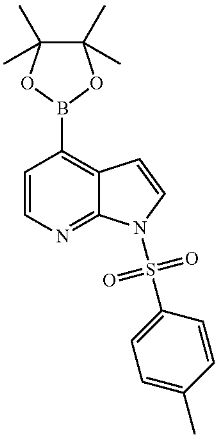

[D002]

4-(4,4,5,5-Tetramethyl-[1,3,2]dioxaborolan-2-yl)-1-(toluene-4-sulfonyl)-1H-pyrrolo[2,3-b]pyridine [D002]

4-Bromo-1-(toluene-4-sulfonyl)-1H-pyrrolo[2,3-b]pyridine (1.57 g, 4.47 mmol), Bis(pinacolato)diboron [D003] (2.71 g, 10.72 mmol), PdCl2.dppf CH2C12 adduct (0.365 g, 0.45 mmol) and potassium acetate (0.876 g, 8.94 mmol) were weighed into a microwave vial. Dioxane (30 mL) was added and the reaction mixture was capped and heated at 130 OC in a microwave reactor for 30 minutes. The solvent was removed under reduced pressure and the residue was partitioned between ammonium chloride 20 mL and ethyl acetate 20 mL. The organics were dried with MgSO4, filtered and evaporated under reduced pressure to a brown oil. This was passed through a short column of silica eluting with 1:4 ethyl acetate:cyclohexane. The fractions were pooled and evaporated to yield the title compound [D002] as a pale yellow solid: LCMS method: 5, RT 4.77 min, MI 317 [M+H for boronic acid intermediate]

Synthesis of Benzenesulfonyl-2-methyl-4-(4,4,5,5-tetramethyl-[1,3,2]dioxaborolan-2-yl)-1H-pyrrolo[2,3-b]pyridine [D004]

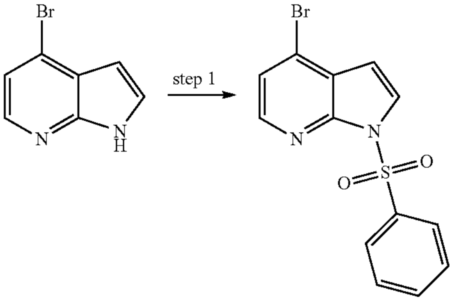

[D005]

1-Benzenesulfonyl-4-bromo-1H-pyrrolo[2,3-b]pyridine [D005]

4-Bromo-7-azaindole (3 g, 15.22 mmol) was weighed into a round bottom flask and dissolved in THF (50 mL) under nitrogen. The reaction mixture was cooled to 0° C. and treated portionwise with sodium hydride (60% in mineral oil, 0.67 g, 16.75 mmol), the addition was accompanied by fizzing. After the addition the reaction mixture was allowed to stir for 30 minutes at room temperature and then treated with benzenesulfonyl chloride (2.14 mL, 16.75 mmol). The reaction mixture was allowed to warm to room temperature and stirred for 2 hours. The reaction mixture was evaporated under reduced pressure and dissolved in DCM 30 mL, the organics were washed with 2×30 mL portions of 2M sodium carbonate, dried with MgSO4, filtered and evaporated to an orange oil. Purified by flash column chromatography eluting with 1:9 ethyl acetate: cyclohexane to provide the title compound [D005] as an off white solid (92%): LCMS method: 5, RT 5.36 min, MI 337 [M+H]; NMR: (1H, 500 MHz, $CDCl_3$) 8.22 (d, 1H), 8.18 (d, 2H), 7.78 (d, 1H), 7.58 (t, 1H), 7.48 (t, 2H), 7.35 (d, 1H), 6.63 (d, 1H).

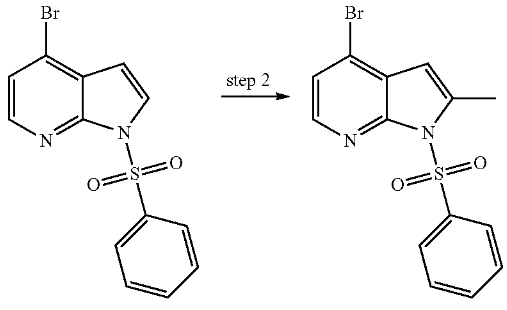

[D005] [D006]

1-Benzenesulfonyl-4-bromo-2-methyl-1H-pyrrolo[2,3-b]pyridine [D006]

To a solution of 1-Benzenesulfonyl-4-bromo-1H-pyrrolo[2,3-b]pyridine [D005](2 g, 5.93 mmol) in THF (50 mL) at −78° C., LDA (2M, 5.9 mL, 11.86 mmol) was added dropwise. The solution was stirred 30 min. The temperature was allowed to warm to 0° C. and Methyl iodide (3.67 mL, 59 mmol) was then added dropwise and the solution was stirred 3 h at 0° C. and was allowed to stir to room temperature overnight. The reaction was quenched with aqueous ammonium chloride solution and extracted with DCM. The combined organic layers were dried over MgSO4 and concentrated in vacuo. The crude was purified by SP1 (eluent, gradient: Cyclohexane/AcOEt: 1/0 to 8/2). The fractions were collected and concentrated under reduced pressure to yield the title compound [D006] a white solid (87%). LCMS method: 5, RT 5.80 min, MI 351 [M+H]; NMR: (1H, 500 MHz, $CDCl_3$) 8.12-8.15 (m, 3H), 7.56 (t, 1H), 7.47 (t, 2H), 7.29 (d, 1H), 6.34 (s, 1H), 2.74 (s, 3H).

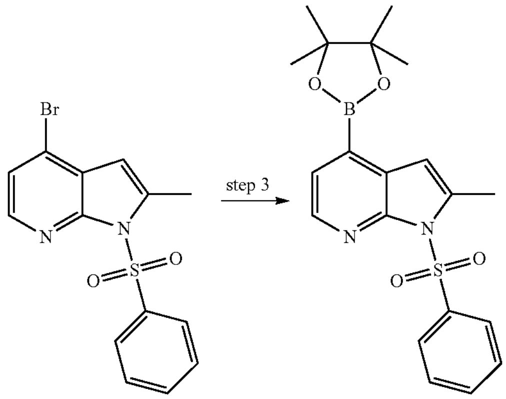

[D006] [D008]

Benzenesulfonyl-2-methyl-4-(4,4,5,5-tetramethyl-[1,3,2]dioxaborolan-2-yl)-1H-pyrrolo[2,3-b]pyridine [D004]

Following the procedure described in scheme D2 replacing 1-Benzenesulfonyl-4-bromo-1H-pyrrolo[2,3-b]pyridine with 1-Benzenesulfonyl-4-bromo-2-methyl-1H-pyrrolo[2,3-b]pyridine gave the title compound [D004](72%%) as a pale yellow solid. LCMS method: 5, RT 6.19 min, MI 399 [M+H]; NMR: (1H, 500 MHz, $CDCl_3$) 8.34 (d, 1H), 8.07 (d, 2H), 7.50 (t, 1H), 7.46 (d, 1H), 7.41 (t, 2H), 6.70 (s, 1H), 2.73 (s, 3H), 1.33 (s, 12H).

The following compounds were prepared according to Scheme D2:

1-Benzenesulfonyl-2-benzyl-4-(4,4,5,5-tetramethyl-[1,3,2]dioxaborolan-2-yl)-1H-pyrrolo[2,3-b]pyridine [D007]

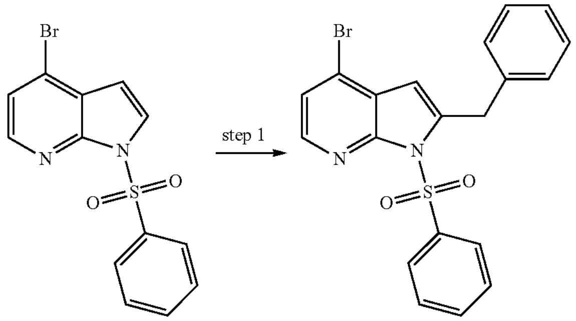

[D008]

1-Benzenesulfonyl-2-benzyl-4-bromo-1H-pyrrolo[2,3-b]pyridine [D008]

Following the procedure described in scheme D2,1-Benzenesulfonyl-4-bromo-1H-pyrrolo[2,3-b]pyridine was reacted with benzyl bromide to give the title compound [D008] which was used crude in the next step. LCMS method: 5, RT 6.62 min, MI 427 [M+H].

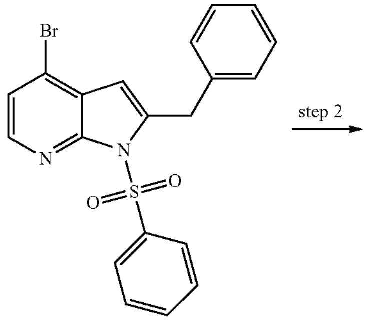

[D008]

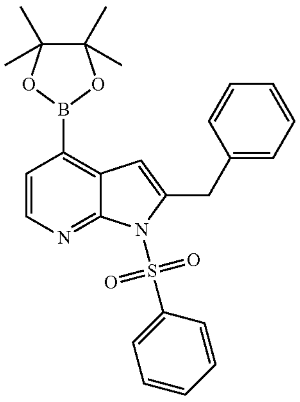

[D007]

1-Benzenesulfonyl-2-benzyl-4-(4,4,5,5-tetramethyl-[1,3,2]dioxaborolan-2-yl)-1H-pyrrolo[2,3-b]pyridine [D007]

Following the procedure described in scheme D2 replacing 1-Benzenesulfonyl-4-bromo-1H-pyrrolo[2,3-b]pyridine with 1-Benzenesulfonyl-2-benzyl-4-bromo-1H-pyrrolo[2,3-b]pyridine gave the title compound [D007] as a pale yellow solid: LCMS method: 5, RT 5.59 min, MI 392 [M+H, Boronic ester hydrolysed into the corresponding boronic acid in the LCMS conditions]; NMR: (1H, 500 MHz, d6-dmso) 8.38 (d, 1H), 7.70 (dd, 1H), 7.49 (d, 1H), 7.42 (t, 1H), 7.23-7.30 (m, 7H), 6.75 (s, 1H), 4.54 (d, 2H), 1.34 (s, 12H).

Synthesis of 1-Benzenesulfonyl-2-(2-fluoro-benzyl)-4-(4,4,5,5-tetramethyl-[1,3,2]dioxaborolan-2-yl)-1H-pyrrolo[2,3-b]pyridine [D009]

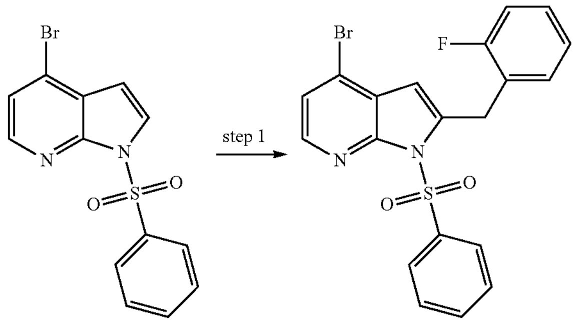

[D010]

Step 1: 1-Benzenesulfonyl-4-bromo-2-(2-fluoro-benzyl)-1H-pyrrolo[2,3-b]pyridine [D010]

Following the procedure described in scheme D2,1-Benzenesulfonyl-4-bromo-1H-pyrrolo[2,3-b]pyridine was reacted with 2-fluorobenzylbromide to give the title compound [D010](75%): LCMS method: 5, RT 6.45 min, MI 445 [M+H].

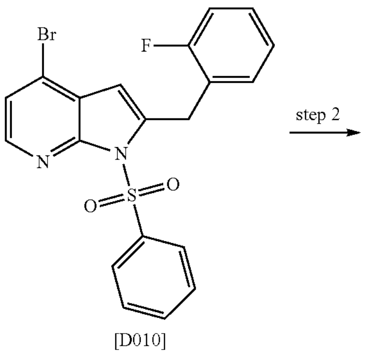

[D010]

-continued

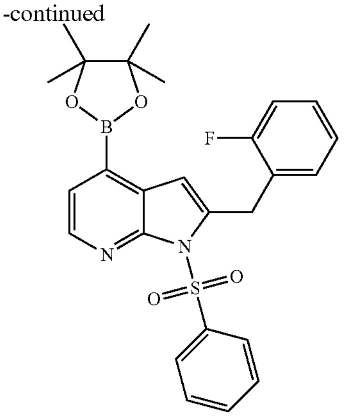

[D009]

Step 2: 1-Benzenesulfonyl-2-(2-fluoro-benzyl)-4-(4,4,5,5-tetramethyl-[1,3,2]dioxaborolan-2-yl)-1H-pyrrolo[2,3-b]pyridine [D009]

Following the procedure described in scheme D2 replacing 1-Benzenesulfonyl-4-bromo-1H-pyrrolo[2,3-b]pyridine with 1-Benzenesulfonyl-4-bromo-2-(2-fluoro-benzyl)-1H-pyrrolo[2,3-b]pyridine gave the title compound [D009] as a white solid. LCMS method: 5, RT 5.50 min, MI 411 [M+1, hydrolysed boronic ester to its corresponding boronic acid].

Synthesis of 1-Benzenesulfonyl-2-ethyl-4-(4,4,5,5-tetramethyl-[1,3,2]dioxaborolan-2-yl)-1H-pyrrolo[2,3-b]pyridine [D011]

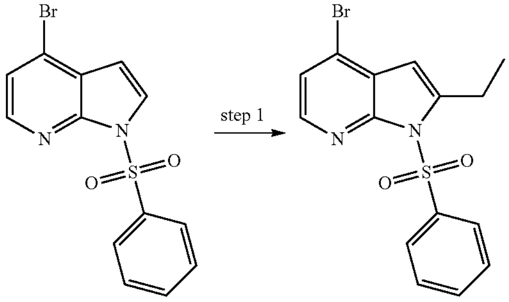

[D012]

1-Benzenesulfonyl-4-bromo-2-ethyl-1H-pyrrolo[2,3-b]pyridine [D012]

Following the procedure described in scheme D 2,1-Benzenesulfonyl-4-bromo-1H-pyrrolo[2,3-b]pyridine was reacted with iodoethane to give the title compound [D012] as a white solid: LCMS method: 5, RT 6.01 min, MI 351 [M+H]; NMR: (1H, 500 MHz, d6-dmso) 8.11-8.15 (m, 3H), 7.56 (d, 1H), 7.45-7.48 (m, 2H), 7.30 (d, 1H), 6.39 (s, 1H), 3.19 (q, 2H), 1.42 (t, 3H).

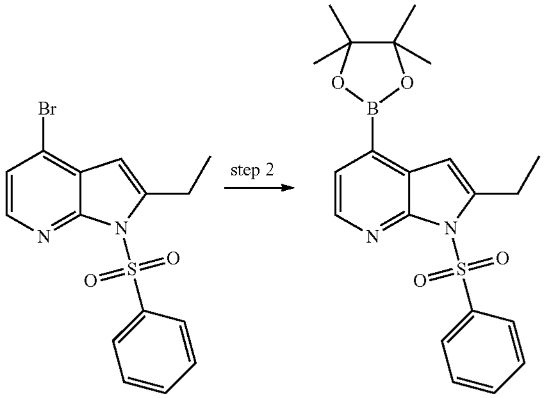

[D012] [D011]

1-Benzenesulfonyl-2-ethyl-4-(4,4,5,5-tetramethyl-[1,3,2]dioxaborolan-2-yl)-1H-pyrrolo[2,3-b]pyridine [D011]

Following the procedure described in scheme D 2 replacing 1-Benzenesulfonyl-4-bromo-1H-pyrrolo[2,3-b]pyridine with 1-Benzenesulfonyl-4-bromo-2-ethyl-1H-pyrrolo[2,3-b]pyridine gave the title compound [D011] as a pale yellow solid. LCMS method: 5, RT 6.42 min, MI 413 [M+H]; LCMS Method 1LCMS5, 6.42 min, MI: 413 [M+1].

The following compounds were synthesised according to the general synthesis shown in scheme [D1]

| | | | Analysis | | |
|---|---|---|---|---|---|
| Ex | Precursor | Boronic ester | LCMS | NMR | Name |
| 1201 | 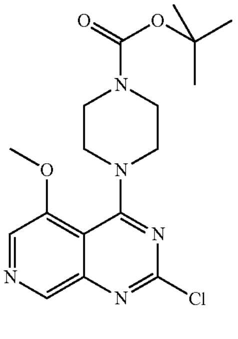 [C011] | 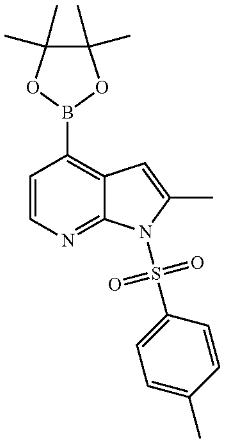 [D004] | Method 5: RT: 2.39 min, MI: 376 [M + H] | (1H, 500 MHz, d6-dmso) 3.44 (brs, 4H), 3.86-(brs, 4H), 4.10 (s, 3H), 7.16 (s, 1H), 8.06 (d, 1H), 8.25 (d, 1H), 8.39 (s, 1H), 8.92 (brs, 2H), 8.98 (s, 1H), 11.77 (brs, 1H). | 5-Methoxy-2-(2-methyl-1H-pyrrolo[2,3-b]pyridin-4-yl)-4-piperazin-1-yl-pyrido[3,4-d]pyrimidine |
| 1202 | 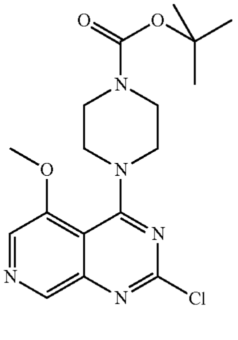 [C011] | 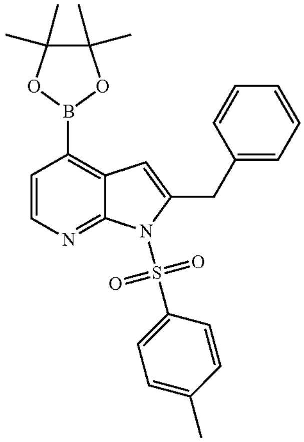 [D007] | Method 5: RT: 3.49 min, MI: 452 [M + H] | (1H, 500 MHz, d6-dmso) 3.19-3.39 (m, 3H), +H2O), 3.77-3.83 (m, 4H), 4.08 (s, 3H), 4.16 (s, 2H), 7.08 (s, 1H), 7.24 (t, 1H), 7.32-7.40 (m, 4H), 8.05 (d, 1H), 8.26 (d, 1H), 8.36 (s, 1H), 8.90 (s, 1H), 8.97 (brs, 2H), 11.86 (s, 1H). | 2-(2-Benzyl-1H-pyrrolo[2,3-b]pyridin-4-yl)-5-methoxy-4-piperazin-1-yl-pyrido[3,4-d]pyrimidine |

-continued

| | | | Analysis | | |
|---|---|---|---|---|---|
| Ex | Precursor | Boronic ester | LCMS | NMR | Name |
| 1203 | 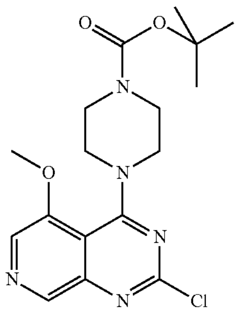 [C011] | 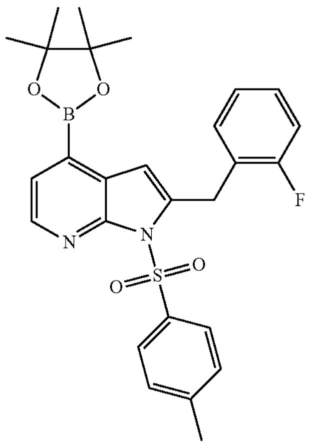 [D009] | Method 5: RT: 3.39 min, MI: 470 [M + H] | (1H, 500 MHz, d6-dmso) 2.96 (brs, 4H), 3.60 (brs, 4H), 4.05 (s, 3H), 4.18 (s, 2H), 6.96 (s, 1H), 7.19-7.23 (m, 2H), 7.32-7.44 (m, 2H), 8.03 (s, 1H), 8.27 (d, 1H), 8.29 (s, 1H), 8.79 (s, 1H), 11.87 (brs, 1H). | 2-[2-(2-Fluoro-benzyl)-1H-pyrrolo[2,3-b]pyridin-4-yl]-5-methoxy-4-piperazin-1-yl-pyrido[3,4-d]pyrimidine |
| 1204 | 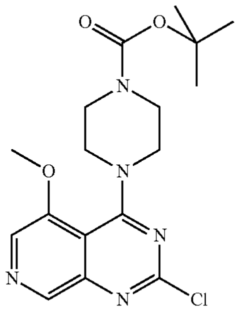 [C011] | 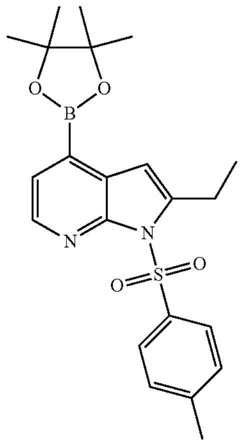 [D011] | | | 2-(2-Ethyl-1H-pyrrolo[2,3-b]pyridin-4-yl)-5methoxy-4-piperazin-1-yl-pyrido[3,4-d]pyrimidine |
| 1205 | 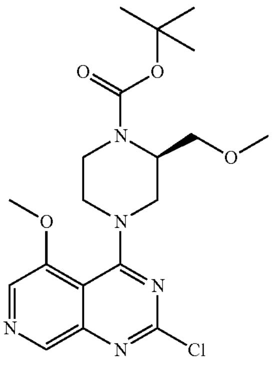 [C019] | 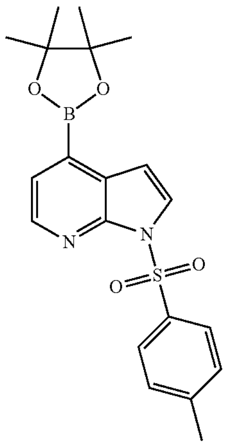 [D002] | Method 5: RT: 2.53 min, MI: 406 [M + H] | | 5-Methoxy-4-((R)-3-methoxymethyl-piperazin-1-yl)-2-(1H-pyrrolo[2,3-b]pyridin-4-yl)-pyrido[3,4-d]pyrimidine |

-continued

| | | | Analysis | | |
|---|---|---|---|---|---|
| Ex | Precursor | Boronic ester | LCMS | NMR | Name |
| 1206 | 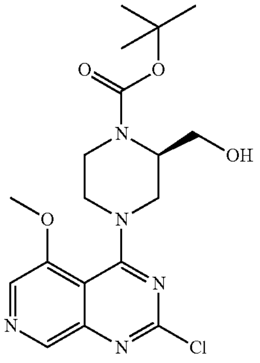 [C020] | 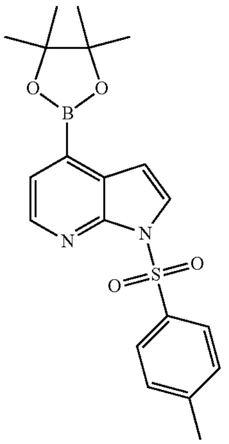 [D002] | Method 5: RT: 2.36 min, MI: 392 [M + H] | (1H, 500 MHz, d6-dmso) 2.86-2.96 (m, 3H), 3.10 (d, 1H), 3.15-3.19 (m, 1H), 3.39-3.45 (m, 2H), 4.06 (s, 3H), 4.15-4.24 (m, 2H), 7.43-7.44 (m, 1H), 7.60-7.61 (m, 1H), 8.08 (d, 1H), 8.19 (s, 1H), 8.32 (s, 1H), 8.35 (d, 1H), 8.89 (s, 1H), 11.89 (brs, 1H). | {(R)-4-[5-Methoxy-2-(1H-pyrrolo[2,3-b]pyridin-4-yl)-pyrido[3,4-d]pyrimidin-4-yl]piperazin-2-yl}-methanol |
| 1207 | 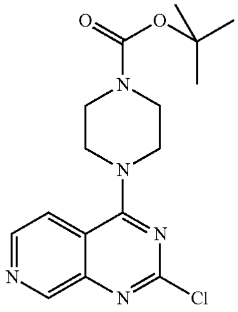 [C013] | 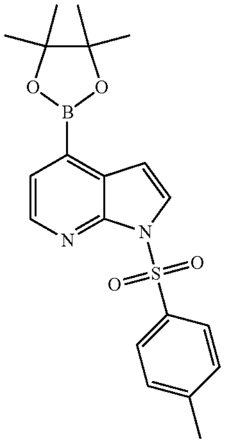 [D002] | Method 5: RT: 1.99 min, MI: 332 [M + H] | (1H, 500 MHz, d6-dmso) 2.94-2.97 (m, 4H), 3.89-3.93 (m, 4H), 7.45 (t, 1H), 7.63 (t, 1H), 7.90 (d, 1H), 8.11 (d, 1H), 8.37 (d, 1H), 8.57 (d, 1H), 9.32 (s, 1H), 11.83 (brs, 1H). | 4-Piperazin-1-yl-2-(1H-pyrrolo[2,3-b]pyridin-4-yl)-pyrido[3,4-d]pyrimidine |
| 1208 | 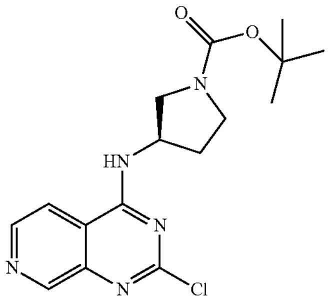 [C021] | 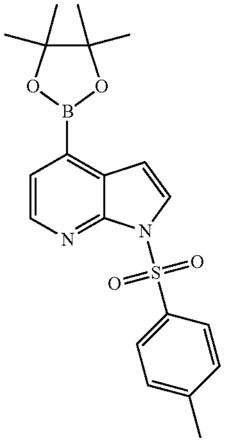 [D002] | Method 5: RT: 1.91 min, MI: 332 [M + H] | (1H, 500 MHz, d6-dmso) 2.21-2.28 (m, 1H), 2.34-2.44 (m, 1H), 3.33-3.50 (m, 3H), 3.67-3.74 (m, 2H), 4.95-5.04 (m, 1H), 7.50 (d, 1H), 7.63 (t, 1H), 8.15 (d, 1H), 8.25 (d, 1H), 8.38 (d, 1H), 8.64 (d, 1H), 8.70 (d, 1H), 9.30 (s, 1H), 11.86 (s, 1H) | (R)-Pyrrolidin-3-yl-[2-(1H-pyrrolo[2,3-b]pyridin-4-yl)-pyrido[3,4-d]pyrimidin-4-yl]-amine |

General synthesis of substituted substituted 4-substituted-2-(1H-pyrrolo[2,3-b]pyridin-4-yl)-azaquinazoline derivatives of general formula [I-001] Scheme D3

The 4-substituted-2-(1H-pyrrolo[2,3-b]pyridin-4-yl)-azaquinazoline derivatives of general formula [I-001] were prepared by the reaction of a halogenated pyridine derivative of general formula [I-010] with a strong base such as LDA, in a polar aprotic solvent such as THF, a symmetrical anhydride such as Di-tert-butyl dicarbonate at low temperature to yield halo-substituted-isonicotinic acid tert-butly ester derivatives of general formula [I-011]. After reaction work up, typically by a liquid-liquid extraction the intermediate was purified by column chromatography. The halo-substituted-isonicotinic acid tert-butly ester derivative of general formula [I-011] was then subjected to a Suzuki type palladium catalysed cross coupling reaction with boronic acid or boronate ester derivative of general formula [I-018] a palladium catalyst such as $Pd(PPh_3)_4$, a base such as $K_2PO_4$ in a polar aprotic solvent such as DMA or DMF at elevated temperature either by heating thermally or using a microwave reactor, to yield the substituted-isonicotinic acid tert-butly ester derivative of general formula [I-012]. After reaction work up, typically by a liquid-liquid extraction the intermediate was purified by column chromatography. The t-butylester inter intermediate [I-012] was then subjected to a deprotection reaction in the presence of a base such as sodium hydroxide in a polar protic solvent such as ethanol to yield the substituted-isonicotinic acid derivative of general formula [I-013], which was then subjected to a coupling reaction with a substituted 1H-pyrrolo[2,3-b]pyridine-4-carboxamidine derivative of general formula [I-014], with a suitable coupling agent such as O-(7-Azabenzotriazol-1-yl)-N,N,N',N'-tetramethyluronium hexafluorophosphate (HATU) in a polar aprotic solvent such as DMA or DMF. The isonicotinoyl-amidine derivative of general formula [I-015] can then be cyclised to displace the relevant halogen group to yield the desired 2-(1H-pyrrolo[2,3-b]pyridine-4-yl)-pyrido[3,4-d]pyrimidin-4-ol derivative of general formula [I-016]. The 4-substituted-2-(1H-pyrrolo[2,3-b]pyridin-4-yl)-azaquinazoline derivatives of general formula [I-001] were prepared by the reaction of a 2-(1H-pyrrolo[2,3-b]pyridine-4-yl)-pyrido[3,4-d]pyrimidin-4-ol derivative of general formula [I-016] with a chlorinatation agent such as phosphorous oxychloride to give compounds of general formula and the intermediate 4-chloro derivative was then further reacted with primary or secondary amino derivative of general formula [I-017], in a polar aprotic solvent such as DMA, DMF, NMP in the presence of a tertiary amine base such as $Et_3N$, DIPEA or NMM at ambient temperature [method A]. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by normal phase silica gel chromatography or reverse phase preparative HPLC. 4-substituted-2-(1H-pyrrolo[2,3-b]pyridin-4-yl)-azaquinazoline derivatives of general formula [I-001] were prepared by the reaction of a -(1H-pyrrolo[2,3-b]pyridine-4-yl)-pyrido[3,4-d]pyrimidin-4-ol derivative of general formula [I-016] with 2,4,6-triisopropylbenzenesulfonyl chloride in a polar aprotic solvent such as DMA, DMF, NMP with a tertiary alkylamine base such as $Et_3N$, DIPEA or NMM and a catalytic amount of DMAP [method B]. The intermediate 6,7-substituted-(2,4,6-triisopropyl-benzenesulfonic acid)-(1H-pyrrolo[2,3-b]pyridine-4-yl)-pyrido[3,4-d]pyrimidin-4-yl ester was then reacted with a primary or secondary amino derivative, of general formula [G-117], in a polar aprotic solvent such as DMA, DMF, NMP in the presence of a tertiary amine base such as $Et_3N$, DIPEA or NMM at ambient temperature. After reaction work up, typically by a liquid-liquid extraction or purification by acidic ion exchange catch-release, the N-Boc derivatives were deprotected under acidic conditions with a strong acid such as TFA, TCA, methanesulfonic acid, HCl or $H_2SO_4$ in a solvent such as DCM, DCE, THF, EtOH or MeOH and the crude reaction product was purified by reverse phase preparative HPLC.

Scheme D3

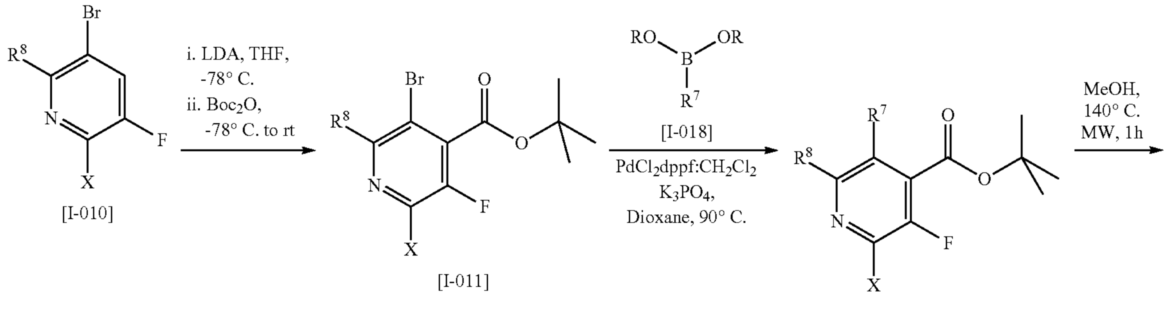

[I-010] [I-011] [I-012]

-continued
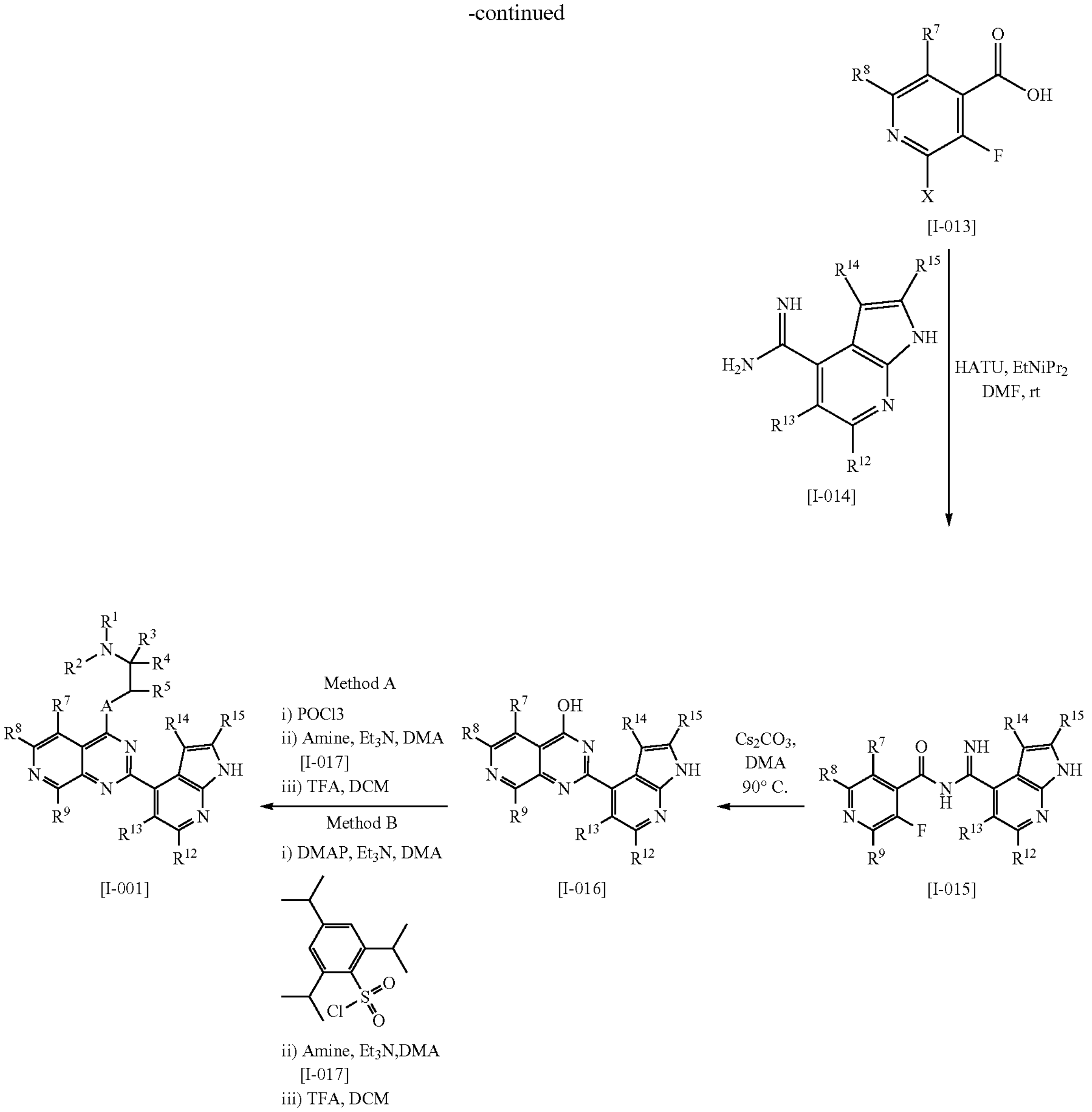
[I-013]
[I-014]
[I-015]
[I-016]
[I-001]
Synthesis of 5-Cyclopropyl-4-piperazin-1-yl-2-(1H-pyrrolo[2,3-b]pyridin-4-yl)-pyrido[3,4-d]pyrimidine [1209]
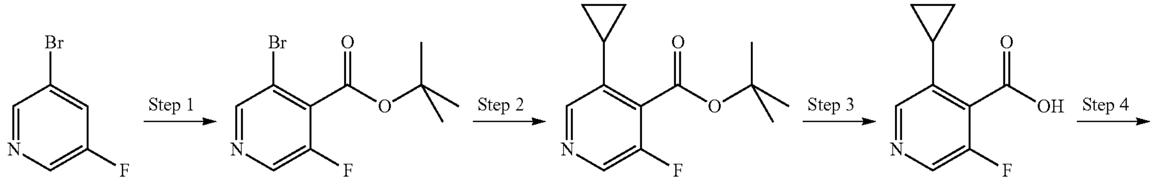
[D013] [D014] [D015]

-continued

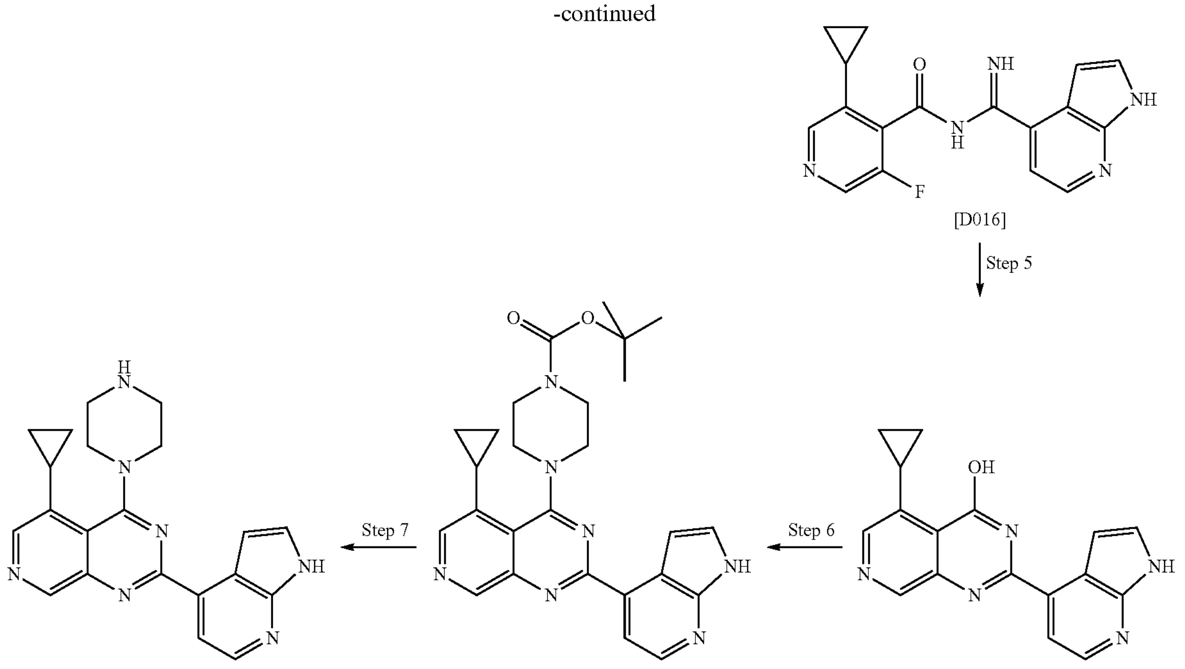

[D016]

[1209] [D018] [D017]

3-Bromo-5-fluoro-isonicotinic acid tert-butyl ester [D013]

To a solution of LDA (2M, 72 mL, 144 mmol) in THF (100 mL) at −78° C. was added dropwise via cannula a solution of 3-bromo-5-fluoropyridine (21.12 g, 120 mmol) in THF (50 mL) pre-cooled at −78° C. During the addition the internal temperature did not rise above −65° C. The dark red-brown solution was stirred for 1 hour. Di-tert-butyldicarbonate (52.4 g, 240 mmol) in THF (50 mL) was cooled to −10° C. in a methanol/ice bath then added dropwise via cannula to the dark red-brown solution. The mixture was stirred for 2 hours then allowed to warm to room temperature and stir for 1 hour. Saturated aqueous ammonium chloride (100 mL) was added slowly and then water (200 mL) and EtOAc (200 mL) and the mixture was vigorously stirred for 45 minutes. The mixture was transferred to a separatory funnel and the layers were separated. The aqueous layer was extracted with EtOAc (200 mL). The THF and EtOAc layers were combined, dried over magnesium sulfate, filtered and evaporated. The recovered dark red-brown oil was purified by column chromatography (Cyclohexane/AcOEt: 1/0 to 97/3). Fractions containing desired material were concentrated in vacuo (14 g, 85%). LCMS method: 5, RT 5.44 min, MI 277 [M+H]; NMR: (1H, 500 MHz, CDCl3) 8.56 (s, 1H), 8.43 (s, 1H), 1.62 (s, 9H).

3-Cyclopropyl-5-fluoro-isonicotinic acid tert-butyl ester [D014]

A solution containing 3-Bromo-5-fluoro-isonicotinic acid tert-butyl ester [D013](5.52 g, 20 mmol), potassium phosphate tribasic (12.74 g, 60 mmol) and cyclopropyl boronic acid (2.58 g, 30 mmol), in dioxane (100 mL) was subjected to vacuum/argon balloon (three times). Dichloro[1,1'-bis(diphenylphosphino)ferrocene]palladium (II) dichloromethane adduct (0.408 g, 0.5 mmol) was added and the reaction heated at 96° C. overnight under positive pressure of nitrogen. The mixture was cooled to room temperature and was filtered through a pad of 200 g silica and washed with EtOAc (1 L). The filtrate was concentrated in vacuo and the crude was purified by column chromatography (Cyclohexane/AcOEt: 98:2 to 96:4). The combined fractions were concentrated under reduced pressure to give the title compound [D014] as a colourless oil (3.42 g, 72%). LCMS method: 5, RT 5.36 min, MI 238 [M+H]; NMR: (1H, 500 MHz, CDCl3) 8.33 (s, 1H), 8.15 (s, 1H), 2.05-2.00 (m, 1H), 1.62 (s, 9H), 1.04-1.00 9 m, 2H), 0.82-0.78 (m, 2H).

3-Cyclopropyl-5-fluoro-isonicotinic acid [D015]

In a microwave vial, 3-cyclopropyl-5-fluoro-isonicotinic acid tert-butyl ester [D014](1.186 g, 5 mmol) was dissolved in methanol and then heated in microwave at 140° C. for 1 hr. The reaction was concentrated in vacuo to yield the title compound [D015] 0.84 g (92%) of white crystalline solid. LC-MS: 1NJM406_1_28Jul2011; 1.51 min, 87%; 182+; 1LCMS5.

3-Cyclopropyl-5-fluoro-N-[imino-(1H-pyrrolo[2,3-b]pyridin-4-yl)-methyl]-isonicotinamide [D016]

3-Cyclopropyl-5-fluoro-isonicotinic acid [D015](0.681 g, 3.76 mmol), HATU (1.43 g, 3.76 mmol) and diisopropyethylamine (2.29 mL, 13.16 mmol) were stirred in DMF (5 mL). After 1 hr, 1H-Pyrrolo[2,3-b]pyridine-4-carboxamidine; acetic acid salt (0.92 g, 3.76 mmol) was added. Having stirred for 18 hr the mixture was poured into water (180 ml), stirred for 2 hours and then a white solid collected by filtration and washed with $H_2O$ to yield the title compound [D016] as a white solid (1.17 g) was used without further purification. LCMS method: 5, RT 3.22 min, MI 324 [M+H].

5-Cyclopropyl-2-pyridin-4-yl-pyrido[3,4-d]pyrimidin-4-ol [D017]

A mixture of N-[(2-Chloro-pyridin-4-yl)-imino-methyl]-3-cyclopropyl-5-fluoro-isonicotinamide [D016](1.164 g, 3.6 mmol) and Cs2CO3 (1.18 g, 3.60 mmol) in DMA (12 mL) was heated thermally at 90° C. overnight. The reaction mixture was poured into $H_2O$ (20 ml) and acidified with dropwise addition of acetic acid at 0 OC. The beige precipitate (0.474, 43%) was collected by filtration and washed with $H_2O$ to yield the title compound [D017] which was used without further purification. LCMS method: 5, RT 4.58 min, MI 304 [M+H]; NMR: (1H, 500 MHz, d6-dmso) 12.12 (brs, 1H), 9.09 (s, 1H), 8.54 (d, 1H), 8.37 (s, 1H), 7.90 (d, 1H), 7.83 (s, 1H), 7.36 (s, 1H), 3.56-3.64 (m, 1H), 1.24-1.30 (m, 2H), 1.08-1.14 (m, 2H).

4-[5-Cyclopropyl-2-(1H-pyrrolo[2,3-b]pyridin-4-yl)-pyrido[3,4-d]pyrimidin-4-yl]-piperazine-1-carboxylic acid tert-butyl ester [D018]

To a solution of 5-Cyclopropyl-2-pyridin-4-yl-pyrido[3,4-d]pyrimidin-4-o [D017]1 (0.47 g, 1.55 mmol) in DMF (25 mL) was added DIPEA (0.809 mL, 4.65 mmol) and DMAP (5 mg). 2,4,6-Triisopropylbenzenesulfonyl chloride (0.563 g, 1.86 mmol) was then added and the mixture was stirred 2 hours. N-Boc-Piperazine (0.318 g, 1.705 mmol) was then added and the mixture was the stirred overnight. Water was added water (60-70 mL) and the solution was stirred at RT for 15 mins. The resulting solid was collected and washed twice with water. The solid was dissolved in DCM and purified by column chromatography (eluent: DCM/MeOH gradient 0% to 10% MeOH) to yield the title compound [D018] as a dark brown gum (0.6 g, 82%) was used without further purification in the next step. LCMS method: 5, RT 5.85 min, MI 472 [M+H].

5-Cyclopropyl-4-piperazin-1-yl-2-(1H-pyrrolo[2,3-b]pyridin-4-yl)-pyrido[3,4-d]pyrimidine To a solution of 4-[5-Cyclopropyl-2-(1H-pyrrolo[2,3-b]pyridin-4-yl)-pyrido[3,4-d]pyrimidin-4-yl]-piperazine-1-carboxylic acid tert-butyl ester [D018](0.6 g, 1.27 mmol) in DCM (15 mL) was added HCl (4N, dioxane, 2 mL) and the resultant bright yellow suspension was stirred at RT for 90 mins. The solution was concentrated under reduced pressure and dissolved in MeOH and added to SCX-2 cartridge (10 g), washed with MeOH/DCM (1:1, 40 mL) and MeOH (20 mL). Then the SCX-2 cartridge was washed with ammonia (7N in MeOH, 30 mL). The ammonia washes were concentrated in vacuo and the material purified on the column chromatography (eluent DCM/MeOH gradient 0-20% MeOH/DCM). The fractions were combined and concentrated under reduced pressure to yield the title compound [1009]: LCMS method: 5, RT 2.65 min, MI 372 [M+H]; NMR: (1H, 500 MHz, d6-dmso) 11.82 (brs, 1H), 9.13 (s, 1H), 8.36 (d, 1H), 8.10 (d, 1H), 7.62 (t, 1H), 7.45 (dd, 1H), 3.50-3.90 (m, 4H), 2.88-2.91 (m, 4H), 2.66-2.69 (m, 1H), 1.22-1.27 (m, 2H), 1.02-1.06

Synthesis of 8-Chloro-5-cyclopropyl-4-piperazin-1-yl-2-(1H-pyrrolo[2,3-b]pyridin-4-yl)-pyrido[3,4-d]pyrimidine [1210]

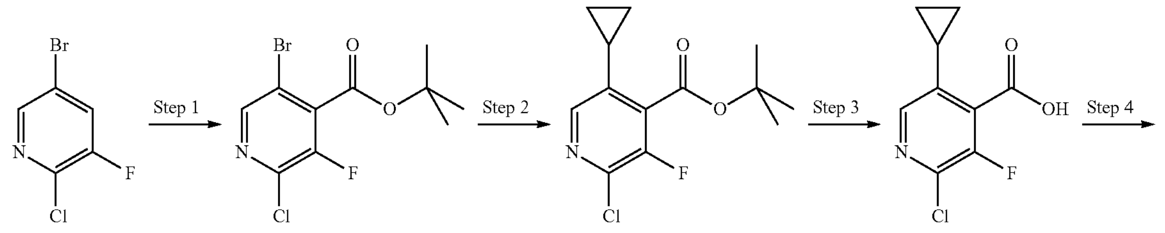

[D019] [D020] [D021]

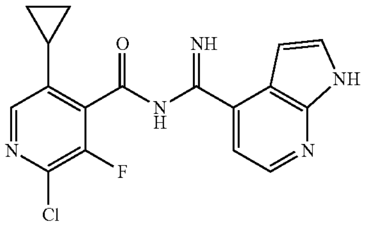

[D022]

Step 5

-continued

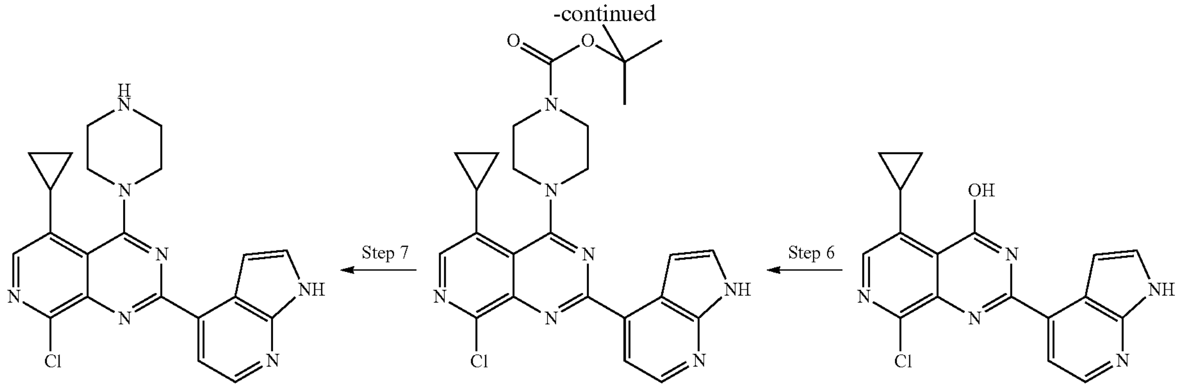

[1210] [D024] [D023]

5-Bromo-2-chloro-3-fluoro-isonicotinic acid tert-butyl ester [D019]

Following the procedure described in scheme D3 1,5-Bromo-2-chloro-3-fluoro-isonicotinic acid tert-butyl ester was prepared [D019] as a colourless oil by reaction of 5-bromo-2-chloro-3-fluoropyridine, LDA (2M), Di-tert-butyldicarbonate, and THF. LCMS method: 5, RT 6.25 min, MI 311 [M+H].

S2-Chloro-5-cyclopropyl-3-fluoro-isonicotinic acid tert-butyl ester [D020]

Following the procedure described in scheme D3,5-Bromo-2-chloro-3-fluoro-isonicotinic acid tert-butyl ester was reacted with cyclopropyl boronic acid to give 2-Chloro-5-cyclopropyl-3-fluoro-isonicotinic acid tert-butyl ester [D020]. LCMS method: 5, RT 6.19 min, MI 272 [M+H].

2-Chloro-5-cyclopropyl-3-fluoro-isonicotinic acid [D021]

2-Chloro-5-cyclopropyl-3-fluoro-isonicotinic acid tert-butyl ester [D020](815 mg, 3.00 mmol) was suspended in 2-propanol (9 mL) and HCl (5 mL of a 4M solution in dioxane) was added. The reaction mixture was heated to 50° C. overnight. The reaction mixture was concentrated under reduced pressure to the title compound [D021](530 mg, 82%) as a white crystalline solid which was used without purification. LCMS method: 5, RT 0.91 min, MI 216 [M+H].

2-Chloro-5-cyclopropyl-3-fluoro-N-[imino-(1H-pyrrolo[2,3-b]pyridin-4-yl)-methyl]-isonicotinamide [D022]

Following the procedure described in scheme D3,2-chloro-5-cyclopropyl-3-fluoro-isonicotinic acid [D021] was reacted with 1H-Pyrrolo[2,3-b]pyridine-4-carboxamidine to give the title compound [D022]. LCMS method: 5, RT 4.45 min, MI 358 [M+H].

8-Chloro-5-cyclopropyl-2-(1H-pyrrolo[2,3-b]pyridin-4-yl)-pyrido[3,4-d]pyrimidin-4-ol [D023]

Following the procedure described in scheme D3,2-Chloro-5-cyclopropyl-3-fluoro-N-[imino-(1H-pyrrolo[2,3-b]pyridin-4-yl)-methyl]-isonicotinamide [D022] was reacted with $Cs_2CO_3$ to give the title compound [D023]. LCMS method: 5, RT 4.87 min, MI 306 [M+H].

4-[8-Chloro-5-cyclopropyl-2-(1H-pyrrolo[2,3-b]pyridin-4-yl)-pyrido[3,4-d]pyrimidin-4-yl]-piperazine-1-carboxylic acid tert-butyl ester [D024]

Following the procedure described in scheme D3,8-Chloro-5-cyclopropyl-2-(1H-pyrrolo[2,3-b]pyridin-4-yl)-pyrido[3,4-d]pyrimidin-4-ol [D023] was reacted with 1-Boc-piperazine to give the title compound [D024]. LCMS method: 5, RT 6.05 min, MI 506 [M+H].

8-Chloro-5-cyclopropyl-4-piperazin-1-yl-2-(1H-pyrrolo[2,3-b]pyridin-4-yl)-pyrido[3,4-d]pyrimidine [1210]

Following the procedure described in scheme D3, 8 4-[8-Chloro-5-cyclopropyl-2-(1H-pyrrolo[2,3-b]pyridin-4-yl)-pyrido[3,4-d]pyrimidin-4-yl]-piperazine-1-carboxylic acid tert-butyl ester [D024] was reacted with 4N HCl in dioxane to give the title compound [1210]: LCMS method: 5, RT 3.22 min, MI 406 [M+H].

Synthesis of -Isopropyl-4-piperazin-1-yl-2-(1H-pyrrolo[2,3-b]pyridin-4-yl)-pyrido[3,4-d]pyrimidine [1211]

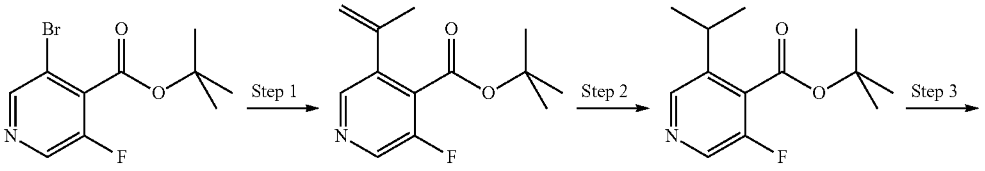

[D013] [D025] [D026]

-continued

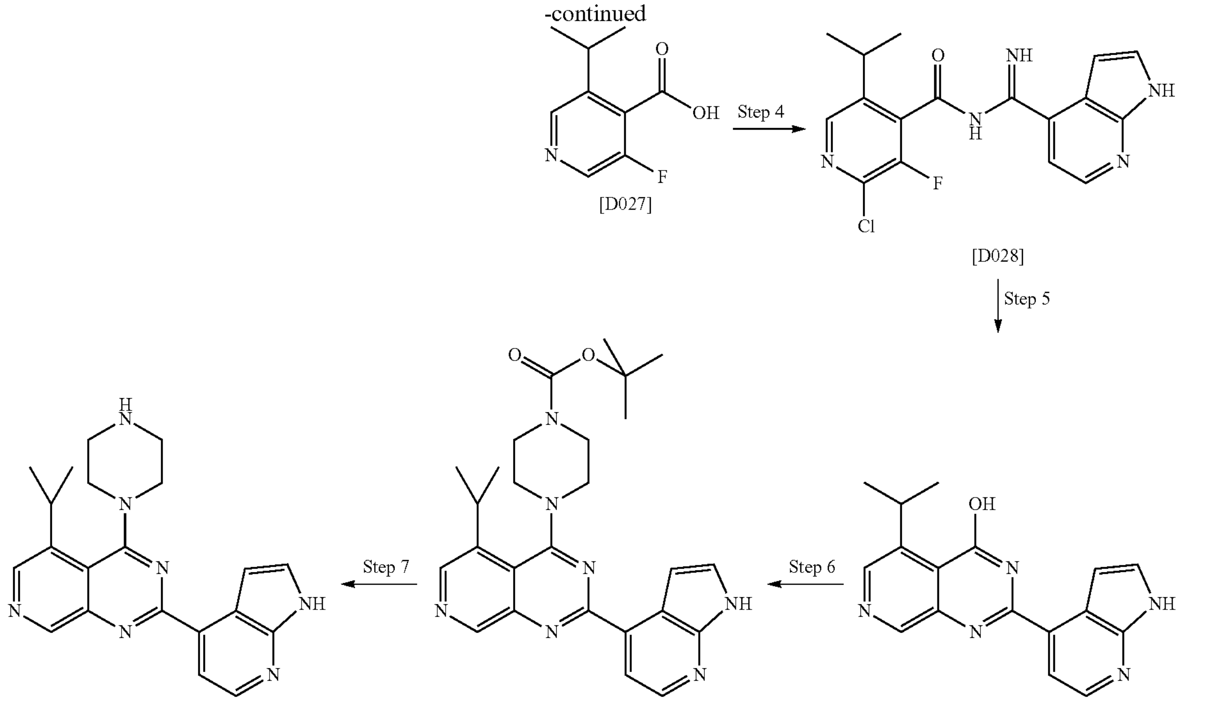

[D027] [D028] [1211] [D030] [D029]

3-Fluoro-5-isopropenyl-isonicotinic acid tert-butyl ester [D025]

Following the procedure described scheme D3,3-Bromo-5-fluoro-isonicotinic acid tert-butyl ester [D013] was reacted with isopropenylboronic acid pinacol ester (contains phenothiazine as stabilizer), with dichloro[1,1'-bis(diphenylphosphino)ferrocene]palladium (II) dichloromethane adduct as catalyst to give 3-Fluoro-5-isopropenyl-isonicotinic acid tert-butyl ester [D025]. LCMS method: 5, RT 5.41 min, MI 238 [M+H].

3-Fluoro-5-isopropyl-isonicotinic acid tert-butyl ester [D026]

To a solution of 3-Fluoro-5-isopropenyl-isonicotinic acid tert-butyl ester [D025] in EtOH was added ammonium formate and palladium on charcoal (5% wt/wt) and the mixture was heated at 60° C. overnight. More ammonium formate was added and the mixture was stirred for a further 45 min at 60° C. then was allowed to cool down to room temperature and was stirred overnight. The mixture was filtered through a celite pad and washed with EtOAc. Water was added to the filtrate and the layers were separated. The organic was dried over MgSO4 and concentrated in vacuo. The crude was purified by column chromatography (gradient Cyclohexane/AcOEt: 1:0 to 92:8). The combined fractions were concentrated under reduced pressure to led the title compound [D026] as a pale yellow oil (0.34 g, 37%). LCMS method: 5, RT 5.55 min, MI 240 [M+H]; NMR: (1H, 500 MHz, CDCl3) 8.42 (1H, s), 8.35 (1H, s), 3.09 (1H, sept), 1.60 (9H, s), 1.33 (6H, d).

3-Fluoro-5-isopropyl-isonicotinic acid [D027]

To a solution of 3-Fluoro-5-isopropyl-isonicotinic acid tert-butyl ester [D026](0.335 g, 1.4 mmol) in isopropyl alcohol (5 mL), a solution of HCl (4N in dioxane, 1 mL) was added and the solution was warmed to 50° C. overnight. LC-MS implies some progress but not complete. HCl (4N in dioxane, 1 mL) was added again and left at 50° C. overnight. The reaction is still not complete so more HCl (4N in dioxane, 1 mL) was added and left through the day (~6-7 hrs). The solution was concentrated in vacuo to yield the title compound [D027] an off-white solid which was used without further purification and analysis.

3-Fluoro-N-[imino-(1H-pyrrolo[2,3-b]pyridin-4-yl)-methyl]-5-isopropyl-isonicotinamide [D028]

Following the procedure described in scheme D3,3-Fluoro-5-isopropyl-isonicotinic acid was reacted [D027] with, 1H-Pyrrolo[2,3-b]pyridine-4-carboxamidine to give 3-Fluoro-N-[imino-(1H-pyrrolo[2,3-b]pyridin-4-yl)-methyl]-5-isopropyl-isonicotinamide [D028]. LCMS method: 5, RT 3.67 min, MI 326 [M+H].

5-Isopropyl-2-(1H-pyrrolo[2,3-b]pyridin-4-yl)-pyrido[3,4-d]pyrimidin-4-ol [D029]

Following the procedure described in scheme D3, 3-Fluoro-N-[imino-(1H-pyrrolo[2,3-b]pyridin-4-yl)-methyl]-5-isopropyl-isonicotinamide [D028] was treated with $Cs_2CO_3$ to give 5-Isopropyl-2-(1H-pyrrolo[2,3-b]pyridin-4-yl)-pyrido[3,4-d]pyrimidin-4-ol [D029] as a brown solid. LCMS method: 5, RT 4.87 min, MI 306 [M+H].

4-[5-Isopropyl-2-(1H-pyrrolo[2,3-b]pyridin-4-yl)-pyrido[3,4-d]pyrimidin-4-yl]-piperazine-1-carboxylic acid tert-butyl ester [D030]

Following the procedure described in scheme D3, 5-Isopropyl-2-(1H-pyrrolo[2,3-b]pyridin-4-yl)-pyrido[3,4-d]pyrimidin-4-ol [D029] was treated with 1-Boc-piperazine to give the title compound [D030] as a brown solid. LCMS method: 5, RT 5.78 min, MI 474 [M+H].

5-Isopropyl-4-piperazin-1-yl-2-(1H-pyrrolo[2,3-b]pyridin-4-yl)-pyrido[3,4-d]pyrimidine Following the procedure described in scheme D3, 4-[5-Isopropyl-2-(1H-pyrrolo[2,3-b]pyridin-4-yl)-pyrido[3,4-d]pyrimidin-4-yl]-piperazine-1-carboxylic acid tert-butyl ester [D030] was treated with 4N HCl to give the title compound [1211] as a brown solid. LCMS method: 5, RT 2.82 min, MI 374 [M+H], NMR: (1H, 500 MHz, CDCl3) 9.28 (1H, s), 9.0 (1H, br s), 8.61 (1H, s), 8.46 (1H, s), 8.23 (1H, d), 7.63 (1H, s), 7.47 (1H, s), 4.07 (1H, m), 3.86 (2H, m), 3.49 (2H, m), 3.11 (4H, m), 1.25 (6H, d).

General synthesis of substituted 1H-pyrrolo[2,3-b]pyridine-4-carboxamidine derivative of general formula [I-012] Scheme D4

The substituted 1H-pyrrolo[2,3-b]pyridine-4-carboxamidine derivatives of general formula [I-012] were prepared by the reaction of 2-methyl pyridine-2-yl carbamic acid tert butyl ester derivative of general formula [I-019] with a strong base such as nBuLi, in a polar aprotic solvent such as THF, and a substituted Weinreb amide derivative of general formula [I-025] at low temperature followed by reaction with a mineral acid such as hydrochloric acid at elevated temperature to yield the 1-H-pyrrolo[2,3-b]pyridine derivative of general formula [I-020], after reaction work up, typically by a liquid-liquid extraction the intermediate was purified by column chromatography. The 1-H-pyrrolo[2,3-b]pyridine derivative of general formula [I-020] was then subjected to a pyridine N-oxidation reaction with an oxidising reagent such as mCPBA in a solvent such as DCM. The intermediate 1-H-pyrrolo[2,3-b]pyridine-7-oxide derivative of general formula [I-021] was then reacted with a chlorinating agent such as methansulfonyl chloride, in a polar aprotic solvent such as DMF at elevated temperature, after reaction work up, typically by a liquid-liquid extraction the intermediate was purified by column chromatography. The intermediate 4-chloro-1H-pyrrolo[2,3-b]pyridine derivative of general formula [I-022] was then submitted to a palladium catalysed cross coupling reaction with a cyanide species such as zinc cyanide, a palladium catalyst such as dichloro[1,1'-bis(diphenylphosphino)ferrocene]palladium (II) dichloromethane adduct, zinc dust, in a polar aprotic solvent such as DMF at elevated temperature, after reaction work up, typically by a liquid-liquid extraction the intermediate was purified by column chromatography. The intermediate 1H-pyrrolo[2,3-b]pyridine-4-carbonitrile derivative of general formula [I-023] was then reacted with hydroxylamine (50% wt/wt in water) and a polar protic solvent such as EtOH at elevated temperature. The intermediate N-hydroxy-1H-pyrrolo[2,3-b]pyridine-4-carboxamide of general formula [I-024] was then subjected to a hydrogenolysis reaction with acetic anhydride in a polar protic solvent such as methanol a palladium catalyst such as palladium on activated charcoal under a atmosphere of hydrogen gas, to yield the substituted 1H-pyrrolo[2,3-b]pyridine-4-carboxamidine derivative of general formula [I-012] Scheme D4.

Scheme D4

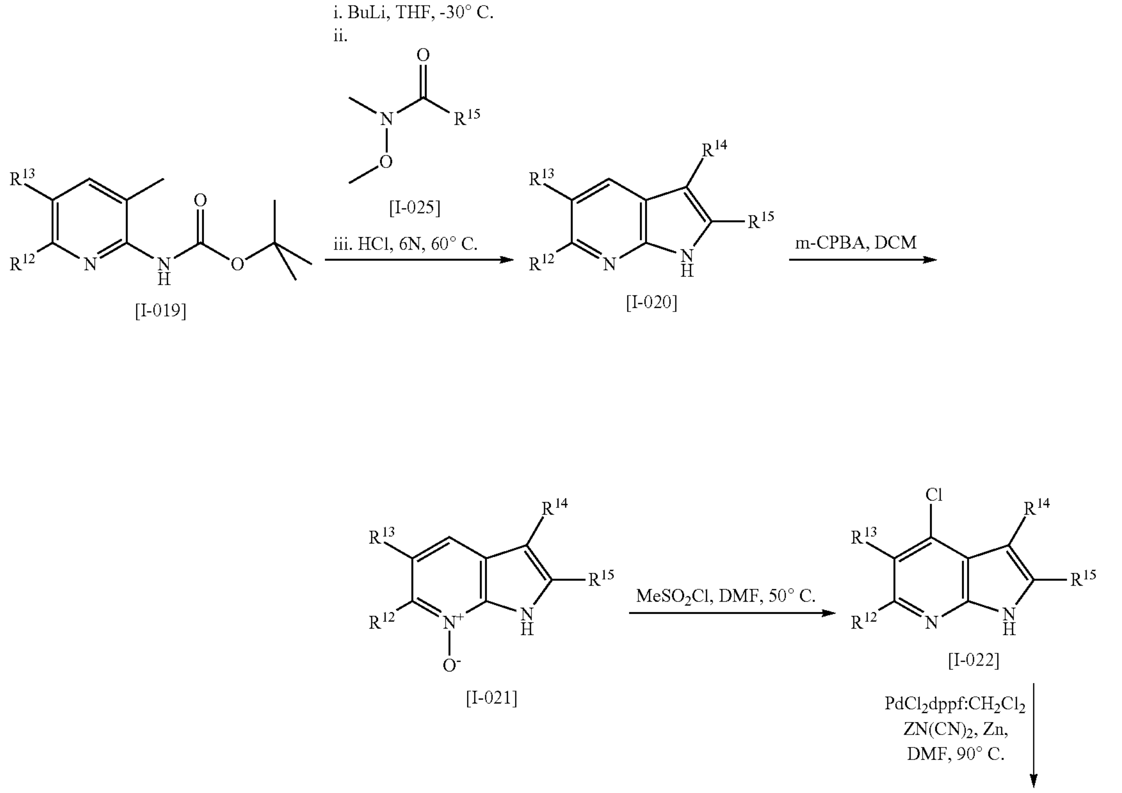

-continued

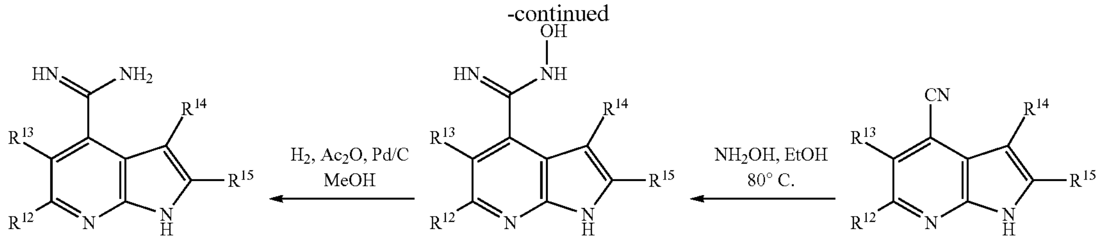

[I-012] [I-024] [I-023]

Synthesis of 2-Trifluoromethyl-1H-pyrrolo[2,3-b]pyridine-4-carboxamidine; acetic acid salt [D036]

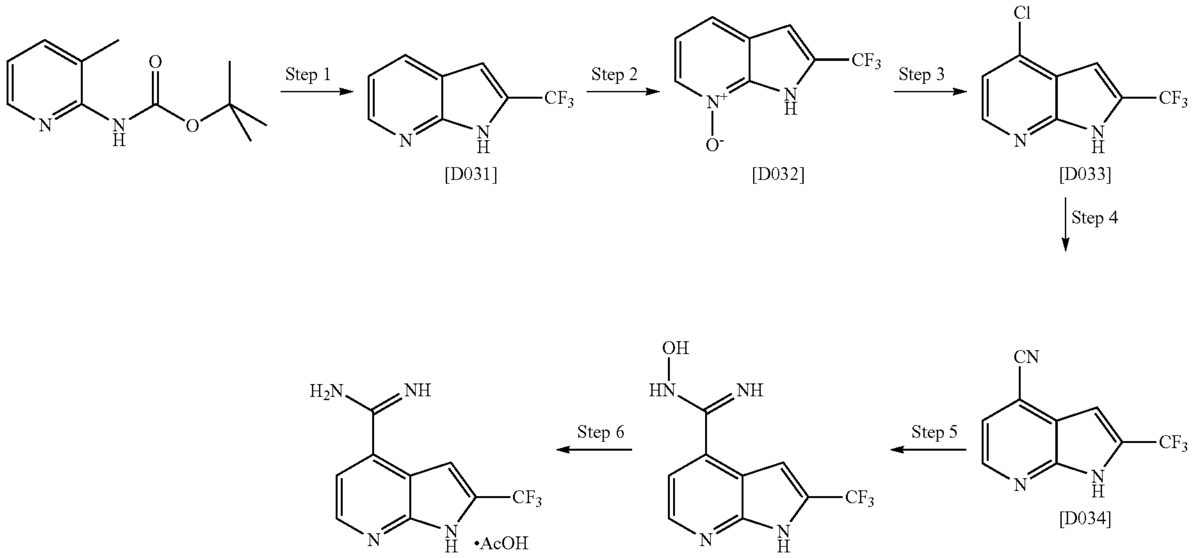

[D031] [D032] [D033] [D034] [D035] [D036]

Step 1: 2-Trifluoromethyl-1H-pyrrolo[2,3-b]pyridine [D031]

To a solution of (3-Methyl-pyridin-2-yl)-carbamic acid tert-butyl ester (5 g, 24 mmol) in THF (50 mL) at −30° C. was added BuLi (2.5M, 28.5 mL, 72 mmol) and the reaction mixture was warmed to 0° C. and stirred for 90 min. A solution of 2,2,2-Trifluoro-N-methoxy-N-methyl-acetamide (2.9 mL, 24 mmol) in THF (10 mL) was slowly added and the reaction was stirred at 0° C. for 3 h. The reaction mixture was slowly treated with HCl (30 mL, 6M) followed by heating at 60° C. for 18 h. The reaction mixture was cooled, the layers were separated and the aqueous layer was made basic with NaOH (5M) and extracted twice with AcOEt. The combined organic layers (plus the one from the first extraction) were dried over MgSO4, concentrated and the residue was purified by Column chromatography (eluent Cyclohexane/AcOEt 1/0 to 8/2) to afford the title compound [D031] as a yellow solid (1.2 g, 27%): LCMS method: 5, RT 4.44 min, MI 187 [M+H], NMR: (1H, 500 MHz, d6-dmso) 14.33 (brs, 1H), 8.49 (d, 1H), 8.09 (d, 1H), 7.27 (dd, 1H), 6.90 (s, 1H).

2-Trifluoromethyl-1H-pyrrolo[2,3-b]pyridine 7-oxide [D032]

To a solution of 2-Trifluoromethyl-1H-pyrrolo[2,3-b]pyridine [D031](1.2 g, 6.45 mmol) in DCM (10 mL), 3-Chloroperoxybenzoic acid (1.22 g, 7.09 mmol) was added and the mixture was stirred overnight. A saturated solution of NaHCO3 was added and the layers were separated. The organic was dried over MgSO4 and concentrated under reduced pressure. To yield the title compound [D032] as yellow solid (0.82 g, 63%) was used without further purification. LCMS method: 5, RT 3.43 min, MI 203 [M+H], NMR: (1H, 500 MHz, d6-dmso) 8.34 (d, 1H), 7.76 (d, 1H), 7.19 (d, 1H), 7.18 (s, 1H), 4-Chloro-2-trifluoromethyl-1H-pyrrolo[2,3-b]pyridine [D033]

To a solution of 2-Trifluoromethyl-1H-pyrrolo[2,3-b]pyridine 7-oxide [D032](0.82 g, 4.05 mmol) in DMF (10 mL) at 50° C., methane sulfonyl chloride (1.57 mL, 20.28 mmol) was added dropwise. The solution was stirred 3 h at 50° C. The reaction was then cooled to room temperature and water (5 mL) was added. A solution of 5M NaOH was added and the solid was collected, dried using an azeotrope with toluene to yield the title compound [D032] which was used without further purification. LCMS: 1LCMS5 5.77 min, 221-223 [M+1, Cl pattern].

2-Trifluoromethyl-1H-pyrrolo[2,3-b]pyridine-4-carbonitrile [D034]

A sealable vial was charged with 4-Chloro-2-trifluoromethyl-1H-pyrrolo[2,3-b]pyridine [D033](0.6 g, 2.72 mmol), Dichloro[1,1'-bis(diphenylphosphino)ferrocene]palladium (II) dichloromethane adduct (0.222 g, 0.27 mmol), zinc cyanide (0.958 g, 8.16 mmol), zinc (dust, 0.036 g, 0.54 mmol) and DMF (15 mL). The vial was capped and heated at 900° C. overnight. The reaction was poured in water and extracted with AcOEt. The aqueous layer was extracted again with AcOEt and the organics were combined, washed with water and brine and dried over MgSO4 to yield the title compound [D043] which was used without further purification: LCMS method: 5, RT 4.98 min, MI 212 [M+H].

N-Hydroxy-2-trifluoromethyl-1H-pyrrolo[2,3-b]pyridine-4-carboxamidine [D035]

A mixture of 2-Trifluoromethyl-1H-pyrrolo[2,3-b]pyridine-4-carbonitrile [D034](0.68 g, 3.22 mmol) and hydroxylamine (50% wt/wt in water, 0.205 mL, 6.44 mmol) and EtOH (5 mL) was heated at 80° C. overnight. Solvent was then evaporated and the mixture azeotroped twice with toluene under vacuum. To yield the title compound [D035] as a yellow solid (0.78 g, 99%) which was used in the next step without further purification: LCMS method: 5, RT 2.22 min, MI 245 [M+H], NMR: (1H, 500 MHz, d6-dmso): 13.14 (brs, 1H), 10.40 (s, 1H), 8.70 (s, 1H), 7.70 (s, 1H), 7.56 (d, 1H), 6.27 (s, 2H).

2-Trifluoromethyl-1H-pyrrolo[2,3-b]pyridine-4-carboxamidine; compound with acetic acid [D036]

To a suspension of N-Hydroxy-2-trifluoromethyl-1H-pyrrolo[2,3-b]pyridine-4-carboxamidine [D035](0.43 g, 1.76 mmol) in MeOH (10 mL) was added dropwise acetic anhydride (0.175 mL, 1.85 mmol) at room temperature. The suspension was stirred 15 min and palladium on charcoal (5% wt/wt, 0.1 g) was added. The vessel was seal and hydrogen (balloon) was bubble in the mixture for 10 min and left stirring at RT under hydrogen atmosphere overnight. The mixture was filtered through celite and concentrated in vacuo to yield the title compound [D036] as a yellow solid (0.51 g, 100%) which was used without further purification. LCMS method: 5, RT 4.45 min, MI 229 [M+H], NMR: (1H, 500 MHz, d6-dmso) 1.79 (s, 3H, $CH_3CO_2H$), 8.50 (s, 1H), 7.35 (s, 1H), 7.03 (s, 1H).

Synthesis of 2-Thiophen-2-yl-1H-pyrrolo[2,3-b]pyridine-4-carboxamidine acetic acid salt [D042]

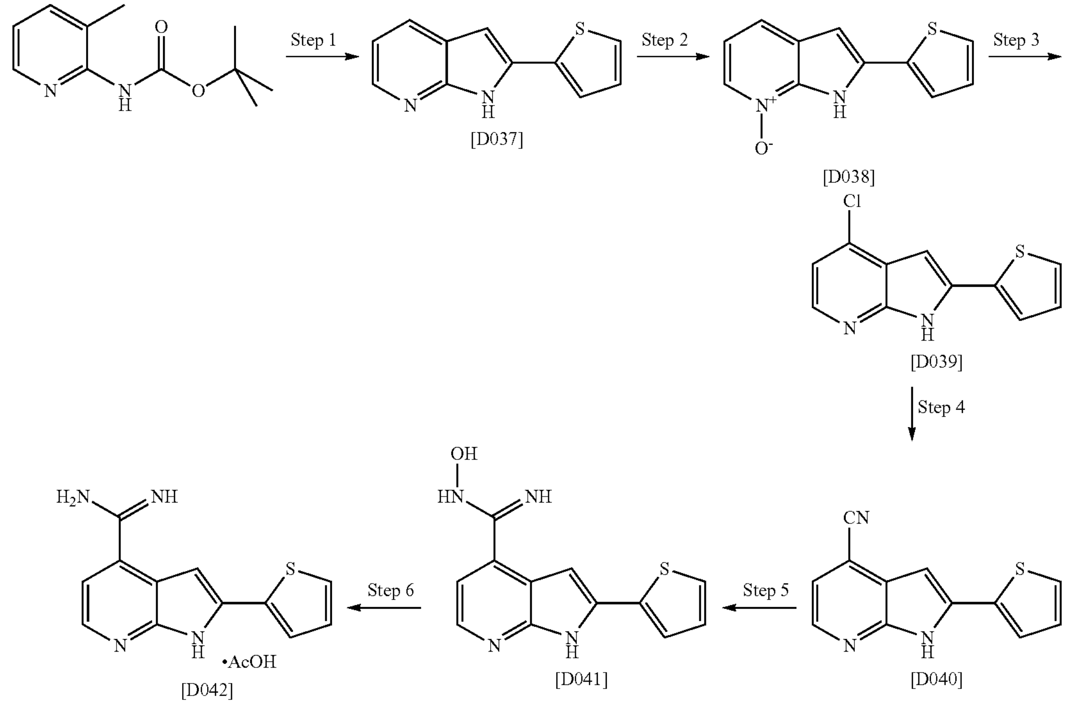

[D037] [D038] [D039] [D040] [D041] [D042]

2-Thiophen-2-yl-1H-pyrrolo[2,3-b]pyridine [D037]

Was prepared, following the procedure described in scheme D4, step 1, by reaction of (3-Methyl-pyridin-2-yl)-carbamic acid tert-butyl ester, thiophene-2-carboxylic acid methoxy-methyl-amide, BuLi and THF to give the title compound as a yellow solid. LCMS method: 5, RT 4.79 min, MI 201 [M+H].

2-Thiophen-2-yl-1H-pyrrolo[2,3-b]pyridine 7-oxide [D038]

Was prepared, following the procedure described in scheme D4, step 2, by reaction of 2-Thiophen-2-yl-1H-pyrrolo[2,3-b]pyridine [D037], m-CPBA and DCM to give the title compound as a yellow solid. LCMS method: 5, RT 3.38 min, MI 217 [M+H].

4-Chloro-2-thiophen-2-yl-1H-pyrrolo[2,3-b]pyridine [D039]

Was prepared, following the procedure described in scheme D4, step 3, by reaction of 2-Thiophen-2-yl-1H-pyrrolo[2,3-b]pyridine 7-oxide [D038], methane sulfonyl chloride and DMF to give the title compound as a yellow solid. LCMS method: 5, RT 6.05 min, MI 235 [M+H].

2-Thiophen-2-yl-1H-pyrrolo[2,3-b]pyridine-4-carbonitrile [D040]

Was prepared, following the procedure described in scheme D4, step 4, by reaction of 4-Chloro-2-thiophen-2-yl-1H-pyrrolo[2,3-b]pyridine [D039], PdCl2dppf:CH2C12, Zinc cyanide, zinc dust and DMA to give the title compound as a yellow solid. LCMS method: 5, RT 5.28 min, MI 226 [M+H].

N-Hydroxy-2-thiophen-2-yl-1H-pyrrolo[2,3-b]pyridine-4-carboxamidine [D041]

Was prepared, following the procedure described in scheme D4, step 5, by reaction of 2-thiophen-2-yl-1H-pyrrolo[2,3-b]pyridine-4-carbonitrile [D040], hydroxylamine and EtOH to give the title compound as a yellow solid. LCMS method: 5, RT 2.38 min, MI 259 [M+H].

2-Thiophen-2-yl-1H-pyrrolo[2,3-b]pyridine-4-carboxamidine acetic acid salt [D042]

Was prepared, following the procedure described in scheme D4, step 6, by reaction of N-Hydroxy-2-thiophen-2-yl-1H-pyrrolo[2,3-b]pyridine-4-carboxamidineacetic anhydride [D041], Pd/C, hydrogen and MeOH to give the title compound as a yellow solid. LCMS method: 5, RT 4.45 min, MI 243 [M+H].

Synthesis of 2-methyl-1H-pyrrolo[2,3-b]pyridine-4-carboxamidine acetic acid salt [D045]

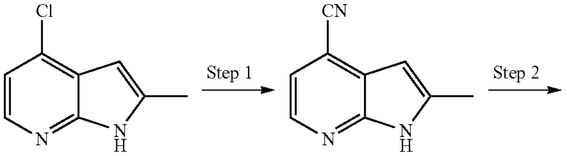

[D043]

-continued

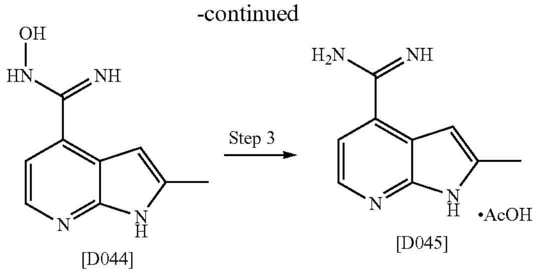

[D044] [D045]

2-Methyl-1H-pyrrolo[2,3-b]pyridine-4-carbonitrile [D043]

Was prepared, following the procedure described in scheme D4, step 4, by reaction of 4-Chloro-2-methyl-1H-pyrrolo[2,3-b]pyridine, PdCl2dppf:CH2Cl2, Zinc cyanide, zinc dust and DMA to give the title compound as a white solid. LCMS method: 5, RT 4.17 min, MI 158 [M+H].

N-Hydroxy-2-methyl-1H-pyrrolo[2,3-b]pyridine-4-carboxamidine [D044]

Was prepared, following the procedure described in scheme D4, step 5, by reaction of 2-Methyl-1H-pyrrolo[2,3-b]pyridine-4-carbonitrile [D043], hydroxylamine and EtOH to give the title compound as a yellow solid. LCMS method: 5, RT 1.92 min, MI 191 [M+H].

2-methyl-1H-pyrrolo[2,3-b]pyridine-4-carboxamidine acetic acid salt [D045]

Was prepared, following the procedure described in scheme D4, step 6, by reaction of N-Hydroxy-2-methyl-1H-pyrrolo[2,3-b]pyridine-4-carboxamidine [D044], acetic anhydride, Pd/C, hydrogen and MeOH to give the title compound as a yellow solid. LCMS method: 5, RT 2.44 min, MI 175 [M+H].

For example Synthesis of 21H-pyrrolo[2,3-b]pyridine-4-carboxamidine acetic acid salt [D047]

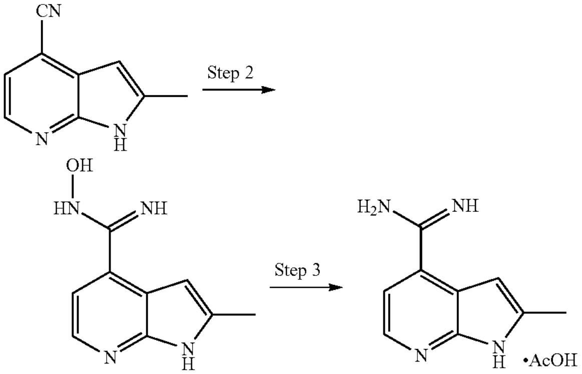

[D046] [D047]

N-Hydroxy-1H-pyrrolo[2,3-b]pyridine-4-carboxamidine [D047]

Was prepared, following the procedure described in scheme D4, step 5, by reaction of 1H-pyrrolo[2,3-b]pyridine-4-carbonitrile, hydroxylamine and EtOH to give the title compound as a yellow solid. LCMS method: 5, RT 1.24 min, MI 162 [M+H].

2-1H-pyrrolo[2,3-b]pyridine-4-carboxamidine acetic acid salt [D047]

Was prepared, following the procedure described in scheme D4, step 6, by reaction of N-Hydroxy-1H-pyrrolo[2,3-b]pyridine-4-carboxamidine [D047], acetic anhydride, Pd/C, hydrogen and MeOH to give the title compound as a yellow solid. LCMS method: 5, RT 1.23 min, MI 161 [M+H], NMR: (1H, 500 MHz, d6-dmso) 8.38 (1H, d), 7.71 (1H, d), 7.30 (1H, d), 6.58 (1H, d), 1.80 (8H, s)

Following the procedures described in Example AZA-9, the following compounds were prepared from 3-Cyclopropyl-5-fluoro-isonicotinic acid:

| | SM | Amidine | Amine | Analysis | | |
|---|---|---|---|---|---|---|
| Ex | [I-013] | [I-014] | [I-017] | LCMS | NMR | Name |
| 1212 | [D015] | 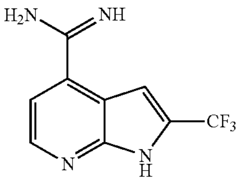 [D036] | 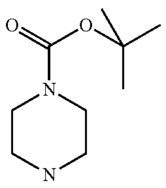 | Method 5: RT: 3.59 min, MI: 440 [M + H] | 1H NMR (DMSO, 500 MHz) 13.17 (s, 1H), 9.19 (s, 1H), 8.63 (d, 1H), 8.25 (d, 1H), 8.19 (s, 1H), 7.95 (s, 1H), 4.10-3.77 (m, 8H), 2.75-2.69 (m, 1H), 1.28-1.22 (m, 2H), 1.13-1.07 (m, 2H). | [5-Cyclopropyl-4-piperazin-1-yl-2-(2-trifluoromethyl-1H-pyrrolo[2,3-b]pyridin-4-yl)-pyrido[3,4-d]pyrimidine |
| 1213 | [D015] | 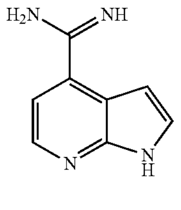 [D047] | 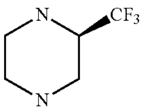 | Method 5: RT: 5.02 min, MI: 440 [M + H] | 1H NMR (400 MHz, d6-DMSO, 90° C.) 11.49 (1H, br. s), 9.10 (1H, s), 8.39 (1H, d, J = 5.0 Hz), 8.16 (1H, s), 8.10 (1H, d, J = 5 Hz), 7.57 (1H, t, J = 2.9 Hz), 7.46 (1H, dd, J = 3.3, 1.9 Hz) 4.43 (1H, br. d, J = 12.8 Hz), 4.01-3.96 (1H, m), 3.77-3.72 (1H, m), 3.48-3.38 (2H, m), 3.10-3.07 (1H, m), 2.93-2.85 (1H, m), 2.75-2.70 (1H, m), 1.34-1.20 (2H, m), 1.08-0.96 (2H, m). | 5-Cyclopropyl-2-(1H-pyrrolo[2,3-b]pyridin-4-yl)-4-((R)-3-trifluoro-methyl-piperazin-1-yl)-pyrido[3,4-d]pyrimidine |
| 1214 | [D015] | 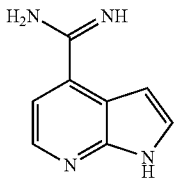 [D047] | 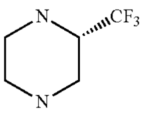 | Method 5: RT: 5.03 min, MI: 440 [M + H] | (1H, 400 MHz, d6-dmso 90° C.) 11.49 (1H, brs), 9.10 (1H, s), 8.39 (1H, d), 8.16 (1H, s), 8.10 (1H, d), 7.57 (1H, t), 7.46 (1H, dd) 4.43 (1H, br. d), 4.01-3.96 (1H, m), 3.77-3.72 (1H, m), 3.48-3.38 (2H, m), 3.10-3.07 (1H, m), 2.93-2.85 (1H, m), 2.75-2.70 (1H, m), 1.34-1.20 (2H, m), 1.08-0.96 (2H, m). | 5-Cyclopropyl-2-(1H-pyrrolo[2,3-b]pyridin-4-yl)-4-((S)-3-trifluoro-methyl-piperazin-1-yl)-pyrido[3,4-d]pyrimidine |
| 1215 | [D015] | 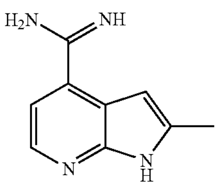 [D045] | 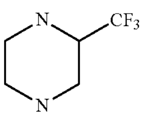 | Method 5: RT: 5.27 min, MI: 454 [M + H] | 1H NMR (DMSO, 500 MHz), 11.67 (brs, 1H), 9.07 (brs, 1H), 8.24 (d, 1H), 8.10 (s, 1H), 8.03 (d, 1H), 7.16 (s, 1H), 4.72-4.18 (m, 1H), 4.05-3.88 (m, 1H), 3.85-3.61 (m, 1H), 3.31 (s, 3H), 3.18-2.72 (m, 4H), 1.33-1.14 (m, 2H), 1.06-0.95 (m, 1H). | 5-Cyclopropyl-2-(2-methyl-1H-pyrrolo[2,3-b]pyridin-4-yl)-4-(3-trifluoro-methyl-piperazin-1-yl)-pyrido[3,4-d]pyrimidine |

-continued

| | SM | Amidine | Amine | Analysis | | |
|---|---|---|---|---|---|---|
| Ex | [I-013] | [I-014] | [I-017] | LCMS | NMR | Name |
| 1216 | [D015] | 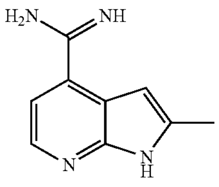<br>[D045] | 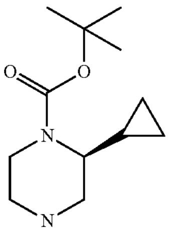 | Method 5: RT: 3.20 min, MI: 426 [M + H] | 1H NMR (DMSO, 500 MHz) 11.68 (brs, 1H), 9.07 (brs, 1H), 8.24 (d, 1H), 8.13 (d, 1H), 8.11 (d, 1H), 7.17 (s, 1H), 4.34-4.08 (m, 2H), 3.60-3.46 (m, 2H), 3.18-2.84 (m, 2H), 3.01 (s, 3H), 1.04-0.88 (m, 3H), 0.60-0.25 (m, 5H). | 5-Cyclopropyl-4-((S)-3-cyclopropyl-piperazin-1-yl)-2-(2-methyl-1H-pyrrolo[2,3-b]pyridin-4-yl)-pyrido[3,4-d]pyrimidine |
| 1217 | [D015] | 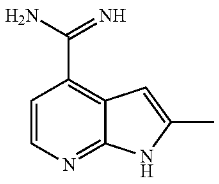<br>[D045] | 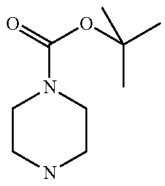 | Method 5: RT: 2.80 min, MI: 386 [M + H] | (1H, 500 MHz, d6-dmso) 11.64 (s, 1H), 9.03 (s, 1H), 8.22 (d, 1H), 8.06 (s, 1H), 8.02 (d, 1H), 7.15 (s, 1H), 3.08 (very broad m, 4H), 2.87-2.92 (m, 4H), 2.65-2.70 (m, 1H), 2.47 (s, 3H), 1.22-1.26 (m, 2H), 1.02-1.07 (m, 2H), | 5-Cyclopropyl-2-(2-methyl-1H-pyrrolo[2,3-b]pyridin-4-yl)-4-piperazin-1-yl-pyrido[3,4-d]pyrimidine |
| 1218 | [D015] | 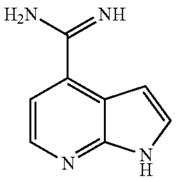<br>[D047] | 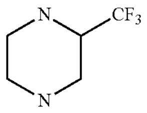 | Method 5: RT: 5.03 min, MI: 440 [M + H] | 1H NMR (400 MHz, d6-DMSO, 90° C.) 11.49 (1H, br. s), 9.10 (1H, s), 8.39 (1H, d, J = 5.0 Hz), 8.16 (1H, s), 8.10 (1H, d, J = 5 Hz), 7.57 (1H, t, J = 2.9 Hz), 7.46 (1H, dd, J = 3.3, 1.9 Hz) 4.43 (1H, br. d, J = 12.8 Hz), 4.01-3.96 (1H, m), 3.77-3.72 (1H, m), 3.48-3.38 (2H, m), 3.10-3.07 (1H, m), 2.93-2.85 (1H, m), 2.75-2.70 (1H, m), 1.34-1.20 (2H, m), 1.08-0.96 (2H, m). | 5-Cyclopropyl-2-(1H-pyrrolo[2,3-b]pyridin-4-yl)-4-(3-trifluoromethyl-piperazin-1-yl)-pyrido[3,4-d]pyrimidine |
| 1219 | [D015] | 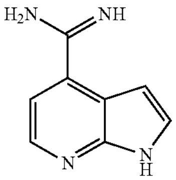<br>[D047] | 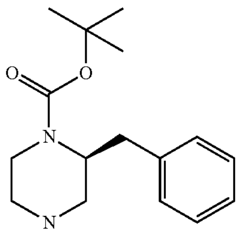 | Method 5: RT: 3.53 min, MI: 462 [M + H] | (1H, 500 MHz, d6-dmso) 11.47 (1H, brs), 9.05 (1H, s), 8.35 (1H, d), 8.06 (1H, s), 7.95 (1H, d), 7.56-7.55 (1H, br. m), 7.43 (1H, d), 7.34-7.30 (2H, m), 7.27-7.24 (3H, m), 4.27 (1H, dr. d), 4.20-4.17 (1H, m), 3.39-3.33 (1H, m), 3.21-3.17 (1H, m), 3.14-3.04 (2H, m), 2.96-2.82 (2H, m), 2.77-2.72 (1H, m), 2.63-2.56 (1H, m), 1.23-1.15 (2H, m), 0.94-0.87 (2H, m). | 4-((S)-3-Benzyl-piperazin-1-yl)-5-cyclopropyl-2-(1H-pyrrolo[2,3-b]pyridin-4-yl)-pyrido[3,4-d]pyrimidine |

-continued

| Ex | SM [I-013] | Amidine [I-014] | Amine [I-017] | Analysis LCMS | NMR | Name |
|---|---|---|---|---|---|---|
| 1220 | [D015] | 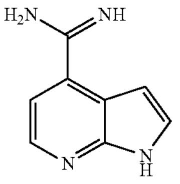 [D047] | 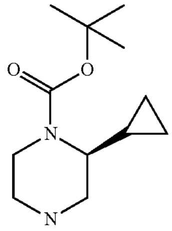 | Method 5: RT: 3.09 min, MI: 412 [M + H] | (1H, 500 MHz, d6-dmso) 11.52 (1H, s, brs), 9.13 (1H, s), 8.41 (1H, d), 8.20 (1H, s), 8.11 (1H, d), 7.60 (1H, d), 7.47 (1H, d), 4.44-4.41 (1H, br. m), 4.28-4.24 (1H, br. m), 3.74-3.68 (1H, br. m), 3.60-3.53 (1H, m), 3.36-3.33 (1H, m), 3.14-3.07 (1H, m), 2.80-2.68 (2H, m), 1.30-1.24 (2H, m), 1.12-1.04 (2H, m), 1.02-0.97 (1H, m), 0.66-0.59 (3H, m), 0.46-0.41 (1H, m). | 5-Cyclopropyl-4-((S)-3-cyclopropyl-piperazin-1-yl)-2-(1H-pyrrolo[2,3-b]pyridin-4-yl)-pyrido[3,4-d]pyrimidine |
| 1221 | [D015] | 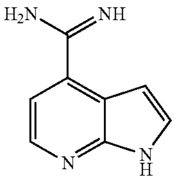 [D047] | 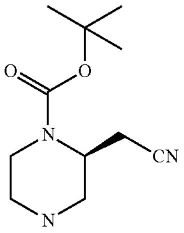 | Method 5: RT: 2.94 min, MI: 411 [M + H] | (1H, 400 MHz, d6-dmso 90° C.) 11.46 (1H, brs), 9.08 (1H, s), 8.38 (1H, d), 8.15 (1H, s), 8.13 (1H, d), 7.57-7.55 (1H, m), 7.48 (1H, dd), 4.34-4.32 (1H, m), 4.13-4.10 (1H, m), 3.31-3.25 (1H, m), 3.21-3.16 (1H, m), 3.11-3.01 (2H, m), 2.95-2.86 (2H, m), 2.72-2.69 (1H, m), 2.61-2.58 (1H, m), 1.30-1.23 (2H, m), 1.03-0.98 (2H, m). | {(S)-4-[5-Cyclopropyl-2-(1H-pyrrolo[2,3-b]pyridin-4-yl)-pyrido[3,4-d]pyrimidin-4-yl]-piperazin-2-yl}-acetonitrile |

The following compounds were synthesised according to the general synthesis shown in scheme [B4]

| Ex | Amine 1 | Amidine 2 | Analysis LCMS | NMR | Name |
|---|---|---|---|---|---|
| 1222 | 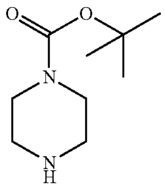 | 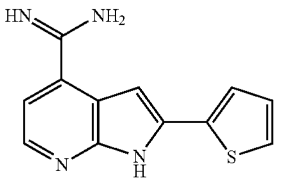 [SMILES: N=C(N)c1ccnc2[nH]c(-c3cccs3)cc12] | method 5: RT 3.59 min, MI: 454 [MH+] | NHM, CDCl3, 500 MHz, 12.06 (brs, 1H), 9.12 (s, 1H), 8.47 (d, 1H), 8.23 (d, 1H), 8.06 (s, 1H), 7.80 (s, 1H), 7.57 (d, 1H), 7.39 (d, 1H), 7.19 (dd, 1H), 4.02-3.61 (m, 4H), 3.12-3.06 (m, 4H), 2.80-2.74 (m, 1H), 1.30-1.26 (m, 2H), 1.05-1.01 | 5-Cyclopropyl-4-piperazin-1-yl-2-(2-thiophen-2-yl-1H-pyrrolo[2,3-b]pyridin-4-yl)-pyrido[3,4-d]pyrimidine |
| 1223 | 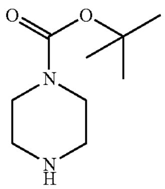 | 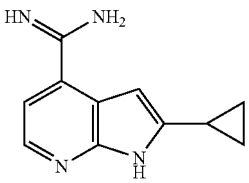 [SMILES: N=C(N)c1ccnc2[nH]c(C3CC3)cc12] | method 5: RT 3.21 min, MI: 412 [MH+] | 1H NMR (400 MHz, 90° C., d6-DMSO) 11.27 (1H, br s), 9.04 (1H, s), 8.23 (1H, d, J = 5.1 Hz), 8.11 (1H, s), 8.02 (1H, d, J = 5.1 Hz), 7.10 (1H, s), 3.74-3.72 (4H, m), 2.95-2.92 (4H, m, overlapping with water signal), 2.74-2.67 (1H, m), 2.18-2.12 (1H, m), 1.28-1.23 (2H, m), 1.09-1.04 (2H, m), 1.00-0.96 (2H, m), 0.95-0.91 (2H, m). | 5-Cyclopropyl-2-(2-cyclopropyl-1H-pyrrolo[2,3-b]pyridin-4-yl)-4-piperazin-1-yl-pyrido[3,4-d]primidine |

-continued

| Ex | Amine 1 | Amidine 2 | Analysis LCMS | NMR | Name |
|---|---|---|---|---|---|
| 1224 | 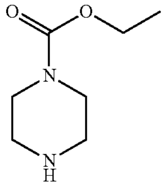 | 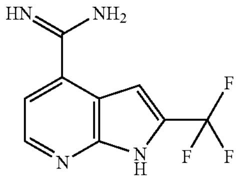 [SMILES: N=C(N)c1ccnc2[nH]c(C(F)(F)F)cc12] | method 5: RT 4.98 min, MI: 412 [MH+] | NMR 1H DMSO 13.11 (brs, 1H), 9.12 (s, 1H), 8.60 (d, 1H), 8.23 (d, 1H), 8.14 (s, 1H), 7.94 (s, 1H), 40.08-4.05 (m, 1H), 3.95-3.55 (m, 8H), 1.26-1.17 (m, 2H), 1.56-1.00 (m, 2H) | 4-[5-Cyclopropyl-2-(2-trifluoromethyl-1H-pyrrolo[2,3-b]pyridin-4-yl)-pyrido[3,4-d]pyrimidin-4-yl]-piperazine-1-carboxylic acid ethyl ester |
| 1225 | — | 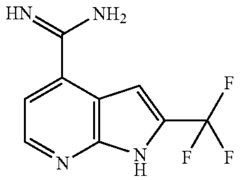 [SMILES: N=C(N)c1ccnc2[nH]c(C(F)(F)F)cc12] | method 5: RT 5.77 min, MI: 372 [MH+] | NMR 1H DMSO 8.97 (s, 1H), 8.62 (d, 1H), 8.24 (s, 1H), 7.88 (d, 1H), 7.67 (s, 1H), 3.45-3.39 (m, 1H), 1.12-1.08 (m, 2H), 0.97-0.92 (m, 2H). | 5-Cyclopropyl-2-(2-trifluoromethyl-1H-pyrrolo[2,3-b]pyridin-4-yl)-pyrido[3,4-d]pyrimidin-4-ol |
| 1226 | 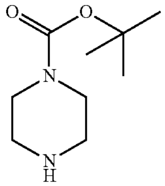 | 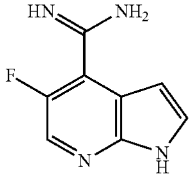 | method 5: RT 2.10 min, MI: 390 [MH+] | 1H NMR (500 MHz, d6-DMSO) 11.92 (1H, s), 8.98 (1H, s), 8.32 (1H, d, J = 3.5 Hz), 8.12 (1H, s), 7.65 (1H, t, J = 2.9 Hz), 6.94 (1H, dd, J = 3.4, 2.0 Hz), 3.84-3.49 (4H, br m), 2.85 (4H, br s), 2.67-2.62 (1H, m), 1.29-1.26 (2H, m), 1.07-1.04 (2H, m). | 5-Cyclopropyl-2-(5-fluoro-1H-pyrrolo[2,3-b]pyridin-4-yl)-4-piperazin-1-yl-pyrido[3,4-d]pyrimidine |
| 1227 | 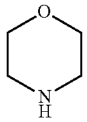 | 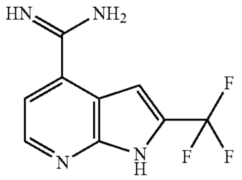 [SMILES: N=C(N)c1ccnc2[nH]c(C(F)(F)F)cc12] | method 5: RT 6.01 min, MI: 441 [MH+] | NMR 1H DMSO 13.11 (s, 1H), 9.12 (s, 1H), 8.62 (s, 1H), 8.22 (d, 1H), 8.13 (s, 1H), 7.93 (s, 1H), 3.80-3.60 (m, 8H), 2.72-2.67 (m, 1H), 1.28-1.23 (m, 2H), 1.06-1.03 (m, 2H). | 5-Cyclopropyl-4-morpholin-4-yl-2-(2-trifluoromethyl-1H-pyrrolo[2,3-b]pyridin-4-yl)-pyrido[3,4-d]pyrimidine |
| 1228 | 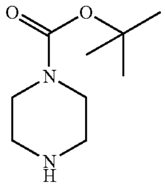 | 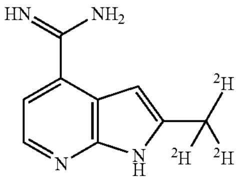 [SMILES: [2H]C([2H])([2H])c1cc2c(C(=N)N)ccnc2[nH]1] | method 5: RT 2.16 min, MI: 389 [MH+] | 1H NMR (400 MHz, d6-DMSO, 90° C.) 11.28 (1H, s), 9.04 (1H, s), 8.24 (1H, d, J = 5.2 Hz), 8.11 (1H, s), 8.03 (1H, d, J = 5.2 Hz), 7.16 (1H, d, J = 1.5 Hz), 3.74-3.72 (4H, m), 2.95-2.93 (4H, m, overlapping with water signal), 2.74-2.69 (1H, m), 1.28-1.23 (2H, m), 1.01-0.97 (2H, m). | 5-Cyclopropyl-4-piperazin-1-yl-2-(2-triduteriomethyl-1H-pyrrolo[2,3-b]pyridin-4-yl)-pyrido[3,4-d]pyrimidine |
| 1229 | 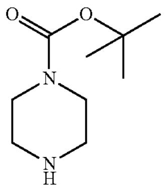 | 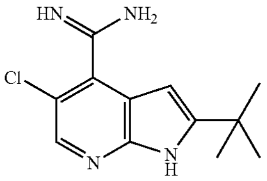 | method 5: RT 3.44 min, MI: 462 [MH+] | 1H NMR (d6-DMSO, 500 MH), 11.87 (1H, s), 8.94 (1H, s), 8.22 (1H, s), 8.11 (1H, s), 3.75-3.55 (4H, m), 2.82 (4H, br s), 2.64-2.59 (1H, m), 1.27 (2H, ddd), 1.05 (2H, ddd) | 2-(2-tert-Butyl-5-chloro-1H-pyrrolo[2,3-b]pyridin-4-yl)-5-cyclopropyl-4-piperazin-1-yl-pyrido[3,4-d]pyrimidine |
| 1230 | 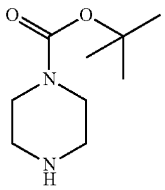 | 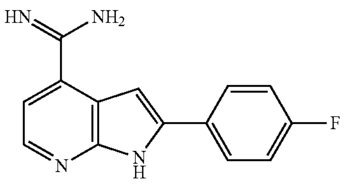 [SMILES: N=C(N)c1ccnc2[nH]c(-c3ccc(F)cc3)cc12] | method 5: RT: 4.02 min, MI: 466 [M + H] | 1H NMR (400 MHz, d6-DMSO, 90° C.) 9.13 (1H, s), 8.38 (1H, d, J = 5.1 Hz), 8.14 (1H, s), 8.11 (1H, d, J = 5.1 Hz), 8.07-8.03 (2H, m), 7.84 (1H, s), 7.32 (2H, t, J = 8.9 Hz), 3.78-3.76 (4H, m), 2.97-2.94 (4H, m, overlapping with water signal), 2.77-2.70 (1H, m), 1.30-1.25 (2H, m), 1.02-0.98 (2H, m). | 5-Cyclopropyl-2-[2-(4-fluoro-phenyl)-1H-pyrrolo[2,3-b]pyridin-4-yl]-4-piperazin-1-yl-pyrido[3,4-d]pyrimidine |

-continued

| Ex | Amine 1 | Amidine 2 | Analysis LCMS | NMR | Name |
|---|---|---|---|---|---|
| 1231 | 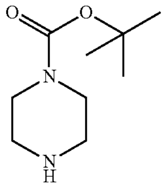 | 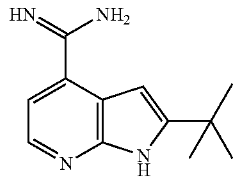 | method 5: RT: 3.51 min, MI: 428 [M + H] | NMR: (1H, d6-DMSO, 500 MHz) 11.71 (1H, br s), 9.03 (1H, s), 8.26 (1H, d), 8.07 (1H, s), 8.02 (1H, d), 7.18 (1H, d), 3.81 (2H, v br s), 3.62 (2H, v br s), 2.90 (4H, br s), 2.70-2.65 (1H, m), 1.41 (9H, s), 1.28-1.22 (2H, m), 1.04-1.01 (2H, dt). | 2-(2-tert-Butyl-1H-pyrrolo[2,3-b]pyridin-4-yl)-5-cyclopropyl-4-piperazin-1-yl-pyrido[3,4-d]pyrimidine |
| 1232 | 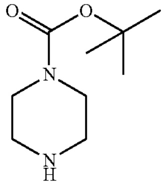 | 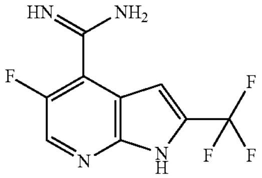 [SMILES: N=C(N)c1c(F)cnc2[nH]c(C(F)(F)F)cc12] | method 5: RT 2.48 min, MI: 458 [MH+] | 1H NMR (400 MHz, d6-DMSO, 90° C.) 9.02 (1H, s), 8.54 (1H, d, J = 3.6 Hz), 8.18 (1H, s), 7.51-7.49 (1H, m), 3.74-3.72 (4H, m), 2.92-2.89 (4H, m), 2.68-2.62 (1H, m), 1.31-1.26 (2H, m), 1.04-1.01 (2H, m). | 5-Cyclopropyl-2-(5-fluoro-2-trifluoromethyl-1H-pyrrolo[2,3-b]pyridin-4-yl)-4-piperazin-1-yl-pyrido[3,4-d]pyrimidine |
| 1233 | 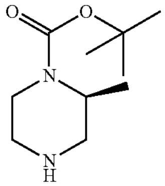 | 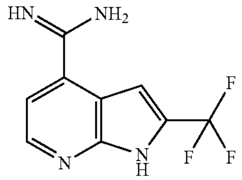 [SMILES: N=C(N)c1ccnc2[nH]c(C(F)(F)F)cc12] | method 5: RT: 3.63 min, MI = 454 [M + H] | | 5-Cyclopropyl-4-((S)-3-methyl-piperazin-1-yl)-2-(2-trifluoromethyl-1H-pyrrolo[2,3-b]pyridin-4-yl)-pyrido[3,4-d]pyrimidine |
| 1234 | 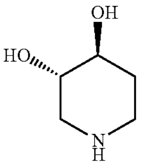 | 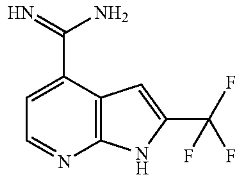 [SMILES: N=C(N)c1ccnc2[nH]c(C(F)(F)F)cc12] | 471.1 (M + H) | ($CDCl_3$) 13.11 (br s, 1H), 9.06 (s, 1H), 8.62 (d, J = 5.0 Hz, 1H), 8.25 (d, J = 5.0 Hz, 1H), 8.10 (s, 1H), 7.98 (d, J = 1.0 Hz, 1H), 5.09-4.67 (m, 1H), 4.67-4.17 (m, 2H), 4.03-3.68 (m, 4H), 3.68-3.38 (m, 2H), 2.63-2.53 (m, 1H), 2.06 (br s, 1H), 1.70 (br s, water), 1.49-0.80 (m, 4H) | (+/−)-(cis)-1-[5-Cyclopropyl-2-(2-trifluoromethyl-1H-pyrrolo[2,3-b]pyridin-4-yl)-pyrido[3,4-d]pyrimidin-4-yl]-piperidine-3,4-diol |
| 1235 | 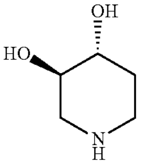 | 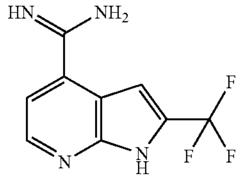 [SMILES: N=C(N)c1ccnc2[nH]c(C(F)(F)F)cc12] | 471.1 (M + H) | ($CDCl_3$): 13.09 (br s, 1H), 9.07 (s, 1H), 8.62 (d, J = 5.0 Hz, 1H), 8.25 (d, J = 5.0 Hz, 1H), 8.11 (s, 1H), 7.98 (d, J = 1.0 Hz, 1H), 5.22-4.71 (m, 2H), 4.22-3.74 (m, 3H), 3.62-3.34 (m, 3H), 2.60-2.53 (m, 1H), 2.30-1.81 (m, 1H), 1.71-1.13 (m, 3H), 1.12-0.95 (m, 2H) | (+/−)-(trans)-1-[5-Cyclopropyl-2-(2-trifluoromethyl-1H-pyrrolo[2,3-b]pyridin-4-l)-pyrido[3,4-d]pyrimidin-4-yl]-piperidine-3,4-diol |
| 1236 | 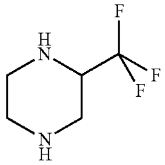 | 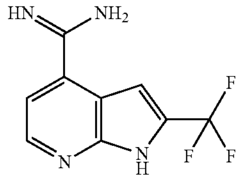 [SMILES: N=C(N)c1ccnc2[nH]c(C(F)(F)F)cc12] | method 5: RT: 4.74 min, MI 508 [M + H] | 1H NMR (DMSO, 500 MHz) 13.14 (s, 1H), 9.12 (s, 1H), 8.61 (d, 1H), 8.21 (d, 1H), 8.14 (s, 1H), 7.91 (s, 1H), 4.70-4.21 (m, 1H), 4.04-3.96 (m, 1H), 3.87-3.46 (m, 2H), 3.19-2.96 (m, 3H), 1.37-1.17 (m, 2H), 1.14-0.96 (m, 2H). | 5-Cyclopropyl-4-(3-trifluoromethyl-piperazin-1-yl)-2-(2-trifluoromethyl-1H-pyrrolo[2,3-b]pyridin-4-yl)-pyrido[3,4-d]pyrimidine |
| 1237 | 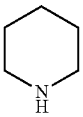 | 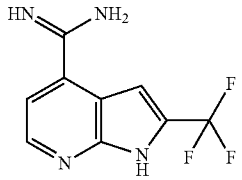 [SMILES: N=C(N)c1ccnc2[nH]c(C(F)(F)F)cc12] | 439.49 | | 5-Cyclopropyl-4-piperidin-1-yl-2-(2-trifluoromethyl-1H-pyrrolo[2,3-b]pyridin-4-yl)-pyrido[3,4-d]pyrimidine |

-continued

| Ex | Amine 1 | Amidine 2 | Analysis LCMS | Analysis NMR | Analysis Name |
|---|---|---|---|---|---|
| 1238 | 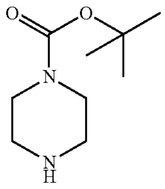 | 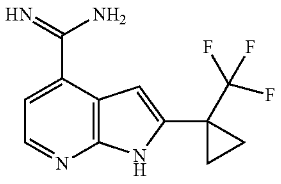 [SMILES: N=C(N)c1ccnc2[nH]c(C3(C(F)(F)F)CC3)cc12] | method 5: RT: 5.31 min, MI 480 [M + H] | 1H NMR (400 MHz, d6-DMSO, 90° C.) 11.66 (1H, br s), 9.04 (1H, s), 8.39 (1H, d, J = 5.0 Hz), 8.13 (1H, s), 8.10 (1H, d, J = 5.0 Hz), 7.55 (1H, s), 3.76-3.73 (4H, m), 2.94-2.91 (4H, m, partly obscured by water signal), 2.73-2.66 (1H, m), 1.49-1.48 (2H, m), 1.47-1.46 (2H, m), 1.29-1.24 (2H, m), 1.01-0.97 (2H, m). | 5-Cyclopropyl-4-piperazin-1-yl-2-[2-(1-trifluoromethyl-cyclopropyl)-1H-pyrrolo[2,3-b]pyridin-4-yl]-pyrido[3,4-d]pyrimidine |
| 1239 | 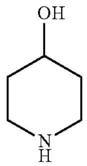 | 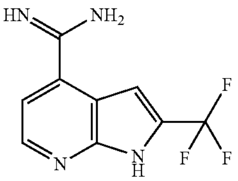 [SMILES: N=C(N)c1ccnc2[nH]c(C(F)(F)F)cc12] | method 5: RT 6.34 min, MI = 455 [M + H] | NMR 1H DMSO 13.12 (s, 1 H), 9.08 (s, 1H), 8.61 (d, 1H), 8.23 (d, 1H), 8.10 (s, 1H), 7.96 (s, 1H), 4.84-4.70 (m, 1H), 4.14-4.04 (m, 1H), 3.88-3.75 (m, 1H), 3.68-3.40 (m, 2H), 1.95-1.84 (m, 1H), 1.67-1.39 (m, 2H), 1.31-1.20 (m, 2H), 1.17-0.99 (m, 4H). | 1-[5-Cyclopropyl-2-(2-trifluoromethyl-1H-pyrrolo[2,3-b]pyridin-4-yl)-pyrido[3,4-d]pyrimidin-4-yl]-piperidin-4-ol |
| 1240 | 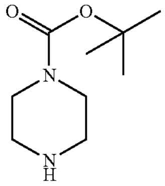 | 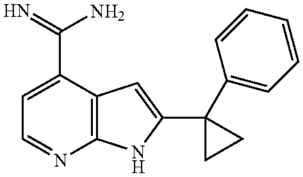 [SMILES: N=C(N)c1ccnc2[nH]c(C3(c4ccccc4)CC3)cc12] | method 5: RT: 3.82 min, MI: 488 [M + H] | 1H NMR (400 MHz, d6-DMSO, 90°) 11.28 (1H, br s), 8.96 (1H, s), 8.27 (1H, d, J = 5.1 Hz), 8.09 (1H, s), 8.05 1H, d, J = 5.1 Hz), 7.45-7.43 (2H, m), 7.38-7.34 (2H, m), 7.29-7.26 (1H, m), 7.02 (1H, m), 3.63-3.60 (4H, m), 2.88-2.85 (4H, m), 2.70-2.64 (1H, m), 1.60-1.57 (2H, m), 1.40-1.37 (2H, m), 1.27-1.22 (2H, m), 1.00-0.96 (2H, m). | 5-Cyclopropyl-2-[2-(1-phenyl-cyclopropyl)-1H-pyrrolo[2,3-b]pyridin-4-yl]-4-piperazin-1-yl-pyrido[3,4-d]pyrimidine |
| 1241 | 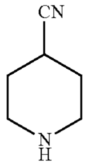 | 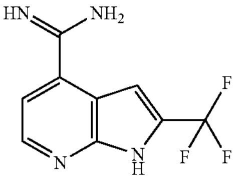 [SMILES: N=C(N)c1ccnc2[nH]c(C(F)(F)F)cc12] | method 5: RT 5.38 min, MI = 464 [M + H] | NMR 1H DMSO, 90°C.,, 12.78 (brs, 1H), 9.12 (s, 1H), 8.62 (d, 1H), 8.24 (d, 1H), 8.18 (s, 1H), 7.95 (d, 1H), 4.04-3.98 (m, 2H), 3.72-3.66 (m, 2H), 3.22-3.15 (m, 1H), 2.72-2.65 (m, 1H), 2.15-2.08 (m, 2H), 2.00-1.91 (m, 2H), 1.31-1.26 (m, 2H), 1.03-0.99 (m, 2H). | 1-[5-Cyclopropyl-2-(2-trifluoromethyl-1H-pyrrolo[2,3-b]pyridin-4-yl)-pyrido[3,4-d]pyrimidin-4-yl]-piperidine-4-carbonitrile |
| 1242 | 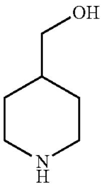 | 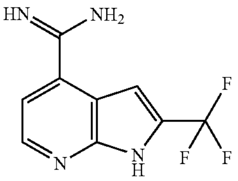 [SMILES: N=C(N)c1ccnc2[nH]c(C(F)(F)F)cc12] | method 5: RT: 5.29 min, MI = 469 [M + H] | NMR 1H DMSO, 90°C., 12.76 (brs, 1H), 9.08 (s, 1H), 8.61 (d, 1H), 8.25 (d, 1H), 8.16 (s, 1H), 7.96 (d, 1H), 4.38-4.35 (m, 2H), 4.12 (t, 1H), 3.37-3.28 (m, 4H), 2.69-2.62 (m, 1H), 1.91-1.73 (m, 3H), 1.46-1.34 (m, 2H), 1.29-1.25 (m, 2H), 1.02-0.98 (m, 2H). | {1-[5-Cyclopropyl-2-(2-trifluoromethyl-1H-pyrrolo[2,3-b]pyridin-4-yl)-pyrido[3,4-d]pyrimidin-4-yl]-piperidin-4-yl}-methanol |
| 1243 | 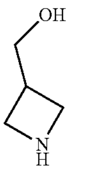 | 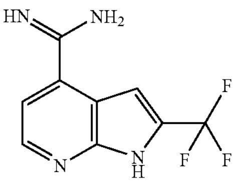 [SMILES: N=C(N)c1ccnc2[nH]c(C(F)(F)F)cc12] | method 5: RT 4.57 min, MI: 441 [M + H] | NMR 1H DMSO, 90° C., 9.03 (s, 1H), 8.60 (d, 1H), 8.26 (d, 1H)m, 8.19 (s, 1H), 7.96 (d, 1H), 4.53 (t, 2H), 4.26 (dd, 2H), 3.62 (d, 2H), 3.00-2.87 (m, 2H), 1.32-1.28 (m, 2H), 0.97-0.93 (m, 2H). | {1-[5-Cyclopropyl-2-(2-trifluoromethyl-1H-pyrrolo[2,3-b]pyridin-4-yl)-pyrido[3,4-d]pyrimidin-4-yl]-azetidin-3-yl}-methanol |

-continued

| Ex | Amine 1 | Amidine 2 | Analysis LCMS | NMR | Name |
|---|---|---|---|---|---|
| 1244 | 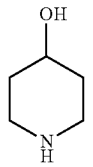 | 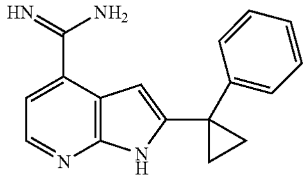 [SMILES: N=C(N)c1ccnc2[nH]c(C3(c4ccccc4)CC3)cc12] | method 5: RT = 5.05 min, MI: 503 [M + H] | 1H NMR (400 MHz, d6-DMSO, 90° C.) 11.27 (1H, s), 8.95 (1H, s), 8.26 (1H, d, J = 5.1 Hz), 8.09 (1H, s), 8.05 (1H, d, J = 5.1 Hz), 7.45-7.42 (2H, m), 7.37-7.34 (2H, m), 7.29-7.25 (1H, m), 7.05 (1H, d, J = 2.2 Hz), 4.40 (1H, d, J = 4.3 Hz), 4.01-3.95 (2H, m), 3.83-3.77 (1H, m), 3.45-3.38 (2H, m), 2.66-2.61 (1H, m), 1.90-1.83 (2H, m), 1.59-1 .49 (4H, q and m overlapping), 1.39-1.37 (2H, m), 1.26-1.21 (2H, m), 0.99-0.95 (2H, m). | 1-[5-Cyclopropyl-2-[2-(1-phenyl-cyclopropyl)-1H-pyrrolo[2,3-b]pyridin-4-yl]-pyrido[3,4-d]pyrimidin-4-yl}-piperidin-4-ol |
| 1245 | 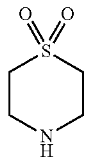 | 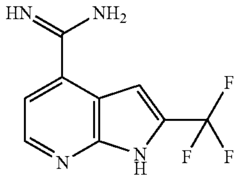 [SMILES: N=C(N)c1ccnc2[nH]c(C(F)(F)F)cc12] | method 5: RT 4.51 min, MI: 489 [M + H] | 1H NMR (DMSO, 500 MHz) 13.15 (s, 1H), 9.19 (s, 1H), 8.63 (d, 1H), 8.25 (d, 1H), 8.16 (s, 1H), 7.97 (s, 1H), 4.41-4.01 (m, 4H), 3.41-3.34 (m, 4H), 2.73-2.66 (m, 1H), 1.32-1.23 (m, 2H), 1.09-1.02 (m, 2H). | 5-Cyclopropyl-4-(1,1-dioxo-1λ$^6$-thiomorpholin-4-yl)-2-(2-trifluoromethyl-1H-pyrrolo[2,3-b]pyridin-4-yl)-pyrido[3,4-d]pyrimidine |
| 1246 | 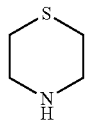 | 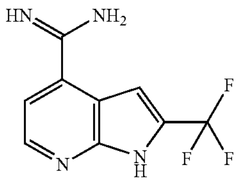 [SMILES: N=C(N)c1ccnc2[nH]c(C(F)(F)F)cc12] | method 5: RT 5.95 min, MI = 457 [M + H] | 1H NMR (DMSO, 500 MHz) 13.12 (s, 1H), 9.10 (s, 1H), 8.61 (d, 1H), 8.22 (d, 1H), 8.11 (s, 1H), 7.94 (s, 1H), 4.09-4.01 (m, 4H), 2.83-2.73 (m, 4H), 2.63-2.57 (m, 1H), 1.31-1.23 (m, 2H), 1.06-0.98 (m, 2H). | 5-Cyclopropyl-4-thiomorpholin-4-yl-2-(2-trifluoromethyl-1H-pyrrolo[2,3-b]pyridin-4-yl)-pyrido[3,4-d]pyrimidine |
| 1247 | 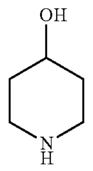 | 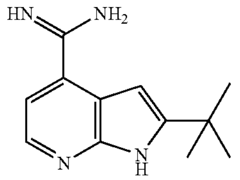 | method 5: RT: 5.61 min, MI: 443 [M + H] | 1H NMR (400 MHz, d6-DMSO, 90° C.) 11.31 (1H, br s), 9.03 (1H, s), 8.27 (1H, d, J = 5.2 Hz), 8.11 (1H, s), 8.06 (1H, d, J = 5.2 Hz), 7.24-7.23 (1H, m), 4.42 (1H, d, J = 4.1 Hz), 4.18-4.08 (2H, m), 3.88-3.83 (1H, m), 360-3.53 (2H, m), 2.71-2.65 (1H, m), 1.95-1.91 (2H, m), 1.65-1.57 (2H, m), 1.46 (9H, s), 1.28-1.23 (2H, m), 1.00-0.96 (2H, m). | 1-[2-(2-tert-Butyl-1H-pyrrolo[2,3-b]pyridin-4-yl)-5-cyclopropyl-pyrido[3,4-d]pyrimidin-4-yl]-piperidin-4-ol |
| 1248 | 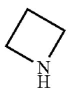 | 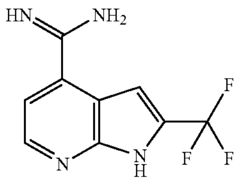 [SMILES: N=C(N)c1ccnc2[nH]c(C(F)(F)F)cc12] | method 5: RT: 5.62 min, MI: 411 [M + H] | 1H NMR (DMSO, 500 MHz) 13.09 (brs, 1H), 9.02 (s, 1H), 8.59 (d, 1H), 8.24 (d, 1H), 8.13 (s, 1H), 7.95 (s, 1H), 7.47 (t, 4H), 2.43-2.33 (m, 3H), 1.31-1.24 (m, 2H), 0.99-0.92 (m, 2H). | 4-Azetidin-1-yl-5-cyclopropyl-2-(2-trifluoromethyl-1H-pyrrolo[2,3-b]pyridin-4-yl)-pyrido[3,4-d]pyrimidine |
| 1249 | 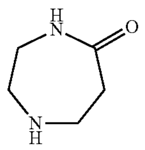 | 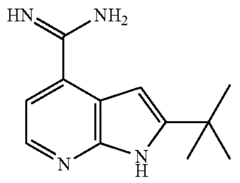 | method 5: RT: 1.76 min, MI: 456 [M + H] | 1H NMR (400 MHz, d6-DMSO, 90° C.) 11.31 (1H, s), 9.05 (1H, s), 8.28 (1H, d, J = 5.0 Hz), 8.15 (1H, s), 8.06 (1H, d, J = 5.0 Hz), 7.29-7.26 (1H, m), 7.19 (1H, d, J = 2.3 Hz), 4.03-4.00 (2H, m), 3.96-3.94 (2H, m), 3.39-3.35 (2H, m), 2.77-2.74 (2H, m), 2.65-2.58 (1H, m), 1.47 (9H, s), 1.28-1.23 (2H, m), 0.99-0.95 (2H, m). | 1-[2-(2-tert-Butyl-1H-pyrrolo[2,3-b]pyridin-4-yl)-5-cyclopropyl-pyrido[3,4-d]pyrimidin-4-yl]-[1,4]diazepan-5-one |

-continued

| | | | Analysis | | |
|---|---|---|---|---|---|
| Ex | Amine 1 | Amidine 2 | LCMS | NMR | Name |
| 1250 | 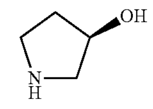 | 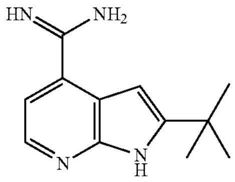 | method 5: RT: 4.78 min, MI: 429 [M + H] | 1H NMR (500 MHz, d6-DMSO), 11.67 (1H, br d, J = 1.8 Hz), 8.92 (1H, s), 8.25 (1H, d, J = 5.2 Hz), 8.07 (1H, s), 8.06 (1H, d, J = 5.2 Hz), 7.22 (1H, d ,J = 2.3 Hz), 4.95 (1H, br, J = 2.9 Hz), 4.35 (1H, br s), 4.19-4.13 (1H, m), 4.09-4.04 (1H, s), 3.77-3.72 (1H, m), 3.48 (1H, d, J = 11.3 Hz), 2.35-2.28 (1H, m), 2.05-1.98 (1H, m), 1.90-1.86 (1H, m), 1.34-1.29 (1H, m), 1.20-1.14 (1H, m), 1.20-1.14 (1H, m), 1.04-0.99 (1H, m), 0.94-0.89 (1H, m). | (R)-1-[2-(2-tert-Butyl-1H-pyrrolo[2,3-b]pyridin-4-yl)-5-cyclopropyl-pyrido[3,4-d]pyrimidin-4-yl]-pyrrolidin-3-ol |
| 1251 | 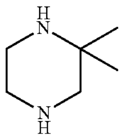 | 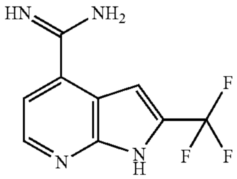 [SMILES: N=C(N)c1ccnc2[nH]c(C(F)(F)F)cc12] | method 5: RT: 3.79 min, MI: 468 [M + H] | 1H NMR (DMSO, 500 MHz) 13.10 (brs, 1H), 9.06 (s, 1H), 8.61 (d, 1H), 8.23 (d, 1H), 8.11 (s, 1H), 7.96 (s, 1H), 4.02-3.75 (m, 1H), 3.70-3.53 (m, 2H), 3.38-3.25 (m, 2H), 2.98-2.85 (m, 2H), 1.29-0.70 (m, 10H). | 5-Cyclopropyl-4-(3,3-dimethyl-piperazin-1-yl)-2-(2-trifluoromethyl-1H-pyrrolo[2,3-b]pyridin-4-yl)-pyrido[3,4-d]pyrimidine |
| 1252 | 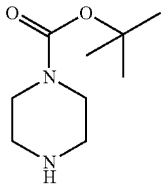 | 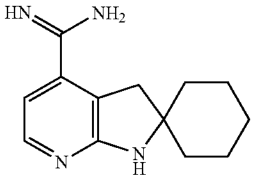 [SMILES: N=C(N)c1ccnc2c1CC1(CCCCC1)N2] | 442 | 1H NMR (400 MHz, d6-DMSO, 90° C.) 8.96 (1H, s), 8.10 (1H, s), 7.82 (1H, d, J = 5.5 Hz), 7.34 (1H, d, J = 5.5 Hz), 6.42 (1H, s), 3.70-3.67 (2H, m), 3.09-3.106 (2H, m), 2.90-2.88 (2H, m), 2.70-2.66 (3H, m), 1.73-1.58 (7H, m), 1.55-1.45 (4H, m), 1.28-1.20 (3H, m), 0.99-0.95 (2H, m). | 4-(5-cyclopropyl-4-piperazin-1-yl-pyrido[3,4-d]pyrimidin-2-yl)spiro[1,3-dihydropyrrolo[2,3-b]pyridine-2,1'-cyclohexane] |
| 1253 | 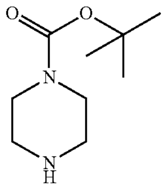 | 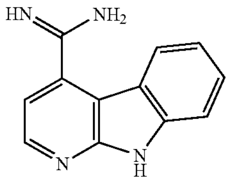 [SMILES: N=C(N)c1ccnc2[nH]c3ccccc3c12] | 422 (M + H) | $^1$H-NMR (DMSO-$d_6$, 400 MHz): δ 12.08 (s, 1H), 9.17 (s, 1H), 8.83 (br s, 1H), 8.68 (d, 1H, J = 8.4 Hz), 8.59 (d, 1H, J = 5.1 Hz), 8.26 (s, 1H), 7.89 (d, 1H, J = 5.1 Hz), 7.55 (d, 1H, J = 7.9 Hz), 7.49 (m, 1H), 7.18 (m, 1lH), 3.68 (br s, 4H), 3.34 (br s, 4H), 2.77 (m, 1H), 1.30 (m, 2H), 1.14 (m ,2H). | 4-(5-Cyclopropyl-4-piperazin-1-yl-pyrido[3,4-d]pyrimidin-2-yl)-9H-pyrido[2,3-b]indole |
| 1254 | 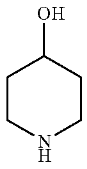 | 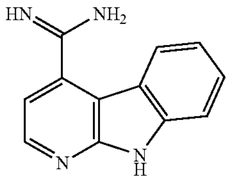 [SMILES: N=C(N)c1ccnc2[nH]c3ccccc3c12] | 437 (M + H) | $^1$H-NMR (DMSO-$d_6$, 400 MHz): δ 12.12 (s, 1H), 9.07 (s, 1H), 8.60 (d, 1H, J = 5.0 Hz) 8.54 (d, 1H, J = 8.1 Hz), 8.22 (s, 1H), 7.84 (d, 1H, J = 5.0 Hz), 7.56 (d, 1H, J = 8.0 Hz), 7.49 (m, 1H), 7.17 (m, 1H), 4.11 (m, 3H), 3.58 (br s, 2H), 2.61 (m, 1H), 1.89 (m, 2H), 1.55 (m, 2H), 1.92 (m, 2H), 1.21 (m, 2H). | 1-[5-Cyclopropyl-2-(9H-pyrido[2,3-b]indol-4-yl)-pyrido[3,4-d]pyrimidine-4-yl]-piperidin-4-ol |
| 1255 | 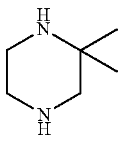 | 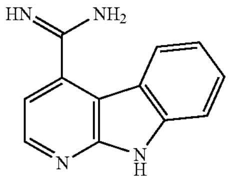 [SMILES: N=C(N)c1ccnc2[nH]c3ccccc3c12] | 450 (M + H) | $^1$H-NMR (DMSO-$d_6$, 400 MHz): δ 12.09 (s, 1H), 9.17 (s, 1H), 9.05 (br s, 2H), 8.67 (d, 1H, J = 8.1 Hz), 8.60 (d, 1H, J = 5.1 Hz), 8.29 (s, 1H), 7.93 (d, 1H, J = 5.1 Hz) 7.55 (d, 1H, J = 7.9 Hz), 7.49 (m, 1H), 7.18 (m, 1H), 3.93 (m, 4H), 3.39 (m, 2H), 2.61 (m,1H), 1.01-1.48 (m, 10H). | 4-[5-Cyclopropyl-4-(3,3-dimethyl-piperazin-1-yl)-pyrido[3,4-d]pyrimidin-2-yl]-9H-pyrido[2,3-b]indole |

Example 1253. 4-(5-Cyclopropyl-4-piperazin-1-yl-pyrido[3,4-d]pyrimidin-2-yl)-9H-pyrido[2,3-b]indole trifluoroacetic acid salt 1253a) A mixture of azeotropically dried (xylene) 4-chloro-9H-pyrido[2,3-b]indole (1.31 g, 6.46 mmol), zinc cyanide (1.21 g, 10.3 mmol), zinc (0.145 g, 2.22 mmol), tris(dibenzylideneacetone)dipalladium(0) (0.479 g, 0.523 mmol) and 1,1'-bis(diphenylphosphino)ferrocene (0.375 g, 0.676 mmol) in N,N-dimethylformamide (27 mL) was vacuum degassed then heated at 100 OC under an atmosphere of argon overnight. The mixture is cooled and poured into water:ethyl acetate (2:1, 150 mL). The layers were separated, the aqueous extracted with ethyl acetate (2×50 mL) and the combined organic extracts are diluted with hexane (15 mL) and brine (100 mL). The fine suspension of solids was removed by filtration of the aqueous layer through Celite, washing with methanol and ethyl acetate. The organic extracts and aqueous/organic rinsate were combined, separated and the organic layer washed with additional brine (100 mL), dried over magnesium sulfate, filtered and concentrated in vacuo onto silica gel (12 g) prior to purification on silica gel (80 g, 5-35% ethyl acetate:hexane). 9H-Pyrido[2,3-b]indole-4-carbonitrile was isolated as a yellow solid (0.830 g, 66% yield). LCMS (ESI): 194 $(M+H)^+$; $^1$H-NMR (DMSO-$d_6$, 400 MHz): δ 12.45 (s, 1H), 8.63 (d, 1H, J=5.0 Hz), 8.32 (d, 1H, J=8.0 Hz), 7.68 (d, 1H, J=5.0 Hz), 7.64 (m, 2H), 7.40 (m, 1H); $^{13}$C-NMR (DMSO-$d_6$, 100 MHz): δ 151.6, 146.2, 139.7, 128.6, 121.1, 120.5, 117.9, 116.9, 116.7, 114.1, 112.0, 109.8.

1253b) Lithium hexamethyldisilazide in tetrahydrofuran (1.0 M, 7.0 mL, 7.0 mmol) was added to a suspension of 9H-pyrido[2,3-b]indole-4-carbonitrile (0.422 g, 2.18 mmol) in tetrahydrofuran (12.0 mL, 148 mmol) at room temperature under an atmosphere of nitrogen. Additional lithium hexamethyldisilazide in tetrahydrofuran (1.0 M, 7 mL) was added at 48 h to drive the reaction to completion. After stirring a total of 72 h, the mixture was diluted with water (50 mL) and the resultant solids were collected by filtration, washed with water and dried on a Buchner funnel and in vacuo. 9H-Pyrido[2,3-b]indole-4-carboxamidine was isolated as beige solids (0.297 g, 65% yield) and was used without further purification. LCMS (ESI): 211 $(M+H)^+$.

1253c) 9H-Pyrido[2,3-b]indole-4-carboxamidine (0.295 g, 1.40 mmol), N,N,N',N'-tetramethyl-O-(7-azabenzotriazol-1-yl)uronium hexafluorophosphate (0.806 g, 2.12 mmol), 3-cyclopropyl-5-fluoro-isonicotinic acid (0.320 g, 1.76 mmol) and N,N-diisopropylethylamine (0.750 mL, 4.30 mmol) were combined in N,N-dimethylformamide (8.0 mL) and stirred for 90 min. The mixture was poured into ethyl acetate (50 mL) and washed with water (2×5 mL). The combined aqueous wash was extracted with ethyl acetate (3×15 mL) which was combined with the first organic extract, washed with brine (30 mL), dried over sodium sulfate, filtered and concentrated in vacuo. The crude 3-cyclopropyl-5-fluoro-N-[imino-(9H-pyrido[2,3-b]indol-4-yl)-methyl]-isonicotinamide was combined with cesium carbonate (0.914 g, 2.81 mmol) in N,N-dimethylformamide (14.0 mL) and was heated at 90 OC under an atmosphere of nitrogen overnight. The mixture was concentrated in vacuo onto silica gel (4.5 g) then purified (silica gel 40 g, 0-10% MeOH:DCM) to afford 5-cyclopropyl-2-(9H-pyrido[2,3-b]indol-4-yl)-3H-pyrido[3,4-d]pyrimidin-4-one (0.230 g; Yield=46.4%). LCMS (ESI): 354 $(M+H)^+$.

1253d) 5-Cyclopropyl-2-(9H-pyrido[2,3-b]indol-4-yl)-3H-pyrido[3,4-d]pyrimidin-4-one (18 mg, 0.051 mmol), 2,4,6-triisopropylbenzenesulfonyl chloride (17.5 mg, 0.0578 mmol), 4-dimethylaminopyridine (1.0 mg, 0.0082 mmol) and triethylamine (35.0 μL, 0.251 mmol) in N,N-dimethylformamide (1.00 mL) was stirred under an atmosphere of nitrogen at room temperature for 1 h, then a solution of piperazine (74.0 mg, 0.859 mmol) in N,N-dimethylformamide (1.0 mL) was added and stirring was continued for 3 h. The mixture was concentrated in vacuo and purified by preparative HPLC (0-45% acetonitrile:water, 0.1% trifluoracetic acid) to afford 4-(5-cyclopropyl-4-piperazin-1-yl-pyrido[3,4-d]pyrimidin-2-yl)-9H-pyrido[2,3-b]indole trifluoroacetic acid salt (10.0 mg; Yield=37%) as a yellow lyophilate. LCMS (ESI): 422 (M+H); $^1$H-NMR (DMSO-$d_6$, 400 MHz): δ 12.08 (s, 1H), 9.17 (s, 1H), 8.83 (br s, 1H), 8.68 (d, 1H, J=8.4 Hz), 8.59 (d, 1H, J=5.1 Hz), 8.26 (s, 1H), 7.89 (d, 1H, J=5.1 Hz), 7.55 (d, 1H, J=7.9 Hz), 7.49 (m, 1H), 7.18 (m, 1H), 3.68 (br s, 4H), 3.34 (br s, 4H), 2.77 (m, 1H), 1.30 (m, 2H), 1.14 (m, 2H).

Example 1254. 1-[5-cyclopropyl-2-(9H-pyrido[2,3-b]indol-4-yl)-pyrido[3,4-d]pyrimidin-4-yl]-piperidin-4-ol trifluoroacetic acid salt Analogous to Example 1253d, 5-cyclopropyl-2-(9H-pyrido[2,3-b]indol-4-yl)-3H-pyrido[3,4-d]pyrimidin-4-one (44.0 mg, 0.124 mmol) was reacted with piperidin-4-ol (34.0 mg, 0.336 mmol) to afford 1-[5-cyclopropyl-2-(9H-pyrido[2,3-b]indol-4-yl)-pyrido[3,4-d]pyrimidin-4-yl]-piperidin-4-ol trifluoroacetic acid salt (32 mg; Yield=47%) as a yellow lyophilate. LCMS (ESI): 437 (M+H); $^1$H-NMR (DMSO-$d_6$, 400 MHz): δ 12.12 (s, 1H), 9.07 (s, 1H), 8.60 (d, 1H, J=5.0 Hz) 8.54 (d, 1H, J=8.1 Hz), 8.22 (s, 1H), 7.84 (d, 1H, J=5.0 Hz), 7.56 (d, 1H, J=8.0 Hz), 7.49 (m, 1H), 7.17 (m, 1H), 4.11 (m, 3H), 3.58 (br s, 2H), 2.61 (m, 1H), 1.89 (m, 2H), 1.55 (m, 2H), 1.92 (m, 2H), 1.21 (m, 2H).

Example 1255. 4-[5-Cyclopropyl-4-(3,3-dimethyl-piperazin-1-yl)-pyrido[3,4-d]pyrimidin-2-yl]-9H-pyrido[2,3-b]indole trifluoroacetic acid salt Analogous to Example 1253d, 5-cyclopropyl-2-(9H-pyrido[2,3-b]indol-4-yl)-3H-pyrido[3,4-d]pyrimidin-4-one (52.5 mg, 0.148 mmol) was reacted with 2,2-dimethylpiperazine (31.4 mg, 0.275 mmol) to afford 4-[5-cyclopropyl-4-(3,3-dimethyl-piperazin-1-yl)-pyrido[3,4-d]pyrimidin-2-yl]-9H-pyrido[2,3-b]indole trifluoroacetic acid salt (17.5 mg; Yield=21%) as a yellow lyophilate. LCMS (ESI): 450 (M+H); $^1$H-NMR (DMSO-d6, 400 MHz): δ 12.09 (s, 1H), 9.17 (s, 1H), 9.05 (br s, 2H), 8.67 (d, 1H, J=8.1 Hz), 8.60 (d, 1H, J=5.1 Hz), 8.29 (s, 1H), 7.93 (d, 1H, J=5.1 Hz) 7.55 (d, 1H, J=7.9 Hz), 7.49 (m, 1H), 7.18 (m, 1H), 3.93 (m, 4H), 3.39 (m, 2H), 2.61 (m, 1H), 1.01-1.48 (m, 10H).

The following compounds were synthesized according to the general syntheses shown in any of the Scheme(s) provided above using analogous procedures, starting materials and intermediates.

| Ex | Structure | Scheme | LCMS | $^1$H-NMR | Name |
|---|---|---|---|---|---|
| 2001 | 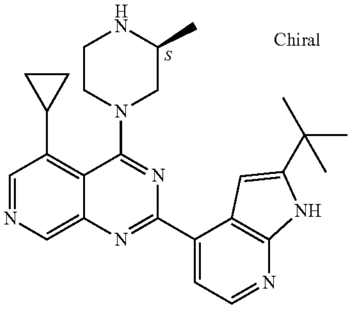 Chiral | [D4], [D3] | Method 5: RT: 3.66 min, MI: 442 [M + H] | (400 MHz, d6-DMSO, 90° C.) 11.32 (1H, s), 9.03 (1H, s), 8.27 (1H, d, J = 5.1 Hz), 8.11 (1H, s), 8.04 (1H, d, J = 5.1 Hz), 7.21 (1H, d, J = 2.2 Hz), 4.21-4.16 (2H, m), 3.23-3.16 (1H, m), 3.06-3.01 (1H, m), 2.94-2.82 (3H, m), 2.74-7.66 (1H, m), 1.28-1.23 (2H, m), 1.07 (3H, d, J = 6.0 Hz), 1.02-0.98 (2H, m). | 2-(2-tert-Butyl-1H-pyrrolo[2,3-b]pyridin-4-yl)-5-cyclopropyl-4-((S)-3-methyl-piperazin-1-yl)-pyrido[3,4-d]pyrimidine |
| 2002 | 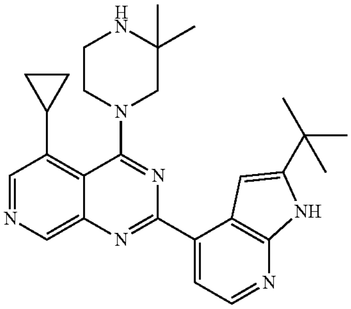 [SMILES: CC1(C)CN(c2nc(-c3ccnc4[nH]c(C(C)(C)C)cc34)nc3cncc(C4CC4)c23)CCN1] | [D4], [D3] | Method 5: RT: 3.75 min, MI: 456 [M + H] | (400 MHz, d6-DMSO, 90° C.) 11.38 (1H, br s), 9.11 (1H, s), 8.30 (1H, d, J = 5.0 Hz), 8.21 (1H, s), 8.07 (1H, d, J = 5.0 Hz), 7.19 (1H, d, J = 2.3 Hz) 3.97-3.94 (2H, m), 3.89 (2H, s), 3.35-3.32 (2H, m), 2.67-2.60 (1H, m), 1.31-1.26 (8 H, m), 1.05-1.00 (2H, m). | 2-(2-tert-Butyl-1H-pyrrolo[2,3-b]pyridin-4-yl)-5-cyclopropyl-4-(3,3-dimethyl-piperazin-1-yl)-pyrido[3,4-d]pyrimidine |
| 2003 | 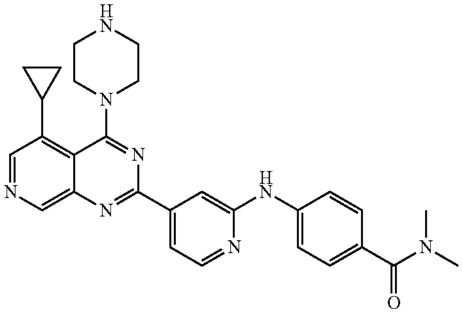 [SMILES: CN(C)C(=O)c1ccc(Nc2cc(-c3nc(N4CCNCC4)c4c(C5CC5)cncc4n3)ccn2)cc1] | [B4] | Method 5: RT: 3.05 min, MI: 495.42 [M + H] | (500 MHz, DMSO) 9.06 (1H, s), 8.37 (1H, d), 8.17 (1H, s), 7.98 (1H, s), 7.82 (1H, s), 7.80 (1H, s), 7.76 (1H, dd), 7.38 (2H, d), 3.92 (4H, s, br), 3.32 (4H, s, br), 2.97 (6H, s), 2.70-2.66 (1H, m), 1.26-1.24 (2H, m), 1.08-1.07 (2H, m). | 4-[4-(5-Cyclopropyl-4-piperazin-1-yl-pyrido[3,4-d]pyrimidin-2-yl)-pyridin-2-ylamino]-N,N-dimethyl-benzamide |
| 2004 | 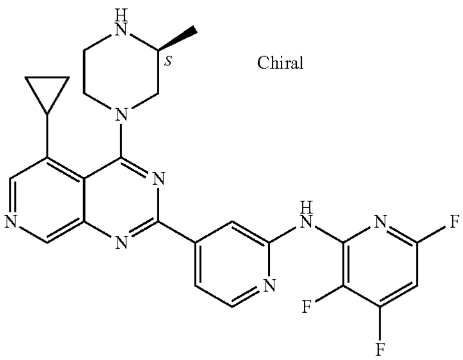 Chiral | [B4] | Method 5: RT: 2.74 min, MI: 493 [M + H] | (DMSO, 500 MHz) 10.13 (1H, s), 9.07 (1H, s), 8.93 (2H, s), 8.48 (1H, s), 8.19 (1H, s), 8.02 (1H, s), 7.02 (1H, m), 4.34 (2H, m), 3.72 (1H, m), 3.48 (4H, m), 3.09 (1H, m), 1.25 (5H, m), 1.09 (2H, m). | {4-[5-Cyclopropyl-4-((S)-3-methyl-piperaizn-1-yl)-pyrido[3,4-d]pyrimidin-2-yl]-pyridin-2-yl}-(3,4,6-trifluoro-pyridin-2-yl)-amine |

Analysis: Scheme, LCMS, $^1$H-NMR, Name

-continued

| Ex | Structure | Scheme | Analysis LCMS | $^1$H-NMR | Name |
|---|---|---|---|---|---|
| 2005 | 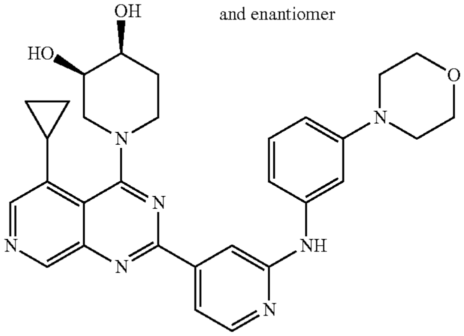 [SMILES: O[C@@H]1CN(c2nc(-c3ccnc(Nc4cccc(N5CCOCC5)c4)c3)nc3cncc(C4CC4)c23)CC[C@@H]1O] and enantiomer | [B4] | LCMS: Purity: 90% RT: min, MI: 540.289978 | ($CDCl_3$): 9.06 (s, 1H), 8.31 (br d, J = 4.4 Hz, 1H), 8.03 (br s, 2H), 7.76 (dd, J = 5.3; 1.3 Hz, 1H), 7.06 (app t, J = 2.0 Hz, 1H), 6.91 (br s, 2H), 6.65 (dd, J = 8.2; 2.0 Hz, 1H), 4.59-3.90 (br m, 4H), 3.89-3.84 (m, 4H), 3.84-3.51 (br s, 2H), 3.22-3.16 (m, 4H), 2.62-2.51 (m, 1H), 1.90-1.50 (br m, 3H), 1.27-1.21 (m, 2H), 0.99-0.95 (m, 2H) | (+/−)-cis-1-{5-Cyclopropyl-2-[2-(3-morpholin-4-yl-phenylamino)-pyridin-4-yl]-pyrido[3,4-d]pyrimidin-4-yl}-piperidine-3,4-diol |
| 2006 | 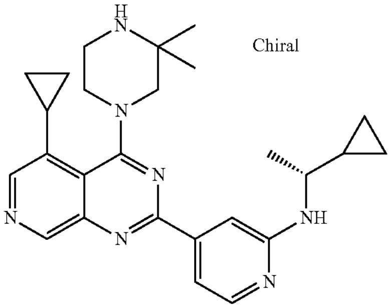 [SMILES: C[C@@H](Nc1cc(-c2nc(N3CCNC(C)(C)C3)c3c(C4CC4)cncc3n2)ccn1)C1CC1] Chiral | [B4] | LCMS: Purity: 92% RT: min, MI: 444.28 (M + H) | (dmso-d6) 9.08 (br s, 2H), 8.83 (br s, 1H), 8.81 (s, 1H), 8.00 (s, 1H), 7.83 (br s, 1H), 7.77 (d, J = 6.7 Hz, 1H), 7.47 (dd, J = 6.7; 1.5 Hz, 1H), 5.98 (br s, exch. H's), 3.69 (br s, 4H), 3.26 (br s, 1H), 3.09 (br s, 2H), 2.25-2.17 (m, 1H), 1.12 (br s, 2H), 1.05 (d, J = 6.4 Hz, 3H), 1.05-0.95 (m, 4H), 0.94-0.70 (m, 5H), 0.40-0.35 (m, 3H), 0.05-(−0.03) (m, 1H). | {4-[5-Cyclopropyl-4-(3,3-dimethyl-piperazin-1-yl)-pyrido[3,4-d]pyrimidin-2-yl]-pyridin-2-yl}-((R)-1-cyclopropyl-ethyl)-amine |
| 2007 | 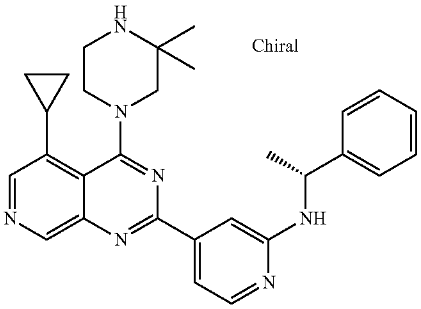 [SMILES: C[C@@H](Nc1cc(-c2nc(N3CCNC(C)(C)C3)c3c(C4CC4)cncc3n2)ccn1)c1ccccc1] Chiral | [B4] | LCMS: Purity: 94%, RT: min, MI: 480.28 (M + H) | (dmso-d6) 9.39 (br s, 3H), 9.09 (s, 1H), 8.28 (s, 1H), 8.13 (d, J = 6.5 Hz, 1H), 8.10 (br s, 1H), 7.79 (d, J = 6.5 Hz, 1H), 7.51 (d, J = 7.4 Hz, 2H), 7.44 (app t, J = 7.4 Hz, 2H), 7.33 (app t, J = 7.4 Hz, 1H), 5.17 (br s, 1H), 4.20-3.80 (m, 4H), 3.38 (br s, 2H), 2.52-2.47 (m, 1H), 1.63 (d, J = 6.7 Hz, 3H), 1.60-1.00 (m, 10H) | {4-[5-Cyclopropyl-4-(3,3-dimethyl-piperazin-1-yl)-pyrido[3,4-d[pyrimidin-2-yl]-pyridin-2-yl}-((R)-1-phenyl-ethyl)-amine |
| 2008 | 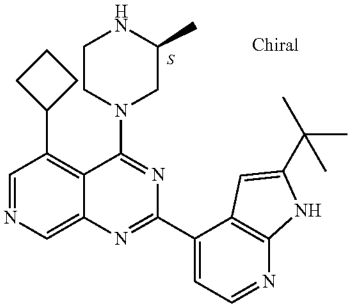 Chiral | [D4], [D3] | Method 5: RT: 3.98 min, MI: 456.43 [M + H] | (d6-DMSO, 400 MHz, 90° C.) 11.34 (1H, s), 9.11 (1H, s), 8.67 (1H, s), 8.28 (1H, d), 8.05 (1H, d), 7.20 (1H, s), 4.36 (1H, m), 3.98 (2H, m), 3.10 (1H, m), 3.02 (2H, m), 2.96 (2H, m), 2.54 (2H, s), 2.22 (2H, m), 2.17 (1H, m), 1.97 (1H, m), 1.47 (9H, s), 1.07 (3H, d). | 2-(2-tert-Butyl-1H-pyrrolo[2,3-b]pyridin-4-yl)-5-cyclobutyl-4-((S)-3-methyl-piperazin-1-yl)-pyrido[3,4-d]pyrimidine |

-continued

| Ex | Structure | Scheme | LCMS (Analysis) | $^1$H-NMR (Analysis) | Name (Analysis) |
|---|---|---|---|---|---|
| 2009 | 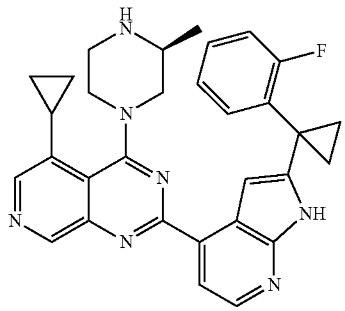 | [D4], [D3] | Method 5: RT: 3.99 min, MI: 506 [M + H] | (400 MHz, d6-DMSO, 90° C.) 11.18 (1H, br s), 8.90 (1H, s), 8.25 (1H, d, J = 5.1 Hz), 8.08 (1H, s), 8.04 (1H, d, J = 5.1 Hz), 7.61 (1H, dt, J = 7.7, 1.8 Hz), 7.43-7.38 (1H, m), 7.25 (1H, dt, J = 7.5, 1.2 Hz), 7.21-7.16 (1H, m), 6.88 (1H, s), 3.60-3.57 (4H, m), 2.89-2.86 (4H, m), 2.68-2.64 (1H, m), 1.69-1.66 (2H, m), 1.40-1.37 (2H, m), 1.26-1.21 (2H, m), 0.98-0.95 (2H, m). | 5-Cyclopropyl-2-{2-[1-(2-fluoro-phenyl)-cyclopropyl]-1H-pyrrolo[2,3-b]pyridin-4-yl}-4-piperazin-1-yl-pyrido[3,4-d]pyrimidine |
| 2010 | 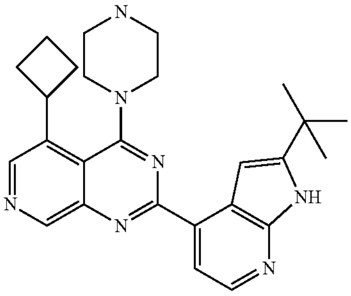 [SMILES: CC(C)(C)c1cc2c(-c3nc(N4CCNCC4)c4c(C5CCC5)cncc4n3)ccnc2[nH]1] | [D4], [D3] | Method 5: RT: 3.90 min, MI: 442.48 [M + H] | (d6-DMSO, 500 MHz) 11.71 (1H, s), 9.07 (1H, s), 8.65 (1H, s), 8.26 (1H, d), 8.04 (1H, d), 7.17 (1H, s), 4.24 (1H, m), 3.84 (1H, m), 3.56 (1H, m), 3.38 (1H, m), 3.36 (1H, m), 2.94 (2H, s), 2.41 (2H, m), 2.15 (2H, m), 2.12 (1H, m), 2.04 (1H, m), 1.41 (9H, s), 1.10 (3H, s), 0.75 (3H, s). | 2-(2-tert-Butyl-1H-pyrrolo[2,3-b]pyridin-4-yl)-5-cyclobutyl-4-piperazin-1-yl-pyrido[3,4-d]pyrimidine |
| 2011 | 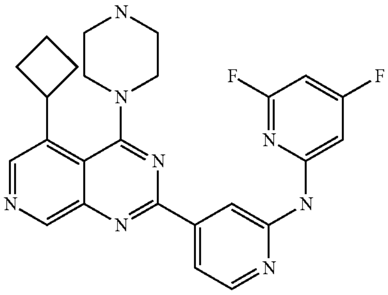 [SMILES: Fc1cc(F)nc(Nc2cc(-c3nc(N4CCNCC4)c4c(C5CCC5)cncc4n3)ccn2)c1] | [B4] | LCMS: Purity: 97%, RT: min, MI: 475.19 (MH)+, | (400 MHz, d6-DMSO, δ): 10.45 (s, 1H), 9.15 (s, 1H), 8.90-8.75 (m, 3H), 8.62 (s, 1H), 8.47 (d, J = 5.3 Hz, 1H), 7.92 (dd, J = 5.2, 1.3 Hz, 1H), 7.80 (dd, J = 11.2, 1.6 Hz, 1H), 6.69 (dt, J = 8.5, 1.6 Hz, 1H), 4.25 (pent, J = 8.8 Hz, 1H), 3.89-3.84 (m, 4H), 3.40-3.17 (m, 4H), 2.52-2.42 (m, 2H), 2.28-2.03 (m, 3H), 1.97-1.87 (m, 1H). | [4-(5-Cyclobutyl-4-piperazin-1-yl-pyrido[3,4-d]pyrimidin-2-yl)-pyridin-2-yl]-(4,6-difluoro-pyridin-2-yl)-amine |
| 2012 | 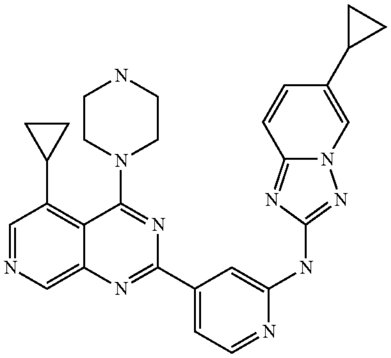 [SMILES: c1cc(-c2nc(N3CCNCC3)c3c(C4CC4)cncc3n2)cc(Nc2nc3ccc(C4CC4)cn3n2)n1] | [B4] | LCMS: Purity: 96%, RT: min, MI: 505.25 (MH)+ | (400 MHz, d6-DMSO, δ): 10.63 (br s, 1H), 9.15 (s, 1H), 9.12 (s, 1H), 8.89 (br s, 2H), 8.68 (s, 1H), 8.45 (d, J = 5.8 Hz, 1H), 8.21 (s, 1H), 7.94 (dd, J = 5.4, 1.3 Hz, 1H), 7.60 (d, J = 9.0 Hz, 1H), 7.42 (dd, J = 9.2, 1.7 Hz, 1H), 3.96 (br s, 4H), 3.36 (br s, 4H), 2.76-2.68 (m, 1H), 2.12-2.05 (m, 1H), 1.30-1.24 (m, 2H), 1.12-1.07 (m ,2H), 1.04-0.98 (m, 2H), 0.85-0.80 (m, 2H). | [4-(5-Cyclopropyl-4-piperazin-1-yl-pyrido[3,4-d]pyrimidin-2-yl)-pyridin-2-yl]-(6-cyclopropyl-[1,2,4]triazolo[1,5-a]pyridin-2-yl)-amine |

-continued

| Ex | Structure | Scheme | Analysis LCMS | $^1$H-NMR | Name |
|---|---|---|---|---|---|
| 2013 | 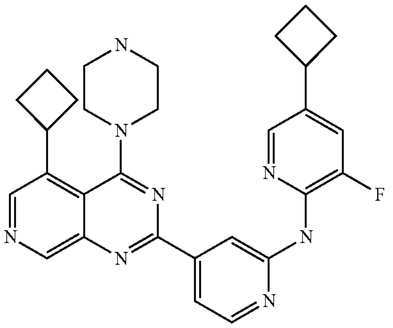 [SMILES: Fc1cc(C2CCC2)cnc1Nc1cc(-c2nc(N3CCNCC3)c3c(C4CCC4)cncc3n2)ccn1] | [B4] | LCMS: Purity: 97%, RT: min, MI: 497.24 (MH)+ | (400 MHz, d6-DMSO, δ): 10.26 (br s, 1H), 9.10 (s, 1H), 8.90 (br s, 2H), 8.83 (s, 1H), 8.44 (d, J = 5.7 Hz, 1H), 8.22 (s, 1H), 8.07 (d, J = 1.5 Hz, 1H), 8.01 (d, J = 5.6 Hz, 1H), 7.83 (d, J = 11.2 Hz, 1H), 3.94 (br s, 4H), 3.61 (pent, J = 8.7 Hz, 1H), 3.34 (br s, 4H), 2.72-2.65 (m, 1H), 2.37-2.28 (m, 2H), 2.22-2.11 (m, 2H), 2.08-1.95 (m, 1H), 1.91-1.82 (m, 1H), 1.30-1.24 (m, 2H), 1.12-1.07 (m, 2H). | (5-Cyclobutyl-3-fluoro-pyridin-2-yl)-[4-(5-cyclopropyl-4-piperazin-1-yl-pyrido[3,4-d] pyrimidin-2-yl)-pyridin-2-yl]-amine |
| 2014 | 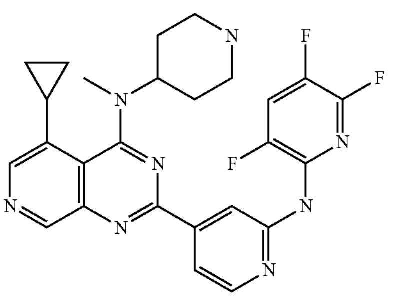 [SMILES: CN(c1nc(-c2ccnc(Nc3nc(F)c(F)cc3F)c2)nc2cncc(C3CC3)c12)C1CCNCC1] | [B4] | LCMS: Purity: >95%, RT: min, MI: 507 (M + H) | 1H-NMR DMSO 9.69 (br s, 1H), 8.93 (s, 1H), 8.60 (s, 1H), 8.40 (m, 1H), 8.27 (m, 1H), 8.12 (s, 1H), 7.91 (m, 1H), 4.62 (br m, 1H), 3.13 (s, 3H), 3.08 (m, 2H), 2.66 (m, 2H), 2.43 (m, 1H), 1.79 (br m, 4H), 1.22 (m, 3H), 0.96 (m, 2H) | {5-Cyclopropyl-2-[2-(3,5,6-trifluoro-pyridin-2-ylamino)-pyridin-4-yl]-pyrido[3,4-d]pyrimidin-4-yl}-methyl-piperidin-4-yl-amine |
| 2015 | 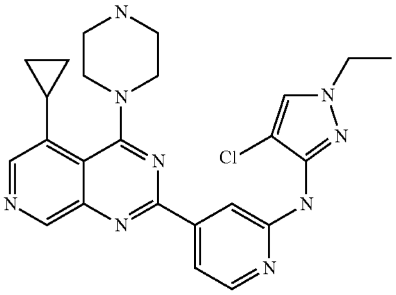 [SMILES: CCn1cc(Cl)c(Nc2cc(-c3nc(N4CCNCC4)c4c(C5CC5)cncc4n3)ccn2)n1] | [B4] | LCMS: Purity: 95%, RT: min, MI: 476.21 (M + H) | (dmso-d6) 9.91 (br s, 1H), 9.13 (br s, 1H), 9.10 (s, 2H), 8.38-8.32 (m, 2H), 8.24 (s, 1H), 8.15 (s, 1H), 7.90 (dd, J = 5.8; 1.1 Hz, 1H), 5.25 (br s, exch. H's), 4.19 (q, J = 7.2 Hz, 2H), 3.96 (br s, 4H), 3.67 (br s, 4H), 2.90-2.60 (m, 1H), 1.47 (t, J = 7.2 Hz, 3H), 1.34-1.25 (m, 2H), 1.41-1.08 (m, 2H) | (4-Chloro-1-ethyl-1H-pyrazol-3-yl)-[4-(5-cyclopropyl-4-piperazin-1-yl-pyrido [3,4-d]pyrimidin-2-yl)-pyridin-2-yl]-amine |
| 2016 | 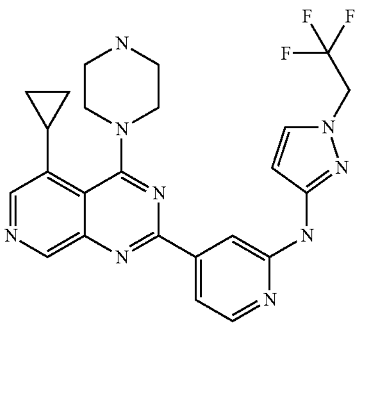 [SMILES: FC(F)(F)Cn1ccc(Nc2cc(-c3nc(N4CCNCC4)c4c(C5CC5)cncc4n3)ccn2)n1] | [B4] | LCMS: Purity: 96%, RT: min, MI: 496.20 (M + H) | (dmso-d6) 10.68 (br s, 1H), 9.09 (br s, 3H), 8.44 (s, 1H), 8.38 (d, J = 5.8 Hz, 1H), 8.22 (s, 1H), 7.87 (d, J = 5.5 Hz, 2H), 6.50 (d, J = 2.4 Hz, 1H), 5.86 (br s, exch. H's), 5.12 (q, J ($CH_2$—$CF_3$) = 9.0 Hz, 2H), 3.96 (br s, 4H), 3.35 (br s, 4H), 2.73-2.65 (m, 1H), 1.32-1.23 (m, 2H), 1.14-1.06 (m, 2H) | [4-(5-Cyclopropyl-4-piperazin-1-yl-pyrido [3,4-d]pyrimidin-2-yl)-pyridin-2-yl]-[1-(2,2,2-trifluoro-ethyl)-1H-pyrazol-3-yl]-amine |

-continued

| Ex | Structure | Scheme | LCMS | $^1$H-NMR | Name |
|---|---|---|---|---|---|
| | | | Analysis | | |
| 2017 | 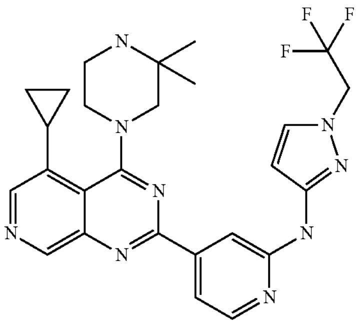 [SMILES: CC1(C)CN(c2nc(-c3ccnc(Nc4ccn(CC(F)(F)F)n4)c3)nc3cncc(C4CC4)c23)CCN1] | [B4] | LCMS: Purity: 95%, RT: min, MI: 524.24 (M + H) | (dmso-d6) 10.79 (br s, 1H), 9.32 (br s, 2H), 9.10 (s, 1H), 8.42-8.36 (m, 2H), 8.26 (s, 1H), 7.93-7.87 (m, 2H), 6.58 (d, J = 2.3 Hz, 1H), 5.56 (br s, exch. H's), 5.14 (q, J(CH2CF3) = 9.0 Hz, 2H), 3.99 (br s, 4H), 3.38 (br s, 2H), 2.58-2.50 (m, overlapping solvent signal, 1H), 1.70-1.00 (m, 10H) | {4-[5-Cyclopropyl-4-(3,3-dimethyl-piperazin-1-yl)-pyrido[3,4-d]pyrimidin-2-yl]-pyridin-2-yl}-[1-(2,2,2-trifluoro-ethyl)-1H-pyrazol-3-yl]-amine |
| 2018 | 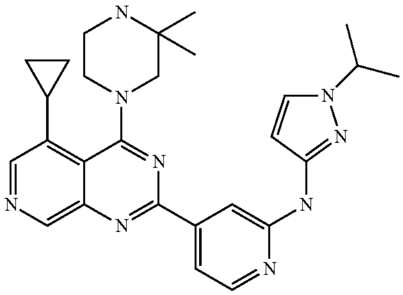 [SMILES: CC(C)n1ccc(Nc2cc(-c3nc(N4CCNC(C)(C)C4)c4c(C5CC5)cncc4n3)ccn2)n1] | [B4] | LCMS: Purity: 97%, RT: min, MI: 484.28 (M + H) | (dmso-d6) 11.37 (br s, 1H), 9.34 (br s, 2H), 9.10 (s, 1H), 8.44 (d, J = 6.3 Hz, 1H), 8.42 (s, 1H), 8.28 (s, 1H), 7.97 (d, J = 6.3 Hz, 1H), 7.88 (d, J = 2.2 Hz, 1H), 6.32 (d, J = 2.3 Hz, 1H), 4.94 (br s, exch. H's), 4.59 (hept, J = 6.6 Hz, 1H), 3.99 (br s, 4H), 3.38 (br s, 2H), 2.55-2.48 (m, partially overlaped by solvent peak, 1H), 1.53 (d, J = 6.6 Hz, 6H), 1.52-1.00 (m, 10H) | {4-[5-Cyclopropyl-4-(3,3-dimethyl-piperazin-1-yl)-pyrido[3,4-d]pyrimidin-2-yl]-pyridin-2-yl}-(1-isopropyl-1H-pyrazol-3-yl)-amine |
| 2019 | 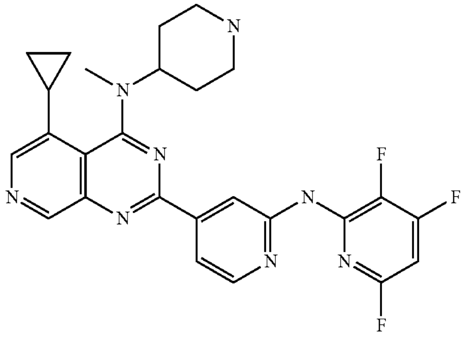 [SMILES: CN(c1nc(-c2ccnc(Nc3nc(F)cc(F)c3F)c2)nc2cncc(C3CC3)c12)C1CCNCC1] | [B4] | LCMS: Purity 92%, RT: min, MI: 507 (M + H) | 1H-NMR: DMSO 10.03 (br s, 1H), 8.93 (s, 1H), 8.73 (s, 1H), 8.45 (m, 1H), 8.12 (s, 1H), 7.97 (m, 1H), 7.01 (m, 1H), 4.59 (br m, 1H), 3.12 (s, 3H), 3.00 (m, 2H), 2.67 (m, 2H), 2.42 (m, 1H), 1.72 (br m, 4H), 1.23 (m, 3H), 0.96 (m, 2H) | {5-Cyclopropyl-2-[2-(3,4,6-trifluoro-pyridin-2-ylamino)-pyridin-4-yl]-pyrido[3,4-d]pyrimidin-4-yl}-methyl-piperidin-4-yl-amine |
| 2020 | 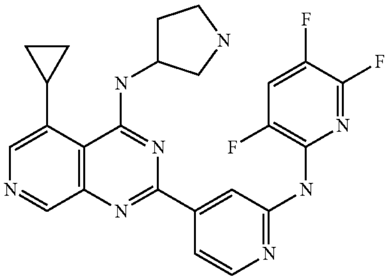 [SMILES: Fc1cc(F)c(Nc2cc(-c3nc(NC4CCNC4)c4c(C5CC5)cncc4n3)ccn2)nc1F] | [B4] | LCMS: Purity: 95%, RT: min, MI: 479 (M + H): | 1H-NMR: DMSO 9.66 (br s, 1H), 9.02 (s, 1H), 8.75 (s, 1H), 8.45 (s, 1H), 8.39 (m, 1H), 8.26 (m, 1H), 7.95 (m, 2H), 4.85 (m, 1H), 3.20 (m, 1H), 3.04 (m, 1H), 2.95 (m, 1H), 2.87 (m, 1H), 2.56 (m, 1H), 2.26 (m, 1H), 1.85 (m, 1H), 1.19 (m, 3H), 1.08 (m, 2H) | {5-Cyclopropyl-2-[2-(3,5,6-trifluoro-pyridin-2-ylamino)-pyridin-4-yl]-pyrido[3,4-d]pyrimidin-4-yl}-pyrrolidin-3-yl-amine |

-continued

| Ex | Structure | Scheme | LCMS | $^1$H-NMR | Name |
| --- | --- | --- | --- | --- | --- |
| | | | Analysis | | |
| 2021 | 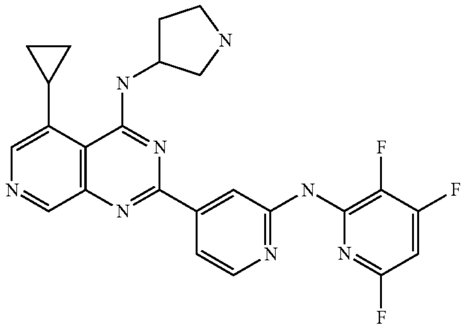 [SMILES: Fc1cc(F)c(F)c(Nc2cc(-c3nc(NC4CCNC4)c4c(C5CC5)cncc4n3)ccn2)n1] | [B4] | LCMS: Purity: >95%, RT: min, MI: 479 (M + H) | 1H-NMR: DMSO 10.07 (s, 1H), 9.08 (s, 1H), 9.03 (br s, 1H), 8.95 (br s, 1H), 8.82 (s, 1H), 8.48 (m, 2H), 8.03 (m, 1H), 7.89 (m, 1H), 7.00 (m, 1H), 5.03 (m, 1H), 3.69 (m, 1H), 3.48 (m, 2H), 3.34 (m, 1H), 2.62 (m, 1H), 2.52 (m, 2H), 2.26 (m, 1H), 1.22 (m, 2H), 1.07 (m, 2H) | {5-Cyclopropyl-2-[2-(3,4,6-trifluoro-pyridin-2-ylamino)-pyridin-4-yl]-pyrido[3,4-d]pyrimidin-4-yl}-pyrrolidin-3-yl-amine |
| 2022 | 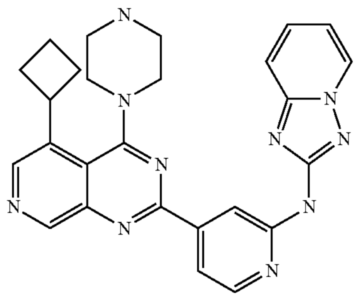 [SMILES: c1ccn2nc(Nc3cc(-c4nc(N5CCNCC5)c5c(C6CCC6)cncc5n4)ccn3)nc2c1] | [B4] | LCMS: Purity: 95%, RT: min, MI: 479.25 (MH)+ | (400 MHz, d6-DMSO, δ): 10.50 (br s, 1H), 9.22 (s, 1H), 9.18 (s, 1H), 8.95-8.75 (m, 4H), 8.44 (d, J = 5.3 Hz, 1H), 7.91 (dd, J = 5.4, 1.4 Hz, 1H), 7.71-7.63 (m, 2H), 7.14 (dt, J = 6.5, 2.0 Hz, 1H), 4.32-4.23 (m, 1H), 3.87 (br s, 4H), 3.41-3.23 (m, 4H), 2.51-2.43 (m, 2H), 2.29-2.05 (m, 3H), 1.98-1.88 (m, 1H). | [4-(5-Cyclobutyl-4-piperazin-1-yl-pyrido[3,4-d]pyrimidin-2-yl)-pyridin-2-yl]-[1,2,4]triazolo[1,5-a]pyridin-2-yl-amine |
| 2023 | 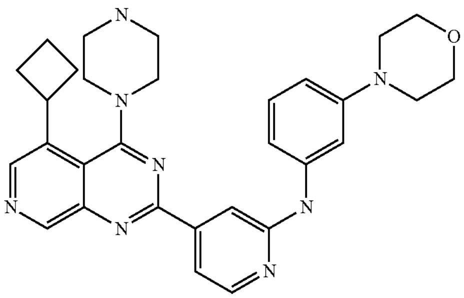 [SMILES: c1cc(Nc2cc(-c3nc(N4CCNCC4)c4c(C5CCC5)cncc4n3)ccn2)cc(N2CCOCC2)c1] | [B4] | LCMS: Purity: 93%, RT: min, MI: 509.3 (M + H) | (dmso-d6) 9.93 (br s, 1H), 9.50-8.5 (broad signal - in the noise), 9.12 (br s, 1H), 9.11 (s, 1H), 8.29 (d, J = 5.8 Hz, 1H), 8.24 (s, 1H), 8.09 (s, 1H), 7.80 (dd, J = 5.8; 1.3 Hz, 1H), 7.33 (br s, 1H), 7.28 (qpp t, J = 8.1 Hz, 1H), 7.15 (d, J = 8.1 Hz, 1H), 6.75 (d, J = 8.1 Hz, 1H), 3.97 (br s, 4H), 3.82-3.78 (m, 4H), 3.37 (br s, 4H), 3.21-3.16 (m, 4H), 2.75-2.68 (m, 1H), 1.33-1.26 (m, 2H), 1.16-1.10 (m, 2H) | [4-(5-Cyclopropyl-4-piperazin-1-yl-pyrido[3,4-d]pyrimidin-2-yl)-pyridin-2-yl]-(3-morpholin-4-yl-phenyl)-amine |
| 2024 | 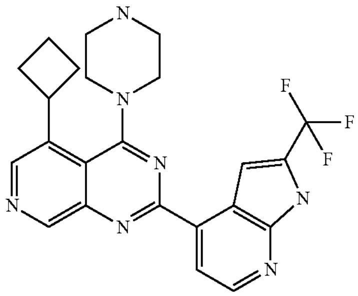 [SMILES: FC(F)(F)c1cc2c(-c3nc(N4CCNCC4)c4c(C5CCC5)cncc4n3)ccnc2[nH]1] | [D4], [D3] | Method 5: RT: 3.93 min, MI: 455.38 [M + H] | (500 MHz, DMSO) 13.20 (1H, s), 8.99 (1H, s, br), 8.88 (1H, s, br), 8.81 (1H, s), 8.69 (1H, d), 8.25 (1H, d), 7.95 (1H, s), 4.30-4.24 (1H, 3.86-3.81 (4H, m), 3.35-3.29 (4H, m), 2.50.2.45 (2H, m), 2.26-2.08 (3H, m), 1.96-1.90 (1H, m). | 5-Cyclobutyl-4-piperazin-1-yl-2-(2-trifluoromethyl-1H-pyrrolo[2,3-b]pyridin-4-yl)-pyrido[3,4-d]pyrimidine |

-continued

| Ex | Structure | Scheme | LCMS (Analysis) | $^1$H-NMR (Analysis) | Name |
|---|---|---|---|---|---|
| 2025 | 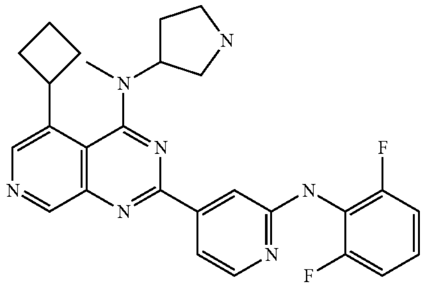 | [B4] | LCMS: Purity: >95%, RT: min, MI: 474 (M + H) | 1H-NMR: DMSO 9.02 (s, 1H), 8.93 (br m, 2H), 8.89 (s, 1H), 8.21 (m, 2H), 7.84 (s, 1H), 7.71 (m, 1H), 7.29 (m, 1H), 7.16 (m, 2H), 5.13 (br m, 1H), 3.79 (m, 1H), 3.45 (m, 1H), 3.29 (br m, 2H), 3.12 (s, 3H), 2.54 (m, 1H), 2.40 (m, 1H), 2.25 (br m, 1H), 1.26 (br m, 2H), 1.01 (m, 2H) | {5-Cyclopropyl-2-[2-(2,6-difluoro-phenylamino)-pyridin-4-yl]-pyrido[3,4-d]pyrimidin-4-yl}-methyl-pyrrolidin-3-yl-amine |
| 2026 | 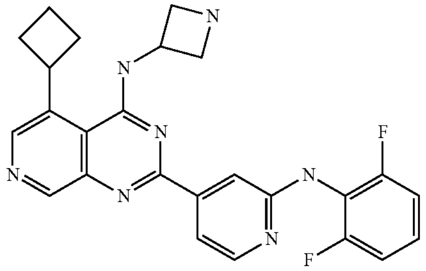 [SMILES: Fc1cccc(F)c1Nc1cc(-c2nc(NC3CNC3)c3c(C4CCC4)cncc3n2)ccn1] | [B4] | LCMS: Purity: >95%, RT: min, MI: 446 (M + H) | 1H-NMR: DMSO 9.07 (s, 1H), 8.90 (br s, 3H), 8.51 (s, 1H), 8.25 (d, 1H, J = 4.6 Hz), 8.17 (d, 1H, J = 5.6 Hz), 7.78 (s, 1H), 7.66 (m, 1H), 7.30 (m, 1H), 7.18 (m, 2H), 5.11 (m, 1H), 4.44 (m, 2H), 4.25 (m, 2H), 2.64 (m, 1H), 2.54 (m, 1H), 1.27 (m, 2H), 1.05 (m, 2H) | Azetidin-3-yl-{5-cyclopropyl-2-[2-(2,6-difluoro-phenylamino)-pyridin-4-yl]-pyrido[3,4-d]pyrimidin-4-yl}-amine |
| 2027 | 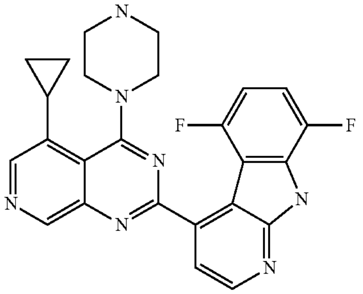 [SMILES: Fc1ccc(F)c2c1[nH]c1nccc(-c3nc(N4CCNCC4)c4c(C5CC5)cncc4n3)c12] | [D3] | LCMS: Purity: 95%, RT: min, MI: 458 (M + H)+ | 1H-NMR (DMSO-d6, 400 MHz): 9.05 (s, 1H), 8.85 (br s, 2H), 8.69 (d, 1H, J = 4.1 Hz), 8.24 (s, 1H), 7.53 (d, 1H, J = 4.9 Hz), 7.34 (m, 1H), 6.78 (m, 1H), 3.73 (m, 4H), 3.25 (m, 4H), 2.77 (m, 1H), 1.29 (m, 2H), 1.14 (m, 2H) | 4-(5-Cyclopropyl-4-piperazin-1-yl-pyrido[3,4-d]pyrimidin-2-yl)-5,8-difluoro-9H-pyrido[2,3-b]indole |
| 2028 | 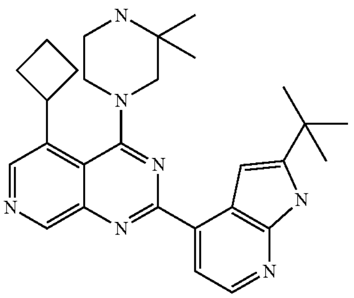 [SMILES: CC1(C)CN(c2nc(-c3ccnc4[nH]c(C(C)(C)C)cc34)nc3cncc(C4CCC4)c23)CCN1] | [D4], [D3] | Method 5: RT: 4.03 min, MI: 470.45 [M + H] | (d6-DMSO, 500 MHz) 11.71 (1H, s), 9.07 (1H, s), 8.65 (1H, s), 8.26 (1H, d), 8.04 (1H, d), 7.17 (1H, s), 4.24 (1H, m), 3.84 (1H, m), 3.56 (1H, m), 3.38 (1H, m), 3.36 (1H, m), 2.94 (2H, s), 2.41 (2H, m), 2.15 (2H, m), 2.12 (1H, m), 2.04 (1H, m), 1.41 (9H, s), 1.10 (3H, s), 0.75 (3H, s). | 2-(2-tert-Butyl-1H-pyrrolo[2,3-b]pyridin-4-yl)-5-cyclobutyl-4-(3,3-dimethyl-piperazin-1-yl)-pyrido[3,4-d]pyrimidine |
| 2029 | 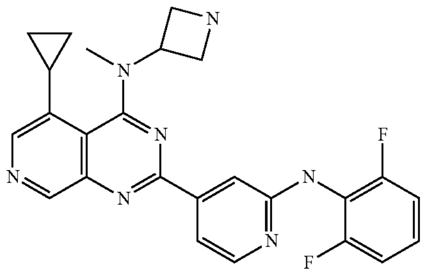 [SMILES: CN(c1nc(-c2ccnc(Nc3c(F)cccc3F)c2)nc2cncc(C3CC3)c12)C1CNC1] | [B4] | LCMS: Purity: >90%, RT: min, MI: 460 (M + H) | (d6-DMSO) 9.04 (s, 1H), 8.88 (s, 1H), 8.85 (br s, 2H), 8.24 (s, 1H), 8.19 (d, 1H, J = 5.3 Hz), 7.73 (s, 1H), 7.61 (m, 1H), 7.29 (m, 1H), 7.18 (m, 2H), 4.74 (m, 1H), 4.24-4.35 (br m, 4H), 3.11 (s, 3H), 2.70 (m, 1H), 1.30 (br m, 2H), 1.07 (m, 2H) | Azetidin-3-yl-{5-cyclopropyl-2-[2-(2,6-difluoro-phenylamino)-pyridin-4-yl]-pyrido[3,4-d]pyrimidin-4-yl}-methyl-amine |

-continued

| Ex | Structure | Scheme | Analysis LCMS | $^1$H-NMR | Name |
|---|---|---|---|---|---|
| 2030 | 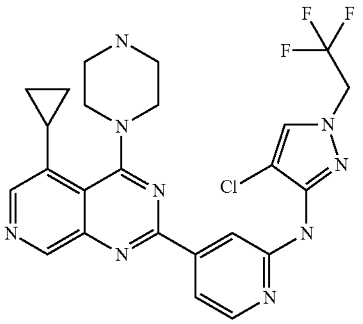 [SMILES: FC(F)(F)Cn1cc(Cl)c(Nc2cc(-c3nc(N4CCNCC4)c4c(C5CC5)cncc4n3)ccn2)n1] | [B4] | LCMS: Purity: 96%, RT: min, MI: 530.15 (M + H) | (dmso-d6) 9.36 (br s, 1H), 9.09 (s, 1H), 9.02 (br s, 2H), 8.35 (d, J = 5.4 Hz, 1H), 8.27 (s, 1H), 8.22 (s, 1H), 8.20 (s, 1H), 7.85 (d, J = 5.4 Hz, 1H), 5.16 (q, J(H, F) = 9.0 Hz, 2H), 3.94 (br s, 4H), 3.36 (br s, 4H), 2.77-2.66 (m, 1H), 1.33-1.25 (m ,2H), 1.15-1.07 (m, 2H) | [4-Chloro-1-(2,2,2-trifluoro-ethyl)-1H-pyrazol-3-yl]-[4-(5-cyclopropyl-4-piperazin-1-yl-pyrido[3,4-d]pyrimidin-2-yl)-pyridin-2-yl]-amine |
| 2031 | 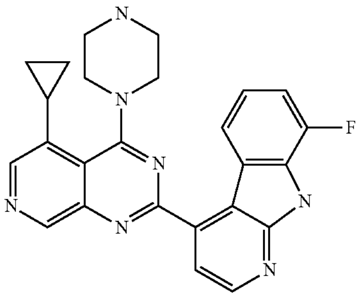 [SMILES: Fc1cccc2c1[nH]c1nccc(-c3nc(N4CCNCC4)c4c(C5CC5)cncc4n3)c12] | [D3] | LCMS: Purity: 95%, RT: min, MI: 440 (M + H)+ | 1H-NMR (DMSO-d6, 400 MHz): 12.60 (s, 1H), 9.18 (s, 1H), 8.88 (br s, 2H), 8.66 (d, 1H, J = 5.1 Hz), 8.53 (d, 1H, J = 8.1 Hz), 8.27 (s, 1H), 7.95 (d, 1H, J = 5.1 Hz), 7.38 (m, 1H), 7.16 (ddd, 1H, J = 5.1, 8.1, 8.1 Hz), 3.92 (br s, 4H), 3.34 (br s, 4H), 2.76 (m, 1H), 1.30 (m, 2H), 1.14 (m, 2H) | 4-(5-Cyclopropyl-4-piperazin-1-yl-pyrido[3,4-d]pyrimidin-2-yl)-8-fluoro-9H-pyrido[2,3-b]indole |
| 2032 | 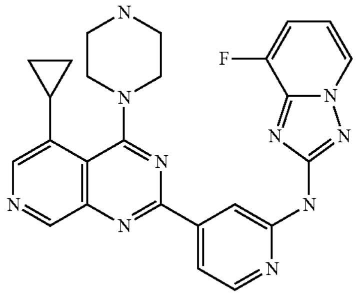 [SMILES: Fc1cccn2nc(Nc3cc(-c4nc(N5CCNCC5)c5c(C6CC6)cncc5n4)ccn3)nc12] | [B4] | LCMS: Purity: 99%, RT: min, MI: 483.21 (MH)+ | (400 MHz, d6-DMSO, δ): 10.62 (s, 1H), 9.27 (s, 1H), 9.13 (s, 1H), 8.90 (br s, 2H), 8.76 (dd, J = 6.7, 0.7 Hz, 1H), 8.46 (dd, J = 5.2, 0.4 Hz, 1H), 8.20 (s, 1H), 7.94 (dd, J = 5.2, 1.4 Hz, 1H), 7.65-7.59 (m, 1H), 7.14-7.08 (m, 1H), 3.97 (br s, 4H), 3.36 (br s, 4H), 2.75-2.68 (m, 1H), 1.30-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-(8-fluoro-[1,2,4]triazolo[1,5-a]pyridin-2-yl)-amine |
| 2033 | 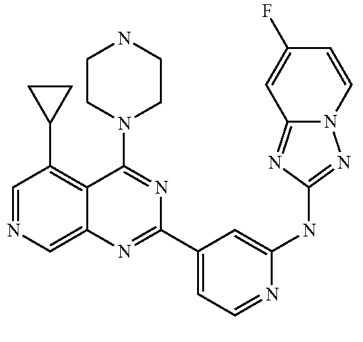 [SMILES: Fc1ccn2nc(Nc3cc(-c4nc(N5CCNCC5)c5c(C6CC6)cncc5n4)ccn3)nc2c1] | [B4] | LCMS: Purity: 98%, RT: min, MI: 483.19 (MH)+ | (400 MHz, d6-DMSO, δ): 10.50 (s, 1H), 9.17 (s, 1H), 9.15 (s, 1H), 8.93 (dd, J = 7.4, 5.5 Hz, 1H), 8.87 (br s, 2H), 8.45 (dd, J = 5.2, 0.5 Hz, 1H), 8.21 (s, 1H), 7.92 (dd, J = 5.3, 1.4 Hz, 1H), 7.60 (dd, J = 9.4, 2.7 Hz, 1H), 7.15 (dt, J = 7.6, 2.8 Hz, 1H), 3.95 (br s, 4H), 3.36 (br s, 4H), 2.75-2.69 (m, 1H), 1.30-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-(7-fluoro-[1,2,4]triazolo[1,5-a]pyridin-2-yl)-amine |

-continued

| Ex | Structure | Scheme | LCMS (Analysis) | $^1$H-NMR (Analysis) | Name (Analysis) |
|---|---|---|---|---|---|
| 2034 | 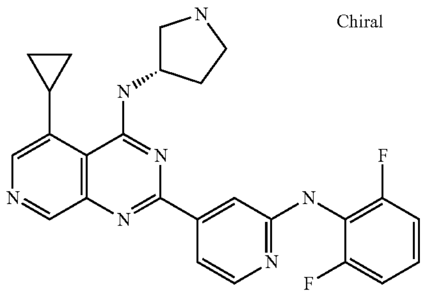 [SMILES: Fc1cccc(F)c1Nc1cc(-c2nc(N[C@H]3CCNC3)c3c(C4CC4)cncc3n2)ccn1] Chiral | [B4] | LCMS: Purity: >95%, RT: min, MI: 460 (M + H) | 1H-NMR: DMSO 9.07 (s, 1H), 9.00 (br s, 2H), 8.90 (s, 1H), 8.50 (s, 1H), 8.19 (d, 1H, J = 4.9 Hz), 7.85 (m, 2H), 7.72 (m, 1H), 7.32 (m, 1H), 7.18 (m, 2H), 4.98 (m, 1H), 3.70 (m, 1H), 3.45 (m, 2H), 3.37 (m, 1H), 2.62 (m, 1H), 2.45 (m, 1H), 2.24 (m, 1H), 1.21 (m, 2H), 1.06 (m, 2H) | {5-Cyclopropyl-2-[2-(2,6-difluoro-phenylamino)-pyridin-4-yl]-pyrido[3,4-d]pyrimidin-4-yl}-(S)-pyrrolidin-3-yl-amine |
| 2035 | 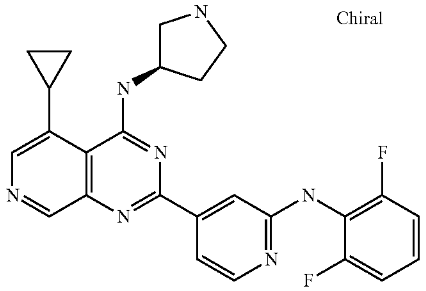 [SMILES: Fc1cccc(F)c1Nc1cc(-c2nc(N[C@@H]3CCNC3)c3c(C4CC4)cncc3n2)ccn1] Chiral | [B4] | LCMS: Purity: >95%, RT: min, MI: 460 (M + H) | 1H-NMR: DMSO 9.07 (s, 1H), 9.01 (br m, 2H), 8.94 (s, 1H), 8.50 (s, 1H), 8.18 (d, 1H, J = 5.2 Hz), 7.85 (m, 2H), 7.73 (m, 1H), 7.30 (m, 1H), 7.19 (m, 2H), 4.97 (m, 1H), 3.70 (m, 1H), 3.44 (m, 3H), 2.61 (m, 1H), 2.47 (m, 1), 2.24 (m, 1H), 1.21 (m, 2H), 1.06 (m, 2H) | {5-Cyclopropyl-2-[2-(2,6-difluoro-phenylamino)-pyridin-4-yl]-pyrido[3,4-d]pyrimidin-4-yl]-(R)-pyrrolidin-3-yl-amine |
| 2036 | 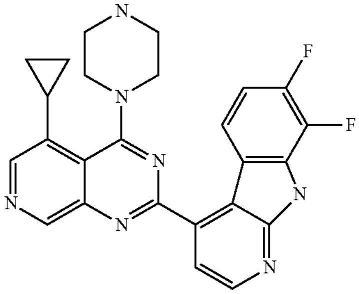 [SMILES: Fc1ccc2c([nH]c3nccc(-c4nc(N5CCNCC5)c5c(C6CC6)cncc5n4)c32)c1F] | [D3] | LCMS: Purity: 95%, RT: min, MI: 458 (M + H)+ | 1H-NMR (DMSO-d6, 400 MHz): 12.84 (s, 1H), 9.20 (s, 1H), 8.87 (br s, 2H), 8.70 (dd, 1H, J = 4.4, 8.8 Hz), 8.65 (d, 1H, J = 5.1 Hz), 8.26 (s, 1H), 8.01 (d, 1H, J = 5.1 Hz), 7.23 (m, 1H), 3.90 (m, 4H), 3.34 (m, 4H), 2.75 (m, 1H), 1.29 (m, 2H), 1.13 (m, 2H) | 4-(5-Cyclopropyl-4-piperaizn-1-yl-pyrido[3,4-d]pyrimidin-2-yl)-7,8-difluoro-9H-pyrido[2,3-b]indole |
| 2037 | 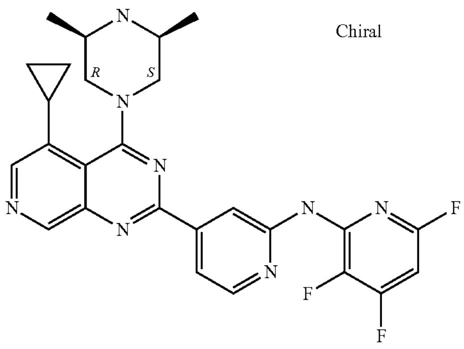 Chiral | [B4] | Method 5: RT: 2.76 min, MI: 507 [M + H] | (DMSO, 500 MHz) 10.02 (1H, s), 8.98 (1H, s), 8.89 (1H, m), 8.45 (1H, d), 8.10 (1H, s), 7.98 (1H, s), 7.01 (1H, m), 4.09 (2H, m), 3.04 (2H, m), 2.69 (1H, m), 1.22 (4H, m), 1.06 (6H, m), unidentified 2 × CH protons. Peaks are too broad. | {4-[5-Cyclopropyl-4-((cis)-3,5-dimethyl-piperazin-1-yl)-pyrido[3,4-d]pyrimidin-2-yl]-pyridin-2-yl}-(3,4,6-trifluoro-pyridin-2-yl)-amine |

-continued

| Ex | Structure | Scheme | Analysis LCMS | Analysis ¹H-NMR | Name |
|---|---|---|---|---|---|
| 2038 | 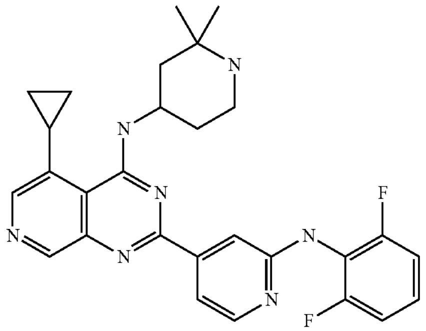 | [B4] | LCMS: Purity: 97%, RT: 2.76 min, MI: 507 (MH)+ | 1H-NMR: DMSO 9.04 (s, 1H), 8.81 (br s, 2H), 8.54 (m, 1H), 8.48 (s, 1H), 8.18 (d, 1H, J = 5.2 Hz), 7.78 (s, 1H), 7.72 (m, 2H), 7.29 (m, 1H), 7.18 (m, 2H), 4.71 (m, 1H), 3.35 (m, 2H), 2.62 (m, 1H), 2.32 (m, 1H), 2.23 (m, 1H), 1.72 (m, 2H), 1.48 (s, 3H), 1.39 (s, 3H), 1.16 (m, 2H), 1.05 (m, 2H) | {5-Cyclopropyl-2-[2-(2,6-difluoro-phenylamino)-pyridin-4-yl]-pyrido[3,4-d]pyrimidin-4-yl}-(2,2-dimethyl-piperidin-4-yl)-amine |
| 2039 | 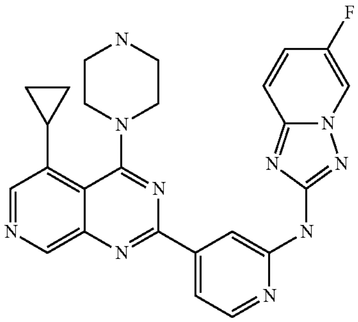 [SMILES: Fc1ccc2nc(Nc3cc(-c4nc(N5CCNCC5)c5c(C6CC6)cncc5n4)ccn3)nn2c1] | [B4] | LCMS: Purity: 97%, RT: 2.76 min, MI: 507 (MH)+ | (400 MHz, d6-DMSO, δ): 10.51 (br s, 1H), 9.23-9.20 (m, 1H), 9.18 (s, 1H), 9.16 (s, 1H), 8.86 (br s, 2H), 8.45 (d, J = 5.2 Hz, 1H), 8.21 (s, 1H), 7.92 (d, J = 5.2 Hz, 1H), 7.80-7.70 (m, 2H), 3.96 (br s, 4H), 3.36 (br s, 4H), 2.76-2.67 (m, 1H), 1.30-1.24 (m, 2H), 1.12-1.07 (m, 2H). | [4-(5-Cyclopropyl--4 piperazin-1-yl-pyrido[3,4-d]pyrimidin-2-yl)-pyridin-2-yl]-(6-fluoro-[1,2,4]triazolo[1,5-a] pyridin-2-yl)-amine |
| 2040 | 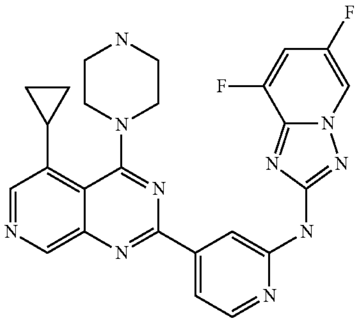 [SMILES: Fc1cc(F)c2nc(Nc3cc(-c4nc(N5CCNCC5)c5c(C6CC6)cncc5n4)ccn3)nn2c1] | [B4] | LCMS: Purity: 97%, RT: 2.76 min, MI: 507 (MH)+ | (400 MHz, d6-DMSO, δ): 10.61 (s, 1H), 9.24 (s, 1H), 9.20-9.17 (m, 1H), 9.14 (s, 1H), 8.87 (br s, 2H), 8.46 (dd, J = 5.1, 0.6 Hz, 1H), 8.20 (s, 1H), 8.04-7.97 (m, 1H), 7.93 (dd, J = 5.2, 1.4 Hz, 1H), 3.96 (br s, 4H), 3.35 (br s, 4H), 2.75-2.67 (m, 1H), 1.30-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-6,8-difluoro-[1,2,4]triazolo[1,5-a] pyridin-2-yl)-amine |
| 2041 | 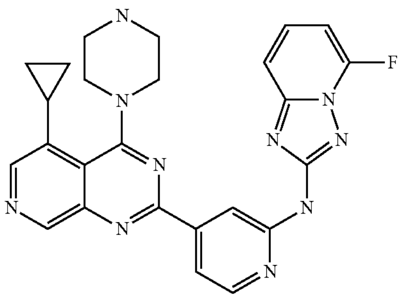 [SMILES: Fc1cccc2nc(Nc3cc(-c4nc(N5CCNCC5)c5c(C6CC6)cncc5n4)ccn3)nn12] | [B4] | LCMS: Purity: 97%, RT: 2.76 min, MI: 507 (MH)+ | (400 MHz, d6-DMSO, δ): 10.61 (s, 1H), 9.31 (s, 1H), 9.10 (s, 1H), 8.90 (br s, 2H), 8.46 (d, J = 5.3 Hz, 1H), 8.20 (s, 1H), 7.95 (dd, J = 5.2, 1.3 Hz, 1H), 7.77-7.70 (m, 1H), 7.56 (dd, J = 8.8, 0.6 Hz, 1H), 7.10-7.05 (m ,1H), 3.97 (br s, 4H), 3.36 (br s, 4H), 2.76-2.67 (m, 1H), 1.30-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-(5-fluoro-[1,2,4]triazolo[1,5-a] pyridin-2-yl)-amine |

-continued

| | | | Analysis | | |
|---|---|---|---|---|---|
| Ex | Structure | Scheme | LCMS | $^1$H-NMR | Name |
| 2042 | 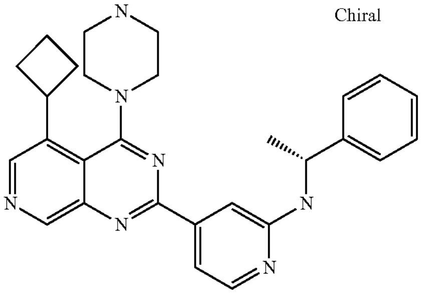 Chiral | [B4] | LCMS: Purity: 97%, RT: 2.76 min, MI: 507 (MH)+ | (dmso-d6) 9.17 (s, 1H), 9.10 (br s, 3H), 8.86 (s, 1H), 8.12 (d, J = 6.3 Hz, 1H), 7.99 (br s, 1H), 7.69 (d, J = 6.3 Hz, 1H), 7.50 (app d, J = 7.3 Hz, 2H), 7.42 (app t, J = 7.3 Hz, 2H), 7.32 (app t, J = 7.3 Hz, 1H), 5.17-5.12 (m, 1H), 4.32-4.20 (m, 1H), 3.90-3.78 (m, 4H), 3.38 (br s, 2H), 3.26 (br s, 2H), 2.51-2.44 (m, 2H), 2.35-2.05 (m, 3H), 2.00-1.92 (m, 1H), 1.60 (d, J = 6.8 Hz, 3H) | [4-(5-Cyclobutyl-4-piperazin-1-yl-pyrido[3,4-d]pyrimidin-2-yl)-pyridin-2-yl]-((R)-1-phenyl-ethyl)-amine |
| 2043 | 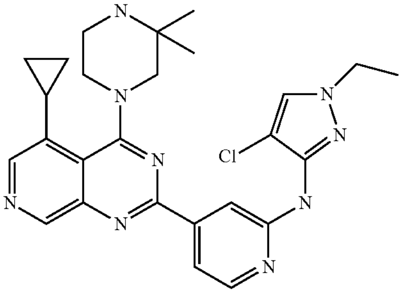 | [B4] | LCMS: Purity: 97%, RT: 2.76 min, MI: 507 (MH)+ | (dmso-d6) 9.83 (br s, 1H), 9.26 (br s, 2H), 9.08 (s, 1H), 8.34 (d, J = 5.8 Hz, 1H), 8.26 (s, 1H), 8.23 (br s, 1H), 8.15 (s, 1H), 7.90 (d, J = 5.8 Hz, 1H), 4.18 (q, J = 7.2 Hz, 2H), 3.96 (br s, 4H), 3.38 (br s, 2H), 2.58-2.49 (m, overlapped w/ solvent signals, 1H), 1.47 (t, J = 7.2 Hz, 3H), 1.49-1.06 (m, 10H) | (4-Chloro-1-ethyl-1H-pyrazol-3-yl)-{4-[5-cyclopropyl-4-(3,3-dimethyl-piperazin-1-yl)-pyrido[3,4-d]pyrimidin-2-yl]-pyridin-2-yl}-amine |
| 2044 | 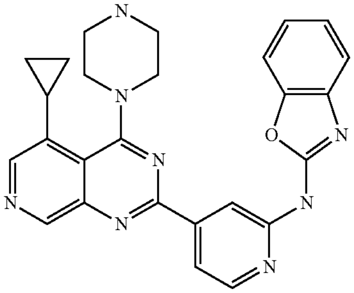 [SMILES: c1ccc2oc(Nc3cc(-c4nc(N5CCNCC5)c5c(C6CC6)cncc5n4)ccn3)nc2c1] | [B4] | LCMS: Purity: 97%, RT: 2.76 min, MI: 507 (MH)+ | (400 MHz, d6-DMSO, δ): 11.50 (br s, 1H), 9.38 (s, 1H), 9.14 (s, 1H), 8.87 (br s, 2H), 8.53 (d, J = 5.3 Hz, 1H), 8.21 (s, 1H), 8.03 (dd, J = 5.2, 1.4 Hz, 1H), 7.59-7.55 (m, 2H), 7.30 (dt, J = 7.6, 1.1 Hz, 1H), 7.21 (dt, J = 7.8, 1.1 Hz, 1H), 3.98 (br s, 4H), 3.38 (br s, 4H), 2.76-2.68 (m ,1H), 1.30-1.24 (m, 2H), 1.12-1.07 (m, 2H). | Benzooxazol-2-yl-[4-(5-cyclopropyl-4-piperazin-1-yl-pyrido [3,4-d]pyrimidin-2-yl)-pyridin-2-yl]-amine |
| 2045 | 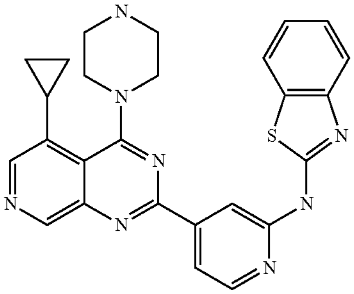 [SMILES: c1ccc2sc(Nc3cc(-c4nc(N5CCNCC5)c5c(C6CC6)cncc5n4)ccn3)nc2c1] | [B4] | LCMS: Purity: 97%, RT: 2.76 min, MI: 507 (MH)+ | (400 MHz, d6-DMSO, δ): 11.75 (br s, 1H), 9.10 (s, 1H), 8.86 (br s, 2H), 8.55 (d, J = 5.8 Hz, 1H), 8.31 (s, 1H), 8.20 (s, 1H), 7.97 (dd, J = 5.3, 1.4 Hz, 1H), 7.92 (d, J = 7.5 Hz, 1H), 7.66 (d, J = 8.1 Hz, 1H), 7.42-7.37 (m, 1H), 7.25-7.20 (m, 1H), 3.95 (br s, 4H), 3.34 (br s, 4H), 2.73-2.65 (m, 1H), 1.29-1.24 (m, 2H), 1.12-1.06 (m, 2H). | Benzothiazol-2-yl-[4-(5-cyclopropyl-4-piperazin-1-yl-pyrido [3,4-d][primidin-2-yl)-pyridin-2-yl]-amine |
| 2046 | 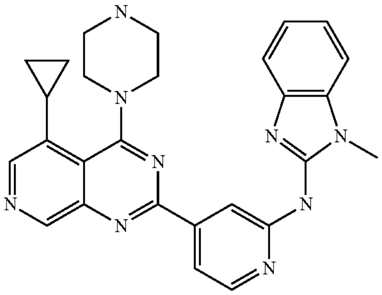 | [B4] | LCMS: Purity: 97%, RT: 2.76 min, MI: 507 (MH)+ | (400 MHz, d6-DMSO, δ): 13.68 (br s, 1H), 11.71 (br s, 1 H), 9.10 (s, 1H), 8.93 (br s, 2H), 8.75-8.62 (m, 1H), 8.60-8.45 (m, 1H), 8.27-8.20 (m, 2H), 7.85-7.65 (m, 2H), 4.15-3.80 (m, 7H), 3.35 (m ,4H), 2.73-2.65 (m, 1H), 1.30-1.24 (m ,2H), 1.13-1.07 (m, 2H). | [4-(5-Cyclopropyl-4-piperazin-1-yl-pyrido[3,4-d]pyrimidin-2-yl)-pyridin-2-yl]-(1-methyl-1H-benzoimidazol-2-yl)-amine |

-continued

| Ex | Structure | Scheme | Analysis LCMS | Analysis $^1$H-NMR | Name |
|---|---|---|---|---|---|
| 2047 | 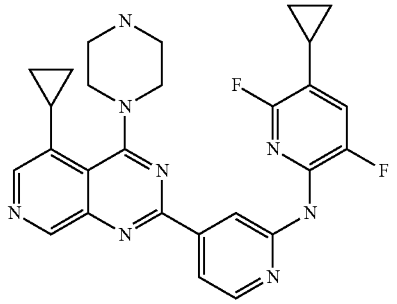 [SMILES: Fc1cc(C2CC2)c(F)nc1Nc1cc(-c2nc(N3CCNCC3)c3c(C4CC4)cncc3n2)ccn1] | [B4] | Method 5: RT: 2.77 min, MI: 501 [M + H] | (DMSO, 400 MHz, 90° C.) 8.98 (1H, s), 8.85 (1H, s), 8.38 (1H, d), 8.13 (1H, s), 7.91 (1H, dd), 7.46 (1H, m), 3.77 (4H, t), 2.91 (4H, t), 2.66 (1H, m), 1.96 (1H, m), 1.27 (2H, m), 0.98 (4H, m), 0.79 (2H, m). | (5-Cyclopropyl-3,6-difluoro-pyridin-2-yl)-[4-(5-cyclopropyl-4-piperazin-1-yl-pyrido [3,4-d]pyrimidin-2-yl)-pyridin-2-yl]-amine |
| 2048 | 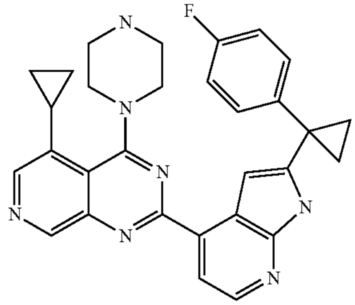 [SMILES: Fc1ccc(C2(c3cc4c(-c5nc(N6CCNCC6)c6c(C7CC7)cncc6n5)ccnc4[nH]3)CC2)cc1] | [D4], [D3] | Method 5: RT: 3.03 min, MI: 506 [M + H] | (400 MHz, d6-DMSO, 90° C.) 11.30 (1H, s), 8.96 (1H, s), 8.27 (1H, d, J = 5.0 Hz), 8.09 (1H, s), 8.05 (1H, d, J = 5.0 Hz), 7.50-7.46 (2H, m), 7.17-7.13 (2H, m), 7.00 (1H, s), 3.62 (4H, m), 2.88-2.85 (4H, m), 2.70-2.67 (1H, m), 1.60-1.57 (2H, m), 1.39-1.36 (2H, m), 1.28-1.23 (2H, m), 1.00-0.96 (2H, m). | 5-Cyclopropyl-2-{2-[1-(4-fluoro-phenyl)-cyclopropyl]-1H-pyrrolo [2,3-b]pyridin-4-yl}-4-piperazin-1-yl-pyrido[3,4-d]pyimidine |
| 2049 | 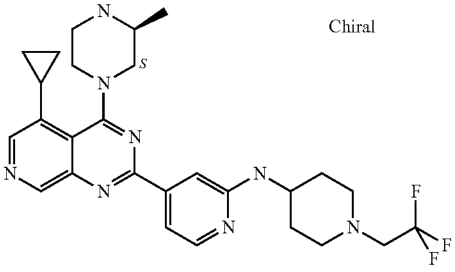 Chiral | [B4] | Method 5: RT: 1.68 min, MI: 527 [M + H] | (DMSO, 500 MHz) 8.95 (1H, s), 8.11 (1H, d), 8.08 (1H, s), 7.52 (1H, s), 7.40 (1H, d), 6.72 (1H, d), 4.17 (2H, s), 3.76 (1H, m), 3.32 (2H, s), 3.16 (3H, m), 2.91 (3H, m), 2.86 (2H, m), 2.46 (1H, m), 1.90 (2H, m), 1.48 (2H, m), 1.23 (2H, m), 1.10 (2H, m), 1.08 (4H, m). | {4-[5-Cyclopropyl-4-((S)-3-methyl-piperazin-1-yl)-pyrido [3,4-d]pyrimidin-2-yl]-pyridin-2-yl}-[1-(2,2,2-trifluoro-ethyl)-piperidin-4-yl]-amine |
| 2050 | 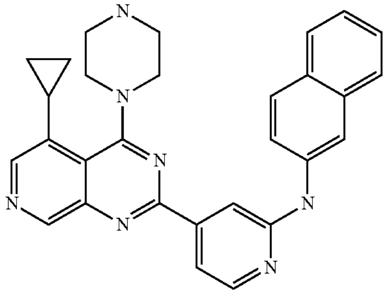 [SMILES: c1ccc2cc(Nc3cc(-c4nc(N5CCNCC5)c5c(C6CC6)cncc5n4)ccn3)ccc2c1] | [B4] | LCMS: Purity: 100%, RT: 1.68 min, MI: 527 (MH)+ | (400 MHz, D6-DMSO, δ): 9.67 (s, 1H), 9.08 (s, 1H), 8.88 (br s, 2H), 8.53 (d, J = 1.6 Hz, 1H), 8.44 (d, J = 5.3 Hz, 1H), 8.19 (s, 1H), 8.05 (s, 1H), 7.86-7.76 (m, 4H), 7.67 (dd, J = 8.9, 2.1 Hz, 1H), 7.47-7.42 (m, 1H), 7.36-7.31 (m, 1H), 3.93 (br s, 4H), 3.34 (br s, 4H), 2.74-2.66 (m, 1H), 1.29-1.23 (m, 2H), 1.12-1.06 (m ,2H). | [4-(5-Cyclopropyl-4-piperazin-1-yl-pyrido[3,4-d]pyrimidin-2-yl)-pyridin-2-yl]-naphthalen-2-yl-amine |
| 2051 | 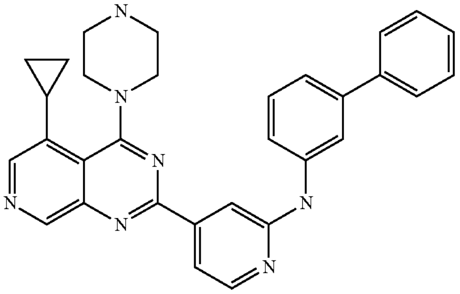 [SMILES: c1ccc(-c2cccc(Nc3cc(-c4nc(N5CCNCC5)c5c(C6CC6)cncc5n4)ccn3)c2)cc1] | [B4] | LCMS: Purity: 100%:, RT: 1.68 min, MI: 527 (MH)+ | (400 MHz, d6-DMSO, δ): 9.52 (s, 1H), 9.07 (s, 1H), 8.86 (br s, 2H), 8.37 (d, J = 5.4 Hz, 1H), 8.19 (s, 1H), 8.06 (t, J = 1.8 Hz, 1H), 8.00 (s, 1H), 7.78-7.73 (m, 2H), 7.67-7.64 (m, 2H), 7.52-7.47 (m, 2H), 7.42-7.36 (m, 2H), 7.22 (d, J = 7.9 Hz, 1H), 3.94 (br s, 4H), 3.32 (br s, 4H), 2.73-2.65 (m, 1H), 1.29-1.23 (m, 2H), 1.11-1.06 (m, 2H). | Biphenyl-3-yl-[4-(5-cyclopropyl-4-piperazin-1-yl-pyrido [3,4-d]pyrimidin-2-yl)-pyridin-2-yl]-amine |

-continued

| | | | Analysis | | |
|---|---|---|---|---|---|
| Ex | Structure | Scheme | LCMS | $^1$H-NMR | Name |
| 2052 | Chiral 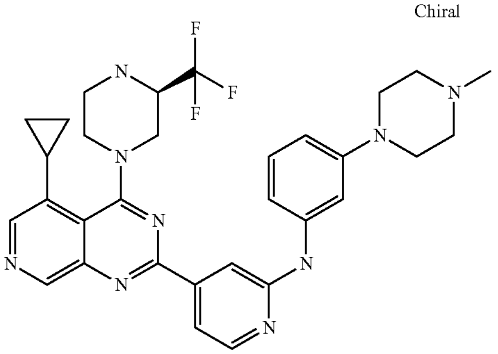 | [B4] | LCMS: Purity: 100%, RT: 1.68 min, MI: 527 (MH)+ | (dmso-d6) 9.86 (br s, 1H), 9.57 (br s, 1H), 9.08 (s, 1H), 8.33 (d, J = 5.5 Hz, 1H), 8.20 (s, 1H), 7.97 (s, 1H), 7.72 (br d, J = 5.0 Hz, 1H), 7.44 (s, 1H), 7.24-7.21 (m, 2H), 6.70-6.66 (m, 1H), 5.25 (br signal, exchangeable protons), 4.80-4.20 (m, 2H), 4.20-3.90 (m, 2H), 3.85-3.79 (m, 2H), 3.59-3.54 (m, 2H), 3.40-3.10 (m, 4H), 3.00 (app t, J = 12.5 Hz, 2H), 2.90 (s, 3H), 2.70 (br s, 1H), 1.33-1.22 (m, 2H), 1.14-1.06 (m, 2H) | {4-[5-Cyclopropyl-4-((R)-3-trifluoromethyl-piperazin-1-yl)-pyrido[3,4-d]pyrimidin-2-yl]-pyridin-2-yl}-[3-(4-methyl-piperazin-1-yl)-phenyl]-amine |
| 2053 | Chiral 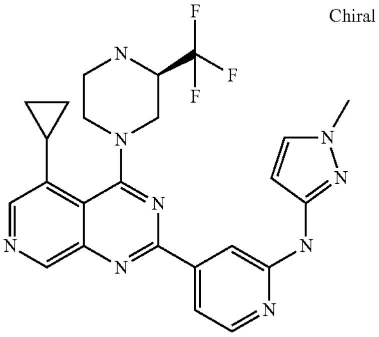 | [B4] | LCMS: Purity: 100%, RT: 1.68 min, MI: 527 (MH)+ | (dmso-d6) 11.25 (br s, 1H), 9.09 (s, 1H), 8.37 (d, J = 6.4 Hz, 1H), 8.34 (s, 1H), 8.21 (s, 1H), 7.88 (d, J = 5.2 Hz, 1H), 7.78 (d, J = 2.0 Hz, 1H), 6.23 (d, J = 2.4 Hz, 1H), 4.70-3.95 (m, 3H), 3.89 (s, 3H), 3.89 (overlapped m, 1H), 3.72 (br s, 1H), 3.25 (br s, 3H), 2.73 (br s, 1H), 1.35-1.20 (m, 2H), 1.15-1.00 (m, 2H) | {4-[5-Cyclopropyl-4-((R)-3-trifluoromethyl-piperazin-1-yl)-pyrido[3,4-d]pyrimidin-2-yl]-pyridin-2-yl}-(1-methyl-1H-pyrazol-3-yl)-amine |
| 2054 | 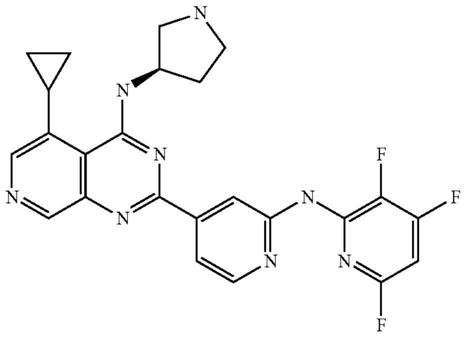 [SMILES: Fc1cc(F)c(F)c(Nc2cc(-c3nc(N[C@@H]4CCNC4)c4c(C5CC5)cncc4n3)ccn2)n1] | [B4] | LCMS: Purity: 95%, MI: 479 (MH)+ | 1H-NMR: DMSO 10.08 (s, 1H), 9.08 (br s, 2H), 9.00 (br s, 1H), 8.82 (s, 1H), 8.51 (s, 1H), 8.48 (d, 1H, J = 5.2 Hz), 8.03 (m, 1H), 7.90 (m, 1H), 7.02 (m, 1H), 5.04 (m, 1H), 3.69 (m, 1H), 3.49 (m, 2H), 3.36 (m, 1H), 2.62 (m, 1H), 2.52 (m, 1H), 2.26 (m, 1H), 1.24 (m, 2H), 1.07 (m, 2H) | {5-Cyclopropyl-2-[2-(3,4,6-trifluoro-pyridin-2-ylamino)-pyridin-4-yl]-pyrido[3,4-d]pyrimidin-4-yl}-(R)-pyrrolidin-3-yl-amine |
| 2055 | 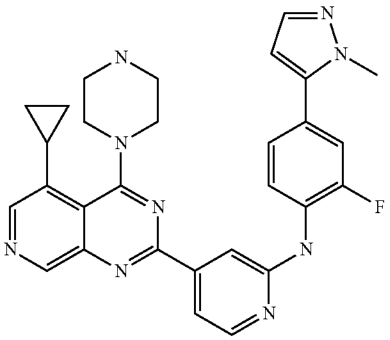 [SMILES: Cn1nccc1-c1ccc(Nc2cc(-c3nc(N4CCNCC4)c4c(C5CC5)cncc4n3)ccn2)c(F)c1] | [B4] | LCMS: Purity: 99.7399 98%, RT: min, MI: 522 | | [4-(5-Cyclopropyl-4-piperazin-1-yl-pyrido[3,4-d]pyrimidin-2-yl)-pyridin-2-yl]-[2-fluoro-4-(2-methyl-2H-pyrazol-3-yl)-phenyl]-amine |

-continued

| Ex | Structure | Scheme | Analysis LCMS | Analysis ¹H-NMR | Analysis Name |
|---|---|---|---|---|---|
| 2056 | 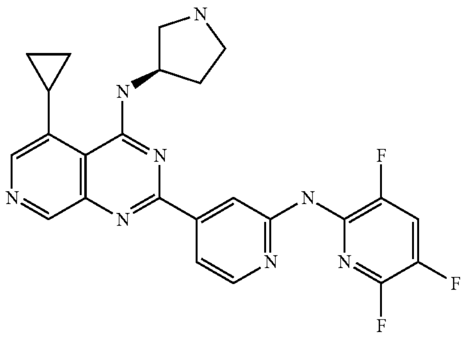 [SMILES: Fc1cc(F)c(Nc2cc(-c3nc(N[C@@H]4CCNC4)c4c(C5CC5)cncc4n3)ccn2)nc1F] | [B4] | LCMS: Purity: 98% RT: min, MI: 465.19 (MH)+ | 1H-NMR: DMSO 9.78 (s, 1H), 9.08 (br s, 2H), 8.97 (br s, 1H), 8.73 (s, 1H), 8.51 (s, 1H), 8.43 (d, 1H, J = 5.2 Hz), 8.29 (m, 1H), 7.98 (m, 1H), 7.90 (m, 1H), 5.04 (m, 1H), 3.72 (m, 1H), 3.48 (m, 2H), 3.37 (m, 1H), 2.62 (m, 1H), 2.52 (m, 1H), 2.26 (m, 1H), 1.24 (m, 2H), 1.06 (m, 2H) | {5-Cyclopropyl-2-[2-(3,5,6-trifluoro-pyridin-2-ylamino)-pyridin-4-yl]-pyrido[3,4-d]pyrimidin-4-yl}-(R)-pyrrolidin-3-yl-amine |
| 2057 | 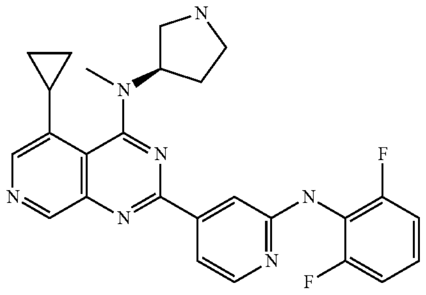 [SMILES: CN(c1nc(-c2ccnc(Nc3c(F)cccc3F)c2)nc2cncc(C3CC3)c12)[C@@H]1CCNC1] | [B4] | LCMS: Purity: 95%, RT: min, MI: 474 (MH)+ | 1H-NMR: DMSO 9.02 (s, 1H), 8.88 (br s, 2H), 8.84 (s, 1H), 8.20 (m, 2H), 7.83 (s, 1H), 7.70 (d, 1H, J = 5.2 Hz), 7.29 (m, 1H), 7.17 (m, 2H), 5.12 (br m, 1H), 3.78 (m, 1H), 3.45 (m, 1H), 3.29 (m, 2H), 3.11 (s, 3H), 2.54 (m, 1H), 2.40 (m, 1H), 2.25 (m, 1H), 1.26 (m, 2H), 1.01 (m, 2H) | {5-Cyclopropyl-2-[2-(2,6-difluoro-phenylamino)-pyridin-4-yl]-pyrido[3,4-d]pyrimidin-4-yl}-methyl-(R)-pyrrolidin-3-yl-amine |
| 2058 | 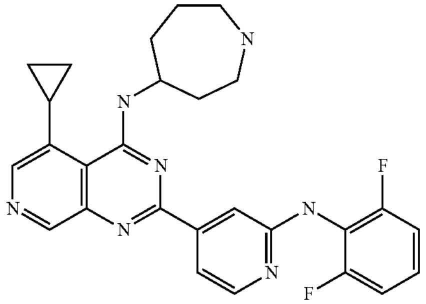 [SMILES: Fc1cccc(F)c1Nc1cc(-c2nc(NC3CCCNCC3)c3c(C4CC4)cncc3n2)ccn1] | [B4] | LCMS: Purity: 100%, RT: min, MI: 465.19 (MH)+ | 1H-NMR: DMSO 9.03 (s, 1H), 8.90 (s, 1H), 8.69 (br s, 2H), 8.48 (s, 1H), 8.19 (d, 1H, J = 5.2 Hz), 7.86 (m, 1H), 7.80 (s, 1H), 7.72 (m, 1H), 7.33 (m, 1H), 7.19 (m, 2H), 4.58 (m, 1H), 3.35 (m, 4H), 2.60 (m, 1H), 2.32 (m, 2H), 2.14 (m, 1H), 1.94 (m, 3H), 1.22 (m, 2H), 1.11 (m, 1H), 1.05 (m, 1H) | Azepan-4-yl-{5-cyclopropyl-2-[2-(2,6-difluoro-phenylamino)-pyridin-4-yl]-pyrido[3,4-d]pyrimidin-4-yl}-amine |
| 2059 | 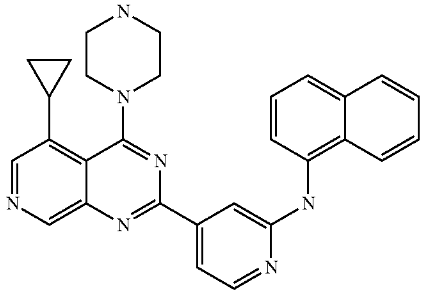 | [B4] | LCMS: Purity: 101%, RT: min, MI: 465.19 (MH)+ | (400 MHz, d6-DMSO, δ): 9.72 (br s, 1H), 9.06 (s, 1H), 8.89 (br s, 2H), 8.23-8.16 (m, 3H), 8.08 (s, 1H), 8.02-7.98 (m, 1H), 7.90 (d, J = 7.3 Hz, 1H), 7.80 (d, J = 7.5 Hz, 1H), 7.76 (d, J = 5.5 Hz, 1H), 7.61-7.53 (m, 3H), 3.88 (br s, 4H), 3.30 (br s, 4H), 2.71-2.63 (m, 1H), 1.28-1.23 (m, 2H), 1.11-1.06 (m, 2H). | [4-(5-Cyclopropyl-4-piperazin-1-yl-pyrido[3,4-d]pyrimidin-2-yl)-pyridin-2-yl]-naphthalen-1-yl-amine |

-continued

| Ex | Structure | Scheme | LCMS | $^1$H-NMR | Name |
|---|---|---|---|---|---|
| | | | Analysis | | |
| 2060 | 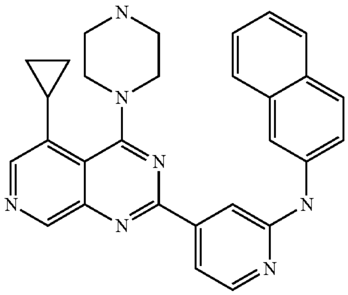 [SMILES: c1ccc2cc(Nc3cc(-c4nc(N5CCNCC5)c5c(C6CC6)cncc5n4)ccn3)ccc2c1] | [B4] | LCMS: Purity: 102%, RT: min, MI: 465.19 (MH)+ | (400 MHz, d6-DMSO, δ): 10.69 (br s, 1H), 9.19 (s, 1H), 9.10 (s, 1H), 8.89 (br s, 2H), 8.49 (d, J = 5.6 Hz, 1H), 8.46 (s, 1H), 8.32 (br s, 1H), 8.21 (s, 1H), 8.09 (d, J = 8.1 Hz, 1H), 7.94-7.87 (m, 2H), 7.71 (t, J = 7.5 Hz, 1H), 7.49 (t, J = 7.4 Hz, 1H), 3.97 (br s, 4H), 3.34 (br s, 4H), 2.73-2.65 (m, 1H), 1.30-1.24 (m, 2H), 1.12-1.07 (m, 2H). | [4-(5-Cyclopropyl-4-piperazin-1-yl-pyrido [3,4-d]pyrimidin-2-yl)-pyridin-2-yl]-iso[D4], [D3]uinolin-3-yl-amine |
| 2061 | 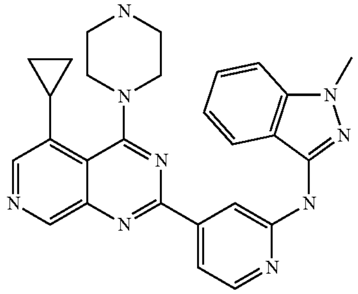 | [B4] | LCMS: Purity: 103%, RT: min, MI: 465.19 (MH)+ | (400 MHz, d6-DMSO, δ): 10.60 (br s, 1H), 9.11 (s, 1H), 9.05-8.80 (m, 3H), 8.41 (d, J = 5.5 Hz, 1H), 8.21 (s, 1H), 8.07 (d, J = 8.1 Hz, 1H), 7.91 (d, J = 5.4 Hz, 1H), 7.61 (d, J = 8.6 Hz, 1H), 7.49-7.44 (m, 1H), 7.13 (t, J = 7.5 Hz, 1H), 4.05 (s, 3H), 3.59 (br s, 4H), 3.36 (br s, 4H), 2.75-2.67 (m, 1H), 1.30-1.24 (m, 2H), 1.12-1.07 (m, 2H). | [4-(5-Cyclopropyl-4-piperazin-1-yl-pyrido[3,4-d]pyrimidin-2-yl)-pyridin-2-yl]-(1-methyl-1H-indazol-3-yl)-amine |
| 2062 | 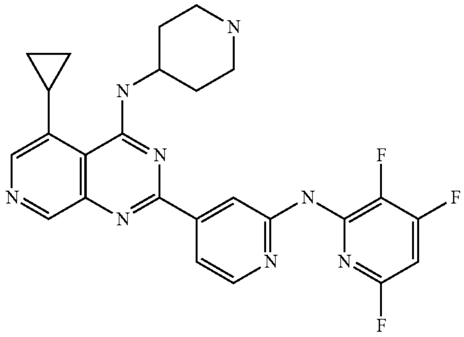 [SMILES: Fc1cc(F)c(F)c(Nc2cc(-c3nc(NC4CCNCC4)c4c(C5CC5)cncc4n3)ccn2)n1] | [B4] | LCMS: Purity: 104%, RT: min, MI: 465.19 (MH)+ | (d6-DMSO) 10.06 (s, 1H), 9.06 (s, 1H), 8.73 (s, 1H), 8.70 (br s, 1H), 8.50 (s, 1H), 8.45 (m, 1H), 8.37 (br m, 1H), 8.02 (m, 1H), 7.82 (m, 1H), 6.99 (m, 1H), 4.59 (m, 1H), 3.40 (m, 2H), 3.13 (m, 2H), 2.66 (m, 1H), 2.34 (m, 2H), 1.90 (m, 2H), 1.19 (m, 2H), 1.07 (m, 2H) | {5-Cyclopropyl-2-[2-(3,4,6-trifluoro-pyridin-2-ylamino)-pyridin-4-yl]-pyrido[3,4-d]pyrimidin-4-yl}-piperidin-4-yl-amine |
| 2063 | 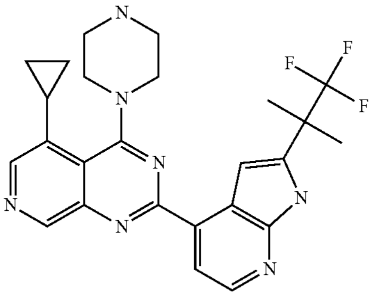 [SMILES: CC(C)(c1cc2c(-c3nc(N4CCNCC4)c4c(C5CC5)cncc4n3)ccnc2[nH]1)C(F)(F)F] | [D4], [D3] | Method 5: RT: 2.75 min, MI: 482 [M + H] | (500 MHz, d6-DMSO) 12.09 (brs, 1H), 9.15 (s, 1H), 8.42 (d, 1H), 8.17 (s, 1H), 8.13 (d, 1H), 7.48 (d, 1H), 4.10-3.71 (m, 4H), 3.41-3.31 (m, 4H), 2.77-2.71 (m, 1H), 1.69 (s, 6H), 1.28-1.21 (m, 2H), 1.10-1.05 (m, 2H). | 5-Cyclopropyl-4-piperazin-1-yl-2-[2-(2,2,2-trifluoro-1,1-dimethyl-ethyl)-1H-pyrrolo[2,3-b]pyridin-4-yl]-pyrido[3,4-d] pyrimidine |

-continued

| Ex | Structure | Scheme | Analysis: LCMS | Analysis: $^1$H-NMR | Analysis: Name |
|---|---|---|---|---|---|
| 2064 | 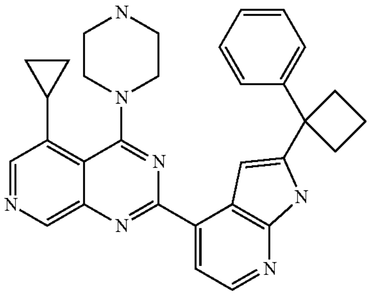 [SMILES: c1ccc(C2(c3cc4c(-c5nc(N6CCNCC6)c6c(C7CC7)cncc6n5)ccnc4[nH]3)CCC2)cc1] | [D4], [D3] | Method 5: RT: 3.05 min, MI: 502 [M + H] | (500 Mhz, d6-DMSO) 11.88 (brs, 1H), 9.12 (s, 1H), 8.29 (d, 1H), 8.16 (s, 1H), 8.07 (d, 1H), 7.44 (dd, 2H), 7.33 (t, 2H), 7.23 (d, 1H), 7.19 (t, 1H), 4.08-3.66 (m, 4H), 3.36-3.27 (m, 4H), 2.94-2.86 (m, 2H), 2.75-2.68 (m, 3H), 2.10-2.00 (m, 1H), 1.96-1.86 (m, 1H), 1.28-1.21 (m, 2H), 1.11-1.03 (m, 2H). | 5-Cyclopropyl-2-[2-(1-phenyl-cyclobutyl)-1H-pyrrolo[2,3-b]pyridin-4-yl]-4-piperazin-1-yl-pyrido[3,4-d]pyrimidine |
| 2065 | 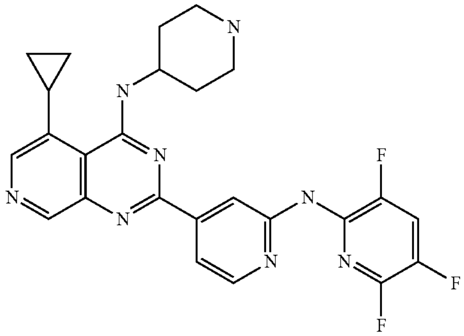 [SMILES: Fc1cc(F)c(Nc2cc(-c3nc(NC4CCNCC4)c4c(C5CC5)cncc4n3)ccn2)nc1F] | [B4] | LCMS: Purity: 105%, RT: min, MI: 465.19 (MH)+ | (d6-DMSO) 9.76 (s, 1H), 9.05 (s, 1H), 8.76 (br m, 1H), 8.63 (s, 1H), 8.50 (s, 1H), 8.40 (br m, 2H), 8.29 (m, 1H), 7.98 (m, 1H), 7.80 (m, 1H), 4.60 (m, 1H), 3.38 (m, 2H), 3.15 (m, 2H), 2.66 (m, 1H), 2.32 (m, 2H), 1.94 (m, 2H), 1.19 (m, 2H), 1.08 (m, 2H) | {5-Cyclopropyl-2-[2-(3,5,6-trifluoro-pyridin-2-ylamino)-pyridin-4-yl]-pyrido[3,4-d]pyrimidin-4-yl}-piperidin-4-yl-amine |
| 2066 | 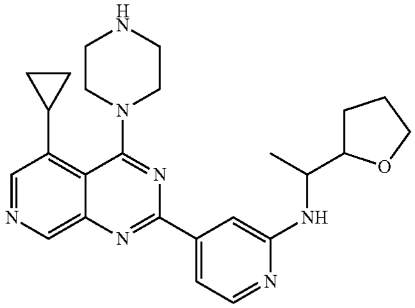 | [B4] | LCMS: Purity: >90%, RT: min, MI: 465.19 (MH)+ | (dmso-d6) 9.16 (br s, 3H), 9.10 (s, 1H), 8.24 (s, 1H), 8.10-8.07 (m, 2H), 7.72 (dd, J = 6.7; 1.3 Hz, 1H), 4.10-3.85 (m, 5H), 3.85-3.75 (m, 1H), 3.70-3.60 (m, 1H), 3.55-3.20 (m, 2H), 3.34 (br s, 4H), 2.67 (m, 1H), 2.10-1.95 (m, 1H), 1.95-1.75 (m, 4H), 1.55-1.45 (m, 1H), 1.30-1.25 (m, 2H), 1.20-1.05 (m, 2H) | [4-(5-Cyclopropyl-4-piperazin-1-yl-pyrido[3,4-d]pyrimidin-2-yl)-pyridin-2-yl]-[1-(tetrahydro-furan-2-yl)-ethyl]-amine |
| 2067 | Chiral 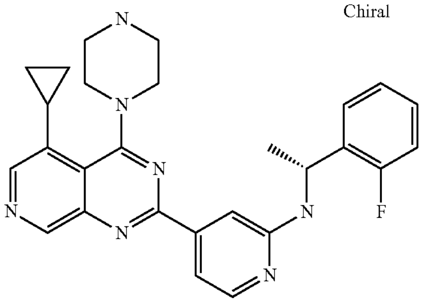 | [B4] | LCMS: Purity: 107%, RT: min, MI: 465.19 (MH)+ | (dmso-d6) 9.18 (br s, 2H), 9.06 (s, 1H), 8.21 (s, 1H), 8.10 (d, J = 6.4 Hz, 1H), 7.98 (br s, 1H), 7.68 (d, J = 5.4 Hz, 1H), 7.51-7.46 (m, 1H), 7.38-7.30 (m, 1H), 7.30-7.17 (m ,2H), 5.33 (br s, 2H), 3.91 (br s, 4H), 3.33 (br s, 4H), 2.70-2.62 (m, 1H), 1.58 (d, J = 6.8 Hz, 3H), 1.30-1.20 (m, 2H), 1.10-1.05 (m, 2H) | [4-(5-Cyclopropyl-4-piperazin-1-yl-pyrido[3,4-d]pyrimidin-2-yl)-pyridin-2-yl]-[(R)-1-(2-fluoro-phenyl)-ethyl]-amine |

-continued

| Ex | Structure | Scheme | LCMS | $^1$H-NMR | Name |
|---|---|---|---|---|---|
| 2068 | 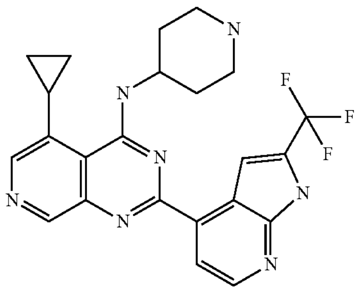 | [D4], [D3] | LCMS: Purity: >95%, RT: min, MI: 454 (M + H), | (d6-DMSO) 13.13 (s, 1H), 9.18 (s, 1H), 8.70 (br m, 1H), 8.63 (d, 1H, J = 4.9 Hz), 8.51 (s, 1H), 8.37 (br m, 1H), 8.30 (m, 1H), 7.96 (s, 1H), 7.83 (m, 1H), 4.62 (m, 1H), 3.43 (m, 2H), 3.20 (m, 2H), 2.67 (m, 1H), 2.35 (m, 2H), 1.94 (m, 2H), 1.20 (m, 2H), 1.08 (m, 2H) | [5-Cyclopropyl-2-(2-trifluoromethyl-1H-pyrrolo[2,3-b]pyridin-4-yl)-pyrido[3,4-d]pyrimidin-4-yl]-piperidin-4-yl-amine |
| 2069 | 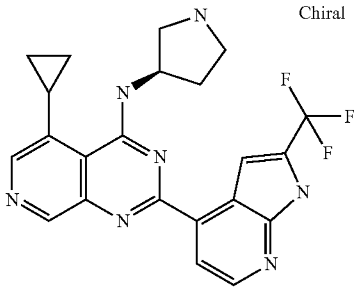 [SMILES: FC(F)(F)c1cc2c(-c3nc(N[C@@H]4CCNC4)c4c(C5CC5)cncc4n3)ccnc2[nH]1] Chiral | [D4], [D3] | LCMS: Purity: >95%, RT: min, MI: 440 (M + H) | 1H-NMR: DMSO 13.15 (s, 1H), 9.22 (s, 1H), 8.99 (br m, 2H), 8.64 (d, 1H, J = 4.9 Hz), 8.52 (s, 1H), 8.28 (m, 1H), 7.99 (s, 1H), 7.89 (m, 1H), 5.08 (m, 1H), 3.73 (m, 1H), 3.45 (m, 4H), 2.63 (m, 1H), 2.26 (m, 1H), 1.23 (m, 2H), 1.10 (m, 2H) | [5-Cyclopropyl-2-(2-trifluoromethyl-1H-pyrrolo[2,3-b]pyridin-4-yl)-pyrido[3,4-d]pyrimidin-4-yl]-(R)-pyrrolidin-3-yl-amine |
| 2070 | 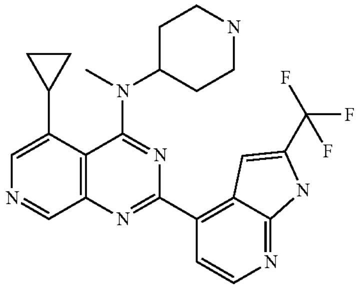 [SMILES: CN(c1nc(-c2ccnc3[nH]c(C(F)(F)F)cc23)nc2cncc(C3CC3)c12)C1CCNCC1] | [D4], [D3] | LCMS: Purity: >95%, RT: min, MI: 468 (M + H) | 1H-NMR: DMSO 13.14 (s, 1H), 9.11 (s, 1H), 8.69 (br m, 1H), 8.63 (d, 1H, J = 4.9 Hz), 8.32 (br m, 1H), 8.28 (m, 1H), 8.19 (s, 1H), 7.97 (s, 1H), 4.88 (m, 1H), 3.46 (m, 2H), 3.12 (m, 5H), 2.07-2.32 (br m, 5H), 1.23 (m, 2H), 0.98 (m, 2H) | [5-Cyclopropyl-2-(2-trifluoromethyl-1H-pyrrolo[2,3-b]pyridin-4-yl)-pyrido[3,4-d]pyrimidin-4-yl]-methyl-piperidin-4-yl-amine |
| 2071 | 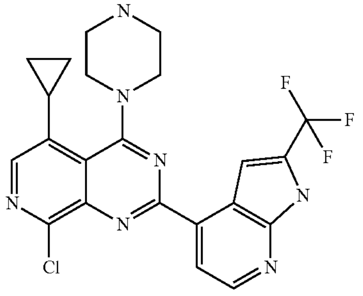 [SMILES: FC(F)(F)c1cc2c(-c3nc(N4CCNCC4)c4c(C5CC5)cnc(Cl)c4n3)ccnc2[nH]1] | [D4], [D3] | LCMS: Purity: 99%, RT: min, MI: 474 (M + H | 1H-NMR (DMSO-d6, 400 MHz): 13.21 (s, 1H), 8.94 (br s, 1H), 8.82 (br s, 1H), 8.67 (d, 1H, J = 4.9 Hz), 8.32 (d, 1H, J = 4.9 Hz), 8.20 (s, 1H), 7.99 (s, 1H), 3.99 (br s, 4H), 3.33 (br s, 4H), 2.64 (m, 1H), 1.26 (m, 2H), 1.07 (m, 2H) | 8-Chloro-5-cyclopropyl-4-piperazin-1-yl-2-(2-trifluoromethyl-1H-pyrrolo[2,3-b]pyridin-4-yl)-pyrido[3,4-d]pyrimidine |

-continued

| Ex | Structure | Scheme | LCMS | $^1$H-NMR | Name |
|---|---|---|---|---|---|
| | | | Analysis | | |
| 2072 | 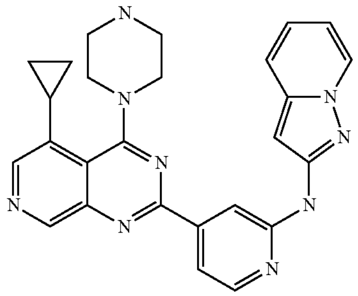 [SMILES: c1ccn2nc(Nc3cc(-c4nc(N5CCNCC5)c5c(C6CC6)cncc5n4)ccn3)cc2c1] | [B4] | LCMS: Purity: >90%, RT: min, MI: 464 (M + H)+ | 1H NMR (400 MHz, DMSO-d6) δ ppm 10.48 (br. s, 1 H) 9.11 (s, 1 H) 8.94 (br. s, 2 H) 8.54 (dd, J = 6.8, 0.8 Hz, 1 H) 8.46 (s, 1 H) 8.41 (d, J = 5.5 Hz, 1 H) 8.20 (s, 1 H) 7.84 (d, J = 5.5 Hz, 1 H) 7.58 (d, J = 8.8 Hz, 1 H) 7.12-7.30 (m, 1 H) 6.68-6.85 (m, 2 H) 3.95 (br. s., 4 H) 3.35 (br. s., 4 H) 2.60-2.79 (m, 1 H) 1.21-1.32 (m, 2 H) 0.98-1.16 (m, 2 H) | [4-(5-Cyclopropyl-4-piperazin-1-yl-pyrido[3,4-d]pyrimidin-2-yl)-pyridin-2-yl]-pyrazolo[1,5-a]pyridin-2-yl-amine |
| 2073 | 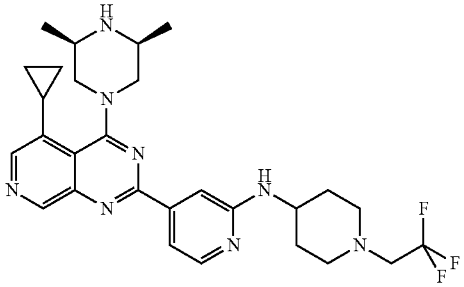 [SMILES: C[C@@H]1CN(c2nc(-c3ccnc(NC4CCN(CC(F)(F)F)CC4)c3)nc3cncc(C4CC4)c23)C[C@H](C)N1] | [B4] | Method 5: RT: 1.7 min, MI: 541 [M + H] | (DMSO, 400 MHz, 90° C.) 8.96 (1H, s), 8.12 (2H, m), 7.51 (1H, s), 7.43 (1H, dd), 4.26 (2H, m), 3.76 (1H, m), 3.16 (3H, m), 2.92 (2H, m), 2.71 (1H, m), 2.46 (1H, m), 1.90 (2H, m), 1.49 (3H, m), 1.08 (9H, m). | {4-[5-Cyclopropyl-4-((cis)-3,5-dimethyl-piperazin-1-yl)-pyrido[3,4-d]pyrimidin-2-yl]-pyridin-2-yl}-[1-(2,2,2-trifluoro-ethyl)-piperidin-4-yl]-amine |
| 2074 | 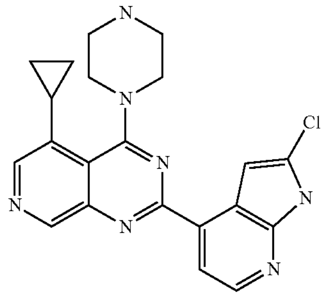 [SMILES: Clc1cc2c(-c3nc(N4CCNCC4)c4c(C5CC5)cncc4n3)ccnc2[nH]1] | [D4], [D3], [D5] | Method 5: RT: 3.29 min, MI: 406 [M + H] | (400 MHz, d6-DMSO, 90° C.) 9.06 (1H, s), 8.37 (1H, d, J = 4.9 Hz), 8.13-8.11 (2H, m), 7.42 (1H, s), 3.74-3.71 (4H, m), 2.94-2.91 (4H, m), 2.72-2.66 (1H, m), 1.28-1.24 (2H, m), 1.01-0.97 (2H, m). | 2-(2-Chloro-1H-pyrrolo[2,3-b]pyridin-4-yl)-5-cyclopropyl-4-piperazin-1-yl-pyrido[3,4-d]pyrimidine |
| 2075 | 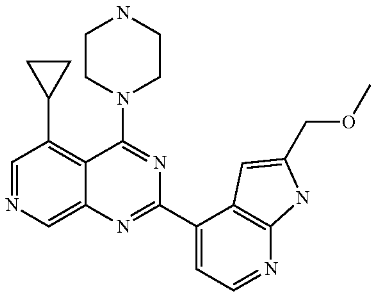 [SMILES: COCc1cc2c(-c3nc(N4CCNCC4)c4c(C5CC5)cncc4n3)ccnc2[nH]1] | [D4], [D3] | LCMS: Purity: 93%, RT: min, MI: 416.22 (M + H) | (dmso-d6) 12.00 (br s, 1H), 9.17 (s, 1H), 8.92 (br s, 2H), 8.40 (d, J = 5.1 Hz, 1H), 8.20 (s, 1H), 8.15 (d, J = 5.1 Hz, 1H), 7.44 (br s, 1H), 4.66 (s, 2H), 3.92 (br s, 4H), 3.39 (br s, 7H), 2.80-2.70 (m, 1H), 1.30-1.25 (m, 2H), 1.12-1.10 (m, 2H) | 5-Cyclopropyl-2-(2-methoxymethyl-1H-pyrrolo[2,3-b]pyridin-4-yl)-4-piperazin-1-yl-pyrido[3,4-d]pyrimidine |

-continued

| | | | Analysis | | |
|---|---|---|---|---|---|
| Ex | Structure | Scheme | LCMS | $^1$H-NMR | Name |
| 2076 | 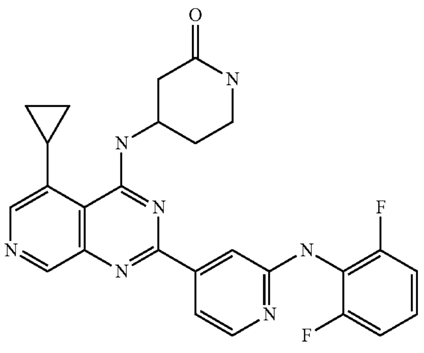 [SMILES: O=C1CC(Nc2nc(-c3ccnc(Nc4c(F)cccc4F)c3)nc3cncc(C4CC4)c23)CCN1] | [B4] | LCMS: Purity: >95%, RT: min, MI: 488 (M + H) | 1H-NMR: DMSO 13.13 (s, 1H), 9.18 (s, 1H), 8.70 (br m, 1H), 8.63 (d, 1H, J = 4.9 Hz), 8.51 (s, 1H), 8.37 (br m, 1H), 8.30 (m, 1H), 7.96 (s, 1H), 7.83 (m, 1H), 4.62 (m, 1H), 3.43 (m, 2H), 3.20 (m, 2H), 2.67 (m, 1H), 2.35 (m, 2H), 1.94 (m, 2H), 1.20 (m, 2H), 1.08 (m, 2H) | 4-{5-Cyclopropyl-2-[2-(2,6-difluoro-phenylamino)-pyridin-4-yl]-pyrido[3,4-d]pyrimidin-4-ylamino}-piperidin-2-one |
| 2077 | 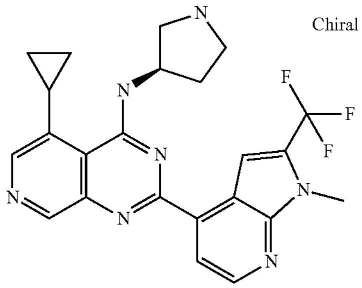 [SMILES: Cn1c(C(F)(F)F)cc2c(-c3nc(N[C@@H]4CCNC4)c4c(C5CC5)cncc4n3)ccnc21] Chiral | [D4], [D3] | LCMS: Purity: 95%, RT: min, MI: 454 (MH)+ | 1H-NMR: DMSO 13.15 (s, 1H), 9.22 (s, 1H), 8.99 (br m, 2H), 8.64 (d, 1H, J = 4.9 Hz), 8.52 (s, 1H), 8.28 (m, 1H), 7.99 (s, 1H), 7.89 (m, 1H), 5.08 (m, 1H), 3.73 (m, 1H), 3.45 (m, 4H), 2.63 (m, 1H), 2.26 (m, 1H), 1.23 (m, 2H), 1.10 (m, 2H) | [5-Cyclopropyl-2-(1-methyl-2-trifluoromethyl-1H-pyrrolo[2,3-b]pyridin-4-yl)-pyrido[3,4-d]pyrimidin-4-yl]-(R)-pyrrolidin-3-yl-amine |
| 2078 | 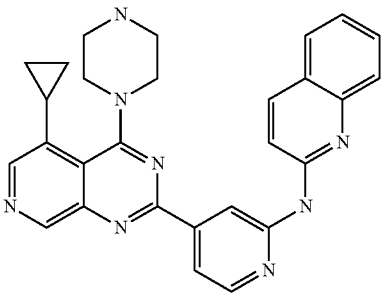 [SMILES: c1ccc2nc(Nc3cc(-c4nc(N5CCNCC5)c5c(C6CC6)cncc5n4)ccn3)ccc2c1] | [B4] | LCMS: Purity: 94%, RT: min, MI: 475.23 (MH)+ | (400 MHz, d6-DMSO, δ): 9.13 (s, 1H), 8.95 (br s, 2H), 8.69-8.64 (m, 1H), 8.51-8.45 (m, 1H), 8.23 (s, 1H), 8.21-8.07 (m, 2H), 7.99 (d, J = 8.3 Hz, 1H), 7.85 (t, J = 8.0 Hz, 1H), 7.60-7.53 (m, 2H), 3.99 (br s, 4H), 3.36 (br s, 4H), 2.75-2.67 (m, 1H), 1.30-1.25 (m, 2H), 1.14-1.07 (m, 2H). | [4-(5-Cyclopropyl-4-piperazin-1-yl-pyrido[3,4-d]pyrimidin-2-yl)-pyridin-2-yl]-[D4], [D3]uinolin-2-yl-amine |
| 2079 | 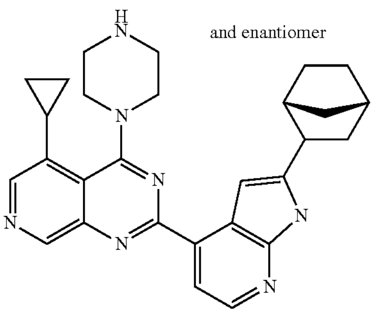 [SMILES: c1cc(-c2nc(N3CCNCC3)c3c(C4CC4)cncc3n2)c2cc(C3C[C@H]4CC[C@@H]3C4)[nH]c2n1] and enantiomer | [D4], [D3] | LCMS: Purity: 95%, RT: min, MI: 466.28 (M + H) | (dmso-d6) 11.76 (s, 1H), 9.19 (s, 1H), 8.93 (br s, 2H), 8.33 (d, J = 5.1 Hz, 1H), 8.22 (s, 1H), 8.11 (d, J = 5.1 Hz, 1H), 7.29 (br s, 1H), 5.08 (very br signal, exch. H's), 3.97 (br s, 4H), 3.40 (br s, 5H), 2.84-2.75 (m, 1H), 2.72 (br s, 1H), 2.40 (br s, 1H), 2.11-2.04 (m, 1H), 1.66-1.46 (m, 4H), 1.33-1.27 (m, 4H), 1.15-1.11 (m, 3H) | (±)-2-((endo)-2-Bicyclo[2.2.1]hept-2-yl-1H-pyrrolo[2,3-b]pyridin-4-yl)-5-cyclopropyl-4-piperazin-1-yl-pyrido[3,4-d]pyrimidine |

-continued

| Ex | Structure | Scheme | Analysis LCMS | Analysis $^1$H-NMR | Name |
|---|---|---|---|---|---|
| 2080 | 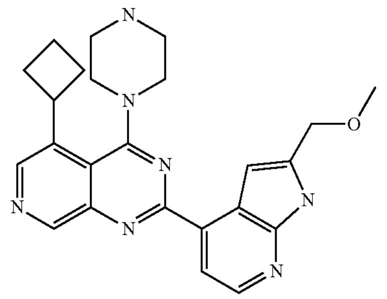 [SMILES: COCc1cc2c(-c3nc(N4CCNCC4)c4c(C5CCC5)cncc4n3)ccnc2[nH]1] | [D4], [D3] | LCMS: Purity: 92%, RT: min, MI: 430.24 (M + H) | (dmso-d6) 11.92 (br s, 1H), 9.17 (s, 1H), 8.90 (br s, 1H), 8.78 (br s, 1H), 8.72 (s, 1H), 8.30 (d, J = 5.0 Hz, 1H), 8.05 (d, J = 5.0 Hz, 1H); 7.34 (br s, 1H), 4.57 (s, 2H), 4.25-4.14 (m, 1H), 3.90-3.60 (m ,4H), 3.40-3.10 (m, 4H), 3.28 (s, 3H), 2.50-2.30 (m, 2H), 2.20-2.10 (m ,2H), 2.10-1.90 (m, 1H), 1.90-1.80 (m, 1H) | 5-Cyclobutyl-2-(2-methoxymethyl-1H-pyrrolo[2,3-b]pyridin-4-yl)-4-piperazin-1-yl-pyrido[3,4-d]pyrimidine |
| 2081 | 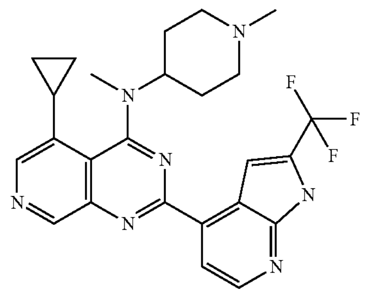 [SMILES: CN1CCC(N(C)c2nc(-c3ccnc4[nH]c(C(F)(F)F)cc34)nc3cncc(C4CC4)c23)CC1] | [D4], [D3] | LCMS: Purity: >95%, RT: min, MI: 482 (M + H) | 1H-NMR: DMSO 13.14 (s, 1H), 9.38 (br m, 1H), 9.12 (s, 1H), 8.63 (d, 1H, J = 4.9 Hz), 8.25 (m, 1H), 8.19 (s, 1H), 7.99 (s, 1H), 4.83 (m, 1H), 3.58 (m ,2H), 3.26 (m, 2H), 3.12 (s, 3H), 2.84 (d, 3H, J = 4.6 Hz), 2.46 (m, 1H), 2.12 (br m, 4H), 1.23 (m, 2H), 1.00 (m, 2H) | [5-Cyclopropyl-2-(2-trifluoromethyl-1H-pyrrolo[2,3-b] pyridin-4-yl)-pyrido [3,4-d]pyrimidin-4-yl]-methyl-(1-methyl-piperidin-4-yl)-amine |
| 2082 | 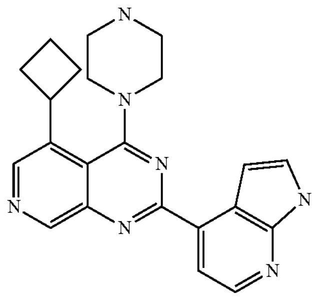 [SMILES: c1cc(-c2nc(N3CCNCC3)c3c(C4CCC4)cncc3n2)c2cc[nH]c2n1] | [D4], [D3] | Method 5: RT: 3.10 min, MI: 386 [M + H] | (500 MHz, d6-DMSO) 11.88 (brs, 1H), 9.22 (s, 1H), 8.99 (brs, 1H), 8.86 (brs, 1H), 8.78 (s, 1H), 8.38 (s, 1H), 8.12 (s, 1H), 7.65 (d, 1H), 7.46 (d, 1H), 4.32-4.24 (m, 1H), 3.93-3.84 (m, 2H), 3.78-3.69 (m, 2H), 3.41-3.34 (m, 2H), 3.32-3.24 (m, 2H), 2.27-2.18 (m, 2H), 2.15-2.06 (m, 1H), 1.96-1.87 (m, 1H). | 5-Cyclobutyl-4-piperazin-1-yl-2-(1H-pyrrolo[2,3-b]pyridin-4-yl)-pyrido [3,4-d]pyrimidine |
| 2083 | 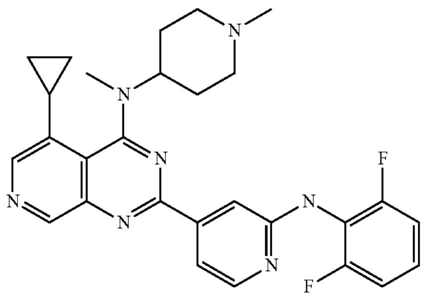 | [B4] | LCMS: Purity: >95%, RT: min, MI: 454 (M + H) | 1H-NMR: DMSO 9.47 (br m, 1H), 8.98 (s, 1H), 8.87 (s, 1H), 8.18 (d, 2H, J = 4.8 Hz), 7.81 (s, 1H), 7.69 (m, 1H), 7.30 (m, 1H), 7.18 (m, 2H), 4.79 (m, 1H), 3.56 (m, 2H), 3.24 (m, 2H), 3.09 (s, 3H), 2.84 (d, 3H, J = 4.4 Hz), 2.44 (m, 1H), 2.10 (br m, 4H), 1.23 (m, 2H), 0.98 (m, 2H) | {5-Cyclopropyl-2-[2-(2,6-difluoro-phenylamino)-pyridin-4-yl]-pyrido[3,4-d]pyrimidin-4-yl}-methyl-(1-methyl-piperidin-4-yl)-amine |
| 2084 | 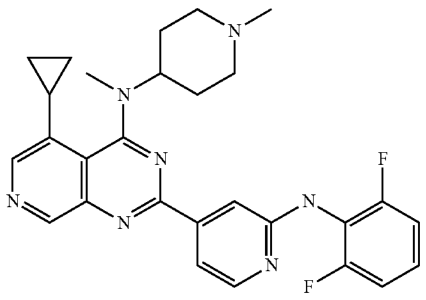 | [B4] | LCMS: Purity: >95%, RT: min, MI: 488 (M + H) | 1H-NMR: DMSO 9.45 (br m, 1H), 9.04 (s, 1H), 8.81 (s, 1H), 8.48 (s, 1H), 8.18 (d, 1H, J = 5.3 Hz), 7.78 (m, 2H), 7.71 (m, 1H), 7.30 (m, 1H), 7.18 (m, 2H), 4.49 (m, 1H), 3.59 (m, 2H), 3.21 (m, 2H), 2.85 (s, 3H), 2.32 (br m, 3H), 1.90 (m, 2H), 1.17 (m, 2H), 1.04 (m, 2H) | {5-Cyclopropyl-2-[2-(2,6-difluoro-phenylamino)-pyridin-4-yl]-pyrido[3,4-d]pyrimidin-4-yl}-(1-methyl-piperidin-4-yl)-amine |

-continued

| Ex | Structure | Scheme | Analysis LCMS | Analysis $^1$H-NMR | Name |
|---|---|---|---|---|---|
| 2085 | 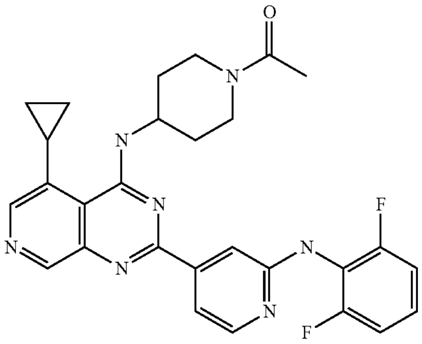 [SMILES: CC(=O)N1CCC(Nc2nc(-c3ccnc(Nc4c(F)cccc4F)c3)nc3cncc(C4CC4)c23)CC1] | [B4] | LCMS: Purity: >95%, RT: min, MI: 516 (M + H) | 1H-NMR: DMSO 9.03 (br s, 2H), 8.46 (s, 1H), 8.19 (d, 1H, J = 5.4 Hz), 7.85 (m, 1H), 7.80 (s, 1H), 7.73 (m, 1H), 7.32 (m, 1H), 7.21 (m, 2H), 4.52 (m, 1H), 4.35 (m, 1H), 3.87 (m, 1H), 3.26 (m, 1H), 2.84 (m, 1H), 2.58 (m, 1H), 2.13 (m, 2H), 2.05 (s, 3H), 1.78 (br m, 2H), 1.18 (br m, 2H), 1.04 (m, 2H) | 1-(4-{5-Cyclopropyl-2-[2-(2,6-difluoro-phenylamino)-pyridin-4-yl]-pyrido[3,4-d]pyrimidin-4-ylamino}-piperidin-1-yl)-ethanone |
| 2086 | 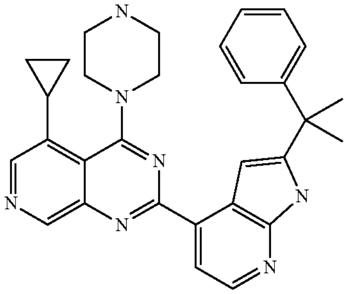 [SMILES: CC(C)(c1ccccc1)c1cc2c(-c3nc(N4CCNCC4)c4c(C5CC5)cncc4n3)ccnc2[nH]1] | [D4], [D3] | Method 5: RT: 4.06 min, MI: 490 [M + H] | (500 MHz, d6-DMSO) 11.72 (s, 1H), 9.10 (s, 1H), 8.30 (d, 1H), 8.16 (s, 1H), 8.09 (d, 1H), 7.34-7.28 (m, 4H), 7.25-7.19 (m, 2H), 4.12-3.67 (m, 4H), 3.38-3.28 (m, 4H), 2.78-2.70 (m, 1H), 1.81 (s, 6H), 1.28-1.20 (m, 2H), 1.10-1.05 (m, 2H). | 5-Cyclopropyl-2-[2-(1-methyl-1-phenyl-ethyl)-1H-pyrrolo [2,3-b]pyridin-4-yl]-4-piperazin-1-yl-pyrido [3,4-d]pyrimidine |
| 2087 | 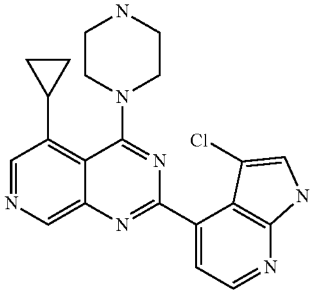 [SMILES: Clc1c[nH]c2nccc(-c3nc(N4CCNCC4)c4c(C5CC5)cncc4n3)c12] | [D3], [D7] | | | 2-(3-Chloro-1H-pyrrolo [2,3-b]pyridin-4-yl)-5-cyclopropyl-4-piperazin-1-yl-pyrido [3,4-d]pyrimidine |
| 2088 | 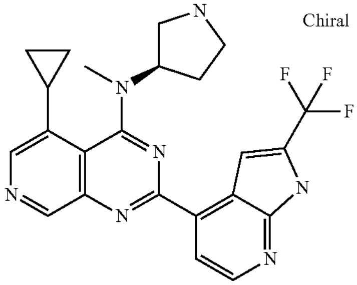 [SMILES: CN(c1nc(-c2ccnc3[nH]c(C(F)(F)F)cc23)nc2cncc(C3CC3)c12)[C@@H]1CCNC1] Chiral | [D4], [D3] | LCMS: Purity: >95%, RT: min, MI: 454 (M + H) | 1H-NMR: DMSO 13.17 (s, 1H), 9.18 (s, 1H), 8.92 (br m, 2H), 8.64 (d, 1H, J = 4.9 Hz), 8.23 (m, 2H), 8.00 (s, 1H), 5.20 (m, 1H), 3.78 (m, 1H), 3.27-3.45 (br m, 3H), 3.14 (s, 3H), 2.42 (m, 1H), 2.26 (br m, 2H), 1.26 (m, 2H), 1.02 (m, 2H) | [5-Cyclopropyl-2-(2-trifluoromethyl-1H-pyrrolo[2,3-b]pyridin-4-yl)-pyrido[3,4-d] pyrimidin-4-yl]-methyl-(R)-pyrrolidin-3-yl-amine |

-continued

| Ex | Structure | Scheme | LCMS | Analysis ¹H-NMR | Name |
|---|---|---|---|---|---|
| 2089 | 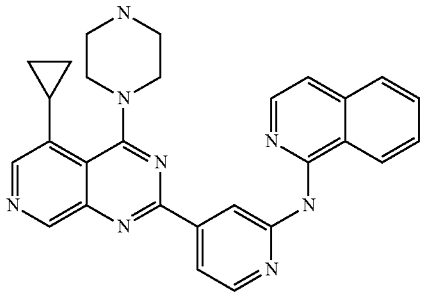 [SMILES: c1ccc2c(Nc3cc(-c4nc(N5CCNCC5)c5c(C6CC6)cncc5n4)ccn3)nccc2c1] | [B4] | LCMS: Purity: 96%, RT: min, MI: 475.21 (MH)+ | (400 MHz, d6-DMSO, δ): 9.13 (s, 1H), 9.05-8.85 (m, 4H), 8.71 (d, J = 4.9 Hz, 1H), 8.35-8.29 (m, 1H), 8.24 (s, 1H), 8.22-8.05 (m, 3H), 8.01-7.94 (m, 1H), 7.74-7.68 (m, 1H), 3.95 (br s, 4H), 3.36 (br s, 4H), 2.72-2.65 (m, 1H), 1.31-1.25 (m, 2H), 1.12-1.08 (m, 2H). | [4-(5-Cyclopropyl-4-piperazin-1-yl-pyrido [3,4-d]pyrimidin-2-yl)-pyridin-2-yl]-iso[D4], [D3]uinolin-1-yl-amine |
| 2090 | 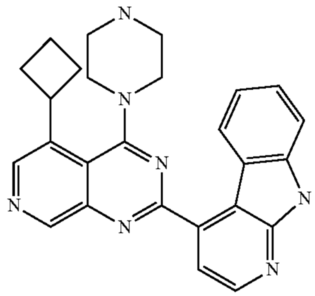 [SMILES: c1ccc2c(c1)[nH]c1nccc(-c3nc(N4CCNCC4)c4c(C5CCC5)cncc4n3)c12] | [D3] | LCMS: Purity: >95%, RT: min, MI: 436 (M + H) | 1H-NMR (DMSO-d6, 400 MHz): 12.09 (s, 1H), 9.26 (s, 1H), 8.8-9.0 (m, 3H), 8.69 (d, 1H, J = 8.2 Hz), 8.59 (d, 1H, J = 5.1 Hz), 7.89 (d, 1H, J = 5.1 Hz), 7.55 (d, 1H, J = 7.9 Hz), 7.49 (m, 1H), 7.19 (m, 1H), 4.32 (m, 1H), 3.83 (m, 4H), 3.30 (m, 4H), 2.57 (m, 2H), 2.28 (m, 2H), 2.13 (m, 1H), 1.95 (m, 1H). | 4-(5-Cyclobutyl-4-piperazin-1-yl-pyrido[3,4-d]pyrimidin-2-yl)-9H-pyrido[2,3-b] indole |
| 2091 | 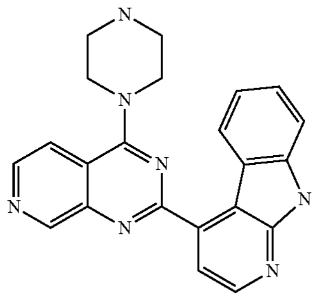 [SMILES: c1ccc2c(c1)[nH]c1nccc(-c3nc(N4CCNCC4)c4ccncc4n3)c12] | [B01] | LCMS: Purity: >95%, RT: min, MI: 382 (M + H) | 1H-NMR (DMSO-d6, 400 MHz): 12.07 (s, 1H), 9.43 (s, 1H), 8.89 (br s, 2H), 8.73 (d, 1H, J = 5.7 Hz), 8.58 (d, 1H, J = 5.1 Hz), 8.55 (d, 1H, J = 8.0 Hz), 8.11 (d, 1H, J = 5.2 Hz), 7.81 (d, 1H, J = 5.1 Hz), 7.55 (d, 1H, J = 8.0 Hz), 7.49 (m, 1H), 7.17 (m, 1H), 4.14 (m, 4H), 3.38 (m, 4H). | 4-(4-Piperazin-1-yl-pyrido[3,4-d]pyrimidin-2-yl)-9H-pyrido[2,3-b] indole |
| 2092 | 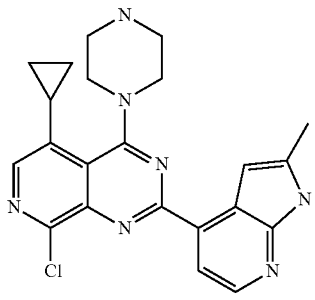 [SMILES: Cc1cc2c(-c3nc(N4CCNCC4)c4c(C5CC5)cnc(Cl)c4n3)ccnc2[nH]1] | [D4], [D3] | LCMS: Purity: >95%, RT: min, MI: 420 (M + H) | 1H-NMR ($CD_3CN$, 400 MHz): 12.80 (s, 1H), 8.38 (d, 1H, J = 5.8) 8.25 (d, 1H, J = 5.8 Hz), 7.87 (s, 1H), 7.57 (s, 1H), 3.99 (m, 4H), 3.24 (m, 4H), 2.55 (m, 4H), 1.20 (m, 2H), 0.94 (m, 2H). | 8-Chloro-5-cyclopropyl-2-(2-methyl-1H-pyrrolo[2,3-b]pyridin-4-yl)-4-piperazin-1-yl-pyrido[3,4-d]pyrimidine |
| 2093 | 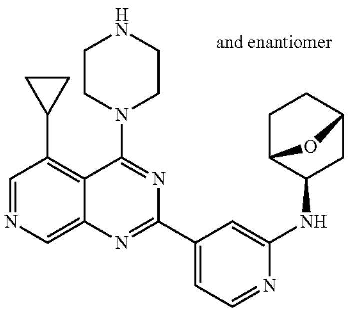 [SMILES: c1cc(-c2nc(N3CCNCC3)c3c(C4CC4)cncc3n2)cc(N[C@@H]2C[C@H]3CC[C@@H]2O3)n1] and enantiomer | [B4] | LCMS: Purity: >95%, RT: min, MI: 444 (M + H) | 1H-NMR (DMSO-d6, 400 MHz): 9.07 (s, 1H), 9.00 (br s, 2H), 8.22 (s, 1H), 8.10 (d, 1H, J = 6.4 Hz), 8.02 (br s, 1H), 7.68 (d, 1H, J = 6.4 Hz), 4.67 (m, 1H), 4.48 (m, 1H), 3.8-4.0 (m, 5H), 3.32 (m, 4H), 2.66 (m, 1H), 2.10 (m, 1H), 1.5-1.7 (m, 4H), 1.47 (m, 1H), 1.25 (m, 2H), 1.08 (m, 2H); | (±)-exo-[4-(5-Cyclopropyl-4-piperazin-1-yl-pyrido [3,4-d]pyrimidin-2-yl)-pyridin-2-yl]--7-oxa-bicyclo[2.2.1]hept-2-yl-amine |

-continued

| Ex | Structure | Scheme | Analysis LCMS | $^1$H-NMR | Name |
|---|---|---|---|---|---|
| 2094 | 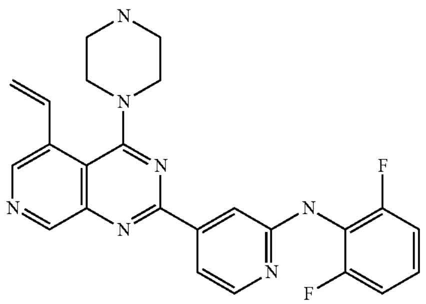 [SMILES: C=Cc1cncc2nc(-c3ccnc(Nc4c(F)cccc4F)c3)nc(N3CCNCC3)c12] | [B4] | LCMS: Purity: >95%, RT: min, MI: 446 (M + H) | 1H-NMR: DMSO 9.22 (s, 1H), 8.86 (br m, 3H), 8.81 (s, 1H), 8.20 (d, 1H, J = 5.2 Hz), 7.84 (s, 1H), 7.71 (m, 1H), 7.38 (m, 1H), 7.27 (m, 1H), 7.17 (m, 2H), 6.11 (br d, 1H, J = 17.8 Hz) 5.64 (d, 1H, 11.8 Hz), 3.74 (br s, 4H), 3.32 (br s, 4H) | (2,6-Difluoro-phenyl)-[4-(4-piperazin-1-yl-5-vinyl-pyrido[3,4-d]pyrimidin-2-yl)-pyridin-2-yl]-amine |
| 2095 | 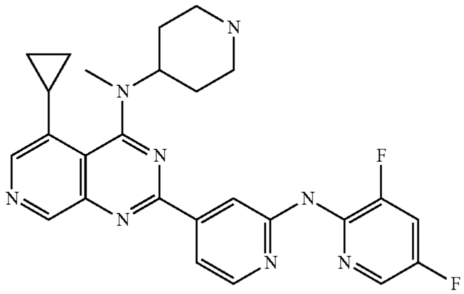 | [B4] | LCMS: Purity: >95%, RT: min, MI: 446 (M + H) | 1H-NMR: DMSO 10.35 (br s, 1H), 9.01 (s, 1H), 8.82 (br m, 1H), 8.64 (s, 1H) 8.41 (m, 2H), 8.30 (m, 1H), 8.20 (s, 1H), 8.08 (m, 1H), 8.02 (m, 1H), 4.85 (m, 1H), 3.44 (m, 2H), 3.15 (m, 2H), 3.12 (s, 3H), 2.44 (m, 1H), 2.07 (br m, 4H), 1.24 (m, 2H), 0.98 (m, 2H) | {5-Cyclopropyl-2-[2-(3,5-difluoro-pyridin-2-ylamino)-pyridin-4-yl]-pyrido[3,4-d]pyrimidin-4-yl}-methyl-piperidin-4-yl-amine |
| 2096 | 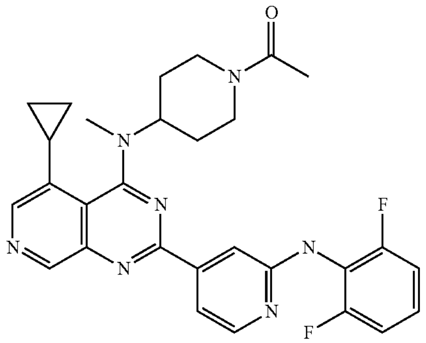 | [B4] | LCMS: Purity: >95%, RT: min, MI: 489 (M + H) | 1H-NMR: DMSO 8.99 (s, 1H), 8.96 (s, 1H), 8.19 (m, 2H), 7.75 (s, 1H), 7.69 (m, 1H), 7.31 (m ,1H), 7.20 (m, 2H), 4.77 (m, 1H), 4.56 (m, 1H), 3.94 (m, 1H), 3.16 (m, 1H), 3.11 (s, 3H), 2.67 (m, 1H), 2.40 (m, 1H), 2.04 (s, 3H), 1.88 (br m, 4H), 1.23 (m, 2H), 0.97 (m ,2H) | 1-[4-({5-Cyclopropyl-2-[2-(2,6-difluoro-phenylamino)-pyridin-4-yl]-pyrido[3,4-d]primidin-4-yl}-methyl-amino)-piperidin-1-yl]-ethanone |
| 2097 | 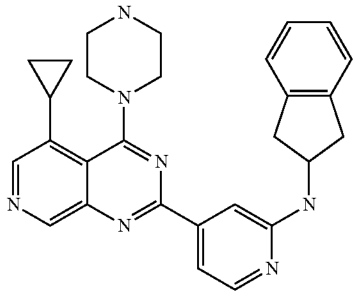 [SMILES: c1ccc2c(c1)CC(Nc1cc(-c3nc(N4CCNCC4)c4c(C5CC5)cncc4n3)ccn1)C2] | [B4] | LCMS: Purity: >95%, RT: min, MI: 530 (M + H) | (400 MHz, d6-DMSO, δ): 9.06 (s, 1H), 8.94 (br s, 2H), 8.21 (s, 1H), 8.13 (d, J = 6.3 Hz, 1H), 8.00-7.90 (m, 1H), 7.67 (d, J = 6.1 Hz, 1H), 7.33-7.28 (m, 2H), 7.23-7.18 (m, 2H), 4.67-4.60 (m, 1H), 3.90 (br s, 4H), 3.42 (dd, J = 16.1, 7.2 Hz, 2H), 3.31 (br s, 4H), 2.96 (dd, J = 16.2, 4.7 Hz, 2H), 2.69-2.62 (m, 1H), 1.28-1.22 (m, 2H), 1.11-1.05 (m, 2H). | 1-[4-({5-Cyclopropyl-2-[2-(2,6-difluoro-phenylamino)-pyridin-4-yl]-pyrido[3,4-d]pyrimidin-4-yl}-methyl-amino)-piperidin-1-yl]-ethanone |

-continued

| Ex | Structure | Scheme | Analysis LCMS | Analysis 1H-NMR | Analysis Name |
|---|---|---|---|---|---|
| 2098 | 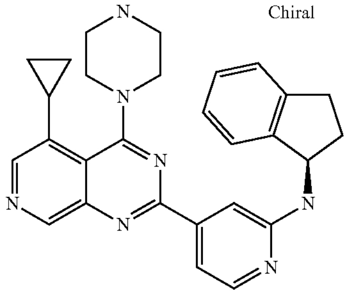 [SMILES: c1ccc2c(c1)CC[C@H]2Nc1cc(-c2nc(N3CCNCC3)c3c(C4CC4)cncc3n2)ccn1] Chiral | [B4] | LCMS: Purity: 98%, RT: min, MI: 464.30 (MH)+ | (400 MHz, d6-DMSO, δ): 9.07 (s, 1H), 8.90 (br s, 2H), 8.21 (s, 1H), 8.15 (d, J = 6.2 Hz, 1H), 8.00-7.90 (m, 1H), 7.70-7.64 (m, 1H), 7.39-7.21 (m, 4H), 5.53-5.45 (m, 1H), 3.86 (br s, 4H), 3.31 (br s, 4H), 3.09-3.00 (m, 1H), 2.95-2.86 (m, 1H), 2.70-2.56 (m, 2H), 1.99-1.90 (m, 1H), 1.29-1.23 (m, 2H), 1.11-1.06 (m, 2H). | [4-(5-Cyclopropyl-4-piperazin-1-yl-pyrido[3,4-d]pyrimidin-2-yl)-pyridin-2-yl]-(R)-indan-1-yl-amine |
| 2099 | 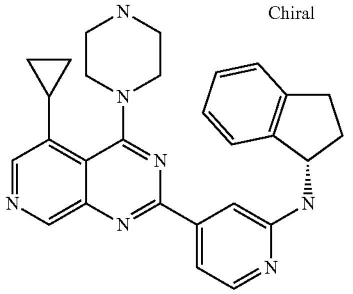 [SMILES: c1ccc2c(c1)CC[C@@H]2Nc1cc(-c2nc(N3CCNCC3)c3c(C4CC4)cncc3n2)ccn1] Chiral | [B4] | LCMS: Purity: 98%, RT: min, MI: 464.29 (MH)+ | (400 MHz, d6-DMSO, δ): 9.07 (s, 1H), 8.96 (br s, 2H), 8.21 (s, 1H), 8.15 (d, J = 6.3 Hz, 1H), 8.03-7.95 (m, 1H), 7.71-7.66 (m, 1H), 7.40-7.22 (m, 4H), 5.52-5.44 (m, 1H), 3.91 (br s, 4H), 3.31 (br s, 4H), 3.09-3.01 (m, 1H), 2.96-2.86 (m, 1H), 2.70-2.57 (m, 2H), 2.01-1.90 (m, 1H), 1.29-1.23 (m, 2H), 1.11-1.06 (m, 2H). | [4-(5-Cyclopropyl-4-piperazin-1-yl-pyrido[3,4-d]pyrimidin-2-yl)-pyridin-2-yl]-(S)-indazn-1-yl-amine |
| 2100 | 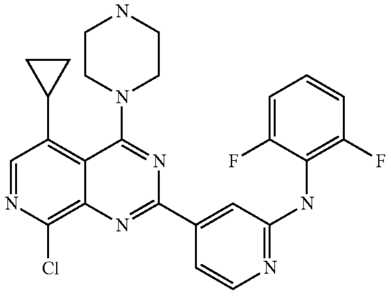 [SMILES: Fc1cccc(F)c1Nc1cc(-c2nc(N3CCNCC3)c3c(C4CC4)cnc(Cl)c3n2)ccn1] | [B4] | LCMS: Purity: 98%, RT: min, MI: 464.27 (MH)+ | 1H-NMR (DMSO-d6, 400 MHz): 9.00 (br s, 1H), 8.91 (s, 1H), 8.89 (br s, 1H), 8.21 (d, 1H, J = ), 7.95 (s, 1H), 7.85 (s, 1H), 7.71 (dd, 1H, J = ), 7.29 (m, 1H), 7.14-7.21 (m, 2H), 3.94 (br s, 4H), 3.30 (br s, 4H), 2.61 (m, 1H), 1.24 (m, 2H), 1.05 (m, 2H) | [4-(8-Chloro-5-cyclopropyl-4-piperazin-1-yl-pyrido[3,4-d]pyrimidin-2-yl)-pyridin-2-yl]-(2,6-difluoro-phenyl)-amine |
| 2101 | 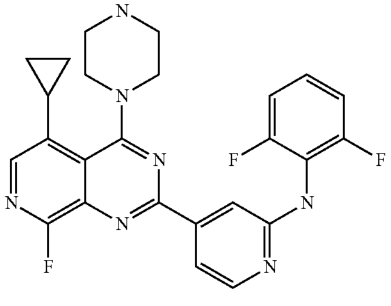 [SMILES: Fc1cccc(F)c1Nc1cc(-c2nc(N3CCNCC3)c3c(C4CC4)cnc(F)c3n2)ccn1] | [B4] | LCMS: Purity: >95%, RT: min, MI: 494 (M + H)+ | 1H-NMR (DMSO-d6, 400 MHz): 8.83 (s, 1H), 8.80 (br s, 2H), 8.20 (d, 1H, J = 5.7 Hz), 7.83 (s, 1H), 7.74 (s, 1H), 7.67 (dd, 1H, J = 1.4, 5.3 Hz), 7.27 (m, 1H), 7.11-7.19 (m, 2H), 3.91 (m, 4H), 3.30 (m, 4H), 2.58 (m, 1H), 1.20 (m, 2H), 1.00 (m, 2H) | [4-(5-Cyclopropyl-8-fluoro-4-piperazin-1-yl-pyrido[3,4-d]pyrimidin-2-yl)-pyridin-2-yl]-(2,6-difluoro-phenyl)-amine |
| 2102 | 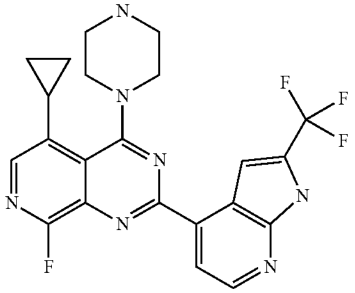 [SMILES: Fc1ncc(C2CC2)c2c(N3CCNCC3)nc(-c3ccnc4[nH]c(C(F)(F)F)cc34)nc12] | [D4], [D3] | LCMS: Purity: >95%, RT: min, MI: 458 (M + H) | 1H-NMR (DMSO-d6, 400 MHz): 13.22 (s, 1H), 8.86 (br s, 2H), 8.66 (d, 1H, J = 5.0 Hz), 8.28 (d, 1H, J = 5.0 Hz), 7.94 (s, 1H), 7.78 (s, 1H), 3.96 (br s, 4H), 3.34 (br s, 4H), 2.61 (m, 1H), 1.21 (m, 2H), 1.03 (m, 2H) | 5-Cyclopropyl-8-fluoro-4-piperazin-1-yl-2-(2-trifluoromethyl-1H-pyrrolo[2,3-b]pyridin-4-yl)-pyrido[3,4-d]pyrimidine |

-continued

| Ex | Structure | Scheme | Analysis LCMS | Analysis $^1$H-NMR | Name |
|---|---|---|---|---|---|
| 2103 | 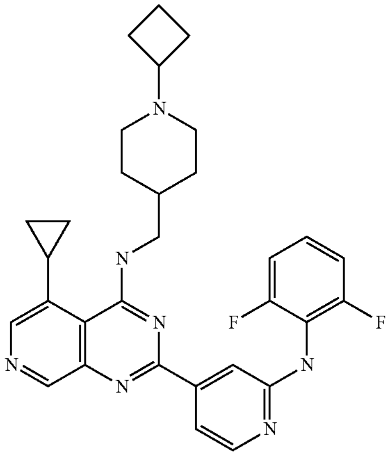 [SMILES: Fc1cccc(F)c1Nc1cc(-c2nc(NCC3CCN(C4CCC4)CC3)c3c(C4CC4)cncc3n2)ccn1] | [B4] | LCMS: Purity: >95%, RT: min, MI: 542 (M + H) | 1H-NMR: DMSO 9.23 (br m, 1H), 9.02 (s, 1H), 8.87 (s, 1H), 8.46 (s, 1H), 8.18 (d, 1H, J = 5.3 Hz), 8.12 (m, 1H), 7.84 (m, 1H), 7.71 (m, 1H), 7.30 (m, 1H), 7.18 (m, 2H), 3.73 (m, 2H), 3.58 (m, 1H), 3.36 (m, 2H), 2.74 (m, 2H), 2.17 (m, 5H), 1.98 (m, 2H), 1.73 (m, 3H), 1.48 (m, 2H), 1.25 (m, 2H), 1.00 (m, 2H) | (1-Cyclobutyl-piperidin-4-ylmethyl)-{5-cyclopropyl-2-[2-(2,6-difluoro-phenylamino)-pyridin-4-yl]-pyrido[3,4-d]pyrimidin-4-yl}-amine |
| 2104 | 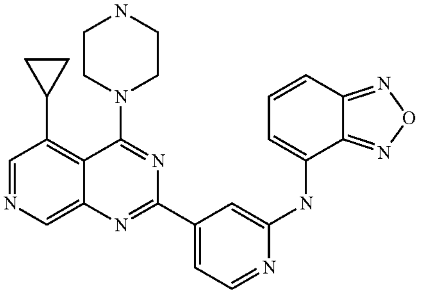 [SMILES: c1cc(Nc2cc(-c3nc(N4CCNCC4)c4c(C5CC5)cncc4n3)ccn2)c2nonc2c1] | [B4] | LCMS: Purity: 98%, RT: min, MI: 466.19 (MH)+ | (400 MHz, d6-DMSO, δ): 10.18 (s, 1H), 9.08 (s, 1H), 8.87 (br s, 2H), 8.54-8.46 (m, 3H), 8.19 (s, 1H), 7.92 (dd, J = 5.2, 1.3 Hz, 1H), 7.59 (dd, J = 8.9, 7.5 Hz, 1H), 7.47 (d, J = 8.8 Hz, 1H), 3.94 (br s, 4H), 3.34 (br s, 4H), 2.73-2.65 (m, 1H), 1.29-1.24 (m, 2H), 1.12-1.07 (m, 2H). | Benzo[1,2,5]oxadiazol-4-yl-[4-(5-cyclopropyl-4-piperazin-1-yl-pyrido[3,4-d]pyrimidin-2-yl)-pyridin-2-yl]-amine |
| 2105 | 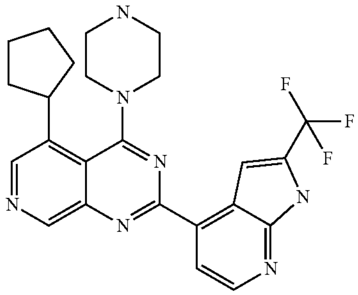 [SMILES: FC(F)(F)c1cc2c(-c3nc(N4CCNCC4)c4c(C5CCCC5)cncc4n3)ccnc2[nH]1] | [D4], [D3] | Method 5: RT: 4.08 min, MI: 468.53 [M + H] | (500 MHz, DMSO) 13.18 (1H, s), 9.27 (1H, s), 8.99 (1H, s, br), 8.88 (1H, s, br), 8.74 (1H, s), 8.63 (1H, d), 8.25 (1H, d), 7.96 (1H, s), 4.31 (4H, s, br), 3.96-3.93 (2H, m, br), 3.89-3.84 (1H, m), 3.77-3.74 (2H, m), 3.61-3.56 (1H, m), 2.13-2.12 (2H, m), 1.89-1.67 (6H, m). | 5-Cyclopentyl-4-piperazin-1-yl-2-(2-trifluoromethyl-1H-pyrrolo[2,3-b]pyridin-4-yl)-pyrido[3,4-d] pyrimidine |
| 2106 | 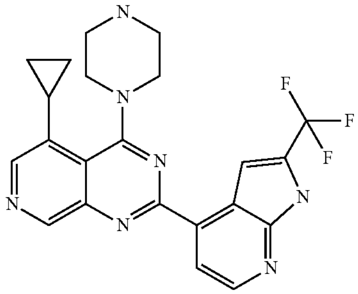 [SMILES: FC(F)(F)c1cc2c(-c3nc(N4CCNCC4)c4c(C5CC5)cncc4n3)ccnc2[nH]1] | [D4], [D3], [D8] | Method 5: RT: 3.19 min, MI: 422 [M + H] | (400 MHz, d6-DMSO 90° C.) 12.58 (1H, s), 9.06 (1H, s), 8.53 (1H, d, J = 4.9 Hz), 8.18 (1H, d, J = 4.9 Hz), 8.11 (1H, s), 7.78 (1H, br m), 7.33 (1H, t, J = 54.2 Hz), 3.93-3.47 (4H, br m), 2.89 (4H, br s), 2.70-2.65 (1H, m), 1.29-1.25 (2H, m), 1.06-1.03 (2H, m). | 5-Cyclopropyl-2-(2-difluoromethyl-1H-pyrrolo[2,3-b] pyridin-4-yl)-4-piperazin-1-yl-pyrido[3,4-d]pyrimidine |

-continued

| Ex | Structure | Scheme | LCMS (Analysis) | $^1$H-NMR (Analysis) | Name |
|---|---|---|---|---|---|
| 2107 | 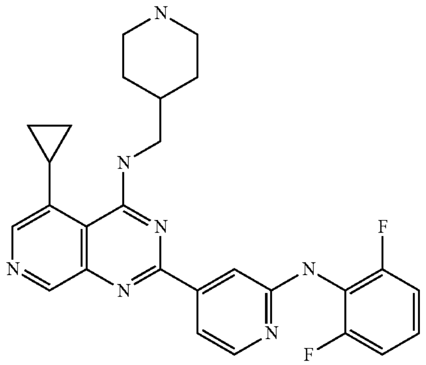 [SMILES: Fc1cccc(F)c1Nc1cc(-c2nc(NCC3CCNCC3)c3c(C4CC4)cncc3n2)ccn1] | [B4] | LCMS: Purity: >95%, RT: min, MI: 488 (M + H) | 1H-NMR: DMSO 9.02 (s, 1H), 8.91 (s, 1H), 8.55 (m, 1H), 8.46 (s, 1H), 8.26 (m, 1H), 8.18 (d, 1H, J = 5.3 Hz), 8.09 (m, 1H), 7.81 (s, 1H), 7.71 (m, 1H), 7.31 (m, 1H), 7.19 (m, 2H), 3.72 (m, 2H), 3.32 (m, 2H), 2.88 (m, 2H), 2.54 (m, 1H), 2.14 (m, 1H), 1.90 (m, 2H), 1.47 (m, 2H), 1.25 (m, 2H), 1.01 (m, 2H) | {5-Cyclopropyl-2-[2-(2,6-difluoro-phenylamino)-pyridin-4-yl]-pyrido[3,4-d]pyrimidin-4-yl}-piperidin-4-ylmethyl-amine |
| 2108 | 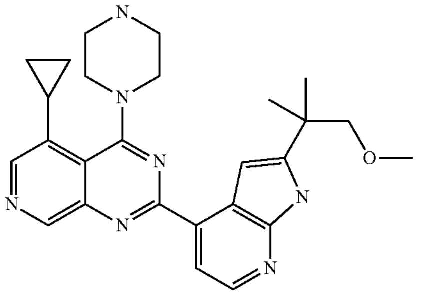 [SMILES: COCC(C)(C)c1cc2c(-c3nc(N4CCNCC4)c4c(C5CC5)cncc4n3)ccnc2[nH]1] | [D4], [D3] | LCMS: Purity: 93%, RT: min, MI: 458.27 (M + H) | (dmso-d6) 11.74 (s, 1H), 9.14 (s, 1H), 8.93 (br s, 2H), 8.32 (d, J = 5.2 Hz, 1H), 8.18 (s, 1H), 8.09 (d, J = 5.2 Hz, 1H), 7.21 (d, J = 2.2 Hz, 1H), 3.93 (br s, 4H), 3.55 (s, 2H), 3.37 (br s, 4H), 3.26 (s, 3H), 2.80-2.71 (m, 1H), 1.40 (s, 6H), 1.30-1.20 (m, 2H), 1.12-1.05 (m, 2H) | 5-Cyclopropyl-2-[2-(2-methoxy-1,1-dimethyl-ethyl)-1H-pyrrolo[2,3-b]pyridin-4-yl]-4-piperazin-1-yl-pyrido[3,4-d]pyrimidine |
| 2109 | 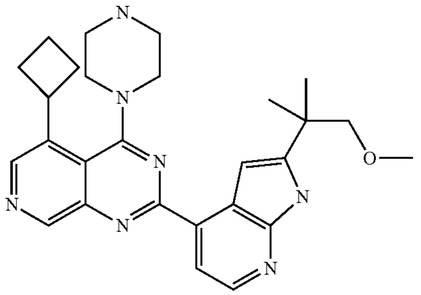 [SMILES: COCC(C)(C)c1cc2c(-c3nc(N4CCNCC4)c4c(C5CCC5)cncc4n3)ccnc2[nH]1] | [D4], [D3] | LCMS: Purity: 97%, RT: min, MI: 472.29 (M + H) | (dmso-d6) 11.74 (br s, 1H), 9.21 (s, 1H), 8.99 (br s, 1H), 8.85 (br s, 1H), 8.79 (s, 1H), 8.31 (d, J = 5.2 Hz, 1H), 8.07 (d, J = 5.2 Hz, 1H), 7.19 (d, J = 2.2 Hz, 1H), 4.29 (quint, 1H), 3.90-3.70 (m, 4H), 3.54 (s, 2H), 3.40-3.25 (m, 4H), 3.26 (s, 3H), 2.47 (m, 2H), 2.30-2.15 (m, 2H), 2.15-2.05 (m, 1H), 1.95-1.85 (m, 1H), 1.40 (s, 6H) | 5-Cyclobutyl-2-[2-(2-methoxy-1,1-dimethyl-ethyl)-1H-pyrrolo[2,3-b]pyridin-4-yl]-4-piperazin-1-yl-pyrido[3,4-d[pyrimidine |
| 2110 | 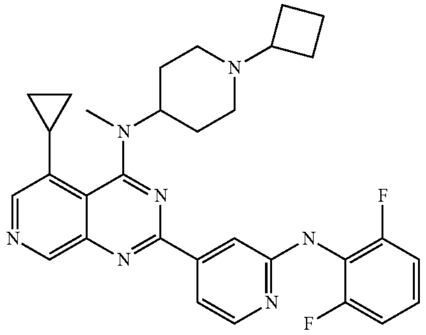 | [B4] | LCMS: Purity: >95%, RT: min, MI: 461 (M + H)+ | 1H-NMR: DMSO 9.60 (br m, 1H), 8.98 (s, 1H), 8.90 (s, 1H), 8.18 (m, 2H), 7.81 (s, 1H), 7.69 (m, 1H), 7.28 (m, 1H), 7.19 (m, 2H), 4.84 (m, 1H), 3.64 (m, 1H), 3.48 (m, 2H), 3.09 (s, 3H), 3.05 (m, 2H), 2.45 (m, 1H), 2.07-2.25 (br m, 8H), 1.77 (m, 2H), 1.24 (m, 2H), 0.99 (m, 2H) | (1-Cyclobutyl-piperidin-4-yl)-{5-cyclopropyl-2-[2-(2,6-difluroo-phenylamino)-pyridin-4-yl]-pyrido[3,4-d]pyrimidin-4-yl}-methyl-amine |

-continued

| Ex | Structure | Scheme | LCMS | Analysis $^1$H-NMR | Name |
|---|---|---|---|---|---|
| 2111 | 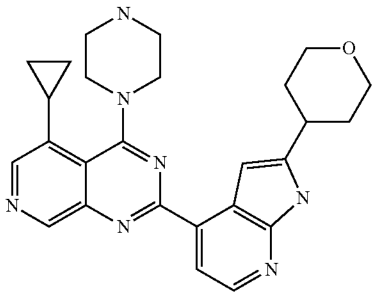 | [D4], [D3] | Method 5: RT: 3.20 min, MI: 456 [M + H] | (500 MHz, d6-DMSO) 11.87 (brs, 1H), 9.16 (s, 1H), 8.31 (d, 1H), 8.16 (s, 1H), 8.08 (d, 1H), 7.21 (s, 1H), 4.11-3.73 (m ,4H), 4.00 (dd, 2H), 3.49 (t, 2H), 3.41-3.32 (m, 4H), 3.12-3.04 (m, 1H), 2.78-2.70 (m, 1H), 2.02-1.97 (m, 2H), 1.87-1.76 (m, 2H), 1.29-1.23 (m, 2H), 1.10-1.05 (m, 2H). | 5-Cyclopropyl-4-piperazin-1-yl-2-[2-(tetrahydro-pyran-4-yl)-1H-pyrrolo[2,3-b]pyridin-4-yl]-pyrido[3,4-d]pyrimidine |
| 2112 | 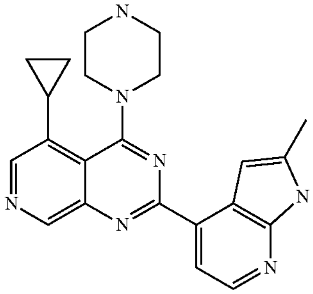 [SMILES: Cc1cc2c(-c3nc(N4CCNCC4)c4c(C5CC5)cncc4n3)ccnc2[nH]1] | [D4], [D3] | Method 5: RT: 3.25 min, MI: 400 [M + H] | (500 MHz, d6-DMSO) 11.99 (1H, s), 9.25 (1H, s), 9.11 (1H, brs), 8.96 (1H, brs), 8.79 (1H, s), 8.31 (1H, d), 8.13-8.12 (1H, m), 7.22 (1H, s), 4.31-4.24 (1H, m), 3.93-3.85 (2H, m), 3.83-3.72 (2H, m), 3.43-3.34 (2H, m), 3.32-3.21 (2H, m), 2.51 (3H, s), 2.47-2.42 (1H, m), 2.26-2.17 (2H, m), 2.15-2.06 (1H, m), 1.94-1.87 (1H, m). | 5-Cyclobutyl-2-(2-methyl-1H-pyrrolo[2,3-b]pyridin-4-yl)-4-piperazin-1-yl-pyrido[3,4-d[pyrimidine |
| 2113 | 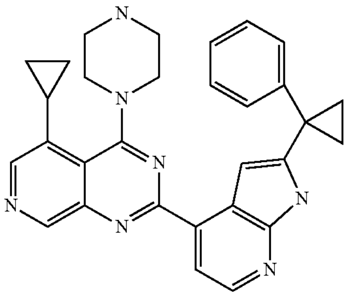 [SMILES: c1ccc(C2(c3cc4c(-c5nc(N6CCNCC6)c6c(C7CC7)cncc6n5)ccnc4[nH]3)CC2)cc1] | [D4], [D3] | Method 5: RT: 3.18 min, MI: 502 [M + H] | (400 MHz, d6-DMSO, 90° C.) 11.25 (1H, s), 9.02 (1H, s), 8.63 (1H, s), 8.26 (1H, d, J = 5.0 Hz), 8.03 (1H, d, J = 5.0 Hz), 7.45-7.42 (2H, m), 7.37-7.34 (2H, m), 7.29-7.25 (1H, m), 7.01 (1H, s), 4.34-4.30 (1H, m), 3.48 (4H, br s), 2.88-2.85 (4H, br. m), 2.55-2.50 (2H, m largely obscured by DMSO peak - visible but broad at lower T), 2.20-2.05 (3H, m), 1.97-1.92 (1H, m), 1.59-1.56 (2H, m), 1.39-1.36 (2H, m). | 5-Cyclobutyl-2-[2-(1-phenyl-cyclopropyl)-1H-pyrrolo[2,3-b]pyridin-4-yl]-4-piperazin-1-yl-pyrido[3,4-d]pyrimidine |
| 2114 | 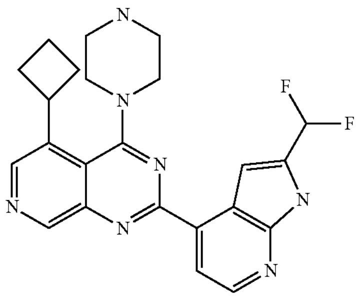 [SMILES: FC(F)c1cc2c(-c3nc(N4CCNCC4)c4c(C5CCC5)cncc4n3)ccnc2[nH]1] | [D4], [D3], [D8] | Method 5: RT: 2.55 min, MI: 436 [M + H] | (400 MHz, d6-DMSO, 90° C.) 9.13 (1H, s), 8.68 (1H, s), 8.51 (1H, d, J = 5.0 Hz), 8.16 (1H, d, J = 5.0 Hz), 7.75 (1H, s), 7.23 (1H, t, J = 54.7 Hz), 4.36-4.32 (1H, m), 3.64-3.61 (4H, br m), 2.95-2.93 (4H, br. m), 2.56-2.49 (2H, m overlapping with DMSO signal), 2.22-2.07 (3H, m), 1.99-1.94 (1H, m). | 5-Cyclobutyl-2-(2-difluoromethyl-1H-pyrrolo[2,3-b]pyridin-4-yl)-4-piperazin-1-yl-pyrido[3,4-d]pyrimidine |

-continued

| Ex | Structure | Scheme | LCMS | $^1$H-NMR | Name |
|---|---|---|---|---|---|
| | | | Analysis | | |
| 2115 | 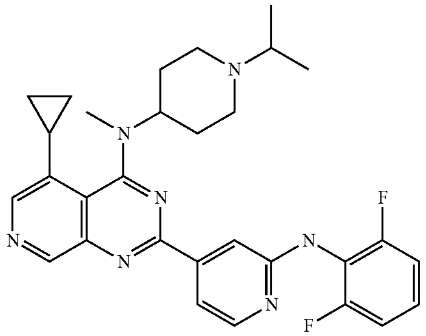 | [B4] | LCMS: Purity: >95%, RT: min, MI: 542 (M + H) | 1H-NMR: DMSO 9.20 (br m, 1H), 8.98 (s, 1H), 8.92 (s, 1H), 8.19 (d, 2H, J = 4.5 Hz), 7.83 (s, 1H), 7.73 (m, 1H), 7.32 (m, 1H), 7.18 (m, 2H), 4.87 (m, 1H), 3.54 (m, 3H), 3.25 (m, 2H), 3.10 (s, 3H), 2.45 (m, 1H), 2.15 (br m, 4H), 1.31 (d, 6H, J = 6.6 Hz), 1.26 (m, 2H), 0.99 (m, 2H) | {5-Cyclopropyl-2-[2-(2,6-difluoro-phenylamino)-pyridin-4-yl]-pyrido[3,4-d]pyrimidin-4-yl}-(1-isopropyl-piperidin-4-yl)-methyl-amine |
| 2116 | 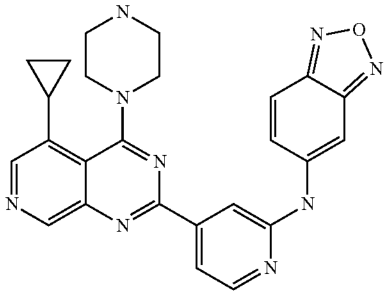 [SMILES: c1cc(-c2nc(N3CCNCC3)c3c(C4CC4)cncc3n2)cc(Nc2ccc3nonc3c2)n1] | [B4] | LCMS: Purity: >95%, RT: min, MI: 530 (M + H) | (400 MHz, d6-DMSO, δ): 10.19 (s, 1H), 9.08 (s, 1H), 8.85 (br s, 2H), 8.76 (s, 1H), 8.57 (d, J = 5.3 Hz, 1H), 8.20 (s, 1H), 8.13 (s, 1H), 7.99 (d, J = 9.6 Hz, 1H), 7.94 (dd, J = 5.4, 1.2 Hz, 1H), 7.56 (dd, J = 9.6, 1.8 Hz, 1H), 3.93 (br s, 4H), 3.34 (br s, 4H), 2.72-2.65 (m, 1H), 1.29-1.23 (m, 2H), 1.12-1.06 (m, 2H). | Benzo[1,2,5]oxadiazol-5-yl-[4-(5-cyclopropyl-4-piperazin-1-yl-pyrido[3,4-d]pyrimidin-2-yl)-pyridin-2-yl]-amine |
| 2117 | 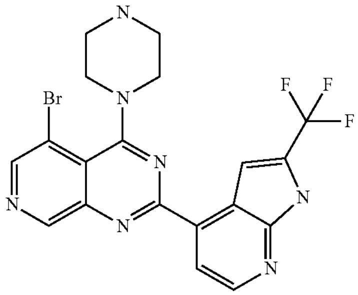 [SMILES: FC(F)(F)c1cc2c(-c3nc(N4CCNCC4)c4c(Br)cncc4n3)ccnc2[nH]1] | [B1] | LCMS: Purity: >95%, RT: min, MI: 478 (M + H)+ | 1H-NMR (DMSO-d6, 400 MHz): 13.23 (s, 1H), 9.44 (s, 1H), 8.97 (br s, 1H), 8.85 (s, 1H), 8.77 (br s, 1H), 8.66 (d, 1H, J = 5.0 Hz), 8.28 (d, 1H, J = 5.0 Hz), 7.97 (s, 1H), 3.7-4.0 (m, 8H) | 5-Bromo-4-piperazin-1-yl-2-(2-trifluoromethyl-1H-pyrrolo[2,3-b]pyridin-4-yl)-pyrido[3,4-d] pyrimidine |
| 2118 | 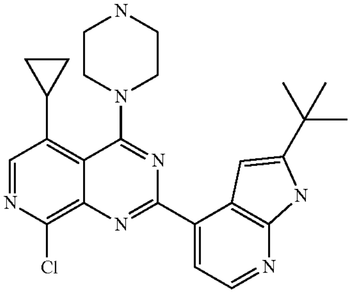 [SMILES: CC(C)(C)c1cc2c(-c3nc(N4CCNCC4)c4c(C5CC5)cnc(Cl)c4n3)ccnc2[nH]1] | [D4], [D3] | LCMS: Purity: >95%, RT: min, MI: 462 (M + H) | 1H-NMR (DMSO-d6, 400 MHz): 11.80 (s, 1H), 8.96 (br s, 1H), 8.77 (br s, 1H), 8.32 (d, 1H, J = 5.1 Hz), 8.11 (d, 1H, J = 5.1 Hz), 7.95 (s, 1H), 7.49 (d, 1H, J = 2.3 Hz), 3.9-4.0 (m, 4H), 3.33 (m, 4H), 2.67 (m, 2H), 1.43 (s, 9H), 1.25 (m, 2H), 1.06 (m, 2H) | 2-(2-tert-Butyl-1H-pyrrolo[2,3-b]pyridin-4-yl)-8-chloro-5-cyclopropyl-4-piperazin-1-yl-pyrido [3,4-d]pyrimidine |

-continued

| Ex | Structure | Scheme | LCMS | $^1$H-NMR | Name |
|---|---|---|---|---|---|
| | | | Analysis | | |
| 2119 | 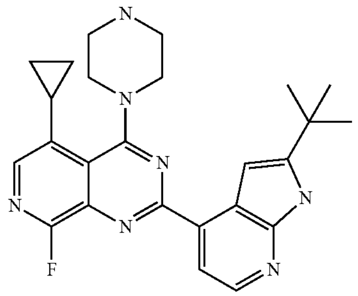 [SMILES: CC(C)(C)c1cc2c(-c3nc(N4CCNCC4)c4c(C5CC5)cnc(F)c4n3)ccnc2[nH]1] | [D4], [D3] | LCMS: Purity: >95%, RT: min, MI: 446 (M + H) | 1H-NMR (DMSO-d6, 400 MHz): 11.80 (s, 1H), 8.88 (br s, 2H), 8.32 (d, 1H, J = 5.1 Hz), 8.08 (d, 1H, J = 5.1 Hz), 7.73 (s, 1H), 7.21 (d, 1H, J = 2.3 Hz), 3.9-4.0 (m, 4H), 3.34 (m ,4H), 2.67 (m, 1H), 1.43 (s, 9H), 1.21 (m, 2H), 1.01 (m, 2H) | 2-(2-tert-Butyl-1H-pyrrolo[2,3-b]pyridin-4-yl)-5-cyclopropyl-8-fluoro-4-piperazin-1-yl-pyrido[3,4-d]pyrimidine |
| 2120 | 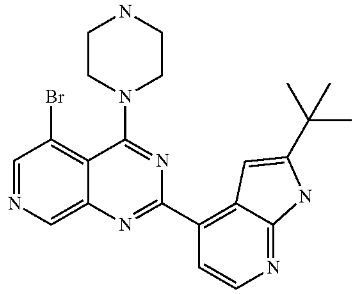 [SMILES: CC(C)(C)c1cc2c(-c3nc(N4CCNCC4)c4c(Br)cncc4n3)ccnc2[nH]1] | [D4], [D3] | LCMS: Purity: >95%, RT: min, MI: 466 (M + H) | 1H-NMR (DMSO-d6, 400 MHz): 11.82 (s, 1H), 9.35 (s, 1H), 9.01 (br s, 1H), 8.81 (s, 1H), 8.79 (br s, 1H), 8.32 (d, 1H, J = 5.2 Hz), 8.08 (d, 1H, J = 5.2 Hz), 7.16 (d, 1H, J = 2.2 Hz), 3.7-4.0 (m ,4H), 3.37 (m, 4H), 1.44 (s, 9H) | 5-Bromo-2-(2-tert-butyl-1H-pyrrolo[2,3-b]pyridin-4-yl)-4-piperazin-1-yl-pyrido[3,4-d]pyrimidine |
| 2121 | 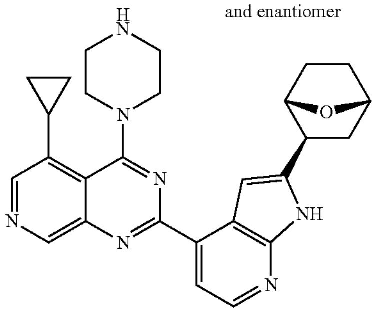 [SMILES: c1cc(-c2nc(N3CCNCC3)c3c(C4CC4)cncc3n2)c2cc([C@@H]3C[C@H]4CC[C@@H]3O4)[nH]c2n1] and enantiomer | [D4], [D3] | LCMS: Purity: 95%, RT: min, MI: 468.26 | (dmso-d6) 11.70 (s, 1H), 9.15 (s, 1H), 8.94 (br s, 2H), 8.30 (d, J = 5.2 Hz, 1H), 8.17 (s, 1H), 8.09 (d, J = 5.2 Hz, 1H), 7.20 (s, 1H), 4.74-4.70 (m, 1H), 4.63 (qpp d, J = 3.7 Hz, 1H), 3.93 (br s, 4H), 3.36 (br s, 4H), 3.24 (dd, J = 8.8; 4.8 Hz, 1H), 2.80-2.70 (m, 1H), 2.10 1.95 (m, 2H), 1.67-1.50 (m, 4H), 1.30-1.20 (m, 2H), 1.15-1.05 (m, 2H) | (±)-exo-5-Cyclopropyl-2-[2-(7-oxa-bicyclo[2.2.1]hept-2-yl)-1H-pyrrolo[2,3-b]pyridin-4-yl]-4-piperazin-1-yl-pyrido[3,4-d]pyrimidine |
| 2122 | 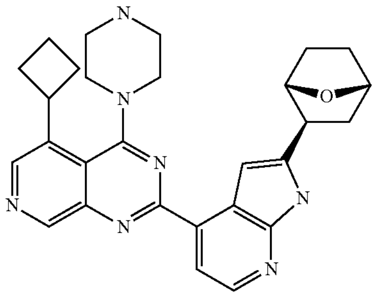 [SMILES: c1cc(-c2nc(N3CCNCC3)c3c(C4CCC4)cncc3n2)c2cc([C@@H]3C[C@H]4CC[C@@H]3O4)[nH]c2n1] | [D4], [D3] | LCMS: Purity: 97%, RT: min, MI: 482.24 (M + H) | (dmso-d6) 11.70 (br s, 1H), 9.22 (s, 1H), 8.98 (br s, 1H), 8.88 (br s, 1H), 8.78 (s, 1H), 8.30 (d, J = 5.2 Hz, 1H), 8.08 (d, J = 5.2 Hz, 1H), 7.18 (s, 1H), 4.73-4.70 (m, 1H), 4.63 (d, J = 3.6 Hz, 1H), 4.28 (app quint, 1H), 3.95-3.75 (m, 4H), 3.45-3.30 (m, 4H), 3.23 (dd, J = 8.8; 4.8 Hz, 1H), 2.50-2.40 (m, 2H), 2.30-2.15 (m, 2H), 2.15-2.00 (m, 2H), 2.00-1.85 (m, 2H), 1.75-1.55 (m, 4H) | (±)-dxo-5-Cyclobutyl-2-[2-(7-oxa-bicyclo[2.2.1]hept-2-yl)-1H-pyrrolo[2,3-b]pyridin-4-yl]-4-piperazin-1-yl-pyrido[3,4-d]pyrimidine |

-continued

| Ex | Structure | Scheme | Analysis LCMS | $^1$H-NMR | Name |
|---|---|---|---|---|---|
| 2123 | 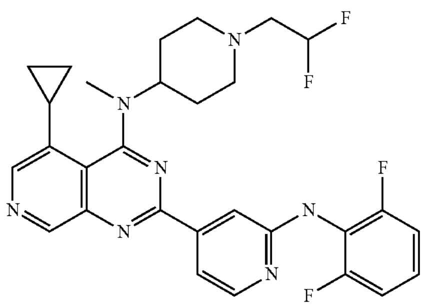 [SMILES: CN(c1nc(-c2ccnc(Nc3c(F)cccc3F)c2)nc2cncc(C3CC3)c12)C1CCN(CC(F)F)CC1] | [B4] | LCMS: Purity: >95%, RT: min, MI: 552 (MH)+ | 1H-NMR: DMSO 8.98 (s, 1H), 8.91 (s, 1H), 8.19 (d, 2H, J = 4.2 Hz), 7.81 (s, 1H), 7.68 (m, 1H), 7.32 (m, 1H), 7.18 (m, 2H), 6.55 (br m, 1H), 4.80 (m, 1H), 3.63 (br m, 4H), 3.31 (m, 2H), 3.10 (s, 3H), 2.44 (m, 1H), 2.08 (br m, 4H), 1.24 (m, 2H), 0.99 (m, 2H) | {5-Cyclopropyl-2-[2-(2,6-difluoro-phenylamino)-pyridin-4-yl]-pyrido[3,4-d]pyrimidin-4-yl}-[1-(2,2-difluoro-ethyl)-piperidin-4-yl]-methyl-amine |
| 2124 | 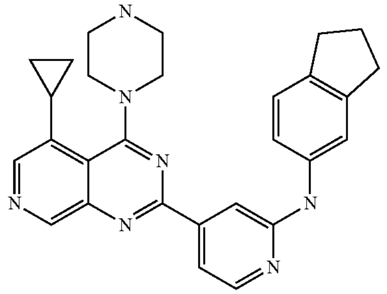 [SMILES: c1cc(-c2nc(N3CCNCC3)c3c(C4CC4)cncc3n2)cc(Nc2ccc3c(c2)CCC3)n1] | [B4] | LCMS: Purity: 96%, RT: min, MI: 464.28 (MH)+ | (400 MHz, d6-DMSO, δ): 9.35 (s, 1H), 9.06 (s, 1H), 8.86 (br s, 2H), 8.26 (d, J = 5.6 Hz, 1H), 8.18 (s, 1H), 7.94 (s, 1H), 7.68 (dd, J = 5.4, 1.3 Hz, 1H), 7.66 (s, 1H), 7.39 (dd, J = 8.0, 1.7 Hz, 1H), 7.16 (d, J = 8.0 Hz, 1H), 3.92 (br s, 4H), 3.33 (br s, 4H), 2.89-2.79 (m, 4H), 2.73-2.65 (m, 1H), 2.07-1.98 (m, 2H), 1.28-1.23 (m, 2H), 1.11-1.06 (m, 2H). | [4-(5-Cyclopropyl-4-piperazin-1-yl-pyrido[3,4-d]pyrimidin-2-yl)-pyridin-2-yl]-indan-5-yl-amine |
| 2125 | 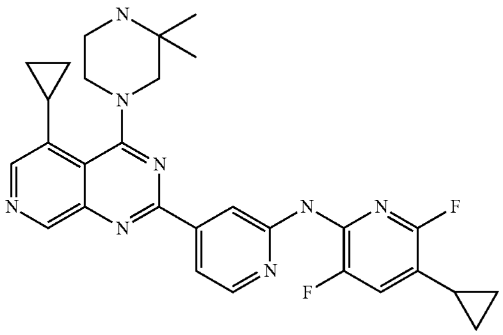 [SMILES: CC1(C)CN(c2nc(-c3ccnc(Nc4nc(F)c(C5CC5)cc4F)c3)nc3cncc(C4CC4)c23)CCN1] | [B4] | Method 5: RT: 2.88 min, MI: 529 [M + H] | (500 MH, d6-DMSO) 9.69 (1H, s), 9.06 (1H, s), 8.82 (1H, s), 8.43 (1H, d), 8.21 (1H, s), 7.98 (1H, dd), 7.56 (1H, m), 3.93 (4H, s), 3.36 (2H, s,), 1.95 (1H, m), 1.39 (3H, m), 1.28 (3H, m), 1.06 (2H, m), 0.98 (2H, m), 0.79 (2H, m). | (5-Cyclopropyl-3,6-difluoro-pyridin-2-yl)-{4-[5-cyclopropyl-4-(3,3-dimethyl-piperazin-1-yl)-pyrido[3,4-d]pyrimidin-2-yl]-pyridin-2-yl}-amine |
| 2126 | 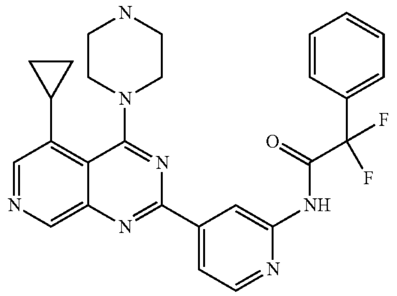 [SMILES: O=C(Nc1cc(-c2nc(N3CCNCC3)c3c(C4CC4)cncc3n2)ccn1)C(F)(F)c1ccccc1] | [B4] | LCMS: Purity: 98%, RT: min, MI: 502.1 (MH)+ | (400 MHz, d6-DMSO, δ): 11.53 (s, 1H), 9.09 (s, 1H), 9.00 (s, 1H), 8.89 (br s, 2H), 8.61 (dd, J = 5.2, 0.5 Hz, 1H), 8.21-8.18 (m, 2H), 7.79-7.75 (m, 2H), 7.64-7.55 (m, 3H), 3.92 (br s, 4H), 3.37-3.28 (m, 4H), 2.72-2.64 (m, 1H), 1.28-1.22 (m, 2H), 1.11-1.05 (m, 2H). | N-[4-(5-Cyclopropyl-4-piperazin-1-yl-pyrido[3,4-d]pyrimidin-2-yl)-pyridin-2-yl]-2,2-difluoro-2-phenyl-acetamide |

-continued

| Ex | Structure | Scheme | Analysis LCMS | $^1$H-NMR | Name |
|---|---|---|---|---|---|
| 2127 | 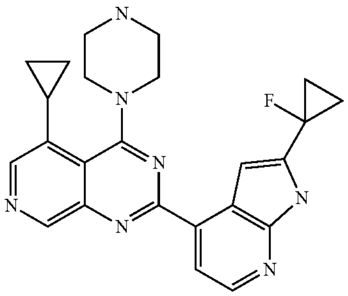 [SMILES: FC1(c2cc3c(-c4nc(N5CCNCC5)c5c(C6CC6)cncc5n4)ccnc3[nH]2)CC1] | [D4], [D3] | Method 5: RT: 3.40 min, MI: 430 [M + H] | (600 MHz, d6-DMSO) 12.06 (1H, s), 9.08 (1H, s), 8.37 (1H, d, J = 5.0 Hz), 9.11-8.10 (2H, m), 7.45 (1H, br d, J = 1.6 Hz), 3.96-3.51 (4H, bery broad m), 2.94 (4H, br s), 2.70-2.66 (1H, m), 1.58-1.542H, m), 1.36-1.34 (2H, m), 1.27-1.24 (2H, m), 1.05-1.04 (2H, m). | 5-Cyclopropyl-2-[2-(1-fluoro-cyclopropyl)-1H-pyrrolo[2,3-b]pyridin-4-yl]-4-piperazin-1-yl-pyrido[3,4-d]pyrimidine |
| 2128 | 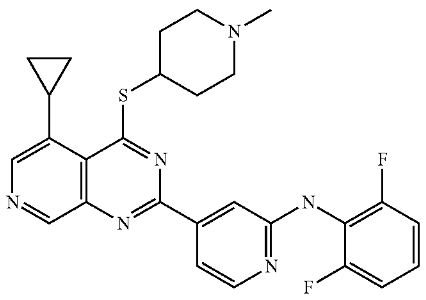 [SMILES: CN1CCC(Sc2nc(-c3ccnc(Nc4c(F)cccc4F)c3)nc3cncc(C4CC4)c23)CC1] | [B4] | LCMS: Purity: >95%, RT: min, MI: 505 (MH)+ | 1H-NMR: DMSO 9.65 (br s, 1H), 9.27 (s, 1H), 8.86 (s, 1H), 8.57 (s, 1H), 8.25 (d, 1H, J = 5.3 Hz), 7.85 (s, 1H), 7.72 (m, 1H), 7.30 (m, 1H), 7.19 (m, 2H), 4.3 5 (m, 1H), 3.61 (m, 2H), 3.30 (m, 2H), 2.88 (s, 3H), 2.46 (m, 1H), 2.27 (m, 2H), 1.93 (m, 2H), 1.22 (m, 2H), 1.07 (m, 2H) | {4-[5-Cyclopropyl-4-(1-methyl-piperidin-4-yslulfanyl)-pyrido[3,4-d]pyrimidin-2-yl]-pyridin-2-yl}-(2,6-difluoro-phenyl)-amine |
| 2129 | 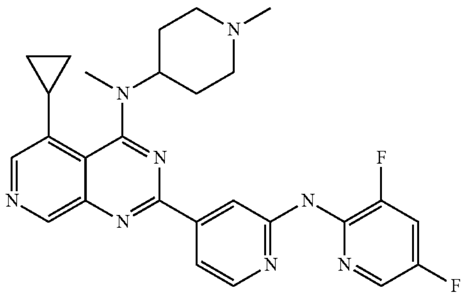 [SMILES: CN1CCC(N(C)c2nc(-c3ccnc(Nc4ncc(F)cc4F)c3)nc3cncc(C4CC4)c23)CC1] | [B4] | LCMS: Purity: >95%, RT: min, MI: 503 (MH)+ | 1H-NMR: DMSO 10.33 (br s, 1H), 9.62 (br s, 1H), 9.01 (s, 1H), 8.61 (s, 1H), 8.41 (d, 1H, J = 5.7 Hz), 8.31 (m, 1H), 8.20 (s, 1H), 8.07 (m, 1H), 7.99 (m, 1H), 4.80 (m, 1H), 3.57 (m, 2H), 3.20 (m, 2H), 3.12 (s, 3H), 2.82 (m, 3H), 2.44 (m, 1H), 2.07 (br m, 4H), 1.25 (m, 2H), 0.99 (m, 2H) | {5-Cyclopropyl-2-[2-(3,5-difluoro-pyridin-2-ylamino)-pyridin-4-yl]-pyrido[3,4-d]pyrimidin-4-yl}-methyl-(1-methyl-piperidin-4-yl)-amine |
| 2130 | 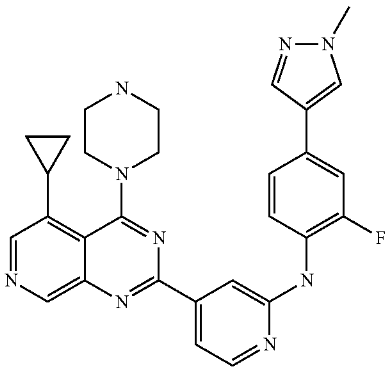 [SMILES: Cn1cc(-c2ccc(Nc3cc(-c4nc(N5CCNCC5)c5c(C6CC6)cncc5n4)ccn3)c(F)c2)cn1] | [B4] | LCMS: Purity: 90.012%, RT: min, MI: 522 | | [4-(5-Cyclopropyl-4-piperazin-1-yl-pyrido[3,4-d] pyrimidin-2-yl)-pyridin-2-yl]-[2-fluoro-4-(1-methyl-1H-pyrazol-4-yl)-phenyl]-amine |

-continued

| Ex | Structure | Scheme | LCMS | $^1$H-NMR | Name |
|---|---|---|---|---|---|
| | | | Analysis | | |
| 2131 | 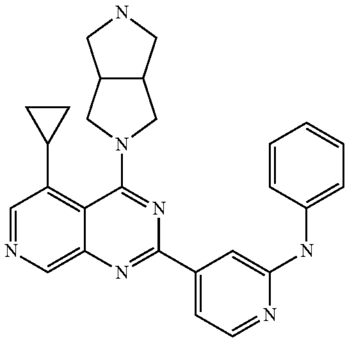 [SMILES: c1ccc(Nc2cc(-c3nc(N4CC5CNCC5C4)c4c(C5CC5)cncc4n3)ccn2)cc1] | [B4] | LCMS: Purity: 98%, RT: min, MI: 450.0 (MH)+ | (400 MHz, d6-DMSO, δ): 9.52 (s, 1H), 8.96 (s, 1H), 8.83 (br s, 2H), 8.31 (d, J = 5.5 Hz, 1H), 8.18 (s, 1H), 7.95 (s, 1H), 7.75-7.70 (m, 3H), 7.34-7.29 (m, 2H), 6.96 (t, J = 8.0 Hz, 1H), 4.12-4.06 (m, 2H), 3.88-3.82 (m, 2H), 3.45-3.35 (m, 2H), 3.15-2.95 (m, 4H), 2.45-2.37 (m, 1H), 1.31-1.25 (m, 2H), 1.04-0.98 (m, 2H). | {4-[5-Cyclopropyl-4-(hexahydro-pyrrolo[3,4-c]pyrrol-2-yl)-pyrido[3,4-d]pyrimidin-2-yl]-pyridin-2-yl}-phenyl-amine |
| 2132 | 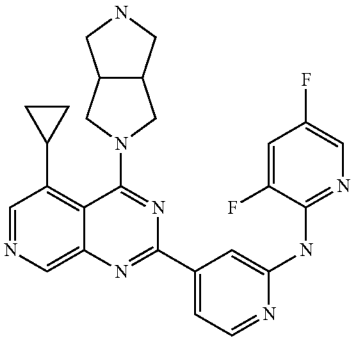 [SMILES: Fc1cnc(Nc2cc(-c3nc(N4CC5CNCC5C4)c4c(C5CC5)cncc4n3)ccn2)c(F)c1] | [B4] | LCMS: Purity: 97%, RT: min, MI: 487.0 (MH)+ | (400 MHz, d6-DMSO, δ): 10.27 (s, 1H), 8.99 (s, 1H), 8.86 (br s, 2H), 8.72 (s, 1H), 8.41 (d, J = 5.5 Hz, 1H), 8.29 (d, J = 2.6 Hz, 1H), 8.20 (s, 1H), 8.10-8.04 (m, 1H), 7.99 (dd, J = 5.7, 1.4 Hz, 1H), 4.14-4.08 (m, 2H), 3.89-3.83 (m, 2H), 3.45-3.35 (m, 2H), 3.15-2.95 (m, 4H), 2.44-2.36 (m, 1H), 1.31-1.26 (m, 2H), 1.04-0.99 (m, 2H). | {4-[5-Cyclopropyl-4-(hexahydro-pyrrolo[3,4-c]pyrrol-2-yl)-pyrido[3,4-d]pyrimidin-2-yl]-pyridin-2-yl}-(3,5-difluoro-pyridin-2-yl)-amine |
| 2133 | 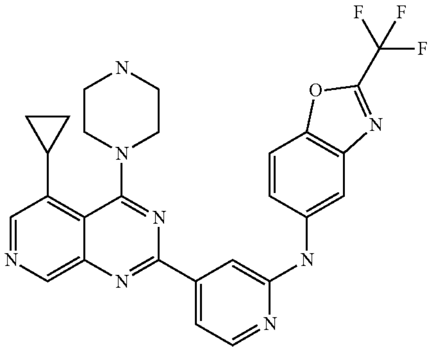 [SMILES: FC(F)(F)c1nc2cc(Nc3cc(-c4nc(N5CCNCC5)c5c(C6CC6)cncc5n4)ccn3)ccc2o1] | [B4] | LCMS: Purity: 96%, RT: min, MI: 533.18 (MH)+ | (400 MHz, d6-DMSO, δ): 9.76 (s, 1H), 9.07 (s, 1H), 8.87 (br s, 2H), 8.67 (d, J = 2.1 Hz, 1H), 8.42 (d, J = 5.3 Hz, 1H), 8.19 (s, 1H), 8.00 (s, 1H), 7.88 (d, J = 9.1 Hz, 1H), 7.80-7.76 (m, 2H), 3.92 (br s, 4H), 3.34 (br s, 4H), 2.74-2.65 (m, 1H), 1.29-1.23 (m, 2H), 1.11-1.06 (m, 2H). | [4-(5-Cyclopropyl-4-piperazin-1-yl-pyrido[3,4-d]pyrimidin-2-yl)-pyridin-2-yl]-(2-trifluoromethyl-benzooxazol-5-yl)-amine |
| 2134 | 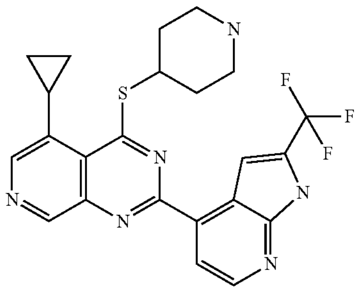 [SMILES: FC(F)(F)c1cc2c(-c3nc(SC4CCNCC4)c4c(C5CC5)cncc4n3)ccnc2[nH]1] | [D4], [D3] | LCMS: Purity: 95%, RT: min, MI: 471 (MH)+ | 1H-NMR: DMSO 13.25 (s, 1H), 9.46 (s, 1H), 8.70 (m, 2H), 8.59 (s, 1H), 8.49 (m, 1H), 8.32 (m, 1H), 8.05 (s, 1H), 4.58 (m, 1H), 3.40 (m, 2H), 3.28 (m, 2H), 2.56 (m, 1H), 2.40 (m, 2H), 1.97 (m, 2H), 1.24 (m, 2H), 1.08 (m, 2H) | 5-Cyclopropyl-4-(piperidin-4-ylsulfanyl)-2-(2-trifluoromethyl-1H-pyrrolo[2,3-b]pyridin-4-yl)-pyrido[3,4-d]pyrimidine |

-continued

| Ex | Structure | Scheme | Analysis LCMS | <br>$^1$H-NMR | Name |
|---|---|---|---|---|---|
| 2135 | 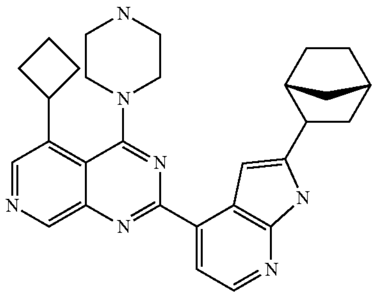 [SMILES: c1cc(-c2nc(N3CCNCC3)c3c(C4CCC4)cncc3n2)c2cc(C3C[C@H]4CC[C@@H]3C4)[nH]c2n1] | [D4], [D3] | LCMS: Purity: 97%, RT: min, MI: 480.1 (M + H) | 1H-NMR (dmso-d6): 11.76 (s, 1H), 9.24 (s, 1H), 9.03 (br s, 1H), 8.92 (br s, 1H), 8.79 (s, 1H), 8.29 (d, J = 5.2 Hz, 1H), 8.07 (d, J = 5.2 Hz, 1H), 7.25 (s, 1H), 4.29 (quint, J = 8.8 Hz, 1H), 3.88 (br s, 2H), 3.79 (br s, 2H), 3.40-3.20 (m, 5H), 2.69 (br s, 1H), 2.50-2.40 (m, 2H), 2.36 (br s, 1H), 2.30-1.80 (m, 5H), 1.70-1.40 (m, 4H), 1.30-1.20 (m, 2H), 1.15-1.05 (m, 1H) | (±) endo-2-(2-Bicyclo[2.2.1]hept-2-yl-1H-pyrrolo[2,3-b]pyridin-4-yl)-5-cyclobutyl-4-piperazin-1-yl-pyrido[3,4-d]pyrimidine |
| 2136 | 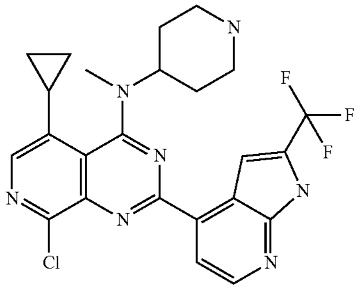 [SMILES: CN(c1nc(-c2ccnc3[nH]c(C(F)(F)F)cc23)nc2c(Cl)ncc(C3CC3)c12)C1CCNCC1] | [D4], [D3] | LCMS: Purity: 95%, RT: min, MI: 502 (M + H) | 1H-NMR: DMSO 13.16 (s, 1H), 8.75 (m, 1H), 8.65 (d, 1H, J = 4.9 Hz), 8.37 (m, 1H), 8.32 (m, 1H), 8.21 (s, 1H), 7.98 (s, 1H), 4.95 (m, 1H), 3.47 (m, 2H), 3.21 (m, 2H), 3.11 (s, 3H), 2.40 (m, 1H), 1.91-2.18 (br m, 4H), 1.14-1.33 (br m, 2H), 0.96 (m, 2H) | [8-Chloro-5-cyclopropyl-2-(2-trifluoromethyl-1H-pyrrolo[2,3-b]pyridin-4-yl)-pyrido[3,4-d]pyrimidin-4-yl]-methyl-piperidin-4-yl-amine |
| 2137 | 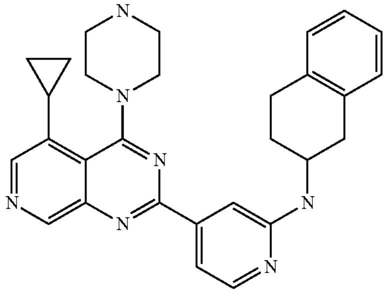 [SMILES: c1ccc2c(c1)CCC(Nc1cc(-c3nc(N4CCNCC4)c4c(C5CC5)cncc4n3)ccn1)C2] | [B4] | LCMS: Purity: 95%, RT: min, MI: 478.27 (MH)+ | (400 MHz, d6-DMSO, δ): 9.07 (s, 1H), 8.94 (br s, 2H), 8.22 (s, 1H), 8.10 (d, J = 6.2 Hz, 1H), 8.02 (br s, 1H), 7.69-7.64 (m, 1H), 7.17-7.11 (m, 4H), 4.21-4.13 (m, 1H), 3.93 (br s, 4H), 3.32 (br s, 4H), 3.20 (dd, J = 16.5, 5.2 Hz, 1H), 2.94 (t, J = 6.3 Hz, 2H), 2.80 (dd, J = 16.4, 8.4 Hz, 1H), 2.70-2.63 (m, 1H), 2.20-2.13 (m, 1H), 1.89-1.77 (m, 1H), 1.29-1.23 (m ,2H), 1.11-1.06 (m, 2H). | [4-(5-Cyclopropyl-4-piperazin-1-yl-pyrido[3,4-d]pyrimidin-2-yl)-pyridin-2-yl]-(1,2,3,4-tetrahydro-naphthalen-2-yl)-amine |
| 2138 | 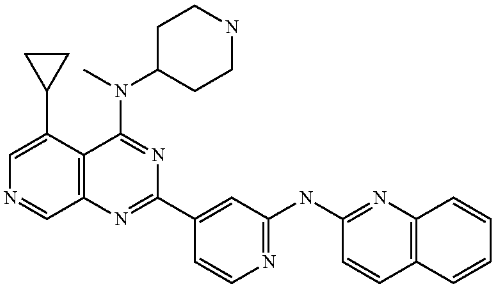 [SMILES: CN(c1nc(-c2ccnc(Nc3ccc4ccccc4n3)c2)nc2cncc(C3CC3)c12)C1CCNCC1] | [B4] | LCMS: Purity: 95%, RT: min, MI: 503 (M + H) | 1H-NMR: DMSO 12.20 (br s, 1H), 9.03 (s, 1H), 8.84 (m, 1H), 8.69 (d, 2H, J = 5.7 Hz), 8.57 (m, 1H), 8.45 (m, 1H), 8.22 (m, 3H), 8.04 (m, 1H), 7.88 (m, 1H), 7.61 (m, 1H), 7.56 (m, 1H), 4.89 (m, 1H), 3.45 (m, 2H), 3.19 (m, 2H), 3.15 (s, 3H), 2.45 (m, 1H), 2.07 (br m, 4H), 1.26 (m, 2H), 1.00 (m, 2H) | {5-Cylcopropyl-2-[2-([D4], [D3]uinolin-2-ylamino)-pyridin-4-yl]-pyrido[3,4-d]pyrimidin-4-yl}-methyl-piperidin-4-yl-amine |

-continued

| Ex | Structure | Scheme | Analysis LCMS | $^1$H-NMR | Name |
|---|---|---|---|---|---|
| 2139 | 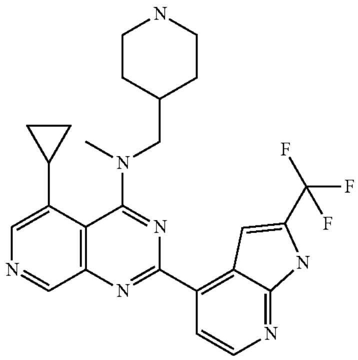 [SMILES: CN(CC1CCNCC1)c1nc(-c2ccnc3[nH]c(C(F)(F)F)cc23)nc2cncc(C3CC3)c12] | [D4], [D3] | LCMS: Purity: 95%, RT: min, MI: 482 (M + H) | 1H-NMR: DMSO 13.15 (s, 1H), 9.09 (s, 1H), 8.63 (d, 1H, J = 4.9 Hz), 8.48 (m, 1H), 8.25 (d, 1H, J = 4.9 Hz), 8.16 (s, 1H), 8.04 (m, 1H), 7.96 (s, 1H), 3.31 (s, 3H), 3.17 (m, 2H), 2.78 (m, 2H), 2.43 (m, 1H), 2.23 (m, 1H), 1.50-1.75 (br m, 2H), 1.30 (br m, 2H), 1.03 (br m, 6H) | [5-Cyclopropyl-2-(2-trifluoromethyl-1H-pyrrolo[2,3-b] pyridin-4-yl)-pyrido [3,4-d]pyrimidin-4-yl]-methyl-piperidin-4-ylmethyl-amine |
| 2140 | Chiral 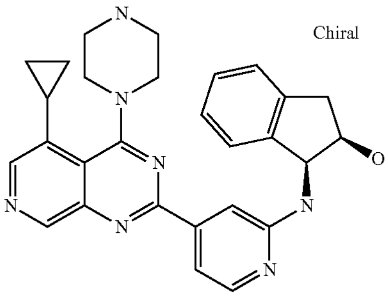 [SMILES: O[C@@H]1Cc2ccccc2[C@@H]1Nc1cc(-c2nc(N3CCNCC3)c3c(C4CC4)cncc3n2)ccn1] | [B4] | LCMS: Purity: 97%, RT: min, MI: 480.1 (MH)+ | (400 MHz, d6-DMSO, δ): 9.08 (s, 1H), 8.94 (br s, 2H), 8.29-8.17 (m, 2H), 8.12 (d, J = 5.9 Hz, 1H), 7.70 (d, J = 6.9 Hz, 1H), 7.36-7.23 (m, 4H), 5.41-5.35 (m, 1H), 4.71-4.66 (m, 1H), 3.92 (br s, 4H), 3.31 (br s, 4H), 3.15 (dd, J = 16.3, 5.7 Hz, 1H), 2.93 (dd, J = 16.3, 2.5 Hz, 1H), 2.70-2.62 (m, 1H), 1.29-1.23 (m, 2H), 1.11-1.06 (m, 2H). | (1S,2R)-1-[4-(5-Cyclopropyl-4-piperazin-1-yl-pyrido[3,4-d]pyrimidin-2-yl)-pyridin-2-ylamino]-indan-2-ol |
| 2141 | Chiral 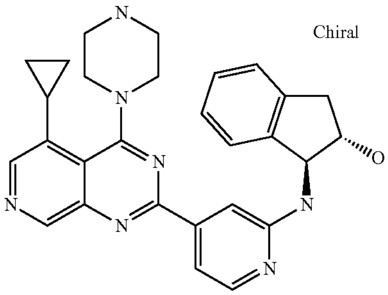 [SMILES: O[C@H]1Cc2ccccc2[C@@H]1Nc1cc(-c2nc(N3CCNCC3)c3c(C4CC4)cncc3n2)ccn1] | [B4] | LCMS: Purity: 98%: RT: min, MI: 480.1 (MH)+ | (400 MHz, d6-DMSO, δ): 9.08 (s, 1H), 8.98 (br s, 2H), 8.22 (s, 1H), 8.15 (d, J = 6.4 Hz, 1H), 8.09 (br s, 1H), 7.72 (d, J = 6.2 Hz, 1H), 7.32-7.22 (m, 4H), 5.30-5.24 (m, 1H), 4.39 (dd, J = 13.9, 7.1 Hz, 1H), 3.92 (br s, 4H), 3.32 (br s, 4H), 3.25 (dd, J = 1.5.7, 7.2 Hz, 1H), 2.83 (dd, J = 15.4, 7.5 Hz, 1H), 2.70-2.62 (m, 1H), 1.29-1.23 (m, 2H), 1.11-1.06 (m, 2H). | (1S,2S)-1-[4-(5-Cyclopropyl-4-piperazin-1-yl-pyrido [3,4-d]pyrimidin-2-yl)-pyridin-2-ylamino]-indan-2-ol |
| 2142 | Chiral 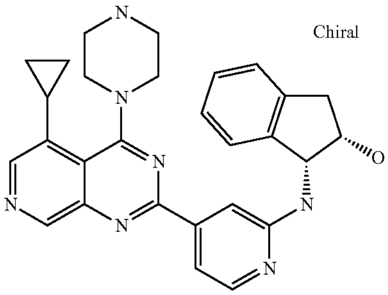 [SMILES: O[C@H]1Cc2ccccc2[C@H]1Nc1cc(-c2nc(N3CCNCC3)c3c(C4CC4)cncc3n2)ccn1] | [B4] | LCMS: Purity: 98%, RT: min, MI: 480.1 (MH)+ | (400 MHz, d6-DMSO, δ): 9.08 (s, 1H), 8.94 (br s, 2H), 8.29-8.17 (m, 2H), 8.13 (d, J = 6.1 Hz, 1H), 7.71 (d, J = 5.6 Hz, 1H), 7.36-7.23 (m, 4H), 5.41-5.35 (m, 1H), 4.70-4.65 (m, 1H), 3.92 (br s, 4H), 3.31 (br s, 4H), 3.15 (dd, J = 16.1, 5.4 Hz, 1H), 2.93 (dd, J = 16.1, 2.6 Hz, 1H), 2.70-2.62 (m, 1H), 1.29-1.23 (m, 2H), 1.11-1.06 (m, 2H). | (1R,2S)-1-[4-(5-Cyclopropyl-4-piperazin-1-yl-pyrido [3,4-d]pyrimidin-2-yl)-pyridin-2-ylamino]-indan-2-ol |

-continued

| Ex | Structure | Scheme | Analysis LCMS | $^1$H-NMR | Name |
|---|---|---|---|---|---|
| 2143 | 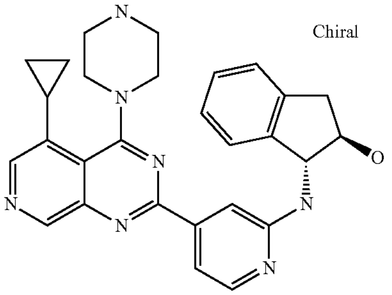 [SMILES: O[C@@H]1Cc2ccccc2[C@H]1Nc1cc(-c2nc(N3CCNCC3)c3c(C4CC4)cncc3n2)ccn1] | [B4] | LCMS: Purity: 99%, RT: min, MI: 480.1 (MH)+ | (400 MHz, d6-DMSO, δ): 9.09 (s, 1H), 9.04 (br s, 2H), 8.23 (s, 1H), 8.16 (d, J = 6.5 Hz, 1H), 8.13 (br s, 1H), 7.74 (d, J = 6.2 Hz, 1H), 7.34-7.23 (m, 4H), 5.27 (t, J = 6.8 Hz, 1H), 4.39 (dd, J = 13.9, 7.1 Hz, 1H), 3.91 (br s, 4H), 3.32 (br s, 4H), 3.25 (dd, J = 15.6, 7.1 Hz, 1H), 2.83 (dd, J = 15.5, 7.6 Hz, 1H), 2.70-2.62 (m, 1H), 1.30-1.23 (m, 2H), 1.11-1.06 (m, 2H). | (1R,2R)-1-[4-(5-Cyclopropyl-4-piperazin-1-yl-pyrido[3,4-d]pyrimidin-2-yl)-pyridin-2-ylamino]-indan-2-ol |
| 2144 | 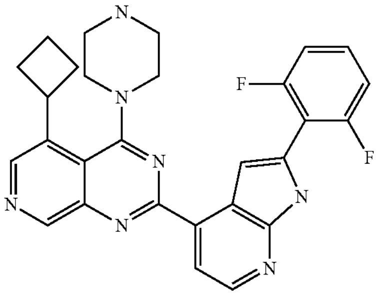 [SMILES: Fc1cccc(F)c1-c1cc2c(-c3nc(N4CCNCC4)c4c(C5CCC5)cncc4n3)ccnc2[nH]1] | [D4], [D3] | LCMS: Purity: 83%, RT: min, MI: 498.0 (M + H) | (dmso-d6) 9.16 (br s, 1H), 8.83 (br s, 1H), 8.74 (br s, 2H), 8.41 (d, J = 4.8 Hz, 1H), 8.12 (d, J = 4.8 Hz, 1H), 7.70 (br s, 1H), 7.55-7.46 (m, 1H), 7.30-7.22 (m, 2H), 4.30-4.15 (m, 1H), 3.90-3.60 (m, 4H), 3.40-3.15 (m, 4H), 2.45-2.35 (m, 2H), 2.20-2.10 (m, 2H), 2.10-1.98 (m, 1H), 1.90-1.80 (m, 1H) | 5-Cyclobutyl-2-[2-(2,6-difluoro-phenyl)-1H-pyrrolo[2,3-b]pyridin-4-yl]-4-piperazin-1-yl-pyrido[3,4-d]pyrimidine |
| 2145 | 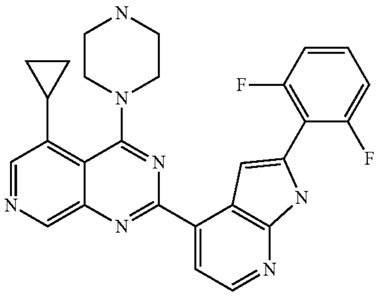 [SMILES: Fc1cccc(F)c1-c1cc2c(-c3nc(N4CCNCC4)c4c(C5CC5)cncc4n3)ccnc2[nH]1] | [D4], [D3] | LCMS: Purity: 95%, RT: min, MI: 484.2 (M + H) | (dmso-d6) 12.23 (d, J = 1.3 Hz, 1H), 9.14 (s, 1H), 8.91 (br s, 2H), 8.49 (d, J = 5.0 Hz, 1H), 8.19 (d, J = 5.0 Hz, 1H), 8.18 (s, 1H), 7.78 (br s, 1H), 7.56 (m, 1H), 7.33 (m, 2H), 3.93 (br s, 4H), 3.36 (br s, 4H), 2.75 (m, 1H), 1.30-1.23 (m, 2H), 1.12-1.06 (m, 2H) | 5-Cyclopropyl-2-[2-(2,6-difluoro-phenyl)-1H-pyrrolo[2,3-b]pyridin-4-yl]-4-piperazin-1-yl-pyrido[3,4-d]pyrimidine |
| 2146 | 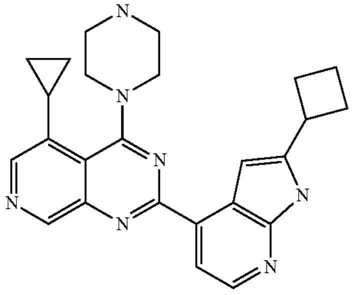 [SMILES: c1cc(-c2nc(N3CCNCC3)c3c(C4CC4)cncc3n2)c2cc(C3CCC3)[nH]c2n1] | [D4], [D3] | LCMS: Purity: 96%, RT: min, MI: 426.1 (M + H) | (dmso-d6) 11.82 (br s, 1H), 9.16 (s, 1H), 8.93 (br s, 2H), 8.30 (d, J = 5.2 Hz, 1H), 8.17 (s, 1H), 8.09 (d, J = 5.2 Hz, 1H), 7.24 (d, J = 1.7 Hz, 1H), 3.91 (br s, 4H), 3.74 (quint, J = 8.4 Hz, 1H), 3.37 (br s, 4H), 2.75 (m, 1H), 2.45-2.75 (m, 4H), 2.35-1.98 (m, 1H), 1.96-1.85 (m, 1H), 1.30-1.22 (m, 2H), 1.12-1.08 (m, 2H) | 2-(2-Cyclobutyl-1H-pyrrolo[2,3-b]pyridin-4-yl)-5-cyclopropyl-4-piperazin-1-yl-pyrido[3,4-d]pyrimidine |
| 2147 | 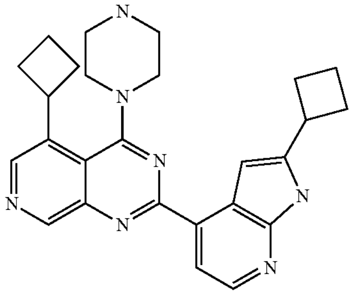 [SMILES: c1cc(-c2nc(N3CCNCC3)c3c(C4CCC4)cncc3n2)c2cc(C3CCC3)[nH]c2n1] | [D4], [D3] | LCMS: Purity: 92%, RT: min, MI: 440.28 (M + H) | (dmso-d6) 11.89 (br s, 1H), 9.25 (s, 1H), 9.10 (br s, 1H), 8.94 (br s, 1H), 8.79 (s, 1H), 8.30 (d, J = 5.2 Hz, 1H), 8.09 (d, J = 5.2 Hz, 1H), 7.23 (d, J = 1.6 Hz, 1H), 4.29 (quint, 1H), 3.88 (br s, 2H), 3.79 (br s, 2H), 3.75 (quint, J = 8.8 Hz, 1H), 3.50-3.20 (m, 4H), 2.50-2.43 (m, 2H), 2.43-2.31 (m, 4H), 2.31-2.16 (m, 2H), 2.16-1.97 (m, 2H), 1.97-1.07 (m, 2H) | 5-Cyclobutyl-2-(2-cyclobutyl-1H-pyrrolo[2,3-b]pyridin-4-yl)-4-piperazin-1-yl-pyrido[3,4-d]pyrimidine |

-continued

| Ex | Structure | Scheme | LCMS | $^1$H-NMR | Name |
|---|---|---|---|---|---|
| | | | Analysis | | |
| 2148 | 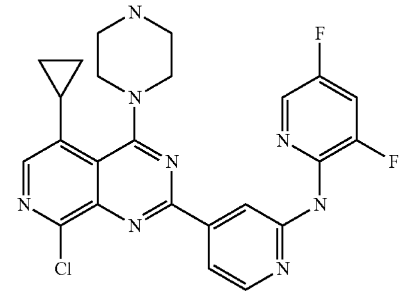 [SMILES: Fc1cnc(Nc2cc(-c3nc(N4CCNCC4)c4c(C5CC5)cnc(Cl)c4n3)ccn2)c(F)c1] | [B4] | LCMS: Purity: 98%, RT: min,, MI: 495 (M + H) | 1H NMR (400 MHz, DMSO-d6) 9.80-10.03 (1 H, m), 8.83-9.14 (2 H, m), 8.81 (1 H, s), 8.43 (1 H, d, J = 5.5 Hz), 8.26 (1 H, d, J = 2.5 Hz), 7.90-8.08 (3 H, m), 3.97 (4 H, br. s.), 3.32 (4 H, br. s.), 2.57-2.64 (1 H, m), 1.18-1.30 (2 H, m), 1.01-1.11 (2 H, m) | [4-(8-Chloro-5-cyclopropyl-4-piperazin-1-yl-pyrido[3,4-d]pyrimidin-2-yl)-pyridin-2-yl]-(3,5-difluoro-pyridin-2-yl)-amine |
| 2149 | 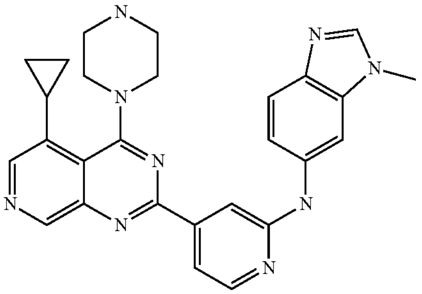 [SMILES: Cn1cnc2ccc(Nc3cc(-c4nc(N5CCNCC5)c5c(C6CC6)cncc5n4)ccn3)cc21] | [B4] | LCMS: Purity: 98%, RT: min, MI: 478.24 (MH)+ | (400 MHz, d6-DMSO, δ): 9.91 (s, 1H), 9.34 (s, 1H), 9.07 (s, 1H), 8.97 (br s, 2H), 8.68 (d, J = 1.4 Hz, 1H), 8.45 (d, J = 5.3 Hz, 1H), 8.20 (s, 1H), 8.04 (s, 1H), 7.82 (dd, J = 5.4, 1.4 Hz, 1H), 7.78 (d, J = 8.9 Hz, 1H), 7.65 (dd, J = 9.0, 1.8 Hz, 1H), 4.03 (s, 3H), 3.93 (br s, 4H), 3.35 (br s, 4H), 2.74-2.65 (m, 1H), 1.29-1.23 (m, 2H), 1.11-1.06 (m, 2H). | [4-(5-Cyclopropyl-4-piperazin-1-yl-pyrido[3,4-d]pyrimidin-2-yl)-pyridin-2-yl]-(3-methyl-3H-benzimidazol-5-yl)-amine |
| 2150 | 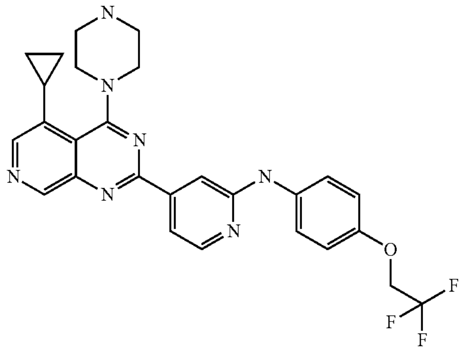 [SMILES: FC(F)(F)COc1ccc(Nc2cc(-c3nc(N4CCNCC4)c4c(C5CC5)cncc4n3)ccn2)cc1] | [B4] | Method 5: RT: 2.34 min, MI: 522 [M + H] | (500 MH, DMSO) 9.43 (1H, s), 9.06 (1H, s), 8.29 (1H, d), 8.18 (1H, s), 7.91 (1H, s), 7.68 (3H, m), 7.05 (2H, d), 4.72 (2H, m), 3.91 (4H, s, broad), 3.33 (4H, s,), 2.69 (1H, m), 1.26 (2H, m), 1.08 (2H, m). | [4-(5-Cyclopropyl-4-piperazin-1-yl-pyrido[3,4-d]pyrimidin-2-yl)-pyridin-2-yl]-[4-(2,2,2-trifluoro-ethoxy)-phenyl]-amine |
| 2151 | 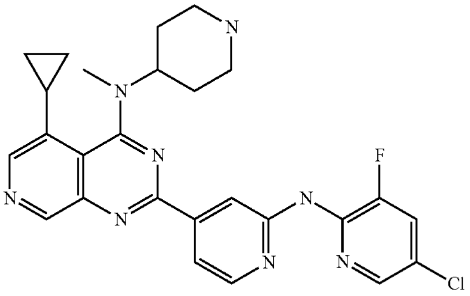 [SMILES: CN(c1nc(-c2ccnc(Nc3ncc(Cl)cc3F)c2)nc2cncc(C3CC3)c12)C1CCNCC1] | [B4] | LCMS: Purity: >95%, RT: min, MI: 506 (MH)+ | 1H-NMR: DMSO 10.29 (br s, 1H), 9.01 (s, 1H), 8.80 (br m, 1H), 8.73 (s, 1H), 8.45 (d, 1H, J = 5.5 Hz), 8.38 (br m, 1H), 8.27 (m, 1H), 8.20 (s, 1H), 8.10 (m, 1H), 8.03 (m, 1H), 4.84 (m, 1H), 3.44 (m, 2H), 3.15 (m, 2H), 3.12 (s, 3H), 2.44 (m, 1H), 2.07 (br m, 4H), 1.25 (m, 2H), 0.98 (m, 2H) | {2-[2-(5-Chloro-3-fluoro-pyridin-2-ylamino)-pyridin-4-yl]-5-cyclopropyl-pyrido[3,4-d]pyrimidin-4-yl}-methyl-piperidin-4-yl-amine |

-continued

| Ex | Structure | Scheme | LCMS | $^1$H-NMR | Name |
|---|---|---|---|---|---|
| 2152 | 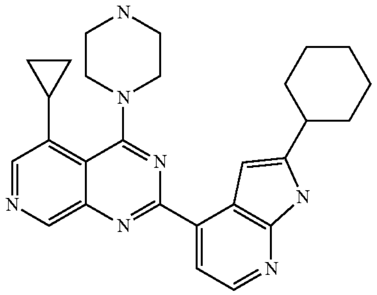 | [D4], [D3] | LCMS: Purity: 95%, RT: min, MI: 454.23 (M + H) | (dmso-d6) 11.71 (d, J = 1.3 Hz, 1H), 9.09 (s, 1H), 8.89 (br s, 2H), 8.23 (d, J = 5.2 Hz, 1H), 8.10 (s, 1H), 8.02 (d, J = 5.2 Hz, 1H), 7.11 (d, J = 1.7 Hz, 1H), 3.84 (br s, 4H), 3.30 (br s, 4H), 2.76 (m, 1H), 2.68 (m, 1H), 2.15 (m, 2H), 1.77 (m, 2H), 1.67 (m, 1H), 1.51 (m, 2H), 1.36 (m, 2H), 1.28-1.13 (m, 3H), 1.06-0.80 (m, 2H) | 5-Cyclopropyl-2-(2-cyclohexyl-1H-pyrrolo[2,3-b]pyridin-4-yl)-4-piperazin-1-yl-pyrido[3,4-d] pyrimidine |
| 2153 | 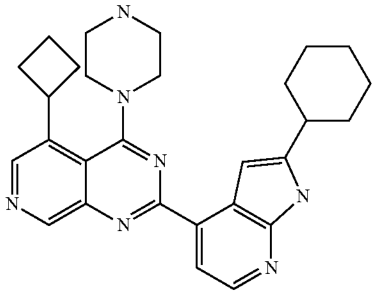 [SMILES: c1cc(-c2nc(N3CCNCC3)c3c(C4CCC4)cncc3n2)c2cc(C3CCCCC3)[nH]c2n1] | [D4], [D3] | LCMS: Purity: 94%, RT: min, MI: 468.28 | (dmso-d6) 11.72 (s, 1H), 9.17 (s, 1H), 8.99 (br s, 1H), 8.84 (br s, 1H), 8.72 (s, 1H), 8.22 (d, J = 5.3 Hz, 1H), 8.01 (d, J = 5.3 Hz, 1H), 7.1 (d, J = 1.8 Hz, 1H), 6.28 (br s, esch. protons), 4.11 (m, 1H), 3.76 (m, 4H), 3.17 (m, 4H), 2.75 (m, 1H), 2.42 (m, 2H), 2.15 (m, 2H), 2.58-1.95 (m, 3H), 1.77 (m, 4H), 1.50 (m, 2H), 1.35 (m, 2H), 1.24 (m, 1H) | 5-Cyclobutyl-2-(2-cyclohexyl-1H-pyrrolo[2,3-b] pyridin-4-yl)-4-piperazin-1-yl-pyrido[3,4-d] pyrimidine |
| 2154 | 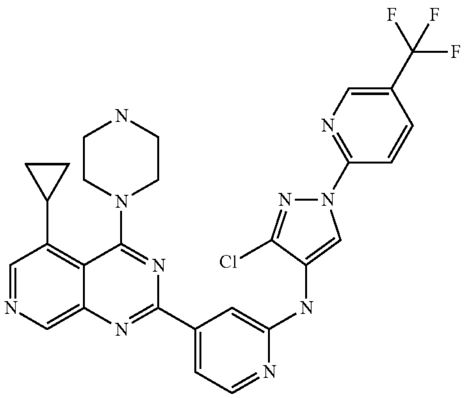 [SMILES: FC(F)(F)c1ccc(-n2cc(Nc3cc(-c4nc(N5CCNCC5)c5c(C6CC6)cncc5n4)ccn3)c(Cl)n2)nc1] | [B4] | LCMS: Purity: 94%, RT: min, MI: 593.17 (M + H) | (dmso-d6) 9.10 (s, 1H), 9.05 (br s, 1H), 9.02 (br s, 1H), 8.92 (br s, 2H), 8.53 (s, 1H), 8.49 (dd, J = 8.3, 2.3 Hz, 1H), 8.36 (d, J = 5.2 Hz, 1H), 8.22 (s, 1H), 8.10 (d, J = 8.3 Hz, 1H), 8.06 (s, 1H), 7.77 (dd, J = 5.3, 1.3 Hz, 1H), 3.88 (br s, 4H), 3.37 (br s,4H), 2.71 (m, 1H), 1.28 (m, 2H), 1.12 (m, 2H) | [3-Chloro-1-(5-trifluoromethyl-pyridin-2-yl)-1H-pyrazol-4-yl]-[4-(5-cyclopropyl-4-piperazin-1-yl-pyrido [3,4-d]pyrimidin-2-yl)-pyridin-2-yl]-amine |
| 2155 | 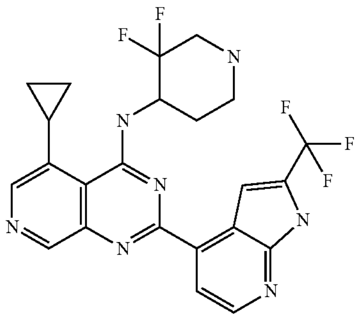 [SMILES: FC(F)(F)c1cc2c(-c3nc(NC4CCNCC4(F)F)c4c(C5CC5)cncc4n3)ccnc2[nH]1] | [D4], [D3] | LCMS: Purity: >95%, RT: min, MI: 490 (M + H) | 1H-NMR: DMSO 13.14 (s, 1H), 9.73 (br m, 1H), 9.35 (br m, 1H), 9.26 (s, 1H), 8.64 (d, 1H, J = 4.9 Hz), 8.56 (s, 1H), 8.34 (d, 1H, J = 4.9 Hz), 7.97 (m, 2H), 5.50 (m, 1H), 4.02 (m, 1H), 3.82-3.90 (br m,1H), 3.45 (m, 2H), 2.61 (m, 1H), 2.54 (m, 1H), 2.08 (m, 1H), 1.21 (m, 3H), 1.05 (m, 1H) | [5-Cyclopropyl-2-(2-trilfuoromethyl-1H-pyrrolo[2,3-b] pyridin-4-yl)-pyrido [3,4-d]pyrimidin-4-yl]-(3,3-difluoro-piperidin-4-yl)-amine |

-continued

| Ex | Structure | Scheme | Analysis LCMS | Analysis ¹H-NMR | Analysis Name |
|---|---|---|---|---|---|
| 2156 | 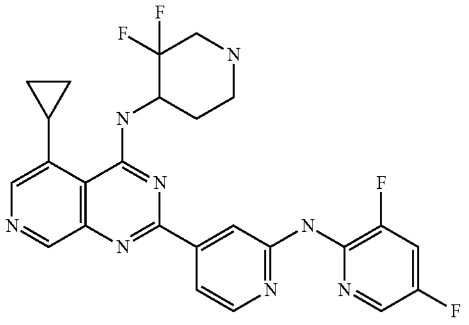 [SMILES: Fc1cnc(Nc2cc(-c3nc(NC4CCNCC4(F)F)c4c(C5CC5)cncc4n3)ccn2)c(F)c1] | [B4] | LCMS: Purity: >95%, RT: min, MI: 511 (M + H) | 1H-NMR: DMSO 10.06 (br s, 1H), 9.84 (br m, 1H), 9.37 (br m, 1H), 9.14 (s, 1H), 8.65 (s, 1H), 8.56 (s, 1H), 8.41 (d, 1H, J = 5.5 Hz), 8.28 (m, 1H), 8.06 (m, 3H), 5.50 (m, 1H), 4.01 (m, 1H), 3.76-3.87 (br m, 1H), 3.45 (m, 1H), 3.35 (m, 1H), 2.60 (m, 1H), 2.46 (m, 1H), 2.07 (m, 1H), 1.20 (m, 3H), 1.03 (m, 1H) | {5-Cyclopropyl-2-[2-(3,5-difluoro-pyridin-2-ylamino)-pyridin-4-yl]-pyrido[3,4-d]pyrimidin-4-yl}-(3,3-difluoro-piperidin-4-yl)-amine |
| 2157 | 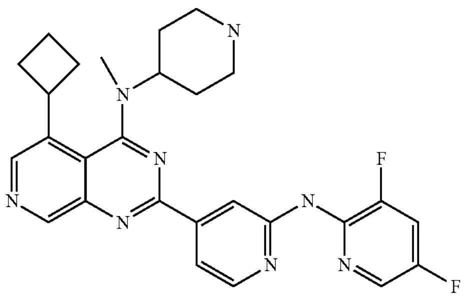 [SMILES: CN(c1nc(-c2ccnc(Nc3ncc(F)cc3F)c2)nc2cncc(C3CCC3)c12)C1CCNCC1] | [B4] | LCMS: Purity: >95%, RT: min, MI: 503 (M + H) | 1H-NMR: DMSO 10.17 (br s, 1H), 9.06 (s, 1H), 8.81(br m, 1H), 8.66 (s, 1H), 8.61 (s, 1H), 8.40 (d, 1H, J = 5.6 Hz), 8.35 (m, 1H), 8.29 (d, 1H, J = 2.5 Hz), 8.05 (m, 1H), 7.99 (m, 1H), 4.82 (m, 1H), 4.16 (m, 1H), 3.51 (m, 1H), 3.39 (m, 1H), 3.15 (m, 2H), 2.98 (s, 3H), 2.64 (m, 1H), 2.22-2.37 (br m, 4H), 1.84-2.11 (br m, 5H) | {5-Cyclobutyl-2-[2-(3,5-difluoro-pyridin-2-ylamino)-pyridin-4-yl]-pyrido[3,4-d]pyrimidin-4-yl}-methyl-piperidin-4-yl-amine |
| 2158 | 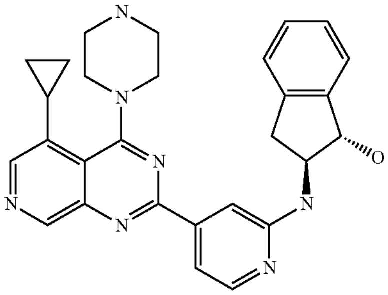 [SMILES: O[C@H]1c2ccccc2C[C@@H]1Nc1cc(-c2nc(N3CCNCC3)c3c(C4CC4)cncc3n2)ccn1] | [B4] | LCMS: Purity: 97%, RT: min, MI: 480.26 (MH)+ | (400 MHz, d6-DMSO, δ): 9.08 (s, 1H), 8.97 (br s, 2H), 8.22 (s, 1H), 8.15 (d, J = 6.5 Hz, 1H), 8.09 (s, 1H), 7.71 (d, J = 6.4 Hz, 1H), 7.40-7.27 (m, 4H), 5.10 (d, J = 6.6 Hz, 1H), 4.40-4.30 (m, 1H), 3.93 (br s, 4H), 3.44 (dd, J = 15.6, 7.7 Hz, 1H), 3.32 (br s, 4H), 2.82 (dd, J = 15.1, 8.1 Hz, 1H), 2.70-2.63 (m, 1H), 1.29-1.23 (m, 2H), 1.11-1.06 (m, 2H). | trans-2-[4-(5-Cyclopropyl-4-piperazin-1-yl-pyrido[3,4-d]pyrimidin-2-yl)-pyridin-2-ylamino]-indan-1-ol |
| 2159 | 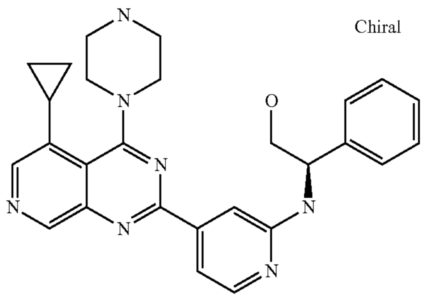 [SMILES: OC[C@H](Nc1cc(-c2nc(N3CCNCC3)c3c(C4CC4)cncc3n2)ccn1)c1ccccc1] Chiral | [B4] | LCMS: Purity: 98%, RT: min, MI: 468.1 (MH)+ | (400 MHz, d6-DMSO, δ): 9.10-8.90 (m, 3H), 8.21 (d, J = 2.7 Hz, 1H), 8.15-7.95 (m, 2H), 7.67 (d, J = 5.2 Hz, 1H), 7.47-7.27 (m, 5H), 5.04 (s, 1H), 4.10-3.65 (m, 6H), 3.32 (br s, 4H), 2.70-2.60 (m, 1H), 1.29-1.22 (m, 2H), 1.10-1.05 (m, 2H). | (R)-2-[4-(5-Cyclopropyl-4-piperazin-1-yl-pyrido[3,4-d]pyrimidin-2-yl)-pyridin-2-ylamino]-2-phenyl-ethanol |

-continued

| Ex | Structure | Scheme | LCMS | $^1$H-NMR | Name |
|---|---|---|---|---|---|
| 2160 | 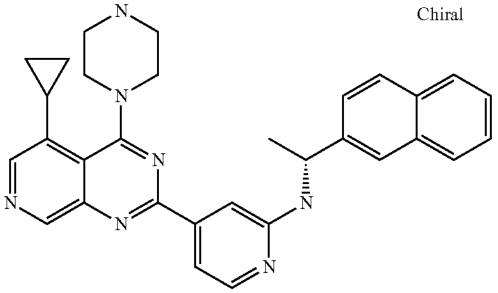 [SMILES: C[C@@H](Nc1cc(-c2nc(N3CCNCC3)c3c(C4CC4)cncc3n2)ccn1)c1ccc2ccccc2c1] Chiral | [B4] | LCMS Purity: 96%, RT: min, MI: 502.1 (MH)+ | (400 MHz, d6-DMSO, δ): 9.04 (s, 1H), 8.82 (br s, 2H), 8.19 (s, 1H), 8.07 (d, J = 5.7 Hz, 1H), 7.95-7.87 (m, 4H), 7.62 (dd, J = 8.6, 1.7 Hz, 1H), 7.58 (br s, 1H), 7.52-7.46 (m, 2H), 5.27-5.22 (m, 1H), 3.83 (br s, 4H), 3.30 (br s, 4H), 2.69-2.61 (m, 1H), 1.63 (d, J = 6.7 Hz, 3H), 1.28-1.22 (m, 2H), 1.10-1.05 (m, 2H). | [4-(5-Cyclopropyl-4-piperazin-1-yl-pyrido[3,4-d]pyrimidin-2-yl)-pyridin-2-yl]-((R)-1-naphthalen-2-yl-ethyl)-amine |
| 2161 | 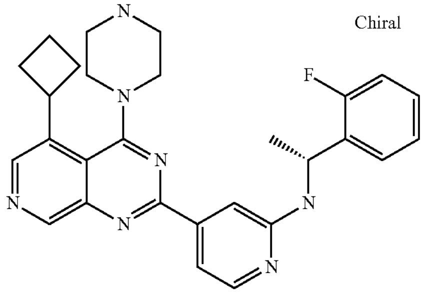 [SMILES: C[C@@H](Nc1cc(-c2nc(N3CCNCC3)c3c(C4CCC4)cncc3n2)ccn1)c1ccccc1F] Chiral | [B4] | LCMS: Purity: >90%, RT: min, MI: 484.1 (M + H) | (dmso-d6) 9.13 (s, 1H), 9.03 (br signal, 2H), 8.81 (s, 1H), 8.08 (d, J = 6.0 Hz, 1H), 7.89 (br s, 1H), 7.62 (d, J = 6.0 Hz, 1H), 7.47 (m, 1H), 7.32 (m, 1H), 7.28-7.13 (m, 2H), 5.33 (m, 1H), 4.23 (m, 1H), 3.80 (m, 4H), 3.30 (m, 4H), 2.45 (m, 2H), 2.24-2.00 (m, 3H), 1.92 (m, 1H), 1.55 (d, J = 6.8 Hz, 3H) | [4-(5-Cyclobutyl-4-piperazin-1-yl-pyrido[3,4-d]pyrimidin-2-yl)-pyridin-2-yl]-[(R)-1-(2-fluoro-phenyl)-ethyl]-amine |
| 2162 | 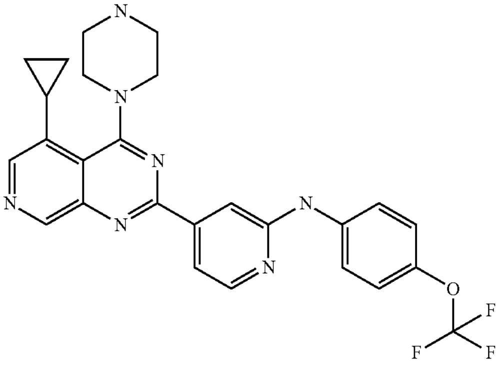 [SMILES: FC(F)(F)Oc1ccc(Nc2cc(-c3nc(N4CCNCC4)c4c(C5CC5)cncc4n3)ccn2)cc1] | [B4] | Method 5: RT: 3.11 min, MI: 508 [M + H] | (500 MH, d6-DMSO) 9.68 (1H, s), 9.07 (1H, s), 8.35 (1H, d), 8.18 (1H, s), 7.97 (1H, s), 7.85 (2H, d), 7.76 (1H, d), 7.30 (2H, d), 3.92 (4H, s, broad), 3.33 (4H, s), 2.69 (1H, m), 1.25 (2H, m), 1.08 (2H, m). | [4-(5-Cyclopropyl-4-piperazin-1-yl-pyrido[3,4-d]pyrimidin-2-yl)-pyridin-2-yl]-(4-trifluoromethoxy-phenyl)-amine |
| 2163 | 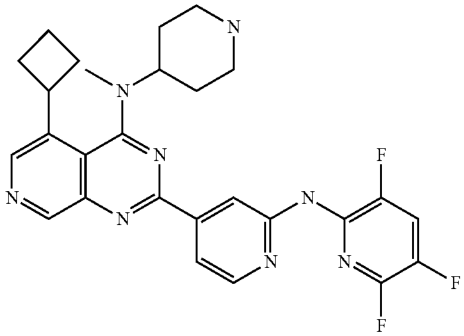 [SMILES: CN(c1nc(-c2ccnc(Nc3nc(F)c(F)cc3F)c2)nc2cncc(C3CCC3)c12)C1CCNCC1] | [B4] | LCMS: Purity: 95%, RT: min, MI: 521 (M + H) | 1H-NMR: 9.80 (s, 1H), 9.05 (s, 1H), 8.73 (m, 1H), 8.65 (s, 1H), 8.56 (s, 1H), 8.41 (d, 1H, J = 5.2 Hz), 8.30 (m, 2H), 7.95 (m, 1H), 4.79 (m, 1H), 4.16 (m, 1H), 3.50 (m, 1H), 3.37 (m, 1H), 3.15 (m, 2H), 2.98 (s, 3H), 2.62 (m, 1H), 2.23-2.37 (br m, 4H), 1.84-2.10 (br m, 5H) | {5-Cyclobutyl-2-[2-(3,5,6-trifluoro-pyridin-2-ylamino)-pyridin-4-yl]-pyrido[3,4-d]pyrimidin-4-yl}-methyl-piperidin-4-yl-amine |

-continued

| | | | Analysis | | |
|---|---|---|---|---|---|
| Ex | Structure | Scheme | LCMS | $^1$H-NMR | Name |
| 2164 | 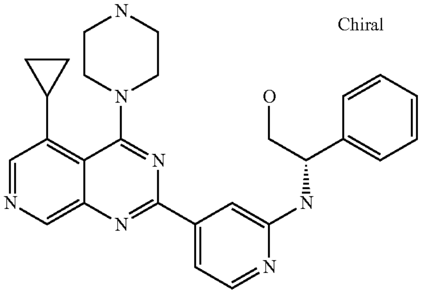 [SMILES: OC[C@@H](Nc1cc(-c2nc(N3CCNCC3)c3c(C4CC4)cncc3n2)ccn1)c1ccccc1] Chiral | [B4] | LCMS: Purity: 90%, RT: min, MI: 468.24 (MH)+ | (400 MHz, d6-DMSO, δ): 9.06 (s, 1H), 8.99 (br s, 2H), 8.21 (s, 1H), 8.12-7.95 (m, 2H), 7.67 (d, J = 6.3 Hz, 1H), 7.49-7.27 (m, 5H), 5.08-5.00 (m, 1H), 4.10-3.65 (m, 6H), 3.33 (br s, 4H), 2.70-2.61 (m, 1H), 1.29-1.23 (m, 2H), 1.11-1.05 (m, 2H). | (S)-2-[5-(5-Cyclopropyl-4-piperazin-1-yl-pyrido[3,4-d]pyrimidin-2-yl)-pyridin-2-ylamino]-2-phenyl-ethanol |
| 2165 | 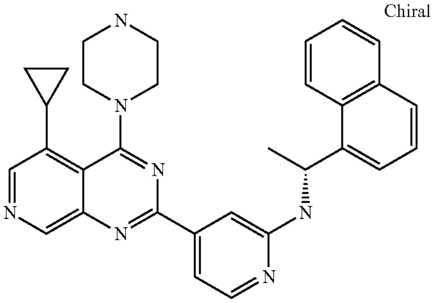 [SMILES: C[C@@H](Nc1cc(-c2nc(N3CCNCC3)c3c(C4CC4)cncc3n2)ccn1)c1cccc2ccccc12] Chiral | [B4] | LCMS: Purity: 95%, RT: min, MI: 502.24 (MH)+ | (400 MHz, d6-DMSO, δ): 9.00 (s, 1H), 8.86 (br s, 2H), 8.27-8.22 (m, 1H), 8.18 (s, 1H), 8.07 (d, J = 6.0 Hz, 1H), 7.85 (d, J = 8.0 Hz, 1H), 7.66-7.47 (m, 4H), 5.91-5.85 (m, 1H), 3.80 (br s, 4H), 3.24 (br s, 4H), 2.66-2.59 (m, 1H), 1.67 (d, J = 6.4 Hz, 3H), 1.27-1.21 (m, 2H), 1.09-1.04 (m, 2H). | [4-(5-Cyclopropyl-4-piperazin-1-yl-pyrido[3,4-d]pyrimidin-2-yl)-pyridin-2-yl]-((R)-1-naphthalen-1-yl-ethyl)-amine |
| 2166 | 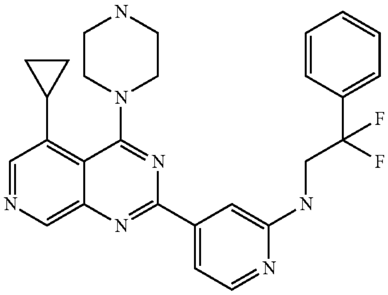 [SMILES: FC(F)(CNc1cc(-c2nc(N3CCNCC3)c3c(C4CC4)cncc3n2)ccn1)c1ccccc1] | [B4] | LCMS: Purity: 96%, RT: min, MI: 488.23 (MH)+ | (400 MHz, d6-DMSO, δ): 9.05 (d, J = 2.2 Hz, 1H), 8.89 (br s, 2H), 8.19 (s, 1H), 8.12 (d, J = 5.8 Hz, 1H), 7.85 (br s, 1H), 7.64-7.49 (m, 6H), 4.30-4.19 (m, 2H), 3.92 (br s, 4H), 3.31 (br s, 4H), 2.74-2.64 (m, 1H), 1.28-1.22 (m, 2H), 1.10-1.05 (m ,2H). | [4-(5-Cyclopropyl-4-piperazin-1-yl-pyrido[3,4-d]pyrimidin-2-yl)-pyridin-2-yl]-(2,2-difluoro-2-phenyl-ethyl)-amine |
| 2167 | 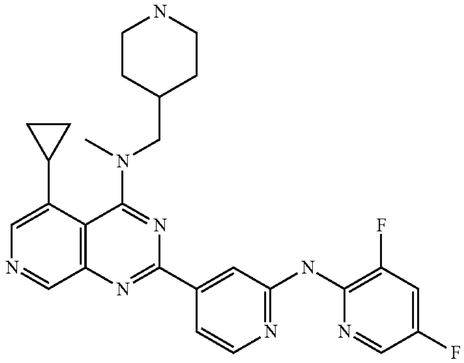 [SMILES: CN(CC1CCNCC1)c1nc(-c2ccnc(Nc3ncc(F)cc3F)c2)nc2cncc(C3CC3)c12] | [B4] | LCMS: Purity: 95%, RT: min, MI: 503 (M + H) | 1H-NMR: DMSO 10.33 (br s, 1H), 9.00 (s, 1H), 8.71 (s, 1H), 8.50 (m, 1H), 8.41 (d, 1H, J = 5.7 Hz), 8.28 (d, 1H, J = 2.5 Hz), 8.17 (s, 1H), 8.08 (m, 2H), 7.99 (m, 1H), 3.30 (s, 3h), 3.16 (m, 2H), 2.80 (m, 2H), 2.38 (m, 1H), 2.19 (m, 1H), 1.57 (br m, 2H), 1.29 (m, 2H), 1.03 (m, 6H) | {5-Cyclopropyl-2-[2-(3,5-difluoro-pyridin-2-ylamino)-pyridin-4-yl]-pyrido[3,4-d]pyrimidin-4-yl}-methyl-piperidin-4-ylmethyl-amine |

-continued

| Ex | Structure | Scheme | Analysis LCMS | $^1$H-NMR | Name |
|---|---|---|---|---|---|
| 2168 | 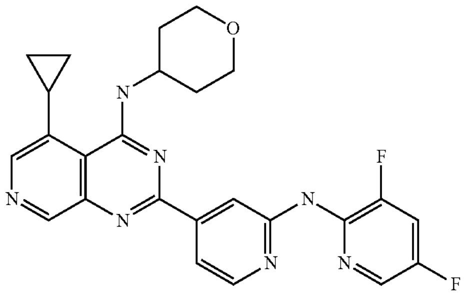 [SMILES: Fc1cnc(Nc2cc(-c3nc(NC4CCOCC4)c4c(C5CC5)cncc4n3)ccn2)c(F)c1] | [B4] | LCMS: Purity: >95%, RT: min, MI: 477 (M + H) | 1H-NMR: DMSO 10.17 (br s, 1H), 9.05 (s, 1H), 8.64 (s, 1H), 8.48 (s, 1H), 8.40 (d, 1H, J = 5.6 Hz), 8.28 (d, 1H, J = 2.5 Hz), 8.06 (m, 1H), 7.98 (m, 1lH), 7.87 (m, 1H), 4.53 (m, 1H), 3.95 (m, 2H), 3.53 (m, 2H), 2.61 (m, 1H), 2.13 (m, 2H), 1.79 (m, 2H), 1.22 (m, 2H), 1.06 (m, 2H) | {5-Cyclopropyl-2-[2-(3,5-difluoro-pyridin-2-ylamino)-pyridin-4-yl]-pyrido[3,4-d]pyrimidin-4-yl}-(tetrahydro-pyran-4-yl)-amine |
| 2169 | 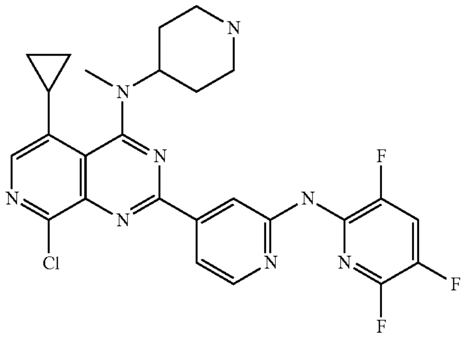 [SMILES: CN(c1nc(-c2ccnc(Nc3nc(F)c(F)cc3F)c2)nc2c(Cl)ncc(C3CC3)c12)C1CCNCC1] | [B4] | LCMS: Purity: 95%, RT: min, MI: 541 (M + H) | 1H-NMR: DMSO 9.76 (s, 1H), 8.73 (s, 1H), 8.71 (m, 1H), 8.43 (d, 1H, J = 5.2 Hz), 8.29 (m, 2H), 7.95 (m, 2H), 4.87 (m, 1H), 3.45 (m, 2H), 3.10 (s, 3H), 2.98 (m, 2H), 2.38 (m, 1H), 1.90-2.28 (br m, 4H), 1.14-1.29 (br m, 2H), 0.95 (m, 2H) | {8-Chloro-5-cyclopropyl-2-[2-(3,5,6-trifluoro-pyridin-2-ylamino)-pyridin-4-yl]-pyrido[3,4-d] pyrimidin-4-yl}-methyl-piperidin-4-yl-amine |
| 2170 | 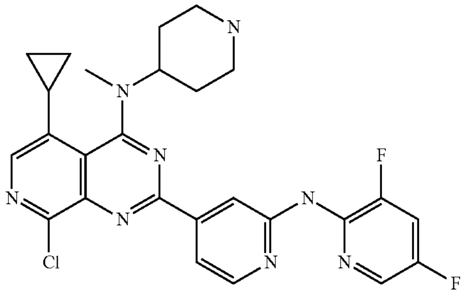 [SMILES: CN(c1nc(-c2ccnc(Nc3ncc(F)cc3F)c2)nc2c(Cl)ncc(C3CC3)c12)C1CCNCC1] | [B4] | LCMS: Purity: 95%, RT: min, MI: 523 (M + H) | 1H-NMR: DMSO 10.02 (br s, 1H), 8.79 (m, 1H), 8.66 (s, 1H), 8.39 (m, 2H), 8.26 (d, 1H, J = 2.5 Hz), 8.03 (m, 1H), 7.96 (2H), 4.89 (m, 1H), 3.45 (m, 2H), 3.12 (m, 2H), 3.10 (s, 3H), 2.37 (m, 1H), 1.90-2.15 (br m, 4H), 1.14-1.29 (br m, 2H), 0.95 (m, 2H) | {8-Chloro-5-cyclopropyl-2-[2-(3,5-difluoro-pyridin-2-ylamino)-pyridin-4-yl]-pyrido[3,4-d]pyrimidin-4-yl}-methyl-piperidin-4-yl-amine |
| 2171 | 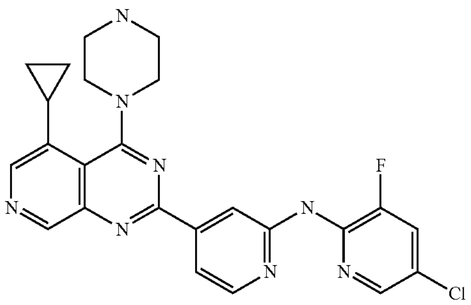 [SMILES: Fc1cc(Cl)cnc1Nc1cc(-c2nc(N3CCNCC3)c3c(C4CC4)cncc3n2)ccn1] | [B4] | LCMS: Purity: 95%, RT: min, MI: 477 (M + H) | 1H-NMR: DMSO 10.16 (s, 1H), 9.05-9.10 (m, 3H), 8.88 (s, 1H), 8.45 (m, 1H), 8.26 (d, 1H, J = 2.1 Hz), 8.20 (s, 1H), 8.10 (m, 1H), 8.02 (m, 1H), 3.94 (m, 4H), 3.34 (m, 4H), 2.69 (m, 1H), 1.27 (m, 2H), 1.09 (m, 2H) | (5-Chloro-3-fluoro-pyridin-2-yl)-[4-(5-cyclopropyl-4-piperazin-1-yl-pyrido[3,4-d]pyrimidin-2-yl)-pyridin-2-yl]-amine |

-continued

| Ex | Structure | Scheme | LCMS | $^1$H-NMR | Name |
|---|---|---|---|---|---|
| | | | Analysis | | |
| 2172 | 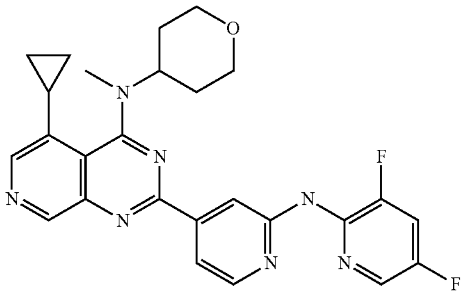 [SMILES: CN(c1nc(-c2ccnc(Nc3ncc(F)cc3F)c2)nc2cncc(C3CC3)c12)C1CCOCC1] | [B4] | LCMS: Purity: 95%, RT: min, MI: 490 (M + H) | 1H-NMR: DMSO 10.48 (br s, 1H), 8.99 (s, 1H), 8.65 (s, 1H), 8.41 (d, 1H, J = 5.8 Hz), 8.30 (d, 1H, J = 2.4 Hz), 8.18 (s, 1H), 8.09 (m, 1H), 7.98 (m, 1H), 4.81 (m, 1H), 3.97 (m, 2H), 3.48 (m, 2H), 3.15 (s, 3H), 2.40 (m, 1H), 1.75-2.07 (br m, 4H), 1.23 (m, 2H), 0.98 (m, 2H) | {5-Cyclopropyl-2-[2-(3,5-difluoro-pyridin-2-ylamino)-pyridin-4-yl]-pyrido[3,4-d]pyrimidin-4-yl}-methyl-(tetrahydro-pyran-4-yl)-amine |
| 2173 | 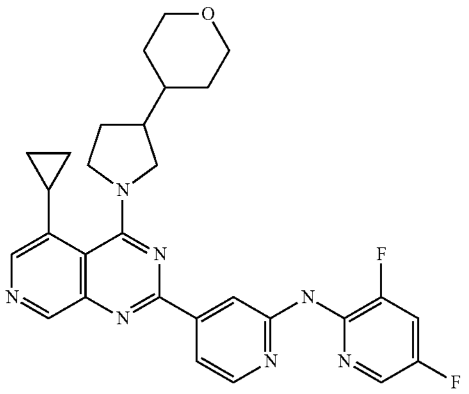 [SMILES: Fc1cnc(Nc2cc(-c3nc(N4CCC(C5CCOCC5)C4)c4c(C5CC5)cncc4n3)ccn2)c(F)c1] | [B4] | LCMS: Purity: 95%, RT: min, MI: 530 (M + H) | 1H-NMR: DMSO 10.73 (br s, 1H), 8.94 (s, 1H), 8.71 (s, 1H), 8.42 (d, 1H, J = 5.9 Hz), 8.29 (d, 1H, J = 2.5 Hz), 8.19 (s, 1H), 8.13 (m, 1H), 8.04 (m, 1H), 4.03 (m, 1H), 3.84 (m, 4H), 3.67 (m, 1H), 3.29 (m, 2H), 2.28 (m, 1H), 2.11 (m, 1H), 1.98 (m, 1H), 1.53 (m ,4H), 1.16-1.37 (br m, 4H), 1.03 (m, 1H), 0.94 (m, 1H) | (4-{5-Cyclopropyl-4-[3-(tetrahydro-pyran-4-yl)-pyrrolidin-1-yl]-pyrido[3,4-d]pyrimidin-2-yl}-pyridin-2-yl)-(3,5-difluoro-pyridin-2-yl)-amine |
| 2174 | 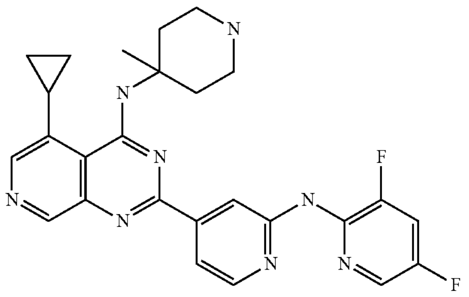 [SMILES: CC1(Nc2nc(-c3ccnc(Nc4ncc(F)cc4F)c3)nc3cncc(C4CC4)c23)CCNCC1] | [B4] | LCMS: Purity: 95%, RT: min, MI: 489 (M + H) | 1H-NMR: DMSO 10.09 (s, 1H), 9.08 (s, 1H), 8.73 (s, 1H), 8.59 (m, 1H), 8.53 (s, 1H), 8.50 (m, 1H), 8.41 (d, 1H, J = 5.5 Hz), 8.24 (d, 1H, J = 2.5 Hz), 8.05 (m, 1H), 7.95 (m, 1H), 7.69 (s, 1H), 3.24 (m, 2H), 3.17 (m, 2H), 2.74 (m, 2H), 2.64 (m, 1H), 2.06 (m, 2H), 1.75 (s, 3H), 1.22 (m, 2H), 1.16 (m, 2H) | {5-Cylcopropyl-2-[2-(3,5-difluoro-pyridin-2-ylamino)-pyridin-4-yl]-pyrido[3,4-d]pyrimidin-4-yl}-(4-methyl-piperidin-4-yl)-amine |
| 2175 | 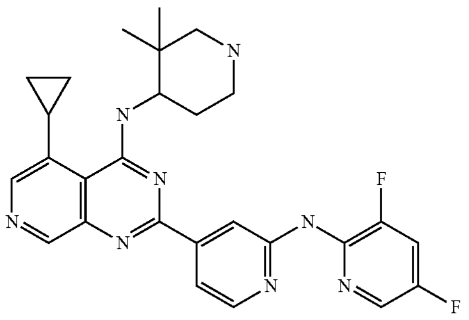 [SMILES: CC1(C)CNCCC1Nc1nc(-c2ccnc(Nc3ncc(F)cc3F)c2)nc2cncc(C3CC3)c12] | [B4] | LCMS: Purity: 95%, RT: min, MI: 503 (M + H) | 1H-NMR: DMSO 10.15 (br s, 1H), 9.09 (s, 1H), 9.07 (m, 1H), 8.63 (s, 1H), 8.52 (s, 1H), 8.41 (d, 1H, J = 5.6 Hz), 8.35 (m, 1H), 8.27 (d, 1H, J = 2.5 Hz), 8.05 (m, 2H), 7.67 (d, 1H, J = 8.7 Hz), 4.82 (m, 1H), 3.37 (m, 1H), 3.20 (m, 2H), 3.06 (m, 1H), 2.60 (m, 1H), 2.12 (m, 1H), 1.96 (m, 1H), 1.26 (m, 1H), 1.19 (s, 3H), 1.16 (m, 3H), 1.11 (s, 3H) | {5-Cyclopropyl-2-[2-(3,5-difluoro-pyridin-2-ylamino)-pyridin-4-yl]-pyrido[3,4-d]pyrimidin-4-yl}-(3,3-dimethyl-piperidin-4-yl)-amine |

-continued

| Ex | Structure | Scheme | Analysis LCMS | Analysis ¹H-NMR | Analysis Name |
|---|---|---|---|---|---|
| 2176 | 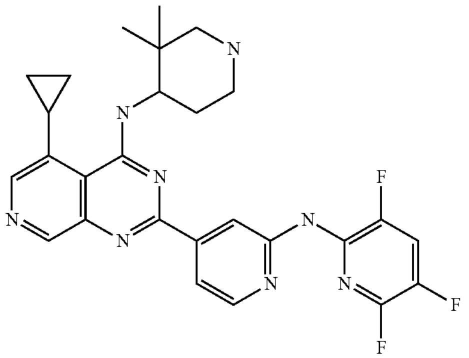 [SMILES: CC1(C)CNCCC1Nc1nc(-c2ccnc(Nc3nc(F)c(F)cc3F)c2)nc2cncc(C3CC3)c12] | [B4] | LCMS: Purity: 95%, RT: min, MI: 521 (M + H) | 1H-NMR: DMSO 9.72 (s, 1H), 9.06 (s, 1H), 8.99 (m, 1H), 8.58 (s, 1H), 8.51 (s, 1H), 8.40 (m, 1H), 8.27 (m, 2H), 8.00 (m, 1H), 7.64 (d, 1H, J = 8.8 Hz), 4.81 (m, 1H), 3.32 (m, 1H), 3.22 (m, 1H), 3.19 (m, 1H), 3.01 (m, 1H), 2.59 (m, 1H), 2.14 (m, 1H), 1.95 (m, 1H), 1.25 (m, 1H), 1.19 (s, 3H), 1.14 (m, 3H), 1.09 (s, 3H) | {5-Cylcopropyl-2-[2-(3,5,6-trifluoro-pyridin-2-ylamino)-pyridin-4-yl]-pyrido[3,4-d]pyrimidin-4-yl}-(3,3-dimethyl-piperidin-4-yl)-amine |
| 2177 | 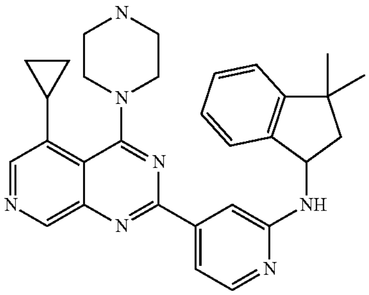 [SMILES: CC1(C)CC(Nc2cc(-c3nc(N4CCNCC4)c4c(C5CC5)cncc4n3)ccn2)c2ccccc21] | [B4] | LCMS: Purity: 92%, RT: min, MI: 492.26 (MH)+ | (400 MHz, d6-DMSO, δ): 9.06 (s, 1H), 8.85 (br s, 2H), 8.20 (s, 1H), 8.16 (d, J = 6.0 Hz, 1H), 7.61 (br s, 1H), 7.34-7.20 (m, 4H), 5.62-5.55 (m, 1H), 3.88 (br s, 4H), 3.31 (br s, 4H), 2.70-2.63 (m, 1H), 1.85-1.79 (m, 1H), 1.40 (s, 3H), 1.28-1.23 (m, 6H), 1.11-1.06 (m, 2H). | [4-(5-Cyclopropyl-4-piperazin-1-yl-pyrido[3,4-d]pyrimidin-2-yl)-pyridin-2-yl]-(3,3-dimethyl-indan-1-yl)-amine |
| 2178 | 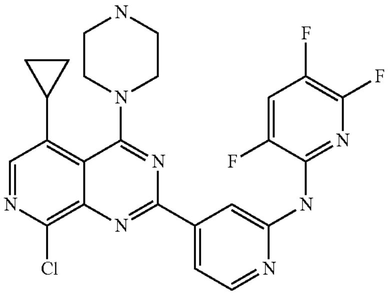 [SMILES: Fc1cc(F)c(Nc2cc(-c3nc(N4CCNCC4)c4c(C5CC5)cnc(Cl)c4n3)ccn2)nc1F] | [B4] | LCMS: Purity: 99%, RT: min, MI: 513 (M + H) | 1H NMR (400 MHz, DMSO-d6) 9.79 (1 H, s), 8.65-9.06 (3 H, m), 8.41-8.51 (1 H, m), 8.20-8.36 (1 H, m), 7.90-8.04 (2 H, m), 3.98 (4 H, br. s.), 3.30 (4 H, br. s.), 2.56-2.65 (1 H, m), 1.19-1.28 (2 H, m), 1.00-1.10 (2 H, m) | [4-(8-Chloro-5-cyclopropyl-4-piperazin-1-yl-pyrido[3,4-d]pyrimidin-2-yl)-pyridin-2-yl]-(3,5,6,-trifluoro-pyridin-2-yl)-amine |
| 2179 | 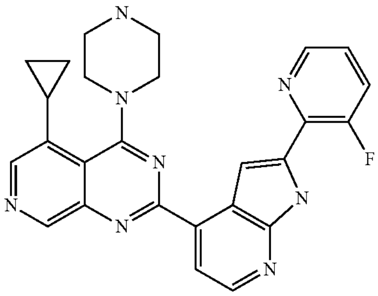 [SMILES: Fc1cccnc1-c1cc2c(-c3nc(N4CCNCC4)c4c(C5CC5)cncc4n3)ccnc2[nH]1] | [D4], [D3] | LCMS: Purity: 96%, RT: min, MI: 467.21 | (dmso-d6) 12.45 (d, J = 1.4 Hz, 1H), 9.13 (s, 1H), 8.96 (br s, 2H), 8.62 (m, 1H), 8.51 (d, J = 5.0 Hz, 1H), 8.20 (m, 3H), 7.93 (m, 1H), 7.53 (m, 1H), 3.98 (br s, 4H), 3.38 (br s, 4H), 2.76 (m, 1H), 1.28 (m, 2H), 1.11 (m, 2H) | 5-Cyclopropyl-2-[2-(3-fluoro-pyridin-2-yl)-1H-pyrrolo[2,3-b]pyridin-4-yl]-4-piperazin-1-yl-pyrido[3,4-d]pyrimidine |

-continued

| Ex | Structure | Scheme | LCMS | $^1$H-NMR | Name |
|---|---|---|---|---|---|
| | | | Analysis | | |
| 2180 | 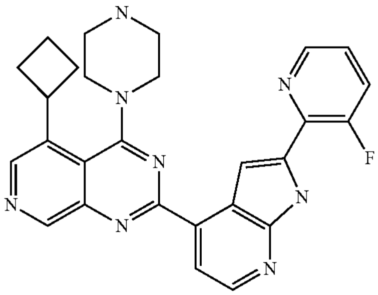 [SMILES: Fc1cccnc1-c1cc2c(-c3nc(N4CCNCC4)c4c(C5CCC5)cncc4n3)ccnc2[nH]1] | [D4], [D3] | LCMS: Purity: 96%, RT: min, MI: 481.22 (M + H) | (dmso-d6) 12.45 (d, J = 1.5 Hz, 1H), 9.20 (s, 1H), 8.99 (br s, 1H), 8.89 (br s, 1H), 8.81 (s, 1H), 8.61 (m, 1H), 8.51 (d, J = 5.0 Hz, 1H), 8.19 (d, J = 5.0 Hz, 1H), 8.17 (m, 1H), 7.93 (m, 1H), 7.53 (m, 1H), 4.30 (m, 1H), 3.87 (m, 4H), 3.35 (m, 4H), 2.47 (m, 2H), 2.24 (m, 2H), 2.12 (m, 1H), 1.93 (m, 1H) | 5-Cyclobutyl-2-[2-(3-fluoro-pyridin-2-yl)-1H-pyrrolo[2,3-b]pyridin-4-yl]-4-piperazin-1-yl-pyrido[3,4-d]pyrimidine |
| 2181 | 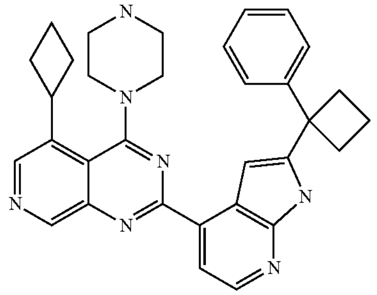 [SMILES: c1ccc(C2(c3cc4c(-c5nc(N6CCNCC6)c6c(C7CCC7)cncc6n5)ccnc4[nH]3)CCC2)cc1] | [D4], [D3] | Method 5: RT: 3.27 min, MI: 516 [M + H] | (500 MHz, d6-DMSO) 11.86 (brs, 1H), 9.19 (s, 1H), 8.97 (brs, 1H), 8.82 (brs, 1H), 8.77 (s, 1H), 8.28 (d, 1H), 8.06 (d, 1H), 7.53-7.40 (m, 2H), 7.38-7.30 (m, 2H), 7.25-7.15 (m, 2H), 4.27 (q, 1H), 3.90-3.56 (m, 5H), 3.40-3.20 (m, 4H), 3.08 (m, 1H), 2.97-2.85 (m, 2H), 2.78-2.67 (m, 2H), 2.27-2.16 (m, 2H), 2.15-2.03 (m, 2H), 1.95-1.87 (m, 2H). | 5-Cyclobutyl-2-[2-(1-phenyl-cyclobutyl)-1H-pyrrolo[2,3-b]pyridin-4-yl]-4-piperazin-1-yl-pyrido[3,4-d]pyrimidine |
| 2182 | 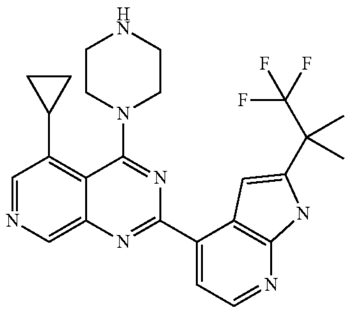 | [D4], [D3] | Method 5: RT: 2.98 min, MI: 496 [M + H] | (500 MHz, d6-DMSO) 12.11 (brs, 1H), 9.25 (s, 1H), 9.07 (brs, 1H), 8.92 (brs, 1H), 8.79 (s, 1H), 8.43 (d, 1H), 8.12 (d, 1H), 7.46 (d, 1H), 4.28 (q, 1H), 3.99-3.70 (m, 4H), 3.45-3.20 (m, 4H), 2.52-2.42 (m, 2H), 2.28-2.16 (m, 2H), 2.10 (m, 1H), 1.92 (m, 1H), 1.69 (s, 6H). | 5-Cyclobutyl-4-piperazin-1-yl-2-[2-(2,2,2-trifluoro-1,1-dimethyl-ethyl)-1H-pyrrolo[2,3- b]pyridin-4-yl]-pyrido [3,4-d]pyrimidine |
| 2183 | 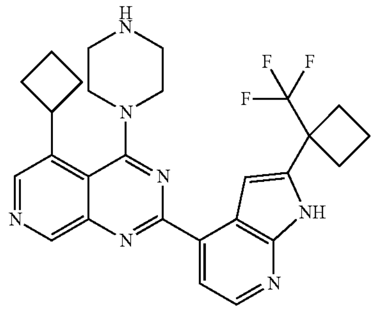 [SMILES: FC(F)(F)C1(c2cc3c(-c4nc(N5CCNCC5)c5c(C6CCC6)cncc5n4)ccnc3[nH]2)CCC1] | [D4], [D3] | Method 5: RT: 3.06 min, MI: 508 [M + H] | (d6-DMSO, 600 MHz) 12.20 (brs, 1H), 9.25 (s, 1H), 8.98 (brs, 1H), 8.84 (brs, 1h), 8.80 (s, 1H), 8.43 (d, 1H), 8.14 (d, 1H), 7.49 (d, 1H), 4.29 (q, 1H), 3.98-3.71 (m, 4H), 3.46-3.21 (m, 4H), 2.84-2.59 (m, 4H), 2.50-2.41 (m, 2H), 2.30-2.18 (m, 2H), 2.18-2.00 (m, 3H), 1.93 (m, 1H). | 5-Cyclobutyl-4-piperazin-1-yl-2-[2-(1-trifluoromethyl-cyclobutyl)-1H-pyrrolo [2,3-b]pyridin-4-yl]-pyrido[3,4-d]pyrimidine |

-continued

| Ex | Structure | Scheme | LCMS | Analysis $^1$H-NMR | Name |
|---|---|---|---|---|---|
| 2184 | 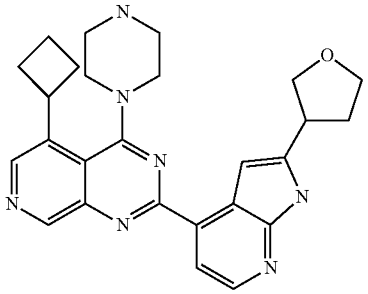 [SMILES: c1cc(-c2nc(N3CCNCC3)c3c(C4CCC4)cncc3n2)c2cc(C3CCOC3)[nH]c2n1] | [D4], [D3] | Method 5: RT: 5.02 min, MI: 456 [M + H] | (500 MHz, d6-DMSO) 11.80 (1H, s), 9.05 (1H, s), 8.29 (1H, d, J = 5.0 Hz), 8.08 (1H, s), 8.06 (1H, d, J = 5.0 Hz), 7.28 (1H, d, J = 1.3 Hz), 4.13 (1H, t, J = 7.6 Hz), 3.98-3.93 (1H, m), 8.89-8.84 (1H, m), 3.80-3.77 (1H, t, J = 7.7 Hz), 3.68-3.61 (1H, m), 3.92-3.50 (4H, very broad s), 2.89 (4H, s), 2.71-2.65 (1H, m), 2.42-2.35 (1H, m), 2.21-2.14 (1H, m), 1.28-1.24 (2H, m), 1.05-1.02 (2H, m). | 5-Cyclobutyl-4-piperazin-1-yl-2-[2-(tetrahydro-furan-3-yl)-1H-pyrrolo[2,3-b]pyridin-4-yl]-pyrido[3,4-d]pyrimidine |
| 2185 | 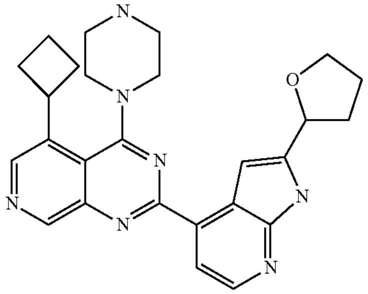 [SMILES: c1cc(-c2nc(N3CCNCC3)c3c(C4CCC4)cncc3n2)c2cc(C3CCCO3)[nH]c2n1] | [D4], [D3] | Method 5: RT: 2.51 min, MI: 456 [M + H] | (500 MHz, d6-DMSO) 11.82 (1H, s), 9.13 (1H, s), 8.70 (1H, s), 8.32 (1H, d, J = 4.9 Hz), 8.06 (1H, d, J = 4.9 Hz), 7.33 (1H, d, J = 1.7 Hz), 5.09 (1H, t, J = 6.8 Hz), 4.32-4.25 (1H, m), 4.03-3.98 (1H, m) 3.87-3.82 (1H, m), 3.68 (2H, br s), 3.51 (2H, br s), 2.94 (2H, br s), 2.87 (2H, br s), 2.38-2.28 (1H, m), 2.23-2.15 (2H, m), 2.12-1.96 (5H, m), 1.93-1.89 (1H, m). | 5-Cyclobutyl-4-piperazin-1-yl-2-[2-(tetrahydro-furan-2-yl)-1H-pyrrolo[2,3-b]pyridin-4-yl]-pyrido[3,4-d]pyrimidine |
| 2186 | 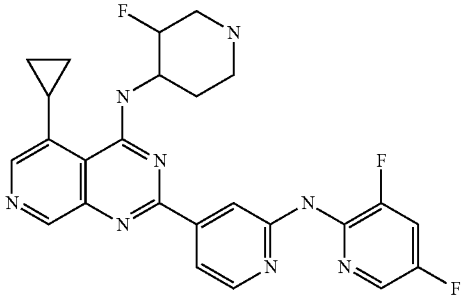 [SMILES: Fc1cnc(Nc2cc(-c3nc(NC4CCNCC4F)c4c(C5CC5)cncc4n3)ccn2)c(F)c1] | [B4] | LCMS: Purity: 95% RT: min, MI: 493 (M + H) | 1H-NMR: DMSO 9.97 (br s, 1H), 9.21 (m, 1H), 9.12 (s, 1H), 8.79 (m, 1H), 8.62 (s, 1H), 8.54 (s, 1H), 8.39 (d, 1H, J = 5.5 Hz), 8.28 (d, 1H, J = 2.5 Hz), 8.02 (m, 3H), 5.37-5.44 (br m, 1H), 4.85-4.96 (br m, 1H), 3.77 (m, 1H), 3.40-3.63 (br m, 2H), 3.27 (m, 1H), 2.59 (m, 1H), 2.33 (m, 1H), 2.07 (m, 1H), 1.21 (m, 2H), 1.13 (m, 2H) | {5-Cyclopropyl-2-[2-(3,5-difluoro-pyridin-2-ylamino)-pyridin-4-yl]-pyrido[3,4-d]pyrimidin-4-yl}-(3-fluoro-piperidin-4-yl)-amine |
| 2187 | 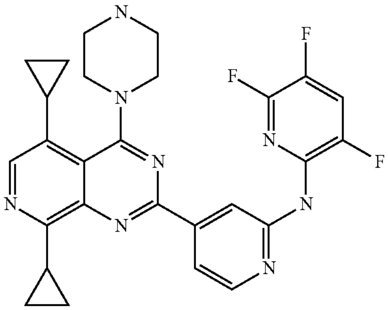 [SMILES: Fc1cc(F)c(Nc2cc(-c3nc(N4CCNCC4)c4c(C5CC5)cnc(C5CC5)c4n3)ccn2)nc1F] | [B4] | LCMS: Purity: 95%, RT: min, MI: 519 (M + H) | 1H NMR (400 MHz, DMSO-d6) 9.76 (1H, s), 9.05 (1H, s), 8.86 (2H, br. s), 8.46 (1H, d, J = 5.0 Hz), 8.20-8.35 (1H, m), 7.95-8.05 (2H, m), 3.74-4.06 (4H, m), 3.49-3.63 (1H, m), 3.31 (4H, br. s.), 2.57-2.70 (1H, m), 1.05-1.25 (6H, m), 0.90-1.03 (2H, m) | [4-(5,8-Dicyclopropyl-4-piperazin-1-yl-pyrido[3,4-d]pyrimidin-2-yl)-pyridin-2-yl]-(3,5,6-trifluoro-pyridin-2-yl)-amine |

-continued

| Ex | Structure | Scheme | LCMS | $^1$H-NMR | Name |
|---|---|---|---|---|---|
| | | | Analysis | | |
| 2188 | 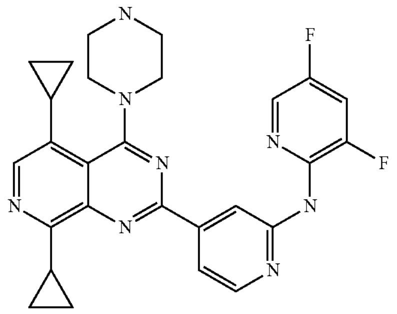 [SMILES: Fc1cnc(Nc2cc(-c3nc(N4CCNCC4)c4c(C5CC5)cnc(C5CC5)c4n3)ccn2)c(F)c1] | [B4] | LCMS: Purity: 90%, RT: min, MI: 501 (M + H) | 1H NMR (400 Mhz, DMSO-d6) 9.84 (1H, br. s), 8.63-9.04 (3H, m), 8.41 (1H, d, J = 5.0 Hz), 8.25 (1H, d, J = 2.5 Hz), 7.92-8.09 (3H, m), 3.90 (4H, br. s), 3.47-3.58 (1H, m), 3.32 (4H, br. s), 2.57-2.65 (1H, m), 1.05-1.26 (6H, m), 0.90-1.00 (2H, m) | [4-(5,8-Dicyclopropyl-4-piperazin-1-yl-pyrido[3,4-d]pyrimidin-2-yl)-pyridin-2-yl]-(3,5-difluoro-pyridin-2-yl)-amine |
| 2189 | 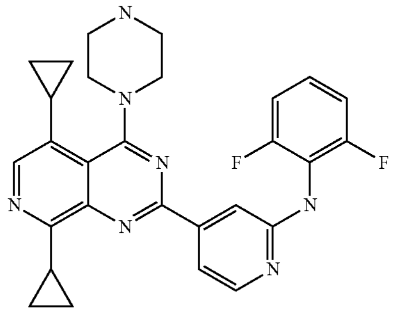 [SMILES: Fc1cccc(F)c1Nc1cc(-c2nc(N3CCNCC3)c3c(C4CC4)cnc(C4CC4)c3n2)ccn1] | [B4] | LCMS: Purity: 90%, RT: min, MI: 500 (M + H) | 1H NMR (400 MHz, DMSO-d6) 8.83 (2H, s), 8.19 (1H, d, J = 5.3 Hz), 8.00 (1H, s), 7.88 (1H, s), 7.73 (1H, dd, J = 5.4, 1.4 Hz), 7.23-7.34 (1H, m), 7.11-7.21 (2H, m), 3.85-3.96 (4H, m), 3.46-3.49 (1H, m), 3.30 (4H, br. s), 2.57-2.65 (1H, m), 1.05-1.23 (6H, m), 0.96 (2H, m) | [4-(5,8-Dicyclopropyl-4-piperazin-1-yl-pyrido[3,4-d]pyrimidin-2-yl)-pyridin-2-yl]-(2,6-difluoro-phenyl)-amine |
| 2190 | 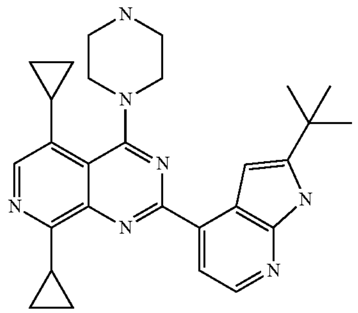 [SMILES: CC(C)(C)c1cc2c(-c3nc(N4CCNCC4)c4c(C5CC5)cnc(C5CC5)c4n3)ccnc2[nH]1] | [D4], [D3] | LCMS: Purity: 95%, RT: min, MI: 468 (M + H) | 1H NMR (400 MHz, DMSO-d6) 11.80 (1H, d, J = 1.8 Hz), 8.48-9.20 (2H, m), 8.32 (1H, d, J = 5.0 Hz), 8.12 (1H, d, J = 5.0 Hz), 8.00 (1H, s), 7.24 (1H, d, J = 2.3 Hz), 3.71-4.20 (4H, m), 3.47-3.59 (1H, m), 3.34 (4H, br. s), 2.63-2.76 (1H, m), 1.41 (9H, s), 1.10-1.28 (6H, m), 0.89-1.00 (2H, m) | 2-(2-tert-Butyl-1H-pyrrolo[2,3- b]pyridin-4-yl)-5,8-dicyclopropyl-4-piperazin-1-yl-pyrido[3,4-d]pyrimidine |
| 2191 | 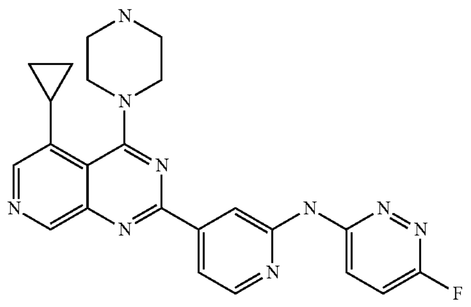 [SMILES: Fc1ccc(Nc2cc(-c3nc(N4CCNCC4)c4c(C5CC5)cncc4n3)ccn2)nn1] | [B4] | Method 5: RT: 1.86 min, MI: 444 [M + H] | (500 MHz, DMSO) 9.08 (1H, s), 9.07 (1H, s), 8.76 (1H, s), 8.46 (1H, d), 8.35 (1H, m), 8.19 (1H, s), 7.93 (1H, dd), 7.63 (1H, dd), 7.43 (2H, dd), 7.17 (2H, m), 3.95 (4H, br s), 3.33 (4H, s), 2.69 (1H, m), 1.25 (2H, m), 1.09 (2H, m). | [4-(5-Cyclopropyl-4-piperazin-1-yl-pyrido[3,4-d]pyrimidin-2-yl)-pyridin-2-yl]-(6-fluoro-pyridazin-3-yl)-amine |

-continued

| Ex | Structure | Scheme | LCMS (Analysis) | ¹H-NMR (Analysis) | Name |
|---|---|---|---|---|---|
| 2192 | 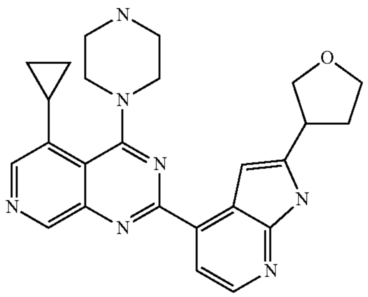 [SMILES: c1cc(-c2nc(N3CCNCC3)c3c(C4CC4)cncc3n2)c2cc(C3CCOC3)[nH]c2n1] | [D4], [D3] | Method 5: RT: 3.08 min, MI: 442 [M + H] | (500 MHz, d6-DMSO) 11.80 (1H, s), 9.05 (1H, s), 8.29 (1H, d, J = 5.0 Hz), 8.08 (1H, s), 8.06 (1H, d, J = 5.0 Hz), 7.28 (1H, d, J = 1.3 Hz), 4.13 (1H, t, J = 7.6 Hz), 3.98-3.93 (1H, m), 8.89-8.84 (1H, m), 3.80-3.77 (1H, t, J = 7.7 Hz), 3.68-3.61 (1H, m), 3.92-3.50 (4H very broad s), 2.89 (4H, s), 2.71-2.65 (1H, m), 2.42-2.35 (1H, m), 2.21-2.14 (1H, m), 1.28-1.24 (2H, m), 1.05-1.02 (2H, m). | 5-Cyclopropyl-4-piperazin-1-yl-2-[2-(tetrahydro-furan-3-yl)-1H-pyrrolo[2,3-b]pyridin-4-yl]-pyrido[3,4-d]pyrimidine |
| 2193 | 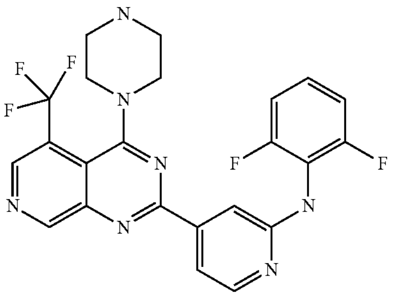 [SMILES: Fc1cccc(F)c1Nc1cc(-c2nc(N3CCNCC3)c3c(C(F)(F)F)cncc3n2)ccn1] | [B1] | LCMS: Purity: 90%, RT: min, MI: 488 (M + H)+ | 1H NMR (400 MHz, DMSO-d6) δ ppm 9.55 (br. s, 1H) 9.05 (br. s, 1H) 8.79-8.87 (m, 2H) 8.21 (d, J = 5.3 Hz, 1H) 7.82 (s, 1H) 7.69 (dd, J = 5.3, 1.3 Hz, 1H) 7.23-7.35 (m, 1H) 7.10-7.22 (m, 2H) 3.51-4.03 (m, 9H) | (2,6-Difluoro-phenyl)-[4-(4-piperazin-1-yl-5-trifluoromethyl-pyrido[3,4-d]pyrimidin-2-yl)-pyridin-2-yl]-amine |
| 2194 | 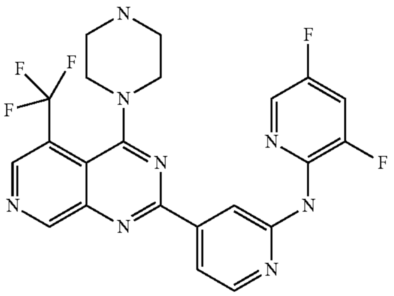 [SMILES: Fc1cnc(Nc2cc(-c3nc(N4CCNCC4)c4c(C(F)(F)F)cncc4n3)ccn2)c(F)c1] | [B1] | LCMS: Purity: 90%, RT: min, MI: 489 (M + H)+ | 1H NMR (400 MHz, DMSO-d6) δ ppm 9.65-9.72 (m, 1H) 9.58 (s, 1H) 9.06 (s, 1H) 8.80-8.98 (m, 2H) 8.76 (br. s, 1H) 8.38-8.47 (m, 1H) 8.27 (br. s, 1H) 7.99 (t, J = 8.4 Hz, 1H) 7.87-7.94 (m, 1H) 3.70-4.04 (m, 8H) | (3,5-Difluoro-pyridin-2-yl)-[4-(4-piperazin-1-yl-5-trifluoromethyl-pyrido[3,4-d]pyrimidin-2-yl)-pyridin-2-yl]-amine |
| 2195 | 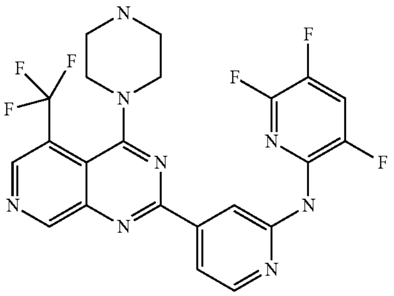 [SMILES: Fc1cc(F)c(Nc2cc(-c3nc(N4CCNCC4)c4c(C(F)(F)F)cncc4n3)ccn2)nc1F] | [B1] | LCMS: Purity: 90%, RT: min, MI: 507 (M + H)+ | 1H NMR (400 MHz, DMSO-d6) δ ppm 9.79-9.83 (m, 1H) 9.56 (s, 1H) 9.04-9.07 (m, 1H) 8.82-8.93 (m, 2H) 8.78-8.81 (m, 1H) 8.47 (d, J = 5.0 Hz, 1 H) 8.23-8.33 (m, 1H) 7.96 (dd, J = 5.3, 1.5 Hz, 1H) 3.70-4.12 (m, 9H) | [4-(4-Piperazin-1-yl-5-trifluoromethyl-pyrido[3,4-d]pyrimidin-2-yl)-pyridin-2-yl]-(3,5,6-trifluoro-pyridin-2-yl)-amine |

-continued

| Ex | Structure | Scheme | Analysis LCMS | Analysis $^1$H-NMR | Analysis Name |
|---|---|---|---|---|---|
| 2196 | 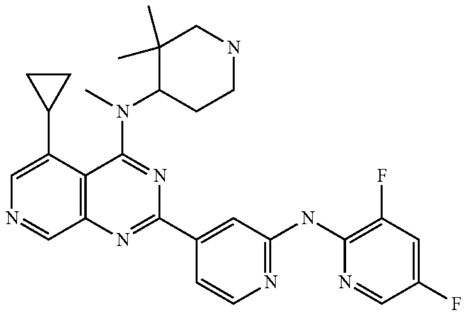 [SMILES: CN(c1nc(-c2ccnc(Nc3ncc(F)cc3F)c2)nc2cncc(C3CC3)c12)C1CCNCC1(C)C] | [B4] | LCMS: Purity: 95%, RT: min, MI: 517 (M + H) | 1H-NMR: DMSO 10.42 (br s, 1H), 9.14 (br m, 1H), 9.01 (s, 1H), 8.61 (br m, 1H), 8.41 (d, 1H, J = 5.7 Hz), 8.30 (br m, 1H), 8.28 (d, 1H, J = 2.4 Hz), 8.16 (s, 1H), 8.07 (m, 2H), 5.56 (m, 1H), 3.45 (m, 1H), 3.30 (m, 2H), 3.16 (s, 3H), 2.78 (m, 1H), 2.41 (m, 1H), 2.22 (m, 1H), 1.91 (m, 1H), 0.98-1.47 (br m, 10H) | {5-Cyclopropyl-2-[2-(3,5-difluoro-pyridin-2-ylamino)-pyridin-4-yl]-pyrido[3,4-d]pyrimidin-4-yl}-(3,3-dimethyl-piperidin-4-yl)-methyl-amine |
| 2197 | 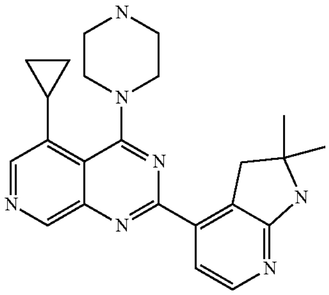 [SMILES: CC1(C)Cc2c(-c3nc(N4CCNCC4)c4c(C5CC5)cncc4n3)ccnc2N1] | [D3] | LCMS: Purity: 90%, RT: min, MI: 402 (M + H)+ | NH protons coalesced with water. 1H NMR (400 MHz, $CDCl_3$) δ ppm 9.10 (s, 1H) 8.04 (s, 1H) 7.95 (d, J = 4.5 Hz, 1H) 7.53 (d, J = 5.5 Hz, 1H) 7.27 (s, 1H) 4.83 (br. s, 1H) 3.54-3.92 (m, 4H), 3.48 (s, 2H) 3.04 (t, J = 4.8 Hz, 4H) 2.73 (tt, J = 8.5, 5.2 Hz, 1H) 1.40 (s, 6H) 0.98-1.05 (m, 2H) 0.85-0.91 (m, 2H) | 5-Cyclopropyl-2-(2,2-dimethyl-2,3-dihydro-1H-pyrrolo[2,3-b]pyridin-4-yl)-4-piperazin-1-yl-pyrido[3,4-d]pyrimidine |
| 2198 | 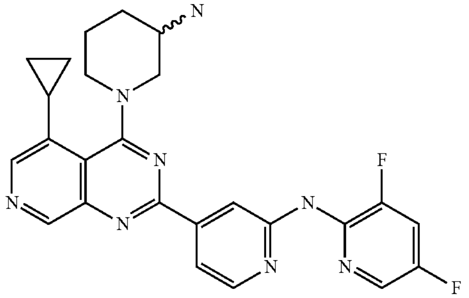 [SMILES: NC1CCCN(c2nc(-c3ccnc(Nc4ncc(F)cc4F)c3)nc3cncc(C4CC4)c23)C1] | [B4] | LCMS: LPurity: 95%, RT: min, MI: 475 (M + H) | 1H-NMR: DMSO 10.23 (br s, 1H), 9.05 (s, 1H), 8.73 (s, 1H), 8.42 (d, 1H, J = 5.6 Hz), 8.29 (d, 1H, J = 2.4 Hz), 8.19 (s, 1H) , 8.08 (br m, 4H), 4.44 (m, 1H), 4.07-4.23 (br m, 2H), 3.22-3.47 (br m, 3H), 2.67 (m ,1H), 2.07 (m, 1H), 1.84 (m, 1H), 1.61 (m, 1H), 1.26 (m, 2H), 1.05 (m, 2H) | {4-[4-(3-Amino-piperidin-1-yl)-5-cyclopropyl-pyrido[3,4-d]pyrimidin-2-yl]-pyridin-2-yl}-(3,5-difluoro-pyridin-2-yl)-amine |
| 2199 | 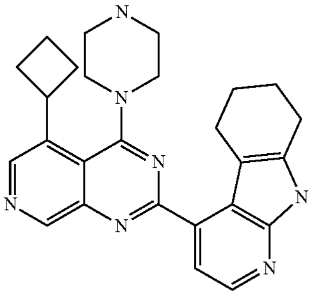 [SMILES: c1cc(-c2nc(N3CCNCC3)c3c(C4CCC4)cncc3n2)c2c3c([nH]c2n1)CCCC3] | [D3], [D9] | Method 5: RT: 3.31 min, MI: 440 [M + H] | (500 MHz, d6-DMSO) 11.59 (brs, 1H), 9.15 (s, 1H), 9.04 (brs, 1H), 8.91 (brs, 1H), 8.79 (s, 1H), 8.11 (d, 1H), 7.58 (d, 1H), 4.32-4.21 (m, 1H), 3.89-3.63 (m, 4H), 3.39-3.19 (m, 4H), 2.78-2.70 (m, 2H), 2.64-2.52 (m, 2H), 2.28-2.16 (m, 2H), 2.15-2.02 (m, 1H), 1.97-1.87 (m, 1H), 1.85-1.72 (m, 2H), 1.70-1.54 (m, 2H). | 4-(5-Cyclobutyl-4-piperazin-1-yl-pyrido[3,4-d]pyrimidin-2-yl)-6,7,8,9-tetrahydro-5H-pyrido[2,3-b]indole |

-continued

| Ex | Structure | Scheme | Analysis LCMS | $^1$H-NMR | Name |
|---|---|---|---|---|---|
| 2200 | 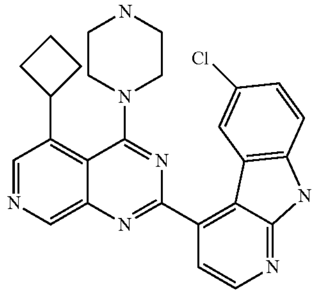 [SMILES: Clc1ccc2[nH]c3nccc(-c4nc(N5CCNCC5)c5c(C6CCC6)cncc5n4)c3c2c1] | [D3] | LCMS: Purity: 98%, RT: min, MI: 470 (M + H) | 1H-NMR (DMSO-d6, 400 MHz): 12.30 (s, 1H), 9.22 (s, 1H), 9.06 (d, 1H, J = 2.1 Hz), 8.90 (br s, 2H), 8.86 (s, 1H), 8.65 (d, 1H, J = 5.1 Hz), 8.03 (5.1 Hz), 7.58 (d, 1H, J = 8.6 Hz), 7.54 (dd, 1H, J = 2.1, 8.6 Hz), 4.30 (pent, 1H, J = 8.6 Hz), 3.86 (m, 4H), 3.2-3.4 (m, 4H), 2.28 (m, 2H), 2.14 (m, 1H), 1.94 (m, 1H) | 6-Chloro-4-(5-cyclobutyl-4-piperazin-1-yl-pyrido[3,4-d]pyrimidin-2-yl)-9H-pyrido[2,3-b]indole |
| 2201 | 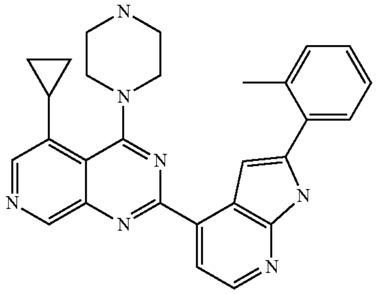 | [D4], [D3] | LCMS: Purity: 95%, RT: min, MI: 410.0 (MH)+ | (dmso-d6) 12.40 (d, J = 1.7 Hz, 1H), 9.14 (s, 1H), 8.95 (br s, 2H), 8.46 (d, J = 5.0 Hz, 1H), 8.18 (m, 2H), 8.10 (m, 1H), 7.98 (m, 1H), 7.52-7.35 (m, 3H), 3.98 (br s, 4H), 3.38 (br s, 4H), 2.76 (m, 1H), 1.27 (m, 2H), 1.10 (m, 2H) | 5-Cyclopropyl-2-[2-(2-fluoro-phenyl)-1H-pyrrolo[2,3-b]pyridin-4-yl]-4-piperazin-1-yl-pyrido[3,4-d]pyrimidine |
| 2202 | 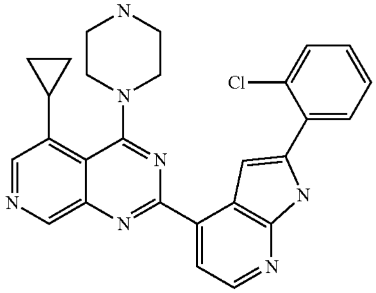 [SMILES: Clc1ccccc1-c1cc2c(-c3nc(N4CCNCC4)c4c(C5CC5)cncc4n3)ccnc2[nH]1] | [D4], [D3] | LCMS: Purity: 95%, RT: min, MI: 466.22 (M + H) | (dmso-d6) 12.32 (d, J = 1.7 Hz, 1H), 9.14 (s, 1H), 8.94 (br s, 2H), 8.47 (d, J = 5.0 Hz, 1H), 8.19 (d, J = 5.0 Hz, 1H), 8.19 (s, 1H), 7.94 (d, J = 2.2 Hz, 1H), 7.85 (dd, J = 7.7, 1.7 Hz, 1H), 7.67 (dd, J = 7.8, 1.4 Hz, 1H), 7.55-7.45 (m, 2H), 3.96 (br s, 4H), 3.37 (br s, 4H), 2.76 (m, 1H), 1.27 (m, 2H), 1.10 (m, 2H) | 2-[2-(2-Chloro-phenyl)-1H-pyrrolo[2,3-b]pyridin-4-yl]-5-cyclopropyl-4-piperazin-1-yl-pyrido[3,4-d]pyrimidine |
| 2203 | 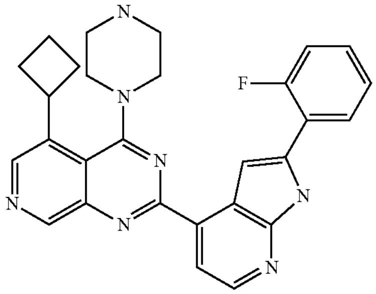 [SMILES: Fc1ccccc1-c1cc2c(-c3nc(N4CCNCC4)c4c(C5CCC5)cncc4n3)ccnc2[nH]1] | [D4], [D3] | LCMS: Purity: 97%, RT: min, MI: 482.18 (M + H) | (dmso-d6) 12.40 (s, 1H), 9.22 (s, 1H), 9.00 (br s, 1H), 8.89 (br s, 1H), 8.80 (s, 1H), 8.46 (d, J = 5.0 Hz, 1H), 8.17 (d, J = 5.0 Hz, 1H), 8.10 (m, 1H), 7.96 (m, 1H), 7.52-7.36 (m, 3H), 4.30 (m, 1H), 3.87 (m, 4H), 3.35 (m, 4H), 2.48 (m, 2H), 2.24 (m, 2H), 2.11 (m, 1H), 1.93 (m, 1H) | 5-Cyclobutyl-2-[2-(2-fluoro-phenyl)-1H-pyrrolo[2,3-b]pyridin-4-yl]-4-piperazin-1-yl-pyrido[3,4-d]pyrimidine |
| 2204 | 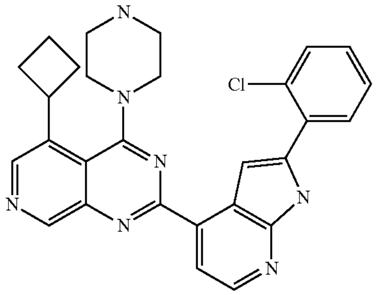 [SMILES: Clc1ccccc1-c1cc2c(-c3nc(N4CCNCC4)c4c(C5CCC5)cncc4n3)ccnc2[nH]1] | [D4], [D3] | LCMS: Purity: 97%, RT: min, MI: 480.22 (M + H) | (dmso-d6) 12.32 (d, J = 1.7 Hz, 1H), 9.22 (s, 1H), 8.98 (br s, 1H), 8.85 (br s, 1H), 8.80 (s, 1H), 8.46 (d, J = 5.0 Hz, 1H), 8.18 (d, J = 5.0 Hz, 1H), 7.92 (d, J = 2.2 Hz, 1H), 7.84 (dd, J = 7.6, 1.8 Hz, 1H), 7.67 (dd, J= 7.9, 1.6 Hz, 1H), 7.56-7.44 (m, 2H), 4.30 (m, 1H), 3.84 (m, 4H), 3.34 (m, 4H), 2.47 (m, 2H), 2.24 (m, 2H), 2.11 (m, 1H), 1.93 (m, 1H) | 2-[2-(2-Chloro-phenyl)-1H-pyrrolo[2,3-b]pyridin-4-yl]-5-cyclobutyl-4-piperazin-1-yl-pyrido[3,4-d]pyrimidine |

-continued

| Ex | Structure | Scheme | LCMS | Analysis $^1$H-NMR | Name |
|---|---|---|---|---|---|
| 2205 | 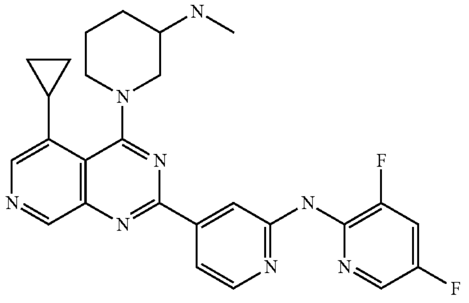 [SMILES: CNC1CCCN(c2nc(-c3ccnc(Nc4ncc(F)cc4F)c3)nc3cncc(C4CC4)c23)C1] | [B4] | LCMS: Purity: 95%, RT: min, MI: 489 (M + H) | 1H-NMR: DMSO 10.08 (br s, 1H), 9.05 (s, 1H), 8.70 (br m, 3H), 8.40 (d, 1H, J = 5.5 Hz), 8.29 (d, 1H, J = 2.2 Hz), 8.18 (s, 1H), 8.00 (m, 2H), 4.56 (br m, 1H), 4.18 (br m, 1H), 3.50 (m, 2H), 3.16 (m, 1H), 2.63 (s, 3H), 2.54 (m, 1H), 2.12 (m, 1H), 1.82 (m, 1H), 1.64 (m, 2H), 1.25 (m, 2H), 1.05 (m, 2H) | {4-[5-Cyclopropyl-4-(3-methylamino-piperidin-1-yl)-pyrido[3,4-d]pyrimidin-2-yl]-pyridin-2-yl}-(3,5-difluoro-pyridin-2-yl)-amine |
| 2206 | 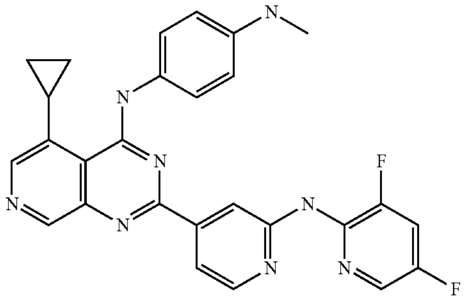 [SMILES: CNc1ccc(Nc2nc(-c3ccnc(Nc4ncc(F)cc4F)c3)nc3cncc(C4CC4)c23)cc1] | [B4] | LCMS: Purity: 95%, RT: min, MI: 497 (M + H) | 1H-NMR: DMSO 10.38 (br s, 1H), 9.66 (s, 1H), 9.09 (s, 1H), 8.67 (s, 1H), 8.55 (s, 1H), 8.43 (d, 1H, J = 5.7 Hz), 8.22 (d, 1H, J = 2.5 Hz), 8.10 (m, 1H), 7.94 (m, 1H), 7.76 (m, 2H), 6.77 (m, 2H), 2.79 (m, 1H), 2.76 (s, 3H), 1.30 (m, 2H), 1.14 (m, 2H) | N-{5-Cyclopropyl-2-[2-(3,5-difluoro-pyridin-2-ylamino)-pyridin-4-yl]-pyrido[3,4-d]pyrimidin-4-yl}-N'-methyl-benzene-1,4-diamine |
| 2207 | 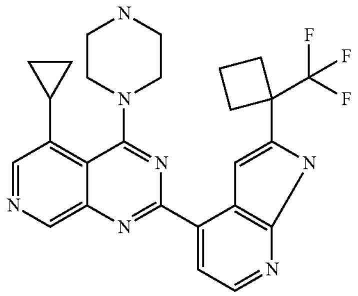 [SMILES: FC(F)(F)C1(c2cc3c(-c4nc(N5CCNCC5)c5c(C6CC6)cncc5n4)ccnc3[nH]2)CCC1] | [D4], [D3] | Method 5: RT: 2.87 min, MI: 494 [M + H] | (500 MHz, d6-DMSO) 12.17 (brs, 1H), 9.17 (s, 1H), 8.89 (brs, 2H), 8.42 (t, 1H), 8.17 (d, 1H), 8.14 (t, 1H), 7.49 (s, 1H), 4.21-3.56 (m, 6H), 2.82-2.64 (m, 6H), 2.17-1.98 (m, 3H), 1.34-1.20 (m, 2H), 1.14-1.03 (m, 2H). | 5-Cyclopropyl-4-piperazin-1-yl-2-[2-(1-trifluoromethyl-cyclobutyl)-1H-pyrrolo[2,3-b]pyridin-4-yl]-pyrido[3,4-d]pyrimidine |
| 2208 | 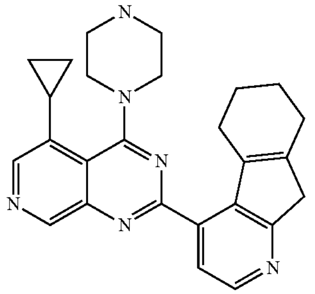 [SMILES: c1cc(-c2nc(N3CCNCC3)c3c(C4CC4)cncc3n2)c2c(n1)CC1=C2CCCC1] | [D3], [D9] | Method 5: RT: 2.88 min, MI: 426 [M + H] | (500 MHz, d6-DMSO) 11.53 (s, 1H), 9.06 (s, 1H), 8.21 (d, 1H), 8.17 (s, 1H), 7.56 (d, 1H), 4.09-3.61 (m, 4H), 3.35-3.28 (m, 4H), 2.78-2.68 (m, 3H), 2.64-2.58 (m, 2H), 1.85-1.77 (m, 2H), 1.69-1.61 (m, 2H), 1.30-1.23 (m, 2H), 1.12-1.07 (m, 2H). | 4-(5-Cyclopropyl-4-piperazin-1-yl-pyrido[3,4-d]pyrimidin-2-yl)-6,7,8,9-tetrahydro-5H-pyrido[2,3-b]indole |
| 2209 | 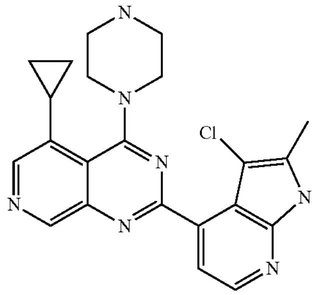 | [D4], [D3], [D7] | Method 5: RT: 3.45 min, MI: 474 [M + H] | (500 MHz, d6-DMSO) 8.96 (1H, s), 8.59 (1H, d), 8.13 (1H, s), 7.57 (1H, d), 3.89-3.46 (4H, m), 2.84 (4H, s), 2.71-2.59 (1H, m), 1.29-1.24 (2H, m), 1.06-1.01 (2H, m). | 2-(3-Chloro-2-methyl-1H-pyrrolo[2,3-b]pyridin-4-yl)-5-cyclopropyl-4-piperazin-1-yl-pyrido[3,4-d]pyrimidine |

-continued

| Ex | Structure | Scheme | Analysis LCMS | Analysis $^1$H-NMR | Analysis Name |
|---|---|---|---|---|---|
| 2210 | 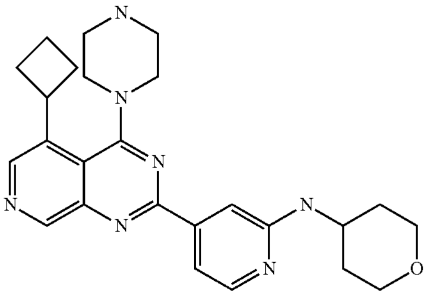 [SMILES: c1cc(-c2nc(N3CCNCC3)c3c(C4CCC4)cncc3n2)cc(NC2CCOCC2)n1] | [B4] | Method 5: RT: 1.44 min, MI: 446 [M + H] | (500 MHz, DMSO) 9.07 (1H, s), 8.74 (1H, s), 8.12 (1H, d), 7.54 (1H, s), 7.42 (1H, dd), 6.79 (1H, d), 4.24 (1H, m), 3.98 (1H, m), 3.89 (2H, m), 3.78-3.67 (4H, m), 3.42 (2H, m), 3.19 (2H, m), 3.09 (2H, m), 2.46 (2H, m), 2.19 (2H, m), 2.09 (1H, m), 1.90 (3H, m), 1.46 (2H, m). | [4-(5-Cyclobutyl-4-piperazin-1-yl-pyrido[3,4-d] pyrimidin-2-yl)-pyridin-2-yl]-(tetrahydro-pyran-4-yl)-amine |
| 2211 | 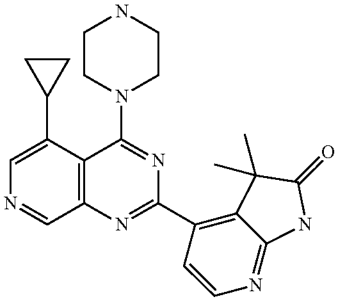 [SMILES: CC1(C)C(=O)Nc2nccc(-c3nc(N4CCNCC4)c4c(C5CC5)cncc4n3)c21] | [D3], [D10] | Method 5: RT: 2.71 min, MI: 416 [M + H] | (300 MHz, DMSO-d6) d 11.20 (s, 1H), 9.08 (s, 1H), 8.94 (bs, 2H), 8.25 (d, J = 5.5 Hz, 1H), 8.21 (s, 1H), 7.80 (d, J = 5.5 Hz, 1H), 3.86 (bs, 4H), 3.32 (bs, 4H), 2.73-2.64 (m, 1H), 1.55 (s, 6H), 1.31-1.19 (m, 2H), 1.14-1.04 (m, 2H) | 4-(5-Cyclopropyl-4-piperazin-1-yl-pyrido[3,4-d]pyrimidin-2-yl)-3,3-dimethyl-1,3-dihydro-pyrrolo[2,3- b] pyridin-2-one |

VI. Biology

PKC$_ι$ IC$_{50}$, Assay

Assays are based on the ability of PKCι to phosphorylate a commercially available peptide substrate in vitro. The peptide substrate is FAM-PKCϵ pseudopeptide derived peptide, and comprises the amino acid sequence 5FAM-ERM-RPRKRQGSVRRRV-$NH_2$. Recombinant, full-length human PKCι expressed in Sf21 insect cells is also commercially available. Recombinant, kinase-domain human PKCι is expressed and purified in-house.

The procedure below explains how dose response curves for inhibitors of PKCι are obtained. The screen described is for a 384 well format but the assay can be adapted to 1536 or other formats as required.

Compounds to be tested are dissolved in 100% DMSO. Compounds are diluted as required to give a final concentration of 4% DMSO (v/v) in the assay. 1 μl is plated into 384 well black low-binding flat bottomed assay plates which are used immediately. Dilutions and additions of compound to assay plates are carried out using Matrix WellMate® and Matrix PlateMate® Plus liquid handling systems.

On the day of the screen PKCι/substrate working solution, and ATP working solution, are prepared in buffer containing 20 mM tris-HCl pH7.5, 10 mM $MgCl_2$, 0.01% Triton X100, 250 μM EGTA and 1 mM DTT. The final concentration of PKCι used varies depending on the batch of protein but is typically 15 pM. The final concentration of peptide substrate in the assay is 100 nM. ATP is used at a final concentration of 150 μM or 25 μM in the assays containing full-length or kinase-domain PKCι respectively, which corresponds to five times or equal to the $K_M^{APP}$ for ATP for each enzyme, respectively. The final buffer concentration in the assay is 18 mM tris-HCl pH7.5, 9 mM $MgCl_2$, 0.009% Triton X100, 225 μM EGTA and 0.9 mM DTT. Relevant controls are included, namely no compound and no enzyme. 5 μl PKCι/substrate working solution at 30 pM and 200 nM, respectively, is added to the wells, followed by 4 μl ATP working solution at 375 μM or 62.5 μM for full-length or kinase-domain PKCι respectively, using a 16 channel Matrix pipette. The reaction is allowed to incubate for 60 minutes at room temperature, before the reaction is stopped and developed by the addition of 20 μl IMAP™ development reagent (Molecular Devices). IMAP development reagent consists of 0.25% (v/v) IMAP progressive binding reagent, 17% (v/v) IMAP progressive binding buffer A and 3% (v/v) IMAP progressive binding buffer B. The plates are then incubated for 2 hours at room temperature before being read using an appropriate plate reader, for example a Molecular Devices HT Analyst or a BMG Pherastar. Plates are read using a fluorescence polarisation protocol with excitation at 485 nm and emission at 530 nm, and dichroic mirror at 505 nm.

Percentage inhibition values are calculated from fluorescence polarisation values, using the no compound and no enzyme control values as 0% and 100% inhibition, respectively. IC50 determination is performed with ExcelFit software (IDBS) using curve fit 205. Z' factors are determined for each plate tested and are all above 0.5.

RESULTS

Biological data for the Example compounds is presented in the following table. Activities are set forth as follows:

IC50 in IMAP assay against full length PKCi at 150 μM ATP:

++++=<100 nM

+++=100 nM to 1,000 nM

++=1,000 nM to 10,000 nM

+=10,000 nM to 40,000 nM

| Example | Activity |
|---|---|
| 1 | +++ |
| 2 | +++ |
| 3 | + |
| 4 | ++ |
| 5 | + |
| 6 | ++++ |
| 7 | ++++ |
| 8 | +++ |
| 9 | ++++ |
| 10 | +++ |
| 11 | ++++ |
| 12 | ++++ |
| 13 | ++ |
| 14 | +++ |
| 15 | ++ |
| 16 | +++ |
| 17 | ++ |
| 18 | + |
| 19 | + |
| 20 | + |
| 21 | + |
| 22 | + |
| 23 | + |
| 24 | + |
| 25 | +++ |
| 26 | + |
| 27 | + |
| 28 | +++ |
| 29 | ++ |
| 30 | ++ |
| 31 | +++ |
| 32 | +++ |
| 33 | ++ |
| 34 | + |
| 35 | + |
| 36 | + |
| 37 | ++++ |
| 38 | +++ |
| 39 | + |
| 40 | ++ |
| 41 | ++++ |
| 42 | + |
| 43 | ++ |
| 44 | +++ |
| 45 | ++ |
| 46 | ++++ |
| 47 | ++++ |
| 48 | ++ |
| 49 | ++ |
| 50 | + |
| 51 | ++ |
| 52 | ++ |
| 53 | +++ |
| 54 | ++ |
| 55 | ++ |
| 56 | + |
| 57 | + |
| 58 | +++ |
| 59 | + |
| 60 | ++ |
| 61 | ++ |
| 62 | ++ |
| 63 | +++ |
| 64 | + |
| 65 | + |

-continued

| Example | Activity |
|---|---|
| 66 | + |
| 67 | + |
| 68 | +++ |
| 69 | + |
| 70 | ++ |
| 71 | ++ |
| 72 | ++ |
| 73 | + |
| 74 | ++++ |
| 75 | ++ |
| 76 | ++++ |
| 77 | ++++ |
| 78 | ++ |
| 79 | + |
| 80 | +++ |
| 81 | +++ |
| 82 | ++ |
| 83 | + |
| 84 | + |
| 85 | + |
| 86 | ++ |
| 87 | + |
| 88 | +++ |
| 89 | ++++ |
| 90 | +++ |
| 91 | +++ |
| 92 | ++ |
| 93 | +++ |
| 94 | +++ |
| 95 | +++ |
| 96 | +++ |
| 97 | +++ |
| 98 | ++ |
| 99 | +++ |
| 100 | +++ |
| 101 | ++ |
| 102 | +++ |
| 103 | +++ |
| 104 | ++ |
| 105 | ++++ |
| 106 | ++ |
| 107 | ++ |
| 108 | +++ |
| 109 | +++ |
| 110 | +++ |
| 111 | +++ |
| 112 | + |
| 113 | +++ |
| 114 | +++ |
| 115 | ++++ |
| 116 | ++ |
| 117 | ++ |
| 118 | ++ |
| 119 | ++ |
| 120 | ++ |
| 121 | +++ |
| 122 | +++ |
| 123 | ++ |
| 124 | ++ |
| 125 | ++ |
| 126 | +++ |
| 127 | + |
| 128 | ++ |
| 129 | +++ |
| 130 | ++ |
| 131 | ++++ |
| 132 | ++++ |
| 133 | ++++ |
| 134 | ++++ |
| 135 | ++++ |
| 136 | ++++ |
| 137 | ++++ |
| 138 | ++++ |
| 139 | ++++ |
| 140 | +++ |
| 141 | +++ |
| 142 | ++ |

-continued

| Example | Activity |
|---|---|
| 143 | ++++ |
| 151 | +++ |
| 152 | ++ |
| 153 | ++ |
| 154 | +++ |
| 155 | ++ |
| 156 | ++ |
| 157 | ++ |
| 158 | ++ |
| 159 | + |
| 160 | + |
| 200 | ++++ |
| 201 | ++++ |
| 202 | ++++ |
| 203 | ++++ |
| 204 | ++++ |
| 205 | +++ |
| 206 | ++++ |
| 207 | +++ |
| 208 | ++++ |
| 209 | +++ |
| 210 | +++ |
| 211 | ++++ |
| 212 | ++++ |
| 213 | +++ |
| 214 | ++++ |
| 215 | +++ |
| 216 | ++++ |
| 217 | +++ |
| 218 | ++++ |
| 219 | +++ |
| 220 | ++++ |
| 221 | ++++ |
| 222 | ++++ |
| 223 | ++ |
| 224 | ++++ |
| 225 | +++ |
| 226 | ++++ |
| 227 | ++++ |
| 228 | ++++ |
| 229 | ++++ |
| 230 | ++++ |
| 231 | + |
| 232 | +++ |
| 233 | +++ |
| 234 | +++ |
| 235 | +++ |
| 236 | +++ |
| 237 | ++ |
| 238 | ++++ |
| 239 | ++++ |
| 240 | ++++ |
| 241 | ++++ |
| 242 | ++++ |
| 243 | ++ |
| 244 | ++ |
| 245 | ++ |
| 246 | +++ |
| 247 | +++ |
| 248 | ++++ |
| 249 | ++++ |
| 250 | +++ |
| 251 | +++ |
| 252 | +++ |
| 253 | ++++ |
| 254 | ++++ |
| 255 | +++ |
| 256 | ++++ |
| 257 | +++ |
| 258 | ++++ |
| 259 | ++++ |
| 260 | + |
| 261 | +++ |
| 262 | +++ |
| 263 | ++++ |
| 264 | ++++ |
| 265 | ++++ |

-continued

| Example | Activity |
|---|---|
| 266 | ++++ |
| 267 | ++++ |
| 268 | +++ |
| 269 | ++++ |
| 270 | +++ |
| 271 | ++++ |
| 272 | ++++ |
| 273 | ++++ |
| 274 | +++ |
| 275 | ++++ |
| 276 | ++++ |
| 277 | ++++ |
| 278 | + |
| 279 | ++++ |
| 280 | ++++ |
| 281 | ++++ |
| 282 | ++++ |
| 283 | ++++ |
| 284 | +++ |
| 285 | ++++ |
| 303 | +++ |
| 304 | +++ |
| 305 | +++ |
| 306 | ++ |
| 307 | +++ |
| 308 | +++ |
| 309 | +++ |
| 310 | +++ |
| 311 | ++++ |
| 313 | ++++ |
| 314 | ++++ |
| 316 | +++ |
| 317 | +++ |
| 318 | ++++ |
| 319 | ++++ |
| 320 | ++++ |
| 321 | ++++ |
| 322 | +++ |
| 323 | ++++ |
| 324 | ++++ |
| 325 | + |
| 326 | +++ |
| 327 | ++++ |
| 328 | ++ |
| 329 | ++++ |
| 330 | ++++ |
| 331 | ++++ |
| 332 | ++++ |
| 333 | ++ |
| 334 | ++ |
| 335 | +++ |
| 336 | +++ |
| 337 | ++++ |
| 338 | ++ |
| 339 | ++++ |
| 341 | ++++ |
| 342 | +++ |
| 343 | +++ |
| 344 | ++++ |
| 345 | ++++ |
| 346 | ++++ |
| 347 | ++++ |
| 348 | ++++ |
| 349 | ++++ |
| 350 | ++++ |
| 351 | ++++ |
| 352 | ++++ |
| 353 | ++++ |
| 354 | ++ |
| 355 | ++++ |
| 356 | ++++ |
| 357 | ++++ |
| 358 | +++ |
| 359 | +++ |
| 360 | +++ |
| 361 | ++++ |
| 362 | ++++ |

-continued

| Example | Activity |
|---|---|
| 363 | ++++ |
| 364 | ++++ |
| 365 | ++++ |
| 366 | ++++ |
| 367 | ++++ |
| 368 | ++++ |
| 369 | ++++ |
| 370 | ++++ |
| 371 | ++++ |
| 372 | ++++ |
| 373 | ++++ |
| 374 | ++++ |
| 375 | ++++ |
| 376 | +++ |
| 377 | +++ |
| 378 | ++++ |
| 379 | ++++ |
| 380 | ++++ |
| 382 | ++++ |
| 383 | ++++ |
| 384 | +++ |
| 385 | +++ |
| 386 | +++ |
| 387 | ++++ |
| 388 | + |
| 389 | +++ |
| 390 | +++ |
| 391 | ++++ |
| 392 | ++++ |
| 393 | ++++ |
| 394 | ++++ |
| 395 | +++ |
| 396 | ++++ |
| 397 | +++ |
| 398 | +++ |
| 399 | ++++ |
| 400 | ++++ |
| 401 | ++++ |
| 402 | +++ |
| 403 | +++ |
| 404 | +++ |
| 405 | ++++ |
| 406 | +++ |
| 407 | +++ |
| 408 | +++ |
| 409 | +++ |
| 410 | +++ |
| 411 | ++++ |
| 412 | ++++ |
| 413 | ++++ |
| 414 | ++++ |
| 415 | ++++ |
| 416 | ++++ |
| 417 | +++ |
| 418 | ++++ |
| 419 | +++ |
| 420 | +++ |
| 421 | ++++ |
| 422 | ++++ |
| 423 | +++ |
| 424 | ++++ |
| 425 | ++ |
| 426 | ++ |
| 427 | ++ |
| 428 | ++ |
| 429 | ++ |
| 430 | +++ |
| 431 | +++ |
| 432 | +++ |
| 433 | ++ |
| 434 | ++++ |
| 435 | +++ |
| 436 | +++ |
| 437 | +++ |
| 438 | ++ |
| 439 | ++++ |
| 440 | ++++ |

-continued

| Example | Activity |
|---|---|
| 441 | ++++ |
| 442 | ++++ |
| 443 | ++ |
| 444 | ++++ |
| 445 | +++ |
| 446 | +++ |
| 447 | ++++ |
| 448 | ++++ |
| 449 | ++++ |
| 450 | ++++ |
| 451 | ++++ |
| 452 | +++ |
| 453 | ++++ |
| 454 | +++ |
| 455 | +++ |
| 456 | +++ |
| 457 | +++ |
| 458 | ++ |
| 459 | + |
| 460 | + |
| 461 | ++ |
| 462 | + |
| 463 | ++ |
| 464 | +++ |
| 465 | ++ |
| 466 | ++ |
| 467 | ++ |
| 468 | +++ |
| 469 | ++ |
| 470 | ++ |
| 471 | ++ |
| 473 | ++++ |
| 474 | ++++ |
| 475 | ++++ |
| 476 | ++++ |
| 477 | ++++ |
| 478 | ++++ |
| 481 | ++++ |
| 482 | +++ |
| 483 | ++++ |
| 484 | ++++ |
| 485 | ++++ |
| 486 | ++++ |
| 487 | ++++ |
| 488 | +++ |
| 489 | ++++ |
| 490 | ++++ |
| 491 | ++++ |
| 492 | ++++ |
| 493 | ++++ |
| 494 | +++ |
| 495 | ++++ |
| 496 | + |
| 497 | + |
| 498 | + |
| 499 | + |
| 500 | +++ |
| 501 | + |
| 502 | ++ |
| 503 | ++ |
| 504 | ++++ |
| 505 | ++++ |
| 506 | +++ |
| 507 | ++++ |
| 508 | ++++ |
| 509 | ++++ |
| 510 | ++++ |
| 511 | +++ |
| 512 | ++++ |
| 513 | ++++ |
| 514 | ++++ |
| 515 | ++++ |
| 516 | ++++ |
| 517 | +++ |
| 518 | ++++ |
| 519 | +++ |
| 520 | ++++ |

-continued

| Example | Activity |
|---|---|
| 521 | ++++ |
| 522 | +++ |
| 523 | ++++ |
| 524 | ++++ |
| 525 | +++ |
| 526 | ++++ |
| 527 | ++++ |
| 528 | +++ |
| 529 | ++++ |
| 530 | ++++ |
| 531 | ++++ |
| 532 | ++++ |
| 533 | +++ |
| 534 | ++++ |
| 535 | +++ |
| 536 | ++ |
| 537 | ++++ |
| 538 | ++++ |
| 539 | ++++ |
| 540 | ++++ |
| 541 | ++++ |
| 542 | +++ |
| 543 | ++++ |
| 544 | ++++ |
| 545 | ++++ |
| 546 | ++++ |
| 547 | ++++ |
| 548 | ++++ |
| 549 | ++++ |
| 550 | ++++ |
| 551 | ++++ |
| 552 | ++++ |
| 553 | ++++ |
| 554 | +++ |
| 555 | +++ |
| 556 | ++++ |
| 557 | ++++ |
| 558 | +++ |
| 559 | ++++ |
| 560 | +++ |
| 561 | ++++ |
| 562 | +++ |
| 563 | ++++ |
| 564 | ++++ |
| 565 | ++++ |
| 566 | ++++ |
| 567 | ++++ |
| 568 | ++++ |
| 569 | ++++ |
| 570 | ++++ |
| 571 | ++++ |
| 572 | ++++ |
| 573 | ++++ |
| 574 | ++++ |
| 575 | ++++ |
| 576 | ++++ |
| 577 | ++++ |
| 578 | ++++ |
| 579 | + |
| 580 | ++++ |
| 581 | ++++ |
| 582 | ++++ |
| 583 | ++++ |
| 584 | ++++ |
| 585 | ++++ |
| 586 | ++++ |
| 587 | ++++ |
| 588 | ++++ |
| 589 | ++++ |
| 590 | ++++ |
| 591 | ++++ |
| 592 | ++++ |
| 593 | + |
| 594 | ++++ |
| 595 | ++++ |
| 596 | + |
| 597 | + |

-continued

| Example | Activity |
|---|---|
| 598 | ++++ |
| 599 | ++++ |
| 600 | ++ |
| 601 | ++++ |
| 602 | ++++ |
| 603 | ++++ |
| 604 | ++++ |
| 605 | ++++ |
| 606 | +++ |
| 607 | +++ |
| 608 | +++ |
| 609 | ++++ |
| 610 | ++++ |
| 611 | +++ |
| 612 | ++++ |
| 613 | ++++ |
| 614 | ++++ |
| 615 | +++ |
| 616 | ++++ |
| 617 | ++++ |
| 618 | ++++ |
| 619 | ++++ |
| 620 | ++++ |
| 621 | ++++ |
| 622 | ++++ |
| 623 | ++++ |
| 624 | +++ |
| 625 | +++ |
| 626 | ++++ |
| 627 | ++++ |
| 628 | ++++ |
| 629 | ++++ |
| 630 | ++++ |
| 631 | +++ |
| 632 | ++++ |
| 633 | ++++ |
| 634 | ++++ |
| 635 | ++++ |
| 636 | ++++ |
| 637 | ++++ |
| 638 | +++ |
| 639 | ++++ |
| 640 | ++++ |
| 641 | ++++ |
| 642 | +++ |
| 643 | ++ |
| 644 | ++++ |
| 645 | ++++ |
| 646 | ++++ |
| 649 | ++++ |
| 650 | ++++ |
| 651 | ++++ |
| 652 | ++++ |
| 653 | ++++ |
| 654 | ++++ |
| 655 | ++ |
| 656 | +++ |
| 657 | +++ |
| 658 | ++ |
| 659 | +++ |
| 660 | + |
| 661 | ++ |
| 662 | ++ |
| 663 | +++ |
| 664 | ++ |
| 665 | ++ |
| 666 | ++ |
| 667 | ++++ |
| 668 | ++++ |
| 669 | ++ |
| 670 | ++++ |
| 671 | ++++ |
| 672 | ++++ |
| 673 | ++++ |
| 674 | ++ |
| 675 | +++ |
| 676 | +++ |

-continued

| Example | Activity |
|---|---|
| 677 | +++ |
| 678 | ++++ |
| 679 | ++ |
| 680 | ++++ |
| 681 | ++++ |
| 682 | +++ |
| 683 | ++ |
| 684 | +++ |
| 685 | +++ |
| 686 | +++ |
| 687 | +++ |
| 688 | ++++ |
| 689 | ++++ |
| 690 | ++++ |
| 691 | ++++ |
| 692 | ++++ |
| 693 | ++++ |
| 694 | ++++ |
| 695 | ++++ |
| 696 | ++++ |
| 697 | +++ |
| 698 | +++ |
| 699 | ++++ |
| 700 | ++++ |
| 701 | + |
| 702 | +++ |
| 703 | ++++ |
| 704 | ++++ |
| 705 | ++++ |
| 706 | +++ |
| 707 | + |
| 708 | +++ |
| 709 | +++ |
| 710 | +++ |
| 711 | +++ |
| 712 | ++++ |
| 713 | +++ |
| 714 | ++++ |
| 715 | ++++ |
| 716 | ++++ |
| 717 | ++++ |
| 718 | ++++ |
| 719 | ++++ |
| 720 | ++++ |
| 721 | ++++ |
| 722 | ++++ |
| 723 | ++ |
| 724 | ++++ |
| 725 | ++++ |
| 726 | +++ |
| 727 | ++++ |
| 728 | +++ |
| 729 | ++++ |
| 730 | ++++ |
| 731 | ++++ |
| 732 | ++++ |
| 733 | ++ |
| 734 | ++++ |
| 735 | +++ |
| 736 | ++++ |
| 737 | ++++ |
| 738 | ++++ |
| 739 | +++ |
| 740 | +++ |
| 741 | +++ |
| 742 | ++++ |
| 743 | ++++ |
| 744 | ++++ |
| 745 | +++ |
| 746 | ++++ |
| 747 | ++++ |
| 748 | ++++ |
| 749 | ++++ |
| 750 | ++++ |
| 751 | ++++ |
| 752 | ++++ |
| 753 | ++++ |

-continued

| Example | Activity |
|---|---|
| 754 | ++++ |
| 756 | ++++ |
| 757 | +++ |
| 758 | ++++ |
| 760 | +++ |
| 761 | +++ |
| 762 | ++++ |
| 763 | ++++ |
| 764 | ++++ |
| 765 | ++++ |
| 766 | +++ |
| 767 | +++ |
| 768 | ++++ |
| 769 | ++++ |
| 770 | +++ |
| 771 | ++ |
| 772 | +++ |
| 773 | +++ |
| 774 | ++++ |
| 775 | ++++ |
| 776 | +++ |
| 777 | +++ |
| 778 | ++++ |
| 779 | ++++ |
| 780 | ++++ |
| 781 | +++ |
| 782 | +++ |
| 783 | ++++ |
| 784 | ++++ |
| 785 | ++++ |
| 786 | ++++ |
| 787 | ++++ |
| 788 | +++ |
| 789 | +++ |
| 790 | ++++ |
| 791 | ++++ |
| 793 | +++ |
| 794 | ++++ |
| 795 | ++++ |
| 796 | ++++ |
| 797 | +++ |
| 798 | ++++ |
| 799 | ++++ |
| 800 | ++++ |
| 801 | ++++ |
| 802 | ++++ |
| 803 | +++ |
| 804 | +++ |
| 805 | +++ |
| 806 | ++ |
| 807 | ++++ |
| 808 | ++++ |
| 809 | ++++ |
| 810 | ++++ |
| 811 | ++++ |
| 812 | ++++ |
| 813 | ++++ |
| 814 | ++++ |
| 815 | ++++ |
| 816 | ++++ |
| 817 | ++++ |
| 818 | ++++ |
| 819 | + |
| 820 | ++++ |
| 821 | ++++ |
| 822 | ++ |
| 823 | ++++ |
| 824 | ++++ |
| 825 | ++++ |
| 826 | +++ |
| 827 | ++++ |
| 828 | ++++ |
| 829 | ++++ |
| 830 | ++ |
| 831 | ++++ |
| 832 | ++++ |
| 833 | ++++ |

-continued

| Example | Activity |
|---|---|
| 834 | ++++ |
| 835 | ++++ |
| 836 | ++++ |
| 837 | ++++ |
| 838 | ++++ |
| 839 | ++++ |
| 840 | ++++ |
| 841 | ++++ |
| 842 | ++++ |
| 843 | ++++ |
| 844 | ++++ |
| 845 | ++++ |
| 846 | ++++ |
| 1000 | ++ |
| 1001 | ++ |
| 1002 | ++++ |
| 1003 | +++ |
| 1004 | ++ |
| 1005 | +++ |
| 1006 | +++ |
| 1007 | ++ |
| 1008 | +++ |
| 1009 | ++ |
| 1010 | +++ |
| 1011 | ++ |
| 1012 | ++ |
| 1013 | +++ |
| 1014 | +++ |
| 1015 | +++ |
| 1016 | ++++ |
| 1017 | ++++ |
| 1018 | ++++ |
| 1200 | ++++ |
| 1201 | ++++ |
| 1202 | ++++ |
| 1203 | ++++ |
| 1204 | +++ |
| 1205 | +++ |
| 1206 | ++++ |
| 1207 | +++ |
| 1208 | +++ |
| 1209 | ++++ |
| 1210 | ++++ |
| 1211 | ++++ |
| 1212 | ++++ |
| 1213 | ++++ |
| 1214 | ++++ |
| 1215 | ++++ |
| 1216 | ++++ |
| 1217 | ++++ |
| 1218 | ++++ |
| 1219 | ++++ |
| 1220 | ++++ |
| 1221 | ++++ |
| 1222 | ++++ |
| 1223 | ++++ |
| 1224 | + |
| 1226 | ++++ |
| 1227 | + |
| 1228 | ++++ |
| 1229 | ++++ |
| 1230 | ++++ |
| 1231 | ++++ |
| 1232 | ++++ |
| 1233 | ++++ |
| 1234 | +++ |
| 1235 | +++ |
| 1236 | ++ |
| 1237 | +++ |
| 1238 | ++++ |
| 1239 | ++++ |
| 1240 | ++++ |
| 1241 | +++ |
| 1242 | ++ |
| 1243 | ++ |
| 1244 | ++++ |
| 1245 | + |

-continued

| Example | Activity |
|---|---|
| 1246 | + |
| 1247 | ++++ |
| 1248 | + |
| 1249 | ++++ |
| 1250 | ++++ |
| 1251 | ++++ |
| 1252 | ++++ |
| 1253 | ++++ |
| 1254 | +++ |
| 1255 | ++++ |
| 2001 | ++++ |
| 2002 | ++++ |
| 2003 | ++++ |
| 2004 | ++++ |
| 2005 | ++++ |
| 2006 | ++++ |
| 2007 | ++++ |
| 2008 | ++++ |
| 2009 | ++++ |
| 2010 | ++++ |
| 2011 | ++++ |
| 2012 | ++++ |
| 2013 | ++++ |
| 2014 | ++++ |
| 2015 | ++++ |
| 2016 | ++++ |
| 2017 | ++++ |
| 2018 | ++++ |
| 2019 | ++++ |
| 2020 | ++++ |
| 2021 | ++++ |
| 2022 | ++++ |
| 2023 | ++++ |
| 2024 | ++++ |
| 2025 | ++++ |
| 2026 | ++++ |
| 2027 | ++++ |
| 2028 | ++++ |
| 2029 | ++++ |
| 2030 | ++++ |
| 2031 | ++++ |
| 2032 | ++++ |
| 2033 | ++++ |
| 2034 | ++++ |
| 2035 | ++++ |
| 2036 | ++++ |
| 2037 | ++++ |
| 2038 | ++++ |
| 2039 | ++++ |
| 2040 | ++++ |
| 2041 | ++++ |
| 2042 | ++++ |
| 2043 | ++++ |
| 2044 | ++++ |
| 2045 | ++++ |
| 2046 | ++++ |
| 2047 | ++++ |
| 2048 | ++++ |
| 2049 | ++++ |
| 2050 | ++++ |
| 2051 | ++++ |
| 2052 | ++++ |
| 2053 | ++++ |
| 2054 | ++++ |
| 2055 | ++++ |
| 2056 | ++++ |
| 2057 | ++++ |
| 2058 | ++++ |
| 2059 | ++++ |
| 2060 | ++++ |
| 2061 | ++++ |
| 2062 | ++++ |
| 2063 | ++++ |
| 2064 | ++++ |
| 2065 | ++++ |
| 2066 | ++++ |
| 2067 | ++++ |

-continued

| Example | Activity |
|---|---|
| 2068 | ++++ |
| 2069 | ++++ |
| 2070 | ++++ |
| 2071 | ++++ |
| 2072 | ++++ |
| 2073 | ++++ |
| 2074 | ++++ |
| 2075 | ++++ |
| 2076 | +++ |
| 2077 | + |
| 2078 | ++++ |
| 2079 | ++++ |
| 2080 | ++++ |
| 2081 | ++++ |
| 2082 | ++++ |
| 2083 | ++++ |
| 2084 | ++++ |
| 2085 | +++ |
| 2086 | ++++ |
| 2087 | ++++ |
| 2088 | ++++ |
| 2089 | ++++ |
| 2090 | +++ |
| 2091 | ++++ |
| 2092 | ++++ |
| 2093 | ++++ |
| 2094 | ++++ |
| 2095 | ++++ |
| 2096 | +++ |
| 2097 | ++++ |
| 2098 | ++++ |
| 2099 | ++++ |
| 2100 | ++++ |
| 2101 | ++++ |
| 2102 | ++++ |
| 2103 | +++ |
| 2104 | ++++ |
| 2105 | ++++ |
| 2106 | ++++ |
| 2107 | ++++ |
| 2108 | ++++ |
| 2109 | ++++ |
| 2110 | +++ |
| 2111 | ++++ |
| 2112 | ++++ |
| 2113 | ++++ |
| 2114 | ++++ |
| 2115 | ++++ |
| 2116 | ++++ |
| 2117 | ++++ |
| 2118 | ++++ |
| 2119 | ++++ |
| 2120 | ++++ |
| 2121 | ++++ |
| 2122 | ++++ |
| 2123 | +++ |
| 2124 | ++++ |
| 2125 | ++++ |
| 2126 | ++++ |
| 2127 | ++++ |
| 2128 | +++ |
| 2129 | ++++ |
| 2130 | ++++ |
| 2131 | ++++ |
| 2132 | ++++ |
| 2133 | ++++ |
| 2134 | ++++ |
| 2135 | ++++ |
| 2136 | ++++ |
| 2137 | ++++ |
| 2138 | ++++ |
| 2139 | ++++ |
| 2140 | ++++ |
| 2141 | ++++ |
| 2142 | +++ |
| 2143 | ++++ |
| 2144 | ++++ |

-continued

| Example | Activity |
|---|---|
| 2145 | ++++ |
| 2146 | ++++ |
| 2147 | ++++ |
| 2148 | ++++ |
| 2149 | ++++ |
| 2150 | ++++ |
| 2151 | ++++ |
| 2152 | ++++ |
| 2153 | ++++ |
| 2154 | ++++ |
| 2155 | +++ |
| 2156 | +++ |
| 2157 | ++++ |
| 2158 | ++++ |
| 2159 | +++ |
| 2160 | ++++ |
| 2161 | ++++ |
| 2162 | ++++ |
| 2163 | ++++ |
| 2164 | ++++ |
| 2165 | ++++ |
| 2166 | ++++ |
| 2167 | ++++ |
| 2168 | + |
| 2169 | ++++ |
| 2170 | ++++ |
| 2171 | ++++ |
| 2172 | ++ |
| 2173 | ++ |
| 2174 | ++++ |
| 2175 | ++++ |
| 2176 | ++++ |
| 2177 | ++++ |
| 2178 | ++++ |
| 2179 | ++++ |
| 2180 | ++++ |
| 2181 | ++++ |
| 2182 | ++++ |
| 2183 | ++++ |
| 2184 | ++++ |
| 2185 | ++++ |
| 2186 | +++ |
| 2187 | +++ |
| 2188 | +++ |
| 2189 | +++ |
| 2190 | ++++ |
| 2191 | ++++ |
| 2192 | ++++ |
| 2193 | ++++ |
| 2194 | ++++ |
| 2195 | ++++ |
| 2196 | ++++ |
| 2198 | ++++ |
| 2199 | +++ |
| 2200 | ++++ |
| 2201 | ++++ |
| 2202 | ++++ |
| 2203 | ++++ |
| 2204 | ++++ |
| 2205 | ++++ |
| 2206 | + |
| 2207 | ++++ |
| 2208 | +++ |
| 2209 | ++++ |
| 2210 | ++++ |
| 2211 | ++ |

Preferably, a compound of the present application (i.e., a compound of formula (I) or a salt thereof) has an $IC_{50}$ in an IMAP assay against full length PKCι at 150 μM ATP of $<40$ μM. In one embodiment, a compound of the present application has an $IC_{50}$ in an IMAP assay against full length PKCι at 150 μM ATP of 40 μM-10 μM. More preferably, a compound of the present application has an $IC_{50}$ in an IMAP assay against full length PKCι at 150 μM ATP of 10 μM-1 μM. In one embodiment, a compound of the present application has an $IC_{50}$ in an IMAP assay against full length PKCι at 150 μM ATP of 1 μM-0.1 μM. More preferably, a compound of the present application has an $IC_{50}$ in an IMAP assay against full length PKCι at 150 μM ATP of <0.1 μM.

Preferably, a compound of the present application (i.e., a compound of formula (I) or a salt thereof) has an $IC_{50}$ in an IMAP assay against kinase domain PKCι at 25 μM ATP of <40 μM. In one embodiment, a compound of the present application has an $IC_{50}$ in an IMAP assay against kinase domain PKCι at 25 μM ATP of 40 μM-10 μM. More preferably, a compound of the present application has an $IC_{50}$ in an IMAP assay against kinase domain PKCι at 25 μM ATP of 10 μM-1 μM. In one embodiment, a compound of the present application has an $IC_{50}$ in an IMAP assay against kinase domain PKCι at 25 μM ATP of 1 μM-0.1 μM. More preferably, a compound of the present application has an $IC_{50}$ in an IMAP assay against kinase domain PKCι at 25 μM ATP of <0.1 μM.

As those skilled in the art will appreciate, numerous modifications and variations of the present application are possible in light of the above teachings. It is therefore understood that within the scope of the appended claims, the application may be practiced otherwise than as specifically described herein, and the scope of the application is intended to encompass all such variations.

Each publication referenced herein is incorporated by reference in its entirety for all purposes.

Additional preferred Embodiments of the present application include:

1. A compound of formula (I)

(I)

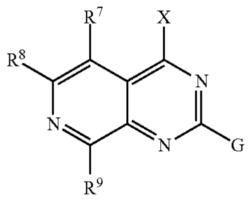

or a salt form thereof, wherein

G is a group of formula

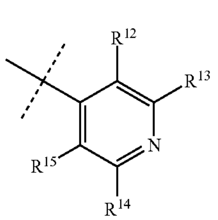

or

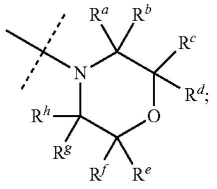

X is chosen from H, $C_{1-10}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{28}$, —C(═O)$OR^{28}$, —C(═O)$NR^{24}R^{28}$, —C(═O)C(═O)$R^{28}$, —$NR^{24}R^{28}$, —$NR^{24}NR^{24}R^{28}$, —N═$NR^{28}$, —$NR^{24}OR^{28}$, —$NR^{24}$C(═O)$R^{28}$, —$NR^{24}$C(═O)C(═O)$R^{28}$, —$NR^{24}$C(═O)$OR^{28}$, —$NR^{24}$C(═O)C(═O)$OR^{28}$, —$NR^{24}$C(═O)$NR^{24}R^{28}$, —$NR^{24}$C(═O)$NR^{24}$C(═O)$R^{28}$, —$NR^{24}$C(═O)$NR^{24}$C(═O)$OR^{28}$, —$NR^{24}$C(═O)C(═O)$NR^{24}R^{28}$, —$NR^{24}$S(═O)$_2R^{28}$, —$NR^{24}$S(═O)$_2NR^{24}R^{28}$, —OR, —OC(═O)$R^{28}$, —OC(═O)$NR^{24}R^{28}$, —OC(═O)$OR^{28}$, —OS(═O)$R^{28}$, —OS(═O)$_2R^{28}$, —OS(═O)$_2OR^{28}$, —OS(═O)$_2NR^{24}R^{28}$, —S(═O)$_nR^{28}$, —S(═O)$_2NR^{24}R^{28}$, and —S(═O)$NR^{24}R^{28}$;

$R^7$, $R^8$, $R^9$, $R^{12}$, $R^{13}$, $R^{14}$, $R^{15}$, $R^a$, $R^b$, $R^c$, $R^d$, $R^e$, $R^f$, $R^g$, and $R^h$ are independently chosen from H, $C_{1-6}$alkyl optionally substituted by 1-13 $R^{19}$, $C_{2-6}$alkenyl optionally substituted by 1-11 $R^{19}$, $C_{2-6}$alkynyl optionally substituted by 1-9 $R^{19}$, $C_{6-11}$aryl optionally substituted by 1-11 $R^{19}$, $C_{7-16}$arylalkyl optionally substituted by 1-19 $R^{19}$, $C_{3-11}$cycloalkyl optionally substituted by 1-21 $R^{19}$, $C_{4-17}$cycloalkylalkyl optionally substituted by 1-32 $R^{19}$, 3-15 membered heterocycloalkyl optionally substituted by 1-28 $R^{19}$, 4-21 membered heterocycloalkylalkyl optionally substituted by 1-40 $R^{19}$, 5-15 membered heteroaryl optionally substituted by 1-15 $R^{19}$, 6-21 membered heteroarylalkyl optionally substituted by 1-27 $R^{19}$, halogen, —CN, —C(═O)$R^{20}$, —C(═O)$OR^{20}$, —C(═O)$NR^{22}R^{23}$, —(═O)C(═O)$R^{20}$, —C(═$NR^{25}$)$R^{20}$, —C(═$NR^{25}$)$NR^{22}R^{23}$, —C(═NOH)$NR^{22}R^{23}$, —C(═$NOR^{26}$)$R^{20}$, —C(═$NNR^{22}R^{23}$)$R^{20}$, —C(═$NNR^{24}$C(═O)$R^{21}$)$R^{20}$, —C(═$NNR^{24}$C(═O)$OR^{21}$)$R^{20}$, —C(═S)$NR^{22}R^{23}$, —NC, —$NO_2$, —$NR^{22}R^{23}$, —$NR^{24}NR^{22}R^{23}$, —N═$NR^{24}$, —$NR^{24}OR^{26}$, —$NR^{24}$C(═O)$R^{20}$, —$NR^{24}$C(═O)C(═O)$R^{20}$, —$NR^{24}$C(═O)$OR^{21}$, —$NR^{24}$C(═O)C(═O)$OR^{21}$, —$NR^{24}$C(═O)$NR^{22}R^{23}$, —$NR^{24}$C(═O)$NR^{24}$C(═O)$R^{20}$, —$NR^{24}$C(═O)$NR^{24}$C(═O)$OR^{20}$, —$NR^{24}$C(═$NR^{25}$)$NR^{22}R^{23}$, —$NR^{24}$C(═O)C(═O)$NR^{22}R^{23}$, —$NR^{24}$C(═S)$R^{20}$, —$NR^{24}$C(═S)$OR^{20}$, —$NR^{24}$C(═S)$NR^{22}R^{23}$, —$NR^{24}$S(═O)$_2R^{21}$, —$NR^{24}$S(═O)$_2NR^{22}R^{23}$, —$NR^{24}$P(═O)$R^{78}R^{78}$, —$NR^{24}$P(═O)($NR^{22}R^{23}$)($NR^{22}R^{23}$), —$NR^{24}$P(═)($OR^{20}$)($OR^{20}$), —$NR^{24}$P(═O)($SR^{20}$)($SR^{20}$), —$OR^{20}$, —OCN, —OC(═O)$R^{20}$, —OC(═O)$NR^{22}R^{23}$, —OC(═O)$OR^{20}$, —OC(═$NR^{25}$)$NR^{22}R^{23}$, —OS(═O)$R^{20}$, —OS(═O)$_2R^{20}$, —OS(═O)$_2OR^{20}$, —OS(═O)$_2NR^{22}R^{23}$, —OP(═O)$R^{78}R^{78}$, —OP(═O)($NR^{22}R^{23}$)($NR^{22}R^{23}$), —OP(═O)($OR^{20}$)($OR^{20}$), —OP(═O)($SR^{20}$)($SR^{20}$), —Si($R^{24}$)$_3$, —SCN, —S(═O)$_nR^{20}$, —S(═O)$_2OR^{20}$, —$SO_3R^{27}$, —S(═O)$_2NR^{22}R^{23}$, —S(═O)$NR^{22}R^{23}$, —SP(═O)$R^{78}R^{78}$, —SP(═O)($NR^{22}R^{23}$)($NR^{22}R^{23}$), —SP(═O)($OR^{20}$)($OR^{20}$), —SP(═O)($SR^{20}$)($SR^{20}$), —P(═O)$R^{78}R^{78}$, —P(═O)($NR^{22}R^{23}$)($NR^{22}R^{23}$), —P(═O)($OR^{20}$)($OR^{20}$), and —P(═O)($SR^{20}$)($SR^{20}$);

or any of $R^7$ and $R^8$, $R^{12}$ and $R^{13}$, $R^{14}$ and $R^{15}$, $R^a$ and $R^b$, $R^a$ and $R^c$, $R^a$ and $R^e$, $R^a$ and $R^g$, $R^b$ and $R^d$, $R^b$ and $R^f$, $R^b$ and $R^h$, $R^c$ and $R^d$, $R^c$ and $R^e$, $R^c$ and $R^g$, $R^d$ and $R^f$, $R^d$ and $R^h$, $R^e$ and $R^f$, $R^e$ and $R^g$, $R^f$ and $R^h$, and $R^g$ and $R^h$ can, together with the atoms linking them, form a $C_{6-11}$aryl optionally substituted by 1-11 $R^{19}$, $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$;

$R^{19}$ at each occurrence is independently chosen from $C_{1-6}$alkyl optionally substituted by 1-13 $R^{39}$, $C_{2-6}$alkenyl optionally substituted by 1-11 $R^{39}$, $C_{2-6}$alkynyl optionally substituted by 1-9 $R^{39}$, $C_{6-11}$aryl optionally substituted by 1-11 $R^{39}$, $C_{7-16}$arylalkyl optionally substituted by 1-19 $R^{39}$, $C_{3-11}$cycloalkyl optionally substituted by 1-21 $R^{39}$, $C_{4-17}$cycloalkylalkyl optionally substituted by 1-32 $R^{39}$, 3-15 membered heterocycloalkyl optionally substituted by 1-28 $R^{39}$, 4-21 membered heterocycloalkylalkyl optionally substituted by 1-40 $R^{39}$, 5-15 membered heteroaryl optionally substituted by 1-15 $R^{39}$, 6-21 membered heteroarylalkyl optionally substituted by 1-27 $R^{39}$, halogen, —CN, —C(═O)$R^{30}$, —C(═O)O$R^{30}$, —C(═O)N$R^{32}R^{33}$, —C(═O)C(═O)$R^{30}$, —C(═N$R^{35}$)$R^{30}$, —C(═N$R^{35}$)N$R^{32}R^{33}$, —C(═NOH)N$R^{32}R^{33}$, —C(═NO$R^{36}$)$R^{30}$, —C(═NN$R^{32}R^{33}$)$R^{30}$, —C(═NN$R^{34}$C(═O)$R^{31}$)$R^{30}$, —C(═NN$R^{34}$C(═O)O$R^{31}$)$R^{30}$, —C(═S)N$R^{32}R^{33}$, —NC, —$NO_2$, —N$R^{32}R^{33}$, —N$R^{34}$N$R^{32}R^{33}$, —N═N$R^{34}$, ═N$R^{30}$, ═NO$R^{30}$, —N$R^{34}$O$R^{36}$, —N$R^{34}$C(═O)$R^{30}$, —N$R^{34}$C(═O)C(═O)$R^{30}$, —N$R^{34}$C(═O)O$R^{31}$, —N$R^{34}$C(═O)C(═O)O$R^{31}$, —N$R^{34}$C(═O)N$R^{32}R^{33}$, —N$R^{34}$C(═O)N$R^{34}$C(═O)$R^{30}$, —N$R^{34}$C(═O)N$R^{34}$C(═O)O$R^{30}$, —N$R^{34}$C(═N$R^{35}$)N$R^{32}R^{33}$, —N$R^{34}$C(═O)C(═O)N$R^{32}R^{33}$, —N$R^{34}$C(═S)$R^{30}$, —N$R^{34}$C(═S)O$R^{30}$, —N$R^{34}$C(═S)N$R^{32}R^{33}$, —N$R^{34}$S(═O)$_2R^{31}$, —N$R^{34}$S(═O)$_2$N$R^{32}R^{33}$, —N$R^{34}$P(═O)$R^{78}R^{78}$, —N$R^{34}$P(═O)(N$R^{32}R^{33}$)(N$R^{32}R^{33}$), —N$R^{34}$P(═)(O$R^{30}$)(O$R^{30}$), —N$R^{34}$P(═O)(S$R^{30}$)(S$R^{30}$), —O$R^{30}$, ═O, —OCN, —OC(═O)$R^{30}$, —OC(═O)N$R^{32}R^{33}$, —OC(═O)O$R^{30}$, —OC(═N$R^{35}$)N$R^{32}R^{33}$, —OS(═O)$R^{30}$, —OS(═O)$_2R^{30}$, —OS(═O)$_2$O$R^{30}$, —OS(═O)$_2$N$R^{32}R^{33}$, —OP(═O)$R^{78}R^{78}$, —OP(═O)(N$R^{32}R^{33}$)(N$R^{32}R^{33}$), —OP(═O)(O$R^{30}$)(O$R^{30}$), —OP(═O)(S$R^{30}$)(S$R^{30}$), —Si($R^{34}$)$_3$, —SCN, ═S, —S(═O)$_nR^{30}$, —S(═O)$_2$O$R^{30}$, —$SO_3R^{37}$, —S(═O)$_2$N$R^{32}R^{33}$, —S(═O)N$R^{32}R^{33}$, —SP(═O)$R^{78}R^{78}$, —SP(═O)(N$R^{32}R^{33}$)(N$R^{32}R^{33}$), —SP(═O)(O$R^{30}$)(O$R^{30}$), —SP(═O)(S$R^{30}$)(S$R^{30}$), —P(═O)$R^{78}R^{78}$, —P(═O)(N$R^{32}R^{33}$)(N$R^{32}R^{33}$), —P(═O)(O$R^{30}$)(O$R^{30}$), and —P(═O)(S$R^{30}$)(S$R^{30}$);

$R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-13 $R^{49}$, $C_{2-6}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$;

$R^{28}$ at each occurrence is independently chosen from $C_{1-10}$alkyl optionally substituted by 1-13 $R^{49}$, $C_{2-10}$alkenyl optionally substituted by 1-11 $R^{49}$, $C_{2-6}$alkynyl optionally substituted by 1-9 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$;

$R^{22}$, $R^{23}$, $R^{32}$ and $R^{33}$ at each occurrence is independently chosen from H, $C_{1-6}$alkyl optionally substituted by 1-13 $R^{59}$, $C_{2-6}$alkenyl optionally substituted by 1-11 $R^{59}$, $C_{2-6}$alkynyl optionally substituted by 1-9 $R^{59}$, $C_{6-11}$aryl optionally substituted by 1-11 $R^{59}$, $C_{7-16}$arylalkyl optionally substituted by 1-19 $R^{59}$, $C_{3-11}$cycloalkyl optionally substituted by 1-21 $R^{59}$, $C_{4-17}$cycloalkylalkyl optionally substituted by 1-32 $R^{59}$, 3-15 membered heterocycloalkyl optionally substituted by 1-28 $R^{59}$, 4-21 membered heterocycloalkylalkyl optionally substituted by 1-40 $R^{59}$, 5-15 membered heteroaryl optionally substituted by 1-15 $R^{59}$, and 6-21 membered heteroarylalkyl optionally substituted by 1-27 $R^{59}$;

or any $R^{22}$ and $R^{23}$ and/or $R^{32}$ and $R^{33}$ may form, together with the nitrogen atom to which they are attached, a 3-15 membered heterocycloalkyl optionally substituted by 1-28 $R^{69}$ or a 5-15 membered heteroaryl optionally substituted by 1-15 $R^{69}$;

$R^{39}$, $R^{49}$, $R^{59}$ and $R^{69}$ at each occurrence is independently chosen from $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(═O)$R^{70}$, —C(═O)O$R^{70}$, —C(═O)N$R^{72}R^{73}$, —C(═O)C(═O)$R^{70}$, —C(═N$R^{75}$)$R^{70}$, —C(═N$R^{75}$)N$R^{72}R^{73}$, —C(═NOH)N$R^{72}R^{73}$, —C(═NO$R^{76}$)$R^{70}$, —C(═NN$R^{72}R^{73}$)$R^{70}$, —C(═NN$R^{74}$C(═O)$R^{71}$)$R^{70}$, —C(═NN$R^{74}$C(═O)O$R^{71}$)$R^{70}$, —C(═S)N$R^{72}R^{73}$, —NC, —$NO_2$, —N$R^{72}R^{73}$, —N$R^{74}$N$R^{72}R^{73}$, —N═N$R^{74}$, ═N$R^{70}$, ═NO$R^{70}$, —N$R^{74}$O$R^{76}$, —N$R^{74}$C(═O)$R^{70}$, —N$R^{74}$C(═O)C(═O)$R^{70}$, —N$R^{74}$C(═O)O$R^{71}$, —N$R^{74}$C(═O)C(═O)O$R^{71}$, —N$R^{74}$C(═O)N$R^{72}R^{73}$, —N$R^{74}$C(═O)N$R^{74}$C(═O)$R^{70}$, —N$R^{74}$C(═O)N$R^{74}$C(═O)O$R^{70}$, —N$R^{74}$C(═N$R^{75}$)N$R^{72}R^{73}$, —N$R^{74}$C(═O)C(═O)N$R^{72}R^{73}$, —N$R^{74}$C(═S)$R^{70}$, —N$R^{74}$C(═S)O$R^{70}$, —N$R^{74}$C(═S)N$R^{72}R^{73}$, —N$R^{74}$S(═O)$_2R^{71}$, —N$R^{74}$S(═O)$_2$N$R^{72}R^{73}$, —N$R^{74}$P(═O)$R^{78}R^{78}$, —N$R^{74}$P(═O)(N$R^{72}$N$R^{73}$)(N$R^{72}R^{73}$), —N$R^{74}$P(═O)(O$R^{70}$)(O$R^{70}$), —N$R^{74}$P(═O)(S$R^{70}$)(S$R^{70}$), —O$R^{70}$, ═O, —OCN, —OC(═O)$R^{70}$, —OC(═O)N$R^{72}R^{73}$, —OC(═O)O$R^{70}$, —OC(═N$R^{75}$)N$R^{72}R^{73}$, —OS(═O)$R^{70}$, —OS(═O)$_2R^{70}$, —OS(═O)$_2$O$R^{70}$, —OS(═O)$_2$N$R^{72}R^{73}$, —OP(═O)$R^{78}R^{78}$, —OP(═O)(N$R^{72}R^{73}$)(N$R^{72}R^{73}$), —OP(═O)(O$R^{70}$)(O$R^{70}$), —OP(═O)(S$R^{70}$)(S$R^{70}$), —Si($R^{74}$)$_3$, —SCN, ═S, —S(═O)$_nR^{70}$, —S(═O)$_2$O$R^{70}$, —$SO_3R^{77}$, —S(═O)$_2$N$R^{72}R^{73}$, —S(═O)N$R^{72}R^{73}$, —SP(═O)$R^{78}R^{78}$, —SP(═O)(N$R^{72}R^{73}$)(N$R^{72}R^{73}$), —SP(═O)(O$R^{70}$)(O$R^{70}$), —SP $(=O)(SR^{70})(SR^{70})$, $—P(=O)R^{78}R^{78}$, $—P(=O)(NR^{72}R^{73})(NR^{72}R^{73})$, $—P(=O)(OR^{70})(OR^{70})$, and $—P(=O)(SR^{70})(SR^{70})$;

$R^{70}$, $R^{71}$, $R^{74}$, $R^{75}$, $R^{76}$ and $R^{77}$ at each occurrence is independently chosen from H, $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

$R^{72}$ and $R^{73}$ at each occurrence is independently chosen from H, $C_{1-6}$alkyl optionally substituted by 1-13 $R^{99}$, $C_{2-6}$alkenyl optionally substituted by 1-11 $R^{99}$, $C_{2-6}$alkynyl optionally substituted by 1-9 $R^{99}$, $C_{6-11}$aryl optionally substituted by 1-11 $R^{99}$, $C_{7-16}$arylalkyl optionally substituted by 1-19 $R^{99}$, $C_{3-11}$cycloalkyl optionally substituted by 1-21 $R^{99}$, $C_{4-17}$cycloalkylalkyl optionally substituted by 1-32 $R^{99}$, 3-15 membered heterocycloalkyl optionally substituted by 1-28 $R^{99}$, 4-21 membered heterocycloalkylalkyl optionally substituted by 1-40 $R^{99}$, 5-15 membered heteroaryl optionally substituted by 1-15 $R^{99}$, and 6-21 membered heteroarylalkyl optionally substituted by 1-27 $R^{99}$;

or any $R^{72}$ and $R^{73}$ may form, together with the nitrogen atom to which they are attached, a 3-15 membered heterocycloalkyl optionally substituted by 1-28 $R^{109}$ or a 5-15 membered heteroaryl optionally substituted by 1-15 $R^{109}$;

$R^{78}$ at each occurrence is independently chosen from $C_{1-6}$alkyl optionally substituted by 1-13 $R^{89}$, $C_{2-6}$alkenyl optionally substituted by 1-11 $R^{89}$, $C_{2-6}$alkynyl optionally substituted by 1-9 $R^{89}$, $C_{6-11}$aryl optionally substituted by 1-11 $R^{89}$, $C_{7-16}$arylalkyl optionally substituted by 1-19 $R^{89}$, $C_{3-11}$cycloalkyl optionally substituted by 1-21 $R^{89}$, $C_{4-17}$cycloalkylalkyl optionally substituted by 1-32 $R^{89}$, 3-15 membered heterocycloalkyl optionally substituted by 1-28 $R^{89}$, 4-21 membered heterocycloalkylalkyl optionally substituted by 1-40 $R^{89}$, 5-15 membered heteroaryl optionally substituted by 1-15 $R^{89}$, and 6-21 membered heteroarylalkyl optionally substituted by 1-27 $R^{89}$;

or any two $R^{78}$ attached to the same phosphorus atom can, together with the phosphorus atom linking them, form a 3-10 membered heterocycloalkyl optionally substituted by 1-6 $R^{89}$;

$R^{79}$, $R^{89}$, $R^{99}$ and $R^{109}$ at each occurrence is independently chosen from $C_{1-6}$alkyl optionally substituted by 1-13 $R^{119}$, $C_{2-6}$alkenyl optionally substituted by 1-11 $R^{119}$, $C_{2-6}$alkynyl optionally substituted by 1-9 $R^{119}$, $C_{6-11}$aryl optionally substituted by 1-11 $R^{119}$, $C_{7-16}$arylalkyl optionally substituted by 1-19 $R^{119}$, $C_{3-11}$cycloalkyl optionally substituted by 1-21 $R^{119}$, $C_{4-17}$cycloalkylalkyl optionally substituted by 1-32 $R^{119}$, 3-15 membered heterocycloalkyl optionally substituted by 1-28 $R^{119}$, 4-21 membered heterocycloalkylalkyl optionally substituted by 1-40 $R^{119}$, 5-15 membered heteroaryl optionally substituted by 1-15 $R^{119}$, 6-21 membered heteroarylalkyl optionally substituted by 1-27 $R^{119}$, halogen, —CN, $—C(=)R^{110}$, $—C(=O)OR^{110}$, $—C(=O)NR^{112}R^{113}$, $—C(=O)C(=O)R^{110}$, $—C(=NR^{115})R^{110}$, $—C(=NR^{115})NR^{112}R^{113}$, $—C(=NOH)NR^{112}R^{113}$, $—C(=NOR^{116})R^{110}$, $—C(=NNR^{112}R^{113})R^{110}$, $—C(=NNR^{114}C(=O)R^{111})R^{110}$, $—C(=NNR^{114}C(=O)OR^{111})R^{110}$, $—C(=S)NR^{112}R^{113}$, —NC, $—NO_2$, $—NR^{112}R^{113}$, $—NR^{114}NR^{112}R^{113}$, $—N=NR^{114}$, $=NR^{110}$, $=NOR^{110}$, $—NR^{114}OR^{116}$, $—NR^{114}C(=O)R^{110}$, $—NR^{114}C(=O)C(=O)R^{110}$, $—NR^{114}C(=O)OR^{111}$, $—NR^{114}C(=O)C(=O)OR^{111}$, $—NR^{114}C(=O)NR^{112}R^{113}$, $—NR^{114}C(=O)NR^{114}C(=O)R^{110}$, $—NR^{114}C(=O)NR^{114}C(=O)OR^{110}$, $—NR^{114}C(=NR^{115})NR^{112}R^{113}$, $—NR^{114}C(=O)C(=O)NR^{112}R^{113}$, $—NR^{114}C(=S)R^{110}$, $—NR^{114}C(=S)OR^{110}$, $—NR^{114}C(=S)NR^{112}R^{113}$, $—NR^{114}S(=O)_2R^{111}$, $—NR^{114}S(=O)_2NR^{112}R^{113}$, $—NR^{114}P(=O)R^{118}R^{18}$, $—NR^{114}P(=O)(NR^{112}R^{113})(NR^{112}R^{113})$, $—NR^{114}P(=O)(OR^{110})(OR^{110})$, $—NR^{114}P(=O)(SR^{110})(SR^{110})$, $—OR^{110}$, =O, —OCN, $—OC(=O)R^{110}$, $—OC(=O)NR^{112}R^{113}$, $—OC(=O)OR^{110}$, $—OC(=NR^{115})NR^{112}R^{113}$, $—OS(=O)R^{110}$, $—OS(=O)_2R^{110}$, $—OS(=O)_2OR^{110}$, $—OS(=O)_2NR^{112}R^{113}$, $—OP(=O)R^{118}R^{118}$, $—OP(=O)(NR^{112}R^{113})(NR^{112}R^{113})$, $—OP(=O)(OR^{110})(OR^{110})$, $—OP(=O)(SR^{110})(SR^{110})$, $—Si(R^{114})_3$, —SCN, =S, $—S(=O)_nR^{110}$, $—S(=O)_2OR^{110}$, $—SO_3R^{111}$, $—S(=O)_2NR^{112}R^{113}$, $—S(=O)NR^{112}R^{113}$, $—SP(=O)R^{118}R^{118}$, $—SP(=O)(NR^{112}R^{113})(NR^{112}R^{113})$, $—SP(=O)(OR^{110})(OR^{110})$, $—SP(=O)(SR^{110})(SR^{110})$, $—P(=O)R^{11}R^{118}$, $—P(=O)(NR^{112}R^{113})(NR^{112}R^{113})$, $—P(=O)(OR^{110})(OR^{110})$, and $—P(=O)(SR^{110})(SR^{110})$;

$R^{110}$, $R^{111}$, $R^{114}$, $R^{115}$, $R^{116}$ and $R^{117}$ at each occurrence is independently chosen from H, $C_{1-6}$alkyl optionally substituted by 1-13 $R^{129}$, $C_{2-6}$alkenyl optionally substituted by 1-11 $R^{129}$, $C_{2-6}$alkynyl optionally substituted by 1-9 $R^{129}$, $C_{6-11}$aryl optionally substituted by 1-11 $R^{129}$, $C_{7-16}$arylalkyl optionally substituted by 1-19 $R^{129}$, $C_{3-11}$cycloalkyl optionally substituted by 1-21 $R^{129}$, $C_{4-17}$cycloalkylalkyl optionally substituted by 1-32 $R^{129}$, 3-15 membered heterocycloalkyl optionally substituted by 1-28 $R^{129}$, 4-21 membered heterocycloalkylalkyl optionally substituted by 1-40 $R^{129}$, 5-15 membered heteroaryl optionally substituted by 1-15 $R^{129}$, and 6-21 membered heteroarylalkyl optionally substituted by 1-27 $R^{129}$;

$R^{112}$ and $R^{113}$ at each occurrence is independently chosen from H, $C_{1-6}$alkyl optionally substituted by 1-13 $R^{139}$, $C_{2-6}$alkenyl optionally substituted by 1-11 $R^{139}$, $C_{2-6}$alkynyl optionally substituted by 1-9 $R^{139}$, $C_{6-11}$aryl optionally substituted by 1-11 $R^{139}$, $C_{7-16}$arylalkyl optionally substituted by 1-19 $R^{139}$, $C_{3-11}$cycloalkyl optionally substituted by 1-21 $R^{139}$, $C_{4-17}$cycloalkylalkyl optionally substituted by 1-32 $R^{139}$, 3-15 membered heterocycloalkyl optionally substituted by 1-28 $R^{139}$, 4-21 membered heterocycloalkylalkyl optionally substituted by 1-40 $R^{139}$, 5-15 membered heteroaryl optionally substituted by 1-15 $R^{139}$, and 6-21 membered heteroarylalkyl optionally substituted by 1-27 $R^{39}$;

or any $R^{112}$ and $R^{113}$ may form, together with the nitrogen atom to which they are attached, a 3-15 membered heterocycloalkyl optionally substituted by 1-28 $R^{149}$ or a 5-15 membered heteroaryl optionally substituted by 1-15 $R^{49}$;

$R^{118}$ at each occurrence is independently chosen from $C_{1-6}$alkyl optionally substituted by 1-13 $R^{129}$, $C_{2-6}$alkenyl optionally substituted by 1-11 $R^{129}$, $C_{2-6}$alkynyl optionally substituted by 1-9 $R^{129}$, $C_{6-11}$aryl optionally substituted by 1-11 $R^{129}$, $C_{7-16}$arylalkyl optionally substituted by 1-19 $R^{129}$, $C_{3-11}$cycloalkyl optionally substituted by 1-21 $R^{129}$, $C_{4-17}$cycloalkylalkyl optionally substituted by 1-32 $R^{129}$, 3-15 membered heterocycloalkyl optionally substituted by 1-28 $R^{129}$, 4-21 membered heterocycloalkylalkyl optionally substituted by 1-40 $R^{129}$, 5-15 membered heteroaryl optionally substituted by 1-15 $R^{129}$, and 6-21 membered heteroarylalkyl optionally substituted by 1-27 $R^{129}$;

$R^{119}$, $R^{129}$, $R^{139}$ and $R^{149}$ at each occurrence is independently chosen from $C_{1-6}$alkyl optionally substituted by 1-13 $R^{159}$, $C_{2-6}$alkenyl optionally substituted by 1-11 $R^{159}$, $C_{2-6}$alkynyl optionally substituted by 1-9 $R^{159}$, $C_{6-11}$aryl optionally substituted by 1-11 $R^{159}$, $C_{7-16}$arylalkyl optionally substituted by 1-19 $R^{159}$, $C_{3-11}$cycloalkyl optionally substituted by 1-21 $R^{159}$, $C_{4-17}$cycloalkylalkyl optionally substituted by 1-32 $R^{159}$, 3-15 membered heterocycloalkyl optionally substituted by 1-28 $R^{159}$, 4-21 membered heterocycloalkylalkyl optionally substituted by 1-40 $R^{159}$, 5-15 membered heteroaryl optionally substituted by 1-15 $R^{159}$, 6-21 membered heteroarylalkyl optionally substituted by 1-27 $R^{159}$, halogen, —CN, —C(═O)$R^{150}$, —C(═O)O$R^{150}$, —C(═O)N$R^{152}R^{153}$, —C(═O)C(═O)$R^{150}$, —C(═N$R^{155}$)$R^{150}$, —C(═N$R^{155}$)N$R^{152}R^{153}$, —C(═NOH)N$R^{152}R^{153}$, —C(═NO$R^{156}$)$R^{150}$, —C(═NN$R^{152}R^{153}$)$R^{150}$, —C(═NN$R^{154}$C(═O)$R^{151}$)$R^{150}$, —C(═NN$R^{154}$C(═O)O$R^{151}$)$R^{150}$, —C(═S)N$R^{152}R^{153}$, —NC, —$NO_2$, —N$R^{152}R^{153}$, —N$R^{154}$N$R^{152}R^{153}$, —N═N$R^{154}$, ═N$R^{150}$, ═NO$R^{15}$, —N$R^{154}$O$R^{156}$, —N$R^{154}$C(═O)$R^{150}$, —N$R^{154}$C(═O)C(═O)$R^{150}$, —N$R^{154}$C(═)O$R^{151}$, —N$R^{154}$C(═O)C(═O)O$R^{151}$, —N$R^{54}$C(═O)N$R^{152}R^{153}$, —N$R^{154}$C(═O)N$R^{154}$C(═O)$R^{150}$, —N$R^{154}$C(═O)N$R^{154}$C(═O)O$R^{150}$, —N$R^{154}$C(═N$R^{155}$)N$R^{152}R^{153}$, —N$R^{154}$C(═O)C(═O)N$R^{152}R^{153}$, —N$R^{154}$C(═S)$R^{150}$, —N$R^{154}$C(═S)O$R^{150}$, —N$R^{154}$C(═S)N$R^{152}R^{153}$, —N$R^{154}$S(═O)$_2$$R^{151}$, —N$R^{154}$S(═O)$_2$N$R^{152}R^{153}$, —N$R^{154}$P(═O)$R^{158}R^{158}$, —N$R^{154}$P(═O)(N$R^{152}R^{153}$)(N$R^{152}R^{153}$), —N$R^{154}$P(═O)(O$R^{150}$)(O$R^{150}$), —N$R^{154}$P(═O)(S$R^{150}$)(S$R^{150}$), —O$R^{150}$, ═O, —OCN, —OC(═O)$R^{150}$, —OC(═O)N$R^{152}R^{153}$, —OC(═O)O$R^{150}$, —OC(═N$R^{155}$)N$R^{152}R^{153}$, —OS(═O)$R^{150}$, —OS(═O)$_2$$R^{150}$, —OS(═O)$_2$O$R^{150}$, —OS(═O)$_2$N$R^{152}R^{153}$, —OP(═O)$R^{158}R^{158}$, —OP(═O)(N$R^{152}R^{153}$)(N$R^{152}R^{153}$), —OP(═O)(O$R^{150}$)(O$R^{150}$), —OP(═O)(SR(S$R^{150}$)(S$R^{150}$), —Si($R^{154}$)$_3$, —SCN, ═S, —S(═O)$_n$$R^{150}$, —S(═O)$_2$O$R^{150}$, —$SO_3$$R^{1515}$, —S(═O)$_2$N$R^{152}R^{153}$, —S(═O)N$R^{152}R^{153}$, —SP(═O)$R^{158}R^{158}$, —SP(═O)(N$R^{152}R^{153}$)(N$R^{152}R^{153}$), —SP(═O)(O$R^{150}$)(O$R^{150}$), —SP(═O)(S$R^{150}$)(S$R^{150}$), —P(═O)$R^{158}R^{158}$, —P(═O)(N$R^{152}R^{153}$)(N$R^{152}R^{153}$), —P(═O)(O$R^{150}$)(O$R^{150}$), and —P(═O)(S$R^{150}$)(S$R^{150}$);

$R^{150}$, $R^{151}$, $R^{154}$, $R^{155}$, $R^{156}$ and $R^{157}$ at each occurrence is independently chosen from H, $C_{1-6}$alkyl optionally substituted by 1-13 $R^{169}$, $C_{2-6}$alkenyl optionally substituted by 1-11 $R^{169}$, $C_{2-6}$alkynyl optionally substituted by 1-9 $R^{169}$, $C_{6-11}$aryl optionally substituted by 1-11 $R^{169}$, $C_{7-16}$arylalkyl optionally substituted by 1-19 $R^{169}$, $C_{3-11}$cycloalkyl optionally substituted by 1-21 $R^{169}$, $C_{4-17}$cycloalkylalkyl optionally substituted by 1-32 $R^{169}$, 3-15 membered heterocycloalkyl optionally substituted by 1-28 $R^{169}$, 4-21 membered heterocycloalkylalkyl optionally substituted by 1-40 $R^{169}$, 5-15 membered heteroaryl optionally substituted by 1-15 $R^{169}$, and 6-21 membered heteroarylalkyl optionally substituted by 1-27 $R^{69}$;

$R^{152}$ and $R^{153}$ at each occurrence is independently chosen from H, $C_{1-6}$alkyl optionally substituted by 1-13 $R^{179}$, $C_{2-6}$alkenyl optionally substituted by 1-11 $R^{179}$, $C_{2-6}$alkynyl optionally substituted by 1-9 $R^{179}$, $C_{6-11}$aryl optionally substituted by 1-11 $R^{179}$, $C_{7-16}$arylalkyl optionally substituted by 1-19 $R^{179}$, $C_{3-11}$cycloalkyl optionally substituted by 1-21 $R^{179}$, $C_{4-17}$cycloalkylalkyl optionally substituted by 1-32 $R^{179}$, 3-15 membered heterocycloalkyl optionally substituted by 1-28 $R^{179}$, 4-21 membered heterocycloalkylalkyl optionally substituted by 1-40 $R^{179}$, 5-15 membered heteroaryl optionally substituted by 1-15 $R^{179}$, and 6-21 membered heteroarylalkyl optionally substituted by 1-27 $R^{179}$;

or any $R^{152}$ and $R^{153}$ may form, together with the nitrogen atom to which they are attached, a 3-15 membered heterocycloalkyl optionally substituted by 1-28 $R^{189}$ or a 5-15 membered heteroaryl optionally substituted by 1-15 $R^{189}$;

$R^{158}$ at each occurrence is independently chosen from $C_{1-6}$alkyl optionally substituted by 1-13 $R^{169}$, $C_{2-6}$alkenyl optionally substituted by 1-11 $R^{169}$, $C_{2-6}$alkynyl optionally substituted by 1-9 $R^{169}$, $C_{6-11}$aryl optionally substituted by 1-11 $R^{169}$, $C_{7-16}$arylalkyl optionally substituted by 1-19 $R^{169}$, $C_{3-11}$cycloalkyl optionally substituted by 1-21 $R^{169}$, $C_{4-17}$cycloalkylalkyl optionally substituted by 1-32 $R^{169}$, 3-15 membered heterocycloalkyl optionally substituted by 1-28 $R^{169}$, 4-21 membered heterocycloalkylalkyl optionally substituted by 1-40 $R^{169}$, 5-15 membered heteroaryl optionally substituted by 1-15 $R^{169}$, and 6-21 membered heteroarylalkyl optionally substituted by 1-27 $R^{69}$;

$R^{159}$, $R^{169}$, $R^{179}$ and $R^{189}$ at each occurrence is independently chosen from $C_{1-6}$alkyl optionally substituted by 1-13 $R^{199}$, $C_{2-6}$alkenyl optionally substituted by 1-11 $R^{199}$, $C_{2-6}$alkynyl optionally substituted by 1-9 $R^{199}$, $C_{6-11}$aryl optionally substituted by 1-11 $R^{199}$, $C_{7-16}$arylalkyl optionally substituted by 1-19 $R^{199}$, $C_{3-11}$cycloalkyl optionally substituted by 1-21 $R^{199}$, $C_{4-17}$cycloalkylalkyl optionally substituted by 1-32 $R^{199}$, 3-15 membered heterocycloalkyl optionally substituted by 1-28 $R^{199}$, 4-21 membered heterocycloalkylalkyl optionally substituted by 1-40 $R^{199}$, 5-15 membered heteroaryl optionally substituted by 1-15 $R^{199}$, 6-21 membered heteroarylalkyl optionally substituted by 1-27 $R^{199}$, halogen, —CN, —C(═O)$R^{190}$, —C(═O)O$R^{190}$, —C(═O)N$R^{192}R^{193}$, —C(═O)C(═O)$R^{190}$, —C(═N$R^{195}$)$R^{190}$, —C(═N$R^{195}$)N$R^{192}R^{193}$, —C(═NOH)N$R^{192}R^{193}$, —C(═NO$R^{196}$)$R^{190}$, —C(═NN$R^{192}R^{193}$)$R^{190}$, —C(═NN$R^{194}$C(═O)$R^{191}$)$R^{190}$, —C(═NN$R^{194}$C(═O)O$R^{191}$)$R^{190}$, —C(═S)N$R^{192}R^{193}$, —NC, —$NO_2$, —N$R^{192}R^{193}$, —N$R^{194}$N$R^{192}R^{193}$, —N═N$R^{194}$, ═N$R^{190}$, ═NO$R^{190}$, —N$R^{194}$O$R^{196}$, —N$R^{194}$C(═O)$R^{190}$, —N$R^{194}$C(═O)C(═O)$R^{190}$, —N$R^{194}$C(═O)O$R^{191}$, —N$R^{194}$C(═O)C(═)O$R^{191}$, —N$R^{194}$C(═O)N$R^{192}R^{193}$, —N$R^{194}$C(═O)N$R^{194}$C(═O)$R^{190}$, —N$R^{194}$C(═O)N$R^{194}$C(═O)O$R^{190}$, —N$R^{194}$C(═N$R^{195}$)N$R^{192}R^{193}$, —N$R^{194}$C(═O)C(═O)N$R^{192}R^{193}$, —N$R^{194}$C(═S)$R^{190}$, —N$R^{194}$C(═S)O$R^{190}$, —N$R^{194}$C(═S)N$R^{192}R^{193}$, —N$R^{194}$S(═O)$_2$$R^{191}$, —N$R^{194}$S(═O)$_2$N$R^{192}R^{193}$, —N$R^{194}$C(═O)$R^{198}R^{198}$, —N$R^{194}$P(═O)(N$R^{192}R^{193}$)(N$R^{192}R^{193}$), —N$R^{194}$P(═O)(O$R^{190}$)(O$R^{190}$), —N$R^{194}$P(═O)

$(SR^{190})(SR^{190})$, $—OR^{190}$, $=O$, —OCN, $—OC(=O)R^{190}$, $—OC(=O)NR^{192}R^{193}$, $—OC(=O)OR^{190}$, $—OC(=NR^{195})NR^{192}R^{193}$, $—OS(=O)R^{190}$, $—OS(=O)_2R^{190}$, $—OS(=O)_2OR^{190}$, $—OS(=O)_2NR^{192}R^{193}$, $—OP(=O)R^{198}R^{198}$, $—OP(=O)(NR^{192}R^{193})(NR^{192}R^{193})$, $—OP(=O)(OR^{190})(OR^{190})$, $—OP(=O)(SR^{190})(SR^{190})$, $—Si(R^{194})_3$, —SCN, =S, $—S(=O)_nR^{190}$, $—S(=O)_2R^{190}$, $—SO_3R^{1919}$, $—S(=O)_2NR^{192}R^{193}$, $—S(=O)NR^{192}R^{193}$, $—SP(=O)R^{198}R^{198}$, $—SP(=O)(NR^{192}R^{193})(NR^{192}R^{193})$, $—SP(=O)(OR^{190})(OR^{190})$, $—SP(=O)(SR^{190})(SR^{190})$, $—P(=O)R^{198}R^{198}$, $—P(=O)(NR^{192}R^{193})(NR^{192}R^{193})$, $—P(=O)(OR^{190})(OR^{190})$, and $—P(=O)(SR^{190})(SR^{190})$;

$R^{190}$, $R^{191}$, $R^{194}$, $R^{195}$, $R^{196}$ and $R^{197}$ at each occurrence is independently chosen from H, $C_{1-6}$alkyl optionally substituted by 1-13 $R^{209}$, $C_{2-6}$alkenyl optionally substituted by 1-11 $R^{209}$, $C_{2-6}$alkynyl optionally substituted by 1-9 $R^{209}$, $C_{6-11}$aryl optionally substituted by 1-11 $R^{209}$, $C_{7-16}$arylalkyl optionally substituted by 1-19 $R^{209}$, $C_{3-11}$cycloalkyl optionally substituted by 1-21 $R^{209}$, $C_{4-17}$cycloalkylalkyl optionally substituted by 1-32 $R^{209}$, 3-15 membered heterocycloalkyl optionally substituted by 1-28 $R^{209}$, 4-21 membered heterocycloalkylalkyl optionally substituted by 1-40 $R^{209}$, 5-15 membered heteroaryl optionally substituted by 1-15 $R^{209}$, and 6-21 membered heteroarylalkyl optionally substituted by 1-27 $R^{209}$;

$R^{192}$ and $R^{193}$ at each occurrence is independently chosen from H, $C_{1-6}$alkyl optionally substituted by 1-13 $R^{219}$, $C_{2-6}$alkenyl optionally substituted by 1-11 $R^{219}$, $C_{2-6}$alkynyl optionally substituted by 1-9 $R^{219}$, $C_{6-11}$aryl optionally substituted by 1-11 $R^{219}$, $C_{7-16}$arylalkyl optionally substituted by 1-19 $R^{219}$, $C_{3-11}$cycloalkyl optionally substituted by 1-21 $R^{219}$, $C_{4-17}$cycloalkylalkyl optionally substituted by 1-32 $R^{219}$, 3-15 membered heterocycloalkyl optionally substituted by 1-28 $R^{219}$, 4-21 membered heterocycloalkylalkyl optionally substituted by 1-40 $R^{219}$, 5-15 membered heteroaryl optionally substituted by 1-15 $R^{219}$, and 6-21 membered heteroarylalkyl optionally substituted by 1-27 $R^{219}$;

or any $R^{192}$ and $R^{193}$ may form, together with the nitrogen atom to which they are attached, a 3-15 membered heterocycloalkyl optionally substituted by 1-28 $R^{229}$ or a 5-15 membered heteroaryl optionally substituted by 1-15 $R^{229}$;

$R^{198}$ at each occurrence is independently chosen from $C_{1-6}$alkyl optionally substituted by 1-13 $R^{209}$, $C_{2-6}$alkenyl optionally substituted by 1-11 $R^{209}$, $C_{2-6}$alkynyl optionally substituted by 1-9 $R^{209}$, $C_{6-11}$aryl optionally substituted by 1-11 $R^{209}$, $C_{7-16}$arylalkyl optionally substituted by 1-19 $R^{209}$, $C_{3-11}$cycloalkyl optionally substituted by 1-21 $R^{209}$, $C_{4-17}$cycloalkylalkyl optionally substituted by 1-32 $R^{209}$, 3-15 membered heterocycloalkyl optionally substituted by 1-28 $R^{209}$, 4-21 membered heterocycloalkylalkyl optionally substituted by 1-40 $R^{209}$, 5-15 membered heteroaryl optionally substituted by 1-15 $R^{209}$, and 6-21 membered heteroarylalkyl optionally substituted by 1-27 $R^{209}$;

$R^{199}$, $R^{209}$, $R^{219}$ and $R^{229}$ at each occurrence is independently chosen from $C_{1-6}$alkyl optionally substituted by 1-13 halogen, $C_{2-6}$alkenyl, $C_{2-6}$alkynyl, $C_{6-11}$aryl, $C_{7-16}$arylalkyl, $C_{3-11}$cycloalkyl, $C_{4-17}$cycloalkylalkyl, 3-15 membered heterocycloalkyl, 4-21 membered heterocycloalkylalkyl, 5-15 membered heteroaryl, 6-21 membered heteroarylalkyl, halogen, —CN, $—C(=O)R^{230}$, $—C(=)OR^{230}$, $—C(=O)NR^{230}R^{230}$, $—C(=O)C(=O)R^{230}$, $—C(=NR^{230})R^{230}$, $—C(=NR^{230})NR^{230}R^{230}$, $—C(=NOH)NR^{230}R^{230}$, $—C(=NOR^{230})R^{230}$, $—C(=NNR^{23}R^{230})R^{230}$, $—C(=NNR^{230}C(=O)R^{230})R^{230}$, $—C(=NNR^{230}C(=O)OR^{230})R^{230}$, $—C(=S)NR^{230}R^{230}$, —NC, $—NO_2$, $—NR^{230}R^{230}$, $—NR^{230}NR^{230}R^{230}$, $—N=NR^{230}$, $=NR^{230}$, $=NOR^{230}$, $—NR^{230}OR^{230}$, $—NR^{230}C(=O)R^{230}$, $—NR^{230}C(=O)C(=O)R^{230}$, $—NR^{230}C(=O)OR^{230}$, $—NR^{230}C(=O)C(=O)OR^{230}$, $—NR^{230}C(=O)NR^{230}R^{230}$, $—NR^{230}C(=O)NR^{230}C(=O)R^{230}C(=O)R^{230}$, $—NR^{230}C(=O)NR^{230}C(=O)OR^{230}$, $—NR^{230}C(=NR^{230})NR^{230}R^{230}$, $—NR^{230}C(=O)C(=O)NR^{230}R^{230}$, $—NR^{230}C(=S)R^{230}$, $—NR^{230}C(=S)OR^{230}$, $—NR^{230}C(=S)NR^{230}R^{230}$, $—NR^{230}S(=O)_2R^{230}$, $—NR^{230}S(=O)_2NR^{230}R^{230}$, $—NR^{230}P(=O)R^{231}R^{231}$, $—NR^{230}P(=O)(NR^{230}R^{230})(NR^{230}R^{230})$, $—NR^{230}P(=O)(OR^{230})(OR^{230})$, $—NR^{230}P(=O)(SR^{230})(SR^{230})$, $—OR^{230}$, =O, —OCN, $—OC(=O)R^{230}$, $—OC(=O)NR^{230}R^{230}$, $—OC(=O)OR^{230}$, $—OC(=NR^{230})NR^{230}R^{230}$, $—OS(=O)R^{230}$, $—OS(=O)_2R^{230}$, $—OS(=O)_2OR^{230}$, $—OS(=O)_2NR^{230}R^{230}$, $—OP(=O)R^{231}R^{231}$, $—OP(=O)(NR^{230}R^{230})(NR^{230}R^{230})$, $—OP(=O)(OR^{230})(OR^{230})$, $—OP(=O)(SR^{230})(SR^{230})$, $—Si(R^{230})_3$, —SCN, =S, $—S(=O)_nR^{230}$, $—S(=O)_2OR^{230}$, $—SO_3R^{230}$, $—S(=O)_2NR^{230}R^{230}$, $—S(=O)NR^{230}R^{230}$, $—SP(=O)R^{231}R^{231}$, $—SP(=O)(NR^{230}R^{230})(NR^{230}R^{230})$, $—SP(=O)(OR^{230})(OR^{230})$, $—SP(=O)(SR^{230})(SR^{230})$, $—P(=O)R^{231}R^{231}$, $—P(=O)(NR^{230}R^{230})(NR^{230}R^{230})$, $—P(=O)(OR^{230})(OR^{230})$, and $—P(=O)(SR^{230})(SR^{230})$;

$R^{230}$ at each occurrence is independently chosen from H, $C_{1-6}$alkyl and $C_{1-6}$-haloalkyl;

$R^{231}$ at each occurrence is independently chosen from $C_{1-6}$alkyl and $C_{1-6}$-haloalkyl; and n at each occurrence is independently chosen from 0, 1, and 2;

with the proviso that the compound is not (a)

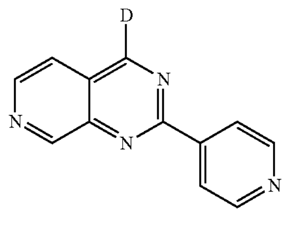

in which D is H or

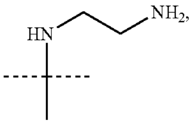

or a salt form thereof;

(b)

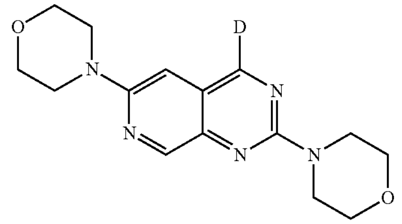

in which D is

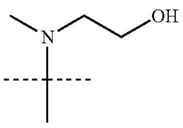

or

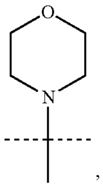

, or a salt form thereof; or (c)

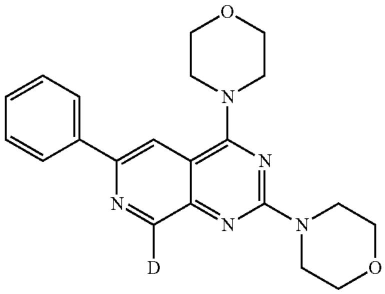

in which D is H or —$CH_3$, or a salt form thereof.

2. A compound as defined in preferred Embodiment 1, wherein X is chosen from 3-10 membered heterocycloalkyl optionally substituted by 1-6 $R^{19}$, 5-10 membered heteroaryl optionally substituted by 1-6 $R^{19}$, —C(═O)$R^{28}$, —C(═O)$NR^{24}R^{28}$, —$NR^{24}R^{28}$, —$NR^{24}$C(═O)$R^{28}$, —$NR^{24}$S(═O)$_2R^{28}$, and —$OR^{28}$.

3. A compound as defined in preferred Embodiment 1, wherein X is chosen from 5-6 membered heterocycloalkyl optionally substituted by 1-6 $R^{19}$, and —$NR^{24}R^{28}$.

4. A compound as defined in preferred Embodiment 1, wherein X is chosen from morpholinyl optionally substituted by 1-6 $R^{19}$, piperidinyl optionally substituted by 1-6 $R^{19}$, piperazinyl optionally substituted by 1-6 $R^{19}$, and —$NR^{24}R^{28}$.

5. A compound as defined in preferred Embodiment 1, wherein X is

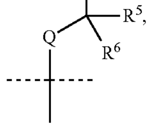

and

A is —$NR^1R^2$, —$CR^iR^jR^k$, —$OR^{18a}$, or —$SR^{18}$b;

Q is —$NR^{11}$—, —$CR^mR^n$—, —O—, or —S—;

$R^k$ is H, halogen, —CN, —$NO_2$, —$NR^{16}R^{17}$, —$OR^{18c}$, —$SR^{18d}$, or —$CR^oR^pR^q$;

$R^q$ is H, halogen, —CN, —$NO_2$, —$NR^{16a}R^{17a}$ or —$OR^{18e}$;

$R^1$, $R^2$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are independently chosen from H, $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, and —$OR^{70}$;

$R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-13 $R^{79}$, $C_{2-6}$alkenyl optionally substituted by 1-11 $R^{79}$, $C_{2-6}$alkynyl optionally substituted by 1-9 $R^{79}$, $C_{6-11}$aryl optionally substituted by 1-11 $R^{79}$, $C_{7-16}$arylalkyl optionally substituted by 1-19 $R^{79}$, $C_{3-11}$cycloalkyl optionally substituted by 1-21 $R^{79}$, $C_{4-17}$cycloalkylalkyl optionally substituted by 1-32 $R^{79}$, 3-15 membered heterocycloalkyl optionally substituted by 1-28 $R^{79}$, 4-21 membered heterocycloalkylalkyl optionally substituted by 1-40 $R^{79}$, 5-15 membered heteroaryl optionally substituted by 1-15 $R^{79}$, 6-21 membered heteroarylalkyl optionally substituted by 1-27 $R^{79}$, halogen, —CN, —C(═O)$R^{70}$, —C(═)$OR^{70}$, —C(═O)$NR^{72}R^{73}$, —C(═O)C(═O)$R^{70}$, —C(═$NR^{75}$)$R^{70}$, —C(═$NR^{75}$)$NR^{72}R^{73}$, —C(═NOH)$NR^{72}R^{73}$, —C(═$NOR^{76}$)$R^{70}$, —C(═$NNR^{72}R^{73}$)$R^{70}$, —C(═$NNR^{74}$C(═O)$R^7$)$R^{71}$)$R^{70}$, —C(═$NNR^{74}$C(═O)$OR^{71}$)$R^{70}$, —C(═S)$NR^{72}R^{73}$, —NC, —$NO_2$, —$NR^{72}R^{73}$, —$NR^{74}NR^{72}R^{73}$, —N═$NR^{74}$, —$NR^{74}OR^{76}$, —$NR^{74}$C(═O)$R^{70}$, —$NR^{74}$C(═O)C(═O)$R^{70}$, —$NR^{74}$C(═O)$OR^{71}$, —$NR^{74}$C(═O)C(═)$OR^{71}$, —$NR^{74}$C(═O)$NR^{72}R^{73}$, —$NR^{74}$C(═O)$NR^{74}$C(═O)$R^{70}$, —$NR^{74}$C(═O)$NR^{74}$C(═O)$OR^{70}$, —$NR^{74}$C(═$NR^{75}$)$NR^{72}R^{73}$, —$NR^{74}$C(═O)C(═O)$NR^{72}R^{73}$, —$NR^{74}$C(═S)$R^{70}$, —$NR^{74}$C(═S)$OR^{70}$, —$NR^{74}$C(═S)$NR^{72}R^{73}$, —$NR^{74}$S(═O)$_2R^{71}$, —$NR^{74}$S(═O)$_2NR^{72}R^{73}$, —$NR^{74}$P(═O)$R^{78}R^{78}$, —$NR^{74}$P(═O)($NR^{72}R^{73}$)($NR^{72}R^{73}$), —$NR^{74}$P(═O)($OR^{70}$)($OR^{70}$), —$NR^{74}$P(═O)($SR^{70}$)($SR^{70}$), —$OR^{70}$, —OCN, —OC(═O)$R^{70}$, —OC(═O)$NR^{72}R^{73}$, —OC(═O)$OR^{70}$, —OC(═$NR^{75}$)$NR^{72}R^{73}$, —OS(═O)$R^{70}$, —OS(═O)$_2R^{70}$, —OS(═O)$_2OR^{70}$, —OS(═O)$_2NR^{72}R^{73}$, —OP(═O)$R^{78}R^{78}$, —OP(═O)($NR^{72}R^{73}$)($NR^{72}R^{73}$), —OP(═O)($OR^{70}$)($OR^{70}$), —OP(═O)($SR^{70}$)($SR^{70}$), —Si($R^{74}$)$_3$, —SCN, —S(═O)$_nR^{70}$, —S(═O)$_2OR^{70}$, —$SO_3R^{77}$, —S(═O)$_2NR^{72}R^{73}$, —S(═O)$NR^{72}R^{73}$, —SP(═O)$R^{78}R^{78}$, —SP(═O)($NR^{72}R^{73}$)($NR^{72}R^{73}$), —SP(═O)($OR^{70}$)($OR^{70}$), —SP(═O)($SR^{70}$)($SR^{70}$), —P(═O)$R^{78}R^{78}$, —P(═O)$R^{73}R^{73}$)($NR^{72}R^{73}$), —P(═O)($OR^{70}$)($OR^{70}$), and —P(═O)($SR^{70}$)($SR^{70}$);

or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and R, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-15 membered heterocycloalkyl optionally substituted by 1-28 $R^{79}$ or a 5-15 membered heteroaryl optionally substituted by 1-15 $R^{79}$;

or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{6-11}$aryl optionally substituted by 1-11 $R^{79}$, $C_{3-11}$cycloalkyl optionally substituted by 1-21 $R^{79}$, 3-15 membered heterocycloalkyl optionally substituted by 1-28 $R^{79}$ or a 5-15 membered heteroaryl optionally substituted by 1-15 $R^{79}$;

or $R^4$ and $R^5$ or $R^n$ and $R^5$ can together form a double bond;

or any of $R^3$ and $R^4$, $R^5$ and $R^6$, $R^i$ and $R^j$, and $R^m$ and $R^n$ can together form ═O, ═$NR^{70}$, ═$NOR^{70}$, or ═S.

6. A compound as defined in preferred Embodiment 5, wherein $R^1$, $R^2$, $R^{11}$, $R^{16}$, $R^{17}$, $R^{16a}$ $R^{17a}$, $R^{18a}$, $R^{18b}$, $R^{18c}$, $R^{18d}$, and $R^{18e}$ are independently chosen from H, $C_{1-6}$alkyl optionally substituted by 1-6 $R^{79}$, and $C_{7-16}$arylalkyl optionally substituted by 1-6 $R^{79}$; $R^3$, $R^4$, $R^5$, $R^6$, $R^i$, $R^j$, $R^m$, $R^n$, $R^o$, and $R^p$ are independently chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, —CN, —C(═O)$OR^{70}$, —C(═O)$NR^{72}R^{73}$, —$NR^{72}R^{73}$, and —$OR^{70}$; or any of $R^1$ and $R^2$, $R^1$ and $R^3$, $R^1$ and $R^5$, $R^1$ and $R^{11}$, $R^1$ and $R^n$, $R^4$ and $R^1$, $R^{16}$ and $R^5$, $R^j$ and $R^{11}$, and $R^{18a}$ and $R^{11}$ can, together with the atoms linking them, form a 3-11 membered heterocycloalkyl optionally substituted by 1-6 $R^{79}$; or $R^3$ and $R^4$ can together form ═O.

7. A compound as defined in preferred Embodiment 5, wherein $R^1$, $R^{11}$, $R^{16}$, $R^{17}$, $R^{16a}$, $R^{17a}$ $R^{18a}$, $R^{18b}$, $R^{18c}$, $R^{18d}$, and $R^{18e}$ are independently chosen from H and $C_{1-6}$alkyl optionally substituted by 1-6 $R^{79}$; $R^2$ is chosen from H, $C_{1-6}$alkyl optionally substituted by 1-6 $R^{79}$, and $C_{7-16}$arylalkyl optionally substituted by 1-6 $R^{79}$; $R^4$, $R^5$, $R^6$, $R^i$, $R^j$, $R^m$, $R^n$, $R^o$, and $R^p$ are independently chosen from H and $C_{1-6}$alkyl optionally substituted by 1-6 $R^{79}$; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-10 membered heterocycloalkyl optionally substituted by 1-6 $R^{79}$, halogen, —CN, —C(═O)$R^{70}$, —C(═O)$OR^{70}$, —C(═O)$NR^{72}R^{73}$, —$NO_2$, —$NR^{72}R^{73}$, —$NR^{74}$C(═O)$R^{70}$, —$NR^{74}$S(═O)$_2R^{71}$, —$OR^{70}$, —OC(═O)$R^{70}$, —S(═O)$_nR^{70}$, and —S(═O)$_2NR^{72}R^{73}$; or any of $R^1$ and $R^2$, $R^1$ and $R^3$, $R^1$ and $R^5$, $R^1$ and R, $R^1$ and $R^{11}$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18c}$ and $R^i$, $R^{18c}$ and $R^3$, $R^{18c}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$ can, together with the atoms linking them, form a 3-11 membered heterocycloalkyl optionally substituted by 1-6 $R^{79}$; or any of $R^3$ and $R^4$, $R^3$ and $R^6$, $R^5$ and $R^6$, $R^i$ and $R^j$, $R^i$ and $R^4$, $R^i$ and $R^5$, $R^i$ and $R^n$, $R^m$ and $R^n$, $R^4$ and $R^m$, and $R^6$ and $R^m$ can, together with the atoms linking them, form a $C_{3-10}$cycloalkyl optionally substituted by 1-6 $R^{79}$, or a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form ═O.

8. A compound as defined in preferred Embodiments 6 or 7, wherein 1-2 of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, $R^{18a}$ and $R^3$, $R^{18a}$ and $R^5$, $R^{18a}$ and $R^{11}$, $R^{18a}$ and $R^n$, $R^{18b}$ and $R^3$, $R^{18b}$ and $R^5$, $R^{18b}$ and $R^{11}$, $R^{18b}$ and $R^n$, $R^{18e}$ and $R^i$, $R^{18e}$ and $R^3$, $R^{18e}$ and $R^5$, $R^{18c}$ and $R^{11}$, $R^{18c}$ and $R^n$, $R^{18d}$ and $R^i$, $R^{18d}$ and $R^3$, $R^{18d}$ and $R^5$, $R^{18d}$ and $R^{11}$, and $R^{18d}$ and $R^n$, together with the atoms linking them, form an optionally substituted heterocycloalkyl.

9. A compound as defined in preferred Embodiment 5, wherein $R^1$, $R^{11}$, $R^{16}$, $R^{17}$, $R^{16a}$, $R^{17a}$, $R^{18a}$, $R^{18b}$, $R^{18c}$, $R^{18d}$, and $R^{18e}$ are H; $R^2$ is chosen from H and $C_{1-6}$alkyl optionally substituted by 1-6 $R^{79}$; $R^4$, $R^5$, $R^6$, $R^i$, $R^j$, $R^m$, $R^n$, $R^o$, and $R^p$ are H; $R^3$ is chosen from H, $C_{1-6}$alkyl optionally substituted by 1-6 $R^{79}$, $C_{2-6}$alkynyl optionally substituted by 1-6 $R^{79}$, $C_{7-16}$arylalkyl optionally substituted by 1-6 $R^{79}$, $C_{3-10}$cycloalkyl optionally substituted by 1-6 $R^{79}$, 3-6 membered heterocycloalkyl optionally substituted by 1-3 $R^{79}$, halogen, —CN, —C(═O)$R^{70}$, —C(═O)$OR^{70}$, —C(═O)$NR^{72}R^{73}$, —$NR^{72}R^{73}$, —$NR^{74}$C(═O)$R^{70}$, —$NR^{74}$S(═O)$_2R^{71}$, —$OR^{70}$, —OC(═O)$R^{70}$, —S(═)$_nR^{70}$, and —S(═O)$_2NR^{72}R^{73}$; or any of $R^1$ and $R^2$, $R^1$ and $R^3$, $R^1$ and $R^5$, $R^1$ and $R^{11}$, $R^1$ and $R^n$, $R^4$ and $R^{11}$, $R^6$ and $R^{11}$, $R^{16}$ and $R^{17}$, $R^{16}$ and $R^i$, $R^{16}$ and $R^3$, $R^{16}$ and $R^5$, $R^{16}$ and $R^{11}$, $R^{16}$ and $R^n$, $R^j$ and $R^{11}$, and $R^{18a}$ and $R^{11}$ can, together with the atoms linking them, form a 3-11 membered heterocycloalkyl optionally substituted by 1-6 $R^{79}$; or any of $R^3$ and $R^4$, $R^5$ and $R^6$, $R^i$ and $R^j$, and $R^m$ and $R^n$ can together form ═O.

10. A compound as defined in any of preferred Embodiments 5-9, wherein $R^q$ is —$NR^{16a}R^{17a}$ or —$OR^{18e}$.

11. A compound as defined in any of preferred Embodiments 5-10, wherein $R^k$ is —$NR^{16}R^{17}$ or —$OR^{18c}$.

12. A compound as defined in any of preferred Embodiments 5-11, wherein A is —$NR^1R^2$, —$CR^iR^jR^k$, or —$OR^{18a}$.

13. A compound as defined in any of preferred Embodiments 5-11, wherein A is —$NR^1R^2$.

14. A compound as defined in any of preferred Embodiments 5-13, wherein Q is —$NR^{11}$—, —$CR^mR^n$—, or —O—.

15. A compound as defined in any of preferred Embodiments 5-13, wherein Q is —$NR^{11}$—.

16. A compound as defined in any of preferred Embodiments 1-15, wherein $R^7$, $R^8$, and $R^9$ are independently chosen from H, $C_{1-6}$alkyl, $C_{2-6}$alkenyl, $C_{2-6}$alkynyl, $C_{6-10}$aryl, $C_{7-11}$arylalkyl, $C_{3-7}$cycloalkyl, $C_{4-8}$cycloalkylalkyl, 3-7 membered heterocycloalkyl, 4-8 membered heterocycloalkylalkyl, 5-6 membered heteroaryl, 6-21 membered heteroarylalkyl, halogen, —CN, —C(═O)$R^{20}$, —C(═O)$OR^{20}$, —C(═O)$NR^{22}R^{23}$, —$NO_2$, —$NR^{22}R^{23}$, —$NR^{24}$C(═O)$R^{20}$, —$NR^{24}$S(═O)$_2R^{21}$, —$OR^{20}$, —S(═O)$_nR^{20}$, and —S(═O)$_2NR^{22}R^{23}$; or $R^7$ and $R^8$ can, together with the atoms linking them, form a $C_{6-10}$aryl, $C_{3-7}$cycloalkyl, 3-7 membered heterocycloalkyl or a 5-6 membered heteroaryl.

17. A compound as defined in any of preferred Embodiments 1-15, wherein $R^7$, $R^8$, and $R^9$ are independently chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —$NR^{22}R^{23}$, —$OR^{20}$, and —S(═O)$_nR^{20}$.

18. A compound as defined in any of preferred Embodiments 1-15, wherein $R^7$ is chosen from H, $C_{1-6}$alkyl optionally substituted by 1-6 $R^{19}$, $C_{2-6}$alkenyl optionally substituted by 1-6 $R^{19}$, $C_{6-10}$aryl optionally substituted by 1-6 $R^{19}$, $C_{3-10}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —C(=O)O$R^{20}$, —C(=O)N$R^{22}R^{23}$, —$NO_2$, —N$R^{22}R^{23}$, —N$R^{24}$C(=O)$R^{20}$, —N$R^{24}$S(=O)$_2R^{21}$, —N$R^{24}$S(=O)$_2$N$R^{22}R^{23}$, —O$R^{20}$, —OC(=O)$R^{20}$, —S(=O)$_nR^{20}$, and —S(=O)$_2$N$R^{22}R^{23}$; $R^8$ is chosen from H, $C_{1-6}$alkyl optionally substituted by 1-6 $R^{19}$, halogen, —N$R^{22}R^{23}$, and —O$R^{20}$; and $R^9$ is chosen from H, $C_{1-6}$alkyl optionally substituted by 1-6 $R^{19}$, $C_{2-6}$alkenyl optionally substituted by 1-6 $R^{19}$, $C_{2-6}$alkynyl optionally substituted by 1-6 $R^{19}$, $C_{6-10}$aryl optionally substituted by 1-6 $R^{19}$, $C_{3-11}$cycloalkyl optionally substituted by 1-6 $R^{19}$, 3-10 membered heterocycloalkyl optionally substituted by 1-6 $R^{19}$, 5-10 membered heteroaryl optionally substituted by 1-6 $R^{19}$, halogen, —CN, —C(=O)$R^{20}$, —(=O)$^{20}$, —C(=O)N$R^{22}R^{23}$, —NC, —$NO_2$, —N$R^{22}R^{23}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —OC(=O)N$R^{22}R^{23}$, —S(=O)$_nR^{20}$, and —S(=O)$_2$N$R^{22}R^{23}$.

19. A compound as defined in any of preferred Embodiments 1-15, wherein $R^7$ is chosen from H, $C_{1-6}$alkyl optionally substituted by 1-3 $R^{19}$, $C_{2-6}$alkenyl optionally substituted by 1-3 $R^{19}$, $C_{3-6}$cycloalkyl optionally substituted by 1-3 $R^{19}$, halogen, —N$R^{22}R^{23}$, and —O$R^{20}$; $R^8$ is chosen from H and halogen; and $R^9$ is chosen from H, $C_{2-6}$alkynyl optionally substituted by 1-3 $R^{19}$, $C_{6-10}$aryl optionally substituted by 1-3 $R^{19}$, 3-6 membered heterocycloalkyl optionally substituted by 1-3 $R^{19}$, 5-9 membered heteroaryl optionally substituted by 1-3 $R^{19}$, halogen, —N$R^{22}R^{23}$, —O$R^{20}$, and —S(=O)$_nR^{20}$.

20. A compound as defined in any of preferred Embodiments 1-19, wherein $R^8$ is H.

21. A compound as defined in any of preferred Embodiments 1-20, wherein G is a group of formula

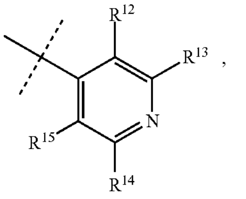

and $R^{12}$, $R^{13}$, $R^{14}$, and $R^{15}$ are independently chosen from H, $C_{1-6}$alkyl optionally substituted by 1-3 $R^{19}$, phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)N$R^{22}R^{23}$, —$NO_2$, —N$R^{22}R^{23}$, —N$R^{24}$C(=O)$R^{20}$, —N$R^{24}$S(=O)$_2R^{21}$, —O$R^{20}$, —S(=O)$_nR^{20}$, and —S(=O)$_2$N$R^{22}R^{23}$; or either or both of $R^{12}$ and $R^{13}$, and/or $R^{14}$ and $R^{15}$, can, together with the atoms linking them, form a phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-6 membered heteroaryl optionally substituted by 1-3 $R^{19}$.

22. A compound as defined in any of preferred Embodiments 1-21, wherein G is a group of formula

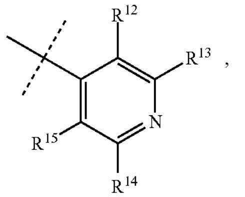

and $R^{12}$, $R^{14}$, and $R^{15}$ are independently chosen from H, $C_{1-6}$alkyl optionally substituted by 1-3 $R^{19}$, and halogen; $R^{13}$ is chosen from H, $C_{1-6}$alkyl optionally substituted by 1-3 $R^{19}$, phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$, 5-6 membered heteroaryl optionally substituted by 1-3 $R^{19}$, halogen, —CN, —C(=O)$R^{20}$, —C(=O)O$R^{20}$, —C(=O)N$R^{22}R^{23}$, —$NO_2$, —N$R^{22}R^{23}$, —N$R^{24}$N$R^{22}R^{23}$, —N$R^{24}$O$R^{26}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —S(=O)$_nR^{20}$, and —S(=O)$_2$N$R^{22}R^{23}$; or $R^{12}$ and $R^{13}$ can, together with the atoms linking them, form a phenyl optionally substituted by 1-3 $R^{19}$, $C_{3-7}$cycloalkyl optionally substituted by 1-3 $R^{19}$, 3-7 membered heterocycloalkyl optionally substituted by 1-3 $R^{19}$ or a 5-10 membered heteroaryl optionally substituted by 1-6 $R^{19}$.

23. A compound as defined in any of preferred Embodiments 1-21, wherein G is a group of formula

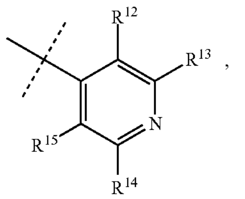

and $R^{12}$ and $R^{14}$ are H; $R^{15}$ is chosen from H and halogen; $R^{13}$ is chosen from H, $C_{1-6}$alkyl optionally substituted by 1-3 $R^{19}$, phenyl optionally substituted by 1-3 $R^{19}$, 5-6 membered heteroaryl optionally substituted by 1-3 $R^{19}$, halogen, —CN, —C(=O)$R^{20}$, —C(=O)O$R^{20}$, —C(=O)N$R^{22}R^{23}$, —$NO_2$, —N$R^{22}R^{23}$, —N$R^{24}$N$R^{22}R^{23}$, —N$R^{24}$O$R^{26}$, —N$R^{24}$C(=O)$R^{20}$, —N$R^{24}$C(=O)O$R^{21}$, —N$R^{24}$C(=O)N$R^{22}R^{23}$, —N$R^{24}$S(=O)$_2R^{21}$, —N$R^{24}$S(=O)$_2$N$R^{22}R^{23}$, —O$R^{20}$, —OC(=O)$R^{20}$, —S(=O)$_nR^{20}$, and —S(=O)$_2$N$R^{22}R^{23}$; or $R^{12}$ and $R^{13}$ can, together with the atoms linking them, form a phenyl optionally substituted by 1-3 $R^{19}$ or a 5-10 membered heteroaryl optionally substituted by 1-6 $R^{19}$.

24. A compound as defined in any of preferred Embodiments 1-21, wherein G is a group of formula

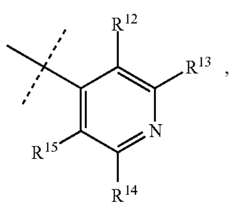

and $R^{14}$ is H; $R^{12}$ and $R^{15}$ are independently chosen from H and halogen; $R^{13}$ is chosen from H, —$NR^{22}R^{23}$, —$NR^{24}C$(═O)$R^{20}$, —$NR^{24}C$(═O)$OR^{21}$, —$NR^{24}C$(═O)$NR^{22}R^{23}$, —$NR^{24}S$(═O)$_2R^{21}$, and —$NR^{24}S$(═O)$_2NR^{22}R^{23}$; or $R^{12}$ and $R^{13}$ can, together with the atoms linking them, form a 5-6 membered heteroaryl optionally substituted by 1-6 $R^{19}$.

25. A compound as defined in any of preferred Embodiments 1-21, wherein G is a group of formula

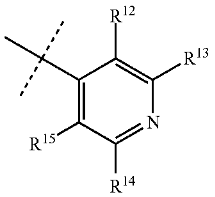
, and $R^{14}$ and $R^{15}$ are H; $R^{12}$ is chosen from H and halogen; $R^{13}$ is chosen from H, —$NR^{22}R^{23}$, and —$NR^{24}C$(═O)$R^{20}$; or $R^{12}$ and $R^{13}$ can, together with the atoms linking them, form a 5 membered heteroaryl optionally substituted by 1-2 $R^{19}$.

26. A compound as defined in any of preferred Embodiments 1-21, wherein G is a group of formula

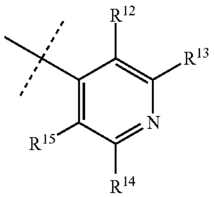
, and $R^{14}$ is H; $R^{12}$ and $R^{15}$ are independently chosen from H and halogen; $R^{13}$ is chosen from H, —$NR^{22}R^{23}$, and —$NR^{24}C$(═O)$R^{20}$; or $R^{12}$ and $R^{13}$ can, together with the atoms linking them, form a pyrrolyl ring optionally substituted by 1 $R^{19}$.

27. A compound as defined in any of preferred Embodiments 1-21, wherein G is a group of formula

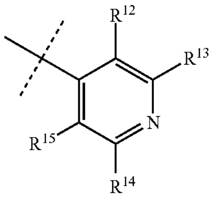
, and $R^{12}$, $R^{13}$, $R^{14}$, and $R^{15}$ are H; or $R^{12}$ and $R^{13}$, together with the atoms linking them, form a pyrrolyl ring.

28. A compound as defined in any of preferred Embodiments 1-21, wherein G is a group of formula

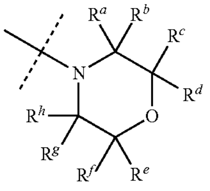
, and $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, 5-10 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}C$(═O)$R^{20}$, —$NR^{24}C$(═O)$NR^{22}R^{23}$, —$NR^{24}S$(═O)$_2R^{21}$, —$NR^{24}S$(═O)$_2NR^{22}R^{23}$, —$OR^{20}$, —OC(═O)$R^{20}$, —OC(═O)$NR^{22}R^{23}$, —OC(═O)$OR^{20}$, —S(═O)$_nR^{20}$, and —S(═O)$_2NR^{22}R^{23}$.

29. A compound as defined in any of preferred Embodiments 1-21, wherein G is a group of formula

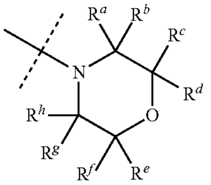
, and $R^a$, $R^b$, $R^c$, $R^d$, $R^e$, $R^f$, $R^g$, and $R^h$ are independently chosen from H, $C_{1-6}$alkyl optionally substituted by 1-3 $R^{19}$, and benzyl optionally substituted by 1-3 $R^{19}$.

30. A compound as defined in any of preferred Embodiments 1-21, wherein G is a group of formula

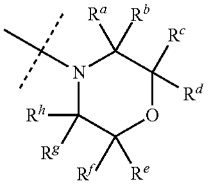
, and $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, $C_{6-10}$aryl optionally substituted by 1-3 $R^{19}$, $C_{7-11}$arylalkyl optionally substituted by 1-3 $R^{19}$, 5-10 membered heteroaryl optionally substituted by 1-3 $R^{19}$, halogen, —CN, —C(═O)$R^{20}$, —C(═O)$OR^{20}$, —C(═O)$NR^{22}R^{23}$, —$NO_2$, —$NR^{22}R^{23}$, —$NR^{24}C$(═O)$R^{20}$, —$NR^{24}C$(═O)$NR^{22}R^{23}$, —$NR^{24}S$(═O)$_2R^{21}$, —$NR^{24}S$(═O)$_2NR^{22}R^{23}$, —$OR^{20}$, —OC(═O)$R^{20}$, —OC(═O)$NR^{22}R^{23}$, —OC(═O)$OR^{20}$, —S(═O)$_nR^{20}$, and —S(═O)$_2NR^{22}R^{23}$.

31. A compound as defined in any of preferred Embodiments 1-21, wherein G is a group of formula

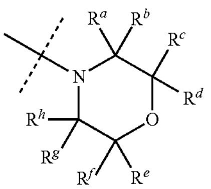
, and $R^a$, $R^b$, $R^c$, $R^e$, $R^f$, $R^g$, and $R^h$ are H; and $R^d$ is chosen from H, $C_{1-6}$alkyl optionally substituted by 1-3 $R^{19}$, and benzyl optionally substituted by 1-3 $R^{19}$.

32. A compound as defined in any of preferred Embodiments 1-21, wherein G is a group of formula

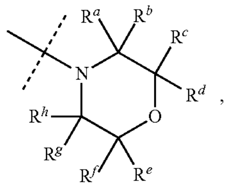

and $R^a$, $R^b$, $R^c$, $R^d$ $R^e$, $R^f$, $R^g$, and $R^h$ are H.

33. A compound as defined in any of preferred Embodiments 1-32, wherein $R^{19}$ at each occurrence is independently chosen from $C_{1-6}$alkyl optionally substituted by 1-3 $R^{39}$, $C_{2-6}$alkenyl optionally substituted by 1-3 $R^{39}$, $C_{2-6}$alkynyl optionally substituted by 1-3 $R^{39}$, $C_{6-10}$aryl optionally substituted by 1-3 $R^{39}$, $C_{7-11}$arylalkyl optionally substituted by 1-3 $R^{39}$, $C_{3-6}$cycloalkyl optionally substituted by 1-3 $R^{39}$, 3-6 membered heterocycloalkyl optionally substituted by 1-3 $R^{39}$, 5-6 membered heteroaryl optionally substituted by 1-3 $R^{39}$, halogen, —CN, —C(═O)$R^{30}$, —C(═O)O$R^{30}$, —C(═O)N$R^{32}R^{33}$, —$NO_2$, —N$R^{32}R^{33}$, —N$R^{34}$C(═O)$R^{30}$, —N$R^{34}$C(═O)N$R^{32}R^{33}$, —N$R^{34}$S(═O)$_2R^{31}$, —N$R^{34}$S(═O)$_2$N$R^{32}R^{33}$, —O$R^{30}$, ═O, —OC(═O)$R^{30}$, —OC(═O)N$R^{32}R^{33}$, —Si($R^{34}$)$_3$, ═S, —S(═O)$_n R^{30}$, and —S(═O)$_2$N$R^{32}R^{33}$.

34. A compound as defined in any of preferred Embodiments 1-32, wherein $R^{19}$ at each occurrence is independently chosen from $C_{1-6}$alkyl, $C_{6-10}$aryl, $C_{7-11}$arylalkyl, $C_{3-6}$cycloalkyl, 3-6 membered heterocycloalkyl, 5-6 membered heteroaryl, halogen, —C(═O)$R^{30}$, —C(═O)O$R^{30}$, —C(═O)N$R^{32}R^{33}$, —N$R^{32}R^{33}$, and —O$R^{30}$.

35. A compound as defined in any of preferred Embodiments 1-32, wherein $R^{19}$ at each occurrence is independently chosen from $C_{1-6}$alkyl, phenyl optionally substituted by 1-3 $R^{39}$, $C_{3-6}$cycloalkyl, 3-6 membered heterocycloalkyl optionally substituted by 1-3 $R^{39}$, 5-6 membered heteroaryl, halogen, —C(═O)O$R^{30}$, —N$R^{32}R^{33}$, and —O$R^{30}$.

36. A compound as defined in any of preferred Embodiments 1-32, wherein $R^{19}$ at each occurrence is independently chosen from $C_{1-6}$alkyl optionally substituted by 1-3 $R^{39}$, $C_{2-6}$alkynyl, $C_{7-11}$arylalkyl optionally substituted by 1-3 $R^{39}$, $C_{3-6}$cycloalkyl, 3-6 membered heterocycloalkyl, 5-6 membered heteroaryl, —CN, —C(═O)O$R^{30}$, —C(═O)N$R^{32}R^{33}$, —N$R^{32}R^{33}$, —N$R^{34}$S(═O)$_2R^{31}$, —O$R^3$ and ═O.

37. A compound as defined in any of preferred Embodiments 1-36, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, and $C_{3-6}$cycloalkyl optionally substituted by 1-3 $R^{49}$.

38. A compound as defined in any of preferred Embodiments 1-36, wherein $R^{20}$ at each occurrence is independently chosen from H, $C_{1-6}$alkyl optionally substituted by 1-3 $R^{49}$, phenyl optionally substituted by 1-3 $R^{49}$, benzyl optionally substituted by 1-3 $R^{49}$, $C_{3-6}$cycloalkyl, 3-6 membered heterocycloalkyl, and 5-6 membered heteroaryl; $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is H.

39. A compound as defined in any of preferred Embodiments 1-36, wherein $R^{20}$, $R^{21}$, $R^{24}$, $R^{25}$, $R^{26}$, $R^{27}$, $R^{30}$, $R^{31}$, $R^{34}$, $R^{35}$, $R^{36}$ and $R^{37}$ at each occurrence is independently chosen from H and $C_{1-6}$alkyl.

40. A compound as defined in any of preferred Embodiments 1-39, wherein $R^{22}$, $R^{23}$, $R^{32}$ and $R^{33}$ at each occurrence is independently chosen from H, $C_{1-6}$alkyl optionally substituted by 1-3 $R^{59}$, phenyl optionally substituted by 1-3 $R^{59}$, and 5-6 membered heteroaryl optionally substituted by 1-3 $R^{59}$.

41. A compound as defined in any of preferred Embodiments 1-39, wherein $R^{22}$ at each occurrence is independently chosen from H, $C_{1-6}$alkyl, phenyl optionally substituted by 1-3 $R^{59}$, and 5-6 membered heteroaryl optionally substituted by 1-3 $R^{59}$; $R^{23}$, $R^{32}$ and $R^{33}$ at each occurrence is independently chosen from H and $C_{1-6}$alkyl.

42. A compound as defined in any of preferred Embodiments 1-39, wherein $R^{22}$, $R^{23}$, $R^{32}$ and $R^{33}$ at each occurrence is independently chosen from H and $C_{1-6}$alkyl.

43. A compound as defined in any of preferred Embodiments 1-42, wherein $R^{39}$, $R^{49}$, $R^{59}$ and $R^{69}$ at each occurrence is independently chosen from $C_{1-6}$alkyl optionally substituted by 1-3 $R^{79}$, phenyl optionally substituted by 1-3 $R^{79}$, benzyl optionally substituted by 1-3 $R^{79}$, $C_{3-6}$cycloalkyl, 3-6 membered heterocycloalkyl, 5-6 membered heteroaryl, halogen, —CN, —C(═O)N$R^{72}R^{73}$, —N$R^{72}R^{73}$, —O$R^{70}$, and —S(═O)$_n R^{70}$.

44. A compound as defined in any of preferred Embodiments 1-42, wherein $R^{39}$, $R^{49}$, $R^{59}$ and $R^{69}$ at each occurrence is independently chosen from $C_{1-6}$alkyl optionally substituted by 1-3 $R^{79}$.

45. A compound as defined in any of preferred Embodiments 1-44, wherein $R^{70}$, $R^{71}$, $R^{74}$, $R^{75}$, $R^{76}$ and $R^{77}$ at each occurrence is independently chosen from H and $C_{1-6}$alkyl optionally substituted by 1-3 $R^{89}$.

46. A compound as defined in any of preferred Embodiments 1-44, wherein $R^{72}$ and $R^{73}$ at each occurrence is independently chosen from H and $C_{1-6}$alkyl.

47. A compound as defined in any of preferred Embodiments 1-46, wherein $R^{79}$ and $R^{89}$, $R^{99}$ and $R^{109}$ at each occurrence is independently chosen from $C_{1-6}$alkyl and phenyl.

48. A compound as defined in any of preferred Embodiments 1-46, wherein $R^{79}$, $R^{89}$, $R^{99}$ and $R^{109}$ at each occurrence is independently $C_{1-6}$alkyl.

49. A compound as defined in any of preferred Embodiments 1 or 33-48, wherein X is chosen from —NH$R^{28}$ and 3-10 membered heterocycloalkyl consisting of carbon atoms and 1 or 2 nitrogen atoms in which the heterocycloalkyl is optionally substituted by 1-6 $R^{19}$; $R^7$ is chosen from H, $C_{3-6}$cycloalkyl, and —O$R^{20}$; $R^8$ is chosen from H and halogen; $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —N$R^{22}R^{23}$, —O$R^{20}$, and —S$R^{20}$; $R^{12}$, $R^{14}$, and $R^{15}$ are H, and $R^{13}$ is chosen from H, $C_{7-16}$arylalkyl optionally substituted by 1-6 $R^{19}$, 5-15 membered heteroaryl optionally substituted by 1-6 $R^{19}$, halogen, —N$R^{22}R^{23}$, and —N$R^{24}$C(═O)$R^{20}$; or $R^{12}$ and $R^{13}$ can, together with the atoms linking them, form a $C_{6-11}$aryl optionally substituted by 1-6 $R^{19}$, 3-15 membered heterocycloalkyl optionally substituted by 1-6 $R^{19}$, or a 5-15 membered heteroaryl optionally substituted by 1-6 $R^{19}$; and $R^a$, $R^b$, $R^c$, $R^d$, $R^e$, $R^f$, $R^g$, and $R^h$ are H.

50. A compound as defined in preferred Embodiment 49, wherein X is chosen from —NH$R^{28}$ and 5-10 membered heterocycloalkyl consisting of carbon atoms and 1 or 2 nitrogen atoms in which the heterocycloalkyl is optionally substituted by 1-6 $R^{19}$.

51. A compound as defined in preferred Embodiment 49, wherein X is chosen from —NH$R^{28}$ and 5-6 membered heterocycloalkyl consisting of carbon atoms and 1 or 2 nitrogen atoms in which the heterocycloalkyl is optionally substituted by 1-6 $R^{19}$.

52. A compound as defined in preferred Embodiment 49, wherein X is chosen from —$NHR^{28}$ and 5-10 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl optionally substituted by 1-3 $R^{39}$, $C_{6-11}$aryl optionally substituted by 1-3 $R^{39}$, $C_{7-16}$arylalkyl optionally substituted by 1-3 $R^{39}$, $C_{3-11}$cycloalkyl optionally substituted by 1-3 $R^{39}$, 3-15 membered heterocycloalkyl optionally substituted by 1-3 $R^{39}$, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

53. A compound as defined in preferred Embodiment 49, wherein X is chosen from —$NHR^{28}$ and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

54. A compound as defined in preferred Embodiment 49, wherein X is chosen from —$NHR^{28}$ and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, and —OH.

55. A compound as defined in preferred Embodiment 49, wherein X is chosen from —NH($C_{1-6}$alkyl optionally substituted by 1-6 $R^{49}$), —NH($C_{7-11}$arylalkyl optionally substituted by 1-6 $R^{4}$), —NH(3-10 membered heterocycloalkyl optionally substituted by 1-6 $R^{49}$), —NH(4-11 membered heterocycloalkylalkyl optionally substituted by 1-6 $R^{49}$), and 3-10 membered heterocycloalkyl consisting of carbon atoms and 1 or 2 nitrogen atoms in which the heterocycloalkyl is optionally substituted by 1-6 $R^{19}$.

56. A compound as defined in preferred Embodiment 49, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-10 membered heterocycloalkyl consisting of carbon atoms and 1 or 2 nitrogen atoms in which the heterocycloalkyl is optionally substituted by 1-6 $R^{19}$.

57. A compound as defined in preferred Embodiment 49, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1-6 $R^{19}$.

58. A compound as defined in preferred Embodiment 49, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-10 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl optionally substituted by 1-3 $R^{39}$, $C_{6-11}$aryl optionally substituted by 1-3 $R^{39}$, $C_{7-16}$arylalkyl optionally substituted by 1-3 $R^{39}$, $C_{3-11}$cycloalkyl optionally substituted by 1-3 $R^{39}$, 3-15 membered heterocycloalkyl optionally substituted by 1-3 $R^{39}$, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

59. A compound as defined in preferred Embodiment 49, wherein X is chosen from —NH($C_{1-6}$alkyl optionally substituted by 1-6 $R^{49}$), —NH($C_{7-11}$arylalkyl optionally substituted by 1-3 $R^{49}$), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═O)$OR^{30}$, —C(═O)$NR^{32}R^{33}$, —$NR^{32}R^{33}$, —$NR^{34}$C(═O)$R^{3}$, and —$OR^{30}$.

60. A compound as defined in preferred Embodiment 49, wherein X is chosen from —NH($C_{1-6}$alkyl optionally substituted by 1-6 $R^{49}$), —NH(5-6 membered heterocycloalkyl), —NH(6-10 membered heterocycloalkylalkyl), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{3}$, and —$OR^{3}$.

61. A compound as defined in preferred Embodiment 49, wherein X is chosen from —NH($C_{1-6}$alkyl optionally substituted by 1-6 $R^{49}$), —NH($C_{7-11}$arylalkyl), —NH(5-6 membered heterocycloalkyl consisting of carbon atoms and 1 or 2 nitrogen atoms), —NH(6-10 membered heterocycloalkylalkyl consisting of carbon atoms and 1 or 2 nitrogen atoms), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-3 $R^{39}$, $C_{2-6}$alkynyl, $C_{6-11}$aryl, $C_{7-16}$arylalkyl optionally substituted by 1-3 $R^{39}$, $C_{3-11}$cycloalkyl optionally substituted by 1-3 $R^{39}$, 5-10 membered heterocycloalkyl, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

62. A compound as defined in preferred Embodiment 49, wherein X is chosen from —NH($C_{1-6}$alkyl optionally substituted by 1-6 $R^{49}$), —NH(5-6 membered heterocycloalkyl consisting of carbon atoms and 1 or 2 nitrogen atoms), —NH(6-10 membered heterocycloalkylalkyl consisting of carbon atoms and 1 or 2 nitrogen atoms), and 5-6 membered heterocycloalkyl consisting of carbon atoms and 1 or 2 nitrogen atoms in which the heterocycloalkyl is optionally substituted by 1 or 2 members chosen from $C_{1-6}$alkyl optionally substituted by 1-6 halogen, halogen, —CN, —C(═O)$OR^{30}$, —C(═O)$NR^{32}R^{33}$, —$NR^{32}R^{33}$, —$NR^{34}$C(═O)$R^{30}$, and —$OR^{30}$.

63. A compound as defined in preferred Embodiment 49, wherein X is chosen from —NH($C_{1-6}$alkyl optionally substituted by 1-6 $R^{49}$) and —NH(5-6 membered heterocycloalkyl consisting of carbon atoms and 1 or 2 nitrogen atoms).

64. A compound as defined in any of preferred Embodiments 1 or 33-63, wherein $R^{7}$ is chosen from H, $C_{3-6}$cycloalkyl, and —O($C_{1-6}$alkyl); $R^{8}$ is chosen from H and halogen; and $R^{9}$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

65. A compound as defined in any of preferred Embodiments 1 or 33-63, wherein $R^7$ is chosen from H, $C_{3-6}$cycloalkyl, and —$OR^{20}$; $R^8$ is H; and $R^9$ is H.

66. A compound as defined in any of preferred Embodiments 1 or 33-63, wherein $R^7$ is chosen from H, $C_{3-6}$cycloalkyl, and —O($C_{1-6}$alkyl); $R^8$ is H; and $R^9$ is H.

67. A compound as defined in any of preferred Embodiments 1 or 33-63, wherein $R^7$ is chosen from H, cyclopropyl, and —O($C_{1-6}$alkyl); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

68. A compound as defined in any of preferred Embodiments 1 or 33-63, wherein $R^7$ is chosen from H, cyclopropyl, and —O($C_{1-6}$alkyl); $R^8$ is H; and $R^9$ is H.

69. A compound as defined in any of preferred Embodiments 1 or 33-63, wherein $R^7$ is chosen from H, cyclopropyl, and —O($CH_3$); $R^8$ is H; and $R^9$ is H.

70. A compound as defined in any of preferred Embodiments 1 or 33-63, wherein $R^7$ is chosen from H, cyclopropyl, and —O($C_{1-6}$alkyl); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

71. A compound as defined in any of preferred Embodiments 1 or 33-63, wherein $R^7$ is chosen from H, $C_{3-6}$cycloalkyl, and —O($CH_3$); $R^8$ is chosen from H and halogen; and $R^9$ is chosen from H, $C_{2-6}$alkynyl optionally substituted by 1-3 $R^{19}$, phenyl optionally substituted by 1-3 $R^{19}$, 3-6 membered heterocycloalkyl optionally substituted by 1-3 $R^{19}$, 5, 6, or 9 membered heteroaryl optionally substituted by 1-3 $R^{19}$, halogen, —$NR^{22}R^{23}$, —$OR^{20}$, and —$SR^{20}$.

72. A compound as defined in any of preferred Embodiments 1 or 33-71, wherein $R^{12}$, $R^{14}$ and $R^{15}$ are H, and $R^{13}$ is chosen from H, $C_{7-16}$arylalkyl optionally substituted by 1-6 $R^{19}$, 5-10 membered heteroaryl optionally substituted by 1-6 $R^{19}$, halogen, —$NR^{22}R^{23}$, and —$NR^{24}C$(═O)$R^{20}$; or $R^{12}$ and $R^{13}$ can, together with the atoms linking them, form a $C_{6-11}$aryl optionally substituted by 1-6 $R^{19}$, 5-10 membered heterocycloalkyl optionally substituted by 1-6 $R^{19}$, or a 5-10 membered heteroaryl optionally substituted by 1-6 $R^{19}$.

73. A compound as defined in any of preferred Embodiments 1 or 33-71, wherein $R^{12}$, $R^{14}$, and $R^{15}$ are H, and $R^{13}$ is chosen from H, $C_{7-16}$arylalkyl optionally substituted by 1-3 $R^{19}$, 5-10 membered heteroaryl optionally substituted by 1-3 $R^{19}$, halogen, —$NR^{22}R^{23}$, and —$NR^{24}C$(═O)$R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

74. A compound as defined in any of preferred Embodiments 1 or 33-71, wherein $R^{12}$, $R^{14}$ and $R^{15}$ are H, and $R^{13}$ is chosen from H, halogen, —$NR^{22}R^{23}$, and —$NR^{24}C$(═O)$R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

75. A compound as defined in any of preferred Embodiments 1 or 33-71, wherein $R^{12}$, $R^{14}$, and $R^{15}$ are H, and $R^{13}$ is chosen from H, halogen, —$NR^{22}R^{23}$, and —$NR^{24}C$(═O)$R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 or 2 nitrogen atoms, or a 5-10 membered heteroaryl optionally substituted by 1-3 $R^{19}$ in which the heteroaryl contains carbon atoms and 1 or 2 nitrogen atoms.

76. A compound as defined in any of preferred Embodiments 1 or 33-71, wherein $R^{12}$, $R^{14}$, and $R^{15}$ are H, and $R^{13}$ is chosen from H, halogen, —$NR^{22}R^{23}$, and —$NR^{24}C$(═O)$R^{20}$; or $R^{12}$ and $R^{13}$, can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 nitrogen atom, or a 5-10 membered heteroaryl optionally substituted by 1-3 $R^{19}$ in which the heteroaryl contains carbon atoms and 1 nitrogen atom.

77. A compound as defined in any of preferred Embodiments 1 or 33-71, wherein $R^{12}$, $R^{14}$, and $R^{15}$ are H, and $R^{13}$ is chosen from H, —$NR^{22}R^{23}$, and —$NR^{24}C$(═O)$R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 or 2 nitrogen atoms, or a 5-10 membered heteroaryl optionally substituted by 1-3 $R^{19}$ in which the heteroaryl contains carbon atoms and 1 or 2 nitrogen atoms.

78. A compound as defined in any of preferred Embodiments 1 or 33-71, wherein $R^{12}$, $R^{14}$, and $R^{15}$ are H, and $R^{13}$ is chosen from H, —$NR^{22}R^{23}$, and —$NR^{24}C$(═O)$R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 nitrogen atom, or a 5-10 membered heteroaryl optionally substituted by 1-3 $R^{19}$ in which the heteroaryl contains carbon atoms and 1 nitrogen atom.

79. A compound as defined in any of preferred Embodiments 1 or 33-71, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a $C_{6-11}$aryl optionally substituted by 1-3 $R^{19}$, 5-10 membered heterocycloalkyl optionally substituted by 1-3 $R^{19}$, or a 5-10 membered heteroaryl optionally substituted by 1-3 $R^{19}$.

80. A compound as defined in any of preferred Embodiments 1 or 33-71, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a phenyl optionally substituted by 1-3 $R^{19}$, 5-10 membered heterocycloalkyl optionally substituted by 1-3 $R^{19}$ in which the heterocycloalkyl contains carbon atoms and 1 or 2 nitrogen atoms, or a 5-10 membered heteroaryl optionally substituted by 1-3 $R^{19}$ in which the heteroaryl contains carbon atoms and 1 or 2 nitrogen atoms.

81. A compound as defined in any of preferred Embodiments 1 or 33-71, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a 5-10 membered heteroaryl optionally substituted by 1-3 $R^{19}$.

82. A compound as defined in any of preferred Embodiments 1 or 33-71, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a 5-10 membered heteroaryl optionally substituted by 1-3 $R^{19}$ in which the heteroaryl contains carbon atoms and 1 or 2 nitrogen atoms.

83. A compound as defined in any of preferred Embodiments 1 or 33-71, wherein $R^{12}$, $R^{14}$, and $R^{15}$ are H, and $R^{13}$ is chosen from H, —$NHR^{23}$, and —NHC(═O)$R^{20}$; or $R^{12}$ and $R^{13}$ can, together with the atoms linking them, form a 5-10 membered heteroaryl optionally substituted by 1-3 $R^{19}$ in which the heteroaryl contains carbon atoms and 1 nitrogen atom.

84. A compound as defined in any of preferred Embodiments 1 or 33-71, wherein $R^{12}$, $R^{14}$, and $R^{15}$ are H, and $R^{13}$ is chosen from H and —$NHR^{23}$; or $R^{12}$ and $R^{13}$ can, together with the atoms linking them, form a 5-10 membered heteroaryl optionally substituted by 1-3 $R^{19}$.

85. A compound as defined in any of preferred Embodiments 1 or 33-71, wherein $R^{12}$, $R^{14}$, and $R^{15}$ are H, and $R^{13}$ is chosen from H and —$NHR^{23}$; or $R^{12}$ and $R^{13}$ can, together with the atoms linking them, form a 5-10 membered heteroaryl optionally substituted by 1-3 $R^{19}$ in which the heteroaryl contains carbon atoms and 1 or 2 nitrogen atoms.

86. A compound chosen from:
1-[2-(pyridin-4-yl)pyrido[3,4-d]pyrimidin-4-yl]piperazine;
(5-Methoxy-2-pyridin-4-yl-pyrido[3,4-d]pyrimidin-4-yl)-(R)-pyrrolidin-3-yl-amine;
N-(2-aminoethyl)-2-(pyridin-4-yl)pyrido[3,4-d]pyrimidin-4-amine;
N-[(2R)-2-aminopropyl]-2-(pyridin-4-yl)pyrido[3,4-d]pyrimidin-4-amine;
N-[(2S)-2-aminopropyl]-2-(pyridin-4-yl)pyrido[3,4-d]pyrimidin-4-amine;
N-[(2S)-2-amino-3-phenylpropyl]-2-(pyridin-4-yl)pyrido[3,4-d]pyrimidin-4-amine;
(3R)—N-[2-(pyridin-4-yl)pyrido[3,4-d]pyrimidin-4-yl]pyrrolidin-3-amine;
(3R)—N-[2-(3-fluoropyridin-4-yl)pyrido[3,4-d]pyrimidin-4-yl]pyrrolidin-3-amine;
N-[(2S)-2-amino-3-phenylpropyl]-5-methoxy-2-(pyridin-4-yl)pyrido[3,4-d]pyrimidin-4-amine;
N-[(2S)-2-amino-3-phenylpropyl]-2-(3-fluoropyridin-4-yl)pyrido[3,4-d]pyrimidin-4-amine;
N-[(2S)-2-amino-3-phenylpropyl]-8-chloro-2-(pyridin-4-yl)pyrido[3,4-d]pyrimidin-4-amine;
N-[(2S)-2-amino-3-phenylpropyl]-6-chloro-2-(pyridin-4-yl)pyrido[3,4-d]pyrimidin-4-amine;
1-[6-chloro-2-(pyridin-4-yl)pyrido[3,4-d]pyrimidin-4-yl]piperazine;
(3S)-3-benzyl-1-[6-chloro-2-(pyridin-4-yl)pyrido[3,4-d]pyrimidin-4-yl]piperazine;
(2S)-1-phenyl-3-{[2-(pyridin-4-yl)pyrido[3,4-d]pyrimidin-4-yl]amino}propan-2-ol;
(3 S)-3-benzyl-1-[2-(pyridin-4-yl)pyrido[3,4-d]pyrimidin-4-yl]piperazine;
(3R)-3-benzyl-1-[2-(pyridin-4-yl)pyrido[3,4-d]pyrimidin-4-yl]piperazine;
1-methyl-4-[2-(pyridin-4-yl)pyrido[3,4-d]pyrimidin-4-yl]piperazine;
1-methyl-4-[2-(pyridin-4-yl)pyrido[3,4-d]pyrimidin-4-yl]-1,4-diazepane;
(2S)-2,4-dibenzyl-1-[2-(pyridin-4-yl)pyrido[3,4-d]pyrimidin-4-yl]piperazine;
4-[2-(pyridin-4-yl)pyrido[3,4-d]pyrimidin-4-yl]morpholine;
tert-butyl 4-[2-(pyridin-4-yl)pyrido[3,4-d]pyrimidin-4-yl]piperazine-1-carboxylate;
tert-butyl 4-[2-(pyridin-4-yl)pyrido[3,4-d]pyrimidin-4-yl]-1,4-diazepane-1-carboxylate;
4-[2-(pyridin-4-yl)pyrido[3,4-d]pyrimidin-4-yl]thiomorpholine;
N,N-Dimethyl[(2S)-1-phenyl-3-{[2-(pyridin-4-yl)pyrido[3,4-d]pyrimidin-4-yl]amino}propan-2-yl]amine;
N-[(2S)-2-amino-3-phenylpropyl]-N-methyl-2-(pyridin-4-yl)pyrido[3,4-d]pyrimidin-4-amine;
4-[2-(pyridin-4-yl)pyrido[3,4-d]pyrimidin-4-yl]piperazin-2-one;
N-[(2S)-1-amino-3-phenylpropan-2-yl]-2-(pyridin-4-yl)pyrido[3,4-d]pyrimidin-4-amine;
(2R)-2-benzyl-1-[2-(pyridin-4-yl)pyrido[3,4-d]pyrimidin-4-yl]piperazine;
(3 S)-3-benzyl-1-[5-methoxy-2-(pyridin-4-yl)pyrido[3,4-d]pyrimidin-4-yl]piperazine;
1-[5-methoxy-2-(pyridin-4-yl)pyrido[3,4-d]pyrimidin-4-yl]piperazine;
1-[8-chloro-2-(pyridin-4-yl)pyrido[3,4-d]pyrimidin-4-yl]piperazine;
1-[2-(pyridin-4-yl)pyrido[3,4-d]pyrimidin-4-yl]-1,4-diazepane;
2-{4-[2-(pyridin-4-yl)pyrido[3,4-d]pyrimidin-4-yl]piperazin-1-yl}ethan-1-ol;
(3 S)-1-[2-(pyridin-4-yl)pyrido[3,4-d]pyrimidin-4-yl]pyrrolidin-3-ol;
(3R)-1-[2-(pyridin-4-yl)pyrido[3,4-d]pyrimidin-4-yl]pyrrolidin-3-ol;
(3R)-3-benzyl-1-[5-methoxy-2-(pyridin-4-yl)pyrido[3,4-d]pyrimidin-4-yl]piperazine;
(2 S)-2-benzyl-1-[2-(pyridin-4-yl)pyrido[3,4-d]pyrimidin-4-yl]piperazine;
methyl (2S,4S)-4-{[2-(pyridin-4-yl)pyrido[3,4-d]pyrimidin-4-yl]amino}pyrrolidine-2-carboxylate;
methyl (2S,4S)-4-[(2S,4S)-4-{[2-(pyridin-4-yl)pyrido[3,4-d]pyrimidin-4-yl]amino}pyrrolidine-2-amido]pyrrolidine-2-carboxylate;
[(2S)-1-{[5-methoxy-2-(pyridin-4-yl)pyrido[3,4-d]pyrimidin-4-yl]amino}-3-phenylpropan-2-yl](methyl)amine;
N-[(3R)-oxolan-3-yl]-2-(pyridin-4-yl)pyrido[3,4-d]pyrimidin-4-amine;
1-[5-methoxy-2-(pyridin-4-yl)pyrido[3,4-d]pyrimidin-4-yl]-3-(trifluoromethyl)piperazine;
(3 S)-1-[5-methoxy-2-(pyridin-4-yl)pyrido[3,4-d]pyrimidin-4-yl]-3-methylpiperazine;
(3R)-1-[5-methoxy-2-(pyridin-4-yl)pyrido[3,4-d]pyrimidin-4-yl]pyrrolidin-3-amine;
[(2R)-4-[5-methoxy-2-(pyridin-4-yl)pyrido[3,4-d]pyrimidin-4-yl]piperazin-2-yl]methanol;
N-[(2R,3R)-2-amino-3-fluoro-3-phenylpropyl]-5-methoxy-2-(pyridin-4-yl)pyrido[3,4-d]pyrimidin-4-amine;
2-[(2S)-2-benzyl-4-[5-methoxy-2-(pyridin-4-yl)pyrido[3,4-d]pyrimidin-4-yl]piperazin-1-yl]acetamide;
[(2S)-1-{[5-methoxy-2-(pyridin-4-yl)pyrido[3,4-d]pyrimidin-4-yl]amino}-3-phenylpropan-2-yl]dimethylamine;
(3 S)-1-[5-methoxy-2-(pyridin-4-yl)pyrido[3,4-d]pyrimidin-4-yl]pyrrolidin-3-ol;
1-[5-methoxy-2-(pyridin-4-yl)pyrido[3,4-d]pyrimidin-4-yl]-3,5-cis-dimethylpiperazine;
(3R)-1-[5-methoxy-2-(pyridin-4-yl)pyrido[3,4-d]pyrimidin-4-yl]-3-methylpiperazine;
(3 S)-1-[5-methoxy-2-(pyridin-4-yl)pyrido[3,4-d]pyrimidin-4-yl]pyrrolidin-3-amine;
3-(fluoromethyl)-1-[5-methoxy-2-(pyridin-4-yl)pyrido[3,4-d]pyrimidin-4-yl]piperazine;
N-(propan-2-yl)-1-[2-(pyridin-4-yl)pyrido[3,4-d]pyrimidin-4-yl]piperidine-4-carboxamide;
4-[2-(pyridin-4-yl)pyrido[3,4-d]pyrimidin-4-yl]piperazine-1-carboxamide;
N-cyclohexyl-4-[2-(pyridin-4-yl)pyrido[3,4-d]pyrimidin-4-yl]piperazine-1-carboxamide;
2-{4-[5-methoxy-2-(pyridin-4-yl)pyrido[3,4-d]pyrimidin-4-yl]piperazin-2-yl}acetonitrile;
1-[2-(pyridin-4-yl)pyrido[3,4-d]pyrimidin-4-yl]-3-(trifluoromethyl)piperazine;

1-[8-chloro-2-(pyridin-4-yl)pyrido[3,4-d]pyrimidin-4-yl]-3-(trifluoromethyl)piperazine;

(3S)-3-ethyl-1-[2-(pyridin-4-yl)pyrido[3,4-d]pyrimidin-4-yl]piperazine;

(3 S)-3-(propan-2-yl)-1-[2-(pyridin-4-yl)pyrido[3,4-d]pyrimidin-4-yl]piperazine;

1-[2-(3-fluoropyridin-4-yl)-5-methoxypyrido[3,4-d]pyrimidin-4-yl]piperazine;

4-{4-[(8aR)-octahydropyrrolo[1,2-a]piperazin-2-yl]pyrido[3,4-d]pyrimidin-2-yl}pyridine;

1-[2-(3-fluoropyridin-4-yl)pyrido[3,4-d]pyrimidin-4-yl]piperazine;

1-[2-(3-fluoropyridin-4-yl)pyrido[3,4-d]pyrimidin-4-yl]-3-(trifluoromethyl)piperazine;

4-{4-[(3aS)-octahydro-1H-pyrrolo[3,2-c]pyridin-5-yl]pyrido[3,4-d]pyrimidin-2-yl}pyridine;

(3S)-3-benzyl-1-[8-chloro-2-(pyridin-4-yl)pyrido[3,4-d]pyrimidin-4-yl]piperazine;

3-phenyl-1-[2-(pyridin-4-yl)pyrido[3,4-d]pyrimidin-4-yl]piperazine;

4-[5-methoxy-2-(pyridin-4-yl)pyrido[3,4-d]pyrimidin-4-yl]morpholine;

3-ethynyl-1-[2-(pyridin-4-yl)pyrido[3,4-d]pyrimidin-4-yl]piperazine;

2-benzyl-4-[5-methoxy-2-(pyridin-4-yl)pyrido[3,4-d]pyrimidin-4-yl]morpholine;

{1-[8-chloro-2-(pyridin-4-yl)pyrido[3,4-d]pyrimidin-4-yl]azetidin-3-yl}methanol;

(3R)-3-[fluoro(phenyl)methyl]-1-[5-methoxy-2-(pyridin-4-yl)pyrido[3,4-d]pyrimidin-4-yl]piperazine;

1-[8-chloro-2-(pyridin-4-yl)pyrido[3,4-d]pyrimidin-4-yl]piperidin-4-ol;

(3R)-3-[fluoro(phenyl)methyl]-1-[5-methoxy-2-(pyridin-4-yl)pyrido[3,4-d]pyrimidin-4-yl]piperazine;

(4-fluorophenyl)[(2R)-4-[5-methoxy-2-(pyridin-4-yl)pyrido[3,4-d]pyrimidin-4-yl]piperazin-2-yl]methanol;

N—[(S)-1-Benzyl-2-(2-pyridin-4-yl-pyrido[3,4-d]pyrimidin-4-ylamino)-ethyl]-formamide;

N—[(S)-1-Benzyl-2-(2-pyridin-4-yl-pyrido[3,4-d]pyrimidin-4-ylamino)-ethyl]-acetamide;

methyl[(2S)-1-phenyl-3-{[2-(pyridin-4-yl)pyrido[3,4-d]pyrimidin-4-yl]amino}propan-2-yl]amine;

(2S)-2-benzyl-4-[5-methoxy-2-(pyridin-4-yl)pyrido[3,4-d]pyrimidin-4-yl]-1-methylpiperazine;

2-{[(2S)-1-phenyl-3-{[2-(pyridin-4-yl)pyrido[3,4-d]pyrimidin-4-yl]amino}propan-2-yl]amino}acetamide;

N-(1-phenyl-3-{[2-(pyridin-4-yl)pyrido[3,4-d]pyrimidin-4-yl]amino}propan-2-yl)methanesulfonamide;

(1-phenyl-3-{[2-(pyridin-4-yl)pyrido[3,4-d]pyrimidin-4-yl]amino}propan-2-yl)urea;

3-ethyl-1-(1-phenyl-3-{[2-(pyridin-4-yl)pyrido[3,4-d]pyrimidin-4-yl]amino}propan-2-yl)urea;

(3aR)-5-[5-methoxy-2-(pyridin-4-yl)pyrido[3,4-d]pyrimidin-4-yl]-hexahydro-1H-[1,3]oxazolo[3,4-a]piperazin-1-one;

2-{4-[5-methoxy-2-(pyridin-4-yl)pyrido[3,4-d]pyrimidin-4-yl]piperazin-1-yl}acetonitrile;

N-{3-[4-((S)-2-Amino-3-phenyl-propylamino)-2-pyridin-4-yl-pyrido[3,4-d]pyrimidin-8-yl]-phenyl}-methanesulfonamide;

N-[(2S)-2-amino-3-phenylpropyl]-8-(1H-pyrazol-5-yl)-2-(pyridin-4-yl)pyrido[3,4-d]pyrimidin-4-amine;

N-[(2S)-2-amino-3-phenylpropyl]-8-phenyl-2-(pyridin-4-yl)pyrido[3,4-d]pyrimidin-4-amine;

4-(4-{[(2S)-2-amino-3-phenylpropyl]amino}-2-(pyridin-4-yl)pyrido[3,4-d]pyrimidin-8-yl)phenol;

3-(4-{[(2S)-2-amino-3-phenylpropyl]amino}-2-(pyridin-4-yl)pyrido[3,4-d]pyrimidin-8-yl)phenol;

N-[(2S)-2-amino-3-phenylpropyl]-8-(2-methoxyphenyl)-2-(pyridin-4-yl)pyrido[3,4-d]pyrimidin-4-amine;

N-[(2S)-2-amino-3-phenylpropyl]-8-(3-methoxyphenyl)-2-(pyridin-4-yl)pyrido[3,4-d]pyrimidin-4-amine;

N-[(2S)-2-amino-3-phenylpropyl]-8-(4-methoxyphenyl)-2-(pyridin-4-yl)pyrido[3,4-d]pyrimidin-4-amine;

N-[(2S)-2-amino-3-phenylpropyl]-8-(2-chlorophenyl)-2-(pyridin-4-yl)pyrido[3,4-d]pyrimidin-4-amine;

N-[(2S)-2-amino-3-phenylpropyl]-8-(1-benzofuran-5-yl)-2-(pyridin-4-yl)pyrido[3,4-d]pyrimidin-4-amine;

N-[(2S)-2-amino-3-phenylpropyl]-8-(1-methyl-1H-pyrazol-4-yl)-2-(pyridin-4-yl)pyrido[3,4-d]pyrimidin-4-amine;

N-[(2S)-2-amino-3-phenylpropyl]-8-(pyridin-3-yl)-2-(pyridin-4-yl)pyrido[3,4-d]pyrimidin-4-amine;

N-[(2S)-2-amino-3-phenylpropyl]-2,8-bis(pyridin-4-yl)pyrido[3,4-d]pyrimidin-4-amine;

N-[(2S)-2-amino-3-phenylpropyl]-8-[1-(2-methylpropyl)-1H-pyrazol-4-yl]-2-(pyridin-4-yl)pyrido[3,4-d]pyrimidin-4-amine;

N-[(2S)-2-amino-3-phenylpropyl]-8-(3-chlorophenyl)-2-(pyridin-4-yl)pyrido[3,4-d]pyrimidin-4-amine;

N-[(2S)-2-amino-3-phenylpropyl]-8-(4-chlorophenyl)-2-(pyridin-4-yl)pyrido[3,4-d]pyrimidin-4-amine;

N-[(2S)-2-amino-3-phenylpropyl]-8-(1-methyl-1H-pyrazol-5-yl)-2-(pyridin-4-yl)pyrido[3,4-d]pyrimidin-4-amine;

2-(4-{[(2S)-2-amino-3-phenylpropyl]amino}-2-(pyridin-4-yl)pyrido[3,4-d]pyrimidin-8-yl)phenol;

N-[(2S)-2-amino-3-phenylpropyl]-8-[3-(3-chlorophenyl)phenyl]-2-(pyridin-4-yl)pyrido[3,4-d]pyrimidin-4-amine;

N-[(2S)-2-amino-3-phenylpropyl]-8-[4-(4-chlorophenyl)phenyl]-2-(pyridin-4-yl)pyrido[3,4-d]pyrimidin-4-amine;

N-[(2S)-2-amino-3-phenylpropyl]-2-(pyridin-4-yl)-8-(pyrimidin-5-yl)pyrido[3,4-d]pyrimidin-4-amine;

N-[(2S)-2-amino-3-phenylpropyl]-8-(3-aminophenyl)-2-(pyridin-4-yl)pyrido[3,4-d]pyrimidin-4-amine;

N-[(2S)-2-amino-3-phenylpropyl]-8-(1-benzofuran-7-yl)-2-(pyridin-4-yl)pyrido[3,4-d]pyrimidin-4-amine;

N-[(2S)-2-amino-3-phenylpropyl]-8-(5-methylthiophen-2-yl)-2-(pyridin-4-yl)pyrido[3,4-d]pyrimidin-4-amine;

N-[(2S)-2-amino-3-phenylpropyl]-8-(dimethyl-1,2-oxazol-4-yl)-2-(pyridin-4-yl)pyrido[3,4-d]pyrimidin-4-amine;

N-[(2S)-2-amino-3-phenylpropyl]-8-(furan-3-yl)-2-(pyridin-4-yl)pyrido[3,4-d]pyrimidin-4-amine;

N-[(2S)-2-amino-3-phenylpropyl]-2-(pyridin-4-yl)-8-(thiophen-3-yl)pyrido[3,4-d]pyrimidin-4-amine;

N-[(2S)-2-amino-3-phenylpropyl]-8-(furan-2-yl)-2-(pyridin-4-yl)pyrido[3,4-d]pyrimidin-4-amine;

N-[(2S)-2-amino-3-phenylpropyl]-8-(1H-1,3-benzodiazol-5-yl)-2-(pyridin-4-yl)pyrido[3,4-d]pyrimidin-4-amine;

N-[(2S)-2-amino-3-phenylpropyl]-8-(3-ethoxyphenyl)-2-(pyridin-4-yl)pyrido[3,4-d]pyrimidin-4-amine;

N-[(2S)-2-amino-3-phenylpropyl]-8-(2-methylphenyl)-2-(pyridin-4-yl)pyrido[3,4-d]pyrimidin-4-amine;

N-[(2S)-2-amino-3-phenylpropyl]-8-(3-methylphenyl)-2-(pyridin-4-yl)pyrido[3,4-d]pyrimidin-4-amine;

N-[(2S)-2-amino-3-phenylpropyl]-8-[3-(1H-pyrazol-5-yl)phenyl]-2-(pyridin-4-yl)pyrido[3,4-d]pyrimidin-4-amine;

N-[(2S)-2-amino-3-phenylpropyl]-8-[5-(aminomethyl)furan-2-yl]-2-(pyridin-4-yl)pyrido[3,4-d]pyrimidin-4-amine;

(R)-3-Phenyl-N-(2-pyridin-4-yl-8-pyridin-2-yl-pyrido[3,4-d]pyrimidin-4-yl)-propane-1,2-diamine;

$N^4$—((R)-2-Amino-3-phenyl-propyl)-$N^8$-phenyl-2-pyridin-4-yl-pyrido[3,4-d]pyrimidine-4,8-diamine;

4-N-[(2S)-2-amino-3-phenylpropyl]-2-(pyridin-4-yl)-8-N-(pyrimidin-2-yl)pyrido[3,4-d]pyrimidine-4,8-diamine;
4-N-[(2S)-2-amino-3-phenylpropyl]-8-N-(3-chlorophenyl)-2-(pyridin-4-yl)pyrido[3,4-d]pyrimidine-4,8-diamine;
4-N-[(2S)-2-amino-3-phenylpropyl]-2-(pyridin-4-yl)-8-N-(1H-1,2,4-triazol-3-yl)pyrido[3,4-d]pyrimidine-4,8-diamine;
(R)—$N^1$-[8-(4-Methyl-piperazin-1-yl)-2-pyridin-4-yl-pyrido[3,4-d]pyrimidin-4-yl]-3-phenyl-propane-1,2-diamine;
(R)-3-Phenyl-$N^1$-(8-phenylsulfanyl-2-pyridin-4-yl-pyrido[3,4-d]pyrimidin-4-yl)-propane-1,2-diamine;
N-[(2S)-2-amino-3-phenylpropyl]-8-phenoxy-2-(pyridin-4-yl)pyrido[3,4-d]pyrimidin-4-amine;
N-[(2S)-2-amino-3-phenylpropyl]-8-(methylsulfanyl)-2-(pyridin-4-yl)pyrido[3,4-d]pyrimidin-4-amine;
4-(4-{[(2S)-2-amino-3-phenylpropyl]amino}-2-(pyridin-4-yl)pyrido[3,4-d]pyrimidin-8-yl)-2-methylbut-3-yn-2-ol;
5-Chloro-4-piperazin-1-yl-2-pyridin-4-yl-pyrido[3,4-d]pyrimidine;
1-[5-bromo-2-(pyridin-4-yl)pyrido[3,4-d]pyrimidin-4-yl]piperazine;
1-[5,8-dichloro-2-(pyridin-4-yl)pyrido[3,4-d]pyrimidin-4-yl]piperazine;
5-Butyl-4-piperazin-1-yl-2-pyridin-4-yl-pyrido[3,4-d]pyrimidine;
1-[5-ethyl-2-(pyridin-4-yl)pyrido[3,4-d]pyrimidin-4-yl]piperazine;
N-[(2S)-2-amino-3-phenylpropyl]-5-ethyl-2-(pyridin-4-yl)pyrido[3,4-d]pyrimidin-4-amine;
1-[5-methyl-2-(pyridin-4-yl)pyrido[3,4-d]pyrimidin-4-yl]piperazine;
1-[5-cyclopropyl-2-(pyridin-4-yl)pyrido[3,4-d]pyrimidin-4-yl]piperazine;
1-{5-[(benzyloxy)methyl]-2-(pyridin-4-yl)pyrido[3,4-d]pyrimidin-4-yl}piperazine;
5-Chloro-4-piperazin-1-yl-8-(1H-pyrazol-3-yl)-2-pyridin-4-yl-pyrido[3,4-d]pyrimidine;
5-chloro-N,N-dimethyl-4-(piperazin-1-yl)-2-(pyridin-4-yl)pyrido[3,4-d]pyrimidin-8-amine;
5-Isopropenyl-4-piperazin-1-yl-2-pyridin-4-yl-pyrido[3,4-d]pyrimidine;
5-Methoxy-4-piperidin-1-yl-2-pyridin-4-yl-pyrido[3,4-d]pyrimidine;
3-Amino-1-(5-methoxy-2-pyridin-4-yl-pyrido[3,4-d]pyrimidin-4-yl)-pyrrolidine-3-carboxylic acid amide;
3-Amino-1-(5-methoxy-2-pyridin-4-yl-pyrido[3,4-d]pyrimidin-4-yl)-pyrrolidine-3-carboxylic acid phenylamide;
4-Amino-1-(5-methoxy-2-pyridin-4-yl-pyrido[3,4-d]pyrimidin-4-yl)-piperidine-4-carboxylic acid;
[(S)-1-(4-chloro-phenyl)-3-hydroxy-propyl]-amide;
4-(5-Methoxy-2-pyridin-4-yl-pyrido[3,4-d]pyrimidin-4-yl)-piperazine-2-carboxylic acid methyl ester;
4-(5-Methoxy-2-pyridin-4-yl-pyrido[3,4-d]pyrimidin-4-yl)-piperazine-2-carboxylic acid phenylamide;
4-(5-Methoxy-2-pyridin-4-yl-pyrido[3,4-d]pyrimidin-4-yl)-piperazine-2-carboxylic acid benzylamide;
4-(5-Methoxy-2-pyridin-4-yl-pyrido[3,4-d]pyrimidin-4-yl)-piperazine-2-carboxylic acid phenethyl-amide;
4-Piperazin-1-yl-8-propyl-2-pyridin-4-yl-pyrido[3,4-d]pyrimidine;
8-Methyl-4-piperazin-1-yl-2-pyridin-4-yl-pyrido[3,4-d]pyrimidine;
[4-(5-Methoxy-4-piperazin-1-yl-pyrido[3,4-d]pyrimidin-2-yl)-pyridin-2-yl]-phenyl-amine;
[4-(5-Methoxy-4-piperazin-1-yl-pyrido[3,4-d]pyrimidin-2-yl)-pyridin-2-yl]-pyrazin-2-yl-amine;
[4-(5-Methoxy-4-piperazin-1-yl-pyrido[3,4-d]pyrimidin-2-yl)-pyridin-2-yl]-(4-trifluoromethyl-oxazol-2-yl)-amine;
(4,5-Dimethyl-oxazol-2-yl)-[4-(5-methoxy-4-piperazin-1-yl-pyrido[3,4-d]pyrimidin-2-yl)-pyridin-2-yl]-amine;
(4-Cyclopropyl-thiazol-2-yl)-[4-(5-methoxy-4-piperazin-1-yl-pyrido[3,4-d]pyrimidin-2-yl)-pyridin-2-yl]-amine;
3-[4-(5-Methoxy-4-piperazin-1-yl-pyrido[3,4-d]pyrimidin-2-yl)-pyridin-2-ylamino]-benzonitrile;
(2-Fluoro-phenyl)-[4-(5-methoxy-4-piperazin-1-yl-pyrido[3,4-d]pyrimidin-2-yl)-pyridin-2-yl]-amine;
[4-(5-Methoxy-4-piperazin-1-yl-pyrido[3,4-d]pyrimidin-2-yl)-pyridin-2-yl]-(4-trifluoromethyl-phenyl)-amine;
4-(5-Methoxy-4-piperazin-1-yl-pyrido[3,4-d]pyrimidin-2-yl)-pyridin-2-ylamine;
N-[4-(5-Methoxy-4-piperazin-1-yl-pyrido[3,4-d]pyrimidin-2-yl)-pyridin-2-yl]-2-morpholin-4-yl-acetamide;
N-[4-(5-Methoxy-4-piperazin-1-yl-pyrido[3,4-d]pyrimidin-2-yl)-pyridin-2-yl]-2-piperidin-1-yl-acetamide;
[4-(5-Methoxy-4-piperazin-1-yl-pyrido[3,4-d]pyrimidin-2-yl)-pyridin-2-yl]-pyrimidin-4-yl-amine;
N-[4-(5-Methoxy-4-piperazin-1-yl-pyrido[3,4-d]pyrimidin-2-yl)-pyridin-2-yl]-benzamide;
[4-(5-Methoxy-4-piperazin-1-yl-pyrido[3,4-d]pyrimidin-2-yl)-pyridin-2-yl]-methyl-amine;
N-[4-(5-Methoxy-4-piperazin-1-yl-pyrido[3,4-d]pyrimidin-2-yl)-pyridin-2-yl]-acetamide;
N-{4-[4-(4-Hydroxy-piperidin-1-yl)-5-methoxy-pyrido[3,4-d]pyrimidin-2-yl]-pyridin-2-yl}-acetamide;
Cyclopropanecarboxylic acid [4-(5-methoxy-4-piperazin-1-yl-pyrido[3,4-d]pyrimidin-2-yl)-pyridin-2-yl]-amide;
N-[4-(5-Methoxy-4-piperazin-1-yl-pyrido[3,4-d]pyrimidin-2-yl)-pyridin-2-yl]-2,2-dimethyl-propionamide;
Tetrahydro-pyran-4-carboxylic acid[4-(5-methoxy-4-piperazin-1-yl-pyrido[3,4-d]pyrimidin-2-yl)-pyridin-2-yl]-amide;
[4-(5-Methoxy-4-piperazin-1-yl-pyrido[3,4-d]pyrimidin-2-yl)-pyridin-2-yl]-thiazol-2-yl-amine;
[4-(5-Methoxy-4-piperazin-1-yl-pyrido[3,4-d]pyrimidin-2-yl)-pyridin-2-yl]-oxazol-2-yl-amine;
[4-(5-Methoxy-4-piperazin-1-yl-pyrido[3,4-d]pyrimidin-2-yl)-pyridin-2-yl]-(4-methyl-oxazol-2-yl)-amine;
{(S)-4-[5-Methoxy-2-(2-phenylamino-pyridin-4-yl)-pyrido[3,4-d]pyrimidin-4-yl]-piperazin-2-yl}-methanol;
1-[5-Methoxy-2-(2-phenylamino-pyridin-4-yl)-pyrido[3,4-d]pyrimidin-4-yl]-4-methyl-piperidin-4-ol;
{4-[4-((S)-3-Isopropyl-piperazin-1-yl)-5-methoxy-pyrido[3,4-d]pyrimidin-2-yl]-pyridin-2-yl}-phenyl-amine;
2-{(S)-4-[5-Methoxy-2-(2-phenylamino-pyridin-4-yl)-pyrido[3,4-d]pyrimidin-4-yl]-piperazin-2-yl}-ethanol;
N-{4-[5-Methoxy-4-((R)-pyrrolidin-3-ylamino)-pyrido[3,4-d]pyrimidin-2-yl]-pyridin-2-yl}-N',N'-dimethyl-benzene-1,4-diamine;
{5-Methoxy-2-[2-(3-morpholin-4-yl-phenylamino)-pyridin-4-yl]-pyrido[3,4-d]pyrimidin-4-yl}-(R)-pyrrolidin-3-yl-amine;
{2-[2-(2-Fluoro-phenylamino)-pyridin-4-yl]-5-methoxy-pyrido[3,4-d]pyrimidin-4-yl}-(R)-pyrrolidin-3-yl-amine;
{5-Methoxy-2-[2-(4-morpholin-4-yl-phenylamino)-pyridin-4-yl]-pyrido[3,4-d]pyrimidin-4-yl}-(R)-pyrrolidin-3-yl-amine;
{2-[2-(4-Fluoro-phenylamino)-pyridin-4-yl]-5-methoxy-pyrido[3,4-d]pyrimidin-4-yl}-(R)-pyrrolidin-3-yl-amine;
{4-[5-Methoxy-4-(3-trifluoromethyl-piperazin-1-yl)-pyrido[3,4-d]pyrimidin-2-yl]-pyridin-2-yl}-phenyl-amine;
{(S)-4-[5-Methoxy-2-(2-phenylamino-pyridin-4-yl)-pyrido[3,4-d]pyrimidin-4-yl]-piperazin-2-yl}-acetonitrile;

{4-[4-((R)-3-Fluoromethyl-piperazin-1-yl)-5-methoxy-pyrido[3,4-d]pyrimidin-2-yl]pyridin-2-yl}-phenyl-amine;
Cyclopropanecarboxylic acid {4-[4-(4-hydroxy-piperidin-1-yl)-5-methoxy-pyrido[3,4-d]pyrimidin-2-yl]-pyridin-2-yl}-amide;
{4-[4-((S)-3-Fluoromethyl-piperazin-1-yl)-5-methoxy-pyrido[3,4-d]pyrimidin-2-yl]-pyridin-2-yl}-phenyl-amine;
{4-[4-((S)-3-Cyclopropyl-piperazin-1-yl)-5-methoxy-pyrido[3,4-d]pyrimidin-2-yl]-pyridin-2-yl}-phenyl-amine;
{4-[4-((R)-3-Fluoromethyl-piperazin-1-yl)-5-methoxy-pyrido[3,4-d]pyrimidin-2-yl]-pyridin-2-yl}-(2,3,6-trifluoro-phenyl)-amine;
[5-Methoxy-2-(2-phenylamino-pyridin-4-yl)-pyrido[3,4-d]pyrimidin-4-yl]-(R)-pyrrolidin-3-yl-amine;
{5-Methoxy-2-[2-(pyrazin-2-ylamino)-pyridin-4-yl]-pyrido[3,4-d]pyrimidin-4-yl}-(R)-pyrrolidin-3-yl-amine;
Thiophene-2-carboxylic acid {4-[5-methoxy-4-((R)-pyrrolidin-3-ylamino)-pyrido[3,4-d]pyrimidin-2-yl]-pyridin-2-yl}-amide;
Cyclopentyl-[4-(5-methoxy-4-piperazin-1-yl-pyrido[3,4-d]pyrimidin-2-yl)-pyridin-2-yl]-amine;
Cyclohexyl-[4-(5-methoxy-4-piperazin-1-yl-pyrido[3,4-d]pyrimidin-2-yl)-pyridin-2-yl]-amine;
{2-[2-(Pyrazin-2-ylamino)-pyridin-4-yl]-pyrido[3,4-d]pyrimidin-4-yl}-(R)-pyrrolidin-3-yl-amine;
{1-[5-Methoxy-2-(2-phenylamino-pyridin-4-yl)-pyrido[3,4-d]pyrimidin-4-yl]-piperidin-4-yl}-methanol;
2-{3-[5-Methoxy-2-(2-phenylamino-pyridin-4-yl)-pyrido[3,4-d]pyrimidin-4-ylamino]-R-pyrrolidin-1-yl}-acetamide;
[4-(5-Chloro-4-piperazin-1-yl-pyrido[3,4-d]pyrimidin-2-yl)-pyridin-2-yl]-phenyl-amine;
[4-(5-Chloro-4-piperazin-1-yl-pyrido[3,4-d]pyrimidin-2-yl)-pyridin-2-yl]-(2-fluoro-phenyl)-amine;
(2-Fluoro-phenyl)-{2-[2-(2-fluoro-phenylamino)-pyridin-4-yl]-4-piperazin-1-yl-pyrido[3,4-d]pyrimidin-5-yl}-amine;
4-{5-(4-Cyano-pyridin-2-ylamino)-2-[2-(4-cyano-pyridin-2-ylamino)-pyridin-4-yl]-pyrido[3,4-d]pyrimidin-4-yl}-piperazine;
{4-[5-Chloro-4-((S)-3-methyl-piperazin-1-yl)-pyrido[3,4-d]pyrimidin-2-yl]-pyridin-2-yl}-phenyl-amine;
N-[4-(5-Chloro-4-piperazin-1-yl-pyrido[3,4-d]pyrimidin-2-yl)-pyridin-2-yl]-acetamide;
[4-(5-Chloro-4-piperazin-1-yl-pyrido[3,4-d]pyrimidin-2-yl)-pyridin-2-yl]-(2,3-difluoro-phenyl)-amine;
[4-(5-Chloro-4-piperazin-1-yl-pyrido[3,4-d]pyrimidin-2-yl)-pyridin-2-yl]-(6-fluoro-pyridin-2-yl)-amine;
[4-(5-Chloro-4-piperazin-1-yl-pyrido[3,4-d]pyrimidin-2-yl)-pyridin-2-yl]-(2,6-difluoro-phenyl)-amine;
[4-(5-Chloro-4-piperazin-1-yl-pyrido[3,4-d]pyrimidin-2-yl)-pyridin-2-yl]-(2,4-difluoro-phenyl)-amine;
[4-(5-Chloro-4-piperazin-1-yl-pyrido[3,4-d]pyrimidin-2-yl)-pyridin-2-yl]-(4-methyl-pyridin-2-yl)-amine;
[4-(5-Chloro-4-piperazin-1-yl-pyrido[3,4-d]pyrimidin-2-yl)-pyridin-2-yl]-(2,3,6-trifluoro-phenyl)-amine;
[4-(5-Chloro-4-piperazin-1-yl-pyrido[3,4-d]pyrimidin-2-yl)-pyridin-2-yl]-(5-fluoro-pyridin-2-yl)-amine;
[4-(5-Chloro-4-piperazin-1-yl-pyrido[3,4-d]pyrimidin-2-yl)-pyridin-2-yl]-(4-trifluoromethyl-pyridin-2-yl)-amine;
5-[4-(5-Chloro-4-piperazin-1-yl-pyrido[3,4-d]pyrimidin-2-yl)-pyridin-2-ylamino]-pyridine-2-carbonitrile;
{4-Piperazin-1-yl-2-[2-(2,3,6-trifluoro-phenylamino)-pyridin-4-yl]-pyrido[3,4-d]pyrimidin-5-yl}-(2,3,6-trifluoro-phenyl)-amine;
(2,6-Difluoro-phenyl)-{2-[2-(2,6-difluoro-phenylamino)-pyridin-4-yl]-4-piperazin-1-yl-pyrido[3,4-d]pyrimidin-5-yl}-amine;
[4-(5-Cyclopropyl-4-piperazin-1-yl-pyrido[3,4-d]pyrimidin-2-yl)-pyridin-2-yl]-(2-fluoro-phenyl)-amine;
[4-(5-Cyclopropyl-4-piperazin-1-yl-pyrido[3,4-d]pyrimidin-2-yl)-pyridin-2-yl]-(2,6-difluoro-phenyl)-amine;
2-[4-(5-Cyclopropyl-4-piperazin-1-yl-pyrido[3,4-d]pyrimidin-2-yl)-pyridin-2-ylamino]-isonicotinonitrile;
[4-(5-Cyclopropyl-4-piperazin-1-yl-pyrido[3,4-d]pyrimidin-2-yl)-pyridin-2-yl]-(2,3,6-trifluoro-phenyl)-amine;
[4-(5-Cyclopropyl-4-piperazin-1-yl-pyrido[3,4-d]pyrimidin-2-yl)-pyridin-2-yl]-(4-methyl-pyridin-2-yl)-amine;
{4-[5-Cyclopropyl-4-(3-trifluoromethyl-piperazin-1-yl)-pyrido[3,4-d]pyrimidin-2-yl]-pyridin-2-yl}-(6-fluoro-pyridin-2-yl)-amine;
[4-(5-Cyclopropyl-4-piperazin-1-yl-pyrido[3,4-d]pyrimidin-2-yl)-pyridin-2-yl]-(4-trifluoromethyl-pyridin-2-yl)-amine;
[4-(5-Cyclopropyl-4-piperazin-1-yl-pyrido[3,4-d]pyrimidin-2-yl)-pyridin-2-yl]-(6-trifluoromethyl-pyridin-3-yl)-amine;
[4-(5-Cyclopropyl-4-piperazin-1-yl-pyrido[3,4-d]pyrimidin-2-yl)-pyridin-2-yl]-(5-fluoro-pyridin-2-yl)-amine;
[4-(5-Cyclopropyl-4-piperazin-1-yl-pyrido[3,4-d]pyrimidin-2-yl)-pyridin-2-yl]-(4,5-dimethyl-oxazol-2-yl)-amine;
{4-[5-Cyclopropyl-4-((S)-3-cyclopropyl-piperazin-1-yl)-pyrido[3,4-d]pyrimidin-2-yl]-pyridin-2-yl}-phenyl-amine;
1-{5-Cyclopropyl-2-[2-(2-fluoro-phenylamino)-pyridin-4-yl]-pyrido[3,4-d]pyrimidin-4-yl}-piperidin-4-ol;
{4-[5-Cyclopropyl-4-((S)-3-isopropyl-piperazin-1-yl)-pyrido[3,4-d]pyrimidin-2-yl]-pyridin-2-yl}-phenyl-amine;
{4-[5-Cyclopropyl-4-((S)-3-cyclopropyl-piperazin-1-yl)-pyrido[3,4-d]pyrimidin-2-yl]-pyridin-2-yl}-(2-fluoro-phenyl)-amine;
{4-[5-Cyclopropyl-4-((S)-3-cyclopropyl-piperazin-1-yl)-pyrido[3,4-d]pyrimidin-2-yl]-pyridin-2-yl}-(6-fluoro-pyridin-2-yl)-amine;
(4-{5-Cyclopropyl-4-[3-(1,1-difluoro-ethyl)-piperazin-1-yl]-pyrido[3,4-d]pyrimidin-2-yl}-pyridin-2-yl)-phenyl-amine;
[4-(5-Cyclopropyl-4-piperazin-1-yl-pyrido[3,4-d]pyrimidin-2-yl)-pyridin-2-yl]-phenyl-amine;
{(S)-4-[5-Cyclopropyl-2-(2-phenylamino-pyridin-4-yl)-pyrido[3,4-d]pyrimidin-4-yl]-piperazin-2-yl}-acetonitrile;
Cyclopentyl-[4-(5-cyclopropyl-4-piperazin-1-yl-pyrido[3,4-d]pyrimidin-2-yl)-pyridin-2-yl]-amine;
Cyclohexyl-[4-(5-cyclopropyl-4-piperazin-1-yl-pyrido[3,4-d]pyrimidin-2-yl)-pyridin-2-yl]-amine;
[4-(5-Cyclopropyl-4-piperazin-1-yl-pyrido[3,4-d]pyrimidin-2-yl)-pyridin-2-yl]-(tetrahydro-pyran-4-yl)-amine;
Cyclopentyl-{4-[5-cyclopropyl-4-(3-trifluoromethyl-piperazin-1-yl)-pyrido[3,4-d]pyrimidin-2-yl]-pyridin-2-yl}-amine;
Adamantan-1-yl-[4-(5-cyclopropyl-4-piperazin-1-yl-pyrido[3,4-d]pyrimidin-2-yl)-pyridin-2-yl]-amine;
2-Amino-N-{4-[4-((R)-pyrrolidin-3-ylamino)-pyrido[3,4-d]pyrimidin-2-yl]-pyridin-2-yl}-benzamide;
4-{4-[4-((R)-Pyrrolidin-3-ylamino)-pyrido[3,4-d]pyrimidin-2-yl]-pyridin-2-ylamino}-benzamide;
4-Amino-N-{4-[4-((R)-pyrrolidin-3-ylamino)-pyrido[3,4-d]pyrimidin-2-yl]-pyridin-2-yl}-benzamide;

{4-[(1S,4S)-4-(2,5-Diaza-bicyclo[2.2.1]hept-2-yl)-pyrido[3,4-d]pyrimidin-2-yl]-pyridin-2-yl}-phenyl-amine;

Pyrazine-2-carboxylic acid {4-[4-((R)-pyrrolidin-3-ylamino)-pyrido[3,4-d]pyrimidin-2-yl]-pyridin-2-yl}-amide;

3-{4-[4-((R)-Pyrrolidin-3-ylamino)-pyrido[3,4-d]pyrimidin-2-yl]-pyridin-2-ylamino}-benzamide;

3-Amino-N-{4-[4-((R)-pyrrolidin-3-ylamino)-pyrido[3,4-d]pyrimidin-2-yl]-pyridin-2-yl}-benzamide;

2-(4-{4-[4-((R)-Pyrrolidin-3-ylamino)-pyrido[3,4-d]pyrimidin-2-yl]-pyridin-2-ylamino}-phenoxy)-acetamide;

2-(3-{4-[4-((R)-Pyrrolidin-3-ylamino)-pyrido[3,4-d]pyrimidin-2-yl]-pyridin-2-ylamino}-phenoxy)-acetamide;

2-(4-{4-[4-((R)-Pyrrolidin-3-ylamino)-pyrido[3,4-d]pyrimidin-2-yl]-pyridin-2-ylamino}-phenyl)-acetamide;

2-(4-Amino-phenyl)-N-{4-[4-((R)-pyrrolidin-3-ylamino)-pyrido[3,4-d]pyrimidin-2-yl]-pyridin-2-yl}-acetamide;

2-(3-{4-[4-((R)-Pyrrolidin-3-ylamino)-pyrido[3,4-d]pyrimidin-2-yl]-pyridin-2-ylamino}-phenyl)-acetamide;

2-(3-Amino-phenyl)-N-{4-[4-((R)-pyrrolidin-3-ylamino)-pyrido[3,4-d]pyrimidin-2-yl]-pyridin-2-yl}-acetamide;

{2-[2-(5-Phenyl-pyridin-2-ylamino)-pyridin-4-yl]-pyrido[3,4-d]pyrimidin-4-yl}-(R)-pyrrolidin-3-yl-amine;

{2-[2-(6-Morpholin-4-yl-pyridin-3-ylamino)-pyridin-4-yl]-pyrido[3,4-d]pyrimidin-4-yl}-(R)-pyrrolidin-3-yl-amine;

(2-{2-[6-(4-Methyl-piperazin-1-yl)-pyridin-3-ylamino]-pyridin-4-yl}-pyrido[3,4-d]pyrimidin-4-yl)-(R)-pyrrolidin-3-yl-amine;

2-{4-[4-((R)-Pyrrolidin-3-ylamino)-pyrido[3,4-d]pyrimidin-2-yl]-pyridin-2-ylamino}-isonicotinonitrile;

{2-[2-(4-Imidazol-1-ylmethyl-phenylamino)-pyridin-4-yl]-pyrido[3,4-d]pyrimidin-4-yl}-(R)-pyrrolidin-3-yl-amine;

2-(3-{4-[5-Methoxy-4-((R)-pyrrolidin-3-ylamino)-pyrido[3,4-d]pyrimidin-2-yl]-pyridin-2-ylamino}-phenoxy)-acetamide;

2-(3-{4-[5-Methoxy-4-((R)-pyrrolidin-3-ylamino)-pyrido[3,4-d]pyrimidin-2-yl]-pyridin-2-ylamino}-phenyl)-acetamide;

2-(3-Amino-phenyl)-N-{4-[5-methoxy-4-((R)-pyrrolidin-3-ylamino)-pyrido[3,4-d]pyrimidin-2-yl]-pyridin-2-yl}-acetamide;

2-(4-{4-[5-Methoxy-4-((R)-pyrrolidin-3-ylamino)-pyrido[3,4-d]pyrimidin-2-yl]-pyridin-2-ylamino}-phenyl)-acetamide;

2-(4-Amino-phenyl)-N-{4-[5-methoxy-4-((R)-pyrrolidin-3-ylamino)-pyrido[3,4-d]pyrimidin-2-yl]-pyridin-2-yl}-acetamide;

1-{4-[4-((R)-Pyrrolidin-3-ylamino)-pyrido[3,4-d]pyrimidin-2-yl]-pyridin-2-yl}-1H-pyrrolo[2,3-b]pyridine-4-carbonitrile;

{5-Methoxy-2-[2-(5-phenyl-pyridin-2-ylamino)-pyridin-4-yl]-pyrido[3,4-d]pyrimidin-4-yl}-(R)-pyrrolidin-3-yl-amine;

{5-Methoxy-2-[2-(6-morpholin-4-yl-pyridin-3-ylamino)-pyridin-4-yl]-pyrido[3,4-d]pyrimidin-4-yl}-(R)-pyrrolidin-3-yl-amine;

(5-Methoxy-2-{2-[6-(4-methyl-piperazin-1-yl)-pyridin-3-ylamino]-pyridin-4-yl}-pyrido[3,4-d]pyrimidin-4-yl)-(R)-pyrrolidin-3-yl-amine;

2-{4-[5-Methoxy-4-((R)-pyrrolidin-3-ylamino)-pyrido[3,4-d]pyrimidin-2-yl]-pyridin-2-ylamino}-isonicotinonitrile;

{2-[2-(4-Imidazol-1-ylmethyl-phenylamino)-pyridin-4-yl]-5-methoxy-pyrido[3,4-d]pyrimidin-4-yl}-(R)-pyrrolidin-3-yl-amine;

2-Phenyl-N-{4-[4-((R)-pyrrolidin-3-ylamino)-pyrido[3,4-d]pyrimidin-2-yl]-pyridin-2-yl}-acetamide;

2-(4-Methoxy-phenyl)-N-{4-[4-((R)-pyrrolidin-3-ylamino)-pyrido[3,4-d]pyrimidin-2-yl]-pyridin-2-yl}-acetamide;

2-(2-Methoxy-phenyl)-N-{4-[4-((R)-pyrrolidin-3-ylamino)-pyrido[3,4-d]pyrimidin-2-yl]-pyridin-2-yl}-acetamide;

2-(3-Methoxy-phenyl)-N-{4-[4-((R)-pyrrolidin-3-ylamino)-pyrido[3,4-d]pyrimidin-2-yl]-pyridin-2-yl}-acetamide;

{2-[2-(4-Methyl-pyridin-2-ylamino)-pyridin-4-yl]-pyrido[3,4-d]pyrimidin-4-yl}-(R)-pyrrolidin-3-yl-amine;

{2-[2-(4-Chloro-pyridin-2-ylamino)-pyridin-4-yl]-pyrido[3,4-d]pyrimidin-4-yl}-(R)-pyrrolidin-3-yl-amine;

6-{4-[4-((R)-Pyrrolidin-3-ylamino)-pyrido[3,4-d]pyrimidin-2-yl]-pyridin-2-ylamino}-nicotinonitrile;

2-[4-(4-Piperazin-1-yl-pyrido[3,4-d]pyrimidin-2-yl)-pyridin-2-ylamino]-isonicotinonitrile;

{2-[2-(4-Morpholin-4-yl-pyridin-2-ylamino)-pyridin-4-yl]-pyrido[3,4-d]pyrimidin-4-yl}-(R)-pyrrolidin-3-yl-amine;

6-{4-[5-Methoxy-4-((R)-pyrrolidin-3-ylamino)-pyrido[3,4-d]pyrimidin-2-yl]-pyridin-2-ylamino}-nicotinonitrile;

{2-[2-(5-Methyl-pyridin-2-ylamino)-pyridin-4-yl]-pyrido[3,4-d]pyrimidin-4-yl}-(R)-pyrrolidin-3-yl-amine;

{2-[2-(5-Chloro-pyridin-2-ylamino)-pyridin-4-yl]-pyrido[3,4-d]pyrimidin-4-yl}-(R)-pyrrolidin-3-yl-amine;

2-[2-(Pyrimidin-4-ylamino)-pyridin-4-yl]-pyrido[3,4-d]pyrimidin-4-yl}-(R)-pyrrolidin-3-yl-amine;

2-(3-Cyano-phenyl)-N-{4-[4-((R)-pyrrolidin-3-ylamino)-pyrido[3,4-d]pyrimidin-2-yl]-pyridin-2-yl}-acetamide;

2-(4-Cyano-phenyl)-N-{4-[4-((R)-pyrrolidin-3-ylamino)-pyrido[3,4-d]pyrimidin-2-yl]-pyridin-2-yl}-acetamide;

(R)-Pyrrolidin-3-yl-{2-[2-(4-trifluoromethyl-pyridin-2-ylamino)-pyridin-4-yl]-pyrido[3,4-d]pyrimidin-4-yl}-amine;

(R)-Pyrrolidin-3-yl-{2-[2-(5-trifluoromethyl-pyridin-2-ylamino)-pyridin-4-yl]-pyrido[3,4-d]pyrimidin-4-yl}-amine;

2-[4-(5-Methoxy-4-piperazin-1-yl-pyrido[3,4-d]pyrimidin-2-yl)-pyridin-2-ylamino]-isonicotinonitrile;

6-[4-(5-Methoxy-4-piperazin-1-yl-pyrido[3,4-d]pyrimidin-2-yl)-pyridin-2-ylamino]-nicotinonitrile;

{4-[5-Methoxy-4-(4-morpholin-4-yl-piperidin-1-yl)-pyrido[3,4-d]pyrimidin-2-yl]-pyridin-2-yl}-phenyl-amine;

2-(4-Cyano-phenyl)-N-[4-(5-methoxy-4-piperazin-1-yl-pyrido[3,4-d]pyrimidin-2-yl)-pyridin-2-yl]-acetamide;

2-(3-Cyano-phenyl)-N-[4-(5-methoxy-4-piperazin-1-yl-pyrido[3,4-d]pyrimidin-2-yl)-pyridin-2-yl]-acetamide;

{2-[2-(5-Morpholin-4-yl-pyridin-2-ylamino)-pyridin-4-yl]-pyrido[3,4-d]pyrimidin-4-yl}-(R)-pyrrolidin-3-yl-amine;

{2-[2-(2-Methoxy-4-morpholin-4-yl-phenylamino)-pyridin-4-yl]-pyrido[3,4-d]pyrimidin-4-yl}-(R)-pyrrolidin-3-yl-amine;

(2-Methoxy-4-morpholin-4-yl-phenyl)-[4-(5-methoxy-4-piperazin-1-yl-pyrido[3,4-d]pyrimidin-2-yl)-pyridin-2-yl]-amine;

{5-Methoxy-2-[2-(2-methoxy-4-morpholin-4-yl-phenylamino)-pyridin-4-yl]-pyrido[3,4-d]pyrimidin-4-yl}-(R)-pyrrolidin-3-yl-amine;

(5-Methoxy-2-{2-[4-(tetrahydro-pyran-4-yl)-phenylamino]-pyridin-4-yl}-pyrido[3,4-d]pyrimidin-4-yl)-(R)-pyrrolidin-3-yl-amine;

[4-(5-Methoxy-4-piperazin-1-yl-pyrido[3,4-d]pyrimidin-2-yl)-pyridin-2-yl]-[4-(tetrahydro-pyran-4-yl)-phenyl]-amine;

[4-(5-Methoxy-4-piperazin-1-yl-pyrido[3,4-d]pyrimidin-2-yl)-pyridin-2-yl]-(4-methyl-pyridin-2-yl)-amine;

[4-(5-Methoxy-4-piperazin-1-yl-pyrido[3,4-d]pyrimidin-2-yl)-pyridin-2-yl]-(5-methyl-pyridin-2-yl)-amine;

(4-Chloro-pyridin-2-yl)-[4-(5-methoxy-4-piperazin-1-yl-pyrido[3,4-d]pyrimidin-2-yl)-pyridin-2-yl]-amine;

(5-Chloro-pyridin-2-yl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-(4-trifluoromethyl-pyridin-2-yl)-amine;

[4-(5-Methoxy-4-piperazin-1-yl-pyrido[3,4-d]pyrimidin-2-yl)-pyridin-2-yl]-(5-trifluoromethyl-pyridin-2-yl)-amine;

2-(4-Chloro-phenyl)-N-[4-(5-methoxy-4-piperazin-1-yl-pyrido[3,4-d]pyrimidin-2-yl)-pyridin-2-yl]-acetamide;

2-(3-Chloro-phenyl)-N-[4-(5-methoxy-4-piperazin-1-yl-pyrido[3,4-d]pyrimidin-2-yl)-pyridin-2-yl]-acetamide;

N-[4-(5-Methoxy-4-piperazin-1-yl-pyrido[3,4-d]pyrimidin-2-yl)-pyridin-2-yl]-2-phenyl-acetamide;

2-(3-Methoxy-phenyl)-N-[4-(5-methoxy-4-piperazin-1-yl-pyrido[3,4-d]pyrimidin-2-yl)-pyridin-2-yl]-acetamide;

N-[4-(5-Methoxy-4-piperazin-1-yl-pyrido[3,4-d]pyrimidin-2-yl)-pyridin-2-yl]-2-(3-trifluoromethyl-phenyl)-acetamide;

2-(4-Methoxy-phenyl)-N-[4-(5-methoxy-4-piperazin-1-yl-pyrido[3,4-d]pyrimidin-2-yl)-pyridin-2-yl]-acetamide;

[4-(5-Methoxy-4-piperazin-1-yl-pyrido[3,4-d]pyrimidin-2-yl)-pyridin-2-yl]-(6-morpholin-4-yl-pyridin-3-yl)-amine;

{2-[2-(Pyridin-3-ylamino)-pyridin-4-yl]-pyrido[3,4-d]pyrimidin-4-yl}-(R)-pyrrolidin-3-yl-amine;

{5-Methoxy-2-[2-(pyridin-3-ylamino)-pyridin-4-yl]-pyrido[3,4-d]pyrimidin-4-yl}-(R)-pyrrolidin-3-yl-amine;

[4-(5-Methoxy-4-piperazin-1-yl-pyrido[3,4-d]pyrimidin-2-yl)-pyridin-2-yl]-pyridin-3-yl-amine;

2-[4-(5-Methoxy-4-piperazin-1-yl-pyrido[3,4-d]pyrimidin-2-yl)-pyridin-2-ylamino]-isonicotinamide;

6-[4-(5-Methoxy-4-piperazin-1-yl-pyrido[3,4-d]pyrimidin-2-yl)-pyridin-2-ylamino]-nicotinamide;

(3-Methoxy-4-morpholin-4-yl-phenyl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-(2-methyl-4-morpholin-4-yl-phenyl)-amine;

5-[4-(5-Methoxy-4-piperazin-1-yl-pyrido[3,4-d]pyrimidin-2-yl)-pyridin-2-ylamino]-pyridine-2-carbonitrile;

{5-Methoxy-2-[2-(pyrimidin-5-ylamino)-pyridin-4-yl]-pyrido[3,4-d]pyrimidin-4-yl}-(R)-pyrrolidin-3-yl-amine;

[4-(5-Methoxy-4-piperazin-1-yl-pyrido[3,4-d]pyrimidin-2-yl)-pyridin-2-yl]-pyrimidin-5-yl-amine;

[4-(5-Methoxy-4-piperazin-1-yl-pyrido[3,4-d]pyrimidin-2-yl)-pyridin-2-yl]-pyrimidin-5-yl-amine;

[4-(5-Methoxy-4-piperazin-1-yl-pyrido[3,4-d]pyrimidin-2-yl)-pyridin-2-yl]-pyridin-2-yl-amine;

2-[4-(5-Methoxy-4-morpholin-4-yl-pyrido[3,4-d]pyrimidin-2-yl)-pyridin-2-ylamino]-isonicotinonitrile;

2-(3-Cyano-phenyl)-N-[4-(5-methoxy-4-morpholin-4-yl-pyrido[3,4-d]pyrimidin-2-yl)-pyridin-2-yl]-acetamide;

[4-(5-Methoxy-4-piperazin-1-yl-pyrido[3,4-d]pyrimidin-2-yl)-pyridin-2-yl]-(3,4,5-trimethoxy-phenyl)-amine;

N-[4-(5-Methoxy-4-piperazin-1-yl-pyrido[3,4-d]pyrimidin-2-yl)-pyridin-2-yl]-2-(4-trifluoromethyl-phenyl)-acetamide;

[4-(5-Methoxy-4-piperazin-1-yl-pyrido[3,4-d]pyrimidin-2-yl)-pyridin-2-yl]-(6-phenyl-pyridin-3-yl)-amine;

[4-(5-Methoxy-4-piperazin-1-yl-pyrido[3,4-d]pyrimidin-2-yl)-pyridin-2-yl]-(6-methyl-pyridin-3-yl)-amine;

[4-(5-Methoxy-4-piperazin-1-yl-pyrido[3,4-d]pyrimidin-2-yl)-pyridin-2-yl]-(6-methoxy-pyridin-3-yl)-amine;

[4-(5-Methoxy-4-piperazin-1-yl-pyrido[3,4-d]pyrimidin-2-yl)-pyridin-2-yl]-(6-trifluoromethyl-pyridin-3-yl)-amine;

N-{4-[5-Methoxy-4-((R)-pyrrolidin-3-ylamino)-pyrido[3,4-d]pyrimidin-2-yl]-pyridin-2-yl}-2-pyridin-3-yl-acetamide;

2-{4-[5-Methoxy-4-(4-methyl-piperazin-1-yl)-pyrido[3,4-d]pyrimidin-2-yl]-pyridin-2-ylamino}-isonicotinonitrile;

2-(3-Chloro-phenyl)-N-{4-[5-methoxy-4-(4-methyl-piperazin-1-yl)-pyrido[3,4-d]pyrimidin-2-yl]-pyridin-2-yl}-acetamide;

N-[4-(5-Methoxy-4-piperazin-1-yl-pyrido[3,4-d]pyrimidin-2-yl)-pyridin-2-yl]-2-pyridin-3-yl-acetamide;

N-[4-(5-Methoxy-4-piperazin-1-yl-pyrido[3,4-d]pyrimidin-2-yl)-pyridin-2-yl]-2-pyridin-4-yl-acetamide;

[4-(5-Methoxy-4-piperazin-1-yl-pyrido[3,4-d]pyrimidin-2-yl)-pyridin-2-yl]-(4-methoxy-pyridin-2-yl)-amine;

2-{4-[4-(4-Hydroxy-piperidin-1-yl)-5-methoxy-pyrido[3,4-d]pyrimidin-2-yl]-pyridin-2-ylamino}-isonicotinonitrile;

2-(3-Cyano-phenyl)-N-{4-[4-(4-hydroxy-piperidin-1-yl)-5-methoxy-pyrido[3,4-d]pyrimidin-2-yl]-pyridin-2-yl}-acetamide;

2-(3-Cyano-phenyl)-N-{4-[5-methoxy-4-(4-methyl-piperazin-1-yl)-pyrido[3,4-d]pyrimidin-2-yl]-pyridin-2-yl}-acetamide;

(6-Chloro-pyridin-3-yl)-[4-(5-methoxy-4-piperazin-1-yl-pyrido[3,4-d]pyrimidin-2-yl)-pyridin-2-yl]-amine;

(R)—N-{4-[5-Methoxy-4-((R)-pyrrolidin-3-ylamino)-pyrido[3,4-d]pyrimidin-2-yl]-pyridin-2-yl}-2-phenyl-propionamide;

(S)—N-{4-[5-Methoxy-4-((R)-pyrrolidin-3-ylamino)-pyrido[3,4-d]pyrimidin-2-yl]-pyridin-2-yl}-2-phenyl-propionamide;

(R)—N-[4-(5-Methoxy-4-piperazin-1-yl-pyrido[3,4-d]pyrimidin-2-yl)-pyridin-2-yl]-2-phenyl-propionamide;

(S)—N-[4-(5-Methoxy-4-piperazin-1-yl-pyrido[3,4-d]pyrimidin-2-yl)-pyridin-2-yl]-2-phenyl-propionamide;

[4-(5-Methoxy-4-piperazin-1-yl-pyrido[3,4-d]pyrimidin-2-yl)-pyridin-2-yl]-(3-methyl-pyridin-2-yl)-amine;

(3-Fluoro-pyridin-2-yl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-(6-piperazin-1-ylpyridin-3-yl)-amine;

[4-(5-Methoxy-4-piperazin-1-yl-pyrido[3,4-d]pyrimidin-2-yl)-pyridin-2-yl]-[2-methyl-4-(4-methyl-piperazin-1-yl)-phenyl]-amine;

[4-(5-Methoxy-4-piperazin-1-yl-pyrido[3,4-d]pyrimidin-2-yl)-pyridin-2-yl]-(1-piperidin-4-yl-1H-pyrazol-4-yl)-amine;

[4-(5-Methoxy-4-piperazin-1-yl-pyrido[3,4-d]pyrimidin-2-yl)-pyridin-2-yl]-(6-methyl-pyridin-2-yl)-amine;

[4-(5-Methoxy-4-piperazin-1-yl-pyrido[3,4-d]pyrimidin-2-yl)-pyridin-2-yl]-(5-methyl-pyridin-3-yl)-amine;

(5-Chloro-pyridin-3-yl)-[4-(5-methoxy-4-piperazin-1-yl-pyrido[3,4-d]pyrimidin-2-yl)-pyridin-2-yl]-amine;

(2-Fluoro-4-morpholin-4-yl-phenyl)-[4-(5-methoxy-4-piperazin-1-yl-pyrido[3,4-d]pyrimidin-2-yl)-pyridin-2-yl]-amine;

3-Fluoro-4-[4-(5-methoxy-4-piperazin-1-yl-pyrido[3,4-d]pyrimidin-2-yl)-pyridin-2-ylamino]-benzonitrile;

4-Fluoro-3-[4-(5-methoxy-4-piperazin-1-yl-pyrido[3,4-d]pyrimidin-2-yl)-pyridin-2-ylamino]-benzonitrile;

(2,6-Difluoro-phenyl)-[4-(5-methoxy-4-piperazin-1-yl-pyrido[3,4-d]pyrimidin-2-yl)-pyridin-2-yl]-amine;

(2-Fluoro-6-methyl-phenyl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-pyrimidin-2-yl-amine;

[4-(5-Methoxy-4-piperazin-1-yl-pyrido[3,4-d]pyrimidin-2-yl)-pyridin-2-yl]-(5-methoxy-pyridin-3-yl)-amine;

(S)-1-[5-Methoxy-2-(2-phenylamino-pyridin-4-yl)-pyrido[3,4-d]pyrimidin-4-yl]-piperidin-3-ol;

2-{4-[4-((S)-3-Hydroxy-piperidin-1-yl)-5-methoxy-pyrido[3,4-d]pyrimidin-2-yl]-pyridin-2-ylamino}-isonicotinonitrile;

1-[5-Methoxy-2-(2-phenylamino-pyridin-4-yl)-pyrido[3,4-d]pyrimidin-4-yl]-piperidin-4-ol;

(R)-1-[5-Methoxy-2-(2-phenylamino-pyridin-4-yl)-pyrido[3,4-d]pyrimidin-4-yl]-piperidin-3-ol;

2-{4-[4-((R)-3-Hydroxy-piperidin-1-yl)-5-methoxy-pyrido[3,4-d]pyrimidin-2-yl]-pyridin-2-ylamino}-isonicotinonitrile;

[5-Methoxy-2-(2-phenylamino-pyridin-4-yl)-pyrido[3,4-d]pyrimidin-4-yl]-(S)-1-pyrrolidin-2-ylmethyl-amine;

[5-Methoxy-2-(2-phenylamino-pyridin-4-yl)-pyrido[3,4-d]pyrimidin-4-yl]-(R)-1-pyrrolidin-2-ylmethyl-amine;

2-{4-[5-Methoxy-2-(2-phenylamino-pyridin-4-yl)-pyrido[3,4-d]pyrimidin-4-yl]-piperazin-1-yl}-ethanol;

{1-[5-Methoxy-2-(2-phenylamino-pyridin-4-yl)-pyrido[3,4-d]pyrimidin-4-yl]-azetidin-3-yl}-methanol;

{(R)-4-[5-Methoxy-2-(2-phenylamino-pyridin-4-yl)-pyrido[3,4-d]pyrimidin-4-yl]-piperazin-2-yl}-methanol;

(R)-7-[5-Methoxy-2-(2-phenylamino-pyridin-4-yl)-pyrido[3,4-d]pyrimidin-4-yl]-hexahydro-oxazolo[3,4-a]pyrazin-3-one;

(±)-cis-1-[5-Methoxy-2-(2-phenylamino-pyridin-4-yl)-pyrido[3,4-d]pyrimidin-4-yl]-piperidine-3,4-diol;

(±)-trans-1-[5-Methoxy-2-(2-phenylamino-pyridin-4-yl)-pyrido[3,4-d]pyrimidin-4-yl]-piperidine-3,4-diol;

4-[5-Methoxy-2-(2-phenylamino-pyridin-4-yl)-pyrido[3,4-d]pyrimidin-4-yl]-piperazin-2-one;

(2,3-Difluoro-phenyl)-[4-(5-methoxy-4-piperazin-1-yl-pyrido[3,4-d]pyrimidin-2-yl)-pyridin-2-yl]-amine;

(2,5-Difluoro-phenyl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-(2,4,6-trifluoro-phenyl)-amine;

((R)-4-{2-[2-(2,6-Difluoro-phenylamino)-pyridin-4-yl]-5-methoxy-pyrido[3,4-d]pyrimidin-4-yl}-piperazin-2-yl)-methanol;

3-Hydroxymethyl-1-[5-methoxy-2-(2-phenylamino-pyridin-4-yl)-pyrido[3,4-d]pyrimidin-4-yl]-piperidin-4-ol;

[4-(5-Methoxy-4-piperazin-1-yl-pyrido[3,4-d]pyrimidin-2-yl)-pyridin-2-yl]-(2,3,6-trifluoro-phenyl)-amine;

[4-(5-Methoxy-4-piperazin-1-yl-pyrido[3,4-d]pyrimidin-2-yl)-pyridin-2-yl]-(2-trifluoromethyl-phenyl)-amine;

[4-(5-Methoxy-4-piperazin-1-yl-pyrido[3,4-d]pyrimidin-2-yl)-pyridin-2-yl]-(3-trifluoromethyl-phenyl)-amine;

(6-Fluoro-pyridin-2-yl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-(6-methoxy-pyridin-2-yl)-amine;

[4-(5-Methoxy-4-piperazin-1-yl-pyrido[3,4-d]pyrimidin-2-yl)-pyridin-2-yl]-(6-trifluoromethyl-pyridin-2-yl)-amine;

(2-Fluoro-pyridin-3-yl)-[4-(5-methoxy-4-piperazin-1-yl-pyrido[3,4-d]pyrimidin-2-yl)-pyridin-2-yl]-amine;

(2-Fluoro-3-methyl-phenyl)-[4-(5-methoxy-4-piperazin-1-yl-pyrido[3,4-d]pyrimidin-2-yl)-pyridin-2-yl]-amine;

(2-Fluoro-3-trifluoromethyl-phenyl)-[4-(5-methoxy-4-piperazin-1-yl-pyrido[3,4-d]pyrimidin-2-yl)-pyridin-2-yl]-amine;

(2,4-Difluoro-phenyl)-[4-(5-methoxy-4-piperazin-1-yl-pyrido[3,4-d]pyrimidin-2-yl)-pyridin-2-yl]-amine;

[4-(5-Methoxy-4-piperazin-1-yl-pyrido[3,4-d]pyrimidin-2-yl)-pyridin-2-yl]-(2,3,4-trifluoro-phenyl)-amine;

[4-(5-Methoxy-4-piperazin-1-yl-pyrido[3,4-d]pyrimidin-2-yl)-pyridin-2-yl]-(2,4,5-trifluoro-phenyl)-amine;

(3S,4S)-1-[5-Methoxy-2-(2-phenylamino-pyridin-4-yl)-pyrido[3,4-d]pyrimidin-4-yl]-piperidine-3,4-diol;

(3R,4R)-1-[5-Methoxy-2-(2-phenylamino-pyridin-4-yl)-pyrido[3,4-d]pyrimidin-4-yl]-piperidine-3,4-diol;

3-[5-Methoxy-2-(2-phenylamino-pyridin-4-yl)-pyrido[3,4-d]pyrimidin-4-ylamino]-propionamide;

[4-(5-Methoxy-4-piperidin-1-yl-pyrido[3,4-d]pyrimidin-2-yl)-pyridin-2-yl]-phenyl-amine;

{4-[4-(4,4-Difluoro-piperidin-1-yl)-5-methoxy-pyrido[3,4-d]pyrimidin-2-yl]-pyridin-2-yl}-phenyl-amine;

1-[5-Methoxy-2-(2-phenylamino-pyridin-4-yl)-pyrido[3,4-d]pyrimidin-4-yl]-piperidine-4-carbonitrile;

{4-[4-(4-Fluoro-piperidin-1-yl)-5-methoxy-pyrido[3,4-d]pyrimidin-2-yl]-pyridin-2-yl}-phenyl-amine;

(3R,4S)-1-[5-Methoxy-2-(2-phenylamino-pyridin-4-yl)-pyrido[3,4-d]pyrimidin-4-yl]-piperidine-3,4-diol;

(3S,4R)-1-[5-Methoxy-2-(2-phenylamino-pyridin-4-yl)-pyrido[3,4-d]pyrimidin-4-yl]-piperidine-3,4-diol;

{(R)-1-[5-Methoxy-2-(2-phenylamino-pyridin-4-yl)-pyrido[3,4-d]pyrimidin-4-yl]-pyrrolidin-3-yl}-methanol;

{(S)-1-[5-Methoxy-2-(2-phenylamino-pyridin-4-yl)-pyrido[3,4-d]pyrimidin-4-yl]-pyrrolidin-3-yl}-methanol;

(meso)-cis-1-[5-Methoxy-2-(2-phenylamino-pyridin-4-yl)-pyrido[3,4-d]pyrimidin-4-yl]-azepane-4,5-diol;

1-{2-[2-(6-Fluoro-pyridin-2-ylamino)-pyridin-4-yl]-5-methoxy-pyrido[3,4-d]pyrimidin-4-yl}-piperidin-4-ol;

1-{5-Methoxy-2-[2-(6-methoxy-pyridin-2-ylamino)-pyridin-4-yl]-pyrido[3,4-d]pyrimidin-4-yl}-piperidin-4-ol;

((S)-1-{2-[2-(6-Fluoro-pyridin-2-ylamino)-pyridin-4-yl]-5-methoxy-pyrido[3,4-d]pyrimidin-4-yl}-pyrrolidin-3-yl)-methanol;

((S)-1-{5-Methoxy-2-[2-(6-methoxy-pyridin-2-ylamino)-pyridin-4-yl]-pyrido[3,4-d]pyrimidin-4-yl}-pyrrolidin-3-yl)-methanol;

2-(4-Cyano-phenyl)-N-[4-(5-cyclopropyl-4-piperazin-1-yl-pyrido[3,4-d]pyrimidin-2-yl)-pyridin-2-yl]-acetamide;

[4-(5-Cyclopropyl-4-piperazin-1-yl-pyrido[3,4-d]pyrimidin-2-yl)-pyridin-2-yl]-(2-methyl-4-morpholin-4-yl-phenyl)-amine;

[4-(5-Cyclopropyl-4-piperazin-1-yl-pyrido[3,4-d]pyrimidin-2-yl)-pyridin-2-yl]-(6-morpholin-4-yl-pyridin-3-yl)-amine;

[4-(5-Cyclopropyl-4-piperazin-1-yl-pyrido[3,4-d]pyrimidin-2-yl)-pyridin-2-yl]-pyridin-3-yl-amine;

(2-Chloro-phenyl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(4-methyl-pyridin-3-yl)-amine;

[4-(5-Cyclopropyl-4-piperazin-1-yl-pyrido[3,4-d]pyrimidin-2-yl)-pyridin-2-yl]-phenyl-amine;

2-{4-[5-Cyclopropyl-4-(4-hydroxy-piperidin-1-yl)-pyrido[3,4-d]pyrimidin-2-yl]-pyridin-2-ylamino}-isonicotinonitrile;

[4-(5-Cyclopropyl-4-piperazin-1-yl-pyrido[3,4-d]pyrimidin-2-yl)-pyridin-2-yl]-(6-fluoro-pyridin-2-yl)-amine;

[4-(5-Cyclopropyl-4-piperazin-1-yl-pyrido[3,4-d]pyrimidin-2-yl)-pyridin-2-yl]-(2-fluoro-phenyl)-amine;

(±)-2-{4-[5-Cyclopropyl-4-cis-3,4-dihydroxy-piperidin-1-yl)-pyrido[3,4-d]pyrimidin-2-yl]-pyridin-2-ylamino}-isonicotinonitrile;

[4-(5-Cyclopropyl-4-piperazin-1-yl-pyrido[3,4-d]pyrimidin-2-yl)-pyridin-2-yl]-o-tolyl-amine;

2-{4-[5-Cyclopropyl-4-((3R,4S)-3,4-dihydroxy-piperidin-1-yl)-pyrido[3,4-d]pyrimidin-2-yl]-pyridin-2-ylamino}-isonicotinonitrile;

2-{4-[5-Cyclopropyl-4-((3S,4R)-3,4-dihydroxy-piperidin-1-yl)-pyrido[3,4-d]pyrimidin-2-yl]-pyridin-2-ylamino}-isonicotinonitrile;

4-(5-Methoxy-4-piperazin-1-yl-pyrido[3,4-d]pyrimidin-2-yl)-N-(1-phenylpyrazol-4-yl)pyridin-2-amine;

(2,3-Dimethyl-2H-indazol-6-yl)-[4-(5-methoxy-4-piperazin-1-yl-pyrido[3, 4-d]pyrimidin-2-yl)-pyridin-2-yl]-amine;

[1-(2-Fluoro-phenyl)-1H-pyrazol-4-yl]-[4-(5-methoxy-4-piperazin-1-yl-pyrido[3, 4-d]pyrimidin-2-yl)-pyridin-2-yl]-amine;

[4-(5-cyclopropyl-4-piperazin-1-yl-pyrido[3,4-d]pyrimidin-2-yl)-pyridin-2-yl]-(1-phenyl-1H-pyrazol-4-yl)-amine;

[4-(5-Cyclopropyl-4-piperazin-1-yl-pyrido[3,4-d]pyrimidin-2-yl)-pyridin-2-yl]-(2,3-dimethyl-2H-indazol-6-yl)-amine;

Phenyl-[4-(4-piperazin-1-yl-pyrido[3,4-d]pyrimidin-2-yl)-pyridin-2-yl]-amine;

[4-(5-cyclopropyl-4-piperazin-1-yl-pyrido[3,4-d]pyrimidin-2-yl)-pyridin-2-yl]-(2-fluoro-pyridin-3-yl)-amine;

[4-(5-Methoxy-4-piperazin-1-yl-pyrido[3,4-d]pyrimidin-2-yl)-pyridin-2-yl]-(5-methyl-isoxazol-3-yl)-amine;

2-[2-(3-Piperazin-1-yl-phenylamino)-pyridin-4-yl]-pyrido[3,4-d]pyrimidin-4-ol;

2-[2-(3-Piperazin-1-ylmethyl-phenylamino)-pyridin-4-yl]-pyrido[3,4-d]pyrimidin-4-ol;

2-[2-(1-Piperidin-4-ylmethyl-1H-pyrazol-4-ylamino)-pyridin-4-yl]-pyrido[3, 4-d]pyrimidin-4-ol;

{5-Methoxy-2-[2-(3-piperazin-1-yl-phenylamino)-pyridin-4-yl]-pyrido[3,4-d]pyrimidin-4-yl}-methyl-amine;

(5-Methoxy-2-{2-[4-(2-pyrrolidin-1-yl-ethoxy)-phenylamino]-pyridin-4-yl}-pyrido[3,4-d]pyrimidin-4-yl)-methyl-amine;

{5-Methoxy-2-[2-(3-piperidin-4-yl-phenylamino)-pyridin-4-yl]-pyrido[3,4-d]pyrimidin-4-yl}-methyl-amine;

[4-(5-Methoxy-pyrido[3,4-d]pyrimidin-2-yl)-pyridin-2-yl]-(3-piperazin-1-yl-phenyl)-amine;

[4-(5-Cyclopropyl-4-piperazin-1-yl-pyrido[3,4-d]pyrimidin-2-yl)-pyridin-2-yl]-(2-fluoro-5-methyl-phenyl)-amine;

[4-(5-Cyclopropyl-4-piperazin-1-yl-pyrido[3,4-d]pyrimidin-2-yl)-pyridin-2-yl]-(2,5-dimethyl-phenyl)-amine;

5-[4-(5-Cyclopropyl-4-piperazin-1-yl-pyrido[3,4-d]pyrimidin-2-yl)-pyridin-2-ylamino]-pyridine-2-carbonitrile;

4-(5-Cyclopropyl-4-piperazin-1-yl-pyrido[3,4-d]pyrimidin-2-yl)-pyridin-2-yl]-pyrazin-2-yl-amine;

Cyclopropyl-{4-[5-cyclopropyl-4-(3-trifluoromethyl-piperazin-1-yl)-pyrido[3,4-d]pyrimidin-2-yl]-pyridin-2-yl}-amine;

[4-(5-Cyclopropyl-4-piperazin-1-yl-pyrido[3,4-d]pyrimidin-2-yl)-pyridin-2-yl]-(R)-tetrahydro-furan-3-yl-amine;

[4-(5-Cyclopropyl-4-piperazin-1-yl-pyrido[3,4-d]pyrimidin-2-yl)-pyridin-2-yl]-(4,4-difluoro-cyclohexyl)-amine;

{4-[5-Cyclopropyl-4-((R)-3-fluoromethyl-piperazin-1-yl)-pyrido[3,4-d]pyrimidin-2-yl]-pyridin-2-yl}-(4-trifluoromethyl-pyridin-2-yl)-amine;

{4-[5-Cyclopropyl-4-((R)-3-fluoromethyl-piperazin-1-yl)-pyrido[3,4-d]pyrimidin-2-yl]-pyridin-2-yl}-(6-fluoro-pyridin-2-yl)-amine;

[4-(5-Cyclopropyl-4-piperazin-1-yl-pyrido[3,4-d]pyrimidin-2-yl)-pyridin-2-yl]-(2-methoxy-pyridin-3-yl)-amine;

(6-Chloro-pyridin-2-yl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(2-methoxy-phenyl)-amine;

[4-(5-Cyclopropyl-4-piperazin-1-yl-pyrido[3,4-d]pyrimidin-2-yl)-pyridin-2-yl]-(2-trifluoromethyl-phenyl)-amine;

[4-(5-Cyclopropyl-4-piperazin-1-yl-pyrido[3,4-d]pyrimidin-2-yl)-pyridin-2-yl]-(2-methoxymethyl-phenyl)-amine;

[4-(5-Cyclopropyl-4-piperazin-1-yl-pyrido[3,4-d]pyrimidin-2-yl)-pyridin-2-yl]-(S)-tetrahydro-furan-3-yl-amine;

2-[4-(5-Cyclopropyl-4-piperazin-1-yl-pyrido[3,4-d]pyrimidin-2-yl)-pyridin-2-ylamino]-benzonitrile;

tert-Butyl-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(2,5-difluoro-phenyl)-amine;

[4-(5-Cyclopropyl-4-piperazin-1-yl-pyrido[3,4-d]pyrimidin-2-yl)-pyridin-2-yl]-(2-fluoro-5-trifluoromethyl-phenyl)-amine;

[4-(5-Cyclopropyl-4-piperazin-1-yl-pyrido[3,4-d]pyrimidin-2-yl)-pyridin-2-yl]-(5-fluoro-2-methyl-phenyl)-amine;

3-[4-(5-Cyclopropyl-4-piperazin-1-yl-pyrido[3,4-d]pyrimidin-2-yl)-pyridin-2-ylamino]-4-methyl-benzonitrile;

7-[5-Cyclopropyl-2-(2-phenylamino-pyridin-4-yl)-pyrido[3,4-d]pyrimidin-4-yl]-hexahydro-oxazolo[3,4-a]pyrazin-3-one;

[4-(5-Cyclopropyl-4-piperazin-1-yl-pyrido[3,4-d]pyrimidin-2-yl)-pyridin-2-yl]-(3-fluoro-pyridin-2-yl)-amine;

(2-Chloro-6-methyl-phenyl)-[4-(5-cyclopropyl-4-piperazin-1-yl-pyrido[3,4-d]pyrimidin-2-yl)-pyridin-2-yl]-amine;

3-[4-(5-Cyclopropyl-4-piperazin-1-yl-pyrido[3,4-d]pyrimidin-2-yl)-pyridin-2-ylamino]-4-fluoro-benzonitrile;

(4-tert-Butyl-2-chloro-phenyl)-[4-(5-cyclopropyl-4-piperazin-1-yl-pyrido[3,4-d]pyrimidin-2-yl)-pyridin-2-yl]-amine;

2-{4-[5-Cyclopropyl-4-((R)-3-fluoromethyl-piperazin-1-yl)-pyrido[3,4-d]pyrimidin-2-yl]-pyridin-2-ylamino}-isonicotinonitrile;

{4-[5-Cyclopropyl-4-((R)-3-fluoromethyl-piperazin-1-yl)-pyrido[3,4-d]pyrimidin-2-yl]-pyridin-2-yl}-(2-fluoro-pyridin-3-yl)-amine;

[4-(5-Cyclopropyl-4-piperazin-1-yl-pyrido[3,4-d]pyrimidin-2-yl)-pyridin-2-yl]-(2,2,2-trifluoro-ethyl)-amine;

2-{4-[5-Cyclopropyl-4-(3-oxo-tetrahydro-oxazolo[3,4-a]pyrazin-7-yl)-pyrido[3,4-d]pyrimidin-2-yl]-pyridin-2-ylamino}-isonicotinonitrile;

[4-(5-Cyclopropyl-4-piperazin-1-yl-pyrido[3,4-d]pyrimidin-2-yl)-pyridin-2-yl]-(6-trifluoromethyl-pyridin-2-yl)-amine;

[4-(5-Cyclopropyl-4-piperazin-1-yl-pyrido[3,4-d]pyrimidin-2-yl)-pyridin-2-yl]-(5-fluoro-pyridin-3-yl)-amine;

[4-(5-Cyclopropyl-4-piperazin-1-yl-pyrido[3,4-d]pyrimidin-2-yl)-pyridin-2-yl]-(2-trifluoromethyl-pyridin-3-yl)-amine;

{4-[5-Cyclopropyl-4-(2,5-diaza-bicyclo[4.1.0]hept-2-yl)-pyrido[3,4-d]pyrimidin-2-yl]-pyridin-2-yl}-phenyl-amine;

{4-[5-Cyclopropyl-4-(2,5-diaza-bicyclo[4.1.0.]hept-2-yl)-pyrido[3,4-d]pyrimidin-2-yl]-pyridin-2-yl}-(2,6-difluoro-phenyl)-amine;

[4-(5-Cyclopropyl-4-piperazin-1-yl-pyrido[3,4-d]pyrimidin-2-yl)-pyridin-2-yl]-(2,6-dichloro-phenyl)-amine;

[4-(5-Cyclopropyl-4-piperazin-1-yl-pyrido[3,4-d]pyrimidin-2-yl)-pyridin-2-yl]-(2,3-dimethyl-phenyl)-amine;

[4-(5-Cyclopropyl-4-piperazin-1-yl-pyrido[3,4-d]pyrimidin-2-yl)-pyridin-2-yl]-(2,6-dimethyl-phenyl)-amine;

[4-(5-Cyclopropyl-4-piperazin-1-yl-pyrido[3,4-d]pyrimidin-2-yl)-pyridin-2-yl]-(2,3-dichloro-phenyl)-amine;

[4-(5-Cyclopropyl-4-piperazin-1-yl-pyrido[3,4-d]pyrimidin-2-yl)-pyridin-2-yl]-(2,3-dichloro-phenyl)-amine;

[4-(5-Cyclopropyl-4-piperazin-1-yl-pyrido[3,4-d]pyrimidin-2-yl)-pyridin-2-yl]-(2-methyl-pyridin-3-yl)-amine;
[4-(5-Cyclopropyl-4-piperazin-1-yl-pyrido[3,4-d]pyrimidin-2-yl)-pyridin-2-yl]-pyridazin-3-yl-amine;
[4-(5-Cyclopropyl-4-piperazin-1-yl-pyrido[3,4-d]pyrimidin-2-yl)-pyridin-2-yl]-(6-methyl-pyridin-3-yl)-amine;
[4-(5-Cyclopropyl-4-piperazin-1-yl-pyrido[3,4-d]pyrimidin-2-yl)-pyridin-2-yl]-(6-methoxy-pyridin-3-yl)-amine;
[4-(5-Cyclopropyl-4-piperazin-1-yl-pyrido[3,4-d]pyrimidin-2-yl)-pyridin-2-yl]-(3,6-difluoro-pyridin-2-yl)-amine;
[4-(5-Cyclopropyl-4-piperazin-1-yl-pyrido[3,4-d]pyrimidin-2-yl)-pyridin-2-yl]-[4-(dimethyl-phosphinoyl)-phenyl]-amine;
[4-(5-Cyclopropyl-4-piperazin-1-yl-pyrido[3,4-d]pyrimidin-2-yl)-pyridin-2-yl]-[4-(diethyl-phosphinoyl)-phenyl]-amine;
$N^5$-[4-(5-Cyclopropyl-4-piperazin-1-yl-pyrido[3,4-d]pyrimidin-2-yl)-pyridin-2-yl]-$N^2$,$N^2$-dimethyl-pyridine-2,5-diamine;
{4-[5-Cyclopropyl-4-((R)-3-fluoromethyl-piperazin-1-yl)-pyrido[3,4-d]pyrimidin-2-yl]-pyridin-2-yl}-phenyl-amine;
[4-(5-Cyclopropyl-4-piperazin-1-yl-pyrido[3,4-d]pyrimidin-2-yl)-pyridin-2-yl]-(5-methoxy-2-methyl-phenyl)-amine;
[4-(5-Cyclopropyl-4-piperazin-1-yl-pyrido[3,4-d]pyrimidin-2-yl)-pyridin-2-yl]-(2-methyl-5-trifluoromethyl-phenyl)-amine;
[4-(5-Cyclopropyl-4-piperazin-1-yl-pyrido[3,4-d]pyrimidin-2-yl)-pyridin-2-yl]-(2-fluoro-5-trifluoromethoxy-phenyl)-amine;
[4-(5-Cyclopropyl-4-piperazin-1-yl-pyrido[3,4-d]pyrimidin-2-yl)-pyridin-2-yl]-(2-fluoro-5-methanesulfonyl-phenyl)-amine;
[4-(5-Cyclopropyl-4-piperazin-1-yl-pyrido[3,4-d]pyrimidin-2-yl)-pyridin-2-yl]-(2,6-difluoro-3-methyl-phenyl)-amine;
[4-(5-Cyclopropyl-4-piperazin-1-yl-pyrido[3,4-d]pyrimidin-2-yl)-pyridin-2-yl]-(5-isopropyl-2-methyl-phenyl)-amine;
[4-(5-Cyclopropyl-4-piperazin-1-yl-pyrido[3,4-d]pyrimidin-2-yl)-pyridin-2-yl]-pent-deuterio-phenyl-amine;
1-{2-[4-(5-Cyclopropyl-4-piperazin-1-yl-pyrido[3,4-d]pyrimidin-2-yl)-pyridin-2-ylamino]-phenyl}-ethanol;
(1R,2S)-2-Amino-cyclopentanecarboxylic acid [4-(5-cyclopropyl-4-piperazin-1-yl-pyrido[3,4-d]pyrimidin-2-yl)-pyridin-2-yl]-amide;
1-{4-[2-(2-Chloro-pyridin-4-yl)-5-cyclopropyl-pyrido[3,4-d]pyrimidin-4-yl]-piperazin-2-yl}-cyclopropanol;
[4-(5-Cyclopropyl-4-piperazin-1-yl-yl-pyridin-2-yl]-pyrazolo[1,5-a]pyridin-6-yl-amine;
[4-(5-Cyclopropyl-4-piperazin-1-yl-yl-pyridin-2-yl]-pyrazolo[1,5-a]pyridin-5-yl-amine;
[4-(5-Cyclopropyl-4-piperazin-1-yl-pyrido[3,4-d]pyrimidin-2-yl)-pyridin-2-yl]-(5-trifluoromethyl-pyridazin-3-yl)-amine;
[4-(5-Cyclopropyl-4-piperazin-1-yl-pyrido[3,4-d]pyrimidin-2-yl)-pyridin-2-yl]-(2,6-difluoro-3-methoxy-phenyl)-amine;
[4-(5-Cyclopropyl-4-piperazin-1-yl-pyrido[3,4-d]pyrimidin-2-yl)-pyridin-2-yl]-(3-ethoxy-2,6-difluoro-phenyl)-amine;
(2-Chloro-3-methyl-phenyl)-[4-(5-cyclopropyl-4-piperazin-1-yl-pyrido[3,4-d]pyrimidin-2-yl)-pyridin-2-yl]-amine;
{4-[5-Cyclopropyl-4-((S)-3-methyl-piperazin-1-yl)-pyrido[3,4-d]pyrimidin-2-yl]-pyridin-2-yl}-phenyl-amine;
(2-Chloro-4-fluoro-phenyl)-[4-(5-cyclopropyl-4-piperazin-1-yl-pyrido[3,4-d]pyrimidin-2-yl)-pyridin-2-yl]-amine;
[4-(5-Cyclopropyl-4-piperazin-1-yl-pyrido[3,4-d]pyrimidin-2-yl)-pyridin-2-yl]-(3-methoxy-phenyl)-amine;
(2-Chloro-4-methyl-phenyl)-[4-(5-cyclopropyl-4-piperazin-1-yl-pyrido[3,4-d]pyrimidin-2-yl)-pyridin-2-yl]-amine;
[4-(5-Cyclopropyl-4-piperazin-1-yl-pyrido[3,4-d]pyrimidin-2-yl)-pyridin-2-yl]-(2,4-dimethyl-phenyl)-amine;
[4-(5-Cyclopropyl-4-piperazin-1-yl-pyrido[3,4-d]pyrimidin-2-yl)-pyridin-2-yl]-(2-fluoro-3-methyl-phenyl)-amine;
[4-(5-Cyclopropyl-4-piperazin-1-yl-pyrido[3,4-d]pyrimidin-2-yl)-pyridin-2-yl]-(2-fluoro-4-methyl-phenyl)-amine;
(2-Chloro-5-fluoro-phenyl)-[4-(5-cyclopropyl-4-piperazin-1-yl-pyrido[3,4-d]pyrimidin-2-yl)-pyridin-2-yl]-amine;
(2-Chloro-5-methyl-phenyl)-[4-(5-cyclopropyl-4-piperazin-1-yl-pyrido[3,4-d]pyrimidin-2-yl)-pyridin-2-yl]-amine;
(2-Chloro-3-fluoro-phenyl)-[4-(5-cyclopropyl-4-piperazin-1-yl-pyrido[3,4-d]pyrimidin-2-yl)-pyridin-2-yl]-amine;
5-Cyclopropyl-2-(6,7-dimethoxy-quinolin-4-yl)-4-piperazin-1-yl-pyrido[3,4-d]pyrimidine;
[4-(5-Cyclopropyl-4-piperazin-1-yl-pyrido[3,4-d]pyrimidin-2-yl)-pyridin-2-yl]-(2-fluoro-5-methoxy-phenyl)-amine;
N-[4-(5-Cyclopropyl-4-piperazin-1-yl-pyrido[3,4-d]pyrimidin-2-yl)-pyridin-2-yl]-acetamide;
4-(5-Cyclopropyl-4-piperazin-1-yl-pyrido[3,4-d]pyrimidin-2-yl)-pyridin-2-ylamine;
N-[4-(5-Cyclopropyl-4-piperazin-1-yl-pyrido[3,4-d]pyrimidin-2-yl)-pyridin-2-yl]-isobutyramide;
Cyclopropanecarboxylic acid [4-(5-cyclopropyl-4-piperazin-1-yl-pyrido[3,4-d]pyrimidin-2-yl)-pyridin-2-yl]-amide;
[4-(5-Cyclopropyl-4-piperazin-1-yl-pyrido[3,4-d]pyrimidin-2-yl)-pyridin-2-yl]-(3,3-difluoro-cyclobutyl)-amine;
[4-(5-Cyclopropyl-4-piperazin-1-yl-pyrido[3,4-d]pyrimidin-2-yl)-pyridin-2-yl]-((R)-1-phenyl-ethyl)-amine;
[4-(5-Cyclopropyl-4-piperazin-1-yl-pyrido[3,4-d]pyrimidin-2-yl)-pyridin-2-yl]-((S)-1-phenyl-ethyl)-amine;
[4-(5-Cyclopropyl-4-piperazin-1-yl-pyrido[3,4-d]pyrimidin-2-yl)-pyridin-2-yl]-(6-methoxy-pyridin-2-yl)-amine;
[4-(5-Cyclopropyl-4-piperazin-1-yl-pyrido[3,4-d]pyrimidin-2-yl)-pyridin-2-yl]-(2-fluoro-3-methoxy-phenyl)-amine;
[4-(5-Cyclopropyl-4-piperazin-1-yl-pyrido[3,4-d]pyrimidin-2-yl)-pyridin-2-yl]-(2,6-difluoro-4-methoxy-phenyl)-amine;
[4-(5-Cyclopropyl-4-piperazin-1-yl-pyrido[3,4-d]pyrimidin-2-yl)-pyridin-2-yl]-(3-methoxy-2-methyl-phenyl)-amine;
(2-Chloro-5-methoxy-phenyl)-[4-(5-cyclopropyl-4-piperazin-1-yl-pyrido[3,4-d]pyrimidin-2-yl)-pyridin-2-yl]-amine;
[4-(5-Cyclopropyl-4-piperazin-1-yl-pyrido[3,4-d]pyrimidin-2-yl)-pyridin-2-yl]-(4-fluoro-phenyl)-amine;
[4-(5-Cyclopropyl-4-piperazin-1-yl-pyrido[3,4-d]pyrimidin-2-yl)-pyridin-2-yl]-(4-trifluoromethyl-phenyl)-amine;
[4-(5-Cyclopropyl-4-piperazin-1-yl-pyrido[3,4-d]pyrimidin-2-yl)-pyridin-2-yl]-(4-trifluoromethyl-phenyl)-amine;
(2-Chloro-5-trifluoromethyl-phenyl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(2,2,2-trifluoro-1,1-dimethyl-ethyl)-amine;

[4-(5-Cyclopropyl-4-piperazin-1-yl-pyrido[3,4-d]pyrimidin-2-yl)-pyridin-2-yl]-(3,4-difluoro-phenyl)-amine;

[4-(5-Cyclopropyl-4-piperazin-1-yl-pyrido[3,4-d]pyrimidin-2-yl)-pyridin-2-yl]-(1-methyl-1H-pyrazol-3-yl)-amine;

[4-(5-Cyclopropyl-4-piperazin-1-yl-pyrido[3,4-d]pyrimidin-2-yl)-pyridin-2-yl]-(4-fluoro-cyclohexyl)-amine;

(+/−)-(cis)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol;

(4-Cyclopropyl-2,6-difluoro-phenyl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(2,6-difluoro-4-methyl-phenyl)-amine;

[4-(5-Cyclopropyl-4-piperazin-1-yl-pyrido[3,4-d]pyrimidin-2-yl)-pyridin-2-yl]-(1-methyl-1H-imidazol-4-yl)-amine;

2-{4-[5-Cyclopropyl-2-(2-phenylamino-pyridin-4-yl)-pyrido[3,4-d]pyrimidin-4-yl]-piperazin-1-yl}-ethanol;

(S)-3-{4-[5-Cyclopropyl-2-(2-phenylamino-pyridin-4-yl)-pyrido[3,4-d]pyrimidin-4-yl]-piperazin-1-yl}-propane-1,2-diol;

(R)-3-{4-[5-Cyclopropyl-2-(2-phenylamino-pyridin-4-yl)-pyrido[3,4-d]pyrimidin-4-yl]-piperazin-1-yl}-propane-1,2-diol;

[4-(5-Cyclopropyl-4-piperazin-1-yl-pyridin-d]pyrimidin-2-yl)-pyridin-2-yl]-(3-methoxy-4-methyl-phenyl)-amine;

[4-(5-Cyclopropyl-4-piperazin-1-yl-pyrido[3,4-d]pyrimidin-2-yl)-pyridin-2-yl]-(3,4-dimethoxy-phenyl)-amine;

[4-(5-Cyclopropyl-4-piperazin-1-yl-pyrido[3,4-d]pyrimidin-2-yl)-pyridin-2-yl]-(3,4,5-trimethoxy-phenyl)-amine;

N-[4-(5-Cyclopropyl-4-piperazin-1-yl-pyrido[3,4-d]pyrimidin-2-yl)-pyridin-2-yl]-2-phenyl-acetamide;

N-[4-(5-Cyclopropyl-4-piperazin-1-yl-pyrido[3,4-d]pyrimidin-2-yl)-pyridin-2-yl]-3,3,3-trifluoro-propionamide;

[4-(5-Cyclopropyl-4-piperazin-1-yl-pyrido[3,4-d]pyrimidin-2-yl)-pyridin-2-yl]-[4-(1-methyl-4-oxo-4$\lambda^5$-[1,4]azaphosphinan-4-yl)-phenyl]-amine;

2-(2-Chloro-pyridin-4-yl)-5-cyclopropyl-4-[3-(2,2,2-trifluoro-ethyl)-piperazin-1-yl]-pyrido[3,4-d]pyrimidine;

(2-Chloro-6-fluoro-phenyl)-[4-(5-cyclopropyl-4-piperazin-1-yl-pyrido[3,4-d]pyrimidin-2-yl)-pyridin-2-yl]-amine;

(6-Chloro-2-fluoro-3-methyl-phenyl)-[4-(5-cyclopropyl-4-piperazin-1-yl-pyrido[3,4-d]pyrimidin-2-yl)-pyridin-2-yl]-amine;

(3-Chloro-2,6-difluoro-phenyl)-[4-(5-cyclopropyl-4-piperazin-1-yl-pyrido[3,4-d]pyrimidin-2-yl)-pyridin-2-yl]-amine;

[4-(5-Cyclobutyl-4-piperazin-1-yl-pyrido[3,4-d]pyrimidin-2-yl)-pyridin-2-yl]-phenyl-amine;

[4-(5-Cyclobutyl-4-piperazin-1-yl-pyrido[3,4-d]pyrimidin-2-yl)-pyridin-2-yl]-(2,6-difluoro-phenyl)-amine;

[4-(5-Cyclopropyl-4-piperazin-1-yl-pyrido[3,4-d]pyrimidin-2-yl)-pyridin-2-yl]-(3,3-difluoro-cyclopentyl)-amine;

[4-(5-Cyclopropyl-4-piperazin-1-yl-pyrido[3,4-d]pyrimidin-2-yl)-pyridin-2-yl]-(3-isopropyl-phenyl)-amine;

[4-(5-Cyclopropyl-4-piperazin-1-yl-pyrido[3,4-d]pyrimidin-2-yl)-pyridin-2-yl]-(3-ethyl-phenyl)-amine;

2-(2-Chloro-pyridin-4-yl)-5-cyclopropyl-4-(3-trifluoromethyl-piperazin-1-yl)-pyrido[3,4-d]pyrimidine;

[4-(5-Cyclopropyl-4-piperazin-1-yl-pyrido[3,4-d]pyrimidin-2-yl)-pyridin-2-yl]-[4-(1-ethyl-4-oxo-4$\lambda^5$-[1,4]azaphosphinan-4-yl)-2-methoxy-phenyl]-amine;

N-(4-{5-Cyclopropyl-4-[3-(2,2,2-trifluoro-ethyl)-piperazin-1-yl]-pyrido[3,4-d]pyrimidin-2-yl}-pyridin-2-yl)-acetamide;

[4-(5-Cyclopropyl-4-piperazin-1-yl-pyrido[3,4-d]pyrimidin-2-yl)-pyridin-2-yl]-(4-fluoro-3-methoxy-phenyl)-amine;

[4-(5-Cyclopropyl-4-piperazin-1-yl-pyrido[3,4-d]pyrimidin-2-yl)-pyridin-2-yl]-(2,4-difluoro-5-methoxy-phenyl)-amine;

Cyclopropylmethyl-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-methyl-amine;

4-[4-(5-Cyclopropyl-4-piperazin-1-yl-pyrido[3,4-d]pyrimidin-2-yl)-pyridin-2-ylamino]-2-fluoro-benzonitrile;

[4-(5-Cyclopropyl-4-[1,4]diazepan-1-yl-pyrido[3,4-d]pyrimidin-2-yl)-pyridin-2-yl]-phenyl-amine;

4-[4-(5-Cyclopropyl-4-piperazin-1-yl-pyrido[3,4-d]pyrimidin-2-yl)-pyridin-2-ylamino]-cyclohexanol;

(2-Chloro-6-fluoro-3-methoxy-phenyl)-[4-(5-cyclopropyl-4-piperazin-1-yl-pyrido[3,4-d]pyrimidin-2-yl)-pyridin-2-yl]-amine;

(2-Chloro-3,6-difluoro-phenyl)-[4-(5-cyclopropyl-4-piperazin-1-yl-pyrido[3,4-d]pyrimidin-2-yl)-pyridin-2-yl]-amine;

{4-[5-Cyclopropyl-4-(2,2,3,3,5,5,6,6-octadeuterio-piperazin-1-yl)-pyrido[3,4-d]pyrimidin-2-yl]-pyridin-2-yl}-phenyl-amine;

(4-Cyclopropyl-3-methoxy-phenyl)-[4-(5-cyclopropyl-4-piperazin-1-yl-pyrido[3,4-d]pyrimidin-2-yl)-pyridin-2-yl]-amine;

4-[5-Cyclopropyl-2-(2-phenylamino-pyridin-4-yl)-pyrido[3,4-d]pyrimidin-4-yl]-piperazine-1-carboxylic acid-amide;

N-[4-(5-Cyclopropyl-4-piperazin-1-yl-pyrido[3,4-d]pyrimidin-2-yl)-pyridin-2-yl]-2-(2,6-difluoro-phenyl)-acetamide;

[4-(5-Cyclopropyl-4-piperazin-1-yl-pyrido[3,4-d]pyrimidin-2-yl)-pyridin-2-yl]-(2-fluoro-5-propyl-phenyl)-amine;

(4-Cyclopropyl-2-fluoro-phenyl)-[4-(5-cyclopropyl-4-piperazin-1-yl-pyrido[3,4-d]pyrimidin-2-yl)-pyridin-2-yl]-amine;

(4-{5-Cyclopropyl-4-[3-(2,2,2-trifluoro-ethyl)-piperazin-1-yl]-pyrido[3,4-d]pyrimidin-2-yl}-pyridin-2-yl)-(2,6-difluoro-phenyl)-amine;

(4-{5-Cyclopropyl-4-[3-(2,2,2-trifluoro-ethyl)-piperazin-1-yl]-pyrido[3,4-d]pyrimidin-2-yl}-pyridin-2-yl)-phenyl-amine;

[4-(5-Cyclopropyl-4-piperazin-1-yl-pyrido[3,4-d]pyrimidin-2-yl)-pyridin-2-yl]-[(R)-1-(3-fluoro-phenyl)-ethyl]-amine;

4-[4-(5-Cyclopropyl-4-piperazin-1-yl-pyrido[3,4-d]pyrimidin-2-yl)-pyridin-2-ylamino]-benzonitrile;

[4-(5-Cyclopropyl-4-piperazin-1-yl-pyrido[3,4-d]pyrimidin-2-yl)-pyridin-2-yl]-(3-trifluoromethyl-phenyl)-amine;

(3-Chloro-2,6-difluoro-phenyl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(2,4,6-trifluoro-phenyl)-amine;

[4-(5-Cyclopropyl-4-piperazin-1-yl-pyrido[3,4-d]pyrimidin-2-yl)-pyridin-2-yl]-(2,4-difluoro-phenyl)-amine;

4-(5-Cyclopropyl-4-piperazin-1-yl-pyrido[3,4-d]pyrimidin-2-yl)-pyridin-2-yl]-[(R)-1-(4-fluoro-phenyl)-ethyl]-amine;

[4-(5-Cyclopropyl-4-piperazin-1-yl-pyrido[3,4-d]pyrimidin-2-yl)-pyridin-2-yl]-[(R)-1-(2,6-difluoro-phenyl)-ethyl]-amine;

[4-(5-Cyclopropyl-4-piperazin-1-yl-pyrido[3,4-d]pyrimidin-2-yl)-5-fluoro-pyridin-2-yl]-phenyl-amine;

1-{5-Cyclopropyl-2-[2-(2,6-difluoro-phenylamino)-pyridin-4-yl]-pyrido[3,4-d]pyrimidin-4-yl}-piperidine-4-carboxylic acid isopropylamide;

1-{5-Cyclopropyl-2-[2-(2,6-difluoro-phenylamino)-pyridin-4-yl]-pyrido[3,4-d]pyrimidin-4-yl}-piperidine-4-carboxylic acid amide;

N-(1-{5-Cyclopropyl-2-[2-(2,6-difluoro-phenylamino)-pyridin-4-yl]-pyrido[3,4-d]pyrimidin-4-yl}-piperidin-4-yl)-acetamide;

1-{5-Cyclopropyl-2-[2-(2,6-difluoro-phenylamino)-pyridin-4-yl]-pyrido[3,4-d]pyrimidin-4-yl}-piperidine-4-carboxylic acid (2-fluoro-ethyl)-amide;

N-{4-[5-Cyclopropyl-4-((S)-3-trifluoromethyl-piperazin-1-yl)-pyrido[3,4-d]pyrimidin-2-yl]-pyridin-2-yl}-acetamide;

2-(2-Chloro-pyridin-4-yl)-5-cyclopropyl-4-((R)-3-trifluoromethyl-piperazin-1-yl)-pyrido[3,4-d]pyrimidine;

(4-{5-Cyclopropyl-4-[4-(2-methoxy-ethyl)-piperazin-1-yl]-pyrido[3,4-d]pyrimidin-2-yl}-pyridin-2-yl)-phenyl-amine;

(4-{5-Cyclopropyl-4-[4-(2-methoxy-ethyl)-piperazin-1-yl]-pyrido[3,4-d]pyrimidin-2-yl}-pyridin-2-yl)-(4-fluoro-phenyl)-amine;

(4-{(5-Cyclopropyl-4-[4-(2-methanesulfonyl-ethyl)-piperazin-1-yl]-pyrido[3,4-d]pyrimidin-2-yl}-pyridin-2-yl)-phenyl-amine;

(4-{(5-Cyclopropyl-4-[4-(2-methanesulfonyl-ethyl)-piperazin-1-yl]-pyrido[3,4-d]pyrimidin-2-yl}-pyridin-2-yl)-(4-fluoro-phenyl)-amine;

Cyclopropanecarboxylic acid (4-{5-cyclopropyl-4-[4-(2-methanesulfonyl-ethyl)-piperazin-1-yl]-pyrido[3,4-d]pyrimidin-2-yl}-pyridin-2-yl)-amide;

Cyclopropanecarboxylic acid (4-{5-cyclopropyl-4-[4-(2-methoxy-ethyl)-piperazin-1-yl]-pyrido[3,4-d]pyrimidin-2-yl}-pyridin-2-yl)-amide;

(5-Cyclopropyl-2-fluoro-phenyl)-[4-(5-cyclopropyl-4-piperazin-1-yl-pyrido[3,4-d]pyrimidin-2-yl)-pyridin-2-yl]-amine;

1-{5-Cyclopropyl-2-[2-(2,6-difluoro-phenylamino)-pyridin-4-yl]-pyrido[3,4-d]pyrimidin-4-yl}-piperidine-4-carboxylic acid (2-pyrrolidin-1-yl-ethyl)-amide;

1-{5-Cyclopropyl-2-[2-(2,6-difluoro-phenylamino)-pyridin-4-yl]-pyrido[3,4-d]pyrimidin-4-yl}-piperidine-4-carboxylic acid methylamide;

[4-(5-Cyclopropyl-4-piperazin-1-yl-pyrido[3,4-d]pyrimidin-2-yl)-pyridin-2-yl]-(2,4-difluoro-pyridin-3-yl)-amine;

[4-(5-Cyclopropyl-4-piperazin-1-yl-pyrido[3,4-d]pyrimidin-2-yl)-pyridin-2-yl]-(2,6-difluoro-pyridin-3-yl)-amine;

[4-(5-Cyclopropyl-4-piperazin-1-yl-pyrido[3,4-d]pyrimidin-2-yl)-pyridin-2-yl]-(6-fluoro-pyridin-3-yl)-amine;

[4-(5-Cyclopropyl-4-piperazin-1-yl-pyrido[3,4-d]pyrimidin-2-yl)-pyridin-2-yl]-(3,3-difluoro-cyclohexyl)-amine;

1-[2-(2-Cyclohexylamino-pyridin-4-yl)-5-cyclopropyl-pyrido[3,4-d]pyrimidin-4-yl]-piperidine-4-carboxylicacid isopropylamide;

(+/−)-(cis)-1-[5-Cyclopropyl-2-(2-phenylamino-pyridin-4-yl)-pyrido[3,4-d]pyrimidin-4-yl]-piperidine-3,4-diol;

(+/−)-(trans)-1-[5-Cyclopropyl-2-(2-phenylamino-pyridin-4-yl)-pyrido[3,4-d]pyrimidin-4-yl]-piperidine-3,4-diol;

(+/−)-2-{4-[5-Cyclopropyl-4-((trans)-3,4-dihydroxy-piperidin-1-yl)-pyrido[3,4-d]pyrimidin-2-yl]-pyridin-2-ylamino}-isonicotinonitrile;

(+/−)-(trans)-1-(5-Cyclopropyl-2-{2-[3-(4-methyl-piperazin-1-yl)-phenylamino]-pyridin-4-yl}-pyrido[3,4d]pyrimidin-4-yl)-piperidine-3,4-diol;

1-[2-(2-Cyclopentylamino-pyridin-4-yl)-5-cyclopropyl-pyrido[3,4-d]pyrimidin-4-yl]-piperidine-4-carboxylicacid isopropylamide;

4-(5-Cyclopropyl-4-piperazin-1-yl-pyrido[3,4-d]pyrimidin-2-yl)-pyridin-2-yl]-(3,5,6-trifluoro-pyridin-2-yl)-amine;

[4-(5-Cyclopropyl-4-piperazin-1-yl-pyrido[3,4-d]pyrimidin-2-yl)-pyridin-2-yl]-[3-(4-methyl-piperazin-1-yl)-phenyl]-amine;

[4-(5-Cyclopropyl-4-piperazin-1-yl-pyrido[3,4-d]pyrimidin-2-yl)-pyridin-2-yl]-(2,3,6-trifluoro-pyridin-4-yl)-amine;

Biphenyl-4-yl-[4-(5-cyclopropyl-4-piperazin-1-yl-pyrido[3,4-d]pyrimidin-2-yl)-pyridin-2-yl]-amine;

4-[4-(5-Cyclopropyl-4-piperazin-1-yl-pyrido[3,4-d]pyrimidin-2-yl)-pyridin-2-ylamino]-benzoic acid;

1-{5-Cyclopropyl-2-[2-(2,6-difluoro-phenylamino)-pyridin-4-yl]-pyrido[3,4-d]pyrimidin-4-yl}-piperidine-4-carboxylic acid (2-hydroxy-ethyl)-amide;

1-{5-Cyclopropyl-2-[2-(2,6-difluoro-phenylamino)-pyridin-4-yl]-pyrido[3,4-d]pyrimidin-4-yl}-piperidine-4-carboxylic acid dimethylamide;

4-(5-Cyclopropyl-2-{2-[3-(4-methyl-piperazin-1-yl)-phenylamino]-pyridin-4-yl}-pyrido[3,4-d]pyrimidin-4-yl)-piperazine-1-carboxylic acid amide;

1-(5-Cyclopropyl-2-{2-[3-(4-methyl-piperazin-1-yl)-phenylamino]-pyridin-4-yl}-pyrido[3,4-d]pyrimidin-4-yl)-piperidin-4-ol;

5-Cyclopropyl-2-(2-fluoro-pyridin-4-yl)-4-piperazin-1-yl-pyrido[3,4-d]pyrimidine;

{4-[4-(4-Amino-piperidin-1-yl)-5-cyclopropyl-pyrido[3,4-d]pyrimidin-2-yl]-pyridin-2-yl}-(2,6-difluoro-phenyl)-amine;

{4-[5-Cyclopropyl-4-((S)-3-methyl-piperazin-1-yl)-pyrido[3,4-d]pyrimidin-2-yl]-pyridin-2-yl}-(2-fluoro-phenyl)-amine;

{4-[5-Cyclopropyl-4-((S)-3-methyl-piperazin-1-yl)-pyrido[3,4-d]pyrimidin-2-yl]-pyridin-2-yl}-(2,6-difluoro-phenyl)-amine;

{4-[5-Cyclopropyl-4-((S)-3-methyl-piperazin-1-yl)-pyrido[3,4-d]pyrimidin-2-yl]-pyridin-2-yl}-(4-fluoro-phenyl)-amine;

{4-[5-Cyclopropyl-4-((S)-3-methyl-piperazin-1-yl)-pyrido[3,4-d]pyrimidin-2-yl]-pyridin-2-yl}-(3,6-difluoro-pyridin-2-yl)-amine;

(+/−)-(1RS,2RS,4SR)-Bicyclo[2.2.1]hept-2-yl-[4-(5-cyclopropyl-4-piperazin-1-yl-pyrido[3,4-d]pyrimidin-2-yl)-pyridin-2-yl]-amine;

{4-[4-(4-Aminomethyl-piperidin-1-yl)-5-cyclopropyl-pyrido[3,4-d]pyrimidin-2-yl]-pyridin-2-yl}-(2,6-difluoro-phenyl)-amine;

[5-Cyclopropyl-2-(2-phenylamino-pyridin-4-yl)-pyrido[3,4-d]pyrimidin-4-yl]-(S)-1-pyrrolidin-2-ylmethyl-amine;

{5-Cyclopropyl-2-[2-(2,6-difluoro-phenylamino)-pyridin-4-yl]-pyrido[3,4-d]pyrimidin-4-yl}-(S)-1-pyrrolidin-2-yl-methyl-amine;

[4-(5-Cyclopropyl-4-[1,4]diazepan-1-yl-pyrido[3,4-d]pyrimidin-2-yl)-pyridin-2-yl]-(4-fluoro-phenyl)-amine;

Bicyclo[1.1.1]pent-1-yl-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-3-fluoro-pyridin-2-yl]-phenyl-amine;

[4-(5-Cyclopropyl-4-[1,4]diazepan-1-yl-pyrido[3,4-d]pyrimidin-2-yl)-pyridin-2-yl]-(2,6-difluoro-phenyl)-amine;

(+/−)-cis-[4-(5-Cyclopropyl-4-piperazin-1-yl-pyrido[3,4-d]pyrimidin-2-yl)-pyridin-2-yl]-(3-fluoro-cyclobutyl)-amine;

[4-(5-Cyclopropyl-4-piperazin-1-yl-pyrido[3,4-d]pyrimidin-2-yl)-pyridin-2-yl]-(3,5-difluoro-pyridin-2-yl)-amine;

[4-(5-Cyclopropyl-4-piperazin-1-yl-pyrido[3,4-d]pyrimidin-2-yl)-pyridin-2-yl]-(3,5-difluoro-pyridin-4-yl)-amine;

[4-(5-Cyclopropyl-4-piperazin-1-yl-pyrido[3,4-d]pyrimidin-2-yl)-pyridin-2-yl]-(2,2,2-trifluoro-1-phenyl-ethyl)-amine;

1-{5-Cyclopropyl-2-[2-(2,6-difluoro-phenylamino)-pyridin-4-yl]-pyrido[3,4-d]pyrimidin-4-yl}-piperidine-3-carboxylic acid methylamide;

{4-[4-(3-Amino-pyrrolidin-1-yl)-5-cyclopropyl-pyrido[3,4-d]pyrimidin-2-yl]-pyridin-2-yl}-(2,6-difluoro-phenyl)-amine;

{4-[4-(5-Cyclopropyl-4-piperazin-1-yl-pyrido[3,4-d]pyrimidin-2-yl)-pyridin-2-ylamino]-phenyl}-acetic acid;

[4-(5-Cyclopropyl-4-piperidin-1-yl-pyrido[3,4d]pyrimidin-2-yl)-pyridin-2-yl]-[3-(4-methyl-piperazin-1-yl)-phenyl]-amine;

3-{4-[5-Cyclopropyl-4-((3R,4S)-3,4-dihydroxy-piperidin-1-yl)-pyrido[3,4-d]pyrimidin-2-yl]-pyridin-2-ylamino}-benzonitrile;

Chroman-4-yl-[4-(5-cyclopropyl-4-piperazin-1-yl-pyrido[3,4-d]pyrimidin-2-yl)-pyridin-2-yl]-amine;

N-(1-{5-Cyclopropyl-2-[2-(2,6-difluoro-phenylamino)-pyridin-4-yl]-pyrido[3,4-d]pyrimidin-4-yl}-pyrrolidin-3-yl)-acetamide;

[4-(5-Cyclopropyl-4-piperazin-1-yl-pyrido[3,4-d]pyrimidin-2-yl)-pyridin-2-yl]-(2-fluoro-4-isopropyl-phenyl)-amine;

[4-(5-Cyclopropyl-4-piperazin-1-yl-pyrido[3,4-d]pyrimidin-2-yl)-pyridin-2-yl]-(5-ethyl-2-fluoro-phenyl)-amine;

[4-(5-Cyclopropyl-4-piperazin-1-yl-pyrido[3,4-d]pyrimidin-2-yl)-pyridin-2-yl]-(2-fluoro-5-isopropyl-phenyl)-amine;

[4-(5-Cyclopropyl-4-piperazin-1-yl-pyrido[3,4-d]pyrimidin-2-yl)-pyridin-2-yl]-(4-ethyl-2-fluoro-phenyl)-amine;

{4-[5-Cyclopropyl-4-(3,3-dimethyl-piperazin-1-yl)-pyrido[3,4-d]pyrimidin-2-yl]-pyridin-2-yl}-(2,6-difluoro-phenyl)-amine;

{4-[5-Cyclopropyl-4-(3,3-dimethyl-piperazin-1-yl)-pyrido[3,4-d]pyrimidin-2-yl]-pyridin-2-yl}-(4-fluoro-phenyl)-amine;

(R)-1-(5-Cyclopropyl-2-{2-[3-(4-methyl-piperazin-1-yl)-phenylamino]-pyridin-4-yl}-pyrido[3,4-d]pyrimidin-4-yl)-piperidin-3-ol;

[(R)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-yl]-methanol;

[(S)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-yl]-methanol;

1-{5-Cyclopropyl-2-[2-(2,6-difluoro-phenylamino)-pyridin-4-yl]-pyrido[3,4-d]pyrimidin-4-yl}-piperidine-4-carboxylic acid ethylamide;

(6-Cyclopropyl-2,4-difluoro-pyridin-3-yl)-[4-(5-cyclopropyl-4-piperazin-1-yl-pyrido[3,4-d]pyrimidin-2-yl)-pyridin-2-yl]-amine;

(6-Cyclopropyl-2-fluoro-pyridin-3-yl)-[4-(5-cyclopropyl-4-piperazin-1-yl-pyrido[3,4-d]pyrimidin-2-yl)-pyridin-2-yl]-amine;

1-{5-Cyclopropyl-2-[2-(2,6-difluoro-phenylamino)-pyridin-4-yl]-pyrido[3,4-d]pyrimidin-4-yl}-pyrrolidine-3-carboxylic acid methylamide;

(S)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-ol;

1-(3-{4-[5-Cyclopropyl-4-(4-methyl-piperazin-1-yl)-pyrido[3,4-d]pyrimidin-2-yl]-pyridin-2-ylamino}-phenyl)-piperidin-4-ol;

1-{5-Cyclopropyl-2-[2-(3-piperazin-1-yl-phenylamino)-pyridin-4-yl]-pyrido[3,4-d]pyrimidin-4-yl}-piperidin-4-ol;

[4-(5-Cyclopropyl-4-piperazin-1-yl-pyrido[3,4-d]pyrimidin-2-yl)-pyridin-2-yl]-[1-(1-methyl-1H-pyrazol-4-yl)-ethyl]-amine;

[4-(5-Cyclopropyl-4-piperazin-1-yl-pyrido[3,4-d]pyrimidin-2-yl)-pyridin-2-yl]-(2-fluoro-6-morpholin-4-yl-pyridin-3-yl)-amine;

1-{5-Cyclopropyl-2-[2-(1-piperidin-4-ylmethyl-1H-pyrazol-4-ylamino)-pyridin-4-yl]-pyrido[3,4-d]pyrimidin-4-yl}-piperidin-4-ol;

4-((R)-3-Benzyloxymethyl-piperazin-1-yl)-2-(2-chloro-pyridin-4-yl)-5-cyclopropyl-pyrido[3,4-d]pyrimidine;

(3-Cyclopropyl-phenyl)-[4-(5-cyclopropyl-4-piperazin-1-yl-pyrido[3,4-d]pyrimidin-2-yl)-pyridin-2-yl]-amine;

(1-{5-Cyclopropyl-2-[2-(2,6-difluoro-phenylamino)-pyridin-4-yl]-pyrido[3,4-d]pyrimidin-4-yl}-piperidin-4-yl)-(4-methyl-piperazin-1-yl)-methanone;

1-{5-Cyclopropyl-2-[2-(2,6-difluoro-phenylamino)-pyridin-4-yl]-pyrido[3,4-d]pyrimidin-4-yl}-piperidine-4-carboxylic acid (2-dimethylamino-ethyl)-amide;

(S)-1-(5-Cyclopropyl-2-{2-[3-(4-methyl-piperazin-1-yl)-phenylamino]-pyridin-4-yl}-pyrido[3,4-d]pyrimidin-4-yl)-piperidin-3-ol;

(R)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidin-3-ol;

1-{5-Cyclopropyl-2-[2-(2,6-difluoro-phenylamino)-pyridin-4-yl]-pyrido[3,4-d]pyrimidin-4-yl}-piperidine-4-carboxylic acid (2-methoxy-ethyl)-amide;

4-[4-(5-Cyclopropyl-4-piperazin-1-yl-pyrido[3,4-d]pyrimidin-2-yl)-pyridin-2-ylamino]-3,5-difluoro-benzonitrile;

(1-{5-Cyclopropyl-2-[2-(2,6-difluoro-phenylamino)-pyridin-4-yl]-pyrido[3,4-d]pyrimidin-4-yl}-piperidin-4-yl)-piperazin-1-yl-methanone;

4-[4-(5-Cyclopropyl-4-piperazin-1-yl-pyrido[3,4-d]pyrimidin-2-yl)-pyridin-2-ylamino]-benzamide;

[4-(5-Cyclopropyl-4-piperazin-1-yl-pyrido[3,4-d]pyrimidin-2-yl)-pyridin-2-yl]-[1,2,4]triazolo[1,5-a]pyridin-2-yl-amine;

1-{5-Cyclopropyl-2-[2-(2,6-difluoro-phenylamino)-pyridin-4-yl]-pyrido[3,4-d]pyrimidin-4-yl}-piperidine-4-carboxylic acid (2-methylamino-ethyl)-amide;

6-{4-[5-Cyclopropyl-4-((cis)-3,4-dihydroxy-piperidin-1-yl)-pyrido[3,4-d]pyrimidin-2-yl]-pyridin-2-ylamino}-pyridine-2-carbonitrile;

6-[4-(5-Cyclopropyl-4-piperazin-1-yl-pyrido[3,4-d]pyrimidin-2-yl)-pyridin-2-ylamino]-pyridine-2-carbonitrile;

1-(5-Cyclopropyl-2-{2-[3-(4-methyl-piperazin-1-yl)-phenylamino]-pyridin-4-yl}-pyrido[3,4-d]pyrimidin-4-yl)-3,3-difluoro-piperidine-4,4-diol;

[4-(5-Cyclopropyl-4-piperazin-1-yl-pyrido[3,4-d]pyrimidin-2-yl)-pyridin-2-yl]-(4,6-difluoro-pyridin-3-yl)-amine;

[4-(5-Cyclopropyl-4-piperazin-1-yl-pyrido[3,4-d]pyrimidin-2-yl)-pyridin-2-yl]-(2,5-difluoro-pyridin-3-yl)-amine;

[4-(5-Cyclopropyl-4-piperazin-1-yl-pyrido[3,4-d]pyrimidin-2-yl)-pyridin-2-yl]-pyridin-2-yl-amine;

(3R,4S)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol;

(3R,4S)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol;

(3S,4S)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol;

(3S,4S)-1-(5-Cyclopropyl-2-{2-[3-(4-methyl-piperazin-1-yl)-phenylamino]-pyridin-4-yl}-pyrido[3,4-d]pyrimidin-4-yl)-piperidine-3,4-diol;

{4-[5-Cyclopropyl-4-(2-methylamino-ethoxy)-pyrido[3,4-d]pyrimidin-2-yl]-pyridin-2-yl}-(2,6-difluoro-phenyl)-amine;

[4-(5-Cyclopropyl-4-piperazin-1-yl-pyrido[3,4-d]pyrimidin-2-yl)-pyridin-2-yl]-(4-fluoro-pyridin-2-yl)-amine;

{4-[5-Cyclopropyl-4-(piperidin-4-yloxy)-pyrido[3,4-d]pyrimidin-2-yl]-pyridin-2-yl}-(2,6-difluoro-phenyl)-amine;

[4-(5-Cyclopropyl-4-piperazin-1-yl-pyrido[3,4-d]pyrimidin-2-yl)-pyridin-2-yl]-(1-methyl-1H-pyrazol-4-ylmethyl)-amine;

[4-(5-Cyclopropyl-4-piperazin-1-yl-pyrido[3,4-d]pyrimidin-2-yl)-pyridin-2-yl]-phenethyl-amine;

[4-(5-Cyclopropyl-4-pyrrolidin-1-yl-pyrido[3,4-d]pyrimidin-2-yl)-pyridin-2-yl]-[3-(4-methyl-piperazin-1-yl)-phenyl]-amine;

[4-(4-Azetidin-1-yl-5-cyclopropyl-pyrido[3,4-d]pyrimidin-2-yl)-pyridin-2-yl]-[3-(4-methyl-piperazin-1-yl)-phenyl]-amine;

[4-(5-Cyclopropyl-4-piperazin-1-yl-pyrido[3,4-d]pyrimidin-2-yl)-pyridin-2-yl]-(3-fluoro-6-methoxy-pyridin-2-yl)-amine;

{4-[5-Cyclopropyl-4-(3,5-dimethyl-piperazin-1-yl)-pyrido[3,4-d]pyrimidin-2-yl]-pyridin-2-yl}-(3,6-difluoro-pyridin-2-yl)-amine;

[4-(5-Cyclopropyl-4-piperazin-1-yl-pyrido[3,4-d]pyrimidin-2-yl)-5-fluoro-pyridin-2-yl]-(2,6-difluoro-phenyl)-amine;

[4-(5-Cyclopropyl-4-piperazin-1-yl-pyrido[3,4-d]pyrimidin-2-yl)-5-fluoro-pyridin-2-yl]-(4-fluoro-phenyl)-amine;

[4-(5-Cyclopropyl-4-pyrrolidin-1-yl-pyrido[3,4-d]pyrimidin-2-yl)-pyridin-2-yl]-(3-piperazin-1-yl-phenyl)-amine;

[4-(4-Azetidin-1-yl-5-cyclopropyl-pyrido[3,4-d]pyrimidin-2-yl)-pyridin-2-yl]-(3-piperazin-1-yl-phenyl)-amine;

N-{4-[4-((R)-3-Benzyloxymethyl-piperazin-1-yl)-5-cyclopropyl-pyrido[3,4-d]pyrimidin-2-yl]-pyridin-2-yl}-acetamide;

{4-[5-Cyclopropyl-4-((R)-3-methanesulfonylmethyl-piperazin-1-yl)-pyrido[3,4-d]pyrimidin-2-yl]-pyridin-2-yl}-phenyl-amine;

N-{4-[5-Cyclopropyl-4-((R)-3-methanesulfonylmethyl-piperazin-1-yl)-pyrido[3,4-d]pyrimidin-2-yl]-pyridin-2-yl}-acetamide;

{4-[5-Cyclopropyl-4-((R)-3-methanesulfonylmethyl-piperazin-1-yl)-pyrido[3,4-d]pyrimidin-2-yl]-pyridin-2-yl}-(4-fluoro-phenyl)-amine;

{4-[5-Cyclopropyl-4-((R)-3-methanesulfonylmethyl-piperazin-1-yl)-pyrido[3,4-d]pyrimidin-2-yl]-pyridin-2-yl}-(2,6-difluoro-phenyl)-amine;

Cyclopropanecarboxylic acid {4-[5-cyclopropyl-4-((R)-3-methanesulfonylmethyl-piperazin-1-yl)-pyrido[3,4-d]pyrimidin-2-yl]-pyridin-2-yl}-amide;

[4-(5-Cyclopropyl-4-piperazin-1-yl-pyrido[3,4-d]pyrimidin-2-yl)-pyridin-2-yl]-(3,4,6-trifluoro-pyridin-2-yl)-amine;

N-{5-Cyclopropyl-2-[2-(2,6-difluoro-phenylamino)-pyridin-4-yl]-pyrido[3,4-d]pyrimidin-4-yl}-N'-methyl-ethane-1,2-diamine;

N-{5-Cyclopropyl-2-[2-(2,6-difluoro-phenylamino)-pyridin-4-yl]-pyrido[3,4-d]pyrimidin-4-yl}-N',N'-dimethyl-ethane-1,2-diamine;

1-(5-Cyclopropyl-2-{2-[3-(4-methyl-piperazin-1-yl)-phenylamino]-pyridin-4-yl}-pyrido[3,4-d]pyrimidin-4-yl)-azetidin-3-ol;

1-{5-Cyclopropyl-2-[2-(3-piperazin-1-yl-phenylamino)-pyridin-4-yl]-pyrido[3,4-d]pyrimidin-4-yl}-azetidin-3-ol;

[4-(5-Cyclopropyl-4-piperazin-1-yl-pyrido[3,4-d]pyrimidin-2-yl)-pyridin-2-yl]-(1-isopropyl-1H-pyrazol-3-yl)-amine;

[4-(5-Cyclopropyl-4-piperazin-1-yl-pyrido[3,4-d]pyrimidin-2-yl)-pyridin-2-yl]-(1-ethyl-5-methyl-1H-pyrazol-3-yl)-amine;

[4-(5-Cyclopropyl-4-piperidin-1-yl-pyrido[3,4-d]pyrimidin-2-yl)-pyridin-2-yl]-[6-(4-methyl-piperazin-1-yl)-pyridin-2-yl]-amine;

[4-(5-Cyclopropyl-4-piperidin-1-yl-pyrido[3,4-d]pyrimidin-2-yl)-pyridin-2-yl]-[6-(4-methyl-piperazin-1-yl)-pyridin-2-yl]-amine;

[4-(5-Cyclobutyl-4-piperazin-1-yl-pyrido[3, 4-d]pyrimidin-2-yl)-pyridin-2-yl]-(3,5-difluoro-pyridin-2-yl)-amine;

[4-(5-Cyclobutyl-4-piperazin-1-yl-pyrido[3,4-d]pyrimidin-2-yl)-pyridin-2-yl]-(3-fluoro-pyridin-2-yl)-amine;

[4-(5-Cyclobutyl-4-piperazin-1-yl-pyrido[3, 4-d]pyrimidin-2-yl)-pyridin-2-yl]-(4-fluoro-pyridin-2-yl)-amine;

[4-(5-Cyclobutyl-4-piperazin-1-yl-pyrido[3,4-d]pyrimidin-2-yl)-pyridin-2-yl]-(3,4,6-trifluoro-pyridin-2-yl)-amine;

{4-[5-Cyclopropyl-4-(3,5-dimethyl-piperazin-1-yl)-pyrido[3,4-d]pyrimidin-2-yl]-pyridin-2-yl}-(2,6-difluoro-phenyl)-amine;

(R)-4-{5-Cyclopropyl-2-[2-(2,6-difluoro-phenylamino)-pyridin-4-yl]-pyrido[3,4-d]pyrimidin-4-yl}-piperazine-2-carbonitrile;

{4-[5-Cyclopropyl-4-(1,2,3,6-tetrahydro-pyridin-4-yl)-pyrido[3,4-d]pyrimidin-2-yl]-pyridin-2-yl}-(2,6-difluoro-phenyl)-amine;

{5-Cyclopropyl-2-[2-(2,6-difluoro-phenylamino)-pyridin-4-yl]-pyrido[3,4-d]pyrimidin-4-yl}-piperidin-4-yl-amine;

{4-[5-Cyclopropyl-4-(piperidin-4-ylsulfanyl)-pyrido[3,4-d]pyrimidin-2-yl]-pyridin-2-yl}-(2,6-difluoro-phenyl)-amine;

(3S,4S)-1-(5-Cyclopropyl-2-{2-[3-(4-methyl-piperazin-1-yl)-phenylamino]-pyridin-4-yl}-pyrido[3,4-d]pyrimidin-4-yl)-pyrrolidine-3,4-diol;

[4-(5-Cyclopropyl-4-piperazin-1-yl-pyrido[3,4-d]pyrimidin-2-yl)-pyridin-2-yl]-(1-cyclopropyl-1H-pyrazol-4-yl)-amine;

[4-(5-Cyclopropyl-4-piperazin-1-yl-pyrido[3,4-d]pyrimidin-2-yl)-pyridin-2-yl]-[1-(tetrahydro-pyran-4-yl)-1H-pyrazol-4-yl]-amine;

(1-Cyclopentyl-1H-pyrazol-4-yl)-[4-(5-cyclopropyl-4-piperazin-1-yl-pyrido[3,4-d]pyrimidin-2-yl)-pyridin-2-yl]-amine;

N-{5-Cyclopropyl-2-[2-(2,6-difluoro-phenylamino)-pyridin-4-yl]-pyrido[3,4-d]pyrimidin-4-yl}-N,N',N'-trimethyl-ethane-1,2-diamine;

{4-[5-Cyclobutyl-4-((S)-3-methyl-piperazin-1-yl)-pyrido[3, 4-d]pyrimidin-2-yl]-pyridin-2-yl}-(3, 6-difluoro-pyridin-2-yl)-amine;

[4-(5-Cyclobutyl-4-piperazin-1-yl-pyrido[3, 4-d]pyrimidin-2-yl)-pyridin-2-yl]-(3,6-difluoro-pyridin-2-yl)-amine;

{4-[5-Cyclopropyl-4-((S)-3-methyl-piperazin-1-yl)-pyrido[3,4-d]pyrimidin-2-yl]-pyridin-2-yl}-(3-fluoro-pyridin-2-yl)-amine;

(6-Chloro-3-fluoro-pyridin-2-yl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-[(R)-1-(3,6-difluoro-pyridin-2-yl)-ethyl]-amine;

N-{5-Cyclopropyl-2-[2-(2,6-difluoro-phenylamino)-pyridin-4-yl]-pyrido[3,4-d]pyrimidin-4-yl}-N',N'-dimethyl-butane-1,4-diamine;

[4-(4-Azepan-1-yl-5-cyclopropyl-pyrido[3,4-d]pyrimidin-2-yl)-pyridin-2-yl]-[3-(4-methyl-piperazin-1-yl)-phenyl]-amine;

1-{5-Cyclopropyl-2-[2-(6-fluoro-pyridin-2-ylamino)-pyridin-4-yl]-pyrido[3,4-d]pyrimidin-4-yl}-piperidin-4-ol;

(R)-1-{5-Cyclopropyl-2-[2-(6-fluoro-pyridin-2-ylamino)-pyridin-4-yl]-pyrido[3,4-d]pyrimidin-4-yl}-piperidin-3-ol;

[4-(5-Cyclobutyl-4-piperazin-1-yl-pyrido[3,4-d]pyrimidin-2-yl)-pyridin-2-yl]-(3,5,6-trifluoro-pyridin-2-yl)-amine;

{4-[5-Cyclobutyl-4-((S)-3-methyl-piperazin-1-yl)-pyrido[3,4-d]pyrimidin-2-yl]-pyridin-2-yl}-(3,5,6-trifluoro-pyridin-2-yl)-amine;

[4-(5-Cyclobutyl-4-piperazin-1-yl-pyrido[3,4-d]pyrimidin-2-yl)-pyridin-2-yl]-(5-trifluoromethyl-pyridin-2-yl)-amine;

((R)-1-Cyclopropyl-ethyl)-[4-(5-cyclopropyl-4-piperazin-1-yl-pyrido[3,4-d]pyrimidin-2-yl)-pyridin-2-yl]-amine;

((R)-1-Cyclohexyl-ethyl)-[4-(5-cyclopropyl-4-piperazin-1-yl-pyrido[3,4-d]pyrimidin-2-yl)-pyridin-2-yl]-amine;

(5-Cyclopropyl-3-fluoro-pyridin-2-yl)-[4-(5-cyclopropyl-4-piperazin-1-yl-pyrido[3,4-d]pyrimidin-2-yl)-pyridin-2-yl]-amine;

1-{4-[4-(5-Cyclopropyl-4-piperazin-1-yl-pyrido[3,4-d]pyrimidin-2-yl)-pyridin-2-ylamino]-piperidin-1-yl}-2,2-dimethyl-propan-1-one;

[4-(5-Cyclopropyl-4-piperazin-1-yl-pyrido[3,4-d]pyrimidin-2-yl)-pyridin-2-yl]-[1-(2,2,2-trifluoro-ethyl)-piperidin-4-yl]-amine;

{4-[5-Cyclopropyl-4-(3,3-dimethyl-piperazin-1-yl)-pyrido[3,4-d]pyrimidin-2-yl]-pyridin-2-yl}-(3,5,6-trifluoro-pyridin-2-yl)-amine;

[4-(5-Cyclopropyl-4-piperazin-1-yl-pyrido[3,4-d]pyrimidin-2-yl]-(1-methanesulfonyl-piperidin-4-yl)-amine;

[4-(5-Cyclopropyl-4-piperazin-1-yl-pyrido[3,4-d]pyrimidin-2-yl)-pyridin-2-yl]-[1-(2-fluoro-phenyl)-1H-pyrazol-4-yl]-amine;

[4-(5-Cyclopropyl-4-piperazin-1-yl-pyrido[3,4-d]pyrimidin-2-yl)-pyridin-2-yl]-[1-(2,6-difluoro-phenyl)-1H-pyrazol-4-yl]-amine;

[4-(5-Cyclopropyl-4-piperazin-1-yl-pyrido[3,4-d]pyrimidin-2-yl)-pyridin-2-yl]-[1-(2,4,6-trifluoro-phenyl)-1H-pyrazol-4-yl]-amine;

1-{5-Cyclopropyl-2-[2-(2-methyl-2,3-dihydro-1H-isoindol-5-ylamino)-pyridin-4-yl]-pyrido[3,4-d]pyrimidin-4-yl}-piperidin-4-ol;

4-[4-(5-Cyclopropyl-4-piperazin-1-yl-pyrido[3,4-d]pyrimidin-2-yl)-pyridin-2-ylamino]-3,5-difluoro-benzamide;

(1 S,2 S,4R)-Bicyclo[2.2.1]hept-2-yl-[4-(5-cyclopropyl-4-piperazin-1-yl-pyrido[3,4-d]pyrimidin-2-yl)-pyridin-2-yl]-amine;

(1 R,2R,4S)-Bicyclo[2.2.1]hept-2-yl-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(5-cyclopropyl-[1,2,4]triazolo[1,5-a]pyridin-2-yl)-amine;

{4-[5-Cyclopropyl-4-(2-dimethylamino-ethoxy)-pyrido[3,4-d]pyrimidin-2-yl]-pyridin-2-yl}-(2,6-difluoro-phenyl)-amine;

[4-(5-Cyclopropyl-4-piperazin-1-yl-pyrido[3,4-d]pyrimidin-2-yl)-pyridin-2-yl]-(5-trifluoromethyl-pyridin-2-yl)-amine;

{4-[5-Cyclopropyl-4-((3R,5S)-3,5-dimethyl-piperazin-1-yl)-pyrido[3,4-d]pyrimidin-2-yl]-pyridin-2-yl}-(3,5,6-trifluoro-pyridin-2-yl)-amine;

{4-[5-Cyclopropyl-4-(4,7-diaza-spiro[2.5]oct-7-yl)-pyrido[3,4-d]pyrimidin-2-yl]-pyridin-2-yl}-(2,6-difluoro-phenyl)-amine;

{4-[5-Cyclopropyl-4-((S)-3-methyl-piperazin-1-yl)-pyrido[3,4-d]pyrimidin-2-yl]-pyridin-2-yl}-(3,5,6-trifluoro-pyridin-2-yl)-amine;

[4-(5-Cyclopropyl-4-piperazin-1-yl-pyrido[3,4-d]pyrimidin-2-yl)-pyridin-2-yl]-(7-cyclopropyl-[1,2,4]triazolo[1,5-a]pyridin-2-yl)-amine;

{4-[5-Cyclopropyl-4-(3,3-dimethyl-piperazin-1-yl)-pyrido[3,4-d]pyrimidin-2-yl]-pyridin-2-yl}-(1-methyl-1H-pyrazol-3-yl)-amine;

{5-Cyclopropyl-2-[2-(2,6-difluoro-phenylamino)-pyridin-4-yl]-pyrido[3,4-d]pyrimidin-4-yl}-methyl-piperidin-4-yl-amine;

1-{5-Cyclopropyl-2-[2-(3-morpholin-4-yl-phenylamino)-pyridin-4-yl]-pyrido[3,4-d]pyrimidin-4-yl}-piperidin-4-ol;

((R)-1-Cyclohexyl-ethyl)-{4-[5-cyclopropyl-4-(3,3-dimethyl-piperazin-1-yl)-pyrido[3,4-d]pyrimidin-2-yl]-pyridin-2-yl}-amine;

[4-(5-Cyclopropyl-4-piperazin-1-yl-pyrido[3,4-d]pyrimidin-2-yl)-pyridin-2-yl]-(4,6-difluoro-pyridin-2-yl)-amine;

{5-Cyclopropyl-2-[2-(2,6-difluoro-phenylamino)-pyridin-4-yl]-pyrido[3,4-d]pyrimidin-4-yl}-pyrrolidin-3-yl-amine;

{4-[5-Cyclopropyl-4-(3,3-dimethyl-piperazin-1-yl)-pyrido[3,4-d]pyrimidin-2-yl]-pyridin-2-yl}-(3,6-difluoro-pyridin-2-yl)-amine;

{4-[5-Cyclopropyl-4-((S)-3-methyl-piperazin-1-yl)-pyrido[3,4-d]pyrimidin-2-yl]-pyridin-2-yl}-(5-trifluoromethyl-pyridin-2-yl)-amine;

{4-[5-Cyclopropyl-4-(3,3-dimethyl-piperazin-1-yl)-pyrido[3,4-d]pyrimidin-2-yl]-pyridin-2-yl}-(3-fluoro-pyridin-2-yl)-amine;

-[4-(5-Cyclopropyl-4-piperazin-1-yl-pyrido[3,4-d]pyrimidin-2-yl)-pyridin-2-ylamino]-N-methyl-benzamide;

{5-Cyclopropyl-2-[2-(2,6-difluoro-phenylamino)-pyridin-4-yl]-pyrido[3,4-d]pyrimidin-4-yl}-piperidin-3-yl-amine;

{4-[5-Cyclopropyl-4-((3R,5S)-3,5-dimethyl-piperazin-1-yl)-pyrido[3,4-d]pyrimidin-2-yl]-pyridin-2-yl}-(2,6-difluoro-phenyl)-amine;

6-[4-(5-Cyclopropyl-4-piperazin-1-yl-pyrido[3,4-d]pyrimidin-2-yl)-pyridin-2-ylamino]-nicotinamide;

{4-[5-Cyclopropyl-4-(3,3-dimethyl-piperazin-1-yl)-pyrido[3,4-d]pyrimidin-2-yl]-pyridin-2-yl}-(3,4,6-trifluoro-pyridin-2-yl)-amine;

[4-(5-Cyclopropyl-4-piperazin-1-yl-pyrido[3,4-d]pyrimidin-2-yl)-pyridin-2-yl]-(8-cyclopropyl-[1,2,4]triazolo[1,5-a]pyridin-2-yl)-amine;

4-((S)-3-Benzyl-piperazin-1-yl)-2-morpholin-4-yl-pyrido[3,4-d]pyrimidine;

[2-(2-Benzyl-morpholin-4-yl)-pyrido[3,4-d]pyrimidin-4-yl]-(R)-pyrrolidin-3-yl-amine;

(S)—N[1]-(5-Methoxy-2-morpholin-4-yl-pyrido[3,4-d]pyrimidin-4-yl)-3-phenyl-propane-1,2-diamine;

5-Methoxy-2-morpholin-4-yl-4-piperazin-1-yl-pyrido[3,4-d]pyrimidine;

5-Methoxy-2-(2-phenoxymethyl-morpholin-4-yl)-4-piperazin-1-yl-pyrido[3,4-d]pyrimidine;

[(R)-4-(5-Methoxy-2-morpholin-4-yl-pyrido[3,4-d]pyrimidin-4-yl)-piperazin-2-yl]-methanol;

5-Methoxy-2-morpholin-4-yl-4-((R)-3-phenoxymethyl-piperazin-1-yl)-pyrido[3,4-d]pyrimidine;

[(S)-1-(5-Methoxy-2-morpholin-4-yl-pyrido[3,4-d]pyrimidin-4-yl)-piperidin-3-yl]-phenyl-amine;

4-[(R)-3-(2-Fluoro-phenoxymethyl)-piperazin-1-yl]-5-methoxy-2-morpholin-4-yl-pyrido[3,4-d]pyrimidine;

5-Methoxy-4-((R)-3-methoxymethyl-piperazin-1-yl)-2-morpholin-4-yl-pyrido[3,4-d]pyrimidine;

4-[(R)-3-(4-Fluoro-phenoxymethyl)-piperazin-1-yl]-5-methoxy-2-morpholin-4-yl-pyrido[3,4-d]pyrimidine;

(2-Morpholin-4-yl-pyrido[3,4-d]pyrimidin-4-yl)-(R)-pyrrolidin-3-yl-amine;

[2-Morpholin-4-yl-8-(2H-pyrazol-3-yl)-pyrido[3,4-d]pyrimidin-4-yl]-(R)-pyrrolidin-3-yl-amine;

N[4]—((S)-2-Amino-3-phenyl-propyl)-2-morpholin-4-yl-pyrido[3,4-d]pyrimidine-4,8-diamine;

(S)—N[1]-(2-Morpholin-4-yl-pyrido[3,4-d]pyrimidin-4-yl)-3-phenyl-propane-1,2-diamine;

5-Bromo-2-morpholin-4-yl-4-piperazin-1-yl-pyrido[3,4-d]pyrimidine;

Synthesis of 5-Cyclopropyl-2-morpholin-4-yl-4-piperazin-1-yl-pyrido[3,4-d]pyrimidine;

4-((S)-3-Benzyl-piperazin-1-yl)-5-cyclopropyl-2-morpholin-4-yl-pyrido[3,4-d]pyrimidine;

[(S)-4-(5-Cyclopropyl-2-morpholin-4-yl-pyrido[3,4-d]pyrimidin-4-yl)-piperazin-2-yl]-acetonitrile;

5-Methoxy-4-piperazin-1-yl-2-(1H-pyrrolo[2,3-b]pyridin-4-yl)-pyrido[3,4-d]pyrimidine;

5-Methoxy-2-(2-methyl-1H-pyrrolo[2,3-b]pyridin-4-yl)-4-piperazin-1-yl-pyrido[3,4-d]pyrimidine;

2-(2-Benzyl-1H-pyrrolo[2,3-b]pyridin-4-yl)-5-methoxy-4-piperazin-1-yl-pyrido[3,4-d]pyrimidine;

2-[2-(2-Fluoro-benzyl)-1H-pyrrolo[2,3-b]pyridin-4-yl]-5-methoxy-4-piperazin-1-yl-pyrido[3,4-d]pyrimidine;

2-(2-Ethyl-1H-pyrrolo[2,3-b]pyridin-4-yl)-5methoxy-4-piperazin-1-yl-pyrido[3,4-d]pyrimidine;

5-Methoxy-4-((R)-3-methoxymethyl-piperazin-1-yl)-2-(1H-pyrrolo[2,3-b]pyridin-4-yl)-pyrido[3,4-d]pyrimidine;

{(R)-4-[5-Methoxy-2-(1H-pyrrolo[2,3-b]pyridin-4-yl)-pyrido[3,4-d]pyrimidin-4-yl]-piperazin-2-yl}-methanol;

4-Piperazin-1-yl-2-(1H-pyrrolo[2,3-b]pyridin-4-yl)-pyrido[3,4-d]pyrimidine;

(R)-Pyrrolidin-3-yl-[2-(1H-pyrrolo[2,3-b]pyridin-4-yl)-pyrido[3,4-d]pyrimidin-4-yl]-amine;

5-Cyclopropyl-4-piperazin-1-yl-2-(1H-pyrrolo[2,3-b]pyridin-4-yl)-pyrido[3,4-d]pyrimidine;

8-Chloro-5-cyclopropyl-4-piperazin-1-yl-2-(1H-pyrrolo[2,3-b]pyridin-4-yl)-pyrido[3,4-d]pyrimidine;

5-Isopropyl-4-piperazin-1-yl-2-(1 H-pyrrolo[2,3-b]pyridin-4-yl)-pyrido[3,4-d]pyrimidine;

[5-Cyclopropyl-4-piperazin-1-yl-2-(2-trifluoromethyl-1H-pyrrolo[2,3-b]pyridin-4-yl)-pyrido[3,4-d]pyrimidine;

5-Cyclopropyl-2-(1H-pyrrolo[2,3-b]pyridin-4-yl)-4-((R)-3-trifluoromethyl-piperazin-1-yl)-pyrido[3,4-d]pyrimidine;

5-Cyclopropyl-2-(1H-pyrrolo[2,3-b]pyridin-4-yl)-4-((S)-3-trifluoromethyl-piperazin-1-yl)-pyrido[3,4-d]pyrimidine;

5-Cyclopropyl-2-(2-methyl-1H-pyrrolo[2,3-b]pyridin-4-yl)-4-(3-trifluoromethyl-piperazin-1-yl)-pyrido[3,4-d]pyrimidine;

5-Cyclopropyl-4-((S)-3-cyclopropyl-piperazin-1-yl)-2-(2-methyl-1H-pyrrolo[2,3-b]pyridin-4-yl)-pyrido[3,4-d]pyrimidine;

5-Cyclopropyl-2-(2-methyl-1H-pyrrolo[2,3-b]pyridin-4-yl)-4-piperazin-1-yl-pyrido[3,4-d]pyrimidine;

5-Cyclopropyl-2-(1H-pyrrolo[2,3-b]pyridin-4-yl)-4-(3-trifluoromethyl-piperazin-1-yl)-pyrido[3,4-d]pyrimidine;

4-((S)-3-Benzyl-piperazin-1-yl)-5-cyclopropyl-2-(1H-pyrrolo[2,3-b]pyridin-4-yl)-pyrido[3,4-d]pyrimidine;

5-Cyclopropyl-4-((S)-3-cyclopropyl-piperazin-1-yl)-2-(1H-pyrrolo[2,3-b]pyridin-4-yl)-pyrido[3,4-d]pyrimidine;

{(S)-4-[5-Cyclopropyl-2-(1H-pyrrolo[2,3-b]pyridin-4-yl)-pyrido[3,4-d]pyrimidin-4-yl]-piperazin-2-yl}-acetonitrile;

5-Cyclopropyl-4-piperazin-1-yl-2-(2-thiophen-2-yl-1H-pyrrolo[2,3-b]pyridin-4-yl)-pyrido[3,4-d]pyrimidine;

5-Cyclopropyl-2-(2-cyclopropyl-1H-pyrrolo[2,3-b]pyridin-4-yl)-4-piperazin-1-yl-pyrido[3,4-d]pyrimidine;

4-[5-Cyclopropyl-2-(2-trifluoromethyl-1H-pyrrolo[2,3-b]pyridin-4-yl)-pyrido[3,4-d]pyrimidin-4-yl]-piperazine-1-carboxylic acid ethyl ester;

5-Cyclopropyl-2-(2-trifluoromethyl-1H-pyrrolo[2,3-b]pyridin-4-yl)-pyrido[3,4-d]pyrimidin-4-ol;

5-Cyclopropyl-2-(5-fluoro-1H-pyrrolo[2,3-b]pyridin-4-yl)-4-piperazin-1-yl-pyrido[3,4-d]pyrimidine;

5-Cyclopropyl-4-morpholin-4-yl-2-(2-trifluoromethyl-1H-pyrrolo[2,3-b]pyridin-4-yl)-pyrido[3,4-d]pyrimidine;

5-Cyclopropyl-4-piperazin-1-yl-2-(2-triduteriomethyl-1H-pyrrolo[2,3-b]pyridin-4-yl)-pyrido[3,4-d]pyrimidine;

2-(2-tert-Butyl-5-chloro-1H-pyrrolo[2,3-b]pyridin-4-yl)-5-cyclopropyl-4-piperazin-1-yl-pyrido[3,4-d]pyrimidine;

5-Cyclopropyl-2-[2-(4-fluoro-phenyl)-1H-pyrrolo[2,3-b]pyridin-4-yl]-4-piperazin-1-yl-pyrido[3,4-d]pyrimidine;

2-(2-tert-Butyl-1H-pyrrolo[2,3-b]pyridin-4-yl)-5-cyclopropyl-4-piperazin-1-yl-pyrido[3,4-d]pyrimidine;

5-Cyclopropyl-2-(5-fluoro-2-trifluoromethyl-1H-pyrrolo[2,3-b]pyridin-4-yl)-4-piperazin-1-yl-pyrido[3,4-d]pyrimidine;

5-Cyclopropyl-4-((S)-3-methyl-piperazin-1-yl)-2-(2-trifluoromethyl-1H-pyrrolo[2,3-b]pyridin-4-yl)-pyrido[3,4-d]pyrimidine;

(+/−)-(cis)-1-[5-Cyclopropyl-2-(2-trifluoromethyl-1H-pyrrolo[2,3-b]pyridin-4-yl)-pyrido[3,4-d]pyrimidin-4-yl]-piperidine-3,4-diol;

(+/−)-(trans)-1-[5-Cyclopropyl-2-(2-trifluoromethyl-1H-pyrrolo[2,3-b]pyridin-4-yl)-pyrido[3,4-d]pyrimidin-4-yl]-piperidine-3,4-diol;

5-Cyclopropyl-4-(3-trifluoromethyl-piperazin-1-yl)-2-(2-trifluoromethyl-1H-pyrrolo[2,3-b]pyridin-4-yl)-pyrido[3,4-d]pyrimidine;

5-Cyclopropyl-4-piperidin-1-yl-2-(2-trifluoromethyl-1H-pyrrolo[2,3-b]pyridin-4-yl)-pyrido[3,4-d]pyrimidine;

5-Cyclopropyl-4-piperazin-1-yl-2-[2-(1-trifluoromethyl-cyclopropyl)-1H-pyrrolo[2,3-b]pyridin-4-yl]-pyrido[3,4-d]pyrimidine;

1-[5-Cyclopropyl-2-(2-trifluoromethyl-1H-pyrrolo[2,3-b]pyridin-4-yl)-pyrido[3,4-d]pyrimidin-4-yl]-piperidin-4-ol;

5-Cyclopropyl-2-[2-(1-phenyl-cyclopropyl)-1H-pyrrolo[2,3-b]pyridin-4-yl]-4-piperazin-1-yl-pyrido[3,4-d]pyrimidine;

1-[5-Cyclopropyl-2-(2-trifluoromethyl-1H-pyrrolo[2,3-b]pyridin-4-yl)-pyrido[3,4-d]pyrimidin-4-yl]-piperidine-4-carbonitrile;

{1-[5-Cyclopropyl-2-(2-trifluoromethyl-1H-pyrrolo[2,3-b]pyridin-4-yl)-pyrido[3,4-d]pyrimidin-4-yl]-piperidin-4-yl}-methanol;

{1-[5-Cyclopropyl-2-(2-trifluoromethyl-1H-pyrrolo[2,3-b]pyridin-4-yl)-pyrido[3,4-d]pyrimidin-4-yl]-azetidin-3-yl}-methanol;

1-{5-Cyclopropyl-2-[2-(1-phenyl-cyclopropyl)-1H-pyrrolo[2,3-b]pyridin-4-yl]-pyrido[3,4-d]pyrimidin-4-yl}-piperidin-4-ol;

5-Cyclopropyl-4-(1,1-dioxo-1λ$^6$-thiomorpholin-4-yl)-2-(2-trifluoromethyl-1H-pyrrolo[2,3-b]pyridin-4-yl)-pyrido[3,4-d]pyrimidine;

5-Cyclopropyl-4-thiomorpholin-4-yl-2-(2-trifluoromethyl-1H-pyrrolo[2,3-b]pyridin-4-yl)-pyrido[3,4-d]pyrimidine;

1-[2-(2-tert-Butyl-1H-pyrrolo[2,3-b]pyridin-4-yl)-5-cyclopropyl-pyrido[3,4-d]pyrimidin-4-yl]-piperidin-4-ol;

4-Azetidin-1-yl-5-cyclopropyl-2-(2-trifluoromethyl-1H-pyrrolo[2,3-b]pyridin-4-yl)-pyrido[3,4-d]pyrimidine;

1-[2-(2-tert-Butyl-1H-pyrrolo[2,3-b]pyridin-4-yl)-5-cyclopropyl-pyrido[3,4-d]pyrimidin-4-yl]-[1,4]diazepan-5-one;

(R)-1-[2-(2-tert-Butyl-1H-pyrrolo[2,3-b]pyridin-4-yl)-5-cyclopropyl-pyrido[3,4-d]pyrimidin-4-yl]-pyrrolidin-3-ol;

5-Cyclopropyl-4-(3,3-dimethyl-piperazin-1-yl)-2-(2-trifluoromethyl-1H-pyrrolo[2,3-b]pyridin-4-yl)-pyrido[3,4-d]pyrimidine;

4-(5-cyclopropyl-4-piperazin-1-yl-pyrido[3,4-d]pyrimidin-2-yl)spiro[1,3-dihydropyrrolo[2,3-b]pyridine-2,1'-cyclohexane];

4-(5-Cyclopropyl-4-piperazin-1-yl-pyrido[3,4-d]pyrimidin-2-yl)-9H-pyrido[2,3-b]indole;

1-[5-Cyclopropyl-2-(9H-pyrido[2,3-b]indol-4-yl)-pyrido[3,4-d]pyrimidin-4-yl]-piperidin-4-ol;

4-[5-Cyclopropyl-4-(3,3-dimethyl-piperazin-1-yl)-pyrido[3,4-d]pyrimidin-2-yl]-9H-pyrido[2,3-b]indole; or a salt form thereof.

87. A compound of formula (I) or a salt form thereof according to embodiment 1 wherein G is

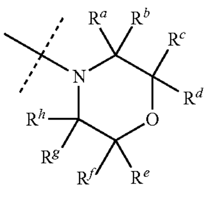

.

88. A compound of formula (I) or a salt form thereof according to embodiment 1 wherein G is

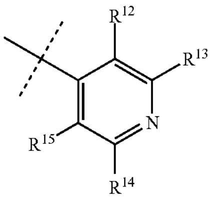

.

89. A compound of formula (I) or a salt form thereof according to embodiment 1 or 88 wherein G is

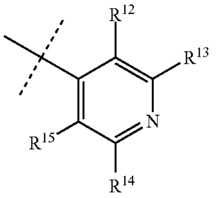

;

X is chosen from 3-15 membered heterocycloalkyl optionally substituted by 1-28 $R^{19}$, —$NR^{24}R^{28}$, and —$S(=O)_nR^{28}$;

$R^7$, $R^8$, $R^9$ are each independently chosen from H, $C_{1-6}$alkyl optionally substituted by 1-13 $R^{19}$, $C_{2-6}$alkenyl optionally substituted by 1-11 $R^{19}$, $C_{3-11}$cycloalkyl optionally substituted by 1-21 $R^{19}$, and halogen.

90. A compound of formula (I) or a salt form thereof according to any of embodiments 1, 88 or 89 wherein $R^{24}$ at each occurrence is independently chosen from H, and $C_{1-6}$alkyl optionally substituted by 1-13 $R^{49}$; and $R^{28}$ is selected from 3-15 membered heterocycloalkyl optionally substituted by 1-28 $R^{49}$, 4-21 membered heterocycloalkylalkyl optionally substituted by 1-40 $R^{49}$ and $C_{6-11}$aryl optionally substituted by 1-11 $R^{49}$.

91. A compound of formula (I) or a salt form thereof according to any of embodiments 1 or 88-90 wherein $R^{12}$ and $R^{13}$ are taken together to form $C_{3-11}$cycloalkyl optionally substituted by 1-21 $R^{19}$, 3-15 membered heterocycloalkyl optionally substituted by 1-28 $R^{19}$ or a 5-15 membered heteroaryl optionally substituted by 1-15 $R^{19}$ 92. A compound of formula (I) or a salt form thereof according to any of embodiments 1 or 88-90 wherein $R^{12}$, $R^{14}$ and $R^{15}$ are each H and $R^{13}$ is —$NR^{22}R^{23}$ or —$NR^{34}C(=O)R^{30}$.

93. A compound of formula (I) or a salt form thereof according to embodiment 92 wherein $R^{22}$ and $R^{23}$ are each independently chosen from H, $C_{1-6}$alkyl optionally substituted by 1-13 $R^{49}$, $C_{6-11}$aryl optionally substituted by 1-11 $R^{49}$, $C_{7-16}$arylalkyl optionally substituted by 1-19 $R^{49}$, $C_{3-11}$cycloalkyl optionally substituted by 1-21 $R^{49}$, $C_{4-17}$cycloalkylalkyl optionally substituted by 1-32 $R^{49}$, 3-15 membered heterocycloalkyl optionally substituted by 1-28 $R^{49}$, 4-21 membered heterocycloalkylalkyl optionally substituted by 1-40 $R^{49}$, 5-15 membered heteroaryl optionally substituted by 1-15 $R^{49}$, and 6-21 membered heteroarylalkyl optionally substituted by 1-27 $R^{49}$.

94. A compound that is selected from:

2-(2-tert-Butyl-H-pyrrolo[2,3-b]pyridin-4-yl)-5-cyclopropyl-4-((S)-3-methyl-piperazin-1-yl)-pyrido[3,4-d]pyrimidine;

2-(2-tert-Butyl-H-pyrrolo[2,3-b]pyridin-4-yl)-5-cyclopropyl-4-(3,3-dimethyl-piperazin-1-yl)-pyrido[3,4-d]pyrimidine;

4-[4-(5-Cyclopropyl-4-piperazin-1-yl-pyrido[3,4-d]pyrimidin-2-yl)-pyridin-2-ylamino]-N,N-dimethyl-benzamide;

{4-[5-Cyclopropyl-4-((S)-3-methyl-piperazin-1-yl)-pyrido[3,4-d]pyrimidin-2-yl]-pyridin-2-yl}-(3,4,6-trifluoro-pyridin-2-yl)-amine;

(+/−)-cis-1-{5-Cyclopropyl-2-[2-(3-morpholin-4-yl-phenylamino)-pyridin-4-yl]-pyrido[3,4-d]pyrimidin-4-yl}-piperidine-3,4-diol;

{4-[5-Cyclopropyl-4-(3,3-dimethyl-piperazin-1-yl)-pyrido[3,4-d]pyrimidin-2-yl]-pyridin-2-yl}-((R)-1-cyclopropyl-ethyl)-amine;

{4-[5-Cyclopropyl-4-(3,3-dimethyl-piperazin-1-yl)-pyrido[3,4-d]pyrimidin-2-yl]-pyridin-2-yl}-((R)-1-phenyl-ethyl)-amine;

2-(2-tert-Butyl-1H-pyrrolo[2,3-b]pyridin-4-yl)-5-cyclobutyl-4-((S)-3-methyl-piperazin-1-yl)-pyrido[3,4-d]pyrimidine;

5-Cyclopropyl-2-{2-[1-(2-fluoro-phenyl)-cyclopropyl]-1H-pyrrolo[2,3-b]pyridin-4-yl}-4-piperazin-1-yl-pyrido[3,4-d]pyrimidine;

2-(2-tert-Butyl-1H-pyrrolo[2,3-b]pyridin-4-yl)-5-cyclobutyl-4-piperazin-1-yl-pyrido[3,4-d]pyrimidine;

[4-(5-Cyclobutyl-4-piperazin-1-yl-pyrido[3,4-d]pyrimidin-2-yl)-pyridin-2-yl]-(4,6-difluoro-pyridin-2-yl)-amine;

[4-(5-Cyclopropyl-4-piperazin-1-yl-pyrido[3,4-d]pyrimidin-2-yl)-pyridin-2-yl]-(6-cyclopropyl-[1,2,4]triazolo[1,5-a]pyridin-2-yl)-amine;

(5-Cyclobutyl-3-fluoro-pyridin-2-yl)-[4-(5-cyclopropyl-4-piperazin-1-yl-pyrido[3,4-d]pyrimidin-2-yl)-pyridin-2-yl]-amine;

{5-Cyclopropyl-2-[2-(3,5,6-trifluoro-pyridin-2-ylamino)-pyridin-4-yl]-pyrido[3,4-d]pyrimidin-4-yl}-methyl-piperidin-4-yl-amine;

(4-Chloro-1-ethyl-1H-pyrazol-3-yl)-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-[1-(2,2,2-trifluoro-ethyl)-1H-pyrazol-3-yl]-amine;

{4-[5-Cyclopropyl-4-(3,3-dimethyl-piperazin-1-yl)-pyrido[3,4-d]pyrimidin-2-yl]-pyridin-2-yl}-[1-(2,2,2-trifluoro-ethyl)-1H-pyrazol-3-yl]-amine;

{4-[5-Cyclopropyl-4-(3,3-dimethyl-piperazin-1-yl)-pyrido[3,4-d]pyrimidin-2-yl]-pyridin-2-yl}-(1-isopropyl-1H-pyrazol-3-yl)-amine;

{5-Cyclopropyl-2-[2-(3,4,6-trifluoro-pyridin-2-ylamino)-pyridin-4-yl]-pyrido[3,4-d]pyrimidin-4-yl}-methyl-piperidin-4-yl-amine;

{5-Cyclopropyl-2-[2-(3,5,6-trifluoro-pyridin-2-ylamino)-pyridin-4-yl]-pyrido[3,4-d]pyrimidin-4-yl}-pyrrolidin-3-yl-amine;

{5-Cyclopropyl-2-[2-(3,4,6-trifluoro-pyridin-2-ylamino)-pyridin-4-yl]-pyrido[3,4-d]pyrimidin-4-yl}-pyrrolidin-3-yl-amine;

[4-(5-Cyclobutyl-4-piperazin-1-yl-pyrido[3,4-d]pyrimidin-2-yl)-pyridin-2-yl]-[1,2,4]triazolo[1,5-a]pyridin-2-yl-amine;

[4-(5-Cyclopropyl-4-piperazin-1-yl-pyrido[3,4-d]pyrimidin-2-yl)-pyridin-2-yl]-(3-morpholin-4-yl-phenyl)-amine;

5-Cyclobutyl-4-piperazin-1-yl-2-(2-trifluoromethyl-1H-pyrrolo[2,3-b]pyridin-4-yl)-pyrido[3,4-d]pyrimidine;

{5-Cyclopropyl-2-[2-(2,6-difluoro-phenylamino)-pyridin-4-yl]-pyrido[3,4-d]pyrimidin-4-yl}-methyl-pyrrolidin-3-yl-amine;

Azetidin-3-yl-{5-cyclopropyl-2-[2-(2,6-difluoro-phenylamino)-pyridin-4-yl]-pyrido[3,4-d]pyrimidin-4-yl}-amine;

4-(5-Cyclopropyl-4-piperazin-1-yl-pyrido[3,4-d]pyrimidin-2-yl)-5,8-difluoro-9H-pyrido[2,3-b]indole;

2-(2-tert-Butyl-1H-pyrrolo[2,3-b]pyridin-4-yl)-5-cyclobutyl-4-(3,3-dimethyl-piperazin-1-yl)-pyrido[3,4-d]pyrimidine;

Azetidin-3-yl-{5-cyclopropyl-2-[2-(2,6-difluoro-phenylamino)-pyridin-4-yl]-pyrido[3,4-d]pyrimidin-4-yl}-methyl-amine;

[4-Chloro-1-(2,2,2-trifluoro-ethyl)-1H-pyrazol-3-yl]-[4-(5-cyclopropyl-4-piperazin-1-yl-pyrido[3,4-d]pyrimidin-2-yl)-pyridin-2-yl]-amine;

4-(5-Cyclopropyl-4-piperazin-1-yl-pyrido[3,4-d]pyrimidin-2-yl)-8-fluoro-9H-pyrido[2,3-b]indole;

[4-(5-Cyclopropyl-4-piperazin-1-yl-pyrido[3,4-d]pyrimidin-2-yl)-pyridin-2-yl]-(8-fluoro-[1,2,4]triazolo[1,5-a]pyridin-2-yl)-amine;

[4-(5-Cyclopropyl-4-piperazin-1-yl-pyrido[3,4-d]pyrimidin-2-yl)-pyridin-2-yl]-(7-fluoro-[1,2,4]triazolo[1,5-a]pyridin-2-yl)-amine;

{5-Cyclopropyl-2-[2-(2,6-difluoro-phenylamino)-pyridin-4-yl]-pyrido[3,4-d]pyrimidin-4-yl}-(S)-pyrrolidin-3-yl-amine;

{5-Cyclopropyl-2-[2-(2,6-difluoro-phenylamino)-pyridin-4-yl]-pyrido[3,4-d]pyrimidin-4-yl}-(R)-pyrrolidin-3-yl-amine;

4-(5-Cyclopropyl-4-piperazin-1-yl-pyrido[3,4-d]pyrimidin-2-yl)-7,8-difluoro-9H-pyrido[2,3-b]indole;

{4-[5-Cyclopropyl-4-((cis)-3,5-dimethyl-piperazin-1-yl)-pyrido[3,4-d]pyrimidin-2-yl]-pyridin-2-yl}-(3,4,6-trifluoro-pyridin-2-yl)-amine;

{5-Cyclopropyl-2-[2-(2,6-difluoro-phenylamino)-pyridin-4-yl]-pyrido[3,4-d]pyrimidin-4-yl}-(2,2-dimethyl-piperidin-4-yl)-amine;

[4-(5-Cyclopropyl-4-piperazin-1-yl-pyrido[3,4-d]pyrimidin-2-yl)-pyridin-2-yl]-(6-fluoro-[1,2,4]triazolo[1,5-a]pyridin-2-yl)-amine;

[4-(5-Cyclopropyl-4-piperazin-1-yl-pyrido[3,4-d]pyrimidin-2-yl)-pyridin-2-yl]-(6,8-difluoro-[1,2,4]triazolo[1,5-a]pyridin-2-yl)-amine;

[4-(5-Cyclopropyl-4-piperazin-1-yl-pyrido[3,4-d]pyrimidin-2-yl)-pyridin-2-yl]-(5-fluoro-[1,2,4]triazolo[1,5-a]pyridin-2-yl)-amine;

[4-(5-Cyclobutyl-4-piperazin-1-yl-pyrido[3,4-d]pyrimidin-2-yl)-pyridin-2-yl]-((R)-1-phenyl-ethyl)-amine;

(4-Chloro-1-ethyl-1H-pyrazol-3-yl)-{4-[5-cyclopropyl-4-(3,3-dimethyl-piperazin-1-yl)-pyrido[3,4-d]pyrimidin-2-yl]-pyridin-2-yl}-amine;

Benzooxazol-2-yl-[4-(5-cyclopropyl-4-piperazin-1-yl-pyrido[3,4-d]pyrimidin-2-yl)-pyridin-2-yl]-amine;

Benzothiazol-2-yl-[4-(5-cyclopropyl-4-piperazin-1-yl-pyrido[3,4-d]pyrimidin-2-yl)-pyridin-2-yl]-amine;

[4-(5-Cyclopropyl-4-piperazin-1-yl-pyrido[3,4-d]pyrimidin-2-yl)-pyridin-2-yl]-(1-methyl-1H-benzoimidazol-2-yl)-amine;

(5-Cyclopropyl-3,6-difluoro-pyridin-2-yl)-[4-(5-cyclopropyl-4-piperazin-1-yl-pyrido[3,4-d]pyrimidin-2-yl)-pyridin-2-yl]-amine;

5-Cyclopropyl-2-{2-[1-(4-fluoro-phenyl)-cyclopropyl]-1H-pyrrolo[2,3-b]pyridin-4-yl}-4-piperazin-1-yl-pyrido[3,4-d]pyrimidine;

{4-[5-Cyclopropyl-4-((S)-3-methyl-piperazin-1-yl)-pyrido[3,4-d]pyrimidin-2-yl]-pyridin-2-yl}-[1-(2,2,2-trifluoro-ethyl)-piperidin-4-yl]-amine;

[4-(5-Cyclopropyl-4-piperazin-1-yl-pyrido[3,4-d]pyrimidin-2-yl)-pyridin-2-yl]-naphthalen-2-yl-amine;

Biphenyl-3-yl-[4-(5-cyclopropyl-4-piperazin-1-yl-pyrido[3,4-d]pyrimidin-2-yl)-pyridin-2-yl]-amine;

{4-[5-Cyclopropyl-4-((R)-3-trifluoromethyl-piperazin-1-yl)-pyrido[3,4-d]pyrimidin-2-yl]-pyridin-2-yl}-[3-(4-methyl-piperazin-1-yl)-phenyl]-amine;

{4-[5-Cyclopropyl-4-((R)-3-trifluoromethyl-piperazin-1-yl)-pyrido[3,4-d]pyrimidin-2-yl]-pyridin-2-yl}-(1-methyl-1H-pyrazol-3-yl)-amine;

{5-Cyclopropyl-2-[2-(3,4,6-trifluoro-pyridin-2-ylamino)-pyridin-4-yl]-pyrido[3,4-d]pyrimidin-4-yl}-(R)-pyrrolidin-3-yl-amine;

[4-(5-Cyclopropyl-4-piperazin-1-yl-pyrido[3,4-d]pyrimidin-2-yl)-pyridin-2-yl]-[2-fluoro-4-(2-methyl-2H-pyrazol-3-yl)-phenyl]-amine;

{5-Cyclopropyl-2-[2-(3,5,6-trifluoro-pyridin-2-ylamino)-pyridin-4-yl]-pyrido[3,4-d]pyrimidin-4-yl}-(R)-pyrrolidin-3-yl-amine;

{5-Cyclopropyl-2-[2-(2,6-difluoro-phenylamino)-pyridin-4-yl]-pyrido[3,4-d]pyrimidin-4-yl}-methyl-(R)-pyrrolidin-3-yl-amine;

Azepan-4-yl-{5-cyclopropyl-2-[2-(2,6-difluoro-phenylamino)-pyridin-4-yl]-pyrido[3,4-d]pyrimidin-4-yl}-amine;

[4-(5-Cyclopropyl-4-piperazin-1-yl-pyrido[3,4-d]pyrimidin-2-yl)-pyridin-2-yl]-naphthalen-1-yl-amine;

[4-(5-Cyclopropyl-4-piperazin-1-yl-pyrido[3,4-d]pyrimidin-2-yl)-pyridin-2-yl]-iso[D3-4]uinolin-3-yl-amine;

[4-(5-Cyclopropyl-4-piperazin-1-yl-pyrido[3,4-d]pyrimidin-2-yl)-pyridin-2-yl]-(1-methyl-1H-indazol-3-yl)-amine;

{5-Cyclopropyl-2-[2-(3,4,6-trifluoro-pyridin-2-ylamino)-pyridin-4-yl]-pyrido[3,4-d]pyrimidin-4-yl}-piperidin-4-yl-amine;

5-Cyclopropyl-4-piperazin-1-yl-2-[2-(2,2,2-trifluoro-1,1-dimethyl-ethyl)-1H-pyrrolo[2,3-b]pyridin-4-yl]-pyrido[3,4-d]pyrimidine;

5-Cyclopropyl-2-[2-(1-phenyl-cyclobutyl)-1H-pyrrolo[2,3-b]pyridin-4-yl]-4-piperazin-1-yl-pyrido[3,4-d]pyrimidine;

{5-Cyclopropyl-2-[2-(3,5,6-trifluoro-pyridin-2-ylamino)-pyridin-4-yl]-pyrido[3,4-d]pyrimidin-4-yl}-piperidin-4-yl-amine;

[4-(5-Cyclopropyl-4-piperazin-1-yl-pyrido[3,4-d]pyrimidin-2-yl)-pyridin-2-yl]-[1-(tetrahydro-furan-2-yl)-ethyl]-amine;

[4-(5-Cyclopropyl-4-piperazin-1-yl-pyrido[3,4-d]pyrimidin-2-yl)-pyridin-2-yl]-[(R)-1-(2-fluoro-phenyl)-ethyl]-amine;

[5-Cyclopropyl-2-(2-trifluoromethyl-1H-pyrrolo[2,3-b]pyridin-4-yl)-pyrido[3,4-d]pyrimidin-4-yl]-piperidin-4-yl-amine;

[5-Cyclopropyl-2-(2-trifluoromethyl-1H-pyrrolo[2,3-b]pyridin-4-yl)-pyrido[3,4-d]pyrimidin-4-yl]-(R)-pyrrolidin-3-yl-amine;

[5-Cyclopropyl-2-(2-trifluoromethyl-1H-pyrrolo[2,3-b]pyridin-4-yl)-pyrido[3,4-d]pyrimidin-4-yl]-methyl-piperidin-4-yl-amine;

8-Chloro-5-cyclopropyl-4-piperazin-1-yl-2-(2-trifluoromethyl-1H-pyrrolo[2,3-b]pyridin-4-yl)-pyrido[3,4-d]pyrimidine;

[4-(5-Cyclopropyl-4-piperazin-1-yl-pyrido[3,4-d]pyrimidin-2-yl)-pyridin-2-yl]-pyrazolo[1,5-a]pyridin-2-yl-amine;

{4-[5-Cyclopropyl-4-((cis)-3,5-dimethyl-piperazin-1-yl)-pyrido[3,4-d]pyrimidin-2-yl]-pyridin-2-yl}-[1-(2,2,2-trifluoro-ethyl)-piperidin-4-yl]-amine;

2-(2-Chloro-1H-pyrrolo[2,3-b]pyridin-4-yl)-5-cyclopropyl-4-piperazin-1-yl-pyrido[3,4-d]pyrimidine;

5-Cyclopropyl-2-(2-methoxymethyl-1H-pyrrolo[2,3-b]pyridin-4-yl)-4-piperazin-1-yl-pyrido[3,4-d]pyrimidine;

4-{5-Cyclopropyl-2-[2-(2,6-difluoro-phenylamino)-pyridin-4-yl]-pyrido[3,4-d]pyrimidin-4-ylamino}-piperidin-2-one;

[5-Cyclopropyl-2-(1-methyl-2-trifluoromethyl-1H-pyrrolo[2,3-b]pyridin-4-yl)-pyrido[3,4-d]pyrimidin-4-yl]-(R)-pyrrolidin-3-yl-amine;

[4-(5-Cyclopropyl-4-piperazin-1-yl-pyrido[3,4-d]pyrimidin-2-yl)-pyridin-2-yl]-[D3-4]uinolin-2-yl-amine;

(±)-2-((endo)-2-Bicyclo[2.2.1]hept-2-yl-1H-pyrrolo[2,3-b]pyridin-4-yl)-5-cyclopropyl-4-piperazin-1-yl-pyrido[3,4-d]pyrimidine;

5-Cyclobutyl-2-(2-methoxymethyl-1H-pyrrolo[2,3-b]pyridin-4-yl)-4-piperazin-1-yl-pyrido[3,4-d]pyrimidine;

[5-Cyclopropyl-2-(2-trifluoromethyl-1H-pyrrolo[2,3-b]pyridin-4-yl)-pyrido[3,4-d]pyrimidin-4-yl]-methyl-(1-methyl-piperidin-4-yl)-amine;

5-Cyclobutyl-4-piperazin-1-yl-2-(1H-pyrrolo[2,3-b]pyridin-4-yl)-pyrido[3,4-d]pyrimidine;

{5-Cyclopropyl-2-[2-(2,6-difluoro-phenylamino)-pyridin-4-yl]-pyrido[3,4-d]pyrimidin-4-yl}-methyl-(1-methyl-piperidin-4-yl)-amine;

{5-Cyclopropyl-2-[2-(2,6-difluoro-phenylamino)-pyridin-4-yl]-pyrido[3,4-d]pyrimidin-4-yl}-(1-methyl-piperidin-4-yl)-amine;

1-(4-{5-Cyclopropyl-2-[2-(2,6-difluoro-phenylamino)-pyridin-4-yl]-pyrido[3,4-d]pyrimidin-4-ylamino}-piperidin-1-yl)-ethanone;

5-Cyclopropyl-2-[2-(1-methyl-1-phenyl-ethyl)-1H-pyrrolo[2,3-b]pyridin-4-yl]-4-piperazin-1-yl-pyrido[3,4-d]pyrimidine;

2-(3-Chloro-1H-pyrrolo[2,3-b]pyridin-4-yl)-5-cyclopropyl-4-piperazin-1-yl-pyrido[3,4-d]pyrimidine;

[5-Cyclopropyl-2-(2-trifluoromethyl-H-pyrrolo[2,3-b]pyridin-4-yl)-pyrido[3,4-d]pyrimidin-4-yl]-methyl-(R)-pyrrolidin-3-yl-amine;

[4-(5-Cyclopropyl-4-piperazin-1-yl-pyrido[3,4-d]pyrimidin-2-yl)-pyridin-2-yl]-iso[D3-4]uinolin-1-yl-amine;

4-(5-Cyclobutyl-4-piperazin-1-yl-pyrido[3,4-d]pyrimidin-2-yl)-9H-pyrido[2,3-b]indole 4-(4-Piperazin-1-yl-pyrido[3,4-d]pyrimidin-2-yl)-9H-pyrido[2,3-b]indole;

8-Chloro-5-cyclopropyl-2-(2-methyl-1H-pyrrolo[2,3-b]pyridin-4-yl)-4-piperazin-1-yl-pyrido[3,4-d]pyrimidine;

(±)-exo-[4-(5-Cyclopropyl-4-piperazin-1-yl-pyrido[3,4-d]pyrimidin-2-yl)-pyridin-2-yl]-7-oxa-bicyclo[2.2.1]hept-2-yl-amine;

(2,6-Difluoro-phenyl)-[4-(4-piperazin-1-yl-5-vinyl-pyrido[3,4-d]pyrimidin-2-yl)-pyridin-2-yl]-amine;

{5-Cyclopropyl-2-[2-(3,5-difluoro-pyridin-2-ylamino)-pyridin-4-yl]-pyrido[3,4-d]pyrimidin-4-yl}-methyl-piperidin-4-yl-amine;

1-[4-({5-Cyclopropyl-2-[2-(2,6-difluoro-phenylamino)-pyridin-4-yl]-pyrido[3,4-d]pyrimidin-4-yl}-methyl-amino)-piperidin-1-yl]-ethanone;

1-[4-({5-Cyclopropyl-2-[2-(2,6-difluoro-phenylamino)-pyridin-4-yl]-pyrido[3,4-d]pyrimidin-4-yl}-methyl-amino)-piperidin-1-yl]-ethanone;

[4-(5-Cyclopropyl-4-piperazin-1-yl-pyrido[3,4-d]pyrimidin-2-yl)-pyridin-2-yl]-(R)-indan-1-yl-amine;

[4-(5-Cyclopropyl-4-piperazin-1-yl-pyrido[3,4-d]pyrimidin-2-yl)-pyridin-2-yl]-(S)-indan-1-yl-amine;

[4-(8-Chloro-5-cyclopropyl-4-piperazin-1-yl-pyrido[3,4-d]pyrimidin-2-yl)-pyridin-2-yl]-(2,6-difluoro-phenyl)-amine;

[4-(5-Cyclopropyl-8-fluoro-4-piperazin-1-yl-pyrido[3,4-d]pyrimidin-2-yl)-pyridin-2-yl]-(2,6-difluoro-phenyl)-amine;

5-Cyclopropyl-8-fluoro-4-piperazin-1-yl-2-(2-trifluoromethyl-1H-pyrrolo[2,3-b]pyridin-4-yl)-pyrido[3,4-d]pyrimidine;

(1-Cyclobutyl-piperidin-4-ylmethyl)-{5-cyclopropyl-2-[2-(2,6-difluoro-phenylamino)-pyridin-4-yl]-pyrido[3,4-d]pyrimidin-4-yl}-amine;

Benzo[1,2,5]oxadiazol-4-yl-[4-(5-cyclopropyl-4-piperazin-1-yl-pyrido[3,4-d]pyrimidin-2-yl)-pyridin-2-yl]-amine;

5-Cyclopentyl-4-piperazin-1-yl-2-(2-trifluoromethyl-1H-pyrrolo[2,3-b]pyridin-4-yl)-pyrido[3,4-d]pyrimidine;

5-Cyclopropyl-2-(2-difluoromethyl-1H-pyrrolo[2,3-b]pyridin-4-yl)-4-piperazin-1-yl-pyrido[3,4-d]pyrimidine;

{5-Cyclopropyl-2-[2-(2,6-difluoro-phenylamino)-pyridin-4-yl]-pyrido[3,4-d]pyrimidin-4-yl}-piperidin-4-ylmethyl-amine;

5-Cyclopropyl-2-[2-(2-methoxy-1,1-dimethyl-ethyl)-1H-pyrrolo[2,3-b]pyridin-4-yl]-4-piperazin-1-yl-pyrido[3,4-d]pyrimidine;

5-Cyclobutyl-2-[2-(2-methoxy-1,1-dimethyl-ethyl)-1H-pyrrolo[2,3-b]pyridin-4-yl]-4-piperazin-1-yl-pyrido[3,4-d]pyrimidine;

(1-Cyclobutyl-piperidin-4-yl)-{5-cyclopropyl-2-[2-(2,6-difluoro-phenylamino)-pyridin-4-yl]-pyrido[3,4-d]pyrimidin-4-yl}-methyl-amine;

5-Cyclopropyl-4-piperazin-1-yl-2-[2-(tetrahydro-pyran-4-yl)-1H-pyrrolo[2,3-b]pyridin-4-yl]-pyrido[3,4-d]pyrimidine;

5-Cyclobutyl-2-(2-methyl-1H-pyrrolo[2,3-b]pyridin-4-yl)-4-piperazin-1-yl-pyrido[3,4-d]pyrimidine;

5-Cyclobutyl-2-[2-(1-phenyl-cyclopropyl)-1H-pyrrolo[2,3-b]pyridin-4-yl]-4-piperazin-1-yl-pyrido[3,4-d]pyrimidine;

5-Cyclobutyl-2-(2-difluoromethyl-1H-pyrrolo[2,3-b]pyridin-4-yl)-4-piperazin-1-yl-pyrido[3,4-d]pyrimidine;

{5-Cyclopropyl-2-[2-(2,6-difluoro-phenylamino)-pyridin-4-yl]-pyrido[3,4-d]pyrimidin-4-yl}-(1-isopropyl-piperidin-4-yl)-methyl-amine;

Benzo[1,2,5]oxadiazol-5-yl-[4-(5-cyclopropyl-4-piperazin-1-yl-pyrido[3,4-d]pyrimidin-2-yl)-pyridin-2-yl]-amine;

5-Bromo-4-piperazin-1-yl-2-(2-trifluoromethyl-1H-pyrrolo[2,3-b]pyridin-4-yl)-pyrido[3,4-d]pyrimidine;

2-(2-tert-Butyl-H-pyrrolo[2,3-b]pyridin-4-yl)-8-chloro-5-cyclopropyl-4-piperazin-1-yl-pyrido[3,4-d]pyrimidine;

2-(2-tert-Butyl-H-pyrrolo[2,3-b]pyridin-4-yl)-5-cyclopropyl-8-fluoro-4-piperazin-1-yl-pyrido[3,4-d]pyrimidine;

5-Bromo-2-(2-tert-butyl-1H-pyrrolo[2,3-b]pyridin-4-yl)-4-piperazin-1-yl-pyrido[3,4-d]pyrimidine;

(±)-exo-5-Cyclopropyl-2-[2-(7-oxa-bicyclo[2.2.1]hept-2-yl)-1H-pyrrolo[2,3-b]pyridin-4-yl]-4-piperazin-1-yl-pyrido[3,4-d]pyrimidine;

(±)-exo-5-Cyclobutyl-2-[2-(7-oxa-bicyclo[2.2.1]hept-2-yl)-1H-pyrrolo[2,3-b]pyridin-4-yl]-4-piperazin-1-yl-pyrido[3,4-d]pyrimidine;

{5-Cyclopropyl-2-[2-(2,6-difluoro-phenylamino)-pyridin-4-yl]-pyrido[3,4-d]pyrimidin-4-yl}-[1-(2,2-difluoro-ethyl)-piperidin-4-yl]-methyl-amine;

[4-(5-Cyclopropyl-4-piperazin-1-yl-pyrido[3,4-d]pyrimidin-2-yl)-pyridin-2-yl]-indan-5-yl-amine;

(5-Cyclopropyl-3,6-difluoro-pyridin-2-yl)-{4-[5-cyclopropyl-4-(3,3-dimethyl-piperazin-1-yl)-pyrido[3,4-d]pyrimidin-2-yl]-pyridin-2-yl}-amine;

N-[4-(5-Cyclopropyl-4-piperazin-1-yl-pyrido[3,4-d]pyrimidin-2-yl)-pyridin-2-yl]-2,2-difluoro-2-phenyl-acetamide;

5-Cyclopropyl-2-[2-(1-fluoro-cyclopropyl)-1H-pyrrolo[2,3-b]pyridin-4-yl]-4-piperazin-1-yl-pyrido[3,4-d]pyrimidine;

{4-[5-Cyclopropyl-4-(1-methyl-piperidin-4-ylsulfanyl)-pyrido[3,4-d]pyrimidin-2-yl]-pyridin-2-yl}-(2,6-difluoro-phenyl)-amine;

{5-Cyclopropyl-2-[2-(3,5-difluoro-pyridin-2-ylamino)-pyridin-4-yl]-pyrido[3,4-d]pyrimidin-4-yl}-methyl-(1-methyl-piperidin-4-yl)-amine;

[4-(5-Cyclopropyl-4-piperazin-1-yl-pyrido[3,4-d]pyrimidin-2-yl)-pyridin-2-yl]-[2-fluoro-4-(1-methyl-1H-pyrazol-4-yl)-phenyl]-amine;

{4-[5-Cyclopropyl-4-(hexahydro-pyrrolo[3,4-c]pyrrol-2-yl)-pyrido[3,4-d]pyrimidin-2-yl]-pyridin-2-yl}-phenyl-amine;

{4-[5-Cyclopropyl-4-(hexahydro-pyrrolo[3,4-c]pyrrol-2-yl)-pyrido[3,4-d]pyrimidin-2-yl]-pyridin-2-yl}-(3, 5-difluoro-pyridin-2-yl)-amine;

[4-(5-Cyclopropyl-4-piperazin-1-yl-pyrido[3,4-d]pyrimidin-2-yl)-pyridin-2-yl]-(2-trifluoromethyl-benzooxazol-5-yl)-amine;

5-Cyclopropyl-4-(piperidin-4-ylsulfanyl)-2-(2-trifluoromethyl-1H-pyrrolo[2, 3-b]pyridin-4-yl)-pyrido[3,4-d]pyrimidine;

(±)-endo-2-(2-Bicyclo[2.2.1]hept-2-yl-1H-pyrrolo[2,3-b]pyridin-4-yl)-5-cyclobutyl-4-piperazin-1-yl-pyrido[3,4-d]pyrimidine;

[8-Chloro-5-cyclopropyl-2-(2-trifluoromethyl-1H-pyrrolo[2,3-b]pyridin-4-yl)-pyrido[3,4-d]pyrimidin-4-yl]-methyl-piperidin-4-yl-amine;

[4-(5-Cyclopropyl-4-piperazin-1-yl-pyrido[3,4-d]pyrimidin-2-yl)-pyridin-2-yl]-(1,2,3,4-tetrahydro-naphthalen-2-yl)-amine;

{5-Cyclopropyl-2-[2-([D3-4]uinolin-2-ylamino)-pyridin-4-yl]-pyrido[3,4-d]pyrimidin-4-yl}-methyl-piperidin-4-yl-amine;

[5-Cyclopropyl-2-(2-trifluoromethyl-1H-pyrrolo[2,3-b]pyridin-4-yl)-pyrido[3,4-d]pyrimidin-4-yl]-methyl-piperidin-4-ylmethyl-amine;

(1S,2R)-1-[4-(5-Cyclopropyl-4-piperazin-1-yl-pyrido[3,4-d]pyrimidin-2-yl)-pyridin-2-ylamino]-indan-2-ol;

(1S,2S)-1-[4-(5-Cyclopropyl-4-piperazin-1-yl-pyrido[3,4-d]pyrimidin-2-yl)-pyridin-2-ylamino]-indan-2-ol;

(1R,2S)-1-[4-(5-Cyclopropyl-4-piperazin-1-yl-pyrido[3,4-d]pyrimidin-2-yl)-pyridin-2-ylamino]-indan-2-ol;

(1R,2R)-1-[4-(5-Cyclopropyl-4-piperazin-1-yl-pyrido[3,4-d]pyrimidin-2-yl)-pyridin-2-ylamino]-indan-2-ol;

5-Cyclobutyl-2-[2-(2,6-difluoro-phenyl)-1H-pyrrolo[2,3-b]pyridin-4-yl]-4-piperazin-1-yl-pyrido[3,4-d]pyrimidine;

5-Cyclopropyl-2-[2-(2,6-difluoro-phenyl)-1H-pyrrolo[2,3-b]pyridin-4-yl]-4-piperazin-1-yl-pyrido[3,4-d]pyrimidine;

2-(2-Cyclobutyl-1H-pyrrolo[2,3-b]pyridin-4-yl)-5-cyclopropyl-4-piperazin-1-yl-pyrido[3,4-d]pyrimidine;

5-Cyclobutyl-2-(2-cyclobutyl-1H-pyrrolo[2,3-b]pyridin-4-yl)-4-piperazin-1-yl-pyrido[3,4-d]pyrimidine;

[4-(8-Chloro-5-cyclopropyl-4-piperazin-1-yl-pyrido[3,4-d]pyrimidin-2-yl)-pyridin-2-yl]-(3,5-difluoro-pyridin-2-yl)-amine;

[4-(5-Cyclopropyl-4-piperazin-1-yl-pyrido[3,4-d]pyrimidin-2-yl)-pyridin-2-yl]-(3-methyl-3H-benzoimidazol-5-yl)-amine;

[4-(5-Cyclopropyl-4-piperazin-1-yl-pyrido[3,4-d]pyrimidin-2-yl)-pyridin-2-yl]-[4-(2,2,2-trifluoro-ethoxy)-phenyl]-amine;

{2-[2-(5-Chloro-3-fluoro-pyridin-2-ylamino)-pyridin-4-yl]-5-cyclopropyl-pyrido[3,4-d]pyrimidin-4-yl}-methyl-piperidin-4-yl-amine;

5-Cyclopropyl-2-(2-cyclohexyl-1H-pyrrolo[2,3-b]pyridin-4-yl)-4-piperazin-1-yl-pyrido[3,4-d]pyrimidine;

5-Cyclobutyl-2-(2-cyclohexyl-1H-pyrrolo[2,3-b]pyridin-4-yl)-4-piperazin-1-yl-pyrido[3,4-d]pyrimidine;

[3-Chloro-1-(5-trifluoromethyl-pyridin-2-yl)-1H-pyrazol-4-yl]-[4-(5-cyclopropyl-4-piperazin-1-yl-pyrido[3,4-d]pyrimidin-2-yl)-pyridin-2-yl]-amine;

[5-Cyclopropyl-2-(2-trifluoromethyl-1H-pyrrolo[2,3-b]pyridin-4-yl)-pyrido[3,4-d]pyrimidin-4-yl]-(3,3-difluoro-piperidin-4-yl)-amine;

{5-Cyclopropyl-2-[2-(3,5-difluoro-pyridin-2-ylamino)-pyridin-4-yl]-pyrido[3,4-d]pyrimidin-4-yl}-(3,3-difluoro-piperidin-4-yl)-amine;

{5-Cyclobutyl-2-[2-(3,5-difluoro-pyridin-2-ylamino)-pyridin-4-yl]-pyrido[3,4-d]pyrimidin-4-yl}-methyl-piperidin-4-yl-amine;

trans-2-[4-(5-Cyclopropyl-4-piperazin-1-yl-pyrido[3,4-d]pyrimidin-2-yl)-pyridin-2-ylamino]-indan-1-ol;

(R)-2-[4-(5-Cyclopropyl-4-piperazin-1-yl-pyrido[3,4-d]pyrimidin-2-yl)-pyridin-2-ylamino]-2-phenyl-ethanol;

[4-(5-Cyclopropyl-4-piperazin-1-yl-pyrido[3,4-d]pyrimidin-2-yl)-pyridin-2-yl]-((R)-1-naphthalen-2-yl-ethyl)-amine;

[4-(5-Cyclobutyl-4-piperazin-1-yl-pyrido[3,4-d]pyrimidin-2-yl)-pyridin-2-yl]-[(R)-1-(2-fluoro-phenyl)-ethyl]-amine;

[4-(5-Cyclopropyl-4-piperazin-1-yl-pyrido[3,4-d]pyrimidin-2-yl)-pyridin-2-yl]-(4-trifluoromethoxy-phenyl)-amine;

{5-Cyclobutyl-2-[2-(3,5,6-trifluoro-pyridin-2-ylamino)-pyridin-4-yl]-pyrido[3,4-d]pyrimidin-4-yl}-methyl-piperidin-4-yl-amine;

(S)-2-[4-(5-Cyclopropyl-4-piperazin-1-yl-pyrido[3,4-d]pyrimidin-2-yl)-pyridin-2-ylamino]-2-phenyl-ethanol;

[4-(5-Cyclopropyl-4-piperazin-1-yl-pyrido[3,4-d]pyrimidin-2-yl)-pyridin-2-yl]-((R)-1-naphthalen-1-yl-ethyl)-amine;

[4-(5-Cyclopropyl-4-piperazin-1-yl-pyrido[3,4-d]pyrimidin-2-yl)-pyridin-2-yl]-(2,2-difluoro-2-phenyl-ethyl)-amine;

{5-Cyclopropyl-2-[2-(3,5-difluoro-pyridin-2-ylamino)-pyridin-4-yl]-pyrido[3,4-d]pyrimidin-4-yl}-methyl-piperidin-4-ylmethyl-amine;

{5-Cyclopropyl-2-[2-(3,5-difluoro-pyridin-2-ylamino)-pyridin-4-yl]-pyrido[3,4-d]pyrimidin-4-yl}-(tetrahydro-pyran-4-yl)-amine;

{8-Chloro-5-cyclopropyl-2-[2-(3,5,6-trifluoro-pyridin-2-ylamino)-pyridin-4-yl]-pyrido[3,4-d]pyrimidin-4-yl}-methyl-piperidin-4-yl-amine;

{8-Chloro-5-cyclopropyl-2-[2-(3,5-difluoro-pyridin-2-ylamino)-pyridin-4-yl]-pyrido[3,4-d]pyrimidin-4-yl}-methyl-piperidin-4-yl-amine;

(5-Chloro-3-fluoro-pyridin-2-yl)-[4-(5-cyclopropyl-4-piperazin-1-yl-pyrido[3,4-d]pyrimidin-2-yl)-pyridin-2-yl]-amine;

{5-Cyclopropyl-2-[2-(3,5-difluoro-pyridin-2-ylamino)-pyridin-4-yl]-pyrido[3,4-d]pyrimidin-4-yl}-methyl-(tetrahydro-pyran-4-yl)-amine;

(4-{5-Cyclopropyl-4-[3-(tetrahydro-pyran-4-yl)-pyrrolidin-1-yl]-pyrido[3,4-d]pyrimidin-2-yl}-pyridin-2-yl)-(3,5-difluoro-pyridin-2-yl)-amine;

{5-Cyclopropyl-2-[2-(3,5-difluoro-pyridin-2-ylamino)-pyridin-4-yl]-pyrido[3,4-d]pyrimidin-4-yl}-(4-methyl-piperidin-4-yl)-amine;

{5-Cyclopropyl-2-[2-(3,5-difluoro-pyridin-2-ylamino)-pyridin-4-yl]-pyrido[3,4-d]pyrimidin-4-yl}-(3,3-dimethyl-piperidin-4-yl)-amine;

{5-Cyclopropyl-2-[2-(3,5,6-trifluoro-pyridin-2-ylamino)-pyridin-4-yl]-pyrido[3,4-d]pyrimidin-4-yl}-(3,3-dimethyl-piperidin-4-yl)-amine;

[4-(5-Cyclopropyl-4-piperazin-1-yl-pyrido[3,4-d]pyrimidin-2-yl)-pyridin-2-yl]-(3,3-dimethyl-indan-1-yl)-amine;

[4-(8-Chloro-5-cyclopropyl-4-piperazin-1-yl-pyrido[3,4-d]pyrimidin-2-yl)-pyridin-2-yl]-(3,5,6-trifluoro-pyridin-2-yl)-amine;

5-Cyclopropyl-2-[2-(3-fluoro-pyridin-2-yl)-1H-pyrrolo[2,3-b]pyridin-4-yl]-4-piperazin-1-yl-pyrido[3,4-d]pyrimidine;

5-Cyclobutyl-2-[2-(3-fluoro-pyridin-2-yl)-1H-pyrrolo[2,3-b]pyridin-4-yl]-4-piperazin-1-yl-pyrido[3,4-d]pyrimidine;

5-Cyclobutyl-2-[2-(1-phenyl-cyclobutyl)-1H-pyrrolo[2,3-b]pyridin-4-yl]-4-piperazin-1-yl-pyrido[3,4-d]pyrimidine;

5-Cyclobutyl-4-piperazin-1-yl-2-[2-(2,2,2-trifluoro-1,1-dimethyl-ethyl)-1H-pyrrolo[2,3-b]pyridin-4-yl]-pyrido[3,4-d]pyrimidine;

5-Cyclobutyl-4-piperazin-1-yl-2-[2-(1-trifluoromethyl-cyclobutyl)-1H-pyrrolo[2,3-b]pyridin-4-yl]-pyrido[3,4-d]pyrimidine;

5-Cyclobutyl-4-piperazin-1-yl-2-[2-(tetrahydro-furan-3-yl)-1H-pyrrolo[2,3-b]pyridin-4-yl]-pyrido[3,4-d]pyrimidine;

5-Cyclobutyl-4-piperazin-1-yl-2-[2-(tetrahydro-furan-2-yl)-1H-pyrrolo[2,3-b]pyridin-4-yl]-pyrido[3,4-d]pyrimidine;

{5-Cyclopropyl-2-[2-(3,5-difluoro-pyridin-2-ylamino)-pyridin-4-yl]-pyrido[3,4-d]pyrimidin-4-yl}-(3-fluoro-piperidin-4-yl)-amine;

[4-(5,8-Dicyclopropyl-4-piperazin-1-yl-pyrido[3,4-d]pyrimidin-2-yl)-pyridin-2-yl]-(3,5,6-trifluoro-pyridin-2-yl)-amine;

[4-(5,8-Dicyclopropyl-4-piperazin-1-yl-pyrido[3,4-d]pyrimidin-2-yl)-pyridin-2-yl]-(3,5-difluoro-pyridin-2-yl)-amine;

[4-(5,8-Dicyclopropyl-4-piperazin-1-yl-pyrido[3,4-d]pyrimidin-2-yl)-pyridin-2-yl]-(2,6-difluoro-phenyl)-amine;

2-(2-tert-Butyl-1H-pyrrolo[2,3-b]pyridin-4-yl)-5,8-dicyclopropyl-4-piperazin-1-yl-pyrido[3,4-d]pyrimidine;

[4-(5-Cyclopropyl-4-piperazin-1-yl-pyrido[3,4-d]pyrimidin-2-yl)-pyridin-2-yl]-(6-fluoro-pyridazin-3-yl)-amine;

5-Cyclopropyl-4-piperazin-1-yl-2-[2-(tetrahydro-furan-3-yl)-1H-pyrrolo[2,3-b]pyridin-4-yl]-pyrido[3,4-d]pyrimidine;

(2,6-Difluoro-phenyl)-[4-(4-piperazin-1-yl-5-trifluoromethyl-pyrido[3,4-d]pyrimidin-2-yl)-pyridin-2-yl]-amine;

(3,5-Difluoro-pyridin-2-yl)-[4-(4-piperazin-1-yl-5-trifluoromethyl-pyrido[3,4-d]pyrimidin-2-yl)-pyridin-2-yl]-amine;

[4-(4-Piperazin-1-yl-5-trifluoromethyl-pyrido[3,4-d]pyrimidin-2-yl)-pyridin-2-yl]-(3,5,6-trifluoro-pyridin-2-yl)-amine;

{5-Cyclopropyl-2-[2-(3,5-difluoro-pyridin-2-ylamino)-pyridin-4-yl]-pyrido[3,4-d]pyrimidin-4-yl}-(3,3-dimethyl-piperidin-4-yl)-methyl-amine;

5-Cyclopropyl-2-(2,2-dimethyl-2,3-dihydro-1H-pyrrolo[2,3-b]pyridin-4-yl)-4-piperazin-1-yl-pyrido[3,4-d]pyrimidine;

{4-[4-(3-Amino-piperidin-1-yl)-5-cyclopropyl-pyrido[3,4-d]pyrimidin-2-yl]-pyridin-2-yl}-(3,5-difluoro-pyridin-2-yl)-amine;

4-(5-Cyclobutyl-4-piperazin-1-yl-pyrido[3,4-d]pyrimidin-2-yl)-6,7,8,9-tetrahydro-5H-pyrido[2,3-b]indole;

6-Chloro-4-(5-cyclobutyl-4-piperazin-1-yl-pyrido[3,4-d]pyrimidin-2-yl)-9H-pyrido[2,3-b]indole;

5-Cyclopropyl-2-[2-(2-fluoro-phenyl)-1H-pyrrolo[2,3-b]pyridin-4-yl]-4-piperazin-1-yl-pyrido[3,4-d]pyrimidine;

2-[2-(2-Chloro-phenyl)-1H-pyrrolo[2,3-b]pyridin-4-yl]-5-cyclopropyl-4-piperazin-1-yl-pyrido[3,4-d]pyrimidine;
5-Cyclobutyl-2-[2-(2-fluoro-phenyl)-1H-pyrrolo[2,3-b]pyridin-4-yl]-4-piperazin-1-yl-pyrido[3,4-d]pyrimidine;
2-[2-(2-Chloro-phenyl)-1H-pyrrolo[2,3-b]pyridin-4-yl]-5-cyclobutyl-4-piperazin-1-yl-pyrido[3,4-d]pyrimidine;
{4-[5-Cyclopropyl-4-(3-methylamino-piperidin-1-yl)-pyrido[3,4-d]pyrimidin-2-yl]-pyridin-2-yl}-(3,5-difluoro-pyridin-2-yl)-amine;
N-{5-Cyclopropyl-2-[2-(3,5-difluoro-pyridin-2-ylamino)-pyridin-4-yl]-pyrido[3,4-d]pyrimidin-4-yl}-N'-methyl-benzene-1,4-diamine;
5-Cyclopropyl-4-piperazin-1-yl-2-[2-(1-trifluoromethyl-cyclobutyl)-1H-pyrrolo[2,3-b]pyridin-4-yl]-pyrido[3,4-d]pyrimidine;
4-(5-Cyclopropyl-4-piperazin-1-yl-pyrido[3,4-d]pyrimidin-2-yl)-6,7,8,9-tetrahydro-5H-pyrido[2,3-b]indole;
2-(3-Chloro-2-methyl-1H-pyrrolo[2,3-b]pyridin-4-yl)-5-cyclopropyl-4-piperazin-1-yl-pyrido[3,4-d]pyrimidine;
[4-(5-Cyclobutyl-4-piperazin-1-yl-pyrido[3,4-d]pyrimidin-2-yl)-pyridin-2-yl]-(tetrahydro-pyran-4-yl)-amine;
4-(5-Cyclopropyl-4-piperazin-1-yl-pyrido[3,4-d]pyrimidin-2-yl)-3,3-dimethyl-1,3-dihydro-pyrrolo[2,3-b]pyridin-2-one;

or a salt thereof.

The invention claimed is:

1. A compound selected from the group consisting of:
(5-Cyclobutyl-3-fluoro-pyridin-2-yl)-[4-(5-cyclopropyl-4-piperazin-1-yl-pyrido[3,4-d]pyrimidin-2-yl)-pyridin-2-yl]-amine;
{5-Cyclopropyl-2-[2-(3,5,6-trifluoro-pyridin-2-ylamino)-pyridin-4-yl]-pyrido[3,4-d]pyrimidin-4-yl}-methyl-piperidin-4-yl-amine;
(4-Chloro-1-ethyl-1H-pyrazol-3-yl)-[4-(5-cyclopropyl-4-piperazin-1-yl-pyrido[3,4-d]pyrimidin-2-yl)-pyridin-2-yl]-amine;
[4-(5-Cyclopropyl-4-piperazin-1-yl-pyrido[3,4-d]pyrimidin-2-yl)-pyridin-2-yl]-[1-(2,2,2-trifluoro-ethyl)-1H-pyrazol-3-yl]-amine;
{4-[5-Cyclopropyl-4-(3,3-dimethyl-piperazin-1-yl)-pyrido[3,4-d]pyrimidin-2-yl]-pyridin-2-yl}-[1-(2,2,2-trifluoro-ethyl)-1H-pyrazol-3-yl]-amine; and
{4-[5-Cyclopropyl-4-(3,3-dimethyl-piperazin-1-yl)-pyrido[3,4-d]pyrimidin-2-yl]-pyridin-2-yl}-(1-isopropyl-1H-pyrazol-3-yl)-amine;

or a pharmaceutically acceptable salt thereof.

2. The compound of claim 1, wherein the compound is (5-(Cyclobutyl-3-fluoro-pyridin-2-yl)-[4-(5-cyclopropyl-4-piperazin-1-yl-pyrido[3,4-d]pyrimidin-2-yl)-pyridin-2-yl]-amine or a pharmaceutically acceptable salt thereof.

3. The compound of claim 1, wherein the compound is {5-Cyclopropyl-2-[2-(3,5,6-trifluoro-pyridin-2-ylamino)-pyridin-4-yl]-pyrido[3,4-d]pyrimidin-4-yl}-methyl-piperidin-4-yl-amine or a pharmaceutically acceptable salt thereof.

4. The compound of claim 1, wherein the compound is (4-Chloro-1-ethyl-1H-pyrazol-3-yl)-[4-(5-cyclopropyl-4-piperazin-1-yl-pyrido[3,4-d]pyrimidin-2-yl)-pyridin-2-yl]-amine or a pharmaceutically acceptable salt thereof.

5. The compound of claim 1, wherein the compound is [4-(5-Cyclopropyl-4-piperazin-1-yl-pyrido[3,4-d]pyrimidin-2-yl)-pyridin-2-yl]-[1-(2,2,2-trifluoro-ethyl)-1H-pyrazol-3-yl]-amine or a pharmaceutically acceptable salt thereof.

6. The compound of claim 1, wherein the compound is {4-[5-Cyclopropyl-4-(3,3-dimethyl-piperazin-1-yl)-pyrido[3,4-d]pyrimidin-2-yl]-pyridin-2-yl}-[1-(2,2,2-trifluoro-ethyl)-1H-pyrazol-3-yl]-amine or a pharmaceutically acceptable salt thereof.

7. The compound of claim 1, wherein the compound is {4-[5-Cyclopropyl-4-(3,3-dimethyl-piperazin-1-yl)-pyrido[3,4-d]pyrimidin-2-yl]-pyridin-2-yl}-(1-isopropyl-1H-pyrazol-3-yl)-amine or a pharmaceutically acceptable salt thereof.

8. A pharmaceutical composition comprising the compound of claim 1 and a pharmaceutically acceptable excipient.

9. The pharmaceutical composition of claim 8, wherein the compound of claim 1 is (5-Cyclobutyl-3-fluoro-pyridin-2-yl)-[4-(5-cyclopropyl-4-piperazin-1-yl-pyrido[3,4-d]pyrimidin-2-yl)-pyridin-2-yl]-amine or a pharmaceutically acceptable salt thereof.

10. The pharmaceutical composition of claim 8, wherein the compound of claim 1 is {5-Cyclopropyl-2-[2-(3,5,6-trifluoro-pyridin-2-ylamino)-pyridin-4-yl]-pyrido[3,4-d]pyrimidin-4-yl}-methyl-piperidin-4-yl-amine or a pharmaceutically acceptable salt thereof.

11. The pharmaceutical composition of claim 8, wherein the compound of claim 1 is (4-Chloro-1-ethyl-1H-pyrazol-3-yl)-[4-(5-cyclopropyl-4-piperazin-1-yl-pyrido[3,4-d]pyrimidin-2-yl)-pyridin-2-yl]-amine or a pharmaceutically acceptable salt thereof.

12. The pharmaceutical composition of claim 8, wherein the compound of claim 1 is [4-(5-Cyclopropyl-4-piperazin-1-yl-pyrido[3,4-d]pyrimidin-2-yl)-pyridin-2-yl]-[1-(2,2,2-trifluoro-ethyl)-1H-pyrazol-3-yl]-amine or a pharmaceutically acceptable salt thereof.

13. The pharmaceutical composition of claim 8, wherein the compound of claim 1 is {4-[5-Cyclopropyl-4-(3,3-dimethyl-piperazin-1-yl)-pyrido[3,4-d]pyrimidin-2-yl]-pyridin-2-yl}-[1-(2,2,2-trifluoro-ethyl)-1H-pyrazol-3-yl]-amine or a pharmaceutically acceptable salt thereof.

14. The pharmaceutical composition of claim 8, wherein the compound of claim 1 is {4-[5-Cyclopropyl-4-(3,3-dimethyl-piperazin-1-yl)-pyrido[3,4-d]pyrimidin-2-yl]-pyridin-2-yl}-(1-isopropyl-1H-pyrazol-3-yl)-amine or a pharmaceutically acceptable salt thereof.

* * * * *